US010946018B2

(12) United States Patent
De Lombaert et al.

(10) Patent No.: US 10,946,018 B2
(45) **Date of Patent: *Mar. 16, 2021**

(54) SPIROCYCLIC COMPOUNDS AS TRYPTOPHAN HYDROXYLASE INHIBITORS

(71) Applicant: Roivant Sciences GmbH, Basel (CH)

(72) Inventors: Stéphane De Lombaert, Brisbane, CA (US); Daniel R. Goldberg, Seattle, WA (US); Kenneth Brameld, Menlo Park, CA (US); Eric Brian Sjogren, Mountain View, CA (US); Andrew Scribner, Durham, NC (US)

(73) Assignee: Roivant Sciences GmbH, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/850,542

(22) Filed: Apr. 16, 2020

(65) Prior Publication Data

US 2020/0237760 A1 Jul. 30, 2020

Related U.S. Application Data

(63) Continuation of application No. 16/426,698, filed on May 30, 2019, now Pat. No. 10,660,893, which is a continuation of application No. 15/978,361, filed on May 14, 2018, now Pat. No. 10,350,208, which is a continuation of application No. 15/645,054, filed on Jul. 10, 2017, now Pat. No. 10,045,988, which is a continuation of application No. 15/278,130, filed on Sep. 28, 2016, now Pat. No. 9,750,740, which is a continuation of application No. 14/841,868, filed on Sep. 1, 2015, now Pat. No. 9,512,122, which is a continuation of application No. 14/477,948, filed on Sep. 5, 2014, now Pat. No. 9,199,994.

(60) Provisional application No. 62/004,385, filed on May 29, 2014, provisional application No. 61/899,943, filed on Nov. 5, 2013, provisional application No. 61/874,545, filed on Sep. 6, 2013.

(51) Int. Cl.

| | |
|---|---|
| ***A61K 31/506*** | (2006.01) |
| ***C07D 471/10*** | (2006.01) |
| ***C07D 519/00*** | (2006.01) |
| ***A61K 9/00*** | (2006.01) |

(52) U.S. Cl.

CPC .......... *A61K 31/506* (2013.01); *A61K 9/0014* (2013.01); *A61K 9/0019* (2013.01); *A61K 9/0053* (2013.01); *A61K 9/0078* (2013.01); *C07D 471/10* (2013.01); *C07D 519/00* (2013.01)

(58) Field of Classification Search

CPC .................................................... A61K 31/506
USPC ..................................................... 514/252.15
See application file for complete search history.

(56) References Cited

U.S. PATENT DOCUMENTS

| | | | | |
|---|---|---|---|---|
| 5,380,927 | A | 1/1995 | Paradies et al. | |
| 7,544,695 | B2 | 6/2009 | Berk et al. | |
| 8,349,825 | B2 | 1/2013 | Mampreian et al. | |
| 9,199,994 | B2 * | 12/2015 | De Lombaert | A61P 19/10 |
| 9,512,122 | B2 * | 12/2016 | De Lombaert | A61P 11/00 |
| 9,750,740 | B2 * | 9/2017 | De Lombaert | A61P 29/00 |
| 10,045,988 | B2 * | 8/2018 | De Lombaert | A61P 1/16 |
| 10,350,208 | B2 * | 7/2019 | De Lombaert | A61P 1/08 |
| 2010/0087431 | A1 | 4/2010 | Brooks et al. | |
| 2010/0173889 | A1 | 7/2010 | Schunk et al. | |
| 2010/0331294 | A1 | 12/2010 | Black et al. | |
| 2012/0101281 | A1 | 4/2012 | Murugesan et al. | |
| 2013/0102611 | A1 | 4/2013 | Charlton et al. | |
| 2015/0080393 | A1 | 3/2015 | De Lombaert et al. | |
| 2016/0096836 | A1 | 4/2016 | De Lombaert et al. | |

FOREIGN PATENT DOCUMENTS

| | | | |
|---|---|---|---|
| CN | 101591332 | A | 12/2009 |
| CN | 104045626 | A | 9/2014 |
| EP | 2634190 | A1 | 9/2013 |
| EP | 3061761 | A1 | 8/2016 |
| WO | 98/008850 | A1 | 3/1998 |
| WO | 2001/066531 | A1 | 9/2001 |
| WO | 2003/051841 | A2 | 6/2003 |
| WO | 2003/051842 | A2 | 6/2003 |
| WO | 2004/035550 | A1 | 4/2004 |
| WO | 2004/111004 | A1 | 12/2004 |
| WO | 2004/111031 | A1 | 12/2004 |
| WO | 2005/073199 | A1 | 8/2005 |
| WO | 2006/074957 | A1 | 7/2006 |
| WO | 2007/089335 | A2 | 8/2007 |
| WO | 2008/073933 | A2 | 6/2008 |

(Continued)

OTHER PUBLICATIONS

Abid et al., "Inhibition of gut- and lung derived serotonin attenuates pulmonary hypertension in mice," Am. J. Physiol Lung Cell Mol Physiol, Jul. 2012, 303:L500-L508.
Alpini et al. "Serotonin metabolism is dysregulated in cholangiocarcinoma, which has implications for tumor growth," Cancer Res., Nov. 2008, 68:9184-9193.
Antic et al., "Treating skin and lung fibrosis in systemic sclerosis: a future filled with promise?" Current Opinion in Pharamacology, 2013, 13:455-462.
Artlett, "Animal models of scleroderma: fresh insights." Curr. Opin. Rheumatol., 2010, 22:677-682.
Ban et al., "Impact of Increased Plasma Serotonin Levels and Carotid Atherosclerosis on Vascular Dementia," Atherosclerosis, 2007, 195, 153-159.

(Continued)

*Primary Examiner* — Kahsay Habte
(74) *Attorney, Agent, or Firm* — Ohlandt, Greeley, Ruggiero & Perle LLP

(57) ABSTRACT

The present invention is directed to spirocyclic compounds which are inhibitors of tryptophan hydroxylase (TPH), particularly isoform 1 (TPH1), that are useful in the treatment of diseases or disorders associated with peripheral serotonin including, for example, gastrointestinal, cardiovascular, pulmonary, inflammatory, metabolic, and low bone mass diseases, as well as serotonin syndrome, and cancer.

18 Claims, No Drawings

(56) References Cited

FOREIGN PATENT DOCUMENTS

| | | | |
|---|---|---|---|
| WO | 2008/100412 | A1 | 8/2008 |
| WO | 2009/009561 | A1 | 1/2009 |
| WO | 2009/014972 | A1 | 1/2009 |
| WO | 2009/040075 | A1 | 4/2009 |
| WO | 2009/123978 | A1 | 10/2009 |
| WO | 2010/046109 | A1 | 4/2010 |
| WO | 2010/056992 | A1 | 5/2010 |
| WO | 2010/065333 | A1 | 6/2010 |
| WO | 2010/147094 | A1 | 12/2010 |
| WO | 2011/053977 | A1 | 5/2011 |
| WO | 2011/056916 | A1 | 5/2011 |
| WO | 2011/063181 | A1 | 5/2011 |
| WO | 2011/100285 | A1 | 8/2011 |
| WO | 2011/103196 | A1 | 8/2011 |
| WO | 2012/048222 | A1 | 4/2012 |
| WO | 2012/061576 | A1 | 5/2012 |
| WO | 2013/030802 | A1 | 3/2013 |
| WO | 2013/059146 | A1 | 4/2013 |
| WO | 2013/074889 | A1 | 5/2013 |
| WO | 2013/105057 | A1 | 7/2013 |
| WO | 2013/105058 | A1 | 7/2013 |
| WO | 2013/105061 | A1 | 7/2013 |
| WO | 2013/105063 | A1 | 7/2013 |
| WO | 2013/105065 | A1 | 7/2013 |
| WO | 2013/105066 | A1 | 7/2013 |
| WO | 2013/111110 | A2 | 8/2013 |
| WO | 2013/148978 | A1 | 10/2013 |
| WO | 2014/082034 | A1 | 5/2014 |
| WO | 2014/124523 | A1 | 8/2014 |
| WO | 2014/195847 | A2 | 12/2014 |
| WO | 2015/075023 | A1 | 5/2015 |
| WO | 2015/075025 | A1 | 5/2015 |
| WO | 2015/089137 | A1 | 6/2015 |
| WO | 2016/177690 | A1 | 11/2016 |

OTHER PUBLICATIONS

Berge et al., "Pharmaceutical Salts," J. Pharm. Sci., 1977, 66(1):1-19.

Brown et al., "The tryptophan hydroxylase inhibitor LX1031 shows clinical benefit in patients with nonconstipating irritable bowel syndrome," Gastroenterology, 2011, 141:507-516.

Camilleri, "LX-1031, A Tryptophan 5-hydroxylase Inhibitor, and Its Potential in Chronic Diarrhea Associated With Increased Serotonin," Neurogastroenterol Motil., Mar. 2011, 23(3):193-200.

Cianchetta et al., "Mechanism of Inhibition of Novel Tryptophan Hydroxylase Inhibitors Revealed by Co-crystal Structures and Kinetic Analysis," Current chemical genomics, 2010, 4:19-26.

Coleiro et al., "Treatment of Raynaud's phenomenon with the selective serotonin reuptake inhibitor fluoxetine," Rheumatology, Sep. 2001 40(9):1038-1043.

Corey and Link, "A General, Catalytic, and Enantioselective Synthesis of Alpha-amino Acids," J. Am. Chem. Soc., 1992, 114:1906-1908.

Costedio et al., "Serotonin and Its Role in Colonic Function and in Gastrointestinal Disorders," Diseases of the Colon and Rectum, Mar. 2007, 50(3): 376-88.

Crowell, "Role of Serotonin in the Pathophysiology of the Irritable Bowel Syndrome," British Journal of Pharmacology, 2004, 141:1285-93.

Dale and Mosher, "Nuclear Magnetic Resonance Enantiomer Regents. Configurational Correlations Via Nuclear Magnetic Resonance Chemical Shifts of Diastereomeric Mandelate, OMethylmandelate, and alpha-Methoxy alpha-Trifluoromethylphenylacetate (MTPA) Esters," J. Am. Chem. Soc., Jan. 1973, 95(2):512-519.

Dees et al., "Platelet-derived serotonin links vascular disease and tissue fibrosis," J. Exp. Med., Apr. 2011, 208(5):961-972.

DeGraw et al., "Experimentally Induced Phenylketonuria. I. Inhibitors of Phenylalanine Hydroxylase," Life Sci., Jan. 1967, 10:64-66.

Derrett-Smith et al. "Animal models of scleroderma: lessons from transgenic and knockout mice." Curr. Opin. Rheumatol., 2009, 21:630-635.

Duerschmied et al., "Platelet Serotonin Promotes The Recruitment of Neutrophils to Sites of Acute Inflammation in Mice," Blood, Feb. 2013, 121(6):1008-1015.

Dürk et al., "Production of serotonin by tryptophan hydroxylase 1 and release via platelets contribute to allergic airway inflammation." Am J Respir Crit Care Med., Jan. 2013, 187(5): 476-485.

Ebrahimkhani et al., "Stimulating Healthy Tissue Regeneration by Targeting the 5-HT2B Receptor In Chronic Liver Disease," Nature Medicine, 2011 17, 1668-1673.

Egermayer et al., "Role of Serotonin in the Pathogenesis of Acute and Chronic Pulmonary Hypertension," Thorax, 1999, 54:161-168.

Engelman et al., "Inhibition of Serotonin Synthesis by Parachlorophenylalanine in Patients With The Carcinoid Syndrome," The New England Journal of Medicine, Nov. 1967, 277:1103-1108.

Fabre et al., "Modulation of bleomycin-induced lung fibrosis by serotonin receptor antagonists in mice," Eur. Resp. Journal, 2008, 32(2):426-436.

Fernandez and Eickelberg, "New Cellular and Molecular Mechanisms of Lung Injury and Fibrosis in Idiopathic Pulmonary Fibrosis," Lancet, Aug. 2012, 380: 680-88.

Fox and Khattar, "Carcinoid Heart Disease: Presentation, Diagnosis, and Management," Heart, 2004, 90:1224-1228.

Galligan and Parkman, "Recent advances in understanding the role of serotonin in gastrointestinal motility and functional bowel disorders," Neurogastroenterol Motil., 2007, 19(Suppl.2):1-4.

Gershon and Tack, "The Serotonin Signaling System: From Basic Understanding to Drug Development for Functional GI Disorders," Gastroenterology, 2007, 132:397-414.

Ghia et al., "Serotonin has a key role in pathogenesis of experimental colitis," Gastroenterology, 2009, 137(5): 1649-1660.

Herrick, "The pathogenesis, diagnosis and treatment of Raynaud phenomenon," Rhematology, Aug. 2012, 8:469-479.

Hicks, "Use of molecular targeted agents for the diagnosis, staging and therapy of neuroendocrine malignancy," Cancer Imaging, Oct. 2010, 10:S83-S91.

International Preliminary Report on Patentability in International Application No. PCT/US2014/054202, dated Mar. 8, 2016, 10 pages.

International Search Report and Written Opinion in International Application No. PCT/US2014/054202 dated Dec. 2, 2014, 14 pages.

Iredale, "Models of liver fibrosis: exploring the dynamic nature of inflammation and repair in a solid organ." J. Clin. Invest., Mar. 2007, 117(3):539-548.

Iwamoto and Distler, "Molecular targets for therapy in systemic sclerosis," Fibrogenesis and Tissue Repair, Jun. 2012, 5(Suppl 1): S19, 6 pages.

Jin et al., "Substituted 3-(4-(1,3,5-triazin-2-yl)phenyl)-2-aminopropanoic Acids As Novel Tryptophan Hydroxylase Inhibitors," Bioorganic & Medicinal Chemistry Letters, 2009, 19:5229-5232.

Jithunsa et all., "Copper (II) chloride-mediated cyclization reaction of N-alkoxy-orthoalkynylbenzamides," Organic Letters 13 (3): 518-521.

Johnson, "The role of transglutaminase in the rat subtotal nephrectomy model of renal fibrosis," J Clin Invest., Jun. 1997, 99(12):2950-2960.

Journal of Pharmaceutical Science, 66, 2 (1977).

Kay et al., "Pulmonary Hypertension Induced in Rats by Monocrotaline and Chronic Hypoxia is Reduced by p-Chlorophenylalanine," Respiration, 1985, 47:48-56.

King et al., "A phase 3 trial of Pirfenidone in patients with idiopathic pulmonary fibrosis," The New England Journal of Medicine, May 2014, 370(22):2083-2092.

Kode et al., "FOXO1 orchestrates the bone-suppressing function of gut-derived serotonin," J. Clinical Investigation, Jul. 2012, 14 pages.

Koizumi et al., "Inhibition of Phenylalanine Hydroxylase, a Pterin-requiring Monooxygenase by Oudenone and its Derivatives," J. Antibiotics, Apr. 1982, 35(4):458-462.

(56) References Cited

OTHER PUBLICATIONS

Konigshoff et al., "Increased expression of 5-hydroxytryptamine2A/B receptors in idiopathic pulmonary fibrosis: a rationale for therapeutic intervention," Thorax, 2010, 65(11):949-55.
Lacerda et al. "Local serotonin mediates cyclic strain-induced phenotype transformation, matrix degradation, and glycosaminoglycan synthesis in cultured sheep mitral valves," Am J Physiol Heart Circ Physiol, 2012, 302(10): H1983-H1990.
Lau et al., "The Role of Circulating Serotonin in the Development of Chronic Obstructive Pulmonary Disease," PloS One, Feb. 2012, 7(2):e31617, 7 pages.
Lesurtel et al., "Role of Serotonin in the Hepato-gastrointestinal Tract: An Old Molecule for New Perspectives," Cell. Mol. Life Sci., 2008 65:940-952.
Li et al., "Serotonin Activates Dendritic Cell Function in the Context of Gut Inflammation," The American Journal of Pathology, Feb. 2011, 178(2):662-671.
Liang et al., "Serotonin Promotes the Proliferation of Serum-deprived Hepatocellular Carcinoma Cells Via Upregulation of FOXO3a," Molecular Cancer, 2013, 12:14, 11 pages.
Liedtke et al., "Experimental liver fibrosis research: update on animal models, legal issues and translational aspects." Fibrogenesis & Tissue Repair, 2013, 6:19, 25 pages.
Liu et al., "Discovery and Characterization of Novel Tryptophan Hydroxylase Inhibitors That Selectively Inhibit Serotonin Synthesis in the Gastrointestinal Tract," J. Pharmacol. Exp. Ther, 2008, 325(1):47-55.
Mann and Oakley, "Serotonin paracrine signaling in tissue fibrosis," Biochimica et Biophysica Acta, 2013, 1832:905-910.
Manocha and Khan, "Serotonin and GI Disorders: An Update on Clinical and Experimental Studies," Clinical and Translational Gastroenterology, 2012, 3:e13, 6 pages.
Margolis et al., "Pharmacological Reduction of Mucosal but Not Neuronal Serotonin Opposes Inflammation in Mouse Intestine," Gut, Jun. 2013, 1-10 (with Supplemental Information).
Maurer and Distler, "Emerging targeted therapies in sleroderma lung and skin fibrosis," Best Practice & Research Clinical Rheumatology, 2011, 25:843-858.
Mawe and Hoffman, "Serotonin signaling in the gut—functions, dysfunctions and therapeutic targets," Gastroenterology & Hepatology, Aug. 2013, 10:473-486.
Mawe et al., "Review article: intestinal serotonin signaling in irritable bowel syndrome," Aliment Pharmacol Ther, 2006, 23:1067-1076.
Moeller et al., "The bleomycin animal model: a useful tool to investigate treatment options for idiopathic pulmonary fibrosis?" Int J Biochem Cell Biol, 2008, 40(3):362-382.
Mouratis and Aidinis, "Modeling pulmonary fibrosis with bleomycin," Current Opinion in Pulmonary Medicine, 2011, 17:355-361.
Nowak et al., "Tryptophan hydroxylase-1 regulates immune tolerance and inflammation," J Exper Med, 2012, 209(11):2127-2135.
Ouadid et al., "Serotonin Increases Calcium Current in Human Atrial Myocytes via the Newly Described 5-Hydroxytyptamine4 Receptors," Molecular Pharmacology, 1992, 41:346-351.
Ouyang et al., "Combined Structure-Based Pharmacophore and 3D-QSAR Studies on Phenylalanine Series Compounds as TPII1 Inhibitors," Int J Molecular Sci, 2012, 13:5348-5363.
Pai et al., "Altered serotonin physiology in human breast cancers favors paradoxical growth and cell survival," Nov. 2009, 11(6):1-17.
Reinhard et al., "A rapid and sensitive assay for Tyrosine-3-Monooxygenase based upon the release of 3H2O and adsorption of [3H]-Tyrosine by charcoal," Life Sciences, 1986, 39(23):2185-2189.
Remington's Pharmaceutical Sciences, 17th ed., Mack Publishing Company, Easton, Pa., 1985, p. 1418.
Richeldi et al., "Efficacy and Safety of Nintedanib in Idiopathic Pulmonary Fibrosis," New England Journal of Medicine, May 2014, 370(22):2071-2082.
Robiolio et al., "Carcinoid Heart Disease: Correlation of High Serotonin Levels with Valvular Abnormalities Detected by Cardiac Catheterization and Echocardiography," Circulation, 1995, 92:790-795.
Shi et al., "Modulation of Peripheral Serotonin Levels by Novel Tryptophan Hydroxylase Inhibitors for the Potential Treatment of Functional Gastrointestinal Disorders," J Med Chem, 2008, 51:3684-3687.
Shinka et al., "Serotonin synthesis and metabolism-related molecules in a human prostate cancer cell line," Oncology Letters, 2011, 2:211-215.
Sikander et al., "Role of serotonin in gastrointestinal motility and irritable bowel syndrome," Clinica Chimica Acta, 2009, 403:47-55.
Skurikhin et al., "Effect of Antiserotonin Drug on the Development of Lung Fibrosis and Blood System Reactions after Intratracheal Administration of Bleomycin," Cell Technologies to Biology and Medicine, Feb. 2012, 4:519-523.
Soll et al., "Serotonin Promotes Tumor Growth in Human Hepatocellular Cancer," Hepatology 2010, 51(4):1244-1254.
Stokes et al., "p-Ethynylphenylalanine: A Potent Inhibitor of Tryptophan Hydroxylase," J Neurology, 2000, 74(5):2067-2073.
Sumara et al., "Gut-derived Serotonin is a Multifunctional Determinant to Fasting Adaptation," Cell Metabolism, Nov. 2012, 16:1-13.
Thomas et al., "Targeting the serotonin pathway for the treatment of pulmonary arterial hypertension," Pharmacology and Therapeutics, 2013, 138:409-417.
Wacker et al., "Structural Features for Functional Selectivity at Serotonin Receptors," Science, May 2013, 340(6132):615-619.
Weber, "p-Chlorophenylalanine depletion of gastrointestinal 5-hydroxytryptamine," Biochem Pharmacol, 1970, 19:2169-2172.
Yadav et al., "Lrp5 Controls Bone Formation by Inhibiting Serotonin Synthesis in the Duodenum," Cell, Nov. 2008, 135:825-837.
Yadav et al., "Pharamacological inhibition of gut-derived serotonin synthesis is a potential bone anabolic treatment for osteoporosis," Nature Medicine, Feb. 2010, 1-14.
Zhong et al., "Molecular Dynamics Simulation of Tryptophan Hydroxylase-1: Binding Modes and Free Energy Analysis to Phenylalanine Derivative Inhibitors," Int. J Molecular Sci, May 2013, 14:9947-9962.
Zhu et al., "3D-QSAR study of pyrrolidine derivatives as matrix metalloproteinase-2 inhibitors," Med Chem Res, 2009, 18:683-701.
Cheng et al., Tetrahedron Letters, 54, 2013, pp. 4483-4486.
Aiello et al"Tryptophan hydroxylase 1 Inhibition Impacts Pulmonary Vascular Remodeling in Two Rat Models of Pulmonary Hypertension" Journal of Pharmacology and Experimental Therapies 360,; 267-279, Feb. 2017.
Goldberg et at ."Optimization of spirocyclic proline tryptophan hydroxlase 1 inhibitors" Bioorganci and Mechanical Chemistry Letters 27 (3): 413-419, 2017.
Yamauchi et al Synthes of 2-aryl-3,3,3-trifluoropropanoic acids using electrochemical carboxylation of (1-bromo,-2,2,2-trilfuoroethyl)arenes and its application to the synthesis of β,β,β-trifluorinated non-steroidal anti-inflammatory drugs,:Tetrahedron 2010 2010 66(2), 473-479.
Kawanami et al., "Efficient prepartion of Ellman's imines from trifluoromethyl1 ketones promoted by ziroconium (IV) tert-butoxide," Tetrahedron, 2013, 54(52): 7202-7205.
Thornber, "Isoterism and Molecular Modification in Drug Design," Chem. Soc. Rev. 1979, 563-580.
Gershon, M. D. "5-hydroxytryptamine (serotonin) in the Gastrointestinal Tract". Current Opinion in Endocrinology, Diabetes, and Obesity 20, 14-21 (2013).
Chinese Office Action for application CN201480060427.9, 8 pages, dated Oct. 18, 2017.
Eurasian Office Action for application EAU201690534, 2 pages, dated Dec. 19, 2017.
Taiwanese Written Opinion and Search Report for tTaiwanese application No. 103130893, 6 pages, dated May 2, 2018.
Chilean Written Opinion and Search Report for Chilean application No. 509-2016, 8 pages, dated Mar. 21, 2018.
Columbian Official Action for Columbian patent application No. 16-072.412, 5 pages.

(56) References Cited

OTHER PUBLICATIONS

Vietnamese Office Action for the corresponding application, 1-2016-01237, 2 pages, dated Feb. 18, 2019.
Ukranian Office Action for the corresponding application a 2016 03580, 7 pages, dated Dec. 4, 2018.
Taiwanese Office Action for the corresponding application TW 103130893, 7 pages, dated Aug. 27, 2018.
Filipino Office Action for the corresponding application PH 1-2016-500416, 4 pages, dated Jun. 27, 2018.
Japanese Office Action for the corresponding application JP2016-540401, 5 pages, dated May 29, 2018.
Singapore Written Opinion for the corresponding application 10201802118Q, 4 pages, dated Mar. 28, 2019.
Singapore Search Report for the corresponding application 10201802118Q, 2 pages, dated Mar. 27, 2019.
Indonesian Examination Report for the corresponding application, P00201602229, 4 pages, dated May 13, 2019.
Indian Office Action for the corresponding Indian application, 201617010637, 6 pages, dated Jul. 26, 2019.
Brazil Office Action for corresponding application BR112016004909-8, 5 pages, dated Dec. 5, 2019.
Argentina Office Action for corresponding application AR20140103327, 4 pages, dated Dec. 3, 2019.
Peru Office Action for corresponding application PR340-2016, 34 pages, dated Oct. 30, 2019.
Malaysian Office Action for corresponding Malaysian Office Action PI 2016000415, dated Feb. 25, 2020, 2 pages.
Singapore Office Action for corresponding Singapore divisional application 10201802118Q, dated Feb. 27, 2020, 4 pages.
Singapore Office Action for corresponding Singapore application 11201601565U, dated Feb. 27, 2020, 3 pages.
Canadian Office Action for corresponding Canadian application No. 2,922,933, 4 pages, dated Jun. 22, 2020.
Costa Rican Office Action for corresponding Costa Rica application No. 2016-0163, 15 pages, dated Jun. 9, 2020.
New Zealand Office Action for corresponding New Zealand application No. 717556, 3 pages, dated Oct. 15, 2020.

* cited by examiner

SPIROCYCLIC COMPOUNDS AS TRYPTOPHAN HYDROXYLASE INHIBITORS

CROSS-REFERENCE TO RELATED APPLICATIONS

The present application is a continuation application of U.S. Ser. No. 16/426,698, filed May 30, 2019; which is a continuation application of U.S. Ser. No. 15/978,361, filed May 14, 2018; which is a continuation application of U.S. Ser. No. 15/645,054, filed Jul. 10, 2017; which is a continuation application of U.S. Ser. No. 15/278,130, filed Sep. 28, 2016 and issued as U.S. Pat. No. 9,750,740; which is a continuation application of U.S. Ser. No. 14/841,868, filed Sep. 1, 2015 and issued as U.S. Pat. No. 9,512,122; which is a continuation application of U.S. Ser. No. 14/477,948, filed Sep. 5, 2014 and issued as U.S. Pat. No. 9,199,994; which claims priority based on U.S. Provisional Application Ser. No. 61/874,545, filed Sep. 6, 2013 and U.S. Provisional Application Ser. No. 61/899,943, filed Nov. 5, 2013, and U.S. Provisional Application Ser. No. 62/004,385, filed May 29, 2014. The contents of the foregoing U.S. applications and patents are incorporated herein in their entireties.

FIELD OF THE INVENTION

The present invention is directed to spirocyclic compounds which are inhibitors of tryptophan hydroxylase (TPH), particularly isoform 1 (TPH1), that are useful in the treatment of diseases or disorders associated with peripheral serotonin including, for example, gastrointestinal, cardiovascular, pulmonary, inflammatory, metabolic, and low bone mass diseases, as well as serotonin syndrome, and cancer.

BACKGROUND OF THE INVENTION

Serotonin (5-hydroxytryptamine, 5-HT) is a neurotransmitter that modulates central and peripheral functions by acting on neurons, smooth muscle, and other cell types. 5-HT is involved in the control and modulation of multiple physiological and psychological processes. In the central nervous system (CNS), 5-HT regulates mood, appetite, and other behavioral functions. In the GI system, 5-HT plays a general prokinetic role and is an important mediator of sensation (e.g., nausea and satiety) between the GI tract and the brain. Dysregulation of the peripheral 5-HT signaling system has been reported to be involved in the etiology of several conditions (see for example: Mawe, G. M. & Hoffman, J. M. Serotonin Signalling In The Gut-functions, Dysfunctions And Therapeutic Targets. *Nature Reviews. Gastroenterology & Hepatology* 10, 473-486 (2013); Gershon, M. D. 5-hydroxytryptamine (serotonin) In The Gastrointestinal Tract. *Current Opinion in Endocrinology, Diabetes, and Obesity* 20, 14-21 (2013); Lesurtel, M., Soll, C., Graf, R. & Clavien, P.-A. Role of Serotonin In The Hepato-gastrointestinal Tract: An Old Molecule For New Perspectives. *Cellular And Molecular Life Sciences: CMLS* 65, 940-52 (2008)). These include osteoporosis (e.g. Kode, A. et al. FOXO1 Orchestrates The Bone-suppressing Function Of Gut-derived Serotonin. *The Journal of Clinical Investigation* 122, 3490-503 (2012); Yadav, V. K. et al. Pharmacological Inhibition Of Gut-derived Serotonin Synthesis Is A Potential Bone Anabolic Treatment For Osteoporosis. *Nature Medicine* 16, 308-12 (2010); Yadav, V. K. et al. Lrp5 Controls Bone Formation By Inhibiting Serotonin Synthesis In The Duodenum. *Cell* 135, 825-37 (2008)), cancer (e.g. Liang, C.

et al. Serotonin Promotes The Proliferation Of Serum-deprived Hepatocellular Carcinoma Cells Via Upregulation Of FOXO3a. *Molecular Cancer* 12, 14 (2013); Soll, C. et al. Serotonin Promotes Tumor Growth In Human Hepatocellular Cancer. *Hepatology* 51, 1244-1254 (2010); Pai, V. P et al. Altered Serotonin Physiology In Human Breast Cancers Favors Paradoxical Growth And Cell Survival. *Breast Cancer Research: BCR* 11, R81 (2009); Engelman, K., Lovenberg, W. & Sjoerdsma, A. Inhibition Of Serotonin Synthesis By Para-chlorophenylalanine In Patients With The Carcinoid Syndrome. *The New England Journal of Medicine* 277, 1103-8 (1967)), cardiovascular (e.g. Robiolio, P. A. et al. Carcinoid Heart Disease: Correlation of High Serotonin Levels With Valvular Abnormalities Detected by Cardiac Catheterization and Echocardiography. *Circulation* 92, 790-795 (1995).), diabetes (e.g. Sumara, G., Sumara, O., Kim, J. K. & Karsenty, G. Gut-derived Serotonin Is A Multifunctional Determinant To Fasting Adaptation. *Cell Metabolism* 16, 588-600 (2012)), atherosclerosis (e.g. Ban, Y. et al. Impact Of Increased Plasma Serotonin Levels And Carotid Atherosclerosis On Vascular Dementia. *Atherosclerosis* 195, 153-9 (2007)), as well as gastrointestinal (e.g. Mancha, M. & Khan, W. I. Serotonin and GI Disorders: An Update on Clinical and Experimental Studies. *Clinical and Translational Gastroenterology* 3, e13 (2012); Ghia, J.-E. et al. Serotonin Has A Key Role In Pathogenesis Of Experimental Colitis. *Gastroenterology* 137, 1649-60 (2009); Sikander, A., Rana, S. V. & Prasad, K. K. Role Of Serotonin In Gastrointestinal Motility And Irritable Bowel Syndrome. *Clinica Chimica Acta; International Journal of Clinical Chemistry* 403, 47-55 (2009); Spiller, R. Recent Advances In Understanding The Role Of Serotonin In Gastrointestinal Motility In Functional Bowel Disorders: Alterations In 5-HT Signalling And Metabolism In Human Disease. *Neurogastroenterology and Motility: The Official Journal of The European Gastrointestinal Motility Society* 19 Suppl 2, 25-31 (2007); Costedio, M. M., Hyman, N. & Mawe, G. M. Serotonin And Its Role In Colonic Function And In Gastrointestinal Disorders. *Diseases of the Colon and Rectum* 50, 376-88 (2007); Gershon, M. D. & Tack, J. The Serotonin Signaling System: From Basic Understanding To Drug Development For Functional GI Disorders. *Gastroenterology* 132, 397-414 (2007); Mawe, G. M., Coates, M. D. & Moses, P. L. Review Article: Intestinal Serotonin Signalling In Irritable Bowel Syndrome. *Alimentary Pharmacology & Therapeutics* 23, 1067-76 (2006); Crowell, M. D. Role Of Serotonin In The Pathophysiology Of The Irritable Bowel Syndrome. *British Journal of Pharmacology* 141, 1285-93 (2004)), pulmonary (e.g. Lau, W. K. W. et al. The Role Of Circulating Serotonin In The Development Of Chronic Obstructive Pulmonary Disease. *PloS One* 7, e31617 (2012); Egermayer, P., Town, G. I. & Peacock, A. J. Role Of Serotonin In The Pathogenesis Of Acute And Chronic Pulmonary Hypertension. *Thorax* 54, 161-168 (1999)), inflammatory (e.g. Margolis, K. G. et al. Pharmacological Reduction of Mucosal but Not Neuronal Serotonin Opposes Inflammation In Mouse Intestine. *Gut* doi:10.1136/gutjnl-2013-304901 (2013); Duerschmied, D. et al. Platelet Serotonin Promotes The Recruitment Of Neutrophils To Sites Of Acute Inflammation In Mice. *Blood* 121, 1008-15 (2013); Li, N. et al. Serotonin Activates Dendritic Cell Function In The Context Of Gut Inflammation. *The American Journal of Pathology* 178, 662-71 (2011)), or liver diseases or disorders (e.g. Ebrahimkhani, M. R. et al. Stimulating Healthy Tissue Regeneration By Targeting The 5-HT2B Receptor In Chronic Liver Disease. *Nature Medicine* 17, 1668-73 (2011)). The large number of pharmaceutical agents that block or stimulate the various 5-HT receptors is also indicative of the wide range of medical disorders that have been associated with 5-HT dysregulation (see for example: Wacker, D. et al. Structural Features For Functional Selectivity At Serotonin Receptors. Science (New York, N.Y.) 340, 615-9 (2013)).

The rate-limiting step in 5-HT biosynthesis is the hydroxylation of tryptophan by dioxygen, which is catalyzed by tryptophan hydroxylase (TPH; EC 1.14.16.4) in the presence of the cofactor (6R)-L-erythro-5,6,7,8-tetrahydrobiopterin (BH4). The resulting oxidized product, 5-hydroxytryptophan (5-HTT) is subsequently decarboxylated by an aromatic amino acid decarboxylase (AAAD; EC 4.1.1.28) to produce 5-HT. Together with phenylalanine hydroxylase (PheOH) and tyrosine hydroxylase (TH), TPH belongs to the pterin-dependent aromatic amino acid hydroxylase family.

Two vertebrate isoforms of TPH, namely TPH1 and TPH2, have been identified. TPH1 is primarily expressed in the pineal gland and non-neuronal tissues, such as enterochromaffin (EC) cells located in the gastrointestinal (GI) tract. $TPH_2$ (the dominant form in the brain) is expressed exclusively in neuronal cells, such as dorsal raphe or myenteric plexus cells. The peripheral and central systems involved in 5-HT biosynthesis are isolated, with 5-HT being unable to cross the blood-brain barrier. Therefore, the pharmacological effects of 5-HT can be modulated by agents affecting TPH in the periphery, mainly TPH1 in the gut.

A small number of phenylalanine-derived TPH1 inhibitors are known. One example, p-chlorophenylalanine (pCPA), a very weak and unselective irreversible inhibitor of TPH, has proven effective in treating chemotherapy-induced emesis, as well as diarrhea, in carcinoid tumor patients. However, pCPA is distibuted centrally and, as a result, its administration has been linked to the onset of depression and other alterations of CNS functions in patients and animals. p-Ethynyl phenylalanine is a more selective and more potent TPH inhibitor than pCPA (Stokes, A. H. et al. p-Ethynylphenylalanine: A Potent Inhibitor Of Tryptophan Hydroxylase. *Journal of Neurochemistry* 74, 2067-73 (2000), but also affects central 5-HT production and, like pCPA, is believed to irreversibly interfere with the synthesis of TPH (and possibly other proteins).

More recently, bulkier phenylalanine-derived TPH inhibitors have been reported to reduce intestinal 5-HT concentration without affecting brain 5-HT levels (Zhong, H. et al. Molecular dynamics simulation of tryptophan hydroxylase-1: binding modes and free energy analysis to phenylalanine derivative inhibitors. *International Journal of Molecular Sciences* 14, 9947-62 (2013); Ouyang, L. et al. Combined Structure-Based Pharmacophore and 3D-QSAR Studies on Phenylalanine Series Compounds as TPH1 Inhibitors. *International Journal of Molecular Sciences* 13, 5348-63 (2012); Camilleri, M. LX-1031, A Tryptophan 5-hydroxylase Inhibitor, And Its Potential In Chronic Diarrhea Associated With Increased Serotonin. *Neurogastroenterology and Motility: The Official Journal of The European Gastrointestinal Motility Society* 23, 193-200 (2011); Cianchetta, G. et al. Mechanism of Inhibition of Novel Tryptophan Hydroxylase Inhibitors Revealed by Co-crystal Structures and Kinetic Analysis. *Current chemical genomics* 4, 19-26 (2010); Jin, H. et al. Substituted 3-(4-(1,3,5-triazin-2-yl)-phenyl)-2-aminopropanoic Acids As Novel Tryptophan Hydroxylase Inhibitors. *Bioorganic & Medicinal Chemistry Letters* 19, 5229-32 (2009); Shi, Z.-C. et al. Modulation Of Peripheral Serotonin Levels By Novel Tryptophan Hydroxylase Inhibitors For The Potential Treatment Of Functional Gastrointestinal Disorders. *Journal of medicinal chemistry* 51, 3684-7 (2008); Liu, Q. et al. Discovery And Characterization of Novel Tryptophan Hydroxylase Inhibitors That Selectively Inhibit Serotonin Synthesis In The Gastrointestinal Tract. *The Journal of Pharmacology and Experimental Therapeutics* 325, 47-55 (2008)).

There is a current need to selectively reduce intestinal 5-HT levels as a means for treating and preventing 5-HT-associated diseases. The TPH1 inhibitors described herein are intended to address this need.

SUMMARY OF THE INVENTION

The present invention relates to a TPH-inhibiting compound of Formula I:

I

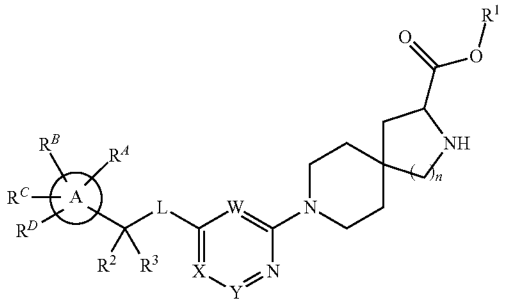

or a pharmaceutically acceptable salt thereof, wherein constituent variables are defined herein.

The present invention further relates to a pharmaceutical composition comprising a TPH-inhibiting compound of the invention, or a pharmaceutically acceptable salt thereof, and at least one pharmaceutically acceptable carrier.

The present invention further relates to a method of inhibiting TPH, such as TPH1, by contacting the TPH enzyme with a compound of Formula I, or a pharmaceutically acceptable salt thereof.

The present invention further relates to a method of lowering peripheral serotonin in a patient comprising administering to the patient an effective amount of a compound of Formula I, or a pharmaceutically acceptable salt thereof.

The present invention further relates to a method of treating or preventing a disease in a patient comprising administering to the patient a therapeutically effective amount of a compound of Formula I, or a pharmaceutically acceptable salt thereof.

The present invention further relates to a compound of Formula I, or a pharmaceutically acceptable salt thereof, for use in the treatment or prevention of disease in a patient.

The present invention further relates to use of a compound of Formula I or a pharmaceutically acceptable salt thereof, for the preparation of a medicament for the treatment or prevention of disease in a patient.

DETAILED DESCRIPTION

Compounds

The present invention relates to a TPH-inhibiting compound of Formula I:

I

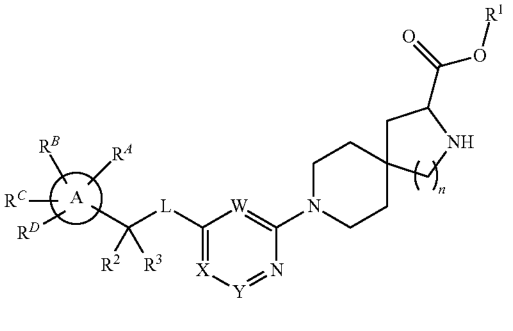

or a pharmaceutically acceptable salt thereof, wherein:

Ring A is $C_{3-10}$ cycloalkyl, $C_{6-10}$ aryl, 4 to 10-membered heterocycloalkyl, or 5 to 10-membered heteroaryl;

L is O or $NR^4$;

W is N or $CR^5$;

X is N or $CR^6$;

Y is N or $CR^7$;

wherein only one of X and Y is N;

$R^1$ is H, $C_{1-10}$ alkyl, $C_{3-10}$ cycloalkyl, 4-10 membered heterocycloalkyl, 5-10 membered heteroaryl, phenyl, —$(CR^8R^9)_pOC(O)R^{10}$, —$(CR^8R^9)_pNR^{11}R^{12}$, or —$(CR^8R^9)_p$ $C(O)NR^{11}R^{12}$, wherein said $C_{1-10}$ alkyl, $C_{3-10}$ cycloalkyl, 4-10 membered heterocycloalkyl, 5-10 membered heteroaryl, and phenyl are each optionally substituted with 1, 2, 3, 4, or 5 substituents independently selected from F, Cl, Br, CN, $C_{1-4}$ alkyl, and $C_{1-4}$ haloalkyl;

$R^2$ and $R^3$ are each independently selected from H, $C_{1-4}$ alkyl, and $C_{1-4}$ haloalkyl;

$R^4$ is H or $C_{1-4}$ alkyl;

$R^5$ and $R^6$ are each independently selected from H, halo, and $C_{1-4}$ alkyl;

$R^7$ is H, $C_{1-4}$ alkyl, $C_{2-6}$ alkenyl, $C_{3-10}$ cycloalkyl, $C_{3-10}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, (5-10 membered heteroaryl)-$C_{1-4}$ alkyl, $NR^{13}R^{14}$,x, $OR^{15}$, $C(O)R^{16}$, $S(O)_qR^{17}$, wherein said $C_{1-4}$ alkyl, $C_{2-6}$ alkenyl, $C_{3-10}$ cycloalkyl, $C_{3-10}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents selected from halo, $C_{1-4}$ alkyl, $C_{2-6}$ alkenyl, amino, $C_{1-4}$ alkylamino, $C_{2-8}$ dialkylamino, hydroxy, and $C_{1-4}$ alkoxy;

$R^8$ and $R^9$ are each independently selected from H and $C_{1-4}$ alkyl;

$R^{10}$ is $C_{1-6}$ alkyl optionally substituted by 1, 2 or 3 substituents independently selected from $C_{1-6}$ haloalkyl, $C_{3-10}$ cycloalkyl, $OR^a$, and $NR^cR^d$;

$R^{11}$ and $R^{12}$ are each independently selected from H and $C_{1-6}$ alkyl;

$R^{13}$ is H or $C_{1-4}$ alkyl;

$R^{14}$ is H, $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, $C(O)R^{b1}$, $C(O)OR^{a1}$, $C(O)NR^{c1}R^{d1}$; $S(O)R^{b1}$, $S(O)_2R^{b1}$, or $S(O)_2NR^{c1}R^{d1}$, wherein said $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{1-4}$ alkyl, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

or $R^{13}$ and $R^{14}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{15}$ is H, $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, wherein said $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{16}$ is $C_{1-4}$ alkyl or $NR^{18a}R^{18b}$ wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{17}$ is $C_{1-4}$ alkyl, $NR^{18a}R^{18b}$, or $OR^{18c}$, wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{18}$a and $R^{18b}$ are each independently selected from H and $C_{1-4}$ alkyl wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, C(O)

$NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

or $R^{18a}$ and $R^{18b}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{18c}$ is H, $C_{1-6}$ alkyl, $C_{3-10}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, wherein said $C_{1-6}$ alkyl, $C_{3-7}$ cycloalkyl, $C_{3-10}$ cycloalkyl-C 1-4 alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{1-4}$ alkyl, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^A$ is H, $Cy^1$, halo, $C_{1-6}$ alkyl, $C_{2-6}$ alkenyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl and $C_{2-6}$ alkenyl are each optionally substituted with 1, 2, 3, 4, or 5 substituents independently selected from $Cy^1$, halo, $C_{1-6}$ alkyl, $C_{2-6}$ alkenyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^B$ is H, $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2 R^{b3}$, and $S(O)_2NR^{c3}R^{d3}$, wherein said $C_{1-6}$ alkyl and $C_{2-6}$ alkenyl are each optionally substituted with 1, 2, 3, 4, or 5 substituents independently selected from $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

$R^C$ and $R^D$ are each independently selected from H, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl and $C_{2-6}$ alkenyl are each optionally substituted with 1, 2, 3, 4, or 5 substituents independently selected from $C_{6-10}$ aryl, $C_{3-10}$ cycloalkyl, 5-10 membered heteroaryl, 4-10 membered heterocycloalkyl, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

$Cy^1$ and $Cy^2$ are each independently selected from $C_{6-10}$ aryl, $C_{3-10}$ cycloalkyl, 5-10 membered heteroaryl, and 4-10 membered heterocycloalkyl, each of which is optionally substituted by 1, 2, 3, 4, or 5 substituents independently selected from $R^{Cy}$;

each $R^{Cy}$ is independently selected from halo, $C_{1-6}$ alkyl, $C_{1-6}$ haloalkyl, $C_{2-6}$ alkenyl, $C_{6-10}$ aryl, $C_{3-10}$ cycloalkyl, 5-10 membered heteroaryl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2 R^{b5}$, and $S(O)_2NR^{c5}R^{d5}$, wherein said $C_{1-6}$ alkyl, $C_{2-6}$ alkenyl $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^a$, $R^{a1}$, $R^{a2}$, $R^{a3}$, $R^{a4}$, and $R^{a5}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{b1}$, $R^{b2}$, $R^{b3}$, $R^{b4}$, and $R^{b5}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^c$, $R^d$, $R^{c1}$, $R^{d1}$, $R^{c2}$, $R^{d2}$, $R^{c3}$, $R^{d3}$, $R^{c4}$, $R^{d4}$, $R^{c5}$, and $R^{d5}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_{1-6}$haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{a6}$, $R^{b6}$, $R^{c6}$, and $R^{d6}$ is independently selected from H, $C_{1-4}$ alkyl, $C_{2-4}$ alkenyl, $C_{3-7}$ cycloalkyl, phenyl, 5-6 membered heteroaryl, and 4-7 membered heterocycloalkyl, wherein said $C_{1-4}$ alkyl, $C_{2-4}$ alkenyl, $C_{3-7}$ cycloalkyl, phenyl, 5-6 membered heteroaryl, and 4-7 membered heterocycloalkyl are each optionally substituted by 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, and di($C_{1-4}$ alkyl)amino;

n is 1 or 2;

p is 1, 2, or 3; and q is 1 or 2;

wherein any aforementioned 4-10 or 4-7 membered heterocycloalkyl group optionally comprises 1, 2, or 3 oxo substituents, wherein each oxo substituent that is present is substituted on a ring-forming carbon, nitrogen, or sulfur atom of the 4-10 or 4-7 membered heterocycloalkyl group.

In some embodiments, the present invention relates to a TPH-inhibiting compound of Formula I:

I

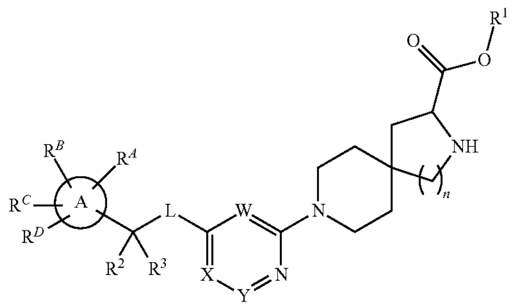

or a pharmaceutically acceptable salt thereof, wherein:

Ring A is $C_{3-10}$ cycloalkyl, $C_{6-10}$ aryl, 4 to 10-membered heterocycloalkyl, or 5 to 10-membered heteroaryl;

L is O or $NR^4$;

W is N or $CR^5$;

X is N or $CR^6$;

Y is N or $CR^7$;

wherein only one of X and Y is N;

$R^1$ is H, $C_{1-10}$ alkyl, $C_{3-10}$ cycloalkyl, phenyl, $—(CR^8R^9)_p OC(O)R^{10}$, $—(CR^8R^9)_p NR^{11}R^{12}$, or $—(CR^8R^9)_p C(O)NR^{11}R^{12}$, wherein said $C_{1-10}$ alkyl, $C_{3-10}$ cycloalkyl, and phenyl are each optionally substituted with 1, 2, 3, 4, or 5 substituents independently selected from F, Cl, Br, CN, C,-4 alkyl, and $C_{1-4}$ haloalkyl;

$R^2$ and $R^3$ are each independently selected from H, $C_{1-4}$ alkyl, and $C_{1-4}$ haloalkyl;

$R^4$ is H or $C_{1-4}$ alkyl;

$R^5$ and $R^6$ are each independently selected from H, halo, and $C_{1-4}$ alkyl;

$R^7$ is H, $C_{1-4}$ alkyl, $C_{2-6}$ alkenyl, $C_{3-10}$ cycloalkyl, $C_{3-10}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, (5-10 membered heteroaryl)-$C_{1-4}$ alkyl, $NR^{13}R^{14}$, OR'5, C(O)R'6, $S(O)_q$ $R^{17}$, wherein said $C_{1-4}$ alkyl, $C_{2-6}$ alkenyl, $C_{3-10}$ cycloalkyl, $C_{3-10}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents selected from halo, $C_{1-4}$ alkyl, $C_{2-6}$ alkenyl, amino, $C_{1-4}$ alkylamino, $C_{2-8}$ dialkylamino, hydroxy, and $C_{1-4}$ alkoxy;

$R^8$ and $R^9$ are each independently selected from H and $C_{1-4}$ alkyl;

$R^{10}$is $C_{1-6}$ alkyl optionally substituted by 1, 2 or 3 substituents independently selected from $C_{1-6}$ haloalkyl, $C_{3-10}$ cycloalkyl, $OR^a$, and $NR^cR^d$;

$R^{11}$ and $R^{12}$ are each independently selected from H and $C_{1-6}$ alkyl;

$R^{13}$ is H or $C_{1-4}$ alkyl;

$R^{14}$ is H, $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, $C(O)R^{b1}$, $C(O)OR^{a1}$, $C(O)NR^{c1}R^{d1}$, $S(O)R^{b1}$, $S(O)_2R^{b1}$, or $S(O)_2NR^{c1}R^{d1}$, wherein said $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{1-4}$ alkyl, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

or $R^{13}$ and $R^{14}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{15}$ is H, $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, wherein said $C_{1-4}$ alkyl, $C_{3-7}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{16}$ is $C_{1-4}$ alkyl or $NR^{18a}R^{18b}$ wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{17}$ is $C_{1-4}$ alkyl, $NR^{18a}R^{18b}$, or $OR^{18c}$, wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{18a}$ and $R^{18b}$ are each independently selected from H and $C_{1-4}$ alkyl wherein said $C_{1-4}$ alkyl is optionally substituted by 1, 2, or 3 substituents independently selected from halo, $C_{3-7}$ cycloalkyl, 4-7 membered heterocycloalkyl, $C_{6-10}$ aryl, 5-6 membered heteroaryl, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c4}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

or $R^{18a}$ and $R^{18b}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)NR^{c1}R^{d1}$, $NR^{c1}C(O)OR^{a1}$, $S(O)R^{b1}$, $S(O)NR^{c1}R^{d1}$, $S(O)_2R^{b1}$, $NR^{c1}S(O)_2R^{b1}$, $NR^{c1}S(O)_2NR^{c1}R^{d1}$, and $S(O)_2NR^{c1}R^{d1}$;

$R^{18c}$ is H, $C_{1-6}$ alkyl, $C_{3-10}$ cycloalkyl, $C_{3-7}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, or (5-10 membered heteroaryl)-$C_{1-4}$ alkyl, wherein said $C_{1-6}$ alkyl, $C_{3-7}$ cycloalkyl, $C_{3-10}$ cycloalkyl-$C_{1-4}$ alkyl, $C_{6-10}$ aryl, $C_{6-10}$ aryl-$C_{1-4}$ alkyl, 4-10 membered heterocycloalkyl, (4-10 membered heterocycloalkyl)-$C_{1-4}$ alkyl, 5-10 membered heteroaryl, and (5-10 membered heteroaryl)-$C_{1-4}$ alkyl are each optionally substituted by 1, 2, or 3 substituents independently selected from halo, $C_{1-4}$ alkyl, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^A$ is H, $Cy^1$, halo, $C_{1-6}$ alkyl, $C_{2-6}$ alkenyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein said $C_{1-6}$ alkyl and $C_{2-6}$ alkenyl are each optionally substituted with 1, 2, 3, 4, or 5 substituents independently selected from $Cy^1$, halo, $C_{1-6}$ alkyl, $C_{2-6}$ alkenyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^B$ is H, $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2 R^{b3}$, or $S(O)_2NR^{c3}R^{d3}$, wherein said $C_{1-6}$ alkyl and $C_{2-6}$ alkenyl are each optionally substituted with 1, 2, 3, 4, or 5 substituents independently selected from $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}{}_R{}^{d3}$, $S(O)_2R^{b3}$, and $S(O)_2NR^{c3}R^{d3}$;

$R^C$ and $R^D$ are each independently selected from H, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}{}_R{}^{d4}$, $S(O)_2R^{b4}$, and $S(O)_2NR^{c4}R^{d4}$; wherein said $C_{1-6}$ alkyl and $C_{2-6}$ alkenyl are each optionally substituted with 1, 2, 3, 4, or 5 substituents independently selected from $C_{6-10}$ aryl, $C_{3-10}$ cycloalkyl, 5-10 membered heteroaryl, 4-10 membered heterocycloalkyl, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}{}_R{}^{d4}$, $S(O)_2R^{b4}$, and $S(O)_2NR^{c4}R^{d4}$;

$Cy^1$ and Cy2 are each independently selected from C6-10 aryl, C3-10 cycloalkyl, 5-10 membered heteroaryl, and 4-10 membered heterocycloalkyl, each of which is optionally substituted by 1, 2, 3, 4, or 5 substituents independently selected from RCy;

each $R^{Cy}$ is independently selected from halo, $C_{1-6}$ alkyl, $C_{1-6}$ haloalkyl, $C_{2-6}$ alkenyl, $C_{6-10}$ aryl, $C_{3-10}$ cycloalkyl, 5-10 membered heteroaryl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}{}_R{}^{d5}$, $S(O)_2 R^{b5}$, and $S(O)_2NR^{c5}R^{d5}$; wherein said $C_{1-6}$ alkyl, $C_{2-6}$ alkenyl $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}{}_R{}^{d5}$, $S(O)_2R^{b5}$, and $S(O)_2NR^{c5}R^{d5}$;

each $R^a$, $R^{a1}$, $R^{a2}$, $R^{a3}$, $R^{a4}$, and $R^{a5}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}{}_R{}^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{b1}$, $R^{b2}$, $R^{b3}$, $R^{b4}$, and $R^{b5}$ is independently selected from H, $C_{1-6}$ alkyl, $C_{1-4}$ haloalkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^c$, $R^d$, $R^{c1}$, $R^{d1}$, $R^{c2}$, $R^{d2}$, $R^{c3}$, $R^{d3}$, $R^{c4}$, $R^{d4}$, $R^{c5}$, and $R^{d5}$ is independently selected from H, $C_{1-6}$ alkyl, $C_{1-4}$ haloalkyl, $C_{2-6}$ alkenyl, $C_{6-10}$ aryl, $C_{3-1}$ocycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, wherein said $C_{1-6}$ alkyl, $C_{2-6}$ alkenyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl are each optionally substituted with 1, 2, 3, 4, or 5 substituents independently selected from $C_{1-4}$ alkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^c$ and $R^d$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-10}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, and 5-6 membered heteroaryl, $C_1$-$_6$haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

or any $R^{c5}$ and $R^{d5}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}R^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$, wherein said $C_{1-6}$ alkyl, $C_{3-7}$ cycloalkyl, 4-7 membered heterocycloalkyl, $C_{6-10}$ aryl, and 5-6 membered heteroaryl are each optionally substituted by 1, 2, or 3 substituents independently selected from halo, CN, $OR^{a6}$, $SR^{a6}$, $C(O)R^{b6}$, $C(O)NR^{c6}R^{d6}$, $C(O)OR^{a6}$, $OC(O)R^{b6}$, $OC(O)NR^{c6}R^{d6}$, $NR^{c6}R^{d6}$, $NR^{c6}C(O)R^{b6}$, $NR^{c6}C(O)NR^{c6}R^{d6}$, $NR^{c6}C(O)OR^{a6}$, $S(O)R^{b6}$, $S(O)NR^{c6}{}_{R}{}^{d6}$, $S(O)_2R^{b6}$, $NR^{c6}S(O)_2R^{b6}$, $NR^{c6}S(O)_2NR^{c6}R^{d6}$, and $S(O)_2NR^{c6}R^{d6}$;

each $R^{a6}$, $R^{b6}$, $R^{c6}$, and $R^{d6}$ is independently selected from H, $C_{1-4}$ alkyl, $C_{2-4}$ alkenyl, $C_{3-7}$ cycloalkyl, phenyl, 5-6 membered heteroaryl, and 4-7 membered heterocycloalkyl, wherein said $C_{1-4}$ alkyl, $C_{2-4}$ alkenyl, $C_{3-7}$ cycloalkyl, phenyl, 5-6 membered heteroaryl, and 4-7 membered heterocycloalkyl are each optionally substituted by 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, and di($C_{1-4}$ alkyl)amino;

n is 1 or 2;

p is 1, 2, or 3; and q is 1 or 2;

wherein any aforementioned 4-10 or 4-7 membered heterocycloalkyl group optionally comprises 1, 2, or 3 oxo substituents, wherein each oxo substituent that is present is substituted on a ring-forming carbon, nitrogen, or sulfur atom of the 4-10 or 4-7 membered heterocycloalkyl group.

In some embodiments, L is O.

In some embodiments, L is $NR^4$.

In some embodiments, W is $CR^5$; X is N; and Y is $CR^7$.

In some embodiments, W is N; X is N; and Y is $CR^7$.

In some embodiments, W is $CR^5$; X is $CR^6$; and Y is N.

In some embodiments, W is $CR^5$; X is $CR^6$; and Y is $CR^7$.

In some embodiments, W is N; X is $CR^6$; and Y is $CR^7$.

In some embodiments, $R^2$ is H and $R^3$ is H.

In some embodiments, $R^2$ is H and $R^3$ is $C_{1-4}$ alkyl.

In some embodiments, $R^2$ is H and $R^3$ is methyl.

In some embodiments, $R^2$ is H and $R^3$ is $C_{1-4}$ haloalkyl.

In some embodiments, $R^2$ is H and $R^3$ is trifluoromethyl.

In some embodiments, n is 1.

In some embodiments, n is 2.

In some embodiments, $R^1$ is H.

In some embodiments, $R^1$ is $C_{1-10}$ alkyl, $C_{3-10}$ cycloalkyl, phenyl, $—(CR^8R^9)_pOC(O)R^{10}$, $—(CR^8R^9)_pNR^{11}R^{12}$, or $—(CR^8R^9)_pC(O)NR^{11}R^{12}$, wherein said $C_{1-10}$ alkyl, $C_{3-10}$ cycloalkyl, and phenyl are each optionally substituted with 1, 2, 3, 4, or 5 substituents independently selected from F, Cl, Br, CN, $C_{1-4}$ alkyl, and $C_{1-4}$ haloalkyl.

In some embodiments, $R^1$ is $C_{1-10}$ alkyl.

In some embodiments, $R^1$ is ethyl.

In some embodiments, $R^4$ is H.

In some embodiments, $R^5$ is H.

In some embodiments, $R^6$ is H.

In some embodiments, $R^7$ is other than H.

In some embodiments, $R^7$ is $C_{1-4}$ alkyl, $NR^{13}R^{14}$, or $OR^{15}$.

In some embodiments, $R^7$ is $NR^{13}R^{14}$.

In some embodiments, $R^7$ is $NH_2$.

In some embodiments, $R^7$ is $C_{1-4}$ alkyl.

In some embodiments, $R^7$ is $OR^{15}$.

In some embodiments, Ring A is $C_{3-10}$ cycloalkyl.

In some embodiments, Ring A is $C_{6-10}$ aryl.

In some embodiments, Ring A is phenyl.

In some embodiments, Ring A is 4 to 10-membered heterocycloalkyl.

In some embodiments, Ring A is phenyl, adamantanyl, naphthyl, 1,2,3,4-tetrahydroquinoxalinyl, 3,4-dihydroqinazolinyl, 1,2,3,4-tetrahydroquinazolinyl, or pyridyl.

In some embodiments, Ring A is 5 to 10-membered heteroaryl.

In some embodiments, at least one of $R^A$, $R^B$, $R^C$, and $R^D$ is other than hydrogen.

In some embodiments, at least two of $R^A$, $R^B$, $R^C$, and $R^D$ are other than hydrogen.

In some embodiments, $R^A$ is $Cy^1$.

In some embodiments, $R^A$ is $C_{6-10}$ aryl or 5-10 membered heteroaryl, each of which is optionally substituted by 1, 2, 3, 4, or 5 substituents independently selected from $R^{Cy}$.

In some embodiments, $R^A$ is 5-10 membered heteroaryl optionally substituted by 1, 2, 3, 4, or 5 substituents independently selected from $R^{Cy}$.

In some embodiments, $R^A$ is 5 to 6-membered heteroaryl optionally substituted by 1, 2, or 3 substituents independently selected from $R^{Cy}$.

In some embodiments, $R^A$ is pyrazolyl which is optionally substituted by 1, 2, 3, 4, or 5 substituents independently selected from $R^{Cy}$.

In some embodiments, $R^A$ is 3-methyl-1H-pyrazol-1-yl.

In some embodiments, $R^A$ is $C_{6-10}$ aryl optionally substituted by 1, 2, or 3 substituents independently selected from $R^{Cy}$.

In some embodiments, $R^A$ is phenyl optionally substituted by 1, 2, or 3 substituents independently selected from $R^{Cy}$.

In some embodiments, $R^B$ is H.

In some embodiments, RB is $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl and $C_{2-6}$ alkenyl are each optionally substituted with 1, 2, 3, 4, or 5 substituents independently selected from $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)^{Rb3}$, $S(O)NR^{c3}R^{d3}$, $S(O)_2R^{b3}$, and $S(O)_2NR^{c3}R^{d3}$.

In some embodiments, $R^B$ is $Cy^2$.

In some embodiments, $R^B$ is $C_{6-10}$ aryl or 5-10 membered heteroaryl, each of which is optionally substituted by 1, 2, 3, 4, or 5 substituents independently selected from $R^{Cy}$.

In some embodiments, $R^B$ is halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl and $C_{2-6}$ alkenyl are each optionally substituted with 1, 2, 3, 4, or 5 substituents independently selected from $Cy^2$, halo, $C_{1-6}$ alkyl, $C_{2-6}$ alkenyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^B$ is halo.

In some embodiments, $R^C$ is H.

In some embodiments, $R^C$ is halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl and $C_{2-6}$ alkenyl are each optionally substituted with 1, 2, 3, 4, or 5 substituents independently selected from $C_{6-10}$ aryl, $C_{3-10}$ cycloalkyl, 5-10 membered heteroaryl, 4-10 membered heterocycloalkyl, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, $R^D$ is H.

In some embodiments, $R^D$ is halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl and $C_{2-6}$ alkenyl are each optionally substituted with 1, 2, 3, 4, or 5 substituents independently selected from $C_{6-10}$ aryl, $C_{3-10}$ cycloalkyl, 5-10 membered heteroaryl, 4-10 membered heterocycloalkyl, halo, $C_{1-6}$ alkyl, $C_{2-6}$ alkenyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$.

In some embodiments, the compounds of the invention have Formula IIa:

IIa

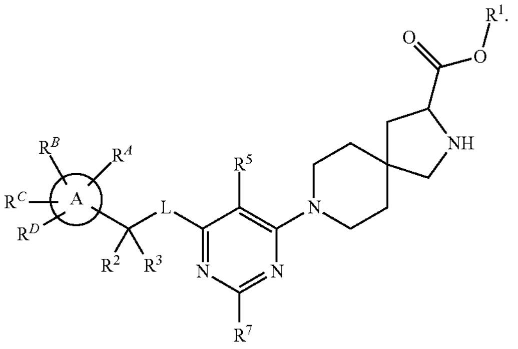

In some embodiments, the compounds of the invention have Formula IIb:

IIb

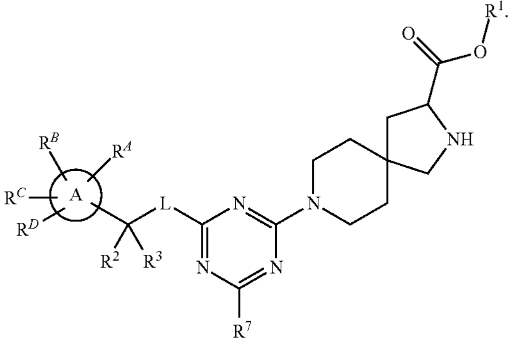

In some embodiments, the compounds of the invention have Formula IIc:

IIc

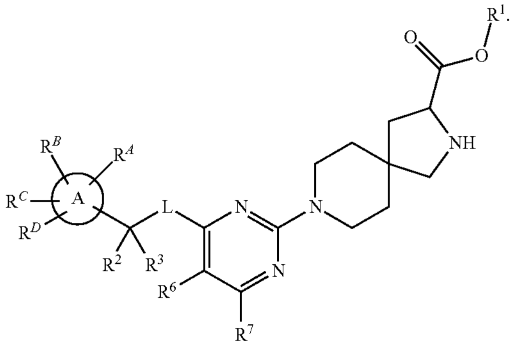

In some embodiments, the compounds of the invention have Formula IId:

IId

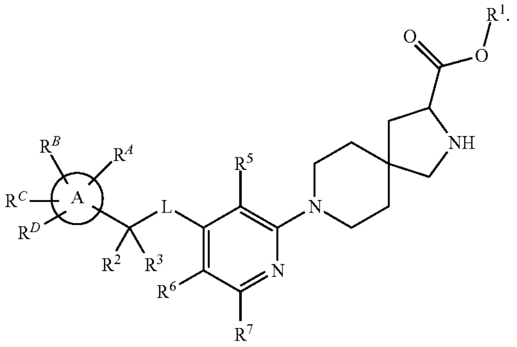

In some embodiments, the compounds of the invention have Formula IIe:

IIe

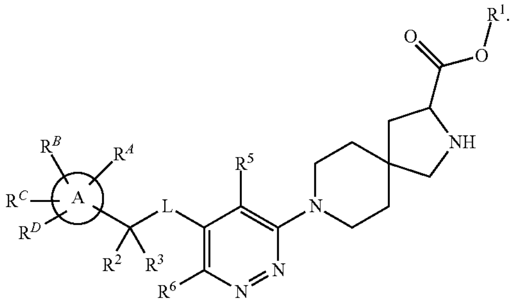

In some embodiments, where the compounds of the invention have Formula IIa, IIb, IIc, IId, or IIe, L is O.

In some embodiments, where the compounds of the invention have Formula IIa, IIb, IIc, IId, or IIe, L is $NR_4$.

In some embodiments, where the compounds of the invention have Formula IIa, IIb, IIc, IId, or IIe, $R^3$ is H.

In some embodiments, where the compounds of the invention have Formula IIa, IIb, IIc, IId, or IIe, $R^2$ is $CF_3$ and $R^3$ is H.

In some embodiments, where the compounds of the invention have Formula IIa, IIb, IIc, IId, or IIe, $R^1$ is H or $C_{1-10}$ alkyl.

In some embodiments, where the compounds of the invention have Formula IIa, IIb, IIc, IId, or IIe, $R^A$ is $Cy^1$.

In some embodiments, where the compounds of the invention have Formula IIa, IIb, IIc, IId, or IIe, $R^A$ is $C_{6-10}$ aryl or 5-10 membered heteroaryl, each of which is optionally substituted by 1, 2, 3, 4, or 5 substituents independently selected from $R^{Cy}$.

In some embodiments, where the compounds of the invention have Formula IIa, IIb, IIc, IId, or IIe, $R^A$ is 5-10 membered heteroaryl optionally substituted by 1, 2, 3, 4, or 5 substituents independently selected from $R^{Cy}$.

In some embodiments, where the compounds of the invention have Formula IIa, IIb, IIc, IId, or IIe, $R^A$ is 5 to 6-membered heteroaryl optionally substituted by 1, 2, or 3 substituents independently selected from $R^{Cy}$.

In some embodiments, where the compounds of the invention have Formula IIa, IIb, IIc, IId, or IIe, $R^A$ is $C_{6-10}$ aryl optionally substituted by 1, 2, or 3 substituents independently selected from $R^{Cy}$.

In some embodiments, where the compounds of the invention have Formula IIa, IIb, IIc, IId, or IIe, $R^A$ is phenyl optionally substituted by 1, 2, or 3 substituents independently selected from $R^{Cy}$.

In some embodiments, where the compounds of the invention have Formula IIa, IIb, IIc, IId, or IIe, $R^B$ is $Cy^2$.

In some embodiments, where the compounds of the invention have Formula IIa, IIb, IIc, IId, or IIe, $R^B$ is H, halo, $C_{1-6}$ alkyl, $C_{2-6}$ alkenyl, $C_{1-6}$ haloalkyl, CN, $OR^{a3}$, C(O)$NR^{c3}R^{d3}$, or C(O)$OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, C(O)$R^{b3}$, C(O)$NR^{c3}R^{d3}$, C(O)$OR^{a3}$, OC(O)$R^{b3}$, OC(O)$NR^{c3}R^{d3}$, $NR^{c3}R^{d3}$, $NR^{c3}$C(O)$R^{b3}$, $NR^{c3}$C(O)$OR^{a3}$, $NR^{c3}$C(O)$NR^{c3}R^{d3}$, $NR^{c3}$S(O)$R^{b3}$, $NR^{c1}$S(O)$_2R^{b3}$, $NR^{c3}$S(O)$_2NR^{c3}R^{d3}$, S(O)$R^{b3}$, S(O)$NR^{c3}R^{d3}$, S(O)$_2$ $R^{b3}$, and S(O)$_2NR^{c3}R^{d3}$.

In some embodiments, where the compounds of the invention have Formula IIa, IIb, IIc, IId, or IIe, $R^C$ is H.

In some embodiments, where the compounds of the invention have Formula IIa, IIb, IIc, IId, or IIe, $R^D$ is H.

In some embodiments, where the compounds of the invention have Formula IIa, IIb, IIc, IId, or IIe, $R^5$ is H.

In some embodiments, where the compounds of the invention have Formula IIa, IIb, IIc, IId, or IIe, $R^6$ is H.

In some embodiments, the compounds of the invention have Formula IIIa or IIIb:

IIIa

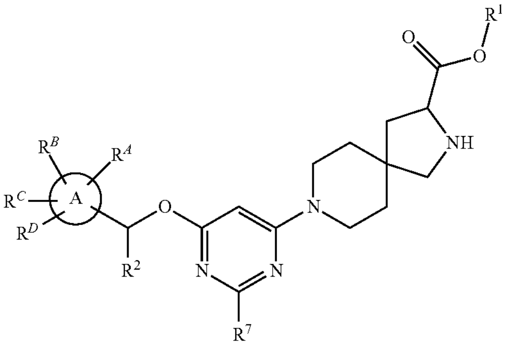

-continued

IIIb

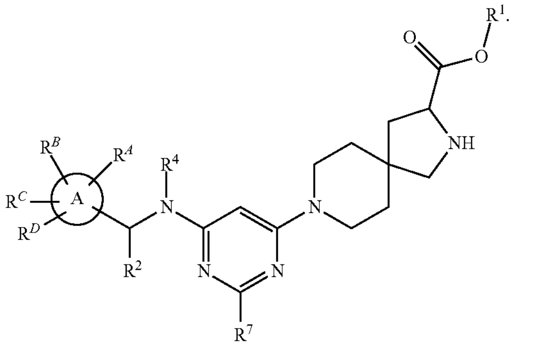

In some embodiments, where the compounds of the invention have Formula IIIa or IIIb, $R^2$ is $CF_3$.

In some embodiments, where the compounds of the invention have Formula IIIa or IIIb, $R^1$ is H or $C_{1-10}$ alkyl.

In some embodiments, where the compounds of the invention have Formula IIIa or IIIb, $R^A$ is $Cy^1$.

In some embodiments, where the compounds of the invention have Formula IIIa or IIIb, $R^A$ is $C_{6-10}$ aryl or 5-10 membered heteroaryl, each of which is optionally substituted by 1, 2, 3, 4, or 5 substituents independently selected from $R^{Cy}$.

In some embodiments, where the compounds of the invention have Formula IIIa or IIIb, $R^A$ is 5-10 membered heteroaryl optionally substituted by 1, 2, 3, 4, or 5 substituents independently selected from $R^{Cy}$.

In some embodiments, where the compounds of the invention have Formula IIIa or IIIb, $R^A$ is 5 to 6-membered heteroaryl optionally substituted by 1, 2, or 3 substituents independently selected from $R^{Cy}$.

In some embodiments, where the compounds of the invention have Formula IIIa or IIIb, $R^A$ is $C_{6-10}$ aryl optionally substituted by 1, 2, or 3 substituents independently selected from $R^{Cy}$.

In some embodiments, where the compounds of the invention have Formula IIIa or IIIb, $R^A$ is phenyl optionally substituted by 1, 2, or 3 substituents independently selected from $R^{Cy}$.

In some embodiments, where the compounds of the invention have Formula IIIa or IIIb, $R^B$ is $Cy^2$.

In some embodiments, where the compounds of the invention have Formula IIIa or IIIb, $R^B$ is H, halo, $C_{1-6}$ alkyl, $C_{2-6}$ alkenyl, $C_{1-6}$ haloalkyl, CN, $OR^{a3}$, C(O)$NR^{c3}R^{d3}$, or C(O)$OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, C(O)$R^{b3}$, C(O)$NR^{c3}R^{d3}$, C(O)$OR^{a3}$, OC(O)$R^{b3}$, OC(O)$NR^{c3}R^{d3}$, $NR^{c3}R^{d3}$, $NR^{c3}$C(O)$R^{b3}$, $NR^{c3}$C(O)$OR^{a3}$, $NR^{c3}$C(O)$NR^{c3}R^{d3}$, $NR^{c3}$S(O)$R^{b3}$, $NR^{c1}$S(O)$_2R^{b3}$, $NR^{c3}$S(O)$_2NR^{c3}R^{d3}$, S(O)$R^{b3}$, S(O)$NR^{c3}R^{d3}$, S(O)$_2R^{b3}$, and S(O)$_2$ $NR^{c3}R^{d3}$.

In some embodiments, where the compounds of the invention have Formula IIIa or IIIb, $R^C$ is H.

In some embodiments, where the compounds of the invention have Formula IIIa or IIIb, $R^D$ is H.

In some embodiments, the compounds of the invention have Formula IV:

IV

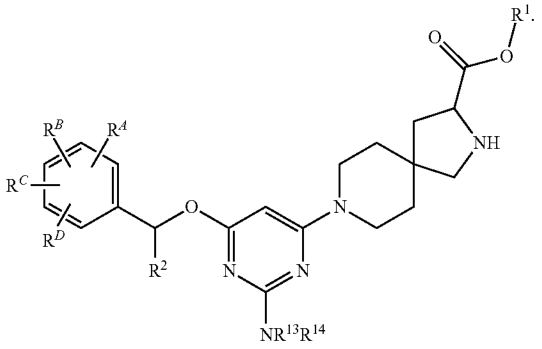

In some embodiments, where the compounds of the invention have Formula IV, $R^2$ is $CF_3$.

In some embodiments, where the compounds of the invention have Formula IV, $R^1$ is H or $C_{1-10}$ alkyl.

In some embodiments, where the compounds of the invention have Formula IV, $R^A$ is $Cy^1$.

In some embodiments, where the compounds of the invention have Formula IV, $R^A$ is $C_{6-10}$ aryl or 5-10 membered heteroaryl, each of which is optionally substituted by 1, 2, 3, 4, or 5 substituents independently selected from $R^{Cy}$.

In some embodiments, where the compounds of the invention have Formula IV, $R^A$ is 5-10 membered heteroaryl optionally substituted by 1, 2, 3, 4, or 5 substituents independently selected from $R^{Cy}$.

In some embodiments, where the compounds of the invention have Formula IV, $R^A$ is 5 to 6-membered heteroaryl optionally substituted by 1, 2, or 3 substituents independently selected from $R^{Cy}$.

In some embodiments, where the compounds of the invention have Formula IV, $R^A$ is $C_{6-10}$ aryl optionally substituted by 1, 2, or 3 substituents independently selected from $R^{Cy}$.

In some embodiments, where the compounds of the invention have Formula IV, $R^A$ is phenyl optionally substituted by 1, 2, or 3 substituents independently selected from $R^{Cy}$.

In some embodiments, where the compounds of the invention have Formula IV, $R^B$ is $Cy^2$.

In some embodiments, where the compounds of the invention have Formula IV, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, where the compounds of the invention have Formula IV, $R^C$ is H.

In some embodiments, where the compounds of the invention have Formula IV, $R^D$ is H.

In some embodiments, the compounds of the invention have Formula Va:

Va

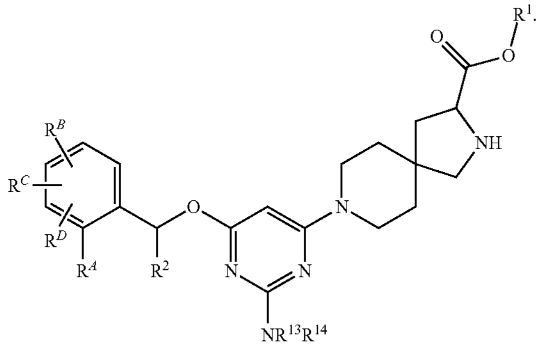

In some embodiments, where the compounds of the invention have Formula Va, $R^2$ is $CF_3$.

In some embodiments, where the compounds of the invention have Formula Va, $R^1$ is H or $C_{1-10}$ alkyl.

In some embodiments, where the compounds of the invention have Formula Va, $R^A$ is $Cy^1$.

In some embodiments, where the compounds of the invention have Formula Va, $R^A$ is $C_{6-10}$ aryl or 5-10 membered heteroaryl, each of which is optionally substituted by 1, 2, 3, 4, or 5 substituents independently selected from $R^{Cy}$.

In some embodiments, where the compounds of the invention have Formula Va, $R^A$ is 5-10 membered heteroaryl optionally substituted by 1, 2, 3, 4, or 5 substituents independently selected from $R^{Cy}$.

In some embodiments, where the compounds of the invention have Formula Va, $R^A$ is 5 to 6-membered heteroaryl optionally substituted by 1, 2, or 3 substituents independently selected from $R^{Cy}$.

In some embodiments, where the compounds of the invention have Formula Va, $R^A$ is $C_{6-10}$ aryl optionally substituted by 1, 2, or 3 substituents independently selected from $R^{Cy}$.

In some embodiments, where the compounds of the invention have Formula Va, $R^A$ is phenyl optionally substituted by 1, 2, or 3 substituents independently selected from $R^{Cy}$.

In some embodiments, where the compounds of the invention have Formula Va, $R^B$ is $Cy^2$.

In some embodiments, where the compounds of the invention have Formula Va, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}Rd^3$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula Vb:

Vb

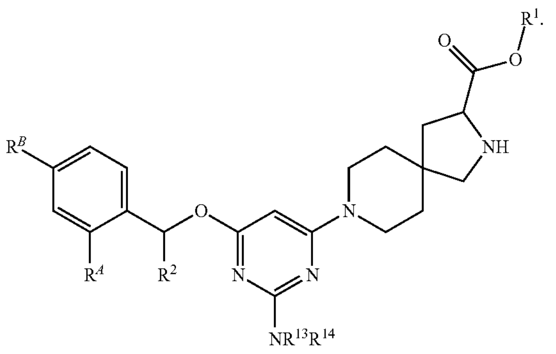

In some embodiments, where the compounds of the invention have Formula Vb, $R^2$ is $CF_3$.

In some embodiments, where the compounds of the invention have Formula Vb, $R^1$ is H or $C_{1-10}$ alkyl.

In some embodiments, where the compounds of the invention have Formula Vb, $R^A$ is $Cy^1$.

In some embodiments, where the compounds of the invention have Formula Vb, $R^A$ is $C_{6-10}$ aryl or 5-10 membered heteroaryl, each of which is optionally substituted by 1, 2, 3, 4, or 5 substituents independently selected from $R^{Cy}$.

In some embodiments, where the compounds of the invention have Formula Vb, $R^A$ is 5-10 membered heteroaryl optionally substituted by 1, 2, 3, 4, or 5 substituents independently selected from $R^{Cy}$.

In some embodiments, where the compounds of the invention have Formula Vb, $R^A$ is 5 to 6-membered heteroaryl optionally substituted by 1, 2, or 3 substituents independently selected from $R^{Cy}$.

In some embodiments, where the compounds of the invention have Formula Vb, $R^A$ is $C_{6-10}$ aryl optionally substituted by 1, 2, or 3 substituents independently selected from $R^{Cy}$.

In some embodiments, where the compounds of the invention have Formula Vb, $R^A$ is phenyl optionally substituted by 1, 2, or 3 substituents independently selected from $R^{Cy}$.

In some embodiments, where the compounds of the invention have Formula Vb, $R^B$ is $Cy^1$.

In some embodiments, where the compounds of the invention have Formula Vb, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula VI:

VI

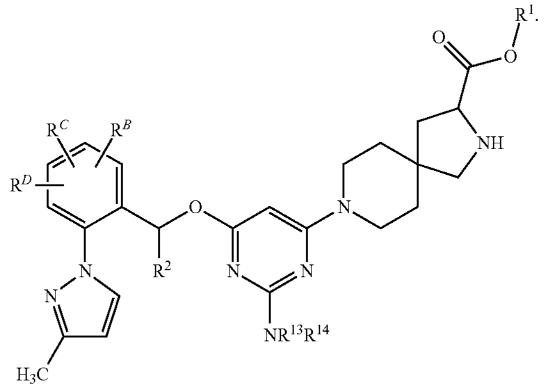

In some embodiments, where the compounds of the invention have Formula VI, $R^2$ is $CF_3$.

In some embodiments, where the compounds of the invention have Formula VI, $R^1$ is H or $C_{1-10}$ alkyl.

In some embodiments, where the compounds of the invention have Formula VI, $R^B$ is $Cy^2$.

In some embodiments, where the compounds of the invention have Formula VI, $Cy^2$ is phenyl optionally substituted by 1, 2, or 3 substituents independently selected from $R^{Cy}$.

In some embodiments, where the compounds of the invention have Formula VI, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, where the compounds of the invention have Formula VI, $R^C$ is H.

In some embodiments, where the compounds of the invention have Formula VI, $R^D$ is H.

In some embodiments, the compounds of the invention have Formula VIA:

VIA

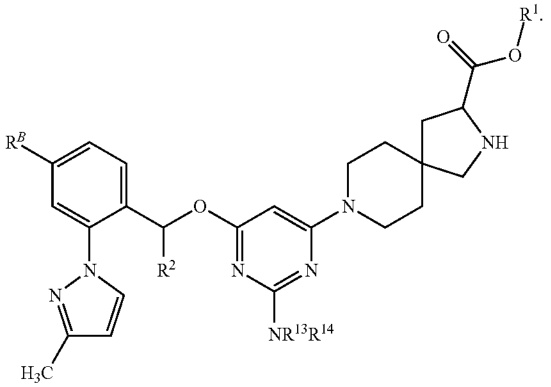

In some embodiments, where the compounds of the invention have Formula VIA, $R^2$ is $CF_3$.

In some embodiments, where the compounds of the invention have Formula VIA, $R^1$ is H or $C_{1-10}$ alkyl.

In some embodiments, where the compounds of the invention have Formula VIA, $R^B$ is $Cy^2$.

In some embodiments, where the compounds of the invention have Formula VIA, $Cy^2$ is phenyl optionally substituted by 1, 2, or 3 substituents independently selected from $R^{Cy}$.

In some embodiments, where the compounds of the invention have Formula VIA, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula VII:

VII

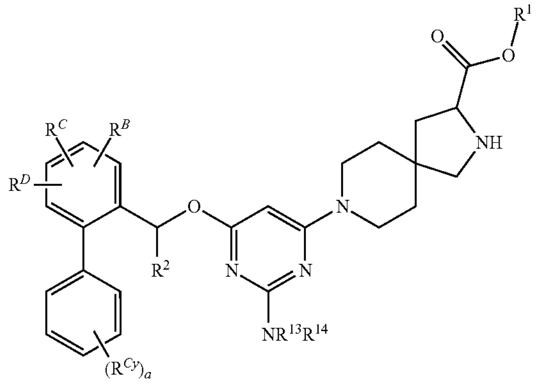

wherein a is 0, 1, 2, or 3.

In some embodiments, where the compounds of the invention have Formula VII, $R^2$ is $CF_3$.

In some embodiments, where the compounds of the invention have Formula VII, $R^1$ is H or $C_{1-10}$ alkyl.

In some embodiments, where the compounds of the invention have Formula VII, $R^B$ is $Cy^2$.

In some embodiments, where the compounds of the invention have Formula VII, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, where the compounds of the invention have Formula VII, $R^B$ is H or halo.

In some embodiments, where the compounds of the invention have Formula VII, $R^B$ is halo.

In some embodiments, where the compounds of the invention have Formula VII, $R^C$ is H.

In some embodiments, where the compounds of the invention have Formula VII, $R^D$ is H.

In some embodiments, where the compounds of the invention have Formula VII, $R^{Cy}$is halo, $C_{1-6}$ alkyl, $C_{1-6}$ haloalkyl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $NR^{c5}R^{d5}$, $S(O)_2R^{b5}$, and $S(O)_2NR^{c5}R^{d5}$, wherein said $C_{1-6}$ alkyl and 4-10 membered heterocycloalkyl are each optionally substituted with 1, 2, 3, 4, or 5 substituents independently selected from halo, $C_{1-6}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$.

In some embodiments, the compounds of the invention have Formula VIII:

VIII

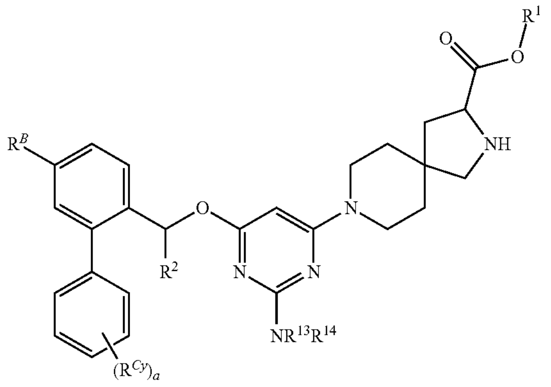

wherein a is 0, 1, 2, or 3.

In some embodiments, where the compounds of the invention have Formula VIII, $R^2$ is $CF_3$.

In some embodiments, where the compounds of the invention have Formula VIII, $R^1$ is H or $C_{1-10}$ alkyl.

In some embodiments, where the compounds of the invention have Formula VIII, $R^B$ is $Cy^2$.

In some embodiments, where the compounds of the invention have Formula VIII, $R^B$ is H, halo, $C_{1-6}$ alkyl, $C_{2-6}$ alkenyl, $C_{1-6}$ haloalkyl, CN, $OR^{a3}$, $C(O)NR^{c3}R^{d3}$, or $C(O)OR^{a3}$, wherein said $C_{1-6}$ alkyl and $C_{2-6}$ alkenyl are each optionally substituted with 1, 2, or 3 substituents independently selected from halo, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c1}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, where the compounds of the invention have Formula VIII, $R^B$ is H or halo.

In some embodiments, where the compounds of the invention have Formula VIII, $R^B$ is halo.

In some embodiments, where the compounds of the invention have Formula VIII, $R^C$ is H.

In some embodiments, where the compounds of the invention have Formula VIII, $R^D$ is H.

In some embodiments, where the compounds of the invention some embodiments have Formula VIII, $R^{Cy}$ is halo, $C_{1-6}$ alkyl, $C_{1-6}$ haloalkyl, 4-10 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $NR^{c5}R^{d5}$, $S(O)_2R^{b5}$, and $S(O)_2NR^{c5}R^{d5}$, wherein said $C_{1-6}$ alkyl and 4-10 membered heterocycloalkyl are each optionally substituted with 1, 2, 3, 4, or 5 substituents independently selected from halo, $C_{1-6}$ alkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2 R^{b5}$, and $S(O)_2NR^{c5}R^{d5}$.

In some embodiments, where the compounds of the invention have Formula VIII, a is 0.

In some embodiments, the chiral carbon to which —C(O)$OR^1$ is attached has an S configuration.

In some embodiments, the carbon to which —$R^2$ is attached is chiral and has an R configuration.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "substituted" means that an atom or group of atoms formally replaces hydrogen as a "substituent" attached to another group. The hydrogen atom is formally removed and replaced by a substituent. A single divalent substituent, e.g., oxo, can replace two hydrogen atoms. The term "optionally substituted" means unsubstituted or substituted. The substituents are independently selected, and substitution may be at any chemically accessible position. It is to be understood that substitution at a given atom is limited by valency. Throughout the definitions, the term "$C_{i-j}$" indicates a range which includes the endpoints, wherein i and j are integers and indicate the number of carbons. Examples include $C_{1-4}$, $C_{1-6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the term "$C_{i-j}$ alkyl," employed alone or in combination with other terms, refers to a saturated hydrocarbon group that may be straight-chain or branched, having i to j carbon atoms. In some embodiments, the alkyl group contains from 1 to 10, 1 to 6, 1 to 4, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i-j}$ alkoxy," employed alone or in combination with other terms, refers to a group of formula —O-alkyl, wherein the alkyl group has i to j carbon atoms. Example alkoxy groups include methoxy, ethoxy, and propoxy (e.g., n-propoxy and isopropoxy). In some embodiments, the alkyl group has 1 to 3 carbon atoms or 1 to 4 carbon atoms.

As used herein, "$C_{i-j}$ alkenyl" refers to an alkyl group having one or more double carbon-carbon bonds and having i to j carbon atoms. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, the term "$C_{i-j}$ alkylamino" refers to a group of formula —NH(alkyl), wherein the alkyl group has i to j carbon atoms. In some embodiments, the alkyl group has 1 to 6 or 1 to 4 carbon atoms.

As used herein, the term "di-$C_{i-j}$-alkylamino" refers to a group of formula —$N(alkyl)_2$, wherein the two alkyl groups each has, independently, i to j carbon atoms. In some embodiments, each alkyl group independently has 1 to 6 or 1 to 4 carbon atoms.

As used herein, the term "thio" refers to a group of formula —SH.

As used herein, the term "$C_{i-j}$ alkylthio" refers to a group of formula —S-alkyl, wherein the alkyl group has i to j carbon atoms. In some embodiments, the alkyl group has 1 to 6 or 1 to 4 carbon atoms.

As used herein, the term "amino" refers to a group of formula —$NH_2$.

As used herein, the term "$C_{i-j}$ aryl," employed alone or in combination with other terms, refers to a monocyclic or polycyclic (e.g., having 2, 3 or 4 fused rings) aromatic hydrocarbon having i to j ring-forming carbon atoms, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "arylalkyl" refers to a group of formula —$C_{i-j}$ alkyl—($C_{i-j}$ aryl). In some embodiments, arylalkyl is $C_{6-10}$ aryl-$C_{1-3}$ alkyl. In some embodiments, arylalkyl is $C_{6-10}$ aryl-$C_{1-4}$ alkyl. In some embodiments, arylalkyl is benzyl.

As used herein, the term "carbonyl," employed alone or in combination with other terms, refers to a —C(=O)— group.

As used herein, the term "carboxy" refers to a group of formula —C(=O)OH.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the defmition of cycloalkyl are moieties that have one or more aromatic rings (aryl or heteroaryl) fused to the cycloalkyl ring, for example, benzo or pyrido derivatives of cyclopentane, cyclopentene, cyclohexane, and the like. Where the cycloalkyl group includes a fused aromatic ring, the cycloalkyl group can be attached at either an atom in the aromatic or non-aromatic portion. One or more ring-forming carbon atoms of a cycloalkyl group can be oxidized to form carbonyl linkages. In some embodiments, cycloalkyl is $C_{3-10}$ or $C_{3-7}$ cycloalkyl, which can be monocyclic or polycyclic. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantanyl and the like. In some embodiments, the cycloalkyl group is cyclopropyl, cyclobutyl, cyclopentyl, or cyclohexyl.

As used herein, the term "cycloalkylalkyl" refers to a group of formula —$C_{i-j}$ cycloalkyl). In some embodiments, cycloalkylalkyl is $C_{3-7}$ cycloalkyl-$C_{1-3}$ alkyl, wherein the cycloalkyl portion is monocyclic. In some embodiments, cycloalkylalkyl is $C_{3-7}$ cycloalkyl-$C_{1-4}$ alkyl.

As used herein, "$C_{i-j}$ haloalkoxy" refers to a group of formula —O-haloalkyl having i to j carbon atoms. An example haloalkoxy group is $OCF_3$. An additional example haloalkoxy group is $OCHF_2$. In some embodiments, the alkyl group has 1 to 6 or 1 to 4 carbon atoms.

As used herein, the term "halo" refers to a halogen atom selected from F, Cl, I or Br. In some embodiments, "halo" refers to a halogen atom selected from F, Cl, or Br. In some embodiments, the halo group is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluoromethyl, difluoromethyl, or trifluoromethyl. In some embodiments, the haloalkyl group is trifluoromethyl. In some embodiments, the haloalkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic moiety, having one or more heteroatom ring members selected from nitrogen, sulfur and oxygen. In some embodiments, the heteroaryl group is a 5- to 10-membered heteroaryl ring, which is monocyclic or bicyclic and which has 1, 2, 3, or 4 heteroatom ring members independently selected from nitrogen, sulfur and oxygen. In some embodiments, the heteroaryl group is a 5- to 6-membered heteroaryl ring, which is monocyclic and which has 1, 2, 3, or 4 heteroatom ring members independently selected from nitrogen, sulfur and oxygen. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, and the like.

A 5-membered heteroaryl is a heteroaryl group having five ring-forming atoms comprising carbon and one or more (e.g., 1, 2, or 3) ring atoms independently selected from N, O and S. Example five-membered heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl is a heteroaryl group having six ring-forming atoms wherein one or more (e.g., 1, 2, or 3) ring atoms are independently selected from N, O, and S. Example six-membered heteroaryls include pyridyl, pyrazinyl, pyrimidinyl, triazinyl and pyridazinyl.

As used herein, the term "heteroarylalkyl" refers to a group of formula —$C_{i-j}$alkyl-(heteroaryl). In some embodiments, heteroarylalkyl 5-10 membered heteteroaryl-$C_{1-4}$ alkyl, wherein the heteroaryl portion is monocyclic or bicyclic and has 1, 2, 3, or 4 heteroatom ring members independently selected from nitrogen, sulfur and oxygen. In some embodiments, the heteroarylalkyl is 5-6 membered heteteroaryl-$C_{1-3}$ alkyl or 5-6 membered heteteroaryl-$C_{1-4}$ alkyl, wherein the heteroaryl portion is monocyclic and has 1, 2, 3, or 4 heteroatom ring members independently selected from nitrogen, sulfur and oxygen.

As used herein, the term "heterocycloalkyl," employed alone or in combination with other terms, refers to a non-aromatic ring or ring system, which optionally contains one or more alkenylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused rings) ring systems, including spiro systems. Also included in the definition of heterocycloalkyl are moieties that have one or more aromatic rings (aryl or heteroaryl) fused to the non-aromatic ring, for example, 1,2,3,4-tetrahydro-quinoline, dihydrobenzofuran and the like. Where the heterocycloalkyl group includes a fused aromatic ring, the heterocycloalkyl group can be attached at either an atom in the aromatic or non-aromatic portion. The carbon atoms or heteroatoms in the ring(s) of the heterocycloalkyl group can be oxidized (e.g. have one or two oxo substituents) to form a carbonyl, or sulfonyl group (or other oxidized linkage) or a nitrogen atom can be quaternized. In some embodiments, the heterocycloalkyl group is 5- to 10-membered, which can be monocyclic or bicyclic and which has 1, 2, 3, or 4 heteroatom ring members independently selected from nitrogen, sulfur and oxygen. In some embodiments, the heterocycloalkyl group is 5- to 6-membered or 5- to 7-membered. Examples of heterocycloalkyl groups include 1, 2, 3, 4-tetrahydroquinoline, dihydrobenzofuran, azetidine, azepane, pyrrolidine, piperidine, piperazine, morpholine, thiomorpholine, and pyran. Further examples of heterocycloalkyl groups include 2-oxotetrahydro furanyl, 2-oxopyrrolidinyl, 2-oxoimidazolidinyl, 1-oxo-1,2,3,4-tetrahydroisoquinolin-6-yl, and 2-oxo-1,3-dioxolan-4-yl.

As used herein, the term "heterocycloalkylalkyl" refers to a group of formula —$C_{i-j}$alkyl-(heterocycloalkyl). In some embodiments, heterocycloalkylalkyl is 5-10 membered heterocycloalkyl-$C_{1-3}$ alkyl or 5-10 membered heterocycloalkyl-$C_{1-4}$alkyl, wherein the heterocycloalkyl portion is monocyclic or bicyclic and has 1, 2, 3, or 4 heteroatom ring members independently selected from nitrogen, sulfur and oxygen. In some embodiments, heterocycloalkylalkyl is 5-6 membered heterocycloalkyl-$C_{1-4}$ alkyl wherein the heterocycloalkyl portion is monocyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention can also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1, 2, 4-triazole, 1H- and 2H- isoindole, and 1H- and 2H-pyrazole.

Compounds of the invention can also include all isotopes of atoms occurring in the intermediates or final compounds. Isotopes include those atoms having the same atomic number but different mass numbers. For example, isotopes of hydrogen include tritium and deuterium.

The term "compound," as used herein, is meant to include all stereoisomers, geometric isomers, tautomers, and isotopes of the structures depicted. Compounds herein identified by name or structure as one particular tautomeric form are intended to include other tautomeric forms unless otherwise specified. Compounds herein identified by name or structure without specifying the particular configuration of a stereocenter are meant to encompass all the possible configurations at the stereocenter. For example, if a particular stereocenter in a compound of the invention could be R or S, but the name or structure of the compound does not designate which it is, than the stereocenter can be either R or S.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, EtOAc, alcohols (e.g., methanol, ethanol, iso-propanol, or butanol) or acetonitrile ($CH_3CN$) are preferred. Lists of suitable salts are found in *Remington's Pharmaceutical Sciences,* 17$^{th}$ Ed., (Mack Publishing Company, Easton, 1985), p. 1418, Berge et al., *J. Pharm. Sci.,* 1977, 66(1), 1-19, and in Stahl et al., *Handbook of Pharmaceutical Salts: Properties, Selection, and Use,* (Wiley, 2002).

The below Table is a key to some abbreviations used throughout.

| Abbreviations | |
|---|---|
| atm | atmosphere |
| BOC | tert-butyl-oxy-carbonyl |
| CAS# | Chemical Abstract Service registry number |
| CBS | Corey-Bakshi-Shibata (catalyst) |
| $CH_3CN$ | Acetonitrile |
| CBZ | Carbobenzyloxy |
| DIPEA | N,N-diisopropylethylamine |
| DMAP | 4-dimethylaminopyridine |
| DME | dimethylether |
| DMF | dimethyl formamide |
| dppf | 1,1'-bis(diphenylphosphino)ferrocene |
| EDCI | 1-ethyl-3-(3-dimethylaminopropyl)carbodiimide hydrochloride |
| ee | enantiomeric excess |
| EtOAc | ethyl acetate |
| h | hour(s) |
| min | minute(s) |
| HOAT | 1-hydroxy-7-azabenzotriazole |
| HOAc | acetic acid |
| HPLC | high-performance liquid chromatography |
| KOAc | potassium acetate |

-continued

| Abbreviations | |
|---|---|
| LAH | lithium aluminum hydride |
| LDA | lithium diisopropylamide |
| mCPBA | 3-meta-chloroperoxybenzoic acid |
| MeOH | Methanol |
| MS | mass spectrometry |
| MTBE | methyl t-butyl ether |
| $NH_4OH$ | ammonium hydroxide |
| NMP | 1-methyl-2-pyrrolidone |
| PAH | pulmonary arterial hypertension |
| PE | petroleum ether |
| PheOH | phenylalanine hydroxylase |
| Prep-TLC | preparative thin-layer chromatography |
| p-TSA | para-toluene sulfonic acid |
| RT | room temperature |
| SNAr | nucleophilic aromatic substitution |
| TBAF | tetrabutylammonium fluoride |
| tBuOH | tert-butanol |
| TBTU | O-(benzotriazol-1-yl)-N,N,N',N'-tetramethyluronium tetrafluoroborate |
| TEA | Triethylamine |
| TFA | trifluoroacetic acid |
| TH | tyrosine hydroxylase |
| THF | Tetrahydrofuran |
| TLC | thin-layer chromatography |
| TMS | Trimethylsilyl |
| TMSI | Trimethyl silyl iodide |
| TPH | tryptophan hydroxylase |

Synthesis

Procedures for making compounds described herein are provided below with reference to Schemes 1-10. Optimum reaction conditions and reaction times may vary depending on the particular reactants used. Unless otherwise specified, solvents, temperatures, pressures and other reaction conditions are readily selected by one of ordinary skill in the art. Specific procedures are provided in the Examples section. Compounds are named using the "structure to name" function included in ChemDraw® v.12 (Perkin-Elmer).

Typically, reaction progress may be monitored by thin layer chromatography (TLC) or HPLC-MS if desired. Intermediates and products may be purified by chromatography on silica gel, recrystallization, HPLC and/or reverse phase HPLC. In the reactions described below, it may be necessary to protect reactive functional groups (such as hydroxy, amino, thio, or carboxy groups) to avoid their unwanted participation in the reactions. The incorporation of such groups, and the methods required to introduce and remove them are known to those skilled in the art (for example, see Greene, Wuts, *Protective Groups in Organic Synthesis.* 2nd Ed. (1999)). One or more deprotection steps in the synthetic schemes may be required to ultimately afford compounds of Formula I. The protecting groups depicted in the schemes are used as examples, and may be replaced by other compatible alternative groups. Starting materials used in the following schemes can be purchased or prepared by methods described in the chemical literature, or by adaptations thereof, using methods known by those skilled in the art. The order in which the steps are performed can vary depending on the protecting or functional groups introduced and the reagents and reaction conditions used, but would be apparent to those skilled in the art.

Compounds of Formula I can be prepared as shown in general in Scheme 1. Briefly, in step 1, an alcohol (where the ring substituted by $R^A$, $R^B$, $R^C$, $R^D$ corresponds to ring A of Formula I) (see, e.g., Intermediate 1) in dioxane is treated with a dichloro heterocycle (e.g., 2-amino-4,6-dichloropyrimidine) in the presence of a base (e.g., $Cs_2CO_3$), and heated for several hours (e.g. 12-24 h) at reflux. In step 2, a spirocycle of formula B (e.g., (S)-2-benzyl 3-ethyl 2,8-diazaspiro[4.5]decane-2,3-dicarboxylate) is added to a solution of compound A in a solvent (e.g., dioxane) in the presence of a base (e.g. $Na_2CO_3$), and heated to reflux to provide a compound of formula C. In step 3, the amino protecting group (P) (e.g. CBZ or BOC) of a compound of formula C is removed (e.g. with TMSI, transition metal-catalyzed hydrogenation, or strong acid depending on the nature of the protecting group). In step 4, a compound of formula D is obtained by ester hydrolysis (e.g. with LiOH in aqueous THF). In some instances, the sequence of steps 3 and 4 can be reversed.

Scheme 1

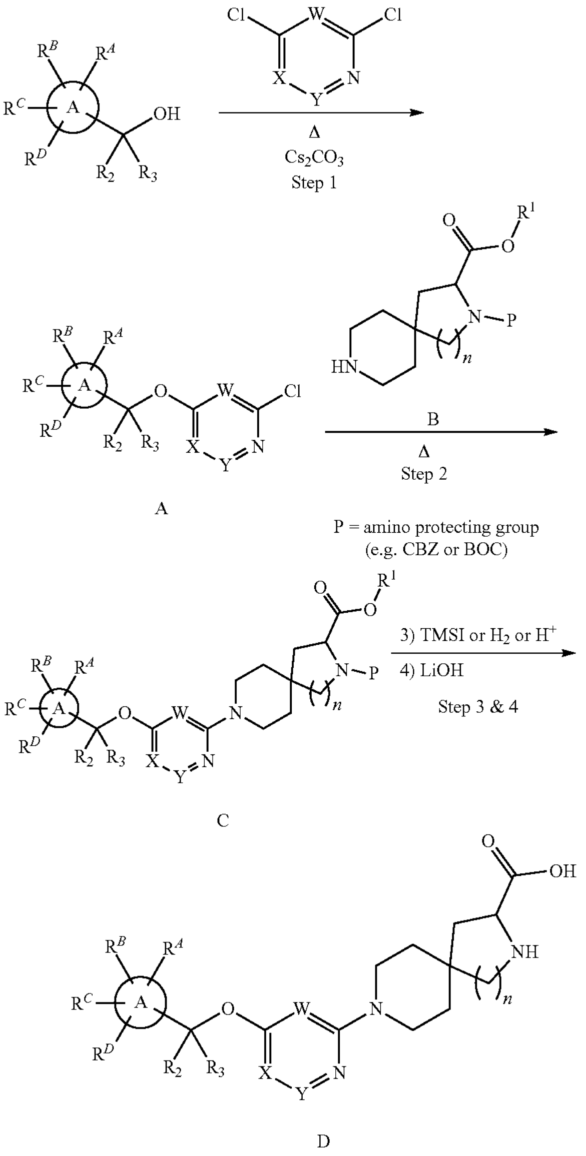

Alcohols (e.g., Intermediate 1) used in Scheme 1 can be prepared as shown in Scheme 2. Briefly, in step 1, to a solution of base (e.g. potassium t-butoxide) in a solvent (e.g. DMSO) is added 3-methyl pyrazole and an aryl bromide E (e.g., 1,4-dibromo-2-fluorobenzene), and the mixture is heated for several hours (e.g. 12-24 h) to provide a compound of formula F. In step 2, a compound of formula F is treated with a a Grignard reagent (e.g., i-PrMgCl) in a solvent (e.g., THF), then reacted with ethyl trifluoroacetate in a solvent (e.g., THF) to provide a ketone of formula G.

Alternatively, a ketone of formula G can be obtained by treating first a fluoro aromatic compound of formula E1 with a strong base (e.g., LDA), then trapping the intermediate aryl lithium with trifluoroacetic acid ethyl ester to give a compound of formula F1 (Step 1a). In a subsequent step 2a, 3-methyl pyrazole can be introduced onto a ketone of formula F1 via an SNAr reaction in the presence of base (e.g., $K_2CO_3$) under solvent reflux (e.g., toluene). In step 3, a ketone of formula G is converted stereospecifically into a chiral alcohol of formula F1 via either chiral transfer hydrogenation (e.g., with potassium formate) in the presence of a transition metal catalyst (e.g., pentamethyl cyclopentadienyl iridium (III) chloride dimer) and a chiral ligand (e.g., (1R,2R)-(−)-N-(4-toluene sulfonyl)-1,2-diphenyl ethylene diamine) in a solvent (e.g., acetonitrile), or alternatively with a borane reagent (e.g. catechol borane) and a chiral catalyst (e.g. (S)-2-methyl-CBS oxazaborolidine) in a solvent (e.g., THF). Alternatively, an alcohol of formula K can be made in a similar fashion starting from a ketone of formula J (step 2c). A ketone of formula J can be prepared in one step (step 2c) by reacting the aryl ester of formula E2 with a nucleophilic silylating agent (e.g., trimethyl(trifluoromethyl)silane) in the presence of a fluoride source (e.g., TBAF) in an inert solvent (e.g., THF).

Scheme 2

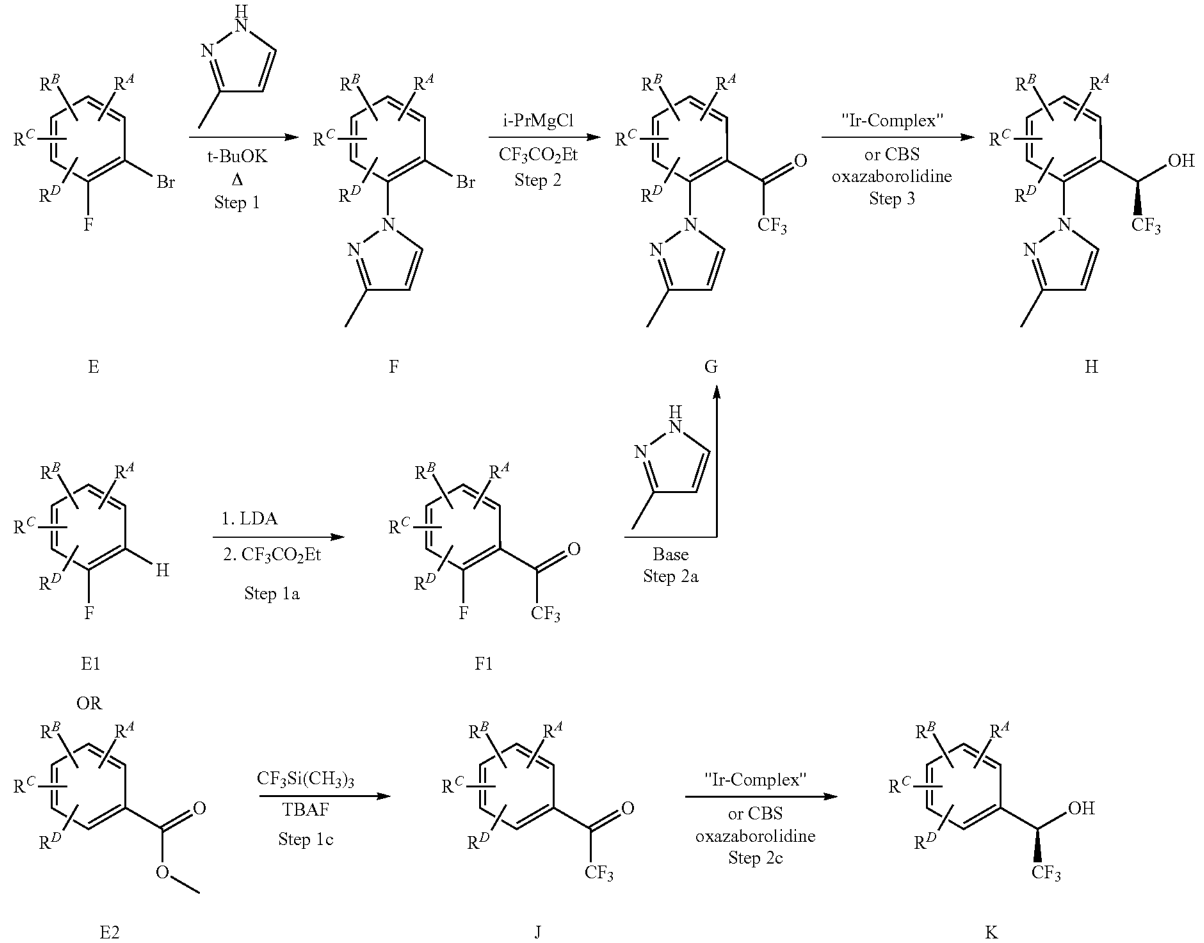

Other types of oxygen or nitrogen linker groups (L-groups) can be installed as shown in Scheme 3. Briefly, in step 1, to a spirocyclic compound of B (e.g., (S)-2-benzyl 3-ethyl 2,8-diazaspiro[4.5]decane-2,3-dicarboxylate) in dioxane is added a di-halo heterocycle (e.g., 2-amino-4,6-dichloropyrimidine) in the presence of a base (e.g., $Cs_2CO_3$) under solvent reflux (e.g., dioxane) to provide a compound of formula M. In step 2, to a compound of formula M in a solvent (e.g., dioxane) is added an alcohol or an amine of formula O (e.g., Intermediate 7 or 16) in the presence of a base (e.g., $Cs_2CO_3$). After heating at reflux for several hours (e.g., 12-24 h), a compound of formula P is obtained. In step 3, the amino protecting group (P) (e.g., CBZ or BOC) of a compound of formula P is removed (e.g., with TMSI, transition metal-catalyzed hydrogenation, or acid). Then, in step 4, a compound of formula Q is obtained by ester hydrolysis (e.g., with LiOH in aqueous THF). In some instances, the sequence of steps 3 and 4 can be reversed.

Scheme 3

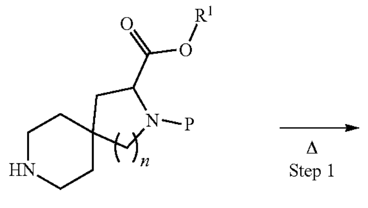

B

P = protecting group
(e.g. CBZ or BOC)

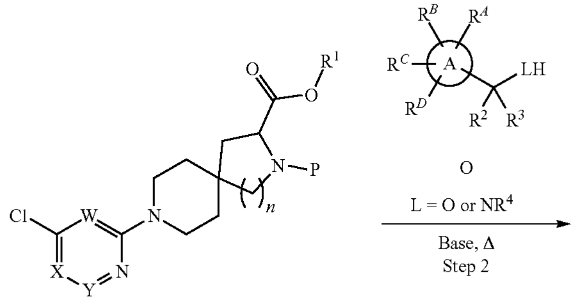

M

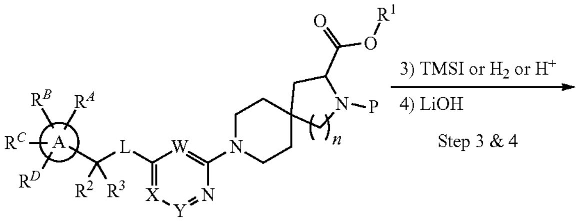

P

-continued

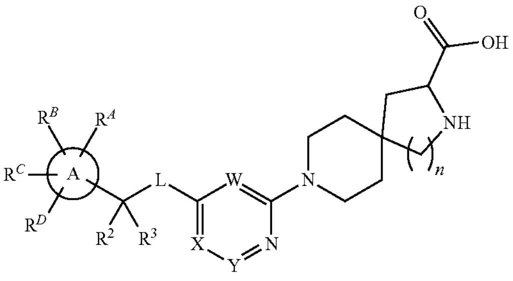

Q

For certain substituents and substitution patterns, palladium-mediated coupling reactions (e.g., Suzuki or Stille reactions) can be used, as shown in Schemes 4a, 4b, and 4c. Briefly, in step 1, to a compound of formula R in a solvent (e.g., aqueous dioxane) is added a boronic acid or boronate (e.g., phenyl boronic acid) in the presence of a palladium catalyst (e.g., $PdCl_2(dppf)$-$CH_2Cl_2$) and a base (e.g., $KHCO_3$), and the mixture heated to reflux for several hours (e.g., 12-24) to provide a compound of formula S. In step 3, the amino protecting group (P) (e.g., CBZ or BOC) of a compound of formula S is removed (e.g., with TMSI, transition metal-catalyzed hydrogenation, or acid). Then, in step 4, a compound of formula T is obtained by ester hydrolysis (e.g., with LiOH in aqueous THF). In some instances, the sequence of steps 2 and 3 can be reversed. A similar set of conditions can be used when starting with a compound of formula U or X, to obtain a compound of formula W or AA, respectively (Schemes 4b and 4c).

Scheme 4a

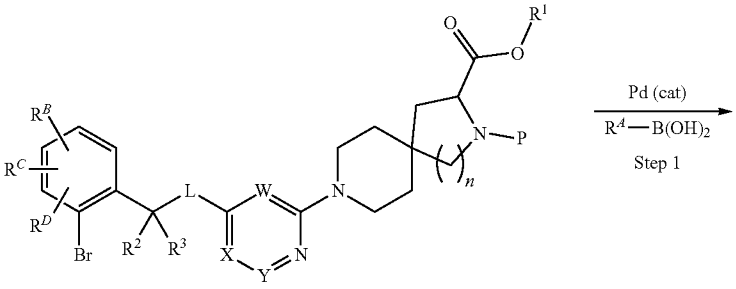

R

P = amino protecting group
(e.g. CBZ or BOC)

-continued
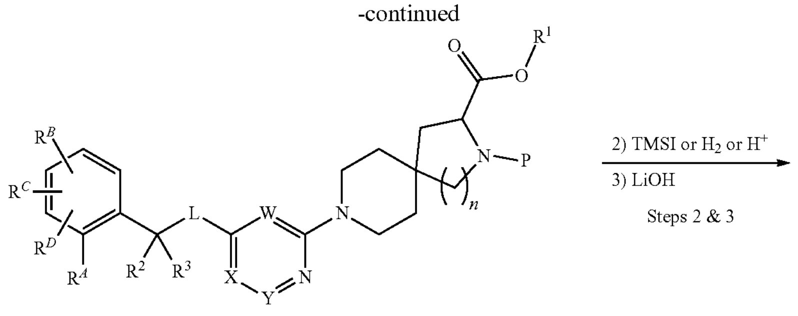
S
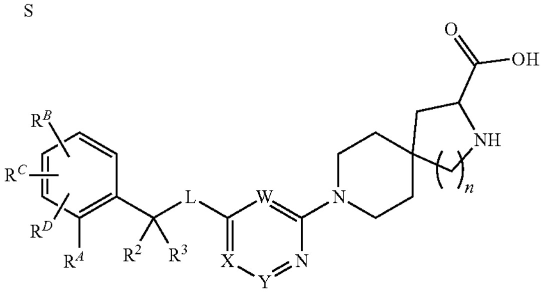
T
Scheme 4b
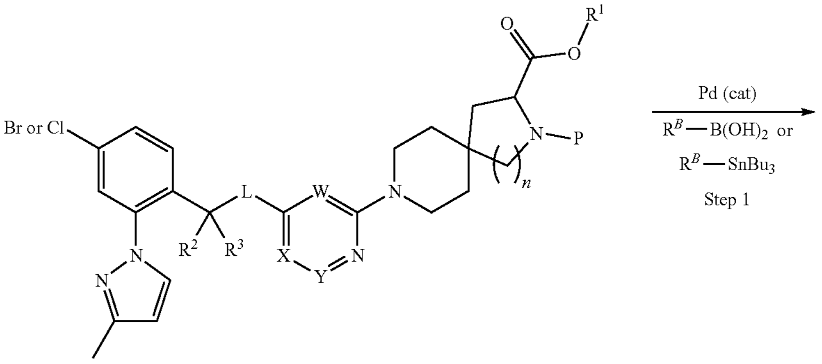
U
P = protecting group
(e.g. CBZ or BOC)
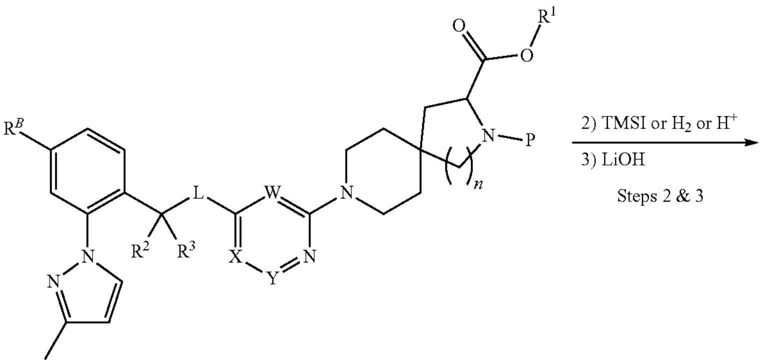
V -continued

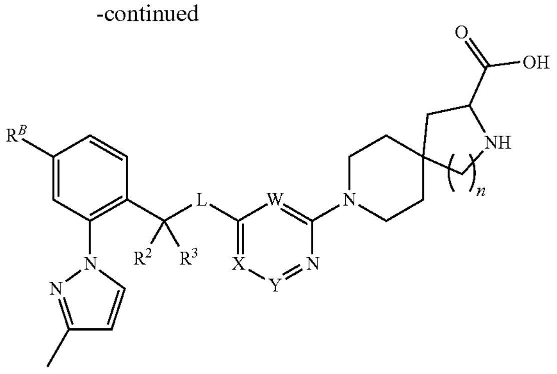

W

Scheme 4c

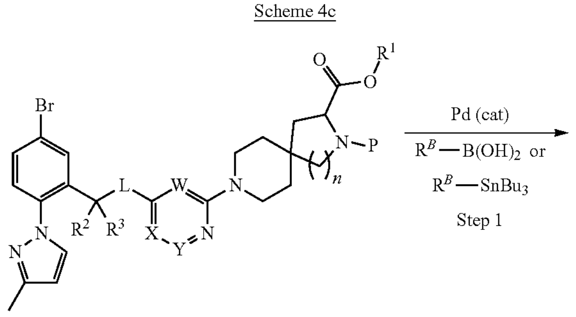

X

P = amino protecting group
(e.g. CBZ or BOC)

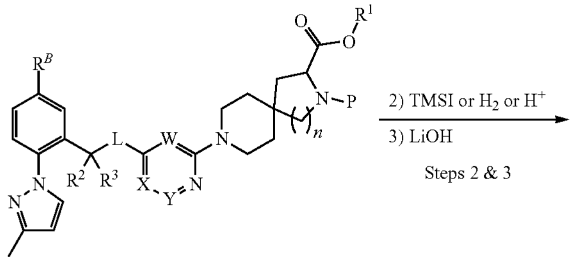

Y

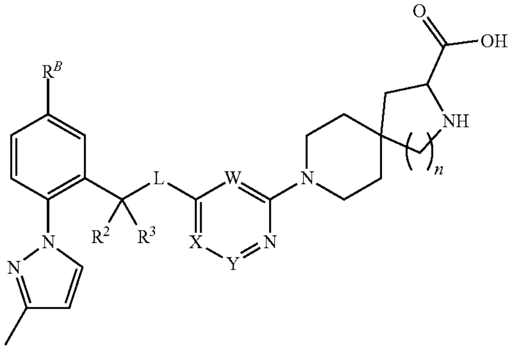

AA

Various substitutions of the central 6-membered ring (e.g., the ring containing W, X, and Y) can be accomplished as shown in Scheme 5. Briefly, in step 1, to a solution of a methyl sulfide of formula AB in an inert solvent (e.g., $CH_2Cl_2$) is added an oxidant (e.g., m-CPBA). The solution is stirred at RT for several hours (e.g., 12-24 h) to provide a sulfone of formula AC. In step 2, to a solution of a compound of formula AC in a solvent (e.g., dioxane) is added a spirocyclic compound of formula B (e.g., (S)-2-benzyl 3-ethyl 2,8-diazaspiro[4.5]decane-2,3-dicarboxylate) in the presence of a base (e.g., $Cs_2CO_3$), and the mixture is heated for several hours (e.g., 12-24 h) to provide a sulfone of formula AD. In step 3, the ester group is saponified (e.g., with LiOH) in an aqueous or alcoholic solvent (e.g., aqueous THF) to provide an acid of formula AE. In step 4, heating an acid of formula AE in the presence of an alcohol or an amine (e.g., phenol) and a base (e.g., $Cs_2CO_3$) for several hours (e.g., 16-24 h) in a solvent (e.g., dioxane), followed in step 5 by deprotection of the amine (e.g. with TMSI, transition metal-catalyzed hydrogenation, or acid) provides a compound of formula AF.

Scheme 5

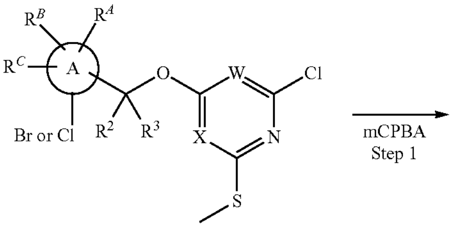

AB

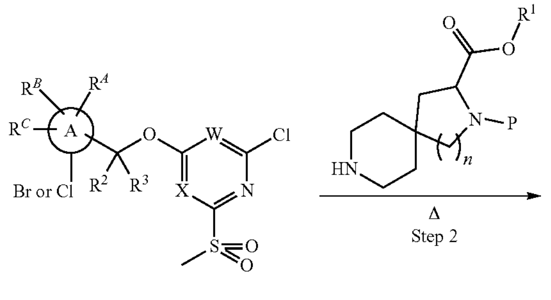

AC

-continued

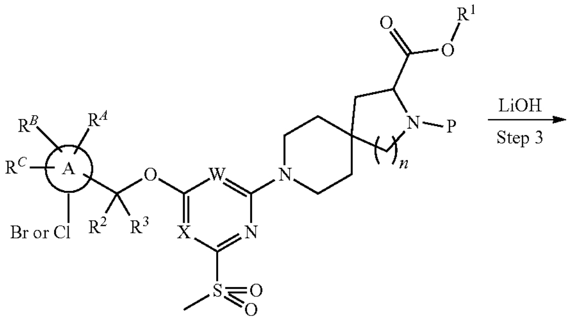

AD

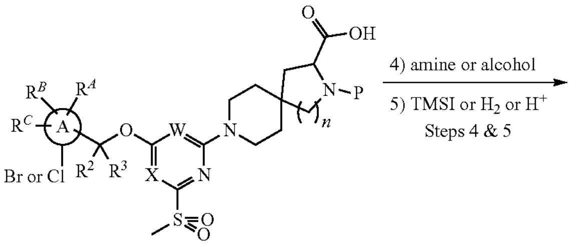

AE

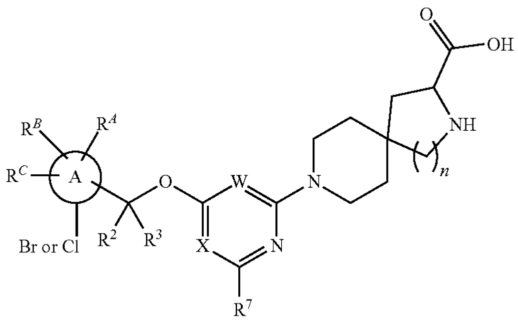

AF

Ester group substituents can be introduced by the general method of Scheme 6. Briefly, in step 1, to a solution of an acid of formula AG in an inert solvent (e.g., $CH_2Cl_2$) is added a coupling reagent (e.g., EDCI and DMAP), followed by an alcohol (e.g., propanol) to provide a compound of formula AH. In step 2, the benzyl groups of the benzyl ester and of the N-CBZ group can be removed with reagents such as TMSI or by transition metal-catalyzed hydrogenation (e.g., $H_2$ with Pd/C), affording a compound of formula AI. In case the amino protecting group is a BOC, an additional step 3, involving treatment with a strong acid (e.g., TFA), can be used for the final deprotection.

Scheme 6

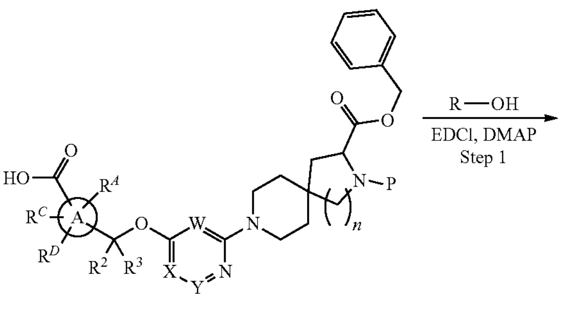

AG

P = amino protecting group (e.g. CBZ or BOC)

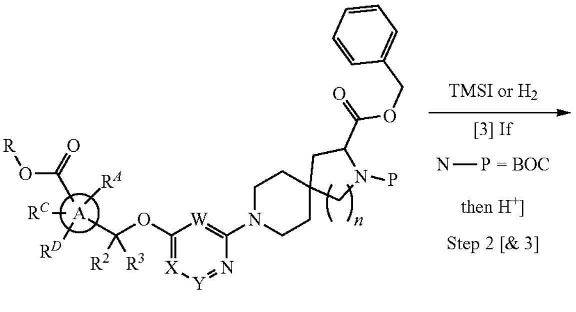

AH

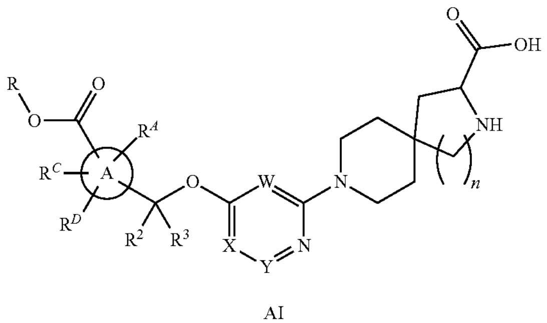

AI

Ethyl esters can be generally prepared according to Scheme 7. Briefly, deprotection of the amino group in a compound of formula AJ, can be accomplished either with the use of a dealkylating agent (e.g., TMSI) or via transition metal-catalyzed hydrogenation (e.g., $H_2$ with Pd/C) if the protecting group is CBZ, or with a strong acid (e.g., TFA or HCl), if the protecting group is BOC, to provide AK. It will be recognized by those skilled in the art that many other protecting groups can be used alternatively (for example, see Greene, Wuts, Protective Groups in Organic Synthesis. 2nd Ed. (1999)).

Scheme 7

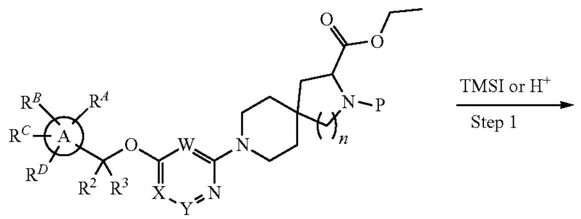

AJ

P = amino protecting group
(e.g. CBZ or BOC)

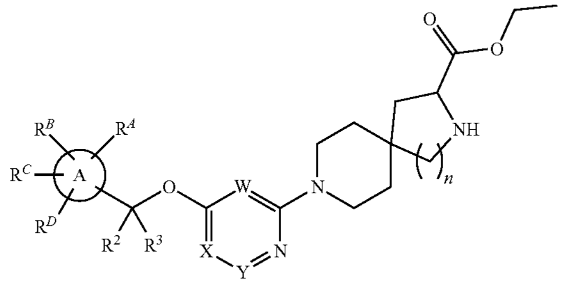

AK

Various esters can be made via direct alcohol coupling to the acid, as shown in Scheme 8, or via alkylation of the acid, as shown in Scheme 9. Briefly, an amino acid of formula AL is dissolved in an alcoholic solvent (e.g., n-octanol), optionally in the presence of a co-solvent (e.g., toluene), and heated in the presence of acid (e.g., p-TSA) for several hours (e.g., 12-24 h), optionally in the presence of a water trapping material (e.g., molecular sieve) or apparatus (e.g., Dean-Stark trap) to produce an ester of formula AM. Alternatively, in step 1, an acid of formula AN is dissolved in a solvent (e.g., DMF) in the presence of a base (e.g., $K_2CO_3$) and treated with an alkyl halide (e.g., 2-chloro-ethyl-dimethyl-amine). After heating the solution for several hours (e.g., 12-24 h), an ester of formula AO is obtained. In step 2, removal of the amino protecting group (e.g., with an acid like TFA in an inert solvent such as $CH_2Cl_2$ in case of a BOC protecting group) provides an ester of formula AP. Other compatible deprotection methods apparent to those skilled in the art can be applied for other types of amino protecting groups.

Scheme 8

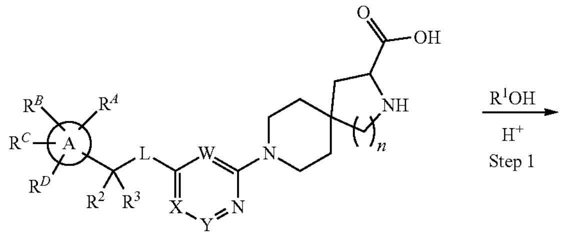

AL

-continued

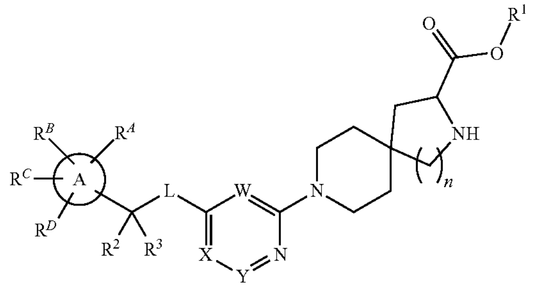

AM

Scheme 9

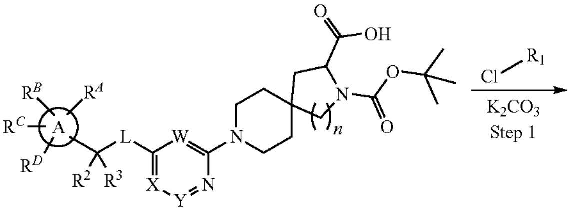

AN

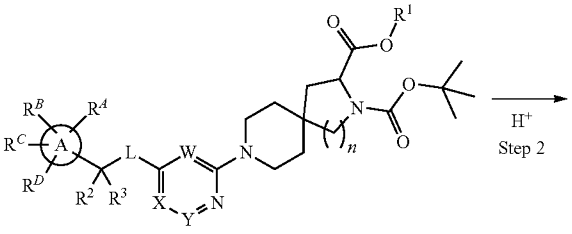

AO

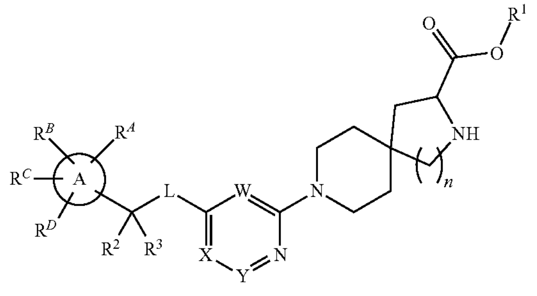

AP t-Butyl esters can be made via direct alcohol coupling to the acid, as shown in Scheme 10. Briefly, in step 1, an acid of formula AQ is dissolved in a solvent (e.g., DMF) in the presence of t-butanol, and treated with a coupling agent (e.g., EDCI and DMAP) to provide a compound of formula AR. In step 2, removal of the amino protecting group is achieved as described earlier to afford a compound of formula AS.

Scheme 10

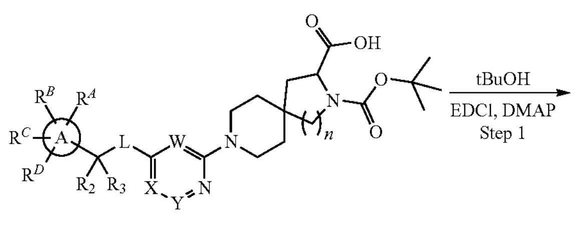

AQ

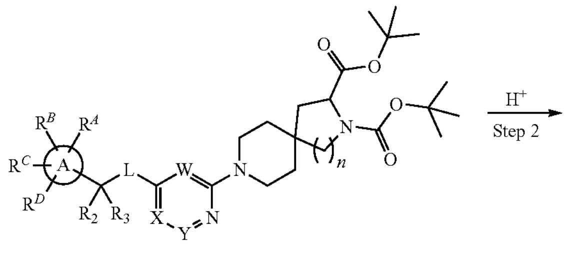

AR

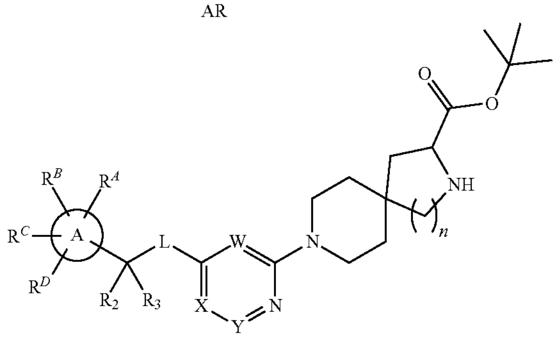

AS

Methods of Use

The compounds of the invention can be used to inhibit the activity of the TPH1 enzyme in a cell by contacting the cell with an inhibiting amount of a compound of the invention. The cell can be part of the tissue of a living organism, or can be in culture, or isolated from a living organism. Additionally, the compounds of the invention can be used to inhibit the activity of the TPH1 enzyme in an animal, individual, or patient, by administering an inhibiting amount of a compound of the invention to the cell, animal, individual, or patient.

Compounds of the invention can also lower peripheral serotonin levels in an animal, individual, or patient, by administering an effective amount of a compound of the invention to the animal, individual, or patient. In some embodiments, the compounds of the invention can lower levels of peripheral serotonin (e.g., 5-HT in the GI tract) selectively over non-peripheral serotonin (e.g., 5-HT in the CNS). In some embodiments, the selectivity is 2-fold or more, 3-fold or more, 5-fold or more, 10-fold or more, 50-fold or more, or 100-fold or more.

As TPH1 inhibitors that can lower peripheral serotonin levels, the compounds of the invention are useful in the treatment and prevention of various diseases associated with abnormal expression or activity of the TPH1 enzyme, or diseases associated with elevated or abnormal peripheral serotonin levels. In some embodiments, the treatment or prevention includes administering to a patient in need thereof a therapeutically effective amount of a TPH1 inhibitor of the invention.

Biological assays, some of which are described herein, can be used to determine the inhibitory effect of compounds against TPH (such as TPH1) in vitro and/or in vivo. In vitro biochemical assays for human, mouse, and rat TPH1 and human TPH2, PheOH, and TH may be used to measure inhibition of enzyme activity and the selectivity among TPH1, TPH2, PheOH, and TH. In addition, the efficacy of these compounds can be determined, for example, by measuring their effect on intestinal 5-HT levels in rodents after oral administration.

Diseases treatable or preventable by administering a TPH1 inhibitor of the invention include bone disease such as, for example, osteoporosis, osteoporosis pseudoglioma syndrome (OPPG), osteopenia, osteomalacia, renal osteodystrophy, Paget's disease, fractures, and bone metastasis. In some embodiments, the disease is osteoporosis, such as primary type 1 (e.g., postmenopausal osteoporosis), primary type 2 (e.g., senile osteoporosis), and secondary (e.g., steroid- or glucocorticoid-induced osteoporosis).

The present invention further includes methods of treating or preventing bone fracture such as, for example, osteoporotic or traumatic fracture, or surgical fractures associated with an orthopedic procedure (e.g., limb lengthening, bunion removal, an increase in bone formation associated with a prosthesis, bone metastasis, or spinal fusion).

Further diseases treatable or preventable by the methods of the invention include cardiovascular diseases such as atherosclerosis and pulmonary hypertension (PH), including idiopathic or familial PH, and also including PH associated with or brought on by other diseases or conditions. In some embodiments, the PH disease is pulmonary arterial hypertension (PAH).

The types of PAH treatable according to the methods of the invention include (1) idiopathic (IPAH), (2) familial (FPAH), and (3) associated (APAH) which is the most common type of PAH. The latter is PAH which is associated with other medical conditions including, for example, (1) collagen vascular disease (or connective tissue disease) which include autoimmune diseases such as scleroderma or lupus; (2) congenital heart and lung disease; (3) portal hypertension (e.g., resulting from liver disease); (4) HIV infection; (5) drugs (e.g., appetite suppressants, cocaine, and amphetamines; (6) other conditions including thyroid disorders, glycogen storage disease, Gaucher disease, hereditary hemorrhagic telangiectasia, hemoglobinopathies, myeloproliferative disorders,and splenectomy. APAH can also be PAH associated with abnormal narrowing in the pulmonary veins and/or capillaries such as in pulmonary veno-occlusive disease (PVOD) and pulmonary capillary hemangiomatosis. Another type of PAH is associatead with persistent pulmonary hypertension of the newborn (PPHN).

Further diseases treatable or preventable by the methods of the invention include metabolic diseases such as diabetes and hyperlipidemia; pulmonary diseases such as chronic obstructive pulmonary disease (COPD), and pulmonary embolism; gastrointestinal diseases such as IBD, colitis, chemotherapy-induced emesis, diarrhea, carcinoid syndrome, celiac disease, Crohn's disease, abdominal pain, dyspepsia, constipation, lactose intolerance, MEN types I and II, Ogilvie's syndrome, pancreatic cholera syndrome, pancreatic insufficiency, pheochromacytoma, scleroderma, somatization disorder, Zollinger-Ellison Syndrome, or other gastrointestinal inflammatory conditions; liver diseases such as chronic liver disease; cancers such as liver cancer, breast cancer, cholangiocarcinoma, colon cancer, colorectal cancer, neuroendocrine tumors, pancreatic cancer, prostate cancer, and bone cancer (e.g., osteosarcoma, chrondrosarcoma, Ewings sarcoma, osteoblastoma, osteoid osteoma, osteochondroma, enchondroma, chondromyxoid fibroma, aneurysmal bone cyst, unicameral bone cyst, giant cell tumor, and bone tumors); blood diseases (e.g., myeoloproliferative syndrome, myelodysplastic syndrome, Hodgkin's lymphoma, non-Hodgkin's lymphoma, myeloma, and anemia such as aplastic anemia and anemia assocated with kidney disease; and blood cancers (e.g., leukemias such as acute lymphocytic leukemia (ALL), chronic lymphocytic leukemica (CLL), acute myeloid leukemia (AML), and chronic myeloid leukemia (CML)).

The compounds of the invention are also useful in the treatment and prevention of serotonin syndrome.

In some embodiments, the present invention includes methods of lowering plasma cholesterol, lowering plasma triglycerides, lowering plasma glycerol, lowering plasma free fatty acids in a patient by administering to said patient a therapeutically effective amount of a compound of the invention.

The compounds of the invention are also useful in the treatment and prevention of inflammatory disease, such as allergic airway inflammation (e.g., asthma).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the enzyme with a compound of the invention includes the administration of a compound of the present invention to an individual or patient, such as a human, having the TPH1 enzyme, as well as, for example, introducing a compound of the invention into a sample containing a cellular or purified preparation containing the TPH1enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein the term "preventing" or "prevention" refers to inhibiting onset or worsening of the disease; for example, in an individual who may be predisposed to the disease, condition or disorder but does not yet experience or display the pathology or symptomatology of the disease.

Combination Therapy

One or more additional pharmaceutical agents or treatment methods can be used in combination with the compounds of the present invention for treatment or prevention of various diseases, disorders or conditions disclosed herein. The agents can be combined with the present compounds in a single dosage form, or the agents can be administered simultaneously or sequentially in separate dosage forms.

Example pharmaceutical agents that may be useful in a combination therapy for blood disorders like blood cancers include parathyroid hormone, anti-sclerostin antibodies, kathepsin K inhibitors, and anti-Dickopff 1.

Example pharmaceutical agents that may be useful in a combination therapy for cancer include leuprolide, goserelin, buserelin, flutamide, nilutamide, ketoconazole, aminoglutethimide, mitoxantrone, estramustine, doxorubicin, etoposide, vinblastine, paclitaxel, carboplatin, and vinorelbine. Therapies that can be combined with TPH inhibition include radiation therapy, high-intensity focused ultrasound, or surgery (e.g., removal of diseased tissues). Other drugs for use in treating cancer include testolactone, anastrozole, letrozole, exemestane, vorozole, formestane, fadrozole, GnRH-analogues, temozolomide, bavituximab, cyclophosphamide, fluorouracil, fulvestrant, gefitinib, trastuzumab, IGF-1 antibodies, lapatinib, methotrexate, olaparib, BSI-201, pazopanib, rapamycin, ribavirin, sorafenib, sunitinib, tamoxifen, docetaxel, vatalinib, bevacizumab, and octreotide.

Example pharmaceutical agents that may be useful in combination therapy for cardiovascular or pulmonary diseases include endothelin receptor antagonists such as ambrisentan, BMS-193884, bosentan, darusentan, SB-234551, sitaxsentan, tezosentan and macitentan. Anticoagulants such as warfarin, acenocoumarol, phenprocoumon, phenindione, heparin, fondaparinux, argatroban, bivalirudin, lepirudin, and ximelagatran may also be useful in combination therapy. Pharmaceutical agents for combination therapy further include calcium channel blockers like amlodipine, felodipine, nicardipine, nifedipine, nimodipine, nisoldipine, nitrendipine, lacidipine, lercanidipine, phenylalkylamines, verapamil, gallopamil, diltiazem, and menthol. Prostacyclins like epoprostenol, iloprost and treprostinil may also be combined with the TPH inhibitors of the invention. Further pharmaceutical agents for combination therapy in cardiovascular or pulmonary diseases include PDE5 inhibitors like sildenafil, tadalafil, and vardenafil; diuretics like furosemide, ethacrynic acid, torasemide, bumetanide, hydrochlorothiazide, spironolactone, mannitol, nitric oxide or nitric oxide releasers, and soluble guanylate cyclase stimulators, such as riociguat. Yet further pharmaceutical agents for combination therapy include APJ receptor agonists (WO 2013/111110); IP receptor agonists (WO 2013/105057; WO 2013/105066; WO 2013/105061; WO 2013/105063; WO 2013/105065; WO 2013/105058); and PDGF receptor inhibitors (WO 2013/030802).

Example pharmaceutical agents that may be useful in combination therapy for metabolic disorders include HSL inhibitors such as those disclosed in International Patent Publications WO2006/074957; WO2005/073199; WO2004/11 1031; WO2004/111004; WO2004/035550; WO2003/051841; WO2003/051842; and WO2001/066531.

Example pharmaceutical agents that may be useful in combination therapy for bone disorders and diseases include bisphosphantes such as etidronate, clodronate, tiludronate, pamidronate, neridronate, olpadronate, alendronate, ibandronate, risedronate, cimadronate, zoledronate, and the like. Serotonin receptor modulators, such as 5-$HT_{1B}$, 5-$HT_{2A}$, and 5-$HT_{2B}$ agonists or antagonists, may also be useful in combination therapy for bone disease. Other useful agents for combination therapy include selective serotonin reuptake inhibitors (SSRI), anti-serotonin antibodies, and beta blockers such as IPS339, ICI1 18,551, butaxamine, metipranolol, nadol, oxprenolol, penbutolol, pindolol, propranolol, timolol, and sotalol. Further useful agents for combination therapy for the treatment of bone disorders, such as osteoporosis, include teriparatide, strontium ranelate, raloxifene, and denosumab.

Administration, Pharmaceutical Formulations, Dosage Forms

The compounds of the invention can be administered to patients (animals and humans) in need of such treatment in appropriate dosages that will provide prophylactic and/or therapeutic efficacy. The dose required for use in the treatment or prevention of any particular disease or disorder will typically vary from patient to patient depending on, for example, particular compound or composition selected, the route of administration, the nature of the condition being treated, the age and condition of the patient, concurrent medication or special diets then being followed by the patient, and other factors. The appropriate dosage can be determined by the treating physician.

A compound of this invention can be administered orally, subcutaneously, topically, parenterally, by inhalation spray or rectally in dosage unit formulations containing conventional non-toxic pharmaceutically acceptable carriers, adjuvants and vehicles. Parenteral administration can involve subcutaneous injections, intravenous or intramuscular injections or infusion techniques.

Treatment duration can be as long as deemed necessary by a treating physician. The compositions can be administered one to four or more times per day. A treatment period can terminate when a desired result, for example a particular therapeutic effect, is achieved. Or a treatment period can be continued indefinitely.

In some embodiments, the pharmaceutical compositions can be prepared as solid dosage forms for oral administration (e.g., capsules, tablets, pills, dragees, powders, granules and the like). A tablet can be prepared by compression or molding. Compressed tablets can include one or more binders, lubricants, glidants, inert diluents, preservatives, disintegrants, or dispersing agents. Tablets and other solid dosage forms, such as capsules, pills and granules, can include coatings, such as enteric coatings.

Compositions for inhalation or insufflation include solutions and suspensions in pharmaceutically acceptable aqueous or organic solvents, or mixtures thereof, and powders. Liquid dosage forms for oral administration can include, for example, pharmaceutically acceptable emulsions, microemulsions, solutions, suspensions, syrups and elixirs. Suspensions can include one or more suspending agents Dosage forms for transdermal administration of a subject composition include powders, sprays, ointments, pastes, creams, lotions, gels, solutions, patches and inhalants.

Compositions and compounds of the present invention can be administered by aerosol which can be administered, for example, by a sonic nebulizer.

Pharmaceutical compositions of this invention suitable for parenteral administration include a compound of the invention together with one or more pharmaceutically acceptable sterile isotonic aqueous or non-aqueous solutions, dispersions, suspensions or emulsions. Alternatively, the composition can be in the form of a sterile powder which can be reconstituted into a sterile injectable solutions or dispersion just prior to use.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TPH1 as described below.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

$^{1}H$ NMR Spectra were acquired on one or more of three instruments: (1) Agilent UnityInova 400 MHz spectrometer equipped with a 5 mm Automation Triple Broadband (ATB) probe (the ATB probe was simultaneously tuned to $^{1}H$, $^{19}F$ and $^{13}C$); (2) Agilent UnityInova 500 MHz spectrometer; or (3) Varian Mercury Plus 400 MHz spectrometer. Several NMR probes were used with the 500 MHz NMR spectrometer, including both 3 mm and 5 mm $^{1}H$, $^{19}F$ and $^{13}C$ probes and a 3 mm $X^{1}H^{19}F$ NMR probe (usually X is tuned to $^{13}C$). For typical $^{1}H$ NMR spectra, the pulse angle was 45 degrees, 8 scans were summed and the spectral width was 16 ppm (−2 ppm to 14 ppm). Typically, a total of about 32768 complex points were collected during the 5.1 second acquisition time, and the recycle delay was set to 1 second. Spectra were collected at 25° C. $^{1}H$ NMR Spectra were typically processed with 0.3 Hz line broadening and zero-filling to about 131072 points prior to Fourier transformation. Chemical shifts were expressed in ppm relative to tetramethylsilane. The following abbreviations are used herein: br=broad signal, s=singlet, d=doublet, dd=double doublet, ddd=double double doublet, dt=double triplet, t=triplet, td=triple doublet, tt=triple triplet q=quartet, m=multiplet.

Liquid chromatography—mass spectrometry (LCMS) experiments to determine retention times and associated mass ions were performed using one or more of the following Methods A, B, and C:

Method A: Waters BEH C18, 3.0×30 mm, 1.7 μm, was used at a temperature of 50° C. and at a flow rate of 1.5 mL/min, 2 μL injection, mobile phase: (A) water with 0.1% formic acid and 1% acetonitrile, mobile phase (B) MeOH with 0.1% formic acid; retention time given in minutes. Method A details: (I) ran on a Binary Pump G1312B with UV/Vis diode array detector G1315C and Agilent 6130 mass spectrometer in positive and negative ion electrospray mode with UV PDA detection with a gradient of 15-95% (B) in a 2.2 min linear gradient (II) hold for 0.8 min at 95% (B) (III) decrease from 95-15% (B) in a 0.1 min linear gradient (IV) hold for 0.29 min at 15% (B);

Method B: An Agilent Zorbax Bonus RP, 2.1×50 mm, 3.5 μm, was used at a temperature of 50° C. and at a flow rate of 0.8 mL/min, 2 μL injection, mobile phase: (A) water with 0.1% formic acid and 1% acetonitrile, mobile phase (B) MeOH with 0.1% formic acid; retention time given in minutes. Method details: (I) ran on a Binary Pump G1312Bwith UVNis diode array detector G1315C and Agilent 6130 mass spectrometer in positive and negative ion electrospray mode with UV-detection at 220 and 254 nm with a gradient of 5-95% (B) in a 2.5 min linear gradient (II) hold for 0.5 min at 95% (B) (III) decrease from 95-5% (B) in a 0.1 min linear gradient (IV) hold for 0.29 min at 5% (B).

Method C: An API 150EX mass spectrometer linked to a Shimadzu LC-10AT LC system with a diode array detector was used. The spectrometer had an electrospray source operating in positive and negative ion mode. LC was carried out using an Agilent ZORBAX XDB 50×2.1 mm C18 column and a 0.5 mL/minute flow rate. Solvent A: 95% water, 5% acetonitrile containing 0.01% formic acid; Solvent B: acetonitrile. The gradient was shown as below. 0-0.5 min: 2% solvent (B); 0.5-2.5 min: 2% solvent B to 95% solvent (B); 2.5-4.0 min: 95% solvent (B); 4.0-4.2 min: 95% solvent (B) to 2% solvent B; 4.2-6.0 min: 2% solvent (B).

Microwave experiments were carried out using a Biotage Initiator™, which uses a single-mode resonator and dynamic field tuning. Temperatures from 40-250° C. were achieved, and pressures of up to 20 bars were reached.

Preparative HPLC purification was carried out using either a C18-reverse-phase column from Genesis (C18) or a C6-phenyl column from Phenomenex (C6 Ph) (100×22.5 mm i.d. with 7 micron particle size, UV detection at 230 or 254 nm, flow 5-15 mL/min), eluting with gradients from 100-0 to 0-100% water/acetonitrile or water/MeOH containing 0.1% formic acid. Fractions containing the required product (identified by LCMS analysis) were pooled, the organic fraction removed by evaporation, and the remaining aqueous fraction lyophilised, to give the product.

Chiral HPLC was carried out using a Chiralpak AD column, 4.4 mm×250 mm, particle size 5 micron Compounds which required column chromatography were purified manually or fully automatically using either a Biotage SP1™ Flash Purification system with Touch Logic Control™ or a Combiflash Companion® with pre-packed silica gel Isolute® SPE cartridge, Biotage SNAP cartridge or Redisep® Rf cartridge respectively.

Preparation of Alcohols and Amines

The chiral alcohols drawn below are shown in their absolute configuration (unless otherwise shown). Their enantiopurity (% ee) can be determined via Mosher ester analysis and analyzed as described in the literature (Dale, J. A. & Mosher, H. S. Nuclear Magnetic Resonance Enantiomer Regents. Configurational Correlations Via Nuclear Magnetic Resonance Chemical Shifts Of Diastereomeric Mandelate, O-Methylmandelate, and alpha-Methoxy alpha-Trifluoromethylphenylacetate (MTPA) Esters. *J. Am. Chem. Soc.* 95, 512-519 (1973)). The chiral alcohols of the invention are preferably enantiomerically enriched, for example, to ≥95% ee.

Representative Mosher Ester Preparation

To a solution of (R)-1-(4-chloro-2-(3-methyl-1H-pyrazol-1-yl)phenyl)-2,2,2-trifluoroethanol (46 mg, 0.20 mmol, Intermediate 3) was added pyridine (138 mg, 1.7 mmol) followed by the addition of either (S or R)-α-methoxy-α-trifluoromethyl-phenylacetyl chloride (10 mg, 0.40 mmol). The reaction was stirred for 12 h, then the material was purified directly on silica gel chromatography (EtOAc/heptane) to provide the "Mosher ester" which was analyzed by $^1$H NMR for enantiomeric purity.

Intermediate 1: (R)-1-(4-Bromo-2-(3-methyl-1H-pyrazol-1-yl)phenyl)-2,2,2-trifluoroethanol

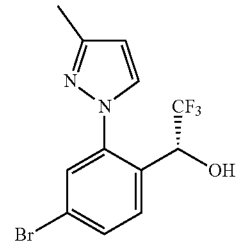

Step 1: Potassium t-butoxide (16.3 g, 145 mmol) was dissolved in DMSO (100 mL). To this solution was added 3-methyl pyrazole (10.4 g, 120 mmol) and the reaction was heated at 50° C. for 30 min. 1,4-Dibromo-2-fluorobenzene (31 g, 120 mmol) was then added and the reaction stirred at 50° C. for 16 h. The reaction was cooled to RT and extracted with water and EtOAc, washed with brine, dried over $Na_2SO_4$, and then filtered and concentrated in vacuo. Purification by normal phase silica gel column chromatography (EtOAc/heptane) provided 1-(2,5-dibromophenyl)-3-methyl-1H-pyrazole.

Step 2: 1-(2,5-dibromophenyl)-3-methyl-1H-pyrazole (23.0 g, 73 mmol) from Step 1 was dissolved in 200 mL of THF and cooled to 0° C. i-Propyl magnesium chloride (2.0 M in THF, 40 mL) was added dropwise and the reaction was stirred for 45 min, then ethyl trifluoroacetate (10.5 mL) was added. The reaction was stirred for 30 min at 0° C., then 10% HCl is added dropwise (400 mL). The reaction was extracted with water and EtOAc, washed with brine, dried over $Na_2SO_4$, filtered, and then concentrated in vacuo. Purification by normal phase silica gel column chromatography (EtOAc/heptane) provided 1-(4-bromo-2-(3-methyl-1H-pyrazol-1-yl)phenyl)-2,2,2-trifluoroethanone.

Step 3: METHOD A: Pentamethylcyclopentadienyl iridium (III) chloride dimer (CAS# 12354-84-6) (10.4 mg) and (1R,2R)-(−)-N-(4-toluene sulfonyl)-1,2-diphenyl ethylene diamine (CAS# 144222-34-4) (9.2 mg) were combined in water (120 mL), then heated to 50° C. for 5 h to provide the "Iridium complex." 1-[4-Bromo-2-(3-methyl-1H-pyrazol-1-yl)phenyl]-2,2,2-trifluoroethanone (16 g, 48 mmol) was dissolved in acetonitrile (120 mL) to which the Iridium complex and potassium formate (3.1 g, 3.7 mmol) were added. The reaction mixture was heated to 50° C. for 8 h. The reaction mixture was then cooled to RT, partitioned between water and EtOAc, and extracted. The combined organic layers were washed with brine, dried over $Na_2SO_4$, filtered, and concentrated in vacuo. Recrystallization from hot heptane (200 mL) provided the title compound.

METHOD B: Alternatively, the trifluoromethyl (or other prochiral) ketones of formula G or J (scheme 2) were asymmetrically reduced as follows (see for example: Corey, E. J. & Link, J. O. A General, Catalytic, and Enantioselective Synthesis of Alpha-amino Acids. *J. Am. Chem. Soc.* 114, 1906-1908 (1992)): Catechol borane (95 mL, 1 M in THF) and (S)-2-methyl-CBS oxazaborolidine (2.6 g, 9.6 mmol) were mixed in a jacketed glass reactor. The mixture was stirred at RT for 20 min, then the jacket was cooled to −78° C. At a reaction temperature of −65° C., 1-[4-bromo-2-(3-methyl-1H-pyrazol-1-yl)phenyl]-2,2,2-trifluoroethanone (16 g, 48 mmol) in THF (150 mL) was added dropwise over 2 h. The reaction was then warmed to −36° C. and held at this temperature for 22 h. Then the reaction was quenched with 3 N NaOH (100 mL) while maintaining a reaction temperature of <−25° C. The reaction was then warmed to 0° C. and $H_2O_2$ (30%, 100 mL) was added over 30 min, then warmed to RT for 4 h. The reaction mixture was quenched with 1 N NaOH, extracted with ether, washed with brine, dried over $Na_2SO_4$, and concentrated in vacuo. Purification on normal phase silica gel chromatography (EtOAc/heptane) provided the product as a viscous oil.

Intermediate 2: (R)-1-(5-Bromo-2-(3-methyl-1H-pyrazol-1-yl)phenyl)-2,2,2-trifluoroethanol

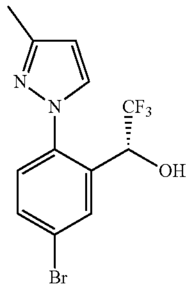 [SMILES: Cc1ccn(-c2ccc(Br)cc2[C@@H](O)C(F)(F)F)n1]

Step 1: Diisopropylamine (4.40 mL, 31.4 mmol) was dissolved in THF (28 mL) and cooled to −40° C. Then n-butyllithium (12.6 mL, 2.5 M in hexanes, 31.4 mmol) was added dropwise, and the reaction was stirred at −40° C. for 1 h, then cooled to −78° C. A solution of 1-bromo-4-fluorobenzene (5 g, 28.6 mmol) in THF (6.0 mL) was added, and the reaction was stirred at −78° C. for 1 h. Trifluoroacetic acid ethyl ester (3.73 mL, 31.4 mmol) in THF (6.0 mL) was then added, and the reaction was slowly warmed to 0° C. over an hour. The reaction was quenched with $NH_4Cl$ (aq. sat), and extracted with EtOAc, washed with brine, and dried over $Na_2SO_4$, filtered, and concentrated in vacuo. Purification by normal phase silica gel column chromatography (EtOAc/heptane) provided 1-(5-bromo-2-fluorophenyl)-2,2,2-trifluoroethanone.

Step 2: 1-(5-bromo-2-fluorophenyl)-2,2,2-trifluoroethanone (2.20 g, 8.12 mmol) from Step 1, $K_2CO_3$ (1.68 g, 12.2 mmol), and 3-methyl-1H-pyrazole (1.33 g, 16.2 mmol) were stirred in toluene (10 mL). The reaction was then heated to 110° C. for 16 h. The reaction was cooled, and water and EtOAc were added. The toluene-EtOAc layer is removed in vacuo, and then the reaction is extracted with water and EtOAc, washed with brine, and dried over $Na_2SO_4$, filtered, and concentrated in vacuo. Purification by normal phase silica gel column chromatography (EtOAc/heptane) provided 1-[5-bromo-2-(3-methyl-pyrazol-1-yl)-phenyl]-2,2,2-trifluoro-ethanone.

Step 3: The title compound was prepared using the Iridium complex-catalyzed hydrogenation as described for Intermediate 1, (R)-1-(4-bromo-2-(3-methyl-1H-pyrazol-1-yl)phenyl)-2,2,2- trifluoroethanol.

Intermediate 3: (R)-1-(4-chloro-2-(3-methyl-1H-pyrazol-1-yl)phenyl)-2,2,2-trifluoroethanol

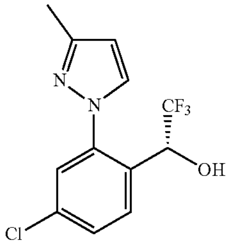 [SMILES: Cc1ccn(-c2cc(Cl)ccc2[C@@H](O)C(F)(F)F)n1]

Step 1: Potassium t-butoxide (3.9 g, 0.33 mmol) was dissolved in DMSO (25 mL). To this solution was added 3-methyl pyrazole (2.7 g, 0.33 mmol) and the reaction was heated at 50° C. for 30 min. 1-Bromo-4-chloro-2-fluorobenzene (4.6 g, 0.22 mmol) was then added and the reaction was stirred at 50° C. for 16 h. The reaction was cooled to RT and extracted with water and EtOAc, washed with brine, and dried over $Na_2SO_4$, filtered and concentrated in vacuo. Purification by normal phase silica gel column chromatography (EtOAc/heptane) provided 1-(2-bromo-5-chlorophenyl)-3-methyl-1H-pyrazole and 1-(2-bromo-5-chlorophenyl)-5-methyl-1H-pyrazole as a 4:1 mixture that was used in the next step directly.

Step 2: The mixture from Step 1 (8 g, 0.39 mmol) was dissolved in 160 mL of THF and cooled to 0° C. i-Propyl magnesium chloride (2.0 M in THF, 23 mL) was added dropwise and the reaction stirred for 45 min, then ethyl trifluoroacetate (6 mL) was added. The reaction was stirred for 30 min at 0° C., then 10% HCl was added dropwise (40 mL). The reaction was extracted with water and EtOAc, washed with brine, and dried over $Na_2SO_4$, filtered, and concentrated in vacuo.

Purification by normal phase silica gel column chromatography (EtOAc/heptane) provided 1-(4-chloro-2-(3-methyl-1H-pyrazol-1-yl)phenyl)-2,2,2-trifluoroethanone as a white solid.

Step 3: The title compound was prepared using the Iridium complex-catalyzed hydrogenation, as described for Intermediate 1 (R)-1-(4-bromo-2-(3-methyl-1H-pyrazol-1-yl)phenyl)-2,2,2-trifluoroethanol.

Intermediate 4: (R)-1-(5-chloro-2-(2,2,2-trifluoro-1-hydroxyethyl)phenyl)pyrrolidin-2-one

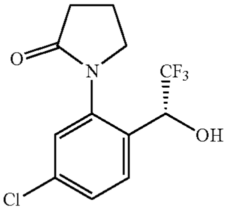 [SMILES: O=C1CCCN1c1cc(Cl)ccc1[C@@H](O)C(F)(F)F]

To a solution of (R)-1-(4)-2,2,2-trifluoroethanol (300 mg, 1.04 mmol) in toluene (7 mL) was added pyrrolidin-2-one (89 mg, 1.04 mmol), (1S,2S)-N1,N2-dimethylcyclohexane-1,2-diamine (74 mg, 0.52 mmol), CuI (50 mg, 0.26 mmol) and $K_2CO_3$ (360 mg, 2.6 mmol). The reaction was heated in a sealed tube to 130° C. for 12 h and then cooled to RT. The solids were filtered and the product was purified by normal phase silica gel chromatography (EtOAc:petroleum ether) to to provide the title compound as a white solid.

Intermediate 5: (R)-2,2,2-Trifluoro-1-(2-methyl-1H-benzo[d]imidazol-4-yl)ethanol

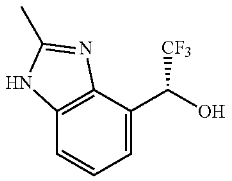 [SMILES: Cc1nc2c([C@@H](O)C(F)(F)F)cccc2[nH]1]

Step 1: 4-Bromo-2-methyl-1H-benzimidazole (500 mg, 2.37 mmol) was dissolved in THF (8 mL) and cooled to −78° C. n-Butyllithium (2.3 mL, 2.5 M in hexanes, 5.7 mmol) was added dropwise and the reaction was stirred at −78° C. for 30 min. Trifluoroacetic acid ethyl ester (339 μL, 2.8 mmol) was added and the reaction was stirred at 0° C. for 1 h. The reaction was quenched with HCl (2 N, 4 mL), then extracted with water and EtOAc, washed with brine, dried over $Na_2SO_4$, filtered, and concentrated in vacuo. Purification by normal phase silica gel column chromatography ($CH_2Cl_2$/MeOH/$NH_4OH$) provided 2,2,2-trifluoro-1-(2-methyl-1H-benzoimidazol-4-yl)-ethanone.

Step 2: The title compound was prepared using the Iridium complex-catalyzed hydrogenation, as described for Intermediate 1 (R)-1-(4-bromo-2-(3-methyl-1H-pyrazol-1-yl)phenyl)-2,2,2-trifluoroethanol.

Intermediate 6: 1-(4-Chloro-2-(3-methyl-1H-pyrazol-1-yl)phenyl)ethanol

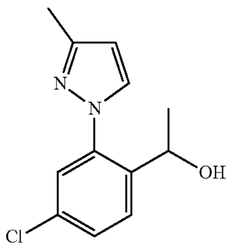 [SMILES: Cc1ccn(-c2cc(Cl)ccc2C(C)O)n1]

Step 1: 1-(2-bromo-5-chlorophenyl)-3-methyl-1H-pyrazole/1-(2-bromo-5-chlorophenyl)-5-methyl-1H-pyrazole mixture (Intermediate 3, step 1) (1.00 g, 3.68 mmol) was dissolved in THF (6 mL) and cooled to 0° C. i-Propyl magnesium chloride (2.76 mL, 2.0 M in THF, 5.52 mmol) was added dropwise and allowed to warm to RT over 30 min. The reaction was then cooled to −15° C. Acetyl chloride (481 μL, 5.5 mmol) was added and the reaction was warmed to RT for 3 h. The reaction was quenched with HCl (2 N, 4 mL), then extracted with water and EtOAc, washed with brine, and dried over $Na_2SO_4$, filtered, and concentrated in vacuo. Purification by normal phase silica gel column chromatography (EtOAc/heptane) provided 1-[4-chloro-2-(3-methyl-pyrazol-1-yl)-phenyl]-ethanone.

Step 2: 1-[4-Chloro-2-(3-methyl-pyrazol-1-yl)-phenyl-]ethanone (400 mg, 1.70 mmol) from Step 1 was dissolved in MeOH (10 mL) and cooled to 0° C. $NaBH_4$ (129 mg, 3.41 mmol) was added portionwise, then the reaction was warmed to RT, stirred for 30 min, then quenched with acetone. The MeOH was removed in vacuo then the residue was partitioned between water and EtOAc and extracted several times. The combined organic layers were washed with brine, dried over $Na_2SO_4$, filtered, and concentrated in vacuo. Purification by normal phase silica gel column chromatography ($CH_2Cl_2$/MeOH/$NH_4OH$) provided the title compound.

Intermediate 7: 1-(2,6-dibromophenyl)ethanol

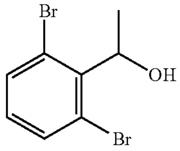

To a solution of 1-(2,6-dibromophenyl)-2,2,2-trifluoroethanone (CAS# 1208078-23-2) (3 g, 9 mmol) in EtOH (50 mL) was added $NaBH_4$ (340 mg, 9 mmol) at 5° C. The reaction was warmed to RT for 1 h, then extracted with EtOAc $NaHCO_3$, brine, and dried over $Na_2SO_4$ filtered and concentrated in vacuo to provide 1-(2,6-dibromophenyl)-2,2,2-trifluoroethanol as a light yellow oil.

Intermediate 8: 1-(2,5-dibromophenyl)ethanol

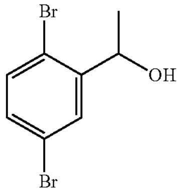

This compound was made as described above for Intermediate 7, 1-(2,6-dibromophenyl)-2,2,2-trifluoroethanol, starting with 1-(2,5-dibromophenyl)-2,2,2-trifluoroethanone to provide a light yellow oil.

Intermediate 9: (4-Chloro-2-(3-methyl-1H-pyrazol-1-yl)phenyl)methanol

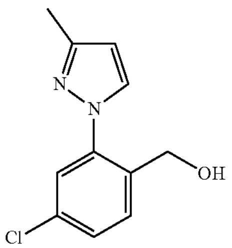

Step 1: 1-(2-bromo-5-chlorophenyl)-3-methyl-1H-pyrazole/1-(2-bromo-5-chlorophenyl)-5-methyl-1H-pyrazole mixture (Intermediate 3, step 1) (1.00 g, 3.68 mmol) was dissolved in THF (6 mL) then cooled to 0° C. i-Propyl magnesium chloride (2.76 mL, 2.0 M in THF, 5.52 mmol) was added dropwise and the reaction was warmed to RT for 30 min. The reaction was then cooled to −15° C. and paraformaldehyde (166 mg, 5.5 mmol) was added. The reaction mixture was allowed to warm to RT and stirred for 1 h. DMF (500 mL) was added and the reaction was stirred for an additional 1 h. The reaction was quenched with HCl (2 N, 4 mL), diluted with water, extracted with EtOAc, washed with brine, dried over $Na_2SO_4$, filtered, and concentrated in vacuo. Purification by normal phase silica gel column chromatography (EtOAc/heptane) provided 4-chloro-2-(3-methyl-pyrazol-1-yl)-benzaldehyde.

Step 2: 4-Chloro-2-(3-methyl-pyrazol-1-yl)-benzaldehyde (446 mg, 2.03 mmol) from Step 1 was dissolved in MeOH (14 mL) and cooled to 0° C. $NaBH_4$ (175 mg, 4.61 mmol)) was added portionwise. The reaction mixture was allowed to warm to RT, and after 90 min was quenched with acetone. The MeOH was removed in vacuo. The residue was partitioned between water and EtOAc and then extracted. The combined organic layers were washed with brine, dried over $Na_2SO_4$, filtered, and concentrated in vacuo. Purification by normal phase silica gel column chromatography (EtOAc/heptane) provided the title compound.

Using the procedure described for Intermediate 3, (R)-1-(4-chloro-2-(3-methyl-1H-pyrazol-1-yl)phenyl)-2,2,2-trifluoroethanol, the following alcohols (Intermediates 10-15) shown in the Table below were prepared starting with the appropriately substituted 1-bromo-2-fluorobenzene.

| No. | Name | Structure | LCMS (MH+) |
|---|---|---|---|
| Intermediate 10 | (R)-2,2,2-trifluoro-1-(4-methyl-2-(3-methyl-1H-pyrazol-1-yl)phenyl)ethanol | 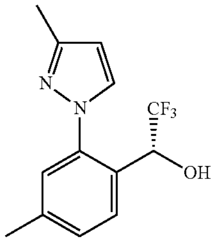 [SMILES: Cc1ccc([C@@H](O)C(F)(F)F)c(-n2ccc(C)n2)c1] | 271 |
| Intermediate 11 | (R)-2,2,2-trifluoro-1-(4-methoxy-2-(3-methyl-1H-pyrazol-1-yl)phenyl)ethanol | 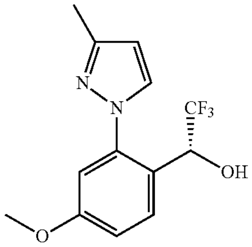 [SMILES: COc1ccc([C@@H](O)C(F)(F)F)c(-n2ccc(C)n2)c1] | 287 |
| Intermediate 12 | (R)-1-(3-chloro-2-(3-methyl-1H-pyrazol-1-yl)phenyl)-2,2,2-trifluoroethanol | 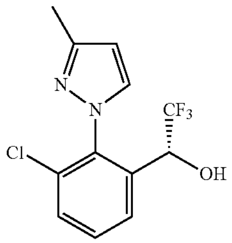 [SMILES: Cc1ccn(-c2c(Cl)cccc2[C@@H](O)C(F)(F)F)n1] | 291 |
| Intermediate 13 | (R)-2,2,2-trifluoro-1-(2-(3-methyl-1H-pyrazol-1-yl)-4-(trifluoromethyl)phenyl)ethanol | 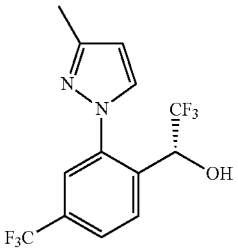 | 325 |
| Intermediate 14 | (R)-2,2,2-trifluoro-1-(4-fluoro-2-(3-methyl-1H-pyrazol-1-yl)phenyl)ethanol | 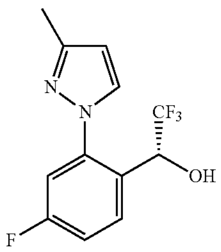 [SMILES: Cc1ccn(-c2cc(F)ccc2[C@@H](O)C(F)(F)F)n1] | 274 |

-continued

| No. | Name | Structure | LCMS (MH+) |
|---|---|---|---|
| Intermediate 15 | (R)-2,2,2-trifluoro-1-(6-methyl-2-(3-methyl-1H-pyrazol-1-yl)pyridin-3-yl)ethanol | 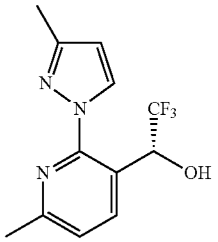 [SMILES: Cc1ccc([C@@H](O)C(F)(F)F)c(-n2ccc(C)n2)n1] | 272 |

Intermediate 16: (2-Phenoxy-6-(piperidin-1-yl)phenyl) methanamine

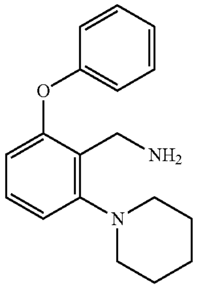 [SMILES: NCc1c(Oc2ccccc2)cccc1N1CCCCC1]

Step 1: To a solution of phenol (415 mg, 4.5 mmol) in 60 mL of DMF was added NaH (60%, 6.0 mmol) at 0° C. The reaction was stirred for 1 h, then 2-fluoro-6-(piperidin-1-yl) benzonitrile (CAS# 646989-68-6) (612 mg, 3.0 mmol) was added and the reaction stirred for 48 h at RT. The reaction mixture was then diluted with water and extracted with EtOAc. The combined organic layers were washed with brine, dried over $Na_2SO_4$, then concentrated in vacuo.

Purification by normal phase silica gel column chromatography (EtOAc/heptane) provided 2-phenoxy-6-(piperidin-1-yl)benzonitrile as an off-white solid.

Step 2: To 2-phenoxy-6-(piperidin-1-yl)benzonitrile (250 mg, 0.9 mmol) from Step 1 in 20 mL of MeOH was added Raney Nickel (5%) and $NH_4OH$ (2 mL). The reaction was stirred under 1 atm of $H_2$ at RT for 2 h. The solid was filtered away and the filtrate was concentrated in vacuo to provide the title compound as a viscous oil.

Intermediate 17: (R)-1-(4-Chloro-2-(2-methoxyethoxy)phenyl)-2,2,2-trifluoroethanol

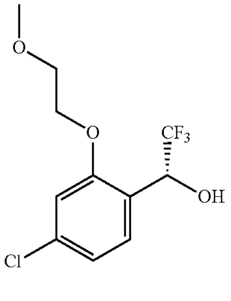 [SMILES: COCCOc1cc(Cl)ccc1[C@@H](O)C(F)(F)F]

Step 1: 1-Bromo-4-chloro-2-(2-methoxy-ethoxy)-benzene (CAS# 1245563-20-5) (5.00 g, 18.8 mmol) was dissolved in THF (30 mL) and cooled to 0° C. i-Propylmagnesium bromide (11.3 mL, 2.0 M in THF, 22.6 mmol) was added dropwise, and the reaction was stirred at 10° C. for 30 min, then warmed to RT for 16 h. The reaction was then cooled to −15° C. and trifluoroacetic acid ethyl ester (3.37 mL, 28.2 mmol) was added. The reaction was stirred at 10° C. for 1 h. The reaction was quenched with HCl (2 N, 38 mL) at 0° C. The reaction mixture was diluted with water and extracted with EtOAc. The combined organic layers were washed with brine, dried over $Na_2SO_4$, then concentrated in vacuo. Purification by normal phase silica gel column chromatography (EtOAc/heptane) provided 1-(4-chloro-2-(2-methoxyethoxy)phenyl)-2,2,2-trifluoroethanone.

Step 2: The title compound was prepared using the Iridium complex-catalyzed hydrogeneation as described for Intermediate 1 (R)-1-(4-bromo-2-(3-methyl-1H-pyrazol-1-yl) phenyl)-2,2,2-trifluoroethanol.

Intermediate 18: (R)-1-(5-chloro-[1,1'-biphenyl]-2-yl)-2,2,2-trifluoroethanol

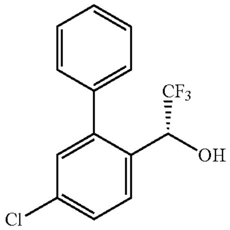 [SMILES: O[C@H](c1ccc(Cl)cc1-c1ccccc1)C(F)(F)F]

To a solution of (R)-1-(2-bromo-4-chlorophenyl)-2,2,2-trifluoroethanol (300 mg, 1.1 mmol) in dioxane (12 mL) was added phenyl boronic acid (185 mg, 1.5 mmol), $Pd_2(dppf)Cl_2$ (35 mg, 0.07 mmol) and $Na_2CO_3$(3 mL, 2.0 M, aq). The reaction was heated to 90° C. for 2 h, then cooled to RT, and concentrated in vacuo. The residue was taken up in $CH_2Cl_2$, washed with brine, and extracted with $CH_2Cl_2$. The combined organic layers were dried over $Na_2SO_4$. Purification by normal phase silica gel column (EtOAc/hexanes) to provide a white solid.

Intermediate 19: (R)-1-(4-chloro-2-(5-chlorothiophen-2-yl)phenyl)-2,2,2-trifluoroethanol

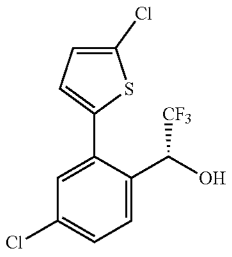 [SMILES: O[C@H](c1ccc(Cl)cc1-c1ccc(Cl)s1)C(F)(F)F]

This compound was made in the same way as described for Intermediate 18 (R)-1-(5-chloro-[1,1'-biphenyl]-2-yl)-2,2,2-trifluoroethanol to provide a white solid.

Intermediate 20: (R)-2,2,2-trifluoro-1-(6-methyl-2-(3-methyl-1H-pyrazol-1-yl)pyridin-3-yl)ethanol

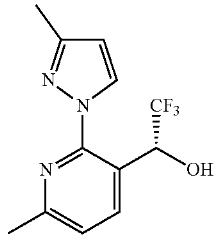 [SMILES: Cc1ccc([C@@H](O)C(F)(F)F)c(-n2ccc(C)n2)n1]

Step 1: To the solution of 2-chloro-6-methylnicotinic acid (5 g, 29.1 mmol) in $CH_2Cl_2$ (40 mL) was added oxalyl dichloride (8.1 g, 63.8 mmol) at 0° C. and the reaction mixture was stirred for 2 h. The mixture was concentrated and 40 mL of methanol was then added at 0° C. and the reaction mixture was stirred at RT for 12 h. The mixture was then concentrated in vacuo and extracted with EtOAc. The combined organic layers were washed with brine, dried over $Na_2SO_4$, filtered, and concentrated in vacuo to provide methyl 2-chloro-6-methylnicotinate that is used without further purification as a light yellow solid.

Step 2: To a solution of 3-methyl-1H-pyrazole (1.1 g, 13.4 mmol) in DMF (5 ml) was added sodium hydride (1.0 g, 60% in oil) at 0° C. The reaction mixture was stirred for 1 h at 0° C. and then . A solution of methyl 2-chloro-6-methylnicotinate (4.3 g, 23.16 mmol) in DMF (5 mL) was added dropwise to the reaction mixture at 0° C. After addition, the mixture was heated to 80° C. and stirred for 12 h. After this time, the mixture was poured into ice-water and extracted and extracted with EtOAc. The combined organic layers were washed with brine, dried over $Na_2SO_4$, filtered, and concentrated in vacuo and then purified by normal phase silica gel column (EtOAc/hepate) to provide methyl 6-methyl-2-(3-methyl-1H-pyrazol-1-yl)nicotinate as a brown semi-solid.

Step 3: To a solution of methyl 6-methyl-2-(3-methyl-1H-pyrazol-1-yl)nicotinate (3.7 g, 16 mmol) and trimethyl(trifluoromethyl)silane (11.4 g, 80.2 mmol) in toluene (60 ml), was added dropwise at −78° C. and then the solution of tetrabutyl ammonium fluoride (1.6 mL,1.0 M in THF) was added dropwise to the reaction mixture at −78° C. After addition, the mixture was warmed slowly up to RT and stirred for 12 h. The reaction mixture was concentrated and the resulting residue was dissolved in methanol (30 mL). 6 N HCl (30 mL) was added to the reaction mixture and the resulting mixture was stirred for 2 h. The reaction mixture was concentrated, adjusted to pH 6 with sat.$NaHCO_3$ and extracted with EtOAc. The combined organic layers were washed with brine, dried over $Na_2SO_4$, filtered, and concentrated in vacuo and purified by normal phase silica gel column (EtOAc/hepate) to provide 2,2,2-trifluoro-1-(6-methyl-2-(3-methyl-1H-pyrazol-1-yl)pyridin-3-yl)ethanone as a brown semi-solid.

Step 4: A solution of (S)-(—)-2-Butyl-CBS-oxazaborolidine solution (3.0 ml 1.0 M in toluene) and catecholborane (30 ml 1.0 M in THF) was stirred at RT for 30 min. The mixture was then cooled to −70° C. and 2,2,2-trifluoro-1-(6-methyl-2-(3-methyl-1H-pyrazol-1-yl)pyridin-3-yl)ethanone (1 g, 2.9 mmol) in THF (16 mL) was added dropwise. After addition, the reaction mixture was warmed up to −32° C. and stirred for 12 h. After this time, 3N NaOH (18 mL) was added followed by $H_2O_2$ (18 mL) and the temperature of the reaction mixture was increased to RT for 30 min and then extracted with ethyl. The combined organic layers were washed with brine, dried over $Na_2SO_4$, filtered, and concentrated in vacuo and purified by normal phase silica gel column (EtOAc/hepate) to provide the title compound as a yellow solid.

Intermediate 38: (R)-1-(5-bromo-[1,1'-biphenyl]-2-yl)-2,2,2-trifluoroethanol

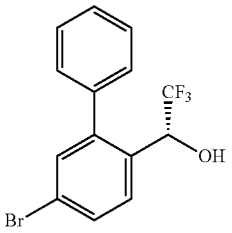

Step 1: A solution of 2,4-dibromo-benzoic acid, (2.3 g, 18.8 mmol), phenyl boronic acid (5 g, 17.9 mmol), $Pd_2(dba)_3$ (818 mg, 8.9 mmol) and LiOH (1.65 g, 39.3 mmol) in a 1:1 mixture of NMP/water (100 mL) was heated to 70° C. for 2 d. After this time, the reaction mixture was cooled to RT, and the reaction mixture was adjusted to pH=4-5 with 3 N HCl. The mixture was then extracted with ethyl acetate and the combined organic layers were washed with brine, dried over $Na_2SO_4$, filtered, and concentrated in vacuo and purified by normal phase silica gel column (EtOAc/PE 10:1 to 1:1) to afford 5-bromo-[1,1'-biphenyl]-2-carboxylic acid as a colorless oil.

Step 2: To a solution of 5-bromo-[1,1'-biphenyl]-2-carboxylic acid (5 g, 18.2 mmol) in MeOH (30 mL) was added $SOCl_2$ (10 mL) dropwise. The reaction mixture was heated to 70° C. for 2 h, then cooled to RT. The mixture was concentrated, adjusted to pH=7-8 with saturated aqueous $NaHCO_3$ and extracted with ethyl acetate. The combined organic layers were washed with brine, dried over $Na_2SO_4$, filtered, and concentrated in vacuo and purified by normal phase silica gel column (EtOAc/PE 50:1) to afford afford methyl 5-bromo-[1,1'-biphenyl]-2-carboxylate as a colorless oil.

Step 3: A solution of methyl 5-bromo-[1,1'-biphenyl]-2-carboxylate (2.2 g, 6.9 mmol) in THF (50 mL) was cooled to 0° C. $LiAlH_4$ (380 mg, 10 mmol) was added slowly. The reaction mixture was stirred at RT for 2 h, after which water (1 mL) was added slowly to quench the reaction. The solid was removed by filtration and the filtrate was concentrated in vacuo to provide (5-bromo-[1,1'-biphenyl]-2-yl)methanol as a white solid that was used directly without further purification.

Step 4: To a solution of (5-bromo-[1,1'-biphenyl]-2-yl) methanol (2.0 g, 8.4 mmol) in $CH_2Cl_2$ (30 mL) was added Dess-Martin Periodinane (4.3 g, 10 mmol). The reaction mixture was stirred at RT for 2 h and then the solids were filtered and the resultant filtrate was concentrated in vacuo. Purification by normal phase silica gel column (EtOAc: PE=1:50) afforded 5-bromo-[1,1'-biphenyl]-2-carbaldehyde as a colorless oil.

Step 5: To a solution of 5-bromo-[1,1'-biphenyl]-2-carbaldehyde (1.9 g, 7.3 mmol) and was added $TMSCF_3$ (1.2g, 8.7 mmol) in THF (20 mL) and cooled to 0° C. To this solution was added TBAF (1.46 mL, 1M in THF) and the reaction mixture was warmed to RT for 3 h. After this time, the mixture was treated with 3 N HCl (5 mL) and stirred for 12 h. Then the reaction mixture was diluted with water and extracted with ethyl acetate. The combined organic layers were washed with brine, dried over $Na_2SO_4$, filtered, concentrated in vacuo and purified by normal phase silica gel column (EtOAc:PE=1:10) to afford 1-(5-bromo-[1,1'-biphenyl]-2-yl)-2,2,2-trifluoroethanol as a colorless oil.

Step 6: To a solution of 1-(5-bromo-[1,1'-biphenyl]-2-yl)-2,2,2-trifluoroethano (1.8 g, 5.5 mmol) in $CH_2Cl_2$ (30 mL) was added Dess-Martin Periodinane (3 g, 7.1 mmol). The reaction mixture was stirred at RT for 2 h and then the solids were filtered. The resultant filtrate was concentrated in vacuo. Purification by normal phase silica gel column (EtOAc:PE=1:50) afforded 1-(5-bromo-[1,1'-biphenyl]-2-yl)-2,2,2-trifluoroethanone as a colorless oil.

Step 7: 1-(5-Bromo-[1,1'-biphenyl]-2-yl)-2,2,2-trifluoroethanone (1.3 g, 3.9 mmol) in $CH_3CN$ (10 mL) was reduced to the chiral alcohol using the chiral iridium catalyst (METHOD A) at RT. The reaction mixture was then charged with potassium formate (725 mg, 8.6 mmol) and the mixture was stirred at 40° C. for 12 h. Then the reaction was diluted with water and extracted with ethyl acetate. The combined organic layers were washed with brine, dried over $Na_2SO_4$, filtered, concentrated in vacuo and purified by normal phase silica gel column (EtOAc:PE=1:10) to afford the title compound as a colorless oil.

Using the procedure described for Intermediate 3, (R)-1-(4-chloro-2-(3-methyl-1H-pyrazol-1-yl)phenyl)-2,2,2-trifluoroethanol, the following alcohols (Intermediates 39-42) shown in the Table below were prepared starting with the appropriately substituted pyrazole.

| No. | Name | Structure | LCMS (MH+) |
|---|---|---|---|
| Intermediate 39 | (R)-1-(4-chloro-2-(3-(trifluoromethyl)-1H-pyrazol-1-yl)phenyl)-2,2,2-trifluoroethanol | 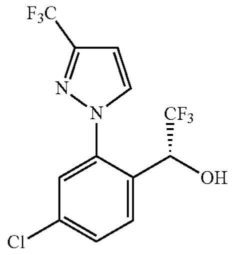 [SMILES: O[C@H](c1ccc(Cl)cc1-n1ccc(C(F)(F)F)n1)C(F)(F)F] | 345 |
| Intermediate 40 | (R)-1-(2-(3-(tert-butyl)-1H-pyrazol-1-yl)-4-chlorophenyl)-2,2,2-trifluoroethanol | 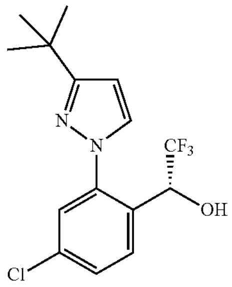 [SMILES: CC(C)(C)c1ccn(-c2cc(Cl)ccc2[C@@H](O)C(F)(F)F)n1] | 334 |
| Intermediate 41 | (R)-1-(4-chloro-2-(3-isopropyl-1H-pyrazol-1-yl)phenyl)-2,2,2-trifluoroethanol | 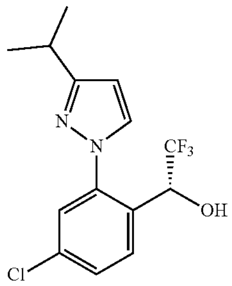 [SMILES: CC(C)c1ccn(-c2cc(Cl)ccc2[C@@H](O)C(F)(F)F)n1] | 319 |

-continued

| No. | Name | Structure | LCMS (MH+) |
|---|---|---|---|
| Intermediate 42 | (R)-1-(4-chloro-2-(3-cyclopropyl-1H-pyrazol-1-yl)phenyl)-2,2,2-trifluoroethanol | 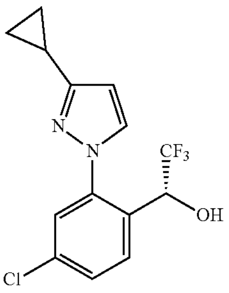 [SMILES: O[C@H](c1ccc(Cl)cc1-n1ccc(C2CC2)n1)C(F)(F)F] | 317 |

Intermediate 43: (R)-1-(2-bromo-4-chlorophenyl)-2,2,2-trifluoroethanol

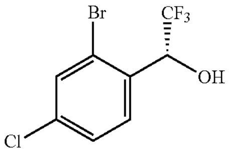 [SMILES: O[C@H](c1ccc(Cl)cc1Br)C(F)(F)F]

A solution of dichloro(pentamethylcyclopentadienyl) iridium (III) dimer ([Cp*IrCl$_2$ ]$_2$, 14 mg, 0.02 mmol) and (IR,2R)-(−)-(4-toluenesulfonyl)-1,2-diphenylethylenediamine (14 mg, 0.04 mmol) in water (7 mL) was prepared at RT. The resulting mixture was heated to 40° C. for 3 h to provide a homogeneous orange solution. To this active catalyst solution at 40° C. was added potassium formate (143 mg, 171 mmol), and a solution of 1-(2-bromo-4-chlorophenyl)-2,2,2-trifluoroethanone (CAS# 1033805-23-0, 98 mg, 0.34 mmol) in $CH_3CN$ (70 mL). The reaction mixture was then stirred at 40° C. for 2 h and then cooled to RT and the layers were separated. The aqueous layer was extracted with MTBE and the combined organic layers were dried over $Na_2SO_4$, filtered, and concentrated in vacuo to provide the title compound that was used without further purification.

The following alcohols and amines in the table below are useful in preparing compounds of the invention. They are either commercially available or can be prepared by known synthetic procedures. CAS registry numbers are provided for each.

| No. | Name | CAS Registry # | Structure | Ex # |
|---|---|---|---|---|
| 21 | (R)-2,2,2-trifluoro-1-(2-(3-methyl-1H-pyrazol-1-yl)phenyl)ethanol | 1033805-15-0 | 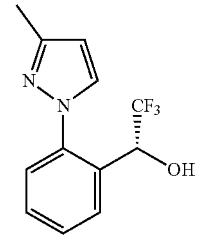 [SMILES: Cc1ccn(-c2ccccc2[C@@H](O)C(F)(F)F)n1] | 10a & 10e |
| 22 | (R)-1-(2-bromo-4-chlorophenyl)-2,2,2-trifluoroethanol | 1033805-25-2 | 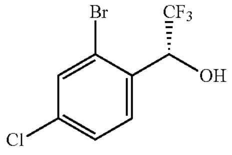 [SMILES: O[C@H](c1ccc(Cl)cc1Br)C(F)(F)F] | 34a-34ae |
| 23 | (R)-1-(5-chloro-2-(3-methyl-1H-pyrazol-1-yl)phenyl)-2,2,2-trifluoroethanol | 1033805-72-9 | 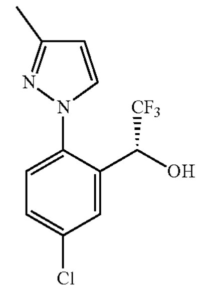 [SMILES: Cc1ccn(-c2ccc(Cl)cc2[C@@H](O)C(F)(F)F)n1] | 10k |

-continued

| No. | Name | CAS Registry # | Structure | Ex # |
|---|---|---|---|---|
| 24 | 1-(adamantan-1-yl)ethanamine | 13392-28-4 | 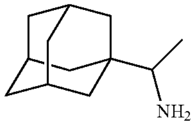 | 38 |
| 25 | (adamantan-1-yl)methanamine | 17768-41-1 | 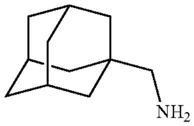 | 41c |
| 26 | [1,1'-biphenyl]-3-ylmethanamine | 177976-49-7 | 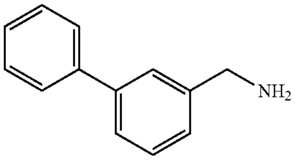 [SMILES: NCc1cccc(-c2ccccc2)c1] | 39d |
| 27 | naphthalen-2-ylmethanamine | 2018-90-8 | 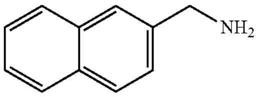 [SMILES: NCc1ccc2ccccc2c1] | 39a |
| 28 | 1-(adamantan-1-yl)ethanol | 26750-08-3 | 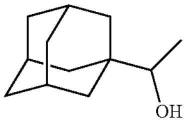 | 41c |
| 29 | (R)-1-(naphthalen-2-yl)ethanamine | 3906-16-9 | 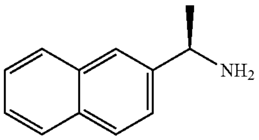 | 39e |
| 30 | (R)-2,2,2-trifluoro-1-(naphthalen-2-yl)ethanol | 68200-42-0 | 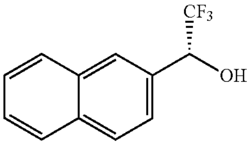 [SMILES: O[C@H](c1ccc2ccccc2c1)C(F)(F)F] | 59b |
| 31 | [1,1'-biphenyl]-4-ylmethanamine | 712-76-5 | 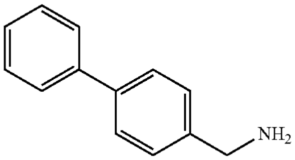 [SMILES: NCc1ccc(-c2ccccc2)cc1] | 39b |
| 32 | (2-(piperidin-1-yl)phenyl)methanamine | 72752-54-6 | 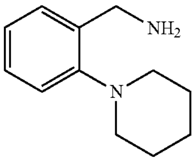 [SMILES: NCc1ccccc1N1CCCCC1] | 41a |
| 33 | (R)-1-(4-bromophenyl)-2,2,2-trifluoroethanol | 80418-12-8 | 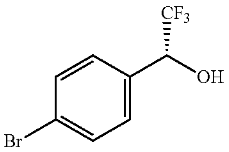 [SMILES: O[C@H](c1ccc(Br)cc1)C(F)(F)F] | 55a-55db |

No. = Intermediate number;

Ex # = Used in the preparation of the following example(s)

Preparation of Boronic Acids and Esters

The boronic acids and esters used in biaryl couplings are either commercially available or can be readily synthesized from the corresponding bromide using routine synthetic methods. The following Intermediate 34 is a representative example.

Intermediate 34: 6-(4,4,5,5-Tetramethyl-1,3,2-dioxaborolan-2-yl)-3,4-dihydroquinolin-2(1H)-one

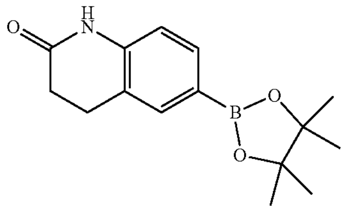 [SMILES: CC1(C)OB(c2ccc3c(c2)CCC(=O)N3)OC1(C)C]

To a solution of 6-bromo-3,4-dihydroquinolin-2(1H)-one (200 mg, 0.89 mmol) in 5 mL of acetonitrile was added pinacoldiboron (300 mg, 1.2 mmol), $Pd(dppf)_2Cl$ (30 mg, 0.09 mmol), KOAc (250 mg, 2.1 mmol) and triethyl amine (1mL). The reaction was heated to 87° C. for 24 h, then cooled to RT. The solids were filtered away, and the solvent was removed in vacuo, then extracted with EtOAc, water, brine and dried over $Na_2SO_4$. The solvent was removed in vacuo to provide an off-white solid which was used without further purification.

Spirocyclic Amino Esters Preparation

Intermediate 35: (S)-2-Benzyl 3-ethyl 2,8-diazaspiro[4.5]decane-2,3-dicarboxylate

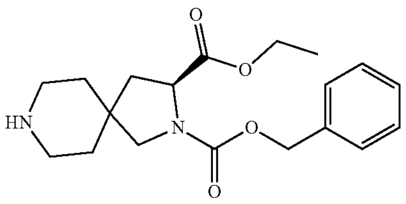 [SMILES: CCOC(=O)[C@@H]1CC2(CCNCC2)CN1C(=O)OCc1ccccc1]

Step 1: (3S)-8-Tert-butyl 3-ethyl 2,8-diazaspiro[4.5]decane-3,8-dicarboxylate [Example 24 in US Pat. Pub. No. 2012/0101280] (50 g, 160 mmol) in $CH_2Cl_2$ (500 mL), and $Et_3N$ (51.7 g, 512 mmol) was cooled to 0° C. Benzyl chloroformate (34.1 g, 205 mmol) was added dropwise and the mixture was stirred at 0° C. for 3 h. The reaction mixture was washed with water, extracted with $CH_2Cl_2$, dried over $Na_2SO_4$, and concentrated in vacuo to provide (S)-2-benzyl 8-tert-butyl 3-ethyl 2,8-diazaspiro[4.5]decane-2,3,8-tricarboxylate as a light yellow oil which was used directly without further purification.

Step 2: To a solution of (S)-2-benzyl 8-tert-butyl 3-ethyl 2,8-diazaspiro[4.5]decane-2,3,8-tricarboxylate (79 g, 160 mmol, Step 1) in $CH_2Cl_2$ (400 mL) was added TFA (182 g, 1600 mmol) dropwise at RT. The reaction mixture was stirred for 3 h then concentrated in vacuo. The residue was quenched with saturated $NaHCO_3$ and solid $NaHCO_3$ was added until no further gas evolution was noted. The mixture was extracted with EtOAc and the combined organic layers were concentrated in vacuo. Purification by normal phase silica gel column chromatography ($CH_2Cl_2$/MeOH/$NH_4OH$) provided the title compound as a light yellow solid.

Intermediate 36: (S)-2-Tert-butyl 3-ethyl 2,8-diazaspiro[4.5]decane-2,3-dicarboxylate

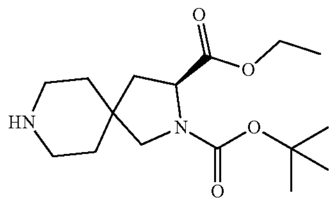 [SMILES: CCOC(=O)[C@@H]1CC2(CCNCC2)CN1C(=O)OC(C)(C)C]

Step 1: (S)-2-Benzyl 3-ethyl 2,8-diazaspiro[4.5]decane-2,3-dicarboxylate (2.4 g, 6.9 mmol) in Hadioxane (50 mL, 3.3 N) was stirred for 2 h at RT. The solvent was then removed in vacuo to provide (S)-2-benzyl 3-ethyl 2,8-diazaspiro[4.5]decane-2,3-dicarboxylate hydrochloride which was used directly without further purification.

Step 2: To a solution of (S)-2-benzyl 3-ethyl 2,8-diazaspiro[4.5]decane-2,3-dicarboxylate hydrochloride and $BOC_2O$ (1.5 g, 6.9 mmol) in EtOH (50 mL) was added Pd/C (10%, 2.4 g) and HOAc (cat.). The mixture was degassed and blanked under $H_2$ then stirred at 45° C. at 50 psi of $H_2$ for 12 h. The solid was filtered away and the filtrate concentrated in vacuo to provide the title compound as a viscous solid.

Intermediate 37: Methyl 3,9-diazaspiro[5.5]undecane-2-carboxylate

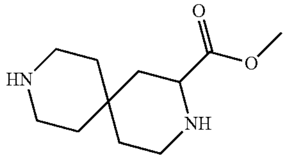

To a solution of 3,9-diazaspiro[5.5]undecane-2-carboxylic acid, 3-[(4-methoxyphenyl)methyl]-9-(phenylmethyl)-methyl ester [CAS# 1314388-32-3] (50 mg, 0.12 mmol) in MeOH (2 mL) and water (2 mL) was added a catalytic amount of TFA. The mixture was hydrogenated using a H-cube apparatus under 80° C./80 bar 2 cycles. The reaction mixture was cooled to RT then concentrated in vacuo to provide the title compound as a white solid which is used directly.

General Synthetic Methods

Methods for Removal of N-Carbobenzyloxy (N-CBZ) Protecting Group

Method A—Hydrogenation over Pd/C: To a solution of N-CBZ protected compound (1 eq.) in EtOAc was added HOAc (100 μL) and 5% (w/w) Pd/C (5 mol %). The reaction mixture was degassed, blanketed under $H_2$ (balloon) 3 times, then stirred at RT for 2 h. The reaction was then filtered through a pad of celite that was rinsed with 1:9 MeOH:EtOAc. The filtrate was concentrated in vacuo. The product was purified by column chromatography using an Isco Gold reversed phase silica cartridge ($H_2O$:HOAc: 99:1 to MeOH:AcOH 99:1).

Method B—Dealkylation with TMSI: To a solution of N-CBZ protected compound (1 eq.) in $CH_3CN$ was added a solution of TMSI (2.2 eq.) in $CH_3CN$ (0.2 M). The reaction mixture was stirred at RT for 2 h then quenched with 1 N HCl to pH 1. The product was purified by column chromatography using an Isco Gold reversed phase silica cartridge ($H_2O$:HOAc: 99:1 to MeOH:AcOH 99:1).

General ester hydrolysis with lithium hydroxide: To a solution of an ethyl ester compound (1 eq) in THF (0.18 M) and water (1.4 M) was added LiOH-$H_2O$ (10 eq). The mixture was stirred at RT for 1 h. Water was added and the pH was adjusted to 6.5 with 1 N HCl. THF was removed in vacuo, then the solid was precipitated, washed with water, and dried in vacuo to yield the corresponding carboxylic acid.

The compounds of the examples were isolated either in the neutral zwitterionic form or as a TFA or HCl salt.

Example 1u (S)-8-(2-amino-6-((R)-2,2,2-trifluoro-1-(3-(3-methyl-1H-pyrazol-1-yl)-[1,1'-biphenyl]-4-yl) ethoxy)pyrimidin-4-yl)-2,8-diazaspiro[4.5]decane-3-carboxylic acid

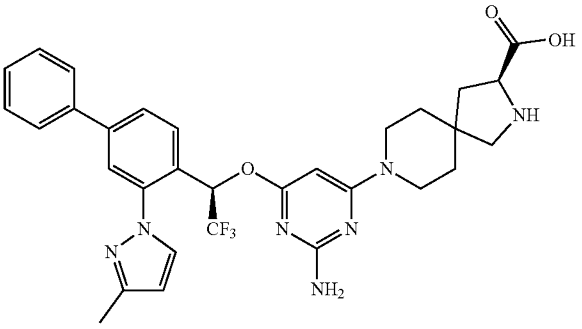 [SMILES: Cc1ccn(-c2cc(-c3ccccc3)ccc2[C@@H](Oc2cc(N3CCC4(CC3)CN[C@H](C(=O)O)C4)nc(N)n2)C(F)(F)F)n1]

Step 1: To a solution of (R)-1-(4-bromo-2-(3-methyl-1H-pyrazol-1-yl)phenyl)-2,2,2-trifluoroethanol (160 mg, 0.2 mmol, Intermediate 1) in dioxane (2 mL) was added 2-amino-4,6-dichloropyrimidine (100 mg, 0.16 mmol) and $Cs_2CO_3$ (48 ,g, 0.16 mmol). The reaction was heated to 80° C. for 16 h, cooled to RT, and filtered. The solvent was removed in vacuo and the residue was dissolved in a mixture of $CH_2Cl_2$ and heptane, concentrated to half the volume, filtered, and concentrated again in vacuo. Purification via normal phase silica gel chromatography ($CH_2Cl_2$/Heptane) provided 4-[(1R)-1-[4-bromo-2-(3-methylpyrazol-1-yl)phenyl]-2,2,2-trifluoro-ethoxy]-6-chloro-pyrimidin-2-amine as an off-white solid.

Step 2: To a solution of 4-[(1R)-1-[4-bromo-2-(3-methylpyrazol-1-yl)phenyl]-2,2,2-trifluoro-ethoxy]-6-chloro-pyrimidin-2-amine (125 mg, 0.3 mmol, Step 1) in dioxane (3 mL) was added (S)-2-benzyl 3-ethyl 2,8-diazaspiro[4.5] decane-2,3-dicarboxylate (95 mg, 0.3 mmol) and $Na_2CO_3$ (182 mg, 0.35 mmol). The reaction was heated to 90° C. for 130 h, then cooled to RT, filtered, and concentrated in vacuo. Purification by normal phase silica gel column (EtOAc/heptane) provided (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a white solid.

Step 3: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (300 mg, 0.4 mmol, Step 2) in ethanol (2 mL) and water (0.5 mL) was added phenylboronic acid (143 mg, 0.8 mmol), $PdCl_2(PPh_3)_2$ (41 mg, 0.058 mmol), and $Cs_2CO_3$ (390 mg, 1.2 mmol). The reaction was heated to 60° C. for 16 h, then cooled to RT, filtered through celite and concentrated in vacuo. Purification by normal phase silica gel column (EtOAc/heptane) provided (S)-2-benzyl 3-ethyl 8-(2-amino-6-((R)-2,2,2-trifluoro-1-(3-(3-methyl-1H-pyrazol -1-yl)-[1,1'-biphenyl]-4-yl)ethoxy)pyrimidin-4-yl)-2,8-diazaspiro[4.5]decane-2,3-dicarboxylate as a white solid.

Step 4: A solution of (S)-2-benzyl 3-ethyl 8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5] decane-2,3-dicarboxylate (240 mg, 0.4 mmol, Step 3) in EtOAc (5 mL) was hyrogenated using an H-Cube apparatus and a 10% (w/w) Pd/C cartridge with a flow rate of 1.0 mL/min at RT. Purification on normal phase silica gel (EtOAc/heptane) provided (S)-ethyl 8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5]decane-3-carboxylate.

Step 5: To a solution of (S)-ethyl 8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5]decane-3-carboxylate (50 mg, 0.08 mmol) from Step 4 in THF (2.0 mL) and water (0.2 mL), was added lithium hydroxide monohydrate (58 mg, 0.05 mmol). The reaction mixture was stirred at RT for 2 h, then the solution was neutralized with 1 N HCl, and concentrated in vacuo. Purification by normal phase silica gel column (EtOAc/heptane) provided the title compound as an off-white solid as the zwitterionic form.

Example 1m (S)-8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid

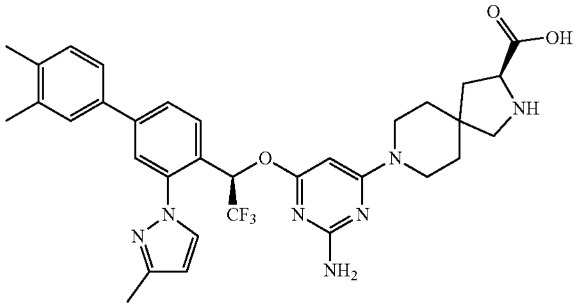 [SMILES: Cc1ccn(-c2cc(-c3ccc(C)c(C)c3)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (Step 2, Example 1u) (300 mg, 0.4 mmol, Step 2) in ethanol (2 mL) and water (0.5 mL) was added (3,4-dimethylphenyl)boronic acid (120 mg, 0.8 mmol), $PdCl_2(PPh_3)_2$ (41 mg, 0.058 mmol), and $Cs_2CO_3$ (390 mg, 1.2 mmol). The reaction was heated to 60° C. for 16 h, then cooled to RT, filtered through celite and concentrated in vacuo. Purification by normal phase silica gel column (EtOAc/heptane) provided (S)-2-benzyl 3-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-2,3-dicarboxylate as a white solid.

Step 2: A solution of (S)-2-benzyl 3-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8- diazaspiro[4.5]decane-2,3-dicarboxylate (220 mg, 0.3 mmol) in EtOAc (5 mL) was hydrogenated using an H-Cube apparatus and a 10% (w/w) Pd/C cartridge with a flow rate of 1.0 mL/min at RT. Purification on normal phase silica gel (EtOAc/heptane) provided (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate.

Step 3: To a solution of (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (50 mg, 0.08 mmol) from Step 2 in THF (2.0 mL) and water (0.2 mL), was added lithium hydroxide monohydrate (58 mg, 0.05 mmol). The reaction mixture was stirred at RT for 2 h, then the solution was neutralized with 1 N HCl and concentrated in vacuo. Purification by normal phase silica gel column (EtOAc/heptane) provided the title compound as an off-white solid as the zwitterionic form.

Example 1 cq (S)-8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro [4.5]decane-3-carboxylic acid

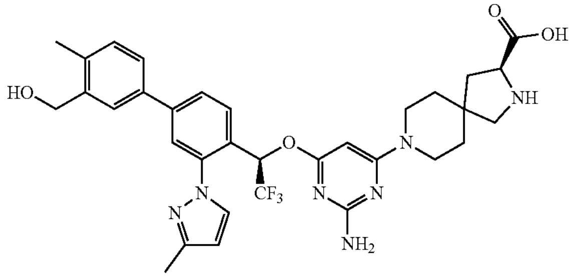 [SMILES: Cc1ccn(-c2cc(-c3ccc(C)c(CO)c3)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (Step 2, Example 1u) (300 mg, 0.4 mmol, Step 2) in ethanol (2 mL) and water (0.5 mL) was added (3-(hydroxymethyl)-4-methylphenyl)boronic acid (CAS# 1451391-54-0; 120 mg, 0.7 mmol), $PdCl_2(PPh_3)_2$ (41 mg, 0.058 mmol), and $Cs_2CO_3$ (390 mg, 1.2 mmol). The reaction was heated to 60° C. for 16 h, then cooled to RT, filtered through celite and concentrated in vacuo. Purification by normal phase silica gel column (EtOAc/heptane) provided (S)-2-benzyl 3-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-2,3-dicarboxylate a white solid.

Step 2: A solution of (S)-2-benzyl 3-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-2,3-dicarboxylate (200 mg, 0.24 mmol,) in EtOAc (5 mL) was hydrogenated using an H-Cube apparatus and a 10% (w/w) Pd/C cartridge with a flow rate of 1.0 mL/min at RT. Purification on normal phase silica gel (EtOAc/heptane) provided (S)-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro [4.5]decane-3-carboxylate.

Step 3: To a solution of (S)-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate (50 mg, 0.08 mmol) from Step 2 in THF (2.0 mL) and water (0.2 mL), was added lithium hydroxide monohydrate (58 mg, 0.05 mmol). The reaction mixture was stirred at RT for 2 h, then the solution was neutralized with 1 N HCl, and concentrated in vacuo. Purification by normal phase silica gel column (EtOAc/heptane) provided the title compound as an off-white solid as the zwitterionic form.

Example 1cr (S)-8-(2-amino-6-((R)-2,2,2-trifluoro-1-(4'-(hydroxymethyl)-3'-methyl-3-(3-methyl-1H-pyrazol-1-yl)-[1,1'-biphenyl]-4-yl)ethoxy)pyrimidin-4-yl)-2,8-diazaspiro [4.5]decane-3-carboxylic acid

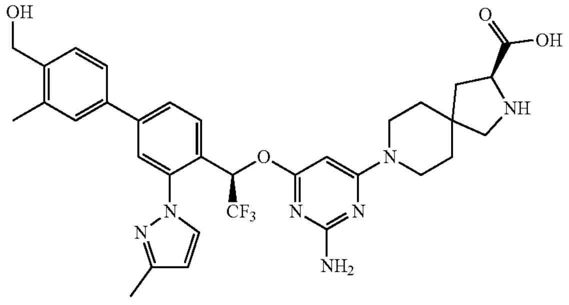 [SMILES: Cc1ccn(-c2cc(-c3ccc(CO)c(C)c3)ccc2[C@@H](Oc2cc(N3CCC4(CC3)CN[C@H](C(=O)O)C4)nc(N)n2)C(F)(F)F)n1]

The title compound was made as described for (S)-8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid (Example lcq) using (4-(hydroxymethyl)-3-methylphenyl)boronic acid (CAS# 1218790-88-5).

Using the generic scheme below, the following examples of Table 1 a were prepared as described above for (S)-8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5]decane-3-carboxylic acid (Example 1u). The boronic acid was generaly used to make the analogues below, however, where it was not available, the corresponding boronate was used.

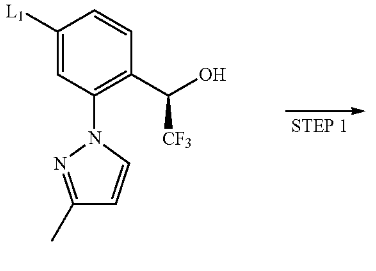

$L_1$ = Br or Cl

-continued

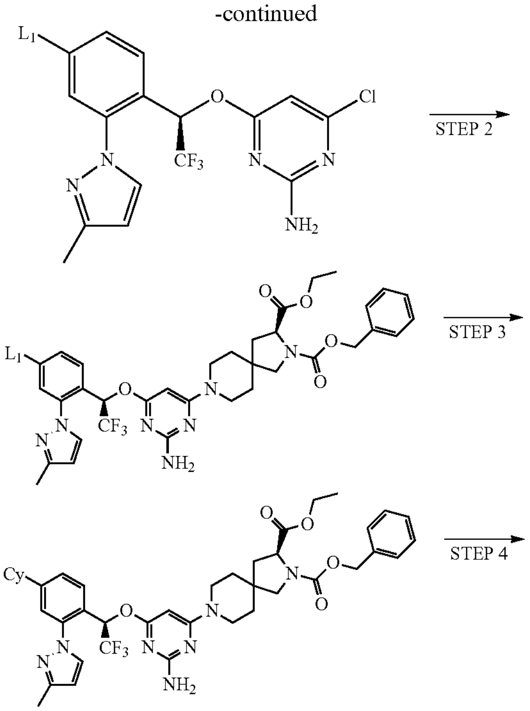

-continued

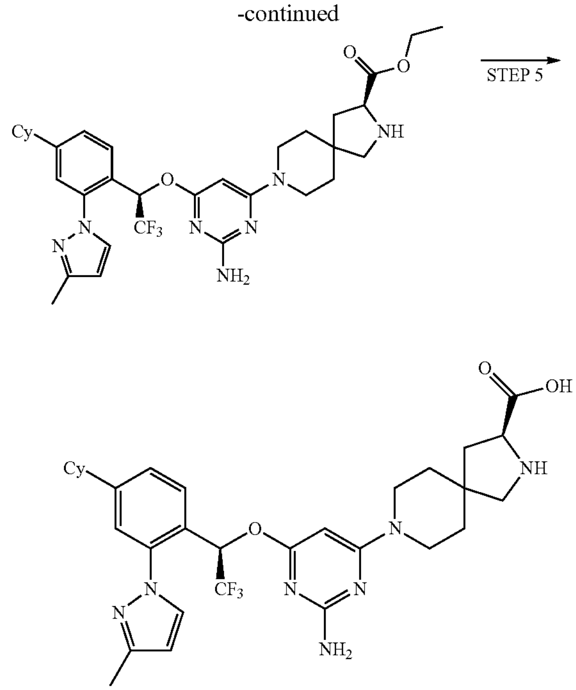

TABLE 1a

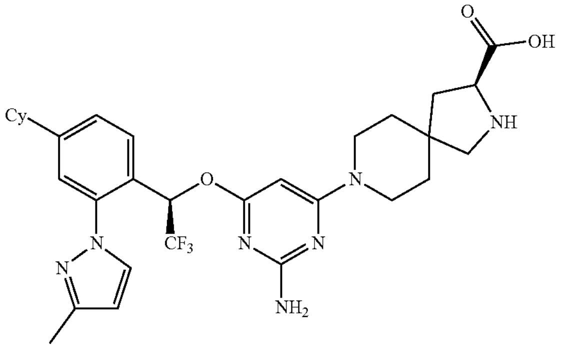

| Ex. No. | Cy | CAS Name | LCMS (MH+) |
|---|---|---|---|
| 1a | 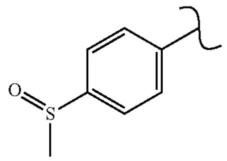 | (3S)-8-(2-amino-6-((1R)-2,2,2-trifluoro-1-(3-(3-methyl-1H-pyrazol-1-yl)-4'-(methylsulfinyl)-[1,1'-biphenyl]-4-yl)ethoxy)pyrimidin-4-yl)-2,8-diazaspiro[4.5]decane-3-carboxylic acid | 671 |
| 1b | 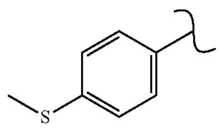 | (S)-8-(2-amino-6-((R)-2,2,2-trifluoro-1-(3-(3-methyl-1H-pyrazol-1-yl)-4'-(methylthio)-[1,1'-biphenyl]-4-yl)ethoxy)pyrimidin-4-yl)-2,8-diazaspiro[4.5]decane-3-carboxylic acid | 655 |
| 1c | 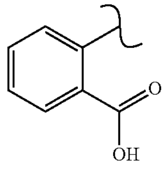 | (S)-8-(2-amino-6-((R)-1-(3'-carboxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652 |

TABLE 1a-continued

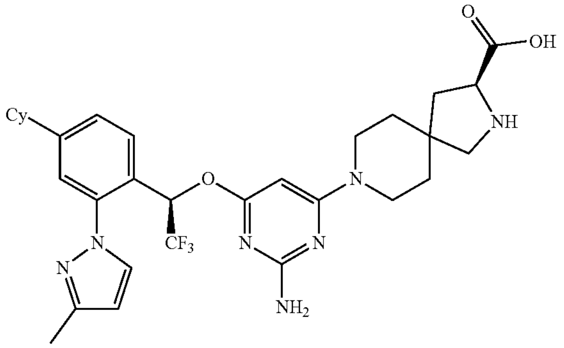

| Ex. No. | Cy | CAS Name | LCMS (MH+) |
|---|---|---|---|
| 1d | 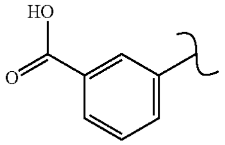 | (S)-8-(2-amino-6-((R)-1-(3'-carboxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652.5 |
| 1e | 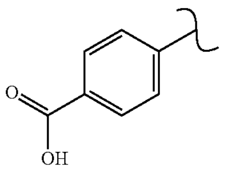 | (S)-8-(2-amino-6-((R)-1-(4'-carboxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652.6 |
| 1f | 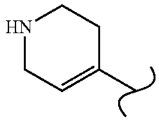 | (S)-8-(2-amino-6-((R)-2,2,2-trifluoro-1-(2-(3-methyl-1H-pyrazol-1-yl)-4-(1,2,3,6-tetrahydropyridin-4-yl)phenyl)ethoxy)pyrimidin-4-yl)-2,8-diazaspiro[4.5]decane-3-carboxylic acid | 613.5 |
| 1g | 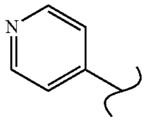 | (S)-8-(2-amino-6-((R)-2,2,2-trifluoro-1-(2-(3-methyl-1H-pyrazol-1-yl)-4-(pyridin-4-yl)phenyl)ethoxy)pyrimidin-4-yl)-2,8-diazaspiro[4.5]decane-3-carboxylic acid | 609.6 |
| 1h | 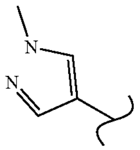 | (S)-8-(2-amino-6-((R)-2,2,2-trifluoro-1-(2-(3-methyl-1H-pyrazol-1-yl)-4-(1-methyl-1H-pyrazol-4-yl)phenyl)ethoxy)pyrimidin-4-yl)-2,8-diazaspiro[4.5]decane-3-carboxylic acid | 612.6 |
| 1i | 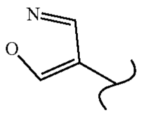 | (S)-8-(2-amino-6-((R)-2,2,2-trifluoro-1-(4-(isoxazol-4-yl)-2-(3-methyl-1H-pyrazol-1-yl)phenyl)ethoxy)pyrimidin-4-yl)-2,8-diazaspiro[4.5]decane-3-carboxylic acid | 599.6 |
| 1j | 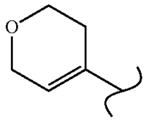 | (S)-8-(2-amino-6-((R)-1-(4-(3,6-dihydro-2H-pyran-4-yl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 614.6 |
| 1k | 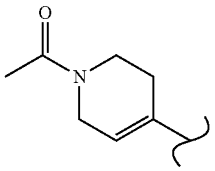 | (S)-8-(6-((R)-1-(4-(1-acetyl-1,2,3,6-tetrahydropyridin-4-yl)-2-(3-methyl-1H-pyrazol-1-yl)phenyl)-2,2,2-trifluoroethoxy)-2-aminopyrimidin-4-yl)-2,8-diazaspiro[4.5]decane-3-carboxylic acid | 655.7 |

TABLE 1a-continued

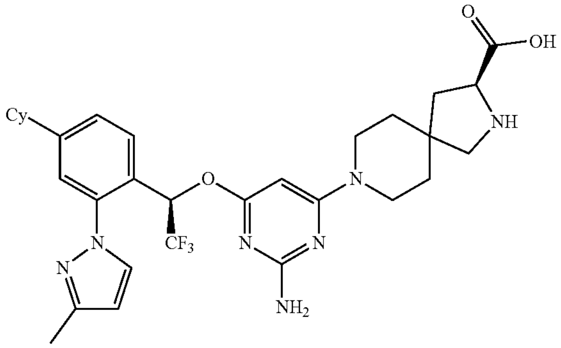

| Ex. No. | Cy | CAS Name | LCMS (MH+) |
|---|---|---|---|
| 1l | 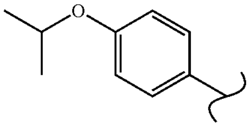 | (S)-8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 666.7 |
| 1m | 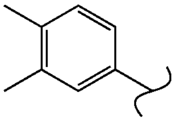 | (S)-8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 636.7 |
| 1n | 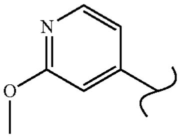 | (S)-8-(2-amino-6-((R)-2,2,2-trifluoro-1-(4-(2-methoxypyridin-4-yl)-2-(3-methyl-1H-pyrazol-1-yl)phenyl)ethoxy)pyrimidin-4-yl)-2,8-diazaspiro[4.5]decane-3-carboxylic acid | 639.6 |
| 1o | 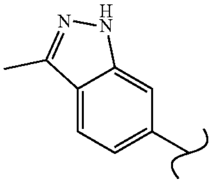 | (S)-8-(2-amino-6-((R)-2,2,2-trifluoro-1-(4-(3-methyl-1H-indazol-6-yl)-2-(3-methyl-1H-pyrazol-1-yl)phenyl)ethoxy)pyrimidin-4-yl)-2,8-diazaspiro[4.5]decane-3-carboxylic acid | 662.3 |
| 1p | 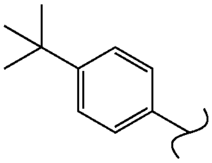 | (S)-8-(2-amino-6-((R)-1-(4'-(tert-butyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 664.8 |
| 1q | 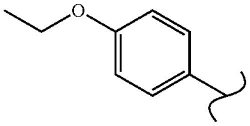 | (S)-8-(2-amino-6-((R)-1-(4'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652.7 |
| 1r | 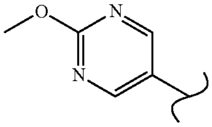 | (S)-8-(2-amino-6-((R)-2,2,2-trifluoro-1-(4-(2-methoxypyrimidin-5-yl)-2-(3-methyl-1H-pyrazol-1-yl)phenyl)ethoxy)pyrimidin-4-yl)-2,8-diazaspiro[4.5]decane-3-carboxylic acid | 639.6 |
| 1s | 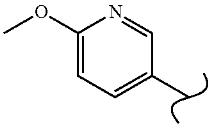 | (S)-8-(2-amino-6-((R)-2,2,2-trifluoro-1-(4-(6-methoxypyridin-3-yl)-2-(3-methyl-1H-pyrazol-1-yl)phenyl)ethoxy)pyrimidin-4-yl)-2,8-diazaspiro[4.5]decane-3-carboxylic acid | 639.6 |

TABLE 1a-continued

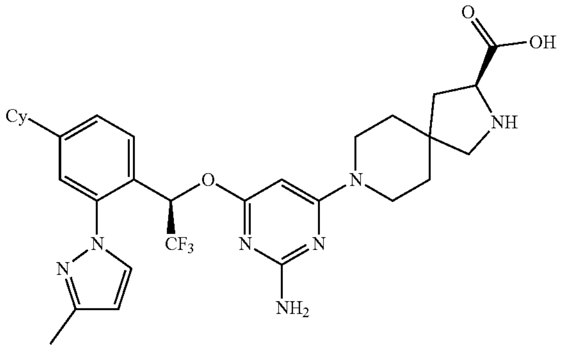

| Ex. No. | Cy | CAS Name | LCMS (MH+) |
|---|---|---|---|
| 1u | 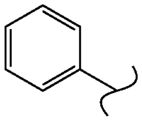 | (S)-8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 608.6 |
| 1v | 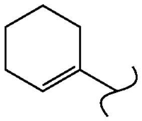 | (S)-8-(2-amino-6-((R)-2,2,2-trifluoro-1-(3-(3-methyl-1H-pyrazol-1-yl)-2',3',4',5'-tetrahydro-[1,1'-biphenyl]-4-yl)ethoxy)pyrimidin-4-yl)-2,8-diazaspiro[4.5]decane-3-carboxylic acid | 636 |
| 1w | 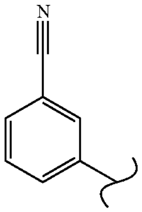 | (S)-8-(2-amino-6-((R)-1-(3'-cyano-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 633 |
| 1x | 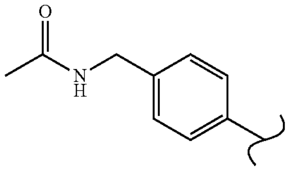 | (S)-8-(6-((R)-1-(4'-(acetamidomethyl)-3-(3-methyl-1H-pyrazol-1-yl)-[1,1'-biphenyl]-4-yl)-2,2,2-trifluoroethoxy)-2-aminopyrimidin-4-yl)-2,8-diazaspiro[4.5]decane-3-carboxylic acid | 679 |
| 1y | 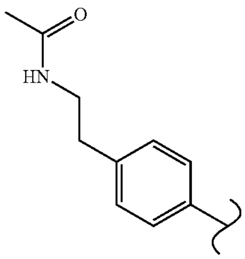 | (S)-8-(6-((R)-1-(4'-(2-acetamidoethyl)-3-(3-methyl-1H-pyrazol-1-yl)-[1,1'-biphenyl]-4-yl)-2,2,2-trifluoroethoxy)-2-aminopyrimidin-4-yl)-2,8-diazaspiro[4.5]decane-3-carboxylic acid | 693 |
| 1z | 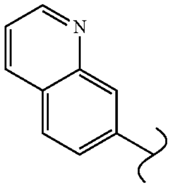 | (S)-8-(2-amino-6-((R)-2,2,2-trifluoro-1-(2-(3-methyl-1H-pyrazol-1-yl)-4-(quinolin-7-yl)phenyl)ethoxy)pyrimidin-4-yl)-2,8-diazaspiro[4.5]decane-3-carboxylic acid | 659 |

TABLE 1a-continued

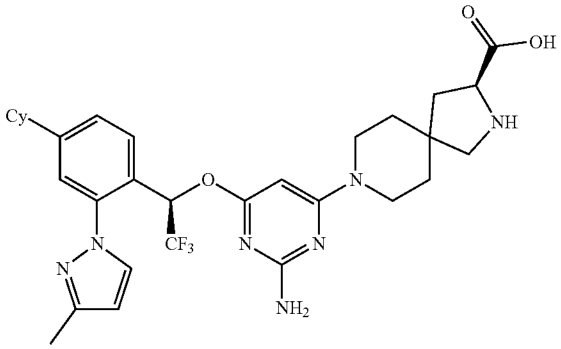

| Ex. No. | Cy | CAS Name | LCMS (MH+) |
|---|---|---|---|
| 1aa | 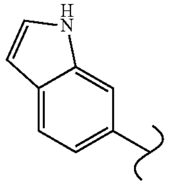 | (S)-8-(6-((R)-1-(4-(1H-indol-6-yl)-2-(3-methyl-1H-pyrazol-1-yl)phenyl)-2,2,2-trifluoroethoxy)-2-aminopyrimidin-4-yl)-2,8-diazaspiro[4.5]decane-3-carboxylic acid | 567 |
| 1ab | 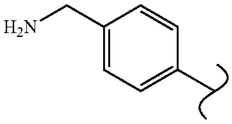 | (S)-8-(2-amino-6-((R)-1-(4'-(aminomethyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 637 |
| 1ac | 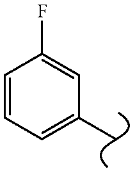 | (S)-8-(2-amino-6-((R)-2,2,2-trifluoro-1-(3'-fluoro-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 626 |
| 1ad | 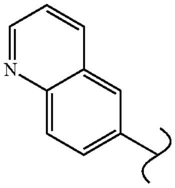 | (S)-8-(2-amino-6-((R)-2,2,2-trifluoro-1-(2-(3-methyl-1H-pyrazol-1-yl)-4-(quinolin-6-yl)phenyl)ethoxy)pyrimidin-4-yl)-2,8-diazaspiro[4.5]decane-3-carboxylic acid | 659 |
| 1ae | 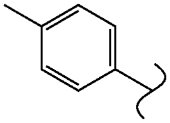 | (S)-8-(2-amino-6-((R)-2,2,2-trifluoro-1-(4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 622 |
| 1af | 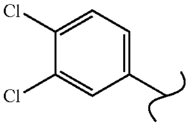 | (S)-8-(2-amino-6-((R)-1-(3',4'-dichloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 677 |
| 1ag | 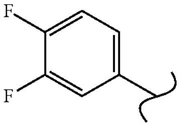 | (S)-8-(2-amino-6-((R)-1-(3',4'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 644 |

TABLE 1a-continued

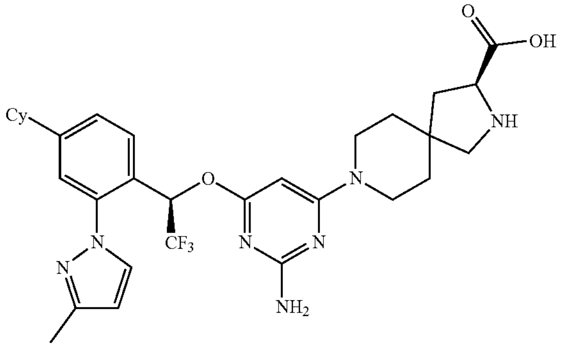

| Ex. No. | Cy | CAS Name | LCMS (MH+) |
|---|---|---|---|
| 1ah | 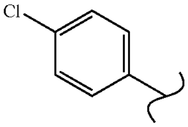 | (S)-8-(2-amino-6-((R)-1-(4'-chloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 643 |
| 1ai | 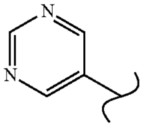 | (S)-8-(2-amino-6-((R)-2,2,2-trifluoro-1-(2-(3-methyl-1H-pyrazol-1-yl)-4-(pyrimidin-5-yl)phenyl)ethoxy)pyrimidin-4-yl)-2,8-diazaspiro[4.5]decane-3-carboxylic acid | 610 |
| 1ak | 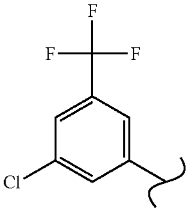 | (S)-8-(2-amino-6-((R)-1-(3'-chloro-3-(3-methyl-1H-pyrazol-1-yl)-5'-(trifluoromethyl)-[1,1'-biphenyl]-4-yl)-2,2,2-trifluoroethoxy)pyrimidin-4-yl)-2,8-diazaspiro[4.5]decane-3-carboxylic acid | 711 |
| 1al | 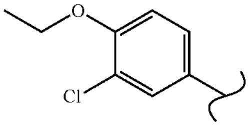 | (S)-8-(2-amino-6-((R)-1-(3'-chloro-4'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 687 |
| 1am | 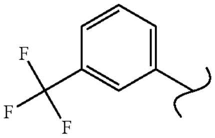 | (S)-8-(2-amino-6-((R)-2,2,2-trifluoro-1-(3-(3-methyl-1H-pyrazol-1-yl)-3'-(trifluoromethyl)-[1,1'-biphenyl]-4-yl)ethoxy)pyrimidin-4-yl)-2,8-diazaspiro[4.5]decane-3-carboxylic acid | 676 |
| 1an | 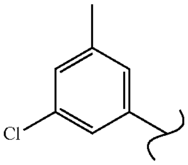 | (S)-8-(2-amino-6-((R)-1-(3'-chloro-5'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 657 |
| 1ao | 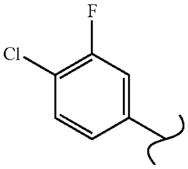 | (S)-8-(2-amino-6-((R)-1-(4'-chloro-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 661 |

TABLE 1a-continued

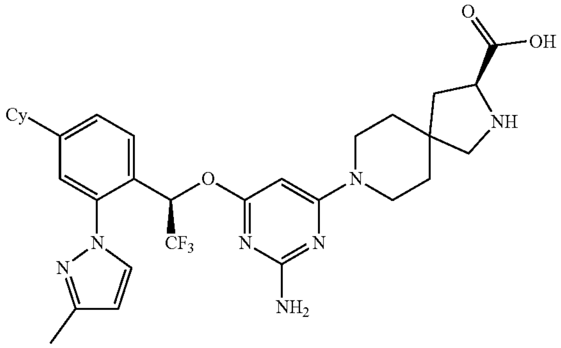

| Ex. No. | Cy | CAS Name | LCMS (MH+) |
|---|---|---|---|
| 1ap | 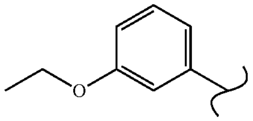 | (S)-8-(2-amino-6-((R)-1-(3'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652 |
| 1aq | 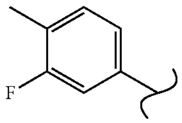 | (S)-8-(2-amino-6-((R)-2,2,2-trifluoro-1-(3'-fluoro-4'-methyl-3-(3-methyl-1H-pyrazol-1-yl)-[1,1'-biphenyl1-4-yl)ethoxy)pyrimidin-4-yl)-2,8-diazaspiro[4.5]decane-3-carboxylic acid | 640 |
| 1ar | 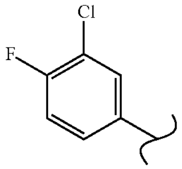 | (S)-8-(2-amino-6-((R)-1-(3'-chloro-4'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 661 |
| 1as | 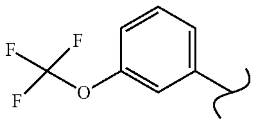 | (S)-8-(2-amino-6-((R)-2,2,2-trifluoro-1-(3-(3-methyl-1H-pyrazol-1-yl)-3'-(trifluoromethoxy)-[1,1'-biphenyl]-4-yl)ethoxy)pyrimidin-4-yl)-2,8-diazaspiro[4.5]decane-3-carboxylic acid | 692 |
| 1at | 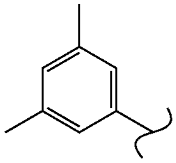 | (S)-8-(2-amino-6-((R)-1-(3',5'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 637 |
| 1au | 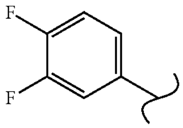 | (S)-8-(2-amino-6-((R)-1-(3',4'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 644 |
| 1av | 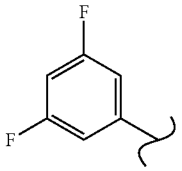 | (S)-8-(2-amino-6-((R)-1-(3',5'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 644 |
| 1aw | 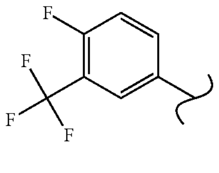 | (S)-8-(2-amino-6-((R)-2,2,2-trifluoro-1-(4'-fluoro-3-(3-methyl-1H-pyrazol-1-yl)-3'-(trifluoromethyl)-[1,1'-biphenyl]-4-yl)ethoxy)pyrimidin-4-yl)-2,8-diazaspiro[4.5]decane-3-carboxylic acid | 694 |

TABLE 1a-continued

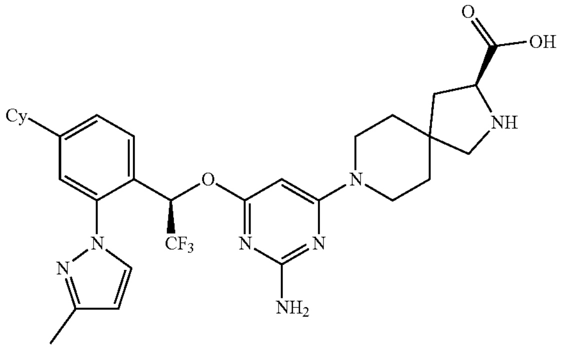

| Ex. No. | Cy | CAS Name | LCMS (MH+) |
|---|---|---|---|
| 1ax | 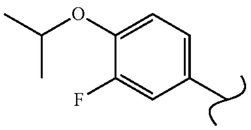 | (S)-8-(2-amino-6-((R)-2,2,2-trifluoro-1-(3'-fluoro-4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 684 |
| 1ay | 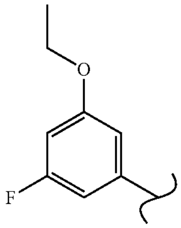 | (S)-8-(2-amino-6-((R)-1-(3'-ethoxy-5'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 670 |
| 1az | 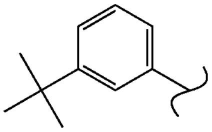 | (S)-8-(2-amino-6-((R)-1-(3'-(tert-butyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 664 |
| 1ba | 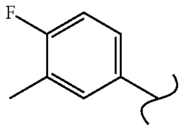 | (S)-8-(2-amino-6-((R)-2,2,2-trifluoro-1-(4'-fluoro-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 640 |
| 1bb | 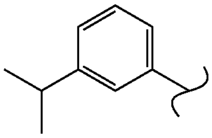 | (S)-8-(2-amino-6-((R)-2,2,2-trifluoro-1-(3'-isopropyl-3-(3-methyl-1H-pyrazol-1-yl)-[1,1'-biphenyl1-4-yl)ethoxy)pyrimidin-4-yl)-2,8-diazaspiro[4.5]decane-3-carboxylic acid | 650 |
| 1bc | 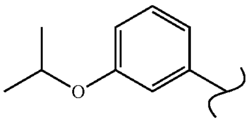 | (S)-8-(2-amino-6-((R)-2,2,2-trifluoro-1-(3'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 666 |
| 1bd | 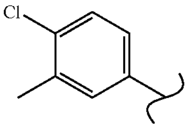 | (S)-8-(2-amino-6-((R)-1-(4'-chloro-3'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 656 |

TABLE 1a-continued

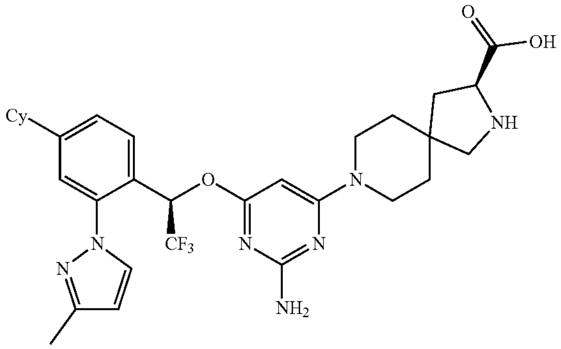

| Ex. No. | Cy | CAS Name | LCMS (MH+) |
|---|---|---|---|
| 1be | 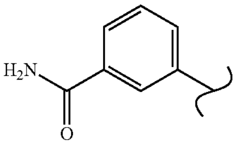 | (S)-8-(2-amino-6-((R)-1-(3'-carbamoyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 651 |
| 1bf | 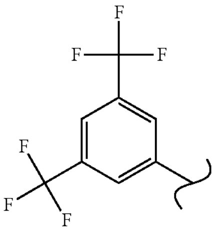 | (S)-8-(2-amino-6-((R)-2,2,2-trifluoro-1-(3-(3-methyl-1H-pyrazol-1-yl)-3',5'-bis(trifluoromethyl)-[1,1'-biphenyl]-4-yl)ethoxy)pyrimidin-4-yl)-2,8-diazaspiro[4.5]decane-3-carboxylic acid | 744 |
| 1bg | 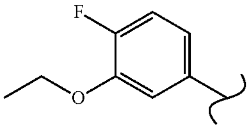 | (S)-8-(2-amino-6-((R)-1-(3'-ethoxy-4'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 670 |
| 1bh | 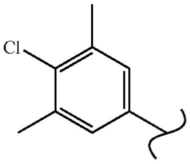 | (S)-8-(2-amino-6-((R)-1-(4'-chloro-3',5'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 671 |
| 1bi | 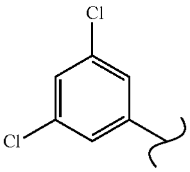 | (S)-8-(2-amino-6-((R)-1-(3',5'-dichloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 677 |
| 1bj | 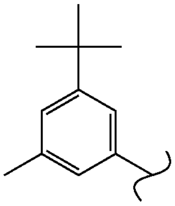 | (S)-8-(2-amino-6-((R)-1-(3'-(tert-butyl)-5'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 778 |

TABLE 1a-continued

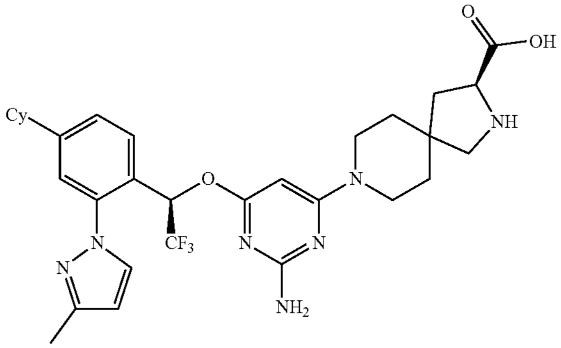

| Ex. No. | Cy | CAS Name | LCMS (MH+) |
|---|---|---|---|
| 1bk | 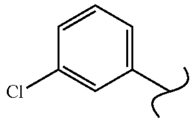 | (S)-8-(2-amino-6-((R)-1-(3'-chloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 642 |
| 1bl | 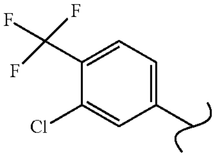 | (S)-8-(2-amino-6-((R)-1-(3'-chloro-3-(3-methyl-1H-pyrazol-1-yl)-4'-(trifluoromethyl)-[1,1'-biphenyl]-4-yl)-2,2,2-trifluoroethoxy)pyrimidin-4-yl)-2,8-diazaspiro[4.5]decane-3-carboxylic acid | 711 |
| 1bm | 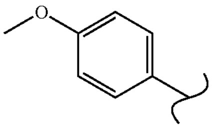 | (S)-8-(2-amino-6-((R)-2,2,2-trifluoro-1-(4'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 638 |
| 1bn | 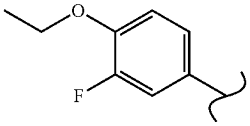 | (S)-8-(2-amino-6-((R)-1-(4'-ethoxy-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 670 |
| 1bo | 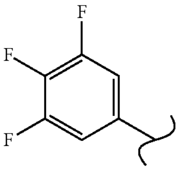 | (S)-8-(2-amino-6-((R)-2,2,2-trifluoro-1-(3',4',5'-trifluoro-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 662 |
| 1bp | 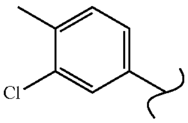 | (S)-8-(2-amino-6-((R)-1-(3'-chloro-4'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 657 |
| 1bq | 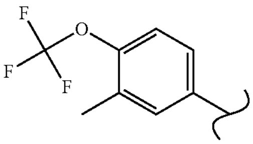 | (S)-8-(2-amino-6-((R)-2,2,2-trifluoro-1-(3'-methyl-3-(3-methyl-1H-pyrazol-1-yl)-4'-(trifluoromethoxy)-[1,1'-biphenyl]-4-yl)ethoxy)pyrimidin-4-yl)-2,8-diazaspiro[4.5]decane-3-carboxylic acid | 706 |
| 1br | 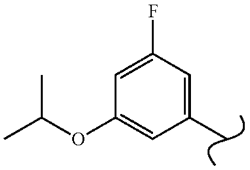 | (S)-8-(2-amino-6-((R)-2,2,2-trifluoro-1-(3'-fluoro-5'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 684 |

TABLE 1a-continued

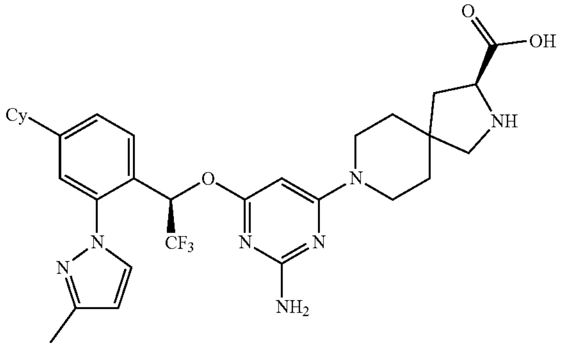

| Ex. No. | Cy | CAS Name | LCMS (MH+) |
|---|---|---|---|
| 1bs | 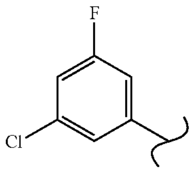 | (S)-8-(2-amino-6-((R)-1-(3'-chioro-5'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 661 |
| 1bt | 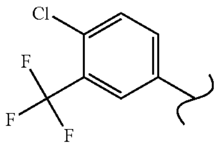 | (S)-8-(2-amino-6-((R)-1-(4'-chloro-3-(3-methyl-1H-pyrazol-1-yl)-3'-(trifluoromethyl)-[1,1'-biphenyl]-4-yl)-2,2,2-trifluoroethoxy)pyrimidin-4-yl)-2,8-diazaspiro[4.5]decane-3-carboxylic acid | 710 |
| 1bu | 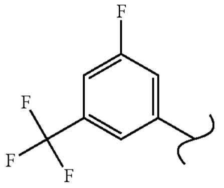 | (S)-8-(2-amino-6-((R)-2,2,2-trifluoro-1-(3'-fluoro-3-(3-methyl-1H-pyrazol-1-yl)-5'-(trifluoromethyl)-[1,1'-biphenyl]-4-yl)ethoxy)pyrimidin-4-yl)-2,8-diazaspiro[4.5]decane-3-carboxylic acid | 694 |
| 1bv | 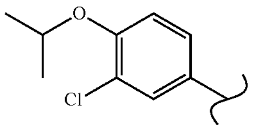 | (S)-8-(2-amino-6-((R)-1-(3'-chloro-4'-isopropoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 701 |
| 1bw | 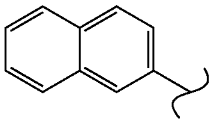 | (S)-8-(2-amino-6-((R)-2,2,2-trifluoro-1-(2-(3-methyl-1H-pyrazol-1-yl)-4-(naphthalen-2-yl)phenyl)ethoxy)pyrimidin-4-yl)-2,8-diazaspiro[4.5]decane-3-carboxylic acid | 659 |
| 1bx | 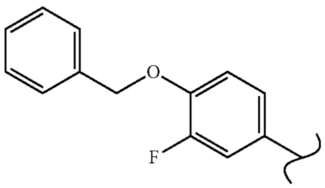 | (S)-8-(2-amino-6-((R)-1-(4'-(benzyloxy)-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 733 |
| 1by | 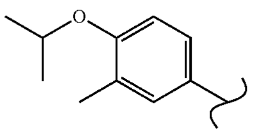 | (S)-8-(2-amino-6-((R)-2,2,2-trifluoro-1-(4'-isopropoxy-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 681 |

TABLE 1a-continued

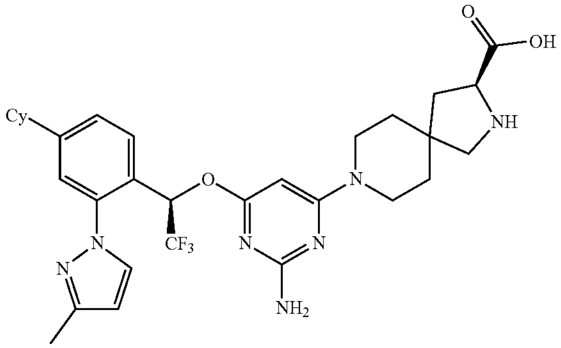

| Ex. No. | Cy | CAS Name | LCMS (MH+) |
|---|---|---|---|
| 1bz | 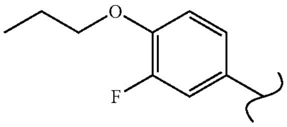 | (S)-8-(2-amino-6-((R)-2,2,2-trifluoro-1-(3'-fluoro-3-(3-methyl-1H-pyrazol-1-yl)-4'-propoxy-[1,1'-biphenyl]-4-yl)ethoxy)pyrimidin-4-yl)-2,8-diazaspiro[4.5]decane-3-carboxylic acid | 685 |
| 1ca | 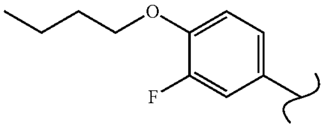 | (S)-8-(2-amino-6-((R)-1-(4'-butoxy-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 698 |
| 1cb | 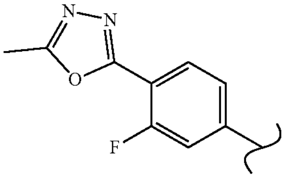 | (S)-8-(2-amino-6-((R)-2,2,2-trifluoro-1-(3'-fluoro-4'-(5-methyl-1,3,4-oxadiazol-2-yl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 709 |
| 1cc | 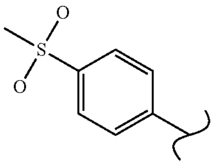 | (S)-8-(2-amino-6-((R)-2,2,2-trifluoro-1-(3-(3-methyl-1H-pyrazol-1-yl)-4'-(methylsulfonyl)-[1,1'-biphenyl]-4-yl)ethoxy)pyrimidin-4-yl)-2,8-diazaspiro[4.5]decane-3-carboxylic acid | 687 |
| 1cd | 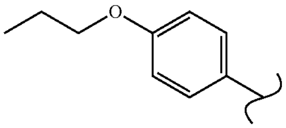 | (S)-8-(2-amino-6-((R)-2,2,2-trifluoro-1-(3-(3-methyl-1H-pyrazol-1-yl)-4'-propoxy-[1,1'-biphenyl]-4-yl)ethoxy)pyrimidin-4-yl)-2,8-diazaspiro[4.5]decane-3-carboxylic acid | 668 |
| 1ce | 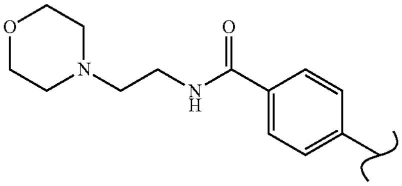 | (S)-8-(2-amino-6-((R)-2,2,2-trifluoro-1-(3-(3-methyl-1H-pyrazol-1-yl)-4'-((2-morpholinoethyl)carbamoyl)-[1,1'-biphenyl]-4-yl)ethoxy)pyrimidin-4-yl)-2,8-diazaspiro[4.5]decane-3-carboxylic acid | 764 |
| 1cf | 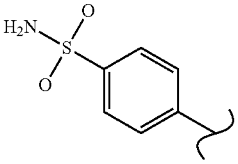 | (S)-8-(2-amino-6-((R)-2,2,2-trifluoro-1-(3-(3-methyl-1H-pyrazol-1-yl)-4'-sulfamoyl-[1,1'-biphenyl]-4-yl)ethoxy)pyrimidin-4-yl)-2,8-diazaspiro[4.5]decane-3-carboxylic acid | 689 |

TABLE 1a-continued

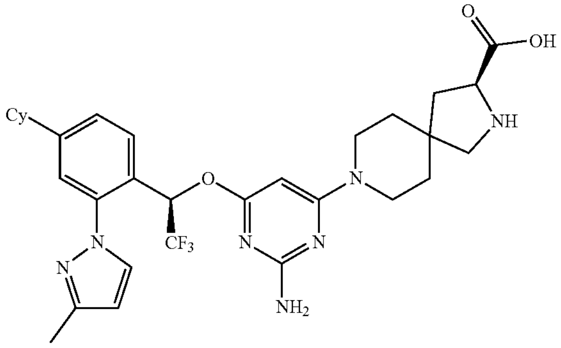

| Ex. No. | Cy | CAS Name | LCMS (MH+) |
|---|---|---|---|
| 1cg | 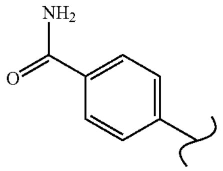 | (S)-8-(2-amino-6-((R)-1-(4'-carbamoyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 652 |
| 1ch | 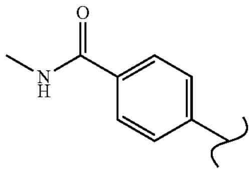 | (S)-8-(2-amino-6-((R)-2,2,2-trifluoro-1-(3-(3-methyl-1H-pyrazol-1-yl)-4'-(methylcarbamoyl)-[1,1'-biphenyl]-4-yl)ethoxy)pyrimidin-4-yl)-2,8-diazaspiro[4.5]decane-3-carboxylic acid | 666 |
| 1ci | 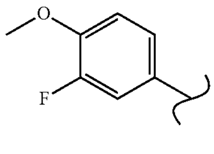 | (S)-8-(2-amino-6-((R)-2,2,2-trifluoro-1-(3'-fluoro-4'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 657 |
| 1cj | 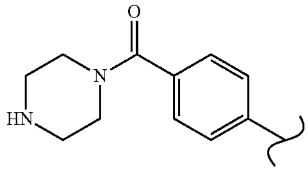 | (S)-8-(2-amino-6-((R)-2,2,2-trifluoro-1-(3-(3-methyl-1H-pyrazol-1-yl)-4'-(piperazine-1-carbonyl)-[1,1'-biphenyl]-4-yl)ethoxy)pyrimidin-4-yl)-2,8-diazaspiro[4.5]decane-3-carboxylic acid | 721 |
| 1ck | 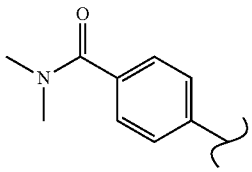 | (S)-8-(2-amino-6-((R)-1-(4'-(dimethylcarbamoyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 680 |
| 1cl | 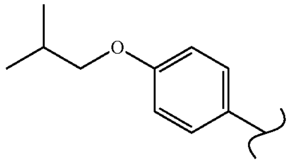 | (S)-8-(2-amino-6-((R)-2,2,2-trifluoro-1-(4'-isobutoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 681 |

TABLE 1a-continued

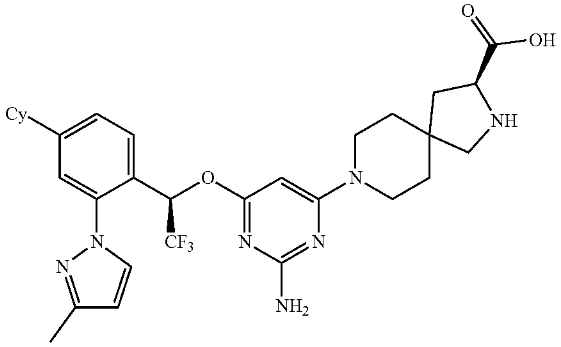

| Ex. No. | Cy | CAS Name | LCMS (MH+) |
|---|---|---|---|
| 1cm | 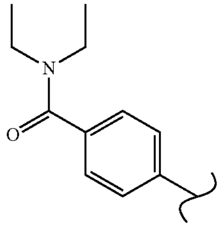 | (S)-8-(2-amino-6-((R)-1-(4'-(diethylcarbamoyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid | 707 |
| 1cn | 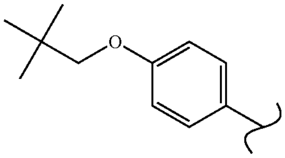 | (S)-8-(2-amino-6-((R)-2,2,2-trifluoro-1-(3-(3-methyl-1H-pyrazol-1-yl)-4'-(neopentyloxy)-[1,1'-biphenyl]-4-yl)ethoxy)pyrimidin-4-yl)-2,8-diazaspiro[4.5]decane-3-carboxylic acid | 695 |
| 1co | 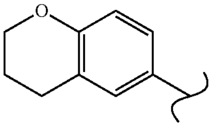 | (S)-8-(2-amino-6-((R)-1-(4-(chroman-6-yl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 665 |
| 1cp | 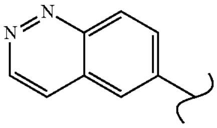 | (S)-8-(2-amino-6-((R)-1-(4-(cinnolin-6-yl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 661 |
| 1cq | 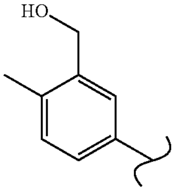 | (S)-8-(2-amino-6-((R)-2,2,2-trifluoro-1-(31-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 652 |
| 1cr | 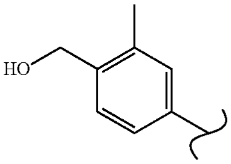 | (S)-8-(2-amino-6-((R)-2,2,2-trifluoro-1-(4'-(hydroxymethyl)-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 653 |

TABLE 1a-continued

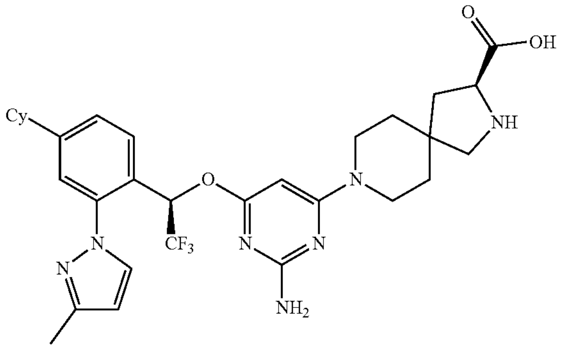

| Ex. No. | Cy | CAS Name | LCMS (MH+) |
|---|---|---|---|
| 1cs | 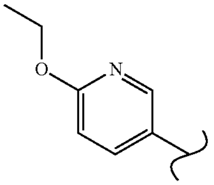 | (S)-8-(2-amino-6-((R)-1-(4-(6-ethoxypyridin-3-yl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 654 |
| 1ct | 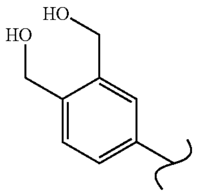 | (S)-8-(2-amino-6-((S)-1-(3',4'-bis(hydroxymethyl)-3-(3-methyl-1H-pyrazol-1-yl)-[1,1'-biphenyl]-4-yl>2,2,2-trifluoroethoxy)pyrimidin-4-yl)-2,8-diazaspiro[4.5]decane-3-carboxylic acid | 669 |

TABLE 1b

1H NMR Data for Compounds of Table 1a

| Ex. No. | 1H NMR |
|---|---|
| 1a | $^1$H NMR (MeOH-d4): δ ppm 1.29 (m, 3H), 1.68 (q, J = 6.3 Hz, 4H), 2.10 (dd, J = 13.6, 8.1 Hz, 1H), 2.41 (s, 4H), 2.85 (s, 3H), 3.24 (m, 2H), 3.62 (m, 1H), 3.71 (s, 2H), 3.79 (dd, J = 13.7, 5.8 Hz, 2H), 4.44 (t, J = 8.5 Hz, 1H), 4.83 (s, 2H), 6.44 (d, J = 2.4 Hz, 1H), 6.92 (q, J = 6.2 Hz, 1H), 7.88 (m, 8H) |
| 1b | $^1$H NMR (400 MHz, MeOH-d4): δ ppm 1.31 (m, 3H), 1.60 (t, J = 5.6 Hz, 4H), 2.06 (dd, J = 13.4, 7.0 Hz, 1H), 2.40 (s, 4H), 2.51 (s, 3H), 2.80 (s, 1H), 3.13 (d, J = 11.5 Hz, 1H), 3.25 (d, J = 11.0 Hz, 1H), 3.53 (dd, J = 22.1, 9.7 Hz, 2H), 3.69 (d, J = 14.9 Hz, 2H), 4.14 (t, J = 8.1 Hz, 1H), 4.93 (s, 1H), 6.42 (d, J = 2.3 Hz, 1H), 6.79 (q, J = 6.5 Hz, 1H), 7.34 (m, 2H), 7.63 (dd, J = 8.9, 2.1 Hz, 3H), 7.77 (m, 2H), 7.97 (d, J = 2.3 Hz, 1H) |
| 1c | $^1$H NMR (400 MHz, MeOH-d4): δ ppm 1.4 (d, J = 18.0 Hz, 1H), 1.68 (q, J = 6.8, 5.6 Hz, 4H), 2.4 (dd, J = 13.6, 8.1 Hz, 1H), 2.41 (s, 4H), 2.85 (s, 1H), 3.25 (m, 2H), 3.64 (m, 1H), 3.72 (s, 1H), 3.79 (d, J = 13.8 Hz, 2H), 4.44 (q, J = 8.6 Hz, 1H), 6.5 (d, J = 2.4 Hz, 1H), 6.92 (dd, J = 10.5, 4.4 Hz, 1H), 7.95 (m, 5H), 8.1 (d, J = 2.5 Hz, 1H), 8.4(m, 2H) |
| 1d | $^1$H NMR (400 MHz, MeOH-d4): δ ppm 1.68 (dt, J = 9.0, 5.8 Hz, 4H), 2.09 (dd, J = 13.6, 8.1 Hz, 1H), 2.41 (s, 4H), 3.24 (m, 2H), 3.72 (m, 4H), 4.45 (t, J = 8.5 Hz, 1H), 6.44 (d, J = 2.3 Hz, 1H), 6.90 (q, J = 6.2 Hz, 1H), 7.61 (t, J = 7.8 Hz, 1H), 7.75 (d, J = 1.7 Hz, 1H), 7.85 (m, 2H), 7.98 (m, 2H), 8.08 (dt, J = 7.8, 1.3 Hz, 1H), 8.34 (t, J = 1.8 Hz, 1H) |
| 1e | $^1$H NMR (400 MHz, MeOH-d4): δ ppm 1.68 (dt, J = 9.0, 5.8 Hz, 4H), 2.09 (dd, J = 13.6, 8.1 Hz, 1H), 2.41 (s, 4H), 3.24 (m, 2H), 3.72 (m, 4H), 4.45 (t, J = 8.5 Hz, 1H), 6.44 (d, J = 2.3 Hz, 1H), 6.90 (q, J = 6.2 Hz, 1H), 7.61 (t, J = 7.8 Hz, 1H), 7.75 (d, J = 1.7 Hz, 1H), 7.85 (m, 2H), 7.98 (m, 2H), 8.08 (dt, J = 7.8, 1.3 Hz, 1H), 8.34 (t, J = 1.8 Hz, 1H) |
| 1f | $^1$H NMR (400 MHz, MeOH-d4): δ ppm 1.47-1.69 (m, 4 H) 1.97-2.13 (m, 1 H) 2.19-2.35 (m, 1 H) 2.37 (d, J = 0.34 Hz, 0 H) 2.66-2.81 (m, 2 H) 3.05-3.17 (m, 1 H) 3.18-3.28 (m, 1 H) 3.33-3.40 (m, 2 H) 3.41-3.72 (m, 4 H) 3.73-3.83 (m, 2 H) 3.99-4.13 (m, 1 H) 5.71 (s, 1 H) 6.32 (d, J = 0.39 Hz, 1 H) 6.41 (d, J = 2.29 Hz, 2 H) 6.67-6.79 (m, 1 H) 7.49 (d, J = 1.81 Hz, 1 H) 7.55-7.64 (m, 1 H) 7.72 (d, J = 8.40 Hz, 2 H) 7.92 (d, J = 2.29 Hz, 1 H) |

TABLE 1b-continued

| Ex. No. | 1H NMR Data for Compounds of Table 1a<br>1H NMR |
|---|---|
| 1g | $^1$H NMR (400 MHz, MeOH-d4): δ ppm 1.49-1.69 (m, 4 H) 2.06 (dd, J = 13.47, 7.03 Hz, 1 H) 2.31 (dd, J = 13.42, 9.32 Hz, 1 H) 2.41 (s, 3 H) 3.12 (d, J = 12.00 Hz, 1 H) 3.25 (d, J = 11.76 Hz, 1 H) 3.38-3.57 (m, 2 H) 3.58-3.76 (m, 2 H) 4.08 (dd, J = 9.13, 7.17 Hz, 1 H) 5.74 (s, 1 H) 6.44 (d, J = 2.34 Hz, 1 H) 6.87 (q, J = 6.62 Hz, 1 H) 7.75-7.80 (m, 2 H) 7.82 (s, 1 H) 7.89 (s, 2 H) 8.02 (d, J = 2.34 Hz, 1 H), 8.57-8.69 (m, 2 H) |
| 1h | $^1$H NMR (400 MHz, MeOH-d4): δ ppm 1.61-1.84 (m, 5 H) 2.10 (dd, J = 13.62, 8.49 Hz, 1 H) 2.40 (s, 3 H) 2.47 (dd, J = 13.76, 8.88 Hz, 1 H) 3.25-3.29 (m, 2 H) 3.73-3.91 (m, 4 H) 3.94 (s, 3 H) 4.53 (t, J = 8.64 Hz, 1 H) 6.42 (d, J = 2.39 Hz, 1 H) 6.81 (q, J = 5.94 Hz, 1 H) 7.61-7.70 (m, 2 H) 7.71-7.78 (m, 1 H) 7.90-7.96 (m, 2 H) 8.12 (s, 1 H) |
| 1i | $^1$H NMR (400 MHz, MeOH-d4): δ ppm 1.35-1.40 (m, 5 H), 1.60-1.65 (m, 8 H), 2.40 (m, 5 H) 2.47 (dd, J = 13.76, 8.88 Hz, 1 H) 3.25-3.29 (m, 2 H) 3.73-3.91 (m, 4 H) 3.94 (s, 3 H) 4.53 (t, J = 8.64 Hz, 1 H), 5.6 (s, 1H), 6.42 (d, J = 2.39 Hz, 2 H) 6.70 (m, 1 H) 7.61-7.70 (m, 2 H) 7.71-7.78 (m, 1 H) 7.90-7.96 (m, 2 H) 8.12 (s, 1 H) |
| 1j | $^1$H NMR (400 MHz, MeOH-d4): δ ppm 1.58-1.86 (m, 4 H) 2.01-2.20 (m, 1 H) 2.40 (s, 3 H) 2.43-2.61 (m, 3 H) 3.61-3.75 (m, 2 H) 3.86 (s, 4 H) 3.93 (t, J = 5.44 Hz, 2 H) 4.25-4.37 (m, 2 H) 4.49-4.69 (m, 1 H) 6.42 (d, J = 2.24 Hz, 2 H) 6.52 (br. s., 1 H) 6.77-6.88 (m, 1 H) 7.51 (d, J = 1.32 Hz, 1 H) 7.60-7.73 (m, 2 H) 7.91 (d, J = 2.34 Hz, 1 H) |
| 1k | $^1$H NMR (400 MHz, MeOH-d4): δ ppm 1.72 (d, J = 18.21 Hz, 4 H) 2.09 (dd, J = 13.62, 8.49 Hz, 1 H) 2.18 (d, J = 14.50 Hz, 3 H) 2.39 (s, 3 H) 2.48 (dd, J = 13.64, 8.91 Hz, 1 H) 2.58 (br. s., 1 H) 2.66 (br. s., 1 H) 3.60-3.95 (m, 6 H) 4.24 (br. s., 2 H) 4.55 (t, J = 8.71 Hz, 1 H) 6.33 (br. s., 1 H) 6.42 (d, J = 2.34 Hz, 1 H) 6.46 (br. s., 1 H) 6.75-6.87 (m, 1 H) 7.52 (s, 1 H) 7.62-7.74 (m, 2 H) 7.92 (d, J = 2.34 Hz, 1 H) |
| 1l | $^1$H NMR (400 MHz, MeOH-d4): δ ppm 1.29 (d, J = 6.05 Hz, 6 H) 1.49 (d, J = 5.47 Hz, 4 H) 1.70-1.86 (m, 1 H) 1.98-2.15 (m, 1 H) 2.37 (s, 3 H) 2.69 (d, J = 11.13 Hz, 1 H) 2.93 (s, 1 H) 3.35-3.52 (m, 2H) 3.53-3.64 (m, 2 H) 3.64-3.73 (m, 1 H) 4.59 (s, 1 H) 5.71 (s, 1 H) 6.38 (d, J = 2.15 Hz, 1 H) 6.68-6.82 (m, 1 H) 6.93 (d, J = 8.79 Hz, 2 H) 7.44-7.58 (m, 3 H) 7.64 (d, J = 1.37 Hz, 1 H) 7.67-7.78 (m, 1 H) 7.93 (d, J = 2.15 Hz, 1 H) |
| 1m | $^1$H NMR (400 MHz, MeOH-d4): δ ppm 1.51 (d, J = 5.47 Hz, 4 H) 1.71-1.86 (m, 1 H) 2.01-2.17 (m, 1 H) 2.28 (s, 3 H) 2.31 (s, 3 H) 2.39 (s, 3 H) 2.64-2.78 (m, 1 H) 2.90-3.05 (m, 1 H) 3.36-3.54 (m, 2 H) 3.55-3.79 (m, 3 H) 5.73 (s, 1 H) 6.41 (d, J = 2.15 Hz, 1 H) 6.69-6.87 (m, 1 H) 7.20 (s, 1 H) 7.33-7.40 (m, 1 H) 7.43 (s, 1 H) 7.59 (d, J = 1.37 Hz, 1 H) 7.70 (s, 1 H) 7.75 (s, 1 H) 7.96 (d, J = 2.15 Hz, 1 H) |
| 1n | $^1$H NMR (400 MHz, MeOH-d4): δ ppm 1.53 (d, J = 5.86 Hz, 4 H) 1.75-1.87 (m, 1 H) 2.04-2.17 (m, 1 H) 2.41 (s, 3 H) 2.64-2.76 (m, 1 H) 2.91-3.04 (m, 1 H) 3.38-3.54 (m, 2 H) 3.55-3.74 (m, 3 H), 3.95 (s, 3 H) 5.72 (s, 1 H) 6.44 (d, J = 2.34 Hz, 1 H) 6.79-6.92 (m, 1 H) 7.12 (s, 1 H) 7.23-7.31 (m, 1 H) 7.74 (d, J = 1.17 Hz, 1 H) 7.79-7.89 (m, 2 H) 8.02 (d, J = 2.15 Hz, 1 H) 8.15-8.25 (m, 1 H) |
| 1o | $^1$H NMR (400 MHz, MeOH-d4): δ ppm 1.60 (br. s., 4 H) 2.02-2.17 (m, 1 H) 2.24-2.39 (m, 1 H) 2.43 (s, 3 H) 2.53-2.66 (m, 4 H) 3.07-3.17 (m, 1 H) 3.21-3.29 (m, 1 H) 3.40-3.59 (m, 2 H) 3.61-3.80 (m, 2 H) 4.00-4.18 (m, 1 H) 5.77 (s, 1 H) 6.45 (d, J = 2.15 Hz, 1 H) 6.75-6.90 (m, 1 H) 7.36-7.56 (m, 1 H) 7.73 (d, J = 4.10 Hz, 2 H) 7.77-7.89 (m, 4 H) 8.01 (d, J = 2.15 Hz, 1 H) |
| 1p | $^1$H NMR (400 MHz, MeOH-d4): δ ppm 1.24-1.42 (m, 9 H) 1.60 (br. s., 4 H) 2.02-2.12 (m, 1 H) 2.42 (s, 4 H) 3.05-3.17 (m, 1 H) 3.20-3.29 (m, 1 H) 3.41-3.79 (m, 4 H) 4.02-4.17 (m, 1 H) 5.78 (s, 1 H) 6.43 (d, J = 2.15 Hz, 1 H) 6.73-6.88 (m, 1 H) 7.51 (d, J = 8.40 Hz, 2 H) 7.57-7.69 (m, 3 H) 7.78 (s, 2 H) 7.98 (d, J = 2.15 Hz, 1 H) |
| 1q | $^1$H NMR (400 MHz, MeOH-d4): δ ppm 1.41 (t, J = 7.03 Hz, 3 H) 1.60 (br. s., 4 H) 1.95-2.14 (m, 1 H) 2.27-2.38 (m, 1 H) 2.41 (s, 3 H) 3.14 (s, 1 H) 3.20-3.29 (m, 1 H) 3.41-3.59 (m, 2 H) 3.60-3.83 (m, 2 H) 3.99-4.20 (m, 3 H) 5.77 (s, 1 H) 6.43 (d, J = 2.34 Hz, 1 H) 6.71-6.85 (m, 1H) 7.00 (d, J = 8.79 Hz, 2 H) 7.52-7.65 (m, 3 H) 7.72 (d, J = 1.56 Hz, 1 H) 7.76 (s, 1 H) 7.97 (d, J = 2.34 Hz, 1 H) |
| 1r | $^1$H NMR (400 MHz, MeOH-d4): δ ppm 1.62 (d, J = 4.88 Hz, 4 H) 2.02-2.13 (m, 1 H) 2.27-2.38 (m, 1 H) 2.42 (s, 3 H) 3.16 (s, 1 H) 3.26 (s, 1H) 3.41-3.59 (m, 2 H) 3.60-3.78 (m, 2 H) 3.99-4.19 (m, 4 H) 5.76 (s, 1 H) 6.45 (d, J = 2.34 Hz, 1 H) 6.82-6.96 (m, 1 H) 7.74 (d, J = 1.56 Hz, 1 H) 7.81 (d, J = 1.56 Hz, 1 H) 7.86 (s, 1 H) 8.03 (d, J = 2.15 Hz, 1 H) 8.92 (s, 2 H)) |
| 1s | $^1$H NMR (400 MHz, MeOH-d4): δ ppm 1.59 (br. s., 4 H) 2.01-2.14 (m, 1 H) 2.31 (br. s., 1 H) 2.41 (s, 3 H) 3.07-3.17 (m, 1 H) 3.21-3.29 (m, 1 H) 3.40-3.59 (m, 2 H) 3.67 (d, J = 5.47 Hz, 2 H) 3.95 (s, 3 H) 4.09 (d, J = 1.17 Hz, 1 H) 5.75 (s, 1 H) 6.43 (d, J = 2.15 Hz, 1 H) 6.82 (d, J = 6.44 Hz, 1 H) 6.88 (d, J = 8.79 Hz, 1 H) 7.64 (d, J = 1.56 Hz, 1 H) 7.68-7.76 (m, 1 H) 7.77-7.87 (m, 1 H) 7.93-8.07 (m, 2 H) 8.45 (d, J = 2.34 Hz, 1 H) |
| 1u | $^1$H NMR (400 MHz, MeOH-d4): δ ppm 1.42-1.74 (m, 4 H) 2.05 (dd, J = 13.50, 7.20 Hz, 1 H) 2.40 (s, 4 H) 3.07-3.16 (m, 1 H) 3.17-3.29 (m, 1 H) 3.38-3.59 (m, 2 H) 3.59-3.78 (m, 2 H) 4.11 (dd, J = 9.10, 7.25 Hz, 1 H) 6.42 (d, J = 2.34 Hz, 1 H) 6.74-6.86 (m, 1 H) 7.34-7.41 (m, 1 H) 7.42-7.50 (m, 2 H) 7.60-7.69 (m, 3 H) 7.71-7.77 (m, 1 H) 7.77-7.83 (m, 1 H) 7.97 (d, J = 2.00 Hz, 1 H) |
| 1v | $^1$H NMR (400 MHz, MeOH-d4): δ ppm 1.24 (t, J = 7.59 Hz, 3 H) 1.50-1.69 (m, 4 H) 2.06 (dd, J = 13.42, 7.13 Hz, 1 H) 2.32 (dd, J = 13.45, 9.20 Hz, 1 H) 2.37 (s, 3 H) 2.72 (q, J = 7.61 Hz, 2 H) 3.08-3.27 (m, 2 H) 3.39-3.78 (m, 4 H) 4.08 (dd, J = 9.13, 7.17 Hz, 1 H) 5.74 (s, 1 H) 6.36 (d, J = 2.34 Hz, 1 H) 6.71 (q, J = 6.65 Hz, 1 H) 7.26-7.34 (m, 1 H) 7.35-7.44 (m, 1 H) 7.56 (s, 1 H) 7.82 (d, J = 2.29 Hz, 1 H) |
| 1w | $^1$H NMR (400 MHz, MeOH-d4): δ ppm 1.51-1.64 (m, 4 H) 1.96 (s, 2 H) 2.04 (dd, J = 13.23, 7.32 Hz, 1 H) 2.25-2.34 (m, 1 H) 2.38 (s, 3 H) 3.09 (d, J = 11.67 Hz, 1 H) 3.23 (d, J = 11.81 Hz, 1 H) 3.38-3.56 (m, 2 H) 3.59-3.73 (m, 2 H) 4.00-4.10 (m, 1 H) 5.73 |

TABLE 1b-continued

| 1H NMR Data for Compounds of Table 1a | |
|---|---|
| Ex. No. | 1H NMR |
| | (s, 1 H) 6.41 (d, J = 2.34 Hz, 1 H) 6.79-6.89 (m, 1 H) 7.61-7.67 (m, 1 H) 7.69-7.88 (m, 4 H) 7.96-8.02 (m, 2 H) 8.08 (t, J = 1.59 Hz, 1 H) |
| 1x | $^{1}$H NMR (400 MHz, MeOH-d4): δ ppm 1.49-1.64 (m, 4 H) 1.97 (s, 3 H) 1.98 (s, 3 H) 2.04 (dd, J = 13.35, 7.15 Hz, 1 H) 2.29 (dd, J = 13.47, 9.18 Hz, 1 H) 2.38 (s, 3 H) 3.05-3.26 (m, 2 H) 3.39-3.73 (m, 4 H) 4.05 (dd, J = 9.18, 7.22 Hz, 1 H) 4.38 (s, 2 H) 5.73 (s, 1 H) 6.40 (d, J = 2.29 Hz, 1 H) 6.77 (q, J = 6.67 Hz, 1 H) 7.37 (d, J = 8.40 Hz, 2 H) 7.59-7.66 (m, 3 H) 7.71-7.81 (m, 2 H) 7.95 (d, J = 2.34 Hz, 1 H) |
| 1y | $^{1}$H NMR (400 MHz, MeOH-d4): δ ppm 1.57 (t, J = 4.44 Hz, 4 H) 1.89 (s, 3 H) 1.97 (s, 4 H) 2.04 (dd, J = 13.37, 7.13 Hz, 1 H) 2.29 (dd, J = 13.28, 9.18 Hz, 1 H) 2.38 (s, 3 H) 2.82 (t, J = 7.32 Hz, 2 H) 3.06-3.25 (m, 2 H) 3.40 (t, J = 7.32 Hz, 2 H) 3.43-3.73 (m, 4 H) 4.05 (dd, J = 9.18, 7.27 Hz, 1 H) 5.74 (s, 1 H) 6.40 (d, J = 2.25 Hz, 1 H) 6.77 (q, J = 6.80 Hz, 1 H) 7.31 (d, J = 8.30 Hz, 2 H) 7.57-7.63 (m, 3H) 7.70-7.80 (m, 2 H) 7.95 (d, J = 2.34 Hz, 1 H) |
| 1z | $^{1}$H NMR (400 MHz, MeOH-d4): δ ppm 1.53-1.61 (m, 4 H) 1.97 (s, 3 H) 2.04 (dd, J = 13.32, 7.03 Hz, 1 H) 2.30 (dd, J = 13.59, 9.30 Hz, 1 H) 2.40 (s, 3 H) 3.06-3.26 (m, 2 H) 3.40-3.72 (m, 4 H) 4.06 (dd, J = 8.91, 7.25 Hz, 1 H) 5.76 (s, 1 H) 6.42 (d, J = 2.29 Hz, 1 H) 6.85 (q, J = 6.51 Hz, 1 H) 7.55 (dd, J = 8.27, 4.32 Hz, 1 H) 7.82 (d, J = 1.71 Hz, 1 H) 7.85-7.99 (m, 3 H) 8.00-8.07 (m, 2 H) 8.29 (s, 1 H) 8.39 (d, J = 7.61 Hz, 1 H) 8.88 (dd, J = 4.30, 1.66 Hz, 1 H) |
| 1aa | $^{1}$H NMR (400 MHz, MeOH-d4): δ ppm 1.59 (d, J = 4.69 Hz, 4 H) 1.99-2.13 (m, 1 H) 2.24-2.39 (m, 1 H) 3.03-3.14 (m, 1 H) 3.17-3.27 (m, 1 H) 3.38-3.54 (m, 2 H) 3.55-3.75 (m, 2 H) 3.99-4.14 (m, 1 H) 5.56 (s, 1 H) 6.46 (d, J = 2.93 Hz, 1 H) 6.58-6.71 (m, 1 H) 7.27 (d, J = 3.12 Hz, 1 H) 7.29-7.36 (m, 1 H) 7.54-7.66 (m, 4 H) 7.70 (d, J = 8.20 Hz, 2 H) |
| 1ab | $^{1}$H NMR (400 MHz, MeOH-d4): δ ppm 1.52-1.62 (m, 4 H) 1.92 (s, 5 H) 1.99-2.09 (m, 1 H) 2.27 (dd, J = 13.42, 9.22 Hz, 1 H) 2.38 (s, 3 H) 3.06-3.26 (m, 2 H) 3.39-3.73 (m, 4 H) 4.00-4.08 (m, 1 H) 4.13 (s, 2 H) 5.72 (s, 1 H) 6.41 (d, J = 2.29 Hz, 1 H) 6.78 (q, J = 6.49 Hz, 1 H) 7.53 (d, J = 8.30 Hz, 2 H) 7.66 (d, J = 1.66 Hz, 1 H) 7.73-7.84 (m, 4 H) 7.97 (d, J = 2.25 Hz, 1 H) |
| 1ac | $^{1}$H NMR (400 MHz, MeOH-d4): δ ppm 1.51-1.70 (m, 4 H) 2.06 (dd, J = 13.37, 7.13 Hz, 1 H) 2.31 (dd, J = 13.28, 9.37 Hz, 1 H) 2.41 (s, 3 H) 3.08-3.19 (m, 1 H) 3.20-3.29 (m, 1 H) 3.39-3.78 (m, 4 H), 4.01-4.19 (m, 1 H) 5.75 (s, 1 H) 6.43 (d, J = 2.15 Hz, 1 H) 6.84 (d, J = 6.64 Hz, 1 H) 7.06-7.19 (m, 1 H) 7.37-7.52 (m, 3 H) 7.65 (d, J = 1.56 Hz, 1 H) 7.70-7.77 (m, 1 H) 7.78-7.86 (m, 1 H) 8.00 (d, J = 2.15 Hz, 1 H) |
| 1ad | $^{1}$H NMR (400 MHz, MeOH-d4): δ ppm 1.53-1.68 (m, 4 H) 2.00-2.11 (m, 1 H) 2.25-2.36 (m, 1 H) 2.44 (s, 3 H) 3.03-3.13 (m, 1 H) 3.18-3.26 (m, 1 H) 3.42-3.60 (m, 2 H) 3.62-3.80 (m, 2 H) 3.98-4.12 (m, 1 H) 5.73-5.86 (m, 1 H) 6.38-6.53 (m, 1 H) 6.80-6.96 (m, 1 H) 7.56-7.64 (m, 1 H) 7.82-7.93 (m, 2 H) 7.93-8.00 (m, 1 H) 8.03-8.09 (m, 1 H) 8.16 (s, 2 H) 8.28-8.38 (m, 1 H), 8.42-8.55 (m, 1 H) 8.80-8.97 (m, 1 H) |
| 1ae | $^{1}$H NMR (400 MHz, MeOH-d4): δ ppm 0.89 (t, J = 6.7 Hz, 1H), 1.30 (d, J = 16.8 Hz, 3H), 1.57 (q, J = 8.1, 5.5 Hz, 4H), 1.98 (m, 1H), 2.24 (m, 1H), 2.38 (d, J = 10.5 Hz, 6H), 2.99 (d, J = 11.6 Hz, 1H), 3.16 (d, J = 11.5 Hz, 1H), 3.48 (ddt, J = 20.2, 13.1, 6.1 Hz, 3H), 3.65 (dd, J = 13.9, 6.2 Hz, 2H), 3.96 (t, J = 8.0 Hz, 1H), 5.75 (s, 1H), 6.41 (d, J = 2.3 Hz, 1H), 6.77 (q, J = 6.6 Hz, 1H), 7.26 (d, J = 7.8 Hz, 2H), 7.58 (m, 3H), 7.74 (m, 2H), 7.96 (d, J = 2.4 Hz, 1H) |
| 1af | $^{1}$H NMR (400 MHz, MeOH-d4): δ ppm 0.90 (m, 1H), 1.27 (m, 5H), 1.51 (dt, J = 10.5, 5.6 Hz, 4H), 1.75 (dd, J = 13.1, 7.2 Hz, 1H), 2.09 (dd, J = 13.1, 8.7 Hz, 1H), 2.40 (s, 3H), 2.76 (d, J = 11.0 Hz, 1H), 2.90 (d, J = 11.0 Hz, 1H), 3.54 (m, 4H), 3.84 (dd, J = 8.7, 7.2 Hz, 1H), 4.19 (qd, J = 7.1, 1.7 Hz, 2H), 5.73 (s, 1H), 6.43 (d, J = 2.4 Hz, 1H), 6.84 (q, J = 6.5 Hz, 1H), 7.64 (m, 3H), 7.80 (m, 3H), 8.01 (d, J = 2.4 Hz, 1H) |
| 1ag | $^{1}$H NMR (400 MHz, MeOH-d4): δ ppm 1.29 (d, J = 14.8 Hz, 1H), 1.58 (s, 8H), 2.05 (m, 2H), 2.39 (s, 8H), 3.12 (d, J = 11.1 Hz, 2H), 3.24 (d, J = 11.2 Hz, 3H), 3.47 (s, 3H), 3.53 (s, 1H), 3.64 (s, 4H), 4.11 (s, 2H), 4.96 (s, 1H), 6.42 (d, J = 2.0 Hz, 2H), 6.83 (q, J = 6.6 Hz, 2H), 7.33 (q, J = 9.0 Hz, 2H), 7.47 (t, J = 6.1 Hz, 2H), 7.65 (m, 6H), 7.79 (d, J = 8.1 Hz, 2H), 7.99 (d, J = 2.0 Hz, 2H) |
| 1ah | $^{1}$H NMR (400 MHz, MeOH-d4): δ ppm 1.29 (d, J = 10.2 Hz, 1H), 1.57 (t, J = 5.3 Hz, 5H), 2.04 (dd, J = 13.2, 6.9 Hz, 1H), 2.34 (m, 5H), 3.09 (d, J = 11.8 Hz, 1H), 3.22 (m, 2H), 3.48 (dd, J = 25.5, 12.5 Hz, 3H), 3.64 (s, 3H), 4.06 (t, J = 7.9 Hz, 1H), 4.83 (s, 2H), 4.93 (s, 1H), 5.74 (s, 1H), 6.41 (d, J = 2.4 Hz, 1H), 6.81 (q, J = 6.7 Hz, 1H), 7.45 (d, J = 8.2 Hz, 2H), 7.65 (m, 3H), 7.76 (m, 3H), 7.98 (d, J = 2.3 Hz, 1H) |
| 1ai | $^{1}$H NMR (400 MHz, MeOH-d4): δ ppm 0.91 (tt, J = 8.8, 4.7 Hz, 1H), 1.32 (m, 3H), 1.58 (h, J = 5.2, 4.4 Hz, 8H), 1.99 (m, 2H), 2.25 (dd, J = 13.4, 9.0 Hz, 2H), 2.40 (s, 6H), 3.03 (d, J = 11.5 Hz, 2H), 3.18 (d, J = 11.5 Hz, 2H), 3.48 (ddt, J = 21.1, 13.0, 5.9 Hz, 5H), 3.62 (dt, J = 11.3, 6.3 Hz, 4H), 3.98 (t, J = 7.9 Hz, 2H), 5.73 (s, 2H), 6.44 (d, J = 2.4 Hz, 2H), 6.90 (q, J = 6.6 Hz, 2H), 7.86 (m, 6H), 8.04 (d, J = 2.4 Hz, 2H), 9.15 (d, J = 11.9 Hz, 6H) |
| 1ak | $^{1}$H NMR (400 MHz, MeOH-d4): δ ppm 1.28 (s, 1H), 1.67 (dt, J = 11.3, 5.3 Hz, 4H), 2.08 (dd, J = 13.6, 8.1 Hz, 1H), 2.40 (m, 4H), 3.25 (q, J = 11.8, 9.3 Hz, 3H), 3.67 (m, 4H), 4.43 (t, J = 8.5 Hz, 1H), 6.44 (d, J = 2.4 Hz, 1H), 6.95 (q, J = 6.3 Hz, 1H), 7.77 (dt, J = 5.4, 1.8 Hz, 2H), 7.86 (d, J = 1.4 Hz, 2H), 7.96 (m, 1H), 8.05 (d, J = 2.4 Hz, 2H) |
| 1al | $^{1}$H NMR (400 MHz, MeOH-d4): δ ppm 1.28 (s, 1H), 1.44 (t, J = 7.0 Hz, 3H), 1.57 (t, J = 5.6 Hz, 4H), 2.02 (dd, J = 13.4, 7.0 Hz, 1H), 2.28 (dd, J = 13.3, 9.1 Hz, 1H), 2.39 (s, 3H), 3.06 (d, J = 11.6 Hz, 1H), 3.21 (d, J = 11.6 Hz, 1H), 3.47 (dd, J = 22.4, 13.7 Hz, |

TABLE 1b-continued

| 1H NMR Data for Compounds of Table 1a | |
|---|---|
| Ex. No. | 1H NMR |
| | 3H), 3.65 (dd, J = 13.8, 6.9 Hz, 2H), 4.03 (t, J = 8.1 Hz, 1H), 4.14 (q, J = 7.0 Hz, 2H), 4.93 (s, 2H), 5.75 (s, 1H), 6.41 (d, J = 2.3 Hz, 1H), 6.78 (q, J = 6.6 Hz, 1H), 7.12 (d, J = 8.7 Hz, 1H), 7.57 (m, 2H), 7.73 (m, 3H), 7.98 (d, J = 2.4 Hz, 1H) |
| 1am | $^{1}$H NMR (400 MHz, MeOH-d4): δ ppm 1.29 (d, J = 3.7 Hz, 2H), 1.55 (m, 4H), 1.92 (dd, J = 13.4, 7.2 Hz, 1H), 2.19 (t, J = 10.6 Hz, 1H), 2.40 (s, 3H), 2.88 (d, J = 11.4 Hz, 1H), 3.10 (d, J = 11.5 Hz, 1H), 3.47 (dd, J = 22.2, 15.6 Hz, 3H), 3.64 (s, 3H), 3.85 (t, J = 8.1 Hz, 1H), 5.74 (s, 1H), 6.43 (d, J = 2.4 Hz, 1H), 6.83 (q, J = 6.6 Hz, 1H), 7.69 (m, 3H), 7.82 (m, 2H), 7.99 (m, 3H) |
| 1an | $^{1}$H NMR (400 MHz, MeOH-d4): δ ppm 1.17 (t, J = 7.0 Hz, 1H), 1.29 (m, 1H), 1.57 (d, J = 5.9 Hz, 4H), 2.00 (dd, J = 13.4, 7.0 Hz, 1H), 2.26 (dd, J = 13.1, 9.4 Hz, 1H), 2.38 (d, J = 9.1 Hz, 6H), 3.03 (d, J = 11.6 Hz, 1H), 3.18 (d, J = 11.5 Hz, 1H), 3.47 (ddt, J = 20.8, 13.2, 6.0 Hz, 2H), 3.62 (h, J = 7.1, 6.4 Hz, 3H), 4.00 (t, J = 7.9 Hz, 1H), 4.89 (s, 9H), 5.74 (s, 1H), 6.41 (d, J = 2.3 Hz, 1H), 6.82 (q, J = 6.9, 6.4 Hz, 1H), 7.21 (s, 1H), 7.40 (s, 1H), 7.45 (s, 1H), 7.60 (d, J = 1.9 Hz, 1H), 7.68 (dd, J = 8.0, 1.8 Hz, 1H), 7.78 (d, J = 8.2 Hz, 1H), 7.99 (d, J = 2.3 Hz, 1H) |
| 1ao | $^{1}$H NMR (400 MHz, MeOH-d4): δ ppm 1.28 (m, 2H), 1.55 (q, J = 7.5, 5.1 Hz, 4H), 1.94 (dd, J = 13.2, 6.9 Hz, 1H), 2.21 (dd, J = 13.1, 8.9 Hz, 1H), 2.39 (s, 3H), 2.94 (d, J = 11.5 Hz, 1H), 3.12 (d, J = 11.2 Hz, 1H), 3.46 (ddt, J = 20.2, 13.0, 5.9 Hz, 2H), 3.63 (dd, J = 13.7, 6.1 Hz, 2H), 3.90 (t, J = 8.0 Hz, 1H), 4.85 (d, J = 9.0 Hz, 1H), 5.73 (s, 1H), 6.42 (d, J = 2.4 Hz, 1H), 6.83 (q, J = 6.6 Hz, 1H), 7.57 (m, 4H), 7.77 (m, 2H), 8.00 (d, J = 2.4 Hz, 1H) |
| 1ap | $^{1}$H NMR (400 MHz, MeOH-d4): δ ppm 1.29 (d, J = 11.9 Hz, 2H), 1.39 (t, J = 7.0 Hz, 3H), 1.59 (t, J = 5.7 Hz, 4H), 2.05 (dd, J = 13.4, 7.2 Hz, 1H), 2.39 (s, 4H), 3.12 (d, J = 11.6 Hz, 1H), 3.24 (d, J = 11.7 Hz, 1H), 3.51 (ddt, J = 25.1, 13.2, 5.8 Hz, 2H), 3.67 (dd, J = 13.8, 5.7 Hz, 2H), 4.10 (dq, J = 14.0, 7.7, 7.0 Hz, 3H), 6.41 (d, J = 2.3 Hz, 1H), 6.79 (q, J = 6.6 Hz, 1H), 6.93 (dd, J = 8.2, 2.5 Hz, 1H), 7.19 (m, 2H), 7.34 (t, J = 7.9 Hz, 1H), 7.62 (d, J = 1.8 Hz, 1H), 7.75 (m, 2H), 7.97 (d, J = 2.4 Hz, 1H) |
| 1aq | $^{1}$H NMR (400 MHz, MeOH-d4): δ ppm 0.89 (t, J = 7.2 Hz, 1H), 1.28 (s, 4H), 1.58 (t, J = 5.6 Hz, 4H), 2.05 (dd, J = 13.5, 7.1 Hz, 1H), 2.29 (d, J = 1.8 Hz, 4H), 2.39 (s, 3H), 3.10 (d, J = 11.8 Hz, 1H), 3.24 (d, J = 11.5 Hz, 1H), 3.49 (ddt, J = 21.1, 12.9, 5.8 Hz, 3H), 3.68 (ddt, J = 18.9, 12.4,6.2 Hz, 3H), 4.07 (m, 1H), 5.75 (s, 1H), 6.41 (d, J = 2.3 Hz, 1H), 6.80 (q, J = 6.5 Hz, 1H), 7.37 (m, 3H), 7.63 (d, J = 1.8 Hz, 1H), 7.76 (m, 2H), 7.98 (d, J = 2.3 Hz, 1H) |
| 1ar | $^{1}$H NMR (400 MHz, MeOH-d4): δ ppm 1.57 (t, J = 5.8 Hz, 4H), 1.99 (dd, J = 13.3, 7.0 Hz, 1H), 2.25 (dd, J = 13.3, 9.1 Hz, 1H), 2.39 (s, 3H), 3.00 (d, J = 11.3 Hz, 1H), 3.17 (d, J = 11.5 Hz, 1H), 3.31 (d, J = 2.4 Hz, 4H), 3.49 (m, 2H), 3.65 (dd, J = 13.8, 6.6 Hz, 2H), 3.97 (t, J = 8.1 Hz, 1H), 5.74 (s, 1H), 6.42 (d, J = 2.3 Hz, 1H), 6.83 (q, J = 6.6 Hz, 1H), 7.33 (t, J = 8.8 Hz, 1H), 7.65 (m, 2H), 7.73 (dd, J = 8.2, 1.9 Hz, 1H), 7.82 (m, 2H), 8.00 (d, J = 2.3 Hz, 1H) |
| 1as | $^{1}$H NMR (400 MHz, MeOH-d4): δ ppm 1.28 (s, 1H), 1.60 (m, 4H), 2.05 (dd, J = 13.4, 7.1 Hz, 1H), 2.32 (dd, J = 13.4, 9.1 Hz, 1H), 2.40 (s, 3H), 3.12 (d, J = 11.7 Hz, 1H), 3.24 (d, J = 11.7 Hz, 1H), 3.51 (dq, J = 24.6, 7.3, 6.5 Hz, 2H), 3.66 (dt, J = 11.7, 6.2 Hz, 2H), 4.11 (dd, J = 9.1, 7.1 Hz, 1H), 6.42 (d, J = 2.3 Hz, 1H), 6.83 (q, J = 6.3 Hz, 1H), 7.32 (m, 1H), 7.58 (dd, J = 15.5, 7.5 Hz, 2H), 7.69 (m, 2H), 7.80 (m, 2H), 8.01 (d, J = 2.3 Hz, 1H) |
| 1at | $^{1}$H NMR (400 MHz, MeOH-d4): δ ppm 1.28 (s, 1H), 1.57 (m, 4H), 1.97 (dd, J = 13.1, 6.8 Hz, 1H), 2.23 (m, 2H), 2.37 (d, J = 18.2 Hz, 9H), 2.98 (d, J = 11.6 Hz, 1H), 3.15 (d, J = 11.5 Hz, 1H), 3.48 (ddt, J = 20.5, 13.0, 5.8 Hz, 2H), 3.65 (dd, J = 13.4, 5.8 Hz, 2H), 3.94 (dd, J = 9.1, 7.1 Hz, 1H), 5.75 (s, 1H), 6.41 (d, J = 2.3 Hz, 1H), 6.78 (q, J = 6.6 Hz, 1H), 7.03 (s, 1H), 7.27 (d, J = 1.6 Hz, 2H), 7.59 (d, J = 1.8 Hz, 1H), 7.73 (m, 2H), 7.97 (d, J = 2.4 Hz, 1H) |
| 1au | $^{1}$H NMR (400 MHz, MeOH-d4): δ ppm 1.29 (d, J = 3.4 Hz, 2H), 1.60 (t, J = 5.7 Hz, 4H), 2.06 (dd, J = 13.5, 7.2 Hz, 1H), 2.39 (s, 4H), 3.13 (d, J = 11.7 Hz, 1H), 3.25 (d, J = 11.7 Hz, 1H), 3.52 (m, 2H), 3.67 (dt, J = 12.0, 6.4 Hz, 2H), 4.14 (dd, J = 9.1, 7.2 Hz, 1H), 4.91 (s, 1H), 6.42 (d, J = 2.4 Hz, 1H), 6.83 (q, J = 6.6 Hz, 1H), 7.36 (dt, J = 10.4, 8.4 Hz, 1H), 7.51 (ddt, J = 8.1, 3.9, 1.6 Hz, 1H), 7.65 (m, 2H), 7.77 (m, 2H), 7.99 (d, J = 2.3 Hz, 1H) |
| 1av | $^{1}$H NMR (400 MHz, MeOH-d4): δ ppm 1.57 (dt, J = 6.7, 3.0 Hz, 4H), 1.98 (dd, J = 13.3, 7.0 Hz, 1H), 2.24 (dd, J = 13.4, 9.2 Hz, 1H), 2.40 (s, 3H), 2.99 (d, J = 11.5 Hz, 1H), 3.16 (d, J = 11.5 Hz, 1H), 3.48 (ddt, J = 20.5, 13.2, 5.9 Hz, 2H), 3.65 (dq, J = 11.1, 5.0 Hz, 2H), 3.95 (t, J = 8.2 Hz, 1H), 5.74 (s, 1H), 6.42 (d, J = 2.4 Hz, 1H), 6.84 (q, J = 6.6 Hz, 1H), 6.99 (tt, J = 9.0, 2.3 Hz, 1H), 7.35 (m, 2H), 7.68 (d, J = 1.9 Hz, 1H), 7.79 (m, 2H), 8.02 (d, J = 2.4 Hz, 1H) |
| 1aw | $^{1}$H NMR (400 MHz, MeOH-d4): δ ppm 0.89 (m, 1H), 1.30 (d, J = 13.3 Hz, 2H), 1.51 (q, J = 6.5, 5.7 Hz, 5H), 1.77 (dd, J = 13.0, 6.9 Hz, 1H), 2.05 (dd, J = 13.0, 8.9 Hz, 1H), 2.40 (s, 3H), 2.62 (d, J = 11.0 Hz, 1H), 2.93 (d, J = 11.0 Hz, 1H), 3.42 (d, J = 14.2 Hz, 2H), 3.49 (s, 1H), 3.62 (dt, J = 16.7, 6.6 Hz, 3H), 5.72 (s, 1H), 6.42 (d, J = 2.4 Hz, 1H), 6.83 (q, J = 6.6 Hz, 1H), 7.44 (m, 1H), 7.69 (d, J = 1.9 Hz, 1H), 7.81 (m, 2H), 8.01 (m, 3H) |
| 1ax | $^{1}$H NMR (400 MHz, MeOH-d4): δ ppm 0.89 (m, 2H), 1.32 (m, 13H), 1.57 (t, J = 5.4 Hz, 4H), 2.01 (m, 1H), 2.29 (dd, J = 13.4, 9.2 Hz, 1H), 2.39 (s, 3H), 2.80 (s, 1H), 3.07 (d, J = 11.6 Hz, 1H), 3.17 (s, 1H), 3.50 (m, 2H), 3.66 (d, J = 13.8 Hz, 2H), 4.03 (t, J = 8.1 Hz, 1H), 4.65 (p, J = 6.1 Hz, 1H), 5.75 (s, 1H), 6.41 (d, J = 2.4 Hz, 1H), 6.78 (q, J = 6.6 Hz, 1H), 7.16 (t, J = 8.6 Hz, 1H), 7.45 (m, 2H), 7.61 (d, J = 1.8 Hz, 1H), 7.74 (m, 2H), 7.98 (d, J = 2.4 Hz, 1H) |

TABLE 1b-continued

| 1H NMR Data for Compounds of Table 1a | |
|---|---|
| Ex. No. | 1H NMR |
| 1ay | $^{1}$H NMR (400 MHz, MeOH-d4): δ ppm 0.88 (m, 2H), 1.28 (s, 2H), 1.39 (t, J = 7.0 Hz, 3H), 1.59 (d, J = 5.6 Hz, 4H), 2.04 (dd, J = 13.5, 7.1 Hz, 1H), 2.39 (s, 4H), 3.10 (d, J = 11.7 Hz, 1H), 3.24 (m, 1H), 3.49 (ddt, J = 25.3, 13.1, 5.9 Hz, 2H), 3.66 (dq, J = 12.1, 5.6 Hz, 2H), 4.07 (dq, J = 12.7, 7.2 Hz, 3H), 5.75 (s, 1H), 6.42 (d, J = 2.4 Hz, 1H), 6.71 (dt, J = 10.8, 2.2 Hz, 1H), 6.80 (p, J = 6.6 Hz, 1H), 7.01 (m, 2H), 7.63 (d, J = 1.8 Hz, 1H), 7.76 (m, 2H), 8.00 (d, J = 2.4 Hz, 1H) |
| 1az | $^{1}$H NMR (400 MHz, MeOH-d4): δ ppm 0.90 (m, 1H), 1.36 (s, 13H), 1.59 (m, 4H), 2.05 (dd, J = 13.4, 6.9 Hz, 1H), 2.33 (dt, J = 13.7, 6.0 Hz, 1H), 2.40 (s, 3H), 3.12 (d, J = 11.4 Hz, 1H), 3.24 (d, J = 12.1 Hz, 1H), 3.40 (s, 1H), 3.53 (d, J = 14.7 Hz, 1H), 3.68 (d, J = 13.4 Hz, 2H), 4.10 (s, 1H), 4.76 (m, 5H), 4.83 (s, 2H), 5.01 (s, 1H), 6.42 (d, J = 2.2 Hz, 1H), 6.77 (q, J = 6.6 Hz, 1H), 7.42 (m, 3H), 7.65 (m, 4H), 7.76 (m, 2H), 7.98 (d, J = 2.3 Hz, 1H) |
| 1ba | $^{1}$H NMR (400 MHz, MeOH-d4): δ ppm 1.30 (d, J = 12.1 Hz, 3H), 1.59 (t, J = 5.2 Hz, 4H), 2.05 (dd, J = 13.4, 7.0 Hz, 1H), 2.34 (m, 7H), 3.11 (d, J = 11.7 Hz, 1H), 3.24 (d, J = 11.8 Hz, 1H), 3.51 (m, 2H), 3.68 (dt, J = 13.1, 6.3 Hz, 2H), 4.09 (dd, J = 9.2, 6.9 Hz, 1H), 6.41 (d, J = 2.3 Hz, 1H), 6.79 (q, J = 6.7 Hz, 1H), 7.11 (t, J = 9.1 Hz, 1H), 7.55 (m, 3H), 7.74 (m, 2H), 7.98 (d, J = 2.3 Hz, 1H) |
| 1bb | $^{1}$H NMR (400 MHz, MeOH-d4): δ ppm 1.28 (d, J = 6.9 Hz, 6H), 1.59 (t, J = 5.6 Hz, 4H), 2.05 (dd, J = 13.4, 6.9 Hz, 1H), 2.32 (dd, J = 13.4, 8.9 Hz, 1H), 2.40 (s, 3H), 2.96 (h, J = 6.8 Hz, 1H), 3.12 (d, J = 11.8 Hz, 1H), 3.24 (d, J = 11.7 Hz, 1H), 3.51 (m, 2H), 3.67 (m, 2H), 4.10 (t, J = 8.3 Hz, 1H), 6.41 (d, J = 2.3 Hz, 1H), 6.78 (q, J = 6.5 Hz, 1H), 7.27 (m, 1H), 7.37 (t, J = 7.7 Hz, 1H), 7.48 (m, 2H), 7.62 (d, J = 1.8 Hz, 1H), 7.76 (m, 2H), 7.98 (d, J = 2.4 Hz, 1H) |
| 1bc | $^{1}$H NMR (400 MHz, MeOH-d4): δ ppm 0.89 (m, 1H), 1.29 (m, 9H), 1.55 (d, J = 5.8 Hz, 4H), 1.99 (m, 1H), 2.26 (dd, J = 13.4, 9.1 Hz, 1H), 2.39 (s, 3H), 3.04 (d, J = 11.6 Hz, 1H), 3.17 (d, J = 11.6 Hz, 1H), 3.47 (ddt, J = 20.9, 13.0, 5.9 Hz, 2H), 3.62 (dq, J = 11.5, 5.7 Hz, 2H), 4.01 (m, 1H), 4.64 (hept, J = 5.9 Hz, 1H), 5.74 (s, 1H), 6.41 (d, J = 2.4 Hz, 1H), 6.79 (q, J = 6.6 Hz, 1H), 6.91 (dd, J = 8.1, 2.4 Hz, 1H), 7.16 (ddd, J = 8.5, 5.3, 1.7 Hz, 2H), 7.32 (t, J = 7.9 Hz, 1H), 7.64 (m, 3H), 7.77 (d, J = 8.3 Hz, 1H), 7.97 (d, J = 2.4 Hz, 1H) |
| 1bd | $^{1}$H NMR (400 MHz, MeOH-d4): δ ppm 1.28 (s, 1H), 1.59 (d, J = 5.6 Hz, 4H), 2.05 (dd, J = 13.4, 7.0 Hz, 1H), 2.31 (dd, J = 13.4, 9.3 Hz, 1H), 2.41 (d, J = 11.1 Hz, 6H), 3.11 (d, J = 11.7 Hz, 1H), 3.24 (d, J = 11.7 Hz, 1H), 3.49 (ddd, J = 27.1, 12.8, 5.9 Hz, 2H), 3.66 (dq, J = 13.8, 6.0 Hz, 2H), 4.07 (dd, J = 9.2, 7.0 Hz, 1H), 5.75 (s, 1H), 6.42 (d, J = 2.4 Hz, 1H), 6.80 (q, J = 6.6 Hz, 1H), 7.45 (m, 2H), 7.63 (dd, J = 7.2, 2.0 Hz, 2H), 7.76 (m, 2H), 7.98 (d, J = 2.3 Hz, 1H) |
| 1be | $^{1}$H NMR (400 MHz, MeOH-d4): δ ppm 1.29 (d, J = 3.9 Hz, 4H), 1.59 (t, J = 5.8 Hz, 7H), 2.05 (dd, J = 13.3, 7.0 Hz, 2H), 2.31 (dd, J = 13.4, 9.2 Hz, 2H), 2.40 (s, 5H), 3.11 (d, J = 11.7 Hz, 2H), 3.24 (m, 4H), 3.50 (dq, J = 23.7, 7.4, 6.5 Hz, 4H), 3.67 (dq, J = 13.1, 6.4 Hz, 4H), 4.09 (t, J = 8.1 Hz, 2H), 4.84 (s, 1H), 4.93 (s, 1H), 6.42 (d, J = 2.3 Hz, 2H), 6.84 (q, J = 6.5 Hz, 2H), 7.57 (t, J = 7.8 Hz, 2H), 7.74 (s, 2H), 7.88 (m, 7H), 7.99 (d, J = 2.4 Hz, 2H), 8.19 (t, J = 1.9 Hz, 2H) |
| 1bf | $^{1}$H NMR (400 MHz, MeOH-d4): δ ppm 1.57 (t, J = 5.7 Hz, 4H), 1.99 (dd, J = 13.3, 7.0 Hz, 1H), 2.25 (dd, J = 13.3, 9.1 Hz, 1H), 2.41 (s, 3H), 3.01 (d, J = 11.6 Hz, 1H), 3.17 (d, J = 11.5 Hz, 1H), 3.48 (dq, J = 23.5, 7.0, 6.5 Hz, 2H), 3.64 (dd, J = 13.0, 5.8 Hz, 2H), 3.97 (dd, J = 9.0, 7.1 Hz, 1H), 5.73 (s, 1H), 6.44 (d, J = 2.4 Hz, 1H), 6.87 (q, J = 6.6 Hz, 1H), 7.79 (d, J = 1.8 Hz, 1H), 7.88 (m, 2H), 8.00 (s, 1H), 8.07 (d, J = 2.3 Hz, 1H), 8.29 (s, 2H) |
| 1bg | $^{1}$H NMR (400 MHz, MeOH-d4): δ ppm 1.28 (s, 1H), 1.43 (t, J = 7.0 Hz, 3H), 1.64 (q, J = 5.8 Hz, 4H), 2.08 (dd, J = 13.5, 7.7 Hz, 1H), 2.40 (s, 4H), 3.23 (m, 2H), 3.64 (m, 4H), 4.18 (q, J = 7.0 Hz, 2H), 4.32 (t, J = 8.4 Hz, 1H), 6.42 (d, J = 2.4 Hz, 1H), 6.83 (q, J = 6.4 Hz, 1H), 7.20 (m, 2H), 7.36 (dd, J = 8.0, 2.1 Hz, 1H), 7.65 (d, J = 1.6 Hz, 1H), 7.77 (m, 2H), 7.99 (d, J = 2.4 Hz, 1H) |
| 1bh | $^{1}$H NMR (400 MHz, MeOH-d4): δ ppm 1.28 (s, 1H), 1.59 (d, J = 5.4 Hz, 4H), 2.04 (dd, J = 13.4, 7.0 Hz, 1H), 2.29 (m, 2H), 2.41 (d, J = 9.6 Hz, 9H), 3.10 (d, J = 11.7 Hz, 1H), 3.24 (m, 1H), 3.49 (ddt, J = 20.7, 13.0, 6.0 Hz, 2H), 3.65 (dt, J = 13.2, 7.2 Hz, 2H), 4.06 (dd, J = 9.2, 7.1 Hz, 1H), 5.75 (s, 1H), 6.41 (d, J = 2.4 Hz, 1H), 6.79 (q, J = 6.6 Hz, 1H), 7.45 (s, 2H), 7.62 (d, J = 1.8 Hz, 1H), 7.75 (m, 2H), 7.98 (d, J = 2.4 Hz, 1H) |
| 1bi | $^{1}$H NMR (400 MHz, MeOH-d4): δ ppm 1.57 (m, 4H), 1.99 (dd, J = 13.4, 7.1 Hz, 1H), 2.26 (dd, J = 13.3, 9.1 Hz, 1H), 2.40 (s, 3H), 3.02 (d, J = 11.6 Hz, 1H), 3.18 (d, J = 11.6 Hz, 1H), 3.48 (dq, J = 23.5, 7.1, 6.6 Hz, 2H), 3.64 (dq, J = 11.4, 5.5 Hz, 2H), 3.99 (dd, J = 9.2, 7.0 Hz, 1H), 5.73 (s, 1H), 6.42 (d, J = 2.4 Hz, 1H), 6.85 (q, J = 6.6 Hz, 1H), 7.46 (t, J = 1.9 Hz, 1H), 7.66 (t, J = 1.8 Hz, 3H), 7.73 (dd, J = 8.3, 2.0 Hz, 1H), 7.82 (d, J = 8.1 Hz, 1H), 8.02 (d, J = 2.4 Hz, 1H) |
| 1bj | $^{1}$H NMR (400 MHz, MeOH-d4): δ ppm 1.28 (m, 1H), 1.34 (s, 10H), 1.61 (t, J = 5.9 Hz, 4H), 2.06 (dd, J = 13.5, 7.3 Hz, 1H), 2.39 (m, 7H), 3.14 (d, J = 11.6 Hz, 1H), 3.25 (m, 1H), 3.55 (m, 2H), 3.68 (s, 2H), 4.18 (dd, J = 9.0, 7.3 Hz, 1H), 6.42 (d, J = 2.3 Hz, 1H), 6.78 (q, J = 6.5 Hz, 1H), 7.28 (m, 2H), 7.45 (t, J = 1.7 Hz, 1H), 7.60 (d, J = 1.8 Hz, 1H), 7.75 (m, 2H), 7.98 (d, J = 2.3 Hz, 1H) |
| 1bk | $^{1}$H NMR (400 MHz, MeOH-d4): δ ppm 1.28 (s, 2H), 1.58 (t, J = 5.5 Hz, 4H), 2.04 (dd, J = 13.3, 6.9 Hz, 1H), 2.30 (dd, J = 13.3, 9.1 Hz, 1H), 2.40 (s, 3H), 3.09 (d, J = 11.7 Hz, 1H), 3.23 (d, J = 12.2 Hz, 1H), 3.51 (m, 2H), 3.66 (dd, J = 13.9, 6.6 Hz, 2H), 4.05 (t, J = 8.2 Hz, 1H), 4.62 (s, 1H), 5.75 (s, 1H), 6.42 (d, J = 2.4 Hz, 1H), 6.82 (q, J = 6.5 Hz, 1H), 7.43 (m, 2H), 7.63 (m, 2H), 7.75 (m, 3H), 8.00 (d, J = 2.3 Hz, 1H) |

TABLE 1b-continued

| 1H NMR Data for Compounds of Table 1a | |
|---|---|
| Ex. No. | 1H NMR |
| 1bl | $^1$H NMR (400 MHz, MeOH-d4): δ ppm 1.57 (t, J = 5.6 Hz, 4H), 2.00 (dd, J = 13.5, 7.0 Hz, 1H), 2.26 (dd, J = 13.3, 9.1 Hz, 1H), 2.40 (s, 3H), 3.03 (d, J = 11.6 Hz, 1H), 3.18 (d, J = 11.5 Hz, 1H), 3.47 (ddd, J = 20.9, 14.0, 6.5 Hz, 2H), 3.64 (t, J = 7.4 Hz, 2H), 3.99 (dd, J = 9.1, 7.1 Hz, 1H), 5.74 (s, 1H), 6.43 (d, J = 2.3 Hz, 1H), 6.86 (q, J = 6.6 Hz, 1H), 7.81 (m, 5H), 7.98 (d, J = 1.6 Hz, 1H), 8.03 (d, J = 2.4 Hz, 1H) |
| 1bm | $^1$H NMR (400 MHz, MeOH-d4): 8 1.54 (d, J = 2.93 Hz, 4 H), 1.82-1.99 (m, 1 H), 2.09-2.24 (m, 1 H), 2.40 (s, 3 H), 2.79-2.93 (m, 1 H), 2.99-3.14 (m, 1 H), 3.37-3.55 (m, 2 H), 3.56-3.72 (m, 2 H), 3.82 (s, 4 H), 5.74 (s, 1 H), 6.41 (d, J = 2.15 Hz, 1 H), 6.70-6.84 (m, 1 H), 6.99 (d, J = 8.79 Hz, 2 H), 7.50-7.63 (m, 3 H), 7.64-7.71 (m, 1 H), 7.71-7.80 (m, 1 H), 7.95 (d, J = 2.15 Hz, 1 H) |
| 1bn | $^1$H NMR (400 MHz, MeOH-d4): δ ppm 0.89 (m, 1H), 1.28 (s, 2H), 1.42 (t, J = 7.0 Hz, 3H), 1.58 (t, J = 5.2 Hz, 4H), 2.05 (dd, J = 13.4, 7.0 Hz, 1H), 2.31 (dd, J = 13.4, 9.0 Hz, 1H), 2.39 (s, 3H), 3.11 (d, J = 11.8 Hz, 1H), 3.24 (d, J = 11.7 Hz, 1H), 3.51 (m, 2H), 3.67 (m, 2H), 4.13 (m, 3H), 4.63 (s, 1H), 5.75 (s, 1H), 6.41 (d, J = 2.3 Hz, 1H), 6.78 (q, J = 6.6 Hz, 1H), 7.15 (t, J = 8.6 Hz, 1H), 7.45 (m, 2H), 7.60 (d, J = 1.8 Hz, 1H), 7.73 (m, 2H), 7.97 (d, J = 2.4 Hz, 1H) |
| 1bo | $^1$H NMR (400 MHz, MeOH-d4): δ ppm 1.29 (d, J = 8.3 Hz, 1H), 1.59 (t, J = 5.3 Hz, 4H), 2.05 (dd, J = 13.5, 7.0 Hz, 1H), 2.32 (dd, J = 13.6, 9.2 Hz, 1H), 2.39 (s, 3H), 3.12 (d, J = 11.6 Hz, 1H), 3.25 (m, 1H), 3.49 (ddd, J = 24.6, 12.8, 5.8 Hz, 2H), 3.66 (dq, J = 12.7, 6.0 Hz, 2H), 4.09 (t, J = 8.1 Hz, 1H), 5.76 (s, 1H), 6.42 (d, J = 2.3 Hz, 1H), 6.85 (q, J = 6.6 Hz, 1H), 7.54 (m, 2H), 7.68 (d, J = 1.8 Hz, 1H), 7.78 (m, 2H), 8.01 (d, J = 2.3 Hz, 1H) |
| 1bp | $^1$H NMR (400 MHz, MeOH-d4): δ ppm 1.29 (d, J = 8.6 Hz, 1H), 1.59 (d, J = 5.9 Hz, 4H), 2.05 (dd, J = 13.5, 7.3 Hz, 1H), 2.39 (m, 7H), 3.13 (d, J = 11.6 Hz, 1H), 3.24 (m, 2H), 3.52 (dq, J = 25.3, 6.3 Hz, 2H), 3.68 (dd, J = 13.7, 5.9 Hz, 2H), 4.16 (m, 1H), 6.42 (d, J = 2.3 Hz, 1H), 6.82 (q, J = 6.5 Hz, 1H), 7.37 (d, J = 7.9 Hz, 1H), 7.51 (dd, J = 7.9, 2.0 Hz, 1H), 7.63 (d, J = 1.9 Hz, 1H), 7.73 (m, 3H), 7.98 (d, J = 2.4 Hz, 1H) |
| 1bq | $^1$H NMR (400 MHz, MeOH-d4): δ ppm 1.29 (d, J = 8.0 Hz, 1H), 1.59 (m, 4H), 2.05 (dd, J = 13.4, 7.0 Hz, 1H), 2.38 (d, J = 13.7 Hz, 7H), 3.13 (d, J = 11.7 Hz, 1H), 3.25 (d, J = 11.6 Hz, 1H), 3.53 (dt, J = 31.7, 10.3 Hz, 2H), 3.67 (dd, J = 13.5, 7.0 Hz, 2H), 4.15 (m, 1H), 4.89 (s, 17H), 6.42 (d, J = 2.4 Hz, 1H), 6.82 (q, J = 6.6 Hz, 1H), 7.32 (m, 1H), 7.61 (m, 4H), 7.76 (m, 2H), 7.99 (d, J = 2.3 Hz, 1H) |
| 1br | $^1$H NMR (400 MHz, MeOH-d4): δ ppm 0.90 (s, 1H), 1.29 (m, 8H), 1.60 (d, J = 7.7 Hz, 4H), 2.02 (m, 2H), 2.39 (s, 4H), 3.14 (d, J = 11.6 Hz, 1H), 3.25 (d, J = 11.4 Hz, 1H), 3.51 (m, 2H), 3.66 (dd, J = 13.6, 6.6 Hz, 2H), 4.11 (dt, J = 21.0, 7.6 Hz, 1H), 4.65 (h, J = 6.0 Hz, 1H), 6.42 (d, J = 2.3 Hz, 1H), 6.69 (dt, J = 10.9, 2.2 Hz, 1H), 6.82 (q, J = 6.3 Hz, 1H), 6.99 (m, 2H), 7.61 (d, J = 1.8 Hz, 1H), 7.71 (m, 1H), 7.78 (d, J = 8.1 Hz, 1H), 7.99 (d, J = 2.3 Hz, 1H) |
| 1bs | $^1$H NMR (400 MHz, MeOH-d4): δ ppm 0.09 (s, 1H), 0.90 (q, J = 8.4, 7.7 Hz, 1H), 1.29 (d, J = 8.6 Hz, 3H), 1.59 (d, J = 5.7 Hz, 5H), 2.05 (dd, J = 13.5, 6.9 Hz, 1H), 2.31 (dd, J = 13.6, 9.4 Hz, 1H), 2.40 (s, 3H), 3.13 (d, J = 11.6 Hz, 1H), 3.25 (m, 1H), 3.61 (m, 5H), 4.08 (m, 1H), 5.74 (s, 1H), 6.43 (d, J = 2.4 Hz, 1H), 6.85 (q, J = 6.7 Hz, 1H), 7.24 (dt, J = 8.5, 2.1 Hz, 1H), 7.45 (dt, J = 9.6, 2.0 Hz, 1H), 7.58 (t, J = 1.7 Hz, 1H), 7.68 (d, J = 1.9 Hz, 1H), 7.79 (m, 2H), 8.02 (d, J = 2.3 Hz, 1H) |
| 1bt | $^1$H NMR (400 MHz, MeOH-d4): δ ppm 1.28 (d, J = 1.7 Hz, 1H), 1.58 (t, J = 5.7 Hz, 4H), 2.03 (dd, J = 13.4, 7.0 Hz, 1H), 2.29 (dd, J = 13.4, 9.2 Hz, 1H), 2.40 (s, 3H), 3.07 (d, J = 11.6 Hz, 1H), 3.22 (d, J = 11.6 Hz, 1H), 3.49 (m, 2H), 3.65 (dd, J = 13.0, 6.7 Hz, 2H), 4.04 (dd, J = 9.2, 7.0 Hz, 1H), 5.73 (s, 1H), 6.43 (d, J = 2.4 Hz, 1H), 6.84 (q, J = 6.6 Hz, 1H), 7.77 (m, 5H), 7.92 (dd, J = 8.4, 2.2 Hz, 1H), 8.04 (dd, J = 14.2, 2.3 Hz, 2H) |
| 1bu | $^1$H NMR (400 MHz, MeOH-d4): δ ppm 1.60 (d, J = 5.4 Hz, 4H), 2.05 (dd, J = 13.5, 7.1 Hz, 1H), 2.40 (s, 4H), 3.11 (d, J = 11.7 Hz, 1H), 3.24 (d, J = 11.7 Hz, 1H), 3.49 (ddt, J = 21.1, 13.3, 6.0 Hz, 2H), 3.67 (dt, J = 12.9, 6.1 Hz, 2H), 4.07 (dd, J = 9.2, 7.1 Hz, 1H), 5.74 (s, 1H), 6.43 (d, J = 2.4 Hz, 1H), 6.86 (q, J = 6.6 Hz, 1H), 7.50 (m, 1H), 7.80 (m, 5H), 8.04 (d, J = 2.4 Hz, 1H) |
| 1bv | $^1$H NMR (400 MHz, MeOH-d4): δ ppm 1.35 (d, J = 6.0 Hz, 7H), 1.55 (d, J = 5.9 Hz, 4H), 1.98 (dd, J = 13.3, 7.0 Hz, 1H), 2.25 (dd, J = 13.3, 9.1 Hz, 1H), 2.39 (s, 2H), 3.01 (d, J = 11.5 Hz, 1H), 3.17 (d, J = 11.6 Hz, 1H), 3.47 (ddt, J = 20.8, 13.0, 6.0 Hz, 2H), 3.64 (dd, J = 13.9, 6.3 Hz, 2H), 3.98 (dd, J = 9.2, 7.1 Hz, 1H), 4.67 (p, J = 6.1 Hz, 1H), 4.89 (s, 11H), 5.74 (s, 1H), 6.41 (d, J = 2.4 Hz, 1H), 6.79 (q, J = 6.6 Hz, 1H), 7.13 (d, J = 8.7 Hz, 1H), 7.55 (m, 2H), 7.71 (m, 4H), 7.98 (d, J = 2.4 Hz, 1H) |
| 1bw | $^1$H NMR (400 MHz, MeOH-d4): δ ppm 1.54 (t, J = 5.7 Hz, 4H), 1.95 (dd, J = 13.3, 7.0 Hz, 1H), 2.22 (dd, J = 13.3, 9.0 Hz, 1H), 2.41 (s, 3H), 2.95 (d, J = 11.5 Hz, 1H), 3.13 (d, J = 11.4 Hz, 1H), 3.47 (ddt, J = 19.9, 12.9, 5.9 Hz, 2H), 3.64 (dd, J = 13.3, 6.4 Hz, 2H), 3.94 (t, J = 8.1 Hz, 1H), 4.91 (s, 10H), 5.77 (s, 1H), 6.43 (d, J = 2.3 Hz, 1H), 6.83 (q, J = 6.6 Hz, 1H), 7.49 (m, 2H), 7.83 (m, 7H), 8.01 (d, J = 2.4 Hz, 1H), 8.13 (d, J = 1.9 Hz, 1H) |
| 1bx | $^1$H NMR (400 MHz, MeOH-d4): δ ppm 1.59 (m, 4H), 2.05 (dd, J = 13.5, 7.2 Hz, 1H), 2.39 (s, 4H), 3.12 (d, J = 11.7 Hz, 1H), 3.24 (d, J = 11.8 Hz, 1H), 3.51 (m, 2H), 3.67 (dd, J = 13.7, 6.2 Hz, 2H), 4.13 (dd, J = 9.1, 7.2 Hz, 1H), 5.19 (s, 2H), 6.41 (d, J = 2.3 Hz, 1H), 6.79 (q, J = 6.5 Hz, 1H), 7.21 (t, J = 8.6 Hz, 1H), 7.42 (m, 7H), 7.60 (d, J = 1.8 Hz, 1H), 7.72 (m, 2H), 7.97 (d, J = 2.3 Hz, 1H) |
| 1by | $^1$H NMR (400 MHz, MeOH-d4): δ ppm 1.33 (dd, J = 6.1, 1.6 Hz, 6H), 1.58 (t, J = 5.2 Hz, 4H), 2.04 (dd, J = 13.5, 7.1 Hz, 1H), 2.22 (s, 3H), 2.35 (m, 4H), 3.10 (d, J = 11.8 Hz, 1H), 3.23 (d, J = 11.8 Hz, 1H), 3.49 (ddt, J = 20.8, 13.6, 5.9 Hz, 2H), 3.66 (dd, J = 13.6, 6.9 Hz, 2H), 4.07 (dd, J = 9.2, 7.1 Hz, 1H), 4.63 (p, J = 6.1 Hz, 1H), 5.76 (s, 1H), |

TABLE 1b-continued

| 1H NMR Data for Compounds of Table 1a | |
|---|---|
| Ex. No. | 1H NMR |
| | 6.41 (d, J = 2.4 Hz, 1H), 6.75 (q, J = 6.7 Hz, 1H), 6.97 (d, J = 8.2 Hz, 1H), 7.45 (d, J = 8.2 Hz, 2H), 7.57 (d, J = 1.8 Hz, 1H), 7.71 (m, 2H), 7.96 (d, J = 2.3 Hz, 1H) |
| 1bz | $^1$H NMR (400 MHz, MeOH-d4): δ ppm 1.06 (t, J = 7.4 Hz, 3H), 1.29 (m, 1H), 1.58 (d, J = 5.9 Hz, 4H), 1.83 (h, J = 7.1 Hz, 2H), 2.02 (dd, J = 13.4, 6.9 Hz, 1H), 2.29 (dd, J = 13.3, 9.1 Hz, 1H), 2.39 (s, 3H), 3.08 (d, J = 11.6 Hz, 1H), 3.21 (d, J = 11.5 Hz, 1H), 3.48 (ddd, J = 21.8, 12.6, 5.8 Hz, 2H), 3.65 (dd, J = 13.6, 7.3 Hz, 2H), 4.04 (q, J = 7.1, 6.4 Hz, 3H), 4.97 (s, 1H), 5.75 (s, 1H), 6.41 (d, J = 2.3 Hz, 1H), 6.78 (q, J = 6.5 Hz, 1H), 7.14 (t, J = 8.6 Hz, 1H), 7.44 (m, 2H), 7.59 (d, J = 1.9 Hz, 1H), 7.72 (m, 2H), 7.98 (d, J = 2.3 Hz, 1H) |
| 1ca | $^1$H NMR (400 MHz, MeOH-d4): δ ppm 0.99 (t, J = 7.4 Hz, 3H), 1.53 (m, 6H), 1.79 (dq, J = 8.6, 6.5 Hz, 2H), 1.93 (dd, J = 13.2, 7.0 Hz, 1H), 2.20 (dd, J = 13.3, 9.1 Hz, 1H), 2.39 (s, 3H), 2.91 (d, J = 11.4 Hz, 1H), 3.11 (d, J = 11.4 Hz, 1H), 3.47 (ddt, J = 20.0, 13.0, 5.9 Hz, 2H), 3.64 (dd, J = 13.8, 5.7 Hz, 2H), 3.88 (t, J = 8.0 Hz, 1H), 4.07 (t, J = 6.4 Hz, 2H), 5.75 (s, 1H), 6.41 (d, J = 2.4 Hz, 1H), 6.78 (q, J = 6.7 Hz, 1H), 7.14 (t, J = 8.6 Hz, 1H), 7.43 (m, 2H), 7.59 (d, J = 1.9 Hz, 1H), 7.71 (m, 2H), 7.98 (d, J = 2.4 Hz, 1H) |
| 1cb | $^1$H NMR (400 MHz, MeOH-d4): δ ppm 0.89 (s, 1H), 1.28 (s, 1H), 1.62 (d, J = 6.2 Hz, 8H), 2.06 (dd, J = 13.3, 7.3 Hz, 2H), 2.41 (s, 8H), 2.65 (s, 5H), 3.15 (d, J = 12.0 Hz, 2H), 3.25 (m, 2H), 3.52 (s, 3H), 3.58 (s, 2H), 3.70 (d, J = 13.3 Hz, 4H), 4.21 (t, J = 8.4 Hz, 2H), 5.89 (s, 1H), 6.00 (m, 1H), 6.44 (d, J = 2.3 Hz, 2H), 6.89 (q, J = 6.4 Hz, 2H), 7.80 (m, 10H), 8.04 (d, J = 2.3 Hz, 2H), 8.12 (t, J = 7.9 Hz, 2H) |
| 1cc | $^1$H NMR (400 MHz, MeOH-d4): δ ppm 1.29 (d, J = 6.2 Hz, 1H), 1.57 (m, 4H), 1.99 (dd, J = 13.4, 7.0 Hz, 1H), 2.25 (dd, J = 13.4, 9.1 Hz, 1H), 2.40 (s, 3H), 3.01 (d, J = 11.6 Hz, 1H), 3.15 (m, 4H), 3.32 (s, 1H), 3.48 (ddt, J = 20.3, 12.8, 5.9 Hz, 2H), 3.65 (dd, J = 13.9, 7.0 Hz, 2H), 3.97 (dd, J = 9.1, 7.0 Hz, 1H), 4.89 (m, 2H), 5.75 (s, 1H), 6.44 (d, J = 2.4 Hz, 1H), 6.85 (q, J = 6.6 Hz, 1H), 7.75 (d, J = 1.7 Hz, 1H), 7.84 (m, 2H), 7.94 (d, J = 8.5 Hz, 2H), 8.03 (m, 3H) |
| 1cd | $^1$H NMR (400 MHz, MeOH-d4): δ ppm 1.05 (t, J = 7.4 Hz, 3H), 1.51 (q, J = 6.5, 5.7 Hz, 4H), 1.80 (h, J = 6.7, 6.1 Hz, 3H), 1.89 (d, J = 1.5 Hz, 1H), 2.07 (dd, J = 12.7, 9.2 Hz, 1H), 2.39 (s, 3H), 2.67 (d, J = 11.2 Hz, 1H), 2.94 (t, J = 11.8 Hz, 1H), 3.40 (m, 3H), 3.64 (m, 3H), 3.96 (t, J = 6.4 Hz, 2H), 4.89 (m, 1H), 5.75 (s, 1H), 6.41 (d, J = 2.3 Hz, 1H), 6.75 (m, 1H), 6.99 (m, 2H), 7.59 (dd, J = 9.0, 2.0 Hz, 3H), 7.71 (m, 2H), 7.97 (d, J = 2.4 Hz, 1H) |
| 1ce | $^1$H NMR (400 MHz, MeOH-d4): δ ppm 1.30 (d, J = 16.9 Hz, 4H), 1.57 (s, 5H), 2.02 (m, 1H), 2.27 (dd, J = 13.3, 8.8 Hz, 1H), 2.40 (s, 3H), 2.60 (m, 6H), 3.06 (d, J = 11.4 Hz, 1H), 3.20 (d, J = 11.3 Hz, 1H), 3.34 (s, 1H), 3.48 (s, 3H), 3.56 (t, J = 6.7 Hz, 2H), 3.70 (m, 7H), 4.02 (s, 1H), 4.98 (d, J = 6.2 Hz, 1H), 5.76 (s, 1H), 6.43 (d, J = 2.3 Hz, 1H), 6.82 (q, J = 6.5 Hz, 1H), 7.71 (s, 1H), 7.80 (m, 4H), 7.93 (d, J = 8.0 Hz, 2H), 8.01 (d, J = 2.3 Hz, 1H) |
| 1cf | $^1$H NMR (400 MHz, MeOH-d4): δ ppm 0.90 (t, J = 6.4 Hz, 1H), 1.30 (dd, J = 12.6, 4.9 Hz, 6H), 1.55 (m, 5H), 1.93 (dd, J = 13.2, 7.0 Hz, 1H), 2.19 (qd, J = 9.4, 3.3 Hz, 1H), 2.40 (s, 3H), 2.92 (d, J = 11.4 Hz, 1H), 3.11 (d, J = 11.3 Hz, 1H), 3.48 (m, 2H), 3.65 (dd, J = 13.7, 6.3 Hz, 2H), 3.88 (dd, J = 8.9, 7.2 Hz, 1H), 4.87 (d, J = 12.3 Hz, 1H), 4.97 (d, J = 12.9 Hz, 2H), 5.75 (s, 1H), 6.43 (d, J = 2.3 Hz, 1H), 6.83 (q, J = 6.7 Hz, 1H), 7.73 (s, 1H), 7.84 (m, 4H), 8.00 (m, 3H) |
| 1cg | $^1$H NMR (400 MHz, MeOH-d4): δ ppm 1.29 (s, 1H), 1.58 (d, J = 5.9 Hz, 4H), 2.03 (dd, J = 13.4, 6.9 Hz, 1H), 2.30 (dd, J = 13.3, 9.2 Hz, 1H), 2.40 (s, 3H), 3.11 (d, J = 11.7 Hz, 1H), 3.23 (d, J = 11.5 Hz, 1H), 3.48 (ddd, J = 28.3, 12.4, 5.7 Hz, 2H), 3.65 (dd, J = 13.7, 7.2 Hz, 2H), 4.07 (m, 1H), 5.76 (s, 1H), 6.43 (d, J = 2.3 Hz, 1H), 6.82 (q, J = 6.5 Hz, 1H), 7.70 (d, J = 1.7 Hz, 1H), 7.79 (dt, J = 13.1, 8.1 Hz, 4H), 7.99 (m, 3H) |
| 1ch | $^1$H NMR (400 MHz, MeOH-d4): δ ppm 1.29 (d, J = 3.6 Hz, 1H), 1.63 (q, J = 5.8 Hz, 5H), 2.07 (dd, J = 13.5, 7.5 Hz, 1H), 2.37 (dd, J = 13.5, 9.0 Hz, 1H), 3.04 (s, 3H), 3.15 (d, J = 24.6 Hz, 6H), 3.27 (m, 1H), 3.52 (dt, J = 24.6, 8.3 Hz, 2H), 3.65 (m, 2H), 4.23 (t, J = 8.1 Hz, 1H), 6.66 (q, J = 7.0 Hz, 1H), 7.51 (d, J = 8.1 Hz, 2H), 7.68 (m, 6H) |
| 1ci | $^1$H NMR (400 MHz, MeOH-d4): δ ppm 1.58 (d, J = 5.6 Hz, 4H), 2.03 (dd, J = 13.3, 7.1 Hz, 1H), 2.30 (dd, J = 13.4, 9.2 Hz, 1H), 2.39 (s, 3H), 3.09 (d, J = 11.7 Hz, 1H), 3.22 (d, J = 11.7 Hz, 1H), 3.49 (ddd, J = 21.1, 12.5, 5.6 Hz, 2H), 3.66 (dd, J = 13.7, 6.7 Hz, 2H), 3.90 (s, 3H), 4.06 (dd, J = 9.2, 7.1 Hz, 1H), 5.76 (s, 1H), 6.41 (d, J = 2.3 Hz, 1H), 6.78 (q, J = 6.6 Hz, 1H), 7.17 (t, J = 8.9 Hz, 1H), 7.46 (m, 2H), 7.60 (d, J = 1.8 Hz, 1H), 7.73 (m, 2H), 7.98 (d, J = 2.3 Hz, 1H) |
| 1cj | $^1$H NMR (400 MHz, MeOH-d4): δ ppm 1.30 (d, J = 17.0 Hz, 1H), 1.57 (d, J = 5.5 Hz, 4H), 2.01 (dd, J = 13.2, 7.0 Hz, 1H), 2.28 (dd, J = 13.3, 9.0 Hz, 1H), 2.40 (s, 3H), 2.79 (s, 2H), 2.91 (s, 2H), 3.07 (d, J = 12.1 Hz, 1H), 3.20 (d, J = 11.4 Hz, 1H), 3.49 (m, 4H), 3.65 (dd, J = 13.5, 6.9 Hz, 2H), 3.74 (s, 2H), 4.02 (t, J = 8.1 Hz, 1H), 4.99 (s, 1H), 5.76 (s, 1H), 6.43 (d, J = 2.4 Hz, 1H), 6.82 (q, J = 6.6 Hz, 1H), 7.52 (d, J = 7.9 Hz, 2H), 7.76 (m, 5H), 8.01 (d, J = 2.4 Hz, 1H) |
| 1ck | $^1$H NMR (400 MHz, MeOH-d4): δ ppm 1.30 (d, J = 11.1 Hz, 1H), 1.51 (q, J = 6.8, 6.0 Hz, 4H), 1.78 (dd, J = 13.0, 7.0 Hz, 1H), 1.89 (s, 2H), 2.07 (dd, J = 13.1, 9.1 Hz, 1H), 2.40 (s, 3H), 2.68 (d, J = 11.1 Hz, 1H), 2.95 (d, J = 11.1 Hz, 1H), 3.03 (s, 3H), 3.11 (s, 3H), 3.22 (s, 2H), 3.45 (m, 3H), 3.63 (q, J = 7.9, 7.5 Hz, 3H), 5.75 (s, 1H), 6.43 (d, J = 2.4 Hz, 1H), 6.82 (q, J = 6.6 Hz, 1H), 7.53 (d, J = 7.9 Hz, 2H), 7.70 (m, 1H), 7.80 (m, 4H), 8.01 (d, J = 2.5 Hz, 1H) |
| 1cl | $^1$H NMR (400 MHz, MeOH-d4): δ ppm 1.04 (d, J = 6.7 Hz, 6H), 1.29 (m, 1H), 1.60 (d, J = 6.0 Hz, 5H), 2.05 (ddd, J = 13.7, 7.0, 3.9 Hz, 2H), 2.36 (m, 4H), 3.13 (d, J = 11.9 Hz, 1H), 3.24 (d, J = 11.6 Hz, 1H), 3.51 (ddd, J = 25.5, 14.3,7.1 Hz, 2H), 3.69 (d, J = |

TABLE 1b-continued

| Ex. No. | 1H NMR |
|---|---|
| | 13.8 Hz, 3H), 3.77 (d, J = 6.4 Hz, 2H), 4.14 (t, J = 8.3 Hz, 1H), 4.93 (s, 8H), 6.41 (d, J = 2.3 Hz, 1H), 6.77 (q, J = 6.6 Hz, 1H), 6.99 (m, 2H), 7.60 (m, 3H), 7.72 (m, 2H), 7.96 (d, J = 2.3 Hz, 1H) |
| 1cm | $^1$H NMR (400 MHz, MeOH-d4): δ 1.14 (t, J = 7.1 Hz, 3H), 1.26 (t, J = 7.3 Hz, 3H), 1.55 (q, J = 4.8 Hz, 4H), 1.90 (m, 1H), 2.18 (dd, J = 13.2, 9.0 Hz, 1H), 2.40 (s, 3H), 2.87 (d, J = 11.4 Hz, 1H), 3.09 (d, J = 11.3 Hz, 1H), 3.30 (m, 4H), 3.54 (dddd, J = 37.2, 30.6, 15.1, 5.9 Hz, 6H), 3.84 (dd, J = 9.0, 6.9 Hz, 1H), 5.76 (s, 1H), 6.42 (d, J = 2.3 Hz, 1H), 6.83 (q, J = 6.6 Hz, 1H), 7.48 (m, 2H), 7.70 (d, J = 1.6 Hz, 1H), 7.80 (m, 4H), 8.01 (d, J = 2.3 Hz, 1H) |
| 1cn | $^1$H NMR (400 MHz, MeOH-d4): δ ppm 0.84 (s, 3H), 1.06 (s, 10H), 1.30 (m, 1H), 1.56 (t, J = 5.4 Hz, 4H), 2.00 (dd, J = 13.4, 6.8 Hz, 1H), 2.27 (dd, J = 13.2, 9.0 Hz, 1H), 2.41 (s, 3H), 3.04 (d, J = 11.5 Hz, 1H), 3.19 (d, J = 11.4 Hz, 1H), 3.48 (ddt, J = 20.4, 13.0, 5.9 Hz, 2H), 3.65 (s, 4H), 4.03 (t, J = 8.1 Hz, 1H), 5.77 (s, 1H), 6.43 (d, J = 2.2 Hz, 1H), 6.79 (q, J = 6.6 Hz, 1H), 6.98 (d, J = 8.4 Hz, 2H), 7.60 (m, 4H), 7.75 (d, J = 8.2 Hz, 1H), 7.97 (d, J = 2.3 Hz, 1H) |
| 1co | $^1$H NMR (400 MHz, MeOH-d4): δ ppm 1.28 (d, J = 5.8 Hz, 1H), 1.55 (t, J = 5.7 Hz, 4H), 1.98 (m, 3H), 2.25 (dd, J = 13.3, 9.2 Hz, 1H), 2.39 (s, 3H), 2.80 (t, J = 6.5 Hz, 2H), 3.02 (d, J = 11.6 Hz, 1H), 3.17 (d, J = 11.6 Hz, 1H), 3.47 (ddt, J = 20.5, 13.0, 5.9 Hz, 2H), 3.64 (dt, J = 13.8, 5.9 Hz, 2H), 4.00 (dd, J = 9.2, 7.1 Hz, 1H), 4.16 (m, 2H), 5.75 (s, 1H), 6.40 (d, J = 2.3 Hz, 1H), 6.76 (m, 2H), 7.33 (d, J = 6.5 Hz, 2H), 7.54 (d, J = 1.8 Hz, 1H), 7.63 (dd, J = 8.3, 1.9 Hz, 1H), 7.71 (d, J = 8.3 Hz, 1H), 7.95 (d, J = 2.4 Hz, 1H) |
| 1cp | $^1$H NMR (400 MHz, MeOH-d4): δ ppm 1.59 (t, J = 5.3 Hz, 4H), 2.05 (dd, J = 13.5, 7.1 Hz, 1H), 2.31 (dd, J = 13.4, 9.3 Hz, 1H), 2.42 (s, 3H), 3.11 (d, J = 11.7 Hz, 1H), 3.24 (d, J = 11.7 Hz, 1H), 3.51 (m, 2H), 3.67 (s, 2H), 4.07 (dd, J = 9.3, 7.1 Hz, 1H), 4.89 (s, 1H), 5.78 (s, 1H), 5.99 (m, 1H), 6.46 (d, J = 2.3 Hz, 1H), 6.89 (q, J = 6.5 Hz, 1H), 7.91 (m, 2H), 8.00 (dd, J = 8.3, 2.0 Hz, 1H), 8.07 (d, J = 2.4 Hz, 1H), 8.34 (m, 3H), 8.55 (d, J = 8.9 Hz, 1H), 9.33 (d, J = 5.9 Hz, 1H) |
| 1cq | $^1$H NMR (400 MHz, MeOH-d4): δ ppm 7.97 (s, 1H), 7.77 (s, 2H), 7.67 (d, J = 15.8 Hz, 2H), 7.51 (s, 1H), 7.26 (d, J = 7.8 Hz, 1H), 6.42 (s, 1H), 4.69 (s, 2H), 4.14 (s, 1H), 3.68 (s, 2H), 3.51 (s, 3H), 3.23 (s, 1H), 3.13 (d, J = 11.6 Hz, 1H), 2.38 (d, J = 14.0 Hz, 6H), 2.05 (s, 1H), 1.60 (s, 4H), 1.29 (s, 3H) |
| 1cr | $^1$H NMR (400 MHz, MeOH-d4): δ ppm 7.97 (s, 2H), 7.74 (q, J = 8.3 Hz, 4H), 7.62 (s, 2H), 7.46 (d, J = 7.4 Hz, 5H), 6.78 (q, J = 6.7 Hz, 2H), 6.41 (s, 2H), 5.75 (s, 2H), 4.65 (s, 3H), 4.07 (t, J = 8.1 Hz, 2H), 3.64 (s, 4H), 3.52 (d, J = 6.9 Hz, 1H), 3.46 (d, J = 16.2 Hz, 4H), 3.22 (d, J = 11.8 Hz, 2H), 3.10 (d, J = 11.8 Hz, 2H), 2.38 (d, J = 7.9 Hz, 10H), 2.29 (s, 1H), 2.03 (dd, J = 13.4, 7.0 Hz, 2H), 1.58 (d, J = 5.6 Hz, 7H), 1.30 (d, J = 13.4 Hz, 5H) |
| 1cs | $^1$H NMR (400 MHz, MeOH-d4): δ ppm 8.43 (d, J = 2.5 Hz, 1H), 7.99 (q, J = 3.3 Hz, 2H), 7.79 (d, J = 8.3 Hz, 1H), 7.72 (d, J = 8.1 Hz, 1H), 7.63 (s, 1H), 6.83 (dd, J = 20.4, 7.6 Hz, 2H), 6.42 (d, J = 2.3 Hz, 1H), 5.74 (s, 1H), 4.35 (q, J = 7.0 Hz, 2H), 3.96 (d, J = 8.9 Hz, 1H), 3.64 (s, 3H), 3.48 (dd, J = 25.9, 11.9 Hz, 2H), 3.15 (d, J = 11.7 Hz, 1H), 2.99 (d, J = 11.4 Hz, 1H), 2.39 (s, 3H), 2.24 (s, 1H), 2.02-1.94 (m, 1H), 1.56 (s, 4H), 1.38 (t, J = 7.1 Hz, 3H), 1.28 (s, 1H). |

Example 1cp (S)-8-(2-amino-6-((R)-1-(3',4'-dimethyl-3-(3-(trifluoromethyl)-1H-pyrazol-1-yl)-[1,1'-biphenyl]-4-yl)-2,2,2-trifluoroethoxy)pyrimidin-4-yl)-2,8-diazaspiro [4.5]decane-3-carboxylic acid

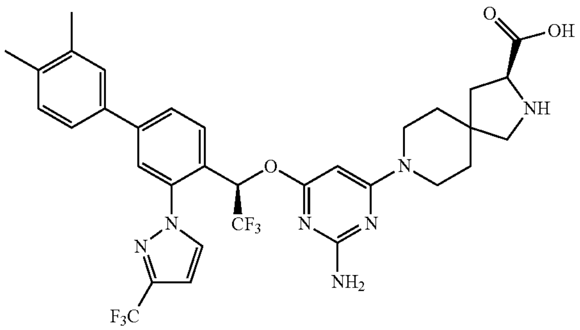 [SMILES: Cc1ccc(-c2ccc([C@@H](Oc3cc(N4CCC5(CC4)CN[C@H](C(=O)O)C5)nc(N)n3)C(F)(F)F)c(-n3ccc(C(F)(F)F)n3)c2)cc1C]

The title compound was prepared as described for (S)-8-(2-amino-6-((R)-2,2,2-trifluoro-1-(3-(3-methyl-1H-pyrazol-1-yl)-[1,1'-biphenyl]-4-yl)ethoxy)pyrimidin-4-yl)-2,8-diazaspiro[4.5]decane-3-carboxylic acid (Example 1u) starting with (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro [4.5]decane-3-carboxylic acid (Example 10d).

$^1$H NMR (400 MHz, MeOH-d4): δ ppm 1.57 (br. s., 4 H) 1.91-2.01 (m, 1 H) 2.18-2.27 (m, 1 H) 2.33 (d, J=11.71 Hz, 6 H) 2.88-3.00 (m, 1 H) 3.08-3.19 (m, 1 H) 3.38-3.56 (m, 2 H) 3.58-3.75 (m, 2 H) 3.85-3.98 (m, 1 H) 5.65 (s, 1 H) 6.55-6.70 (m, 1 H) 6.92-7.04 (m, 1 H) 7.19-7.28 (m, 1 H) 7.38-7.46 (m, 1 H) 7.46-7.53 (m, 1 H) 7.72 (s, 1 H) 7.83 (s, 2 H) 8.22-8.35 (m, 1 H)LCMS (MH+): 690.

Example 2

(S)-8-(2-amino-6-((R)-2,2,2-trifluoro-1-(2-(3-methyl-1H-pyrazol-1-yl)-4-(piperidin-4-yl)phenyl)ethoxy)pyrimidin-4-yl)-2,8-diazaspiro[4.5]decane-3-carboxylic acid

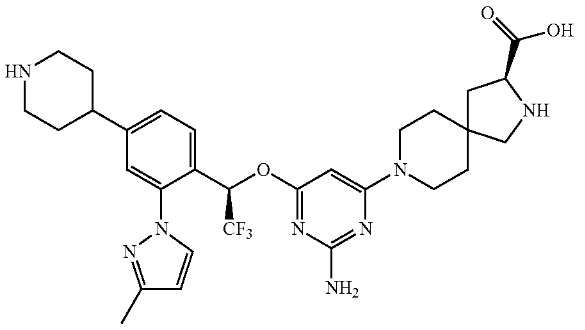 [SMILES: Cc1ccn(-c2cc(C3CCNCC3)ccc2[C@@H](Oc2cc(N3CCC4(CC3)CN[C@H](C(=O)O)C4)nc(N)n2)C(F)(F)F)n1]

Step 1: A solution of (S)-2-benzyl 3-ethyl 8-(2-amino-6-((R)-2,2,2-trifluoro-1-(2-(3-methyl-1H-pyrazol-1-yl)-4-(1,2,3,6-tetrahydropyridin-4-yl)phenyl)ethoxy)pyrimidin-4-yl)-2,8-diazaspiro[4.5]decane-2,3-dicarboxylate (Example 1f) (150 mg, 0.15 mmol) in MeOH (5 mL) was hydrogenated in an H-Cube apparatus using a 10% (w/w) Pd/C cartridge with a flow rate of 1.0 mL/min at RT. The resulting eluent was concentrated in vacuo and The product was purified by column chromatography using an Isco Gold reversed phase silica cartridge (100% $CH_2Cl_2$ to 90:9:1 $CH_2Cl_2$:MeOH:conc. $NH_4OH$) to provide (S)-2-benzyl 3-ethyl 8-(2-amino-6-((R)-2,2,2-trifluoro-1-(2-(3-methyl-1H-pyrazol-1-yl)-4-(1,2,3,6-tetrahydropyridin-4-yl)phenyl)ethoxy)pyrimidin-4-yl)-2,8-diazaspiro[4.5]decane-2,3-dicarboxylate.

Step 2: Hydrolysis of (S)-2-benzyl 3-ethyl 8-(2-amino-6-((R)-2,2,2-trifluoro-1-(2-(3-methyl-1H-pyrazol-1-yl)-4-(1,2,3,6-tetrahydropyridin-4-yl)phenyl)ethoxy)pyrimidin-4-yl)-2,8-diazaspiro[4.5]decane-2,3-dicarboxylate using the LiOH general method provided the title compound as an off-white solid.

$^1$H NMR (400 MHz, MeOH-d4): δ ppm 1.49-1.69 (m, 4 H) 2.00-2.18 (m, 3 H) 2.21-2.35 (m, 1 H) 2.38 (s, 3 H) 2.92-3.05 (m, 1 H) 3.08 (d, J=0.44 Hz, 2 H) 3.10-3.18 (m, 2 H) 3.25 (d, J=11.71 Hz, 1 H) 3.38-3.72 (m, 7 H) 4.09 (t, J=7.88 Hz, 1 H) 5.69 (s, 1 H) 6.41 (d, J=2.29 Hz, 1 H) 6.74 (q, J=6.80 Hz, 1 H) 7.34 (d, J=1.12 Hz, 1 H) 7.43 (d, J=8.15 Hz, 1 H) 7.71 (d, J=8.44 Hz, 1 H) 7.91 (d, J=2.20 Hz, 1 H). LCMS (MH+): 613.

Example 3a (S)-8-(2-amino-6-((R)-2,2,2-trifluoro-1-(2-(3-methyl-1H-pyrazol-1-yl)-4-(1-(methylsulfonyl)piperidin-4-yl)phenyl)ethoxy)pyrimidin-4-yl)-2,8-diazaspiro[4.5]decane-3-carboxylic acid

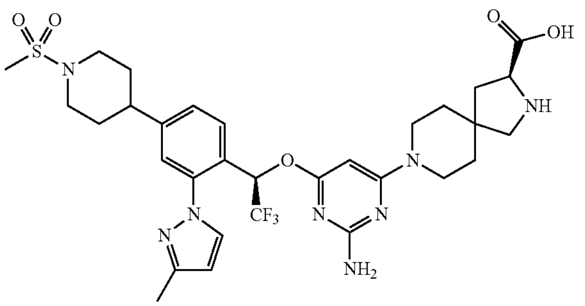 [SMILES: Cc1ccn(-c2cc(C3CCN(S(C)(=O)=O)CC3)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-2,2,2-trifluoro-1-(2-(3-methyl-1H-pyrazol-1-yl)-4-(1,2,3,6-tetrahydropyridin-4-yl)phenyl)ethoxy)pyrimidin-4-yl)-2,8-diazaspiro[4.5]decane-2,3-dicarboxylate (320 mg, 0.413 mmol) in $CH_2Cl_2$ (5.0 mL) was added methanesulfonyl chloride (47 mg, 0.41 mmol) and triethylamine (94 mg, 0.83 mmol), and the reaction was stirred for 1.5 h at RT and then concentrated in vacuo. The product was purified by column chromatography using an Isco Gold reversed phase silica cartridge (100% $CH_2Cl_2$ to 90:9:1 $CH_2Cl_2$:MeOH: conc. $NH_4OH$) to provide (S)-2-benzyl 3-ethyl 8-(2-amino-6-((R)-2,2,2-trifluoro-1-(2-(3-methyl-1H-pyrazol-1-yl)-4-(1-(methylsulfonyl)-1,2,3,6-tetrahydropyridin-4-yl)phenyl)ethoxy)pyrimidin-4-yl)-2,8-diazaspiro[4.5]decane-2,3-dicarboxylate as an off-white solid.

Step 2: A solution of (S)-2-benzyl 3-ethyl 8-(2-amino-6-((R)-2,2,2-trifluoro-1-(2-(3-methyl-1H-pyrazol-1-yl)-4-(1-(methylsulfonyl)-1,2,3,6-tetrahydropyridin-4-yl)phenyl)ethoxy)pyrimidin-4-yl)-2,8-diazaspiro[4.5]decane-2,3-dicarboxylate (290 mg, 0.340 mmol, Step 1) in MeOH (10 mL) was hydrogenated in an H-Cube apparatus using a 10% (w/w) Pd/C cartridge with a flow rate of 1.0 mL/min at RT. The resulting eluent was concentrated in vacuo and The product was purified by column chromatography using an Isco Gold reversed phase silica cartridge (100% $CH_2Cl_2$ to 90:9:1 $CH_2Cl_2$:MeOH:conc. $NH_4OH$) to provide (S)-ethyl 8-(2-amino-6-((R)-2,2,2-trifluoro-1-(2-(3-methyl-1H-pyrazol-1-yl)-4-(1-(methylsulfonyl)piperidin-4-yl)phenyl)ethoxy)pyrimidin-4-yl)-2,8-diazaspiro[4.5]decane-3-carboxylate.

Step 3: Hydrolysis of (S)-ethyl 8-(2-amino-6-((R)-2,2,2-trifluoro-1-(2-(3-methyl-1H-pyrazol-1-yl)-4-(1-(methylsulfonyl)piperidin-4-yl)phenyl)ethoxy)pyrimidin-4-yl)-2,8-diazaspiro[4.5]decane-3-carboxylate using the LiOH general method provided the title compound as an off-white solid.

1H NMR (400 MHz, MeOH-d4): δ ppm 1.53-1.65 (m, 4 H) 1.80 (qd, J=12.57, 3.98 Hz, 2 H) 1.94-2.02 (m, 2 H) 2.02-2.12 (m, 1 H) 2.31 (dd, J=13.42, 9.27 Hz, 1 H) 2.38 (s, 3 H) 2.67-2.94 (m, 3 H) 2.86 (s, 3 H) 3.07-3.28 (m, 2 H) 3.37-3.74 (m, 4 H) 3.78-3.92 (m, 2 H) 4.08 (dd, J=9.15, 7.20 Hz, 1 H) 5.71 (s, 1 H) 6.39 (d, J=2.29 Hz, 1 H) 6.64-6.82 (m, 1 H) 7.31 (d, J=1.71 Hz, 1 H) 7.42 (dd, J=8.25, 1.76 Hz, 1 H) 7.67 (d, J=8.10 Hz, 1 H) 7.89 (d, J=2.29 Hz, 1 H). LCMS (MH+): 693.

Using the generic scheme below, the following examples of Table 2a can be prepared as described above for (S)-8-(2-amino-6-((R)-2,2,2-trifluoro-1-(2-(3-methyl-1H-pyrazol-1-yl)-4-(1-(methylsulfonyl)piperidin-4-yl)phenyl)ethoxy)pyrimidin-4-yl)-2,8-diazaspiro[4.5]decane-3-carboxylic acid (Example 3a).

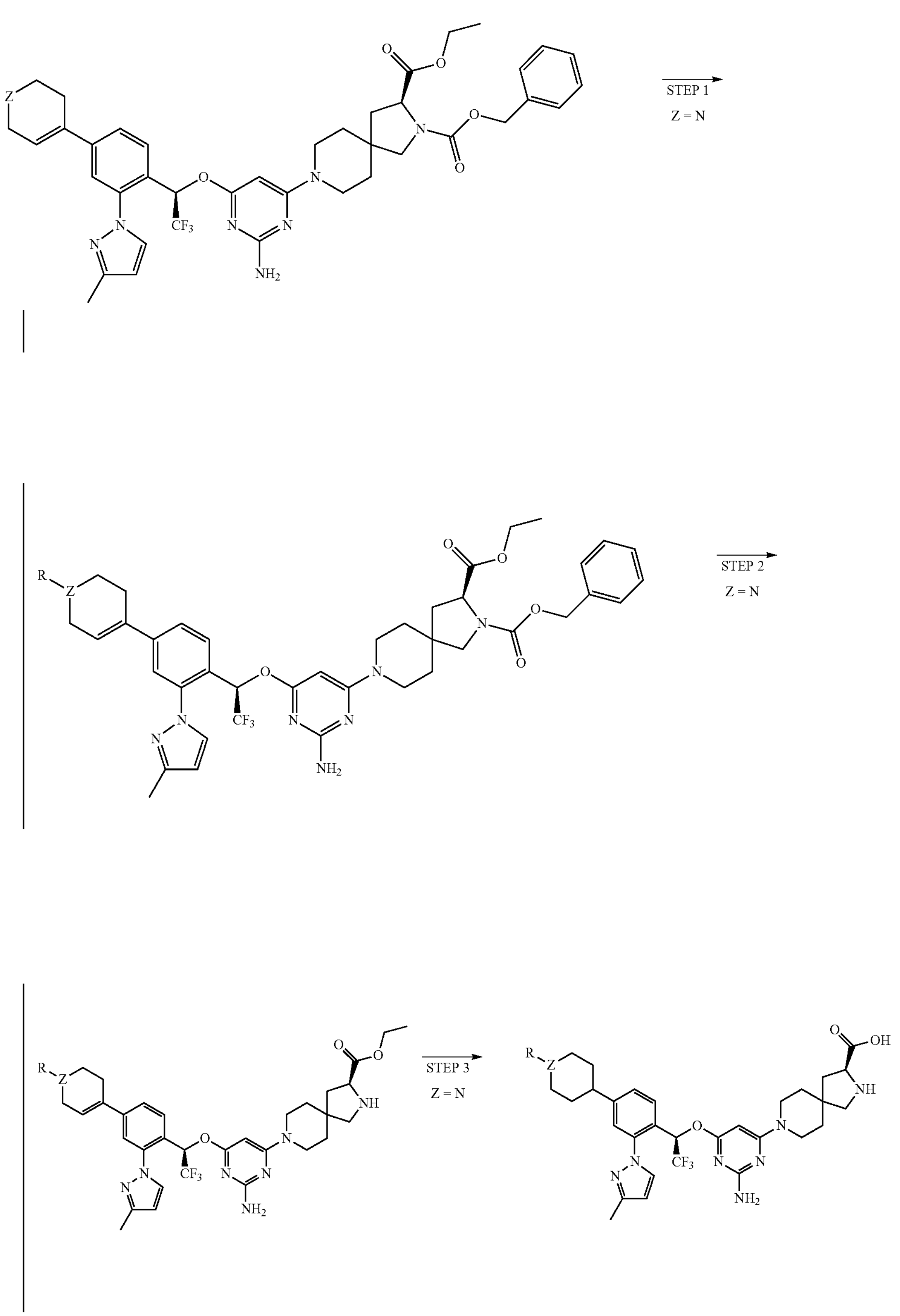
STEP 1
Z = N
STEP 2
Z = N
STEP 3
Z = N

-continued

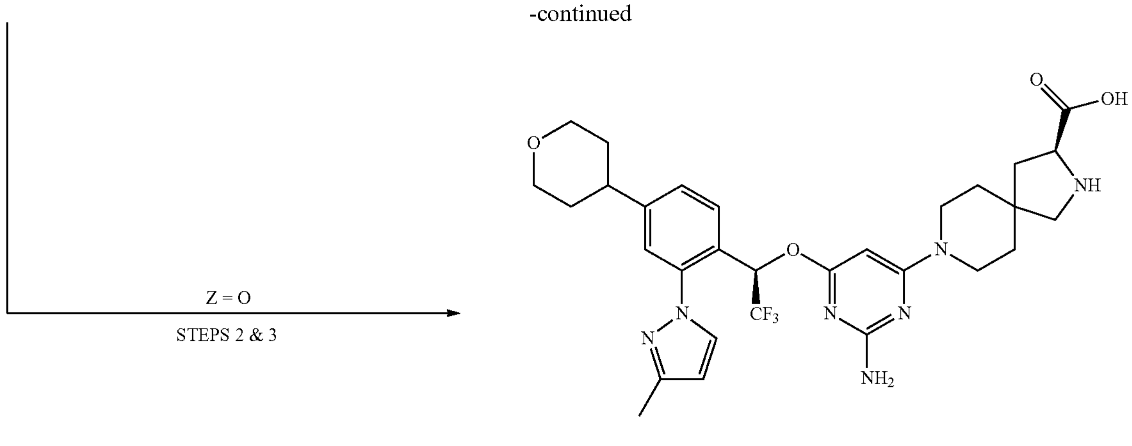

TABLE 2a

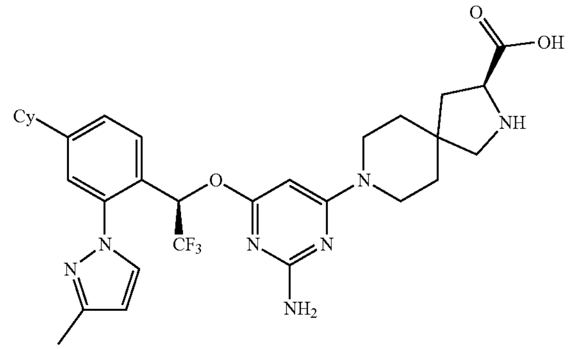

| Ex. No. | Cy | CAS Name | LCMS (MH+) |
|---|---|---|---|
| 3b | 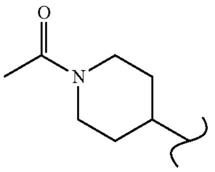 | (S)-8-(6-((R-1-(4-(1-acetylpiperidin-4-yl)-2-(3-methyl-1H-pyrazol-1-yl)phenyl)-2,2,2-trifluoroethoxy)-2-aminopyrimidin-4-yl)-2,8-diazaspiro[4.5]decane-3-carboxylic acid | 656.7 |
| 3c | 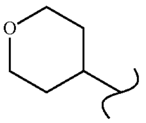 | (S)-8-(2-amino-6-((R)-2,2,2-trifluoro-1-(2-(3-methyl-1H-pyrazol-1-yl)-4-(tetrahydro-2H-pyran-4-yl)phenyl)ethoxy)pyrimidin-4-yl)-2,8-diazaspiro[4.5]decane-3-carboxylic acid | 615.6 |

TABLE 2b

NMR Data for Compounds of Table 2a

| Ex. No. | 1H NMR |
|---|---|
| 3b | $^1$H NMR (400 MHz, MeOH-d4): δ ppm 1.54-1.82 (m, 6 H) 1.86-1.99 (m, 2 H) 2.05-2.18 (m, 4 H) 2.36-2.38 (m, 3 H) 2.48 (dd, J = 13.69, 8.86 Hz, 1 H) 2.66-2.81 (m, 1 H) 2.88-3.03 (m, 1 H) 3.19-3.27 (m, 1 H) 3.31-3.40 (m, 1 H) 3.60-3.95 (m, 4 H) 4.05 (d, J = 13.08 Hz, 1 H) 4.55 (t, J = 8.66 Hz, 1 H) 4.67 (d, J = 13.13 Hz, 1 H) 6.39 (d, J = 2.39 Hz, 1 H) 6.50 (br. s., 1 H) 6.79-6.87 (m, 1 H), 7.36 (s, 1 H) 7.47 (dd, J = 8.22, 1.64 Hz, 1 H) 7.64 (d, J = 8.30 Hz, 1 H) 7.86 (d, J = 2.39 Hz, 1 H) |
| 3c | $^1$H NMR (400 MHz, MeOH-d4): δ ppm 1.59 (d, J = 5.08 Hz, 4 H) 1.72-1.89 (m, 4 H) 2.06 (dd, J = 13.45, 7.15 Hz, 1 H) 2.32 (dd, J = 13.45, 9.25 Hz, 1 H) 2.38 (s, 3 H) 2.82- |

TABLE 2b-continued

NMR Data for Compounds of Table 2a

| Ex. No. | 1H NMR |
|---|---|
| | 2.95 (m, 1 H) 3.07-3.16 (m, 1 H) 3.25 (d, J = 11.76 Hz, 1 H) 3.36-3.74 (m, 6 H) 4.03 (dt, J = 11.16, 2.96 Hz, 2 H) 4.08 (dd, J = 9.15, 7.20 Hz, 1 H) 5.71 (s, 1 H) 6.39 (d, J = 2.29 Hz, 1 H) 6.72 (q, J = 6.75 Hz, 1 H) 7.29 (d, J = 1.71 Hz, 1 H) 7.41 (dd, J = 8.20, 1.76 Hz, 1 H) 7.67 (d, J = 8.10 Hz, 1 H) 7.88 (d, J = 2.34 Hz, 1 H) |

Example 4

(S)-8-(2-amino-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2,8-diazaspiro [4.5]decane-3-carboxylic acid

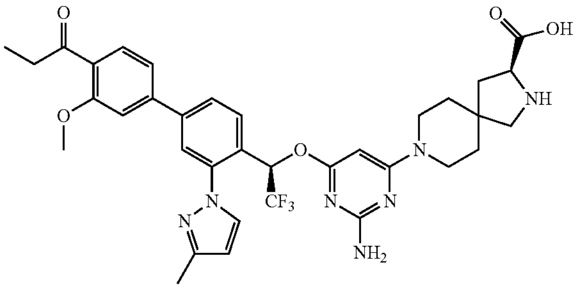 [SMILES: CCC(=O)c1ccc(-c2ccc([C@@H](Oc3cc(N4CCC5(CC4)CN[C@H](C(=O)O)C5)nc(N)n3)C(F)(F)F)c(-n3ccc(C)n3)c2)cc1OC]

Step 1: To a solution of (S)-8-(2-amino-6-((R)-1-(4-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro [4.5]decane-3-carboxylic acid (product of Step 3, Example 10m) (135 mg, 0.18 mmol) in dioxane (2 mL) was added (3-methoxy-4-(methoxycarbonyl)phenyl)boronic acid (84 mg, 0.4 mmol) and $Cs_2CO_3$ (48 mg, 0.16 mmol). The reaction was heated to 80° C. for 16 h, cooled to RT, and filtered. The solvent was removed in vacuo. Purification via normal phase silica gel chromatography ($CH_2Cl_2$/Heptane) provided (S)-8-(2-amino-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2-((benzyloxy) carbonyl)-2,8-diazaspiro[4.5]decane-3-carboxylic acid as an off-white solid.

Step 2: N-CBZ Deprotection was accomplished via method B to yield (S)-8-(2-amino-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid as an off-white solid.

$^{1}$H NMR (400 MHz, MeOH-d4): δ ppm 1.66 (d, J=5.47 Hz, 4 H) 2.03-2.17 (m, 1 H) 2.42 (s, 4 H) 3.16-3.30 (m, 2 H) 3.47-3.81 (m, 4 H) 3.89 (s, 3 H) 3.97 (s, 3 H) 4.26-4.45 (m, 1 H) 6.40-6.52 (m, 1 H) 6.82-6.96 (m, 1 H) 7.30-7.37 (m, 1 H) 7.40 (s, 1 H) 7.76 (s, 1 H) 7.80-7.93 (m, 4 H) 7.99-8.09 (m, 1 H). LCMS: 696.7.

Example 5a (S)-8-(2-amino-6-((R)-1-(3'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid

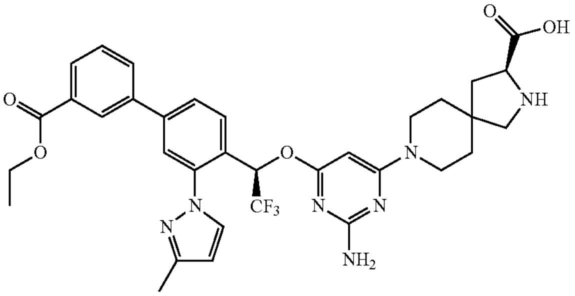 [SMILES: CCOC(=O)c1cccc(-c2ccc([C@@H](Oc3cc(N4CCC5(CC4)CN[C@H](C(=O)O)C5)nc(N)n3)C(F)(F)F)c(-n3ccc(C)n3)c2)c1]

The title compound was made according to the procedures described for (S)-8-(2-amino-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid (Example 4). $^{1}$H NMR (400 MHz, MeOH-d4): δ ppm 1.42 (t, J=7.13 Hz, 3 H) 1.61 (br. s., 4 H) 2.02-2.14 (m, 1 H) 2.28-2.40 (m, 1 H) 2.42 (s, 3 H) 3.06-3.19 (m, 1 H) 3.21-3.30 (m, 1 H) 3.40-3.60 (m, 2 H) 3.62-3.80 (m, 2 H) 4.01-4.19 (m, 1 H) 4.41 (d, J=7.22 Hz, 2 H) 5.76 (s, 1 H) 6.45 (d, J=2.34 Hz, 1 H) 6.79-6.92 (m, 1 H) 7.60 (s, 1 H) 7.70 (d, J=1.56 Hz, 1 H) 7.80 (d, J=1.56 Hz, 1 H) 7.84 (s, 1 H) 7.90-7.97 (m, 1 H) 8.02 (d, J=2.15 Hz, 1 H) 8.05 (s, 1 H) 8.31 (s, 1 H) 680.7. LCMS (MH+): 578.7.

Example 5b (S)-8-(2-amino-6-((R)-1-(4'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5] decane-3-carboxylic acid

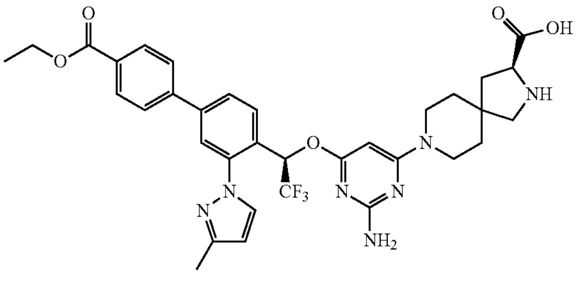 [SMILES: CCOC(=O)c1ccc(-c2ccc([C@@H](Oc3cc(N4CCC5(CC4)CN[C@H](C(=O)O)C5)nc(N)n3)C(F)(F)F)c(-n3ccc(C)n3)c2)cc1]

The title compound was made according to the procedures described for (S)-8-(2-amino-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid (Example 4).

$^1$H NMR (400 MHz, MeOH-d4): δ ppm 0.88 (m, 4H), 1.30 (d, J=17.4 Hz, 10H), 1.40 (t, J=7.1 Hz, 4H), 1.59 (d, J=5.8 Hz, 5H), 2.05 (dd, J=13.5, 7.2 Hz, 1H), 2.35 (m, 5H), 3.11 (d, J=11.7 Hz, 1H), 3.24 (d, J=11.7 Hz, 1H), 3.49 (ddd, J=28.1, 12.7, 5.7 Hz, 2H), 3.66 (dd, J=13.2, 7.3 Hz, 3H), 4.07 (t, J=8.1 Hz, 1H), 4.38 (q, J=7.1 Hz, 2H), 4.82 (d, J=9.7 Hz, 1H), 4.91 (s, 2H), 5.75 (s, 1H), 6.42 (d, J=2.4 Hz, 1H), 6.83 (q, J=6.5 Hz, 1H), 7.72 (d, J=1.6 Hz, 1H), 7.81 (m, 4H), 8.00 (d, J=2.4 Hz, 1H), 8.10 (m, 2H). LCMS (MH+): 681.

Example 6

(S)-8-(2-amino-6-((R)-1-(4-(3-carboxypropyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

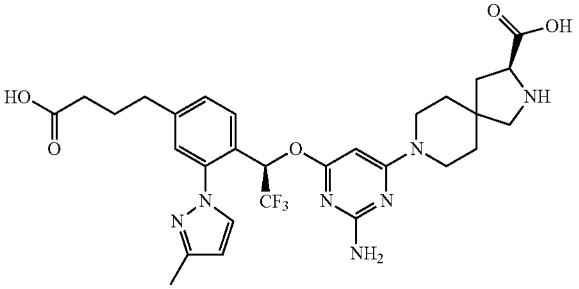 [SMILES: Cc1ccn(-c2cc(CCCC(=O)O)ccc2[C@@H](Oc2cc(N3CCC4(CC3)CN[C@H](C(=O)O)C4)nc(N)n2)C(F)(F)F)n1]

Step 1: To a solution of 9-borabicyclo[3.3.1]nonane (2.0 mL, 0.5 M in THF, 1.0 mmol) was added methyl but-3-enoate (100 μL, 1.0 mmol) and stirred at RT for 2 h to prepare the 9-BBN/butane solution.

Step 2: To a solution of (S)-8-(2-amino-6-((R)-1-(4-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro [4.5]decane-3-carboxylic acid (product of Step 3, Example 10m) (250 mg, 0.32 mmol) in THF (2 mL) was added sequentially $PdCl_2(dppf)CH_2Cl_2$ (8 mg, 0.01 mmol), NaOEt (66 mg, 1 mmol) and the prepared 9-BBN/butene solution from Step 1. The reaction was heated to 65° C. for 2 h, then cooled to RT. The reaction was extracted with EtOAc, brine and dried over $Na_2SO_4$ and concentrated in vacuo. The product was purified by column chromatography using an Isco Gold reversed phase silica cartridge (100% $CH_2Cl_2$ to 90:9:1 $CH_2Cl_2$:MeOH:conc. $NH_4OH$) to provide (S)-2-benzyl 3-ethyl 8-(2-amino-6-((R)-2,2,2-trifluoro-1-(4-(4-methoxy-4-oxobutyl)-2-(3-methyl-1H-pyrazol-1-yl)phenyl)ethoxy) pyrimidin-4-yl)-2,8-diazaspiro[4.5]decane-2,3-dicarboxylate as an off-white solid.

Step 3: N-CBZ Deprotection was accomplished via method B to provide (S)-ethyl 8-(2-amino-6-((R)-2,2,2-trifluoro-1-(4-(4-methoxy-4-oxobutyl)-2-(3-methyl-1H-pyrazol-1-yl) phenyl) ethoxy)pyrimidin-4-yl)-2,8-diazaspiro[4.5]decane-3-carboxylate as an off-white solid.

Step 4: Hydrolysis of (S)-ethyl 8-(2-amino-6-((R)-2,2,2-trifluoro-1-(4-(4-methoxy-4-oxobutyl)-2-(3-methyl-1H-pyrazol-1-yl)phenyl)ethoxy)pyrimidin-4-yl)-2,8-diazaspiro [4.5]decane-3-carboxylate was carried out using the LiOH general method providing the title compound as an off-white solid.

$^1$H NMR (400 MHz, DMSO-d6): δ ppm 1.40-1.61 (m, 4 H) 1.76-1.93 (m, 3 H) 2.24 (t, J=7.35 Hz, 2 H) 2.27-2.37 (m, 4 H) 2.58-2.74 (m, 2 H) 3.10 (br. s., 2 H) 3.53 (br. s., 4 H) 4.42 (br. s., 1 H) 5.71 (br. s., 1 H) 6.00 (br. s., 2 H) 6.38 (d, J=2.20 Hz, 1 H) 7.00 (q, J=6.87 Hz, 1 H) 7.29 (d, J=1.51 Hz, 1 H) 7.32-7.41 (m, 1 H) 7.60 (s, 1 H) 8.05 (d, J=2.29 Hz, 1 H) 8.94 (br. s., 1 H) 10.20 (br. s, 1 H) 12.14 (br. s., 1 H). LCMS (MH+): 618.6.

Example 7

(S)-8-(2-amino-6-((R)-1-(4-(2-carboxyethyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

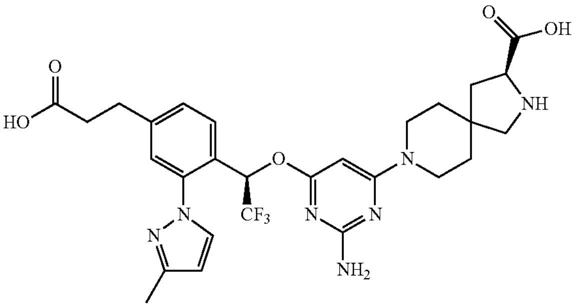 [SMILES: Cc1ccn(-c2cc(CCC(=O)O)ccc2[C@@H](Oc2cc(N3CCC4(CC3)CN[C@H](C(=O)O)C4)nc(N)n2)C(F)(F)F)n1]

The title compound was made as described for (S)-8-(2-amino-6-((R)-1-(4-(3-carboxypropyl)-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 6).

$^1$H NMR (400 MHz, MeOH-d4): δ ppm 1.56 (t, J=5.54 Hz, 4 H) 1.97 (s, 2 H) 2.04 (dd, J=13.30, 7.10 Hz, 1 H) 2.29 (dd, J=13.67, 9.18 Hz, 1H) 2.35 (s, 3 H) 2.59-2.68 (m, 2 H) 2.97 (t, J=7.49 Hz, 2 H) 3.06-3.13 (m, 1 H) 3.23 (d, J=11.86 Hz, 1 H) 3.39-3.55 (m, 2 H) 3.57-3.75 (m, 2H) 4.06 (dd, J=9.05, 7.30 Hz, 1 H) 5.72 (s, 1 H) 6.36 (d, J=2.29 Hz, 1 H) 6.71 (q, J=6.61 Hz, 1 H) 7.28 (d, J=1.61 Hz, 1 H) 7.37 (dd, J=8.20, 1.46 Hz, 1 H) 7.62 (d, J=8.10 Hz, 1 H) 7.83 (d, J=2.25 Hz, 1 H). LCMS (MH+): 604.

Example 9

(S)-8-(2-amino-6-((R)-1-(4-(3-ethoxy-3-oxopropyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

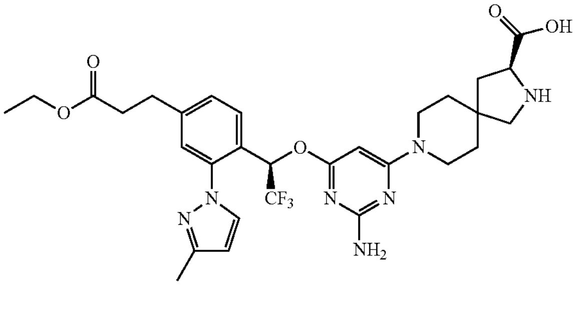 [SMILES: CCOC(=O)CCc1ccc([C@@H](Oc2cc(N3CCC4(CC3)CN[C@H](C(=O)O)C4)nc(N)n2)C(F)(F)F)c(-n2ccc(C)n2)c1]

Step 1: To a solution of (S)-8-(2-amino-6-((R)-1-(4-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid (product of Step 3, Example 10m) (240 mg, 0.33 mmol) in ethanol (8 mL) was added (E)-ethyl 3-(4,4,5,5-tetramethyl-1,3,2-dioxaborolan-2-yl)acrylate (110 mg, 0.49 mmol), $PdCl_2(PPh_3)_2$ (20 mg, 0.049 mmol) and $KHCO_3$ (170 mg, 0.05 mmol). The reaction was heated to 80° C. for 2 h, cooled to RT, and filtered. The solvent was removed in vacuo. Purification via normal phase silica gel chromatography ($CH_2Cl_2$/heptane) provided ((S)-8-(2-amino-6-((R)-1-(4-((E)-3-ethoxy-3-oxoprop-1-en-1-yl)-2-(3-methyl-1H-pyrazol-1-yl)phenyl)-2,2,2-trifluoroethoxy)pyrimidin-4-yl)-2-(4-yl)-2-((((2E,4Z)-2-vinylhexa-2,4-dien-1-yl)oxy)carbonyl)-2,8-diazaspiro[4.5]decane-3-carboxylic acid as a white solid.

Step 2: To a solution of ((S)-8-(2-amino-6-((R)-1-(4-((E)-3-ethoxy-3-oxoprop-1-en-1-yl)-2-(3-methyl-1H-pyrazol-1-yl)phenyl)-2,2,2-trifluoroethoxy)pyrimidin-4-yl)-2-((((2E,4Z)-2-vinylhexa-2,4-dien-1-yl)oxy)carbonyl)-2,8-diazaspiro[4.5]decane-3-carboxylic acid (180 mg, 0.15 mmol) in MeOH (5 mL) was hydrogenated in an H-Cube apparatus using a 10% (w/w) Pd/C cartridge with a flow rate of 1.0 mL/min at RT. The resulting eluent was concentrated in vacuo and the product was purified by column chromatography using an Isco Gold reversed phase silica cartridge (100% $CH_2Cl_2$ to 90:9:1 $CH_2Cl_2$:MeOH:conc. $NH_4OH$) to provide the title compound as a white solid.

$^1$H NMR (400 MHz, MeOH-d4): δ ppm 1.14 (t, J=7.15 Hz, 3 H) 1.50-1.68 (m, 4 H) 1.94-1.99 (m, 2 H) 2.04 (dd, J=13.45, 7.20 Hz, 1 H) 2.30 (dd, J=13.47, 9.27 Hz, 1 H) 2.35 (s, 3 H) 2.66 (t, J=7.54 Hz, 2 H) 2.97 (t, J=7.52 Hz, 2 H) 3.07-3.14 (m, 1 H) 3.23 (d, J=11.76 Hz, 1 H) 3.39-3.72 (m, 4 H) 4.01-4.11 (m, 3 H) 5.70 (s, 1 H) 6.36 (d, J=2.34 Hz, 1 H) 6.72 (q, J=6.72 Hz, 1 H) 7.27 (d, J=1.61 Hz, 1 H) 7.35 (dd, J=8.15, 1.61 Hz, 1 H) 7.62 (d, J=8.05 Hz, 1 H) 7.83 (d, J=2.34 Hz, 1 H). LCMS (MH+): 632.1

Example 10d (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid

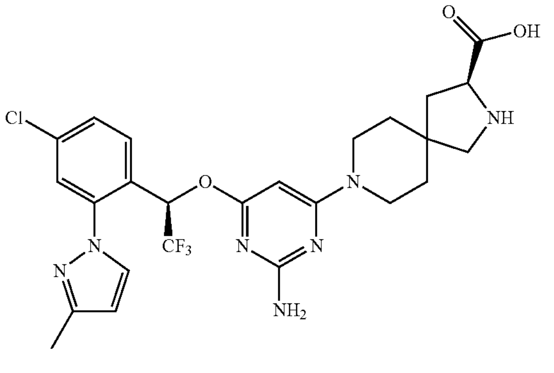 [SMILES: Cc1ccn(-c2cc(Cl)ccc2[C@@H](Oc2cc(N3CCC4(CC3)CN[C@H](C(=O)O)C4)nc(N)n2)C(F)(F)F)n1]

Step 1: To a solution of (1R)-1-[4-chloro-2-(3-methylpyrazol-1-yl)phenyl]-2,2,2-trifluoro-ethanol (40 g, 138 mmol) in dioxane (400 mL) was added 4,6-dichloropyrimidin-2-amine (113 g, 690 mmol) and $Cs_2CO_3$ (132 g, 405 mmol). The mixture was heated for 24 h at 80° C. The reaction was then cooled to RT and filtered. The solvent was removed in vacuo, then $CH_2Cl_2$ and heptane was added. The solvent volume was reduced until a solid precipitated out. The solid was filtered and the procedure repeated several times to provide 4-chloro-6-[(1R)-1-[4-chloro-2-(3-methylpyrazol-1-yl)phenyl]-2,2,2-trifluoro-ethoxy]pyrimidin-2-amine as a white solid.

Step 2: To a solution of 4-chloro-6-[(1R)-1-[4-chloro-2-(3-methylpyrazol-1-yl)phenyl]-2,2,2-trifluoroethoxy]pyrimidin-2-amine (57.3 g, 137 mmol, Step 1) in dioxane (500 mL) was added (S)-2-benzyl 3-ethyl 2,8-diazaspiro[4.5]decane-2,3-dicarboxylate (48 g, 124.9 mmol), and $NaHCO_3$ (31.5 g, 375 mmol). After 5 h, an additional amount of $NaHCO_3$ (31.5 g, 375 mmol) was added and the reaction mixture was heated to 90° C. for 36 h. The reaction was then cooled to RT and filtered. Purification by normal phase silica gel column (EtOAc/heptane) provided (S)-2-benzyl 3-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a white solid.

Step 3: N-CBZ Deprotection was accomplished via method B to provide (S)-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate an off-white solid.

Step 4: Hydrolysis of (S)-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate using the LiOH general method provided the title compound as an off-white solid.

Using the generic scheme below, the following examples of Table 3a were prepared as described above for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d).

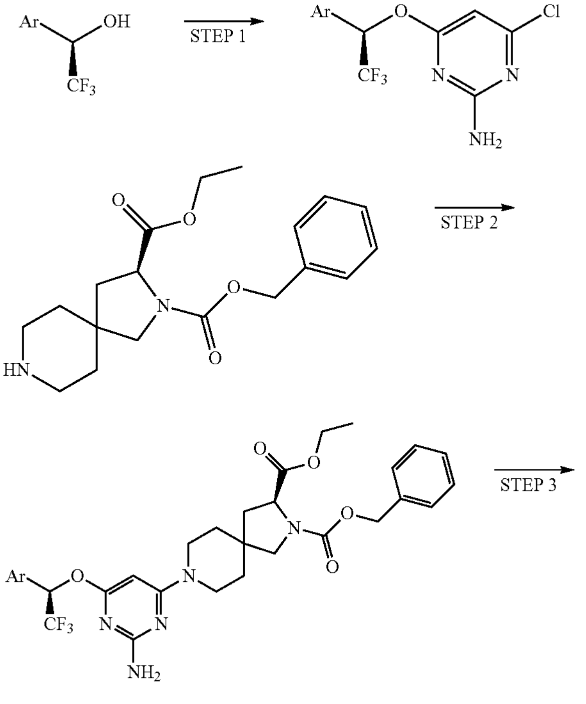

-continued

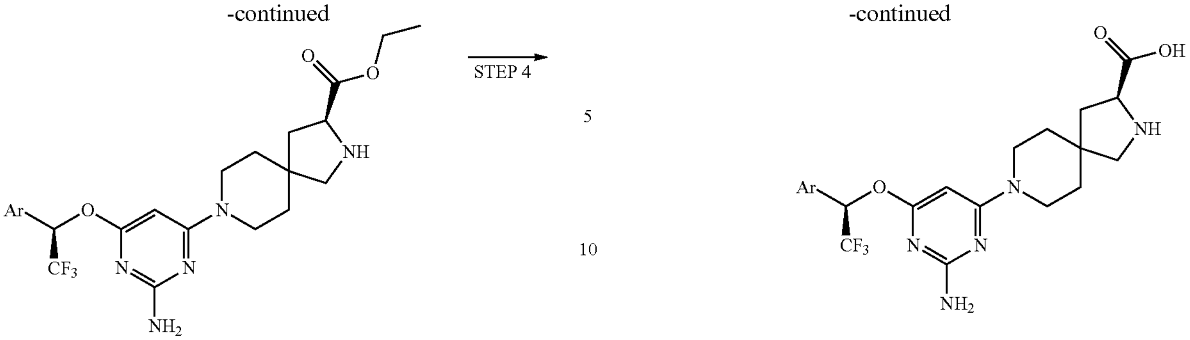

-continued

TABLE 3a

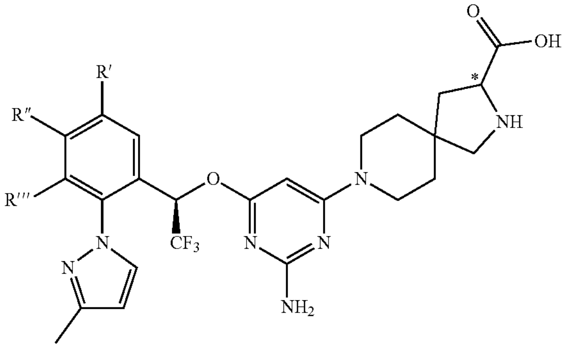

*Stereochemistry defined in name in table below

| Ex. No. | R' | R'' | R''' | CAS Name | LCMS (MH+) |
|---|---|---|---|---|---|
| 10a | H | H | H | 8-(2-amino-6((R)-2,2,2-trifluoro-1-(2-(3-methyl-1H-pyrazol-1-yl)phenyl)ethoxy)pyrimidin-4-yl)-2,8-diazaspiro[4.5]decane-3-carboxylic acid | 532 |
| 10b | H | Cl | H | 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid | 566 |
| 10c | H | Cl | H | (R)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid R-Spiro | 566 |
| 10d | H | Cl | H | (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid | 566 |
| 10e | H | H | H | (S)-8-(2-amino-6-((R)-2,2,2-trifluoro-1-(2-(3-methyl-1H-pyrazol-1-yl)phenyl)ethoxy)pyrimidin-4-yl)-2,8-diazaspiro[4.5]decane-3-carboxylic acid | 532 |
| 10f | H | H | Cl | (S)-8-(2-amino-6-((R)-1-(3-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid | 566.9 |
| 10g | H | $CF_3$ | H | (S)-8-(2-amino-6-((R)-2,2,2-trifluoro-1-(2-(3-methyl-1H-pyrazol-1-yl)-4-(trifluoromethyl)phenyl)ethoxy)pyrimidin-4-yl)-2,8-diazaspiro[4.5]decane-3-carboxylic acid | 600.6 |
| 10h | H | $CH_3$ | H | (S)-8-(2-amino-6-((R)-2,2,2-trifluoro-1-(4-methyl-2-(3-methyl-1H-pyrazol-1-yl)phenyl)ethoxy)pyrimidin-4-yl)-2,8-diazaspiro[4.5]decane-3-carboxylic acid | 546.6 |
| 10i | H | F | H | 8-(2-amino-64(R)-2,2,2-trifluoro-1-(4-fluoro-2-(3-methyl-1H-pyrazol-1-yl)phenyl)ethoxy)pyrimidin-4-yl)-2,8-diazaspiro[4.5]decane-3-carboxylic acid | 550.5 |
| 10j | H | 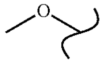 | H | 8-(2-amino-64(R)-2,2,2-trifluoro-1-(4-methoxy-2-(3-methyl-1H-pyrazol-1-yl)phenyl)ethoxy)pyrimidin-4-yl)-2,8-diazaspiro[4.5]decane-3-carboxylic acid | 564.6 |

TABLE 3a-continued

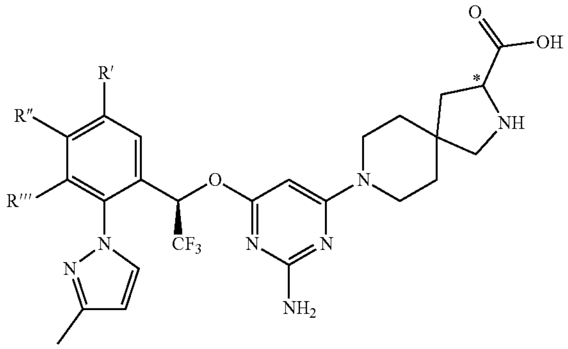

*Stereochemistry defined in name in table below

| Ex. No. | R' | R'' | R''' | CAS Name | LCMS (MH+) |
|---|---|---|---|---|---|
| 10k | Cl | H | H | 8-(2-amino-6-((R)-1-(5-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid | 566.9 |
| 10l | H | 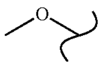 | H | (S)-8-(2-amino-6-((R)-2,2,2-trifluoro-1-(4-methoxy-2-(3-methyl-1H-pyrazol-1-yl)phenyl)ethoxy)pyrimidin-4-yl)-2,8-diazaspiro[4.5]decane-3-carboxylic acid | 564.6 |
| 10m | H | Br | H | (S)-8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-3-carboxylic acid | 611 |
| 10n | Br | H | H | (S)-8-(2-amino-6-((R)-1-(5-bromo-2-(3-methyl-1H-pyrazol-1-yl)phenyl)-2,2,2-trifluoroethoxy)pyrimidin-4-yl)-2,8-diazaspiro[4.5]decane-3-carboxylic acid | 611.5 |

TABLE 3b

NMR Data for Compounds of Table 3a

| Ex. No. | NMR |
|---|---|
| 10a | $^1$H NMR (400 MHz, MeOH-d4): δ ppm 1.59 (br. s., 4 H) 1.97-2.12 (m, 1 H) 2.24-2.35 (m, 1 H) 2.39 (s, 3 H) 3.11 (s, 1 H) 3.22 (s, 1 H) 3.40-3.58 (m, 2 H) 3.66 (br. s., 2 H) 3.95-4.17 (m, 1 H), 5.73 (s, 1 H) 6.39 (s, 1 H) 6.70-6.88 (m, 1 H) 7.42 (d, J = 7.52 Hz, 1 H) 7.53 (dd, J = 12.93, 7.57 Hz, 2 H) 7.75 (d, J = 7.52 Hz, 1 H) 7.87 (s, 1 H) |
| 10b | $^1$H NMR (400 MHz, MeOH-d4) δ ppm 1.44-1.74 (m, 4 H) 1.88-2.06 (m, 1 H) 2.17-2.31 (m, 1 H) 2.39 (s, 3 H) 2.86-3.04 (m, 1 H) 3.09 3.21 (m, 1 H) 3.41-3.57 (m, 2 H) 3.58-3.77 (m, 2H) 3.85-4.05 (m, 1H) 5.63-5.76 (m, 1 H )6.36-6.48 (m, 1 H) 6.76 6.91 (m, 1 H) 7.46-7.60 (m, 2 H) 7.67-7.79 (m, 1 H) 7.90-8.03 (m, 1 H) |
| 10c | $^1$H NMR (400 MHz, MeOH-d4): δ ppm 1.62 (br. s., 4 H) 2.04-2.17 (m, 1 H) 2.41 (s, 4 H) 3.10-3.21 (m, 1 H) 3.27 (s, 1 H) 3.44-3.58 (m, 2 H) 3.60-3.79 (m, 2 H) 4.05-4.18 (m, 1 H) 5.71 (s, 1 H) 6.44 (d, J = 2.15 Hz, 1 H) 6.75-6.91 (m, 1 H) 7.52 (s, 2 H) 7.66-7.80 (m, 1 H) 7.96 (d, J = 2.15 Hz, 1 H) |
| 10d | $^1$H NMR (400 MHz, MeOH-d4): δ ppm 1.59 (t, J = 5.30 Hz, 4 H) 1.97-2.12 (m, 1 H) 2.31 (dd, J = 13.45, 9.25 Hz, 1 H) 2.38 (s, 3 H) 3.11 (d, J = 11.76 Hz, 1 H) 3.25 (d, J = 11.71 Hz, 1 H) 3.38-3.57 (m, 2 H), 3.58-3.74 (m, 2 H) 4.08 (dd, J = 9.15, 7.15 Hz, 1 H) 5.69 (s, 1 H) 6.41 (d, J = 2.39 Hz, 1 H) 6.82 (q, J = 6.61 Hz, 1 H) 7.44-7.57 (m, 2 H) 7.71 (d, J = 8.35 Hz, 1 H) 7.93 (d, J = 2.34 Hz, 1 H) |
| 10e | $^1$H NMR (400 MHz, MeOH-d4): δ ppm 1.71 (dt, J = 18.13, 5.48 Hz, 4 H) 2.08 (dd, J = 13.62, 8.49 Hz, 1 H) 2.37 (s, 3 H) 2.47 (dd, J = 13.59, 8.96 Hz, 1 H) 3.62-3.90 (m, 4 H) 4.54 (t, J = 8.71 Hz, 1 H) 6.38 (d, J = 2.34 Hz, 1 H) 6.48 (br. s., 1 H) 6.85 (q, J = 6.04 Hz, 1 H) 7.46 (dd, J = 7.86, 1.07 Hz, 1 H) 7.52-7.59 (m, 1 H) 7.61-7.67 (m, 1 H) 7.70 (d, J = 7.76 Hz, 1 H) 7.84 (d, J = 2.39 Hz, 1 H) |
| 10f | $^1$H NMR (400 MHz, MeOH-d4): δ ppm 1.49-1.68 (m, 4 H) 2.04 (dd, J = 13.45, 7.15 Hz, 1 H) 2.30 (dd, J = 13.45, 9.25 Hz, 1 H) 2.35 (s, 3 H) 3.05-3.26 (m, 2 H) 3.38-3.77 (m, 5 H) 4.06 (dd, J = 9.10, 7.15 Hz, 1 H) 5.60 (s, 1 H) 6.18 (q, J = 6.56 Hz, 1 H) 6.39 (d, J = 2.34 Hz, 1 H) 7.49-7.59 (m, 1 H) 7.60-7.74 (m, 3 H) |
| 10g | $^1$H NMR (400 MHz, MeOH-d4): δ ppm 1.51-1.64 (m, 4 H) 2.03 (dd, J = 13.45, 7.15 Hz, 1 H) 2.29 (dd, J = 13.47, 9.27 Hz, 1 H) 2.37 (s, 3 H) 3.03-3.25 (m, 2 H) 3.37-3.54 (m, 2 H) 3.56-3.75 (m, 2 H), 4.04 (dd, J = 9.08, 7.22 Hz, 1 H) 5.66 (s, 1 H) 6.42 (d, J = 2.34 Hz, 1 |

TABLE 3b-continued

| Ex. No. | NMR Data for Compounds of Table 3a NMR |
|---|---|
| | H) 6.90 (q, J = 6.54 Hz, 1 H) 7.73 (s, 1 H) 7.78 (d, J = 8.25 Hz, 1 H) 7.91 (d, J = 8.35 Hz, 1 H) 7.98 (d, J = 2.34 Hz, 1 H) |
| 10h | $^1$H NMR (400 MHz, MeOH-d4): δ ppm 1.58 (t, J = 5.25 Hz, 4 H) 2.05 (dd, J = 13.45, 7.15 Hz, 1 H) 2.30 (dd, J = 1.00 Hz, 1 H) 2.37 (s, 3 H) 2.40 (s, 3 H) 3.05-3.17 (m, 1 H) 3.21-3.29 (m, 1 H) 3.36-3.75 (m, 4 H) 4.09 (dd, J = 9.10, 7.25 Hz, 1 H) 5.73 (s, 1 H) 6.37 (d, J = 2.25 Hz, 1 H) 6.71 (d, J = 6.69 Hz, 1 H) 7.23 (d, J = 0.68 Hz, 1 H) 7.31 (d, J = 8.10 Hz, 1 H) 7.60 (d, J = 8. 05 Hz, 1 H) 7.84 (d, J = 2.29 Hz, 1 H) |
| 10i | $^1$H NMR (400 MHz, MeOH-d4): δ ppm 1.52-1.91 (m, 4 H) 2.05-2.16 (m, 1 H) 2.40 (s, 3 H) 2.45-2.69 (m, 1 H) 3.52-4.13 (m, 4 H) 4.57 (d, J = 17.28 Hz, 1 H) 6.43 (d, J = 2.25 Hz, 1 H) 6.88-7.09 (m, 1 H) 7.23-7.51 (m, 2 H) 7.68-7.83 (m, 1 H) 7.92 (d, J = 2.29 Hz, 1 H) |
| 10j | $^1$H NMR (400 MHz, MeOH-d4): δ ppm 1.59 (d, J = 4.54 Hz, 4 H) 2.00-2.12 (m, 1 H) 2.27-2.35 (m, 1 H) 2.38 (s, 3 H) 3.05-3.17 (m, 1 H) 3.25 (d, J = 11.71 Hz, 1 H) 3.48 (dd, J = 1.17, 0.20 Hz, 2 H) 3.66 (d, J = 5.52 Hz, 2 H) 3.85 (s, 3 H) 4.08 (dd, J = 9.08, 7.27 Hz, 1 H) 5.72 (s, 1 H) 6.38 (d, J = 2.29 Hz, 1 H) 6.67 (d, J = 6.69 Hz, 1 H) 6.94 (d, J = 2.64 Hz, 1 H) 7.06 (dd, J = 8.83, 2.59 Hz, 1 H) 7.63 (d, J = 8.83 Hz, 1 H) 7.87 (d, J = 2.29 Hz, 1 H) |
| 10k | $^1$H NMR (400 MHz, CHLOROFORM-d): δ ppm 1.18-1.36 (m, 3 H) 1.43 (t, J = 6.74 Hz, 3 H) 1.54-2.29 (m, 6 H) 2.39 (br. s., 3 H) 3.78 (br. s., 4 H) 4.26 (br. s., 2 H) 4.42 (d, J = 6.15 Hz, 2 H) 5.53 (br. s., 1 H), 6.36 (s, 1 H) 6.59 (br. s., 1 H) 7.48 (d, J = 7.96 Hz, 1 H), 7.61 (br. s. 1 H) 8.16 (d, J = 8.05 Hz, 1 H) 8.34 (br. s., 1 H) |
| 10l | $^1$H NMR (400 MHz, DICHLOROMETHANE-d2): δ ppm 1.40-1.61 (m, 4 H) 1.95 (dd, J = 12.89, 5.86 Hz, 1 H) 2.14-2.28 (m, 1 H) 2.36 (s, 3 H) 3.07 (d, J = 1.00 Hz, 1 H) 3.16 (d, J = 1.00 Hz, 1 H) 3.36 (br. s., 2 H), 3.54 (br. s., 2 H) 3.79 (s, 3 H) 4.08 (t, J = 7.71 Hz, 1 H) 4.71-5.04 (m, 2 H) 5.47 (s, 1 H) 6.30 (d, J = 2.10 Hz, 1 H) 6.65 (q, J = 7.11 Hz, 1 H) 6.87 (d, J = 2.64 Hz, 1 H) 6.95 (dd, J = 8.86, 2.61 Hz, 1 H), 7.61 (d, J = 8.74 Hz, 1 H) 7.65 (d, J = 2.20 Hz, 1 H) |
| 10m | $^1$H NMR (400 MHz, MeOH-d4): δ ppm 1.64 (d, J = 4.69 Hz, 4 H) 2.03-2.15 (m, 1 H) 2.40 (s, 4 H) 3.12-3.31 (m, 2 H) 3.43-3.63 (m, 2 H) 3.64-3.78 (m, 2 H) 4.16-4.34 (m, 1 H) 6.43 (d, J = 2.34 Hz, , 1 H) 6.76-6.91 (m, 1 H) 7.67 (dd, J = 5.76, 4.20 Hz, 3 H) 7.94 (d, J = 2.15 Hz, 1 H) |
| 10n | $^1$H NMR (400 MHz, DMSO-d6): δ ppm 1.47-1.71 (m, 4 H) 1.90 (dd, J = 13.15, 9.15 Hz, 1 H) 2.24-2.39 (m, 4 H) 3.13 (t, J = 5.25 Hz, 2 H) 3.66 (br. s., 4 H) 4.39-4.51 (m, 2 H) 6.05 (s, 1 H) 6.42 (d, J = 2.34 Hz, 1 H) 7.25 (d, J = 5.27 Hz, 1 H) 7.51 (d, J = 8.59 Hz, 1 H) 7.78 (s, 1 H) 7.85 (dd, J = 8.54, 2.29 Hz, 1 H) 8.11 (d, J = 2.34 Hz, 1 H) 8.95 (d, J = 6.69 Hz, 1 H) 10.20 (br. s., 1 H) |

Example 10o (S)-8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-3-carboxylic acid

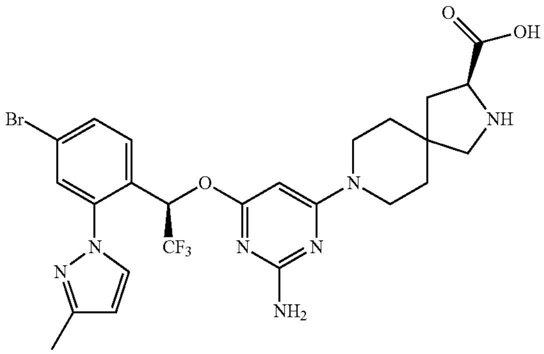

The title compound was prepared as described for (S)-8-(2-amino-6-((R)-1-(4-chloro-2-(3-methyl-1H-pyrazol -1-yl) phenyl)-2,2,2-trifluoroethoxy)pyrimidin-4-yl)-2,8-diazaspiro[4.5]decane-3-carboxylic acid (Example 10d) starting with (R)-1-(5-bromo-[1,1'-biphenyl]-2-yl)-2,2,2-trifluoroethanol(Intermediate 38).

$^1$H NMR (400 MHz, MeOH-d4): δ ppm 1.29 (d, J=7.7 Hz, 2H), 1.61 (q, J=6.5, 5.3 Hz, 4H), 2.06 (dd, J=13.5, 7.4 Hz, 1H), 2.36 (dd, J=13.5, 9.1 Hz, 1H), 3.15 (d, J=11.9 Hz, 1H), 3.26 (d, J=11.7 Hz, 1H), 3.47 (ddt, J=21.7, 13.4, 5.8 Hz, 2H), 3.63 (m, 2H), 4.18 (t, J=8.2 Hz, 1H), 6.63 (q, J=6.8 Hz, 1H), 7.50 (m, 7H). LCMS (MH+): 607.

Example 10p (S)-8-(2-amino-6-((R)-1-(4-chloro-2-(3-(trifluoromethyl)-1H-pyrazol-1-yl)phenyl)-2,2,2-trifluoroethoxy)pyrimidin-4-yl)-2,8-diazaspiro[4.5]decane-3-carboxylic acid

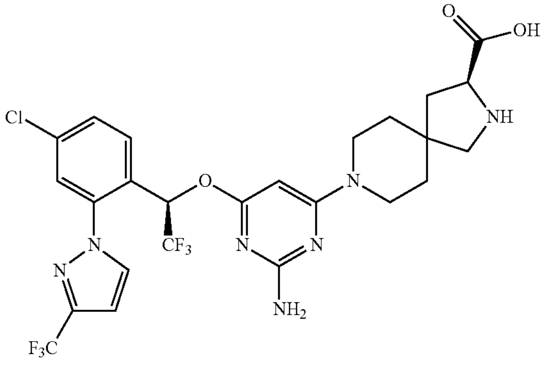 [SMILES: Nc1nc(O[C@H](c2ccc(Cl)cc2-n2ccc(C(F)(F)F)n2)C(F)(F)F)cc(N2CCC3(CC2)CN[C@H](C(=O)O)C3)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro [4.5]decane-3-carboxylic acid (Example 10d) starting with (R)-1-(4-chloro-2-(3-(trifluoromethyl)-1H-pyrazol-1-yl)phenyl)-2,2,2-trifluoroethanol (Intermediate 39).

$^1$H NMR (400 MHz, MeOH-d4): δ ppm 1.53 (d, J=5.08 Hz, 4 H) 1.77-1.87 (m, 1 H) 2.03-2.20 (m, 1 H) 2.75 (s, 1 H) 2.99 (s, 1 H) 3.37-3.53 (m, 2 H) 3.54-3.66 (m, 2 H) 3.66-3.77 (m, 1 H) 5.56 (s, 1 H) 6.53-6.70 (m, 1 H) 6.96 (d, J=2.34 Hz, 1 H) 7.62 (dd, J=4.30, 2.34 Hz, 2 H), 7.76 (s, 1 H) 8.25 (d, J=1.37 Hz, 1 H). LCMS (MH+): 620.

Example 10pa (S)-8-(2-amino-6-((R)-1-(2-(3-(tert-butyl)-1H-pyrazol-1-yl)-4-chlorophenyl)-2,2,2-trifluoroethoxy)pyrimidin-4-yl)-2,8-diazaspiro[4.5]decane-3-carboxylic acid

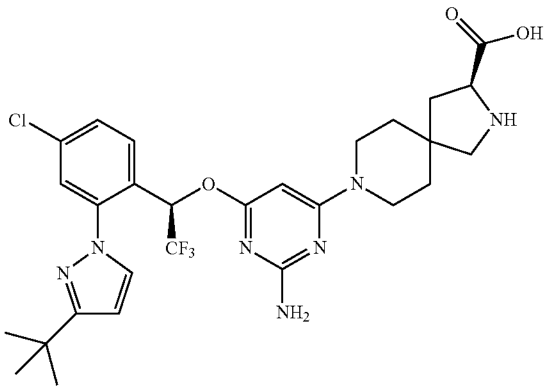 [SMILES: CC(C)(C)c1ccn(-c2cc(Cl)ccc2[C@@H](Oc2cc(N3CCC4(CC3)CN[C@H](C(=O)O)C4)nc(N)n2)C(F)(F)F)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro [4.5]decane-3-carboxylic acid (Example 10d) starting with (R)-1-(2-(3-(tert-butyl)-1H-pyrazol-1-yl)-4-chlorophenyl)-2,2,2-trifluoroethanol (Intermediate 40).

$^1$H NMR (400 MHz, MeOH-d4): δ ppm 1.40 (s, 9 H) 1.51-1.68 (m, 4 H) 1.99-2.12 (m, 1 H) 2.25-2.41 (m, 1 H) 3.05-3.16 (m, 1 H) 3.20-3.28 (m, 1 H) 3.38-3.55 (m, 2 H) 3.56-3.73 (m, 2 H) 4.00-4.16 (m, 1 H) 5.57 (s, 1 H) 6.52 (d, J=2.34 Hz, 1 H) 7.15-7.28 (m, 1 H) 7.44-7.53 (m, 1 H) 7.56 (d, J=1.95 Hz, 1 H) 7.68-7.79 (m, 1 H) 7.95 (d, J=2.34 Hz, 1 H). LCMS (MH+): 609.

Example 10q (S)-8-(2-amino-6-((R)-1-(4-chloro-2-(3-isopropyl-1H-pyrazol-1-yl)phenyl)-2,2,2-trifluoroethoxy)pyrimidin-4-yl)-2,8-diazaspiro[4.5]decane-3-carboxylic acid

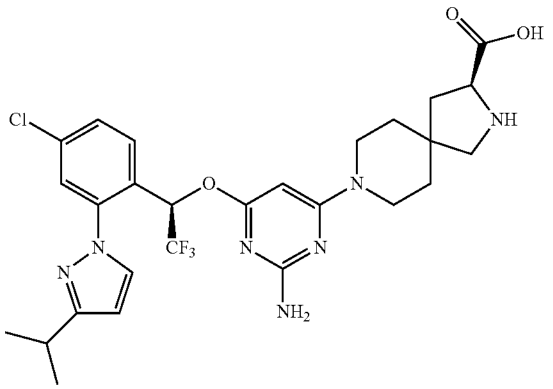 [SMILES: CC(C)c1ccn(-c2cc(Cl)ccc2[C@@H](Oc2cc(N3CCC4(CC3)CN[C@H](C(=O)O)C4)nc(N)n2)C(F)(F)F)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d) starting with (R)-1-(4-chloro-2-(3-isopropyl-1H-pyrazol-1-yl)phenyl)-2,2,2-trifluoroethanol (Intermediate 41).

$^1$H NMR (400 MHz, MeOH-d4): δ ppm 1.36 (dd, J=6.93, 1.07 Hz, 6 H) 1.57 (br. s., 4 H) 1.86-2.03 (m, 1 H) 2.15-2.30 (m, 1 H) 2.86-3.00 (m, 1 H) 3.02-3.19 (m, 2 H) 3.39-3.55 (m, 2 H) 3.57-3.73 (m, 2 H) 3.82-3.98 (m, 1 H) 5.63 (s, 1 H) 6.40-6.56 (m, 1 H) 6.93-7.10 (m, 1 H) 7.54 (s, 2 H) 7.67-7.78 (m, 1 H) 7.91-8.02 (m, 1 H). LCMS (MH+): 595.

Example 10r (S)-8-(2-amino-6-((R)-1-(4-chloro-2-(3-cyclopropyl-1H-pyrazol-1-yl)phenyl)-2,2,2-trifluoroethoxy)pyrimidin-4-yl)-2,8-diazaspiro[4.5]decane-3-carboxylic acid

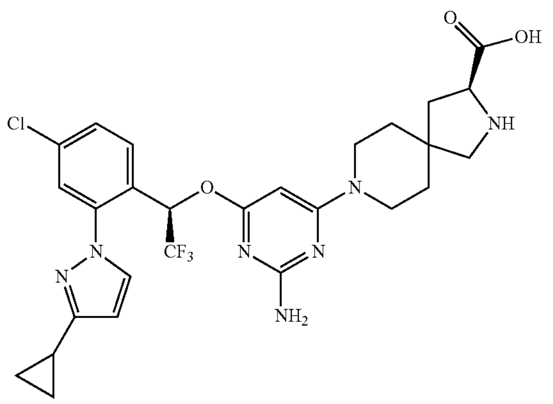 [SMILES: Nc1nc(O[C@H](c2ccc(Cl)cc2-n2ccc(C3CC3)n2)C(F)(F)F)cc(N2CCC3(CC2)CN[C@H](C(=O)O)C3)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d) starting with (R)-1-(4-chloro-2-(3-cyclopropyl-1H-pyrazol-1-yl)phenyl)-2,2,2-trifluoroethanol (Intermediate 42).

$^1$H NMR (400 MHz, MeOH-d4): δ ppm 0.77-0.90 (m, 2 H) 0.95-1.08 (m, 2 H) 1.49-1.65 (m, 4 H) 1.80-1.95 (m, 1 H) 1.99-2.10 (m, 1 H) 2.10-2.24 (m, 1 H) 2.74-2.85 (m, 1 H) 3.00-3.11 (m, 1 H) 3.38-3.69 (m, 4 H) 3.72-3.84 (m, 1 H) 5.56-5.70 (m, 1 H) 6.29-6.38 (m, 1 H) 6.89-7.05 (m, 1 H) 7.52 (s, 2 H) 7.67-7.77 (m, 1 H) 7.86-7.98 (m, 1 H). LCMS (MH+): 593.

Example 11

(S)-8-(2-amino-6-((R)-2,2,2-trifluoro-1-(6-methyl-2-(3-methyl-1H-pyrazol-1-yl)pyridin-3-yl)ethoxy)pyrimidin-4-yl)-2,8-diazaspiro[4.5]decane-3-carboxylic acid

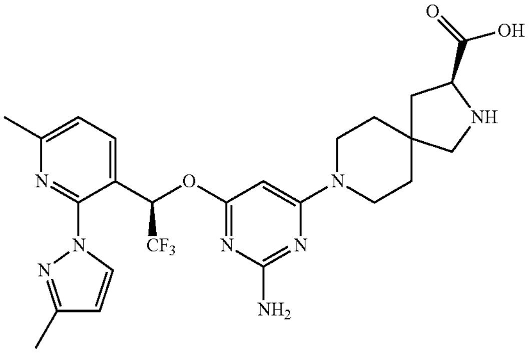 [SMILES: Cc1ccc([C@@H](Oc2cc(N3CCC4(CC3)CN[C@H](C(=O)O)C4)nc(N)n2)C(F)(F)F)c(-n2ccc(C)n2)n1]

The title compound was prepared as described for (S)-8-(2-amino-6-((R)-1-(4-chloro-2-(3-methyl-1H-pyrazol -1-yl)phenyl)-2,2,2-trifluoroethoxy)pyrimidin-4-yl)-2,8-diazaspiro[4.5]decane-3-carboxylic acid (Example 10d) starting with (S)-2,2,2-trifluoro-1-(6-methyl-2-(3-methyl-1H-pyrazol-1-yl)pyridin-3-yl)ethanol (Intermediate 20)

Example 12a (S)-8-(2-amino-6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-3-carboxylic acid

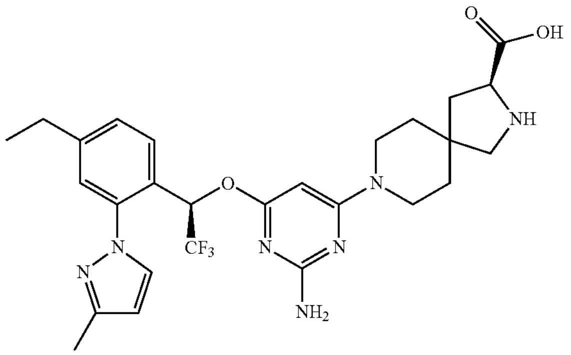 [SMILES: CCc1ccc([C@@H](Oc2cc(N3CCC4(CC3)CN[C@H](C(=O)O)C4)nc(N)n2)C(F)(F)F)c(-n2ccc(C)n2)c1]

Step 1: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (300 mg, 0.388 mmol, see Example 1u) in EtOH:$H_2O$ (15 mL) was added 4,4,5,5-tetramethyl-2-vinyl-1,3,2-dioxaborolane (90 mg, 0.58 mmol), $KHCO_3$ (389 mg, 3.88 mmol), and $PdCl_2(PPh_3)_2$ (41 mg, 0.058 mmol). The reaction mixture was heated to 80° C. for 1 h, then cooled to RT. The reaction was diluted with water, extracted with EtOAc. The combined organic layers were washed with brine, dried over $Na_2SO_4$, filtered, and concentrated in vacuo. Purification with a 40 g Isco RediSep silica cartridge (EtOAc:heptane) provided (S)-2-benzyl 3-ethyl 8-(2-amino-6-((R)-2,2,2-trifluoro-1-(2-(3-methyl-1H-pyrazol-1-yl)-4-vinylphenyl)ethoxy)pyrimidin-4-yl)-2,8-diazaspiro[4.5]decane-2,3-dicarboxylate as a white solid.

Step 2: N-CBZ Deprotection was accomplished via method A, which also reduced the olefin, to provide (S)-2-benzyl 3-ethyl 8-(2-amino-6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a white solid.

Step 3: Hydrolysis of (S)-2-benzyl 3-ethyl 8-(2-amino-6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-2,3-dicarboxylate using the LiOH general method provided the title compound as a white solid.

Using the same scheme below, the following examples of Table 4a were prepared as described above for (S)-8-(2-amino -6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 12a).

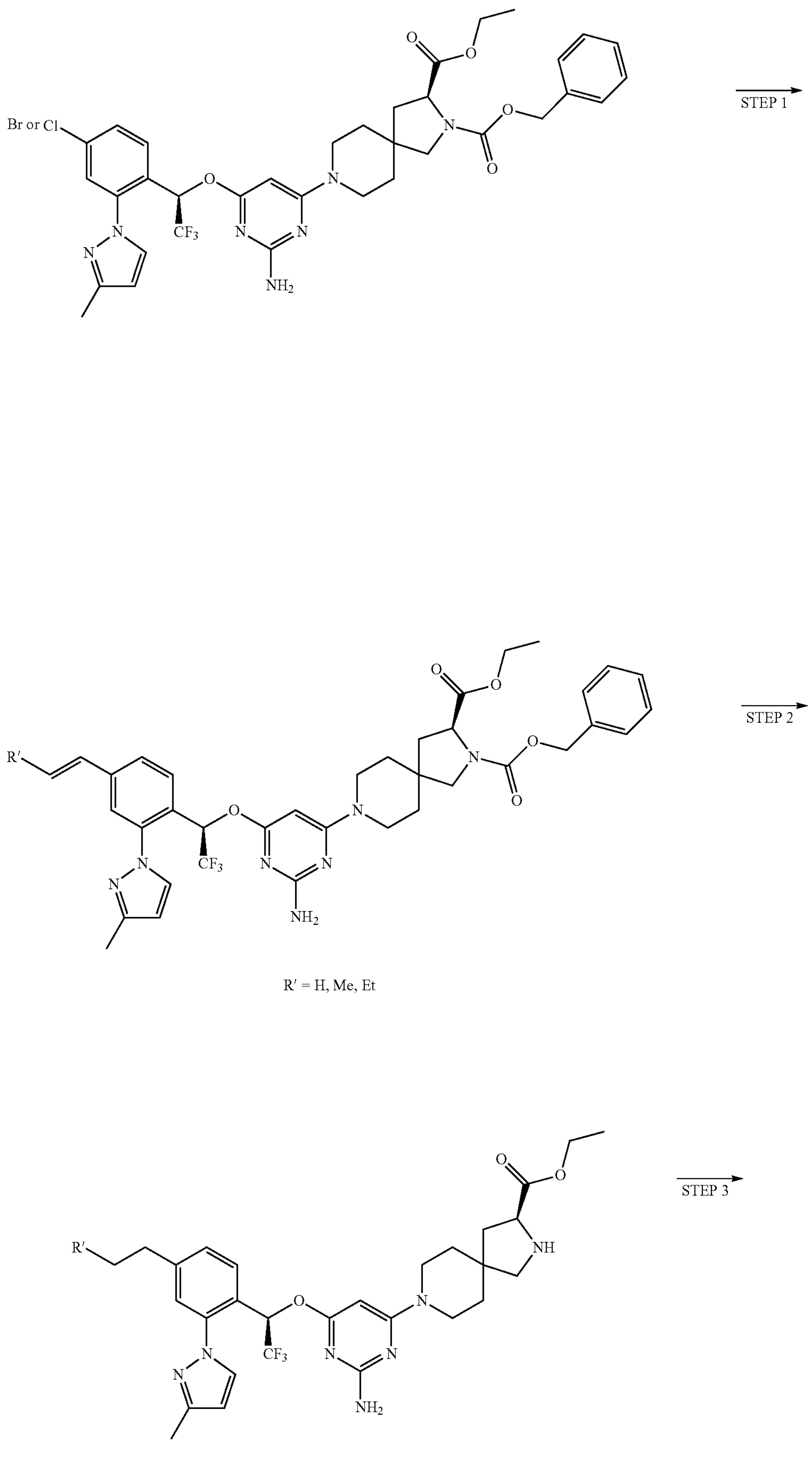
STEP 1
STEP 2
R′ = H, Me, Et
STEP 3

-continued

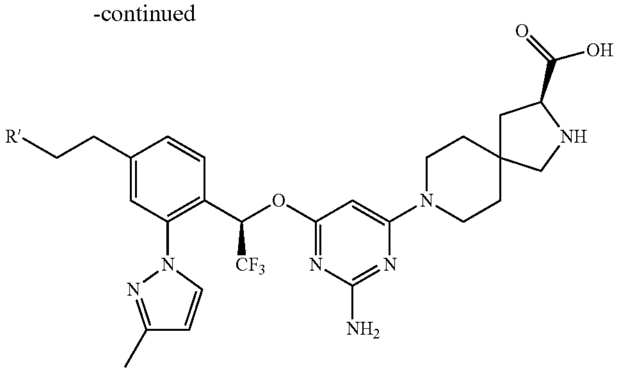

TABLE 4a

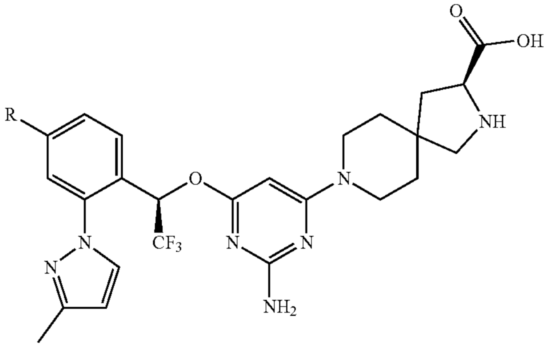

| Ex. No. | R | CAS Name | LCMS (MH+) |
|---|---|---|---|
| 12a | 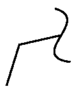 | (S)-8-(2-amino-6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-3-carboxylic acid | 560 |
| 12b | 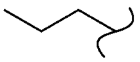 | (S)-8-(2-amino-6-((R)-2,2,2-trifluoro-1-(2-(3-methyl-1H-pyrazol-1-yl)-4-propylphenyl)ethoxy)pyrimidin-4-yl)-2,8-diazaspiro[4.5]decane-3-carboxylic acid | 575 |
| 12c | 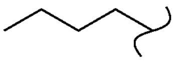 | (S)-8-(2-amino-6-((R)-1-(4-butyl-2-(3-methyl-1H-pyrazol-1-yl)phenyl)-2,2,2-trifluoroethoxy)pyrimidin-4-yl)-2,8-diazaspiro[4.5]decane-3-carboxylic acid | 588 |

TABLE 4b

NMR Data for Compounds of Table 4a

| Ex. No. | NMR |
|---|---|
| 12a | $^1$H NMR (400 MHz, MeOH-d4): δ ppm 1.26 (t, J = 7.59 Hz, 3 H), 1.50-1.69 (m, 4 H), 2.01-2.35 (m, 2 H), 2.37 (s, 3 H), 2.72 (q, J = 7.57 Hz, 2 H), 3.05-3.28 (m, 2 H), 3.40-3.76 (m, 4 H), 4.08 (dd, J = 8.88, 7.32 Hz, 1 H), 5.72 (s, 1 H), 6.38 (d, J = 2.25 Hz, 1 H), 6.71 (q, J = 6.70 Hz, 1 H), 7.25 (d, J = 1.56 Hz, 1 H), 7.35 (dd, J = 8.18, 1.59 Hz, 1 H), 7.63 (d, J = 8.15 Hz, 1 H), 7.85 (d, J = 2.29 Hz, 1 H) |
| 12b | $^1$H NMR (400 MHz, MeOH-d4): δ ppm 0.96 (t, J = 7.35 Hz, 3 H), 1.49-1.62 (m, 4 H), 1.62-1.77 (m, 2 H), 2.01-2.35 (m, 2 H), 2.37 (s, 3 H), 2.59-2.74 (m, 2 H), 3.06-3.29 (m, 2 H), 3.39-3.77 (m, 4 H), 4.08 (dd, J = 9.05, 7.30 Hz, 1 H), 5.72 (s, 1 H), 6.37 (d, J = 2.29 Hz, 1 H), 6.71 (q, J = 6.72 Hz, 1 H), 7.23 (d, J = 1.56 Hz, 1 H), 7.33 (dd, J = 8.15, 1.56 Hz, 1 H), 7.63 (d, J = 8.05 Hz, 1 H), 7.85 (d, J = 2.29 Hz, 1 H) |

TABLE 4b-continued

| Ex. No. | NMR |
|---|---|
| | NMR Data for Compounds of Table 4a |
| 12c | $^1$H NMR (400 MHz, MeOH-d4): δ ppm 0.94 (t, J = 7.35 Hz, 3 H), 1.38 (dq, J = 14.92, 7.39 Hz, 2 H), 1.49-1.72 (m, 6 H), 2.01-2.35 (m, 2 H), 2.37 (s, 3 H), 2.60-2.74 (m, 2 H), 3.07-3.28 (m, 2 H), 3.40-3.74 (m, 4 H), 4.08 (dd, J = 9.15, 7.20 Hz, 1 H), 5.71 (s, 1 H), 6.38 (d, J = 2.15 Hz, 1 H), 6.63-6.77 (m, 1 H), 7.23 (d, J = 1.61 Hz, 1 H), 7.33 (dd, J = 8.10, 1.66 Hz, 1 H), 7.63 (d, J = 8.05 Hz, 1 H), 7.85 (d, J = 2.29 Hz, 1 H) |

Example 13

(3S)-8-(2-amino-6-((1R)-1-(4-(1,2-dihydroxyethyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

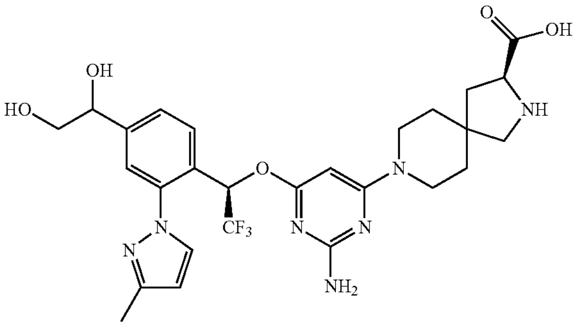 [SMILES: Cc1ccn(-c2cc(C(O)CO)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-2,2,2-trifluoro-1-(2-(3-methyl-1H-pyrazol-1-yl)-4-vinylphenyl)ethoxy)pyrimidin-4-yl)-2,8-diazaspiro[4.5]decane-2,3-dicarboxylate (product of Step 1, Example 12b) (373 mg, 0.518 mmol) in 4:1 acetone:$H_2O$ (20 mL) was added $OsO_4$ (313 μL of a 4% (w/w) aqueous solution, 325 mg, 0.0518 mmol) and N-methylmorpholine-N-oxide (214 μL of a 50% (w/w) aqueous solution, 242 mg, 1.04 mmol). The reaction was stirred at RT for 24 h, concentrated in vacuo, and the residue was purified by chromatography on a 50 g Isco Gold RediSep reversed phase silica cartridge ($H_2O$:HOAc: 99:1 to EtOH:HOAc 99:1). A second purification on a 40 g Isco RediSep silica cartridge eluting ($CH_2Cl_2$ 100% to 90:9:1 $CH_2Cl_2$:EtOH:$NH_4OH$) provided (3S)-2-benzyl 3-ethyl 8-(2-amino-6-((1R)-1-(4-(1,2-dihydroxyethyl)-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a white solid.

Step 2: N-CBZ deprotection was accomplished via method A to provide (3S)-ethyl 8-(2-amino-6-((1R)-1-(4-(1,2-dihydroxyethyl)-2-(3-methyl-1H-pyrazol-1-yl)phenyl)-2,2,2-trifluoroethoxy)pyrimidin-4-yl)-2,8-diazaspiro[4.5]decane-3-carboxylate as a white solid.

Step 3: Hydrolysis of (3S)-ethyl 8-(2-amino-6-((1R)-1-(4-(1,2-dihydroxyethyl)-2-(3-methyl-1H-pyrazol-1-yl)phenyl)-2,2,2-trifluoroethoxy)pyrimidin-4-yl)-2,8-diazaspiro[4.5]decane-3-carboxylate using the LiOH general method provides the title compound as a white solid.

$^1$H NMR (400 MHz, MeOH-d4): δ ppm 1.49-1.66 (m, 4 H) 2.05 (dd, J=13.50, 7.20 Hz, 1 H) 2.31 (dd, J=13.45, 9.20 Hz, 1 H) 2.38 (s, 3 H) 3.04-3.28 (m, 2 H) 3.38-3.76 (m, 6 H) 4.08 (dd, J=8.98, 7.27 Hz, 1 H) 4.67-4.79 (m, 1 H) 5.72 (d, J=2.15 Hz, 1 H) 6.39 (d, J=2.29 Hz, 1 H) 6.77 (q, J=6.65 Hz, 1 H) 7.45 (s, 1 H) 7.52 (d, J=8.20 Hz, 1 H) 7.71 (d, J=8.15 Hz, 1 H) 7.88 (dd, J=4.20, 2.34 Hz, 1 H). LCMS (MH+): 592.

Example 14

(S)-8-(2-amino-6-((R)-1-(4-cyano-2-(3-methyl-1H-pyrazol-1-yl)phenyl)-2,2,2-trifluoroethoxy)pyrimidin-4-yl)-2,8-diazaspiro[4.5]decane-3-carboxylic acid

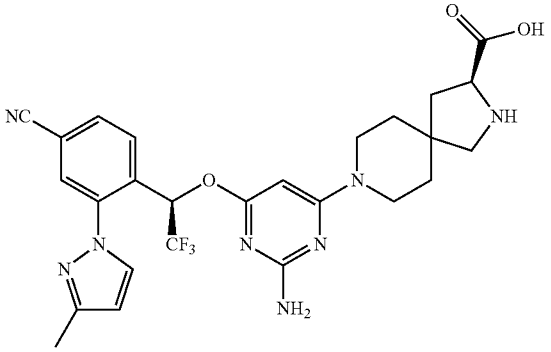 [SMILES: Cc1ccn(-c2cc(C#N)ccc2[C@@H](Oc2cc(N3CCC4(CC3)CN[C@H](C(=O)O)C4)nc(N)n2)C(F)(F)F)n1]

Step 1: To a solution of (3S)-2-benzyl 3-ethyl 8-(2-amino-6-(1-(4-chloro-2-(3-methyl-1H-pyrazol-1-yl)phenyl)-2,2,2-trifluoroethoxy)pyrimidin-4-yl)-2,8-diazaspiro[4.5]decane-2,3-dicarboxylate (730 mg, 1.0 mmol), was added $ZnCN_2$ (280 mg, 2.4 mmol), Zn (64 mg, 1.0 mmol), DMA (10 mL), and $Pd(P\text{-}t\text{-}Bu_3)_2$ (78 mg, 0.15 mmol). The reaction mixture was heated in a sealed vial at 115° C. for 2 h, then cooled to RT, filtered, and concentrated in vacuo. Purification by normal phase silica gel column (EtOAc/hepate) provided (3S)-2-benzyl 3-ethyl 8-(2-amino-6-(1-(4-cyano-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a viscous oil.

Step 2: N-CBZ Deprotection was accomplished via Method A to provide (3S)-ethyl 8-(2-amino-6-(1-(4-cyano-2-(3-methyl-1H-pyrazol-1-yl)phenyl)-2,2,2-trifluoroethoxy)pyrimidin-4-yl)-2,8-diazaspiro[4.5]decane-3-carboxylate as an off-white solid.

Step 3: Hydrolysis of (3S)-ethyl 8-(2-amino-6-(1-(4-cyano-2-(3-methyl-1H-pyrazol-1-yl)phenyl)-2,2,2-trifluoroethoxy)pyrimidin-4-yl)-2,8-diazaspiro[4.5]decane-3-carboxylate using the LiOH general method provides the title compound as an off-white solid.

$^1$H NMR (400 MHz, MeOH-d4): δ ppm 1.47-1.71 (m, 4 H) 1.95-2.10 (m, 1 H) 2.20-2.33 (m, 1 H) 2.36 (s, 3 H) 2.96-3.24 (m, 2 H) 3.35-3.54 (m, 2 H) 3.55-3.79 (m, 2 H) 3.92-4.13 (m, 1 H) 5.65 (s, 1 H) 6.42 (d, J=2.15 Hz, 1 H) 6.95 (q, J=6.72 Hz, 1 H) 7.70-7.91 (m, 3 H) 7.97 (d, J=2.25 Hz, 1 H). LCMS (MH+): 556.

Example 15

(S)-8-(2-amino-6-((R)-1-(4-carbamoyl-2-(3-methyl-1H-pyrazol-1-yl)phenyl)-2,2,2-trifluoroethoxy)pyrimidin-4-yl)-2,8-diazaspiro[4.5]decane-3-carboxylic acid

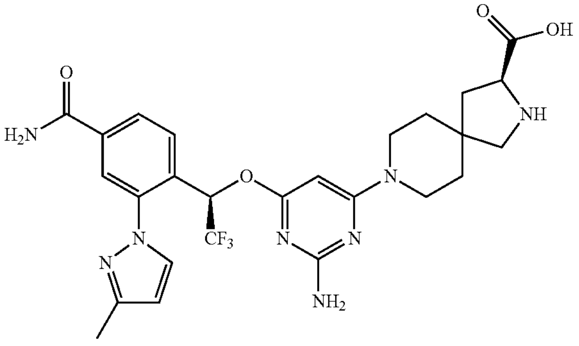 [SMILES: Cc1ccn(-c2cc(C(N)=O)ccc2[C@@H](Oc2cc(N3CCC4(CC3)CN[C@H](C(=O)O)C4)nc(N)n2)C(F)(F)F)n1]

Step 1: To a solution of (3S)-2-benzyl 3-ethyl 8-(2-amino-6-(1-(4-cyano-2-(3-methyl-1H-pyrazol-1-yl)phenyl)-2,2,2-trifluoroethoxy)pyrimidin-4-yl)-2,8-diazaspiro[4.5]decane-2,3-dicarboxylate (150 mg, 0.2 mmol, see Ex. 14) in toluene (10 mL) was added acetaldehyde oxime (240 mg, 4 mmol) and $InCl_3$ (44 mg, 0.2 mmol). The reaction was heated to 110° C. for 3 h, then cooled to RT, and concentrated in vacuo. Purification by normal phase silica gel column (EtOAc/hepate) provided (3S)-2-benzyl 3-ethyl 8-(2-amino-6-(1-(4-carbamoyl-2-(3-methyl-1H-pyrazol-1-yl)phenyl)-2,2,2-trifluoroethoxy)pyrimidin-4-yl)-2,8-diazaspiro [4.5]decane-2,3-dicarboxylate as a white solid.

Step 2: N-CBZ Deprotection was accomplished via Method A to provide (3S)-ethyl 8-(2-amino-6-(1-(4-carbamoyl-2-(3-methyl-1H-pyrazol-1-yl)phenyl)-2,2,2-trifluoroethoxy)pyrimidin-4-yl)-2,8-diazaspiro[4.5]decane-3-carboxylate as a white solid.

Step 3: Hydrolysis of (3S)-ethyl 8-(2-amino-6-(1-(4-carbamoyl-2-(3-methyl-1H-pyrazol-1-yl)phenyl)-2,2,2-trifluoroethoxy)pyrimidin-4-yl)-2,8-diazaspiro[4.5]decane-3-carboxylate using the LiOH general method provides the title compound as a white solid.

$^1$H NMR (400 MHz, MeOH-d4): δ ppm 1.56 (t, J=4.98 Hz, 5 H) 2.03 (dd, J=13.47, 7.03 Hz, 1 H) 2.23-2.33 (m, 2 H) 2.35-2.39 (m, 3 H) 3.04-3.12 (m, 1 H) 3.22 (d, J=11.71 Hz, 1 H) 3.37-3.72 (m, 5 H) 4.05 (dd, J=9.20, 7.05 Hz, 1 H) 5.70 (s, 1 H) 6.40 (d, J=2.39 Hz, 1 H) 6.82-6.92 (m, 1 H) 7.80 (d, J=8.10 Hz, 1 H) 7.87-7.97 (m, 4 H). LCMS (MH+): 575.

Example 16

(S)-8-(2-amino-6-((R)-1-(4-carboxy-2-(3-methyl-1H-pyrazol-1-yl)phenyl)-2,2,2-trifluoroethoxy)pyrimidin-4-yl)-2,8-diazaspiro[4.5]decane-3-carboxylic acid

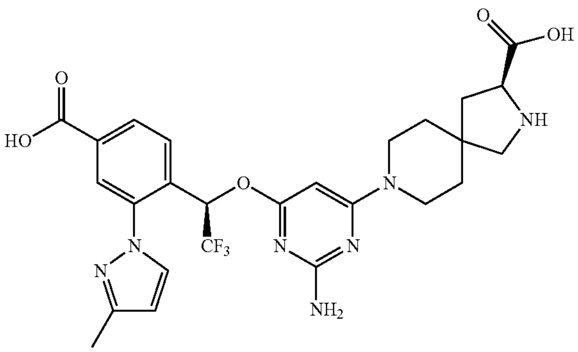 [SMILES: Cc1ccn(-c2cc(C(=O)O)ccc2[C@@H](Oc2cc(N3CCC4(CC3)CN[C@H](C(=O)O)C4)nc(N)n2)C(F)(F)F)n1]

Step 1: To a solution of (3S)-2-benzyl 3-ethyl 8-(2-amino-6-(1-(4-cyano-2-(3-methyl-1H-pyrazol-1-yl)phenyl)-2,2,2-trifluoroethoxy)pyrimidin-4-yl)-2,8-diazaspiro[4.5]decane-2,3-dicarboxylate (0.35 g , 0.50 mmol, see Ex. 14) in MeOH (5 mL) and water (1 mL) was added LiOH-$H_2O$ (0.20 g, 5 mmol). The mixture was heated to 50° C. overnight. The reaction was then cooled to RT, and the reaction was acidified with 6N HCl to pH=1. Concentration in vacuo followed by reverse phase HPLC purification (MeOH/water/HOAc) provided (3S)-8-(2-amino-6-(1-(4-carboxy-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid as a white solid.

Step 2: N-CBZ Deprotection was accomplished via Method A to provide the title compound as a white solid.

$^1$H NMR (400 MHz, MeOH-$d_4$): δ ppm 1.57 (t, J=5.42 Hz, 4 H) 2.03 (dd, J=13.42, 7.42 Hz, 1 H) 2.25-2.35 (m, 2 H) 2.37 (s, 2 H) 3.04-3.13 (m, 1 H) 3.16-3.25 (m, 1 H) 3.38-3.75 (m, 5 H) 4.06 (dd, J=9.03, 7.32 Hz, 1 H) 5.72 (s, 1 H) 6.39 (d, J=2.29 Hz, 1 H) 6.78-6.89 (m, 1 H) 7.76 (d, J=8.15 Hz, 1 H) 7.90 (d, J=2.34 Hz, 1 H) 7.95 (d, J=1.42 Hz, 1 H) 8.04 (dd, J=8.13, 1.59 Hz, 1 H). LCMS (MH+): 576.

Example 17

(S)-8-(2-amino-6-((R)-1-(4-(ethoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

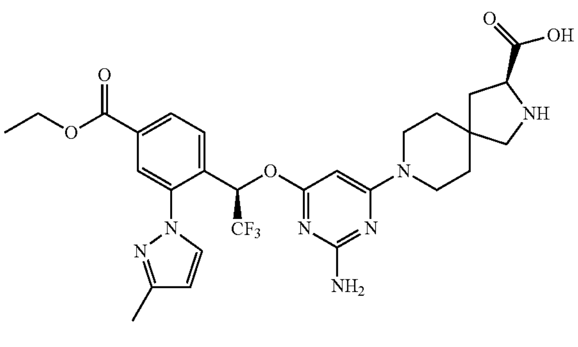 [SMILES: CCOC(=O)c1ccc([C@@H](Oc2cc(N3CCC4(CC3)CN[C@H](C(=O)O)C4)nc(N)n2)C(F)(F)F)c(-n2ccc(C)n2)c1]

Step 1: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (1.50 g, 1.94 mmol, See Ex. lu) in THF (20 mL), MeOH (10 mL) and water (10 mL) was added LiOH-$H_2O$ (0.80 g, 19.4 mmol), and the reaction was stirred at RT for 4 h. The pH of the reaction mixture was adjusted to 6.5 with 6 N HCl, and the organic solvents were removed in vacuo to provide a white solid that is filtered away. The reaction mixture was then partitioned between water and EtOAc, and extracted. The combined organic layers were washed with brine, dried over $Na_2SO_4$, filtered, then concentrated in vacuo to provide (2S)-8-[2-amino-6-[(1R)-1-[4-bromo-2-(3-methylpyrazol -1-yl)phenyl]-2,2,2-trifluoro-ethoxy]pyrimidin-4-yl]-3-benzyloxycarbonyl-3,8-diazaspiro [4.5]decane-2-carboxylic acid as a white solid that is used directly without further purification.

Step 2: To a solution of (2S)-8-[2-amino-6-[(1R)-1-[4-bromo-2-(3-methylpyrazol-1-yl)phenyl]-2,2,2-trifluoro-ethoxy]pyrimidin-4-yl]-3-benzyloxycarbonyl-3,8-diazaspiro [4.5]decane-2-carboxylic acid (74 mg, 0.10 mmol, Step 2) in EtOH (4 mL) was added $KHCO_3$ (84 mg, 1.0 mmol). The reaction mixture was degassed, fitted with a 1 atm CO balloon, then treated with $PdCl_2(PPh_3)_2$ (14 mg, 0.02 mmol). The reaction was degassed once more with 1 atm CO and then heated to 80° C. for 12 h. The reaction was cooled to RT, concentrated in vacuo and the residue was partitioned between water and EtOAc, and extracted. The combined organic layers were washed with brine, dried over $Na_2SO_4$, filtered, and concentrated in vacuo. Purification by normal phase silica gel column ($CH_2Cl_2$/AcOH/EtOH) provided (2S)-8-[2-amino-6-[(1R)-1-[4-ethoxycarbonyl-2-(3-methylpyrazol-1-yl)phenyl]-2,2,2-trifluoro-ethoxy] pyrimidin-4-yl]-3-benzyloxycarbonyl-3,8-diazaspiro[4.5]decane-2-carboxylic acid as a white solid.

Step 3: N-CBZ Deprotection was accomplished via Method A to provide the title compound as a white solid.

$^1$H NMR (400 MHz, MeOH-d4): δ ppm 1.37 (t, J=7.13 Hz, 3 H) 1.58 (d, J=4.30 Hz, 4 H) 1.97 (s, 2 H) 2.04 (dd, J=13.47, 7.27 Hz, 1 H) 2.30 (dd, J=13.59, 9.25 Hz, 1 H) 2.38 (s, 3 H) 3.05-3.27 (m, 2 H) 3.39-3.76 (m, 4 H) 3.99-4.10 (m, 1 H) 4.37 (q, J=7.13 Hz, 2 H) 5.68 (s, 1 H) 6.41 (d, J=2.34 Hz, 1 H) 6.84 (q, J=6.67 Hz, 1 H) 7.83 (d, J=8.10 Hz, 1 H) 7.94 (d, J=2.34 Hz, 1 H) 7.99 (d, J=1.61 Hz, 1 H) 8.09 (dd, J=8.27, 1.68 Hz,1 H). LCMS (MH+): 604.

Example 18a (S)-8-(2-amino-6-((R)-2,2,2-trifluoro-1-(4-(((1,1,1,3,3,3-hexafluoro-2-methylpropan-2-yl)oxy)carbonyl)-2-(3-methyl-1H-pyrazol-1-yl)phenyl)ethoxy)pyrimidin-4-yl)-2,8-diazaspiro[4.5]decane-3-carboxylic acid

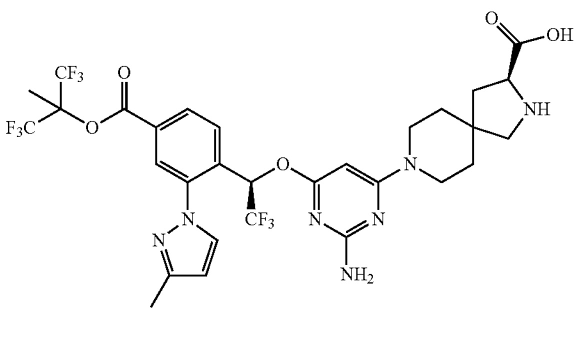 [SMILES: Cc1ccn(-c2cc(C(=O)OC(C)(C(F)(F)F)C(F)(F)F)ccc2[C@@H](Oc2cc(N3CCC4(CC3)CN[C@H](C(=O)O)C4)nc(N)n2)C(F)(F)F)n1]

Step 1: To a solution of (S)-8-(2-amino-6-((R)-1-(4-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid (product of Step 3, Example 10m) (1.2 g, 1.6 mmol) in DMF (16 mL) was added benzyl bromide (0.27 g, 1.6 mmol) and $NaHCO_3$ (0.67 g, 8.0 mmol). The reaction was then heated to 60° C. for 2 h, cooled to RT, and stirred for 12 h. The precipitate was filtered, washed with EtOAc and the filtrate concentrated in vacuo. The residue was partitioned between water and EtOAc, and extracted. The combined organic layers were washed with brine, dried over $Na_2SO_4$, filtered, and concentrated in vacuo. Purification by normal phase silica gel column (EtOAc/heptane) provided (S)-dibenzyl 8-(2-amino-6-((R)-1-(4-bromo-2-(3-methyl-1H-pyrazol-1-yl) phenyl)-2,2,2-trifluoroethoxy)pyrimidin-4-yl)-2,8-diazaspiro[4.5]decane-2,3-dicarboxylate as the white solid.

Step 2: To a solution of (S)-dibenzyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate from Step 1 (415 mg, 0.50 mmol) in 1,4-dioxane (8 mL) and water (4 mL) was added $KHCO_3$ (420 mg, 5.0 mmol), and the reaction was degassed with 1 atm CO. Then $PdCl_2(PPh_3)_2$ (140 mg, 0.10 mmol) was added and the reaction mixture was treated with 1 atm CO (balloon). The reaction mixture was heated to 80° C. for 12 h, then cooled to RT, and concentrated in vacuo. The residue was partitioned between water and EtOAc, and extracted. The combined organic layers were washed with brine, dried over $Na_2SO_4$, filtered, and concentrated in vacuo. Purification by normal phase silica gel column ($CH_2Cl_2$/MeOH/$NH_4OH$) provided 4-[(1R)-1-[2-amino-6-[(2S)-2,3-bis(benzyloxycarbonyl)-3,8-diazaspiro [4.5]decan-8-yl]pyrimidin-4-yl]oxy-2,2,2-trifluoro-ethyl]-3-(3-methylpyrazol-1-yl) benzoic acid as a white solid.

Step 3: To a solution of 4-[(1R)-1-[2-amino-6-[(2S)-2,3-bis (benzyloxycarbonyl)-3,8-diazaspiro[4.5]decan-8-yl]pyrimidin-4-yl]oxy-2,2,2-trifluoro-ethyl]-3-(3-methylpyrazol-1-yl)benzoic acid (80 mg, 0.1 mmol) in $CH_2Cl_2$ (4 mL) was added DMAP (73 mg, 0.6 mmol), $(CF_3)_2$MeCOH (108 mg, 0.6 mmol), followed by EDCI (114 mg, 0.6 mmol). The reaction mixture was stirred at RT for 12 h, diluted with $CH_2Cl_2$ and washed with water. The aqueous solution was extracted with $CH_2Cl_2$. The combined organic layers were washed with brine, dried over $Na_2SO_4$, filtered, and concentrated in vacuo. Purification by normal phase silica gel column (EtOAc/heptane) provided dibenzyl (2S)-8-[2-amino-6-[(1R)-2,2,2-trifluoro-1-[2-(3-methylpyrazol-1-yl)-4-[2,2,2-trifluoro-1-methyl-1-(trifluoromethyl)ethoxy] carbonyl-phenyl]ethoxy]pyrimidin-4-yl]-3,8-diazaspiro[4.5] decane-2,3-dicarboxylate as a white solid.

Step 4: N-CBZ Deprotection was accomplished via Method A to provide the title compound as a white solid.

Using the generic scheme below, the following examples of Table 5a were prepared as described above for (S)-8-(2-amino-6-((R)-2,2,2-trifluoro-1-(4-(((1,1,1,3,3,3-hexafluoro-2-methylpropan-2-yl)oxy)carbonyl)-2-(3-methyl-1H-pyrazol-1-yl)phenyl)ethoxy)pyrimidin-4-yl)-2,8-diazaspiro[4.5] decane-3-carboxylic acid (Example 18a).

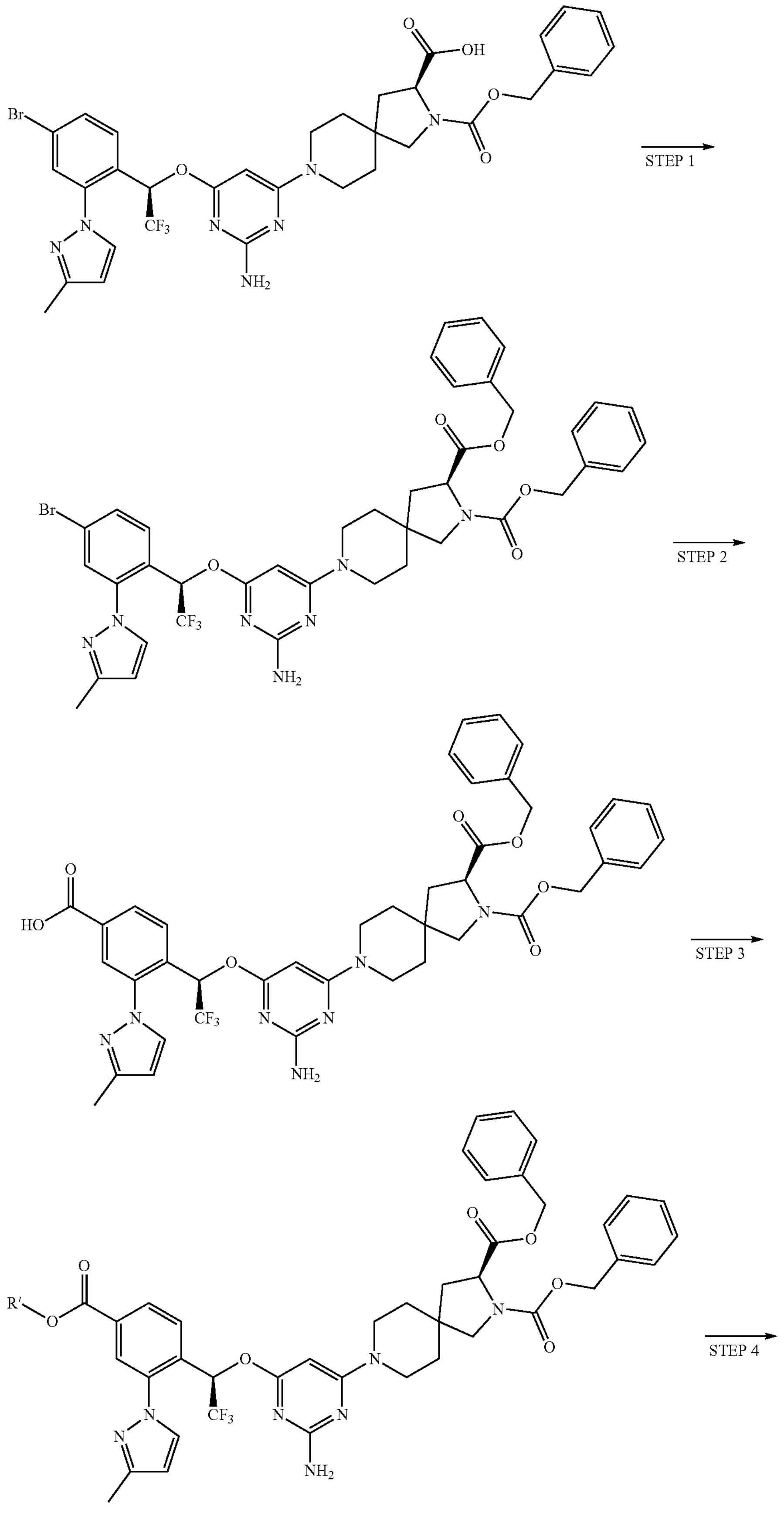
STEP 1
STEP 2
STEP 3
STEP 4

-continued

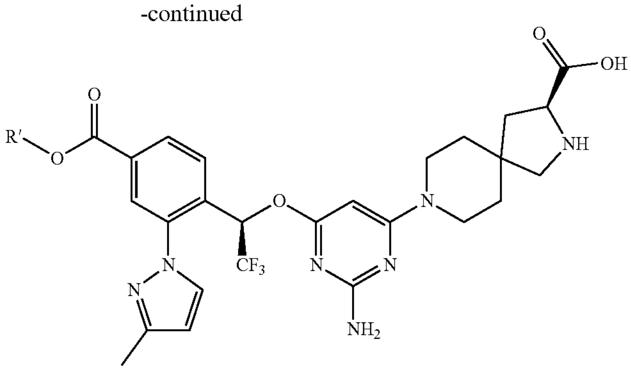

R' = $(CF_3)_2C(CH_3)$, nPr, nBu, $(CH_3)_2CH_2CH$, tBu, cPent

TABLE 5A

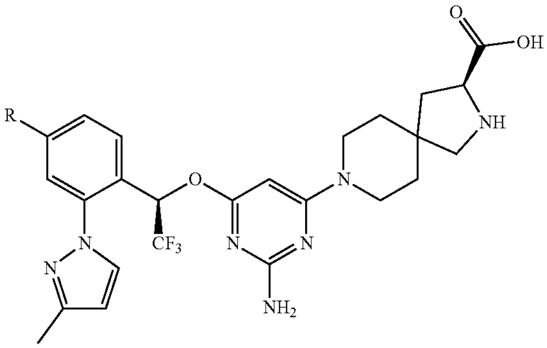

| Ex. No. | R | CAS Name | LCMS (MH+) |
|---|---|---|---|
| 18a | 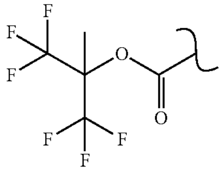 | (S)-8-(2-amino-6-((R)-2,2,2-trifluoro-1-(4-(((1,1,1,3,3,3-hexafluoro-2-methylpropan-2-yl)oxy)carbonyl)-2-(3-methyl-1H-pyrazol-1-yl)phenyl)ethoxy)pyrimidin-4-yl)-2,8-diazaspiro[4.5]decane-3-carboxylic acid | 740 |
| 18b | 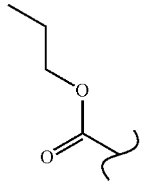 | (S)-8-(2-amino-6-((R)-2,2,2-trifluoro-1-(2-(3-methyl-1H-pyrazol-1-yl)-4-(propoxycarbonyl)phenyl)ethoxy)pyrimidin-4-yl)-2,8-diazaspiro[4.5]decane-3-carboxylic | 618 |
| 18c | 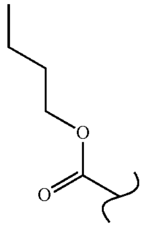 | (S)-8-(2-amino-6-((R)-1-(4-(butoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 632 |
| 18d | 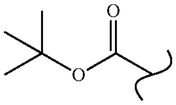 | (S)-8-(2-amino-6-((R)-1-(4-(tert-butoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 632 |

TABLE 5A-continued

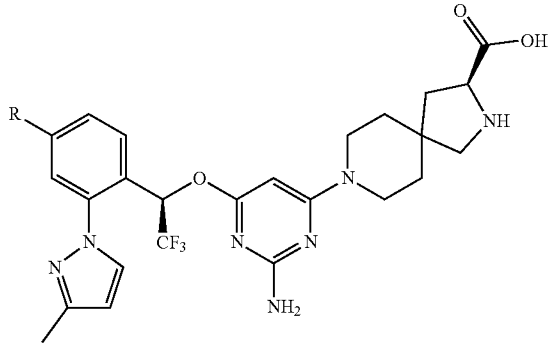

| Ex. No. | R | CAS Name | LCMS (MH+) |
|---|---|---|---|
| 18e | 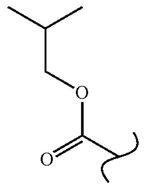 | (S)-8-(2-amino-6-((R)-2,2,2-trifluoro-1-(4-(isobutoxycarbonyl)-2-(3-methyl-1H-pyrazol-1-yl)phenyl)ethoxy)pyrimidin-4-yl)-2,8-diazaspiro[4.5]decane-3-carboxylic acid | 632 |
| 18f | 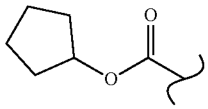 | (S)-8-(2-amino-6-((R)-1-(4-((cyclopentyloxy)carbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 644 |

TABLE 5b

NMR Data for Compounds of Table 5a

| Ex. No. | NMR |
|---|---|
| 18a | $^1$H NMR (400 MHz, MeOH-d4): δ ppm 1.58 (br. s., 4 H) 1.97 (s, 1 H) 2.04 (dd, J = 13.50, 7.20 Hz, 1 H) 2.12 (s, 3 H) 2.31 (dd, J = 13.45, 9.30 Hz, 1 H) 2.38 (s, 3 H) 3.04-3.27 (m, 2 H) 3.38-3.55 (m, 2 H) 3.64 (dd, J = 13.23, 5.56 Hz, 2 H) 4.07 (t, J = 8.08 Hz, 1 H) 5.67 (s, 1 H) 6.43 (d, J = 2.34 Hz, 1 H) 6.85 (q, J = 6.69 Hz, 1 H) 7.90 (d, J = 8.20 Hz, 1 H) 7.96 (dd, J = 8.20, 2.00 Hz, 2 H) 8.06 (dd, J = 8.27, 1.73 Hz, 1 H) |
| 18b | $^1$H NMR (400 MHz, MeOH-d4): δ ppm 1.01 (t, J = 7.44 Hz, 3 H) 1.58 (d, J = 4.49 Hz, 4 H) 1.72-1.85 (m, 2 H) 1.97 (s, 1 H) 2.04 (dd, J = 13.35, 7.25 Hz, 1 H) 2.30 (dd, J = 13.52, 9.13 Hz, 1 H) 2.38 (s, 3 H), 3.06-3.26 (m, 2 H) 3.38-3.72 (m, 4 H) 4.00-4.12 (m, 1 H) 4.29 (t, J = 6.64 Hz, 2 H) 5.68 (s, 1 H) 6.42 (d, J = 2.44 Hz, 1 H) 6.84 (q, J = 6.57 Hz, 1 H) 7.84 (d, J = 8.20 Hz, 1 H) 7.95 (d, J = 2.34 Hz, 1H) 7.98 (d, J = 1.61 Hz, 1 H) 8.09 (dd, J = 8.22, 1.64 Hz, 1 H) |
| 18c | $^1$H NMR (400 MHz, MeOH-d4): δ ppm 0.97 (t, J = 7.42 Hz, 3 H) 1.46 (dq, J = 15.01, 7.48 Hz, 2 H) 1.58 (d, J = 4.83 Hz, 4 H) 1.68-1.82 (m, 2 H) 1.97 (s, 1 H) 2.04 (dd, J = 13.52, 7.03 Hz, 1 H) 2.30 (dd, J = 13.42, 9.18 Hz, 1 H) 2.38 (s, 3 H) 3.07-3.25 (m, 2 H) 3.38-3.71 (m, 4 H) 4.06 (dd, J = 9.15, 7.00 Hz, 1 H) 4.33 (t, J = 6.61 Hz, 2 H) 5.68 (s, 1 H) 6.42 (d, J = 2.39 Hz, 1 H) 6.84 (q, J = 6.44 Hz, 1 H) 7.84 (d, J = 8.30 Hz, 1 H) 7.95 (d, J = 2.29 Hz, 1 H) 7.98 (d, J = 1.61 Hz, 1 H) 8.08 (dd, J = 8.25, 1.71 Hz, 1 H) |
| 18d | $^1$N MR (400 MHz, MeOH-d4): δ ppm 1.57 (s, 13 H) 1.97 (s, 2 H) 2.04 (dd, J = 13.50, 7.15 Hz, 1 H) 2.30 (dd, J = 14.06, 9.96 Hz, 1 H) 2.38 (s, 3 H) 3.08-3.26 (m, 2 H) 3.38-3.74 (m, 4 H) 4.01-4.14 (m, 1 H) 5.68 (s, 1 H) 6.41 (d, J = 2.34 Hz, 1 H) 6.80 (q, J = 6.64 Hz, 1 H) 7.80 (d, J = 8.15 Hz, 1 H) 7.92 (dd, J = 7.88, 1.93 Hz, 2 H) 8.02 (dd, J = 8.27, 1.59 Hz, 1 H) |
| 18e | $^1$H NMR (400 MHz, MeOH-d4): δ ppm 1.00 (d, J = 6.74 Hz, 6 H) 1.52-1.64 (m, 4 H) 1.97 (s, 2 H) 2.00-2.12 (m, 2 H) 2.30 (dd, J = 13.45, 9.35 Hz, 1 H) 2.38 (s, 3 H) 3.07-3.26 (m, 2 H) 3.37-3.55 (m, 2 H) 3.58-3.70 (m, 2 H) 4.06 (dd, J = 9.03, 7.17 Hz, 1 H) 4.12 (d, J = 6.59 Hz, 2 H) 5.68 (s, 1 H) 6.42 (d, J = 2.39 Hz, 1 H) 6.84 (q, J = 6.51 Hz, 1 H) 7.84 (d, J = 8.35 Hz, 1 H) 7.95 (d, J = 2.34 Hz, I H) 7.98 (d, J = 1.61 Hz, 1 H) 8.09 (dd, J = 8.27, 1.68 Hz, 1 H) |
| 18f | $^1$H NMR (400 MHz, MeOH-d4): δ ppm 1.54-1.94 (m, 11 H) 1.97 (s, 3 H) 2.04 (dd, J = 13.35, 7.15 Hz, 1 H) 2.24-2.35 (m, 1 H) 2.38 (s, 3 H) 3.02-3.27 (m, 2 H) 3.37-3.81 (m, 4 H) 3.95-4.22 (m, 1H) 5.32-5.44 (m, 1 H) 5.67 (s, 1 H) 6.41 (d, J = 2.39 Hz, |

TABLE 5b-continued

| NMR Data for Compounds of Table 5a | |
|---|---|
| Ex. No. | NMR |
| | 1 H) 6.82 (d, J = 6.39 Hz, 1 H) 7.82 (d, J = 8.30 Hz, 1 H) 7.94 (d, J = 1.85 Hz, 2 H) 8.06 (dd, J = 8.15, 1.71 Hz, 1 H) |

Example 19a

(S)-8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylic acid

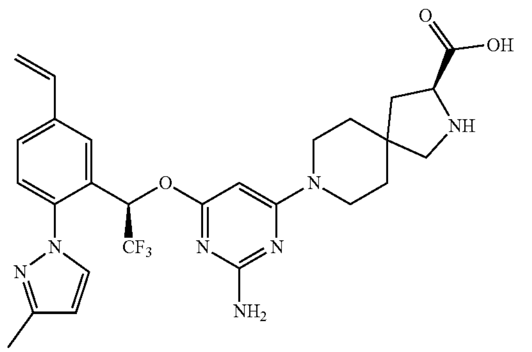 [SMILES: C=Cc1ccc(-n2ccc(C)n2)c([C@@H](Oc2cc(N3CCC4(CC3)CN[C@H](C(=O)O)C4)nc(N)n2)C(F)(F)F)c1]

Step 1: To a solution of (S)-2-benzyl 3-ethyl 8-(2-amino-6-((R)-1-(5-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (500 mg, 0.65 mmol) in 4:1 EtOH:$H_2O$ (25 mL) was added 4,4,5,5-tetramethyl-2-vinyl-1,3,2-dioxaborolane (150 mg, 0.971 mmol), $KHCO_3$ (648 mg, 6.47 mmol), and $PdCl_2(PPh_3)_2$ (68 mg, 0.097 mmol). The reaction mixture was heated to 80° C. for 1.75 h, then cooled to RT, and extracted with EtOAc. The combined organic layers were washed with brine, dried over $Na_2SO_4$, filtered, and concentrated in vacuo. Purification via a 40 g Isco RediSep silica cartridge eluting (EtOAc/hepate) provides (S)-2-benzyl 3-ethyl 8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-2,3-dicarboxylate as an off-white solid.

Step 2: N-CBZ Deprotection was accomplished via Method B to provide (S)-ethyl 8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylate as an off-white solid.

Step 3: Hydrolysis of (S)-ethyl 8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylate using the LiOH general method provided the title compound as a white solid.

Using the generic scheme below, the following examples of Table 6a were prepared as described above for (S)-8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylic acid (Example 19a).

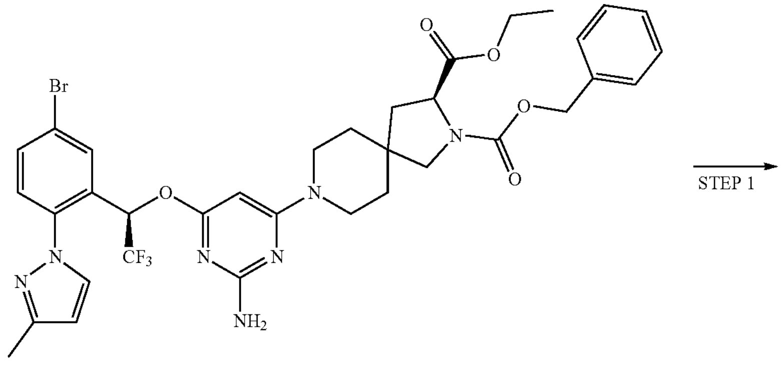

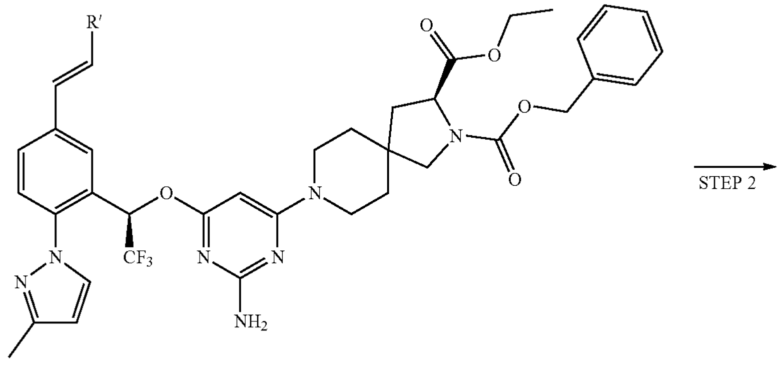

-continued
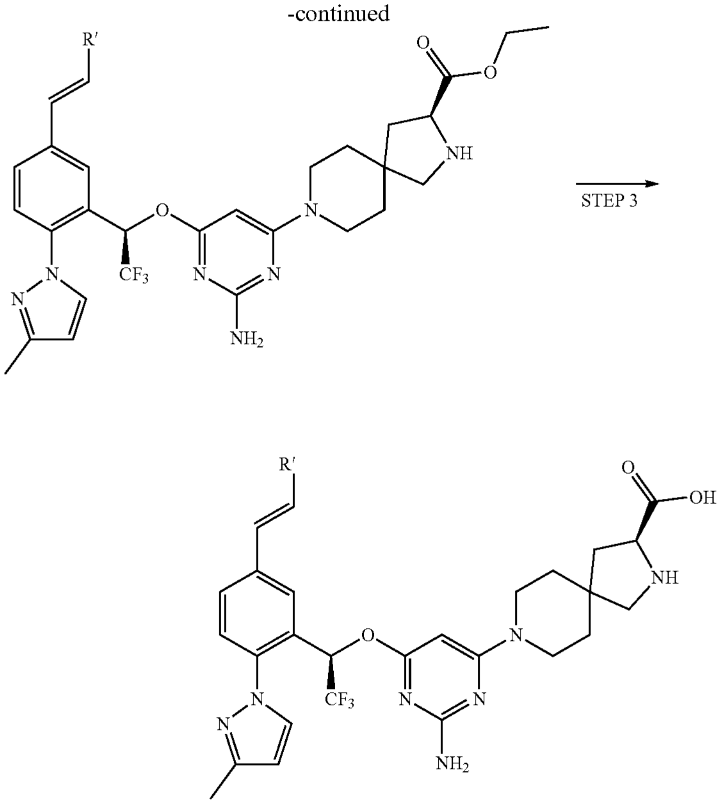
R' = H, Me, Et, COOH
TABLE 6A
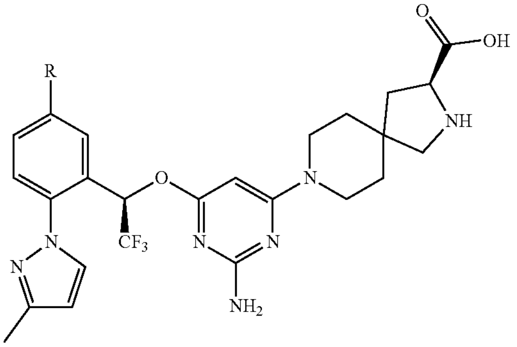
| Ex. No. | R | CAS Name | LCMS (MH+) |
|---|---|---|---|
| 19a | 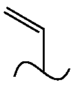 | (S)-8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylic acid | 558.6 |
| 19b | 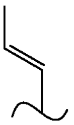 | (S)-8-(2-amino-6-((R)-2,2,2-trifluoro-1-(2-(3-methyl-1H-pyrazol-1-yl)-5-((E)-prop-1-en-1-yl)phenyl)ethoxy)pyrimidin-4-yl)-2,8-diazaspiro[4.5]decane-3-carboxylic acid | 572.6 |

TABLE 6A-continued

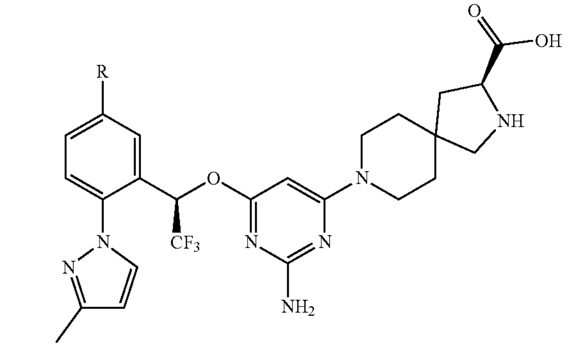

| Ex. No. | R | CAS Name | LCMS (MH+) |
|---|---|---|---|
| 19c | 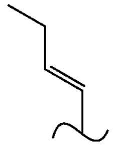 | (S)-8-(2-amino-6-((R)-1-(5-((E)-but-1-en-1-yl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 585.5 |
| 19d | 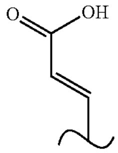 | (S)-8-(2-amino-6-((R)-1-(5-((E)-2-carboxyvinyl)-2-(3-methyl-1H-pyrazol-1-yl)phenyl)-2,2,2-trifluoroethoxy)pyrimidin-4-yl)-2,8-diazaspiro[4.5]decane-3-carboxylic acid | 602.6 |

TABLE 6b

NMR Data for Compounds of Table 6a

| Ex. No. | NMR |
|---|---|
| 19a | $^{1}H$ NMR (400 MHz, MeOH- d4): δ ppm 1.59 (m, 4 H) 2.06 (dd, J = 13.42, 7.17 Hz, 1 H) 2.31 (dd, J = 13.42, 9.18 Hz, 1 H) 2.38 (s, 3 H) 3.18 (m, 2 H) 3.59 (m, 4 H) 4.07 (dd, J = 9.20, 7.20 Hz, 1 H) 5.36 (d, J = 10.98 Hz, 1 H) 5.75 (s, 1 H) 5.85 (d, J = 17.62 Hz, 1 H) 6.39 (d, J = 2.34 Hz, 1 H) 6.80 (m, 2 H) 7.38 (d, J = 8.30 Hz, 1 H) 7.63 (dd, J = 8.25, 2.00 Hz, 1 H) 7.74 (s, 1 H) 7.87 (d, J = 2.29 Hz, 1 H) |
| 19b | $^{1}H$ NMR (400 MHz, MeOH- d4): δ ppm 1.59 (m, 3 H) 1.90 (dd, J = 6.32, 1.20 Hz, 3 H) 2.06 (dd, J = 13.47, 7.13 Hz, 1 H) 2.31 (dd, J = 13.45, 9.25 Hz, 1 H) 2.37 (s, 3 H) 3.18 (m, 2 H) 3.57 (m, 4 H) 4.08 (dd, J = 9.18, 7.17 Hz, 1 H) 5.75 (s, 1 H) 6.39 (m, 3 H) 6.75 (q, J = 6.67 Hz, 1 H) 7.32 (d, J = 8.25 Hz, 1 H) 7.52 (dd, J = 8.30, 2.00 Hz, 1 H) 7.65 (s, 1 H) 7.84 (d, J = 2.34 Hz, 1 H) |
| 19c | $^{1}H$ NMR (400 MHz, MeOH- d4): δ ppm 1.11 (t, J = 7.47 Hz, 3 H) 1.59 (d, J = 4.59 Hz, 4 H) 2.06 (dd, J = 13.37, 7.22 Hz, 1 H) 2.28 (m, 3 H) 2.37 (s, 3 H) 3.18 (m, 2 H) 3.59 (m, 4 H) 4.07 (dd, J = 9.10, 7.20 Hz, 1 H) 5.76 (s, 1 H) 6.40 (m, 3 H) 6.76 (m, 1 H) 7.33 (d, J = 8.25 Hz, 1 H) 7.54 (dd, J = 8.30, 2.05 Hz, 1 H) 7.66 (s, 1 H) 7.84 (d, J = 2.29 Hz, 1 H) |
| 19d | $^{1}H$ NMR (400 MHz, MeOH-d4): δ ppm 1.57 (t, J = 5.44 Hz, 4 H) 1.97 (s, 3 H) 2.04 (dd, J = 13.72, 7.27 Hz, 1 H) 2.30 (dd, J = 13.32, 9.18 Hz, 1H) 2.37 (s, 3 H) 3.07-3.25 (m, 2 H) 3.40-3.55 (m, 2 H) 3.65 (dd, J = 9.27, 4.73 Hz, 2 H) 4.07 (t, J = 7.98 Hz, 1 H) 5.75 (s, 1 H) 6.40 (d, J = 2.34 Hz, 1 H) 6.51 (d, J = 16.20 Hz, 1 H) 6.94 (q, J = 6.52 Hz, 1 H) 7.46 (d, J = 8.30 Hz, 1 H) 7.66 (d, J = 15.86 Hz, 1 H) 7.78 (dd, J = 8.32, 1.88 Hz, 1 H) 7.87 (s, 1 H) 7.92 (d, J = 2.34 Hz, 1 H) |

Using the generic scheme below, the following examples of Table 7a can be prepared as described above for (S)-8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylic acid (Example 19a), by substituting the alkylidene borolane with a boronic acid or ester.

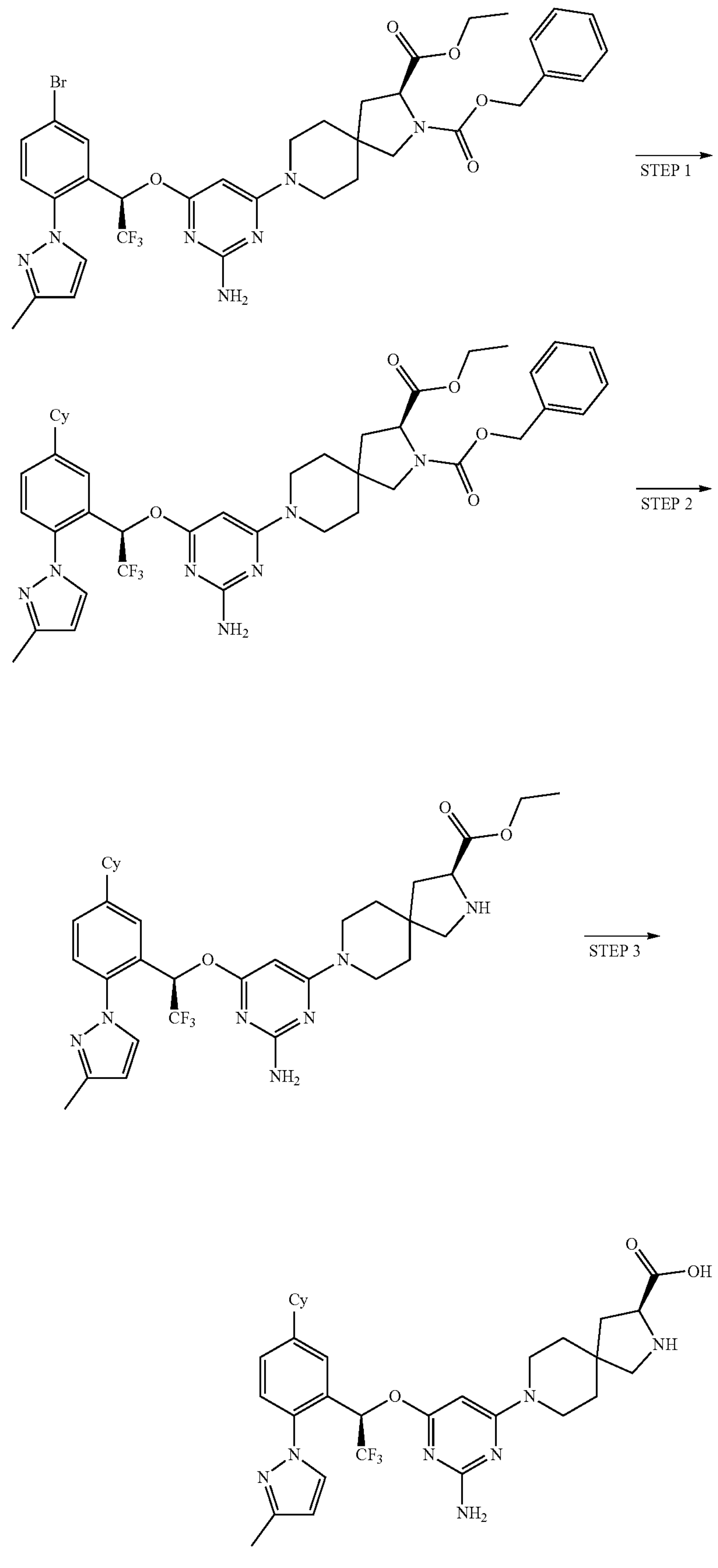
STEP 1
STEP 2
STEP 3

TABLE 7A

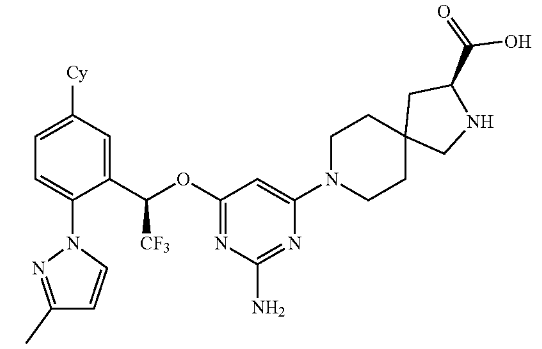

| Ex. No. | Cy | CAS Name | LCMS (MH+) |
|---|---|---|---|
| 19e | 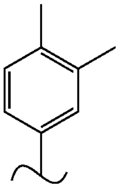 | (S)-8-(2-amino-6-((R)-1-(3',4'-dimethyl-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid | 536.7 |
| 19f | 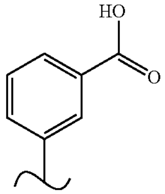 | (S)-8-(2-amino-6-((R)-1-(3'-carboxy-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid | 652 |
| 19g | 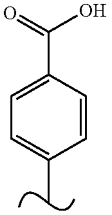 | (S)-8-(2-amino-6-((R)-1-(4'-carboxy-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid | 652 |
| 19h | 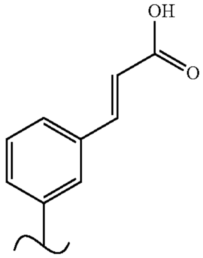 | (S)-8-(2-amino-6-((R)-1-(3'-((E)-2-carboxyvinyl)-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 678 |
| 19i | 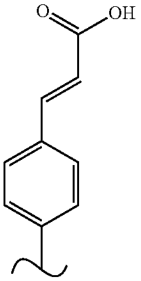 | (S)-8-(2-amino-6-((R)-1-(4'-((E)-2-carboxyvinyl)-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 678 |

TABLE 7A-continued

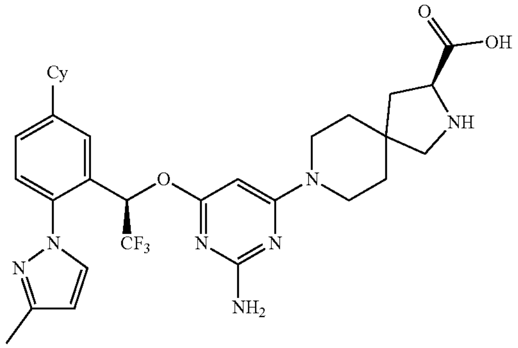

| Ex. No. | Cy | CAS Name | LCMS (MH+) |
|---|---|---|---|
| 19j | 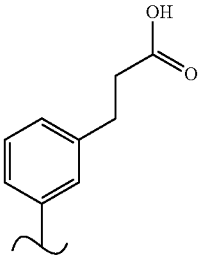 | (S)-8-(2-amino-6-((R)-1-(3'-(2-carboxyethyl)-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 680 |
| 19k | 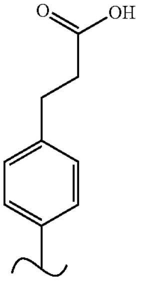 | (S)-8-(2-amino-6-((R)-1-(4'-(2-carboxyethyl)-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 680 |
| 19l | 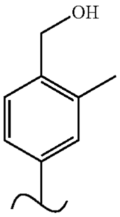 | (S)-8-(2-amino-6-((R)-2,2,2-trifluoro-1-(4'-(hydroxymethyl)-3'-methyl-4-(3-methyl-1H-pyrazol-1-yl)-[1,1'-biphenyl]-3-yl)ethoxy)pyrimidin-4-yl)-2,8-diazaspiro[4.5]decane-3-carboxylic | 652 |
| 19m | 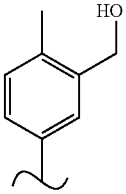 | (S)-8-(2-amino-6-((R)-2,2,2-trifluoro-1-(3'-(hydroxymethyl)-4'-methyl-4-(3-methyl-1H-pyrazol-1-yl)-[1,1'-biphenyl]-3-yl)ethoxy)pyrimidin-4-yl)-2,8-diazaspiro[4.5]decane-3-carboxylic acid | 652 |
| 19n | 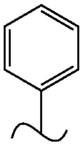 | (S)-8-(2-amino-64(R)-2,2,2-trifluoro-1-(4-(3-methyl-1H-pyrazol-1-yl)[1,1'-biphenyl]-3-yl)ethoxy)pyrimidin-4-yl)-2,8-diazaspiro[4.5]decane-3-carboxylic acid | 608 |

TABLE 7A-continued

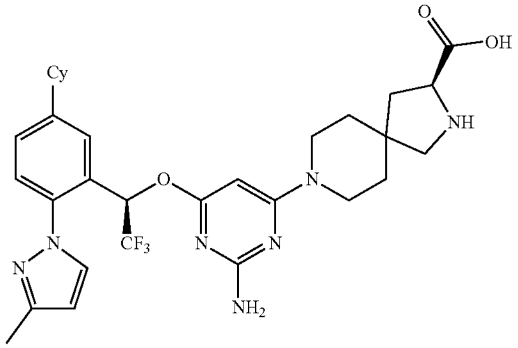

| Ex. No. | Cy | CAS Name | LCMS (MH+) |
|---|---|---|---|
| 19o | 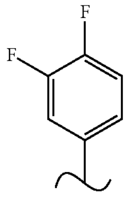 | (S)-8-(2-amino-6-((R)-1-(3',4'-difluoro-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 644 |
| 19p | 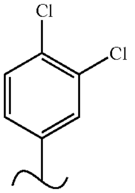 | (S)-8-(2-amino-6-((R)-1-(3',4'-dichloro-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 677 |
| 19q | 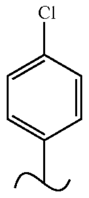 | (S)-8-(2-amino-6-((R)-1-(4'-chloro-4-(3-methyl-1H-pyrazol-1-yl)[1,1'-biphenyl]-3-yl)-2,2,2-trifluoroethoxy)pyrimidin-4-yl)-2,8-diazaspiro[4.5]decane-3-carboxylic acid | 643 |
| 19r | 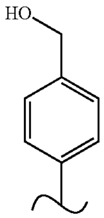 | (S)-8-(2-amino-64(R)-2,2,2-trifluoro-1-(4'-(hydroxymethyl)-4-(3-methyl-1H-pyrazol-1-yl)[1,1'-biphenyl]-3-yl)ethoxy)pyrimidin-4-yl)-2,8-diazaspiro[4.5]decane-3-carboxylic acid | 639 |

TABLE 7b

NMR Data for Compounds of Table 7a

| Ex. No. | NMR |
|---|---|
| 19e | $^1$H NMR (400 MHz, MeOH- d4): δ ppm 1.57 (m, 4 H) 2.04 (dd, J = 13.62, 6.98 Hz, 1 H) 2.32 (d, J = 11.96 Hz, 6 H) 2.40 (s, 3 H) 3.16 (m, 2 H) 3.55 (m, 4 H) 4.07 (dd, J = 9.18, 7.22 Hz, 1 H) 5.79 (s, 1 H) 6.40 (d, J = 2.29 Hz, 1 H) 6.85 (m, 1 H) 7.21 (d, J = 7.76 Hz, 1 H) 7.31 (m, 1 H) 7.36 (s, 1 H) 7.45 (d, J = 8.25 Hz, 1 H) 7.75 (dd, J = 8.27, 2.12 Hz, 1 H) 7.90 (d, J = 2.20 Hz, 2 H) |

TABLE 7b-continued

| NMR Data for Compounds of Table 7a | |
|---|---|
| Ex. No. | NMR |
| 19f | $^{1}$H NMR (400 MHz, MeOH-d4): δ ppm 1.53-1.67 (m, 4 H) 2.05 (dd, J = 13.42, 7.17 Hz, 1 H) 2.30 (dd, J = 13.42, 9.22 Hz, 1 H) 2.40 (s, 3 H) 3.06-3.27 (m, 2 H) 3.39-3.74 (m, 4 H) 4.08 (dd, J = 9.13, 7.27 Hz, 1 H) 5.79 (s, 1 H) 6.42 (d, J = 2.29 Hz, 1 H) 6.92 (q, J = 6.62 Hz, 1 H) 7.53 (d, J = 8.25 Hz, 1 H) 7.57 (t, J = 7.76 Hz, 1 H) 7.77-7.87 (m, 2 H) 7.94 (d, J = 2.34 Hz, 1 H) 7.97 (d, J = 1.42 Hz, 1 H) 8.04 (dt, J = 7.79, 1.23 Hz, 1 H) 8.24 (t, J = 1.61 Hz, 1 H) |
| 19g | $^{1}$H NMR (400 MHz, MeOH-d4): δ ppm 1.47-1.67 (m, 4 H) 2.05 (dd, J = 13.45, 7.20 Hz, 1 H) 2.31 (dd, J = 13.37, 9.27 Hz, 1 H) 2.40 (s, 3 H) 2.99-3.28 (m, 2 H) 3.39-3.78 (m, 4 H) 4.08 (dd, J = 9.08, 7.27 Hz, 1 H) 5.79 (s, 1 H) 6.42 (d, J = 2.29 Hz, 1 H) 6.86-7.01 (m, 1 H) 7.53 (d, J = 8.30 Hz, 1 H) 7.64-7.77 (m, 2 H) 7.85 (dd, J = 8.30, 2.15 Hz, 1 H) 7.94 (d, J = 2.34 Hz, 1 H) 7.99 (d, J = 1.32 Hz, 1 H) 8.08-8.18 (m, 2 H) |
| 19h | $^{1}$H NMR (400 MHz, MeOH-d4): δ ppm 1.59 (t, J = 5.54 Hz, 4 H) 2.04 (dd, J = 13.45, 7.39 Hz, 1 H) 2.32 (dd, J = 13.50, 9.25 Hz, 1 H) 2.41 (s, 3 H) 3.07-3.26 (m, 2 H) 3.41-3.76 (m, 4 H) 4.08 (dd, J = 9.01, 7.30 Hz, 1 H) 5.81 (s, 1 H) 6.42 (d, J = 2.29 Hz, 1 H) 6.57 (d, J = 16.01 Hz, 1 H) 6.86-6.97 (m, 1 H) 7.48-7.57 (m, 2 H) 7.60-7.68 (m, 2 H) 7.73 (d, J = 16.01 Hz, 1 H) 7.77 (bs, 1 H) 7.83 (dd, J = 8.25, 2.10 Hz, 1 H) 7.93-7.96 (m, 2 H) |
| 19i | $^{1}$H NMR (400 MHz, MeOH-d4): δ ppm 1.50-1.65 (m, 4 H) 2.05 (dd, J = 13.45, 7.20 Hz, 1 H) 2.31 (dd, J = 13.40, 9.30 Hz, 1 H) 2.40 (s, 3 H) 3.05-3.28 (m, 2 H) 3.40-3.74 (m, 4 H) 4.07 (dd, J = 9.10, 7.25 Hz, 1 H) 5.79 (s, 1 H) 6.42 (d, J = 2.29 Hz, 1 H) 6.54 (d, J = 16.01 Hz, 1 H) 6.91 (q, J = 6.72 Hz, 1 H) 7.51 (d, J = 8.25 Hz, 1 H) 7.61-7.75 (m, 5 H) 7.82 (dd, J = 8.30, 2.15 Hz, 1 H) 7.93 (d, J = 2.34 Hz, 1 H) 7.97 (s, 1 H) |
| 19j | $^{1}$H NMR (400 MHz, MeOH-d4): δ ppm 1.51-1.66 (m, 4 H) 2.04 (dd, J = 13.50, 7.15 Hz, 1 H) 2.31 (dd, J = 13.37, 9.18 Hz, 1 H) 2.40 (s, 3 H) 2.65 (t, J = 7.61 Hz, 2 H) 2.99 (t, J = 7.59 Hz, 2 H) 3.06-3.27 (m, 2 H) 3.40-3.78 (m, 4 H) 4.08 (dd, J = 8.98, 7.42 Hz, 1 H) 5.80 (s, 1 H) 6.41 (d, J = 2.34 Hz, 1 H) 6.88 (q, J = 6.61 Hz, 1 H) 7.27 (d, J = 7.32 Hz, 1 H) 7.35-7.41 (m, 1 H) 7.41-7.51 (m, 3 H) 7.77 (dd, J = 8.27, 2.12 Hz, 1 H) 7.88-7.97 (m, 2 H) |
| 19k | $^{1}$H NMR (400 MHz, MeOH-d4): δ ppm 1.57 (d, J = 3.37 Hz, 4 H) 2.04 (dd, J = 13.40, 7.20 Hz, 1 H) 2.30 (dd, J = 13.35, 9.20 Hz, 1 H) 2.40 (s, 3 H) 2.63 (t, J = 7.61 Hz, 2 H) 2.96 (t, J = 7.57 Hz, 2 H) 3.03-3.26 (m, 2 H) 3.39-3.76 (m, 4 H) 4.07 (dd, J = 9.03, 7.32 Hz, 1 H) 5.78 (s, 1 H) 6.41 (d, J = 2.29 Hz, 1 H) 6.86 (q, J = 6.54 Hz, 1 H) 7.34 (d, J = 8.25 Hz, 2 H) 7.46 (d, J = 8.30 Hz, 1 H) 7.52 (d, J = 8.25 Hz, 2 H) 7.76 (dd, J = 8.27, 2.12 Hz, 1 H) 7.89-7.92 (m, 2 H) |
| 19l | $^{1}$H NMR (400 MHz, MeOH-d4): δ ppm 1.45-1.65 (m, 4 H) 2.00-2.09 (m, 1 H) 2.30 (dd, J = 13.40, 9.25 Hz, 1 H) 2.40 (s, 6 H) 3.03-3.27 (m, 2 H) 3.39-3.76 (m, 4 H) 4.07 (dd, J = 9.10, 7.25 Hz, 1 H), 4.67 (s, 2 H) 5.79 (s, 1 H) 6.41 (d, J = 2.25 Hz, 1 H) 6.86 (q, J = 6.64 Hz, 1 H) 7.36-7.53 (m, 4 H) 7.77 (dd, J = 8.30, 2.15 Hz, 1 H) 7.91 (d, J = 2.44 Hz, 2 H) |
| 19m | $^{1}$H NMR (400 MHz, MeOH-d4): δ ppm 1.46-1.69 (m, 4 H) 2.00-2.10 (m, 1 H) 2.30 (dd, J = 13.45, 9.25 Hz, 1 H) 2.37 (s, 3 H) 2.40 (s, 3 H) 3.03-3.27 (m, 2 H) 3.39-3.76 (m, 4 H) 4.07 (dd, J = 9.13, 7.22 Hz, 1 H) 4.70 (s, 2 H) 5.78 (s, 1 H) 6.41 (d, J = 2.25 Hz, 1 H) 6.85 (q, J = 6.57 Hz, 1 H) 7.26 (d, J = 7.91 Hz, 1 H) 7.43 (dd, J = 7.81, 1.95 Hz, 1 H) 7.47 (d, J = 8.30 Hz, 1 H) 7.64 (d, J = 1.81 Hz, 1 H) 7.79 (dd, J = 8.27, 2.12 Hz, 1 H) 7.91 (d, J = 2.29 Hz, 1 H) 7.94 (s, 1 H) |
| 19n | $^{1}$H NMR (400 MHz, MeOH-d4): δ ppm 1.29 (d, J = 7.2 Hz, 1H), 1.56 (d, J = 6.3 Hz, 4H), 2.03 (d, J = 12.8 Hz, 1H), 2.30 (d, J = 12.4 Hz, 1H), 2.39 (s, 3H), 3.09 (d, J = 11.5 Hz, 1H), 3.22 (d, J = 11.7 Hz, 1H), 3.47 (t, J = 18.6 Hz, 2H), 3.63 (s, 2H), 4.07 (s, 1H), 4.64 (s, 1H), 5.78 (s, 1H), 6.41 (d, J = 2.1 Hz, 1H), 6.87 (q, J = 6.5 Hz, 1H), 7.44 (m, 4H), 7.59 (d, J = 7.4 Hz, 2H), 7.64 (s, 1H), 7.77 (m, 1H), 7.91 (m, 2H) |
| 19o | $^{1}$H NMR (400 MHz, MeOH-d4): δ ppm 1.30 (d, J = 18.0 Hz, 1H), 1.57 (d, J = 6.1 Hz, 4H), 2.04 (dd, J = 13.9, 6.4 Hz, 1H), 2.30 (dd, J = 13.5, 8.4 Hz, 1H), 2.39 (s, 3H), 3.11 (d, J = 11.6 Hz, 1H), 3.23 (d, J = 11.4 Hz, 1H), 3.48 (dq, J = 21.6, 7.6, 6.8 Hz, 2H), 3.64 (dd, J = 13.8, 6.9 Hz, 2H), 4.08 (m, 1H), 4.87 (s, 12H), 5.78 (s, 1H), 6.41 (d, J = 2.0 Hz, 1H), 6.91 (q, J = 6.6 Hz, 1H), 7.36 (m, 2H), 7.50 (t, J = 9.3 Hz, 2H), 7.74 (dd, J = 8.3, 2.2 Hz, 1H), 7.90 (dd, J = 7.9, 2.1 Hz, 2H) |
| 19p | $^{1}$H NMR (400 MHz, MeOH-d4): δ ppm 1.27 (s, 1H), 1.44 (s, 1H), 1.52 (q, J = 5.9 Hz, 4H), 1.85 (m, 1H), 2.11 (dd, J = 13.2, 8.8 Hz, 1H), 2.39 (s, 3H), 2.77 (d, J = 11.3 Hz, 1H), 3.01 (d, J = 11.3 Hz, 1H), 3.45 (ddt, J = 19.8, 12.8, 5.8 Hz, 2H), 3.61 (m, 2H), 3.74 (t, J = 8.0 Hz, 1H), 5.78 (s, 1H), 6.42 (d, J = 2.4 Hz, 1H), 6.93 (q, J = 6.6 Hz, 1H), 7.54 (m, 3H), 7.75 (m, 2H), 7.92 (dd, J = 11.1, 2.0 Hz, 2H) |
| 19q | $^{1}$H NMR (400 MHz, MeOH-d4): δ ppm 1.28 (s, 1H), 1.57 (t, J = 5.0 Hz, 4H), 2.03 (dd, J = 13.3, 6.9 Hz, 1H), 2.29 (dd, J = 13.4, 9.0 Hz, 1H), 2.39 (s, 3H), 3.08 (d, J = 11.6 Hz, 1H), 3.22 (d, J = 11.6 Hz, 1H), 3.48 (ddt, J = 20.4, 13.2, 5.9 Hz, 2H), 3.65 (dd, J = 13.7, 6.5 Hz, 2H), 4.05 (t, J = 8.0 Hz, 1H), 5.77 (s, 1H), 6.41 (d, J = 2.3 Hz, 1H), 6.89 (q, J = 6.6 Hz, 1H), 7.47 (m, 3H), 7.58 (m, 2H), 7.77 (dd, J = 8.3, 2.2 Hz, 1H), 7.91 (t, J = 2.4 Hz, 2H) |
| 19r | $^{1}$H NMR (400 MHz, MeOH-d4): δ ppm 7.94-7.80 (m, 9H), 7.60 (d, J = 8.1 Hz, 6H), 7.50 (dd, J = 20.7, 8.1 Hz, 9H), 6.94 (q, J = 6.2 Hz, 3H), 6.42 (d, J = 2.3 Hz, 3H), 4.66 (s, 5H), 4.38 (t, J = 8.4 Hz, 3H), 3.73 (s, 6H), 3.63-3.55 (m, 1H), 3.29-3.18 (m, 5H), 2.40 (s, 9H), 2.07 (dd, J = 13.5, 7.8 Hz, 3H), 1.70-1.61 (m, 10H), 1.28 (s, 1H). |

Example 20

(S)-8-(2-amino-6-((R)-1-(2'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid

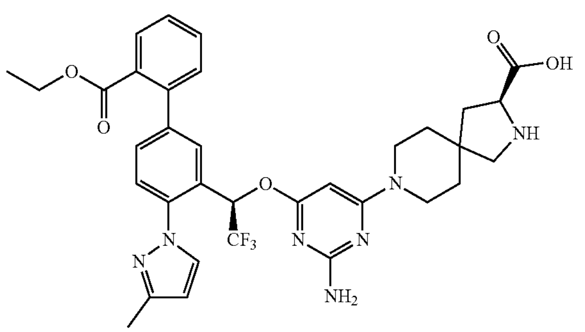 [SMILES: CCOC(=O)c1ccccc1-c1ccc(-n2ccc(C)n2)c([C@@H](Oc2cc(N3CCC4(CC3)CN[C@H](C(=O)O)C4)nc(N)n2)C(F)(F)F)c1]

The title compound was made using the procedure described for (S)-8-(2-amino-6-((R)-1-(3'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid (Example 5a) starting with (S)-8-(2-amino-6-((R)-1-(5-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid.

$^1$H NMR (400 MHz, MeOH-d4): δ ppm 0.89 (t, J=7.15 Hz, 3 H) 1.60 (t, J=5.54 Hz, 4 H) 2.06 (dd, J=13.50, 7.25 Hz, 1 H) 2.33 (dd, J=13.42, 9.27 Hz, 1 H) 2.40 (s, 3 H) 3.08-3.28 (m, 2 H) 3.39-3.73 (m, 4 H) 3.74-3.98 (m, 2 H) 4.08 (dd, J=9.08, 7.32 Hz, 1 H) 5.74 (s, 1 H) 6.42 (d, J=2.34 Hz, 1 H) 6.88 (q, J=6.75 Hz, 1 H) 7.38 (dd, J=7.71, 0.93 Hz, 1 H) 7.45-7.56 (m, 4 H) 7.58-7.65 (m, 1 H) 7.82 (dd, J=7.69, 1.20 Hz, 1 H) 7.95 (d, J=2.34 Hz, 1 H). LCMS (MH+): 680.

Example 21

(S)-8-(2-amino-6-((R)-1-(4'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid

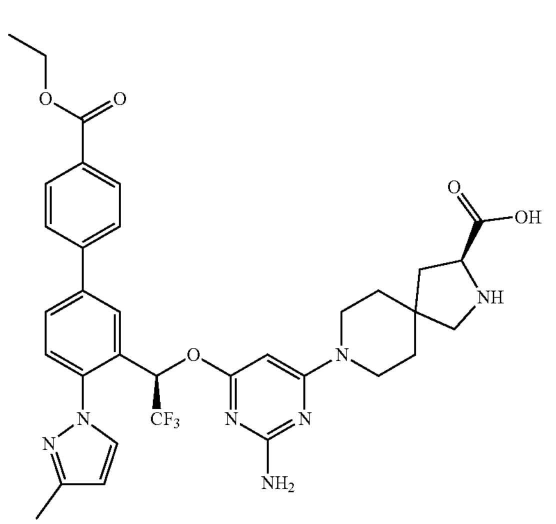 [SMILES: CCOC(=O)c1ccc(-c2ccc(-n3ccc(C)n3)c([C@@H](Oc3cc(N4CCC5(CC4)CN[C@H](C(=O)O)C5)nc(N)n3)C(F)(F)F)c2)cc1]

The title compound was made using the procedure described for (S)-8-(2-amino-6-((R)-1-(3'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid (Example 5) starting with (S)-8-(2-amino-6-((R)-1-(5-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid.

$^1$H NMR (400 MHz, MeOH-d4): δ ppm 1.41 (t, J=7.15 Hz, 3 H) 1.58 (br. s., 4 H) 2.05 (dd, J=13.50, 7.15 Hz, 1 H) 2.30 (dd, J=13.42, 9.18 Hz, 1 H) 2.40 (s, 3 H) 3.03-3.28 (m, 2 H) 3.37-3.76 (m, 4 H) 4.07 (dd, J=9.13, 7.22 Hz, 1 H) 4.39 (q, J=7.13 Hz, 2 H) 5.78 (s, 1 H) 6.42 (d, J=2.25 Hz, 1 H) 6.86-7.01 (m, 1 H) 7.53 (d, J=8.30 Hz, 1 H) 7.66-7.77 (m, 2 H) 7.84 (dd, J=8.30, 2.20 Hz, 1 H) 7.94 (d, J=2.29 Hz, 1 H) 7.99 (d, J=1.51 Hz, 1 H) 8.06-8.17 (m, 2 H). LCMS (MH+): 680.

Example 22a (S)-8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro[4.5]decane-3-carboxylic acid

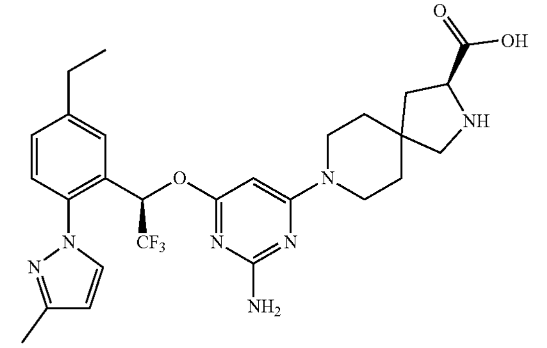 [SMILES: CCc1ccc(-n2ccc(C)n2)c([C@@H](Oc2cc(N3CCC4(CC3)CN[C@H](C(=O)O)C4)nc(N)n2)C(F)(F)F)c1]

Step 1: (S)-Ethyl 8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylate (100 mg, 0.171 mmol) in MeOH (2 mL) was hydrogenated via an H-Cube apparatus using a 10% (w/w) Pd/C cartridge with a flow rate of 1.0 mL/min at RT. The catalyst was filtered and the filtrate was concentrated in vacuo. The resisdue was lyophilized from 1:1 $H_2O$:$CH_3CN$ to provide (S)-ethyl 8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro[4.5]decane-3-carboxylate as a white solid which was used directly in the next step.

Step 2: Hydrolysis of (S)-ethyl 8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro [4.5]decane-3-carboxylate using the LiOH general method provided the title compound as a white solid.

Using the same generic scheme below, the following examples of Table 8a can be prepared as described above for (S)-8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro [4.5]decane-3-carboxylic acid (Example 22a).

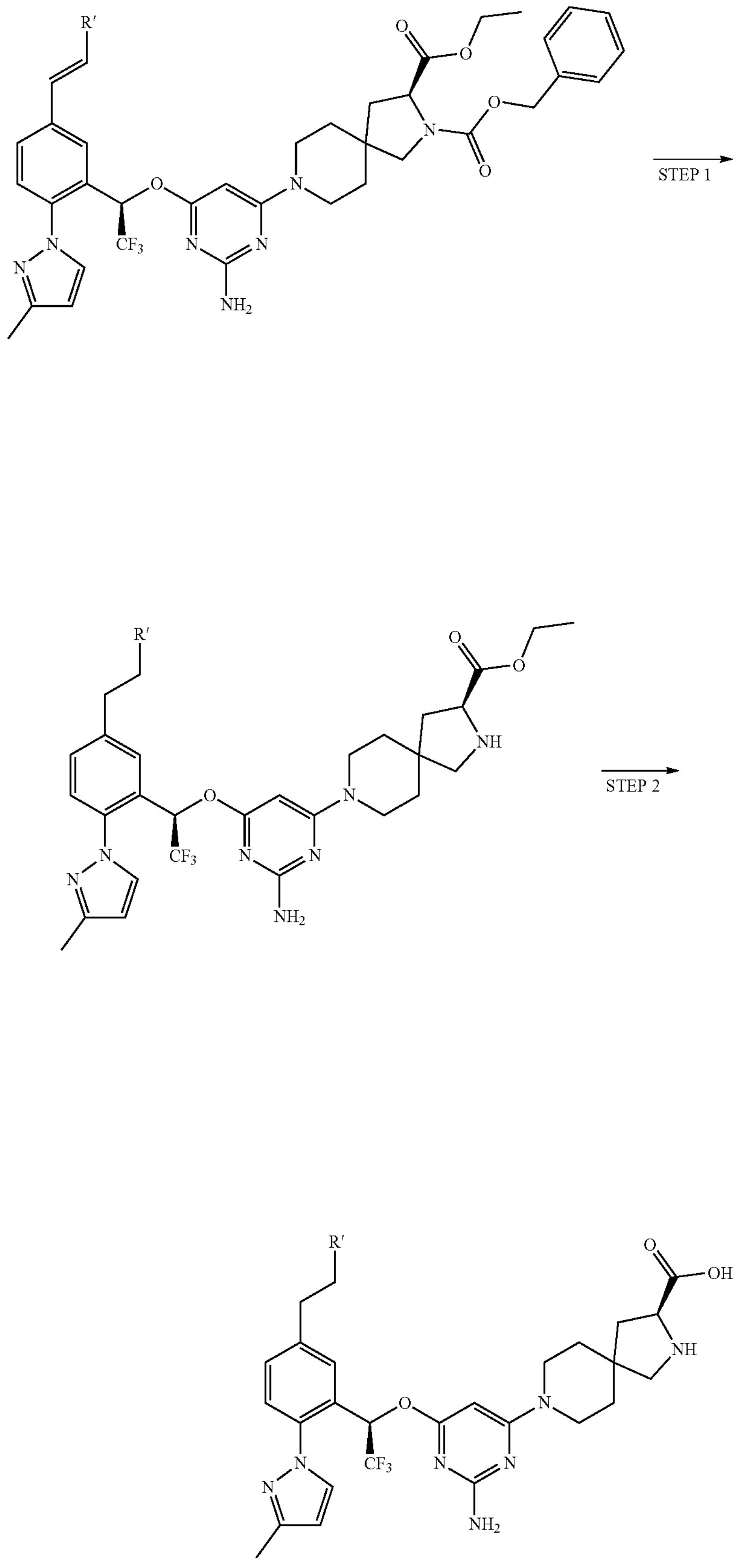
R' = H, Me, Et

TABLE 8A

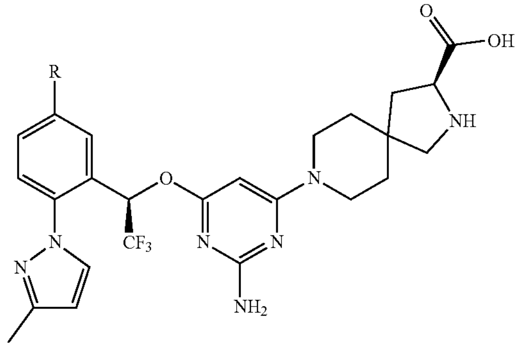

| Ex. No. | R | CAS Name | LCMS (MH+) |
|---|---|---|---|
| 22a | 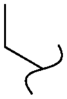 | (S)-8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro[4.5]decane-3-carboxylic acid | 561 |
| 22b | 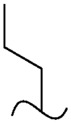 | S)-8-(2-amino-6-((R)-2,2,2-trifluoro-1-(2-(3-methyl-1H-pyrazol-1-yl)-5-propylphenyl)ethoxy)pyrimidin-4-yl)-2,8-diazaspiro[4.5]decane-3-carboxylic acid | 575 |
| 22c | 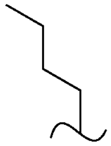 | (S)-8-(2-amino-6-((R)-1-(5-butyl-2-(3-methyl-1H-pyrazol-1-yl)phenyl)-2,2,2-trifluoroethoxy)pyrimidin-4-yl)-2,8-diazaspiro[4.5]decane-3-carboxylic acid | 589 |

TABLE 8b

| NMR Data for Compounds of Table 8a | |
|---|---|
| Ex. No. | NMR |
| 22a | $^1$H NMR (400 MHz, MeOH-d4): δ ppm 1.24 (t, J = 7.59 Hz, 3 H) 1.57 (m, 4 H) 2.06 (dd, J = 13.42, 7.13 Hz, 1 H) 2.32 (dd, J = 13.45, 9.20 Hz, 1 H) 2.37 (s, 3 H) 2.72 (q, J = 7.61 Hz, 2 H) 3.18 (m, 2 H) 3.57 (m, 4 H) 4.08 (dd, J = 9.13, 7.17 Hz, 1 H) 5.74 (s, 1 H) 6.36 (d, J = 2.34 Hz, 1 H) 6.71 (q, J = 6.65 Hz, 1 H) 7.31 (m, 1 H) 7.39 (m, 1 H) 7.56 (s, 1 H) 7.82 (d, J = 2.29 Hz, 1 H) |
| 22b | $^1$H NMR (400 MHz, MeOH-d4): δ ppm 0.91 (t, J = 7.35 Hz, 2 H) 1.62 (m, 6 H) 2.06 (dd, J = 13.52, 7.17 Hz, 1 H) 2.31 (dd, J = 13.45, 9.25 Hz, 1 H) 2.37 (s, 3 H) 2.66 (t, J = 7.52 Hz, 2 H) 3.18 (m, 2 H) 3.56 (m, 4 H) 4.08 (dd, J = 9.13, 7.17 Hz, 1 H) 5.74 (s, 1 H) 6.36 (d, J = 2.29 Hz, 1 H) 6.70 (q, J = 6.70 Hz, 1 H) 7.31 (m, 1 H) 7.37 (m, 1 H) 7.53 (s, 1 H) 7.82 (d, J = 2.29 Hz, 1 H) |
| 22c | $^1$H NMR (400 MHz, MeOH-d4): δ ppm 0.92 (t, J = 7.37 Hz, 2 H) 1.32 (dq, J = 14.94, 7.38 Hz, 2 H) 1.60 (m, 6 H) 2.06 (dd, J = 13.37, 7.22 Hz, 1 H) 2.31 (dd, J = 13.45, 9.25 Hz, 1 H) 2.37 (s, 3 H) 2.69 (t, J = 7.59 Hz, 2 H) 3.18 (m, 2 H) 3.58 (m, 4 H) 4.08 (dd, J = 9.20, 7.25 Hz, 1 H) 5.75 (s, 1 H) 6.36 (d, J = 2.15 Hz, 1 H) 6.69 (q, J = 6.62 Hz, 1 H) 7.30 (m, 1 H) 7.37 (m, 1 H) 7.53 (s, 1 H) 7.82 (d, J = 2.29 Hz, 1 H) |

Example 23

(S)-8-(2-Amino-6-((R)-1-(5-(ethoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

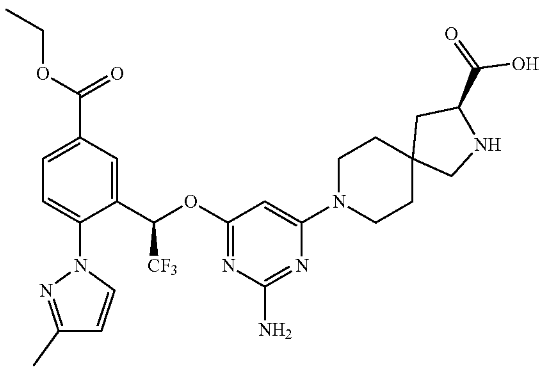 [SMILES: CCOC(=O)c1ccc(-n2ccc(C)n2)c([C@@H](Oc2cc(N3CCC4(CC3)CN[C@H](C(=O)O)C4)nc(N)n2)C(F)(F)F)c1]

Step 1: To a solution of (S)-8-(2-amino-6-((R)-1-(5-bromo-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid (product of Step 3, Example 10m) (180 mg, 0.24 mmol) in ethanol (2 mL) was added $Pd(PPh_3)_2Cl_2$ (34 mg, 0.048 mmol), $KHCO_3$ (242 mg, 2.4 mmol). A balloon of CO was fitted and the reaction mixture was heated to 80° C. for 20 h, then cooled to RT. The reaction was quenched with water, and extracted with EtOAc. The combined organic layers were washed with brine, dried over $MgSO_4$, filtered, and concentrated in vacuo. Purification by normal phase silica gel column ($CH_2Cl_2$/MeOH/AcOH) provided (S)-8-(2-amino-6-((R)-1-(5-(ethoxycarbonyl)-2-(3-methyl-1H-pyrazol-1-yl)phenyl)-2,2,2-trifluoroethoxy) pyrimidin-4-yl)-2-((benzyloxy)carbonyl)-2,8-diazaspiro[4.5]decane-3-carboxylic acid as an off-white solid.

Step 2: N-CBZ Deprotection of (S)-8-(2-amino-6-((R)-1-(5-(ethoxycarbonyl)-2-(3-methyl-1H-pyrazol-1-yl)phenyl)-2,2,2-trifluoroethoxy) pyrimidin-4-yl)-2-((benzyloxy)carbonyl)-2,8-diazaspiro[4.5]decane-3-carboxylic acid was accomplished via Method A to provide the title compound as an off-white solid.

$^1$H NMR (400 MHz, DMSO-d6): δ ppm 1.34 (t, J=7.10 Hz, 3 H) 1.51-1.71 (m, 4 H) 1.90 (dd, J=13.28, 9.18 Hz, 1 H) 2.26-2.40 (m, 4 H) 3.13 (br. s., 2 H) 3.66 (br. s., 4 H) 4.29-4.52 (m, 4 H) 6.07 (s, 1 H) 6.47 (d, J=2.39 Hz, 1 H) 7.48 (d, J=6.05 Hz, 1 H) 7.72 (d, J=8.40 Hz, 1 H) 8.15 (dd, J=8.40, 1.95 Hz, 1 H) 8.19-8.29 (m, 2 H) 8.96 (d, J=5.56 Hz, 1 H) 10.36 (d, J=4.49 Hz, 1 H). LCMS (MH+): 604.

Example 24

(S)-8-(2-Amino-6-((R)-1-(5-carboxy-2-(3-methyl-1H-pyrazol-1-yl)phenyl)-2,2,2-trifluoroethoxy) pyrimidin-4-yl)-2,8-diazaspiro[4.5]decane-3-carboxylic acid

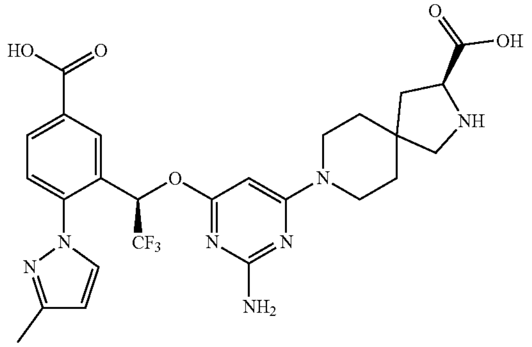 [SMILES: Cc1ccn(-c2ccc(C(=O)O)cc2[C@@H](Oc2cc(N3CCC4(CC3)CN[C@H](C(=O)O)C4)nc(N)n2)C(F)(F)F)n1]

Hydrolysis of (S)-8-(2-amino-6-((R)-1-(5-(ethoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 23) using the LiOH general method provides the title compound as a white solid.

$^1$H NMR (400 MHz, DMSO-d6): δ ppm 1.45-1.65 (m, 4 H) 1.83-1.95 (m, 1 H) 2.26-2.38 (m, 4 H) 3.12 (br. s., 2 H) 3.61 (br. s., 4 H) 4.36-4.51 (m, 1 H) 5.93 (br. s., 1 H) 6.46 (d, J=2.39 Hz, 1 H) 7.40 (m, J=5.80 Hz, 1 H) 7.67 (d, J=8.35 Hz, 1 H) 8.11 (dd, J=8.35, 1.95 Hz, 1 H) 8.21 (d, J=2.39 Hz, 1 H) 8.25 (s, 1 H) 8.93 (m, J=4.40 Hz, 1 H) 10.09 (br. s., 1 H). LCMS (MH+): 576.

Example 25

(S)-8-(2-Amino-6-((R)-2,2,2-trifluoro-1-(4-(hydroxymethyl)-2-(3-methyl-1H-pyrazol-1-yl)phenyl) ethoxy) pyrimidin-4-yl)-2,8-diazaspiro[4.5]decane-3-carboxylic acid

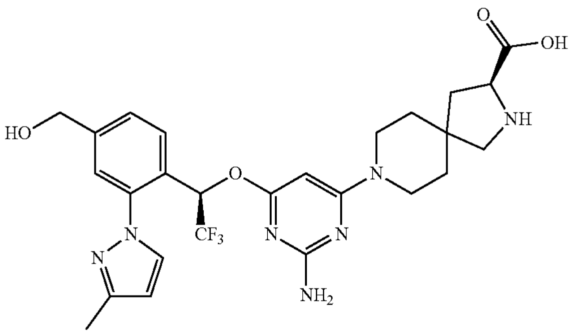 [SMILES: Cc1ccn(-c2cc(CO)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-1-(4-bromo-2-(3-methyl-1H-pyrazol-1-yl)phenyl)-2,2,2-trifluoroethoxy)pyrimidin-4-yl)-2,8-diazaspiro[4.5]decane-2,3-dicarboxylate (386 mg, 0.50 mmol) in DMF (10 mL) and $Et_3N$ (0.35 mL, 2.5 mmol) was added $(n\text{-octyl})_3SiH$ (368 mg, 1.0 mmol). The mixture was degassed under 1 atm of CO balloon and $PdCl_2(PPh_3)_2$ (72 mg, 0.10 mmol) was added, then degassed again with 1 atm of CO, and heated to 80° C. for 12 h. The reaction was cooled to RT and concentrated in vacuo. The residue was diluted with water then extracted with EtOAc. The combined organic layers were dried over $Na_2SO_4$, filtered, and concentrated in vacuo. Normal phase column chromatography on silica gel (EtOAc/heptane) provided (S)-2-benzyl 3-ethyl 8-(2-amino-6-((R)-2,2,2-trifluoro-1-(4-formyl-2-(3-methyl-1H-pyrazol-1-yl)phenyl)ethoxy)pyrimidin-4-yl)-2,8-diazaspiro[4.5]decane-2,3-dicarboxylate as a light yellow solid contaminated with about 25% of (S)-2-benzyl 3-ethyl 8-(2-amino-6-((R)-2,2,2-trifluoro-1-(2-(3-methyl-1H-pyrazol -1-yl)phenyl)ethoxy)pyrimidin-4-yl)-2,8-diazaspiro[4.5]decane-2,3-dicarboxylate as by-product. The mixture was used directly in the next step.

Step 2: To a solution of (S)-2-benzyl 3-ethyl 8-(2-amino-6-((R)-2,2,2-trifluoro-1-(4-formyl-2-(3-methyl-1H-pyrazol-1-yl)phenyl)ethoxy)pyrimidin-4-yl)-2,8-diazaspiro[4.5]decane-2,3-dicarboxylate (36 mg, 0.05 mmol) in dichloroethane (2 mL) was added $NaCNBH_3$ (1M in THF, 1 mL, 0.5 mmol), followed by a few drops of HOAc. The mixture was stirred at RT for 3 h then concentrated in vacuo. The residue was dissolved in MeOH and purified on reverse phase HPLC (MeOH/$H_2O$/HOAc) to provide (S)-2-benzyl 3-ethyl 8-(2-amino-6-((R)-2,2,2-trifluoro-1-(4-(hydroxymethyl)-2-(3-methyl-1H-pyrazol-1-yl)phenyl)ethoxy)pyrimidin-4-yl)-2,8-diazaspiro[4.5]decane-2,3-dicarboxylate as a sticky solid that was used without further purification.

Step 3: N-CBZ Deprotection was accomplished via Method B to provide (S)-ethyl 8-(2-amino-6-((R)-2,2,2-trifluoro-1-(4-(hydroxymethyl)-2-(3-methyl-1H-pyrazol-1-yl)phenyl)ethoxy)pyrimidin-4-yl)-2,8-diazaspiro[4.5]decane-3-carboxylate as a white solid.

Step 4: Hydrolysis of (S)-ethyl 8-(2-amino-6-((R)-2,2,2-trifluoro-1-(4-(hydroxymethyl)-2-(3-methyl-1H-pyrazol-1-yl)phenyl)ethoxy)pyrimidin-4-yl)-2,8-diazaspiro[4.5]decane-3-carboxylate using the LiOH general method provided the title compound as a white solid.

$^1$H NMR (400 MHz, MeOH-d4): δ ppm 1.57 (t, J=5.15 Hz, 4 H) 1.91-2.12 (m, 7 H) 2.30 (dd, J=13.23, 9.42 Hz, 1 H) 2.36 (s, 3 H) 3.07-3.26 (m, 2 H) 3.39-3.54 (m, 2 H) 3.58-3.70 (m, 2 H) 3.99-4.13 (m, 1 H) 4.65 (s, 2 H) 5.71 (s, 1 H) 6.37 (d, J=2.34 Hz, 1 H) 6.74 (q, J=6.65 Hz, 1 H) 7.39 (s, 1 H) 7.45 (d, J=8.20 Hz, 1 H) 7.68 (d, J=8.10 Hz, 1 H) 7.84 (d, J=2.34 Hz, 1 H). LCMS (MH+): 562.

Example 26

(S)-8-(2-amino-6-((R)-1-(4-((dimethylamino)methyl)-2-(3-methyl-1H-pyrazol-1-yl)phenyl)-2,2,2-trifluoroethoxy)pyrimidin-4-yl)-2,8-diazaspiro[4.5]decane-3-carboxylic acid

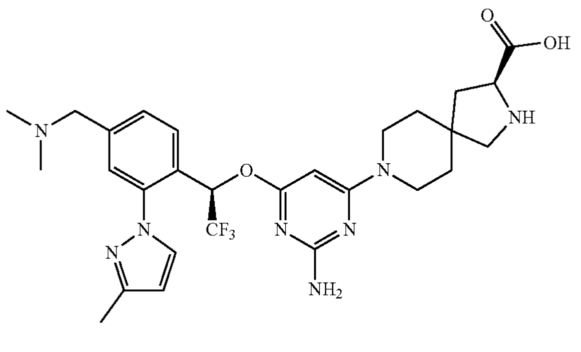 [SMILES: Cc1ccn(-c2cc(CN(C)C)ccc2[C@@H](Oc2cc(N3CCC4(CC3)CN[C@H](C(=O)O)C4)nc(N)n2)C(F)(F)F)n1]

Step 1: To a solution of (S)-2-benzyl 3-ethyl 8-(2-amino-6-((R)-2,2,2-trifluoro-1-(4-formyl-2-(3-methyl-1H-pyrazol-1-yl)phenyl)ethoxy)pyrimidin-4-yl)-2,8-diazaspiro [4.5] decane-2,3-dicarboxylate (166 mg, 0.23 mmol, see Ex. 25) in dichloroethane (4 mL) and HOAc (10 mg) was added NaBH(OAc)3 (242 mg, 1.15 mmol) and Me2NH (2M in THF, 0.58 mL, 1.15 mmol). The reaction mixture was stirred at RT for 20 h then concentrated in vacuo. The residue was dissolved in MeOH (1 mL) and purified by reverse phase HPLC (MeOH/$H_2O$/HOAc) to provide (S)-2-benzyl 3-ethyl 8-(2-amino-6-((R)-1-(4-((dimethylamino) methyl)-2-(3-methyl-1H-pyrazol-1-yl)phenyl)-2,2,2-trifluoroethoxy)pyrimidin-4-yl)-2,8-diazaspiro[4.5]decane-2,3-dicarboxylate as a white solid.

Step 2: N-CBZ Deprotection was accomplished via Method A to provide (S)-ethyl 8-(2-amino-6-((R)-1-(4-((dimethylamino)methyl)-2-(3-methyl-1H-pyrazol-1-yl)phenyl)-2,2,2-trifluoroethoxy)pyrimidin-4-yl)-2,8-diazaspiro[4.5]decane-3-carboxylate as a white solid.

Step 3: Hydrolysis of (S)-ethyl 8-(2-amino-6-((R)-1-(4-((dimethylamino)methyl)-2-(3-methyl-1H-pyrazol-1-yl)phenyl)-2,2,2-trifluoroethoxy)pyrimidin-4-yl)-2,8-diazaspiro [4.5]decane-3-carboxylate using the LiOH general method provided the title compound as a white solid.

$^1$H NMR (400 MHz, MeOH-d4): δ ppm 1.66-1.81 (m, 4 H) 2.10 (dd, J=13.62, 8.54 Hz, 1 H) 2.38 (s, 3 H) 2.49 (dd, J=13.62, 8.88 Hz, 1 H) 2.88 (s, 3 H) 2.90 (s, 3 H) 3.58-3.90 (m, 4 H) 4.37-4.49 (m, 2 H) 4.56 (t, J=8.69 Hz, 1 H) 6.37 (br. s., 1 H) 6.43 (d, J=2.34 Hz, 1 H) 7.06-7.12 (m, 1 H) 7.71-7.78 (m, 2 H) 7.85 (d, J=8.10 Hz, 1 H) 7.98 (d, J=2.39 Hz, 1 H). LCMS (MH+): 589.

Example 27

(S)-8-(6-((R)-1-(4-Bromo-2-(3-methyl-1H-pyrazol -1-yl)phenyl)-2,2,2-trifluoroethoxy)-2-methylpyrimidin-4-yl)-2,8-diazaspiro [4.5]decane-3-carboxylic acid

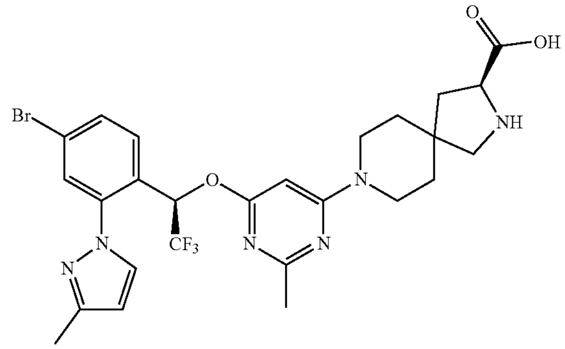 [SMILES: Cc1ccn(-c2cc(Cl)ccc2[C@@H](Oc2cc(N3CCC4(CC3)CN[C@H](C(=O)O)C4)nc(C)n2)C(F)(F)F)n1]

Step 1: To a solution of 1 (R)-1-[4-bromo-2-(3-methyl-1H-pyrazol-1-yl)phenyl]-2,2,2-trifluoroethanol (15.7 g, 46.3 mmol, Intermediate 1) in dioxane (200 mL) was added 4,6-dichloro-2-methylpyrimidine (30.6 g, 51 mmol) and $Cs_2CO_3$ (61.2 g, 187 mmol). The reaction mixture was heated to 80° C. for 30 h, then cooled to RT, and filtered. The residue was concentrated in vacuo and purified by normal phase column chromatography on silica gel ($CH_2Cl_2$/heptane) to provide (R)-4-(1-(4-bromo-2-(3-methyl-1H-pyrazol-1-yl)phenyl)-2,2,2-trifluoroethoxy)-6-chloro-2-methylpyrimidine as a white solid.

Step 2: To a solution of (R)-4-(1-(4-bromo-2-(3-methyl-1H-pyrazol-1-yl)phenyl)-2,2,2-trifluoroethoxy)-6-chloro-2-methylpyrimidine (21 g) in dioxane (200 ml) was added (S)-2-benzyl 3-ethyl 2,8-diazaspiro[4.5]decane-2,3-dicarboxylate (15 g) and $Na_2CO_3$ (14 g). The reaction was heated to 90° C. for 48 h, then cooled to RT, filtered, and concentrated in vacuo. Purification of the residue on normal phase column chromatography on silica gel (EtOAc/heptane) provided (S)-2-benzyl 3-ethyl 8-(6-((R)-1-(4-bromo-2-(3-methyl-1H-pyrazol-1-yl)phenyl)-2,2,2-trifluoroethoxy)-2-methylpyrimidin-4-yl)-2,8-diazaspiro[4.5]decane-2,3-dicarboxylate as an off-white solid.

Step 4: N-CBZ Deprotection was accomplished via Method A to provide (S)-ethyl 8-(6-((R)-1-(4-bromo-2-(3-methyl-1H-pyrazol-1-yl)phenyl)-2,2,2-trifluoroethoxy)-2-methylpyrimidin-4-yl)-2,8-diazaspiro[4.5]decane-3-carboxylate an off-white solid.

Step 5: Hydrolysis of(S)-ethyl 8-(6-((R)-1-(4-bromo-2-(3-methyl-1H-pyrazol-1-yl)phenyl)-2,2,2-trifluoroethoxy)-2-methylpyrimidin-4-yl)-2,8-diazaspiro [4.5 ]decane-3-carboxylate using the LiOH general method provided the title compound as an off-white solid.

$^1$H NMR (400 MHz, MeOH-d4): δ ppm 1.64 (br. s., 4 H) 2.10 (d, J=7.03 Hz, 1 H) 2.28 (s, 3 H) 2.35 (dd, J=13.37, 9.27 Hz, 1 H) 2.39 (s, 3 H) 3.10-3.20 (m, 1 H) 3.28 (d, J=11.91 Hz, 1 H) 3.45-3.67 (m, 2 H) 3.75 (br. s., 2 H) 4.10 (dd, J=8.98, 7.22 Hz, 1 H) 6.17 (s, 1 H) 6.43 (d, J=2.15 Hz, 1 H) 7.01 (d, J=6.44 Hz, 1 H) 7.58-7.75 (m, 3 H) 8.03 (d, J=2.15 Hz, 1 H). LCMS (MH+): 609.

Example 28

(S)-8-(6-((R)-1-(4-chloro-2-(3-methyl-1H-pyrazol-1-yl)phenyl)-2,2,2-trifluoroethoxy)-2-methyl pyrimidin-4-yl)-2,8-diazaspiro[4.5]decane-3-carboxylic acid

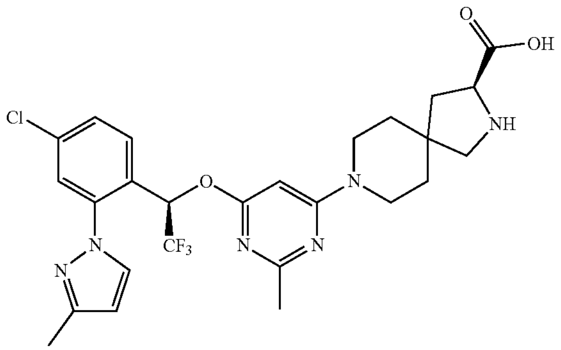

The title compound was prepared as described above for (S)-8-(6-((R)-1-(4-bromo-2-(3-methyl-1H-pyrazol-1-yl) phenyl)-2,2,2-trifluoroethoxy)-2-methylpyrimidin-4-yl)-2,8-diazaspiro[4.5]decane-3-carboxylic acid (byr replacing 1(R)-1-[4-bromo-2-(3-methyl-1H-pyrazol-1-yl)phenyl]-2,2,2-trifluoroethanol with 1(R)-1-[4-chloro-2-(3-methyl-1H-pyrazol-1-yl)phenyl]-2,2,2-trifluoroethanol, Intermediate 3) and obtained as an off-white solid.

$^1$H NMR (400 MHz, DMSO-d6): δ ppm 1.34-1.54 (m, 4 H) 1.82 (dd, J=13.01, 6.76 Hz, 1 H) 1.99-2.08 (m, 1 H) 2.11 (s, 3 H) 2.30 (s, 3 H) 2.92 (d, J=11.52 Hz, 1 H) 3.06 (d, J=11.52 Hz, 1 H) 3.42-3.65 (m, 4 H) 3.70 (dd, J=8.91, 7.00 Hz, 1 H) 6.15 (s, 1 H) 6.42 (s, 1 H) 7.43 (q, J=6.93 Hz, 1 H) 7.54-7.61 (m, 1 H) 7.64 (d, J=2.10 Hz, 1 H) 7.70 (d, J=8.44 Hz, 1 H) 8.19 (d, J=2.39 Hz, 1 H) 8.70 (br. s., 1 H). LCMS (MH+): 565.

General Biaryl Coupling (Suzuki) Procedures

Biaryl Coupling Method A

Step 1: To a mixture of (S)-2-((benzyloxy)carbonyl)-8-(6-((R)-1-(4-bromo-2-(3-methyl-1H-pyrazol-1-yl)phenyl)-2,2,2-trifluoroethoxy)-2-methylpyrimidin-4-yl)-2,8-diazaspiro[4.5]decane-3-carboxylic acid (product of Step 3, Example 10m) (150 mg, 0.2 mmol), an arylboronic acid (0.4 mmol), Pd(N,N-dimethyl μ-alaninate)$_2$ (3.42 mg, 0.01 mmol), and K3PO4 (128 mg, 0.6 mmol) were added water (3.0 mL) and EtOH (3.0 mL). The mixture was stirred at 50° C. for 12 h. The reaction was then cooled to RT, diluted with water, and extracted with EtOAc. The combined organic layers were dried over $Na_2SO_4$, filtered, and concentrated in vacuo. The target biaryl compounds were purified by normal phase silica gel column ($CH_2Cl_2$:MeOH).

Step 2: Subsequent N-CBZ deprotection via method A afforded the final target spirocyclic amino acids.

Biaryl Coupling Method B

Step 1: To a mixture of (S)-2-((benzyloxy)carbonyl)-8-(6-((R)-1-(4-bromo-2-(3-methyl-1H-pyrazol-1-yl)phenyl)-2,2,2-trifluoroethoxy)-2-methylpyrimidin-4-yl)-2,8-diazaspiro[4.5]decane-3-carboxylic acid (product of Step 3, Example 10m) (150 mg, 0.2 mmol), an arylboronic acid (0.4 mmol), $Pd(OAc)_2$·(1,1,3,3-tetramethyl-2-N-butylguanidine)$_2$ (5.7 mg, 0.01 mmol), and $K_2CO_3$ (83.5 mg, 0.61 mmol) was added water (1.0 mL) and dioxane (3.0 mL). The reaction mixture was stirred at 44° C. for 24 h. The reaction mixture was then cooled to RT, diluted with water, and extracted with EtOAc. The combined organic layers were dried over $Na_2SO_4$, filtered, and concentrated in vacuo. The target biaryl compounds were purified by normal phase silica gel column ($CH_2Cl_2$:MeOH).

Step 2: Subsequent N-CBZ deprotection via method A afforded the final target spirocyclic amino acids.

Using the generic scheme below and employing the biaryl coupling method A, the following examples of Table 9 were prepared.

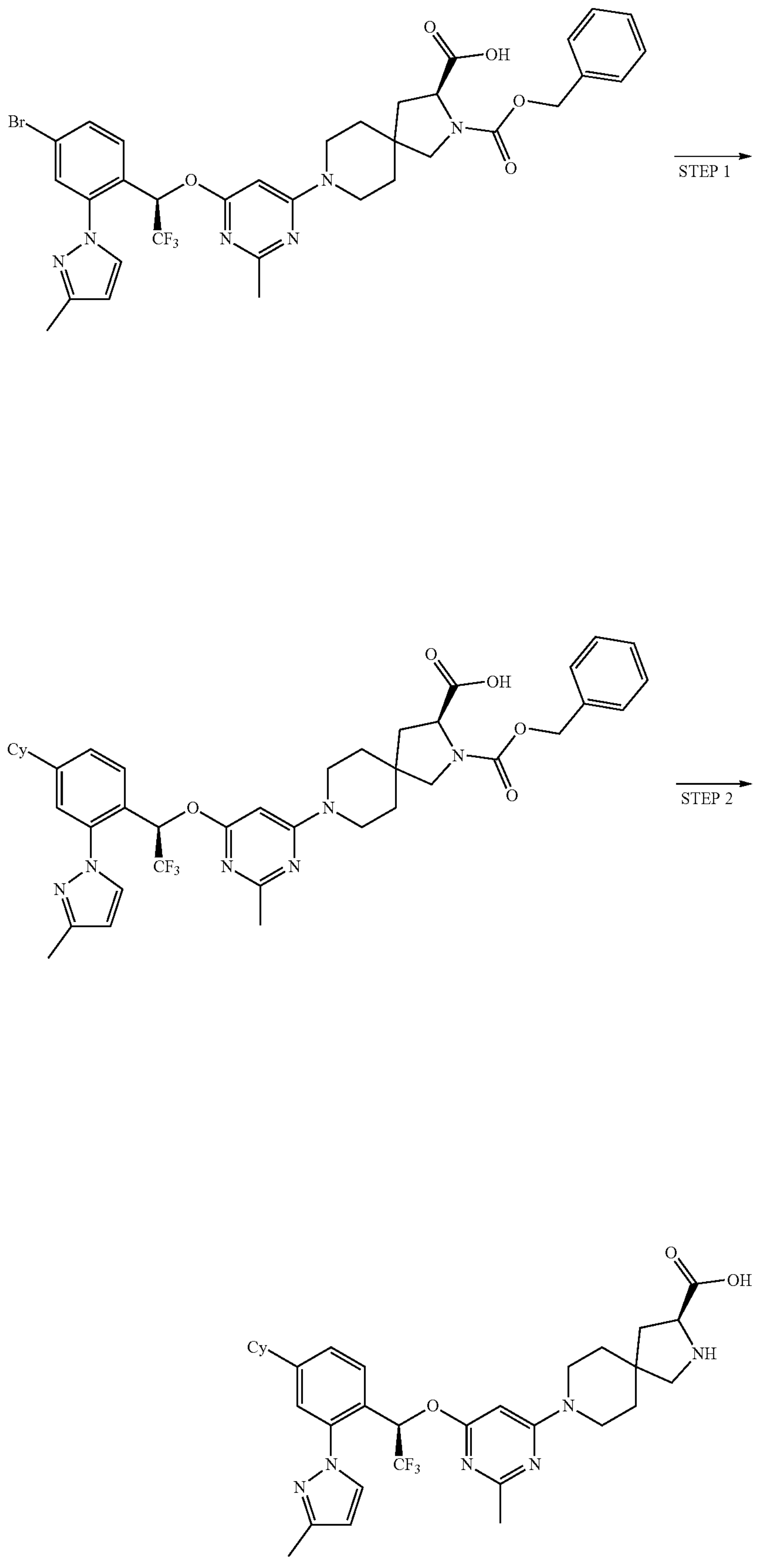
STEP 1
STEP 2

TABLE 9

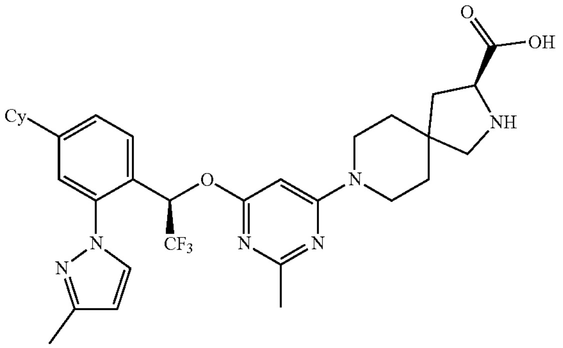

| Ex. No. | Cy | CAS Name | LCMS (MH+) |
|---|---|---|---|
| 29a | 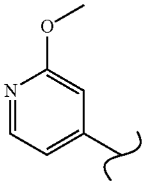 | (S)-8-(2-methyl-6-4R)-2,2,2-trifluoro-1-(4-(2-methoxypyridin-4-yl)-2-(3-methyl-1H-pyrazol-1-yl)phenyl)ethoxy)pyrimidin-4-yl)-2,8-diazaspiro[4.5]decane-3-carboxylic acid | 638 |
| 29b | 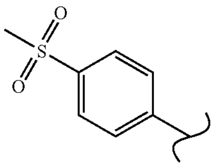 | (S)-8-(2-methyl-6-((R)-2,2,2-trifluoro-1-(3-(3-methyl-1H-pyrazol-1-yl)-4'-(methylsulfonyl)-[1,1'-biphenyl]-4-yl)ethoxy)pyrimidin-4-yl)-2,8-diazaspiro[4.5]decane-3-carboxylic acid | 686 |
| 29c | 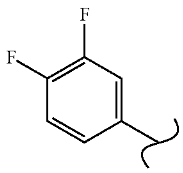 | (S)-8-(6-((R)-1-(3',4'-difluoro-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 645 |
| 29d | 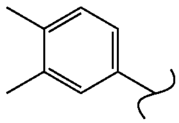 | (S)-8-(6-((R)-1-(3',4'-dimethyl-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 635 |
| 29e | 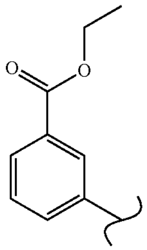 | (S)-8-(6-((R)-1-(3'-(ethoxycarbonyl)-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 680 |
| 29f | 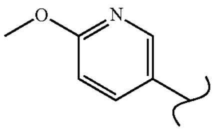 | (S)-8-(2-methyl-6-((R)-2,2,2-trifluoro-1-(4-(6-methoxypyridin-3-yl)-2-(3-methyl-1H-pyrazol-1-yl)phenyl)ethoxy)pyrimidin-4-yl)-2,8-diazaspiro[4.5]decane-3-carboxylic acid | 639 |
| 29g | 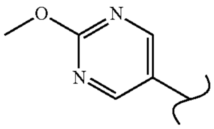 | (S)-8-(2-methyl-6-((R)-2,2,2-trifluoro-1-(4-(2-methoxypyrimidin-5-yl)-2-(3-methyl-1H-pyrazol-1-yl)phenyl)ethoxy)pyrimidin-4-yl)-2,8-diazaspiro[4.5]decane-3-carboxylic acid | 640 |

TABLE 9-continued

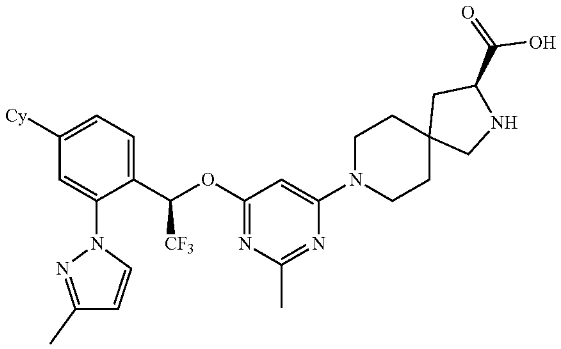

| Ex. No. | Cy | CAS Name | LCMS (MH+) |
|---|---|---|---|
| 29h | 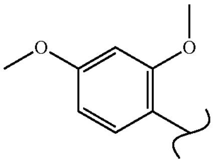 | (S)-8-(6-((R)-1-(2',4'-dimethoxy-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 668 |
| 29i | 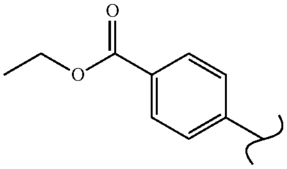 | (S)-8-(6-((R)-1-(4'-(ethoxycarbonyl)-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 679 |
| 29j | 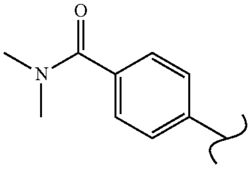 | (S)-8-(6-((R)-1-(4'-(dimethylcarbamoyl)-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 678 |
| 29k | 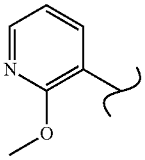 | (S)-8-(2-methyl-6-4R)-2,2,2-trifluoro-1-(4-(2-methoxypyridin-3-yl)-2-(3-methyl-1H-pyrazol-1-yl)phenyl)ethoxy)pyrimidin-4-yl)-2,8-diazaspiro[4.5]decane-3-carboxylic acid | 639 |
| 29l | 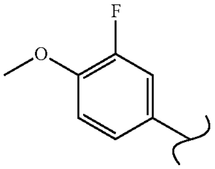 | (S)-8-(2-methyl-6-((R)-2,2,2-trifluoro-1-(3'-fluoro-4'-methoxy-3-(3-methyl-1H-pyrazol-1-yl)-[1,1'-biphenyl]-4-ypethoxy)pyrimidin-4-yl)-2,8-diazaspiro[4.5]decane-3-carboxylic acid | 655.6 |
| 29m | 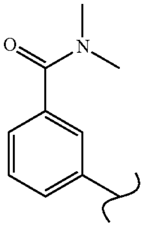 | (S)-8-(6-((R)-1-(3'-(dimethylcarbamoyl)-3-(3-methyl-1H-pyrazol-1-yl)[1,1'-biphenyl]-4-yl)-2,2,2-trifluoroethoxy)-2-methylpyrimidin-4-yl)-2,8-diazaspiro[4.5]decane-3-carboxylic acid | 679 |

Using the generic scheme above with the biaryl coupling method B, the following examples of Table 10 were prepared.

TABLE 10

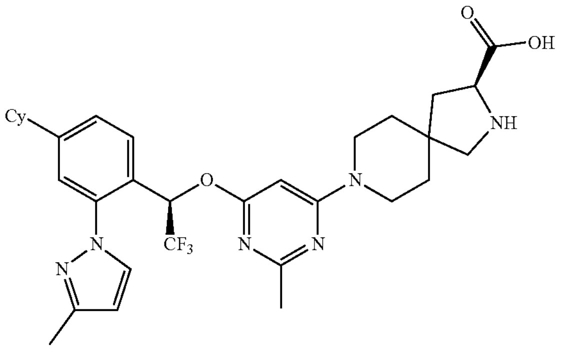

| Ex. No. | Cy | CAS Name | LCMS (MH+) |
|---|---|---|---|
| 29n | 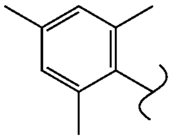 | (S)-8-(2-methyl-6-((R)-2,2,2-trifluoro-1-(2',4',6'-trimethyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 650 |
| 29o | 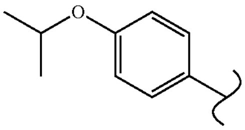 | (S)-8-(2-methyl-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 666 |
| 29p | 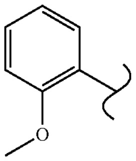 | (S)-8-(2-methyl-6-((R)-2,2,2-trifluoro-1-(2'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 638 |
| 29q | 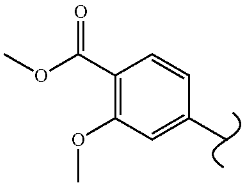 | (S)-8-(2-methyl-6-((R)-2,2,2-trifluoro-1-(3'-methoxy-4'-(methoxycarbonyl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 695 |
| 29r | 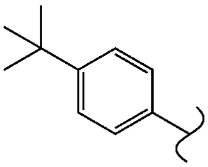 | (S)-8-(6-((R)-1-(4'-(tert-butyl)-3-(3-methyl-1H-pyrazol-1-yl)-[1,1'-biphenyl]-4-yl)-2,2,2-trifluoroethoxy)-2-methylpyrimidin-4-yl)-2,8-diazaspiro[4.5]decane-3-carboxylic acid | 663 |
| 29s | 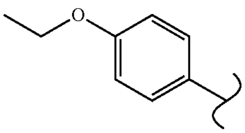 | (S)-8-(6-((R)-1-(4'-ethoxy-3-(3-methyl-1H-pyrazol-1-yl)-[1,1'-biphenyl]-4-yl)-2,2,2-trifluoroethoxy)-2-methylpyrimidin-4-yl)-2,8-diazaspiro[4.5]decane-3-carboxylic acid | 652 |
| 29t | 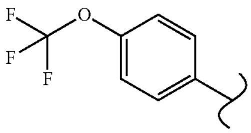 | (S)-8-(2-methyl-6-((R)-2,2,2-trifluoro-1-(3-(3-methyl-1H-pyrazol-1-yl)-4'-(trifluoromethoxy)-[1,1'-biphenyl]-4-yl)ethoxy)pyrimidin-4-yl)-2,8-diazaspiro[4.5]decane-3-carboxylic acid | 692 |

TABLE 10-continued

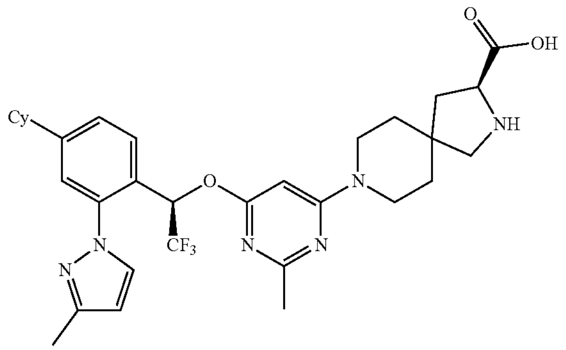

| Ex. No. | Cy | CAS Name | LCMS (MH+) |
|---|---|---|---|
| 29u | 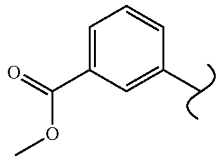 | (S)-8-(2-methyl-6-((R)-2,2,2-trifluoro-1-(3'-(methoxycarbonyl)-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 666 |
| 29v | 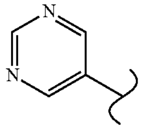 | (S)-8-(2-methyl-6-((R)-2,2,2-trifluoro-1-(2-(3-methyl-1H-pyrazol-1-yl)-4-(pyrimidin-5-yl)phenyl)ethoxy)pyrimidin-4-yl)-2,8-diazaspiro[4.5]decane-3-carboxylic acid | 609 |
| 29w | 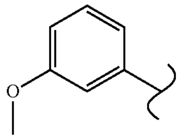 | (S)-8-(2-methyl-6-((R)-2,2,2-trifluoro-1-(3'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 637 |
| 29x | 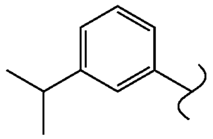 | (S)-8-(2-methyl-6-((R)-2,2,2-trifluoro-1-(3'-isopropyl-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 650 |
| 29y | 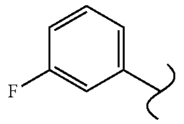 | (S)-8-(2-methyl-6-((R)-2,2,2-trifluoro-1-(3'-fluoro-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 626 |
| 29z | 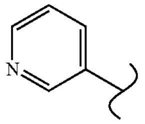 | (S)-8-(2-methyl-6-((R)-2,2,2-trifluoro-1-(2-(3-methyl-1H-pyrazol-1-yl)-4-(pyridin-3-yl)phenyl)ethoxy)pyrimidin-4-yl)-2,8-diazaspiro[4.5]decane-3-carboxylic acid | 609 |
| 29aa | 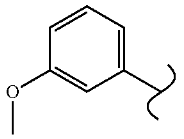 | (S)-8-(2-methyl-6-((R)-2,2,2-trifluoro-1-(3'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylic acid | 638 |
| 29ab | 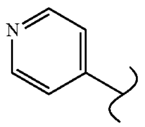 | (S)-8-(2-methyl-6-((R)-2,2,2-trifluoro-1-(2-(3-methyl-1H-pyrazol-1-yl)-4-(pyridin-4-yl)phenyl)ethoxy)pyrimidin-4-yl)-2,8-diazaspiro[4.5]decane-3-carboxylic acid | 608 |

Example 30a 8-(6-((R)-1-(4-chloro-2-(3-methyl-1H-pyrazol-1-yl)phenyl)-2,2,2-trifluoroethoxy)-2-phenoxypyrimidin-4-yl)-2,8-diazaspiro[4.5]decane-3-carboxylic acid

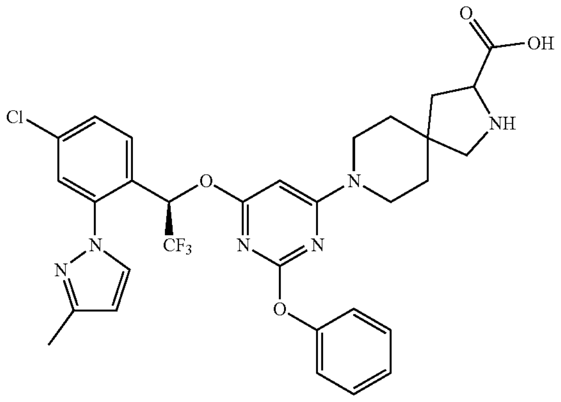 [SMILES: Cc1ccn(-c2cc(Cl)ccc2[C@@H](Oc2cc(N3CCC4(CC3)CNC(C(=O)O)C4)nc(Oc3ccccc3)n2)C(F)(F)F)n1]

Step 1: To a solution of (R)-1-[4-chloro-2-(3-methylpyrazol-1-yl)phenyl]-2,2,2-trifluoroethanol (5.00 g, 17.2 mmol) and 4,6-dichloro-2-(methylthio)pyrimidine (3.36 g, 17.2 mmol) in dioxane (250 mL) was added $Cs_2CO_3$ (16.8 g, 51.6 mmol). The reaction mixture was then heated to 70° C. for 90 h, then cooled to RT. The reaction mixture was quenched with water and extracted with EtOAc. The combined organic layers were washed with brine, dried over $Na_2SO_4$, filtered, and concentrated in vacuo. Purification on a 120 g Isco RediSep silica cartridge (EtOAc:heptane) provided 4-chloro-6-[(R)-1-[4-chloro-2-(3-methylpyrazol-1-yl)phenyl]-2,2,2-trifluoroethoxy]-2-methylsulfanylpyrimidine as a white solid.

Step 2: To a solution of 4-chloro-6-[(R)-1-[4-chloro-2-(3-methylpyrazol-1-yl)phenyl]-2,2,2-trifluoroethoxy]-2-methylsulfanylpyrimidine (4 g, 8.95 mmol) in $CH_2Cl_2$ (200 mL) was added m-CPBA (4.2 g of a 77% (w/w) source, 18.8 mmol) and the reaction was stirred at RT for 15 h. The reaction was then diluted with saturated $NaHCO_3$, and extracted with $CH_2Cl_2$. The combined organic layers were washed with brine, dried over $Na_2SO_4$, filtered, and concentrated in vacuo. Purification on a 120 g Isco RediSep silica cartridge (EtOAc:heptane) provided 4-chloro-6-[(1R)-1-[4-chloro-2-(3-methylpyrazol-1-yl)phenyl]-2,2,2-trifluoroethoxy]-2-methylsulfonylpyrimidine as an off-white solid.

Step 3: To a solution of 4-chloro-6-[(1R)-1-[4-chloro-2-(3-methylpyrazol-1-yl)phenyl]-2,2,2-trifluoroethoxy]-2-methylsulfonylpyrimidine (2.49 g, 5.17 mmol) in dioxane (100 mL) was added 2-benzyl 3-ethyl 2,8-diazaspiro[4.5]decane-2,3-dicarboxylate (1.8 g, 5.2 mmol), $Cs_2CO_3$ (5.06 g, 15.5 mmol), and the reaction mixture was heated to 100° C. for 1.5 h. The reaction mixture was cooled to RT, quenched with brine, and extracted with EtOAc. The combined organic layers were dried over $Na_2SO_4$, filtered, and concentrated in vacuo. Purification on a 120 g Isco RediSep silica cartridge (EtOAc:heptane) provided (S)-2-benzyl 3-ethyl 8-(6-((R)-1-(4-chloro-2-(3-methyl-1H-pyrazol-1-yl)phenyl)-2,2,2-trifluoroethoxy)-2-(methylsulfonyl) pyrimidin-4-yl)-2,8-diazaspiro[4.5]decane-2,3-dicarboxylate as a white solid (1.3 g) in addition to (S)-2-benzyl 3-ethyl 8-(4-chloro-6-((R)-1-(4-chloro-2-(3-methyl-1H-pyrazol-1-yl)phenyl)-2,2,2-trifluoroethoxy)pyrimidin-2-yl)-2,8-diazaspiro[4.5]decane-2,3-dicarboxylate.

Step 4: To a solution of 2-benzyl 3-ethyl 8-(6-((R)-1-(4-chloro-2-(3-methyl-1H-pyrazol-1-yl)phenyl)-2,2,2-trifluoroethoxy)-2-(methylsulfonyl)pyrimidin-4-yl)-2,8-diazaspiro[4.5]decane-2,3-dicarboxylate (2.10 g, 2.65 mmol) in 2:1 THF:$H_2O$ (90 mL) was added LiOH (127 mg, 5.3 mmol), and the reaction was stirred at RT for 21 h, afer which additional LiOH (65 mg, 2.6 mmol) was added, and the reaction was stirred for 8 h longer. The reaction was then quenched with 1 N HCl to pH<1, and extracted with EtOAc. The combined organic layers were dried over $Na_2SO_4$, filtered, and concentrated in vacuo to provide 2-((benzyloxy)carbonyl)-8-(6-((R)-1-(4-chloro-2-(3-methyl-1H-pyrazol-1-yl)phenyl)-2,2,2-trifluoroethoxy)-2-(methylsulfonyl) pyrimidin-4-yl)-2,8-diazaspiro[4.5]decane-3-carboxylic acid as an off-white solid which was used directly without further purification.

Step 5: To a solution of 2-((benzyloxy)carbonyl)-8-(6-((R)-1-(4-chloro-2-(3-methyl-1H-pyrazol-1-yl)phenyl)-2,2,2-trifluoroethoxy)-2-(methylsulfonyl)pyrimidin-4-yl)-2,8-diazaspiro[4.5]decane-3-carboxylic acid (300 mg, 0.393 mmol) in 1,4-dioxane (10 mL) was added phenol (74 mg, 0.79 mmol), $Cs_2CO_3$ (512 mg, 1.5 mmol), and the reaction was heated to 70° C. for 21 h. The reaction was then cooled to RT, diluted with water, acidified to pH<1 with 1 N HCl, and extracted with EtOAc. The combined organic layers were dried over $Na_2SO_4$, filtered, and concentrated in vacuo. Purification on a 50 g Isco Gold RediSep reverse phase silica cartridge ($H_2O$:HOAc: 99:1 MeOH:HOAc 99:1) provided 2-((benzyloxy)carbonyl)-8-(6-((R)-1-(4-chloro-2-(3-methyl-1H-pyrazol-1-yl)phenyl)-2,2,2-trifluoroethoxy)-2-phenoxypyrimidin-4-yl)-2,8-diazaspiro[4.5]decane-3-carboxylic acid as an off-white solid.

Step 6: N-CBZ Deprotection was accomplished via Method B to provide the title compound as an off-white solid.

Using the generic scheme below, the following examples of Table 11a were prepared as described above for 8-(6-((R)-1-(4-chloro-2-(3-methyl-1H-pyrazol-1-yl)phenyl)-2,2,2-trifluoroethoxy)-2-phenoxypyrimidin-4-yl)-2,8-diazaspiro[4.5]decane-3-carboxylic acid (Example 30a).

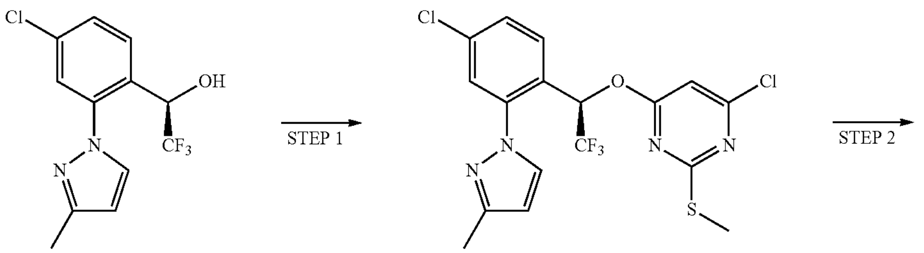

-continued
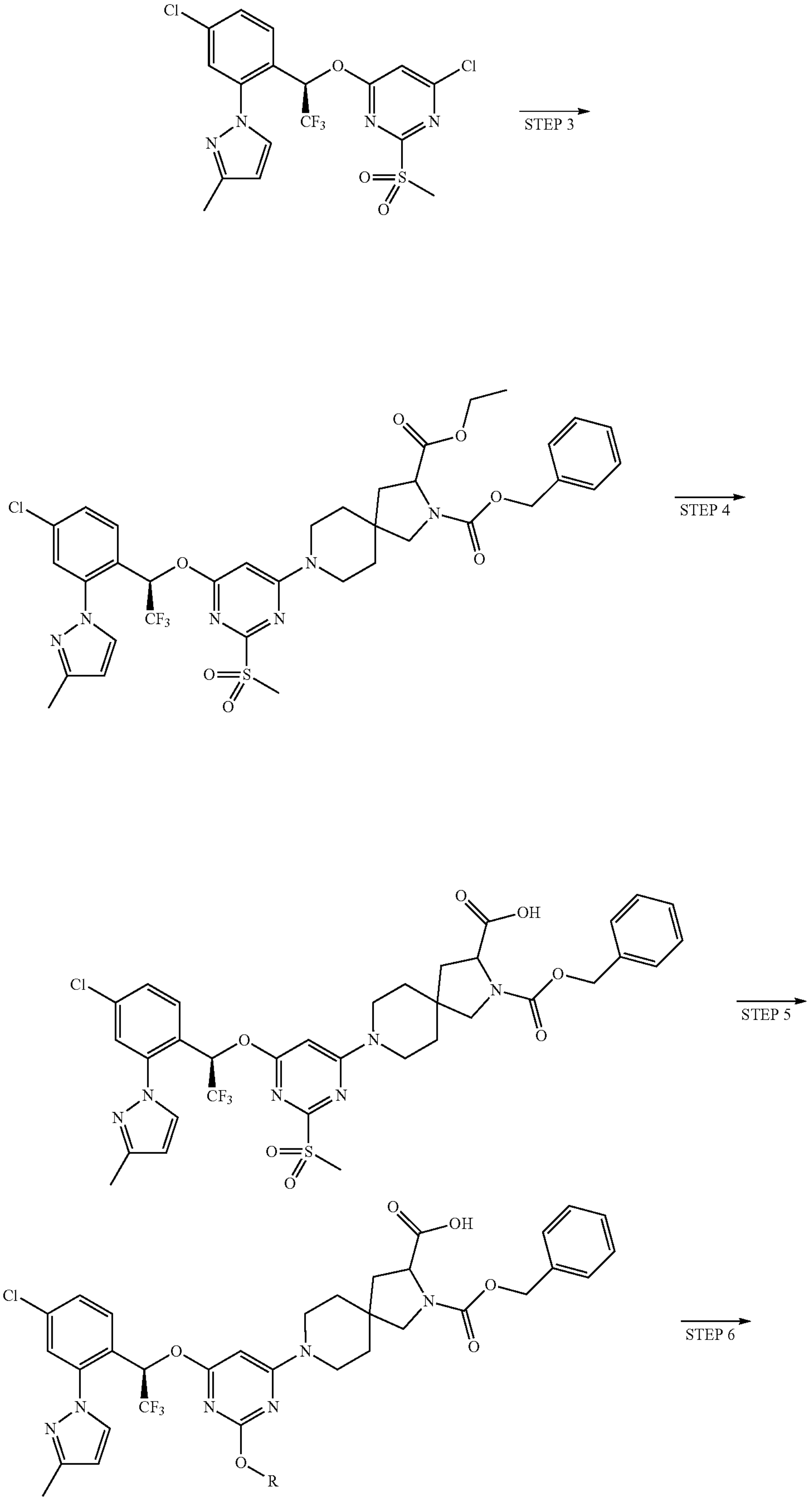

-continued

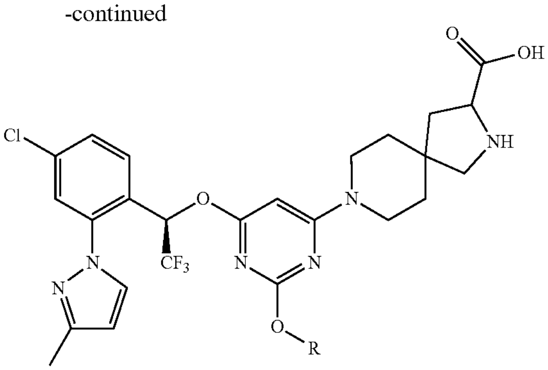

TABLE 11a

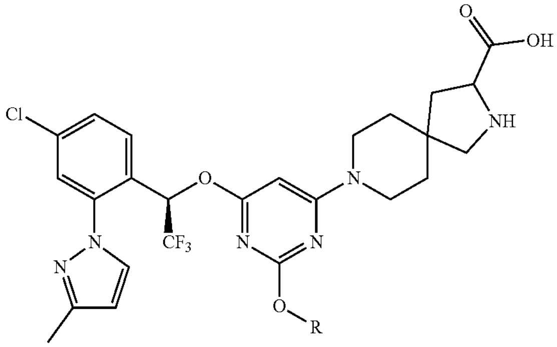

| Ex. No. | Cy | CAS Name | LCMS (MH+) |
|---|---|---|---|
| 30a | 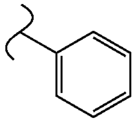 | 8-(6-((R)-1-(4-chloro-2-(3-methyl-1H-pyrazol-1-yl)phenyl)-2,2,2-trifluoroethoxy)-phenoxypyrimidin-4-yl)-2,8-diazaspiro[4.5]decane-3-carboxylic acid | 644 |
| 30b | 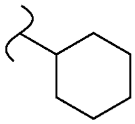 | 8-(6-((R)-1-(4-chloro-2-(3-methyl-1H-pyrazol-1-yl)phenyl)-2,2,2-trifluoroethoxy)-2-(cyclohexyloxy)pyrimidin-4-yl)-2,8-diazaspiro[4.5]decane-3-carboxylic acid | 649 |

TABLE 11b

NMR Data for Compounds of Table 11a

| Ex. No. | NMR |
|---|---|
| 30a | $^1$H NMR (400 MHz, MeOH-d4): δ ppm 1.57 (br. s., 4 H), 2.00-2.31 (m, 2 H), 2.32 (s, 3 H), 3.06-3.28 (m, 2 H), 3.36-3.71 (m, 4 H), 4.07 (dd, J = 8.83, 7.37 Hz, 1 H), 6.11 (s, 1 H), 6.30 (d, J = 2.34 Hz, 1 H), 6.70 (q, J = 6.43 Hz, 1 H), 6.97-7.06 (m, 2 H), 7.10-7.20 (m, 1 H), 7.26-7.36 (m, 2 H), 7.47 (d, J = 2.15 Hz, 1 H), 7.54 (dd, J = 8.54, 2.15 Hz, 1 H), 7.71 (d, J = 8.54 Hz, 1 H), 7.86 (d, J = 2.39 Hz, 1 H). |
| 30b | $^1$H NMR (400 MHz, MeOH-d4): δ ppm 1.16-1.95 (m, 14 H), 2.04-2.35 (m, 2 H), 2.36 (s, 3 H), 3.07-3.30 (m, 2 H), 3.43-3.82 (m, 4 H), 4.09 (dd, J = 8.86, 7.39 Hz, 1 H), 4.80-4.95 (m, 1 H), 5.98 (s, 1 H), 6.37 (d, J = 2.39 Hz, 1 H), 7.01-7.13 (m, 1 H), 7.45-7.55 (m, 2 H), 7.70 (d, J = 9.08 Hz, 1 H), 8.12 (d, J = 2.34 Hz, 1 H) |

Example 31

8-(6-((R)-1-(4-chloro-2-(3-methyl-1H-pyrazol-1-yl) phenyl)-2,2,2-trifluoroethoxy)-2-(cyclohexylamino) pyrimidin-4-yl)-2,8-diazaspiro[4.5]decane-3-carboxylic acid

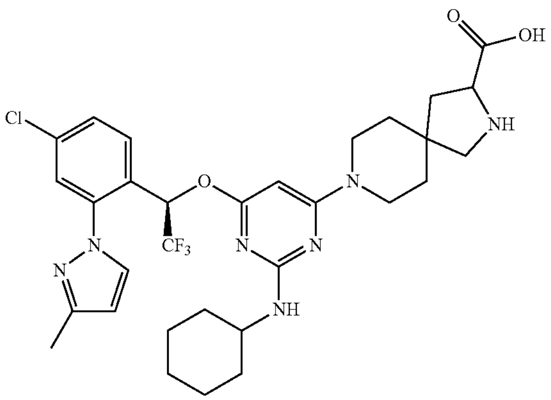 [SMILES: Cc1ccn(-c2cc(Cl)ccc2[C@@H](Oc2cc(N3CCC4(CC3)CNC(C(=O)O)C4)nc(NC3CCCCC3)n2)C(F)(F)F)n1]

The title compound was prepared as described above by replacing the alcohol in Step 5 of Example 30a with cyclohexyl amine.

$^1$H NMR (400 MHz, MeOH-d4): δ ppm 0.99-1.95 (m, 14 H), 2.02-2.37 (m, 2 H), 2.38 (s, 3 H), 3.07-3.29 (m, 2 H), 3.41-3.77 (m, 5 H), 4.09 (dd, J=9.10, 7.15 Hz, 1 H), 5.60 (s, 1 H), 6.39 (d, J=2.39 Hz, 1 H), 6.87-7.21 (m, 1 H), 7.49 (dtd, J=4.48, 2.26, 2.26, 2.12 Hz, 2 H), 7.70 (d, J=9.03 Hz, 1 H), 7.87 (d, J=2.34 Hz, 1 H). LCMS (MH+): 650.

Example 32

(S)- 8-(6-((R)-1-(4-chloro-2-(3-methyl-1H-pyrazol-1-yl)phenyl)-2,2,2-trifluoroethoxy)-2-(cyclobutanecarboxamido)pyrimidin-4-yl)-2,8-diazaspiro [4.5] decane-3-carboxylic acid

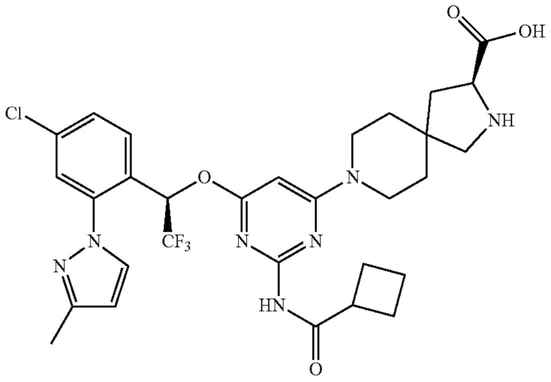 [SMILES: Cc1ccn(-c2cc(Cl)ccc2[C@@H](Oc2cc(N3CCC4(CC3)CN[C@H](C(=O)O)C4)nc(NC(=O)C3CCC3)n2)C(F)(F)F)n1]

Step 1: To a solution of (S)-8-(2-amino-6-((R)-1-(4-chloro-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid (product of Step 3, Example 10m) (300 mg, 0.412 mmol) in pyridine (1.0 mL) was added cyclobutanecarbonyl chloride (54 mg, 0.045 mmol). The reaction mixture was stirred at RT for 3 h, then diluted with EtOAc, and washed with 0.5 N HCl. The organic layer was dried over $Na_2SO_4$, filtered, and concentrated in vacuo. Purification on a 40 g Isco RediSep silica cartridge (EtOAc/heptane) provides (S)-2-benzyl 3-ethyl 8-(6-((R)-1-(4-chloro-2-(3-methyl-1H-pyrazol-1-yl)phenyl)-2,2,2-trifluoroethoxy)-2-(cyclobutanecarboxamido) pyrimidin-4-yl)-2,8-diazaspiro[4.5]decane-2,3-dicarboxylate as an off-white solid.

Step 2: The title compound was prepared by the N-CBZ removal using the general method B to provide a white solid. $^1$H NMR (400 MHz, MeOH-d4): δ ppm 1.66 (d, J=4.30 Hz, 4 H), 1.78-1.99 (m, 2 H), 2.03-2.38 (m, 6 H), 2.39 (s, 3 H), 3.12-3.32 (m, 2 H), 3.47-3.90 (m, 5 H), 4.10 (dd, J=9.10, 7.20 Hz, 1 H), 6.03 (s, 1 H), 6.41 (d, J=2.34 Hz, 1 H), 6.82-6.98 (m, 1 H), 7.45-7.57 (m, 2 H), 7.73 (d, J=8.49 Hz, 1 H), 7.97 (d, J=2.34 Hz, 1 H). LCMS (MH+): 649.

Example 33

(S)-8-(2-amino-6-((R)-1-(4-chloro-2-(2-oxopyrrolidin-1-yl)phenyl)-2,2,2-trifluoroethoxy) pyrimidin-4-yl)-2,8-diazaspiro[4.5]decane-3-carboxylic acid

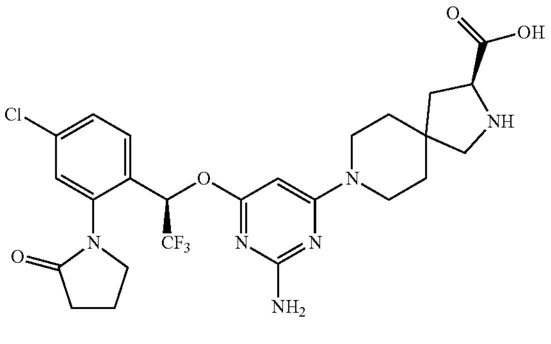 [SMILES: Nc1nc(O[C@H](c2ccc(Cl)cc2N2CCCC2=O)C(F)(F)F)cc(N2CCC3(CC2)CN[C@H](C(=O)O)C3)n1]

The title compound was prepared as described for (S)-8-(2-amino-6-((R)-1-(4-chloro-2-(3-methyl-1H-pyrazol-1-yl) phenyl)-2,2,2-trifluoroethoxy)pyrimidin-4-yl)-2,8-diazaspiro[4.5]decane-3-carboxylic acid (Example 10d) starting with (R)-1-(5-chloro-2-(2,2,2-trifluoro-1-hydroxyethyl)phenyl)pyrrolidin-2-one.

$^1$H NMR (DMSO-d6): δ ppm 1.23 (m, 1H), 1.40 (m, 4H), 1.81 (dd, J=13.2, 6.9 Hz, 1H), 2.07 (m, 4H), 2.45 (d, J=8.1 Hz, 2H), 2.91 (d, J=11.5 Hz, 3H), 3.06 (d, J=11.6 Hz, 1H), 3.47 (d, J=6.9 Hz, 3H), 3.66 (m, 3H), 5.54 (s, 1H), 6.09 (s, 2H), 6.74 (q, J=6.9 Hz, 1H), 7.55 (m, 3H). LCMS (MH+): 570.

Example 34c (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid

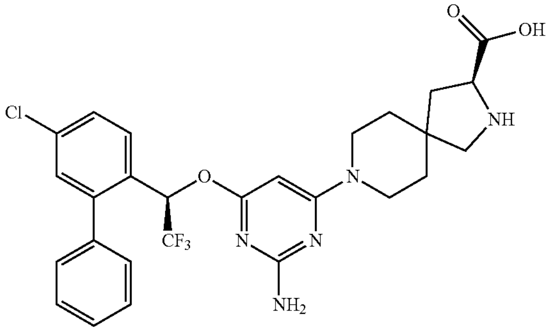 [SMILES: Nc1nc(O[C@H](c2ccc(Cl)cc2-c2ccccc2)C(F)(F)F)cc(N2CCC3(CC2)CN[C@H](C(=O)O)C3)n1]

Step 1: To a solution of (R)-1-(2-bromo-4-chlorophenyl)-2,2,2-trifluoroethanol (Intermediate 43) (400 mg, 1.4 mmol) in dioxane (25 mL) was added 4,6-dichloropyrimidin-2-amine (1.1 g, 7 mmol) and $Cs_2CO_3$ (1.3 g, 4 mmol). The mixture was heated for 24 h at 80° C. The reaction was then cooled to RT and filtered. The solvent was removed in vacuo, then $CH_2Cl_2$ and heptane was added. The solvent volume was reduced until a solid precipitated out. The solid was filtered and the procedure repeated several times to provide (R)-4-(1-(2-bromo-4-chlorophenyl)-2,2,2-trifluoroethoxy)-6-chloropyrimidin-2-amine as a white solid.

Step 2: To a solution of (R)-4-(1-(2-bromo-4-chlorophenyl)-2,2,2-trifluoroethoxy)-6-chloropyrimidin-2-amine (100 mg, 0.24 mmol, Step 1) in dioxane (5 mL) was added (S)-2-benzyl 3-ethyl 2,8-diazaspiro[4.5]decane-2,3-dicarboxylate (100 mg, 0.29 mmol), and $NaHCO_3$ (300 mg, 3.5 mmol). After 5 h, an additional amount of $NaHCO_3$ (300 mg, 3.5 mmol) was added and the reaction mixture was heated to 90° C. for 36 h. The reaction was then cooled to RT and filtered. Purification by normal phase silica gel column (EtOAc/heptane) provided (S)-2-benzyl 3-ethyl 8-(2-amino-6-((R)-1-(2-bromo-4-chlorophenyl)-2,2,2-trifluoroethoxy)pyrimidin-4-yl)-2,8-diazaspiro[4.5]decane-2,3-dicarboxylate as a white solid.

Step 3: To a solution of (S)-2-benzyl 3-ethyl 8-(2-amino-6-((R)-1-(2-bromo-4-chlorophenyl)-2,2,2-trifluoroethoxy)pyrimidin-4-yl)-2,8-diazaspiro[4.5]decane-2,3-dicarboxylate (100 mg, 0.13 mmol) in 10:1 dioxane:water (5 mL) was phenyl boronic acid (33 mg, 0.27 mmol), $KHCO_3$ (27 mg, 0.3 mmol), and $PdCl_2(dppf)-CH_2Cl_2$ (6 mg, 0.007 mmol). The reaction was heated to 100° C. for 15 h, cooled to RT, and concentrated in vacuo. The residue was diluted with water, and extracted with EtOAc. The combined organic layers were dried over $Na_2SO_4$, filtered, and concentrated in vacuo. Purification by normal phase silica gel column (EtOAc/heptane) provided (5)-2-benzyl 3-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-2,3-dicarboxylate as an off-white solid.

Step 4: N-CBZ Deprotection was accomplished via method B to provide (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate an off-white solid.

Step 5: Hydrolysis of (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate using the LiOH general method provided the title compound as an off-white solid as the zwitterionic form.

Example 34u (S)-8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylic acid

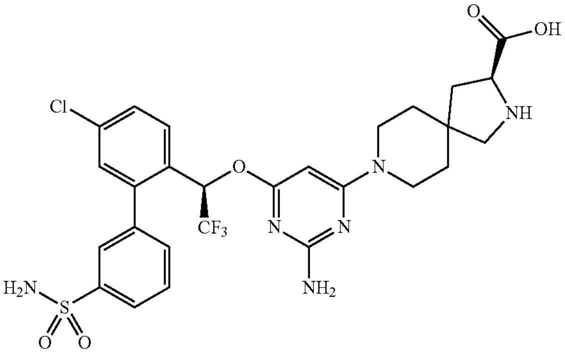 [SMILES: Nc1nc(O[C@H](c2ccc(Cl)cc2-c2cccc(S(N)(=O)=O)c2)C(F)(F)F)cc(N2CCC3(CC2)CN[C@H](C(=O)O)C3)n1]

Step 1: To a solution of (S)-2-benzyl 3-ethyl 8-(2-amino-6-((R)-1-(2-bromo-4-chlorophenyl)-2,2,2-trifluoroethoxy)pyrimidin-4-yl)-2,8-diazaspiro[4.5]decane-2,3-dicarboxylate (500 mg, 0.688 mmol) in 10:1 dioxane:water (11 mL) was added 3-(4,4,5,5-tetramethyl-1,3,2-dioxaborolan-2-yl)benzenesulfonamide (195 mg, 0.7 mmol), $KHCO_3$ (207 mg, 2.06 mmol), and $PdCl_2(dppf)-CH_2Cl_2$ (56 mg, 0.069 mmol). The reaction was heated to 100° C. for 15 h, cooled to RT, and concentrated in vacuo. The residue was diluted with water, and extracted with EtOAc. The combined organic layers were dried over $Na_2SO_4$, filtered, and concentrated in vacuo. Purification by normal phase silica gel column (EtOAc/heptane) provided (S)-2-benzyl 3-ethyl 8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-2,3-dicarboxylate as an off-white solid.

Step 2: N-CBZ Deprotection was accomplished via method B to provide (S)-ethyl 8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylate as a white solid.

Step 3: Hydrolysis of (S)-ethyl 8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylate using the LiOH general method provided the title compound as an off-white solid.

Using the generic scheme below, the following examples of Table 12a can be prepared as described above for (S)-8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylic acid (Example 34u).

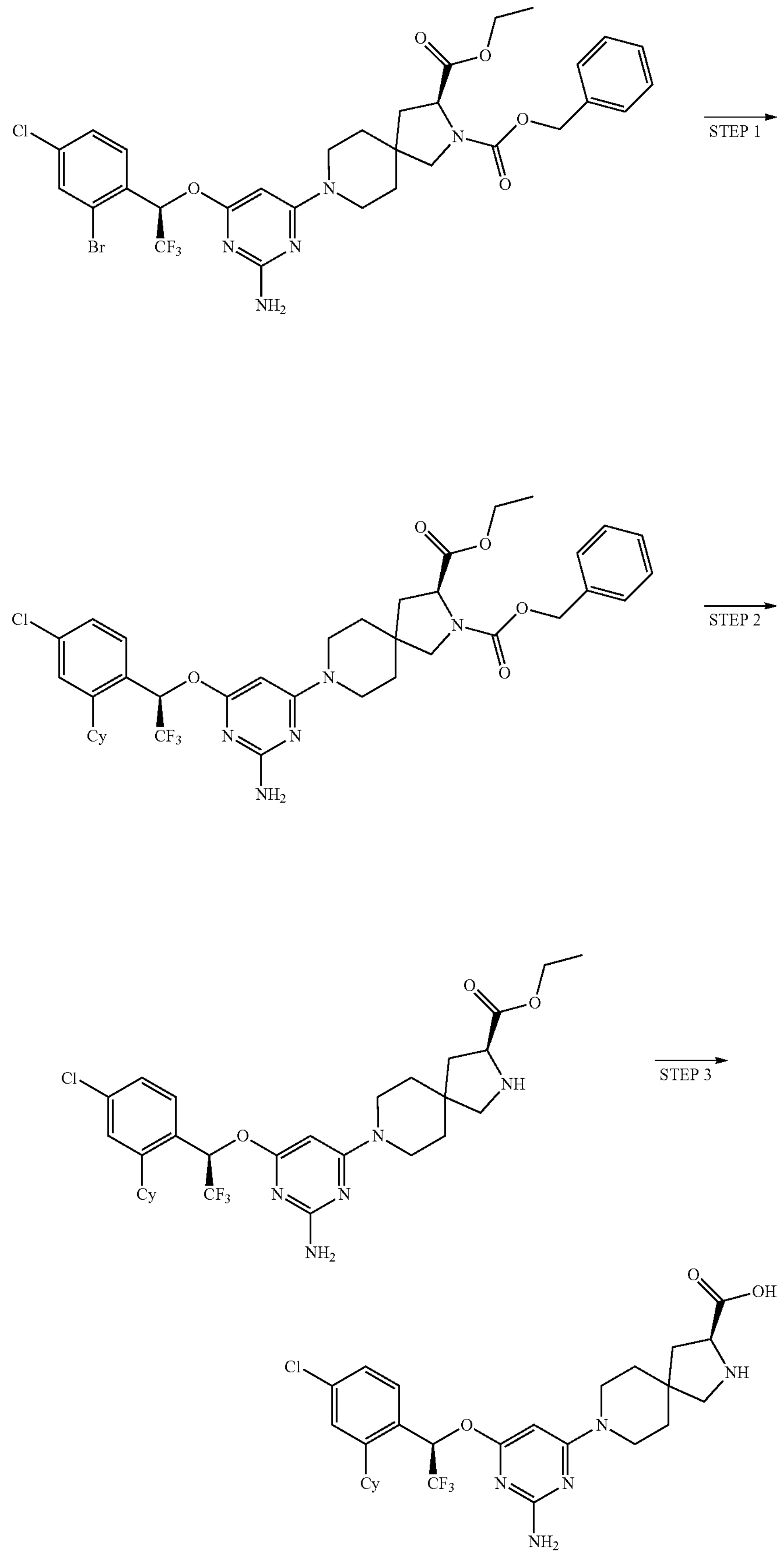
STEP 1
STEP 2
STEP 3

TABLE 12a

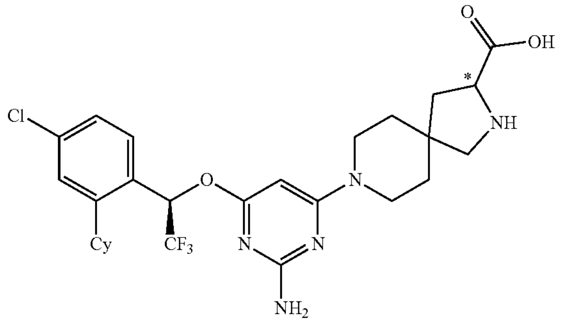

* Stereochemistry defined in name in table below

| Ex. No. | Cy | CAS Name | LCMS (MH+) |
| --- | --- | --- | --- |
| 34a | 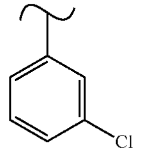 | (S)-8-(2-amino-6-((R)-1-(3',5-dichloro-[1,1'-biphenyl]-2-yl)-2,2,2-trifluoroethoxy)pyrimidin-4-yl)-2,8-diazaspiro[4.5]decane-3-carboxylic acid | 597 |
| 34b | 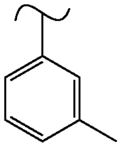 | (S)-8-(2-amino-6-((R)-1-(5-chloro-3'-methyl-[1,1'-biphenyl]-2-yl)-2,2,2-trifluoroethoxy)pyrimidin-4-yl)-2,8-diazaspiro[4.5]decane-3-carboxylic acid | 577 |
| 34c | 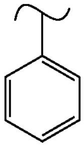 | 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid | 563 |
| 34d | 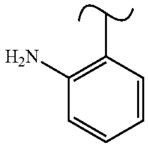 | 8-(2-amino-6-((R)-1-(2'-amino-5-chloro-[1,1'-biphenyl]-2-yl)-2,2,2-trifluoroethoxy)pyrimidin-4-yl)-2,8-diazaspiro[4.5]decane-3-carboxylic acid | 577 |
| 34e | 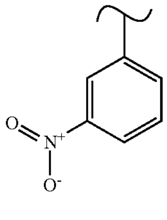 | 8-(2-amino-6-((R)-1-(5-chloro-3'-nitro-[1,1'-biphenyl]-2-yl)-2,2,2-trifluoroethoxy)pyrimidin-4-yl)-2,8-diazaspiro[4.5]decane-3-carboxylic acid | 606 |
| 34f | 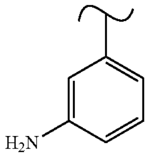 | 8-(2-amino-6-((R)-1-(3'-amino-5-chloro-[1,1'-biphenyl]-2-yl)-2,2,2-trifluoroethoxy)pyrimidin-4-yl)-2,8-diazaspiro[4.5]decane-3-carboxylic acid | 577 |

TABLE 12a-continued

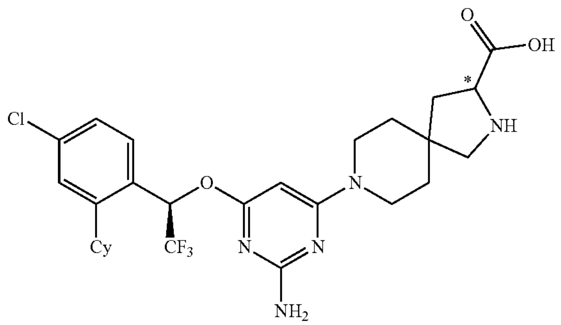

* Stereochemistry defined in name in table below

| Ex. No. | Cy | CAS Name | LCMS (MH+) |
|---|---|---|---|
| 34g | 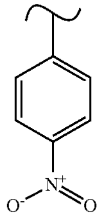 | 8-(2-amino-6-((R)-1-(5-chloro-4'-nitro-[1,1'-biphenyl]-2-yl)-2,2,2-trifluoroethoxy)pyrimidin-4-yl)-2,8-diazaspiro[4.5]decane-3-carboxylic acid | 607 |
| 34h | 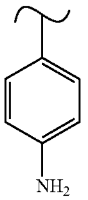 | 8-(2-amino-6-((R)-1-(4'-amino-5-chloro-[1,1'-biphenyl]-2-yl)-2,2,2-trifluoroethoxy)pyrimidin-4-yl)-2,8-diazaspiro[4.5]decane-3-carboxylic acid | 577 |
| 34i | 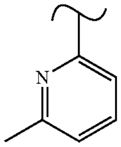 | (S)-8-(2-amino-6-((R)-1-(4-chloro-2-(6-methylpyridin-2-yl)phenyl)-2,2,2-trifluoroethoxy)pyrimidin-4-yl)-2,8-diazaspiro[4.5]decane-3-carboxylic acid | 578 |
| 34j | 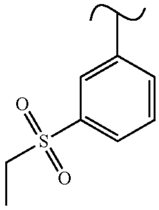 | (S)-8-(2-amino-6-((R)-1-(5-chloro-3'-(ethylsulfonyl)-[1,1'-biphenyl]-2-yl)-2,2,2-trifluoroethoxy)pyrimidin-4-yl)-2,8-diazaspiro[4.5]decane-3-carboxylic acid | 655 |
| 34k | 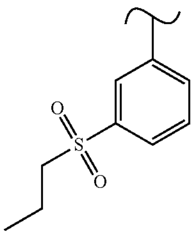 | (S)-8-(2-amino-6-((R)-1-(5-chloro-3'-(propylsulfonyl)-[1,1'-biphenyl]-2-yl)-2,2,2-trifluoroethoxy)pyrimidin-4-yl)-2,8-diazaspiro[4.5]decane-3-carboxylic acid | 669 |

TABLE 12a-continued

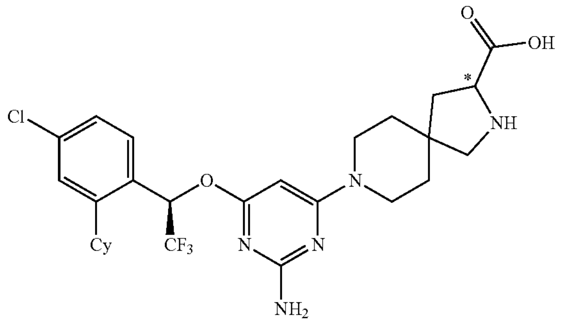

* Stereochemistry defined in name in table below

| Ex. No. | Cy | CAS Name | LCMS (MH+) |
|---|---|---|---|
| 34l | 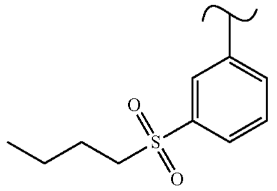 | (S)-8-(2-amino-6-((R)-1-(3'-(butylsulfonyl)-5-chloro-[1,1'-biphenyl]-2-yl)-2,2,2-trifluoroethoxy)pyrimidin-4-yl)-2,8-diazaspiro[4.5]decane-3-carboxylic acid | 682 |
| 34m | 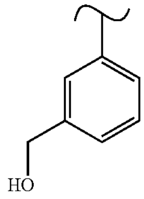 | (S)-8-(2-amino-6-((R)-1-(5-chloro-3'-(hydroxymethyl)-[1,1'-biphenyl]-2-yl)-2,2,2-trifluoroethoxy)pyrimidin-4-yl)-2,8-diazaspiro[4.5]decane-3-carboxylic acid | 592 |
| 34n | 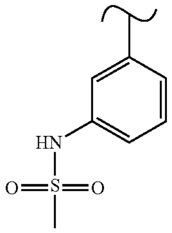 | (S)-8-(2-amino-6-((R)-1-(5-chloro-3'-(methylsulfonamido)-[1,1'-biphenyl]-2-yl)-2,2,2-trifluoroethoxy)pyrimidin-4-yl)-2,8-diazaspiro[4.5]decane-3-carboxylic acid | 656 |
| 34o | 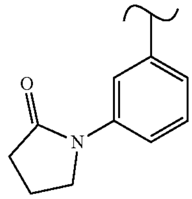 | (S)-8-(2-amino-6-((R)-1-(5-chloro-3'-(2-oxopyrrolidin-1-yl)-[1,1'-biphenyl]-2-yl)-2,2,2-trifluoroethoxy)pyrimidin-4-yl)-2,8-diazaspiro[4.5]decane-3-carboxylic acid | 646 |
| 34p | 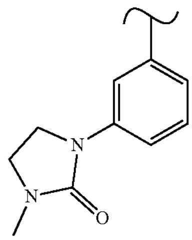 | (S)-8-(2-amino-6-((R)-1-(5-chloro-3'-(3-methyl-2-oxoimidazolidin-1-yl)-[1,1'-biphenyl]-2-yl)-2,2,2-trifluoroethoxy)pyrimidin-4-yl)-2,8-diazaspiro[4.5]decane-3-carboxylic acid | 660.5 |

TABLE 12a-continued

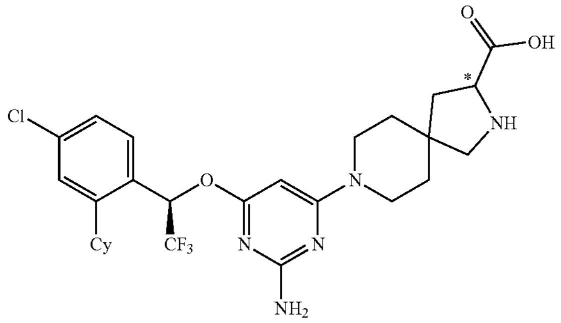

* Stereochemistry defined in name in table below

| Ex. No. | Cy | CAS Name | LCMS (MH+) |
|---|---|---|---|
| 34q | 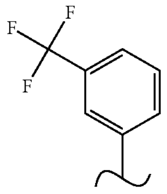 | (S)-8-(2-amino-6-((R)-1-(5-chloro-3'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 630 |
| 34r | 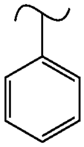 | (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid | 563 |
| 34s | 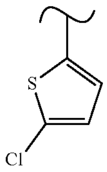 | (S)-8-(2-amino-6-((R)-1-(4-chloro-2-(5-chlorothiophen-2-yl)phenyl)-2,2,2-trifluoroethoxy)pyrimidin-4-yl)-2,8-diazaspiro[4.5]decane-3-carboxylic acid | 604 |
| 34t | 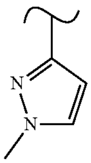 | (S)-8-(2-amino-6-((R)-1-(4-chloro-2-(1-methyl-1H-pyrazol-3-yl)phenyl)-2,2,2-trifluoroethoxy)pyrimidin-4-yl)-2,8-diazaspiro[4.5]decane-3-carboxylic acid | 566 |
| 34u | 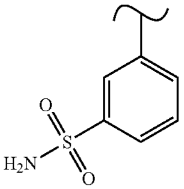 | (S)-8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylic acid | 641 |
| 34v | 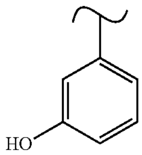 | (S)-8-(2-amino-6-((R)-1-(5-chloro-3'-hydroxy-[1,1'-biphenyl]-2-yl)-2,2,2-trifluoroethoxy)pyrimidin-4-yl)-2,8-diazaspiro[4.5]decane-3-carboxylic acid | 578 |

TABLE 12a-continued

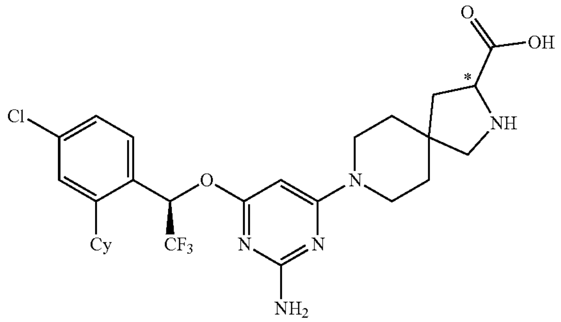

* Stereochemistry defined in name in table below

| Ex. No. | Cy | CAS Name | LCMS (MH+) |
|---|---|---|---|
| 34w | 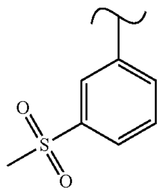 | (S)-8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-3-carboxylic acid | 640 |
| 34x | 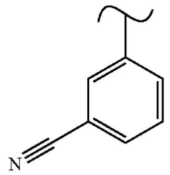 | (S)-8-(2-amino-6-((R)-1-(5-chloro-3'-cyano-[1,1'-biphenyl]-2-yl)-2,2,2-trifluoroethoxy)pyrimidin-4-yl)-2,8-diazaspiro[4.5]decane-3-carboxylic acid | 587 |
| 34y | 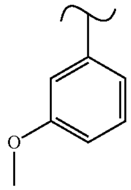 | (S)-8-(2-amino-6-((R)-1-(5-chloro-3'-methoxy-[1,1'-biphenyl]-2-yl)-2,2,2-trifluoroethoxy)pyrimidin-4-yl)-2,8-diazaspiro[4.5]decane-3-carboxylic acid | 592 |
| 34z | 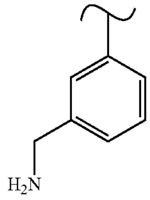 | (S)-8-(2-amino-6-((R)-1-(3'-(aminomethyl)-5-chloro-[1,1'-biphenyl]-2-yl)-2,2,2-trifluoroethoxy)pyrimidin-4-yl)-2,8-diazaspiro[4.5]decane-3-carboxylic acid | 591 |
| 34aa | 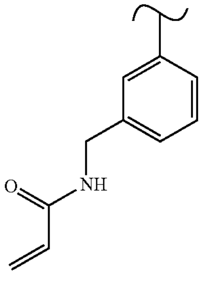 | (S)-8-(6-((R)-1-(3'-(acrylamidomethyl)-5-chloro-[1,1'-biphenyl]-2-yl)-2,2,2-trifluoroethoxy)-2-aminopyrimidin-4-yl)-2,8-diazaspiro[4.5]decane-3-carboxylic acid | 645 |

TABLE 12a-continued

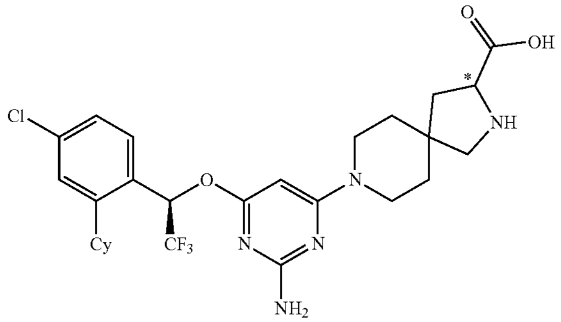

* Stereochemistry defined in name in table below

| Ex. No. | Cy | CAS Name | LCMS (MH+) |
|---|---|---|---|
| 34ab | 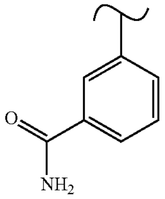 | (S)-8-(2-amino-6-((R)-1-(3'-carboxy-5-chloro-[1,1'-biphenyl]-2-yl)-2,2,2-trifluoroethoxy)pyrimidin-4-yl)-2,8-diazaspiro[4.5]decane-3-carboxylic acid | 606 |
| 34ac | 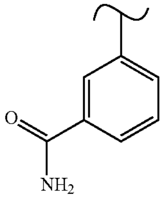 | (S)-8-(2-amino-6-((R)-1-(3'-carbamoyl-5-chloro-[1,1'-biphenyl]-2-yl)-2,2,2-trifluoroethoxy)pyrimidin-4-yl)-2,8-diazaspiro[4.5]decane-3-carboxylic acid | 605 |
| 34ad | 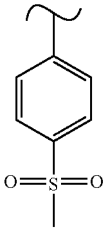 | (S)-8-(2-amino-6-((R)-]-(5-chloro-4'-(methylsulfonyl)-[1,1'-biphenyl]-2-yl)-2,2,2-trifluoroethoxy)pyrimidin-4-yl)-2,8-diazaspiro[4.5]decane-3-carboxylic acid | 640 |
| 34ae | 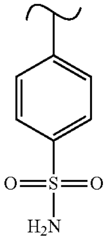 | (S)-8-(2-amino-6-((R)-1-(5-chloro-4'-sulfamoyl-[1,1'-biphenyl]-2-yl)-2,2,2-trifluoroethoxy)pyrimidin-4-yl)-2,8-diazaspiro[4.5]decane-3-carboxylic acid | 641 |
| 34af | 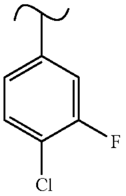 | (S)-8-(2-amino-6-((R)-1-(4',5-dichloro-3'-fluoro-[1,1'-biphenyl]-2-yl)-2,2,2-trifluoroethoxy)pyrimidin-4-yl)-2,8-diazaspiro[4.5]decane-3-carboxylic acid | 615 |

TABLE 12a-continued

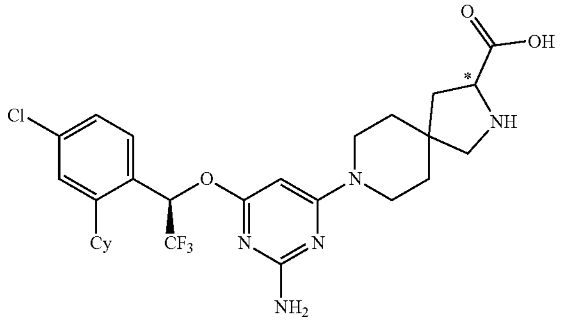

* Stereochemistry defined in name in table below

| Ex. No. | Cy | CAS Name | LCMS (MH+) |
|---|---|---|---|
| 34ag | 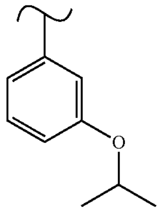 | (S)-8-(2-amino-6-((R)-1-(5-chloro-3'-isopropoxy-[1,1'-biphenyl]-2-yl)-2,2,2-trifluoroethoxy)pyrimidin-4-yl)-2,8-diazaspiro[4.5]decane-3-carboxylic acid | 621 |
| 34ah | 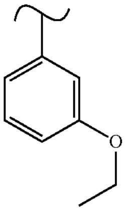 | (S)-8-(2-amino-6-((R)-1-(5-chloro-3'-ethoxy-[1,1'-biphenyl]-2-yl)-2,2,2-trifluoroethoxy)pyrimidin-4-yl)-2,8-diazaspiro[4.5]decane-3-carboxylic acid | 607 |
| 34ai | 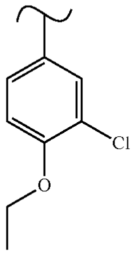 | (S)-8-(2-amino-6-((R)-1-(3',5-dichloro-4'-ethoxy-[1,1'-biphenyl]-2-yl)-2,2,2-trifluoroethoxy)pyrimidin-4-yl)-2,8-diazaspiro[4.5]decane-3-carboxylic acid | 642 |
| 34aj | 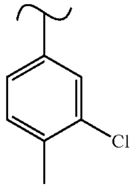 | (S)-8-(2-amino-6-((R)-1-(3',5-dichloro-4'-methyl-[1,1'-biphenyl]-2-yl)-2,2,2-trifluoroethoxy)pyrimidin-4-yl)-2,8-diazaspiro[4.5]decane-3-carboxylic acid | 611 |
| 34ak | 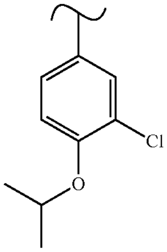 | (S)-8-(2-amino-6-((R)-1-(3',5-dichloro-4'-isopropoxy-[1,1'-biphenyl]-2-yl)-2,2,2-trifluoroethoxy)pyrimidin-4-yl)-2,8-diazaspiro[4.5]decane-3-carboxylic acid | 655 |

TABLE 12a-continued

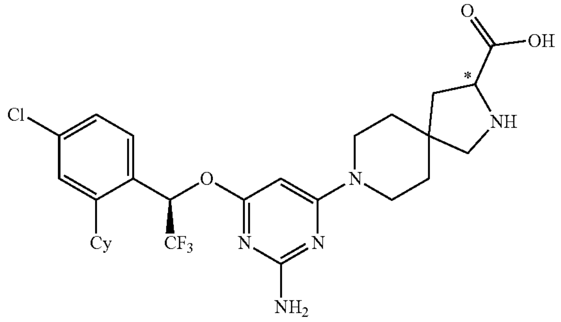

* Stereochemistry defined in name in table below

| Ex. No. | Cy | CAS Name | LCMS (MH+) |
|---|---|---|---|
| 34al | 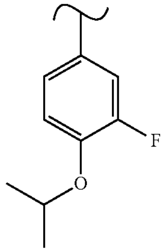 | (S)-8-(2-amino-6-((R)-1-(5-chloro-3'-fluoro-4'-isopropoxy-[1,1'-biphenyl]-2-yl)-2,2,2-trifluoroethoxy)pyrimidin-4-yl)-2,8-diazaspiro[4.5]decane-3-carboxylic acid | 639 |
| 34am | 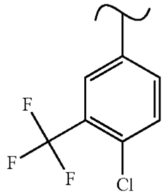 | (S)-8-(2-amino-6-((R)-1-(4',5-dichloro-3'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 665 |
| 34an | 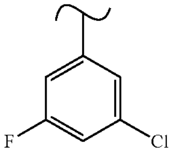 | (S)-8-(2-amino-6-((R)-1-(3',5-dichloro-5'-fluoro-[1,1'-biphenyl]-2-yl)-2,2,2-trifluoroethoxy)pyrimidin-4-yl)-2,8-diazaspiro[4.5]decane-3-carboxylic acid | 615 |
| 34ao | 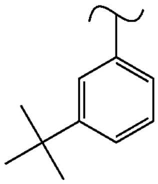 | (S)-8-(2-amino-6-((R)-1-(3'-(tert-butyl)-5-chloro-[1,1'-biphenyl]-2-yl)-2,2,2-trifluoroethoxy)pyrimidin-4-yl)-2,8-diazaspiro[4.5]decane-3-carboxylic acid | 619 |
| 34ap | 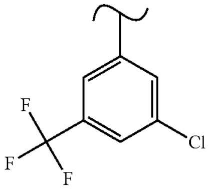 | (S)-8-(2-amino-6-((R)-1-(3',S-dichloro-5'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 665 |
| 34aq | 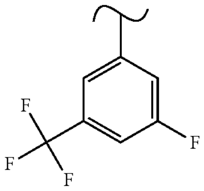 | (S)-8-(2-amino-6-((R)-1-(5-chloro-3'-fluoro-5'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 648 |

TABLE 12a-continued

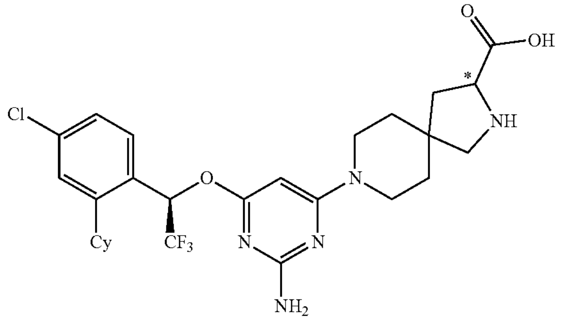

* Stereochemistry defined in name in table below

| Ex. No. | Cy | CAS Name | LCMS (MH+) |
|---|---|---|---|
| 34ar | 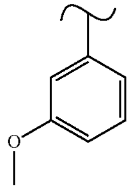 | (S)-8-(2-amino-6-((R)-1-(5-chloro-3'-methoxy-[1,1'-biphenyl]-2-yl)-2,2,2-trifluoroethoxy)pyrimidin-4-yl)-2,8-diazaspiro[4.5]decane-3-carboxylic acid | 593 |
| 34as | 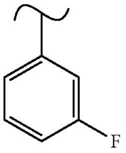 | (S)-8-(2-amino-6-((R)-1-(5-chloro-3'-fluoro-[1,1'-biphenyl]-2-yl)-2,2,2-trifluoroethoxy)pyrimidin-4-yl)-2,8-diazaspiro[4.5]decane-3-carboxylic acid | 580 |
| 34at | 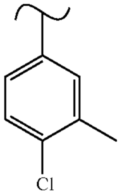 | (S)-8-(2-amino-6-((R)-1-(4',5-dichloro-3'-methyl-[1,1'-biphenyl]-2-yl)-2,2,2-trifluoroethoxy)pyrimidin-4-yl)-2,8-diazaspiro[4.5]decane-3-carboxylic acid | 611 |
| 34au | 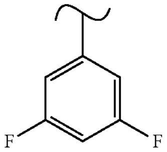 | (S)-8-(2-amino-6-((R)-1-(5-chloro-3',5'-difluoro-[1,1'-biphenyl]-2-yl)-2,2,2-trifluoroethoxy)pyrimidin-4-yl)-2,8-diazaspiro[4.5]decane-3-carboxylic acid | 598 |
| 34av | 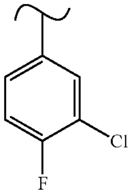 | (S)-8-(2-amino-6-((R)-1-(3',5-dichloro-4'-fluoro-[1,1'-biphenyl]-2-yl)-2,2,2-trifluoroethoxy)pyrimidin-4-yl)-2,8-diazaspiro[4.5]decane-3-carboxylic acid | 615 |
| 34aw | 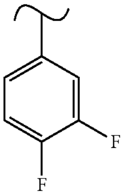 | (S)-8-(2-amino-6-((R)-1-(5-chloro-3',4'-difluoro-[1,1'-biphenyl]-2-yl)-2,2,2-trifluoroethoxy)pyrimidin-4-yl)-2,8-diazaspiro[4.5]decane-3-carboxylic acid | 598 |

TABLE 12a-continued

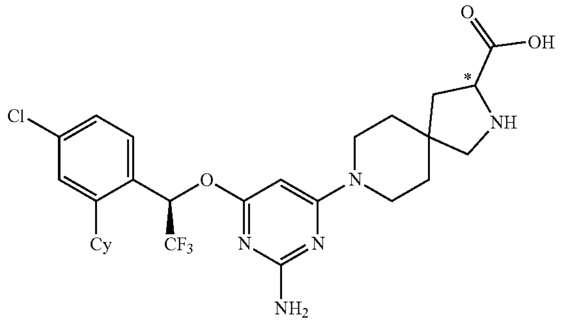

* Stereochemistry defined in name in table below

| Ex. No. | Cy | CAS Name | LCMS (MH+) |
|---|---|---|---|
| 34ax | 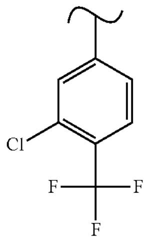 | (S)-8-(2-amino-6-((R)-1-(3',5-dichloro-4'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 665 |
| 34ay | 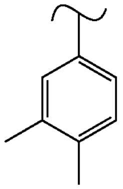 | (S)-8-(2-amino-6-((R)-1-(5-chloro-3',4'-dimethyl-[1,1'-biphenyl]-2-yl)-2,2,2-trifluoroelhoxy)pyrimidin-4-yl)-2,8-diazaspiro[4.5]decane-3-carboxylic acid | 591 |
| 34az | 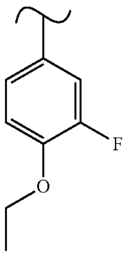 | (S)-8-(2-amino-6-((R)-1-(5-chloro-4'-ethoxy-3'-fluoro-[1,1'-biphenyl]-2-yl)-2,2,2-trifluoroethoxy)pyrimidin-4-yl)-2,8-diazaspiro[4.5]decane-3-carboxylic acid | 625 |
| 34ba | 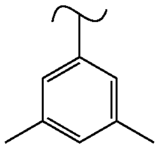 | (S)-8-(2-amino-6-((R)-1-(5-chloro-3',5'-dimethyl-[1,1'-biphenyl]-2-yl)-2,2,2-trifluoroethoxy)pyrimidin-4-yl)-2,8-diazaspiro[4.5]decane-3-carboxylic acid | 591 |
| 34bb | 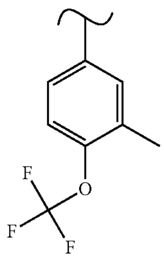 | (S)-8-(2-amino-6-((R)-1-(5-chloro-3'-methyl-4'-(trifluoromethoxy)-[1,1'-biphenyl]-2-yl)-2,2,2-trifluoroethoxy)pyrimidin-4-yl)-2,8-diazaspiro[4.5]decane-3-carboxylic acid | 661 |

TABLE 12a-continued

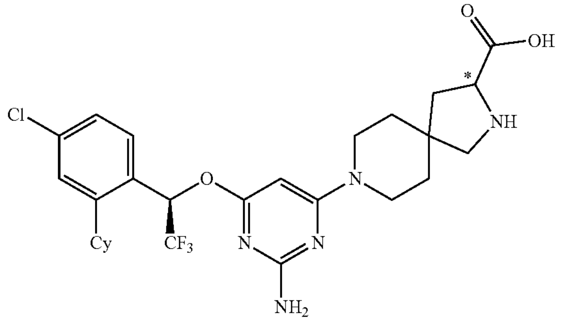

* Stereochemistry defined in name in table below

| Ex. No. | Cy | CAS Name | LCMS (MH+) |
|---|---|---|---|
| 34bc | 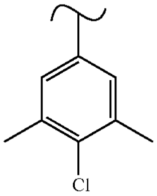 | (S)-8-(2-amino-6-((R)-1-(4',5-dichloro-3',5'-dimethyl-[1,1'-biphenyl]-2-yl)-2,2,2-trifluoroethoxy)pyrimidin-4-yl)-2,8-diazaspiro[4.5]decane-3-carboxylic acid | 625 |
| 34bd | 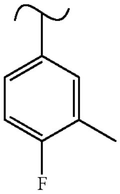 | (S)-8-(2-amino-6-((R)-1-(5-chloro-4'-fluoro-3'-methyl-[1,1'-biphenyl]-2-yl)-2,2,2-trifluoroethoxy)pyrimidin-4-yl)-2,8-diazaspiro[4.5]decane-3-carboxylic acid | 595 |
| 34be | 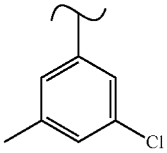 | (S)-8-(2-amino-6-((R)-1-(3',5-dichloro-5'-methyl-[1,1'-biphenyl]-2-yl)-2,2,2-trifluoroethoxy)pyrimidin-4-yl)-2,8-diazaspiro[4.5]decane-3-carboxylic acid | 611 |
| 34bf | 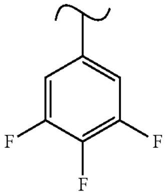 | (S)-8-(2-amino-6-((R)-1-(5-chloro-3',4',5'-trifluoro-[1,1'-biphenyl]-2-yl)-2,2,2-trifluoroethoxy)pyrimidin-4-yl)-2,8-diazaspiro[4.5]decane-3-carboxylic acid | 616 |
| 34bg | 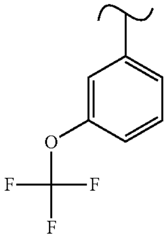 | (S)-8-(2-amino-6-((R)-1-(5-chloro-3'-(trifluoromethoxy)-[1,1'-biphenyl]-2-yl)-2,2,2-trifluoroethoxy)pyrimidin-4-yl)-2,8-diazaspiro[4.5]decane-3-carboxylic acid | 696 |
| 34bh | 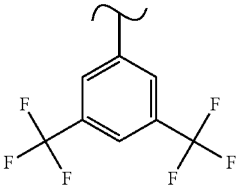 | (S)-8-(2-amino-6-((R)-1-(5-chloro-3',5'-bis(trifluoromethyl)-[1,1'-biphenyl]-2-yl)-2,2,2-trifluoroethoxy)pyrimidin-4-yl)-2,8-diazaspiro[4.5]decane-3-carboxylic acid | 698 |

TABLE 12a-continued

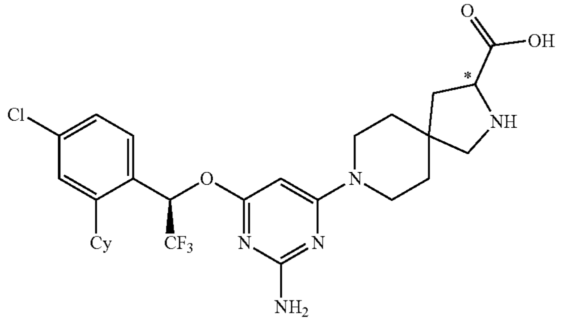

* Stereochemistry defined in name in table below

| Ex. No. | Cy | CAS Name | LCMS (MH+) |
|---|---|---|---|
| 34bi | 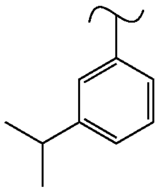 | (S)-8-(2-amino-6-((R)-1-(5-chloro-3'-isopropyl-[1,1'-biphenyl]-2-yl)-2,2,2-trifluoroethoxy)pyrimidin-4-yl)-2,8-diazaspiro[4.5]decane-3-carboxylic acid | 605 |
| 34bj | 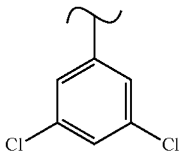 | (S)-8-(2-amino-6-((R)-2,2,2-trifluoro-1-(3',5,5'-trichloro-[1,1'-biphenyl]-2-yl)ethoxy)pyrimidin-4-yl)-2,8-diazaspiro[4.5]decane-3-carboxylic acid | 631 |
| 34bk | 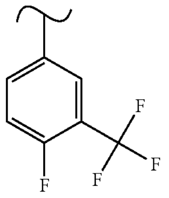 | (S)-8-(2-amino-6-((R)-1-(5-chloro-4'-fluoro-3'-(trifluoromethyl)-[1,1'-biphenyl]-2-yl)-2,2,2-trifluoroethoxy)pyrimidin-4-yl)-2,8-diazaspiro[4.5]decane-3-carboxylic acid | 648 |
| 34bl | 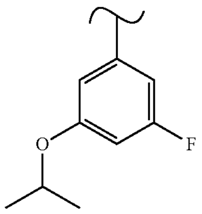 | (S)-8-(2-amino-6-((R)-1-(5-chloro-3'-fluoro-5'-isopropoxy-[1,1'-biphenyl]-2-yl)-2,2,2-trifluoroethoxy)pyrimidin-4-yl)-2,8-diazaspiro[4.5]decane-3-carboxylic acid | 639 |
| 34bm | 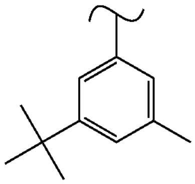 | (S)-8-(2-amino-6-((R)-1-(3'-(tert-butyl)-5-chloro-5'-methyl-[1,1'-biphenyl]-2-yl)-2,2,2-trifluoroethoxy)pyrimidin-4-yl)-2,8-diazaspiro[4.5]decane-3-carboxylic acid | 633 |
| 34bn | 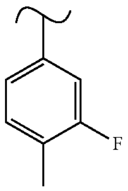 | (S)-8-(2-amino-6-((R)-1-(5-chloro-3'-fluoro-4'-methyl-[1,1'-biphenyl]-2-yl)-2,2,2-trifluoroethoxy)pyrimidin-4-yl)-2,8-diazaspiro[4.5]decane-3-carboxylic acid | 595 |

TABLE 12a-continued

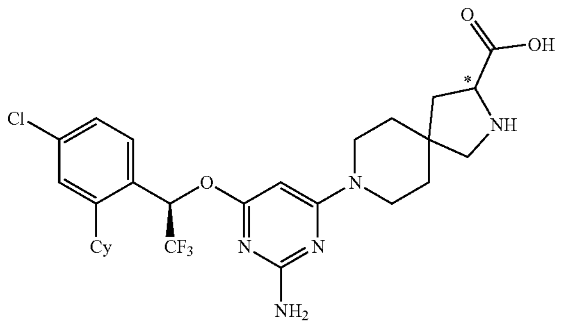

* Stereochemistry defined in name in table below

| Ex. No. | Cy | CAS Name | LCMS (MH+) |
|---|---|---|---|
| 34bo | 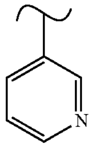 | (S)-8-(2-amino-6-((R)-1-(4-chloro-2-(pyridin-3-yl)phenyl)-2,2,2-trifluoroethoxy)pyrimidin-4-yl)-2,8-diazaspiro[4.5]decane-3-carboxylic acid | 563 |
| 34bp | 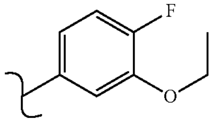 | (S)-8-(2-amino-6-((R)-1-(5-chloro-3'-ethoxy-4'-fluoro-[1,1'-biphenyl]-2-yl)-2,2,2-trifluoroethoxy)pyrimidin-4-yl)-2,8-diazaspiro[4.5]decane-3-carboxylic acid | 625 |
| 34bq | 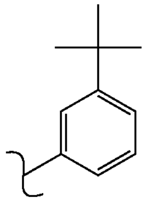 | (S)-8-(2-amino-6-((R)-1-(3'-(tert-butyl)-5-chloro-[1,1'-biphenyl]-2-yl)-2,2,2-trifluoroethoxy)pyrimidin-4-yl)-2,8-diazaspiro[4.5]decane-3-carboxylic acid | 619 |
| 34br | 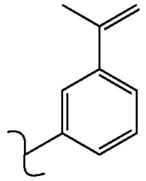 | (S)-8-(2-amino-6-((R)-1-(5-chloro-3'-(prop-1-en-2-yl)-[1,1'-biphenyl]-2-yl)-2,2,2-trifluoroethoxy) pyrimidin-4-yl)-2,8-diazaspiro [4.5]decane-3-carboxylic acid | 603 |
| 34bs | 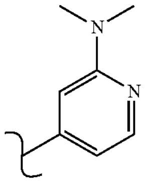 | (S)-8-(2-amino-6-((R)-1-(4-chloro-2-(2-(dimethylamino)pyridin-4-yl)phenyl)-2,2,2-trifluoroethoxy)pyrimidin-4-yl)-2,8-diazaspiro[4.5]decane-3-carboxylic acid | 603 |
| 34bt | 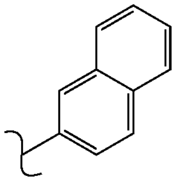 | (S)-8-(2-amino-6-((R)-1-(4-chloro-2-(naphthalen-2-yl)phenyl)-2,2,2-trifluoroethoxy)pyrimidin-4-yl)-2,8-diazaspiro[4.5]decane-3-carboxylic acid | 613 |

TABLE 12a-continued

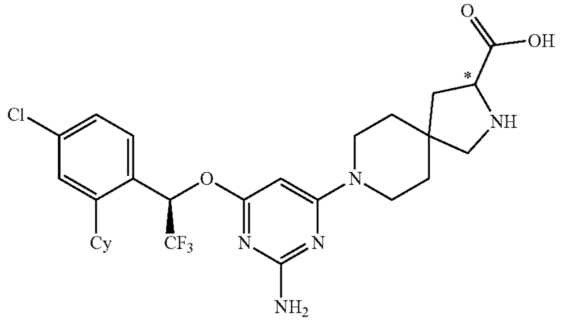

* Stereochemistry defined in name in table below

| Ex. No. | Cy | CAS Name | LCMS (MH+) |
|---|---|---|---|
| 34bu | 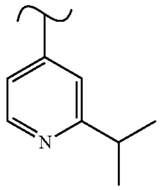 | (S)-8-(2-amino-6-((R)-1-(4-chloro-2-(2-isopropylpyridin-4-yl)phenyl)-2,2,2-trifluoroethoxy)pyrimidin-4-yl)-2,8-diazaspiro[4.5]decane-3-carboxylic acid | 606 |
| 34bv | 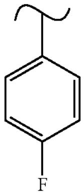 | (S)-8-(2-amino-6-((R)-1-(5-chloro-4'-fluoro-[1,1'-biphenyl]-2-yl)-2,2,2-trifluoroethoxy)pyrimidin-4-yl)-2,8-diazaspiro[4.5]decane-3-carboxylic acid | 525 |
| 34bw | 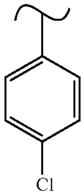 | (S)-8-(2-amino-6-((R)-1-(4',5-dichloro-[1,1'-biphenyl]-2-yl)-2,2,2-trifluoroethoxy)pyrimidin-4-yl)-2,8-diazaspiro[4.5]decane-3-carboxylic acid | 597 |
| 34bx | 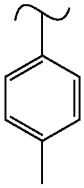 | (S)-8-(2-amino-6-((R)-1-(5-chloro-4'-methyl-[1,1'-biphenyl]-2-yl)-2,2,2-trifluoroethoxy)pyrimidin-4-yl)-2,8-diazaspiro[4.5]decane-3-carboxylic acid | 577 |
| 34by | 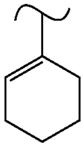 | (S)-8-(2-amino-6-((R)-1-(5-chloro-2',3',4',5'-tetrahydro-[1,1'-biphenyl]-2-yl)-2,2,2-trifluoroethoxy)pyrimidin-4-yl)-2,8-diazaspiro[4.5]decane-3-carboxylic acid | 567 |
| 34bz | 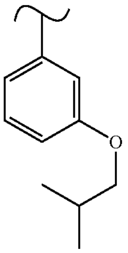 | (S)-8-(2-amino-6-((R)-1-(5-chloro-3'-isobutoxy-[1,1'-biphenyl]-2-yl)-2,2,2-trifluoroethoxy)pyrimidin-4-yl)-2,8-diazaspiro[4.5]decane-3-carboxylic acid | 635 |

TABLE 12a-continued

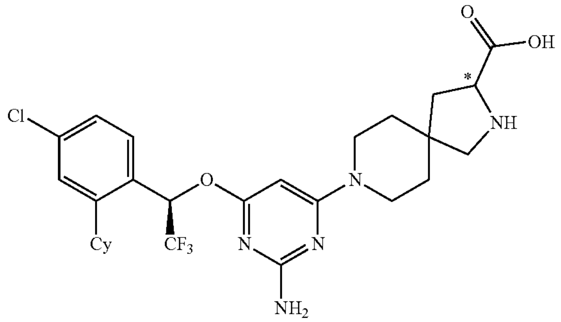

* Stereochemistry defined in name in table below

| Ex. No. | Cy | CAS Name | LCMS (MH+) |
|---|---|---|---|
| 34ca | 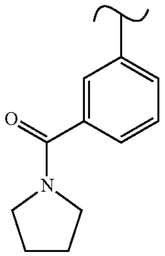 | (S)-8-(2-amino-6-((R)-1-(5-chloro-3'-(pyrrolidine-1-carbonyl)-[1,1'-biphenyl]-2-yl)-2,2,2-trifluoroethoxy)pyrimidin-4-yl)-2,8-diazaspiro[4.5]decane-3-carboxylic acid | 660 |
| 34cb | 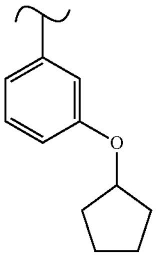 | (S)-8-(2-amino-6-((R)-1-(5-chloro-3'-(cyclopentyloxy)-[1,1'-biphenyl]-2-yl)-2,2,2-trifluoroethoxy)pyrimidin-4-yl)-2,8-diazaspiro[4.5]decane-3-carboxylic acid | 647 |
| 34cc | 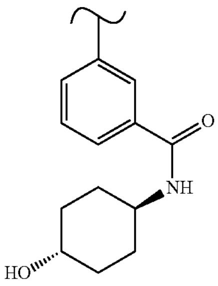 | (S)-8-(2-amino-6-((R)-1-(5-chloro-3'-(((1R,4R)-4-hydroxycyclohexyl)carbamoyl)-[1,1'-biphenyl]-2-yl)-2,2,2-trifluoroethoxy)pyrimidin-4-yl)-2,8-diazaspiro[4.5]decane-3-carboxylic acid | 740 |
| 34cd | 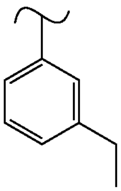 | (S)-8-(2-amino-6-((R)-1-(5-chloro-3'-ethyl-[1,1'-biphenyl]-2-yl)-2,2,2-trifluoroethoxy)pyrimidin-4-yl)-2,8-diazaspiro[4.5]decane-3-carboxylic acid | 591 |

TABLE 12a-continued

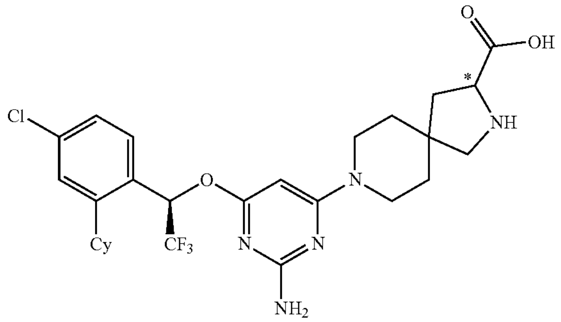

* Stereochemistry defined in name in table below

| Ex. No. | Cy | CAS Name | LCMS (MH+) |
|---|---|---|---|
| 34ce | 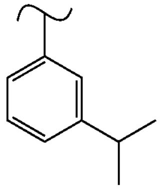 | (S)-8-(2-amino-6-((R)-1-(5-chloro-3'-isopropyl-[1,1'-biphenyl]-2-yl)-2,2,2-trifluoroethoxy)pyrimidin-4-yl)-2,8-diazaspiro[4.5]decane-3-carboxylic acid | 633 |
| 34cf | 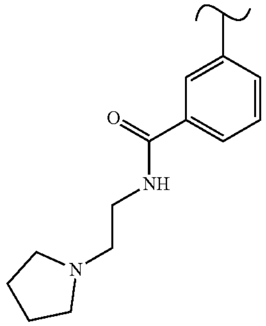 | (S)-8-(2-amino-6-((R)-1-(5-chloro-3'-((2-(pyrrolidin-1-yl)ethyl)carbamoyl)-[1,1'-biphenyl]-2-yl)-2,2,2-trifluoroethoxy)pyrimidin-4-yl)-2,8-diazaspiro[4.5]decane-3-carboxylic acid | 703 |
| 34cg | 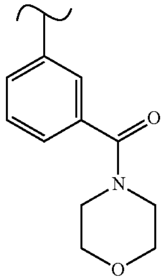 | (S)-8-(2-amino-6-((R)-1-(5-chloro-3'-(morpholine-4-carbonyl)-[1,1'-biphenyl]-2-yl)-2,2,2-trifluoroethoxy)pyrimidin-4-yl)-2,8-diazaspiro[4.5]decane-3-carboxylic acid | 676 |
| 34ch | 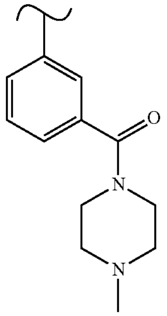 | (S)-8-(2-amino-6-((R)-1-(5-chloro-3'-(4-methylpiperazine-1-carbonyl)-[1,1'-biphenyl]-2-yl)-2,2,2-trifluoroethoxy)pyrimidin-4-yl)-2,8-diazaspiro[4.5]decane-3-carboxylic acid | 689 |

TABLE 12a-continued

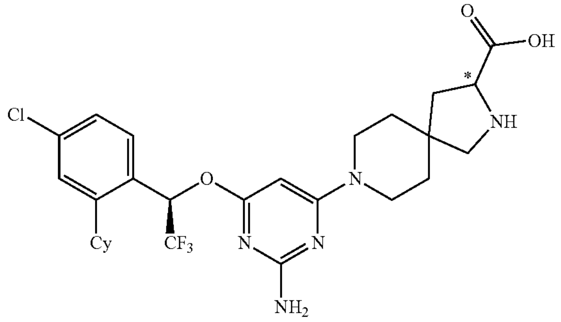

* Stereochemistry defined in name in table below

| Ex. No. | Cy | CAS Name | LCMS (MH+) |
|---|---|---|---|
| 34ci | 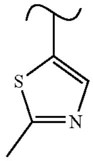 | (S)-8-(2-amino-6-((R)-1-(4-chloro-2-(2-methylthiazol-5-yl)phenyl)-2,2,2-trifluoroethoxy)pyrimidin-4-yl)-2,8-diazaspiro[4.5]decane-3-carboxylic acid | 584 |
| 34cj | 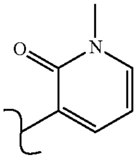 | (S)-8-(2-amino-6-((R)-1-(4-chloro-2-(1-methyl-2-oxo-1,2-dihydropyridin-3-yl)phenyl)-2,2,2-trifluoroethoxy)pyrimidin-4-yl)-2,8-diazaspiro[4.5]decane-3-carboxylic acid | 594 |
| 34ck | 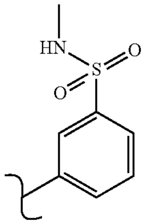 | (S)-8-(2-amino-6-((R)-1-(5-chloro-3'-(N-methylsulfamoyl)-[1,1'-biphenyl]-2-yl)-2,2,2-trifluoroethoxy)pyrimidin-4-yl)-2,8-diazaspiro[4.5]decane-3-carboxylic acid | 656 |
| 34cl | 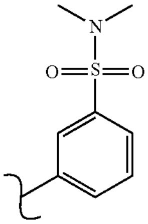 | (S)-8-(2-amino-6-((R)-1-(5-chloro-3'-(N,N-dimethylsulfamoyl)-[1,1'-biphenyl]-2-yl)-2,2,2-trifluoroethoxy)pyrimidin-4-yl)-2,8-diazaspiro[4.5]decane-3-carboxylic acid | 670 |
| 34cm | 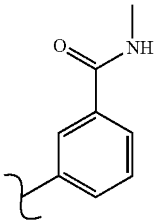 | (S)-8-(2-amino-6-((R)-1-(5-chloro-3'-(methylcarbamoyl)-[1,1'-biphenyl]-2-yl)-2,2,2-trifluoroethoxy)pyrimidin-4-yl)-2,8-diazaspiro[4.5]decane-3-carboxylic acid | 620 |
| 34cn | 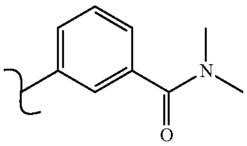 | (S)-8-(2-amino-6-((R)-1-(5-chloro-3'-(dimethylcarbamoyl)-[1,1'-biphenyl]-2-yl)-2,2,2-trifluoroethoxy)pyrimidin-4-yl)-2,8-diazaspiro[4.5]decane-3-carboxylic acid | 634 |

TABLE 12a-continued

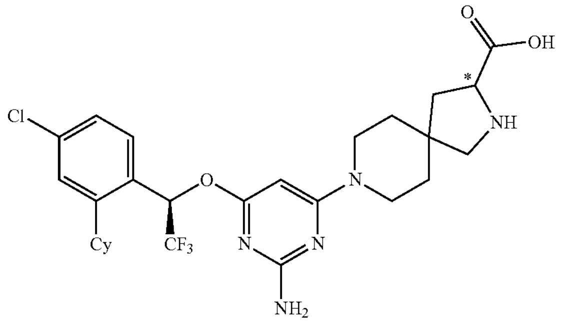

* Stereochemistry defined in name in table below

| Ex. No. | Cy | CAS Name | LCMS (MH+) |
|---|---|---|---|
| 34co | 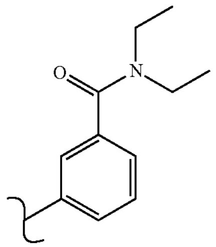 | (S)-8-(2-amino-6-((R)-1-(5-chloro-3'-(diethylcarbamoyl)-[1,1'-biphenyl]-2-yl)-2,2,2-trifluoroethoxy)pyrimidin-4-yl)-2,8-diazaspiro[4.5]decane-3-carboxylic acid | 662 |
| 34cp | 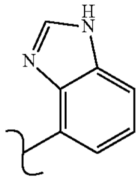 | (S)-8-(6-((R)-1-(2-(1H-benzo[d]imidazol-4-yl)-4-chlorophenyl)-2,2,2-trifluoroethoxy)-2-aminopyrimidin-4-yl)-2,8-diazaspiro[4.5]decane-3-carboxylic acid | 603 |
| 34cq | 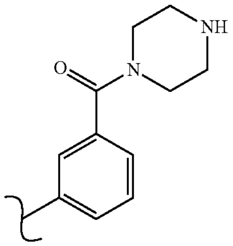 | (S)-8-(2-amino-6-((R)-1-(5-chloro-3'-(piperazine-1-carbonyl)-[1,1'-biphenyl]-2-yl)-2,2,2-trifluoroethoxy)pyrimidin-4-yl)-2,8-diazaspiro[4.5]decane-3-carboxylic acid | 675 |
| 34cr | 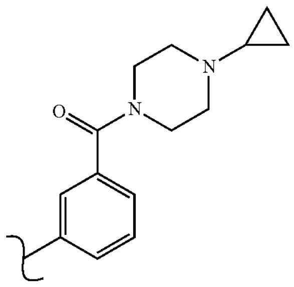 | (S)-8-(2-amino-6-((R)-1-(5-chloro-3'-(4-cyclopropylpiperazine-1-carbonyl)-[1,1'-biphenyl]-2-yl)-2,2,2-trifluoroethoxy)pyrimidin-4-yl)-2,8-diazaspiro[4.5]decane-3-carboxylic acid | 716 |
| 34cs | 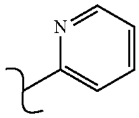 | (S)-8-(2-amino-6-((R)-1-(4-chloro-2-(pyridin-2-yl)phenyl)-2,2,2-trifluoroethoxy)pyrimidin-4-yl)-2,8-diazaspiro[4.5]decane-3-carboxylic acid | 564 |

TABLE 12a-continued

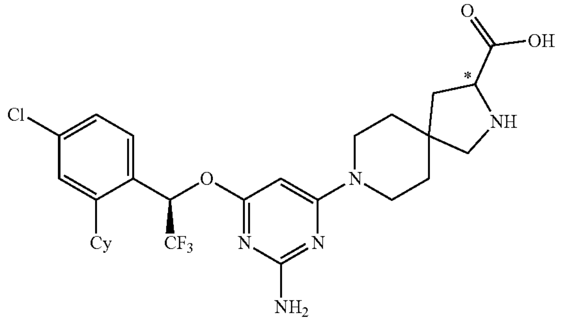

* Stereochemistry defined in name in table below

| Ex. No. | Cy | CAS Name | LCMS (MH+) |
|---|---|---|---|
| 34ct | 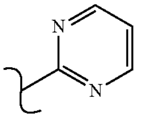 | (S)-8-(2-amino-6-((R)-1-(4-chloro-2-(pyrimidin-2-yl)phenyl)-2,2,2-trifluoroethoxy)pyrimidin-4-yl)-2,8-diazaspiro[4.5]decane-3-carboxylic acid | 564 |
| 34cu | 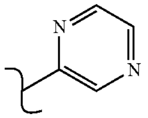 | (S)-8-(2-amino-6-((R)-1-(4-chloro-2-(pyrazin-2-yl)phenyl)-2,2,2-trifluoroethoxy)pyrimidin-4-yl)-2,8-diazaspiro[4.5]decane-3-carboxylic acid | 565 |
| 34cv | 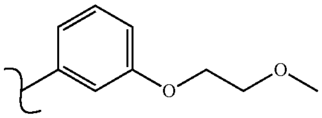 | (S)-8-(2-amino-6-((R)-1-(5-chloro-3'-(2-methoxyethoxy)-[1,1'-biphenyl]-2-yl)-2,2,2-trifluoroethoxy)pyrimidin-4-yl)-2,8-diazaspiro[4.5]decane-3-carboxylic acid | 637 |

TABLE 12b

NMR Data for Compounds of Table 12a

| Ex. No. | NMR |
|---|---|
| 34a | $^1$H NMR (400 MHz, MeOH-d4): δ ppm 1.31 (d, J = 15.3 Hz, 1H), 1.67 (d, J = 7.3 Hz, 4H), 2.10 (dd, J = 13.6, 8.1 Hz, 1H), 2.46 (m, 1H), 3.25 (t, J = 12.0 Hz, 2H), 3.52 (s, 2H), 3.63 (m, 3H), 4.45 (t, J = 8.6 Hz, 1H), 4.83 (d, J = 3.0 Hz, 1H), 6.59 (q, J = 6.5 Hz, 1H), 7.32 (q, J = 1.8 Hz, 1H), 7.39 (m, 1H), 7.52 (m, 4H), 7.70 (d, J = 8.4 Hz, 1H) |
| 34b | $^1$H NMR (400 MHz, MeOH-d4): δ ppm 1.60 (q, J = 5.6 Hz, 4H), 2.06 (dd, J = 13.4, 7.2 Hz, 1H), 2.33 (dd, J = 13.5, 9.2 Hz, 1H), 2.43 (s, 3H), 3.13 (d, J = 11.8 Hz, 1H), 3.26 (d, J = 11.7 Hz, 1H), 3.47 (m, 2H), 3.62 (tt, J = 9.2, 4.9 Hz, 2H), 4.10 (dd, J = 9.1, 7.1 Hz, 1H), 4.61 (s, 1H), 5.48 (s, 1H), 6.66 (q, J = 6.9 Hz, 1H), 7.27 (m, 4H), 7.42 (m, 2H), 7.67 (d, J = 8.5 Hz, 1H) |
| 34c | $^1$H NMR (400 MHz, MeOH -d4): δ ppm 1.62 (d, J = 4.88 Hz, 4 H) 2.08 (dd, J = 13.47, 7.22 Hz, 1 H) 2.34 (dd, J = 13.37, 9.27 Hz, 1 H) 3.08-3.19 (m, 1H) 3.28 (d, J = 11.71 Hz, 1 H) 3.38-3.56 (m, 2 H) 3.63 (d, J = 5.66 Hz, 2 H) 4.11 (dd, J = 8.98, 7.22 Hz, 1 H) 5.51 (s, 1 H) 6.66 (d, J = 6.83 Hz, 1 H) 7.30 (d, J = 2.15 Hz, 1 H) 7.41-7.52 (m, 4 H) 7.52-7.61 (m, 2 H) 7.69 (d, J = 8.59 Hz, 1 H) |
| 34d | $^1$H-NMR (400 MHz, MeOH -d4): δ ppm 1.9 (m, 4H), 1.98 (m, 1H), 2.26 (m, 1H), 3.01 (m, 1H), 3.17 (m, 1H), 3.48 (m, 2H), 3.60 (m, 2H), 3.95 (m, 1H), 5.53-5.52 (d, 1H), 6.26-6.22 (q, 1H), 6.97-6.69 (m, 3H), 7.31-7.17(m, 2H), 7.47-7.44 (m, 1H), 7.74-7.63 (m, 1H) |
| 34e | $^1$H NMR (400 MHz, DMSO-d6): δ ppm 1.61 (m, 4 H), 2.07-2.04 (m, 1 H), 2.37-2.33 (m, 1 H), 3.15-3.12 (d, 1 H, J = 11.8 Hz), 3.25 (d, 1 H, J = 11.8 Hz), 3.50-3.47 (m, 2 H), 3.67-3.66 (m, 2 H), 4.11-4.07 (t, 1H), 5.58 (s, 1 H), 6.58-6.53 (q, 1 H, J = 6.8 Hz), 7.36 (s, 1 H), 7.53-7.51 (d, 1 H, J = 8.4 Hz), 7.70-7.67 (d, 1 H, J = 8.0 Hz), 7.82-7.78 (m, 2 H), 8.38-8.36 (d, 1 H, J = 8.0 Hz), 8.58 (s, 1 H) |
| 34f | $^1$H NMR (400 MHz, MeOH -d4): δ ppm 1.58 (m, 4 H), 2.05-2.02 (m, 1 H), 2.31-2.30 (m, 1 H), 3.28-3.21 (d, 1 H, J = 11.8 Hz), 3.48-3.46 (m, 2 H, J = 11.8 Hz), 3.68-3.51 (m, 2 H), 4.08-4.01 (q, 1 H, J = 7.0 Hz), 5.44 (s, 1 H), 6.76-6.69 (m, 4 H), 7.26-7.21 (m, 2 H), 7.41-7.40 (d, 1 H, J = 8.4 Hz), 7.66-7.64 (d, 1 H, J = 8.4 Hz) |
| 34g | $^1$H-NMR 400 MHz, MeOH -d4): δ ppm 1.28 (m, 2H), 1.63 (m 4H), 2.10-2.04 (m, 1H), 2.42-2.36 (m, 1H), 3.19-3.16 (d, J = 6.0, 2H), 3.26 (s, 1H), 3.65 (m, 2H), 4.28-4.24 (t, J = 16.0, 1H), 5.58 (s 1H), 6.62-6.57 (m, 1H), 7.37-7.36 (d, J = 4.0, 1H), 7.54-7.51 (dd, J = 12.0, 4.0, 1H), 7.72-7.70 (d, J = 8.0, 1H), 7.78-7.76 (d, J = 8.0, 2H), 8.43-8.41 (d, J = 8.0, 2H) |

TABLE 12b-continued

| NMR Data for Compounds of Table 12a | |
|---|---|
| Ex. No. | NMR |
| 34h | $^{1}$H-NMR (400 MHz, MeOH -d4): δ ppm 1.29 (m, 2H), 1.58 (m, 4H), 2.07-2.02 (m, 1H), 2.33-2.28(m, 1H), 3.11-3.08 (d, J = 12.0, 1H), 3.24-3.21 (d, J = 12.0, 1H), 3.48-3.41(m, 2H), 3.60-3.55(m, 2H), 4.08-4.04 (t, J = 16.0, 1H), 5.39 (d, J = 2.0, 1H), 6.66-6.63 (m, 1H), ), 6.86-6.84 (d, J = 8.02H), 7.19-7.17 (d, J = 8.0, 2H), 7.25-7.24 (d, J = 4.0, 1H), 7.37-7.35 (dd, J = 8.0, 6.0, 1H), 7.63-7.61(d, J = 8.0, 1H) |
| 34i | $^{1}$H NMR (400 MHz, MeOH-d4): δ 7.88 (t, J = 7.68 Hz, 1 H), 7.70 (d, J = 8.52 Hz, 1 H), 7.50 (m, 3 H), 7.35 (d, J = 7.76 Hz, 1 H), 6.99 (q, J = 6.96 Hz, 1H), 5.69 (s, 1 H), 4.06 (t, J = 7.48 Hz, 2 H), 3.62 (m, 2 H), 3.48 (m, 2 H), 3.22 (d,J = 11.64 Hz, 1H), 3.09 (d, J = 11.44 Hz, 1 H), 2.61 (s, 3 H), 2.30 (m, 1 H), 2.03 (m, 1H), 1.57 (m, 4 H). |
| 34j | $^{1}$H NMR (400 MHz, MeOH-d4): δ ppm 1.25 (t, J = 7.4 Hz, 3H), 1.63 (m, 4H), 2.11-2.06 (m, 1H), 2.38-2.31 (m, 1H), 3.16-3.13 (m, 1H), 3.26 (m, 1H), 3.31 (m, 2H), 3.55-3.50 (m, 2H), 3.71-3.64 (m, 2H), 4.11 (M, 1H), 5.61 (s, 1H), 6.63 (m, 1H), 7.36 (s, 1H), 7.52-7.50 (m, 1H), 7.71-7.68 (m, 1H), 7.76-7.75 (m, 1H), 7.83 (t, J = 7.8 Hz, 1H), 8.04 (d, J = 7.2 Hz, 1H) 8.43 (s, 1H) |
| 34k | $^{1}$H NMR (400 MHz, MeOH -d4): δ ppm 0.96 (t, J = 12.0, 4H), 1.70-1.62 (m, 8H), 2.06 (s, 1H), 2.32 (s, 1H), 3.24 (d, J = 12.0, 1H), 3.50(s, 2H), 3.67(s, 2H), 4.07 (s, 1H), 4.63 (s, 1H), 5.61 (s, 1H), 6.62 (q, J = 8.0, 1H), 7.37(s, 1H), 7.50 (d, 1H, J = 8.0), 7.79-7.69 (m, 2H), 7.83(t, 1H, J = 8.0), 8.03(d, 1H, J = 8.0), 8.45 (s, 1H) |
| 34l | $^{1}$H NMR (400 MHz, MeOH-d4): δ ppm 8.47 (s, 1 H), 8.03 (d, 1 H), 7.74 (t, 1 H), 7.67 (m, 2 H), 7.51-7.49 (d, 1 H), 7.37 (s, 1 H), 6.64-6.59 (q, 1 H), 5.62 (s, 1 H), 4.12-4.08 (t, 1 H), 3.67 (m, 2 H), 3.50 (m, 2 H), 3.26 (d, 1 H), 3.13 (d, 1 H), 2.35-2.32 (m, 1 H), 2.05 (m, 1 H), 1.63 (m, 6 H), 1.34 (q, 2 H), 0.84-0.80 (t, 3 H) |
| 34m | $^{1}$H NMR (400 MHz, MeOH -d4): δ ppm 7.74-7.66 (m, 2H), 7.48-7.39 (m, 3H), 7.27 (m, 2H), 6.73-6.71 (m, 1H), 5.53 (s, 1H), 4.73 (s, 2H), 4.08 (t, J = 7.1 Hz, 1H), 3.63 (m, 2H), 3.47 (m, 2H), 3.27-3.24 (m, 1H), 3.14-3.11 (m, 1H), 2.36-2.30 (m, 1H), 2.08-2.03 (m, 1H), 1.60 (m, 4H) |
| 34n | $^{1}$H NMR (400 MHz, MeOH -d4)δ ppm 7.66 (d, 1 H, J = 8.6 Hz), 7.50 (m, 3 H), 7.31 (m, 2 H), 7.24 (d, 1 H, J = 8.2 Hz), 6.61 (m, 1 H), 4.21 (m, 1 H), 3.63 (m, 2 H), 3.48 (m, 2 H), 3.21 (m, 1 H), 3.18 (m, 1 H), 3.01 (s, 3 H), 2.37 (m, 1 H), 2.07 (m, 1 H), 1.62 (m, 4 H) |
| 34o | $^{1}$H-NMR (400 MHz, MeOH-d4): δ ppm 7.97 (s, 1H), 7.60-7.67 (m, 2H), 7.52-7.54 (m, 1H), 7.40-7.46 (m, 1H), 7.31-7.31 (m, 1H), 7.22-7.24 (m, 1H), 6.61-6.66 (m, 1H), 5.51 (s, 1H), 4.39-4.04 (m, 4H), 3.52-3.60 (m, 2H), 3.42-3.50 (m, 2H), 3.15-3.18 (d, 1H), 2.96-2.99 (d, 1H), 2.60-2.64 (m, 2H), 2.18-2.28 (m, 3H), 1.96-2.00 (m, 1H), 1.58-1.59 (m, 4H) |
| 34p | $^{1}$H-NMR (400 MHz, DMSO-d6): δ ppm 8.00 (s, 1H), 7.56-7.58 (m, 1H), 7.43-7.49 (m, 2H), 7.26-7.27 (m, 2H), 6.97-7.97 (m, 1H), 6.59-6.55 (m, 1H), 5.48 (s, 1H), 3.78-3.82 (m, 1H), 3.70 -3.74 (m, 2H), 3.39-3.44 (m, 6H), 2.98-3.02 (d, 1H), 2.82-2.85 (d, 1H), 2.70 (s, 3H), 2.04-2.11 (m, 1H), 1.69-1.75 (m, 1H), 1.36-1.40 (m, 4H) |
| 34q | $^{1}$H NMR (400 MHz, MeOH-d4): δ ppm 1.64 (t, J = 5.8 Hz, 4H), 2.08 (dd, J = 13.5, 7.6 Hz, 1H), 2.40 (dd, J = 13.5, 9.0 Hz, 1H), 3.19 (d, J = 11.8 Hz, 1H), 3.28 (d, J = 12.2 Hz, 1H), 3.51 (m, 2H), 3.66 (m, 2H), 4.28 (t, J = 8.4 Hz, 1H), 4.87 (s, 16H), 6.53 (q, J = 6.7 Hz, 1H), 7.34 (d, J = 2.3 Hz, 1H), 7.51 (dd, J = 8.6, 2.3 Hz, 1H), 7.75 (m, 5H) |
| 34r | $^{1}$H NMR (400 MHz, MeOH-d) δ ppm 1.62 (d, J = 4.88 Hz, 4 H) 2.08 (dd, J = 13.47, 7.22 Hz, 1 H) 2.34 (dd, J = 13.37, 9.27 Hz, 1 H) 3.08-3.19 (m, 1H) 3.28 (d, J = 11.71 Hz, 1 H) 3.38-3.56 (m, 2 H) 3.63 (d, J = 5.66 Hz, 2 H) 4.11 (dd, J = 8.98, 7.22 Hz, 1 H) 5.51 (s, 1 H) 6.66 (d, J = 6.83 Hz, 1 H) 7.30 (d, J = 2.15 Hz, 1 H) 7.41-7.52 (m, 4 H) 7.52-7.61 (m, 2 H) 7.69 (d, J = 8.59 Hz, 1 H) |
| 34s | $^{1}$H NMR (400 MHz, MeOH-d4): δ ppm 1.60 (d, J = 5.47 Hz, 4 H) 1.98-2.12 (m, 1 H) 2.26-2.39 (m, 1 H) 3.07-3.17 (m, 1 H) 3.20-3.29 (m, 1 H) 3.38-3.55 (m, 2 H) 3.56-3.71 (m, 2 H) 4.01-4.15 (m, 1 H) 5.51 (s, 1 H) 6.74-6.89 (m, 1 H) 7.11 (s, 1 H) 7.14 (s, 1 H) 7.42 (d, J = 2.15 Hz, 11 H) 7.44-7.53 (m, 1 H) 7.61-7.73 (m, 1 H) |
| 34t | $^{1}$H NMR (400 MHz, MeOH-d4): δ ppm 1.51 (d, J = 4.69 Hz, 4 H) 1.84-2.00 (m, 1 H) 2.09-2.31 (m, 1 H) 2.82-3.00 (m, 1 H) 3.02-3.20 (m, 1 H) 3.32-3.64 (m, 4 H) 3.84-3.94 (m, 1 H) 3.98 (s, 3 H), 5.50 (s, 1 H) 6.63 (d, J = 1.95 Hz, 1 H) 7.13-7.27 (m, 1 H) 7.39 (d, J = 1.56 Hz, 1 H) 7.55 (d, J = 1.76 Hz, 1 H) 7.64 (d, J = 8.59 Hz, 1 H) 7.71 (d, J = 1.76 Hz, 1 H) |
| 34u | $^{1}$H NMR (400 MHz, MeOH-d4): δ ppm 1.52-1.75 (m, 4 H) 2.07 (dd, J = 13.40, 7.30 Hz, 1 H) 2.34 (dd, J = 13.42, 9.18 Hz, 1 H) 3.07-3.29 (m, 2 H) 3.40-3.78 (m, 4 H) 4.10 (dd, J = 9.10, 7.25 Hz, 1 H) 5.59 (s, 1 H) 6.61 (q, J = 6.59 Hz, 1 H) 7.31 (d, J = 2.20 Hz, 1 H) 7.49 (dd, J = 8.52, 2.22 Hz, 1 H) 7.61 (d, J = 7.03 Hz, 1 H) 7.65-7.80 (m, 2 H) 7.97-8.10 (m, 1 H) 8.32 (br. s., 1 H) |
| 34v | $^{1}$H NMR (400 MHz, MeOH-d4): δ ppm 1.52-1.71 (m, 4 H) 2.07 (dd, J = 13.42, 7.27 Hz, 1 H) 2.33 (dd, J = 13.47, 9.27 Hz, 1 H) 3.08-3.29 (m, 2 H) 3.36-3.76 (m, 4 H) 4.09 (dd, J = 9.15, 7.20 Hz, 1 H) 5.48 (s, 1 H) 6.74 (q, J = 7.00 Hz, 1 H) 6.87 (d, J = 7.47 Hz, 1 H) 6.91 (ddd, J = 8.19, 2.48, 0.85 Hz, 1 H) 7.05 (d, J = 0.73 Hz, 1 H) 7.28 (d, J = 2.20 Hz, 1 H) 7.32 (t, J = 7.88 Hz, 1 H) 7.43 (dd, J = 8.49, 2.25 Hz, 1 H) 7.67 (d, J = 8.49 Hz, 1 H) |
| 34w | $^{1}$H NMR (400 MHz, MeOH-d4): δ ppm 1.43-1.76 (m, 4 H) 2.08 (dd, J = 13.45, 7.15 Hz, 1 H) 2.34 (dd, J = 13.42, 9.22 Hz, 1 H) 3.13-3.29 (m, 5 H) 3.41-3.77 (m, 4 H) 4.10 (dd, J = 9.18, 7.17 Hz, 1 H) 5.60 (s, 1 H) 6.57 (q, J = 6.57 Hz, 1 H) 7.35 (d, J = 2.15 Hz, 1 H) 7.51 (dd, J = 8.52, 2.17 Hz, 1 H) 7.70 (d, J = 8.54 Hz, 1 H) 7.72-7.78 (m, 1 H) 7.78-7.87 (m, 1 H) 8.04-8.15 (m, 1 H) 8.41 (d, J = 0.39 Hz, 1 H) |

TABLE 12b-continued

NMR Data for Compounds of Table 12a

| Ex. No. | NMR |
|---|---|
| 34x | $^1$H NMR (400 MHz, DMSO-d6): δ ppm 1.46-1.69 (m, 4 H) 1.90 (dd, J = 13.25, 9.20 Hz, 1 H) 2.35 (dd, J = 13.35, 8.66 Hz, 1 H) 3.14 (br. s., 2 H) 3.64 (br. s., 4 H) 4.45 (t, J = 6.49 Hz, 1 H) 5.84 (br. s., 1 H), 6.56 (q, J = 6.77 Hz, 1 H) 7.48 (d, J = 1.07 Hz, 1 H) 7.62-7.69 (m, 2 H) 7.75-7.82 (m, 1 H) 7.83-7.91 (m, 1 H) 7.92-8.00 (m, 2 H) 8.97 (br. s., 1 H) 10.23 (br. s., 1 H) |
| 34y | $^1$H NMR (400 MHz, DMSO-d6): δ ppm 1.46-1.71 (m, 4 H) 1.91 (dd, J = 13.32, 9.27 Hz, 1 H) 2.27-2.40 (m, 1 H) 3.14 (br. s., 2 H) 3.63 (d, J = 5.37 Hz, 4 H) 3.81 (s, 3 H) 4.36-4.53 (m, 1 H) 5.85 (br. s., 1 H) 6.72 (q, J = 6.62 Hz, 1 H) 6.94-7.10 (m, 3 H) 7.40 (d, J = 2.05 Hz, 1 H) 7.49 (t, J = 7.96 Hz, 1 H) 7.57-7.70 (m, 2 H) 8.96 (d, J = 5.71 Hz, 1 H) 10.27 (br. s., 1 H) |
| 34z | $^1$H NMR (400 MHz, DMSO-d6): δ ppm 1.43-1.76 (m, 4 H) 1.92 (dd, J = 13.18, 9.32 Hz, 1 H) 2.35 (dd, J = 13.30, 8.57 Hz, 1 H) 3.14 (br. s., 2 H) 3.67 (br. s., 4 H) 3.97-4.18 (m, 2 H) 4.44 (t, J = 6.88 Hz, 1H) 5.93 (br. s., 1 H) 6.75 (q, J = 6.57 Hz, 1 H) 7.39 (d, J = 1.66 Hz, 1 H) 7.53 (br. s., 1 H) 7.57-7.71 (m, 5 H) 8.58 (br. s., 3 H) 9.01 (br. s., 1 H) 10.55 (br. s., 1 H) |
| 34aa | $^1$H NMR (400 MHz, MeOH-d4): δ ppm 1.68-1.86 (m, 5 H) 2.13 (dd, J = 13.69, 8.66 Hz, 1 H) 2.54 (dd, J = 13.72, 8.98 Hz, 1 H) 3.56 (br. s., 1 H) 3.67 (br. s., 3 H) 4.44-4.63 (m, 3 H) 5.70 (dd, 1 = 9.42, 2.54 Hz, 1 H) 6.19-6.35 (m, 2 H) 6.58 (br. s., 1 H) 7.28 (d, J = 7.57 Hz, 1 H) 7.34-7.40 (m, 2 H) 7.43 (d, J = 7.86 Hz, 1 H) 7.47-7.56 (m, 2 H) 7.71 (d, J = 8.64 Hz, 1 H) |
| 34ab | $^1$H NMR (400 MHz, DMSO-d6): δ ppm 1.44-1.69 (m, 4 H) 1.91 (dd, J = 13.28, 9.18 Hz, 1 H) 2.35 (dd, J = 13.15, 8.61 Hz, 1 H) 3.14 (br. s., 2 H) 3.64 (br. s., 4 H) 4.37-4.53 (m, 1 H) 5.87 (br. s., 1 H) 6.62 (q, J = 6.78 Hz, 1 H) 7.43 (t, J = 1.22 Hz, 1 H) 7.65 (s, 2 H) 7.70 (d, J = 4.78 Hz, 2 H) 7.99-8.12 (m, 1 H) 8.26 (br. s., 1 H) 8.96 (d, J = 5.03 Hz, 1 H) 10.25 (br. s., 1 H) |
| 34ac | $^1$H NMR (400 MHz, MeOH-d4): δ ppm 1.62 (d, J = 4.15 Hz, 4 H) 2.02-2.14 (m, 1 H) 2.26-2.43 (m, 1 H) 3.08-3.29 (m, 2 H) 3.40-3.77 (m, 4 H) 4.09 (dd, J = 8.98, 7.27 Hz, 1 H) 5.55 (s, 1 H) 6.55-6.70 (m, 1 H) 7.30 (d, J = 2.05 Hz, 1 H) 7.47 (dd, J = 8.47, 2.07 Hz, 1 H) 7.51-7.59 (m, 1 H) 7.59-7.65 (m, 1 H) 7.67 (d, J = 8.30 Hz, 1 H) 7.96 (dd, J = 8.52, 1.00 Hz, 1 H) 8.32-8.50 (m, 1 H) |
| 34ad | $^1$H NMR (400 MHz, MeOH-d4): δ ppm 1.50-1.76 (m, 4 H) 2.07 (dd, J = 13.20, 7.15 Hz, 1 H) 2.34 (dd, J = 13.47, 9.27 Hz, 1 H) 3.14 (d, J = 11.71 Hz, 1 H) 3.23 (s, 3 H) 3.27 (d, J = 11.86 Hz, 1 H) 3.40-3.76 (m, 4 H) 4.09 (dd, J = 9.03, 7.27 Hz, 1 H) 5.54 (s, 1 H) 6.60 (q, J = 6.64 Hz, 1 H) 7.34 (d, J = 2.15 Hz, 1 H) 7.52 (dd, J = 8.49, 2.20 Hz, 1 H) 7.72 (d, J = 8.54 Hz, 1 H) 7.78 (d, J = 7.76 Hz, 2 H) 8.14 (d, J = 8.64 Hz, 2 H) |
| 34ae | $^1$H NMR (400 MHz, MeOH-d4): δ ppm 1.61 (q, J = 4.88 Hz, 4 H) 2.07 (dd, J = 13.37, 7.13 Hz, 1 H) 2.33 (dd, J = 13.42, 9.22 Hz, 1 H) 3.08-3.30 (m, 2 H) 3.38-3.74 (m, 4 H) 4.10 (dd, J = 8.91, 7.35 Hz, 1 H), 5.52 (s, 1 H) 6.53-6.69 (m, 1 H) 7.33 (d, J = 2.20 Hz, 1 H) 7.50 (dd, J = 8.52, 2.22 Hz, 1 H) 7.67 (d, J = 7.96 Hz, 2 H) 7.71 (d, J = 8.54 Hz, 1 H) 8.08 (d, J = 8.64 Hz, 2 H) |
| 34af | $^1$H NMR (400 MHz, MeOH-d4): δ ppm 1.62 (q, J = 6.0, 5.0 Hz, 17H), 2.07 (dd, J = 13.4, 7.2 Hz, 5H), 2.33 (dd, J = 13.4, 9.2 Hz, 5H), 3.15 (d, J = 11.8 Hz, 5H), 3.27 (d, J = 11.8 Hz, 13H), 3.49 (m, 9H), 3.64 (ddt, J = 15.7, 10.7, 5.2 Hz, 9H), 4.11 (dd, J = 9.2, 7.1 Hz, 5H), 6.61 (q, J = 6.7 Hz, 4H), 7.33 (m, 7H), 7.47 (m, 8H), 7.66 (m, 8H) |
| 34ag | $^1$H NMR (400 MHz, MeOH-d4): δ ppm 0.86 (m, 1H), 1.34 (dd, J = 9.4, 6.0 Hz, 7H), 1.58 (t, J = 5.7 Hz, 4H), 1.98 (dd, J = 13.3, 7.0 Hz, 1H), 2.26 (dd, J = 13.3, 9.0 Hz, 1H), 3.00 (d, J = 11.5 Hz, 1H), 3.16 (d, J = 11.5 Hz, 1H), 3.46 (ddt, J = 19.2, 12.6, 5.9 Hz, 2H), 3.62 (dt, J = 12.8, 7.1 Hz, 2H), 3.96 (t, J = 8.1 Hz, 1H), 4.69 (p, J = 6.0 Hz, 1H), 5.50 (s, 1H), 6.73 (q, J = 6.9 Hz, 1H), 6.95 (m, 1H), 7.04 (dd, J = 8.5, 2.4 Hz, 1H), 7.20 (s, 1H), 7.28 (d, J = 2.3 Hz, 1H), 7.42 (m, 2H), 7.66 (d, J = 8.5 Hz, 1H) |
| 34ah | $^1$H NMR (400 MHz, MeOH-d4): δ ppm 1.29 (d, J = 7.3 Hz, 1H), 1.41 (t, J = 7.0 Hz, 3H), 1.61 (q, J = 6.2, 5.4 Hz, 4H), 2.07 (dd, J = 13.5, 7.3 Hz, 1H), 2.35 (dd, J = 13.5, 9.1 Hz, 1H), 3.14 (d, J = 11.8 Hz, 1H), 3.26 (d, J = 11.7 Hz, 1H), 3.33 (s, 1H), 3.48 (m, 2H), 3.66 (dd, J = 14.5, 6.2 Hz, 2H), 4.13 (tt, J = 9.7, 7.2 Hz, 3H), 4.87 (s, 17H), 6.74 (q, J = 6.9 Hz, 1H), 6.97 (d, J = 7.6 Hz, 1H), 7.04 (dd, J = 8.3, 2.5 Hz, 1H), 7.19 (s, 1H), 7.29 (d, J = 2.2 Hz, 1H), 7.44 (m, 2H), 7.67 (d, J = 8.5 Hz, 1H) |
| 34ai | $^1$H NMR (400 MHz, MeOH-d4): δ ppm 1.48 (t, J = 7.0 Hz, 3H), 1.60 (m, 4H), 2.06 (dd, J = 13.4, 6.9 Hz, 1H), 2.33 (dd, J = 13.4, 8.9 Hz, 1H), 3.13 (d, J = 11.6 Hz, 1H), 3.25 (d, J = 11.4 Hz, 1H), 3.48 (ddd, J = 21.0, 14.2, 7.2 Hz, 2H), 3.64 (q, J = 8.9, 8.1 Hz, 2H), 4.09 (t, J = 8.3 Hz, 1H), 4.20 (q, J = 6.9 Hz, 2H), 4.88 (s, 15H), 5.52 (s, 1H), 6.63 (q, J = 6.7 Hz, 1H), 7.24 (m, 2H), 7.34 (d, J = 8.3 Hz, 1H), 7.43 (dd, J = 8.5, 2.3 Hz, 2H), 7.57 (s, 1H), 7.65 (d, J = 8.4 Hz, 1H) |
| 34aj | $^1$H NMR (400 MHz, MeOH-d4): δ ppm 1.28 (s, 1H), 1.58 (dd, J = 7.1, 4.1 Hz, 4H), 1.99 (dd, J = 13.4, 7.1 Hz, 1H), 2.29 (m, 1H), 2.46 (s, 3H), 3.02 (d, J = 11.6 Hz, 1H), 3.18 (d, J = 11.6 Hz, 1H), 3.46 (ddt, J = 21.0, 13.5, 6.0 Hz, 2H), 3.63 (m, 2H), 3.98 (dd, J = 9.2, 7.1 Hz, 1H), 5.52 (s, 1H), 6.60 (q, J = 6.6 Hz, 1H), 7.28 (m, 2H), 7.45 (dd, J = 8.3, 2.4 Hz, 2H), 7.56 (m, 1H), 7.66 (d, J = 8.5 Hz, 1H) |
| 34ak | $^1$H NMR (400 MHz, MeOH-d4): δ ppm 1.29 (d, J = 6.2 Hz, 1H), 1.40 (d, J = 6.0 Hz, 6H), 1.60 (d, J = 5.2 Hz, 4H), 2.03 (dd, J = 13.4, 6.8 Hz, 1H), 2.30 (dd, J = 13.3, 8.9 Hz, 1H), 2.81 (s, 1H), 3.07 (d, J = 11.6 Hz, 1H), 3.22 (d, J = 11.8 Hz, 1H), 3.48 (m, 2H), 3.64 (d, J = 9.7 Hz, 2H), 4.03 (t, J = 7.9 Hz, 1H), 4.75 (m, 1H), 5.53 (s, 1H), 6.63 (q, J = 6.8 Hz, 1H), 7.29 (m, 3H), 7.43 (dd, J = 8.6, 2.3 Hz, 1H), 7.58 (s, 1H), 7.65 (d, J = 8.5 Hz, 1H) |

TABLE 12b-continued

NMR Data for Compounds of Table 12a

| Ex. No. | NMR |
| --- | --- |
| 34al | $^{1}$H NMR (400 MHz, MeOH-d4): δ ppm 1.39 (d, J = 6.0 Hz, 6H), 1.60 (m, 4H), 2.06 (dd, J = 13.5, 7.2 Hz, 1H), 2.33 (dd, J = 13.4, 9.2 Hz, 1H), 3.13 (d, J = 11.7 Hz, 1H), 3.26 (d, J = 11.7 Hz, 1H), 3.48 (m, 2H), 3.64 (q, J = 12.4, 10.4 Hz, 2H), 4.10 (dd, J = 9.2, 7.2 Hz, 1H), 4.70 (hept, J = 5.9 Hz, 1H), 5.53 (s, 1H), 6.67 (q, J = 6.8 Hz, 1H), 7.25 (m, 4H), 7.43 (dd, J = 8.5, 2.3 Hz, 1H), 7.65 (d, J = 8.4 Hz, 1H) |
| 34am | $^{1}$H NMR (400 MHz, MeOH-d4): δ ppm 1.28 (s, 1H), 1.61 (q, J = 5.7 Hz, 4H), 2.06 (dd, J = 13.4, 7.1 Hz, 1H), 2.33 (dd, J = 13.4, 9.2 Hz, 1H), 3.12 (d, J = 11.7 Hz, 1H), 3.26 (d, J = 11.6 Hz, 1H), 3.48 (ddt, J = 18.1, 13.6, 6.0 Hz, 2H), 3.65 (tt, J = 11.7, 4.8 Hz, 2H), 4.08 (dd, J = 9.2, 7.1 Hz, 1H), 5.54 (s, 1H), 6.49 (q, J = 6.6 Hz, 1H), 7.35 (d, J = 2.2 Hz, 1H), 7.51 (dd, J = 8.5, 2.3 Hz, 1H), 7.69 (d, J = 8.5 Hz, 1H), 7.82 (td, J = 17.6, 16.6, 4.9 Hz, 3H) |
| 34an | $^{1}$H NMR (400 MHz, MeOH-d4): δ ppm 0.88 (d, J = 7.8 Hz, 1H), 1.29 (d, J = 6.7 Hz, 2H), 1.62 (q, J = 5.9, 5.4 Hz, 4H), 2.07 (dd, J = 13.4, 7.2 Hz, 1H), 2.33 (dd, J = 13.4, 9.2 Hz, 1H), 3.13 (d, J = 11.7 Hz, 1H), 3.26 (d, J = 11.7 Hz, 1H), 3.49 (ddd, J = 21.4, 12.5, 5.9 Hz, 2H), 3.65 (td, J = 12.3, 10.3, 5.5 Hz, 2H), 4.10 (dd, J = 9.2, 7.1 Hz, 1H), 5.55 (s, 1H), 6.59 (q, J = 6.7 Hz, 1H), 7.25 (d, J = 14.9 Hz, 1H), 7.35 (m, 2H), 7.44 (s, 1H), 7.51 (dd, J = 8.5, 2.2 Hz, 1H), 7.69 (d, J = 8.5 Hz, 1H) |
| 34ao | $^{1}$H NMR (400 MHz, MeOH-d4): δ ppm 0.89 (m, 2H), 1.30 (d, J = 11.8 Hz, 3H), 1.36 (s, 10H), 1.60 (m, 5H), 2.34 (s, 1H), 2.81 (s, 1H), 3.14 (d, J = 11.6 Hz, 1H), 3.28 (m, 4H), 3.45 (s, 2H), 3.62 (s, 3H), 4.15 (t, J = 8.1 Hz, 1H), 4.85 (s, 38H), 6.62 (t, J = 6.7 Hz, 1H), 7.28 (m, 2H), 7.46 (m, 5H), 7.66 (d, J = 8.5 Hz, 1H) |
| 34ap | $^{1}$H NMR (400 MHz, MeOH-d4): δ ppm 1.29 (d, J = 7.5 Hz, 2H), 1.65 (s, 3H), 2.08 (dd, J = 13.5, 7.9 Hz, 1H), 2.44 (t, J = 11.2 Hz, 1H), 3.24 (dd, J = 14.0, 11.6 Hz, 1H), 3.61 (m, 4H), 4.41 (t, J = 8.4 Hz, 1H), 6.48 (q, J = 6.6 Hz, 1H), 7.38 (d, J = 2.2 Hz, 1H), 7.54 (dd, J = 8.5, 2.2 Hz, 1H), 7.71 (d, J = 8.6 Hz, 1H), 7.86 (t, J = 1.5 Hz, 2H) |
| 34aq | $^{1}$H NMR (400 MHz, MeOH-d4): δ ppm 1.28 (d, J = 2.2 Hz, 1H), 1.60 (s, 4H), 2.03 (d, J = 13.1 Hz, 1H), 2.30 (t, J = 11.1 Hz, 1H), 3.08 (d, J = 11.6 Hz, 1H), 3.23 (d, J = 12.3 Hz, 1H), 3.50 (dt, J = 24.2, 8.0 Hz, 2H), 3.64 (d, J = 10.2 Hz, 2H), 4.03 (t, J = 7.8 Hz, 1H), 4.58 (s, 1H), 5.55 (s, 1H), 6.52 (q, J = 6.7 Hz, 1H), 7.37 (d, J = 2.2 Hz, 1H), 7.53 (dd, J = 8.5, 2.3 Hz, 1H), 7.66 (m, 4H) |
| 34ar | $^{1}$H NMR (400 MHz, MeOH-d4): δ ppm 1.57 (q, J = 7.9, 6.6 Hz, 4H), 1.92 (dd, J = 13.2, 7.0 Hz, 1H), 2.19 (dd, J = 13.2, 9.0 Hz, 1H), 2.88 (d, J = 11.4 Hz, 1H), 3.10 (d, J = 11.4 Hz, 1H), 3.45 (ddt, J = 20.3, 13.1, 6.1 Hz, 2H), 3.61 (m, 2H), 3.87 (s, 4H), 5.48 (s, 1H), 6.70 (q, J = 6.9 Hz, 1H), 7.04 (m, 2H), 7.16 (s, 1H), 7.29 (d, J = 2.2 Hz, 1H), 7.45 (m, 2H), 7.67 (d, J = 8.5 Hz, 1H) |
| 34as | $^{1}$H NMR (400 MHz, MeOH-d4): δ ppm 1.29 (d, J = 10.0 Hz, 2H), 1.61 (d, J = 5.6 Hz, 5H), 2.06 (dd, J = 13.4, 7.2 Hz, 1H), 2.33 (dd, J = 13.4, 9.2 Hz, 1H), 3.13 (d, J = 11.7 Hz, 1H), 3.26 (d, J = 11.7 Hz, 1H), 3.49 (dt, J = 21.9, 7.2 Hz, 3H), 3.65 (ddt, J = 15.1, 10.1, 5.2 Hz, 3H), 4.09 (dd, J = 9.2, 7.1 Hz, 1H), 4.86 (s, 26H), 5.53 (s, 1H), 6.64 (q, J = 6.8 Hz, 1H), 7.28 (m, 5H), 7.47 (dd, J = 8.5, 2.3 Hz, 1H), 7.55 (m, 1H), 7.68 (d, J = 8.5 Hz, 1H) |
| 34at | $^{1}$H NMR (400 MHz, MeOH-d4): δ ppm 1.28 (s, 1H), 1.35 (s, 1H), 1.60 (q, J = 5.1 Hz, 4H), 2.03 (dd, J = 13.3, 7.1 Hz, 1H), 2.30 (dd, J = 13.4, 9.1 Hz, 1H), 2.45 (s, 3H), 3.08 (d, J = 11.6 Hz, 1H), 3.23 (d, J = 11.7 Hz, 1H), 3.31 (s, 3H), 3.47 (ddt, J = 19.8, 12.7, 5.7 Hz, 2H), 3.63 (dt, J = 12.9, 7.5 Hz, 2H), 4.04 (dd, J = 9.0, 7.3 Hz, 1H), 5.51 (s, 1H), 6.62 (q, J = 6.8 Hz, 1H), 7.30 (m, 3H), 7.45 (dd, J = 8.5, 2.3 Hz, 1H), 7.52 (d, J = 8.1 Hz, 1H), 7.66 (d, J = 8.5 Hz, 1H) |
| 34au | $^{1}$H NMR (400 MHz, MeOH-d4): δ ppm 1.29 (d, J = 6.2 Hz, 1H), 1.62 (q, J = 5.5 Hz, 4H), 2.07 (dd, J = 13.5, 7.3 Hz, 1H), 2.35 (dd, J = 13.5, 9.2 Hz, 1H), 3.15 (d, J = 11.8 Hz, 1H), 3.27 (d, J = 11.7 Hz, 1H), 3.49 (ddt, J = 21.6, 13.6, 6.3 Hz, 2H), 3.66 (ddt, J = 15.6, 10.1, 4.9 Hz, 2H), 4.14 (dd, J = 9.1, 7.3 Hz, 1H), 4.85 (d, J = 3.1 Hz, 16H), 6.63 (q, J = 6.8 Hz, 1H), 7.12 (m, 3H), 7.34 (d, J = 2.2 Hz, 1H), 7.50 (dd, J = 8.5, 2.2 Hz, 1H), 7.69 (d, J = 8.5 Hz, 1H) |
| 34av | $^{1}$H NMR (400 MHz, MeOH-d4): δ ppm 0.88 (m, 1H), 1.28 (s, 3H), 1.61 (q, J = 6.1 Hz, 4H), 2.07 (dd, J = 13.4, 7.1 Hz, 1H), 2.33 (dd, J = 13.5, 9.0 Hz, 1H), 3.13 (d, J = 11.6 Hz, 1H), 3.26 (d, J = 11.8 Hz, 2H), 3.48 (ddt, J = 20.7, 12.7, 5.7 Hz, 2H), 3.65 (q, J = 8.9, 6.2 Hz, 2H), 4.10 (m, 1H), 4.90 (s, 1H), 5.55 (s, 1H), 6.57 (q, J = 6.8 Hz, 1H), 7.42 (m, 5H), 7.67 (d, J = 8.3 Hz, 2H) |
| 34aw | $^{1}$H NMR (400 MHz, MeOH-d4): δ ppm 1.29 (t, J = 7.7 Hz, 2H), 1.60 (q, J = 6.1, 4.9 Hz, 4H), 2.03 (dd, J = 13.3, 7.1 Hz, 1H), 2.30 (dd, J = 13.4, 9.0 Hz, 1H), 3.07 (d, J = 11.6 Hz, 1H), 3.22 (d, J = 11.6 Hz, 1H), 3.48 (ddt, J = 20.9, 13.3, 5.7 Hz, 2H), 3.64 (tt, J = 10.8, 5.3 Hz, 2H), 4.03 (t, J = 8.1 Hz, 1H), 4.87 (s, 17H), 5.54 (s, 1H), 6.61 (q, J = 6.7 Hz, 1H), 7.32 (t, J = 5.0 Hz, 2H), 7.46 (m, 3H), 7.54 (s, 1H), 7.67 (d, J = 8.5 Hz, 1H) |
| 34ax | $^{1}$H NMR (400 MHz, MeOH-d4): δ ppm 1.30 (dd, J = 17.9, 6.7 Hz, 2H), 1.54 (m, 4H), 1.79 (dd, J = 12.9, 7.0 Hz, 1H), 2.06 (td, J = 16.5, 14.8, 7.8 Hz, 1H), 2.66 (d, J = 11.0 Hz, 1H), 2.97 (d, J = 11.1 Hz, 1H), 3.45 (ddt, J = 20.1, 13.2, 6.0 Hz, 2H), 3.62 (m, 3H), 5.50 (d, J = 16.5 Hz, 1H), 6.54 (q, J = 6.7 Hz, 1H), 7.34 (d, J = 2.3 Hz, 1H), 7.52 (dd, J = 8.5, 2.3 Hz, 1H), 7.68 (dd, J = 24.2, 8.1 Hz, 2H), 7.84 (m, 1H), 7.97 (d, J = 8.1 Hz, 1H) |
| 34ay | $^{1}$H NMR (400 MHz, MeOH-d4): δ ppm 0.89 (m, 2H), 1.28 (s, 2H), 1.40 (s, 10H), 1.60 (q, J = 5.5 Hz, 4H), 2.06 (dd, J = 13.5, 7.1 Hz, 1H), 2.35 (d, J = 3.7 Hz, 7H), 3.13 (d, J = 11.6 Hz, 1H), 3.25 (d, J = 11.6 Hz, 1H), 3.47 (dq, J = 22.4, 7.8, 6.8 Hz, 2H), 3.63 (dd, J = 13.9, 7.3 Hz, 2H), 4.11 (t, J = 8.3 Hz, 1H), 6.66 (q, J = 6.8 Hz, 1H), 7.17 (d, J = 7.1 Hz, 2H), 7.26 (m, 2H), 7.41 (dd, J = 8.5, 2.2 Hz, 1H), 7.65 (d, J = 8.5 Hz, 1H) |
| 34az | $^{1}$H NMR (400 MHz, MeOH-d4): δ ppm 0.88 (q, J = 10.5, 8.0 Hz, 1H), 1.30 (d, J = 12.4 Hz, 4H), 1.46 (t, J = 7.0 Hz, 5H), 1.61 (d, J = 5.7 Hz, 8H), 2.06 (dd, J = 13.4, 7.1 Hz, |

TABLE 12b-continued

| NMR Data for Compounds of Table 12a | |
|---|---|
| Ex. No. | NMR |
| | 2H), 2.33 (dd, J = 13.3, 8.8 Hz, 2H), 3.13 (d, J = 11.5 Hz, 2H), 3.26 (d, J = 11.8 Hz, 2H), 3.48 (m, 4H), 3.62 (d, J = 12.9 Hz, 3H), 4.19 (m, 5H), 4.84 (s, 2H), 6.67 (q, J = 6.7 Hz, 2H), 7.27 (m, 7H), 7.43 (dd, J = 8.6, 2.2 Hz, 2H), 7.65 (d, J = 8.5 Hz, 2H) |
| 34ba | 1H NMR (400 MHz, MeOH-d4): δ ppm 1.59 (m, 4H), 2.04 (dd, J = 13.4, 7.2 Hz, 1H), 2.38 (s, 7H), 3.08 (d, J = 11.7 Hz, 1H), 3.23 (d, J = 11.7 Hz, 1H), 3.46 (m, 2H), 3.64 (dt, J = 14.7, 5.8 Hz, 2H), 4.04 (dd, J = 9.2, 7.1 Hz, 1H), 5.48 (s, 1H), 6.67 (q, J = 6.9 Hz, 1H), 7.03 (s, 2H), 7.12 (s, 1H), 7.25 (d, J = 2.3 Hz, 1H), 7.42 (dd, J = 8.5, 2.3 Hz, 1H), 7.66 (d, J = 8.5 Hz, 1H) |
| 34bb | $^{1}$H NMR (400 MHz, MeOH-d4): δ ppm1.28 (s, 3H), 1.58 (m, 4H), 1.98 (dd, J = 13.2, 7.1 Hz, 1H), 2.25 (dd, J = 13.3, 9.1 Hz, 1H), 2.40 (s, 3H), 2.98 (d, J = 11.5 Hz, 1H), 3.17 (d, J = 11.5 Hz, 1H), 3.46 (ddt, J = 20.0, 13.0, 6.1 Hz, 2H), 3.63 (dq, J = 12.7, 6.3 Hz, 2H), 3.95 (dd, J = 9.1, 7.0 Hz, 1H), 4.89 (s, 17H), 5.52 (s, 1H), 6.61 (q, J = 6.7 Hz, 1H), 7.30 (d, J = 2.3 Hz, 1H), 7.46 (m, 4H), 7.67 (d, J = 8.4 Hz, 1H) |
| 34bc | $^{1}$H NMR (400 MHz, MeOH-d4): δ ppm0.88 (d, J = 7.5 Hz, 1H), 1.28 (s, 3H), 1.60 (q, J = 5.5 Hz, 4H), 2.05 (dd, J = 13.6, 7.3 Hz, 1H), 2.30 (m, 1H), 2.44 (d, J = 2.6 Hz, 6H), 3.10 (d, J = 11.7 Hz, 1H), 3.26 (m, 2H), 3.47 (ddd, J = 16.0, 12.4, 6.6 Hz, 2H), 3.62 (d, J = 12.7 Hz, 2H), 4.06 (dd, J = 9.2, 7.2 Hz, 1H), 5.50 (d, J = 2.5 Hz, 1H), 6.64 (q, J = 6.7 Hz, 1H), 7.21 (s, 2H), 7.27 (d, J = 2.3 Hz, 1H), 7.44 (dd, J = 8.5, 2.3 Hz, 1H), 7.66 (d, J = 8.5 Hz, 1H) |
| 34bd | $^{1}$H NMR (400 MHz, MeOH-d4): δ ppm 0.89 (t, J = 7.7 Hz, 1H), 1.29 (d, J = 5.9 Hz, 5H), 1.61 (q, J = 5.6 Hz, 4H), 2.06 (dd, J = 13.5, 7.2 Hz, 1H), 2.33 (m, 4H), 2.84 (s, 1H), 3.12 (d, J = 11.7 Hz, 1H), 3.25 (d, J = 11.7 Hz, 1H), 3.48 (m, 2H), 3.64 (ddt, J = 15.0, 10.2, 5.1 Hz, 2H), 4.08 (dd, J = 9.2, 7.1 Hz, 1H), 5.52 (s, 1H), 6.63 (q, J = 6.8 Hz, 1H), 7.26 (m, 4H), 7.43 (dd, J = 8.5, 2.3 Hz, 1H), 7.66 (d, J = 8.5 Hz, 1H) |
| 34be | $^{1}$H NMR (400 MHz, MeOH-d4): δ ppm 1.28 (s, 1H), 1.58 (m, 4H), 1.99 (dd, J = 13.3, 7.1 Hz, 1H), 2.27 (dd, J = 13.3,9.1 Hz, 1H), 2.42 (s, 3H), 3.01 (d, J = 11.6 Hz, 1H), 3.19 (d, J = 11.5 Hz, 1H), 3.47 (ddt, J = 21.2, 13.6, 6.9 Hz, 2H), 3.64 (dq, J = 12.3, 5.8 Hz, 2H), 3.98 (dd, J = 9.1, 7.1 Hz, 1H), 5.52 (s, 1H), 6.61 (q, J = 6.8 Hz, 1H), 7.18 (s, 1H), 7.31 (m, 3H), 7.46 (dd, J = 8.5, 2.3 Hz, 1H), 7.68 (d, J = 8.3 Hz, 1H) |
| 34bf | $^{1}$H NMR (400 MHz, MeOH-d4): δ ppm 0.89 (t, J = 6.6 Hz, 1H), 1.29 (d, J = 7.9 Hz, 4H), 1.62 (s, 8H), 2.09 (d, J = 6.9 Hz, 1H), 2.34 (t, J = 10.9 Hz, 2H), 3.15 (d, J = 8.2 Hz, 2H), 3.25 (m, 1H), 3.32 (s, 2H), 3.48 (s, 4H), 3.54 (s, 1H), 3.66 (s, 5H), 4.12 (s, 2H), 5.56 (s, 1H), 6.60 (q, J = 6.7 Hz, 2H), 7.34 (m, 5H), 7.50 (dd, J = 8.6, 2.2 Hz, 2H), 7.68 (d, J = 8.5 Hz, 2H) |
| 34bg | $^{1}$H NMR (400 MHz, MeOH-d4): δ ppm 0.89 (m, 2H), 1.30 (d, J = 14.2 Hz, 7H), 1.61 (s, 12H), 2.07 (m, 3H), 2.36 (dd, J = 13.3, 8.3 Hz, 3H), 2.80 (s, 1H), 3.15 (d, J = 11.8 Hz, 3H), 3.26 (d, J = 11.5 Hz, 3H), 3.46 (d, J = 16.1 Hz, 5H), 3.52 (d, J = 7.0 Hz, 2H), 3.64 (s, 7H), 4.18 (s, 3H), 4.92 (s, 1H), 4.98 (s, 1H), 6.58 (q, J = 6.7 Hz, 3H), 7.33 (d, J = 2.0 Hz, 3H), 7.47 (m, 12H), 7.67 (m, 6H) |
| 34bh | $^{1}$H NMR (400 MHz, MeOH-d4): δ ppm 0.89 (t, J = 6.4 Hz, 1H), 1.29 (d, J = 4.7 Hz, 2H), 1.62 (q, J = 6.3, 5.4 Hz, 4H), 2.07 (dd, J = 13.4, 7.3 Hz, 1H), 2.36 (dd, J = 13.5, 9.1 Hz, 1H), 3.15 (d, J = 11.8 Hz, 1H), 3.26 (m, 1H), 3.50 (ddd, J = 20.3, 10.5, 6.5 Hz, 2H), 3.65 (m, 2H), 4.16 (t, J = 8.2 Hz, 1H), 4.68 (s, 1H), 4.95 (t, J = 11.4 Hz, 1H), 6.40 (q, J = 6.5 Hz, 1H), 7.41 (d, J = 2.2 Hz, 1H), 7.56 (dd, J = 8.5, 2.3 Hz, 1H), 7.71 (d, J = 8.6 Hz, 1H), 8.12 (s, 3H) |
| 34bi | $^{1}$H NMR 400 MHz, MeOH-d4): δ ppm 0.89 (d, J = 6.7 Hz, 1H), 1.15 (s, 1H), 1.28 (m, 9H), 1.57 (d, J = 6.4 Hz, 5H), 1.92 (dt, J = 13.9, 6.8 Hz, 1H), 2.21 (dd, J = 13.2, 9.1 Hz, 1H), 2.95 (m, 2H), 3.11 (d, J = 11.4 Hz, 1H), 3.44 (ddt, J = 20.6, 13.0, 6.2 Hz, 2H), 3.60 (dd, J = 13.8, 6.6 Hz, 2H), 3.87 (dd, J = 9.0, 7.0 Hz, 1H), 5.46 (s, 1H), 6.61 (q, J = 6.8 Hz, 1H), 7.39 (m, 6H), 7.66 (d, J = 8.5 Hz, 1H) |
| 34bj | $^{1}$H NMR400 MHz, MeOH-d4): δ ppm 1.29 (d, J = 5.0 Hz, 3H), 1.55 (m, 6H), 1.82 (dd, J = 12.9, 6.9 Hz, 1H), 2.10 (dd, J = 13.0, 9.0 Hz, 1H), 2.71 (d, J = 11.1 Hz, 1H), 3.00 (d, J = 11.1 Hz, 1H), 3.32 (s, 3H), 3.45 (tt, J = 13.0, 6.3 Hz, 3H), 3.65 (ddd, J = 18.3, 10.9, 7.1 Hz, 4H), 4.88 (s, 17H), 5.53 (s, 2H), 6.54 (q, J = 6.6 Hz, 1H), 7.32 (d, J = 2.3 Hz, 1H), 7.51 (m, 5H), 7.59 (t, J = 1.9 Hz, 1H), 7.70 (d, J = 8.5 Hz, 1H) |
| 34bk | $^{1}$H NMR (400 MHz, MeOH-d4): δ ppm1.28 (s, 1H), 1.62 (q, J = 5.5 Hz, 4H), 2.07 (dd, J = 13.5, 7.3 Hz, 1H), 2.35 (dd, J = 13.6, 9.1 Hz, 1H), 3.15 (d, J = 11.8 Hz, 1H), 3.26 (d, J = 11.7 Hz, 1H), 3.49 (ddt, J = 21.5, 14.0, 6.1 Hz, 2H), 3.65 (m, 2H), 4.15 (dd, J = 9.1, 7.4 Hz, 1H), 6.49 (q, J = 6.6 Hz, 1H), 7.34 (d, J = 2.2 Hz, 1H), 7.52 (m, 2H), 7.68 (d, J = 8.5 Hz, 1H), 7.81 (s, 2H) |
| 34bl | $^{1}$H NMR (400 MHz, MeOH-d4): δ ppm 1.33 (m, 8H), 1.56 (q, J = 5.9, 5.2 Hz, 4H), 1.89 (dd, J = 13.1, 7.0 Hz, 1H), 2.18 (dd, J = 13.1, 9.0 Hz, 1H), 2.86 (d, J = 11.3 Hz, 1H), 3.08 (d, J = 11.4 Hz, 1H), 3.46 (ddd, J = 15.1, 12.2, 6.6 Hz, 2H), 3.61 (dd, J = 13.4, 6.0 Hz, 2H), 3.82 (dd, J = 9.0, 7.0 Hz, 1H), 4.68 (hept, J = 6.0 Hz, 1H), 5.51 (s, 1H), 6.72 (q, J = 8.2, 7.0 Hz, 2H), 6.82 (dt, J = 11.1, 2.3 Hz, 1H), 7.02 (s, 1H), 7.28 (d, J = 2.2 Hz, 1H), 7.44 (dd, J = 8.5, 2.3 Hz, 1H), 7.67 (d, J = 8.6 Hz, 1H) |
| 34bm | $^{1}$H NMR (400 MHz, MeOH-d4): δ ppm1.32 (d, J = 18.8 Hz, 11H), 1.60 (q, J = 5.8 Hz, 4H), 2.05 (dd, J = 13.5, 7.2 Hz, 1H), 2.33 (m, 2H), 2.43 (s, 3H), 3.12 (d, J = 11.7 Hz, 1H), 3.25 (d, J = 11.7 Hz, 1H), 3.45 (ddt, J = 21.7, 13.4, 6.5 Hz, 2H), 3.62 (dq, J = 11.4, 5.5 Hz, 2H), 4.09 (dd, J = 9.2, 7.2 Hz, 1H), 6.64 (q, J = 6.8 Hz, 1H), 7.05 (s, 1H), 7.26 (m, 2H), 7.34 (d, J = 1.8 Hz, 1H), 7.42 (dd, J = 8.5, 2.3 Hz, 1H), 7.66 (d, J = 8.5 Hz, 1H) |
| 34bm | $^{1}$H NMR (400 MHz, MeOH-d4): δ ppm 1.28 (s, 2H), 1.53 (t, J = 6.1 Hz, 4H), 1.80 (dd, J = 13.0, 6.9 Hz, 1H), 2.09 (dd, J = 13.0, 8.9 Hz, 1H), 2.36 (d, J = 2.0 Hz, 3H), 2.68 (d, J = 10.8 Hz, 1H), 2.98 (d, J = 11.1 Hz, 1H), 3.42 (m, 2H), 3.63 (m, 3H), 5.49 (s, 1H), 6.64 (q, J = 6.8 Hz, 1H), 7.24 (m, 3H), 7.43 (m, 2H), 7.67 (d, J = 8.5 Hz, 1H) |

TABLE 12b-continued

| NMR Data for Compounds of Table 12a | |
|---|---|
| Ex. No. | NMR |
| 34bo | 1H NMR (400 MHz, MeOH-d4): δ ppm 1.30 (d, J = 13.0 Hz, 1H), 1.53 (m, 4H), 1.79 (dd, J = 12.9, 6.9 Hz, 1H), 2.08 (dd, J = 12.9, 8.9 Hz, 1H), 2.66 (d, J = 11.1 Hz, 1H), 2.97 (d, J = 11.0 Hz, 1H), 3.42 (m, 3H), 3.62 (m, 3H), 5.50 (d, J = 15.0 Hz, 1H), 6.53 (q, J = 6.9 Hz, 1H), 7.36 (d, J = 2.3 Hz, 1H), 7.53 (dd, J = 8.4, 2.2 Hz, 1H), 7.63 (dd, J = 8.0, 5.0 Hz, 1H), 7.72 (d, J = 8.5 Hz, 1H), 7.98 (m, 1H), 8.67 (m, 1H), 8.74 (s, 1H) |
| 34bp | $^1$H NMR (400 MHz, MeOH-d4): δ ppm 1.41 (t, J = 6.9 Hz, 3H), 1.65 (dt, J = 10.9, 5.8 Hz, 4H), 2.08 (dd, J = 13.6, 8.2 Hz, 1H), 2.44 (dd, J = 13.6, 8.9 Hz, 1H), 3.24 (m, 2H), 3.57 (m, 4H), 4.13 (qd, J = 7.0, 4.1 Hz, 2H), 4.42 (t, J = 8.5 Hz, 1H), 6.66 (q, J = 6.7 Hz, 1H), 7.00 (s, 1H), 7.16 (d, J = 8.0 Hz, 1H), 7.28 (m, 2H), 7.46 (dd, J = 8.5, 2.3 Hz, 1H), 7.67 (d, J = 8.5 Hz, 1H) |
| 34bq | $^1$H NMR (400 MHz, MeOH-d4): δ ppm 1.36 (s, 1H), 1.59 (q, J = 5.8, 4.7 Hz, 0H), 2.05 (dd, J = 13.4, 7.2 Hz, 0H), 2.31 (m, 0H), 3.12 (d, J = 11.6 Hz, 0H), 3.24 (d, J = 11.7 Hz, 0H), 3.42 (d, J = 9.4 Hz, 0H), 3.49 (m, 0H), 3.59 (d, J = 12.4 Hz, 0H), 4.09 (dd, J = 9.1, 7.1 Hz, 0H), 4.90 (s, 2H), 5.44 (s, 0H), 6.65 (q, J = 7.0 Hz, 0H), 7.27 (m, 0H), 7.45 (m, 0H), 7.54 (s, 0H), 7.69 (m, 0H) |
| 34br | $^1$H NMR (400 MHz, MeOH-d4): δ ppm 1.29 (d, J = 7.7 Hz, 3H), 1.59 (m, 6H), 2.04 (dd, J = 13.5, 7.0 Hz, 1H), 2.19 (s, 2H), 2.31 (dd, J = 13.5, 9.2 Hz, 1H), 3.11 (d, J = 11.5 Hz, 1H), 3.24 (d, J = 11.8 Hz, 1H), 3.34 (s, 1H), 3.47 (dt, J = 24.1, 8.0 Hz, 2H), 3.63 (m, 2H), 4.07 (t, J = 7.9 Hz, 1H), 4.73 (s, 1H), 5.16 (m, 1H), 5.47 (d, J = 10.8 Hz, 2H), 6.62 (q, J = 6.8 Hz, 1H), 7.33 (m, 1H), 7.51 (m, 3H), 7.68 (d, J = 8.6 Hz, 1H) |
| 34bs | $^1$H NMR (400 MHz, MeOH-d4): δ ppm 1.28 (s, 1H), 1.60 (q, J = 5.9, 5.4 Hz, 4H), 2.04 (m, 1H), 2.31 (dd, J = 13.5, 9.2 Hz, 1H), 3.11 (s, 7H), 3.24 (d, J = 11.6 Hz, 1H), 3.47 (m, 2H), 3.63 (s, 2H), 4.06 (t, J = 8.1 Hz, 1H), 5.50 (s, 1H), 6.69 (m, 3H), 7.34 (d, J = 2.2 Hz, 1H), 7.48 (dd, J = 8.6, 2.3 Hz, 1H), 7.69 (d, J = 8.4 Hz, 1H), 8.18 (d, J = 5.2 Hz, 1H) |
| 34bt | $^1$H NMR (400 MHz, MeOH-d4): δ ppm 1.56 (t, J = 5.4 Hz, 4H), 1.99 (dd, J = 13.3, 7.0 Hz, 1H), 2.26 (dd, J = 13.3, 9.1 Hz, 1H), 3.01 (d, J = 11.5 Hz, 1H), 3.18 (d, J = 11.5 Hz, 1H), 3.43 (ddt, J = 20.5, 13.2, 6.0 Hz, 2H), 3.60 (dd, J = 13.4, 5.7 Hz, 2H), 3.98 (dd, J = 9.1, 7.0 Hz, 1H), 4.85 (m, 1H), 5.47 (s, 1H), 6.68 (q, J = 6.7 Hz, 1H), 7.39 (d, J = 2.3 Hz, 1H), 7.54 (m, 4H), 7.72 (d, J = 8.5 Hz, 1H), 7.97 (m, 4H) |
| 34bu | $^1$H NMR (400 MHz, $CDCl_3$): δ ppm 1.36 (dd, J = 6.9, 3.7 Hz, 6H), 1.73 (dd, J = 13.1, 6.7 Hz, 1H), 2.05 (dd, J = 13.1, 8.8 Hz, 1H), 2.81 (d, J = 10.5 Hz, 1H), 2.94 (d, J = 10.5 Hz, 1H), 3.14 (p, J = 6.9 Hz, 1H), 3.47 (dt, J = 12.2, 5.6 Hz, 4H), 3.85 (dd, J = 8.8, 6.7 Hz, 1H), 4.19 (q, J = 7.1 Hz, 2H), 4.34 (s, 2H), 5.42 (s, 1H), 6.53 (q, J = 6.7 Hz, 1H), 7.25 (m, 3H), 7.42 (dd, J = 8.5, 2.2 Hz, 1H), 7.68 (d, J = 8.5 Hz, 1H), 8.65 (dd, J = 5.0, 0.8 Hz, 1H) |
| 34bv | $^1$H NMR (400 MHz, MeOH-d4): δ ppm 1.30 (d, J = 13.8 Hz, 1H), 1.54 (q, J = 6.0, 5.4 Hz, 4H), 1.80 (dd, J = 13.0, 6.9 Hz, 1H), 2.08 (dd, J = 12.8, 8.9 Hz, 1H), 2.66 (d, J = 11.2 Hz, 1H), 2.97 (d, J = 11.1 Hz, 1H), 3.38 (m, 3H), 3.61 (dt, J = 13.8, 7.1 Hz, 3H), 5.49 (d, J = 1.5 Hz, 1H), 6.60 (q, J = 6.7 Hz, 1H), 7.28 (m, 3H), 7.47 (m, 3H), 7.66 (d, J = 8.4 Hz, 1H) |
| 34bw | $^1$H NMR (400 MHz, MeOH-d4): δ ppm 1.63 (d, J = 7.6 Hz, 4H), 2.07 (dd, J = 13.4, 7.6 Hz, 1H), 2.39 (dd, J = 13.6, 9.0 Hz, 1H), 3.17 (d, J = 11.9 Hz, 1H), 3.28 (m, 2H), 3.51 (dt, J = 23.6, 8.6 Hz, 2H), 3.62 (d, J = 14.5 Hz, 2H), 4.25 (t, J = 8.4 Hz, 1H), 6.60 (q, J = 6.6 Hz, 1H), 7.29 (d, J = 2.3 Hz, 1H), 7.51 (m, 6H), 7.66 (d, J = 8.7 Hz, 1H) |
| 34bx | $^1$H NMR (400 MHz, MeOH-d4): δ ppm 1.61 (m, 4H), 2.06 (dd, J = 13.5, 7.5 Hz, 1H), 2.39 (m, 4H), 3.15 (d, J = 11.8 Hz, 1H), 3.26 (d, J = 11.7 Hz, 1H), 3.47 (m, 2H), 3.62 (ddd, J = 15.6, 9.4, 5.2 Hz, 2H), 4.18 (dd, J = 9.1, 7.4 Hz, 1H), 6.64 (q, J = 6.7 Hz, 1H), 7.26 (d, J = 2.3 Hz, 1H), 7.38 (m, 4H), 7.65 (d, J = 8.5 Hz, 1H) |
| 34by | $^1$H NMR (400 MHz, MeOH-d4): δ ppm: 1.30 (d, J = 17.9 Hz, 1H), 1.58 (q, J = 4.3, 2.7 Hz, 4H), 1.78 (m, 4H), 1.98 (dd, J = 13.3, 7.1 Hz, 1H), 2.24 (m, 4H), 2.41 (m, 1H), 3.02 (d, J = 11.6 Hz, 1H), 3.18 (d, J = 11.6 Hz, 1H), 3.47 (m, 2H), 3.62 (dq, J = 12.8, 5.9 Hz, 2H), 3.98 (dd, J = 9.1, 7.0 Hz, 1H), 5.49 (s, 1H), 5.75 (q, J = 2.6, 1.7 Hz, 1H), 6.94 (q, J = 6.9 Hz, 1H), 7.15 (d, J = 2.3 Hz, 1H), 7.29 (dd, J = 8.5, 2.3 Hz, 1H), 7.58 (d, J = 8.5 Hz, 1H) |
| 34bz | $^1$H NMR (400 MHz, MeOH-d4): δ ppm 1.02 (m, 7H), 1.28 (d, J = 5.2 Hz, 1H), 1.60 (q, J = 6.1, 5.6 Hz, 4H), 2.06 (ddt, J = 14.1, 11.3, 6.7 Hz, 2H), 2.33 (dd, J = 13.4, 9.2 Hz, 1H), 3.12 (d, J = 11.7 Hz, 1H), 3.27 (d, J = 25.3 Hz, 3H), 3.47 (ddt, J = 20.4, 13.1, 5.7 Hz, 2H), 3.65 (m, 2H), 3.81 (m, 2H), 4.08 (dd, J = 9.1, 7.3 Hz, 1H), 5.51 (s, 1H), 6.71 (q, J = 6.8 Hz, 1H), 7.01 (m, 2H), 7.18 (s, 1H), 7.29 (d, J = 2.1 Hz, 1H), 7.43 (m, 2H), 7.66 (d, J = 8.6 Hz, 1H) |
| 34ca | $^1$H NMR (400 MHz, MeOH-d4): δ ppm 1.00 (t, J = 7.3 Hz, 1H), 1.28 (m, 1H), 1.60 (m, 5H), 1.97 (m, 5H), 2.30 (t, J = 11.2 Hz, 1H), 2.83 (t, J = 7.4 Hz, 1H), 3.07 (d, J = 11.5 Hz, 1H), 3.22 (d, J = 11.4 Hz, 1H), 3.54 (m, 8H), 4.04 (d, J = 8.7 Hz, 1H), 5.08 (s, 1H), 5.56 (s, 1H), 6.69 (q, J = 6.6 Hz, 1H), 7.31 (d, J = 2.1 Hz, 1H), 7.48 (m, 2H), 7.65 (m, 3H), 7.93 (s, 1H) |
| 34cb | $^1$H NMR (400 MHz, MeOH-d4): δ ppm 1.29 (m, 1H), 1.62 (m, 6H), 1.90 (m, 8H), 2.32 (dd, J = 13.4, 9.1 Hz, 1H), 3.11 (d, J = 11.7 Hz, 1H), 3.25 (d, J = 11.6 Hz, 1H), 3.47 (ddt, J = 21.4, 13.3, 6.4 Hz, 2H), 3.65 (dq, J = 13.0, 6.2 Hz, 2H), 4.08 (dd, J = 9.1, 7.1 Hz, 1H), 5.51 (s, 1H), 6.72 (q, J = 6.9 Hz, 1H), 6.94 (d, J = 7.7 Hz, 1H), 7.02 (dd, J = 8.2, 2.6 Hz, 1H), 7.18 (s, 1H), 7.28 (d, J = 2.3 Hz, 1H), 7.42 (m, 2H), 7.66 (d, J = 8.5 Hz, 1H) |
| 34cc | $^1$H NMR (400 MHz, MeOH-d4): δ ppm 1.29 (m, 1H), 1.49 (m, 8H), 2.02 (m, 5H), 2.33 (dd, J = 13.3, 9.0 Hz, 1H), 3.13 (d, J = 11.6 Hz, 1H), 3.25 (d, J = 12.3 Hz, 1H), 3.58 (ddd, J = 32.1, 26.0, 15.3 Hz, 5H), 3.88 (td, J = 10.6, 10.2, 3.9 Hz, 1H), 4.08 (t, J = 8.1 Hz, 1H), 5.56 (s, 1H), 6.63 (q, J = 6.7 Hz, 1H), 7.29 (d, J = 2.2 Hz, 1H), 7.56 (m, 4H), 7.89 (d, J = 7.7 Hz, 1H), 8.34 (s, 1H) |

TABLE 12b-continued

NMR Data for Compounds of Table 12a

| Ex. No. | NMR |
| --- | --- |
| 34cd | $^1$H NMR (400 MHz, MeOH-d4): δ$^{ppm}$ 1.28 (q, J = 7.6, 6.7 Hz, 4H), 1.57 (p, J = 3.8 Hz, 4H), 1.99 (dd, J = 13.3, 7.1 Hz, 1H), 2.27 (dd, J = 13.3, 9.1 Hz, 1H), 2.73 (q, J = 7.6 Hz, 2H), 3.01 (d, J = 11.5 Hz, 1H), 3.18 (d, J = 11.6 Hz, 1H), 3.45 (ddt, J = 21.2, 13.1, 5.9 Hz, 2H), 3.60 (dt, J = 12.5, 6.8 Hz, 2H), 3.98 (dd, J = 9.1, 7.1 Hz, 1H), 4.93 (s, 11H), 5.47 (s, 1H), 6.64 (q, J = 6.8 Hz, 1H), 7.30 (m, 4H), 7.43 (m, 2H), 7.66 (d, J = 8.5 Hz, 1H) |
| 34ce | $^1$H NMR (400 MHz, MeOH-d4): δ ppm 1.28 (m, 9H), 1.52 (ddd, J = 11.5, 7.0, 4.8 Hz, 4H), 1.74 (dd, J = 13.1, 7.2 Hz, 1H), 2.10 (dd, J = 13.1, 8.8 Hz, 1H), 2.75 (d, J = 10.9 Hz, 1H), 2.95 (m, 2H), 3.50 (m, 4H), 3.83 (dd, J = 8.8, 7.2 Hz, 1H), 4.18 (qd, J = 7.1, 1.5 Hz, 2H), 4.92 (s, 8H), 5.47 (d, J = 14.2 Hz, 1H), 6.61 (q, J = 6.8 Hz, 1H), 7.32 (m, 4H), 7.44 (m, 2H), 7.66 (d, J = 8.5 Hz, 1H) |
| 34cf | $^1$H NMR (400 MHz, MeOH-d4): δ ppm 0.09 (s, 0H), 0.89 (t, J = 6.5 Hz, 0H), 1.31 (d, J = 12.8 Hz, 1H), 1.59 (m, 0H), 1.84 (s, 0H), 2.02 (d, J = 6.4 Hz, 0H), 2.19 (t, J = 7.8 Hz, 0H), 2.65 (s, 0H), 2.76 (t, J = 6.7 Hz, 0H), 2.87 (d, J = 14.6 Hz, 0H), 3.06 (s, 0H), 3.30 (s, 1H), 3.49 (m, 0H), 3.61 (m, 0H), 3.82 (s, 0H), 4.98 (s, 0H), 5.33 (m, 0H), 5.55 (s, 0H), 7.30 (s, 0H), 7.38 (d, J = 7.9 Hz, 0H), 7.46 (t, J = 7.3 Hz, 0H), 7.54 (t, J = 7.8 Hz, 0H), 7.64 (m, 0H), 7.81 (t, J = 8.6 Hz, 0H), 7.93 (m, 0H), 8.40 (s, 0H) |
| 34cg | $^1$H NMR (400 MHz, MeOH-d4): δ ppm 1.73 (p, J = 7.2, 6.3 Hz, 4H), 2.10 (dd, J = 13.7, 8.5 Hz, 1H), 2.50 (dd, J = 13.6, 8.9 Hz, 1H), 3.26 (m, 4H), 3.61 (m, 11H), 3.78 (d, J = 16.7 Hz, 4H), 4.53 (t, J = 8.7 Hz, 1H), 6.61 (m, 1H), 7.36 (d, J = 2.2 Hz, 1H), 7.58 (m, 6H) |
| 34ch | $^1$H NMR (400 MHz, DMSO-d6): δ ppm 1.43 (m, 4H), 1.79 (dd, J = 13.3, 7.5 Hz, 1H), 2.13 (m, 1H), 2.30 (s, 3H), 2.48 (m, 3H), 2.95 (d, J = 11.8 Hz, 1H), 3.09 (m, 1H), 3.38 (s, 1H), 3.44 (s, 6H), 3.66 (s, 2H), 3.82 (t, J = 8.3 Hz, 1H), 5.54 (s, 1H), 6.57 (q, J = 6.8 Hz, 1H), 7.34 (d, J = 2.1 Hz, 1H), 7.55 (m, 6H) |
| 34ci | $^1$H NMR (400 MHz, MeOH-d4): δ ppm 1.29 (d, J = 4.2 Hz, 2H), 1.59 (m, 5H), 1.99 (dd, J = 13.4, 6.9 Hz, 1H), 2.27 (dd, J = 13.3, 8.9 Hz, 1H), 2.80 (s, 3H), 3.01 (d, J = 11.5 Hz, 1H), 3.18 (d, J = 11.4 Hz, 1H), 3.48 (m, 3H), 3.62 (q, J = 6.8, 5.6 Hz, 2H), 3.98 (t, J = 8.0 Hz, 1H), 5.52 (s, 1H), 6.75 (q, J = 6.7 Hz, 1H), 7.49 (m, 3H), 7.69 (d, J = 8.5 Hz, 1H), 7.76 (s, 1H) |
| 34cj | $^1$H NMR (400 MHz, MeOH-d4): δ ppm 1.29 (m, 1H), 1.58 (s, 8H), 2.06 (dd, J = 10.2, 6.4 Hz, 2H), 2.30 (m, 2H), 3.12 (s, 2H), 3.23 (d, J = 9.6 Hz, 2H), 3.49 (m, 4H), 3.64 (s, 9H), 4.07 (t, J = 7.9 Hz, 2H), 5.64 (s, 1H), 6.24 (d, J = 7.2 Hz, 2H), 6.50 (t, J = 6.8 Hz, 2H), 7.31 (d, J = 2.2 Hz, 2H), 7.46 (dd, J = 14.7, 7.7 Hz, 3H), 7.65 (d, J = 8.5 Hz, 2H), 7.78 (dd, J = 12.8, 6.1 Hz, 2H) |
| 34ck | $^1$H NMR (400 MHz, MeOH-d4): δ ppm 1.62 (q, J = 6.1, 5.6 Hz, 4H), 2.06 (dd, J = 13.4, 7.2 Hz, 1H), 2.34 (dd, J = 13.5, 9.2 Hz, 1H), 2.58 (s, 3H), 3.13 (d, J = 11.7 Hz, 1H), 3.26 (d, J = 11.7 Hz, 2H), 3.51 (m, 2H), 3.68 (td, J = 14.8, 14.3, 7.0 Hz, 2H), 4.08 (dd, J = 9.2, 7.1 Hz, 1H), 4.87 (d, J = 7.3 Hz, 1H), 4.97 (s, 1H), 5.60 (s, 1H), 6.65 (q, J = 6.6 Hz, 1H), 7.34 (d, J = 2.3 Hz, 1H), 7.50 (dd, J = 8.6, 2.2 Hz, 1H), 7.67 (dd, J = 12.0, 8.0 Hz, 2H), 7.77 (t, J = 7.8 Hz, 1H), 7.94 (dt, J = 7.9, 1.4 Hz, 1H), 8.31 (s, 1H) |
| 34cl | $^1$H NMR (400 MHz, MeOH-d4): δ ppm 1.61 (d, J = 5.5 Hz, 5H), 2.04 (dd, J = 13.3, 7.1 Hz, 1H), 2.31 (dd, J = 13.4, 9.2 Hz, 1H), 2.73 (s, 6H), 3.08 (d, J = 11.6 Hz, 1H), 3.23 (d, J = 11.7 Hz, 1H), 3.53 (m, 2H), 3.68 (d, J = 14.2 Hz, 2H), 4.04 (dd, J = 9.1, 7.0 Hz, 1H), 5.62 (s, 1H), 6.69 (q, J = 6.6 Hz, 1H), 7.36 (d, J = 2.3 Hz, 1H), 7.50 (dd, J = 8.5, 2.3 Hz, 1H), 7.70 (dd, J = 12.4, 7.7 Hz, 2H), 7.86 (m, 2H), 8.33 (s, 1H) |
| 34cm | $^1$H NMR (400 MHz, MeOH-d4): δ ppm 1.27 (s, 1H), 1.57 (p, J = 7.6, 6.8 Hz, 4H), 1.86 (dd, J = 13.0, 6.9 Hz, 1H), 2.15 (dd, J = 13.2, 9.0 Hz, 1H), 2.81 (d, J = 11.2 Hz, 1H), 2.95 (s, 4H), 3.05 (d, J = 11.2 Hz, 1H), 3.32 (s, 1H), 3.46 (ddt, J = 17.4, 13.1, 5.7 Hz, 2H), 3.62 (dq, J = 11.5, 5.5 Hz, 2H), 3.76 (dd, J = 9.0, 6.9 Hz, 1H), 5.54 (s, 1H), 6.63 (q, J = 6.7 Hz, 1H), 7.29 (d, J = 2.3 Hz, 1H), 7.46 (dd, J = 8.5, 2.3 Hz, 1H), 7.62 (m, 3H), 7.89 (dt, J = 7.7, 1.5 Hz, 1H), 8.36 (s, 1H) |
| 34cn | $^1$H NMR (400 MHz, MeOH-d4): δ ppm 1.28 (s, 2H), 1.62 (q, J = 5.7, 5.0 Hz, 12H), 2.07 (dd, J = 13.4, 7.1 Hz, 3H), 2.35 (dd, J = 13.4, 9.1 Hz, 3H), 3.09 (d, J = 26.8 Hz, 23H), 3.26 (s, 2H), 3.53 (m, 6H), 3.64 (d, J = 13.0 Hz, 7H), 4.15 (s, 3H), 4.88 (d, J = 3.3 Hz, 1H), 4.97 (s, 1H), 5.56 (s, 1H), 6.71 (q, J = 6.7 Hz, 3H), 7.32 (d, J = 2.2 Hz, 3H), 7.56 (m, 15H), 7.78 (s, 3H) |
| 34co | $^1$H NMR (400 MHz, MeOH-d4): δ ppm 1.13 (t, J = 7.1 Hz, 3H), 1.26 (m, 4H), 1.61 (q, J = 6.1, 5.6 Hz, 4H), 2.05 (dd, J = 13.4, 7.2 Hz, 1H), 2.33 (dd, J = 13.4, 9.3 Hz, 1H), 3.13 (d, J = 11.7 Hz, 1H), 3.47 (m, 10H), 4.09 (t, J = 8.3 Hz, 1H), 5.55 (s, 1H), 6.74 (q, J = 6.8 Hz, 1H), 7.32 (d, J = 2.2 Hz, 1H), 7.48 (m, 3H), 7.65 (m, 3H) |
| 34cp | $^1$H NMR (400 MHz, MeOH-d4): δ ppm 1.28 (m, 7H), 1.58 (d, J = 13.6 Hz, 14H), 2.05 (m, 3H), 2.31 (s, 4H), 2.88 (s, 1H), 3.11 (d, J = 12.1 Hz, 3H), 3.25 (d, J = 12.8 Hz, 3H), 3.38 (s, 10H), 3.48 (s, 3H), 3.63 (m, 5H), 4.09 (t, J = 8.2 Hz, 3H), 4.48 (s, 2H), 4.98 (s, 3H), 5.10 (s, 1H), 5.42 (s, 2H), 5.54 (s, 2H), 6.50 (d, J = 13.3 Hz, 2H), 6.79 (m, 1H), 7.22 (s, 2H), 7.44 (s, 5H), 7.53 (d, J = 8.4 Hz, 5H), 7.76 (s, 7H), 8.11 (m, 3H) |
| 34cq | $^1$H NMR (400 MHz, MeOH-d4): δ ppm 1.31 (s, 3H), 1.62 (s, 8H), 2.08 (dd, J = 13.3, 7.1 Hz, 2H), 2.35 (t, J = 11.4 Hz, 2H), 3.16 (d, J = 11.8 Hz, 2H), 3.32 (m, 23H), 3.49 (s, 4H), 3.63 (d, J = 19.6 Hz, 3H), 3.83 (s, 4H), 3.90 (s, 2H), 3.97 (s, 2H), 4.05 (s, 1H), 4.13 (t, J = 7.7 Hz, 2H), 6.67 (m, 2H), 7.35 (s, 2H), 7.51 (d, J = 8.7 Hz, 2H), 7.66 (dq, J = 31.2, 9.5, 9.1 Hz, 7H), 7.84 (s, 2H) |
| 34cr | $^1$H NMR (400 MHz, MeOH-d4): δ ppm 0.46 (m, 4H), 1.28 (s, 1H), 1.58 (s, 4H), 1.69 (d, J = 7.3 Hz, 1H), 1.97 (d, J = 9.1 Hz, 1H), 2.24 (dd, J = 13.1, 9.0 Hz, 1H), 2.58 (s, 2H), |

TABLE 12b-continued

| NMR Data for Compounds of Table 12a | |
|---|---|
| Ex. No. | NMR |
| | 2.73 (s, 2H), 2.96 (d, J = 11.3 Hz, 1H), 3.15 (d, J = 11.6 Hz, 1H), 3.32 (m, 1H), 3.48 (t, J = 12.1 Hz, 4H), 3.63 (s, 2H), 3.76 (s, 2H), 3.92 (t, J = 8.1 Hz, 1H), 5.55 (s, 1H), 6.71 (q, J = 6.7 Hz, 1H), 7.33 (d, J = 2.2 Hz, 1H), 7.50 (m, 3H), 7.66 (m, 2H), 7.80 (s, 1H) |
| 34cl | $^1$H NMR (400 MHz, MeOH-d4): δ ppm 8.71 (d, J = 4.7 Hz, 1H), 8.02 (t, J = 7.9 Hz, 1H), 7.72 (t, J = 7.3 Hz, 2H), 7.52 (d, J = 10.9 Hz, 3H), 6.92 (d, J = 6.7 Hz, 1H), 5.87 (s, 1H), 4.80 (s, 7H), 4.10 (d, J = 8.7 Hz, 1H), 3.66 (s, 2H), 3.50 (s, 2H), 3.30 (s, 5H), 3.25 (d, J = 11.8 Hz, 1H), 3.12 (d, J = 11.7 Hz, 1H), 2.35-2.27 (m, 1H), 2.06 (dd, J = 13.3, 7.1 Hz, 1H), 1.59 (s, 3H), 1.59 (d, J = 11.4 Hz, 1H) |
| 34cm | $^1$H NMR (400 MHz, MeOH-d4): δ ppm 8.99 (d, J = 4.9 Hz, 2H), 8.03 (s, 1H), 7.75 (d, J = 9.4 Hz, 2H), 7.60-7.49 (m, 2H), 5.71 (s, 1H), 4.10 (s, 1H), 3.59 (d, J = 18.5 Hz, 2H), 3.30 (d, J = 3.1 Hz, 9H), 3.11 (d, J = 12.0 Hz, 1H), 2.31 (t, J = 11.6 Hz, 1H), 2.06 (s, 1H), 1.57 (s, 5H), 1.28 (s, 1H) |
| 34cu | $^1$H NMR (400 MHz, MeOH-d4): δ ppm 8.96 (d, J = 1.5 Hz, 1H), 8.83-8.77 (m, 1H), 8.71 (d, J = 2.6 Hz, 1H), 7.77 (d, J = 8.4 Hz, 1H), 7.64-7.55 (m, 2H), 6.87 (q, J = 6.7 Hz, 1H), 5.64 (s, 1H), 3.99 (t, J = 8.2 Hz, 1H), 3.46 (s, 1H), 3.19 (d, J = 11.6 Hz, 1H), 3.03 (d, J = 11.6 Hz, 1H), 2.27 (dd, J = 13.3, 9.2 Hz, 1H), 2.00 (dd, J = 13.4, 7.0 Hz, 1H), 1.57 (s, 3H), 1.29 (s, 1H). |
| 34cv | $^1$H NMR (400 MHz, MeOH-d4): δ ppm 7.67 (d, J = 8.5 Hz, 2H), 7.44 (ddd, J = 8.0, 4.8, 2.6 Hz, 3H), 7.32-7.23 (m, 3H), 7.07 (dd, J = 8.4, 2.6 Hz, 2H), 6.98 (d, J = 7.6 Hz, 1H), 6.76 (d, J = 7.0 Hz, 2H), 4.26-4.05 (m, 5H), 3.75 (t, J = 4.7 Hz, 3H), 3.42 (s, 4H), 3.36 (s, 1H), 3.26 (d, J = 11.7 Hz, 3H), 3.13 (d, J = 11.7 Hz, 2H), 2.33 (dd, J = 13.5, 9.1 Hz, 2H), 2.06 (dd, J = 13.4, 7.1 Hz, 2H), 1.61 (d, J = 5.6 Hz, 5H). |

Example 35

(S)-8-(2-amino-6-((R)-1-(5-chloro-3'-(ethoxycarbonyl)-[1,1'-biphenyl]-2-yl)-2,2,2-trifluoroethoxy)pyrimidin-4-yl)-2,8-diazaspiro[4.5]decane-3-carboxylic acid

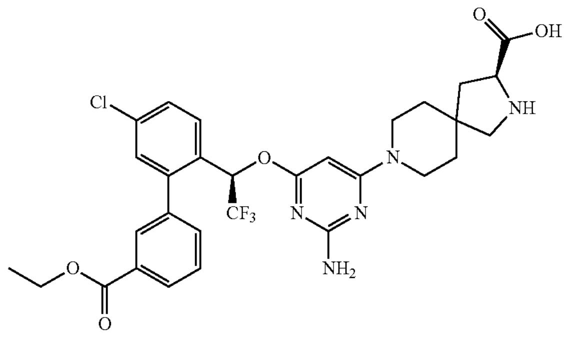 [SMILES: CCOC(=O)c1cccc(-c2cc(Cl)ccc2[C@@H](Oc2cc(N3CCC4(CC3)CN[C@H](C(=O)O)C4)nc(N)n2)C(F)(F)F)c1]

The title compound was prepared as described for (S)-8-(2-amino-6-((R)-1-(2'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylic acid (Example 20) starting with (S)-8-(2-amino-6-((R)-1-(2-bromo-4-chlorophenyl)-2,2,2-trifluoroethoxy)pyrimidin-4-yl)-2-((benzyloxy)carbonyl)-2,8-diazaspiro[4.5]decane-3-carboxylic acid.

1H NMR (400 MHz, DMSO-d6): δ ppm 1.29-1.38 (m, 3 H) 1.47-1.72 (m, 4 H) 1.91 (dd, J=13.28, 9.18 Hz, 1 H) 2.35 (dd, J=13.25, 8.61 Hz, 1 H) 3.14 (br. s., 2 H) 3.65 (br. s., 4 H) 4.30-4.40 (m, 2 H) 4.40-4.50 (m, 1 H) 5.90 (br. s., 1 H) 6.59 (q, J=6.67 Hz, 1 H) 7.11 (br. s., 1 H) 7.44 (t, J=1.22 Hz, 1 H) 7.66 (s, 2 H) 7.70-7.79 (m, 2 H) 8.08 (dt, J=6.37, 2.14 Hz, 1 H) 8.14 (br. s., 1 H) 8.98 (d, J=5.61 Hz, 1 H) 10.36 (d, J=5.08 Hz, 1 H). LCMS (MH+): 634.

Example 36

(S)-8-(2-amino-6-((R)-1-(4-chloro-2-(2-methoxyethoxy)phenyl)-2,2,2-trifluoroethoxy)pyrimidin-4-yl)-2,8-diazaspiro[4.5]decane-3-carboxylic acid

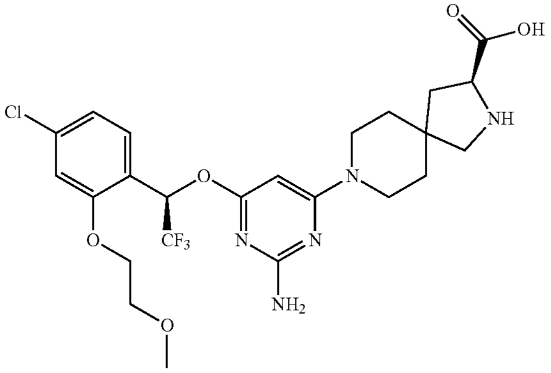 [SMILES: COCCOc1cc(Cl)ccc1[C@@H](Oc1cc(N2CCC3(CC2)CN[C@H](C(=O)O)C3)nc(N)n1)C(F)(F)F]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d) starting with (R)-1-(4-bromo-2-(2-methoxyethoxy)phenyl)-2,2,2-trifluoroethanol and obtained as a white solid.

$^1$H NMR (400 MHz, DMSO-d6): δ ppm 1.44-1.66 (m, 4 H) 1.83-1.95 (m, 1 H) 2.34 (dd, J=13.08, 8.79 Hz, 1 H) 3.14 (br. s., 2 H) 3.33 (s, 3 H) 3.42-3.65 (m, 4 H) 3.67-3.79 (m, 2 H) 4.19-4.27 (m, 1 H) 4.27-4.36 (m, 1 H) 4.48 (t, J=6.49 Hz, 1 H) 5.74 (s, 1 H) 6.99 (q, J=6.78 Hz, 1 H) 7.07-7.16 (m, 1 H) 7.27 (s, 1 H) 7.43 (d, J=8.35 Hz, 1 H) 8.93 (d, J=5.42 Hz, 1 H) 9.81 (br. s., 1 H). LCMS (MH+): 560.

Example 36b (S)-8-(6-((R)-1-(2-(1H-benzo[d]imidazol-1-yl)-4-chlorophenyl)-2,2,2-trifluoroethoxy)-2-aminopyrimidin-4-yl)-2,8-diazaspiro[4.5]decane-3-carboxylic acid

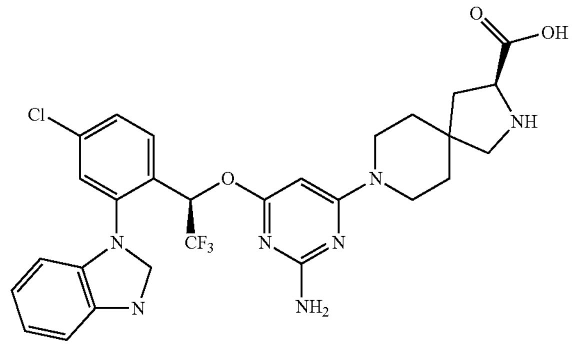 [SMILES: Nc1nc(O[C@H](c2ccc(Cl)cc2N2CNc3ccccc32)C(F)(F)F)cc(N2CCC3(CC2)CN[C@H](C(=O)O)C3)n1]

Step 1: To a solution of (R)-1-(2-bromo-4-chlorophenyl)-2,2,2-trifluoroethanol (1 g, 3.5 mmol) and 1H-benzo[d]imidazole (408 mg, 3.5 mmol) in toluene (24 mL) was added sequentially, CuI (131 mg, 0.69 mmol), $K_2CO_3$ (1.19 g, 8.63 mmol), and (1R,2R)-N1,N2-dimethylcyclohexane-1,2-diamine (196 mg, 1.38 mmol). The reaction mixture was purged with $N_2$ and then heated at 130° C. in a sealed tube for 12 h. Afterward, the reaction was cooled to RT. The solid was removed by filtration and the filtrate was concentrated and purified by flash column (EtOAc in hexane=0 to 50%) to afford -(R)-1-(2-(1H-benzo[d]imidazol-1-yl)-4-chlorophenyl)-2,2,2-trifluoroethanol as a white solid.

Steps 2-5: The title compound was made as described for Example 10d (Steps 1-4) to provide a white solid.

$^1$H NMR (400 MHz, DMSO-d6): δ ppm 1.59 (m, 4H), 2.05 (dt, J=13.7, 6.9 Hz, 1H), 2.33 (dt, J=14.5, 8.5 Hz, 1H), 3.13 (dd, J=11.7, 7.6 Hz, 1H), 3.26 (m, 2H), 3.49 (m, 3H), 3.63 (m, 2H), 4.10 (q, J=7.0, 5.2 Hz, 1H), 5.48 (d, J=3.9 Hz, 1H), 6.43 (p, J=6.4 Hz, 1H), 7.22 (dd, J=7.8, 4.0 Hz, 1H), 7.38 (m, 2H), 7.61 (dd, J=5.3, 2.2 Hz, 1H), 7.81 (m, 3H), 8.54 (s, 1H). LCMS ($MH^+$): 603.

Example 36c (S)-8-(2-amino-6-((R)-1-(4-chloro-2-(1H-indazol-1-yl)phenyl)-2,2,2-trifluoroethoxy)pyrimidin-4-yl)-2,8-diazaspiro[4.5]decane-3-carboxylic acid

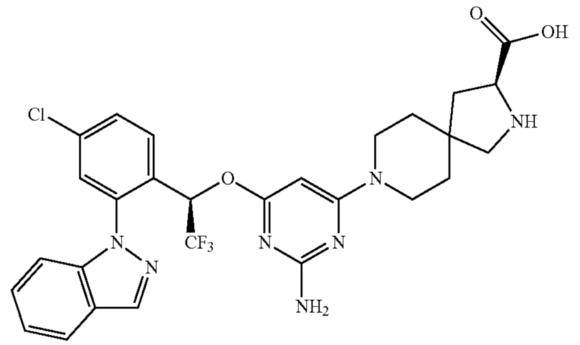 [SMILES: Nc1nc(O[C@H](c2ccc(Cl)cc2-n2ncc3ccccc32)C(F)(F)F)cc(N2CCC3(CC2)CN[C@H](C(=O)O)C3)n1]

The title compound was prepared as described for (S)-8-(6-((R)-1-(2-(1H-benzo[d]imidazol-1-yl)-4-chlorophenyl)-2,2,2-trifluoroethoxy)-2-aminopyrimidin-4-yl)-2,8-diazaspiro[4.5]decane-3-carboxylic acid (Example 36b) starting with 1H-indazole and obtained as a white solid.

$^1$H NMR (400 MHz, DMSO-d6): δ ppm 1.57 (m, 5H), 2.05 (dd, J=13.4, 7.1 Hz, 1H), 2.32 (dd, J=13.5, 9.2 Hz, 1H), 3.12 (d, J=11.7 Hz, 1H), 3.24 (d, J=11.7 Hz, 1H), 3.52 (dddd, J=44.5, 25.8, 14.0, 7.1 Hz, 5H), 4.13 (dd, J=9.1, 7.1 Hz, 1H), 4.92 (s, 1H), 6.68 (q, J=6.5 Hz, 1H), 7.31 (t, J=7.4 Hz, 1H), 7.46 (m, 2H), 7.72 (m, 5H), 8.39 (s, 1H). LCMS ($MH^+$): 603.

Example 36d (S)-8-(2-amino-6-((R)-1-(4-bromo-2-(piperazin-1-yl)phenyl)-2,2,2-trifluoroethoxy)pyrimidin-4-yl)-2,8-diazaspiro[4.5]decane-3-carboxylic acid

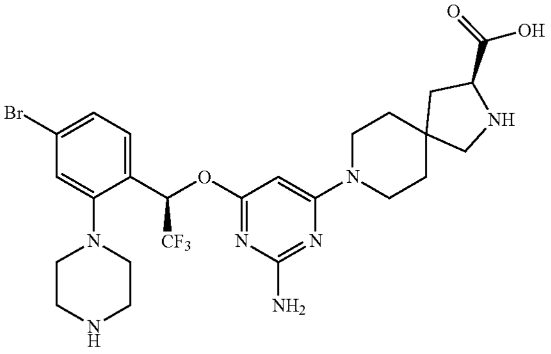 [SMILES: Nc1nc(O[C@H](c2ccc(Br)cc2N2CCNCC2)C(F)(F)F)cc(N2CCC3(CC2)CN[C@H](C(=O)O)C3)n1]

Step 1: A mixture of 4-bromo-2-fluorobenzoic acid (2 g, 9.1 mmol), benzyl piperazine-1-carboxylate (2.4 g, 10.9 mmol) and $K_2CO_3$ (2.5 g, 18.26 mmol) in DMF (40 mL) was stirred at 150° C. for 36 h. The reaction was then cooled to RT and extracted with ethyl acetate, 3 N HCl, brine, dried over $Na_2SO_4$, filtered and concentrated in vacuo to provide 2-(4-((benzyloxy) carbonyppiperazin-1-yl)-4-bromobenzoic acid as yellow oil that was used without further purification.

Step 2: To a mixture of 2-(4-((benzyloxy) carbonyppiperazin-1-yl)-4-bromobenzoic acid (2 g, 9.1 mmol) in THF (20 mL) was added dropwise BH3/THF (1.0 M, 40 mL) at 0° C. The mixture was refluxed for 2 h, then cooled to RT, quenched with $H_2O$, and extracted with ethyl acetate, 3 N HCl, brine, then dried over $Na_2SO_4$, filtered and concentrated. Purification by normal phase silica gel (ethyl acetate/hexanes) provided benzyl 4-(5-bromo-2-(hydroxymethyl)phenyl)piperazine-1-carboxylate as a white solid.

Steps 3-10: The title compound was prepared as described for (S)-8-(2-amino-6-((R)-2,2,2-trifluoro-1-(5-(methylsulfonyl)-[1,1'-biphenyl]-2-yl)ethoxy)pyrimidin-4-yl)-2,8-diazaspiro[4.5]decane-3-carboxylic acid (Example 54d) following Steps 4-11.

$^1$H NMR (MeOH-d4): δ ppm 0.90 (dt, J=16.0, 8.0 Hz, 1H), 1.31 (s, 2H), 1.62 (t, J=5.6 Hz, 5H), 2.03 (dd, J=13.6, 6.9 Hz, 1H), 2.30 (dd, J=13.4, 9.1 Hz, 1H), 2.76 (dd, J=10.1, 6.3 Hz, 2H), 3.08 (m, 8H), 3.22 (d, J=11.6 Hz, 1H), 3.47 (s, 1H), 3.54 (m, 1H), 3.65 (dd, J=13.9, 6.8 Hz, 2H), 4.01 (t, J=8.0 Hz, 1H), 5.56 (s, 1H), 7.31 ($_q$, J=6.9 Hz, 1H), 7.41 (dd, J=8.4, 1.9 Hz, 1H), 7.50 (m, 2H). LCMS (MH+): 615.

Example 36e (S)-8-(2-amino-6-((R)-2,2,2-trifluoro-1-(4'-isopropoxy-3-(piperazin-1-yl)-[1,1'-biphenyl]-4-yl)ethoxy)pyrimidin-4-yl)-2,8-diazaspiro[4.5]decane-3-carboxylic acid

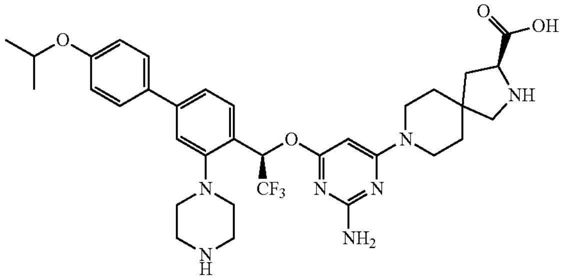 [SMILES: CC(C)Oc1ccc(-c2ccc([C@@H](Oc3cc(N4CCC5(CC4)CN[C@H](C(=O)O)C5)nc(N)n3)C(F)(F)F)c(N3CCNCC3)c2)cc1]

The title compound was prepared starting with (S)-2-benzyl 3-ethyl 8-(2-amino-6-((R)-1-(2-(4-((benzyloxy)carbonyl)piperazin-1-yl)-4-bromophenyl)-2,2,2-trifluoroethoxy)pyrimidin-4-yl)-2,8-diazaspiro[4.5]decane-2,3-dicarboxylate (intermediate from Step 8, Example 36d] via a Suzuki coupling with (4-isopropoxyphenyl)boronic acid as as described for example 54b.

$^1$H NMR (MeOH-d4): δ ppm 0.90 (m, 1H), 1.33 (m, 8H), 1.40 (s, 1H), 1.59 (q, J=5.7 Hz, 4H), 2.06 (dd, J=13.7, 7.0 Hz, 1H), 2.31 (dd, J=13.5, 9.2 Hz, 1H), 3.11 (m, 3H), 3.26 (d, J=11.7 Hz, 1H), 3.51 (m, 10H), 4.09 (dd, J=9.3, 6.8 Hz, 1H), 4.64 (p, J=6.0 Hz, 1H), 5.56 (s, 1H), 6.98 (m, 2H), 7.32 (q, J=7.0 Hz, 1H), 7.53 (m, 4H), 7.64 (d, J=8.2 Hz, 1H). LCMS (MH+): 671.

Example 36f (S)-8-(2-amino-6-((R)-2,2,2-trifluoro-1-(4'-isopropoxy-3-morpholino-[1,1'-biphenyl]-4-yl)ethoxy)pyrimidin-4-yl)-2,8-diazaspiro[4.5]decane-3-carboxylic acid

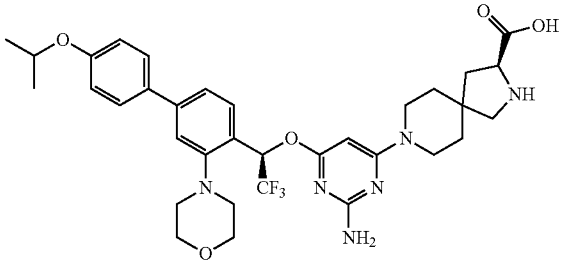 [SMILES: CC(C)Oc1ccc(-c2ccc([C@@H](Oc3cc(N4CCC5(CC4)CN[C@H](C(=O)O)C5)nc(N)n3)C(F)(F)F)c(N3CCOCC3)c2)cc1]

The title compound was prepared as described for (S)-8-(2-amino-6-((R)-2,2,2-trifluoro-1-(4'-isopropoxy-3-(piperazin-1-yl)-[1,1'-biphenyl]-4-yl)ethoxy)pyrimidin-4-yl)-2,8-diazaspiro[4.5]decane-3-carboxylic acid (Example 36e) substituting morpholine for benzyl piperazine-1-carboxylate.

$^1$H NMR (MeOH-d4): δ ppm 1.32 (d, J=6.0 Hz, 7H), 1.58 (d, J=6.0 Hz, 4H), 1.98 (m, 1H), 2.25 (dd, J=13.3, 9.0 Hz, 1H), 2.83 (m, 2H), 2.99 (d, J=11.5 Hz, 1H), 3.19 (m, 3H), 3.32 (s, 1H), 3.48 (ddt, J=18.5, 8.9, 5.0 Hz, 2H), 3.62 (s, 2H), 3.92 (m, 5H), 4.63 (h, J=6.0 Hz, 1H), 4.88 (m, 1H), 5.54 (s, 1H), 6.97 (m, 2H), 7.41 (m, 2H), 7.54 (m, 4H). LCMS (MH+): 672

Example 36g (S)-8-(6-((R)-1-([1,1'-biphenyl]-2-yl)-2,2,2-trifluoroethoxy)-2-amino pyrimidin-4-yl)-2,8-diazaspiro[4.5]decane-3-carboxylic acid

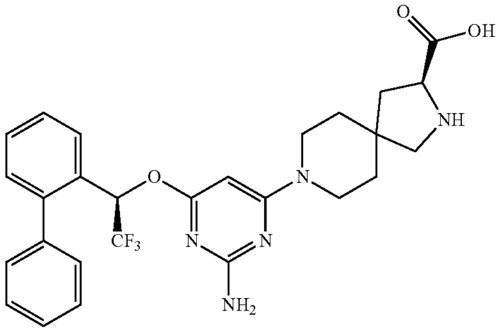 [SMILES: Nc1nc(O[C@H](c2ccccc2-c2ccccc2)C(F)(F)F)cc(N2CCC3(CC2)CN[C@H](C(=O)O)C3)n1]

The title compound was prepared as described for (S)-8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylic acid (Example 34u) starting with 1-(2-bromophenyl)-2,2,2-trifluoroethanone.

$^1$H NMR (MeOH-d4): δ ppm 1.58 (d, J=5.4 Hz, 4H), 2.00 (dd, J=13.4, 7.1 Hz, 1H), 2.27 (dd, J=13.3, 9.2 Hz, 1H), 3.02 (d, J=11.6 Hz, 1H), 3.19 (d, J=11.5 Hz, 1H), 3.30 (q, J=1.8 Hz, 3H), 3.45 (td, J=14.5, 6.3 Hz, 1H), 3.61 (m, 2H), 3.99 (m, 1H), 5.46 (s, 1H), 6.67 (q, J=6.8 Hz, 1H), 7.26 (dd, J=6.2, 2.4 Hz, 1H), 7.45 (m, 7H), 7.70 (d, J=7.3 Hz, 1H). LCMS (MH+): 528.

Example 37

(3S)-8-(6-(1-((1r,3r,5S,7S)-adamantan-2-yl)ethoxy)-2-aminopyrimidin-4-yl)-2,8-diazaspiro[4.5]decane-3-carboxylic acid

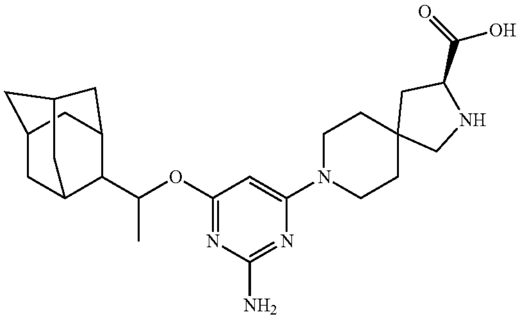 [SMILES: CC(Oc1cc(N2CCC3(CC2)CN[C@H](C(=O)O)C3)nc(N)n1)C1C2CC3CC(C2)CC1C3]

Step 1: A solution of adamantan-1-yl-methanol (100 mg, 0.60 mmol) in THF (5 mL) was cooled to 0° C. 15-Crown-5 ether (99 mg, 0.5 mmol) and NaH (60% in oil, 92 mg, 2.4 mmol) were added sequentially. The reaction was warmed to RT for 1 h, cooled to 0° C., and 4,6-dichloro-pyrimidin-2-ylamine (247 mg, 1.5 mmol) was added. The reaction was heated to 65° C. for 16 h, cooled to RT, quenched with water, and extracted with EtOAc. The combined organic layers were washed with brine, dried over $Na_2SO_4$, filtered, and concentrated in vacuo. Purification by normal phase chromatography (EtOAc/heptane) provided 4-(adamantan-1-ylmethoxy)-6-chloro-pyrimidin-2-ylamine as a white solid.

Step 2: 4-(Adamantan-1-ylmethoxy)-6-chloro-pyrimidin-2-ylamine (89 mg, 0.30 mmol), (S)-2-benzyl 3-ethyl 2,8-diazaspiro[4.5]decane-2,3-dicarboxylate (157 mg, 0.45 mmol) and $NaHCO_3$ (76 mg, 0.9 mmol) were dissolved in dioxane (1.5 mL) and heated to 95° C. for 64 h. Then the reaction was cooled to RT, quenched with water, and extracted with EtOAc. The organic layers were washed with brine, dried over $Na_2SO_4$, filtered, and concentrated in vacuo. Purification by normal phase silica gel column (EtOAc/heptane) provides (S)-2-benzyl 3-ethyl 8-(6-(adamantan-1-ylmethoxy)-2-aminopyrimidin-4-yl)-2,8-diazaspiro[4.5]decane-2,3-dicarboxylate as a white solid.

Step 3: N-CBZ Deprotection was accomplished via Method B to provide (S)-ethyl 8-(6-(adamantan-1-ylmethoxy)-2-aminopyrimidin-4-yl)-2,8-diazaspiro [4.5]decane-3-carboxylate as a white solid.

Step 4: Hydrolysis of (S)-ethyl 8-(6-(adamantan-1-ylmethoxy)-2-aminopyrimidin-4-yl)-2,8-diazaspiro[4.5]decane-3-carboxylate using the LiOH general method provides the title compound as a white solid.

$^1$H NMR (400 MHz, DMSO-d6): δ ppm 1.12 (d, J=6.25 Hz, 3 H) 1.42-1.76 (m, 17 H) 1.82-2.02 (m, 4 H) 2.34 (dd, J=13.32, 8.59 Hz, 1 H) 3.12 (br. s., 2 H) 3.67 (br. s., 4 H) 4.35-4.48 (m, 1 H) 5.85 (br. s., 1 H) 8.97 (br. s., 1 H) 10.44 (br. s., 1 H). LCMS (MH+): 456.

Example 38

(S)-8-(6-((1r,3r,5S,7S)-adamantan-2-ylmethoxy)-2-aminopyrimidin-4-yl)-2,8-diazaspiro[4.5]decane-3-carboxylic acid

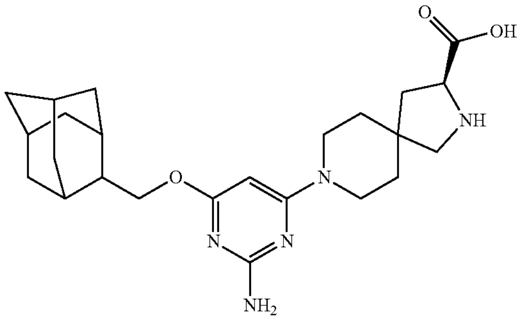 [SMILES: Nc1nc(OCC2C3CC4CC(C3)CC2C4)cc(N2CCC3(CC2)CN[C@H](C(=O)O)C3)n1]

The title compound was made as described above for (3S)-8-(6-(1-((1r,3r,5S,7S)-adamantan-2-yl)ethoxy)-2-aminopyrimidin-4-yl)-2,8-diazaspiro[4.5]decane-3-carboxylic acid (Example 37) using (1r,3r,5r,7r)-adamantan-2-ylmethanol.

$^1$H NMR (400 MHz, DMSO-d6): δ ppm 1.39-1.76 (m, 16 H) 1.83-2.01 (m, 4 H) 2.34 (dd, J=13.18, 8.44 Hz, 1 H) 3.13 (br. s., 2 H) 3.69 (br. s., 4 H) 3.79 (s, 2 H) 4.42 (br. s., 1 H) 5.83 (br. s., 1 H) 8.97 (br. s., 1 H) 10.40 (br. s., 1 H). LCMS (MH+): 442.

Example 39a 8-(4-Amino-6-((naphthalen-2-ylmethyl)amino)-1,3,5-triazin-2-yl)-2,8-diazaspiro[4.5]decane-3-carboxylic acid

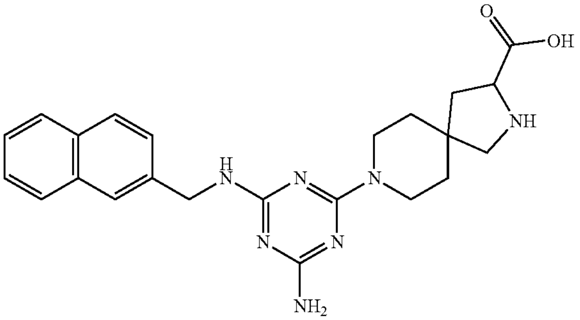 [SMILES: Nc1nc(NCc2ccc3ccccc3c2)nc(N2CCC3(CC2)CNC(C(=O)O)C3)n1]

Step 1: To a solution of 4,6-dichloro-1,3,5-triazin-2-amine (1.6 g) in isopropanol (14 mL) was added 2-benzyl 3-ethyl 2,8-diazaspiro[4.5]decane-2, 3-dicarboxylate (1.28 g, 3.7 mmol) and $Et_3N$ (7 mL). The solution was heated to reflux for 72 h, then cooled to RT, and concentrated in vacuo. Purification by normal phase chromatography ($CH_2Cl_2$/MeOH=50/1) afforded 2-benzyl 3-ethyl 8-(4-amino-6-chloro-1,3,5-triazin-2-yl)-2,8-diazaspiro[4.5]decane-2,3-dicarboxylate as a colorless oil.

Step 2: To a solution of 2-benzyl 3-ethyl 8-(4-amino-6-chloro-1,3,5-triazin-2-yl)-2,8-diazaspiro[4.5]decane-2,3-dicarboxylate (265 mg, 0.56 mmol) in isopropanol (3 mL) were added naphthalen-2-ylmethanamine (105 mg, 0.67 mmol) and $Et_3N$ (1.4 mL). The reaction mixture was heated to reflux for 12 h, then cooled to RT, and concentrated in vacuo. Purification by normal phase chromatography ($CH_2Cl_2$/MeOH) provided 2-benzyl 3-ethyl 8-(4-amino-6-((naphthalen-2-ylmethyl)amino)-1,3,5-triazin-2-yl)-2,8-diazaspiro[4.5]decane-2,3-dicarboxylate as a white solid.

Step 3: Hydrolysis of 2-benzyl 3-ethyl 8-(4-amino-6-((naphthalen-2-ylmethyl)amino)-1,3,5-triazin-2-yl)-2,8-diazaspiro [4.5]decane-2,3-dicarboxylate using the LiOH general method provided 8-(4-amino-6-((naphthalen-2-ylmethyl)amino)-1,3,5-triazin-2-yl)-2-((benzyloxy)carbonyl)-2,8-diazaspiro[4.5]decane-3-carboxylic acid as a white solid.

Step 4: N-CBZ Deprotection was accomplished via Method B to provide the title compound as a white solid.

Using the generic scheme below, the following examples of Table 13a were prepared as described above for 8-(4-amino-6-((naphthalen-2-ylmethyl)amino)-1,3,5-triazin-2-yl)-2,8-diazaspiro[4.5]decane-3-carboxylic acid (Example 39a).

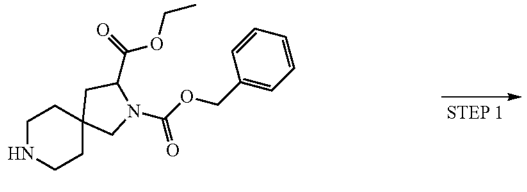

-continued
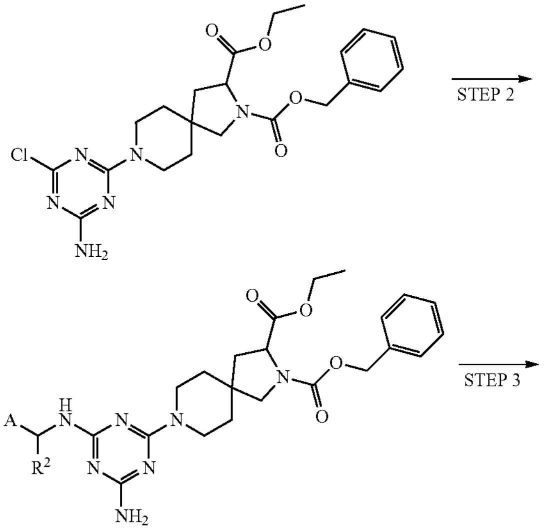
-continued
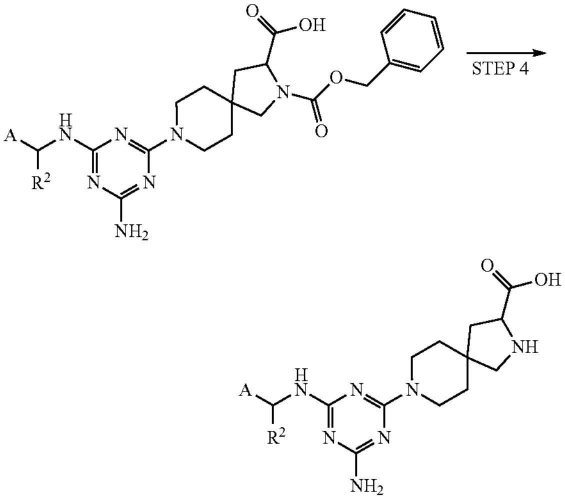
TABLE 13a
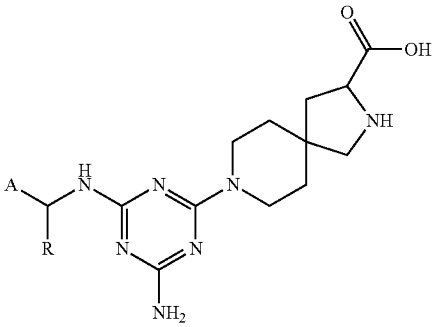
| Ex. No. | A—CH(R)—NH— | CAS Name | LCMS (MH+) |
|---|---|---|---|
| 39a | 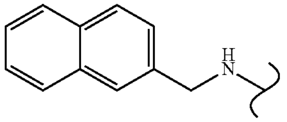 | 8-(4-amino-6-((naphthalen-2-ylmethyl)amino)-1,3,5-triazin-2-yl)-2,8-diazaspiro[4.5]decane-3-carboxylic acid | 435 |
| 39b | 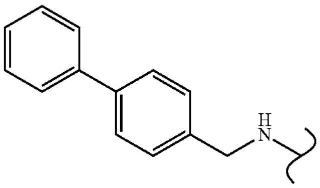 | 8-(4-(([1,1'-biphenyl]-4-ylmethyl)amino)-6-amino-1,3,5-triazin-2-yl)-2,8-diazaspiro[4.5]decane-3-carboxylic acid | 460 |
| 39c | 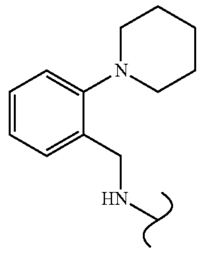 | 8-(4-amino-6-((2-(piperidin-1-yl)benzyl)amino)-1,3,5-triazin-2-yl)-2,8-diazaspiro[4.5]decane-3-carboxylic acid | 467 |

TABLE 13a-continued

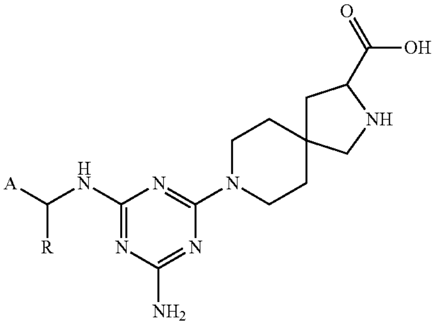

| Ex. No. | A—CH(R)—NH— | CAS Name | LCMS (MH+) |
|---|---|---|---|
| 39d | 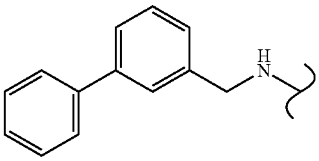 | 8-(4-(([1,1'-biphenyl]-3-ylmethyl)amino)-6-amino-1,3,5-triazin-2-yl)-2,8-diazaspiro[4.5]decane-3-carboxylic acid | 460 |
| 39e | 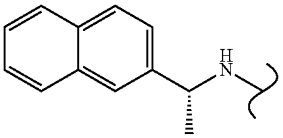 | 8-(4-amino-6-(((R)-1-(naphthalen-2-yl)ethyl)amino)-1,3,5-triazin-2-yl)-2,8-diazaspiro[4.5]decane-3-carboxylic acid | 448 |

TABLE 13b

| NMR Data for Compounds of Table 13a | |
|---|---|
| Ex. No. | NMR |
| 39a | 1H NMR (400 MHz, DMSO-d6): δ ppm 1.5 (br.s. 4 H), 1.6-1.8 (m, 1H), 2.1-2.2 (m, 1H), 3.0-3.1 (br.s. 3H), 3.5-3.8 (br.s. 5 H), 4.1 (t, J = 4.8 Hz, 1 H), 4.5 (d, J = 5.5 Hz, 2 H), 6.0-6.3 (br.s. 2 H), 7.1-7.3 (m, 3H), 7.5-7.9 (m, 4 H). |
| 39b | 1H NMR (400 MHz, MeOH-d4): δ ppm 1.54-1.79 (m, 4 H) 2.02-2.19 (m, 1 H) 2.44-2.60 (m, 1 H) 3.74-3.92 (m, 2 H) 3.93-4.08 (m, 2 H) 4.49-4.62 (m, 1 H) 4.63-4.71 (m, 2 H) 7.30-7.40 (m, 1 H) 7.40-7.51 (m, 4 H) 7.55-7.68 (m, 4 H) |
| 39c | 1H NMR (400 MHz, MeOH-d4): δ ppm 1.66 (br. s., 6 H) 1.86 (br. s., 4 H) 2.03-2.16 (m, 1 H) 2.40-2.54 (m, 1 H) 3.06-3.22 (m, 4 H) 3.66-3.87 (m, 2 H) 3.87-4.02 (m, 2 H) 4.46-4.59 (m, 1 H), 4.75 (s, 2 H) 7.12-7.27 (m, 1 H) 7.29-7.45 (m, 3 H) |
| 39d | 1H NMR (400 MHz, MeOH-d4): δ ppm 1.29-1.79 (m, 4 H) 1.88-2.15 (m, 1 H) 2.25-2.54 (m, 1 H) 3.22 (br. s., 2 H) 3.60-4.01 (m, 4 H) 4.35-4.54 (m, 1 H) 4.62 (s, 2 H) 7.25-7.35 (m, 1 H) 7.36-7.46 (m, 3 H) 7.51 (d, J = 7.61 Hz, 1 H) 7.57 (d, J = 8.59 Hz, 3 H) |
| 39e | 1H NMR (400 MHz, MeOH-d4): δ ppm 1.63 (d, J = 6.83 Hz, 9 H) 3.01-3.21 (m, 1 H) 3.50-4.07 (m, 5 H) 4.32-4.65 (m, 1 H) 5.14-5.33 (m, 1 H) 7.32-7.54 (m, 3 H) 7.81 (d, J = 5.08 Hz, 4 H) |

Example 40

8-(4-amino-6-((R)-1-(4-chloro-2-(3-methyl-1H-pyrazol-1-yl)phenyl)-2,2,2-trifluoroethoxy)-1,3,5-triazin-2-yl)-2,8-diazaspiro[4.5]decane-3-carboxylic acid

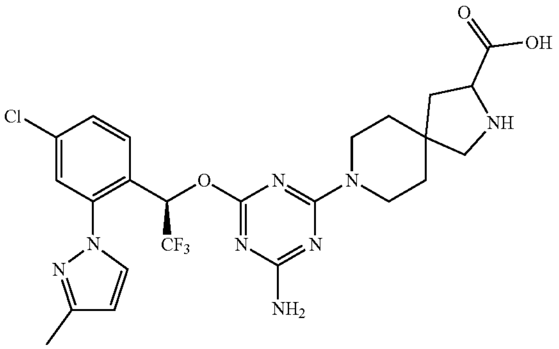 [SMILES: Cc1ccn(-c2cc(Cl)ccc2[C@@H](Oc2nc(N)nc(N3CCC4(CC3)CNC(C(=O)O)C4)n2)C(F)(F)F)n1]

Step 1: To a solution of (R)-1-(4-chloro-2-(3-methyl-1H-pyrazol-1-yl)phenyl)-2,2,2-trifluoroethanol (380 mg, 1.3 mmol) in 10 mL of THF was added NaH (60 mg, 1.4 mmol) and the reaction was stirred at RT for 30 min. After this time, 2-benzyl 3-ethyl 8-(4-amino-6-chloro-1,3,5-triazin-2-yl)-2,8-diazaspiro[4.5]decane-2,3-dicarboxylate (product from Step 1, Example 39a) (570 mg, 1.2 mmol) was added and the reaction was heatd to 50° C. for 12 h. After this time, the reaction was cooled to RT, quenched with methanol and concentrated in vacuo. Normal phase silica gel chromatography (EtOAc/heptane) provided 2-benzyl 3-ethyl 8-(4-amino-6-((R)-1-(4-chloro-2-(3-methyl-1H-pyrazol-1-yl)phenyl)-2,2,2-trifluoroethoxy)-1,3,5-triazin-2-yl)-2,8-diazaspiro[4.5]decane-2,3-dicarboxylate as a white solid.

Step 2: N-CBZ Deprotection was accomplished via Method B to provide ethyl 8-(4-amino-6-((R)-1-(4-chloro-2-(3-methyl-1H-pyrazol-1-yl)phenyl)-2,2,2-trifluoroethoxy)-1,3,5-triazin-2-yl)-2,8-diazaspiro[4.5]decane-3-carboxylate as a white solid.

Step 3: Step 3: Hydrolysis of ethyl 8-(4-amino-6-((R)-1-(4-chloro-2-(3-methyl-1H-pyrazol-1-yl)phenyl)-2,2,2-trifluoroethoxy)-1,3,5-triazin-2-yl)-2,8-diazaspiro[4.5]decane-3-carboxylate using the LiOH general method provided the title compound as a white solid.

$^{1}$H NMR (400 MHz, MeOH-d4): δ ppm 1.55 (br. s., 4 H) 1.98 (s, 1 H) 2.02-2.15 (m, 1 H) 2.30 (dd, J=13.42, 9.27 Hz, 1 H) 2.36 (s, 3 H) 3.10 (d, J=11.71 Hz, 1 H) 3.23-3.28 (m, 1 H) 3.40-4.01 (m,4 H) 4.08 (dd, J=9.27, 6.88 Hz, 1 H) 6.39 (d, J=2.25 Hz, 1 H) 7.36-7.63 (m, 3 H) 7.76 (d, J=8.54 Hz, 1 H) 7.91 (d, J=2.10 Hz, 1 H). LCMS (MH+): 567.

Example 41a (S)-8-(2-Amino-6-((2-(piperidin-1-yl)benzyl)amino)pyrimidin-4-yl)-2,8-diazaspiro[4.5]decane-3-carboxylic acid

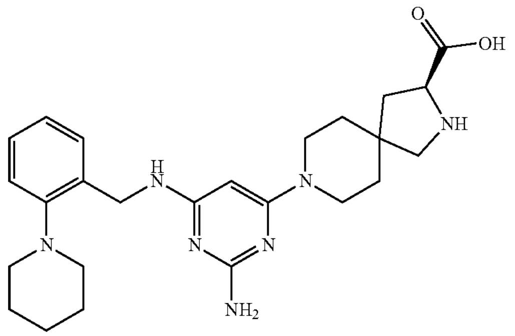 [SMILES: Nc1nc(NCc2ccccc2N2CCCCC2)cc(N2CCC3(CC2)CN[C@H](C(=O)O)C3)n1]

Step 1: To a solution of (S)-2-benzyl 3-ethyl 8-(2-amino-6-chloropyrimidin-4-yl)-2,8-diazaspiro [4.5]decane-2,3-dicarboxylate (200 mg, 0.6 mmol) and [2-(1-piperidinyl)phenyl]methanamine (CAS#: 72752-54-6) (105 mg, 0.8 mmol) in i-PrOH (2 mL) was added diisopropylethyl amine (0.5 mL). The reaction was heated to 120° C. for 2 h followed by heating to 140° C. for 1 h under microwave conditions, then cooled to RT and concentrated in vacuo. Purification by normal phase silica gel column (EtOAc/heptane) provided (S)-2-benzyl 3-ethyl 8-(2-amino-6-((2-(piperidin-1-yl)benzyl)amino) pyrimidin-4-yl)-2,8-diazaspiro[4.5]decane-2,3-dicarboxylate as a white solid.

Step 2: N-CBZ Deprotection was accomplished via Method B to provide (S)-ethyl 8-(2-amino-6-((2-(piperidin-1-yl)benzyl)amino)pyrimidin-4-yl)-2,8-diazaspiro[4.5]decane-3-carboxylate as a white solid.

Step 3: Hydrolysis of (S)-ethyl 8-(2-amino-6-((2-(piperidin-1-yfibenzyl)amino)pyrimidin-4-yl)-2,8-diazaspiro[4.5]decane-3-carboxylate using the LiOH general method provided the title compound as a white solid.

Using the generic scheme below, the following examples of Table 14a were prepared as described above for (S)-8-(2-amino-6-((2-(piperidin-1-yl)benzyl)amino)pyrimidin-4-yl)-2,8-diazaspiro[4.5]decane-3-carboxylic acid (Example 41a).

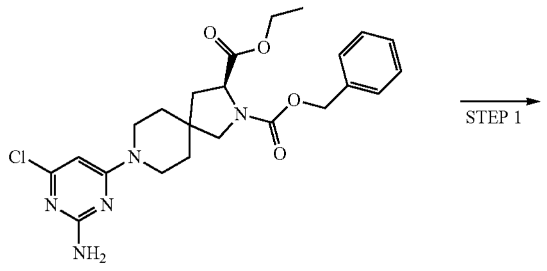
-continued
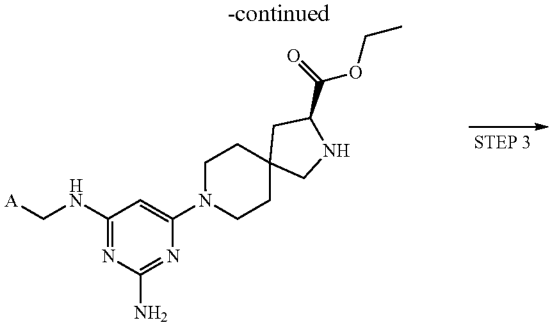
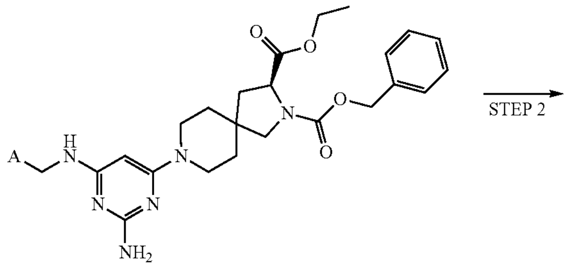
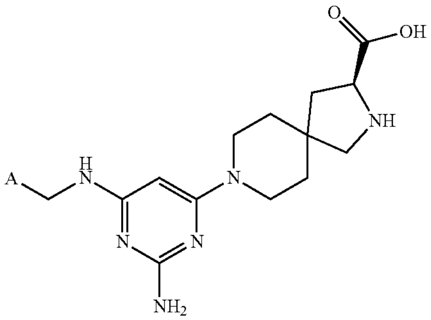
TABLE 14a
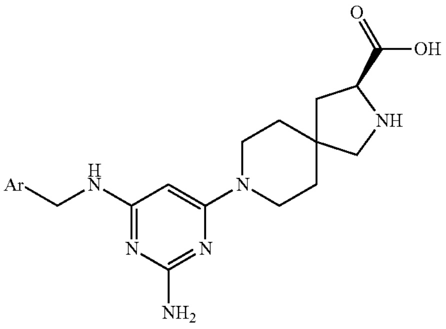
| Ex. No. | Ar | CAS Name | LCMS (MH+) |
| --- | --- | --- | --- |
| 41a | 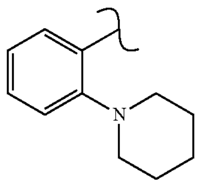 | (S)-8-(2-amino-6-((2-(piperidin-1-yl)benzyl)amino)pyrimidin-4-yl)-2,8-diazaspiro[4.5]decane-3-carboxylic acid | 446 |

TABLE 14a-continued

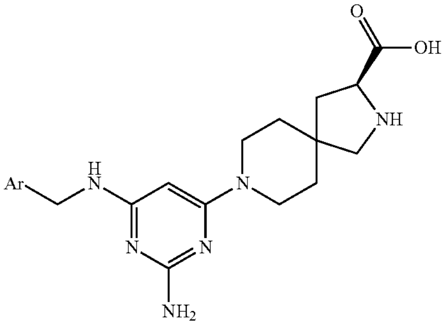

| Ex. No. | Ar | CAS Name | LCMS (MH+) |
|---|---|---|---|
| 41b | 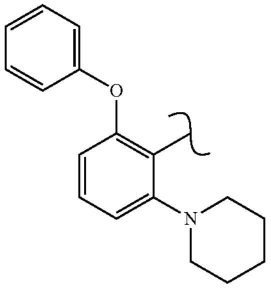 | (S)-8-(2-amino-6-((2-phenoxy-6-(piperidin-1-yl)benzyl)amino)pyrimidin-4-yl)-2,8-diazaspiro[4.5]decane-3-carboxylic acid | 558 |
| 41c | 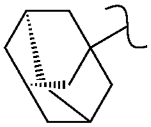 | (3S)-8-(6-(((3S,5S)-adamantan-1-ylmethyl)amino)-2-aminopyrimidin-4-yl)-2,8-diazaspiro[4.5]decane-3-carboxylic acid | 441 |
| 41d | 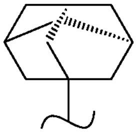 | (3S)-8-(6-((1-((1R,3S,5S)-adamantan-1-yl)ethyl)amino)-2-aminopyrimidin-4-yl)-2,8-diazaspiro[4.5]decane-3-carboxylic acid | 456 |

TABLE 14b

| NMR Data for Compounds of Table 14a | |
|---|---|
| Ex. No. | NMR |
| 41a | $^1$H NMR (400 MHz, MeOH-d4): δ ppm 1.39-1.66 (m, 6 H) 1.67-1.85 (m, 4 H) 1.95-2.11 (m, 1 H) 2.18-2.35 (m, 1 H) 2.69-2.95 (m, 4 H) 3.09 (s, 1 H) 3.20 (s, 1 H) 3.35 (s, 4 H) 3.94-4.14 (m, 1 H) 4.43 (s, 2 H) 6.93-7.05 (m, 1 H) 7.11 (s, 1 H) 7.14-7.24 (m, 1 H) 7.26-7.38 (m, 1 H) |
| 41b | $^1$H NMR (400 MHz, MeOH-d4): δ ppm 1.43-1.66 (m, 6 H) 1.67-1.85 (m, 4H) 1.94-2.09 (m, 1 H) 2.18-2.34 (m, 1 H) 2.89 (d, J = 4.49 Hz, 4 H) 3.07 (s, 1 H) 3.14-3.25 (m, 1 H) 3.32-3.63 (m, 4 H) 3.95-4.08 (m, 1 H) 4.46 (s, 2 H) 6.49-6.58 (m, 1 H) 6.84-6.97 (m, 3 H) 7.03-7.09(m, 1 H) 7.18 (s, 1 H) 7.28 (d, J = 7.91 Hz, 2 H) |
| 41c | $^1$H NMR (400 MHz, MeOH-d4): δ ppm 0.00 (br. s., 6 H) 0.03-0.26 (m, 10 H) 0.27-0.44 (m, 9 H) 0.48-0.58 (m, 1 H) 0.68-0.85 (m, 1 H) 1.33 (s, 2 H) 1.50-1.64 (m, 1 H) 1.84-2.03 (m, 2 H) 2.11(br. s., 2 H) 2.42-2.62 (m, 1 H) |
| 41d | $^1$H NMR (400 MHz, MeOH-d4): δ ppm 1.08 (d, J = 6.83 Hz, 3 H) 1.52-1.71 (m, 13 H) 1.73 (br. s., 3 H) 1.93 (s, 2 H) 1.97 (br. s., 3 H) 2.04-2.19 (m, 1 H) 2.24-2.43 (m, 1 H) 3.06-3.21 (m, 1 H) 3.22-3.28 (m, 1 H) 3.36-3.58 (m, 3 H) 3.59-3.75 (m, 2 H) 4.02-4.20 (m, 1 H) |

Example 42a (S)-8-(2-amino-6-((R)-1-(3'-chloro-[1,1'-biphenyl]-2-yl)-2,2,2-trifluoroethoxy)pyrimidin-4-yl)-2,8-diazaspiro[4.5]decane-3-carboxylic acid

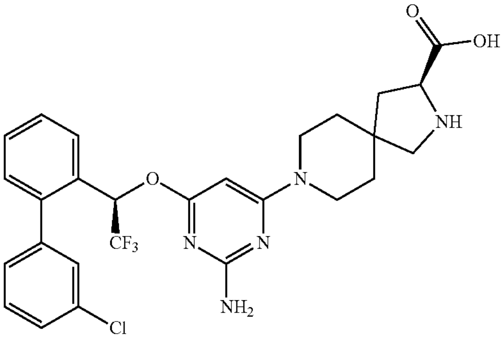 [SMILES: Nc1nc(O[C@H](c2ccccc2-c2cccc(Cl)c2)C(F)(F)F)cc(N2CCC3(CC2)CN[C@H](C(=O)O)C3)n1]

The title compound was made as described for (S)-8-(2-amino-6-((R)-1-(5-chloro-3'-(ethoxycarbonyl)-[1,1'-biphenyl]-2-yl)-2,2,2-trifluoroethoxy)pyrimidin-4-yl)-2,8-diazaspiro[4.5]decane-3-carboxylic acid (Example 35) starting with (S)-2-benzyl 3-ethyl 8-(2-amino-6-((R)-1-(2-bromophenyl)-2,2,2-trifluoroethoxy)pyrimidin-4-yl)-2,8-diazaspiro[4.5]decane-2,3-dicarboxylate.

$^1$H NMR (400 MHz, DMSO-d6): δ ppm 1.43 (h, J=8.5, 6.5 Hz, 4H), 1.80 (dd, J=13.3, 7.4 Hz, 1H), 2.12 (dd, J=13.2, 9.0 Hz, 1H), 2.48 (d, J=1.8 Hz, 1H), 2.95 (d, J=11.7 Hz, 1H), 3.08 (d, J=11.7 Hz, 1H), 3.37 (d, J=16.1 Hz, 1H), 3.48 (d, J=11.2 Hz, 3H), 3.79 (m, 2H), 5.57 (s, 1H), 6.62 (q, J=6.9 Hz, 1H), 7.27 (dd, J=5.8, 3.3 Hz, 1H), 7.51 (m, 7H). LCMS (MH+): 563.

Example 42b (S)-8-(2-amino-6-((R)-2,2,2-trifluoro-1-(3'-fluoro-[1,1'-biphenyl]-2-yl)ethoxy)pyrimidin-4-yl)-2,8-diazaspiro[4.5]decane-3-carboxylic acid

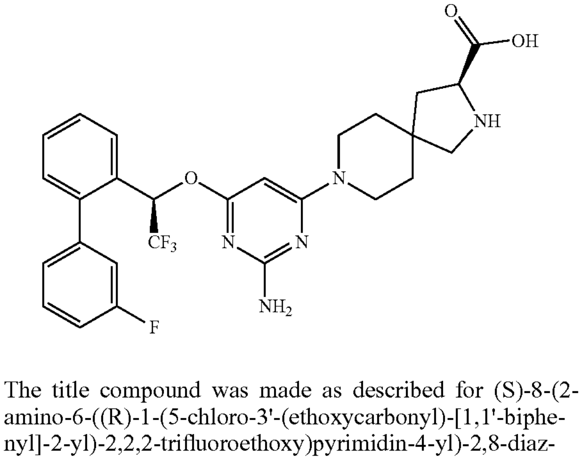

The title compound was made as described for (S)-8-(2-amino-6-((R)-1-(5-chloro-3'-(ethoxycarbonyl)-[1,1'-biphenyl]-2-yl)-2,2,2-trifluoroethoxy)pyrimidin-4-yl)-2,8-diazaspiro[4.5]decane-3-carboxylic acid (Example 35) starting with (S)-2-benzyl 3-ethyl 8-(2-amino-6-((R)-1-(2-bromophenyl)-2,2,2-trifluoroethoxy)pyrimidin-4-yl)-2,8-diazaspiro[4.5]decane-2,3-dicarboxylate.

$^1$H NMR (400 MHz, DMSO-d6): δ ppm 0.89 (m, 1H), 1.30 (d, J=16.3 Hz, 3H), 1.60 (q, J=5.9 Hz, 4H), 2.05 (dd, J=13.4, 7.2 Hz, 1H), 2.32 (dd, J=13.4, 9.1 Hz, 1H), 3.11 (d, J=11.7 Hz, 1H), 3.24 (d, J=11.7 Hz, 1H), 3.47 (ddt, J=20.6, 13.4, 6.5 Hz, 2H), 3.64 (ddt, J=15.8, 10.8, 5.2 Hz, 2H), 4.07 (dd, J=9.2, 7.1 Hz, 1H), 5.51 (s, 1H), 6.68 (q, J=6.9 Hz, 1H), 7.25 (m, 4H), 7.48 (m, 3H), 7.71 (m, 1H). LCMS (MH+): 546.

Example 43

(S)-8-(5-((R)-1-(4-chloro-2-(3-methyl-1H-pyrazol-1-yl)phenyl)-2,2,2-trifluoroethoxy)pyridazin-3-yl)-2,8-diazaspiro[4.5]decane-3-carboxylic acid

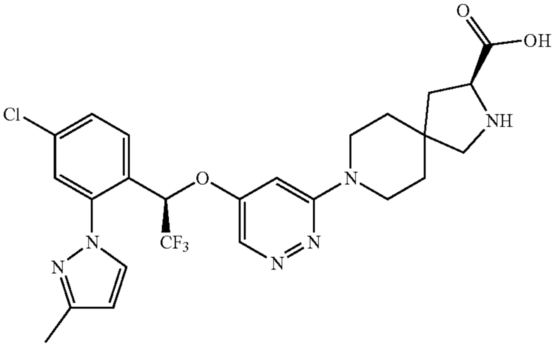 [SMILES: Cc1ccn(-c2cc(Cl)ccc2[C@@H](Oc2cnnc(N3CCC4(CC3)CN[C@H](C(=O)O)C4)c2)C(F)(F)F)n1]

Step 1: To (R)-1-(4-chloro-2-(3-methyl-1H-pyrazol-1-yl)phenyl)-2,2,2-trifluoroethanol(1.00 g, 3.44 mmol, Intermediate 3) in 1,4-dioxane (100 mL) was added 3,5-dichloropyridazine (512 mg, 3.44 mmol) and $Cs_2CO_3$ (3.36 g, 10.3 mmol). The reaction mixture was then heated at 100° C. for 182 h. During this time, the reaction was charged with additional 3,5-dichloropyridazine (2.56 g, 17.2 mmol) at t=86 h. Then the reaction mixture was cooled to RT, diluted with water, and extracted with EtOAc. The combined organic layers were dried over $Na_2SO_4$, filtered, and concentrated in vacuo. Purification on a 120 g Isco RediSep silica cartridge (EtOAc/heptane) provided 3-chloro-5-[(1R)-1-[4-chloro-2-(3-methylpyrazol-1-yl)phenyl]-2,2,2-trifluoroethoxy]pyridazine as a 3:2 mixture of (R)-3-chloro-5-(1-(4-chloro-2-(3-methyl-1H-pyrazol-1-yl)phenyl)-2,2,2-trifluoroethoxy)pyridazine and (R)-5-chloro-3-(1-(4-chloro-2-(3-methyl-1H-pyrazol-1-yl)phenyl)-2,2,2-trifluoroethoxy)pyridazine respectively.

Step 2: To a solution of the (R)-3-chloro-5-(1-(4-chloro-2-(3-methyl-1H-pyrazol-1-yl)phenyl)-2,2,2-trifluoroethoxy)pyridazine/(R)-5-chloro-3-(1-(4-chloro-2-(3-methyl-1H-pyrazol-1-yl)phenyl)-2,2,2-trifluoroethoxy)pyridazine mixture from step 1 in 1,4-dioxane (19 mL) was added 2-benzyl 3-ethyl 2,8-diazaspiro[4.5]decane-2,3-dicarboxylate (980 mg, 2.83 mmol), $Cs_2CO_3$ (2.30 g, 7.07 mmol), $Pd_2(dba)_3$ (432 mg, 0.471 mmol), and rac-BINAP (587 mg, 0.940 mmol), and the reaction mixture was heated to 60° C. for 60 h. Then the reaction mixture was cooled to RT, filtered through celite, washed with EtOAc, and the filtrate concentrated in vacuo. Purification on a 120 g Isco RediSep silica cartridge (EtOAc/heptane) provided (S)-2-benzyl 3-ethyl 8-(5-((R)-1-(4-chloro-2-(3-methyl-1H-pyrazol-1-yl)phenyl)-2,2,2-trifluoroethoxy)pyridazin-3-yl)-2,8-diazaspiro[4.5]decane-2,3-dicarboxylate as a white solid.

Step 3: N-CBZ Deprotection was accomplished via Method B to provide (S)-8-(5-((R)-1-(4-chloro-2-(3-methyl-1H- pyrazol-1-yl)phenyl)-2,2,2-trifluoroethoxy)pyridazin-3-yl)-3-(ethoxycarbonyl)-2,8-diazaspiro[4.5]decane-2-carboxylic acid as a white solid.

Step 4: Hydrolysis of (S)-8-(5-((R)-1-(4-chloro-2-(3-methyl-1H-pyrazol-1-yl)phenyl)-2,2,2- trifluoroethoxy) pyridazin-3-yl)-3-(ethoxycarbonyl)-2,8-diazaspiro[4.5]decane-2-carboxylic acid using the LiOH general method provided the title compound as an off-white solid.

$^1$H NMR (400 MHz, MeOH-d4): δ ppm 1.66-1.80 (m, 4 H), 2.11 (dd, J=13.45, 7.05 Hz, 1 H), 2.30-2.40 (m, 1 H), 2.36 (s, 3 H), 3.16 (d, J=11.81 Hz, 1 H), 3.25-3.35 (m, 1 H), 3.37-3.65 (m, 4 H), 4.03-4.19 (m, 1 H), 6.39 (d, J=2.34 Hz, 1 H), 6.63 (d, J=2.39 Hz, 1 H), 6.95 (q, J=6.39 Hz, 1 H), 7.43-7.57 (m, 2 H), 7.76 (d, J=8.35 Hz, 1 H), 8.22 (d, J=2.39 Hz, 1 H), 8.63 (d, J=2.49 Hz, 1 H). LCMS (MH+): 551

Example 44

(S)-8-(4-((R)-2,2,2-trifluoro-1-(2-(3-methyl-1H-pyrazol-1-yl)phenyl)ethoxy)pyridin-2-yl)-2,8-diazaspiro[4.5]decane-3-carboxylic acid and

Example 45

(S)-8-(4-((R)-1-(4-chloro-2-(3-methyl-1H-pyrazol-1-yl)phenyl)-2,2,2-trifluoroethoxy)pyridin-2-yl)-2,8-diazaspiro[4.5]decane-3-carboxylic acid

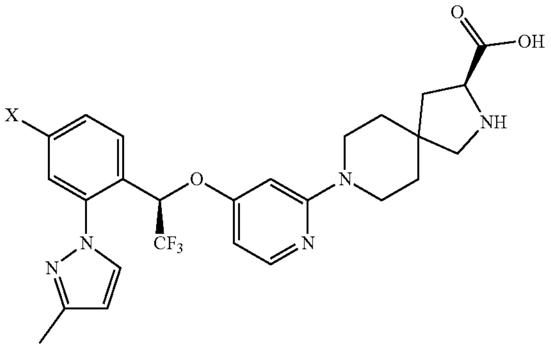

Example 45 X = Cl
Example 44: X = H

Step 1: To a solution of 2-chloro-4-nitropyridine (200 mg, 1.00 mmol) in 1,4-dioxane (6 mL) was added (R)-1-(4-chloro-2-(3-methyl-1H-pyrazol-1-yl)phenyl)-2,2,2-trifluoroethanol (368 mg, 1.27 mmol), and $Cs_2CO_3$ (828 mg, 2.54 mmol). The reaction was heated to 80° C. for 12 h, then cooled to RT, diluted with water, and extracted with EtOAc. The combined organic layers were dried over $Na_2SO_4$, filtered, and concentrated in vacuo. Purification by normal phase silica gel column (EtOAc/heptane) provided (R)-2-chloro-4-(1-(4-chloro-2-(3-methyl-1H-pyrazol-1-yl)phenyl)-2,2,2-trifluoroethoxy)pyridine as an off-white solid.

Step 2: To a solution of (R)-2-chloro-4-(1-(4-chloro-2-(3-methyl-1H-pyrazol-1-yl)phenyl)-2,2,2-trifluoroethoxy)pyridine (227 mg, 0.57 mmol) in 1,4-dioxane (5 mL) was added 2-benzyl 3-ethyl 2,8-diazaspiro[4.5]decane-2,3-dicarboxylate (237 mg, 0.68 mmol), $Cs_2CO_3$ (557 mg, 1.71 mmol), BINAP (142 mg, 0.23 mmol), and $Pd_2(dba)_3$. The reaction was heated to 60° C. for 3 d, then cooled to RT, and concentrated in vacuo. Purification by normal phase silica gel column (EtOAc/heptane) provided 2-benzyl 3-ethyl 8-(4-((R)-1-(4-chloro-2-(3-methyl-1H-pyrazol-1-yl)phenyl)-2,2,2-trifluoroethoxy)pyridin-2-yl)-2,8-diazaspiro[4.5]decane-2,3-dicarboxylate as a white solid.

Step 3: Hydrolysis of 2-benzyl 3-ethyl 8-(4-((R)-1-(4-chloro-2-(3-methyl-1H-pyrazol-1-yl)phenyl)-2,2,2-trifluoroethoxy)pyridin-2-yl)-2,8-diazaspiro[4.5]decane-2,3-dicarboxylate using the LiOH general method provided 2-((benzyloxy)carbonyl)-8-(4-((R)-1-(4-chloro-2-(3-methyl-1H-pyrazol-1-yl)phenyl)-2,2,2-trifluoroethoxy)pyridin-2-yl)-2,8-diazaspiro[4.5]decane-3-carboxylic acid.

Step 4: N-CBZ Deprotection was accomplished via Method A followed by normal phase silica gel purification (EtOAc: heptane) providing both of the title compounds as white solids (120 mg and 75 mg for the des-chloro analog).

8-(4-((R)-2,2,2-trifluoro-1-(2-(3-methyl-1H-pyrazol-1-yl)phenyl)ethoxy)pyridin-2-yl)-2,8-diazaspiro[4.5]decane-3-carboxylic acid:

$^1$H NMR (400 MHz, MeOH-d4): δ ppm 1.52-1.76 (m, 4 H) 1.95-2.15 (m, 1 H) 2.23-2.37 (m, 1 H) 2.39 (s, 3 H) 2.87 (s, 1 H) 3.05-3.16 (m, 1 H) 3.19-3.27 (m, 1 H) 3.38-3.72 (m, 4 H) 3.77-4.13 (m, 1 H) 6.39 (d, J=2.44 Hz, 1 H) 6.44-6.52 (m, 1 H) 6.79 (d, J=2.20 Hz, 1 H) 6.83-6.97 (m, 1 H) 7.43-7.51 (m, 1 H) 7.54 (d, J=2.05 Hz, 1 H) 7.66 (d, J=8.74 Hz, 1 H) 7.81-8.00 (m, 2 H). LCMS (MH+): 550.

8-(4-((R)-2,2,2-trifluoro-1-(2-(3-methyl-1H-pyrazol-1-yl)phenyl)ethoxy)pyridin-2-yl)-2,8-diazaspiro[4.5]decane-3-carboxylic acid:

$^1$H NMR (400 MHz, MeOH-d4): δ ppm 1.47-1.71 (m, 4 H) 1.95-2.04 (m, 1 H) 2.21-2.31 (m, 1 H) 2.39 (s, 3 H) 2.73 (s, 1 H) 3.02 (d, J=11.52 Hz, 1 H) 3.14-3.22 (m, 1 H) 3.37-4.03 (m, 4 H) 6.36 (d, J=2.34 Hz, 1 H) 6.43-6.51 (m, 1 H) 6.72-6.85 (m, 2 H) 7.30-7.51 (m, 3 H) 7.52-7.61 (m, 1 H) 7.67 (d, J=7.86 Hz, 1 H) 7.81 (d, J=2.34 Hz, 1 H) 7.86-7.91 (m, 1 H). LCMS (MH+): 516.

Example 46

8-(4-((R)-1-(4-chloro-2-(3-methyl-1H-pyrazol-1-yl)phenyl)-2,2,2-trifluoroethoxy)-6-phenoxypyrimidin-2-yl)-2,8-diazaspiro[4.5]decane-3-carboxylic acid

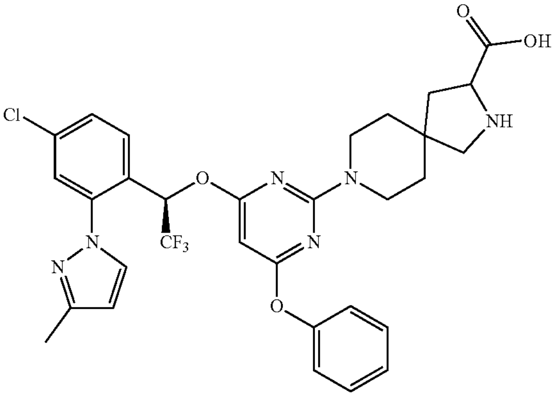

Step 1: To a solution of 2-benzyl 3-ethyl 8-(4-chloro-6-((R)-1-(4-chloro-2-(3-methyl-1H-pyrazol-1-yl)phenyl)-2,2,2-trifluoroethoxy)pyrimidin-2-yl)-2,8-diazaspiro[4.5]decane-2,3-dicarboxylate (by-product from Step 3, Example 30a) (250 mg, 0.347 mmol) in 1,4-dioxane (9.0 mL) was added phenol (1.00 g, 10.6 mmol) and $Cs_2CO_3$ (3.65 g, 11.2 mmol). The reaction was heated at 80° C. for 12 h, then cooled to RT diluted with water, and extracted with EtOAc. The combined organic layers were dried over $Na_2SO_4$, filtered, and concentrated in vacuo. Purification on a 12 g Isco RediSep silica cartridge (EtOAc/heptane) provided 2-benzyl 3-ethyl 8-(4-((R)-1-(4-chloro-2-(3-methyl-1H-pyrazol-1-yl)phenyl)-2,2,2-trifluoroethoxy)-6-phenoxypyrimidin-2-yl)-2,8-diazaspiro[4.5]decane-2,3-dicarboxylate as an off-white solid.

Step 2: N-CBZ Deprotection was accomplished via Method A to provide (ethyl 8-(4-((R)-1-(4-chloro-2-(3-methyl-1H-pyrazol-1-yl)phenyl)-2,2,2-trifluoroethoxy)-6-phenoxypyrimidin-2-yl)-2,8-diazaspiro[4.5]decane-3-carboxylate as a white solid.

Step 3: Hydrolysis of ethyl 8-(4-((R)-1-(4-chloro-2-(3-methyl-1H-pyrazol-1-yl)phenyl)-2,2,2-trifluoroethoxy)-6-phenoxypyrimidin-2-yl)-2,8-diazaspiro[4.5]decane-3-carboxylate using the LiOH general method provided the title compound as an off-white solid.

$^1$H NMR (400 MHz, MeOH-d4): δ ppm 1.36 (br. s., 4 H), 1.90-1.99 (m, 1 H), 2.11-2.21 (m, 1H), 2.26 (s, 3 H), 2.92-3.17 (m, 2 H), 3.24-3.60 (m, 4 H), 3.96 (dd, J=9.13, 6.88 Hz, 1 H), 5.44 (d, J=2.29 Hz, 1 H), 6.27-6.33 (m, 1 H), 7.00 (d, J=8.00 Hz, 2 H), 7.08-7.16 (m, 1 H), 7.24-7.32 (m, 2 H), 7.38 (dd, J=8.44, 1.90 Hz, 1 H), 7.44 (d, J=2.00 Hz, 1 H), 7.54-7.62 (m, 1 H), 7.64 (d, J=8.49 Hz, 1 H), 7.81 (d, J=2.25 Hz, 1 H). LCMS (MH+): 642.

Example 47

(3S)-8-(2-Amino-6-(1-(2,6-dibromophenyl)-2,2,2-trifluoroethoxy)pyrimidin-4-yl)-2,8-diazaspiro[4.5]decane-3-carboxylic acid

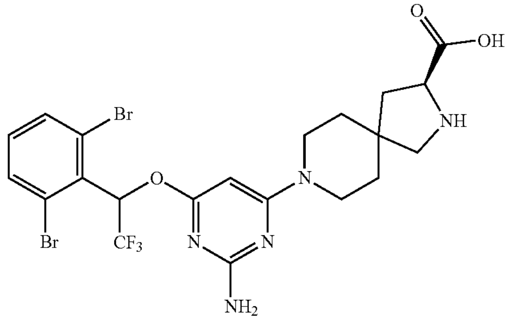 [SMILES: Nc1nc(OC(c2c(Br)cccc2Br)C(F)(F)F)cc(N2CCC3(CC2)CN[C@H](C(=O)O)C3)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d) starting with 1-(2,6-dibromophenyl)-2,2,2-trifluoroethanol.

$^1$H NMR (400 MHz, MeOH-d4): δ ppm 1.29 (m, 1H), 1.62 (q, J=5.7 Hz, 4H), 2.06 (m, 1H), 2.33 (dd, J=13.5, 9.2 Hz, 1H), 3.13 (d, J=11.7 Hz, 1H), 3.26 (d, J=11.7 Hz, 1H), 3.49 (m, 2H), 3.65 (dq, J=10.7, 5.4 Hz, 2H), 4.09 (dd, J=9.2, 7.2 Hz, 1H), 5.56 (s, 1H), 7.15 (t, J=8.0 Hz, 1H), 7.28 (q, J=8.0 Hz, 1H), 7.69 (m, 2H). LCMS (MH+): 611.

Example 48

(S)-8-(2-Amino-6-((R)-1-(2,5-dibromophenyl)-2,2,2-trifluoroethoxy)pyrimidin-4-yl)-2,8-diazaspiro[4.5]decane-3-carboxylic acid

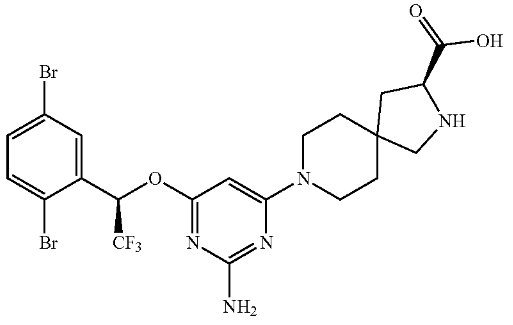 [SMILES: Nc1nc(O[C@H](c2cc(Br)ccc2Br)C(F)(F)F)cc(N2CCC3(CC2)CN[C@H](C(=O)O)C3)n1]

The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d) starting with 1-(2,5-dibromophenyl)-2,2,2-trifluoroethanol.

$^1$H NMR (400 MHz, MeOH-d4): δ ppm 1.62 (q, J=5.8, 5.2 Hz, 4H), 2.06 (dd, J=13.5, 7.2 Hz, 1H), 2.34 (dd, J=13.4, 9.2 Hz, 1H), 3.13 (d, J=11.7 Hz, 1H), 3.26 (d, J=11.8 Hz, 1H), 3.50 (m, 2H), 3.66 (ddt, J=15.0, 10.7, 5.2 Hz, 2H), 4.09 (dd, J=9.2, 7.2 Hz, 1H), 4.83 (s, 1H), 5.58 (s, 1H), 6.97 (q, J=6.6 Hz, 1H), 7.47 (dd, J=8.6, 2.4 Hz, 1H), 7.58 (d, J=8.6 Hz, 1H), 7.69 (d, J=2.4 Hz, 1H). LCMS (MH+): 611.

Example 49

(S)-8-(2-Amino-6-((R)-2,2,2-trifluoro-1-(3'-(methylsulfonyl)-4-propyl-[1,1'-biphenyl]-2-yl)ethoxy)pyrimidin-4-yl)-2,8-diazaspiro[4.5]decane-3-carboxylic acid

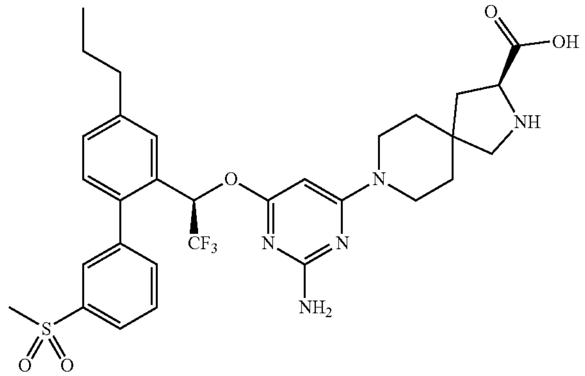 [SMILES: CCCc1ccc(-c2cccc(S(C)(=O)=O)c2)c([C@@H](Oc2cc(N3CCC4(CC3)CN[C@H](C(=O)O)C4)nc(N)n2)C(F)(F)F)c1]

Step 1: To a solution of (S)-2-tert-butyl 3-ethyl 8-(2-amino-6-((R)-1-(2-bromo-5-chlorophenyl)-2,2,2-trifluoroethoxy)pyrimidin-4-yl)-2,8-diazaspiro[4.5]decane-2,3-dicarboxylate (660 mg, 0.95 mmol) in dioxane (12 mL) was added (3-(methylsulfonyl)phenyl)boronic acid (285 mg, 1.43 mmol), $Pd_2(dppf)Cl_2$ (70 mg, 0.095 mmol) and $Na_2CO_3$(6.0 mL, 2.0 M, aq). The reaction was heated to 90° C. for 2 h, then cooled to RT, concentrated in vacuo. The residue was taken up in $CH_2Cl_2$, washed with brine, and extracted with $CH_2Cl_2$. The combined organic layers were dried over $Na_2SO_4$. Purification by normal phase silica gel column (EtOAc/heptane) provided (S)-2-tert-butyl 3-ethyl 8-(2-amino-6-((R)-1-(4-chloro-3'-(methylsulfonyl)-[1,1'-biphenyl]-2-yl)-2,2,2-trifluoroethoxy)pyrimidin-4-yl)-2,8-diazaspiro[4.5]decane-2,3-dicarboxylate as a white solid.

Step 2: To a solution of (S)-2-tert-butyl 3-ethyl 8-(2-amino-6-((R)-1-(4-chloro-3'-(methylsulfonyl)-[1,1'-biphenyl]-2-yl)-2,2,2-trifluoroethoxy)pyrimidin-4-yl)-2,8-diazaspiro [4.5]decane-2,3-dicarboxylate (500 mg, 0.65 mmol) in DMF (10 mL) was added tributyl(prop-1-enyl)stannane (258 mg, 0.78 mmol), $Pd(t\text{-}Bu_3P)_2$ (33 mg, 0.065 mmol), and CsF (217 mg, 1.43 mmol). The reaction was heated to 130° C. in a sealed tube for 3 h, then cooled to RT. The reaction mixture was partitioned between water and $CH_2Cl_2$, and extracted. The combined organic layers were washed with brine, dried over $Na_2SO_4$, filtered, and concentrated in vacuo. Purification by normal phase silica gel column (EtOAc/heptane) provided (S)-2-tert-butyl 3-ethyl 8-(2-amino-6-((R)-2,2,2-trifluoro-1-(3'-(methylsulfonyl)-4-(prop-1-en-1-yl)-[1,1'-biphenyl]-2-yl)ethoxy)pyrimidin-4-yl)-2,8-diazaspiro[4.5]decane-2,3-dicarboxylate as a white solid.

Step 3: To a solution of (S)-2-tert-butyl 3-ethyl 8-(2-amino-6-((R)-2,2,2-trifluoro-1-(3'-(methylsulfonyl)-4-(prop-1-en-1-yl)-[1,1'-biphenyl]-2-yl)ethoxy)pyrimidin-4-yl)-2,8-diazaspiro[4.5]decane-2,3-dicarboxylate (200 mg, 0.26 mmol) in EtOH (10 mL) was added 10% Pd/C (200 mg) and the reaction mixture was stirred under 1 atm $H_2$ for 12 h. The solids were filtered and the filtrate was concentrated to afford (S)-2-tert-butyl 3-ethyl 8-(2-amino-6-((R)-2,2,2-trifluoro-1-(3'-(methylsulfonyl)-4-propyl-[1,1'-biphenyl]-2-yl)ethoxy) pyrimidin-4-yl)-2,8-diazaspiro[4.5]decane-2,3-dicarboxylate as a white solid that is used directly without further purification.

Step 4: To a solution of (S)-2-tert-butyl 3-ethyl 8-(2-amino-6-((R)-2,2,2-trifluoro-1-(3'-(methylsulfonyl)-4-propyl-[1,1'-biphenyl]-2-yl)ethoxy)pyrimidin-4-yl)-2,8-diazaspiro [4.5] decane-2,3-dicarboxylate in $CH_2Cl_2$ (4 mL) was added TFA (2.0 mL) dropwise at 0° C. The reaction mixture was stirred at RT for 2 h, then concentrated in vacuo. The pH was adjusted to 7-8 with saturated aqueous $NaHCO_3$ solution. The aqueous layer was extracted with $CH_2Cl_2$. The combined organic layers were washed with brine, dried over $Na_2SO_4$, filtered, and concentrated in vacuo. Purification by normal phase silica gel column ($CH_2Cl_2$/MeOH) provided the title compound as a white solid.

$^1$H NMR (400 MHz, MeOH-d4): δ ppm 8.41 (m, 1H), 8.04 (d, J=7.8 Hz, 1H), 7.79 (t, J=7.8 Hz, 1H), 7.73-7.71 (m, 1H), 7.53 (s, 1H), 7.33 (d, J=7.8 Hz, 1H), 7.20 (d, J=7.8 Hz, 1H), 6.61 (q, J=6.7 Hz, 1H), 5.61 (s, 1H), 4.10 (t, J=8.4 Hz, 1H), 3.72-3.63 (m, 2H), 3.55-3.46 (m, 2H), 3.26 (m, 1H), 3.21 (s, 3H), 3.16-3.13 (m, 1H), 2.66 (t, J=7.6 Hz, 2H), 2.38-2.32 (m, 1H), 2.10-2.05 (m, 2H), 1.65-1.60 (m, 3H). LCMS (MH+): 649.

Example 50

(S)-8-(2-Amino-6-((R)-2,2,2-trifluoro-1-(3'-(methylsulfonyl)-4-((E)-prop-1-en-1-yl)-[1,1'-biphenyl]-2-yl)ethoxy)pyrimidin-4-yl)-2,8-diazaspiro[4.5]decane-3-carboxylic acid

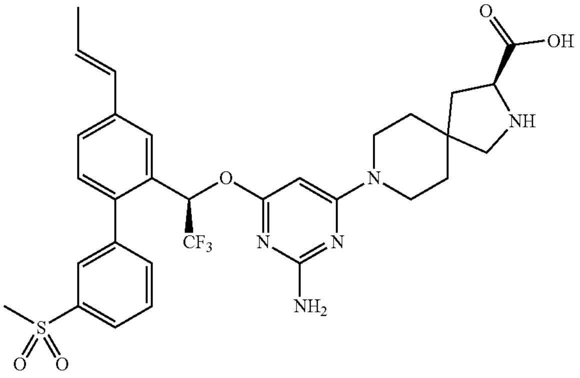 [SMILES: C/C=C/c1ccc(-c2cccc(S(C)(=O)=O)c2)c([C@@H](Oc2cc(N3CCC4(CC3)CN[C@H](C(=O)O)C4)nc(N)n2)C(F)(F)F)c1]

The title compound was prepared as described for (S)-2-tert-butyl 3-ethyl 8-(2-amino-6-((R)-2,2,2-trifluoro-1-(3'-(methylsulfonyl)-4-(prop-1-en-1-yl)-[1,1'-biphenyl]-2-yl) ethoxy)pyrimidin-4-yl)-2,8-diazaspiro[4.5]decane-2,3-dicarboxylate (Example 49) by omitting the olefin hydrogenation reaction of Step 3.

$^1$H NMR (400 MHz, CD3OD-d4): δ ppm 8.46-8.42 (m, 1H), 8.06-8.03 (m, 1H), 7.82-7.71 (m, 2H), 7.64 (s, 1H), 7.45 (dd, J1=8.2 Hz, J2=33.2 Hz, 1H), 7.25 (dd, J1=7.9 Hz, J2=23.9 Hz, 1H), 6.64-6.62 (m, 1H), 6.49-6.45 (m, 1H), 6.39-5.86 (m, 1H), 5.62 (d, J=5.3 Hz, 1H), 4.12-4.08 (m, 1H), 3.70-3.62 (m, 2H), 3.54-3.45 (m, 2H), 3.29-3.26 (m, 1H), 3.22-3.21 (m, 3H), 3.16-3.13 (m, 1H), 2.37-2.31 (m, 1H), 2.10-2.05 (m, 1H), 1.91-1.87 (m, 3H), 1.62 (m, 4H). LCMS (MH+): 647.

Example 51a

(S)-8-(6-((R)-1-([1,1':4',1"-terphenyl]-2'-yl)-2,2,2-trifluoroethoxy)-2-aminopyrimidin-4-yl)-2,8-diazaspiro[4.5]decane-3-carboxylic acid

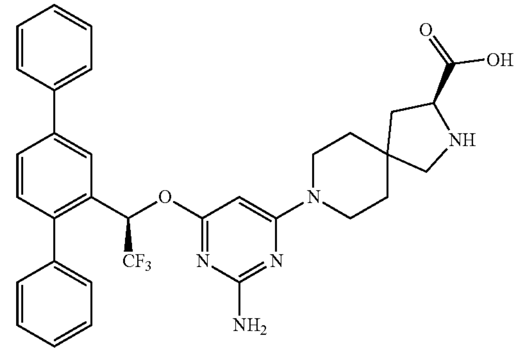 [SMILES: Nc1nc(O[C@H](c2cc(-c3ccccc3)ccc2-c2ccccc2)C(F)(F)F)cc(N2CCC3(CC2)CN[C@H](C(=O)O)C3)n1]

Step 1: To a solution of (S)-2-tert-butyl 3-ethyl 8-(2-amino-6-((R)-1-(2,5-dibromophenyl)-2,2,2-trifluoroethoxy)pyrimidin-4-yl)-2,8-diazaspiro[4.5]decane-2,3-dicarboxylate (660 mg, 0.95 mmol) in dioxane (12 mL) was added phenyl boronic acid (290 mg, 2.4 mmol), $Pd_2(dppf)Cl_2$ (70 mg, 0.095 mmol), and $Na_2CO_3$(6.0 mL, 2.0 M, aq). The reaction mixture was heated to 90° C. for 2 h, then cooled to RT, concentrated in vacuo, and extracted with $CH_2Cl_2$. The combined organic layers were washed with brine, and dried over $Na_2SO_4$. Purification by normal phase silica gel column (EtOAc/heptane) provided (S)-2-tert-butyl 3-ethyl 8-(6-((R)-1-([1,1':4',1"-terphenyl]-2'-yl)-2,2,2-trifluoroethoxy)-2-aminopyrimidin-4-yl)-2,8-diazaspiro[4.5]decane-2,3-dicarboxylate as a white solid.

Step 2: To a solution of (S)-2-tert-butyl 3-ethyl 8-(6-((R)-1-([1,1':4',1"-terphenyl]-2'-yl)-2,2,2-trifluoroethoxy)-2-aminopyrimidin-4-yl)-2,8-diazaspiro[4.5]decane-2,3-dicarboxylate (550 mg, 0.75 mmol) in $CH_2Cl_2$ (4 mL) was added TFA (2.0 mL) dropwise at 0° C. The reaction mixture was stirred at RT for 2 h, and concentrated in vacuo. The pH was adjusted to 7-8 with a saturated aqueous $NaHCO_3$ solution. The aqueous layer was extracted with $CH_2Cl_2$. The organic layer is wahed with brine, dried over $Na_2SO_4$, filtered, and concentrated in vacuo. Purification by normal phase silica gel column ($CH_2Cl_2$/MeOH) provided (S)-ethyl 8-(6-((R)-1-([1,1':4',1"-terphenyl]-2'-yl)-2,2,2-trifluoroethoxy)-2-aminopyrimidin-4-yl)-2,8-diazaspiro[4.5]decane-3-carboxylate as a white solid.

Step 3: Hydrolysis of (S)-ethyl 8-(6-((R)-1-([1,1':4',1"-terphenyl]-2'-yl)-2,2,2-trifluoroethoxy)-2-aminopyrimidin-4-yl)-2,8-diazaspiro[4.5]decane-3-carboxylate using the LiOH general method provided the title compound as a white solid. $^1$H NMR (400 MHz, $CD_3OD$-d4): δ ppm 7.91 (s, 1H), 7.70 (dd, J1=6.08 Hz, J=1.88 Hz, 1H),7.62 (m,2H), 7.56-7.44 (m,7H),7.39-7.35 (m, 2H), 6.72 (q, J=6.52 Hz, 1H), 5.48(s, 1H), 4.18 (q, J=6.96 Hz, 2H), 3.67 (m, 1H), 3.58 (m, 2H),3.41(m,2H), 2.98 (d, J=10.96 Hz, 1H), 2.69 (d,J=11.24 Hz,1H), 2.12-2.06 (m,1H), 1.83-1.78 (m, 1H), 1.52 (m, 4H). LCMS (MH+): 604.5

Example 51b (S)-8-(6-((R)-1-([1,1':3',1"-terphenyl]-2'-yl)-2,2,2-trifluoroethoxy)-2-aminopyrimidin-4-yl)-2,8-diazaspiro[4.5]decane-3-carboxylic acid

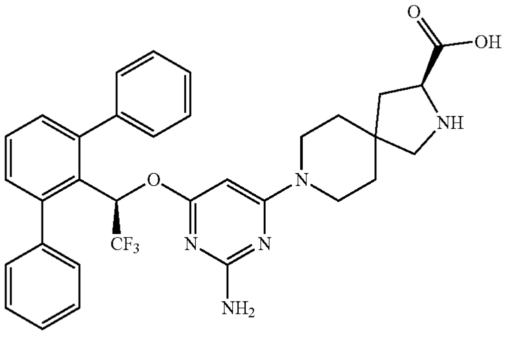 [SMILES: Nc1nc(O[C@H](c2c(-c3ccccc3)cccc2-c2ccccc2)C(F)(F)F)cc(N2CCC3(CC2)CN[C@H](C(=O)O)C3)n1]

The title compound was prepared as described for (S)-8-(6-((R)-1-([1,1':4',1"-terphenyl]-2'-yl)-2,2,2-trifluoroethoxy)-2-aminopyrimidin-4-yl)-2,8-diazaspiro[4.5]decane-3-carboxylic acid (Example 51a) starting with (S)-2-tert-butyl 3-ethyl 8-(2-amino-6-((R)-1-(2,6-dibromophenyl)-2,2,2-trifluoroethoxy)pyrimidin-4-yl)-2,8-diazaspiro[4.5]decane-2,3-dicarboxylate (product of Step 4, example 63ao).

$^1$H NMR (400 MHz, $CD_3OD$-d4): δ ppm 1.32 (dd, J=15.5, 7.9 Hz, 1H), 1.70 (dd, J=7.9, 4.3 Hz, 5H), 2.12 (m, 1H), 2.49 (ddd, J=12.3, 9.0, 2.6 Hz, 1H), 3.25 (dd, J=11.9, 2.2 Hz, 1H), 3.60 (s, 9H), 4.48 (t, J=8.6 Hz, 1H), 6.89 (q, J=7.8 Hz, 1H), 7.21 (d, J=7.6 Hz, 2H), 7.42 (m, 14H). LCMS (MH+): 604.

Example 52a (S)-8-(2-Amino-6-((R)-1-(3,4-dimethyl-3"-(methylsulfonyl)-[1,1':3',1"-terphenyl]-4'-yl)-2,2,2-trifluoroethoxy)pyrimidin-4-yl)-2,8-diazaspiro[4.5]decane-3-carboxylic acid

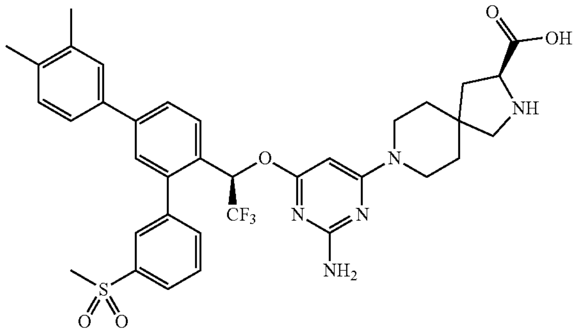 [SMILES: Cc1ccc(-c2ccc([C@@H](Oc3cc(N4CCC5(CC4)CN[C@H](C(=O)O)C5)nc(N)n3)C(F)(F)F)c(-c3cccc(S(C)(=O)=O)c3)c2)cc1C]

Step 1: To a solution of (S)-2-benzyl 3-ethyl 8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-2,3-dicarboxylate (product of Step 1, Example 34w) (273 mg, 0.34 mmol) in 1,4-dioxane (5 mL) was added (3,4-dimethylphenyl)boronic acid (77 mg, 0.51 mmol), $KHCO_3$ (341 mg, 3.40 mmol), and $Pd(PCy_3)_2$ (34 mg, 0.051 mmol). The reaction was heated to 100° C. for 44 h. The reaction was charged with additional $Pd(PCy_3)_2$ (68 mg, 0.10 mmol) at t=16 and 39 h. Then the reaction was cooled to RT and extracted with EtOAc. The combined organic layers were dried over $Na_2SO_4$, filtered, and concentrated in vacuo. Purification on a 12 g Isco RediSep silica cartridge (EtOAc/heptane) provided (S)-2-benzyl 3-ethyl 8-(2-amino-6-((R)-1-(3,4-dimethyl-3"-(methylsulfonyl)-[1,1':3',1"-terphenyl]-4'-yl)-2,2,2-trifluoroethoxy)pyrimidin-4-yl)-2,8-diazaspiro[4.5]decane-2,3-dicarboxylate as an white solid.

Step 2: N-CBZ Deprotection was accomplished via Method B to provide (S)-ethyl 8-(2-amino-6-((R)-1-(3,4-dimethyl-3"-(methylsulfonyl)-[1,1':3',1"-terphenyl]-4'-yl)-2,2,2-trifluoroethoxy) pyrimidin-4-yl)-2,8-diazaspiro[4.5]decane-3-carboxylate as a white solid.

Step 3: Hydrolysis of (S)-ethyl 8-(2-amino-6-((R)-1-(3,4-dimethyl-3"-(methylsulfonyl)-[1,1':3',1"-terphenyl]-4'-yl)-2,2,2-trifluoroethoxy) pyrimidin-4-yl)-2,8-diazaspiro[4.5]decane-3-carboxylate using the LiOH general method provided the title compound as an off-white solid.

Using the generic scheme below, the following examples of Table 16a were prepared as described above for (S)-8-(2-amino-6-((R)-1-(3,4-dimethyl-3"-(methylsulfonyl)-[1,1':3',1"-terphenyl]-4'-yl)-2,2,2-trifluoroethoxy)pyrimidin-4-yl)-2,8-diazaspiro[4.5]decane-3-carboxylic acid (Example 52a).

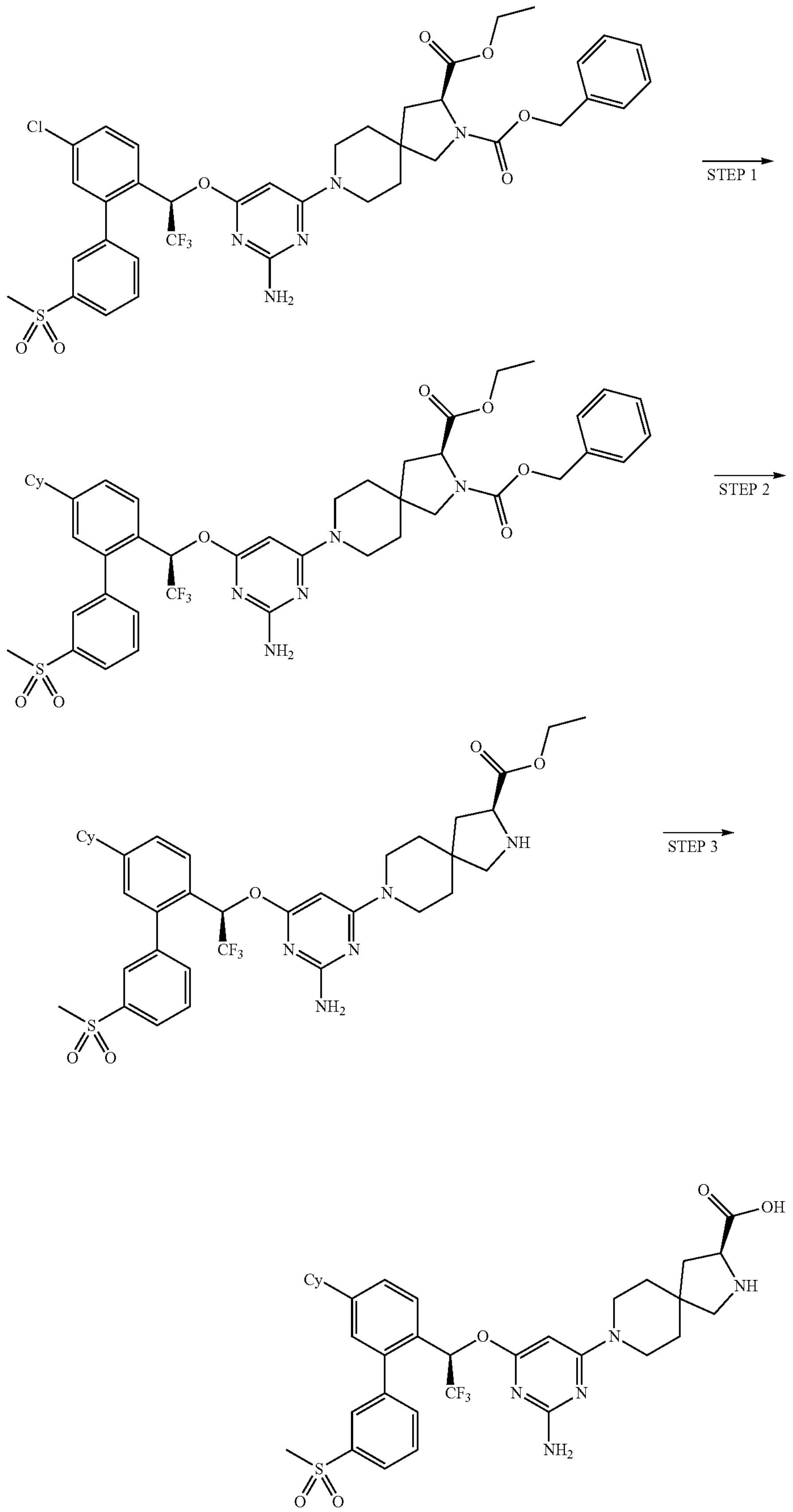
STEP 1
STEP 2
STEP 3

TABLE 16a

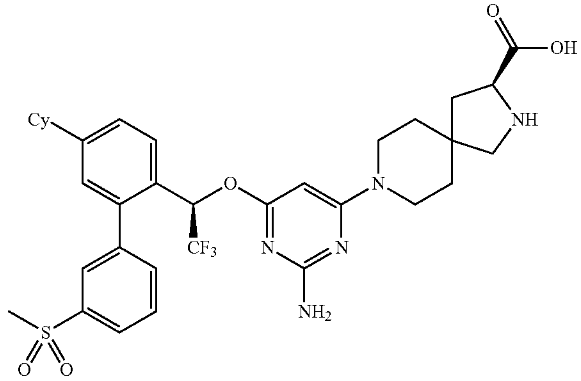

| Ex. No. | Cy | CAS Name | LCMS (MH+) |
|---|---|---|---|
| 52a | 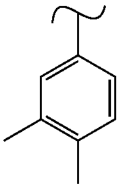 | (S)-8-(2-amino-6-((R)-1-(3,4-dimethyl-3''-(methylsulfonyl)-[1,1':3',1''-terphenyl]-4'-yl)-2,2,2-trifluoroethoxy)pyrimidin-4-yl)-2,8-diazaspiro[4.5]decane-3-carboxylic acid | 710 |
| 52b | 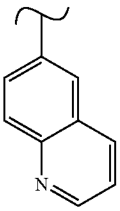 | (S)-8-(2-amino-6-((R)-2,2,2-trifluoro-1-(3'-(methylsulfonyl)-5-(quinolin-6-yl)-[1,1'-biphenyl]-2-yl)ethoxy)pyrimidin-4-yl)-2,8-diazaspiro[4.5]decane-3-carboxylic acid | 733 |

TABLE 16b

NMR Data for Compounds of Table 16a

| Ex. No. | NMR |
|---|---|
| 52a | $^1$H NMR (400 MHz, MeOH-d4): δ ppm 1.46-1.73 (m, 4 H) 2.07 (dd, J = 13.45, 7.15 Hz, 1 H) 2.28 (s, 3 H) 2.30 (s, 3 H) 2.32-2.40 (m, 1 H) 3.14 (d, J = 11.76 Hz, 1 H) 3.22 (s, 3 H) 3.27 (d, J = 11.76 Hz, 1 H) 3.40-3.77 (m, 4 H) 4.09 (dd, J = 9.08, 7.27 Hz, 1 H) 5.62 (s, 1 H) 6.63 (q, J = 6.64 Hz, 1 H) 7.18 (d, J = 7.96 Hz, 1 H) 7.35 (dd, J = 7.81, 1.81 Hz, 1 H) 7.40 (s, 1 H) 7.47 (d, J = 1.85 Hz, 1 H) 7.63-7.72 (m, 1 H) 7.72-7.77 (m, 1 H) 7.80-7.85 (m, 2 H) 8.07 (dt, J = 6.97, 1.96 Hz, 1 H) 8.48 (br. s., 1 H) |
| 52b | $^1$H NMR (400 MHz, MeOH-d4): δ ppm 1.59 (t, J = 5.54 Hz, 4 H) 1.92 (dd, J = 13.13, 7.03 Hz, 1 H) 2.20 (dd, J = 13.15, 9.10 Hz, 1 H) 2.81-3.17 (m, 2 H) 3.24 (s, 3 H) 3.38-3.74 (m, 4 H) 3.84 (dd, J = 8.96, 7.05 Hz, 1 H) 5.64 (s, 1 H) 6.67 (q, J = 6.64 Hz, 1 H) 7.55 (dd, J = 8.35, 4.34 Hz, 1 H) 7.67 (d, J = 1.61 Hz, 1 H) 7.78-7.92 (m, 4 H) 8.04-8.15 (m, 3 H) 8.21 (s, 1 H) 8.41 (dd, J = 8.40, 1.56 Hz, 1 H) 8.54 (br. s., 1 H) 8.84 (dd, J = 4.32, 1.68 Hz, 1 H) |

Example 53

(S)-8-(2-Amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro[4.5]decane-3-carboxylic acid

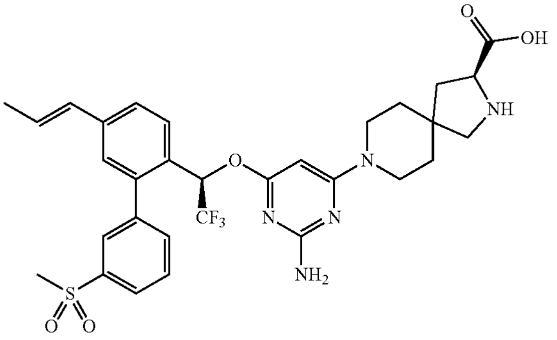 [SMILES: C/C=C/c1ccc([C@@H](Oc2cc(N3CCC4(CC3)CN[C@H](C(=O)O)C4)nc(N)n2)C(F)(F)F)c(-c2cccc(S(C)(=O)=O)c2)c1]

Step 1: To a solution of (S)-2-tert-butyl 3-ethyl 8-(2-amino-6-((R)-1-(2-bromo-4-chlorophenyl)-2,2,2-trifluoroethoxy) pyrimidin-4-yl)-2,8-diazaspiro[4.5]decane-2,3-dicarboxylate (600 mg, 0.89 mmol) in dioxane (12 mL) was added (3-(methylsulfonyl)phenyl)boronic acid (275 mg, 1.3 mmol), $Pd_2(dppf)Cl_2$ (65 mg, 0.095 mmol), and $Na_2CO_3$ (6.0 mL, 2.0 M, aq). The reaction was heated to 90° C. for 2 h, then cooled to RT, and concentrated in vacuo. The residue was taken up in $CH_2Cl_2$, wahed with brine, and dried over $Na_2SO_4$. Purification by normal phase silica gel column (EtOAc/heptane) provides (S)-2-tert-butyl 3-ethyl 8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-2,3-dicarboxylate as a white solid.

Step 2: To a solution (S)-2-tert-butyl 3-ethyl 8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5] decane-2,3-dicarboxylate (500 mg, 0.65 mmol) in DMF (10 mL) was added tributyl(prop-1-enyl)stannane (258 mg, 0.78 mmol), Pd(t-Bu3P) 2 (33 mg, 0.065 mmol), and CsF (217 mg, 1.43 mmol). The reaction was heated to 130° C. in a sealed tube for 3 h, then cooled to RT, and partitioned between between water and $CH_2Cl_2$. The combined organic layers were washed with brine, dried over $Na_2SO_4$, filtered, and concentrated in vacuo. Purification by normal phase silica gel column (EtOAc/heptane) provided (S)-2-tert-butyl 3-ethyl 8-(2-amino-6-((R)-2,2,2-trifluoro-1-(3'-(methylsulfonyl)-5-((E)-prop-1-en-1-yl)-[1,1'-biphenyl]-2-yl) ethoxy)pyrimidin-4-yl)-2,8-diazaspiro[4.5]decane-2,3-dicarboxylate as a white solid.

Step 3: To a solution of (S)-2-tert-butyl 3-ethyl 8-(2-amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro[4.5]decane-2,3-dicarboxylate in $CH_2Cl_2$ (4 mL) was added TFA (2.0 mL) dropwise at 0° C. The reaction mixture was stirred at RT for 2 h, then concentrated in vacuo. The pH was adjusted to 7-8 with a saturated aqueous $NaHCO_3$ solution. The aqueous layer was extracted with $CH_2Cl_2$, washed with brine, dried over $Na_2SO_4$, filtered, and concentrated in vacuo. Purification by normal phase silica gel column ($CH_2Cl_2$/MeOH) provided (S)-ethyl 8-(2-amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro[4.5]decane-3-carboxylate as a white solid.

Step 4: Hydrolysis of (S)-8-(2-amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro [4.5]decane-3-carboxylic acid using the LiOH general method provided the title compound as an off-white solid.

$^1$H NMR (400 MHz, CD3OD-d4): δ ppm 8.40 (s, 1 H), 8.02 (d, 1 H,J=7.4 Hz), 7.50 (m, 3 H), 7.40 (m, 1 H), 7.20 (m, 1 H), 6.58 (m, 1 H), 5.58 (m, 1 H), 4.09 (m, 1 H), 3.55 (m, 2 H), 3.48 (m, 2 H), 3.21 (m, 4H), 3.10 (m, 1 H), 2.59 (m, 2 H), 2.29 (m, 1 H),1.95 (m, 1 H), 1.86 (m, 3 H), 1.30 (m, 4 H). LCMS (MH+): 646.

Example 54a (S)-8-(2-Amino-6-((R)-2,2,2-trifluoro-1-(3'-(methylsulfonyl)-5-propyl-[1,1'-biphenyl]-2-yl)ethoxy)pyrimidin-4-yl)-2,8-diazaspiro[4.5]decane-3-carboxylic acid

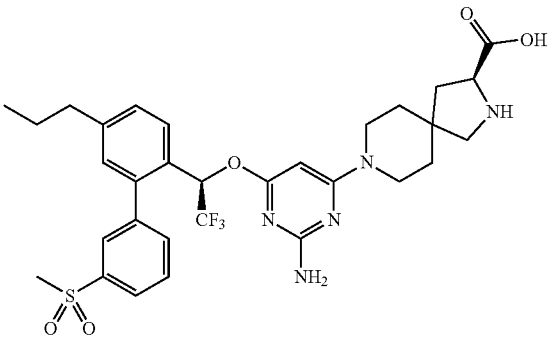 [SMILES: CCCc1ccc([C@@H](Oc2cc(N3CCC4(CC3)CN[C@H](C(=O)O)C4)nc(N)n2)C(F)(F)F)c(-c2cccc(S(C)(=O)=O)c2)c1]

Step 1: To a solution of (S)-2-tert-butyl 3-ethyl 8-(2-amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro[4.5]decane-2,3-dicarboxylate (product from Step 2, Example 53) (200 mg, 0.26 mmol) in EtOH (10 mL) is added 10% Pd/C (200 mg), and the reaction mixture was stirred under 1 atm $H_2$ for 12 h. The solids were filtered and the filtrate was concentrated in vacuo to provide (S)-2-tert-butyl 3-ethyl 8-(2-amino-6-((R)-2,2,2-trifluoro-1-(3'-(methylsulfonyl)-5-propyl-[1,1'-biphenyl]-2-yl)ethoxy)pyrimidin-4-yl)-2,8-diazaspiro[4.5]decane-2,3-dicarboxylate as a white solid that is used directly without further purification.

Step 2: To a solution of (S)-2-tert-butyl 3-ethyl 8-(2-amino-6-((R)-2,2,2-trifluoro-1-(3'-(methylsulfonyl)-5-propyl-[1,1'-biphenyl]-2-yl)ethoxy)pyrimidin-4-yl)-2,8-diazaspiro[4.5] decane-2,3-dicarboxylate in $CH_2Cl_2$ (4 mL) was added TFA (2.0 mL) dropwise at 0° C. The reaction mixture was stirred at RT for 2 h, then concentrated in vacuo. The pH was adjusted to 7-8 with saturated aqueous $NaHCO_3$ solution. The aqueous layer was extracted with $CH_2Cl_2$, washed with brine, dried over $Na_2SO_4$, filtered, and concentrated in vacuo. Purification by normal phase silica gel column ($CH_2Cl_2$/MeOH) provided (S)-ethyl 8-(2-amino-6-((R)-2,2,2-trifluoro-1-(3'-(methylsulfonyl)-5-propyl-[1,1'-biphenyl]-2-yl)ethoxy)pyrimidin-4-yl)-2,8-diazaspiro[4.5]decane-3-carboxylate as a white solid.

Step 3: Hydrolysis of (S)-ethyl 8-(2-amino-6-((R)-2,2,2-trifluoro-1-(3'-(methylsulfonyl)-5-propyl-[1,1'-biphenyl]-2-yl) ethoxy)pyrimidin-4-yl)-2,8-diazaspiro[4.5]decane-3-carboxylate using the LiOH general method provides the title compound as an off-white solid.

$^1$H NMR (400 MHz, $CD_3OD$-d4): δ ppm 8.40 (s, 1 H), 8.02 (d, 1 H,J=7.8 Hz), 7.60 (m, 3 H), 7.29 (m, 1 H), 7.08 (s, 1 H), 6.58 (m, 1 H), 5.56 (s, 1 H), 4.00 (m, 1 H), 3.55 (m, 2 H), 3.48 (m, 2 H), 3.31 (m, 4H), 3.30 (m, 1 H), 2.59 (m, 2 H), 2.29 (m, 1 H),1.95 (m, 1 H), 1.54 (m, 6 H), 0.95 (m, 3 H). LCMS (MH+): 649.

Example 54b (S)-8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylic acid

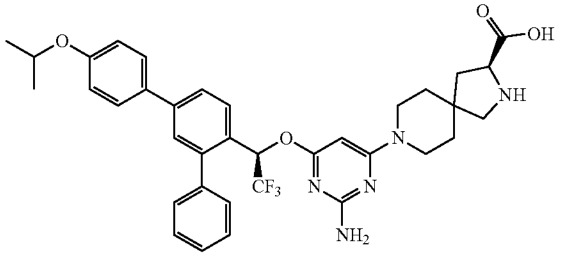 [SMILES: CC(C)Oc1ccc(-c2ccc([C@@H](Oc3cc(N4CCC5(CC4)CN[C@H](C(=O)O)C5)nc(N)n3)C(F)(F)F)c(-c3ccccc3)c2)cc1]

Step 1: To a solution of (S)-ethyl 8-(2-amino-6-((R)-1-(5-bromo-[1,1'-biphenyl]-2-yl)-2,2,2-trifluoroethoxy)pyrimidin-4-yl)-2,8-diazaspiro[4.5]decane-3-carboxylate (350 mg, 0.56 mmol) in $CH_2Cl_2$ (20 mL) was added $Boc_2O$ (436 mg, 2.0 mmol) and $Et_3N$ (306 mg, 3.03 mmol) at 0° C. The reaction mixture was stirred at RT for 3 h, then concentrated in vacuo and purified on normal phase silica gel (ethyl acetate/hexanes) to afford (S)-2-tert-butyl 3-ethyl 8-(2-amino-6-((R)-1-(5-bromo-[1,1'-biphenyl]-2-yl)-2,2,2-trifluoroethoxy)pyrimidin-4-yl)-2,8-diazaspiro[4.5]decane-2,3-dicarboxylate as a yellow solid.

Step 2: A solution of (S)-2-tert-butyl 3-ethyl 8-(2-amino-6-((R)-1-(5-bromo-[1,1'-biphenyl]-2-yl)-2,2,2-trifluoroethoxy)pyrimidin-4-yl)-2,8-diazaspiro[4.5]decane-2,3-dicarboxylate (150 mg, 0.2 mmol), 4-isopropoxyphenyl boronic acid (44 mg, 0.25 mmol) and $Pd(dppf)Cl_2$ (15 mg, 0.02 mmol) in dioxane (3.0 mL)/aqueous $Na_2CO_3$ solution (3.0 mL, 2.0 M, aq.) was stirred at 90° C. for 2 h. The aqueous layer was extracted with $CH_2Cl_2$, washed with brine, dried over $Na_2SO_4$, filtered, and concentrated in vacuo. Purification by normal phase silica gel column (EtOAc/ Hex=10 to 50%) to (S)-2-tert-butyl 3-ethyl 8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-2,3-dicarboxylate as a white solid.

Step 3: To a solution of (S)-2-tert-butyl 3-ethyl 8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-2,3-dicarboxylate (130mg, 0.164 mmol) in $CH_2Cl_2$ (4 mL) was added TFA (1 mL), and the reaction mixture was stirred at 25° C. for 12 h. The mixture was concentrated, and neutralized to pH 7-8 with saturated aqueous $NaHCO_3$. The aqueous layer was extracted with $CH_2Cl_2$, washed with brine, dried over $Na_2SO_4$, filtered, and concentrated in vacuo to provide (S)-ethyl 8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylate as a light yellow solid that is used without further purification.

Step 4: Hydrolysis of (S)-ethyl 8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylate using the LiOH general method provided the title compound as an off-white solid.

$^1$H NMR (400 MHz, MeOH-d4): δ ppm 1.31 (d, J=6.0 Hz, 6H), 1.58 (m, 4H), 2.04 (dd, J=13.4, 7.2 Hz, 1H), 2.32 (dd, J=13.4, 9.2 Hz, 1H), 3.11 (d, J=11.7 Hz, 1H), 3.24 (d, J=11.7 Hz, 1H), 3.45 (ddd, J=21.2, 10.1, 6.4 Hz, 2H), 3.60 (td, J=12.4, 11.2, 6.0 Hz, 2H), 4.08 (dd, J=9.1, 7.1 Hz, 1H), 4.62 (p, J=6.1 Hz, 1H), 6.67 (q, J=6.8 Hz, 1H), 6.95 (m, 2H), 7.54 (m, 9H), 7.72 (d, J=8.3 Hz, 1H). LCMS (MH+): 663.

Example 54c (S)-8-(2-amino-6-((R)-2,2,2-trifluoro-1-(4-propoxy-[1,1':3',1"-terphenyl]-4'-yl)ethoxy)pyrimidin-4-yl)-2,8-diazaspiro[4.5]decane-3-carboxylic acid

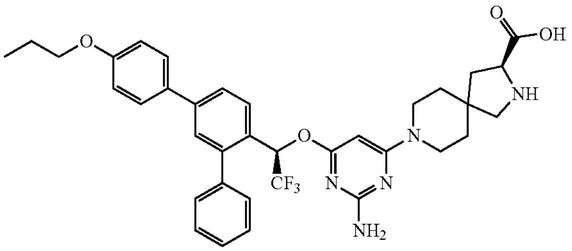 [SMILES: CCCOc1ccc(-c2ccc([C@@H](Oc3cc(N4CCC5(CC4)CN[C@H](C(=O)O)C5)nc(N)n3)C(F)(F)F)c(-c3ccccc3)c2)cc1]

The title compound was prepared as described above for (S)-8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylic acid (Example 54b) by substituting 4-propoxyphenyl boronic acid for 4-isopropoxyphenyl boronic acid in Step 2.

$^1$H NMR (400 MHz, MeOH-d4): δ ppm 1.04 (t, J=7.4 Hz, 3H), 1.57 (m, 4H), 1.80 (h, J=6.7 Hz, 2H), 1.99 (dd, J=13.3, 7.3 Hz, 1H), 2.27 (dd, J=13.3, 9.1 Hz, 1H), 3.02 (d, J=11.6 Hz, 1H), 3.18 (d, J=11.5 Hz, 1H), 3.30 (d, J=3.2 Hz, 1H), 3.45 (q, J=15.9, 11.4 Hz, 2H), 3.60 (s, 2H), 3.97 (dt, J=13.1, 7.3 Hz, 3H), 4.88 (m, 1H), 5.47 (s, 1H), 6.66 (q, J=6.9 Hz, 1H), 6.97 (d, J=8.3 Hz, 2H), 7.54 (m, 9H), 7.72 (m, 1H). LCMS (MH+): 662.

Example 54d (S)-8-(2-amino-6-((R)-2,2,2-trifluoro-1-(5-(methylsulfonyl)-[1,1'-biphenyl]-2-yl)ethoxy)pyrimidin-4-yl)-2,8-diazaspiro[4.5]decane-3-carboxylic acid

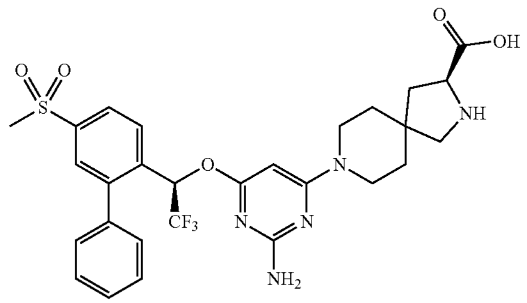 [SMILES: CS(=O)(=O)c1ccc([C@@H](Oc2cc(N3CCC4(CC3)CN[C@H](C(=O)O)C4)nc(N)n2)C(F)(F)F)c(-c2ccccc2)c1]

Step 1: To a mixture of 2-chloro-4-(methylsulfonyl)benzoic acid (5 g, 21.3 mmol) in anhydrous methanol (100 mL) was added concentrated sulfuric acid (0.5 mL). The resulting solution was stirred for 18 h at reflux. Upon cooling, the mixture was concentrated under reduced pressure, dissolved in $CH_2Cl_2$ and washed with $NaHCO_3$ solution and brine. The organic phase was dried over sodium sulfate and concentrated to afford methyl 2-chloro-4-(methylsulfonyl)benzoate as a white solid.

Step 2: To a mixture of methyl 2-chloro-4-(methylsulfonyl) benzoate (2.2 g, 8.9 mmol), $PhB(OH)_2$ (1.31 g, 10.8 mmol), DME (12 mL), and 2M $Na_2CO_3$ (6 mL) was added $Pd(PPh_3)_4$ (515 mg). The mixture was heated for 20 min at 160° C. in a microwave reactor, and then extracted with EtOAc, dried over sodium sulfate and concentrated in vacuo. Purification on normal phase silica gel (hexane/EtOAc) provided methyl 5-(methylsulfonyl)-[1,1'-biphenyl]-2-carboxylate as a white solid.

Step 3: To a solution of $CaCl_2$ (1.52 g, 13.78 mmol) in EtOH (50 mL) at RT was added methyl 5-(methylsulfonyl)-[1,1'-biphenyl]-2-carboxylate (2 g, 6.9 mmol) in THF (50 mL) followed by the addition of $NaBH_4$ (1.0 g, 27.6 mmol). The reaction was stirred at RT for 24 h, then concentrated in vacuo and extracted with ethyl acetate, 5% HCl, and brine. Purification on normal phase silica gel provided (5-(methylsulfonyl)-[1,1'-biphenyl]-2-yl)methanol as a white solid.

Step 4: To a solution of (5-(methylsulfonyl)-[1,1'-biphenyl]-2-yl)methanol (1 g, 3.8 mmol) in $CH_2Cl_2$ (50 mL) was added Dess-Martin periodinane (2.4 g, 5.71mmol). The reaction was stirred for 2 h at RT, then concentrated in vacuo and purified directly on normal phase silica gel to provide 5-(methylsulfonyl)-[1,1'-biphenyl]-2-carbaldehyde as a white solid.

Step 5: To a solution of 5-(methylsulfonyl)-[1,1'-biphenyl]-2-carbaldehyde (1 g, 3.8 mmol) was added TMS-$CF_3$ (1.0 g, 7.7 mmol) in THF (10 mL). The reaction was cooled to 0° C. to and TBAF (0.57 mL, 0.57 mmol) was added dropwise. The reaction mixture was stirred for 2 h, then 3 N HCl (2 mL) was added to the mixture and the reaction mixture was stirred for an additional 30 min. The mixture was extracted with ethyl acetate, washed with brine, dried over $Na_2SO_4$, filtered, and concentrated in vacuo. Purification on normal phase silica gel provided 2,2,2-trifluoro-1-(5-(methylsulfonyl)-[1,1'-biphenyl]-2-yl)ethanol as a white solid.

Step 6: To a mixture of 2,2,2-trifluoro-1-(5-(methylsulfonyl)-[1,1'-biphenyl]-2-yl)ethanol (720 mg, 2.2 mmol)) in $CH_2Cl_2$ (50 mL) was added Dess-Martin periodinane (1.1 g, 2.6 mmol). The reaction was stirred for 2 h at RT, then concentrated in vacuo and purified directly on normal phase silica gel to provide 2,2,2-trifluoro-1-(5-(methylsulfonyl)-[1,1'-biphenyl]-2-yl)ethanone as a white solid.

Step 7: Chiral reduction of 2,2,2-trifluoro-1-(5-(methylsulfonyl)-[1,1'-biphenyl]-2-yl)ethanone using the Iridium complex-catalyzed hydrogenation as described for Intermediate 1, (R)-1-(4-bromo-2-(3-methyl-1H-pyrazol-1-yl)phenyl)-2,2,2-trifluoroethanol, provided (R)-2,2,2-trifluoro-1-(5-(methylsulfonyl)-[1,1'-biphenyl]-2-yl)ethanol as a white solid.

Steps 8-11: The title compound was prepared as described for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 10d), Steps 1-4.

$^1$H NMR (400 MHz, MeOH-d4): δ ppm 1.63 (q, J=5.7, 4.9 Hz, 4H), 2.10 (m, 1H), 2.36 (dd, J=13.5, 9.2 Hz, 1H), 3.23 (d, J=31.0 Hz, 5H), 3.50 (dddd, J=18.0, 13.4, 9.5, 5.1 Hz, 2H), 3.66 (ddt, J=15.9, 10.6, 4.6 Hz, 2H), 4.16 (dd, J=9.2, 7.2 Hz, 1H), 6.78 (q, J=6.7 Hz, 1H), 7.57 (m, 5H), 7.86 (d, J=1.9 Hz, 1H), 8.01 (m, 2H), 8.17 (s, 1H). LCMS (MH+): 607.

Example 54e (S)-8-(2-amino-6-((R)-2,2,2-trifluoro-1-(3-fluoro-4-propoxy-[1,1':3',1"-terphenyl]-4'-yl)ethoxy)pyrimidin-4-yl)-2,8-diazaspiro[4.5]decane-3-carboxylic acid

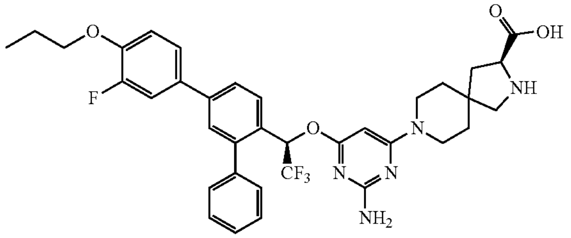 [SMILES: CCCOc1ccc(-c2ccc([C@@H](Oc3cc(N4CCC5(CC4)CN[C@H](C(=O)O)C5)nc(N)n3)C(F)(F)F)c(-c3ccccc3)c2)cc1F]

The title compound was prepared as described above for (S)-8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylic acid (Example 54b) by replacing the 4-isopropoxyphenyl boronic acid in Step 2 with (3-fluoro-4-propoxyphenyl)boronic acid (CAS# 192376-68-4).

$^1$H NMR (400 MHz, MeOH-d4): δ ppm 0.86 (m, 1H), 1.05 (t, J=7.4 Hz, 3H), 1.26 (s, 1H), 1.59 (s, 4H), 1.83 (h, J=7.1 Hz, 2H), 2.06 (dd, J=13.4, 7.2 Hz, 1H), 2.33 (m, 1H), 3.10 (d, J=11.9 Hz, 1H), 3.23 (d, J=12.0 Hz, 1H), 3.43 (s, 2H), 3.60 (s, 2H), 4.02 (t, J=6.5 Hz, 2H), 4.12 (s, 1H), 6.62 (d, J=6.8 Hz, 1H), 7.09 (t, J=8.7 Hz, 1H), 7.34 (s, 1H), 7.43 (m, 4H), 7.50 (s, 3H), 7.60 (m, 1H), 7.76 (m, 2H). LCMS (MH+): 681.

Example 54f (S)-8-(2-amino-6-((R)-1-(3,4-dimethyl-[1,1':3',1"-terphenyl]-4'-yl)-2,2,2-trifluoroethoxy)pyrimidin-4-yl)-2,8-diazaspiro[4.5]decane-3-carboxylic acid

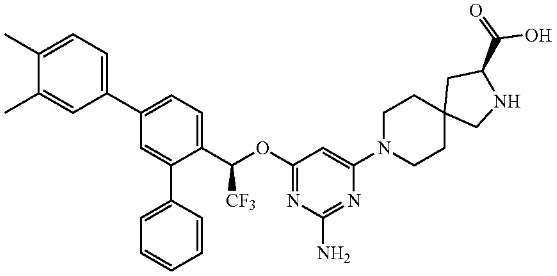 [SMILES: Cc1ccc(-c2ccc([C@@H](Oc3cc(N4CCC5(CC4)CN[C@H](C(=O)O)C5)nc(N)n3)C(F)(F)F)c(-c3ccccc3)c2)cc1C]

The title compound was prepared as described above for (S)-8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro[4.5]decane-3-carboxylic acid (Example 54b) by replacing the 4-isopropoxyphenyl boronic acid in Step 2 with 3,4-dimethylphenyl boronic acid.

$^1$H NMR (400 MHz, MeOH-d4): δ ppm 1.62 (s, 4H), 2.06 (dd, J=13.5, 7.6 Hz, 1H), 2.29 (d, J=9.7 Hz, 5H), 2.37 (m, 1H), 3.17 (d, J=11.8 Hz, 1H), 3.26 (d, J=11.7 Hz, 1H), 3.63 (d, J=14.2 Hz, 2H), 4.27 (t, J=8.3 Hz, 1H), 6.66 (q, J=6.8 Hz, 1H), 7.18 (d, J=7.9 Hz, 1H), 7.36 (m, 2H), 7.49 (m, 5H), 7.64 (dd, J=8.2, 2.0 Hz, 1H), 7.74 (d, J=8.2 Hz, 1H). LCMS (MH+): 633.

Example 54g (S)-8-(6-((R)-1-([1,1':3',1"-terphenyl]-4'-yl)-2,2,2-trifluoroethoxy)-2-aminopyrimidin-4-yl)-2,8-diazaspiro[4.5]decane-3-carboxylic acid

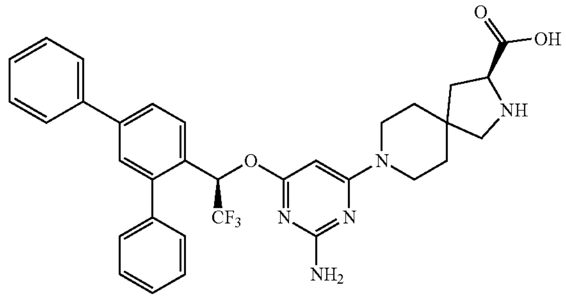 [SMILES: Nc1nc(O[C@H](c2ccc(-c3ccccc3)cc2-c2ccccc2)C(F)(F)F)cc(N2CCC3(CC2)CN[C@H](C(=O)O)C3)n1]

The title compound was prepared as described above for (S)-8-(2-amino-6-((R)-2,2,2-trifluoro-1-(4-isopropoxy-[1,1':3',1"-terphenyl]-4'-yl)ethoxy)pyrimidin-4-yl)-2,8-diazaspiro [4.5]decane-3-carboxylic acid (Example 54b) by substituting phenyl boronic acid for 4-isopropoxyphenyl boronic acid in Step 2.

$^1$H NMR (400 MHz, MeOH-d4): δ ppm 1.62 (s, 4H), 2.06 (dd, J=13.5, 7.7 Hz, 1H), 2.38 (dd, J=13.5, 9.1 Hz, 1H), 3.16 (d, J=11.8 Hz, 1H), 3.26 (d, J=11.8 Hz, 1H), 3.47 (s, 2H), 3.62 (s, 2H), 4.26 (t, J=8.4 Hz, 1H), 6.68 (q, J=6.9 Hz, 1H), 7.35 (m, 1H), 7.47 (m, 4H), 7.53 (s, 3H), 7.66 (m, 3H), 7.77 (d, J=8.2 Hz, 1H). LCMS (MH+): 604.

Example 54h (R)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid

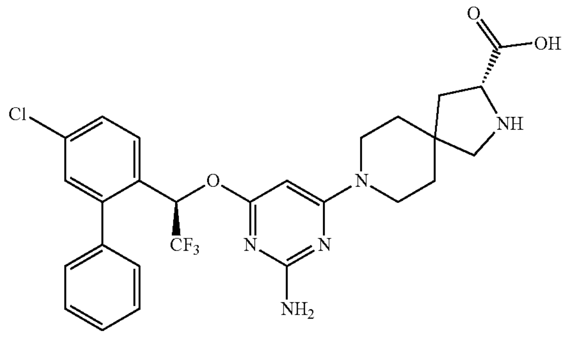 [SMILES: Nc1nc(O[C@H](c2ccc(Cl)cc2-c2ccccc2)C(F)(F)F)cc(N2CCC3(CC2)CN[C@@H](C(=O)O)C3)n1]

The title compound was prepared as described above for (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid (Example 34c) by using (R)-2-benzyl 3-ethyl 8-(2-amino-6-((R)-1-(2-bromo-4-chlorophenyl)-2,2,2-trifluoroethoxy)pyrimidin-4-yl)-2,8-diazaspiro[4.5]decane-2,3-dicarboxylate.

$^1$H NMR (400 MHz, MeOH-d4): δ ppm 1.59 (d, J=5.5 Hz, 4H), 2.03 (dd, J=13.4, 7.1 Hz, 1H), 2.31 (dd, J=13.4, 9.2 Hz, 1H), 3.09 (d, J=11.8 Hz, 1H), 3.23 (d, J=11.6 Hz, 1H), 3.46 (dt, J=15.3, 8.2 Hz, 2H), 3.62 (s, 2H), 4.06 (dd, J=9.1, 7.1 Hz, 1H), 5.49 (s, 1H), 6.64 (q, J=6.9 Hz, 1H), 7.28 (d, J=2.2 Hz, 1H), 7.46 (m, 5H), 7.53 (s, 1H), 7.67 (d, J=8.5 Hz, 1H). LCMS (MH+): 562.

Example 54i (R)-8-(2-amino-6-((S)-1-(5-chloro-[1,1'-biphenyl]-2-yl)-2,2,2-trifluoroethoxy)pyrimidin-4-yl)-2,8-diazaspiro [4.5]decane-3-carboxylic acid

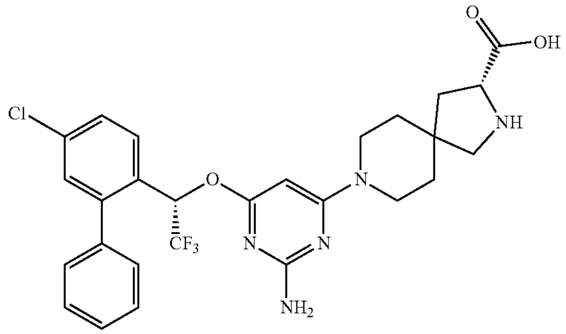 [SMILES: Nc1nc(O[C@@H](c2ccc(Cl)cc2-c2ccccc2)C(F)(F)F)cc(N2CCC3(CC2)CN[C@@H](C(=O)O)C3)n1]

The title compound was prepared as described above for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 34c) by using (R)-2-benzyl 3-ethyl 8-(2-amino-6-((S)-1-(2-bromo-4-chlorophenyl)-2,2,2-trifluoroethoxy)pyrimidin-4-yl)-2,8-diazaspiro[4.5]decane-2,3-dicarboxylate.

$^1$H NMR (400 MHz, MeOH-d4): δ ppm 7.70 (d, J=8.5 Hz, 1H), 7.59-7.44 (m, 4H), 7.47-7.40 (m, 2H), 7.32 (d, J=2.2 Hz, 1H), 6.61 (q, J=6.5 Hz, 1H), 4.51 (t, J=8.7 Hz, 1H), 3.72-3.59 (m, 1H), 3.56 (s, 1H), 3.28 (s, 1H), 2.49 (dd, J=13.6, 8.9 Hz, 1H), 2.10 (dd, J=13.6, 8.4 Hz, 1H), 1.71 (dt, J=16.0, 6.6 Hz, 4H), 1.28 (s, 0H).LCMS (MH+): 562.

Example 54j (S)-8-(2-amino-6-((S)-1-(5-chloro-[1,1'-biphenyl]-2-yl)-2,2,2-trifluoroethoxy)pyrimidin-4-yl)-2,8-diazaspiro[4.5]decane-3-carboxylic acid

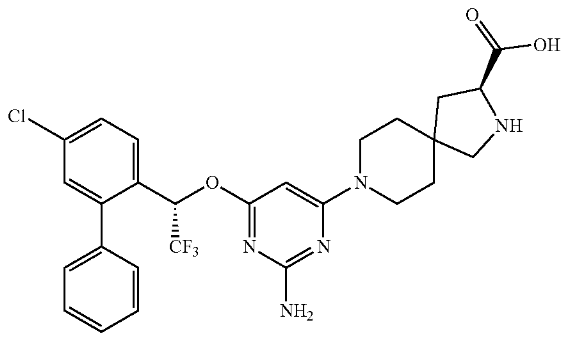 [SMILES: Nc1nc(O[C@@H](c2ccc(Cl)cc2-c2ccccc2)C(F)(F)F)cc(N2CCC3(CC2)CN[C@H](C(=O)O)C3)n1]

The title compound was prepared as described above for (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (Example 34c) by using (S)-2-benzyl 3-ethyl 8-(2-amino-6-((S)-1-(2-bromo-4-chlorophenyl)-2,2,2-trifluoroethoxy)pyrimidin-4-yl)-2,8-diazaspiro[4.5]decane-2,3-dicarboxylate.

$^1$H NMR (400 MHz, MeOH-d4): δ ppm 7.70 (d, J=8.5 Hz, 1H), 7.61-7.42 (m, 6H), 7.32 (d, J=2.3 Hz, 1H), 6.66 (q, J=6.7 Hz, 1H), 4.25 (dd, J=9.0, 7.6 Hz, 1H), 3.72-3.60 (m, 1H), 3.29 (d, J=11.7 Hz, 1H), 3.18 (d, J=11.8 Hz, 1H), 2.40 (dd, J=13.5, 9.2 Hz, 1H), 2.09 (dd, J=13.5, 7.6 Hz, 1H), 1.64 (s, 2H).LCMS (MH+): 562.

Example 54k (S)-8-(2-amino-6-((S)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid

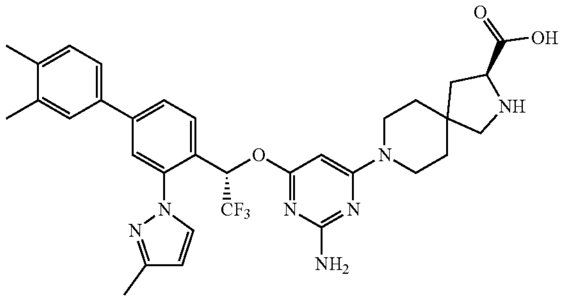 [SMILES: Cc1ccn(-c2cc(-c3ccc(C)c(C)c3)ccc2[C@H](Oc2cc(N3CCC4(CC3)CN[C@H](C(=O)O)C4)nc(N)n2)C(F)(F)F)n1]

The title compound was prepared as described above for (S)-8-(2-amino-6-((R)-1-(3',4'-dimethyl-3-(3-methyl-1H-pyrazol-1-yl)-[1,1'-biphenyl]-4-yl)-2,2,2-trifluoroethoxy) pyrimidin-4-yl)-2,8-diazaspiro [4.5]decane-3-carboxylic acid (Example 1m) by using (S)-2-benzyl 3-ethyl 8-(2-amino-6-((S)-1-(4-chloro-2-(3-methyl-1H-pyrazol-1-yl) phenyl)-2,2,2-trifluoroethoxy)pyrimidin-4-yl)-2,8-diazaspiro[4.5]decane-2,3-dicarboxylate.

$^1$H NMR (400 MHz, MeOH-d4): δ ppm 1.58 (s, 6H), 2.04 (dd, J=13.4, 7.2 Hz, 1H), 2.30 (d, J=11.1 Hz, 9H), 2.40 (s, 3H), 3.10 (d, J=11.8 Hz, 1H), 3.23 (d, J=11.7 Hz, 1H), 3.48 (s, 2H), 3.66 (d, J=15.7 Hz, 3H), 4.08 (t, J=8.2 Hz, 1H),6.41 (d, J=2.4 Hz, 1H), 6.77 (q, J=6.5 Hz, 1H), 7.20 (d, J=7.8 Hz, 1H), 7.38 (d, J=8.0 Hz, 1H), 7.44 (d, J=2.0 Hz, 1H), 7.60 (d, J=1.8 Hz, 1H), 7.73 (m, 2H), 7.97 (d, J=2.4 Hz, 1H). LCMS (MH+): 635.

Example 54l (R)-8-(2-amino-6-((S)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylic acid

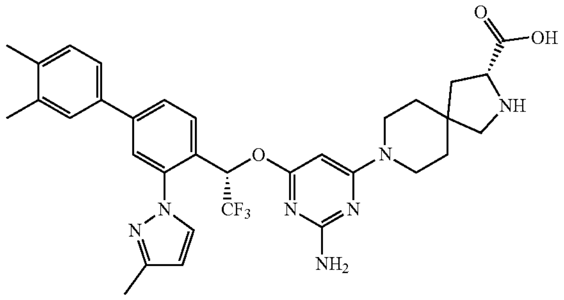 [SMILES: Cc1ccn(-c2cc(-c3ccc(C)c(C)c3)ccc2[C@H](Oc2cc(N3CCC4(CC3)CN[C@@H](C(=O)O)C4)nc(N)n2)C(F)(F)F)n1]

The title compound was prepared as described above for (R)-8-(2-amino-6-((R)-1-(3',4'-dimethyl-3-(3-methyl-1H-pyrazol-1-yl)-[1,1'-biphenyl]-4-yl)-2,2,2-trifluoroethoxy) pyrimidin-4-yl)-2,8-diazaspiro [4.5]decane-3-carboxylic acid (Example 1m) by using (R)-2-benzyl 3-ethyl 8-(2-amino-6-((S)-1-(4-chloro-2-(3-methyl-1H-pyrazol-1-yl) phenyl)-2,2,2-trifluoro ethoxy)pyrimidin-4-yl)-2,8-diazaspiro[4.5]decane-2,3-dicarboxylate.

$^1$H NMR (400 MHz, MeOH-d4): δ ppm 7.97 (d, J=2.3 Hz, 0H), 7.79-7.69 (m, 0H), 7.61 (d, J=1.6 Hz, 0H), 7.45 (s, 0H), 7.42-7.35 (m, 0H), 7.21 (d, J=7.9 Hz, 0H), 6.77 (q, J=6.5 Hz, OH), 6.41 (d, J=2.3 Hz, 0H), 4.10 (t, J=8.2 Hz, 0H), 3.68 (dd, J=13.9, 6.3 Hz, 0H), 3.58-3.43 (m, 0H), 3.24 (d, J=11.7 Hz, 0H), 3.11 (d, J=11.8 Hz, 0H), 2.42-2.27 (m, 1H), 2.05 (dd, J=13.5, 7.2 Hz, 0H), 1.59 (d, J=11.4 Hz, 0H), 1.59 (s, 0H). LCMS (MH+): 635.

Example 54m (R)-8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazasp iro [4.5] decane-3-carboxylic acid

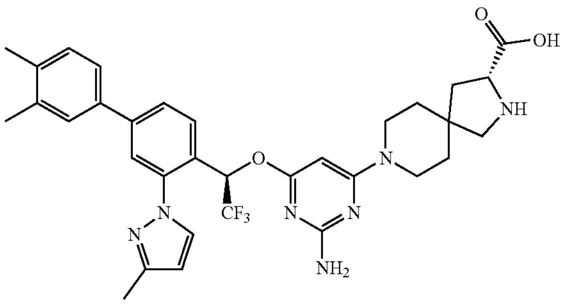 [SMILES: Cc1ccn(-c2cc(-c3ccc(C)c(C)c3)ccc2[C@@H](Oc2cc(N3CCC4(CC3)CN[C@@H](C(=O)O)C4)nc(N)n2)C(F)(F)F)n1]

The title compound was prepared as described above for (R)-2-benzyl 3-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro [4.5]decane-2,3-dicarboxylate (Example 1m) by using (R)-2-benzyl 3-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-2,3-dicarboxylate.

$^1$H NMR (400 MHz, MeOH-d4): δ ppm 7.97 (d, J=2.4 Hz, 1H), 7.79-7.68 (m, 2H), 7.60 (d, J=1.7 Hz, 1H), 7.44 (s, 1H), 7.38 (d, J=8.0 Hz, 1H), 7.20 (d, J=7.8 Hz, 1H), 6.76 (q, J=6.7 Hz, 1H), 6.41 (d, J=2.3 Hz, 1H), 5.75 (s, 1H), 3.98 (t, J=8.1 Hz, 1H), 3.64 (d, J=15.5 Hz, 3H), 3.47 (s, 2H), 3.33-3.27 (m, 6H), 3.17 (d, J=11.6 Hz, 1H), 3.01 (d, J=11.6 Hz, 1H), 2.39 (s, 3H), 2.34-2.18 (m, 8H), 1.99 (dd, J=13.4, 7.1 Hz, 1H), 1.56 (s, 5H). LCMS (MH+): 635.

Example 55an (S)-8-(2-amino-6-((R)-2,2,2-trifluoro-1-(3'-methoxy-[1,1'-biphenyl]-4-yl)ethoxy)pyrimidin-4-yl)-2,8-diazaspiro[4.5]decane-3-carboxylic acid

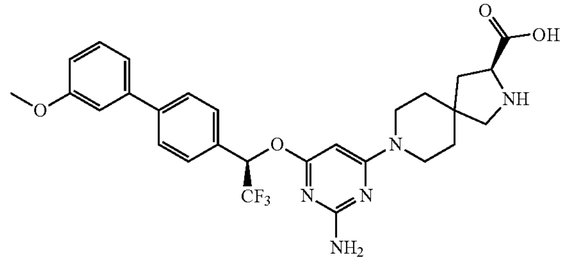 [SMILES: COc1cccc(-c2ccc([C@@H](Oc3cc(N4CCC5(CC4)CN[C@H](C(=O)O)C5)nc(N)n3)C(F)(F)F)cc2)c1]

Step 1: To a solution of (R)-1-(4-bromophenyl)-2,2,2-trifluoroethanol (150 mg, 0.60 mmol) in dioxane (10 mL) was added 4,6-dichloropyrimidin-2-amine (120 mg g, 0.71 mmol) and $Cs_2CO_3$ (290 mg, 0.88 mmol), and the reaction mixture was heated to 80° C. for 30 h. Then the reaction was cooled to RT. EtOAc was added and the organic layer was washed with brine, dried over $Na_2SO_4$, filtered, and concentrated in vacuo. Purification by normal phase silica gel column (EtOAc/heptane) provided (R)-4-(1-(4-bromophenyl)-2,2,2-trifluoroethoxy)-6-chloropyrimidin-2-amine as a colorless oil.

Step 2: To a solution of (R)-4-(1-(4-bromophenyl)-2,2,2-trifluoroethoxy)-6-chloropyrimidin-2-amine (19 mg, 0.50 mmol) in dioxane (25 ml) was added (S)-2-benzyl 3-ethyl 2,8-diazaspiro[4.5]decane-2,3-dicarboxylate (175 mg, 0.50 mmol) and sodium bicarbonate (210 mg, 0.25 mmol), and the reaction mixture was heated to 100° C. for 48 h. Then the reaction mixture was cooled to RT, and extracted with EtOAc. The combined organic layers were washed with brine, dried over $Na_2SO_4$, filtered, and concentrated in vacuo. Purification by normal phase silica gel column (EtOAc/heptane) provided (S)-2-benzyl 3-ethyl 8-(2-amino-6-((R)-1-(4-bromophenyl)-2,2,2-trifluoroethoxy)-pyrimidin-4-yl)-2,8-diazaspiro[4.5]decane-2,3-dicarboxylate as white solid.

Step 3: To a solution of (S)-2-benzyl 3-ethyl 8-(2-amino-6-((R)-1-(4-bromophenyl)-2,2,2-trifluoroethoxy)-pyrimidin-4-yl)-2,8-diazaspiro[4.5]decane-2,3-dicarboxylate (190 mg, 0.27 mmol) was added NaOH (100 mg, 0.26 mmol) in 15 mL THF/EtOH/$H_2O$ (2/1/2.5), and the reaction was stirred for 12 h at RT. Then, the reaction mixture was concentrated in vacuo to remove most of the organic solvents, and the pH was adjusted to 6 with 1 N HCl. EtOAc was added, and the organic layer was washed with brine, dried over $Na_2SO_4$, filtered, and concentrated in vacuo to provide (S)-8-(2-amino-6-((R)-1-(4-bromophenyl)-2,2,2-trifluoroethoxy) pyrimidin-4-yl)-2-(benzyloxycarbonyl)-2,8-diazaspiro[4.5] decane-3-carboxylic acid as a white solid which was used without further purification.

Step 4: To a solution of (S)-8-(2-amino-6-((R)-1-(4-bromophenyl)-2,2,2-trifluoroethoxy) pyrimidin-4-yl)-2-((benzyloxy)carbonyl)-2,8-diazaspiro[4.5]decane-3-carboxylic acid (80 mg, 0.12 mmol) in dioxane (1 mL)/ $Na_2CO_3$(1.0 mL, 2 M, aq) were added (3-methoxyphenyl)boronic acid (22 mg, 0.14 mmol) and Pd(dppf)$_2$ (8 mg, 0.01 mmol). The reaction flask was degassed and refilled with argon via balloon 3 times, and the reaction mixture was refluxed for 4 h. Then the reaction was cooled to RT, concentrated in vacuo, and extracted with EtOAc. The combined organic layers were are washed with brine, dried over $Na_2SO_4$, filtered, and concentrated in vacuo. Purification by reverse phase silica gel column ($H_2O$/$NH_4OH$/MeOH) provided (S)-8-(2-amino-6-((S)-2,2,2-trifluoro-1-(3'-methoxy-[1,1'-biphenyl]-4-yl)ethoxy)pyrimidin-4-yl)-2-((benzyloxy)carbonyl)-2,8-diazaspiro[4.5]decane-3-carboxylic acid as a white solid.

Step 5: N-CBZ Deprotection was accomplished via Method A to provide the title compound as an off-white solid isolated as the zwitterionic form.

Using the generic scheme below, the following examples of Table 17a were prepared as described above for (S)-8-(2-amino-6-((R)-2,2,2-trifluoro-1-(3'-methoxy-[1,1'-biphenyl]-4-yl)ethoxy)pyrimidin-4-yl)-2,8-diazaspiro[4.5]decane-3-carboxylic acid (Example 55an) using the appropriate boronic acid or boronate In some cases, the Cy coupling reaction was performed prior to ethyl ester and N-CBz removal (see alternative Steps 3a and 4a) as noted in the scheme. In the cases of example 55al and 55am, racemic 1-(4-bromophenyl)-2,2,2-trifluoroethanol was used as opposed to (R)-1-(4-bromophenyl)-2,2,2-trifluoroethanol for all other examples.

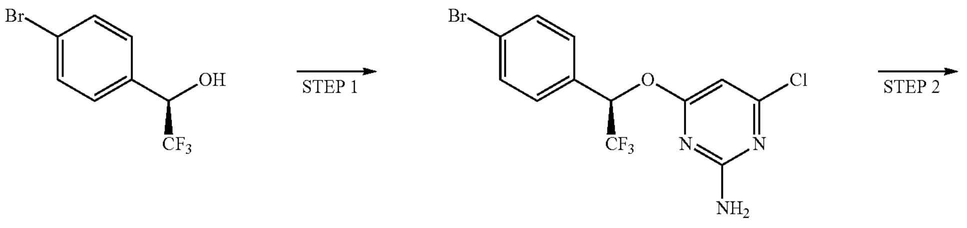

-continued
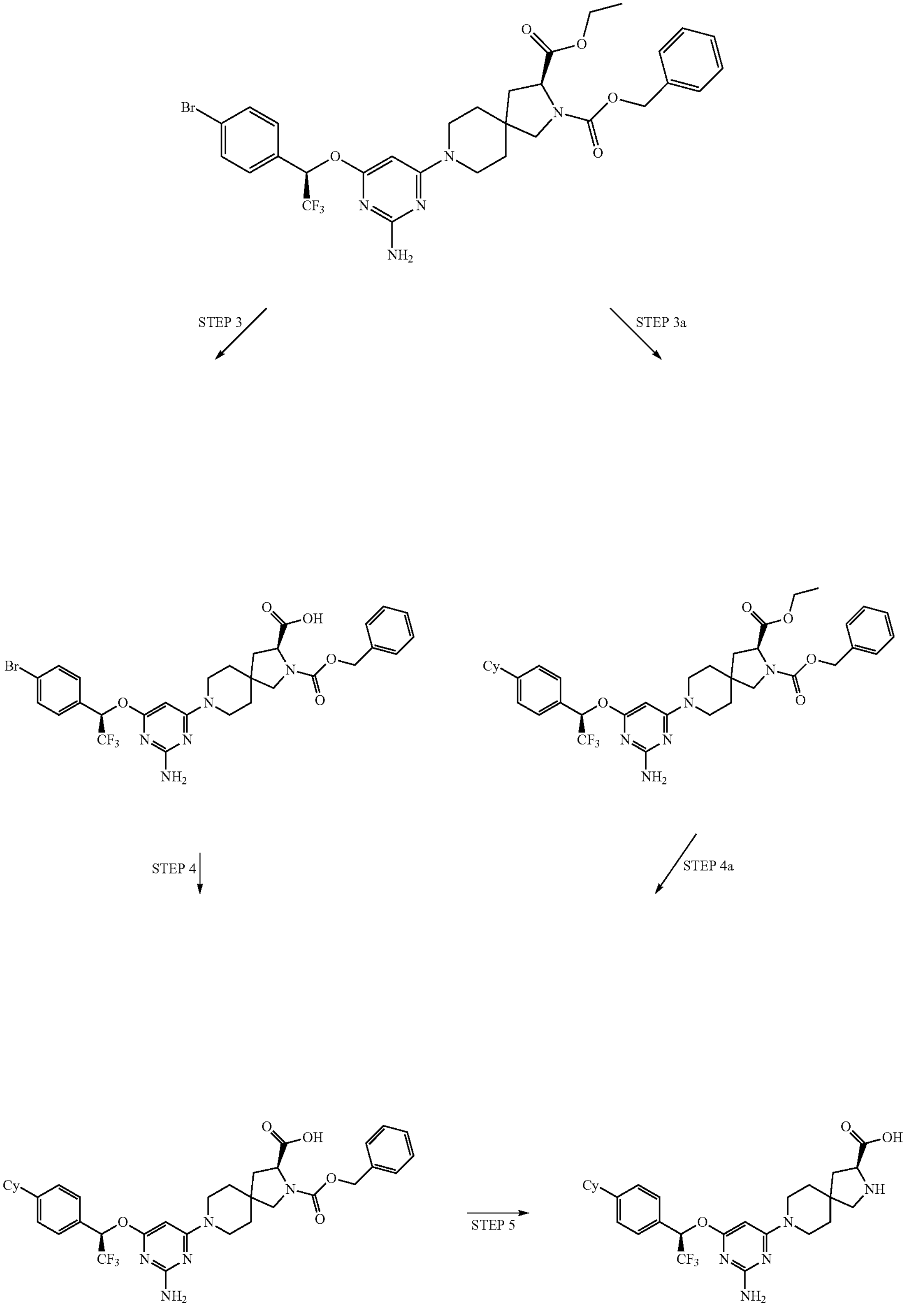

TABLE 17a

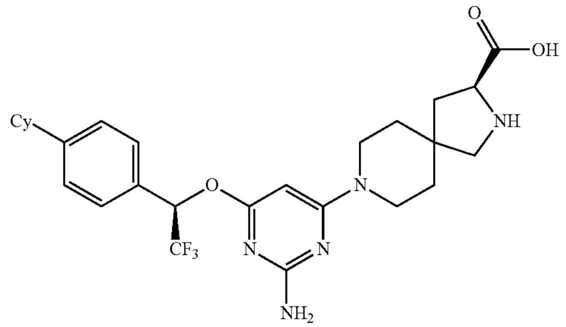

| Ex. No. | Cy | CAS Name | LCMS (MH+) |
|---|---|---|---|
| 55a | 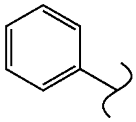 | (S)-8-(6-((R)-1-([1,1'-biphenyl]-4-yl)-2,2,2-trifluoroethoxy)-2-aminopyrimidin-4-yl)-2,8-diazaspiro[4.5]decane-3-carboxylic acid | 529 |
| 55b | 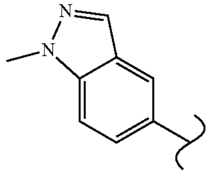 | (S)-8-(2-amino-6-((R)-2,2,2-trifluoro-1-(4-(1-methyl-1H-indazol-5-yl)phenyl)ethoxy)pyrimidin-4-yl)-2,8-diazaspiro[4.5]decane-3-carboxylic acid | 583 |
| 55c | 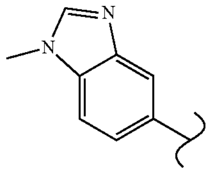 | (S)-8-(2-amino-6-((R)-2,2,2-trifluoro-1-(4-(1-methyl-1H-benzo[d]imidazol-5-yl)phenyl)ethoxy)pyrimidin-4-yl)-2,8-diazaspiro[4.5]decane-3-carboxylic acid | 583 |
| 55d | 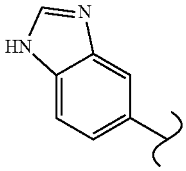 | (S)-8-(6-((R)-1-(4-(1H-benzo[d]imidazol-5-yl)phenyl)-2,2,2-trifluoroethoxy)-2-aminopyrimidin-4-yl)-2,8-diazaspiro[4.5]decane-3-carboxylic acid | 569 |
| 55e | 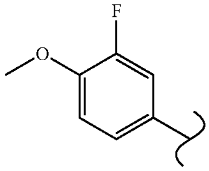 | (S)-8-(2-amino-6-((R)-2,2,2-trifluoro-1-(3'-fluoro-4'-methoxy-[1,1'-biphenyl]-4-yl)ethoxy)pyrimidin-4-yl)-2,8-diazaspiro[4.5]decane-3-carboxylic acid | 577 |
| 55f | 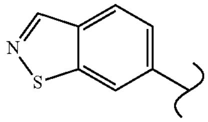 | (S)-8-(2-amino-6-((R)-1-(4-(benzo[d]isothiazol-6-yl)phenyl)-2,2,2-trifluoroethoxy)pyrimidin-4-yl)-2,8-diazaspiro[4.5]decane-3-carboxylic acid | 586 |
| 55g | 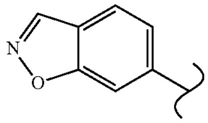 | (S)-8-(2-amino-6-((R)-1-(4-(benzo[d]isoxazol-6-yl)phenyl)-2,2,2-trifluoroethoxy)pyrimidin-4-yl)-2,8-diazaspiro[4.5]decane-3-carboxylic acid | 570 |

TABLE 17a-continued

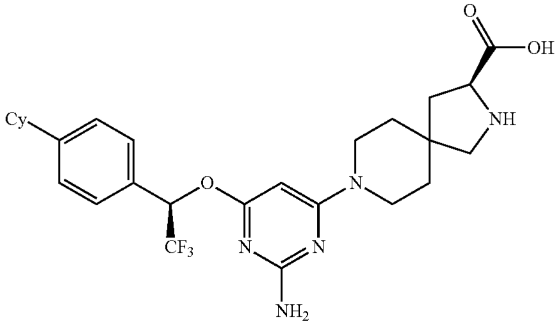

| Ex. No. | Cy | CAS Name | LCMS (MH+) |
|---|---|---|---|
| 55h | 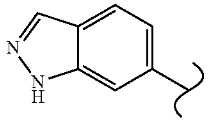 | (S)-8-(6-((R)-1-(4-(1H-indazol-6-yl)phenyl)-2,2,2-trifluoroethoxy)-2-aminopyrimidin-4-yl)-2,8-diazaspiro[4.5]decane-3-carboxylic acid | 569 |
| 55i | 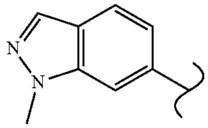 | (S)-8-(2-amino-6-((R)-2,2,2-trifluoro-1-(4-(1-methyl-1H-indazol-6-yl)phenyl)ethoxy)pyrimidin-4-yl)-2,8-diazaspiro[4.5]decane-3-carboxylic acid | 583 |
| 55j | 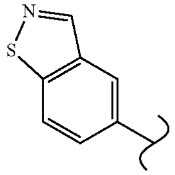 | (S)-8-(2-amino-6-((R)-1-(4-(benzo[d]isothiazol-5-yl)phenyl)-2,2,2-trifluoroethoxy)pyrimidin-4-yl)-2,8-diazaspiro[4.5]decane-3-carboxylic acid | 586 |
| 55k | 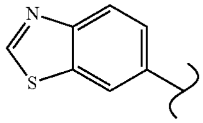 | (S)-8-(2-amino-6-((R)-1-(4-(benzo[d]thiazol-6-yl)phenyl)-2,2,2-trifluoroethoxy)pyrimidin-4-yl)-2,8-diazaspiro[4.5]decane-3-carboxylic acid | 586 |
| 55l | 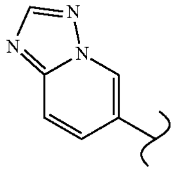 | (S)-8-(6-((R)-1-(4-([1,2,4]triazolo[1,5-a]pyridin-6-yl)phenyl)-2,2,2-trifluoroethoxy)-2-aminopyrimidin-4-yl)-2,8-diazaspiro[4.5]decane-3-carboxylic acid | 570 |
| 55m | 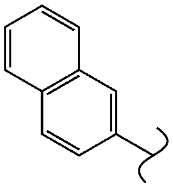 | (S)-8-(2-amino-6-((R)-2,2,2-trifluoro-1-(4-(naphthalen-2-yl)phenyl)ethoxy)pyrimidin-4-yl)-2,8-diazaspiro[4.5]decane-3-carboxylic acid | 579 |
| 55n | 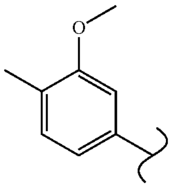 | (S)-8-(2-amino-6-((R)-2,2,2-trifluoro-1-(3'-methoxy-4'-methyl-[1,1'-biphenyl]-4-yl)ethoxy)pyrimidin-4-yl)-2,8-diazaspiro[4.5]decane-3-carboxylic acid | 573 |

TABLE 17a-continued

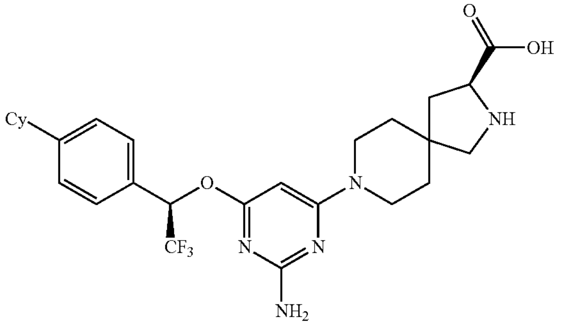

| Ex. No. | Cy | CAS Name | LCMS (MH+) |
|---|---|---|---|
| 55o | 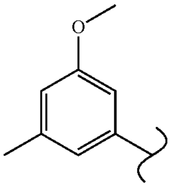 | (S)-8-(2-amino-6-((R)-2,2,2-trifluoro-1-(3'-methoxy-5'-methyl-[1,1'-biphenyl]-4-yl)ethoxy)pyrimidin-4-yl)-2,8-diazaspiro[4.5]decane-3-carboxylic acid | 573 |
| 55p | 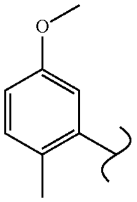 | (S)-8-(2-amino-6-((R)-2,2,2-trifluoro-1-(5'-methoxy-2'-methyl-[1,1'-biphenyl]-4-yl)ethoxy)pyrimidin-4-yl)-2,8-diazaspiro[4.5]decane-3-carboxylic acid | 573 |
| 55q | 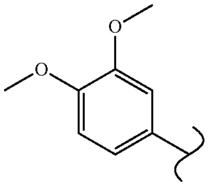 | (S)-8-(2-amino-6-((R)-1-(3',4'-dimethoxy-[1,1'-biphenyl]-4-yl)-2,2,2-trifluoroethoxy)pyrimidin-4-yl)-2,8-diazaspiro[4.5]decane-3-carboxylic acid | 589 |
| 55r | 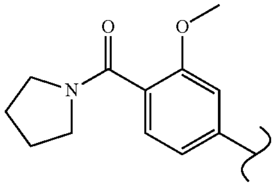 | (S)-8-(2-amino-6-((R)-2,2,2-trifluoro-1-(3'-methoxy-4'-(pyrrolidine-1-carbonyl)-[1,1'-biphenyl]-4-yl)ethoxy)pyrimidin-4-yl)-2,8-diazaspiro[4.5]decane-3-carboxylic acid | 656 |
| 55s | 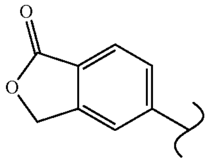 | (S)-8-(2-amino-6-((R)-2,2,2-trifluoro-1-(4-(1-oxo-1,3-dihydroisobenzofuran-5-yl)phenyl)ethoxy)pyrimidin-4-yl)-2,8-diazaspiro[4.5]decane-3-carboxylic acid | 585 |
| 55t | 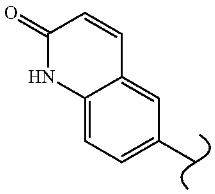 | (S)-8-(2-amino-6-((R)-2,2,2-trifluoro-1-(4-(2-oxo-1,2-dihydroquinolin-6-yl)phenyl)ethoxy)pyrimidin-4-yl)-2,8-diazaspiro[4.5]decane-3-carboxylic acid | 596 |

TABLE 17a-continued

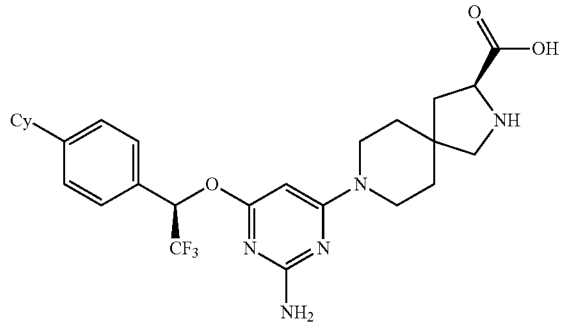

| Ex. No. | Cy | CAS Name | LCMS (MH+) |
|---|---|---|---|
| 55u | 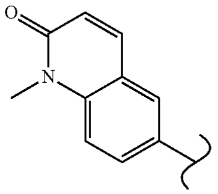 | (S)-8-(2-amino-6-((R)-2,2,2-trifluoro-1-(4-(1-methyl-2-oxo-1,2-dihydroquinolin-6-yl)phenyl)ethoxy)pyrimidin-4-yl)-2,8-diazaspiro[4.5]decane-3-carboxylic acid | 610 |
| 55v | 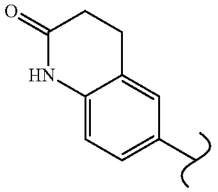 | (S)-8-(2-amino-6-((R)-2,2,2-trifluoro-1-(4-(2-oxo-1,2,3,4-tetrahydroquinolin-6-yl)phenyl)ethoxy)pyrimidin-4-yl)-2,8-diazaspiro[4.5]decane-3-carboxylic acid | 598 |
| 55w | 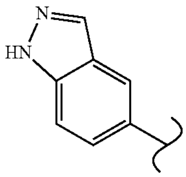 | (S)-8-(6-((R)-1-(4-(1H-indazol-5-yl)phenyl)-2,2,2-trifluoroethoxy)-2-aminopyrimidin-4-yl)-2,8-diazaspiro[4.5]decane-3-carboxylic acid | 569 |
| 55x | 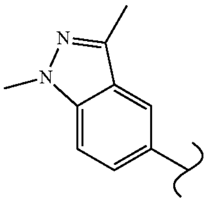 | (S)-8-(2-amino-6-((R)-1-(4-(1,3-dimethyl-1H-indazol-5-yl)phenyl)-2,2,2-trifluoroethoxy)pyrimidin-4-yl)-2,8-diazaspiro[4.5]decane-3-carboxylic acid | 597 |
| 55y | 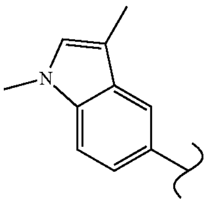 | (S)-8-(2-amino-6-((R)-1-(4-(1,3-dimethyl-1H-indol-5-yl)phenyl)-2,2,2-trifluoroethoxy)pyrimidin-4-yl)-2,8-diazaspiro[4.5]decane-3-carboxylic acid | 596 |
| 55z | 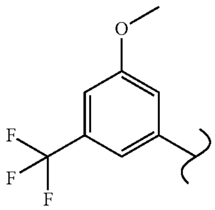 | (S)-8-(2-amino-6-((R)-2,2,2-trifluoro-1-(3'-methoxy-5'-(trifluoromethyl)-[1,1'-biphenyl]-4-yl)ethoxy)pyrimidin-4-yl)-2,8-diazaspiro[4.5]decane-3-carboxylic acid | 627 |

TABLE 17a-continued

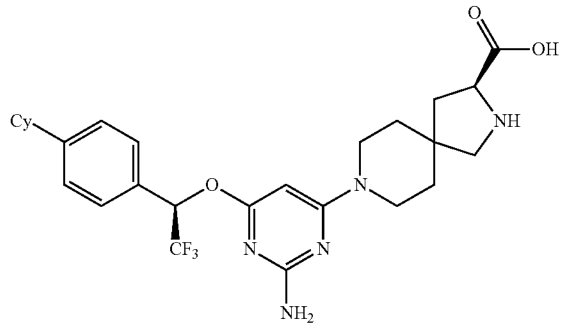

| Ex. No. | Cy | CAS Name | LCMS (MH+) |
|---|---|---|---|
| 55aa | 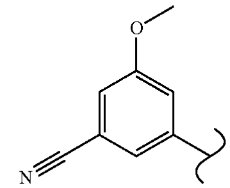 | (S)-8-(2-amino-6-((R)-1-(3'-cyano-5'-methoxy-[1,1'-biphenyl]-4-yl)-2,2,2-trifluoroethoxy)pyrimidin-4-yl)-2,8-diazaspiro[4.5]decane-3-carboxylic acid | 584 |
| 55ab | 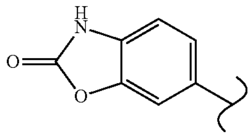 | (S)-8-(2-amino-6-((R)-2,2,2-trifluoro-1-(4-(2-oxo-2,3-dihydrobenzo[d]oxazol-6-yl)phenyl)ethoxy)pyrimidin-4-yl)-2,8-diazaspiro[4.5]decane-3-carboxylic acid | 586 |
| 55ac | 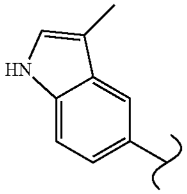 | (S)-8-(2-amino-6-((R)-2,2,2-trifluoro-1-(4-(3-methyl-1H-indol-5-yl)phenyl)ethoxy)pyrimidin-4-yl)-2,8-diazaspiro[4.5]decane-3-carboxylic acid | 1 |
| 55ad | 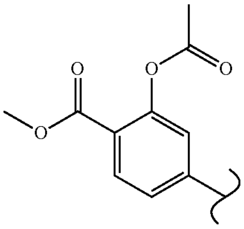 | (S)-8-(6-((R)-1-(3'-acetoxy-4'-(methoxycarbonyl)-[1,1'-biphenyl]-4-yl)-2,2,2-trifluoroethoxy)-2-aminopyrimidin-4-yl)-2,8-diazaspiro[4.5]decane-3-carboxylic acid | 645 |
| 55ae | 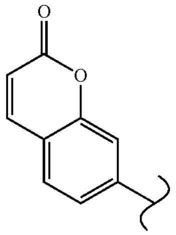 | (S)-8-(2-amino-6-((R)-2,2,2-trifluoro-1-(4-(2-oxo-2H-chromen-7-yl)phenyl)ethoxy)pyrimidin-4-yl)-2,8-diazaspiro[4.5]decane-3-carboxylic acid | 596 |
| 55af | 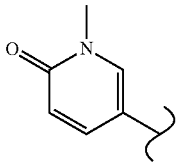 | (S)-8-(2-amino-6-((R)-2,2,2-trifluoro-1-(4-(1-methyl-6-oxo-1,6-dihydropyridin-3-yl)phenyl)ethoxy)pyrimidin-4-yl)-2,8-diazaspiro[4.5]decane-3-carboxylic acid | 560 |

TABLE 17a-continued

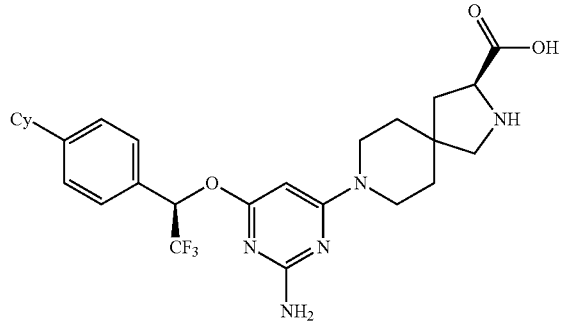

| Ex. No. | Cy | CAS Name | LCMS (MH+) |
|---|---|---|---|
| 55ag | 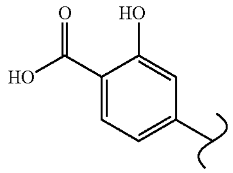 | (S)-8-(2-amino-6-((R)-1-(4'-carboxy-3'-hydroxy-[1,1'-biphenyl]-4-yl)-2,2,2-trifluoroethoxy)pyrimidin-4-yl)-2,8-diazaspiro[4.5]decane-3-carboxylic acid | 588 |
| 55ah | 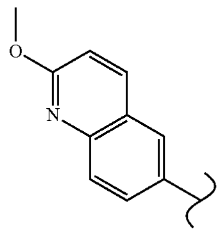 | (S)-8-(2-amino-6-((R)-2,2,2-trifluoro-1-(4-(2-methoxyquinolin-6-yl)phenyl)ethoxy)pyrimidin-4-yl)-2,8-diazaspiro[4.5]decane-3-carboxylic acid | 610 |
| 55ai | 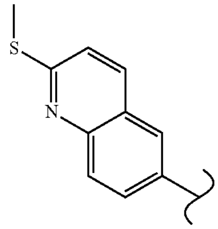 | (S)-8-(2-amino-6-((R)-2,2,2-trifluoro-1-(4-(2-(methylthio)quinolin-6-yl)phenyl)ethoxy)pyrimidin-4-yl)-2,8-diazaspiro[4.5]decane-3-carboxylic acid | 626 |
| 55aj | 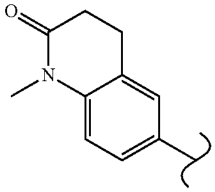 | (S)-8-(2-amino-6-((R)-2,2,2-trifluoro-1-(4-(1-methyl-2-oxo-1,2,3,4-tetrahydroquinolin-6-yl)phenyl)ethoxy)pyrimidin-4-yl)-2,8-diazaspiro[4.5]decane-3-carboxylic acid | 612 |
| 55ak | 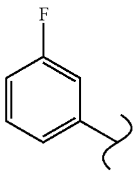 | (3S)-8-(2-amino-6-(2,2,2-trifluoro-1-(3'-fluoro-[1,1'-biphenyl]-4-yl)ethoxy)pyrimidin-4-yl)-2,8-diazaspiro[4.5]decane-3-carboxylic acid | 547 |
| 55al | 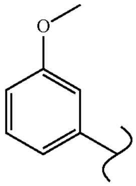 | (3S)-8-(2-amino-6-(2,2,2-trifluoro-1-(3'-methoxy-[1,1'-biphenyl]-4-yl)ethoxy)pyrimidin-4-yl)-2,8-diazaspiro[4.5]decane-3-carboxylic acid | 559 |

TABLE 17a-continued

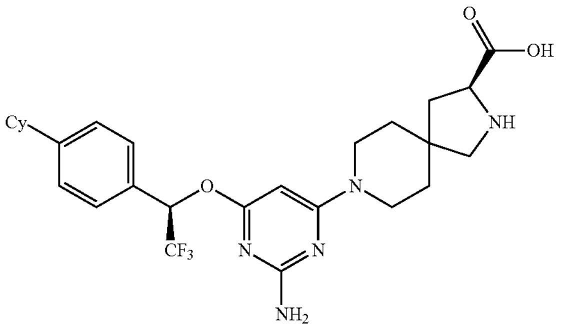

| Ex. No. | Cy | CAS Name | LCMS (MH+) |
|---|---|---|---|
| 55am | 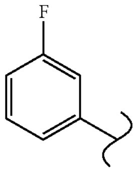 | (S)-8-(2-amino-6-((R)-2,2,2-trifluoro-1-(3'-fluoro-[1,1'-biphenyl]-4-yl)ethoxy)pyrimidin-4-yl)-2,8-diazaspiro[4.5]decane-3-carboxylic acid | 547 |
| 55an | 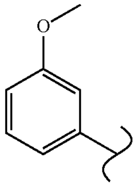 | (S)-8-(2-amino-6-((R)-2,2,2-trifluoro-1-(3'-methoxy-[1,1'-biphenyl]-4-yl)ethoxy)pyrimidin-4-yl)-2,8-diazaspiro[4.5]decane-3-carboxylic acid | 559 |
| 55ao | 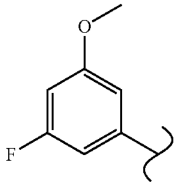 | (S)-8-(2-amino-6-((R)-2,2,2-trifluoro-1-(3'-fluoro-5'-methoxy-[1,1'-biphenyl]-4-yl)ethoxy)pyrimidin-4-yl)-2,8-diazaspiro[4.5]decane-3-carboxylic acid | 577 |
| 55ap | 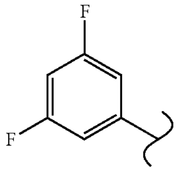 | (S)-8-(2-amino-6-((R)-1-(3',5'-difluoro-[1,1'-biphenyl]-4-yl)-2,2,2-trifluoroethoxy)pyrimidin-4-yl)-2,8-diazaspiro[4.5]decane-3-carboxylic acid | 565 |
| 55aq | 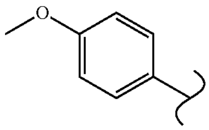 | (S)-8-(2-amino-6-((R)-2,2,2-trifluoro-1-(4'-methoxy-[1,1'-biphenyl]-4-yl)ethoxy)pyrimidin-4-yl)-2,8-diazaspiro[4.5]decane-3-carboxylic acid | 559 |
| 55ar | 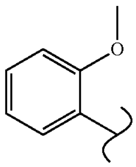 | (S)-8-(2-amino-6-((R)-2,2,2-trifluoro-1-(2'-methoxy-[1,1'-biphenyl]-4-yl)ethoxy)pyrimidin-4-yl)-2,8-diazaspiro[4.5]decane-3-carboxylic acid | 559 |

TABLE 17a-continued

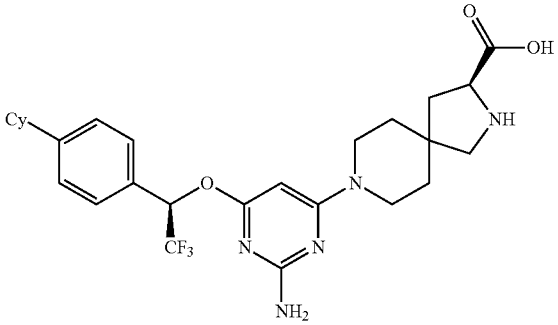

| Ex. No. | Cy | CAS Name | LCMS (MH+) |
|---|---|---|---|
| 55as | 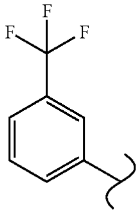 | (S)-8-(2-amino-6-((R)-2,2,2-trifluoro-1-(3'-(trifluoromethyl)-[1,1'-biphenyl]-4-yl)ethoxy)pyrimidin-4-yl)-2,8-diazaspiro[4.5]decane-3-carboxylic acid | 597 |
| 55at | 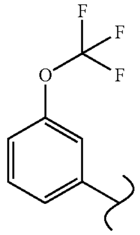 | (S)-8-(2-amino-6-((R)-2,2,2-trifluoro-1-(3'-(trifluoromethoxy)-[1,1'-biphenyl]-4-yl)ethoxy)pyrimidin-4-yl)-2,8-diazaspiro[4.5]decane-3-carboxylic acid | 613 |
| 55au | 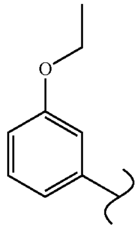 | (S)-8-(2-amino-6-((R)-1-(3'-ethoxy-[1,1'-biphenyl]-4-yl)-2,2,2-trifluoroethoxy)pyrimidin-4-yl)-2,8-diazaspiro[4.5]decane-3-carboxylic acid | 573 |
| 55av | 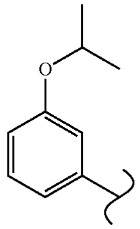 | (S)-8-(2-amino-6-((R)-2,2,2-trifluoro-1-(3'-isopropoxy-[1,1'-biphenyl]-4-yl)ethoxy)pyrimidin-4-yl)-2,8-diazaspiro[4.5]decane-3-carboxylic acid | 587 |
| 55aw | 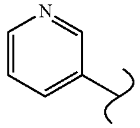 | (S)-8-(2-amino-6-((R)-2,2,2-trifluoro-1-(4-(pyridin-3-yl)phenyl)ethoxy)pyrimidin-4-yl)-2,8-diazaspiro[4.5]decane-3-carboxylic acid | 530 |
| 55ax | 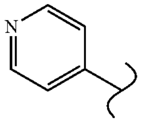 | (S)-8-(2-amino-6-((R)-2,2,2-trifluoro-1-(4-(pyridin-4-yl)phenyl)ethoxy)pyrimidin-4-yl)-2,8-diazaspiro[4.5]decane-3-carboxylic acid | 530 |

TABLE 17a-continued

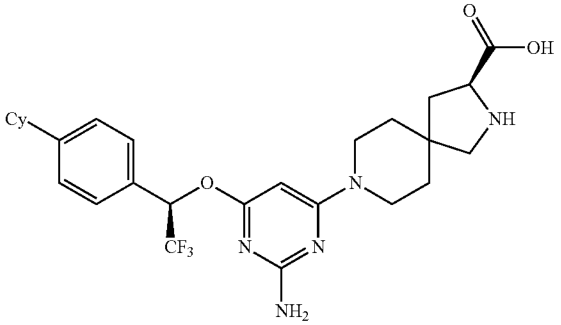

| Ex. No. | Cy | CAS Name | LCMS (MH+) |
|---|---|---|---|
| 55ay | 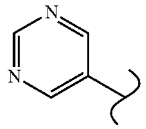 | (S)-8-(2-amino-6-((R)-2,2,2-trifluoro-1-(4-(pyrimidin-5-yl)phenyl)ethoxy)pyrimidin-4-yl)-2,8-diazaspiro[4.5]decane-3-carboxylic acid | 531 |
| 55az | 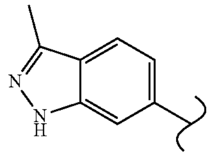 | (S)-8-(2-amino-6-((R)-2,2,2-trifluoro-1-(4-(3-methyl-1H-indazol-6-yl)phenyl)ethoxy)pyrimidin-4-yl)-2,8-diazaspiro[4.5]decane-3-carboxylic acid | 583 |
| 55ba | 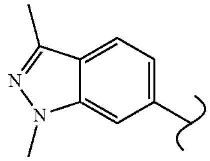 | (S)-8-(2-amino-6-((R)-1-(4-(1,3-dimethyl-1H-indazol-6-yl)phenyl)-2,2,2-trifluoroethoxy)pyrimidin-4-yl)-2,8-diazaspiro[4.5]decane-3-carboxylic acid | 597 |
| 55bb | 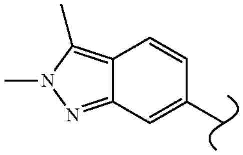 | S)-8-(2-amino-6-((R)-1-(4-(2,3-dimethyl-2H-indazol-6-yl)phenyl)-2,2,2-trifluoroethoxy)pyrimidin-4-yl)-2,8-diazaspiro[4.5]decane-3-carboxylic acid | 597 |
| 55bc | 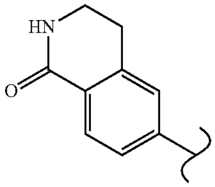 | (S)-8-(2-amino-6-((R)-2,2,2-trifluoro-1-(4-(1-oxo-1,2,3,4-tetrahydroisoquinolin-6-yl)phenyl)ethoxy)pyrimidin-4-yl)-2,8-diazaspiro[4.5]decane-3-carboxylic acid | 598 |
| 55bd | 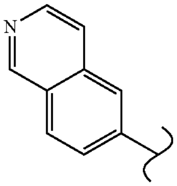 | (S)-8-(2-amino-6-((R)-2,2,2-trifluoro-1-(4-(isoquinolin-6-yl)phenyl)ethoxy)pyrimidin-4-yl)-2,8-diazaspiro[4.5]decane-3-carboxylic acid | 580 |
| 55be | 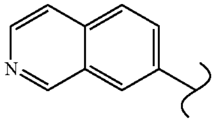 | (S)-8-(2-amino-6-((R)-2,2,2-trifluoro-1-(4-(isoquinolin-7-yl)phenyl)ethoxy)pyrimidin-4-yl)-2,8-diazaspiro[4.5]decane-3-carboxylic acid | 580 |

TABLE 17a-continued

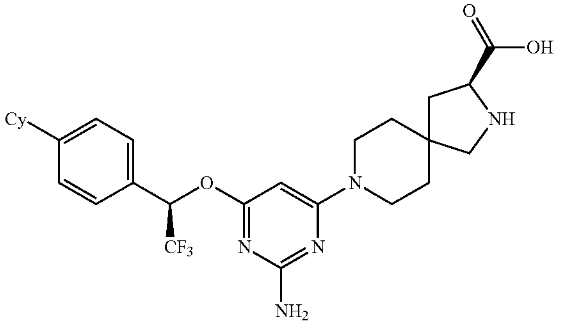

| Ex. No. | Cy | CAS Name | LCMS (MH+) |
|---|---|---|---|
| 55bf | 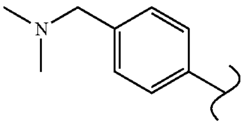 | (S)-8-(2-amino-6-((R)-1-(4'-((dimethylamino)methyl)-[1,1'-biphenyl]-4-yl)-2,2,2-trifluoroethoxy)pyrimidin-4-yl)-2,8-diazaspiro[4.5]decane-3-carboxylic acid | 586 |
| 55bg | 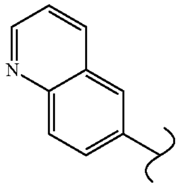 | (S)-8-(2-amino-6-((R)-2,2,2-trifluoro-1-(4-(quinolin-6-yl)phenyl)ethoxy)pyrimidin-4-yl)-2,8-diazaspiro[4.5]decane-3-carboxylic acid | 580 |
| 55bh | 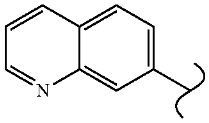 | (S)-8-(2-amino-6-((R)-2,2,2-trifluoro-1-(4-(quinolin-7-yl)phenyl)ethoxy)pyrimidin-4-yl)-2,8-diazaspiro[4.5]decane-3-carboxylic acid | 580 |
| 55bi | 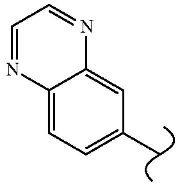 | (S)-8-(2-amino-6-((R)-2,2,2-trifluoro-1-(4-(quinoxalin-6-yl)phenyl)ethoxy)pyrimidin-4-yl)-2,8-diazaspiro[4.5]decane-3-carboxylic acid | 581 |
| 55bj | 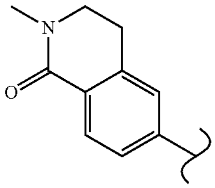 | (S)-8-(2-amino-6-((R)-2,2,2-trifluoro-1-(4-(2-methyl-1-oxo-1,2,3,4-tetrahydroisoquinolin-6-yl)phenyl)ethoxy)pyrimidin-4-yl)-2,8-diazaspiro[4.5]decane-3-carboxylic acid | 612 |
| 55bk | 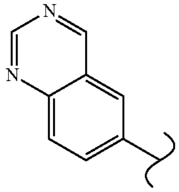 | (S)-8-(2-amino-6-((R)-2,2,2-trifluoro-1-(4-(quinazolin-6-yl)phenyl)ethoxy)pyrimidin-4-yl)-2,8-diazaspiro[4.5]decane-3-carboxylic acid | 581 |
| 55bl | 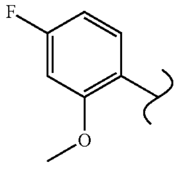 | (S)-8-(2-amino-6-((R)-2,2,2-trifluoro-1-(4'-fluoro-2'-methoxy-[1,1'-biphenyl]-4-yl)ethoxy)pyrimidin-4-yl)-2,8-diazaspiro[4.5]decane-3-carboxylic acid | 577 |

TABLE 17a-continued

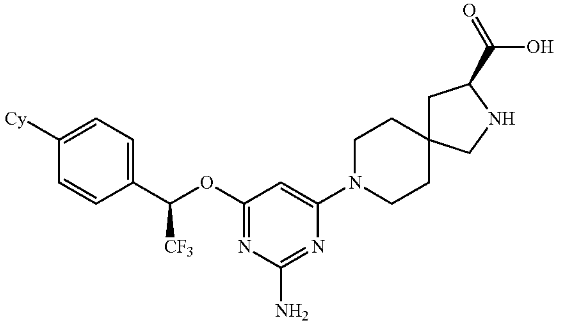

| Ex. No. | Cy | CAS Name | LCMS (MH+) |
|---|---|---|---|
| 55bm | 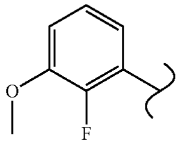 | (S)-8-(2-amino-6-((R)-2,2,2-trifluoro-1-(2'-fluoro-3'-methoxy-[1,1'-biphenyl]-4-yl)ethoxy)pyrimidin-4-yl)-2,8-diazaspiro[4.5]decane-3-carboxylic acid | 577 |
| 55bn | 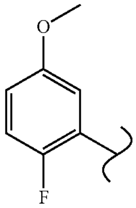 | (S)-8-(2-amino-6-((R)-2,2,2-trifluoro-1-(2'-fluoro-5'-methoxy-[1,1'-biphenyl]-4-yl)ethoxy)pyrimidin-4-yl)-2,8-diazaspiro[4.5]decane-3-carboxylic acid | 577 |
| 55bo | 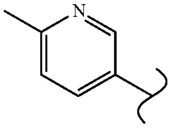 | (S)-8-(2-amino-6-((R)-2,2,2-trifluoro-1-(4-(6-methylpyridin-3-yl)phenyl)ethoxy)pyrimidin-4-yl)-2,8-diazaspiro[4.5]decane-3-carboxylic acid | 544 |
| 55bp | 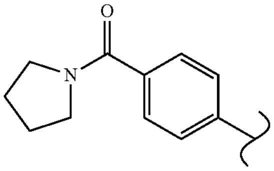 | (S)-8-(2-amino-6-((R)-2,2,2-trifluoro-1-(4'-(pyrrolidine-1-carbonyl)-[1,1'-biphenyl]-4-yl)ethoxy)pyrimidin-4-yl)-2,8-diazaspiro[4.5]decane-3-carboxylic acid | 626 |
| 55bq | 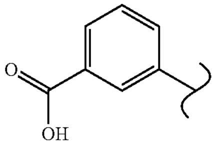 | (S)-8-(2-amino-6-((R)-1-(3'-carboxy-[1,1'-biphenyl]-4-yl)-2,2,2-trifluoroethoxy)pyrimidin-4-yl)-2,8-diazaspiro[4.5]decane-3-carboxylic acid | 573 |
| 55br | 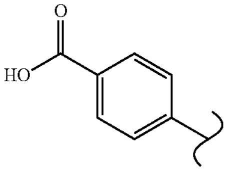 | (S)-8-(2-amino-6-((R)-1-(4'-carboxy-[1,1'-biphenyl]-4-yl)-2,2,2-trifluoroethoxy)pyrimidin-4-yl)-2,8-diazaspiro[4.5]decane-3-carboxylic acid | 573 |
| 55bs | 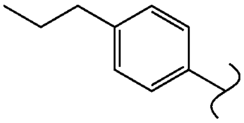 | (S)-8-(2-amino-6-((R)-2,2,2-trifluoro-1-(4'-propyl-[1,1'-biphenyl]-4-yl)ethoxy)pyrimidin-4-yl)-2,8-diazaspiro[4.5]decane-3-carboxylic acid | 571 |

TABLE 17a-continued

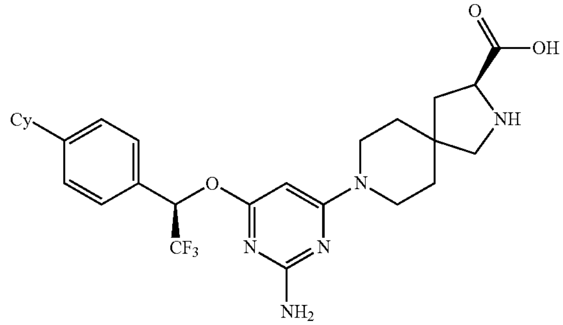

| Ex. No. | Cy | CAS Name | LCMS (MH+) |
|---|---|---|---|
| 55bt | 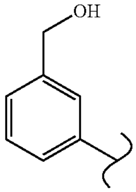 | (S)-8-(2-amino-6-((R)-2,2,2-trifluoro-1-(3'-(hydroxymethyl)-[1,1'-biphenyl]-4-yl)ethoxy)pyrimidin-4-yl)-2,8-diazaspiro[4.5]decane-3-carboxylic acid | 559 |
| 55bu | 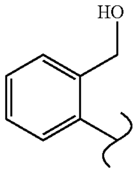 | (S)-8-(2-amino-6-((R)-2,2,2-trifluoro-1-(2'-(hydroxymethyl)-[1,1'-biphenyl]-4-yl)ethoxy)pyrimidin-4-yl)-2,8-diazaspiro[4.5]decane-3-carboxylic acid | 559 |
| 55bv | 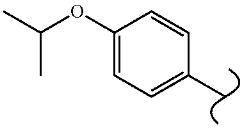 | (S)-8-(2-amino-6-((R)-2,2,2-trifluoro-1-(4'-isopropoxy-[1,1'-biphenyl]-4-yl)ethoxy)pyrimidin-4-yl)-2,8-diazaspiro[4.5]decane-3-carboxylic acid | 587 |
| 55bw | 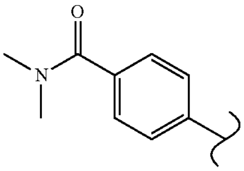 | (S)-8-(2-amino-6-((R)-1-(4'-(dimethylcarbamoyl)-[1,1'-biphenyl]-4-yl)-2,2,2-trifluoroethoxy)pyrimidin-4-yl)-2,8-diazaspiro[4.5]decane-3-carboxylic acid | 600 |
| 55bx | 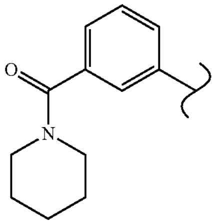 | (S)-8-(2-amino-6-((R)-2,2,2-trifluoro-1-(3'-(piperidine-1-carbonyl)-[1,1'-biphenyl]-4-yl)ethoxy)pyrimidin-4-yl)-2,8-diazaspiro[4.5]decane-3-carboxylic acid | 640 |
| 55by | 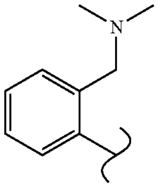 | (S)-8-(2-amino-6-((R)-1-(2'-((dimethylamino)methyl)-[1,1'-biphenyl]-4-yl)-2,2,2-trifluoroethoxy)pyrimidin-4-yl)-2,8-diazaspiro[4.5]decane-3-carboxylic acid | 586 |

TABLE 17a-continued

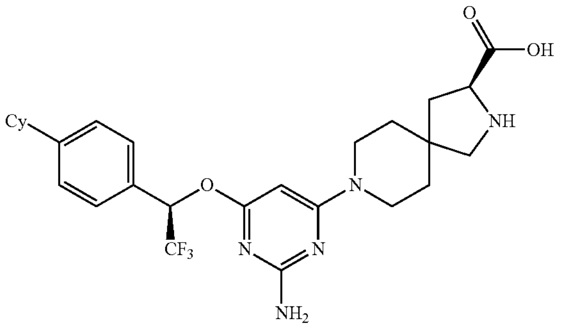

| Ex. No. | Cy | CAS Name | LCMS (MH+) |
|---|---|---|---|
| 55bz | 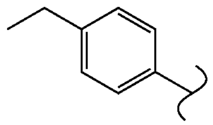 | (S)-8-(2-amino-6-((R)-1-(4'-ethyl-[1,1'-biphenyl]-4-yl)-2,2,2-trifluoroethoxy)pyrimidin-4-yl)-2,8-diazaspiro[4.5]decane-3-carboxylic acid | 557 |
| 55ca | 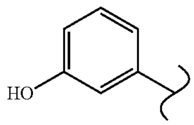 | (S)-8-(2-amino-6-((R)-2,2,2-trifluoro-1-(3'-hydroxy-[1,1'-biphenyl]-4-yl)ethoxy)pyrimidin-4-yl)-2,8-diazaspiro[4.5]decane-3-carboxylic acid | 545 |
| 55cb | 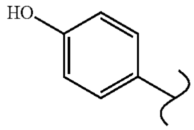 | (S)-8-(2-amino-6-((R)-2,2,2-trifluoro-1-(4'-hydroxy-[1,1'-biphenyl]-4-yl)ethoxy)pyrimidin-4-yl)-2,8-diazaspiro[4.5]decane-3-carboxylic acid | 545 |
| 55cc | 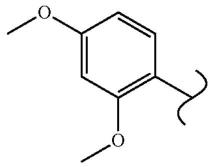 | (S)-8-(2-amino-6-((R)-1-(2',4'-dimethoxy-[1,1'-biphenyl]-4-yl)-2,2,2-trifluoroethoxy)pyrimidin-4-yl)-2,8-diazaspiro[4.5]decane-3-carboxylic acid | 589 |
| 55cd | 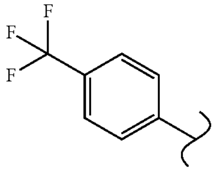 | (S)-8-(2-amino-6-((R)-2,2,2-trifluoro-1-(4'-(trifluoromethyl)-[1,1'-biphenyl]-4-yl)ethoxy)pyrimidin-4-yl)-2,8-diazaspiro[4.5]decane-3-carboxylic acid | 597 |
| 55ce | 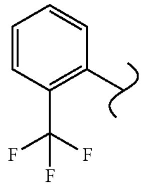 | (S)-8-(2-amino-6-((R)-2,2,2-trifluoro-1-(2'-(trifluoromethyl)-[1,1'-biphenyl]-4-yl)ethoxy)pyrimidin-4-yl)-2,8-diazaspiro[4.5]decane-3-carboxylic acid | 597 |
| 55cf | 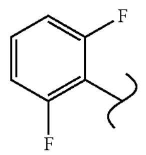 | (S)-8-(2-amino-6-((R)-1-(2',6'-difluoro-[1,1'-biphenyl]-4-yl)-2,2,2-trifluoroethoxy)pyrimidin-4-yl)-2,8-diazaspiro[4.5]decane-3-carboxylic acid | 565 |

TABLE 17a-continued

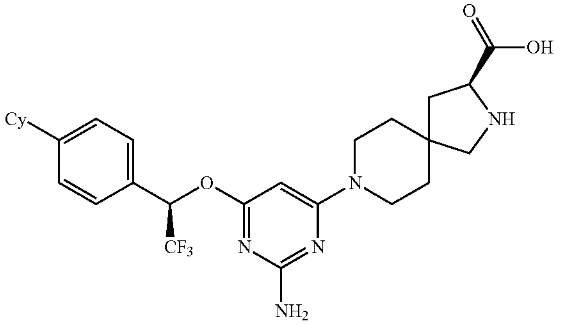

| Ex. No. | Cy | CAS Name | LCMS (MH+) |
|---|---|---|---|
| 55cg | 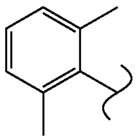 | (S)-8-(2-amino-6-((R)-1-(2',6'-dimethyl-[1,1'-biphenyl]-4-yl)-2,2,2-trifluoroethoxy)pyrimidin-4-yl)-2,8-diazaspiro[4.5]decane-3-carboxylic acid | 557 |
| 55ch | 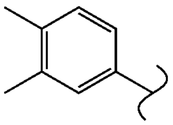 | (S)-8-(2-amino-6-((R)-1-(3',4'-dimethyl-[1,1'-biphenyl]-4-yl)-2,2,2-trifluoroethoxy)pyrimidin-4-yl)-2,8-diazaspiro[4.5]decane-3-carboxylic acid | 557 |
| 55ci | 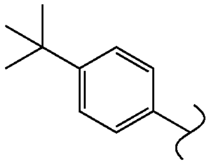 | (S)-8-(2-amino-6-((R)-1-(4'-(tert-butyl)-[1,1'-biphenyl]-4-yl)-2,2,2-trifluoroethoxy)pyrimidin-4-yl)-2,8-diazaspiro[4.5]decane-3-carboxylic acid | 585 |
| 55cj | 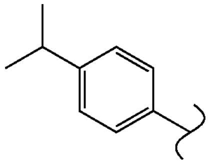 | (S)-8-(2-amino-6-((R)-2,2,2-trifluoro-1-(4'-isopropyl-[1,1'-biphenyl]-4-yl)ethoxy)pyrimidin-4-yl)-2,8-diazaspiro[4.5]decane-3-carboxylic acid | 571 |
| 55ck | 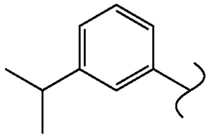 | (S)-8-(2-amino-6-((R)-2,2,2-trifluoro-1-(3'-isopropyl-[1,1'-biphenyl]-4-yl)ethoxy)pyrimidin-4-yl)-2,8-diazaspiro[4.5]decane-3-carboxylic acid | 571 |
| 55cl | 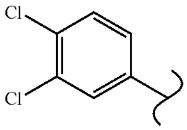 | (S)-8-(2-amino-6-((R)-1-(3',4'-dichloro-[1,1'-biphenyl]-4-yl)-2,2,2-trifluoroethoxy)pyrimidin-4-yl)-2,8-diazaspiro[4.5]decane-3-carboxylic acid | 597 |
| 55cm | 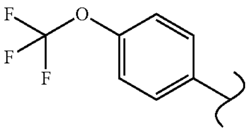 | (S)-8-(2-amino-6-((R)-2,2,2-trifluoro-1-(4'-(trifluoromethoxy)-[1,1'-biphenyl]-4-yl)ethoxy)pyrimidin-4-yl)-2,8-diazaspiro[4.5]decane-3-carboxylic acid | 613 |
| 55cn | 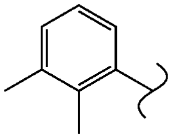 | (S)-8-(2-amino-6-((R)-1-(2',3'-dimethyl-[1,1'-biphenyl]-4-yl)-2,2,2-trifluoroethoxy)pyrimidin-4-yl)-2,8-diazaspiro[4.5]decane-3-carboxylic acid | 557 |

TABLE 17a-continued

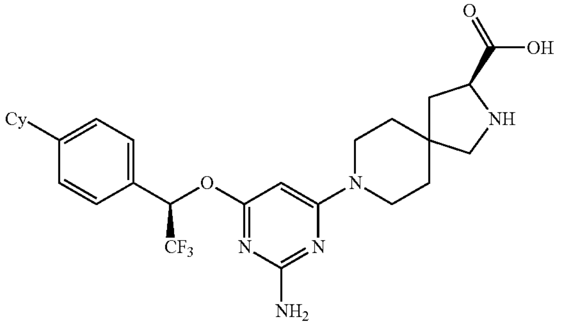

| Ex. No. | Cy | CAS Name | LCMS (MH+) |
|---|---|---|---|
| 55co | 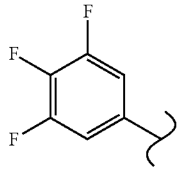 | (S)-8-(2-amino-6-((R)-2,2,2-trifluoro-1-(3',4',5'-trifluoro-[1,1'-biphenyl]-4-yl)ethoxy)pyrimidin-4-yl)-2,8-diazaspiro[4.5]decane-3-carboxylic acid | 583 |
| 55cp | 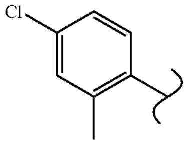 | (S)-8-(2-amino-6-((R)-1-(4'-chloro-2'-methyl-[1,1'-biphenyl]-4-yl)-2,2,2-trifluoroethoxy)pyrimidin-4-yl)-2,8-diazaspiro[4.5]decane-3-carboxylic acid | 577 |
| 55cq | 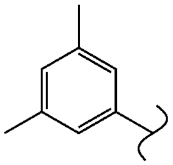 | (S)-8-(2-amino-6-((R)-1-(3',5'-dimethyl-[1,1'-biphenyl]-4-yl)-2,2,2-trifluoroethoxy)pyrimidin-4-yl)-2,8-diazaspiro[4.5]decane-3-carboxylic acid | 557 |
| 55cr | 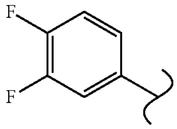 | (S)-8-(2-amino-6-((R)-1-(3',4'-difluoro-[1,1'-biphenyl]-4-yl)-2,2,2-trifluoroethoxy)pyrimidin-4-yl)-2,8-diazaspiro[4.5]decane-3-carboxylic acid | 565 |
| 55cs | 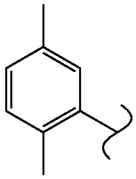 | (S)-8-(2-amino-6-((R)-1-(2',5'-dimethyl-[1,1'-biphenyl]-4-yl)-2,2,2-trifluoroethoxy)pyrimidin-4-yl)-2,8-diazaspiro[4.5]decane-3-carboxylic acid | 557 |
| 55ct | 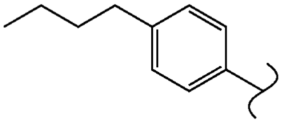 | (S)-8-(2-amino-6-((R)-1-(4'-butyl-[1,1'-biphenyl]-4-yl)-2,2,2-trifluoroethoxy)pyrimidin-4-yl)-2,8-diazaspiro[4.5]decane-3-carboxylic acid | 585 |
| 55cu | 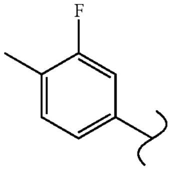 | (S)-8-(2-amino-6-((R)-2,2,2-trifluoro-1-(3'-fluoro-4'-methyl-[1,1'-biphenyl]-4-yl)ethoxy)pyrimidin-4-yl)-2,8-diazaspiro[4.5]decane-3-carboxylic acid | 561 |

TABLE 17a-continued

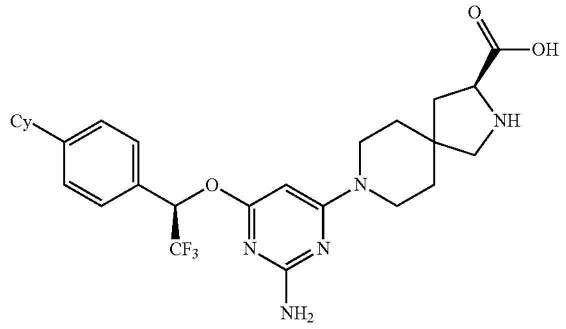

| Ex. No. | Cy | CAS Name | LCMS (MH+) |
|---|---|---|---|
| 55cv | 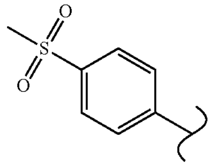 | (S)-8-(2-amino-6-((R)-2,2,2-trifluoro-1-(4'-(methylsulfonyl)-[1,1'-biphenyl]-4-yl)ethoxy)pyrimidin-4-yl)-2,8-diazaspiro[4.5]decane-3-carboxylic acid | 607 |
| 55cw | 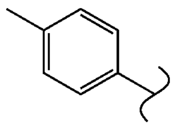 | (S)-8-(2-amino-6-((R)-2,2,2-trifluoro-1-(4'-methyl-[1,1'-biphenyl]-4-yl)ethoxy)pyrimidin-4-yl)-2,8-diazaspiro[4.5]decane-3-carboxylic acid | 543 |
| 55cx | 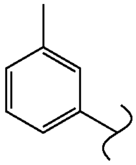 | (S)-8-(2-amino-6-((R)-2,2,2-trifluoro-1-(3'-methyl-[1,1'-biphenyl]-4-yl)ethoxy)pyrimidin-4-yl)-2,8-diazaspiro[4.5]decane-3-carboxylic acid | 543 |
| 55cy | 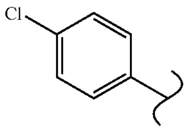 | (S)-8-(2-amino-6-((R)-1-(4'-chloro-[1,1'-biphenyl]-4-yl)-2,2,2-trifluoroethoxy)pyrimidin-4-yl)-2,8-diazaspiro[4.5]decane-3-carboxylic acid | 563 |
| 55cz | 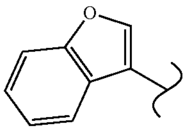 | (S)-8-(2-amino-6-((R)-1-(4-(benzofuran-3-yl)phenyl)-2,2,2-trifluoroethoxy)pyrimidin-4-yl)-2,8-diazaspiro[4.5]decane-3-carboxylic acid | 569 |
| 55da | 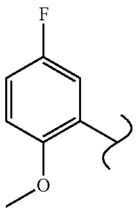 | (S)-8-(2-amino-6-((R)-2,2,2-trifluoro-1-(5'-fluoro-2'-methoxy-[1,1'-biphenyl]-4-yl)ethoxy)pyrimidin-4-yl)-2,8-diazaspiro[4.5]decane-3-carboxylic acid | 577 |
| 55db | 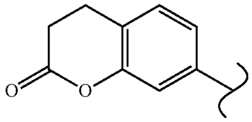 | (S)-8-(2-amino-6-((R)-2,2,2-trifluoro-1-(4-(2-oxochroman-7-yl)phenyl)ethoxy)pyrimidin-4-yl)-2,8-diazaspiro[4.5]decane-3-carboxylic acid | 599 |

TABLE 17a-continued

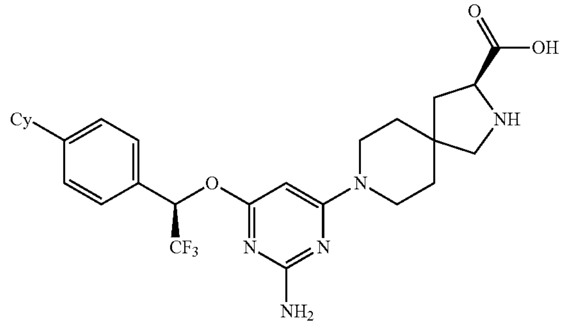

| Ex. No. | Cy | CAS Name | LCMS (MH+) |
|---|---|---|---|
| 55dc | 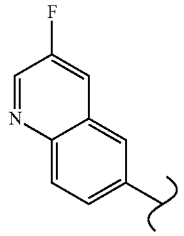 | (S)-8-(2-amino-6-((R)-2,2,2-trifluoro-1-(4-(3-fluoroquinolin-6-yl)phenyl)ethoxy)pyrimidin-4-yl)-2,8-diazaspiro[4.5]decane-3-carboxylic acid | 597 |
| 55dd | 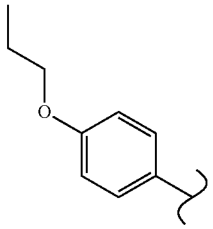 | (S)-8-(2-amino-6-((R)-2,2,2-trifluoro-1-(4'-propoxy-[1,1'-biphenyl]-4-yl)ethoxy)pyrimidin-4-yl)-2,8-diazaspiro[4.5]decane-3-carboxylic acid | 587 |
| 55de | 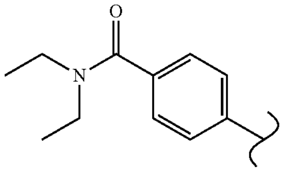 | (S)-8-(2-amino-6-((R)-1-(4'-(diethylcarbamoyl)-[1,1'-biphenyl]-4-yl)-2,2,2-trifluoroethoxy) pyrimidin-4-yl)-2,8-diazaspiro[4.5]decane-3-carboxylic acid | 628 |
| 55df | 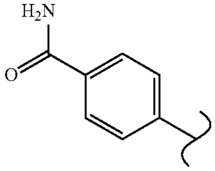 | (S)-8-(2-amino-6-((R)-1-(4'-carbamoyl-[1,1'-biphenyl]-4-yl)-2,2,2-trifluoroethoxy)pyrimidin-4-yl)-2,8-diazaspiro[4.5]decane-3-carboxylic acid | 572 |
| 55dg | 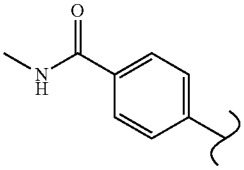 | (S)-8-(2-amino-6-((R)-2,2,2-trifluoro-1-(4'-(methylcarbamoyl)-[1,1'-biphenyl]-4-yl)ethoxy)pyrimidin-4-yl)-2,8-diazaspiro[4.5]decane-3-carboxylic acid | 585 |
| 55dh | 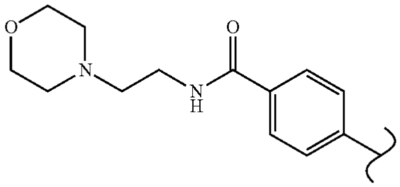 | (S)-8-(2-amino-6-((R)-2,2,2-trifluoro-1-(4'-((2-morpholinoethyl)carbamoyl)-[1,1'-biphenyl]-4-yl)ethoxy)pyrimidin-4-yl)-2,8-diazaspiro[4.5]decane-3-carboxylic acid | 685 |

TABLE 17a-continued

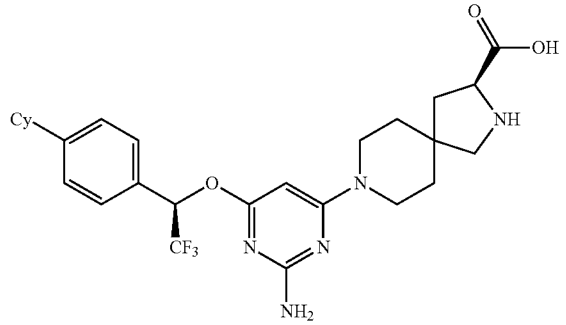

| Ex. No. | Cy | CAS Name | LCMS (MH+) |
|---|---|---|---|
| 55di | 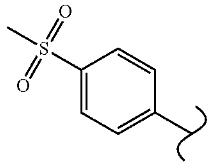 | (S)-8-(2-amino-6-((R)-2,2,2-trifluoro-1-(4'-(methylsulfonyl)-[1,1'-biphenyl]-4-yl)ethoxy)pyrimidin-4-yl)-2,8-diazaspiro[4.5]decane-3-carboxylic acid | 606 |
| 55dj | 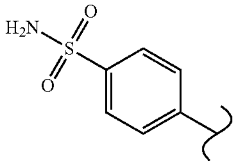 | (S)-8-(2-amino-6-((R)-2,2,2-trifluoro-1-(4'-sulfamoyl-[1,1'-biphenyl]-4-yl)ethoxy)pyrimidin-4-yl)-2,8-diazaspiro[4.5]decane-3-carboxylic acid | 607 |
| 55dk | 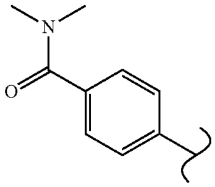 | (S)-8-(2-amino-6-((R)-1-(4'-(dimethylcarbamoyl)-[1,1'-biphenyl]-4-yl)-2,2,2-trifluoroethoxy)pyrimidin-4-yl)-2,8-diazaspiro[4.5]decane-3-carboxylic acid | 600 |
| 55dl | 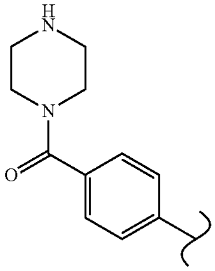 | (S)-8-(2-amino-6-((R)-2,2,2-trifluoro-1-(4'-(piperazine-1-carbonyl)-[1,1'-biphenyl]-4-yl)ethoxy)pyrimidin-4-yl)-2,8-diazaspiro[4.5]decane-3-carboxylic acid | 641 |
| 55dm | 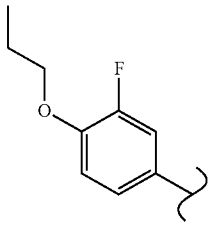 | (S)-8-(2-amino-6-((R)-2,2,2-trifluoro-1-(3'-fluoro-4'-propoxy-[1,1'-biphenyl]-4-yl)ethoxy)pyrimidin-4-yl)-2,8-diazaspiro[4.5]decane-3-carboxylic acid | 605 |
| 55dn | 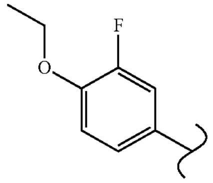 | (S)-8-(2-amino-6-((R)-1-(4'-ethoxy-3'-fluoro-[1,1'-biphenyl]-4-yl)-2,2,2-trifluoroethoxy)pyrimidin-4-yl)-2,8-diazaspiro[4.5]decane-3-carboxylic acid | 591 |

TABLE 17a-continued

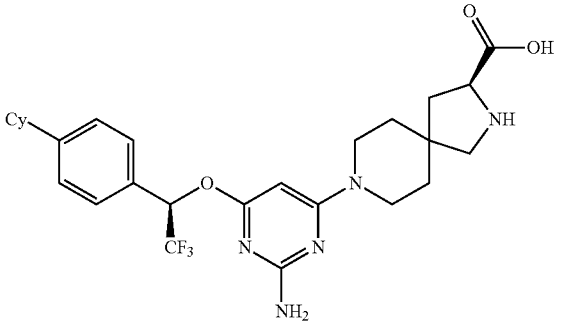

| Ex. No. | Cy | CAS Name | LCMS (MH+) |
|---|---|---|---|
| 55do | 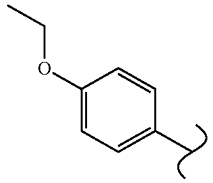 | (S)-8-(2-amino-6-((R)-1-(4'-ethoxy-[1,1'-biphenyl]-4-yl)-2,2,2-trifluoroethoxy)pyrimidin-4-yl)-2,8-diazaspiro[4.5]decane-3-carboxylic acid | 573 |
| 55dp | 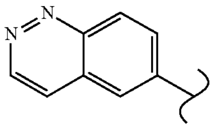 | (S)-8-(2-amino-6-((R)-1-(4-(cinnolin-6-yl)phenyl)-2,2,2-trifluoroethoxy)pyrimidin-4-yl)-2,8-diazaspiro[4.5]decane-3-carboxylic acid | 580 |
| 55dq | 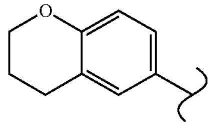 | (S)-8-(2-amino-6-((R)-1-(4-(chroman-6-yl)phenyl)-2,2,2-trifluoroethoxy)pyrimidin-4-yl)-2,8-diazaspiro[4.5]decane-3-carboxylic acid | 584 |

TABLE 17b

| NMR Data for Compounds of Table 17a | |
|---|---|
| Ex. No. | NMR |
| 55a | $^1$H NMR (400 MHz, MeOH-d4): δ ppm 7.66-7.58 (m, 6H), 7.45-7.41 (m, 2H), 7.36-7.32 (m, 1H), 6.64 (q, J = 6.8 Hz, 1H), 5.56 (s, 1H), 4.00 (m, 1H), 3.67-3.60 (m, 2H), 3.52-3.44 (m, 2H), 3.20-3.02 (m, 2H), 2.31-2.25 (m, 1H), 2.01 (m, 1H), 1.58 (s, 4H) |
| 55b | $^1$H NMR (400 MHz, MeOH-d4): δ ppm 8.02 (s, 1 H), 7.92 (s, 1 H), 7.67-7.65 (m, 3 H), 7.61-7.55(m, 4H), 6.60 (m, 1 H), 5.47 (s, 1 H), 3.97 (s, 4 H), 3.53 (m, 2 H), 3.35 (m, 2 H), 3.15-3.12 (m, 1 H), 3.13-3.00 (m, 1 H), 2.21 (m, 1 H), 1.95(m, 1H), 1.50 (m, 4H) |
| 55c | $^1$H NMR (400 MHz, MeOH-d4): δ ppm 8.16 (s, 1 H), 7.89 (s, 1 H), 7.71-7.69 (d, 2 H), 7.63-7.60 (m, 4 H), 6.67-6.66 (q, 1 H), 5.52 (s, 1 H), 4.00 (m, 1 H), 3.87 (s, 3 H), 3.62 (m, 2 H), 3.44 (m, 2 H), 3.12 (d, 1 H), 3.06 (d, 1 H), 2.23 (m, 1 H), 1.99 (m, 1 H), 1.54(m, 4 H), 1.23 (m, 3 H). |
| 55d | $^1$H NMR (400 MHz, MeOH-d4): δ ppm 8.56 (s, 1H), 7.90 (s, 1H), 7.76-7.61 (m, 6H), 6.66 (q, J = 6.6 Hz, 1H), 5.59 (s, 1H), 4.17-4.13 (m, 1H), 3.69-3.57 (m, 2H), 3.52-3.43 (m, 2H), 3.27-3.24 (m, 1H), 3.16-3.13 (m, 1H), 2.37-2.31 (m, 1H), 2.09-2.04 (m, 5H), 1.61 (m, 4H) |
| 55e | $^1$H NMR (400 MHz, MeOH -d4): δ ppm 7.62-7.56 (m, 4 H), 7.40 (m, 2 H), 7.15 (m, 1 H), 6.61 (m, 1 H), 5.56 (m, 1 H), 4.07 (m, 1 H), 3.90 (s, 3 H), 3.63 (m, 2 H), 3.48 (m, 2 H), 3.25 (m, 1 H), 3.13 (m, 1 H), 2.30 (m, 1 H), 2.04 (m, 1 H), 1.60 (s, 4 H) |
| 55f | $^1$H NMR (400 MHz, DMSO-d6): δ ppm 9.09 (s, 1 H), 8.45 (s, 1 H), 8.26 (m, 1 H), 7.83-7.77(m, 3 H), 7.64 (m, 2 H), 6.73 (m, 1H), 6.06 (s, 1H), 5.57 (s. 1H), 3.45 (m, 4H), 2.99 (m, 2 H), 2.10 (m, 1 H), 1.79 (m, 1 H), 1.42 (m, 4 H). |
| 55g | $^1$H NMR (400 MHz, MeOH-d4): δ ppm 7.66-7.56 (m, 6H), 7.19-7.17 (m, 2H), 6.66 (q, J = 6.7 Hz, 1H), 5.56-5.55 (m, 1H), 4.08 (m, 1H), 3.64-3.59 (m, 2H), 3.53-3.43 (m, 2H), 3.23-3.13 (m, 1H), 2.98-2.92 (m, 1H), 2.35-2.19 (m, 1H), 2.08-2.03 (m, 1H), 1.59 (m, 4H). |
| 55h | $^1$H NMR (400 MHz, MeOH-d4): δ ppm 8.06 (s, 1H), 7.83 (d, J = 8.3 Hz, 1H), 7.73 (d, J = 7.7 Hz, 3H), 7.62 (d, J = 7.5 Hz, 2H), 7.44 (d, J = 8.6 Hz, 1H), 6.67 (q, J = 7.4 Hz, 1H), 5.58 (s, 1H), 4.08 (m, 1H), 3.69-3.61 (m, 2H), 3.52-3.43 (m, 2H), 3.23-3.10 (m, 2H), 2.35-2.30 (m, 1H), 2.08-2.03 (m, 1H), 1.60 (s, 4H). |

TABLE 17b-continued

| NMR Data for Compounds of Table 17a | |
|---|---|
| Ex. No. | NMR |
| 55i | $^1$H NMR (400 MHz, DMSO-d6): δ ppm 8.03 (s, 1 H), 7.83-7.82 (d, 2 H, J = 4.5 Hz), 7.81-7.79 (d, 2 H, J = 7.6 Hz), 7.62-7.60 (d, 2 H, J = 7.6 Hz), 7.43-7.41 (d, 2 H, J = 8.6 Hz), 6.71-6.70 (q, 1 H, J = 6.8 Hz), 5.55 (s, 1 H), 4.02 (s, 3 H), 3.71 (m, 1 H), 3.55-.344 (m, 4 H), 2.85 (m, 1 H), 2.12 (m, 1 H), 1.71 (m, 1 H), 1.40 (m, 4 H). |
| 55j | $^1$H NMR (400 MHz, MeOH-d4): δ ppm 8.96 (s, 1 H), 8.33 (s, 1 H), 8.09-8.07 (d, 1 H, J = 8.8 Hz), 7.81-7.79(dd, 1 H, J = 8.0 Hz), 7.71-7.69 (d, 2 H, J = 8.0 Hz), 7.60-7.58 (d, 2 H, J = 8.0 Hz), 6.63-6.58 (q, 1 H), 5.51 (s. 1H), 4.00-3.96 (m, 1 H), 3.57 (m, 2 H), 3.40 (m, 2 H), 3.17-3.14 (d, 1 H, J = 11.7 Hz), 3.13-3.00 (d, 1 H, J = 11.7 Hz), 2.23-2.21 (m, 1 H), 1.99-1.94 (m, 1 H), 1.53 (m, 5 H). |
| 55k | $^1$H NMR (400 MHz, MeOH-d4): δ ppm 9.26 (S, 1 H), 8.33 (s, 1 H), 8.13-8.11 (d, 1 H, J = 8.5 Hz), 7.84-7.82(dd, 1 H, J = 8.5 Hz), 7.76-7.74 (d, 2 H, J = 8.3 Hz), 7.65-7.63 (d, 2 H, J = 8.3 Hz), 6.67-6.65 (q, 1 H, J = 7.2 Hz), 4.15-4.11 (m, 1 H), 3.53 (m, 2 H), 3.49 (m, 2 H), 3.27-3.24 (d, 1 H, J = 11.7 Hz), 3.15-3.12 (d, 1 H, J = 11.7 Hz), 3.33-2.31 (m, 1 H), 2.07-2.03 (m, 1 H), 1.61 (m, 5 H). |
| 55l | $^1$H-NMR (400 MHz, MeOH-d4): δ ppm 9.08 9(s, 1H), 8.44 (s, 1H), 8.02-8.03 (m, 1H), 7.83-7.86 (m, 2H), 7.66-7.75 (m, 2H), 6.66-6.69 (m, 1H), 5.50 (s, 1H), 4.07-4.07 (m, 1H), 3.64-3.66 (m, 2H), 3.44-3.48 (m, 2H), 3.19-3.24 (m, 1H), 3.16-3.46 (m, 1H), 2.29-2.55 (m, 1H), 2.03-2.08 (m, 1H), 1.60-1.61 (m, 4H) |
| 55m | $^1$H-NMR (400 MHz, DMSO-d6): δ ppm 8.19 (s, 1H), 7.84-7.97 (m, 6H), 7.63-7.82 (m, 2H), 7.50-7.61 (m, 2H), 6.70-6.76 (m, 1H), 5.58 (s, 1H), 3.38-3.47 (S, 1H), 3.00-3.00 (m, 1H), 2.91-2.94 (m, 1H), 2.06-2.13 (m, 1H), 1.74-1.78 (m, 1H), 1.37-1.44 (m, 4H) |
| 55n | $^1$H-NMR (400 MHz, MeOH-d4): δ ppm 7.63-7.65 (m, 2H), 7.56-7.58 (m, 2H), 7.15-7.20 (m, 1H), 7.07-7.09 (m, 2H), 6.60-6.65 (m, 1H), 4.11-4.16 (m, 1H), 3.87 (s, 3H), 3.48-3.66 (m, 4H), 3.23-3.26 (m, 1H), 3.11-3.16 (m, 1H), 2.31-3.41 (m, 1H), 2.20 (s, 3H), 2.02-2.10 (m, 1H), 1.59-1.61 (m, 4H), 1.27-1.31 (m, 1H) |
| 55o | $^1$H NMR (400 MHz, MeOH-d4): δ ppm 7.62-7.56 (m, 4H), 7.00 (s, 1H), 6.93 (s, 1H), 6.74(s, 1H), 6.64 (q, 1H, J = 8.0), 5.56 (d, 1H, J = 4.0), 4.08-4.04 (m, 1H), 3.80 (s, 3H), 3.63 (s, 2H), 3.47 (s, 2H) 3.23 (d, 1H, J = 16.0), 3.10 (d, 1H, J = 12.0 Hz), 2.36 (s, 3H), 2.04 (s, 1H), 1.59 (s, 1H), 1.28 (s, 1H) |
| 55p | $^1$H NMR (400 MHz, MeOH-d4): δ ppm 0.89 (m, 1H), 1.30 (d, J = 15.5 Hz, 3H), 1.62 (d, J = 5.7 Hz, 5H), 2.06 (m, 1H), 2.14 (s, 3H), 2.33 (dd, J = 13.5, 9.2 Hz, 1H), 3.13 (d, J = 11.7 Hz, 1H), 3.25 (d, J = 11.3 Hz, 1H), 3.51 (dt, J = 20.9, 6.7 Hz, 2H), 3.66 (d, J = 13.3 Hz, 2H), 3.76 (s, 3H), 4.09 (t, J = 8.2 Hz, 1H), 5.57 (s, 1H), 6.69 (m, 2H), 6.81 (dd, J = 8.4, 2.8 Hz, 1H), 7.15 (d, J = 8.4 Hz, 1H), 7.35 (m, 2H), 7.57 (d, J = 7.9 Hz, 2H) |
| 55q | $^1$H NMR (400 MHz, MeOH-d4): δ ppm 7.62 (d, 2H, J = 8.0), 7.56(d, 2H, J = 8.0), 7.18(m, 2H), 7.02(d, 1H, J = 8.0), 6.62 (q, 1H, J = 8.0), 5.55 (s, 1H), 4.01-3.97 (m, 1H), 3.31-3.23 (m, 1H), 3.89 (s, 3H), 3.86 (s, 3H), 3.67-3.60 (m, 2H), 3.49-3.43(m, 2H) 3.19 (d, 1H, J = 12.0), 3.02 (d, 1H, J = 12.0 Hz), 2.27(dd, 1H, J = 12.0, 8.0), 2.00 (dd, 1H, J = 14.0, 4.0), 1.58 (s, 1H), 1.28 (s, 1H) |
| 55r | $^1$H NMR (400 MHz, MeOH-d4): δ ppm 7.70-7.61 (m, 4H), 7.28 (m, 3H), 6.67 (q, J = 7.6 Hz, 1H), 5.56 (s, 1H), 4.08 (m, 1H), 3.91 (s, 3H), 3.63-3.46 (m, 8H), 3.13 (m, 1H), 2.35-2.29 (m, 1H), 2.01-1.99 (m, 1H), 1.97-1.87 (m, 5H), 1.59 (m, 4H). |
| 55s | $^1$H-NMR (400 MHz, MeOH-d4): δ ppm 1.74-1.73 (m, 4H), 2.13-2.07 (m, 1H), 2.52-2.46 (m, 1H), 3.60-3.55 (m, 1H), 3.70-3.66 (m, 2H), 4.55-4.50 (m, 1H), 5.44 (s, 2H), 6.66-6.63 (m, 1H), 7.74-7.69 (m, 2H), 7.88-7.80 (m, 4H), 7.96-7.92 (m, 1H) |
| 55t | $^1$H NMR (400 MHz, MeOH-d4): δ ppm 8.03-8.05 (m, 1H), 7.95 (s, 1H), 7.84-7.86 (m, 1H), 7.71-7.73 (m, 2H), 7.60-7.62 (m, 2H), 7.43-7.45 (m, 1H), 6.62-6.65 (m, 2H), 5.57 (s, 1H), 4.05-4.10 (m, 1H), 3.61-3.70 (m, 3H), 3.42-3.52 (m, 3H), 3.09-3.12 (m, 1H), 2.29-2.36 (m, 1H), 2.02-2.07 (m, 1H), 1.60 (m, 4H) |
| 55u | $^1$H NMR (400 MHz, DMSO-d6): δ ppm 8.02 (s, 1H), 7.93-7.98 (m, 2H), 7.76-7.78 (m, 2H), 7.59-7.63 (m, 3H), 6.63-6.73 (m, 2H), 5.55 (s, 1H), 3.74-3.79 (m, 1H), 3.61 (s, 3H), 3.32-3.47 (m, 5H), 2.89-3.07 (m, 2H), 2.08-2.14 (m, 1H), 1.73-1.80 (m, 1H), 1.41 (m, 4H). |
| 55v | $^1$H NMR (400 MHz, MeOH-d4): δ ppm 7.62(d, 2H, J = 8.0), 7.56 (d, 2H, J = 8.0), 7.45 (m, 2H), 6.93 (d, 1H, J = 8.0), 6.62 (q, 1H, J = 8.0), 5.56 (s, 1H), 4.07 (t, 1H, J = 8.0), 3.64δ3.58 (m, 2H), 3.52-3.45(m, 2H), 3.24 (d, 1H, J = 12.0), 3.11 (d, 1H, J = 8.0 Hz), 3.01 (t, 2H, J = 8.0), 2.59-2.57 (m, 2H), 2.32(dd, 1H, J = 12.0, 8.0), 2.05(dd, 1H, J = 12.0, 8.0), 1.58 (s, 4H), 1.28 (s, 1H) |
| 55w | $^1$H NMR (400 MHz, DMSO-d6): δ 1.59 (m, 4 H), 2.05-2.01 (m, 1 H, J = 11.6 Hz), 2.32-2.28 (m, 1 H, J = 11.6 Hz), 3.11-3.08 (d, 1 H), 3.25-3.22 (d, 1 H), 3.50-3.47 (m, 2 H), 3.68-3.65 (m, 2 H), 4.08-4.04 (q, 1 H), 5.57 (s, 1 H), 6.66-6.65 (q, 1 H), 8.10 (s, 1 H), 7.61-7.60 (m, 3 H, J = 8.6 Hz), 7.71-7.69 (m, 3 H, J = 8.6 Hz), 8.01 (s, 1 H) |
| 55x | $^1$H NMR (400 MHz, MeOH-d4): δ ppm 1.61 (d, J = 5.7 Hz, 4H), 2.06 (dd, J = 13.5, 7.3 Hz, 1H), 2.35 (dd, J = 13.5, 9.2 Hz, 1H), 2.56 (s, 3H), 3.15 (d, J = 11.8 Hz, 1H), 3.25 (d, J = 11.7 Hz, 1H), 3.54 (m, 5H), 3.99 (s, 3H), 4.17 (t, J = 8.3 Hz, 1H), 5.00 (s, 1H), 6.66 (q, J = 7.1 Hz, 1H), 7.53 (d, J = 8.8 Hz, 1H), 7.61 (d, J = 8.1 Hz, 2H), 7.70 (m, 3H), 7.91 (s, 1H) |
| 55y | $^1$H NMR (400 MHz, MeOH-d4): δ ppm 1.54 (m, 4 H), 2.10 (m, 1 H), 2.26 (m, 4 H), 3.04 (m, 1 H), 3.17 (m, 1 H), 3.40 (m, 2 H), 3.56 (m, 2 H), 3.69 (s, 3 H), 4.07-4.03 (m, 1 H), 6.65-6.59 (m, 1 H), 6.93 (s, 1 H), 7.37-7.34(m, 1 H), 7.45-7.42 (m, 1 H), 7.57-7.55 (m, 2 H), 7.72-7.68 (m, 3 H) |

TABLE 17b-continued

| Ex. No. | NMR |
|---|---|
| | NMR Data for Compounds of Table 17a |
| 55z | $^1$H NMR (400 MHz, MeOH-d4): δ ppm 7.72-7.63(m, 4H), 7.45(s, 1H), 7.40 (s, 1H), 7.18 (s, 1H), 6.66 (q, 1H, J = 8.0), 4.30 (d, 1H, J = 8.0), 3.91 (s, 3H), 3.66 (s, 2H), 3.55(s, 2H), 3.26 (s, 1H), 3.19(d, 1H, J = 12.0 Hz), 2.43-2.37 (m, 1H), 2.10-2.05 (m, 1H), 1.65 (s, 5H), 1.28 (s, 1H) |
| 55aa | $^1$H NMR (400 MHz, MeOH-d4): δ ppm 7.94 (d, 1H, J = 4.0), 7.71 (d, 1H, J = 4.0), 7.53-7.50 (m, 2H), 6.82 (q, 1H, J = 8.0), 6.41 (d, 1H, J = 4.0), 5.68 (d, 1H, J = 4.0), 4.41 (s, 1H), 3.09 (s, 1H), 2.75(t, 2H, J = 8.0), 2.46 (d, 1H, J = 16.0), 2.38 (s, 3H), 2.22(dd, 1H, J = 16.0, 8.0), 1.23-1.19 (m, 3H) |
| 55ab | $^1$H NMR (400 MHz, MeOH-d4): δ ppm 1.60 (m, 4 H), 2.03-2.05 (m, 1 H), 2.33-2.32 (m, 1 H), 3.14-3.11 (d, 1 H, J = 11.9 Hz), 3.26-3.23 (d, 1 H, J = 11.9 Hz), 3.52-3.47 (m, 2 H), 3.65-3.54 (m, 2 H), 4.10-4.06 (m, 1H), 5.57 (s, 1 H), 6.65-6.64 (q, 1 H), 7.16-7.14 (d, 2 H, J = 8.2 Hz), 7.51-7.44 (dd, 2 H, J = 8.2 Hz), 7.51 (s, 1 H), 7.60-7.57 (d, 2 H, J = 8.3 Hz), 7.65-7.63 (d, 2 H, J = 8.3 Hz) |
| 55ac | $^1$H NMR (400 MHz, MeOH-d4): δ ppm 7.72-7.69 (m, 3 H), 7.58-7.56 (m, 2 H), 7.38 (s, 2 H), 7.02(m, 1 H), 6.61 (m, 1 H), 4.23(m, 1 H), 3.65 (m, 2 H), 3.48 (m, 2 H), 3.30 (m, 1 H), 3.14 (m, 1 H), 2.31 (m, 4H), 2.06 (m, 1 H), 1.62 (s, 4 H). |
| 55ad | $^1$H NMR (400 MHz, MeOH-d4): δ ppm 8.08 (d, J = 8.2 Hz, 1H), 7.77 (d, J = 8.2 Hz, 2H), 7.67-7.65 (m, 3H), 7.46 (m, 1H), 6.67-6.61 (m, 1H), 4.47 (m, 1H), 3.87 (s, 3H), 3.73-3.52 (m, 4H), 3.27-3.22 (m, 2H), 2.50-2.44 (m, 1H), 2.33 (s, 3H), 2.12-2.06 (m, 1H), 1.68 (m, 4H). |
| 55ae | $^1$H NMR (400 MHz, DMSO-d6): δ ppm 1.22 (d, J = 5.3 Hz, 2H), 1.42 (m, 4H), 1.82 (d, J = 13.2 Hz, 1H), 1.98 (dd, J = 17.4, 8.5 Hz, 1H), 2.91 (m, 1H), 3.03 (d, J = 11.0 Hz, 1H), 3.55 (s, 1H), 3.68 (s, 1H), 3.80 (s, 1H), 5.62 (s, 1H), 6.13 (s, 2H), 6.49 (d, J = 9.6 Hz, 1H), 6.75 (q, J = 7.3 Hz, 1H), 7.67 (m, 4H), 7.83 (dd, J = 22.1, 8.1 Hz, 3H), 8.09 (d, J = 9.5 Hz, 1H) |
| 55af | $^1$H NMR (400 MHz, MeOH-d4): δ ppm 8.01(d, J = 2.6 Hz, 1H), 7.89(dd, J = 2.72, 6.8 Hz, 1H), 7.58(m, 4H), 6.64(m, 2H), 5.56(s, 1H), 4.08(m, 1H), 3.64(s, 3H), 3.53(m, 4H), 3.12(m, 2H), 2.33(m, 1H), 2.06(m, 1H), 1.60(m, 4H). |
| 55ag | $^1$H NMR (400 MHz, MeOH-d4): δ ppm 7.92 (d, J = 8.8 Hz, 1H), 7.65 (dd, J1 = 8.4 Hz, J2 = 31.9 Hz, 4H), 7.17-7.14 (m, 2H), 6.66-6.63 (m, 1H), 4.14-4.10 (m, 1H), 3.66-3.59 (m, 2H), 3.54-3.43 (m, 2H), 3.26-3.24 (m, 1H), 3.15-3.12 (m, 1H), 2.37-2.32 (m, 1H), 2.08-2.03 (m, 1H), 1.61 (m, 4H) |
| 55ah | $^1$H NMR (400 MHz, MeOH-d4): δ ppm 8.16 (d, J = 8.92 Hz, 1H), 8.02 (d, J = 1.56 Hz, 1H), 7.93-7.86 (m, 2H), 7.76 (d, J = 8.16 Hz, 2H), 7.64(d, J = 8.08 Hz, 2H), 6.96 (d, J = 8.88 Hz, 1H), 6.66 (q, J = 7.12 Hz, 1H), 5.57(s, 1H), 4.06(s, 3H), 3.97 (m, 1H), 3.64(m, 2H), 3.47(m, 2H), 3.17 (d, J = 10.92 Hz, 1H), 3.00 (d, J = 12.04 Hz, 1H), 2.26 (m, 1H), 2.01 (m, 1H), 1.58 (s, 4H) |
| 55ai | $^1$H NMR (400 MHz, MeOH-d4): δ ppm 8.06 (d, J = 8.76 Hz, 1H), 8.01 (s, 1H), 7.93 (s, 2H), 7.76 (d, J = 8.04 Hz, 2H), 7.64 (d, J = 8.16 Hz, 2H), 7.31 (d, J = 8.76 Hz, 1H), 6.68 (q, J = 8.48 Hz, 1H), 5.58 (s, 1H), 4.08 (m, 1H), 3.63-3.50 (m, 4H), 3.24 (d, J = 11.64 Hz, 1H), 3.12 (d, J = 11.64 Hz, 1H), 2.68(s, 3H), 2.31 (m, 1H), 2.05 (m, 1H), 1.59 (m, 4H). |
| 55aj | $^1$H NMR (400 MHz, MeOH-d4): δ ppm δ7.67(d, 2H, J = 8.0), 7.61-7.57(m, 4H), 7.51(s, 1H), 7.20(d, 1H, J = 8.0), 6.63 (q, 1H, J = 8.0), 4.29 (t, 1H, J = 12.0), 3.67δ3.58 (m, 2H), 3.53-3.48(m, 2H), 3.38(s, 3H), 3.27 (d, 1H, J = 12.0), 3.19 (d, 1H, J = 8.0 Hz), 2.99-2.95 (m, 2H), 2.65-2.63 (m, 2H), 2.40(dd, 1H, J = 12.0, 8.0), 2.09(dd, 1H, J = 12.0, 8.0), 1.66 (s, 5H), 1.31 (s, 2H) |
| 55ak | $^1$H NMR (400 MHz, MeOH-d4): δ ppm 1.52-1.67 (m, 4 H) 2.05 (dd, J = 13.42, 7.13 Hz, 1 H) 2.32 (dd, J = 13.54, 9.30 Hz, 1 H) 3.07-3.16 (m, 1 H) 3.24 (d, J = 11.76 Hz, 1 H) 3.38-3.55 (m, 2 H) 3.56-3.76 (m, 2 H) 4.10 (t, J = 8.18 Hz, 1 H) 5.56 (s, 1 H) 6.63 (q, J = 6.96 Hz, 1 H) 7.06 (qd, J = 5.74, 3.29 Hz, 1 H) 7.35 (dd, J = 9.30, 1.44 Hz, 1 H) 7.38-7.48 (m, 2 H) 7.55-7.69 (m, 4 H) |
| 55al | $^1$H NMR (400 MHz, MeOH-d4): δ ppm 1.59 (d, J = 4.59 Hz, 4 H) 2.04 (dd, J = 13.50, 7.30 Hz, 1 H) 2.31 (dd, J = 13.30, 9.01 Hz, 1 H) 3.05-3.25 (m, 2 H) 3.37-3.53 (m, 2 H) 3.54-3.69 (m, 2 H) 3.81 (s, 3 H) 4.05 (dd, J = 9.18, 7.32 Hz, 1 H) 5.54 (s, 1 H) 6.61 (q, J = 7.29 Hz, 1 H) 6.89 (dd, J = 7.83, 2.12 Hz, 1 H) 7.05-7.21 (m, 2 H) 7.26-7.38 (m, 1 H) 7.46-7.68 (m, 4 H) |
| 55am | $^1$H NMR (400 MHz, MeOH-d4): δ ppm 1.63 (d, J = 5.08 Hz, 4 H) 2.08 (dd, J = 13.32, 7.18 Hz, 1 H) 2.35 (dd, J = 13.32, 9.22 Hz, 1 H) 3.07-3.20 (m, 1 H) 3.27 (d, J = 11.71 Hz, 1 H) 3.40-3.58 (m, 2 H) 3.59-3.80 (m, 2 H) 4.11 (t, J = 7.96 Hz, 1 H) 5.58 (s, 1 H) 6.68 (d, J = 7.13 Hz, 1 H) 7.10 (dt, J = 6.00, 2.95 Hz, 1 H) 7.38 (d, J = 10.35 Hz, 1 H) 7.42-7.52 (m, 2 H) 7.56-7.79 (m, 4 H) |
| 55an | $^1$H NMR (400 MHz, MeOH-d4): δ ppm 1.48-1.66 (m, 4 H) 2.01 (dd, J = 13.37, 7.17 Hz, 1 H) 2.28 (dd, J = 13.35, 9.20 Hz, 1 H) 3.06 (d, J = 11.71 Hz, 1 H) 3.20 (d, J = 11.67 Hz, 1 H) 3.35-3.52 (m, 2 H) 3.53-3.69 (m, 2 H) 3.81 (s, 3 H) 4.02 (dd, J = 9.15, 7.20 Hz, 1 H) 5.53 (s, 1 H) 6.61 (q, J = 7.21 Hz, 1 H) 6.89 (dd, J = 8.20, 2.49 Hz, 1 H) 7.06-7.21 (m, 2 H) 7.26-7.38 (m, 1 H) 7.47-7.68 (m, 4 H) |
| 55ao | $^1$H NMR (400 MHz, MeOH-d4): δ ppm 1.63-1.87 (m, 4 H) 2.10 (dd, J = 13.72, 8.69 Hz, 1 H) 2.48-2.62 (m, 1 H) 3.33 (s, 0 H) 3.52-3.81 (m, 4 H) 3.84 (s, 3 H) 4.55 (t, J = 8.81 Hz, 1 H) 5.93 (s, 0 H) 6.59 (d, J = 6.25 Hz, 1 H) .71 (dt, J = 10.75, 2.26 Hz, 1 H) 6.90-7.02 (m, 2 H) 7.51-7.80 (m, 4 H). |
| 55ap | $^1$H NMR (400 MHz, MeOH-d4): δ ppm 1.63-1.85 (m, 4 H) 2.10 (dd, J = 13.64, 8.66 Hz, 1 H) 2.50 (dd, J = 13.64, 8.81 Hz, 1 H) 3.51-3.88 (m, 5 H) 4.55 (t, J = 8.71 Hz, 1 H) 5.93 (s, 1 H) 6.63 (q, J = 6.61 Hz, 1 H) 6.96 (tt, J = 9.06, 2.31 Hz, 1 H) 7.20-7.33 (m, 2 H) 7.62-7.80 (m, 4 H). |

TABLE 17b-continued

| NMR Data for Compounds of Table 17a | |
|---|---|
| Ex. No. | NMR |
| 55aq | $^1$H NMR (400 MHz, MeOH-d4): δ ppm 1.60-1.87 (m, 4 H) 2.09 (dd, J = 13.64, 8.76 Hz, 1 H) 2.50 (dd, J = 13.59, 8.86 Hz, 1 H) 3.51-3.79 (m, 4 H) 3.81 (s, 3 H) 4.56 (t, J = 8.74 Hz, 1 H) 5.88-5.99 (m, 1 H) 5.93 (s, 1 H) 6.57 (d, J = 6.39 Hz, 1 H) 6.94-7.04 (m, 2 H) 7.50-7.70 (m, 6 H) |
| 55ar | $^1$H NMR (400 MHz, MeOH-d4): δ ppm 1.67-1.87 (m, 4 H) 2.10 (dd, J = 13.64, 8.71 Hz, 1 H) 2.51 (dd, J = 13.59, 8.86 Hz, 1 H) 3.54-3.77 (m, 4 H) 3.78 (s, 4 H) 4.57 (t, J = 8.76 Hz, 1 H) 5.95 (s, 1 H) 6.59 (q, J = 6.22 Hz, 1 H) 7.00 (td, J = 7.46, 0.95 Hz, 1 H) 7.06 (d, J = 8.10 Hz, 1 H) 7.19-7.38 (m, 2 H) 7.48-7.66 (m, 4 H) |
| 55as | $^1$H NMR (400 MHz, MeOH-d4): δ ppm 1.60-1.86 (m, 4 H) 2.10 (dd, J = 13.64, 8.66 Hz, 1 H) 2.50 (dd, J = 13.62, 8.83 Hz, 1 H) 3.53-3.87 (m, 4 H) 4.54 (t, J = 8.71 Hz, 1 H) 5.93 (s, 0 H) 6.64 (q, J = 6.65 Hz, 1 H) 7.61-7.72 (m, 4 H) 7.73-7.80 (m, 2 H) 7.84-7.94 (m, 2 H) |
| 55at | $^1$H NMR (400 MHz, MeOH-d4): δ ppm 1.67-1.84 (m, 4 H) 2.10 (dd, J = 13.67, 8.69 Hz, 1 H) 2.51 (dd, J = 13.69, 8.81 Hz, 1 H) 3.55-3.82 (m, 4 H) 4.56 (t, J = 8.76 Hz, 1 H) 5.95 (s, 1 H) 6.63 (q, J = 6.56 Hz, 1 H) 7.29 (dt, J = 8.19, 1.15 Hz, 1 H) 7.48-7.58 (m, 2 H) 7.61-7.76 (m, 5 H) |
| 55au | $^1$H NMR (400 MHz, MeOH-d4): δ ppm 1.39 (t, J = 7.00 Hz, 3 H) 1.65-1.86 (m, 4 H) 2.09 (dd, J = 13.64, 8.76 Hz, 1 H) 2.50 (dd, J = 13.62, 8.79 Hz, 1 H) 3.51-3.84 (m, 4 H) 4.07 (q, J = 6.98 Hz, 2 H) 4.57 (t, J = 8.74 Hz, 1 H) 5.94 (s, 1 H) 6.61 (q, J = 6.57 Hz, 1 H) 6.82-6.95 (m, 1 H) 7.06-7.20 (m, 2 H) 7.28-7.43 (m, 1 H) 7.55-7.73 (m, 4 H) |
| 55av | $^1$H NMR (400 MHz, MeOH-d4): δ ppm 1.32 (d, J = 6.05 Hz, 6 H) 1.65-1.86 (m, 4 H) 2.09 (dd, J = 13.67, 8.69 Hz, 1 H) 2.50 (dd, J = 13.64, 8.86 Hz, 1 H) 3.48-3.85 (m, 4 H) 4.55 (t, J = 8.71 Hz, 1 H) 4.65 (dt, J = 12.08, 6.06 Hz, 1 H) 5.92 (s, 1 H) 6.59 (q, J = 6.43 Hz, 1 H) 6.91 (dd, J = 8.22, 1.93 Hz, 1 H) 7.11 (t, J = 2.03 Hz, 1 H) 7.15 (d, J = 7.71 Hz, 1 H) 7.29-7.39 (m, 1 H) 7.56-7.73 (m, 4 H) |
| 55aw | $^1$H NMR (400 MHz, MeOH-d4): δ ppm 1.62-1.93 (m, 4 H) 2.11 (dd, J = 13.69, 8.76 Hz, 1 H) 2.54 (dd, J = 13.69, 8.86 Hz, 1 H) 3.46-4.00 (m, 4 H) 4.59 (t, J = 8.74 Hz, 1 H) 6.01 (s, 1 H) 6.74 (q, J = 6.65 Hz, 1 H) 7.75-8.02 (m, 4 H) 8.20 (dd, J = 8.22, 5.78 Hz, 1 H) 8.87 (d, J = 5.71 Hz, 1 H)8.97 (dt, J = 8.27, 1.72 Hz, 1 H) 9.24 (d, J = 2.00 Hz, 1 H) |
| 55ax | $^1$H NMR (400 MHz, MeOH-d4): δ ppm 1.64-1.90 (m, 4 H) 2.11 (dd, J = 13.67, 8.79 Hz, 1 H) 2.52 (dd, J = 13.64, 8.86 Hz, 1 H) 3.49-4.02 (m, 4 H) 4.57 (t, J = 8.71 Hz, 1 H) 6.01 (s, 1 H) 6.76 (d, J = 6.54 Hz, 1 H) 7.85 (d, J = 8.35 Hz, 2 H) 8.09 (d, J = 8.49 Hz, 2 H) 8.33-8.54 (m, 2 H) 8.80-8.99 (m, 2 H) |
| 55ay | $^1$H NMR (400 MHz, MeOH-d4): δ ppm 1.56-1.91 (m, 4 H) 2.10 (dd, J = 13.69, 8.66 Hz, 1 H) 2.51 (dd, J = 13.81, 8.83 Hz, 1 H) 3.53-3.94 (m, 5 H) 4.56 (dt, J = 8.48, 4.37 Hz, 1 H) 5.89-6.14 (m, 1 H) 6.51-6.82 (m, 1 H) 7.48-8.01 (m, 4 H) 9.19 (s, 1 H) 9.24 (s, 1 H) |
| 55az | $^1$H NMR (400 MHz, MeOH-d4): δ ppm 1.60 (t, J = 5.08 Hz, 4 H) 2.00 (s, 2 H) 2.03-2.13 (m, 1 H) 2.26-2.39 (m, 1 H) 2.52-2.64 (m, 4 H) 3.07-3.18 (m, 1 H) 3.26 (d, J = 11.71 Hz, 1 H) 3.39-3.57 (m, 2 H) 3.57-3.77 (m, 2 H) 4.01-4.20 (m, 1 H) 5.58 (s, 1 H) 6.67 (s, 1 H) 7.40 (dd, J = 8.49, 1.07 Hz, 1 H) 7.59-7.68 (m, 3 H) 7.69-7.79 (m, 3 H) |
| 55ba | $^1$H NMR (400 MHz, MeOH-d4): δ ppm 1.47-1.74 (m, 4 H) 1.99-2.13 (m, 1 H) 2.26-2.40 (m, 1 H) 2.55 (s, 3 H) 3.07-3.19 (m, 1 H) 3.21 3.29 (m, 1H) 3.48 (d, J = 4.88 Hz, 2 H) 3.65 (d, J = 3.32 Hz, 2 H) 4.01 (s, 3 H) 4.10 (dd, J = 8.98, 7.22 Hz, 1 H) 5.59 (s, 1 H) 6.69 (d, J = 7.03 Hz, 1 H) 7.41 (dd, J = 8.49, 1.07 Hz, 1 H) 7.58-7.70 (m, 3 H) 7.70-7.84 (m, 3 H) |
| 55bb | $^1$H NMR (400 MHz, MeOH-d4): δ ppm 1.58 (br. s., 4 H) 1.95-2.09 (m, 1 H) 2.24-2.38 (m, 1 H) 2.63 (s, 3 H) 3.01-3.14 (m, 1 H) 3.17 3.25 (m, 1 H) 3.38-3.54 (m, 2 H) 3.55-3.74 (m, 2H) |
| 55bc | $^1$H NMR (400 MHz, MeOH-d4): δ ppm 1.62 (br. s., 4 H) 1.97-2.09 (m, 1 H) 2.24-2.36 (m, 1 H) 3.07 (s, 3 H) 3.18-3.27 (m, 1 H) 3.55 (s, 4 H) 3.60-3.75 (m, 2 H) 3.96-4.07 (m, 1 H) 5.59 (s, 1 H), 6.61-6.75 (m, 1 H) 7.54-7.61 (m, 1 H) 7.66 (s, 3 H) 7.72 (s, 2 H) 7.95-8.08 (m, 1 H) |
| 55bd | $^1$H NMR (400 MHz, MeOH-d4): δ ppm 1.50-1.68 (m, 4 H) 1.86-2.01 (m, 1 H) 2.11-2.28 (m, 1 H) 2.77-2.91 (m, 1 H) 3.04-3.13 (m, 1 H) 3.40-3.57 (m, 2 H) 3.59-3.74 (m, 2 H) 3.76-3.88 (m, 1 H) 5.54-5.66 (m, 1 H) 6.61-6.79 (m, 1 H) 7.67-7.77 (m, 2 H) 7.81-7.97 (m, 3 H) 7.99-8.09 (m, 1 H) 8.16-8.27 (m, 2 H) 8.41-8.53 (m, 1 H) 9.21-9.33 (m, 1 H) |
| 55be | $^1$H NMR (400 MHz, MeOH-d4): δ ppm 1.50-1.65 (m, 4 H) 1.92-2.00 (m, 1 H) 2.14-2.28 (m, 1 H) 2.84-2.94 (m, 1 H) 3.04-3.16 (m, 1 H) 3.40-3.57 (m, 2 H) 3.58-3.73 (m, 2 H) 3.79-3.91 (m, 1 H) 5.59 (s, 1 H) 6.62-6.78 (m, 1 H) 7.64-7.75 (m, 2 H) 7.86 (d, J = 8.59 Hz, 3 H) 8.01-8.09 (m, 1 H) 8.10-8.20 (m, 1 H) 8.35-8.42 (m, 1 H) 8.43-8.48 (m, 1 H) 9.25-9.37 (m, 1 H) |
| 55bf | $^1$H NMR (400 MHz, MeOH-d4): δ ppm 1.61 (br. s., 4 H) 1.94-2.04 (m, 1 H) 2.28 (s, 7 H) 2.92-3.06 (m, 1 H) 3.11-3.23 (m, 1 H) 3.53 (s, 4 H) 3.59-3.75 (m, 2 H) 3.89-4.02 (m, 1 H) 5.58 (s, 1 H) 6.60-6.70 (m, 1 H) 7.43 (s, 2 H) 7.57-7.74 (m, 6 H) |
| 55bg | $^1$H NMR (400 MHz, MeOH-d4): δ ppm 1.56 (d, J = 4.69 Hz, 4 H) 1.78-1.95 (m, 1 H) 2.07-2.22 (m, 1 H) 2.69-2.83 (m, 1 H) 2.96-3.09 (m, 1 H) 3.38-3.54 (m, 2 H) 3.56-3.69 (m, 2 H) 3.70-3.79 (m, 1 H) 5.57 (s, 1 H) 6.59-6.77 (m, 1 H) 7.51-7.61 (m, 1 H) 7.68 (d, J = 8.00 Hz, 2 H) 7.83 (d, J = 8.20 Hz, 2 H) 8.11 (s, 2 H) 8.20 (s, 1 H) 8.38-8.50 (m, 1 H) 8.77-8.92 (m, 1 H) |
| 55bh | $^1$H NMR (400 MHz, MeOH-d4): δ ppm 1.57 (br. s., 4 H) 1.84-2.03 (m, 1 H) 2.12-2.29 (m, 1 H) 2.91 (s, 1 H) 3.04-3.16 (m, 1 H) 3.38-3.55 (m, 2 H) 3.56-3.73 (m, 2 H) 3.78-3.96 (m, 1 H) 5.58 (s, 1 H) 6.60-6.80 (m, 1 H) 7.47-7.58 (m, 1 H) 7.69 (d, |

TABLE 17b-continued

NMR Data for Compounds of Table 17a

| Ex. No. | NMR |
|---|---|
| | J = 8.20 Hz, 2 H) 7.83 (d, J = 8.20 Hz, 2 H) 7.93 (d, J = 1.17 Hz, 1 H) 8.02 (d, J = 8.59 Hz, 1 H) 8.25 (s, 1 H) 8.37 (s, 1 H) 8.87 (d, J = 2.93 Hz, 1 H) |
| 55bi | $^1$H NMR (400 MHz, MeOH-d 4): δ ppm 1.56 (d, J = 5.08 Hz, 4 H) 1.76-1.88 (m, 1 H) 2.05-2.20 (m, 1 H) 2.63-2.81 (m, 1 H) 2.94-3.07 (m, 1 H) 3.37-3.54 (m, 2 H) 3.55-3.79 (m, 3 H) 5.58 (s, 1H) 6.61-6.78 (m, 1 H) 7.71 (d, J = 8.20 Hz, 2 H) 7.86 (d, J = 8.40 Hz, 2 H) 8.17 (s, 2 H) 8.32 (s, 1 H) 8.89 (dd, J = 12.98, 1.66 Hz, 2 H) |
| 55bj | $^1$H NMR (400 MHz, MeOH-d4): δ ppm 1.54-1.72 (m, 4 H) 2.01-2.13 (m, 1 H) 2.27-2.41 (m, 1 H) 3.06-3.16 (m, 3 H) 3.18 (s, 3 H) 3.22-3.30 (m, 1 H) 3.41-3.59 (m, 2 H) 3.67 (s, 4 H) 4.02-4.16 (m, 1 H) 5.53-5.66 (m, 1 H) 6.61-6.74 (m, 1 H) 7.54-7.57 (m, 1 H) 7.61-7.67 (m, 3 H) 7.70-7.80 (m, 2 H) 7.96-8.06 (m, 1 H) |
| 55bk | $^1$H NMR (400 MHz, MeOH-d4): δ ppm 1.54-1.72 (m, 4 H) 2.05-2.18 (m, 1 H) 2.29-2.43 (m, 1 H) 3.08-3.20 (m, 1 H) 3.24-3.29 (m, 1 H) 3.43-3.76 (m, 4 H) 4.05-4.17 (m, 1 H) 5.57-5.67 (m, 1 H) 6.64-6.79 (m, 1 H) 7.65-7.76 (m, 2 H) 7.83-7.94 (m, 2 H) 8.08-8.19 (m, 1 H) 8.32-8.48 (m, 2 H) 9.21-9.33 (m, 1 H) 9.56-9.67 (m, 1 H) |
| 55bp | $^1$H NMR (400 MHz, MeOH-d4): δ ppm 1.60 (q, J = 5.9, 5.2 Hz, 4H), 1.98 (m, 5H), 2.32 (dd, J = 13.4, 9.3 Hz, 1H), 3.12 (d, J = 11.8 Hz, 1H), 3.25 (d, J = 11.7 Hz, 1H), 3.50 (m, 4H), 3.61 (m, 4H), 4.08 (dd, J = 9.2, 7.2 Hz, 1H), 5.57 (s, 1H), 6.67 (q, J = 7.1 Hz, 1H), 7.61 (ddd, J = 356.8, 7.9, 5.7 Hz, 4H), 7.71 (m, 4H) |
| 55cc | $^1$H NMR (400 MHz, MeOH-d4): δ ppm 0.09 (d, 1 = 1.2 Hz, 0H), 1.28 (s, 0H), 1.61 (q, J = 5.3 Hz, 0H), 1.92 (m, 0H), 2.05 (dd, J = 13.3, 7.3 Hz, 0H), 2.32 (m, 0H), 3.10 (s, 0H), 3.29 (s, 2H), 3.53 (s, 0H), 3.65 (s, 1H), 3.80 (dd, J = 16.8, 1.2 Hz, 0H), 4.07 (t, J = 8.2 Hz, 0H), 4.89 (d, J = 3.8 Hz, 0H), 5.56 (d, J = 1.2 Hz, 0H), 5.99 (m, 0H), 6.60 (m, 0H), 7.21 (dd, J = 8.4, 1.2 Hz, 0H), 7.48 (d, J = 1.2 Hz, 1H) |
| 55ce | $^1$H NMR (400 MHz, DMSO-d6): δ ppm 1.58 (q, J = 6.7, 6.1 Hz, 4H), 1.94 (dd, J = 13.2, 9.1 Hz, 1H), 2.39 (dd, J = 13.3, 8.6 Hz, 1H), 3.20 (s, 2H), 3.80 (m, 3H), 4.54 (t, J = 8.4 Hz, 1H), 5.74 (s, 1H), 6.31 (s, 2H), 6.90 (q, J = 7.2 Hz, 1H), 7.49 (t, J = 6.5 Hz, 3H), 7.76 (m, 6H), 9.01 (dt, J = 21.8, 11.9 Hz, 1H), 9.74 (d, J = 11.9 Hz, 1H) |
| 55cg | $^1$H NMR (400 MHz, DMSO-d6): δ ppm 1.59 (m, 4H), 2.00 (s, 7H), 2.41 (m, 1H), 3.20 (s, 2H), 3.60 (m, 4H), 3.83 (m, 1H), 4.53 (d, J = 8.7 Hz, 1H), 5.74 (s, 1H), 6.34 (dd, J = 28.1, 14.7 Hz, 2H), 6.91 (q, J = 7.4 Hz, 1H), 7.24 (m, 5H), 7.67 (d, J = 7.8 Hz, 2H), 8.99 (s, 1H), 9.77 (d, J = 8.4 Hz, 1H) |
| 55cj | $^1$H NMR (400 MHz, DMSO-d6): δ ppm 1.29 (d, J = 6.8 Hz, 6H), 1.58 (m, 4H), 1.94 (dd, J = 13.2, 9.2 Hz, 1H), 2.39 (dd, J = 13.4, 8.6 Hz, 1H), 2.99 (hept, J = 7.1 Hz, 1H), 3.19 (s, 2H), 3.59 (m, 4H), 4.55 (d, J = 9.2 Hz, 1H), 5.73 (s, 1H), 6.28 (m, 2H), 6.81 (q, J = 7.4 Hz, 1H), 7.41 (d, J = 7.9 Hz, 2H), 7.65 (m, 4H), 7.78 (d, J = 8.0 Hz, 2H), 8.97 (d, J = 13.6 Hz, 1H), 9.76 (s, 1H) |
| 55ck | $^1$H NMR (400 MHz, DMSO-d6): δ ppm 0.99 (s, 1H), 1.31 (d, J = 6.9 Hz, 7H), 1.58 (m, 4H), 1.94 (dd, J = 13.2, 9.2 Hz, 1H), 2.39 (dd, J = 13.4, 8.6 Hz, 1H), 3.02 (hept, J = 7.2 Hz, 1H), 3.19 (s, 2H), 3.55 (ddd, J = 19.7, 12.2, 5.9 Hz, 2H), 3.86 (s, 2H), 4.05 (s, 1H), 4.54 (q, J = 8.9, 6.7 Hz, 1H), 5.73 (s, 1H), 6.31 (m, 2H), 6.81 (q, J = 7.3 Hz, 1H), 7.46 (m, 5H), 7.65 (d, J = 8.0 Hz, 2H), 7.79 (d, J = 8.0 Hz, 2H), 8.96 (dt, J = 20.8, 8.6 Hz, 1H), 9.77 (d, J = 8.5 Hz, 1H) |
| 55cp | $^1$H NMR (400 MHz, DMSO-d6): δ ppm 1.29 (s, 1H), 1.57 (dd, J = 9.4, 5.0 Hz, 12H), 1.94 (dd, J = 13.3, 9.1 Hz, 3H), 2.28 (s, 9H), 2.41 (m, 4H), 2.61 (d, J = 7.4 Hz, 1H), 3.19 (s, 7H), 3.59 (m, 13H), 4.15 (s, 1H), 4.55 (d, J = 8.4 Hz, 4H), 5.75 (s, 3H), 6.38 (m, 5H), 6.87 (q, J = 7.4 Hz, 3H), 7.46 (m, 22H), 8.98 (m, 3H), 9.76 (m, 3H) |
| 55cq | $^1$H NMR (400 MHz, MeOH-d4): δ ppm 1.60 (m, 4H), 2.05 (m, 1H), 2.34 (s, 7H), 3.12 (d, J = 11.5 Hz, 1H), 3.24 (d, J = 11.5 Hz, 1H), 3.49 (m, 2H), 3.64 (dq, J = 12.6, 6.5, 4.7 Hz, 2H), 4.08 (t, J = 8.2 Hz, 1H), 5.56 (s, 1H), 6.64 (q, J = 7.1 Hz, 1H), 6.99 (s, 1H), 7.21 (s, 2H), 7.59 (m, 5H) |
| 55cr | $^1$H NMR (400 MHz, DMSO-d6): δ ppm 1.29 (s, 1H), 1.58 (dq, J = 11.6, 7.5, 7.1 Hz, 11H), 1.94 (dd, J = 13.3, 9.1 Hz, 3H), 2.15 (s, 0H), 2.39 (dd, J = 13.3, 8.6 Hz, 3H), 2.61 (d, J = 8.8 Hz, 3H), 3.05 (s, 0H), 3.19 (s, 6H), 3.40 (s, 1H), 3.54 (h, J = 6.4 Hz, 3H), 3.81 (m, 4H), 4.01 (dd, J = 19.9, 11.7 Hz, 1H), 4.16 (s, 1H), 4.54 (t, J = 8.6 Hz, 3H), 5.73 (s, 3H), 6.28 (d, J = 15.5 Hz, 5H), 6.81 (q, J = 7.3 Hz, 3H), 7.63 (m, 11H), 7.86 (dd, J = 17.4, 7.8 Hz, 8H), 8.99 (dq, J = 23.7, 15.7, 12.4 Hz, 2H), 9.72 (s, 3H) |
| 55cs | $^1$H NMR (400 MHz, DMSO-d6): δ ppm 1.57 (m, J = 8.0, 6.2 Hz, 8H), 1.94 (dd, J = 13.2, 9.2 Hz, 2H), 2.23 (s, 6H), 2.34 (s, 8H), 3.20 (s, 5H), 3.57 (dp, J = 22.0, 7.4, 6.0 Hz, 9H), 4.54 (t, J = 8.4 Hz, 3H), 5.76 (s, 2H), 6.34 (d, J = 14.9 Hz, 1H), 6.45 (s, 1H), 6.86 (q, J = 7.4 Hz, 2H), 7.18 (m, 6H), 7.56 (dd, J = 46.1, 7.8 Hz, 8H), 8.99 (m, 2H), 9.77 (d, J = 15.0 Hz, 2H) |
| 55ct | $^1$H NMR (400 MHz, DMSO-d6): δ ppm 0.97 (t, J = 7.3 Hz, 3H), 1.50 (m, 9H), 1.94 (dd, J = 13.3, 9.2 Hz, 1H), 2.39 (dd, J = 13.3, 8.6 Hz, 1H), 2.67 (q, J = 6.9, 6.2 Hz, 2H), 3.19 (s, 2H), 3.57 (m, 5H), 3.85 (m, 1H), 4.06 (d, J = 16.1 Hz, 1H), 4.54 (m, 1H), 5.74 (s, 1H), 6.31 (s, 2H), 6.81 (q, J = 7.3 Hz, 1H), 7.35 (d, J = 7.8 Hz, 2H), 7.64 (d, J = 7.8 Hz, 4H), 7.78 (d, J = 8.0 Hz, 2H), 8.96 (m, 1H), 9.73 (d, J = 8.2 Hz, 1H) |
| 55cv | $^1$H NMR (400 MHz, DMSO-d6): δ ppm 1.29 (s, 1H), 1.38 (s, 1H), 1.58 (qd, J = 12.6, 8.1, 7.6 Hz, 11H), 1.95 (m, 8H), 2.43 (m, 5H), 2.94 (t, J = 10.0 Hz, 1H), 3.08 (dd, J = 16.3, 7.0 Hz, 1H), 3.19 (s, 6H), 3.33 (s, 8H), 3.52 (m, 4H), 3.82 (m, 5H), 4.11 (m, 4H), 4.53 (dt, J = 12.6, 6.0 Hz, 3H), 5.75 (s, 2H), 6.20 (s, 1H), 6.28 (d, J = 9.3 Hz, 2H), 6.48 (s, 3H), 6.84 (q, J = 7.3 Hz, 2H), 7.56 (s, 1H), 7.93 (m, 21H), 8.98 (dd, J = 13.6, 8.0 Hz, 2H), 9.71 (m, 2H) |
| 55cw | $^1$H NMR (400 MHz, DMSO-d6): δ ppm 1.29 (s, 1H), 1.58 (dd, J = 7.3, 4.2 Hz, 8H), 1.94 (dd, J = 13.2, 9.1 Hz, 2H), 2.14 (d, J = 1.4 Hz, 0H), 2.40 (s, 8H), 2.49 (d, J = 9.3 Hz, 0H), 3.03 (m, 1H), 3.19 (s, 5H), 3.55 (m, 3H), 3.81 (t, J = 8.1 Hz, 0H), 4.00 (m, |

TABLE 17b-continued

| NMR Data for Compounds of Table 17a | |
|---|---|
| Ex. No. | NMR |
| | 8H), 4.24 (m, 0H), 4.35 (m, 1H), 4.54 (m, 2H), 5.74 (s, 2H), 6.31 (m, 3H), 6.80 (q, J = 7.3 Hz, 2H), 7.34 (d, J = 7.8 Hz, 4H), 7.64 (d, J = 8.1 Hz, 8H), 7.78(m, 4H), 8.99 (q, J = 8.5, 7.4 Hz, 2H), 9.74 (s, 2H) |
| 55cx | $^{1}$H NMR (400 MHz, DMSO-d6): δ ppm 1.29 (s, 1H), 1.59 (m, 11H), 1.94 (dd, J = 13.3, 9.1 Hz, 3H), 2.43 (s, 11H), 2.61 (d, J = 9.0 Hz, 1H), 3.19 (s, 6H), 3.58 (m, 11H), 4.13 (s, 1H), 4.54 (m, 6H), 5.75 (s, 2H), 6.26 (s, 1H), 6.34 (s, 1H), 6.42 (s, 2H), 6.81 (q, J = 7.3 Hz, 3H), 7.27 (d, J = 7.5 Hz, 3H), 7.58 (m, 20H), 8.98 (s, 3H), 9.77 (d, J = 9.9 Hz, 3H) |
| 55db | $^{1}$H NMR (400 MHz, MeOH-d4): δ ppm 1.24 (m, 8H), 1.76 (dd, J = 12.6, 6.8 Hz, 9H), 2.01 (s, 3H), 2.12 (m, 4H), 2.51 (dd, J = 13.6, 8.8 Hz, 3H), 2.63 (td, J = 7.6, 5.4 Hz, 4H), 2.90 (m, 6H), 3.36 (d, J = 12.8 Hz, 7H), 3.63 (dt, J = 11.5, 5.0 Hz, 4H), 3.76 (m, 4H), 4.11 (qd, J = 7.1, 3.6 Hz, 4H), 4.56 (t, J = 8.7 Hz, 3H), 4.94 (s, 2H), 6.62 (dq, J = 19.2, 6.7 Hz, 3H), 7.02 (dt, J = 6.2, 2.0 Hz, 3H), 7.16 (m, 2H), 7.38 (m, 2H), 7.65 (m, 9H), 7.84 (m, 1H) |
| 55dc | $^{1}$H NMR (400 MHz, MeOH-d4): δ ppm 1.58 (t, J = 5.4 Hz, 4H), 2.02 (dd, J = 13.4, 7.0 Hz, 1H), 2.29 (dd, J = 13.4, 9.1 Hz, 1H), 3.08 (d, J = 11.6 Hz, 1H), 3.21 (d, J = 11.5 Hz, 1H), 3.46 (ddt, J = 20.6, 13.2, 5.7 Hz, 2H), 3.61 (d, J = 16.6 Hz, 2H), 4.05 (t, J = 8.1 Hz, 1H), 4.94 (s, 10H), 5.58 (s, 1H), 6.69 (q, J = 7.2 Hz, 1H), 7.66 (d, J = 8.0 Hz, 2H), 7.79 (d, J = 7.9 Hz, 2H), 8.00 (dd, J = 8.9, 1.9 Hz, 1H), 8.12 (m, 3H), 8.79 (d, J = 2.7 Hz, 1H) |
| 55dd | $^{1}$H NMR (400 MHz, MeOH-d4): δ ppm 1.05 (t, J = 7.4 Hz, 3H), 1.29 (d, J = 5.8 Hz, 1H), 1.59 (q, J = 5.8, 5.0 Hz, 4H), 1.80 (h, J = 6.9 Hz, 2H), 2.04 (dd, J = 13.5, 7.1 Hz, 1H), 2.32 (dd, J = 13.4, 9.2 Hz, 1H), 3.11 (d, J = 11.8 Hz, 1H), 3.23 (d, J = 12.0 Hz, 1H), 3.47 (ddt, J = 20.6, 13.1, 6.1 Hz, 2H), 3.64 (m, 2H), 3.96 (t, J = 6.4 Hz, 2H), 4.07 (dd, J = 9.1, 7.3 Hz, 1H), 5.55 (s, 1H), 6.62 (q, J = 7.1 Hz, 1H), 6.97 (m, 2H), 7.56 (m, 6H) |
| 55de | $^{1}$H NMR (400 MHz, MeOH-d4): δ ppm 1.15 (t, J = 7.0 Hz, 3H), 1.26 (t, J = 7.1 Hz, 3H), 1.61 (q, J = 5.9, 5.1 Hz, 4H), 2.05 (dd, J = 13.4, 7.2 Hz, 1H), 2.32 (dd, J = 13.4, 9.2 Hz, 1H), 3.11 (d, J = 11.8 Hz, 1H), 3.24 (d, J = 11.6 Hz, 1H), 3.35 (m, 3H), 3.56 (dddd, J = 47.5, 27.9, 14.5, 7.8 Hz, 6H), 4.07 (dd, J = 9.2, 7.1 Hz, 1H), 4.92 (s, 17H), 5.57 (s, 1H), 6.66 (q, J = 7.1 Hz, 1H), 7.46 (m, 2H), 7.62 (d, J = 8.1 Hz, 2H), 7.71 (m, 4H) |
| 55df | $^{1}$H NMR (400 MHz, MeOH-d4): δ ppm 1.28 (s, 1H), 1.64 (m, 4H), 2.07 (dd, J = 13.5, 7.6 Hz, 1H), 2.39 (dd, J = 13.5, 9.0 Hz, 1H), 3.17 (d, J = 11.7 Hz, 1H), 3.27 (d, J = 12.0 Hz, 2H), 3.53 (dt, J = 22.9, 7.5 Hz, 2H), 3.67 (td, J = 13.8, 13.2, 6.4 Hz, 2H), 4.26 (t, J = 8.3 Hz, 1H), 4.87 (m, 3H), 6.66 (q, J = 7.0 Hz, 1H), 7.63 (d, J = 8.1 Hz, 2H), 7.74 (m, 4H), 7.96 (m, 2H) |
| 55dg | $^{1}$H NMR (400 MHz, MeOH-d4): δ ppm 1.31 (dd, J = 17.3, 3.8 Hz, 2H), 1.62 (m, 4H), 2.06 (dd, J = 13.5, 7.4 Hz, 1H), 2.36 (dd, J = 13.5, 9.1 Hz, 1H), 2.93 (s, 3H), 3.15 (d, J = 11.9 Hz, 1H), 3.26 (d, J = 11.6 Hz, 1H), 3.51 (m, 2H), 3.64 (dq, J = 12.1, 6.4, 5.1 Hz, 2H), 4.18 (dd, J = 9.1, 7.5 Hz, 1H), 4.93 (d, J = 1.7 Hz, 19H), 6.66 (q, J = 7.1 Hz, 1H), 7.63 (d, J = 8.1 Hz, 2H), 7.72 (dd, J = 8.3, 5.9 Hz, 4H), 7.89 (m, 2H) |
| 55dh | $^{1}$H NMR (400 MHz, MeOH-d4): δ ppm 1.60 (q, J = 6.0, 5.0 Hz, 4H), 2.03 (dd, J = 13.4, 7.2 Hz, 1H), 2.31 (dd, J = 13.4, 9.2 Hz, 1H), 2.59 (dt, J = 24.2, 5.7 Hz, 6H), 3.10 (d, J = 11.7 Hz, 1H), 3.23 (d, J = 11.9 Hz, 1H), 3.62 (m, 10H), 4.06 (dd, J = 9.2, 7.2 Hz, 1H), 4.87 (s, 1H), 5.57 (s, 1H), 6.66 (q, J = 7.1 Hz, 1H), 7.62 (d, J = 8.1 Hz, 2H), 7.72 (m, 4H), 7.91 (m, 2H) |
| 55di | $^{1}$H NMR (400 MHz, MeOH-d4): δ ppm 1.61 (d, J = 5.5 Hz, 4H), 2.05 (dd, J = 13.4, 7.1 Hz, 1H), 2.32 (dd, J = 13.4, 9.3 Hz, 1H), 3.15 (s, 4H), 3.25 (d, J = 11.6 Hz, 1H), 3.50 (dt, J = 20.2, 7.0 Hz, 2H), 3.64 (m, 2H), 4.09 (dd, J = 9.2, 7.1 Hz, 1H), 5.58 (s, 1H), 6.68 (q, J = 7.2 Hz, 1H), 7.65 (d, J = 8.0 Hz, 2H), 7.73 (d, J = 8.4 Hz, 2H), 7.88 (d, J = 8.4 Hz, 2H), 8.01 (m, 2H) |
| 55dj | $^{1}$H NMR (400 MHz, MeOH-d4): δ ppm 1.28 (s, 1H), 1.60 (q, J = 6.4, 5.0 Hz, 4H), 2.03 (dd, J = 13.4, 7.1 Hz, 1H), 2.31 (dd, J = 13.4, 9.2 Hz, 1H), 3.10 (d, J = 11.7 Hz, 1H), 3.23 (d, J = 11.8 Hz, 1H), 3.48 (m, 2H), 3.63 (m, 2H), 4.06 (dd, J = 9.2, 7.1 Hz, 1H), 5.57 (s, 1H), 6.67 (q, J = 7.1 Hz, 1H), 7.68 (m, 4H), 7.79 (m, 2H), 7.96 (m, 2H) |
| 55dk | $^{1}$H NMR (400 MHz, MeOH-d4): δ ppm 1.29 (d, J = 3.6 Hz, 1H), 1.63 (q, J = 5.8 Hz, 5H), 2.07 (dd, J = 13.5, 7.5 Hz, 1H), 2.37 (dd, J = 13.5, 9.0 Hz, 1H), 3.04 (s, 3H), 3.15 (d, J = 24.6 Hz, 6H), 3.27 (m, 1H), 3.52 (dt, J = 24.6, 8.3 Hz, 2H), 3.65 (m, 2H), 4.23 (t, J = 8.1 Hz, 1H), 6.66 (q, J = 7.0 Hz, 1H), 7.51 (d, J = 8.1 Hz, 2H), 7.68 (m, 6H) |
| 55dl | $^{1}$H NMR (400 MHz, MeOH-d4): δ ppm 1.29 (m, 3H), 1.60 (q, J = 6.1, 4.7 Hz, 4H), 2.05 (dd, J = 13.2, 7.0 Hz, 1H), 2.32 (dd, J = 13.5, 9.2 Hz, 1H), 3.13 (d, J = 11.6 Hz, 1H), 3.26 (m, 5H), 3.48 (ddd, J = 26.8, 12.6, 5.3 Hz, 2H), 3.64 (td, J = 19.2, 16.1, 9.2 Hz, 2H), 3.78 (s, 1H), 3.90 (m, 3H), 4.10 (dd, J = 9.2, 7.1 Hz, 1H), 4.95 (s, 13H), 5.56 (s, 1H), 6.67 (q, J = 7.0 Hz, 1H), 7.67 (m, 7H) |
| 55dm | $^{1}$H NMR (400 MHz, MeOH-d4): δ ppm 1.06 (t, J = 7.4 Hz, 4H), 1.59 (d, J = 6.1 Hz, 5H), 1.82 (dq, J = 14.1, 6.6 Hz, 2H), 2.02 (dd, J = 13.4, 7.2 Hz, 1H), 2.30 (dd, J = 13.5, 9.2 Hz, 1H), 3.07 (d, J = 11.6 Hz, 1H), 3.21 (m, 2H), 3.48 (dt, J = 20.5, 6.6 Hz, 2H), 3.65 (d, J = 15.7 Hz, 2H), 4.03 (td, J = 7.7, 6.5, 5.1 Hz, 3H), 4.91 (m, 1H), 5.55 (s, 1H), 6.63 (q, J = 7.2 Hz, 1H), 7.13 (t, J = 8.7 Hz, 1H), 7.38 (m, 2H), 7.59 (q, J = 8.4 Hz, 4H) |
| 55dn | $^{1}$H NMR (400 MHz, MeOH-d4): δ ppm 1.28 (d, J = 2.6 Hz, 1H), 1.43 (t, J = 6.9 Hz, 3H), 1.60 (q, J = 5.8 Hz, 4H), 2.05 (dd, J = 13.1, 7.0 Hz, 1H), 2.33 (dd, J = 13.4, 9.0 Hz, 1H), 3.12 (d, J = 11.4 Hz, 1H), 3.25 (d, J = 11.4 Hz, 1H), 3.48 (m, 2H), 3.65 (q, J = 12.5, 10.8 Hz, 2H), 4.11 (dq, J = 16.7, 8.5, 7.7 Hz, 3H), 5.56 (s, 1H), 6.63 (q, J = 7.0 Hz, 1H), 7.13 (t, J = 8.6 Hz, 1H), 7.38 (m, 2H), 7.59 (q, J = 8.1 Hz, 4H) |
| 55do | $^{1}$H NMR (400 MHz, MeOH-d4): δ ppm 1.40 (t, J = 7.0 Hz, 3H), 1.60 (q, J = 5.9, 5.1 Hz, 4H), 2.05 (dd, J = 13.4, 7.2 Hz, 1H), 2.33 (dd, J = 13.4, 9.2 Hz, 1H), 3.12 (d, J = 11.7 Hz, 1H), 3.24 (d, J = 11.7 Hz, 1H), 3.47 (ddt, J = 20.2, 12.7, 5.6 Hz, 2H), 3.64 (m, |

TABLE 17b-continued

| NMR Data for Compounds of Table 17a | |
|---|---|
| Ex. No. | NMR |
| | 2H), 4.07 (p, J = 7.1 Hz, 3H), 5.56 (s, 1H), 6.62 (q, J = 7.1 Hz, 1H), 6.97 (m, 2H), 7.57 (m, 6H) |
| 55dp | $^1$H NMR (400 MHz, MeOH-d4): δ ppm 1.28 (s, 1H), 1.64 (d, J = 6.8 Hz, 5H), 2.07 (dd, J = 13.5, 7.6 Hz, 1H), 2.38 (dd, J = 13.5, 9.1 Hz, 1H), 3.17 (d, J = 11.8 Hz, 1H), 3.27 (d, J = 11.8 Hz, 1H), 3.52 (m, 1H), 3.66 (m, 1H), 4.24 (t, J = 8.3 Hz, 1H), 6.70 (p, J = 7.2 Hz, 1H), 7.72 (d, J = 8.1 Hz, 3H), 7.90 (m, 3H), 8.28 (m, 3H), 8.53 (m, 1H), 9.31 (d, J = 5.9 Hz, 1H) |
| 55dq | $^1$H NMR (400 MHz, MeOH-d4): δ ppm 7.62-7.49 (m, 4H), 7.33-7.24 (m, 2H), 6.76 (d, J = 8.3 Hz, 1H), 6.62 (q, J = 7.2 Hz, 1H), 5.53 (s, 1H), 4.19-4.12 (m, 2H), 4.08 (dd, J = 9.1, 7.3 Hz, 1H), 3.61 (s, 2H), 3.44 (ddt, J = 20.8, 13.4, 6.0 Hz, 2H), 3.22 (d, J = 11.7 Hz, 1H), 3.10 (d, J = 11.7 Hz, 1H), 2.80 (t, J = 6.5 Hz, 2H), 2.30 (dd, J = 13.5, 9.2 Hz, 1H), 2.00 (ddd, J = 17.2, 12.5, 6.7 Hz, 3H), 1.57 (q, J = 5.9, 4.6 Hz, 4H), 1.27 (s, 1H) |

Example 56

(S)-8-(2-amino-6-((R)-2,2,2-trifluoro-1-(4-(1,2,3,4-tetrahydroquinoxalin-6-yl) phenyl)ethoxy)pyrimidin-4-yl)-2,8-diazaspiro[4.5]decane-3-carboxylic acid

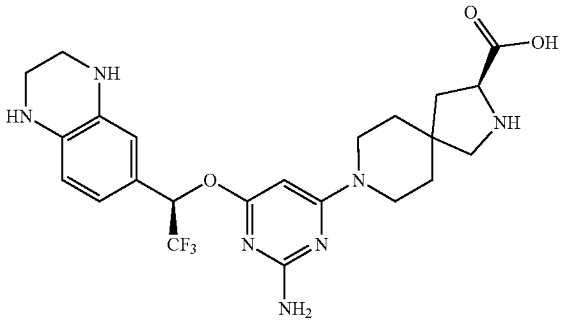 [SMILES: Nc1nc(O[C@H](c2ccc3c(c2)NCCN3)C(F)(F)F)cc(N2CCC3(CC2)CN[C@H](C(=O)O)C3)n1]

Hydrolysis of (S)-ethyl 8-(2-amino-6-((R)-2,2,2-trifluoro-1-(1,2,3,4-tetrahydroquinoxalin-6-yl)ethoxy)pyrimidin-4-yl)-2,8-diazaspiro[4.5]decane-3-carboxylate (a by-product from the N-CBZ deprotection of Example 55bi) using the LiOH general method provided the title compound as an off-white solid.

$^1$H NMR (400 MHz, MeOH-d4): δ ppm 1.54-1.72 (m, 4 H) 2.07-2.14 (m, 1 H) 2.29-2.41 (m, 1 H) 3.09-3.18 (m, 1 H) 3.22-3.29 (m, 1 H) 3.36-3.42 (m, 4 H) 3.43-3.58 (m, 2 H) 3.60-3.80 (m, 2 H) 4.03-4.17 (m, 1 H) 5.49-5.65 (m, 1 H) 6.50-6.67 (m, 2 H) 6.77-6.92 (m, 2 H) 7.43-7.63 (m, 4 H). LCMS (MH+): 585.

Example 57

(S)-8-(2-amino-6-((R)-1-(3,4-dihydroquinazolin-6-yl)-2,2,2-trifluoroethoxy)pyrimidin-4-yl)-2,8-diazaspiro [4.5]decane-3-carboxylic acid

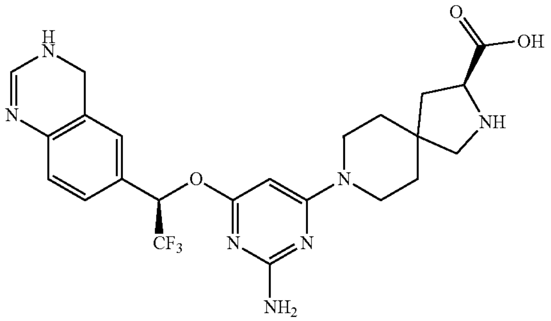 [SMILES: Nc1nc(O[C@H](c2ccc3c(c2)CNC=N3)C(F)(F)F)cc(N2CCC3(CC2)CN[C@H](C(=O)O)C3)n1]

Hydrolysis of (S)-ethyl 8-(2-amino-6-((R)-1-(3,4-dihydroquinazolin-6-yl)-2,2,2-trifluoroethoxy)pyrimidin-4-yl)-2,8-diazaspiro[4.5]decane-3-carboxylate (a by-product from the N-CBZ deprotection of Example 55bk) using the LiOH general method provided the title compound as an off-white solid.

$^1$H NMR (400 MHz, MeOH-d4) δ ppm 1.54-1.66 (m, 4 H) 1.98-2.08 (m, 1 H) 2.23-2.34 (m, 1 H) 3.02-3.11 (m, 1 H) 3.17-3.25 (m, 1 H) 3.37-3.54 (m, 2 H) 3.55-3.72 (m, 2 H) 3.97-4.08 (m, 1 H) 4.62-4.70 (m, 2 H) 5.50-5.58 (m, 1 H) 6.56-6.66 (m, 1 H) 6.86-6.93 (m, 1 H) 7.19-7.24 (m, 1 H) 7.25-7.31 (m, 1 H) 7.38-7.44 (m, 1 H) 7.51-7.57 (m, 2 H) 7.57-7.64 (m, 2 H). LCMS (MH+): 583

Example 58

(S)-8-(2-amino-6-((R)-2,2,2-trifluoro-1-(1,2,3,4-tetrahydroquinazolin-6-yl)ethoxy) pyrimidin-4-yl)-2,8-diazaspiro[4.5]decane-3-carboxylic acid

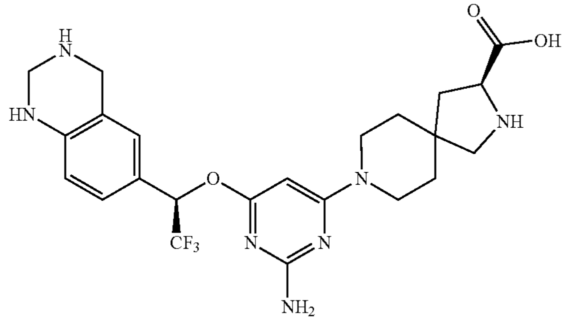 [SMILES: Nc1nc(O[C@H](c2ccc3c(c2)CNCN3)C(F)(F)F)cc(N2CCC3(CC2)CN[C@H](C(=O)O)C3)n1]

Hydrolysis of (S)-ethyl 8-(2-amino-6-((R)-1-(3,4-dihydroquinazolin-6-yl)-2,2,2-trifluoroethoxy)pyrimidin-4-yl)-2,8-diazaspiro[4.5]decane-3-carboxylate (a by-product from the N-CBZ deprotection of Example 55bk) using the LiOH general method provided the title compound as an off-white solid.
$^1$H NMR (400 MHz, MeOH-d4) δ ppm 1.57-1.68 (m, 4 H) 1.93-2.03 (m, 1 H) 2.18-2.30 (m, 1 H) 2.90-3.01 (m, 1 H) 3.12-3.19 (m, 1 H) 3.43-3.75 (m, 4 H) 3.86-3.95 (m, 1 H) 4.00-4.07 (m, 2 H) 4.15-4.23 (m, 2 H) 5.45-5.64 (m, 1 H) 6.56-6.67 (m, 2 H) 7.17-7.23 (m, 1 H) 7.27-7.33 (m, 1 H) 7.49-7.55 (m, 2 H) 7.55-7.62 (m, 2 H). LCMS (MH+): 585.

Example 59a (S)-8-(2-amino-6-((R)-1-(4-bromophenyl)-2,2,2-trifluoroethoxy)pyrimidin-4-yl)-2,8-diazaspiro[4.5]decane-3-carboxylic acid

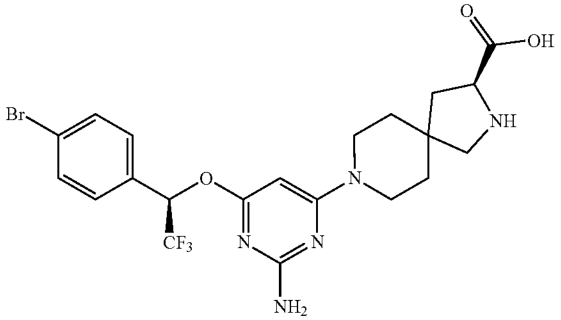 [SMILES: Nc1nc(O[C@H](c2ccc(Br)cc2)C(F)(F)F)cc(N2CCC3(CC2)CN[C@H](C(=O)O)C3)n1]

N-CBZ Deprotection was carried out using Method B with (S)-8-(2-amino-6-((R)-1-(4-bromophenyl)-2,2,2-trifluoroethoxy) pyrimidin-4-yl)-2-(benzyloxycarbonyl)-2,8-diazaspiro[4.5]decane-3-carboxylic acid (75 mg, product of Step 3, Example 55an) providing the title compound as a white solid.
$^1$H NMR (400 MHz, MeOH-d4): δ ppm 1.50-1.68 (m, 4 H) 1.96 (s, 2 H) 2.04 (dd, J=13.35, 7.20 Hz, 1 H) 2.31 (dd, J=13.35, 9.10 Hz, 1 H) 3.07-3.26 (m, 2 H) 3.35-3.55 (m, 2 H) 3.55-3.73 (m, 2 H), 4.06 (dd, J=9.13, 7.17 Hz, 1 H) 5.52 (s, 1 H) 6.57 (q, J=7.11 Hz, 1 H) 7.41 (d, J=8.44 Hz, 2 H) 7.51-7.58 (m, 2 H); LCMS (MH+): 531.

Example 59b (S)-8-(2-amino-6-((R)-2,2,2-trifluoro-1-(naphthalen-2-yl)ethoxy)pyrimidin-4-yl)-2,8-diazaspiro[4.5]decane-3-carboxylic acid

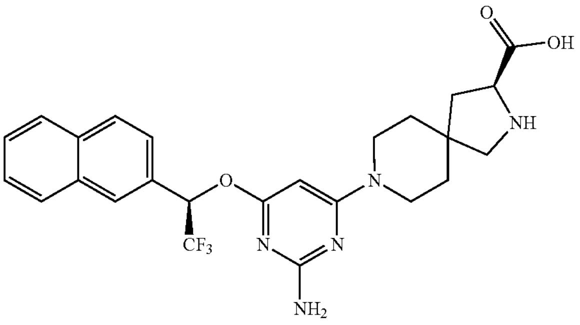 [SMILES: Nc1nc(O[C@H](c2ccc3ccccc3c2)C(F)(F)F)cc(N2CCC3(CC2)CN[C@H](C(=O)O)C3)n1]

The title compound was made as described for Example 10e, starting with (R)-2,2,2-trifluoro-1-(naphthalen-2-yl)ethanol. $^1$H NMR (400 MHz, DMSO-d6): δ ppm 1.20 (dt, J=12.5, 5.3 Hz, 2H), 1.47 (m, 3H), 1.88 (dd, J=12.4, 8.0 Hz, 1H), 2.57 (s, 1H), 2.69 (s, 1H), 2.80 (d, J=12.4 Hz, 1H), 3.36 (m, 3H), 3.97 (dt, J=12.3, 5.2 Hz, 2H), 6.05 (s, 1H), 6.37 (m, 3H), 7.53 (m, 2H), 7.77 (dd, J=7.5, 1.5 Hz, 1H), 7.93 (m, 4H); LCMS (MH+): 562.

Example 59c (S)-8-(2-amino-6-((R)-2,2,2-trifluoro-1-(4-(3-fluoroquinolin-6-yl)-2-methylphenyl)ethoxy)pyrimidin-4-yl)-2,8-diazaspiro[4.5]decane-3-carboxylic acid

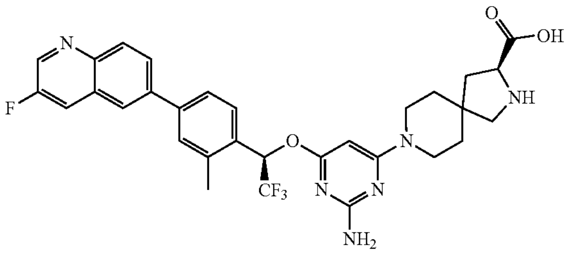 [SMILES: Cc1cc(-c2ccc3ncc(F)cc3c2)ccc1[C@@H](Oc1cc(N2CCC3(CC2)CN[C@H](C(=O)O)C3)nc(N)n1)C(F)(F)F]

Step 1: To a solution of 4-bromo-2-methylbenzoic acid (5.0 g, 23.2 mmol) in DMF (50 mL) was added potassium carbonate (6.4 g,46.4 mmol) and iodomethane (6.6 g, 46.479 mmol). The mixture was stirred at RT for 12 h then diluted with water and extracted with ethyl acetate. The combined organic layer was washed with brine, dried over $Na_2SO_4$ and concentrated in vacuo. Purification by normal phase silica gel column provided methyl 4-bromo-2-methylbenzoate as a colorless oil.
Step 2: To a solution of methyl 4-bromo-2-methylbenzoate (2 g, 8.7 mmol) in THF (20 mL) was added LAH (663 mg,17.5 mmol) at 0° C. The mixture was stirred at RT for 1 h, then diluted with NaOH (1.0M, 10 mL) and extracted with ethyl acetate. The combined organic layer was washed with brine, dried over $Na_2SO_4$ and concentrated in vacuo. Purification by normal phase silica gel column provided (4-bromo-2-methylphenyl)methanol as a colorless oil.

Step 3: To the solution of (4-bromo-2-methylphenyl)methanol (1.8 g, 8.1 mmol) in $CH_2Cl_2$ (20 mL) was added Dess-Martin Periodinane (5.1 g, 12.1 mmol) at 0° C. The mixture was stirred at RT for 1 h, then diluted with water, and the solid was removed by filtration. The filtrate was extracted with $CH_2Cl_2$. The combined organic layer was washed with brine, dried over $Na_2SO_4$ and concentrated in vacuo. Purification by normal phase silica gel column provided 4-bromo-2-methylbenzaldehyde as a yellow oil.

Step 4: To a solution of 4-bromo-2-methylbenzaldehyde (1.5 g, 7.5 mmol) in THF (20 mL) was added $TMSCF_3$ (2.2 g, 15.5 mmol) at 0° C. and then TBAF (1.1 mL, 1.0 M in THF). The mixture was stirred at RT for 1 h, then diluted with HCl (3.0 M, 10 mL), stirred at RT for 1 h and extracted with ethyl acetate. The combined organic layer was washed with brine, dried over $Na_2SO_4$ and concentrated in vacuo. Purification by normal phase silica gel column provided 1-(4-bromo-2-methylphenyl)-2,2,2-trifluoroethanol as an off-white solid.

Step 5: To a solution of 1-(4-bromo-2-methylphenyl)-2,2,2-trifluoroethanol (1.8 g, 6.7 mmol) in $CH_2Cl_2$ (20 mL) was added Dess-Martin Periodinane (3.4 g, 8.1 mmol) at 0° C. The mixture was stirred at RT for 2 h, then diluted with water (10 mL) and filtered. The filtrate was extracted with $CH_2Cl_2$. The combined organic layer was washed with brine, dried over $Na_2SO_4$ and concentrated in vacuo. Purification by normal phase silica gel column provided 1-(4-bromo-2-methylphenyl)-2,2,2-trifluoroethanone as a yellow oil.

Step 6: Chiral reduction of 1-(4-bromo-2-methylphenyl)-2,2,2-trifluoroethanone using the Iridium complex-catalyzed hydrogenation as described for Intermediate 1, (R)-1-(4-bromo-2-(3-methyl-1H-pyrazol-1-yl)phenyl)-2,2,2-trifluoroethanol provides (R)-1-(4-bromo-2-methylphenyl)-2,2,2-trifluoroethanol.

Steps 7: The title compound was prepared as described for (S)-8-(2-amino-6-((R)-2,2,2-trifluoro-1-(3'-methoxy-[1,1'-biphenyl]-4-yl)ethoxy)pyrimidin-4-yl)-2,8-diazaspiro[4.5]decane-3-carboxylic acid (Example 55an) Steps 4-5. 3-Fluoro-6-(4,4,5,5-tetramethyl-1,3,2-dioxaborolan-2-yl)quinolone was used as the Suzuki coupling partner (CAS# 1251731-31-3).

$^1$H NMR (400 MHz, MeOH-d4): δ ppm 1.28 (s, 1H), 1.59 (s, 4H), 2.04 (dd, J=13.5, 7.0 Hz, 1H), 2.31 (dd, J=13.3, 9.3 Hz, 1H), 2.65 (s, 3H), 3.10 (d, J=11.7 Hz, 1H), 3.23 (d, J=11.5 Hz, 1H), 3.47 (t, J=14.3 Hz, 2H), 3.63 (t, J=13.8 Hz, 2H), 4.07 (t, J=8.1 Hz, 1H), 5.56 (s, 1H), 6.87 (q, J=7.0 Hz, 1H), 7.63 (d, J=4.6 Hz, 3H), 8.01 (d, J=8.9 Hz, 1H), 8.12 (m, 3H), 8.80 (m, 1H). LCMS (MH+): 611.

Example 59d (S)-8-(2-amino-6-((R)-1-(2-ethyl-4-(3-fluoroquinolin-6-yl)phenyl)-2,2,2-trifluoroethoxy)pyrimidin-4-yl)-2,8-diazaspiro[4.5]decane-3-carboxylic acid

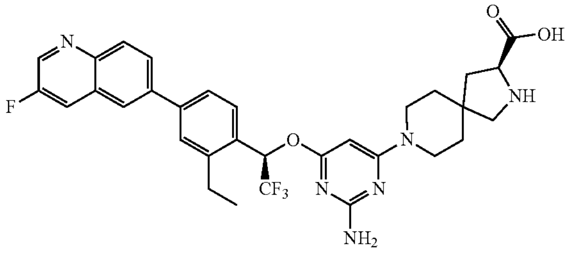

Step 1: To a 0° C. solution of LDA (10.7 mL, 21.39 mmol) in THF (20 mL) was added 4-bromo-2-methylbenzoic acid (2 g, 9.3 mmol) in THF (5 mL). The mixture was stirred at 0° C. for 1 h, cooled to −70° C., and then MeI (2.3 mL, 37.20 mmol) was added dropwise. The mixture was allowed to warm up to 0° C., stirred for 3 h, then quenched with $H_2O$, and the pH was adjusted to 1-2 with 3 N HCl. The mixture was then diluted with water and extracted with ethyl acetate. The combined organic layer was washed with brine, dried over $Na_2SO_4$and concentrated in vacuo. Purification by normal phase silica gel column provided 4-bromo-2-ethylbenzoic acid as a white solid.

Step 2: The title compound was prepared as described above for (S)-8-(2-amino-6-((R)-2,2,2-trifluoro-1-(4-(3-fluoroquinolin-6-yl)-2- methylphenyl)ethoxy)pyrimidin-4-yl)-2,8-diazaspiro[4.5]decane-3-carboxylic acid (Example 59c) starting with 4-bromo-2-ethylbenzoic acid in place of 4-bromo-2-methylbenzoic acid.

$^1$H NMR (400 MHz, MeOH-d4): δ ppm 1.29 (m, 1H), 1.41 (t, J=7.5 Hz, 3H), 1.59 (q, J=6.1, 5.6 Hz, 4H), 2.04 (dd, J=13.5, 7.1 Hz, 1H), 2.32 (dd, J=13.4, 9.1 Hz, 1H), 3.01 (dt, J=12.1, 7.0 Hz, 2H), 3.12 (d, J=11.6 Hz, 1H), 3.24 (d, J=11.8 Hz, 1H), 3.48 (dt, J=21.5, 6.9 Hz, 2H), 3.62 (m, 2H), 4.08 (dd, J=9.1, 7.0 Hz, 1H), 4.94 (s, 15H), 5.56 (s, 1H), 7.00 (q, J=6.9 Hz, 1H), 7.67 (m, 3H), 8.11 (m, 5H), 8.80 (d, J=2.8 Hz, 1H). LCMS (MH+): 626.

Example 60

9-(2-Amino-6-((R)-1-(4-chloro-2-(3-methyl-1H-pyrazol-1-yl)phenyl)-2,2,2-trifluoroethoxy)pyrimidin-4-yl)-3,9-diazaspiro[5.5]undecane-2-carboxylic acid

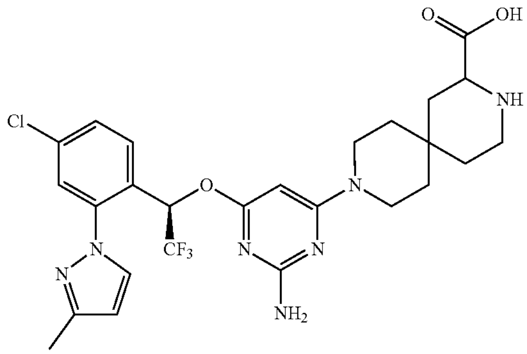 [SMILES: Cc1ccn(-c2cc(Cl)ccc2[C@@H](Oc2cc(N3CCC4(CCNC(C(=O)O)C4)CC3)nc(N)n2)C(F)(F)F)n1]

Step 1: To a solution of methyl 3,9-diazaspiro[5.5]undecane-10-carboxylate (30 mg, 0.14 mmol) in dioxane (2 mL)/i-PrOH (2 mL) was added 4-chloro-6-[(1R)-1-[4-chloro-2-(3-methylpyrazol-1-yl)phenyl]-2,2,2-trifluoro-ethoxy]pyrimidin-2-amine (92 mg, 0.22 mmol), and the reaction was heated at 100° C. under microwave for 3 h. The reaction was cooled to RT, and concentrated in vacuo. The residue was purified by reversed phase HPLC (MeOH/$H_2O$/0.5% TFA) to provide methyl 9-(2-amino-6-((R)-1-(4-chloro-2-(3-methyl-1H-pyrazol-1-yl)phenyl)-2,2,2-trifluoroethoxy)pyrimidin-4-yl)-3,9-diazaspiro[5.5]undecane-2-carboxylate as an off-white solid.

Step 2: Hydrolysis of methyl 9-(2-amino-6-((R)-1-(4-chloro-2-(3-methyl-1H-pyrazol-1-yl)phenyl)-2,2,2-trifluoroethoxy)pyrimidin-4-yl)-3,9-diazaspiro[5.5]undecane-2- carboxylate using the LiOH general method provides the title compound as an off-white solid.

$^1$H NMR (400 MHz, MeOH-d4): δ ppm 1.22-1.37 (m, 1 H) 1.30-1.30 (m, 1 H) 1.46-1.68 (m, 4 H) 1.68-1.90 (m, 2 H) 2.29 (dd, J=12.59, 6.83 Hz, 1 H) 2.37 (d, J=1.90 Hz, 3 H) 3.07-3.24 (m, 2 H) 3.59-3.90 (m, 4 H) 4.03-4.19 (m, 1 H) 6.29-6.38 (m, 1 H) 6.40 (d, J=2.29 Hz, 1 H), 6.88-7.02 (m, 1 H) 7.52-7.61 (m, 2 H) 7.65-7.74 (m, 1 H) 7.89 (d, J=2.34 Hz, 1 H). LCMS (MH+): 581.

Example 61

(S)-8-(2-Amino-6-((4-(3-methyl-1H-indazol-6-yl) phenoxy)methyl)pyrimidin-4-yl)-2,8-diazaspiro[4.5] decane-3-carboxylic acid

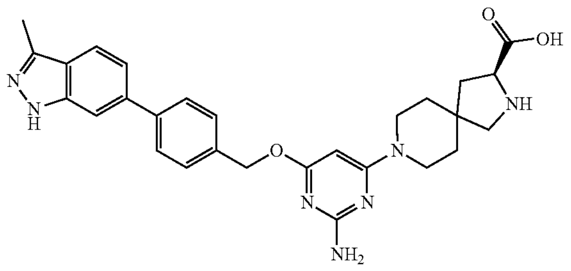 [SMILES: Cc1n[nH]c2cc(-c3ccc(COc4cc(N5CCC6(CC5)CN[C@H](C(=O)O)C6)nc(N)n4)cc3)ccc12]

Step 1: A mixture of 4-bromophenol (173 mg, 1.00 mmol), 4-chloro-6-(chloromethyl)pyrimidin-2-amine (CAS#: 92311-35-8) (178 mg, 1.16 mmol) and $K_2CO_3$ (175 mg, 1.00 mmol) in DMF (5 mL) was heated to 100° C. for 12 h. The reaction was cooled to RT, concentrated in vacuo, and the residue taken up in and EtOAc. The organic layer was washed with brine, dried over $Na_2SO_4$ and concentrated in vacuo. Purification on normal phase silica gel (EtOAc/petroleum ether) provided 4-((4-bromophenoxy)methyl)-6-chloropyrimidin-2-amine as a white solid.

Step 2: A mixture of 4-((4-Bromophenoxy)methyl)-6-chloropyrimidin-2-amine (454 mg, 1.4 mmol), (S)-2-benzyl 3-ethyl 2,8-diazaspiro[4.5]decane-2,3-dicarboxylate (500 mg, 1.44 mmol) and $NaHCO_3$(605 mg,7 mmol) in dioxane (5 mL) was heated to 100° C. for 12 h. The reaction was cooled to RT, concentrated in vacuo, and extracted with EtOAc. The combined organic layers were washed with brine, dried over $Na_2SO_4$, and concentrated in vacuo. Purification on normal phase silica gel (EtOAc/petroleum ether) provided (S)-2-benzyl 3-ethyl 8-(2-amino-6-((4-bromophenoxy)methyl)pyrimidin-4-yl)-2,8-diazaspiro[4.5]decane-2, 3-dicarboxylate as a white solid.

Step 3: To a solution of (S)-2-benzyl 3-ethyl 8-(2-amino-6-((4-bromophenoxy)methyl)pyrimidin-4-yl)-2,8-diazaspiro [4.5]decane-2,3-dicarboxylate (550 mg, 0.9 mmol) in acetonitrile (5 mL) was added TMSI (705 mg, 3.5 mmol) dropwise at 0° C. The mixture was stirred at 0° C. for 2 h, then concentrated in vacuo. The residue was dissolved in $CH_2Cl_2$ (20 mL) followed by the sequential addition of $Et_3N$ (267 mg, 2.6 mmol), and $(BOC)_2O$ (285 mg, 1.3 mmol). The reaction mixture was stirred at RT for 16 h then concentrated in vacuo. Purification on normal phase silica gel ($CH_2Cl_2$/MeOH) provides (S)-2-tert-butyl 3-ethyl 8-(2-amino-6-((4-bromophenoxy) methyl)pyrimidin-4-yl)-2,8-diazaspiro[4.5] decane-2,3-dicarboxylate as a light yellow solid.

Step 4: A mixture of (S)-2-tert-butyl 3-ethyl 8-(2-amino-6-((4-bromophenoxy) methyl)pyrimidin-4-yl)-2,8-diazaspiro [4.5]decane-2,3-dicarboxylate (350 mg, 0.56 mmol), 3-methyl-6-(4,4,5,5-tetramethyl-1,3,2-dioxaborolan-2-yl)-1H-indazole (285 mg, 1.1 mmol) and Pd(dppf)$Cl_2$ (62 mg, 0.09 mmol) in dioxane (5 mL)/aq. $Na_2CO_3$ solution (2.0 M, 5 mL) was heated to 90° C. for 4 h. The reaction was cooled to RT, the solids filtered away, and the solution concentrated in vacuo. Purification on normal phase silica gel ($CH_2Cl_2$/MeOH) provided (S)-2-tert-butyl 3-ethyl 8-(2-amino-6-((4-(3-methyl-1H-indazol-6-yl)phenoxy)methyl)pyrimidin-4-yl)-2,8-diazaspiro[4.5]decane-2,3-dicarboxylate as a brown solid.

Step 5: To a solution of (S)-2-tert-butyl 3-ethyl 8-(2-amino-6-((4-(3-methyl-1H-indazol-6-yl)phenoxy)methyl)pyrimidin-4-yl)-2,8-diazaspiro[4.5]decane-2,3-dicarboxylate (150 mg, 0.19 mmol) in $CH_2Cl_2$ (5 mL) was added TFA (3 mL), and the resulting mixture was stirred at RT for 1 h. The reaction mixture was concentrated in vacuo, and the resulting material partitioned bewteen $CH_2Cl_2$ and saturated $NaHCO_3$, and extracted. The combined organic layers were dried over $Na_2SO_4$, filtered, and concentrated in vacuo. Purification by prep-TLC ($CH_2Cl_2$/MeOH) provided (S)-ethyl 8-(2-amino-6-((4-(3-methyl-1H-indazol-6-yl)phenoxy)methyl)pyrimidin-4-yl)-2,8-diazaspiro[4.5]decane-3-carboxylate as a brown solid.

Step 6: To a solution of (S)-ethyl 8-(2-amino-6-((4-(3-methyl-1H-indazol-6-yl)phenoxy)methyl) pyrimidin-4-yl)-2,8-diazaspiro[4.5]decane-3-carboxylate (70 mg, 0.11 mmol) in MeOH (3 mL) is added 4 N NaOH (3 mL), and the reaction mixture was stirred at RT for 4 h. The reaction mixture was then concentrated in vacuo. The residue was diluted with water (5 mL) and the pH adjusted to 6-7. The precipitated solid was collected by filtration, and the filter cake was washed with cold water, then dried to afford the title compound as an off-white solid.

$^1$H NMR (400 MHz, DMSO-d6): δ ppm 7.72-7.70 (d, 1 H), 7.61-7.59 (d, 3 H), 7.31-7.30 (d, 1 H), 7.06-7.04 (d, 2 H), 6.14 (s, 1 H), 4.76 (s, 2 H), 3.87-3.83 (q, 1 H), 3.46-3.41 (m, 4 H), 3.08-3.06 (d, 1 H), 2.98-2.95 (d, 1 H), 2.43 (s, 1 H), 2.16-2.13 (m, 1 H), 1.82-1.80 (m, 1 H), 1.44 (m, 4 H). LCMS (MH+): 514.

Example 62

(S)-8-(2-amino-6-((5-chloro-3'-(methylsulfonyl)-[1, 1'-biphenyl]-2-yl)methoxy)pyrimidin-4-yl)-2,8-diazaspiro[4.5]decane-3-carboxylic acid

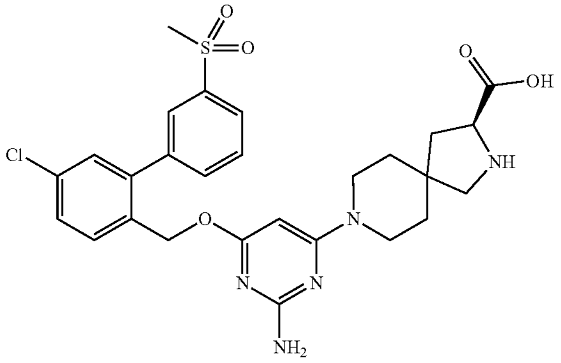 [SMILES: CS(=O)(=O)c1cccc(-c2cc(Cl)ccc2COc2cc(N3CCC4(CC3)CN[C@H](C(=O)O)C4)nc(N)n2)c1]

Step 1: A mixture of (2-bromo-4-chlorophenyl)methanol (173 mg, 1 mmol), 4-chloro-6-(chloromethyl)pyrimidin-2-amine (178 mg, 1.16 mmol) and $K_2CO_3$ (175 mg, 1.00 mmol) in DMF (5 mL) was heated to 100° C. for 12 h. The reaction was cooled to RT, concentrated in vacuo, and extracted with EtOAc. The combined organic layers were washed with brine, dried over $Na_2SO_4$, and concentrated in vacuo. Purification on normal phase silica gel (EtOAc/petroleum ether) provided 4-((2-bromo-4-chlorobenzyl)oxy)-6-chloropyrimidin-2-amine as a white solid.

Step 2: A mixture of 4-((2-bromo-4-chlorobenzyl)oxy)-6-chloropyrimidin-2-amine (300 mg, 1.1 mmol), (S)-2-benzyl 3-ethyl 2,8-diazaspiro[4.5]decane-2,3-dicarboxylate (400 mg, 1.2 mmol), and $NaHCO_3$(550 mg,7 mmol) in dioxane (5 mL) was heated to 100° C. for 12 h. The reaction was cooled to RT, concentrated in vacuo, and extracted with EtOAc. The combined organic layers were washed with brine, water, dried over $Na_2SO_4$, and concentrated in vacuo. Purification on normal phase silica gel (EtOAc/petroleum ether) provided (S)-2-benzyl 3-ethyl 8-(2-amino-6-((2-bromo-4-chlorobenzyl)oxy)pyrimidin-4-yl)-2,8-diazaspiro[4.5]decane-2,3-dicarboxylate as a white solid.

Step 3: To a solution of (S)-2-benzyl 3-ethyl 8-(2-amino-6-((2-bromo-4-chlorobenzyl)oxy)pyrimidin-4-yl)-2,8-diazaspiro[4.5]decane-2,3-dicarboxylate (500 mg, 0.8 mmol) in acetonitrile (5 mL) was added TMSI (705 mg, 3.5 mmol) dropwise at 0° C. The reaction mixture was stirred at 0° C. for 2 h, then concentrated in vacuo. The residue was dissolved in $CH_2Cl_2$ (20 mL), followed by the sequential addition of $Et_3N$ (267 mg, 2.6 mmol), and $(BOC)_2O$ (285 mg, 1.3 mmol). The reaction mixture was stirred at RT for 16 h, then concentrated in vacuo. Purification on normal phase silica gel ($CH_2Cl_2$/MeOH) provided (S)-2-tert-butyl 3-ethyl 8-(2-amino-6-((2-bromo-4-chlorobenzyl)oxy)pyrimidin-4-yl)-2,8-diazaspiro[4.5]decane-2,3-dicarboxylate as a light yellow solid.

Step 4: A mixture of (S)-2-tert-butyl 3-ethyl 8-(2-amino-6-((2-bromo-4-chlorobenzyl) oxy)pyrimidin-4-yl)-2,8-diazaspiro[4.5]decane-2,3-dicarboxylate (300 mg, 0.4 mmol), (3-(methylsulfonyl)phenyl)boronic acid (280 mg, 1 mmol), and $Pd(dppf)Cl_2$ (62 mg, 0.09 mmol) in dioxane (5 mL)/aq. $Na_2CO_3$ solution (2.0 M, 5 mL) was heated to 90° C. for 4 h. The reaction was then cooled to RT, the solids filtered away, and the filtrate concentrated in vacuo. Purification on normal phase silica gel ($CH_2Cl_2$/MeOH) provided (S)-2-tert-butyl 3-ethyl 8-(2-amino-6-((5-chloro-3'-(methylsulfonyl)-[1,1'-biphenyl]-2-yl)methoxy)pyrimidin-4-yl)-2,8-diazaspiro[4.5]decane-2,3-dicarboxylate as an off-white solid.

Step 5: To a solution of (S)-2-tert-butyl 3-ethyl 8-(2-amino-6-((5-chloro-3'-(methylsulfonyl)-[1,1'-biphenyl]-2-yl)methoxy)pyrimidin-4-yl)-2,8-diazaspiro[4.5]decane-2,3-dicarboxylate (200 mg, 0.25 mmol) in $CH_2Cl_2$ (5 ml) was added TFA (3 mL), and the resulting mixture was stirred at RT for 1 h. The reaction mixture was concentrated in vacuo, and the residue was partitioned between $CH_2Cl_2$ and saturated $NaHCO_3$. The organic layer was dried over $Na_2SO_4$, filtered, and concentrated in vacuo. Purification by prep-TLC ($CH_2Cl_2$/MeOH) provided (S)-ethyl 8-(2-amino-6-((5-chloro-3'-(methylsulfonyl)-[1,1'-biphenyl]-2-yl)methoxy)pyrimidin-4-yl)-2,8-diazaspiro[4.5]decane-3-carboxylate as an off-white solid.

Step 6: To a solution (S)-ethyl 8-(2-amino-6-((5-chloro-3'-(methylsulfonyl)-[1,1'-biphenyl]-2-yl)methoxy)pyrimidin-4-yl)-2,8-diazaspiro[4.5]decane-3-carboxylate (100 mg, 0.13 mmol) in MeOH (3 mL) was added 4 N NaOH (3 mL), and the mixture was stirred at RT for 4 h. The reaction mixture was then concentrated in vacuo. The residue was diluted with water (5 mL) and the pH adjusted to 6-7. The precipitated solid was collected by filtration, the filter cake was washed with cold water, then dried to afford the title compound as an off-white solid isolated as the zwitterionic form.

$^1H$ NMR (400 MHz, MeOH-d4): δ ppm 7.94 (m, 2 H), 7.59-7.57 (m, 3 H), 7.44-7.40 (m, 1 H), 7.33 (m, 1 H), 5.33 (m, 1 H), 4.07 (m, 1 H), 3.59 (m, 2 H), 3.45 (m, 2 H), 3.30 (m, 1 H), 3.15 (m, 1 H),2.32 (m, 1 H), 2.06 (m, 1 H), 1.61 (s, 4 H). LCMS (MH+): 573.

The following esters were isolated as either a TFA or HCl salt formed during the HPLC purification procedure used to isolate the final compounds.

Example 63bd (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5] decane-3-carboxylate

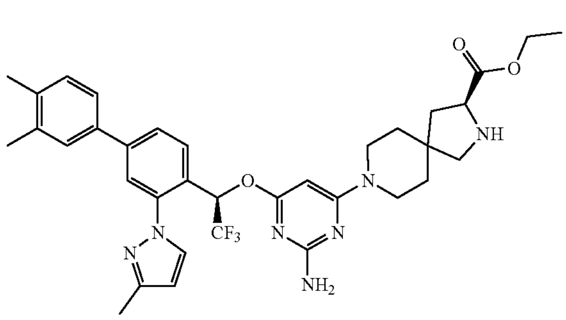 [SMILES: CCOC(=O)[C@@H]1CC2(CCN(c3cc(O[C@H](c4ccc(-c5ccc(C)c(C)c5)cc4-n4ccc(C)n4)C(F)(F)F)nc(N)n3)CC2)CN1]

A solution of (S)-2-benzyl 3-ethyl 8-(2-amino-6-((R)-1-(3',4'-dimethyl-3-(3-methyl-1H-pyrazol-1-yl)-[ 1,1'-biphenyl]-4-yl)-2,2,2-trifluoroethoxy)pyrimidin-4-yl)-2,8-diazaspiro[4.5]decane-2,3-dicarboxylate (from Step 3, Example 1m, 220 mg, 0.3 mmol,) in EtOAc (5 mL) was hydrogenated using Method A by using an H-Cube apparatus and a 10% (w/w) Pd/C cartridge with a flow rate of 1.0 mL/min at RT. Purification on normal phase silica gel (EtOAc/heptane) provided (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy) pyrimidin-4-yl)-2,8-diazaspiro[4.5]decane-3-carboxylate.

Example 63kp (S)-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate

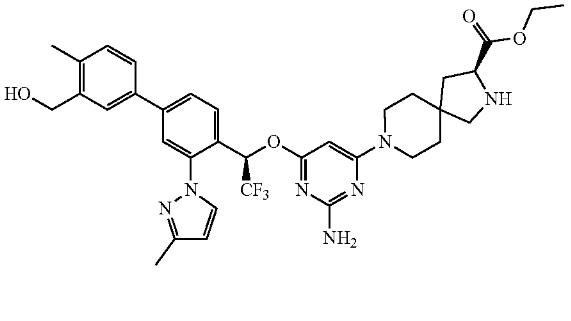 [SMILES: CCOC(=O)[C@@H]1CC2(CCN(c3cc(O[C@H](c4ccc(-c5ccc(C)c(CO)c5)cc4-n4ccc(C)n4)C(F)(F)F)nc(N)n3)CC2)CN1]

The title compound was prepared as described for (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 63bd) using Method A to remove the N-CBz group.

Example 63i (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate

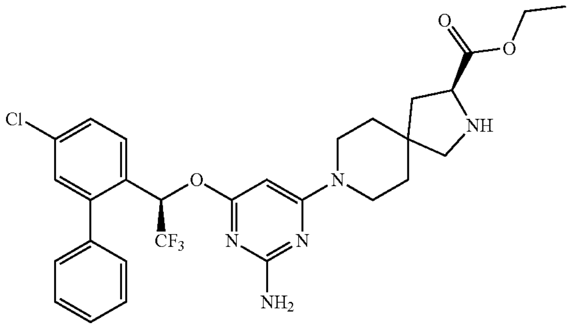 [SMILES: CCOC(=O)[C@@H]1CC2(CCN(c3cc(O[C@H](c4ccc(Cl)cc4-c4ccccc4)C(F)(F)F)nc(N)n3)CC2)CN1]

A solution of (S)-2-benzyl 3-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-2,3-dicarboxylate (from Step 3, Example 34c, 315 mg, 0.43 mmol) in acetonitrile (300 mL) was added TMSI (0.13 mL, 0.9 mmol) [Method B]. The reaction mixture was then warmed to RT for an additional 30-40 min, then cooled to 0-5° C., and 2 M HCl in diethyl ether (0.5 mL) was added. The reaction mixture was the allowed to warm RT and then concentrated in vacuo. Normal phase silica gel chromatography provide the title compound as an off-white solid.

Ethyl ester prodrugs in Table 18a were prepared by removing the N-CBZ group by either method A or method B, as shown below.

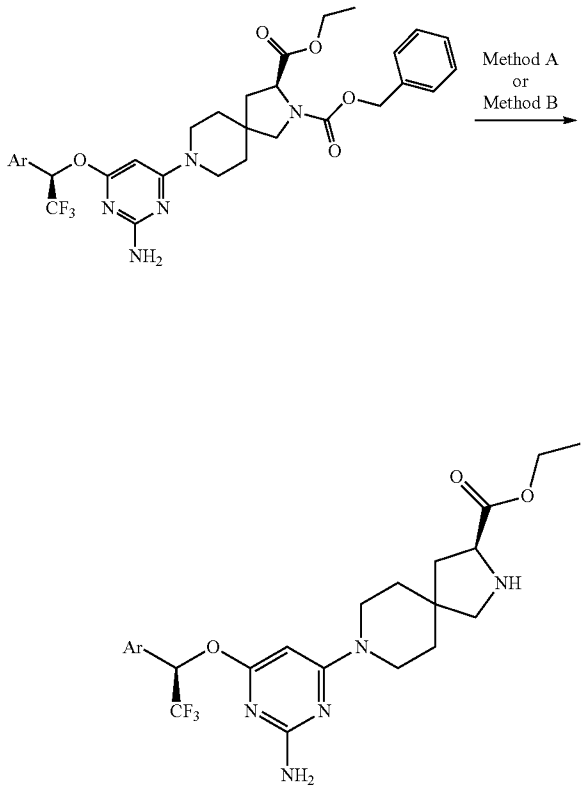

TABLE 18a

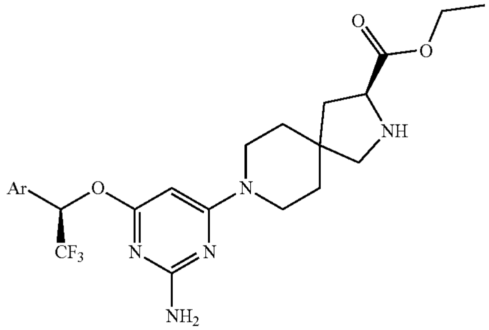

| Ex. No. | Ar | Method A or B | CAS Name | LCMS (MH+) |
|---|---|---|---|---|
| 63a | 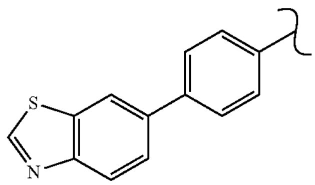 | A | (S)-ethyl 8-(2-amino-6-((R)-1-(4-(benzo[d]thiazol-6-yl)phenyl)-2,2,2-trifluoroethoxy)pyrimidin-4-yl)-2,8-diazaspiro[4.5]decane-3-carboxylate | 613 |

TABLE 18a-continued

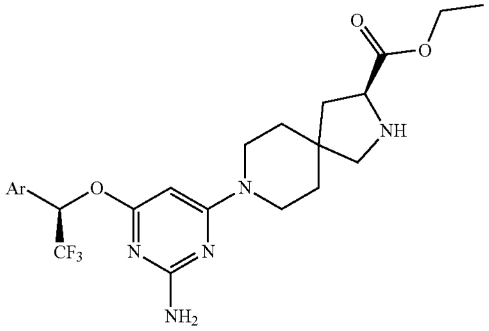

| Ex. No. | Ar | Method A or B | CAS Name | LCMS (MH+) |
|---|---|---|---|---|
| 63b | 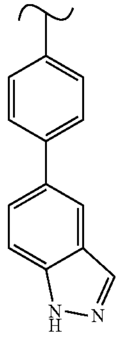 | A | (S)-ethyl 8-(6-((R)-1-(4-(1H-indazol-5-yl)phenyl)-2,2,2-trifluoroethoxy)-2-aminopyrimidin-4-yl)-2,8-diazaspiro[4.5]decane-3-carboxylate | 596 |
| 63c | 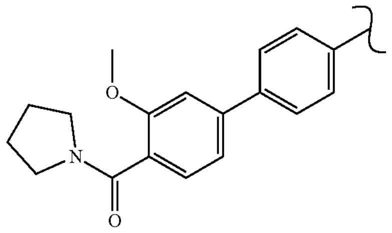 | A | (S)-ethyl 8-(2-amino-6-((R)-2,2,2-trifluoro-1-(3'-methoxy-4'-(pyrrolidine-1-carbonyl)-[1,1'-biphenyl]-4-yl)ethoxy)pyrimidin-4-yl)-2,8-diazaspiro[4.5]decane-3-carboxylate | 683 |
| 63d | 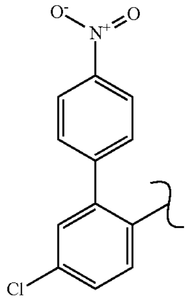 | A | (S)-ethyl 8-(2-amino-6-((R)-1-(5-chloro-4'-nitro-[1,1'-biphenyl]-2-yl)-2,2,2-trifluoroethoxy)pyrimidin-4-yl)-2,8-diazaspiro[4.5]decane-3-carboxylate | 631 |
| 63e | 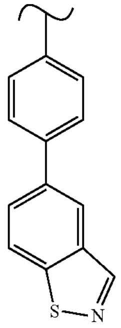 | B | (S)-ethyl 8-(2-amino-6-((R)-1-(4-(benzo[d]isothiazol-5-yl)phenyl)-2,2,2-trifluoroethoxy)pyrimidin-4-yl)-2,8-diazaspiro[4.5]decane-3-carboxylate | 613 |

TABLE 18a-continued

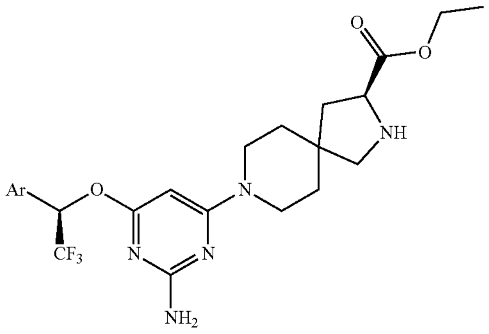

| Ex. No. | Ar | Method A or B | CAS Name | LCMS (MH+) |
|---|---|---|---|---|
| 63f | 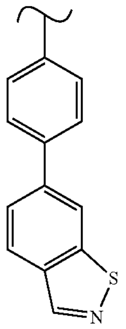 | A | (S)-ethyl 8-(2-amino-6-((R)-1-(4-(benzo[d]isothiazol-6-yl)phenyl)-2,2,2-trifluoroethoxy)pyrimidin-4-yl)-2,8-diazaspiro[4.5]decane-3-carboxylate616 | 616 |
| 63g | 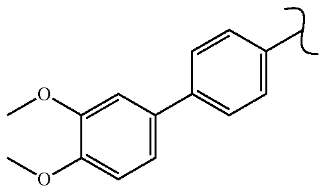 | A | (S)-ethyl 8-(2-amino-6-((R)-1-(3',4'-dimethoxy-[1,1'-biphenyl]-4-yl)-2,2,2-trifluoroethoxy)pyrimidin-4-yl)-2,8-diazaspiro[4.5]decane-3-carboxylate | 616 |
| 63h | 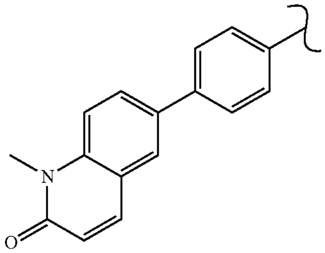 | A | (S)-ethyl 8-(2-amino-6-((R)-2,2,2-trifluoro-1-(4-(1-methyl-2-oxo-1,2-dihydroquinolin-6-yl)phenyl)ethoxy)pyrimidin-4-yl)-2,8-diazaspiro[4.5]decane-3-carboxylate | 637 |
| 63i | 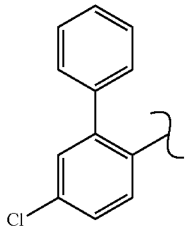 | B | (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate | 591 |

TABLE 18a-continued

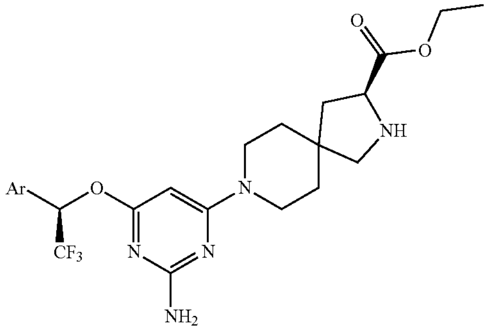

| Ex. No. | Ar | Method A or B | CAS Name | LCMS (MH+) |
|---|---|---|---|---|
| 63j | 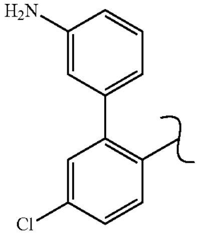 | B | (S)-ethyl 8-(2-amino-6-((R)-1-(3'-amino-5-chloro-[1,1'-biphenyl]-2-yl)-2,2,2-trifluoroethoxy)pyrimidin-4-yl)-2,8-diazaspiro[4.5]decane-3-carboxylate | 606 |
| 63k | 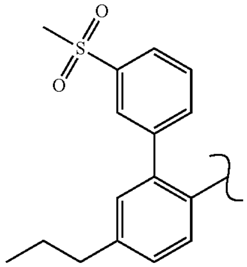 | A | (S)-ethyl 8-(2-amino-6-((R)-2,2,2-trifluoro-1-(3'-(methylsulfonyl)-5-propyl-[1,1'-biphenyl]-2-yl)ethoxy)pyrimidin-4-yl)-2,8-diazaspiro[4.5]decane-3-carboxylate | 676 |
| 63l | 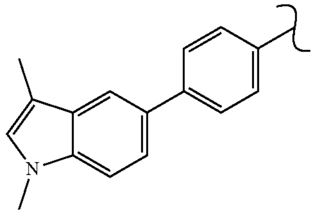 | A | (S)-ethyl 8-(2-amino-6-((R)-1-(4-(1,3-dimethyl-1H-indol-5-yl)phenyl)-2,2,2-trifluoroethoxy)pyrimidin-4-yl)-2,8-diazaspiro[4.5]decane-3-carboxylate | 622 |
| 63m | 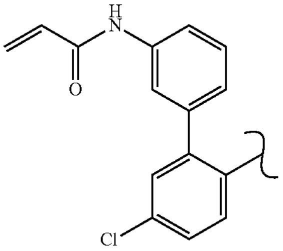 | A | (S)-ethyl 8-(6-((R)-1-(3'-acrylamido-5-chloro-[1,1'-biphenyl]-2-yl)-2,2,2-trifluoroethoxy)-2-aminopyrimidin-4-yl)-2,8-diazaspiro[4.5]decane-3-carboxylate | 659.1 |
| 63n | 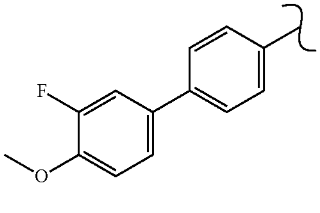 | A | (S)-ethyl 8-(2-amino-6-((R)-2,2,2-trifluoro-1-(3'-fluoro-4'-methoxy-[1,1'-biphenyl]-4-yl)ethoxy)pyrimidin-4-yl)-2,8-diazaspiro[4.5]decane-3-carboxylate | 604 |

TABLE 18a-continued

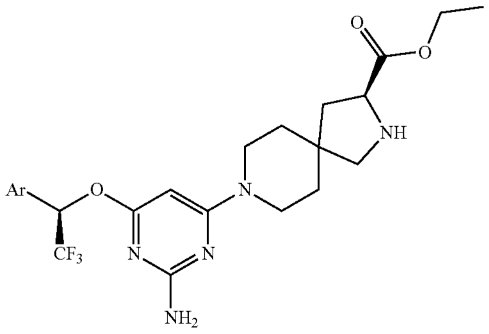

| Ex. No. | Ar | Method A or B | CAS Name | LCMS (MH+) |
|---|---|---|---|---|
| 63o | 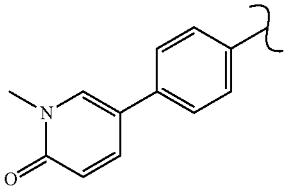 | A | (S)-ethyl 8-(2-amino-6-((R)-2,2,2-trifluoro-1-(4-(1-methyl-6-oxo-1-6-dihydropyridin-3-yl)phenyl)ethoxy)pyrimidin-4-yl)-2,8-diazaspiro[4.5]decane-3-carboxylate | 587 |
| 63p | 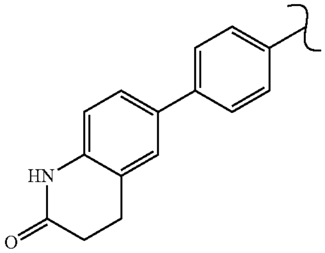 | A | (S)-ethyl 8-(2-amino-6-((R)-2,2,2-trifluoro-1-(4-(2-oxo-1,2,3,4-tetrahydroquinolin-6-yl)phenyl)ethoxy)pyrimidin-4-yl)-2,8-diazaspiro[4.5]decane-3-carboxylate | 626 |
| 63q | 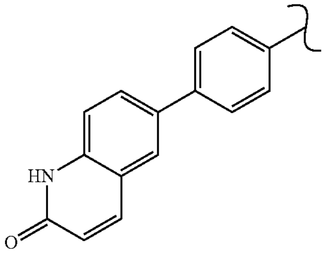 | A | (S)-ethyl 8-(2-amino-6-((R)-2,2,2-trifluoro-1-(4-(2-oxo-1,2-dihydroquinolin-6-yl)phenyl)ethoxy)pyrimidin-4-yl)-2,8-diazaspiro[4.5]decane-3-carboxylate | 623 |
| 63r | 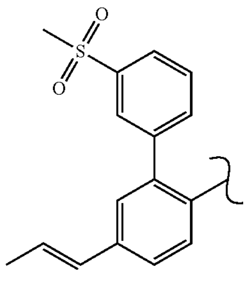 | B | (S)-ethyl 8-(2-amino-6-((R)-2,2,2-trifluoro-1-(3'-(methylsulfonyl)-5-((E)-prop-1-en-1-yl)-[1,1'-biphenyl]-2-yl)ethoxy)pyrimidin-4-yl)-2,8-diazaspiro[4.5]decane-3-carboxylate | 674 |

TABLE 18a-continued

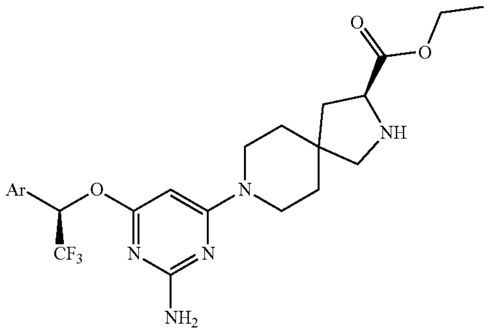

| Ex. No. | Ar | Method A or B | CAS Name | LCMS (MH+) |
|---|---|---|---|---|
| 63s | 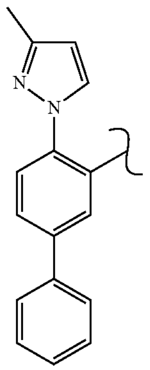 | A | (S)-ethyl 8-(2-amino-6-((R)-2,2,2-trifluoro-1-(4-(3-methyl-1H-pyrazol-1-yl)-[1,1'-biphenyl]-3-yl)ethoxy)pyrimidin-4-yl)-2,8-diazaspiro[4.5]decane-3-carboxylate | 583 |
| 63t | 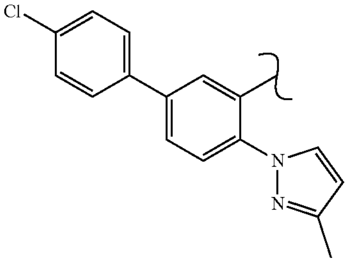 | B | (S)-ethyl 8-(2-amino-6-((R)-1-(4'-chloro-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 671 |
| 63u | 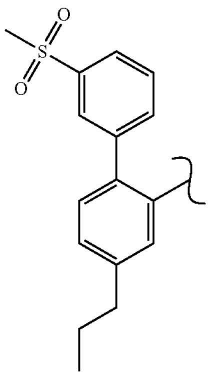 | A | (S)-ethyl 8-(2-amino-6-((R)-2,2,2-trifluoro-1-(3'-(methylsulfonyl)-4-propyl-[1,1'-biphenyl]-2-yl)ethoxy)pyrimidin-4-yl)-2,8-diazaspiro[4.5]decane-3-carboxylate | 677 |

TABLE 18a-continued

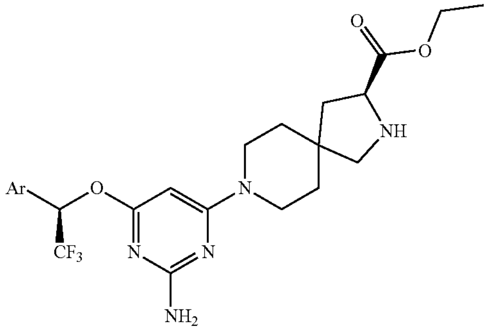

| Ex. No. | Ar | Method A or B | CAS Name | LCMS (MH+) |
|---|---|---|---|---|
| 63v | 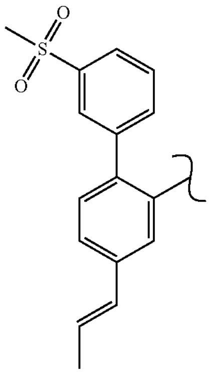 | B | (S)-ethyl 8-(2-amino-6-((R)-2,2,2-trifluoro-1-(3'-(methylsulfonyl)-4-((E)-prop-1-en-1-yl)-[1,1'-biphenyl]-2-yl)ethoxy)pyrimidin-4-yl)-2,8-diazaspiro[4.5]decane-3-carboxylate | 675 |
| 63w | 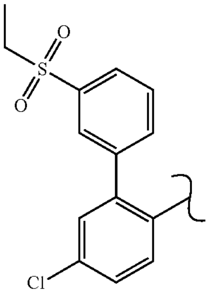 | B | (S)-ethyl 8-(2-amino-6-((R)-1-(5-chloro-3'-(ethylsulfonyl)-[1,1'-biphenyl]-2-yl)-2,2,2-trifluoroethoxy)pyrimidin-4-yl)-2,8-diazaspiro[4.5]decane-3-carboxylate | 683 |
| 63x | 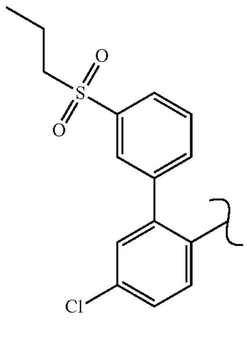 | B | (S)-ethyl 8-(2-amino-6-((R)-1-(5-chloro-3'-(propylsulfonyl)-[1,1'-biphenyl]-2-yl)-2,2,2-trifluoroethoxy)pyrimidin-4-yl)-2,8-diazaspiro[4.5]decane-3-carboxylate | 697 |

TABLE 18a-continued

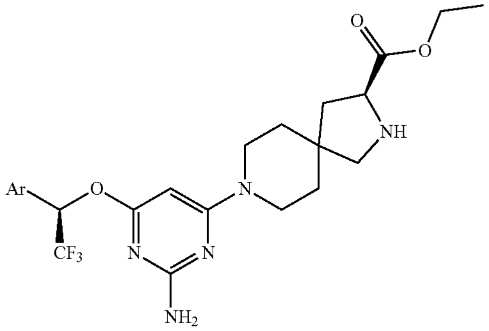

| Ex. No. | Ar | Method A or B | CAS Name | LCMS (MH+) |
|---|---|---|---|---|
| 63y | 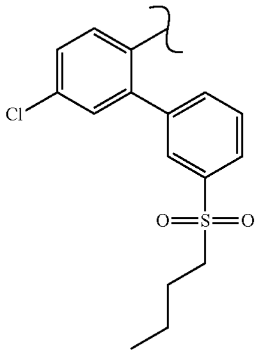 | A | (S)-ethyl 8-(2-amino-6-((R)-1-(5-chloro-3'-(butylsulfonyl)-[1,1'-biphenyl]-2-yl)-2,2,2-trifluoroethoxy)pyrimidin-4-yl)-2,8-diazaspiro[4.5]decane-3-carboxylate | 711 |
| 63z | 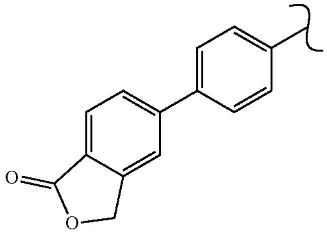 | A | (S)-ethyl 8-(2-amino-6-((R)-2,2,2-trifluoro-1-(4-(1-oxo-1,3-dihydroisobenzofuran-5-yl)phenyl)ethoxy)pyrimidin-4-yl)-2,8-diazaspiro[4.5]decane-3-carboxylate | 612 |
| 63aa | 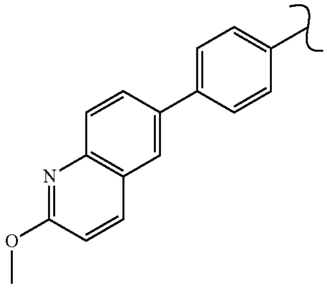 | A | (S)-ethyl 8-(2-amino-6-((R)-2,2,2-trifluoro-1-(4-(2-methoxyquinolin-6-yl)phenyl)ethoxy)pyrimidin-4-yl)-2,8-diazaspiro[4.5]decane-3-carboxylate | 638 |
| 63ab | 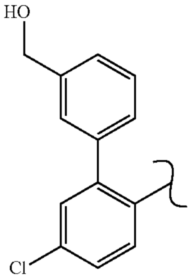 | A | (S)-ethyl 8-(2-amino-6-((R)-1-(5-chloro-3'-(hydroxymethyl)-[1,1'-biphenyl]-2-yl)-2,2,2-trifluoroethoxy)pyrimidin-4-yl)-2,8-diazaspiro[4.5]decane-3-carboxylate | 621 |

TABLE 18a-continued

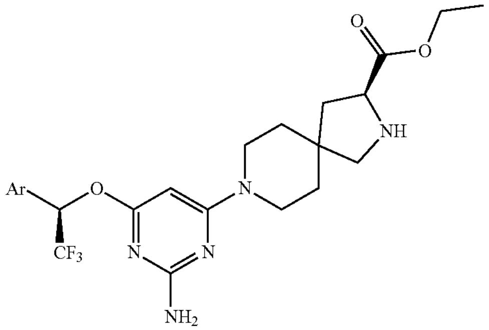

| Ex. No. | Ar | Method A or B | CAS Name | LCMS (MH+) |
|---|---|---|---|---|
| 63ac | 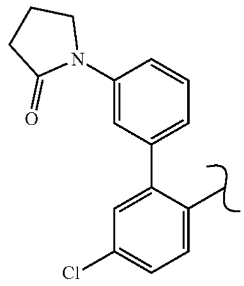 | A | (S)-ethyl 8-(2-amino-6-((R)-1-(5-chloro-3'-(2-oxopyrrolidin-1-yl)-[1,1'-biphenyl]-2-yl)-2,2,2-trifluoroethoxy)pyrimidin-4-yl)-2,8-diazaspiro[4.5]decane-3-carboxylate | 673 |
| 63ad | 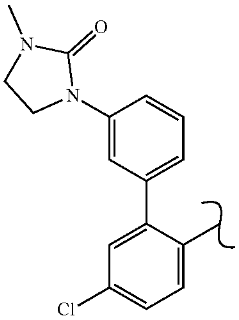 | B | (S)-ethyl 8-(2-amino-6-((R)-1-(5-chloro-3'-(3-methyl-2-oxoimidazolidin-1-yl)-[1,1'-biphenyl]-2-yl)-2,2,2-trifluoroethoxy)pyrimidin-4-yl)-2,8-diazaspiro[4.5]decane-3-carboxylate | 688 |
| 63ae | 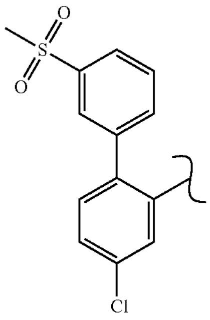 | B | (S)-ethyl 8-(2-amino-6-((R)-1-(4-chloro-3'-(methylsulfonyl)-[1-1'-biphenyl]-2-yl)-2,2,2-trifluoroethoxy)pyrimidin-4-yl)-2,8-diazaspiro[4.5]decane-3-carboxylate | 668 |
| 63af | 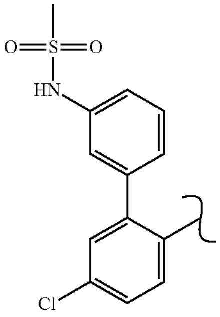 | B | (S)-ethyl 8-(2-amino-6-((R)-1-(5-chloro-3'-(methylsulfonamido)-[1,1'-biphenyl]-2-yl)-2,2,2-trifluoroethoxy)pyrimidin-4-yl)-2,8-diazaspiro[4.5]decane-3-carboxylate | 683 |

TABLE 18a-continued

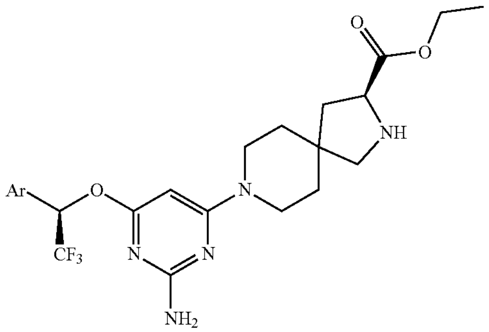

| Ex. No. | Ar | Method A or B | CAS Name | LCMS (MH+) |
|---|---|---|---|---|
| 63ag | 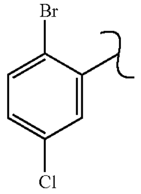 | A | (S)-ethyl 8-(2-amino-6-((R)-1-(2-bromo-5-chlorophenyl)-2,2,2-trifluoroethoxy)pyrimidin-4-yl)-2,8-diazaspiro[4.5]decane-3-carboxylate | 593 |
| 63ah | 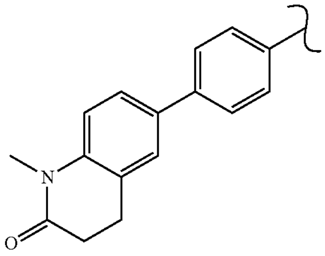 | A | (S)-ethyl 8-(2-amino-6-((R)-2,2,2-trifluoro-1-(4-(1-methyl-2-oxo-1,2,3,4-tetrahydroquinolin-6-yl)phenyl)ethoxy)pyrimidin-4-yl)-2,8-diazaspiro[4.5]decane-3-carboxylate ( | 595 |
| 63ai | 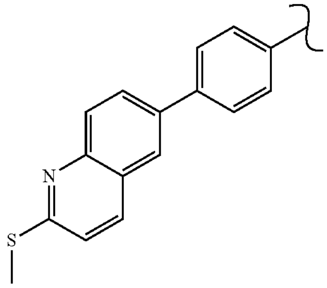 | A | (S)-ethyl 8-(2-amino-6-((R)-2,2,2-trifluoro-1-(4-(2-(methylthio)quinolin-6-yl)phenyl)ethoxy)pyrimidin-4-yl)-2,8-diazaspiro[4.5]decane-3-carboxylate | 554 |
| 63aj | 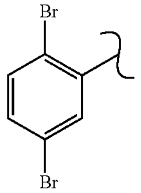 | B | (S)-ethyl 8-(2-amino-6-((R)-1-(2,5-dibromophenyl)-2,2,2-trifluoroethoxy)pyrimidin-4-yl)-2,8-diazaspiro[4.5]decane-3-carboxylate | 638 |
| 63ak | 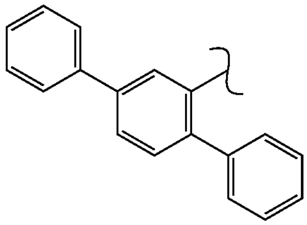 | A | (S)-ethyl 8-(6-((R)-1-([1,1';4',1''-terphenyl]-2'-yl)-2,2,2-trifluoroethoxy)-2-aminopyrimidin-4-yl)-2,8-diazaspiro[4.5]decane-3-carboxylate | 633 |

TABLE 18a-continued

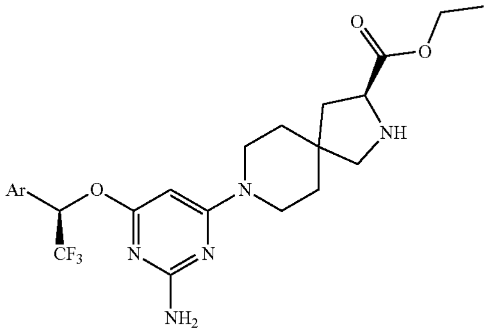

| Ex. No. | Ar | Method A or B | CAS Name | LCMS (MH+) |
|---|---|---|---|---|
| 63al | 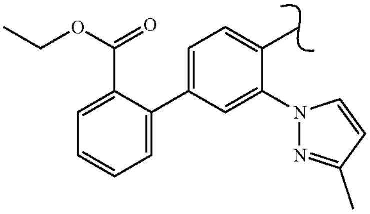 | A | (S)-ethyl 8-(2-amino-6-((R)-1-(2'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 708 |
| 63am | 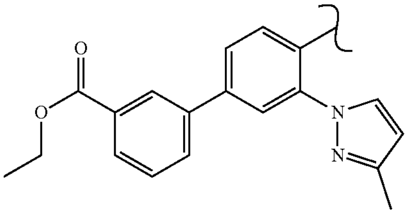 | A | (S)-ethyl 8-(2-amino-6-((R)-1-(3'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 708 |
| 63an | 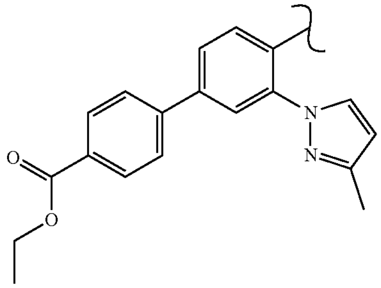 | A | (S)-ethyl 8-(2-amino-6-((R)-1-(4'-(ethoxycarbonyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 708 |
| 63ao | 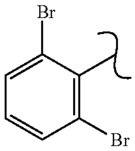 | B | (S)-ethyl 8-(2-amino-6-((R)-1-(2,6-dibromophenyl)-2,2,2-trifluoroethoxy)pyrimidin-4-yl)-2,8-diazaspiro[4.5]decane-3-carboxylate | 638 |
| 63ap | 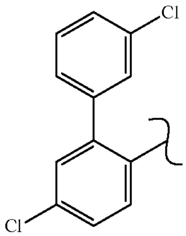 | B | (S)-ethyl 8-(2-amino-6-((R)-1-(3',5-dichloro-[1,1'-biphenyl]-2-yl)-2,2,2-trifluoroethoxy)pyrimidin-4-yl)-2,8-diazaspiro[4.5]decane-3-carboxylate | 625 |

TABLE 18a-continued

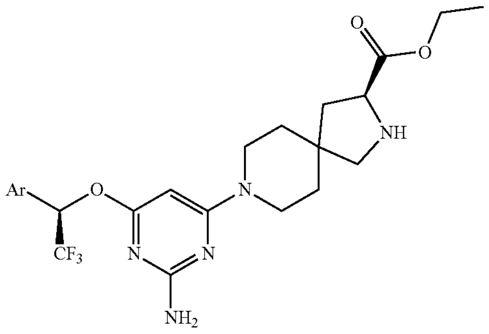

| Ex. No. | Ar | Method A or B | CAS Name | LCMS (MH+) |
|---|---|---|---|---|
| 63aq | 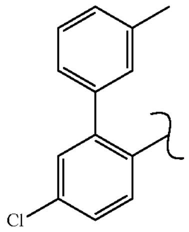 | B | (S)-ethyl 8-(2-amino-6-((R)-1-(5-chloro-3'-methyl-[1,1'-biphenyl]-2-yl)-2,2,2-trifluoroethoxy)pyrimidin-4-yl)-2,8-diazaspiro[4.5]decane-3-carboxylate | 605 |
| 63ar | 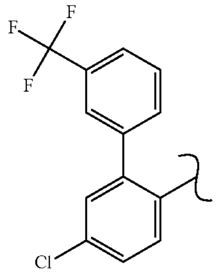 | B | (S)-ethyl 8-(2-amino-6-((R)-1-(5-chloro-3'-(trifluoromethyl)-[1,1'-biphenyl]-2-yl)-2,2,2-trifluoroethoxy)pyrimidin-4-yl)-2,8-diazaspiro[4.5]decane-3-carboxylate | 659 |
| 63as | 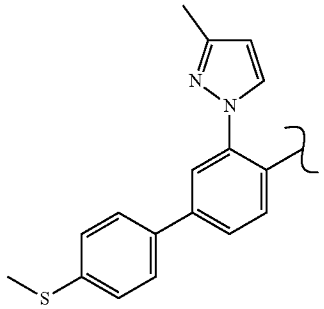 | A | (S)-ethyl 8-(2-amino-6-((R)-2,2,2-trifluoro-1-(3-(3-methyl-1H-pyrazol-1-yl)-4'-(methylthio)-[1,1'-biphenyl]-4-yl)ethoxy)pyrimidin-4-yl)-2,8-diazaspiro[4.5]decane-3-carboxylate | 583 |
| 63at | 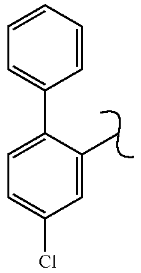 | B | (S)-ethyl 8-(2-amino-6-((R)-1-(4-chloro-[1,1'-biphenyl]-2-yl)-2,2,2-trifluoroethoxy)pyrimidin-4-yl)-2,8-diazaspiro[4.5]decane-3-carboxylate | 591 |

TABLE 18a-continued

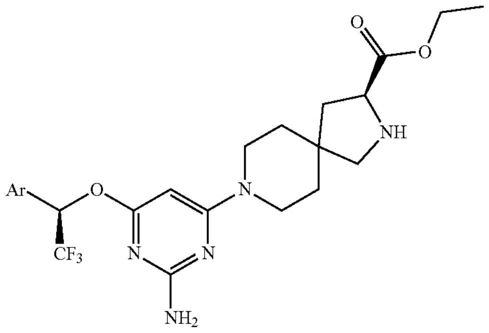

| Ex. No. | Ar | Method A or B | CAS Name | LCMS (MH+) |
|---|---|---|---|---|
| 63au | 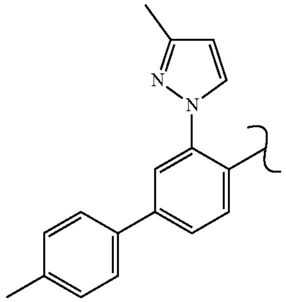 | A | (S)-ethyl 8-(2-amino-6-((R)-2,2,2-trifluoro-1-(4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 651 |
| 63av | 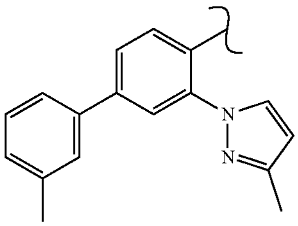 | A | (S)-ethyl 8-(2-amino-6-((R)-2,2,2-trifluoro-1-(3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 651 |
| 63aw | 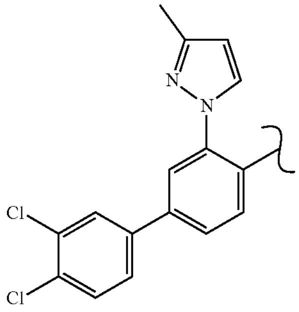 | B | (S)-ethyl 8-(2-amino-6-((R)-1-(3',4'-dichloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 705 |
| 63ax | 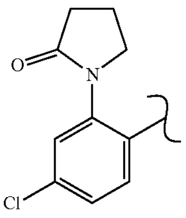 | B | (S)-ethyl 8-(2-amino-6-((R)-1-(4-chloro-2-(2-oxopyrrolidin-1-yl)phenyl)-2,2,2-trifluoroethoxy)pyrimidin-4-yl)-2,8-diazaspiro[4.5]decane-3-carboxylate | 598 |

TABLE 18a-continued

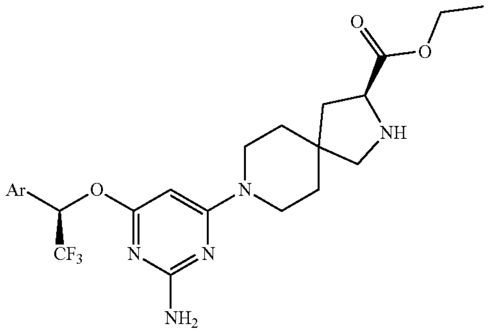

| Ex. No. | Ar | Method A or B | CAS Name | LCMS (MH+) |
|---|---|---|---|---|
| 63ay | 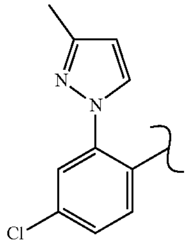 | B | ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 594 |
| 63az | 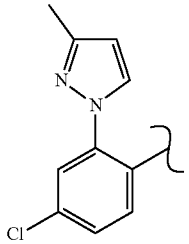 | B | (S)-ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 594 |
| 63ba | 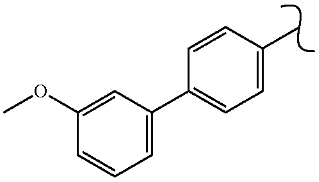 | A | (S)-ethyl 8-(2-amino-6-((R)-2,2,2-trifluoro-1-(3'-methoxy-[1,1'-biphenyl]-4-yl)ethoxy)pyrimidin-4-yl)-2,8-diazaspiro[4.5]decane-3-carboxylate | 587 |
| 63bb | 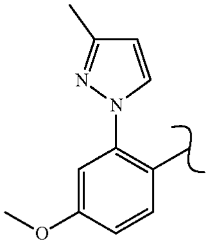 | A | (S)-ethyl 8-(2-amino-6-((R)-2,2,2-trifluoro-1-(4-methoxy-2-(3-methyl-1H-pyrazol-1-yl)phenyl)ethoxy)pyrimidin-4-yl)-2,8-diazaspiro[4.5]decane-3-carboxylate | 591 |
| 63bc | 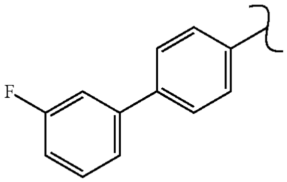 | A | (S)-ethyl 8-(2-amino-6-((R)-2,2,2-trifluoro-1-(3'-fluoro-[1,1'-biphenyl]-4-yl)ethoxy)pyrimidin-4-yl)-2,8-diazaspiro[4.5]decane-3-carboxylate | 575 |

TABLE 18a-continued

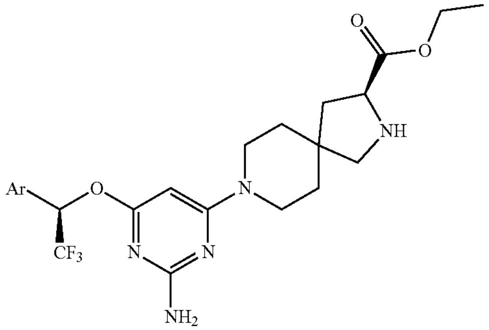

| Ex. No. | Ar | Method A or B | CAS Name | LCMS (MH+) |
|---|---|---|---|---|
| 63bd | 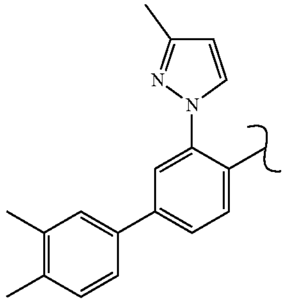 | A | (S)-ethyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 665 |
| 63be | 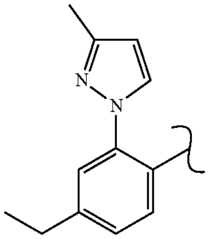 | A | (S)-ethyl 8-(2-amino-6-((R)-1-(4-ethyl-2-(3-methyl-1H-pyrazol-1-yl)phenyl)-2,2,2-trifluoroethoxy)pyrimidin-4-yl)-2,8-diazaspiro[4.5]decane-3-carboxylate | 589 |
| 63bf | 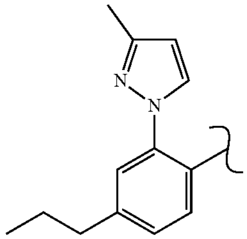 | A | (S)-ethyl 8-(2-amino-6-((R)-2,2,2-trifluoro-1-(2-(3-methyl-1H-pyrazol-1-yl)-4-propylphenyl)ethoxy)pyrimidin-4-yl)-2,8-diazaspiro[4.5]decane-3-carboxylate | 603 |
| 63bg | 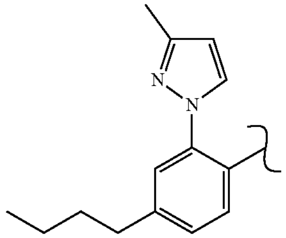 | A | (S)-ethyl 8-(2-amino-6-((R)-1-(4-butyl-2-(3-methyl-1H-pyrazol-1-yl)phenyl)-2,2,2-trifluoroethoxy)pyrimidin-4-yl)-2,8-diazaspiro[4.5]decane-3-carboxylate | 617 |

TABLE 18a-continued

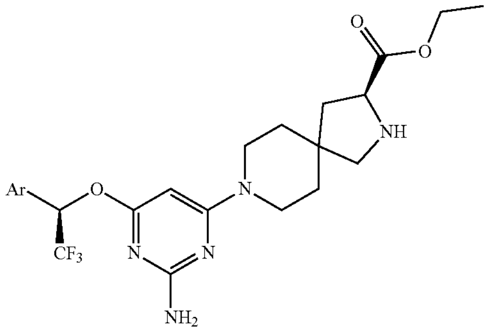

| Ex. No. | Ar | Method A or B | CAS Name | LCMS (MH+) |
|---|---|---|---|---|
| 63bh | 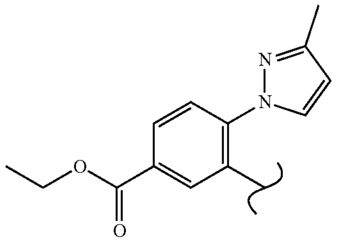 | A | (S)-ethyl 8-(2-amino-6-((R)-1-(5-(ethoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylate | 633 |
| 63bi | 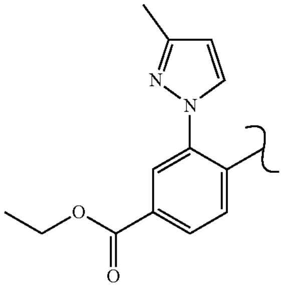 | A | (S)-ethyl 8-(2-amino-6-((R)-1-(4-(ethoxycarbonyl)-2-(3-methyl-1H-pyrazol-1-yl)phenyl)-2,2,2-trifluoroethoxy)pyrimidin-4-yl)-2,8-diazaspiro[4.5]decane-3-carboxylate | 632 |
| 63bj | 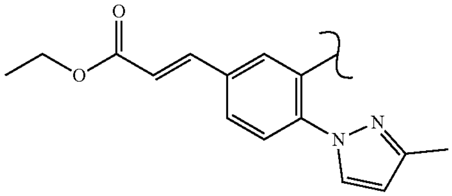 | A | (S)-ethyl 8-(2-amino-6-((R)-1-(5-((E)-3-ethoxy-3-oxoprop-1-en-1-yl)-2-(3-methyl-1H-pyrazol-1-yl)phenyl)-2,2,2-trifluoroethoxy)pyrimidin-4-yl)-2,8-diazaspiro[4.5]decane-3-carboxylate | 559 |
| 63bk | 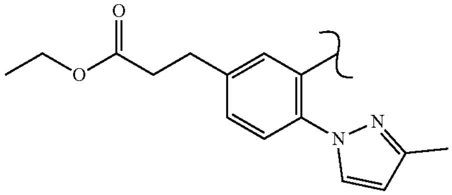 | A | (S)-ethyl 8-(2-amino-6-((R)-1-(5-(3-ethoxy-3-oxopropyl)-2-(3-methyl-1H-pyrazol-1-yl)phenyl)-2,2,2-trifluoroethoxy)pyrimidin-4-yl)-2,8-diazaspiro[4.5]decane-3-carboxylate | 588 |
| 63bl | 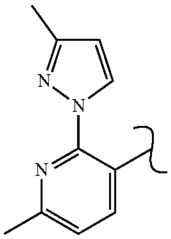 | A | (S)-ethyl 8-(2-amino-6-((R)-2,2,2-trifluoro-1-(6-methyl-2-(3-methyl-1H-pyrazol-1-yl)pyridin-3-yl)ethoxy)pyrimidin-4-yl)-2,8-diazaspiro[4.5]decane-3-carboxylate | 618 |

TABLE 18a-continued

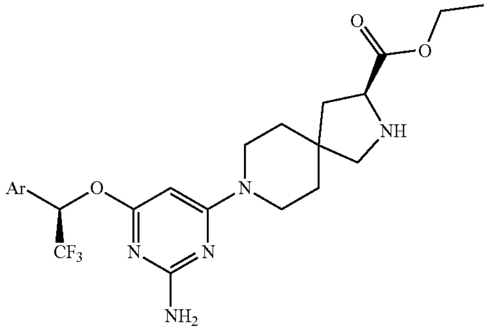

| Ex. No. | Ar | Method A or B | CAS Name | LCMS (MH+) |
|---|---|---|---|---|
| 63bm | 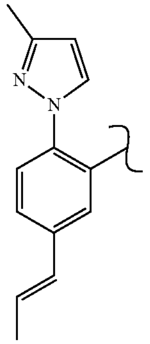 | B | (S)-ethyl 8-(2-amino-6-((R)-2,2,2-trifluoro-1-(2-(3-methyl-1H-pyrazol-1-yl)-5-((E)-prop-1-en-1-yl)phenyl)ethoxy)pyrimidin-4-yl)-2,8-diazaspiro[4.5]decane-3-carboxylate | 600 |
| 63bn | 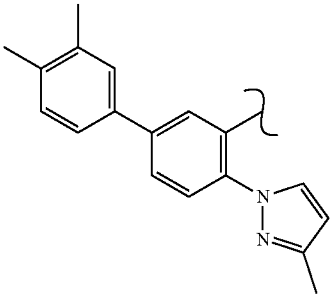 | A | (S)-ethyl 8-(2-amino-6-((R)-1-(3',4'-dimethyl-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 664 |
| 63bo | 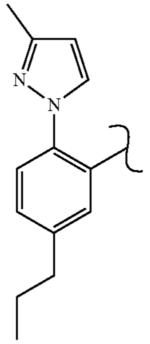 | A | (S)-ethyl 8-(2-amino-6-((R)-2,2,2-trifluoro-1-(2-(3-methyl-1H-pyrazol-1-yl)-5-propylphenyl)ethoxy)pyrimidin-4-yl)-2,8-diazaspiro[4.5]decane-3-carboxylate | 602 |

TABLE 18a-continued

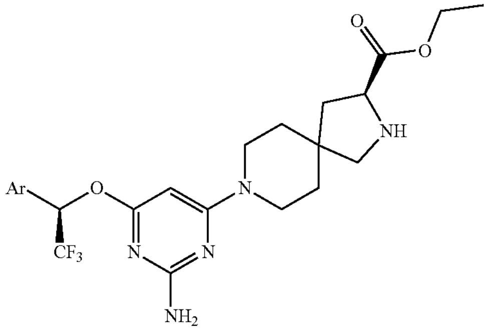

| Ex. No. | Ar | Method A or B | CAS Name | LCMS (MH+) |
|---|---|---|---|---|
| 63bp | 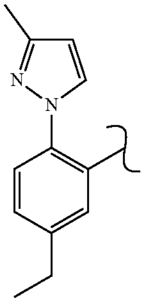 | A | (S)-ethyl 8-(2-amino-6-((R)-1-(5-ethyl-2-(3-methyl-1H-pyrazol-1-yl)phenyl)-2,2,2-trifluoroethoxy)pyrimidin-4-yl)-2,8-diazaspiro[4.5]decane-3-carboxylate | 588 |
| 63bq | 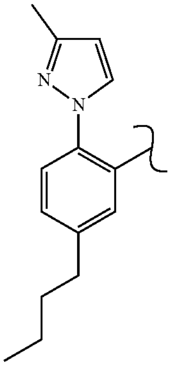 | A | (S)-ethyl 8-(2-amino-6-((R)-1-(5-butyl-2-(3-methyl-1H-pyrazol-1-yl)phenyl)-2,2,2-trifluoroethoxy)pyrimidin-4-yl)-2,8-diazaspiro[4.5]decane-3-carboxylate | 616 |
| 63br | 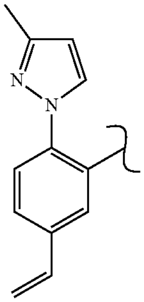 | B | (S)-ethyl 8-(2-amino-6-((R)-2,2,2-trifluoro-1-(2-(3-methyl-1H-pyrazol-1-yl)-5-vinylphenyl)ethoxy)pyrimidin-4-yl)-2,8-diazaspiro[4.5]decane-3-carboxylate | 586 |

TABLE 18a-continued

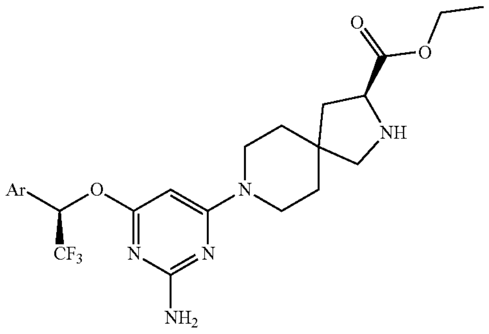

| Ex. No. | Ar | Method A or B | CAS Name | LCMS (MH+) |
|---|---|---|---|---|
| 63bs | 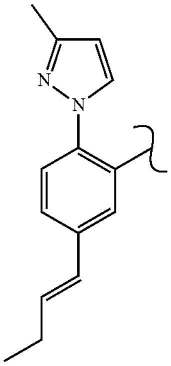 | B | (S)-ethyl 8-(2-amino-6-((R)-1-(5-((E)-but-1-en-1-yl)-2-(3-methyl-1H-pyrazol-1-yl)phenyl)-2,2,2-trifluoroethoxy)pyrimidin-4-yl)-2,8-diazaspiro[4.5]decane-3-carboxylate | 614 |
| 63bt | 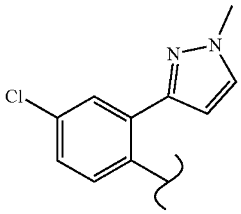 | B | (S)-ethyl 8-(2-amino-6-((R)-1-(4-chloro-2-(1-methyl-1H-pyrazol-3-yl)phenyl)-2,2,2-trifluoroethoxy)pyrimidin-4-yl)-2,8-diazaspiro[4.5]decane-3-carboxylate | 594 |
| 63bu | 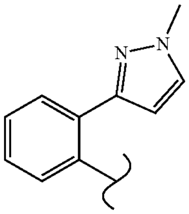 | A | (S)-ethyl 8-(2-amino-6-((R)-2,2,2-trifluoro-1-(2-(1-methyl-1H-pyrazol-3-yl)phenyl)ethoxy)pyrimidin-4-yl)-2,8-diazaspiro[4.5]decane-3-carboxylate | 560 |
| 63bv | 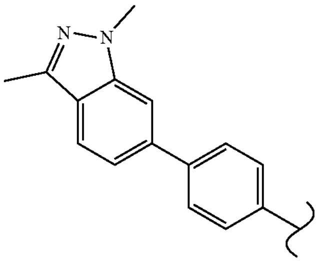 | A | (S)-ethyl 8-(2-amino-6-((R)-1-(4-(1,3-dimethyl-1H-indazol-6-yl)phenyl)-2,2,2-trifluoroethoxy)pyrimidin-4-yl)-2,8-diazaspiro[4.5]decane-3-carboxylate | 624 |

TABLE 18a-continued

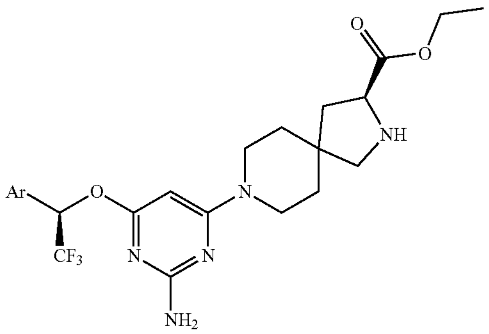

| Ex. No. | Ar | Method A or B | CAS Name | LCMS (MH+) |
|---|---|---|---|---|
| 63bw | 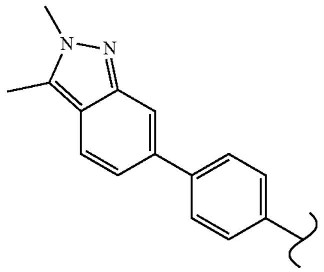 | A | (S)-ethyl 8-(2-amino-6-((R)-1-(4-(2,3-dimethyl-2H-indazol-6-yl)phenyl)-2,2,2-trifluoroethoxy)pyrimidin-4-yl)-2,8-diazaspiro[4.5]decane-3-carboxylate | 624 |
| 63bx | 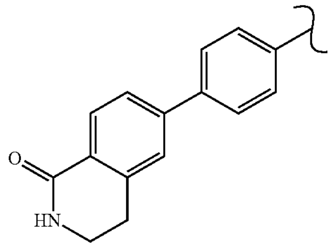 | A | (S)-ethyl 8-(2-amino-6-((R)-2,2,2-trifluoro-1-(4-(1-oxo-1,2,3,4-tetrahydroisoquinolin-6-yl)phenyl)ethoxy)pyrimidin-4-yl)-2,8-diazaspiro[4.5]decane-3-carboxylate | 625 |
| 63by | 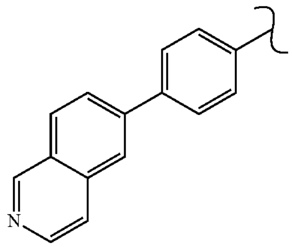 | A | (S)-ethyl 8-(2-amino-6-((R)-2,2,2-trifluoro-1-(4-(isoquinolin-6-yl)phenyl)ethoxy)pyrimidin-4-yl)-2,8-diazaspiro[4.5]decane-3-carboxylate | 607 |
| 63bz | 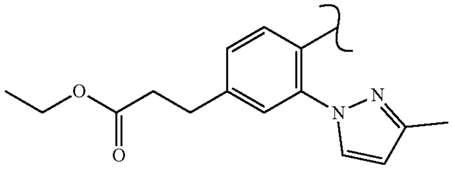 | A | (S)-ethyl 8-(2-amino-6-((R)-1-(4-(3-ethoxy-3-oxopropyl)-2-(3-methyl-1H-pyrazol-1-yl)phenyl)-2,2,2-trifluoroethoxy)pyrimidin-4-yl)-2,8-diazaspiro[4.5]decane-3-carboxylate | 660 |
| 63ca | 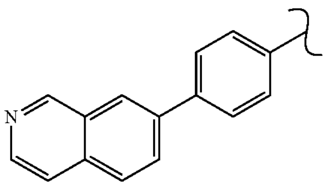 | A | (S)-ethyl 8-(2-amino-6-((R)-2,2,2-trifluoro-1-(4-(isoquinolin-7-yl)phenyl)ethoxy)pyrimidin-4-yl)-2,8-diazaspiro[4.5]decane-3-carboxylate | 607 |

TABLE 18a-continued

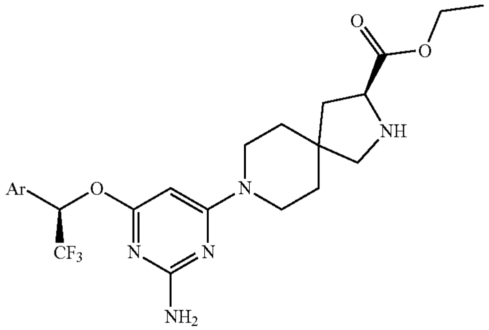

| Ex. No. | Ar | Method A or B | CAS Name | LCMS (MH+) |
|---|---|---|---|---|
| 63cb | 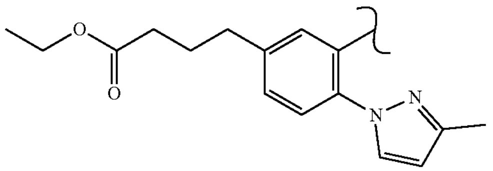 | A | (S)-ethyl 8-(2-amino-6-((R)-1-(5-(4-ethoxy-4-oxobutyl)-2-(3-methyl-1H-pyrazol-1-yl)phenyl)-2,2,2-trifluoroethoxy)pyrimidin-4-yl)-2,8-diazaspiro[4.5]decane-3-carboxylate | 674 |
| 63cc | 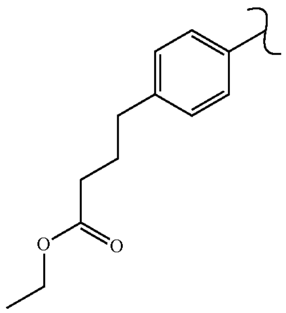 | A | (S)-ethyl 8-(2-amino-6-((R)-1-(4-(4-ethoxy-4-oxobutyl)phenyl)-2,2,2-trifluoroethoxy)pyrimidin-4-yl)-2,8-diazaspiro[4.5]decane-3-carboxylate | 594 |
| 63cd | 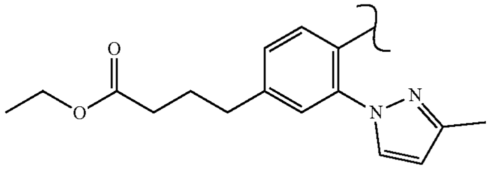 | A | (S)-ethyl 8-(2-amino-6-((R)-1-(4-(4-ethoxy-4-oxobutyl)-2-(3-methyl-1H-pyrazol-1-yl)phenyl)-2,2,2-trifluoroethoxy)pyrimidin-4-yl)-2,8-diazaspiro[4.5]decane-3-carboxylate | 674 |
| 63ce | 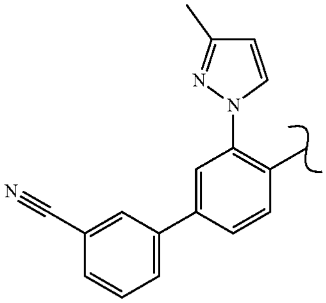 | A | (S)-ethyl 8-(2-amino-6-((R)-1-(3'-cyano-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 661 |
| 63cf | 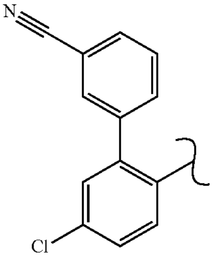 | B | (S)-ethyl 8-(2-amino-6-((R)-1-(5-chloro-3'-cyano-[1,1'-biphenyl]-2-yl)-2,2,2-trifluoroethoxy)pyrimidin-4-yl)-2,8-diazaspiro[4.5]decane-3-carboxylate | 615 |

TABLE 18a-continued

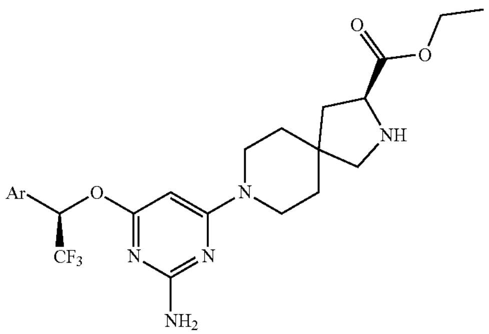

| Ex. No. | Ar | Method A or B | CAS Name | LCMS (MH+) |
|---|---|---|---|---|
| 63cg | 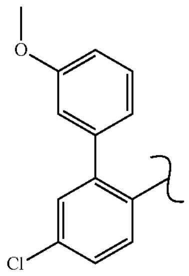 | B | (S)-ethyl 8-(2-amino-6-((R)-1-(5-chloro-3'-methoxy-[1,1'-biphenyl]-2-yl)-2,2,2-trifluoroethoxy)pyrimidin-4-yl)-2,8-diazaspiro[4.5]decane-3-carboxylate | 620 |
| 63ch | 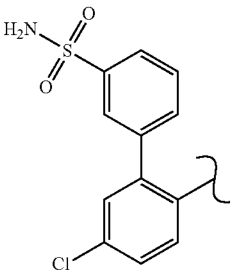 | B | (S)-ethyl 8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylate | 669 |
| 63ci | 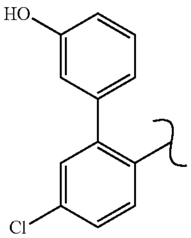 | B | (S)-ethyl 8-(2-amino-6-((R)-1-(5-chloro-3'-hydroxy-[1,1'-biphenyl]-2-yl)-2,2,2-trifluoroethoxy)pyrimidin-4-yl)-2,8-diazaspiro[4.5]decane-3-carboxylate | 606 |
| 63cj | 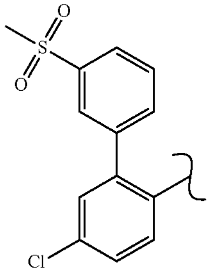 | B | (S)-ethyl 8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-3-carboxylate | 668 |

TABLE 18a-continued

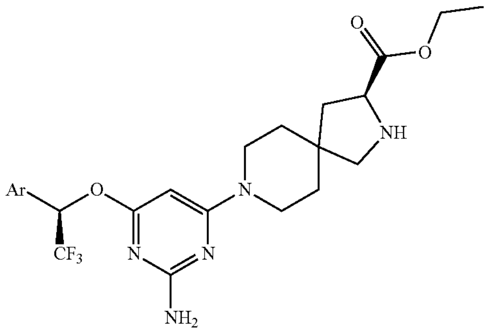

| Ex. No. | Ar | Method A or B | CAS Name | LCMS (MH+) |
|---|---|---|---|---|
| 63ck | 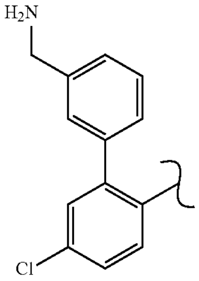 | B | (S)-ethyl 8-(2-amino-6-((R)-1-(3'-(aminomethyl)-5-chloro-[1,1'-biphenyl]-2-yl)-2,2,2-trifluoroethoxy)pyrimidin-4-yl)-2,8-diazaspiro[4.5]decane-3-carboxylate | 619 |
| 63cl | 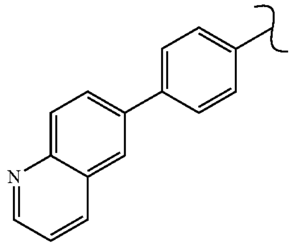 | A | (S)-ethyl 8-(2-amino-6-((R)-2,2,2-trifluoro-1-(4-(quinolin-6-yl)phenyl)ethoxy)pyrimidin-4-yl)-2,8-diazaspiro[4.5]decane-3-carboxylate | 608 |
| 63cm | 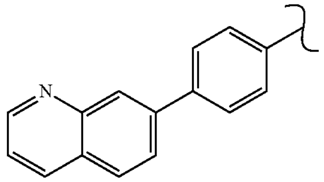 | A | (S)-ethyl 8-(2-amino-6-((R)-2,2,2-trifluoro-1-(4-(quinolin-7-yl)phenyl)ethoxy)pyrimidin-4-yl)-2,8-diazaspiro[4.5]decane-3-carboxylate | 608 |
| 63cn | 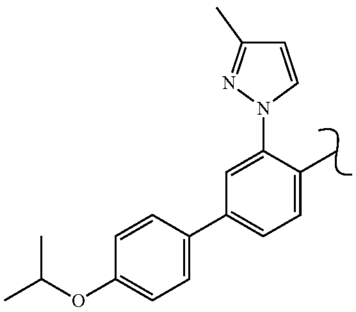 | A | (S)-ethyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 694 |

TABLE 18a-continued

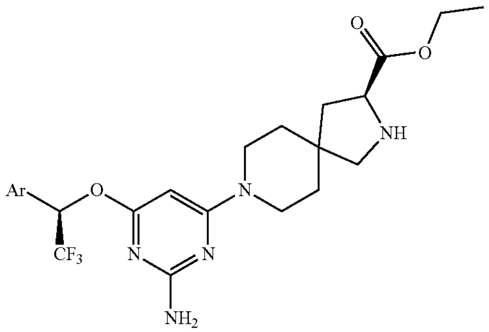

| Ex. No. | Ar | Method A or B | CAS Name | LCMS (MH+) |
|---|---|---|---|---|
| 63co | 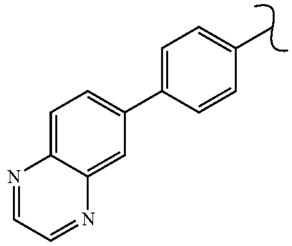 | A | (S)-ethyl 8-(2-amino-6-((R)-2,2,2-trifluoro-1-(4-(quinoxalin-6-yl)phenyl)ethoxy)pyrimidin-4-yl)-2,8-diazaspiro[4.5]decane-3-carboxylate | 608 |
| 63cp | 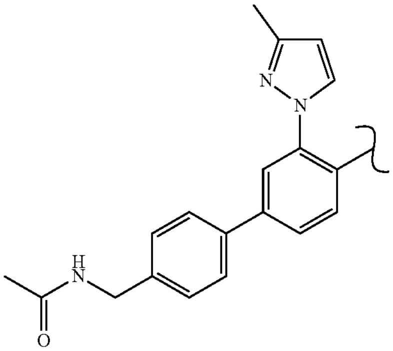 | A | (S)-ethyl 8-(6-((R)-1-(4'-(acetamidomethyl)-3-(3-methyl-1H-pyrazol-1-yl)-[1,1'-biphenyl]-4-yl)-2,2,2-trifluoroethoxy)-2-aminopyrimidin-4-yl)-2,8-diazaspiro[4.5]decane-3-carboxylate | 707 |
| 63cq | 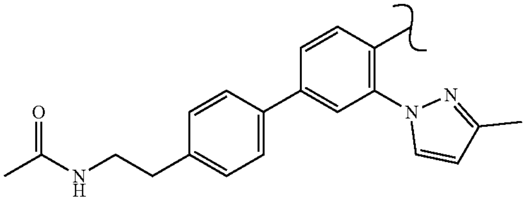 | A | (S)-ethyl 8-(6-((R)-1-(4'-(2-acetamidoethyl)-3-(3-methyl-1H-pyrazol-1-yl)-[1,1'-biphenyl]-4-yl)-2,2,2-trifluoroethoxy)-2-aminopyrimidin-4-yl)-2,8-diazaspiro[4.5]decane-3-carboxylate | 721 |
| 63cr | 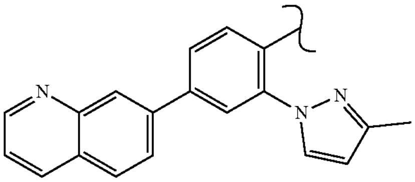 | A | (S)-ethyl 8-(2-amino-6-((R)-2,2,2-trifluoro-1-(2-(3-methyl-1H-pyrazol-1-yl)-4-(quinolin-7-yl)phenyl)ethoxy)pyrimidin-4-yl)-2,8-diazaspiro[4.5]decane-3-carboxylate | 687 |

TABLE 18a-continued

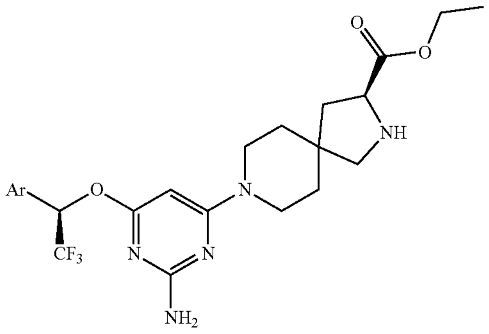

| Ex. No. | Ar | Method A or B | CAS Name | LCMS (MH+) |
|---|---|---|---|---|
| 63cs | 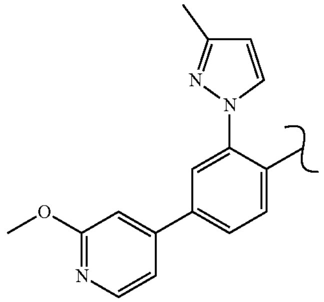 | A | (S)-ethyl 8-(2-amino-6-((R)-2,2,2-trifluoro-1-(4-(2-methoxypyridin-4-yl)-2-(3-methyl-1H-pyrazol-1-yl)phenyl)ethoxy)pyrimidin-4-yl)-2,8-diazaspiro[4.5]decane-3-carboxylate | 666 |
| 63ct | 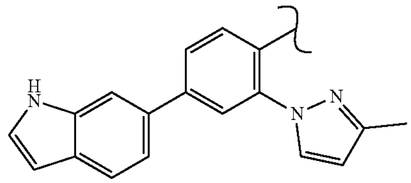 | A | (S)-ethyl 8-(6-((R)-1-(4-(1H-indol-6-yl)-2-(3-methyl-1H-pyrazol-1-yl)phenyl)-2,2,2-trifluoroethoxy)-2-aminopyrimidin-4-yl)-2,8-diazaspiro[4.5]decane-3-carboxylate | 595 |
| 63cu | 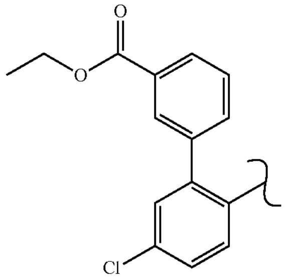 | B | (S)-ethyl 8-(2-amino-6-((R)-1-(5-chloro-3'-(ethoxycarbonyl)-[1,1'-biphenyl]-2-yl)-2,2,2-trifluoroethoxy)pyrimidin-4-yl)-2,8-diazaspiro[4.5]decane-3-carboxylate | 662 |
| 63cv | 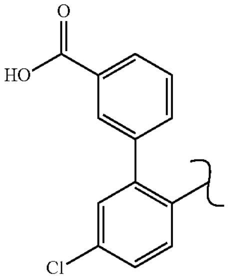 | B | 2'-((R)-1-((2-amino-6-((S)-3-(ethoxycarbonyl)-2,8-diazaspiro[4.5]decan-8-yl)pyrimidin-4-yl)oxy)-2,2,2-trifluoroethyl)-5'-chloro-[1,1'-biphenyl]-3-carboxylic acid | 634 |

TABLE 18a-continued

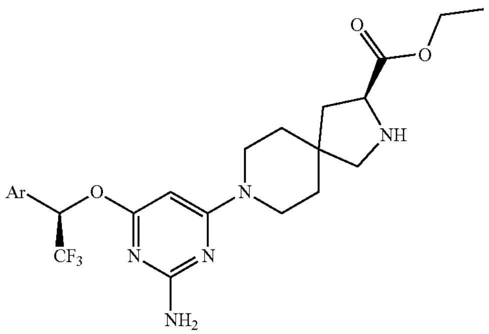

| Ex. No. | Ar | Method A or B | CAS Name | LCMS (MH+) |
|---|---|---|---|---|
| 63cw | 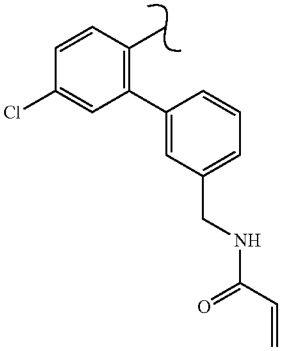 | B | (S)-ethyl 8-(6-((R)-1-(3'-(acrylamidomethyl)-5-chloro-[1,1'-biphenyl]-2-yl)-2,2,2-trifluoroethoxy)-2-aminopyrimidin-4-yl)-2,8-diazaspiro[4.5]decane-3-carboxylate | 673 |
| 63cx | 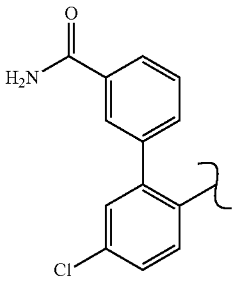 | B | (S)-ethyl 8-(2-amino-6-((R)-1-(3'-carbamoyl-5-chloro-[1,1'-biphenyl]-2-yl)-2,2,2-trifluoroethoxy)pyrimidin-4-yl)-2,8-diazaspiro[4.5]decane-3-carboxylate | 633 |
| 63cy | 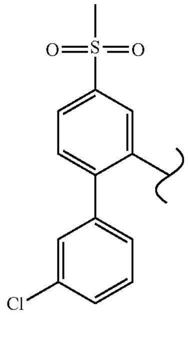 | B | (S)-ethyl 8-(2-amino-6-((R)-1-(5-chloro-4'-(methylsulfonyl)-[1,1'-biphenyl]-2-yl)-2,2,2-trifluoroethoxy)pyrimidin-4-yl)-2,8-diazaspiro[4.5]decane-3-carboxylate | 668 |

TABLE 18a-continued

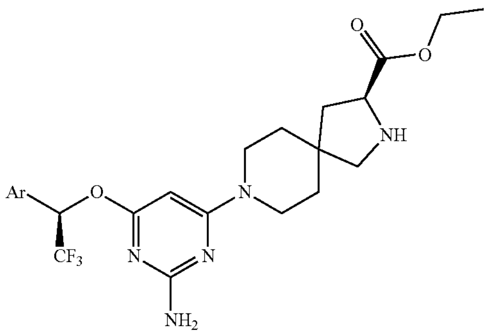

| Ex. No. | Ar | Method A or B | CAS Name | LCMS (MH+) |
|---|---|---|---|---|
| 63cz | 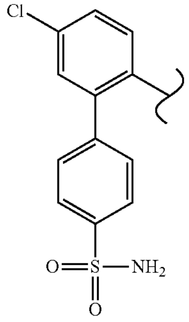 | B | (S)-ethyl 8-(2-amino-6-((R)-1-(5-chloro-4'-sulfamoyl-[1,1'-biphenyl]-2-yl)-2,2,2-trifluoroethoxy)pyrimidin-4-yl)-2,8-diazaspiro[4.5]decane-3-carboxylate | 669 |
| 63da | 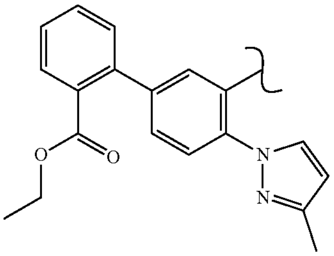 | A | (S)-ethyl 8-(2-amino-6-((R)-1-(2'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 708 |
| 63db | 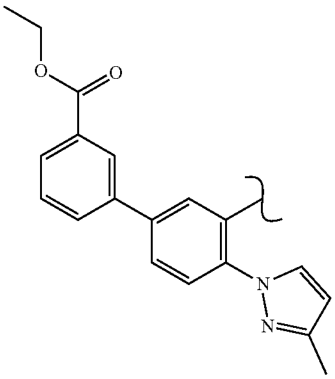 | A | (S)-ethyl 8-(2-amino-6-((R)-1-(3'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 708 |

TABLE 18a-continued

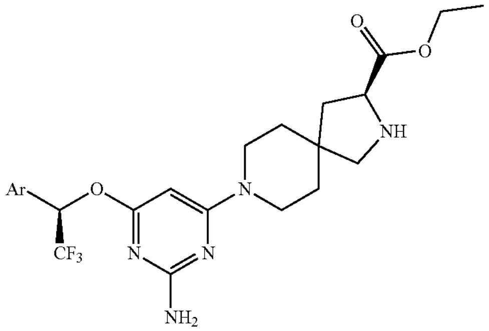

| Ex. No. | Ar | Method A or B | CAS Name | LCMS (MH+) |
|---|---|---|---|---|
| 63dc | 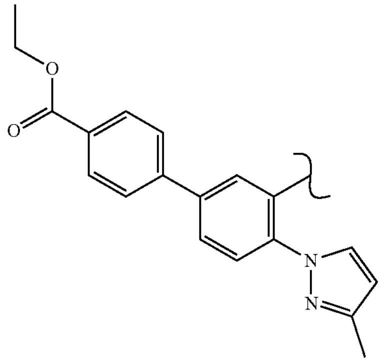 | A | (S)-ethyl 8-(2-amino-6-((R)-1-(4'-(ethoxycarbonyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 708 |
| 63dd | 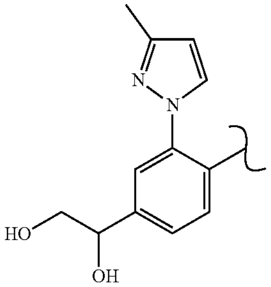 | A | (3S)-ethyl 8-(2-amino-6-((1R)-1-(4-(1,2-dihydroxyethyl)-2-(3-methyl-1H-pyrazol-1-yl)phenyl)-2,2,2-trifluoroethoxy)pyrimidin-4-yl)-2,8-diazaspiro[4.5]decane-3-carboxylate | 620 |
| 63de | 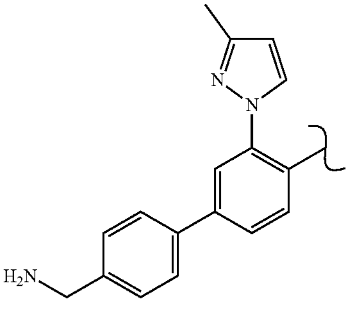 | A | (S)-ethyl 8-(2-amino-6-((R)-1-(4'-(aminomethyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 666 |
| 63df | 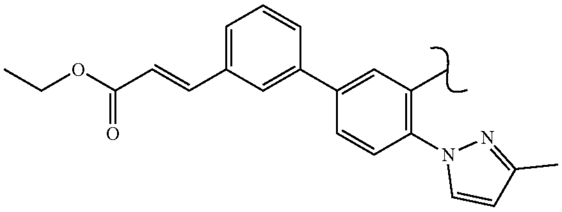 | A | (S)-ethyl 8-(2-amino-6-((R)-1-(3'-((E)-3-ethoxy-3-oxoprop-1-en-1-yl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 734 |

TABLE 18a-continued

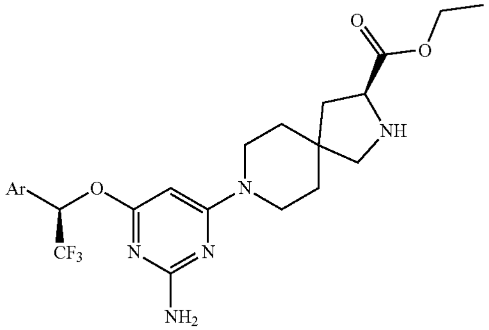

| Ex. No. | Ar | Method A or B | CAS Name | LCMS (MH+) |
|---|---|---|---|---|
| 63dg | 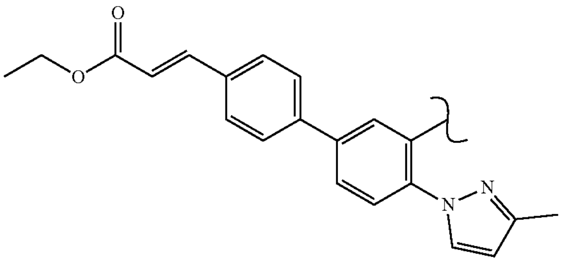 | A | (S)-ethyl 8-(2-amino-6-((R)-1-(4'-((E)-3-ethoxy-3-oxoprop-1-en-1-yl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 734 |
| 63dh | 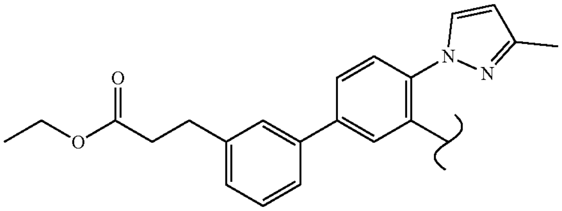 | A | (S)-ethyl 8-(2-amino-6-((R)-1-(3'-(3-ethoxy-3-oxopropyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 736 |
| 63di | 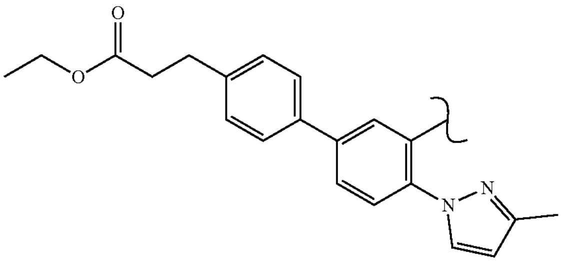 | A | (S)-ethyl 8-(2-amino-6-((R)-1-(4'-(3-ethoxy-3-oxopropyl)-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 736 |
| 63dj | 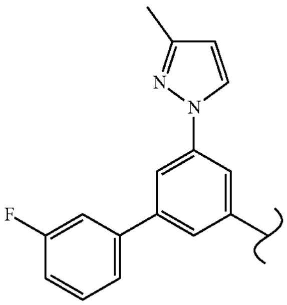 | A | (S)-ethyl 8-(2-amino-6-((R)-2,2,2-trifluoro-1-(3'-fluoro-3-(3-methyl-1H-pyrazol-1-yl)-[1,1'-biphenyl]-4-yl)ethoxy)pyrimidin-4-yl)-2,8-diazaspiro[4.5]decane-3-carboxylate | 654 |

TABLE 18a-continued

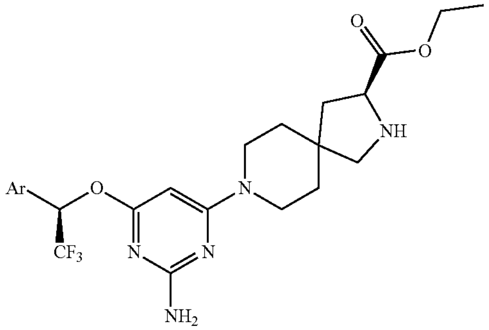

| Ex. No. | Ar | Method A or B | CAS Name | LCMS (MH+) |
|---|---|---|---|---|
| 63dk | 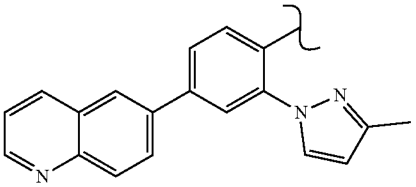 | A | (S)-ethyl 8-(2-amino-6-((R)-2,2,2-trifluoro-1-(2-(3-methyl-1H-pyrazol-1-yl)-4-(quinolin-6-yl)phenyl)ethoxy)pyrimidin-4-yl)-2,8-diazaspiro[4.5]decane-3-carboxylate | 687 |
| 63dl | 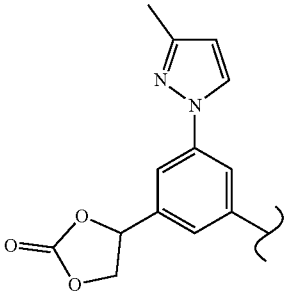 | A | (3S)-ethyl 8-(2-amino-6-((1R)-2,2,2-trifluoro-1-(2-(3-methyl-1H-pyrazol-1-yl)-4-(2-oxo-1,3-dioxolan-4-yl)phenyl)ethoxy)pyrimidin-4-yl)-2,8-diazaspiro[4.5]decane-3-carboxylate | 646 |
| 63dm | 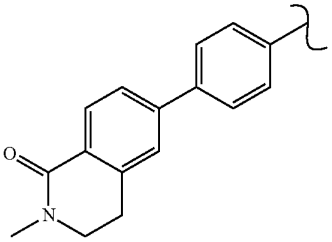 | A | (S)-ethyl 8-(2-amino-6-((R)-2,2,2-trifluoro-1-(4-(2-methyl-1-oxo-1,2,3,4-tetrahydroisoquinolin-6-yl)phenyl)ethoxy)pyrimidin-4-yl)-2,8-diazaspiro[4.5]decane-3-carboxylate | 639 |
| 63dn | 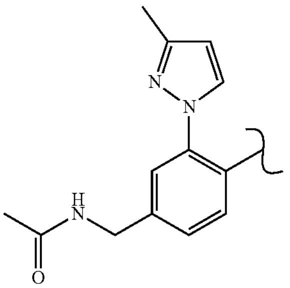 | A | (S)-ethyl 8-(6-((R)-1-(4-(acetamidomethyl)-2-(3-methyl-1H-pyrazol-1-yl)phenyl)-2,2,2-trifluoroethoxy)-2-aminopyrimidin-4-yl)-2,8-diazaspiro[4.5]decane-3-carboxylate | 631 |

TABLE 18a-continued

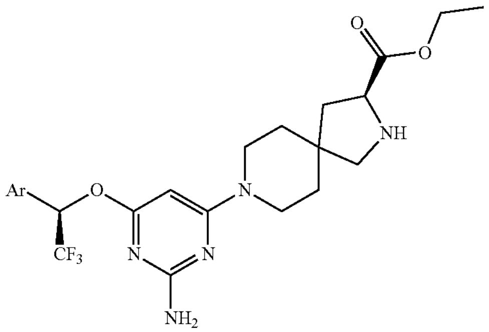

| Ex. No. | Ar | Method A or B | CAS Name | LCMS (MH+) |
|---|---|---|---|---|
| 63do | 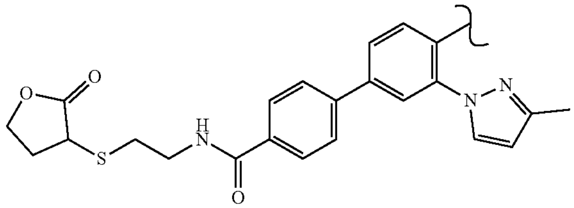 | A | (3S)-ethyl 8-(2-amino-6-((1R)-2,2,2-trifluoro-1-(3-(3-methyl-1H-pyrazol-1-yl)-4'-((2-((2-oxotetrahydrofuran-3-yl)thio)ethyl)carbamoyl)-[1,1'-biphenyl]-4-yl)ethoxy)pyrimidin-4-yl)-2,8-diazaspiro[4.5]decane-3-carboxylate | 823 |
| 63dp | 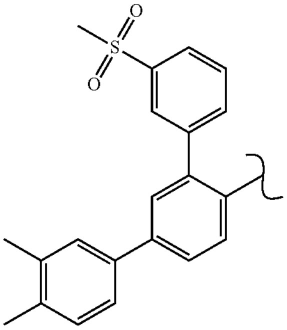 | A | (S)-ethyl 8-(2-amino-6-((R)-1-(3,4-dimethyl-3''-(methylsulfonyl)-[1,1':3',1''-terphenyl]-4'-yl)-2,2,2-trifluoroethoxy)pyrimidin-4-yl)-2,8-diazaspiro[4.5]decane-3-carboxylate | 738 |
| 63dq | 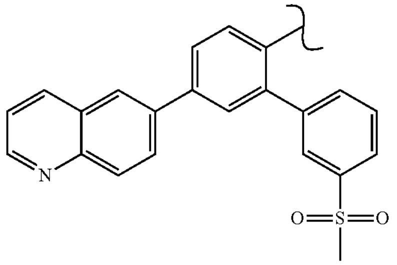 | A | (S)-ethyl 8-(2-amino-6-((R)-2,2,2-trifluoro-1-(3'-(methylsulfonyl)-5-(quinolin-6-yl)-[1,1'-biphenyl]-2-yl)ethoxy)pyrimidin-4-yl)-2,8-diazaspiro[4.5]decane-3-carboxylate | 761 |
| 63dr | 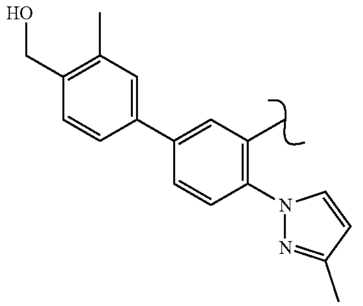 | A | (S)-ethyl 8-(2-amino-6-((R)-2,2,2-trifluoro-1-(4'-(hydroxymethyl)-3'-methyl-4-(3-methyl-1H-pyrazol-1-yl)-[1,1'-biphenyl]-3-yl)ethoxy)pyrimidin-4-yl)-2,8-diazaspiro[4.5]decane-3-carboxylate | 680 |

TABLE 18a-continued

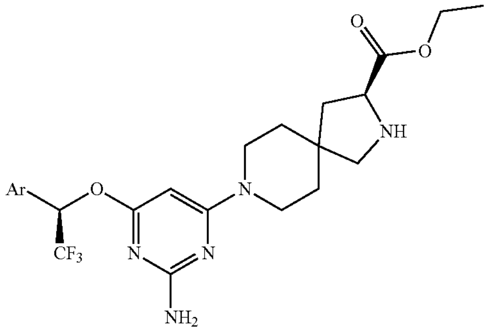

| Ex. No. | Ar | Method A or B | CAS Name | LCMS (MH+) |
|---|---|---|---|---|
| 63ds | 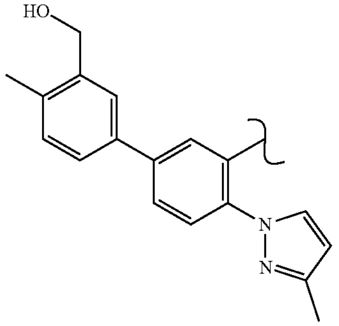 | A | (S)-ethyl 8-(2-amino-6-((R)-2,2,2-trifluoro-1-(3'-(hydroxymethyl)-4'-methyl-4-(3-methyl-1H-pyrazol-1-yl)-[1,1'-biphenyl]-3-yl)ethoxy)pyrimidin-4-yl)-2,8-diazaspiro[4.5]decane-3-carboxylate | 680 |
| 63dt | 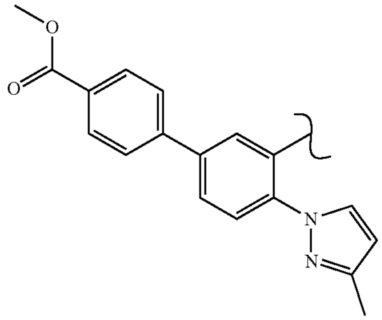 | A | (S)-ethyl 8-(2-amino-6-((R)-2,2,2-trifluoro-1-(4'-(methoxycarbonyl)-4-(3-methyl-1H-pyrazol-1-yl)-[1,1'-biphenyl]-3-yl)ethoxy)pyrimidin-4-yl)-2,8-diazaspiro[4.5]decane-3-carboxylate | 694 |
| 63du | 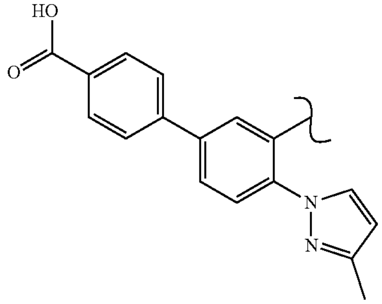 | A | 3'-((S)-1-((2-amino-6-((R)-3-(ethoxycarbonyl)-2,8-diazaspiro[4.5]decan-8-yl)pyrimidin-4-yl)oxy)-2,2,2-trifluoroethyl)-4'-(3-methyl-1H-pyrazol-1-yl)-[1,1'-biphenyl]-4-carboxylic acid | 680 |
| 63dv | 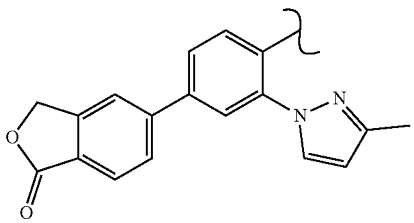 | A | (S)-ethyl 8-(2-amino-6-((R)-2,2,2-trifluoro-1-(2-(3-methyl-1H-pyrazol-1-yl)-4-(1-oxo-1,3-dihydroisobenzofuran-5-yl)phenyl)ethoxy)pyrimidin-4-yl)-2,8-diazaspiro[4.5]decane-3-carboxylate | 693 |

TABLE 18a-continued

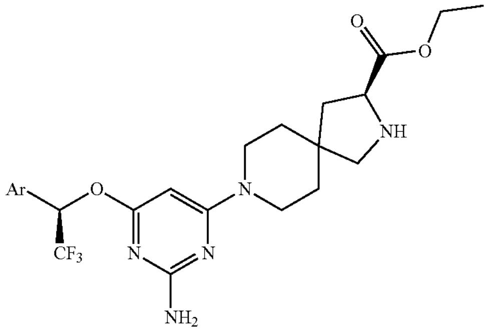

| Ex. No. | Ar | Method A or B | CAS Name | LCMS (MH+) |
|---|---|---|---|---|
| 63dw | 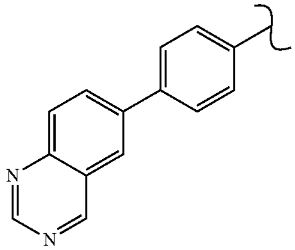 | A | (S)-ethyl 8-(2-amino-6-((R)-2,2,2-trifluoro-1-(4-(quinazolin-6-yl)phenyl)ethoxy)pyrimidin-4-yl)-2,8-diazaspiro[4.5]decane-3-carboxylate | 608 |
| 63dx | 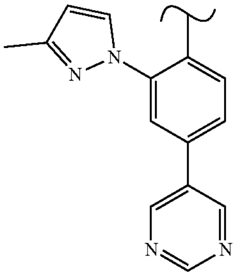 | A | (S)-ethyl 8-(2-amino-6-((R)-2,2,2-trifluoro-1-(2-(3-methyl-1H-pyrazol-1-yl)-4-(pyrimidin-5-yl)phenyl)ethoxy)pyrimidin-4-yl)-2,8-diazaspiro[4.5]decane-3-carboxylate | 638 |
| 63dy | 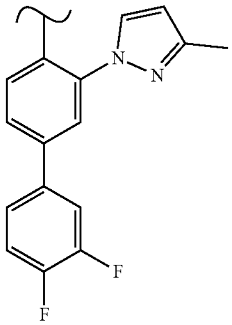 | A | (S)-ethyl 8-(2-amino-6-((R)-1-(3',4'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 672 |
| 63dz | 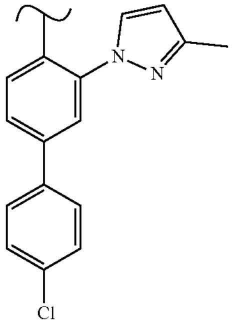 | B | (S)-ethyl 8-(2-amino-6-((R)-1-(4'-chloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 671 |

TABLE 18a-continued

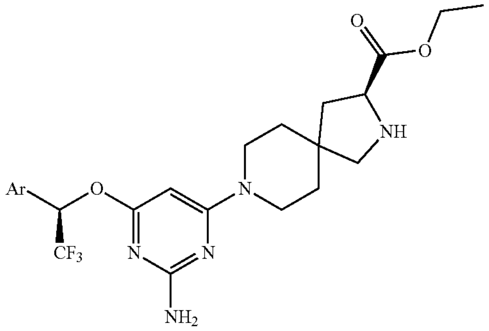

| Ex. No. | Ar | Method A or B | CAS Name | LCMS (MH+) |
|---|---|---|---|---|
| 63ea | 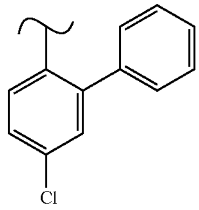 | B | (S)-ethyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate | 591 |
| 63eb | 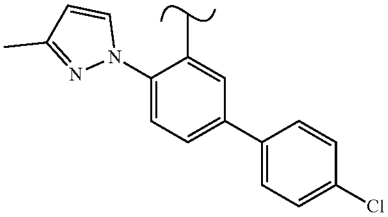 | B | (S)-ethyl 8-(2-amino-6-((R)-1-(4'-chloro-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 671 |
| 63ec | 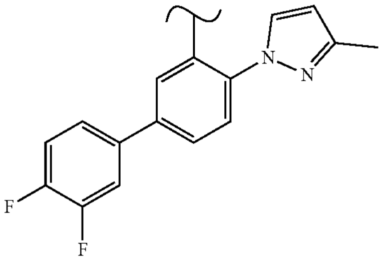 | A | (S)-ethyl 8-(2-amino-6-((R)-1-(3',4'-difluoro-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 672 |
| 63ed | 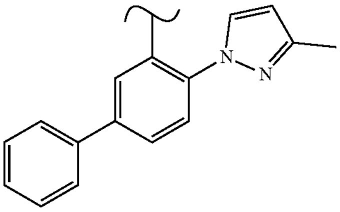 | A | (S)-ethyl 8-(2-amino-6-((R)-2,2,2-trifluoro-1-(4-(3-methyl-1H-pyrazol-1-yl)-[1,1'-biphenyl]-3-yl)ethoxy)pyrimidin-4-yl)-2,8-diazaspiro[4.5]decane-3-carboxylate | 636 |
| 63ee | 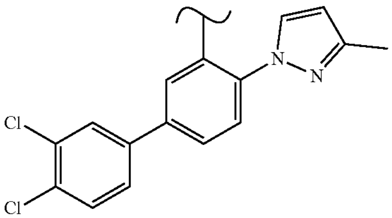 | B | (S)-ethyl 8-(2-amino-6-((R)-1-(3',4'-dichloro-4-(3-methyl-1H-pyrazol-1-yl)-[1,1'-biphenyl]-3-yl)-2,2,2-trifluoroethoxy)pyrimidin-4-yl)-2,8-diazaspiro[4.5]decane-3-carboxylate | 705 |

TABLE 18a-continued

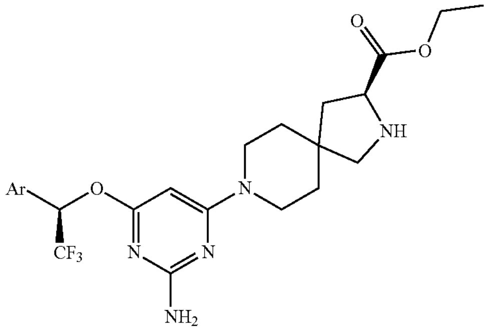

| Ex. No. | Ar | Method A or B | CAS Name | LCMS (MH+) |
|---|---|---|---|---|
| 63ef | 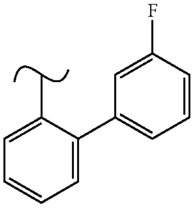 | A | (S)-ethyl 8-(2-amino-6-((R)-2,2,2-trifluoro-1-(3'-fluoro-[1,1'-biphenyl]-2-yl)ethoxy)pyrimidin-4-yl)-2,8-diazaspiro[4.5]decane-3-carboxylate | 574 |
| 63eg | 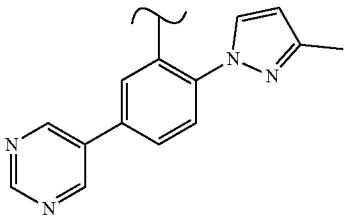 | A | (S)-ethyl 8-(2-amino-6-((R)-2,2,2-trifluoro-1-(2-(3-methyl-1H-pyrazol-1-yl)-5-(pyrimidin-5-yl)phenyl)ethoxy)pyrimidin-4-yl)-2,8-diazaspiro[4.5]decane-3-carboxylate | 638 |
| 63eh | 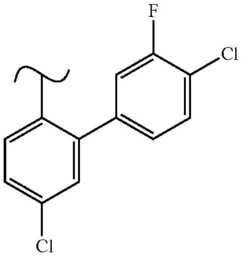 | B | (S)-ethyl 8-(2-amino-6-((R)-1-(4',5-dichloro-3'-fluoro-[1,1'-biphenyl]-2-yl)-2,2,2-trifluoroethoxy)pyrimidin-4-yl)-2,8-diazaspiro[4.5]decane-3-carboxylate | 643 |
| 63ei | 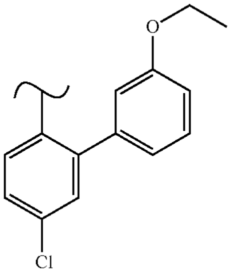 | B | (S)-ethyl 8-(2-amino-6-((R)-1-(5-chloro-3'-ethoxy-[1,1'-biphenyl]-2-yl)-2,2,2-trifluoroethoxy)pyrimidin-4-yl)-2,8-diazaspiro[4.5]decane-3-carboxylate | 635 |
| 63ej | 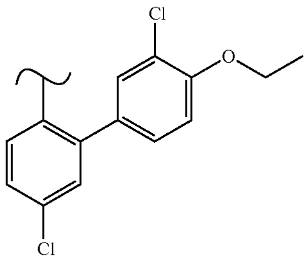 | B | (S)-ethyl 8-(2-amino-6-((R)-1-(3',5-dichloro-4'-ethoxy-[1,1'-biphenyl]-2-yl)-2,2,2-trifluoroethoxy)pyrimidin-4-yl)-2,8-diazaspiro[4.5]decane-3-carboxylate | 669 |

TABLE 18a-continued

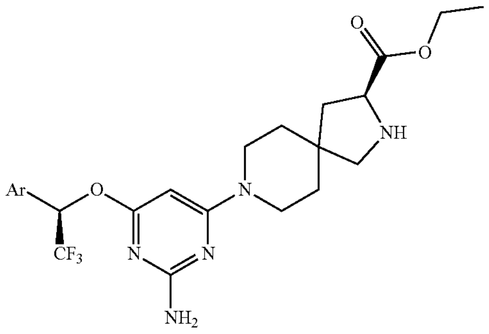

| Ex. No. | Ar | Method A or B | CAS Name | LCMS (MH+) |
|---|---|---|---|---|
| 63ek | 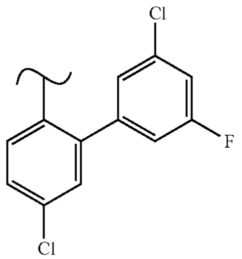 | B | (S)-ethyl 8-(2-amino-6-((R)-1-(3',5-dichloro-5'-fluoro-[1,1'-biphenyl]-2-yl)-2,2,2-trifluoroethoxy)pyrimidin-4-yl)-2,8-diazaspiro[4.5]decane-3-carboxylate | 643 |
| 63el | 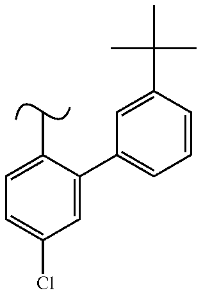 | B | (S)-ethyl 8-(2-amino-6-((R)-1-(3'-(tert-butyl)-5-chloro-[1,1'-biphenyl]-2-yl)-2,2,2-trifluoroethoxy)pyrimidin-4-yl)-2,8-diazaspiro[4.5]decane-3-carboxylate | 647 |
| 63em | 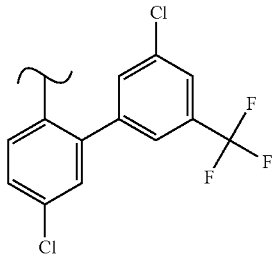 | B | (S)-ethyl 8-(2-amino-6-((R)-1-(3',5-dichloro-5'-(trifluoromethyl)-[1,1'-biphenyl]-2-yl)-2,2,2-trifluoroethoxy)pyrimidin-4-yl)-2,8-diazaspiro[4.5]decane-3-carboxylate | 693 |
| 63en | 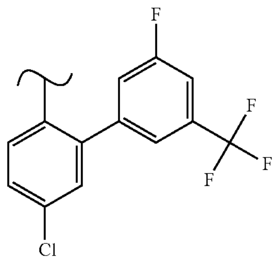 | B | (S)-ethyl 8-(2-amino-6-((R)-1-(5-chloro-3'-fluoro-5'-(trifluoromethyl)-[1,1'-biphenyl]-2-yl)-2,2,2-trifluoroethoxy)pyrimidin-4-yl)-2,8-diazaspiro[4.5]decane-3-carboxylate | 677 |

TABLE 18a-continued

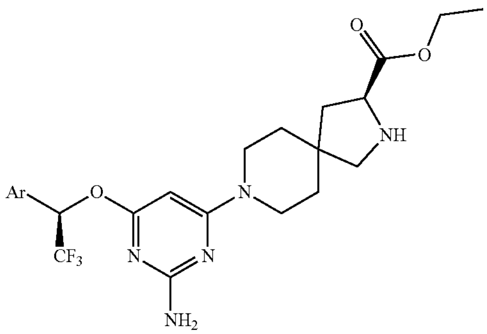

| Ex. No. | Ar | Method A or B | CAS Name | LCMS (MH+) |
|---|---|---|---|---|
| 63eo | 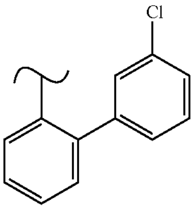 | B | (S)-ethyl 8-(2-amino-6-((R)-1-(3'-chloro-[1,1'-biphenyl]-2-yl)-2,2,2-trifluoroethoxy)pyrimidin-4-yl)-2,8-diazaspiro[4.5]decane-3-carboxylate | 591 |
| 63ep | 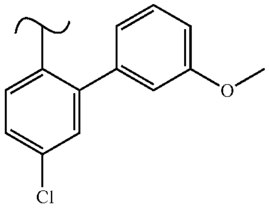 | B | (S)-ethyl 8-(2-amino-6-((R)-1-(5-chloro-3'-methoxy-[1,1'-biphenyl]-2-yl)-2,2,2-trifluoroethoxy)pyrimidin-4-yl)-2,8-diazaspiro[4.5]decane-3-carboxylate | 621 |
| 63eq | 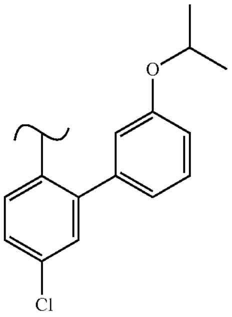 | B | (S)-ethyl 8-(2-amino-6-((R)-1-(5-chloro-3'-isopropoxy-[1,1'-biphenyl]-2-yl)-2,2,2-trifluoroethoxy)pyrimidin-4-yl)-2,8-diazaspiro[4.5]decane-3-carboxylate | 649 |
| 63er | 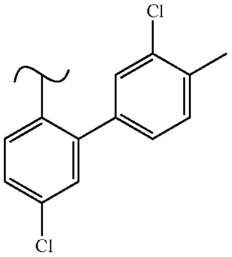 | B | (S)-ethyl 8-(2-amino-6-((R)-1-(3',5-dichloro-4'-methyl-[1,1'-biphenyl]-2-yl)-2,2,2-trifluoroethoxy)pyrimidin-4-yl)-2,8-diazaspiro[4.5]decane-3-carboxylate | 639 |

TABLE 18a-continued

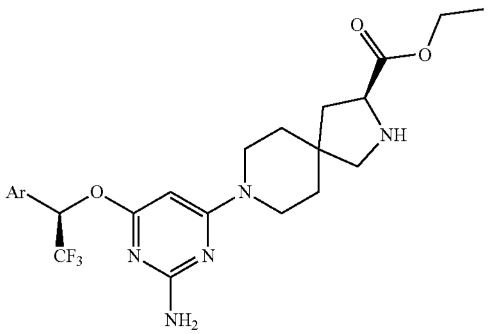

| Ex. No. | Ar | Method A or B | CAS Name | LCMS (MH+) |
|---|---|---|---|---|
| 63es | 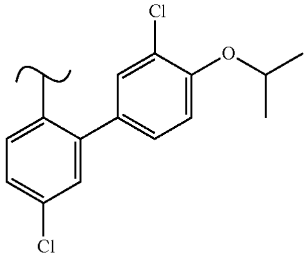 | B | (S)-ethyl 8-(2-amino-6-((R)-1-(3',5-dichloro-4'-isopropoxy-[1,1'-biphenyl]-2-yl)-2,2,2-trifluoroethoxy)pyrimidin-4-yl)-2,8-diazaspiro[4.5]decane-3-carboxylate | 683 |
| 63et | 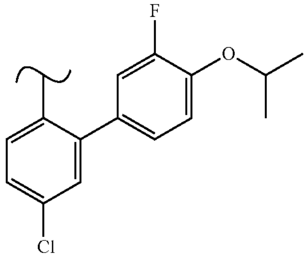 | B | (S)-ethyl 8-(2-amino-6-((R)-1-(5-chloro-3'-fluoro-4'-isopropoxy-[1,1'-biphenyl]-2-yl)-2,2,2-trifluoroethoxy)pyrimidin-4-yl)-2,8-diazaspiro[4.5]decane-3-carboxylate | 667 |
| 63eu | 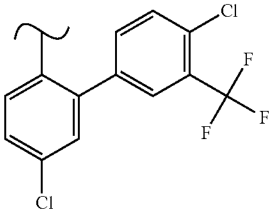 | B | (S)-ethyl 8-(2-amino-6-((R)-1-(4',5-dichloro-3'-(trifluoromethyl)-(1,1'-biphenyl]-2-yl)-2,2,2-trifluoroethoxy)pyrimidin-4-yl)-2,8-diazaspiro[4.5]decane-3-carboxylate | 693 |
| 63ev | 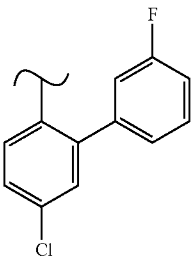 | B | (S)-ethyl 8-(2-amino-6-((R)-1-(5-chloro-3'-fluoro-[1,1'-biphenyl]-2-yl)-2,2,2-trifluoroethoxy)pyrimidin-4-yl)-2,8-diazaspiro[4.5]decane-3-carboxylate | 609 |

TABLE 18a-continued

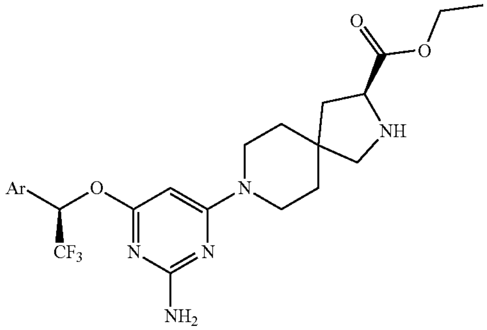

| Ex. No. | Ar | Method A or B | CAS Name | LCMS (MH+) |
|---|---|---|---|---|
| 63ew | 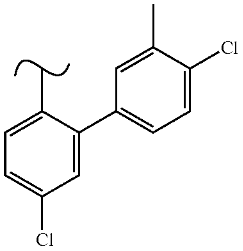 | B | (S)-ethyl 8-(2-amino-6-((R)-1-(4',5-dichloro-3'-methyl-[1,1'-biphenyl]-2-yl)-2,2,2-trifluoroethoxy)pyrimidin-4-yl)-2,8-diazaspiro[4.5]decane-3-carboxylate | 639 |
| 63ex | 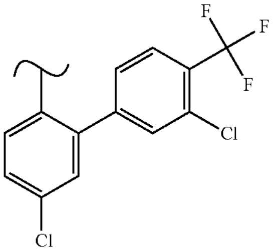 | B | (S)-ethyl 8-(2-amino-6-((R)-1-(3',5-dichloro-4'-(trifluoroinethyl)-[1,1'-biphenyl]-2-yl)-2,2,2-trifluoroethoxy)pyrimidin-4-yl)-2,8-diazaspiro[4.5]decane-3-carboxylate | 693 |
| 63ey | 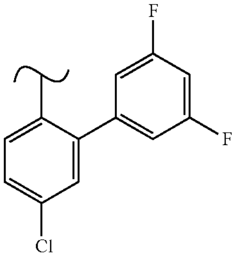 | B | (S)-ethyl 8-(2-amino-6-((R)-1-(5-chloro-3',5'-difluoro-[1,1'-biphenyl]-2-yl)-2,2,2-trifluoroethoxy)pyrimidin-4-yl)-2,8-diazaspiro[4.5]decane-3-carboxylate | |
| 63ez | 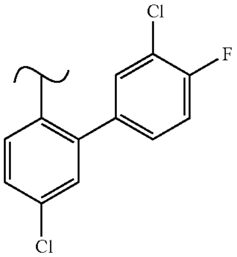 | B | (S)-ethyl 8-(2-amino-6-((R)-1-(3',5-dichloro-4'-fluoro-[1,1'-biphenyl]-2-yl)-2,2,2-trifluoroethoxy)pyrimidin-4-yl)-2,8-diazaspiro[4.5]decane-3-carboxylate | |

TABLE 18a-continued

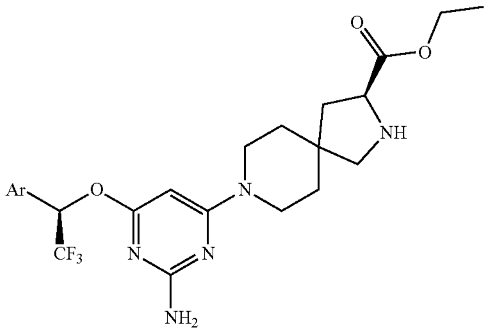

| Ex. No. | Ar | Method A or B | CAS Name | LCMS (MH+) |
|---|---|---|---|---|
| 63fa | 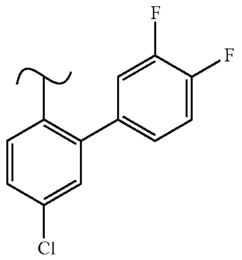 | B | (S)-ethyl 8-(2-amino-6-((R)-1-(5-chloro-3',4'-difluoro-[1,1'-biphenyl]-2-yl)-2,2,2-trifluoroethoxy)pyrimidin-4-yl)-2,8-diazaspiro[4.5]decane-3-carboxylate | |
| 63fb | 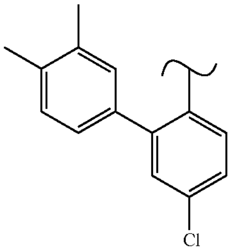 | B | (S)-ethyl 8-(2-amino-6-((R)-1-(5-chloro-3',4'-dimethyl-[1,1'-biphenyl]-2-yl)-2,2,2-trifluoroethoxy)pyrimidin-4-yl)-2,8-diazaspiro[4.5]decane-3-carboxylate | 619 |
| 63fc | 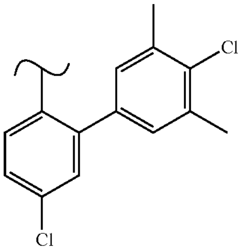 | B | (S)-ethyl 8-(2-amino-6-((R)-1-(4',5-dichloro-3',5'-dimethyl-[1,1'-biphenyl]-2-yl)-2,2,2-trifluoroethoxy)pyrimidin-4-yl)-2,8-diazaspiro[4.5]decane-3-carboxylate | 653 |
| 63fd | 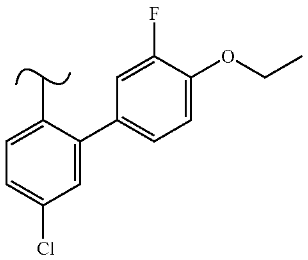 | B | (S)-ethyl 8-(2-amino-6-((R)-1-(5-chloro-4'-ethoxy-3'-fluoro-[1,1'-biphenyl]-2-yl)-2,2,2-trifluoroethoxy)pyrimidin-4-yl)-2,8-diazaspiro[4.5]decane-3-carboxylate | 653 |

TABLE 18a-continued

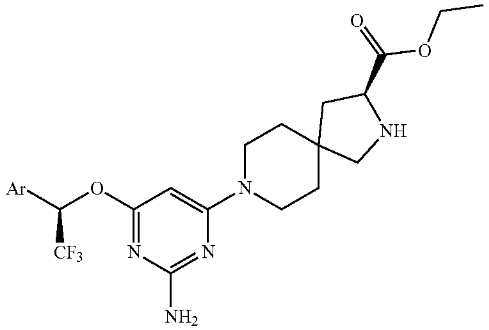

| Ex. No. | Ar | Method A or B | CAS Name | LCMS (MH+) |
|---|---|---|---|---|
| 63fe | 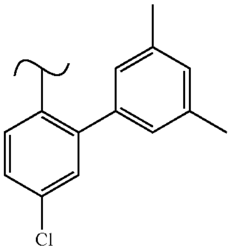 | B | (S)-ethyl 8-(2-amino-6-((R)-1-(5-chloro-3',5'-dimethyl-[1,1'-biphenyl]-2-yl)-2,2,2-trifluoroethoxy)pyrimidin-4-yl)-2,8-diazaspiro[4.5]decane-3-carboxylate | 619 |
| 63ff | 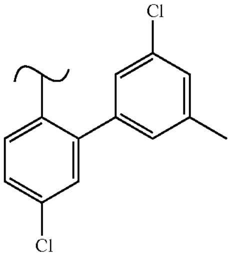 | B | (S)-ethyl 8-(2-amino-6-((R)-1-(3',5-dichloro-5'-methyl-[1,1'-biphenyl]-2-yl)-2,2,2-trifluoroethoxy)pyrimidin-4-yl)-2,8-diazaspiro[4.5]decane-3-carboxylate | 639 |
| 63fg | 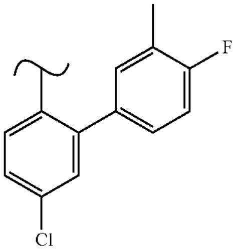 | | (S)-ethyl 8-(2-amino-6-((R)-1-(5-chloro-4'-fluoro-3'-methyl-[1,1'-biphenyl]-2-yl)-2,2,2-trifluoroethoxy)pyrimidin-4-yl)-2,8-diazaspiro[4.5]decane-3-carboxylate | 623 |
| 63fh | 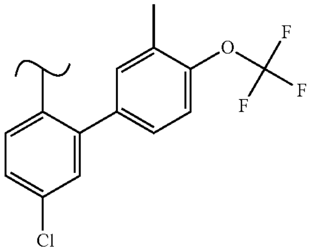 | B | (S)-ethyl 8-(2-amino-6-((R)-1-(5-chloro-3'-methyl-4'-(trifluoromethoxy)-[1,1'-biphenyl]-2-yl)-2,2,2-trifluoroethoxy)pyrimidin-4-yl)-2,8-diazaspiro[4.5]decane-3-carboxylate | 689 |

TABLE 18a-continued

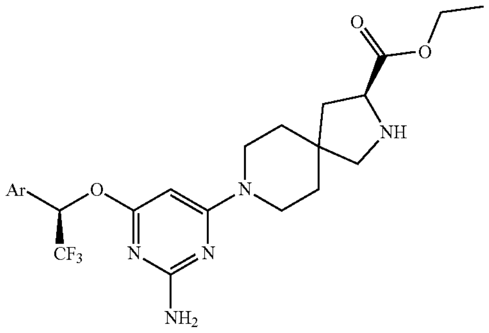

| Ex. No. | Ar | Method A or B | CAS Name | LCMS (MH+) |
|---|---|---|---|---|
| 63fi | 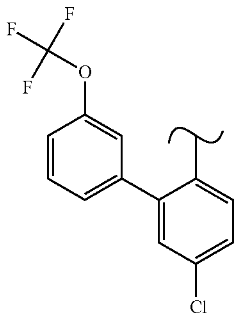 | B | (S)-ethyl 8-(2-amino-6-((R)-1-(5-chloro-3'-(trifluoromethoxy)-[1,1'-biphenyl]-2-yl)-2,2,2-trifluoroethoxy)pyrimidin-4-yl)-2,8-diazaspiro[4.5]decane-3-carboxylate | 675 |
| 63fj | 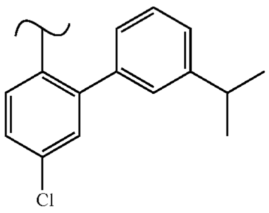 | B | (S)-ethyl 8-(2-amino-6-((R)-1-(5-chloro-3'-isopropyl-[1,1'-biphenyl]-2-yl)-2,2,2-trifluoroethoxy)pyrimidin-4-yl)-2,8-diazaspiro[4.5]decane-3-carboxylate | 633 |
| 63fk | 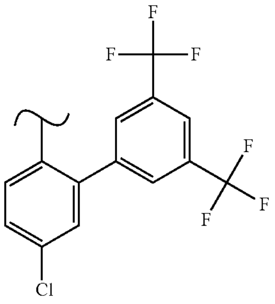 | B | (S)-ethyl 8-(2-amino-6-((R)-1-(5-chloro-3',5'-bis(trifluoromethyl)-[1,1'-biphenyl]-2-yl)-2,2,2-trifluoroethoxy)pyrimidin-4-yl)-2,8-diazaspiro[4.5]decane-3-carboxylate | 727 |
| 63fl | 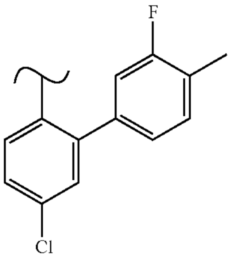 | B | (S)-ethyl 8-(2-amino-6-((R)-1-(5-chloro-3'-fluoro-4'-methyl-[1,1'-biphenyl]-2-yl)-2,2,2-trifluoroethoxy)pyrimidin-4-yl)-2,8-diazaspiro[4.5]decane-3-carboxylate | 623 |

TABLE 18a-continued

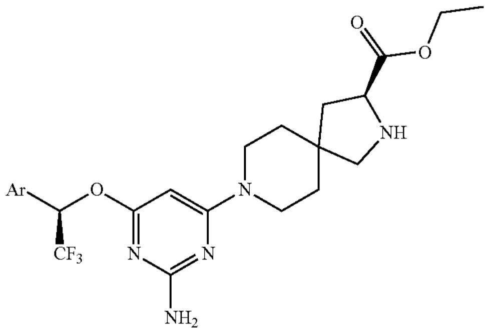

| Ex. No. | Ar | Method A or B | CAS Name | LCMS (MH+) |
|---|---|---|---|---|
| 63fm | 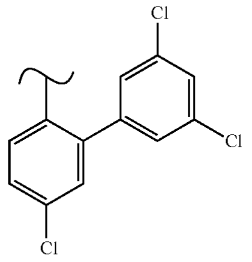 | B | (S)-ethyl 8-(2-amino-6-((R)-2,2,2-trifluoro-1-(3',5,5'-trichloro-[1,1'-biphenyl]-2-yl)ethoxy)pyrimidin-4-yl)-2,8-diazaspiro[4.5]decane-3-carboxylate | 659 |
| 63fn | 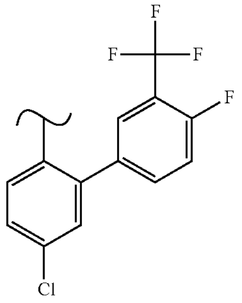 | B | (S)-ethyl 8-(2-amino-6-((R)-1-(5-chloro-4'-fluoro-3'-(trifluoromethyl)-[1,1'-biphenyl]-2-yl)-2,2,2-trifluoroethoxy)pyrimidin-4-yl)-2,8-diazaspiro[4.5]decane-3-carboxylate | 677 |
| 63fo | 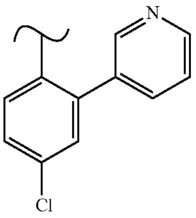 | B | (S)-ethyl 8-(2-amino-6-((R)-1-(4-chloro-2-(pyridin-3-yl)phenyl)-2,2,2-trifluoroethoxy)pyrimidin-4-yl)-2,8-diazaspiro[4.5]decane-3-carboxylate | 592 |
| 63fp | 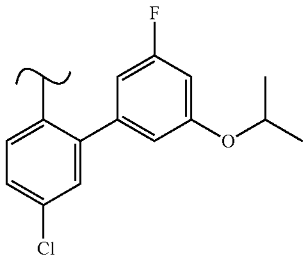 | B | (S)-ethyl 8-(2-amino-6-((R)-1-(5-chloro-3'-fluoro-5'-isopropoxy-[1,1'-biphenyl]-2-yl)-2,2,2-trifluoroethoxy)pyrimidin-4-yl)-2,8-diazaspiro[4.5]decane-3-carboxylate | 667 |

TABLE 18a-continued

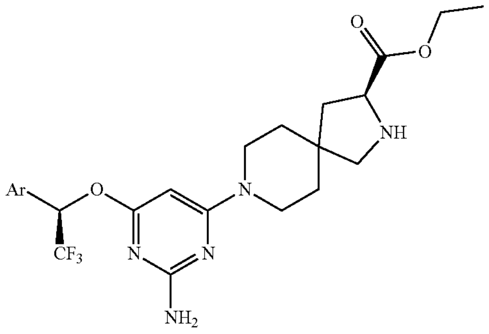

| Ex. No. | Ar | Method A or B | CAS Name | LCMS (MH+) |
|---|---|---|---|---|
| 63fq | 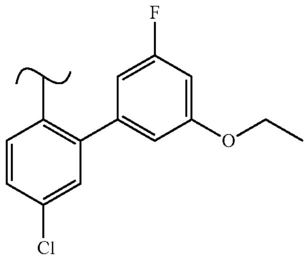 | B | (S)-ethyl 8-(2-amino-6-((R)-1-(5-chloro-3'-ethoxy-5'-fluoro-[1,1'-biphenyl]-2-yl)-2,2,2-trifluoroethoxy)pyrimidin-4-yl)-2,8-diazaspiro[4.5]decane-3-carboxylate | 653 |
| 63fr | 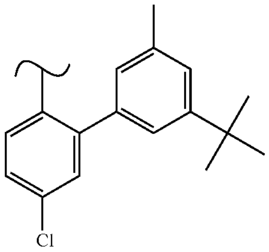 | B | (S)-ethyl 8-(2-amino-6-((R)-1-(3'-(tert-butyl)-5-chloro-5'-methyl-[1,1'-biphenyl]-2-yl)-2,2,2-trifluoroethoxy)pyrimidin-4-yl)-2,8-diazaspiro[4.5]decane-3-carboxylate | 661 |
| 63fs | 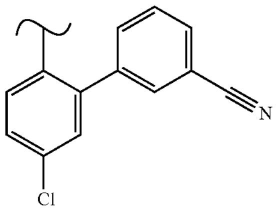 | B | (S)-ethyl 8-(2-amino-6-((R)-1-(5-chloro-3'-cyano-[1,1'-biphenyl]-2-yl)-2,2,2-trifluoroethoxy)pyrimidin-4-yl)-2,8-diazaspiro[4.5]decane-3-carboxylate | 616 |
| 63ft | 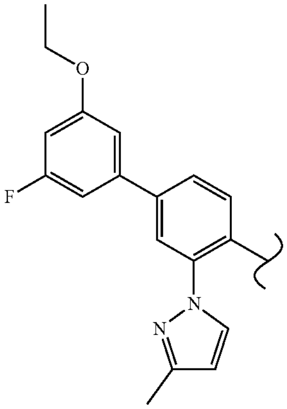 | A | (S)-ethyl 8-(2-amino-6-((R)-1-(3'-ethoxy-5'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 698 |

TABLE 18a-continued

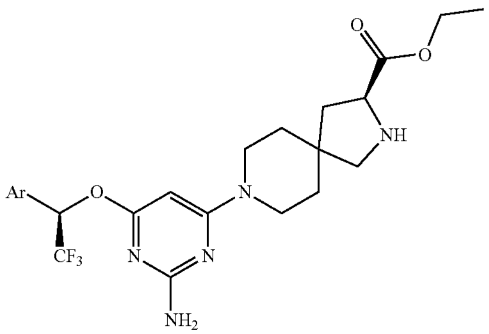

| Ex. No. | Ar | Method A or B | CAS Name | LCMS (MH+) |
|---|---|---|---|---|
| 63fv | 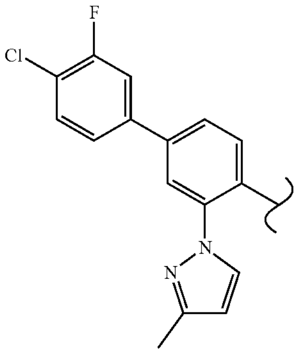 | B | (S)-ethyl 8-(2-amino-6-((R)-1-(4'-chloro-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 689 |
| 63fw | 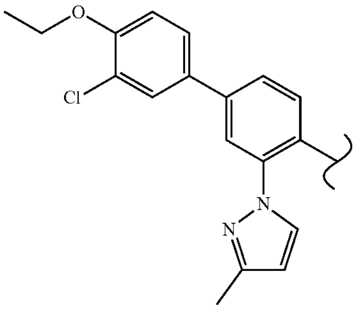 | B | (S)-ethyl 8-(2-amino-6-((R)-1-(3'-chloro-4'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 715 |
| 63fx | 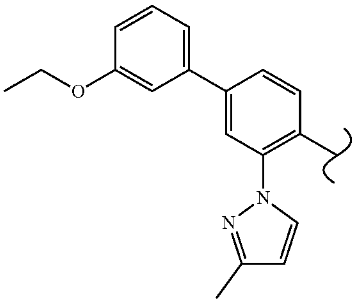 | A | (S)-ethyl 8-(2-amino-6-((R)-1-(3'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 680 |

TABLE 18a-continued

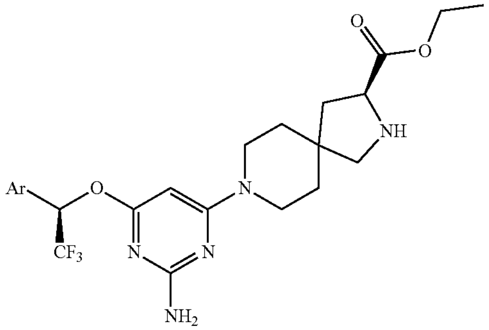

| Ex. No. | Ar | Method A or B | CAS Name | LCMS (MH+) |
|---|---|---|---|---|
| 63fy | 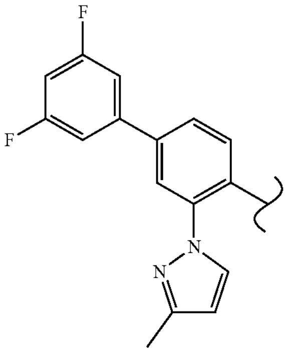 | A | (S)-ethyl 8-(2-amino-6-((R)-1-(3',5'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 672 |
| 63fz | 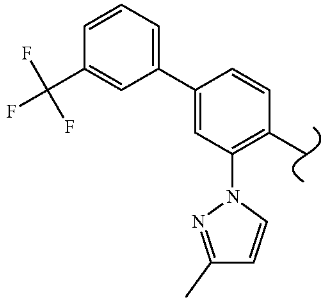 | A | (S)-ethyl 8-(2-amino-6-((R)-2,2,2-trifluoro-1-(3-(3-methyl-1H-pyrazol-1-yl)-3'-(trifluoromethyl)-[1,1'-biphenyl]-4-yl)ethoxy)pyrimidin-4-yl)-2,8-diazaspiro[4.5]decane-3-carboxylate | 704 |
| 63ga | 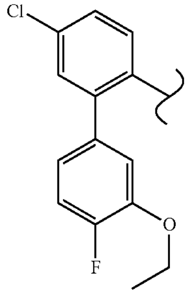 | B | (S)-ethyl 8-(2-amino-6-((R)-1-(5-chloro-3'-ethoxy-4'-fluoro-[1,1'-biphenyl]-2-yl)-2,2,2-trifluoroethoxy)pyrimidin-4-yl)-2,8-diazaspiro[4.5]decane-3-carboxylate | 653 |

TABLE 18a-continued

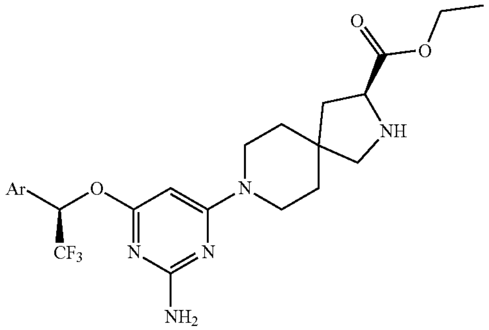

| Ex. No. | Ar | Method A or B | CAS Name | LCMS (MH+) |
|---|---|---|---|---|
| 63gb | 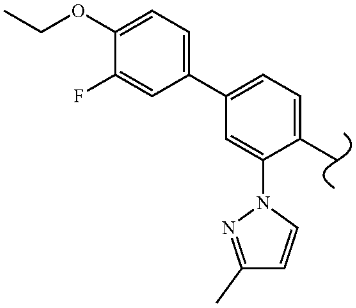 | A | (S)-ethyl 8-(2-amino-6-((R)-2,2,2-trifluoro-1-(3'-fluoro-4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 712 |
| 63gc | 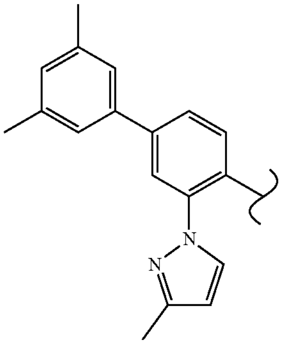 | A | (S)-ethyl 8-(2-amino-6-((R)-1-(3',5'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 664 |
| 63gd | 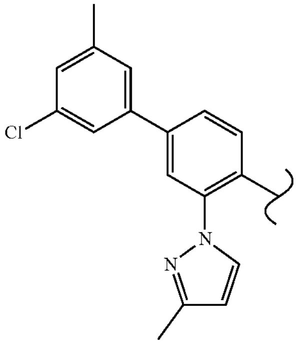 | B | (S)-ethyl 8-(2-amino-6-((R)-1-(3'-chloro-5'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 685 |
| 63ge | 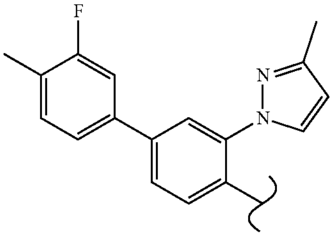 | A | (S)-ethyl 8-(2-amino-6-((R)-2,2,2-trifluoro-1-(3'-fluoro-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 678 |

TABLE 18a-continued

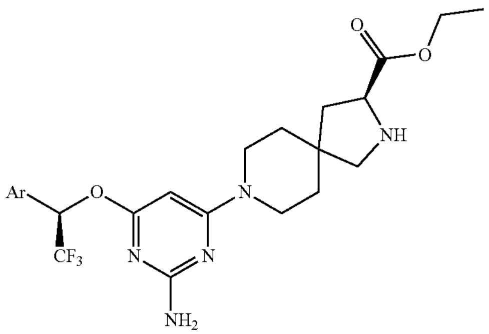

| Ex. No. | Ar | Method A or B | CAS Name | LCMS (MH+) |
|---|---|---|---|---|
| 63gf | 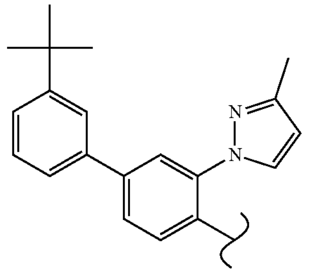 | A | (S)-ethyl 8-(2-amino-6-((R)-1-(3'-(tert-butyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 692 |
| 63gg | 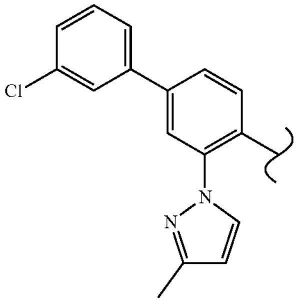 | B | (S)-ethyl 8-(2-amino-6-((R)-1-(3'-chloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 671 |
| 63gh | 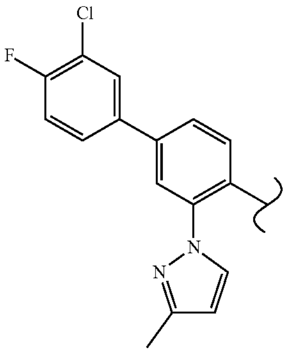 | B | (S)-ethyl 8-(2-amino-6-((R)-1-(3'-chloro-4'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 689 |

TABLE 18a-continued

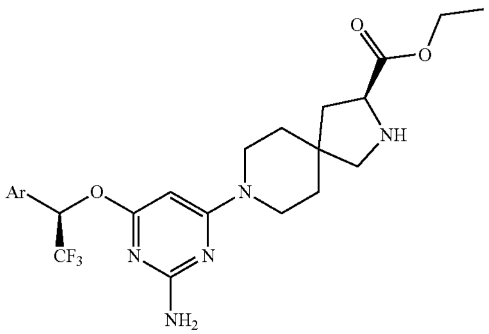

| Ex. No. | Ar | Method A or B | CAS Name | LCMS (MH+) |
|---|---|---|---|---|
| 63gi | 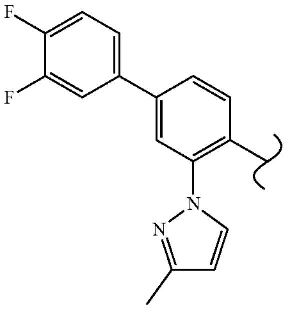 | A | (S)-ethyl 8-(2-amino-6-((R)-1-(3',4'-difluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 672 |
| 63gj | 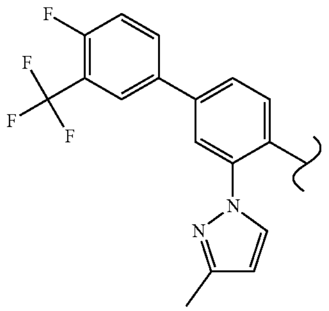 | A | (S)-ethyl 8-(2-amino-6-((R)-2,2,2-trifluoro-1-(4'-fluoro-3-(3-methyl-1H-pyrazol-1-yl)-3'-(trifluoromethyl)-[1,1'-biphenyl]-4-yl)ethoxy)pyrimidin-4-yl)-2,8-diazaspiro[4.5]decane-3-carboxylate | 722 |
| 63gk | 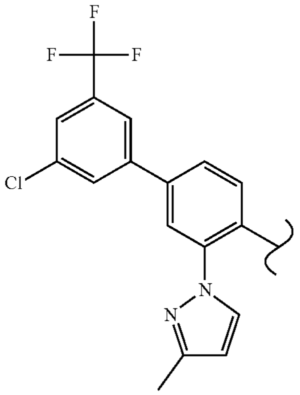 | B | (S)-ethyl 8-(2-amino-6-((R)-1-(3-chloro-3-(3-methyl-1H-pyrazol-1-yl)-5'-(trifluoromethyl)-[1,1'-biphenyl]-4-yl)-2,2,2-trifluoroethoxy)pyrimidin-4-yl)-2,8-diazaspiro[4.5]decane-3-carboxylate | 739 |

TABLE 18a-continued

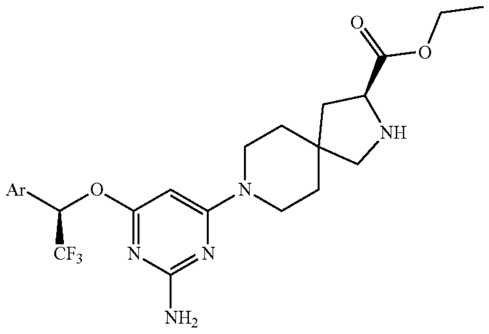

| Ex. No. | Ar | Method A or B | CAS Name | LCMS (MH+) |
|---|---|---|---|---|
| 63gl | 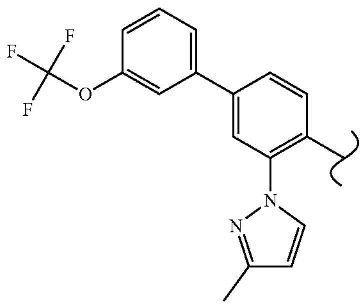 | A | (S)-ethyl 8-(2-amino-6-((R)-2,2,2-trifluoro-1-(3-(3-methyl-1H-pyrazol-1-yl)-3'-(trifluoromethoxy)-[1,1'-biphenyl]-4-yl)ethoxy)pyrimidin-4-yl)-2,8-diazaspiro[4.5]decane-3-carboxylate | 720 |
| 63gm | 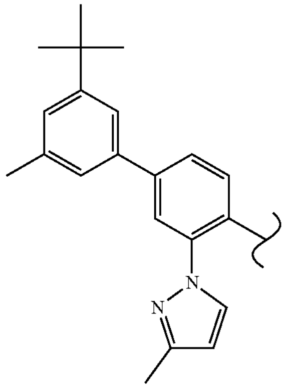 | A | (S)-ethyl 8-(2-amino-6-((R)-1-(3'-(tert-butyl)-5'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 706 |
| 63gn | 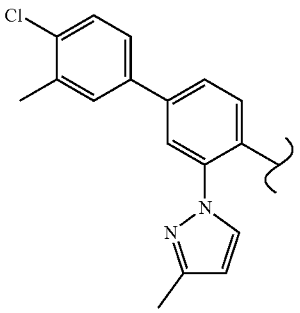 | B | (S)-ethyl 8-(2-amino-6-((R)-1-(4'-chloro-3'-methyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 685 |

TABLE 18a-continued

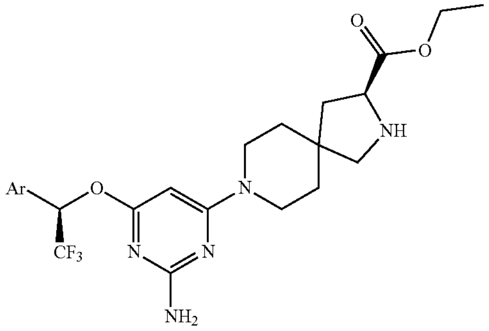

| Ex. No. | Ar | Method A or B | CAS Name | LCMS (MH+) |
|---|---|---|---|---|
| 63go | 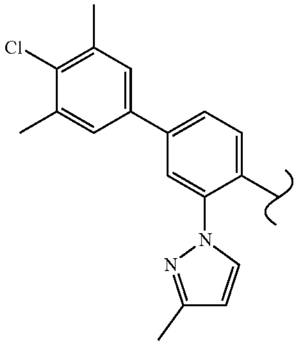 | B | (S)-ethyl 8-(2-amino-6-((R)-1-(4'-chloro-3',5'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 699 |
| 63gp | 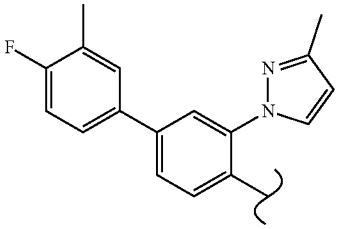 | A | (S)-ethyl 8-(2-amino-6-((R)-2,2,2-trifluoro-1-(4'-fluoro-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 668 |
| 63gq | 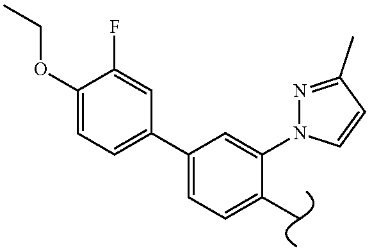 | A | (S)-ethyl 8-(2-amino-6-((R)-1-(4'-ethoxy-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 698 |
| 63gr | 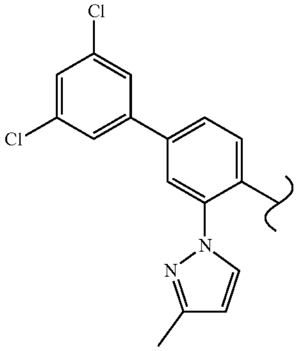 | B | (S)-ethyl 8-(2-amino-6-((R)-1-(3',5'-dichloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 705 |

TABLE 18a-continued

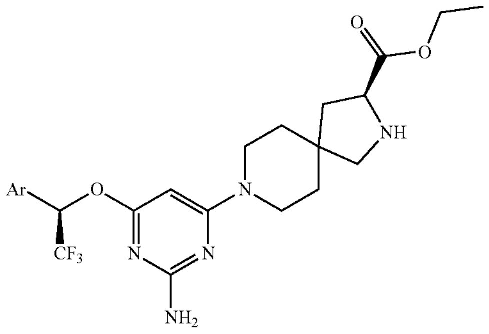

| Ex. No. | Ar | Method A or B | CAS Name | LCMS (MH+) |
|---|---|---|---|---|
| 63gs | 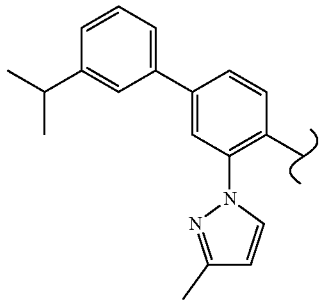 | A | (S)-ethyl 8-(2-amino-6-((R)-2,2,2-tritluoro-1-(3'-isopropyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 678 |
| 63gt | 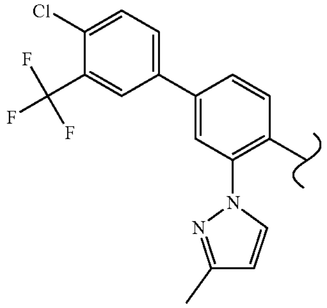 | B | (S)-ethyl 8-(2-amino-6-((R)-1-(4'-chloro-3-(3-methyl-1H-pyrazol-1-yl)-3'-(trifluoromethyl)-[1,1'-biphenyl]-4-yl)-2,2,2-trifluoroethoxy)pyrimidin-4-yl)-2,8-diazaspiro[4.5]decane-3-carboxylate | 739 |
| 63gu | 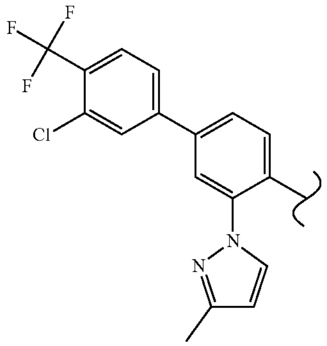 | B | (S)-ethyl 8-(2-amino-6-((R)-1-(3'-chloro-3-(3-methyl-1H-pyrazol-1-yl)-4'-(trifluoromethyl)-[1,1-biphenyl]-4-yl)-2,2,2-trifluoroethoxy)pyrimidin-4-yl)-2,8-diazaspiro[4.5]decane-3-carboxylate | 738 |

TABLE 18a-continued

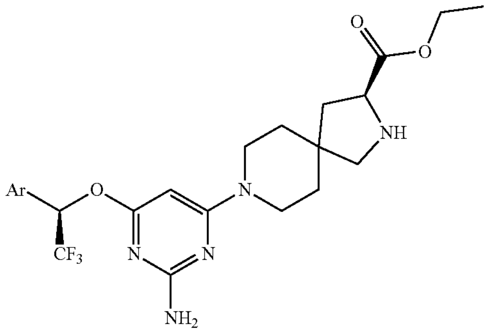

| Ex. No. | Ar | Method A or B | CAS Name | LCMS (MH+) |
|---|---|---|---|---|
| 63gv | 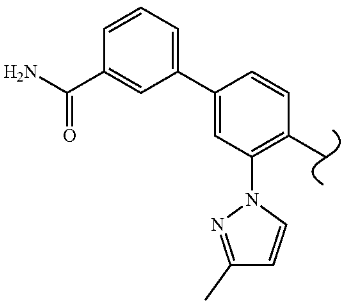 | A | (S)-ethyl 8-(2-amino-6-((R)-1-(3'-carbamoyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 679 |
| 63gw | 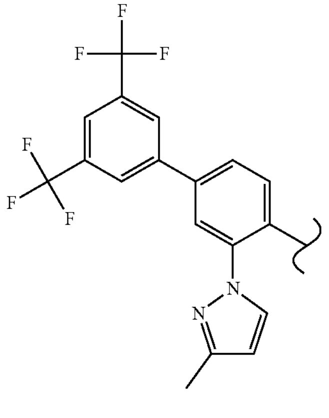 | A | (S)-ethyl 8-(2-amino-6-((R)-2,2,2-trifluoro-1-(3-(3-methyl-1H-pyrazol-1-yl)-3',5'-bis(trifluoromethy!)-[1,1'-biphenyl]-4-yl)ethoxy)pyrimidin-4-yl)-2,8-diazaspiro[4.5]decane-3-carboxylate | 772 |
| 63gx | 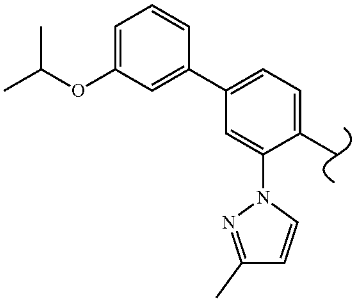 | A | (S)-ethyl 8-(2-amino-6-((R)-2,2,2-trifluoro-1-(3'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 694 |

TABLE 18a-continued

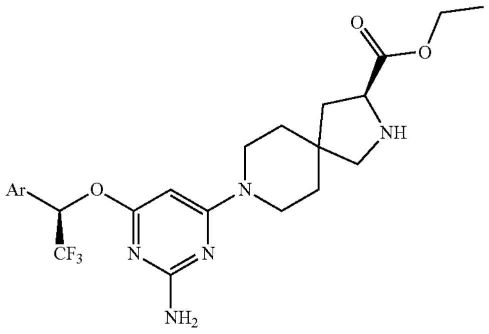

| Ex. No. | Ar | Method A or B | CAS Name | LCMS (MH+) |
|---|---|---|---|---|
| 63gy | 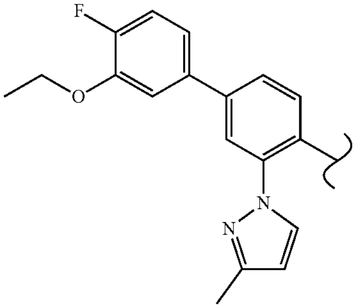 | A | (S)-ethyl 8-(2-amino-6-((R)-1-(3'-ethoxy-4'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 698 |
| 63gz | 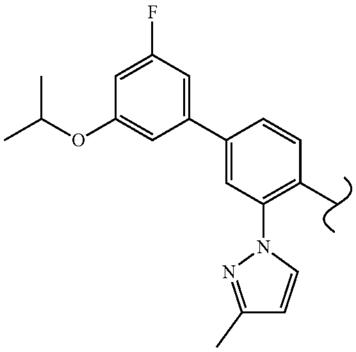 | A | (S)-ethyl 8-(2-amino-6-((R)-2,2,2-trifluoro-1-(3'-fluoro-5'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 712 |
| 63ha | 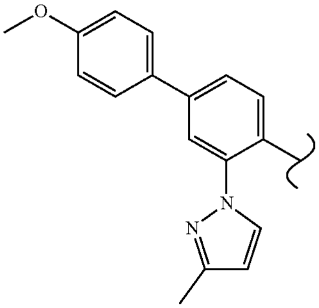 | A | (S)-ethyl 8-(2-amino-6-((R)-2,2,2-trifluoro-1-(4'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 666 |

TABLE 18a-continued

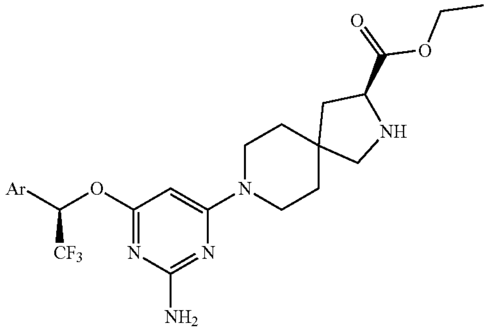

| Ex. No. | Ar | Method A or B | CAS Name | LCMS (MH+) |
|---|---|---|---|---|
| 63hb | 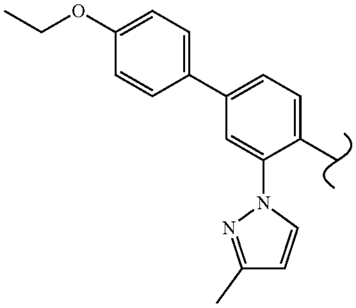 | A | (S)-ethyl 8-(2-amino-6-((R)-1-(4'-ethoxy-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 680 |
| 63hc | 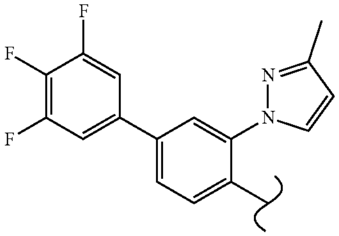 | A | (S)-ethyl 8-(2-amino-6-((R)-2,2,2-trifluoro-1-(3',4',5'-trifluoro-3-(3-methyl-1H-pyrazol-1-yl)-[1,1'-biphenyl]-4-yl)ethoxy)pyrimidin-4-yl)-2,8-diazaspiro[4.5]decane-3-carboxylate | 690 |
| 63hd | 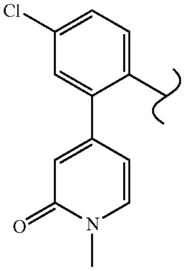 | B | (S)-ethyl 8-(2-amino-6-((R)-1-(4-chloro-2-(1-methyl-2-oxo-1,2-dihydropyridin-4-yl)phenyl)-2,2,2-trifluoroethoxy)pyrimidin-4-yl)-2,8-diazaspiro[4.5]decane-3-carboxylate | 622 |
| 63he | 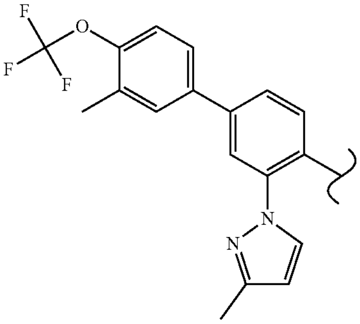 | A | (S)-ethyl 8-(2-amino-6-((R)-2,2,2-trifluoro-1-(3'-methyl-3-(3-methyl-1H-pyrazol-1-yl)-4'-(trifluoromethoxy)-[1,1'-biphenyl]-4-yl)ethoxy)pyrimidin-4-yl)-2,8-diazaspiro[4.5]decane-3-carboxylate | 734 |

TABLE 18a-continued

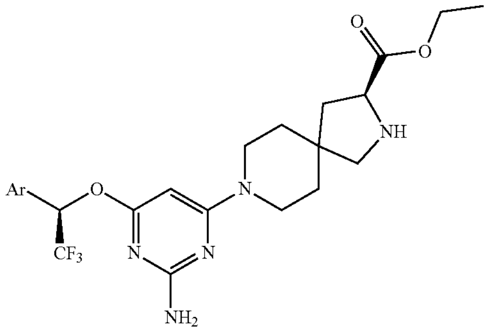

| Ex. No. | Ar | Method A or B | CAS Name | LCMS (MH+) |
|---|---|---|---|---|
| 63hf | 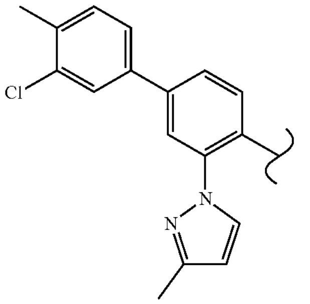 | B | (S)-ethyl 8-(2-amino-6-((R)-1-(3'-chloro-4'-methyl-3-(3-methyl-1H-pyrazol-1-yl)-[1,1'-biphenyl]-4-yl)-2,2,2-trifluoroethoxy) pyrimidin-4-yl)-2,8-diazaspiro[4.5]decane-3-carboxylate | 685 |
| 63hg | 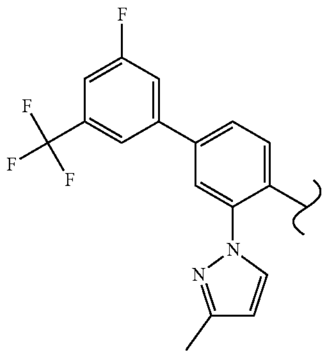 | A | (S)-ethyl 8-(2-amino-6-((R)-2,2,2-trifluoro-1-(3'-fluoro-3-(3-methyl-1H-pyrazol-1-yl)-5'-(trifluoromethyl)-[1,1'-biphenyl]-4-yl)ethoxy)pyrimidin-4-yl)-2,8-diazaspiro[4.5]decane-3-carboxylate | 722 |
| 63hh | 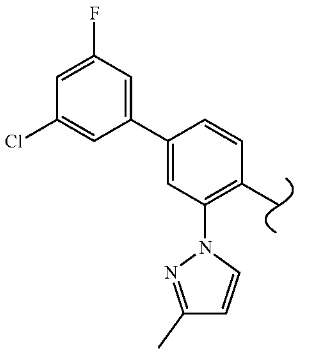 | A | (S)-ethyl 8-(2-amino-6-((R)-1-(3'-chloro-5'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 689 |
| 63hi | 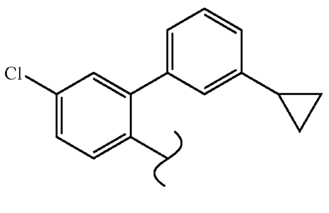 | B | (S)-ethyl 8-(2-amino-6-((R)-1-(5-chloro-3'-cyclopropyl-[1,1'-biphenyl]-2-yl)-2,2,2-trifluoroethoxy)pyrimidin-4-yl)-2,8-diazaspiro[4.5]decane-3-carboxylate | 631 |

TABLE 18a-continued

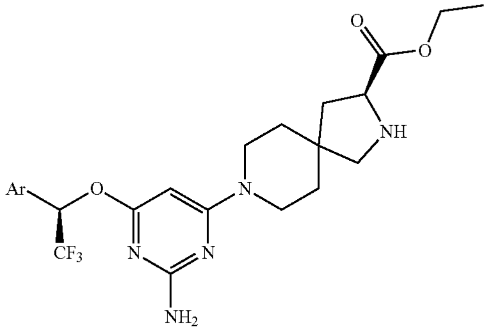

| Ex. No. | Ar | Method A or B | CAS Name | LCMS (MH+) |
|---|---|---|---|---|
| 63hj | 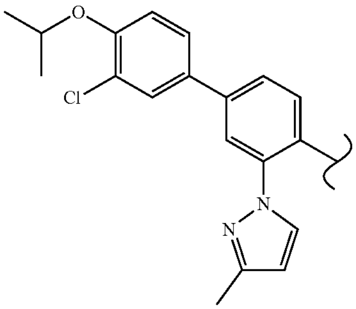 | B | (S)-ethyl 8-(2-amino-6-((R)-1-(3-chloro-4'-isopropoxy-3-(3-methyl-1H-pyrazol-1-yl)-[1,1'-biphenyl]-4-yl)-2,2,2-trifluoroethoxy) pyrimidin-4-yl)-2,8-diazaspiro[4.5]decane-3-carboxylate | 729 |
| 63hk | 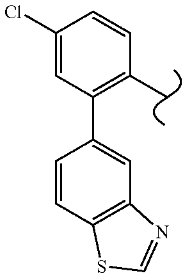 | B | (S)-ethyl 8-(2-amino-6-((R)-1-(2-(benzo[d]thiazol-5-yl)-4-chlorophenyl)-2,2,2-trifluoroethoxy)pyrimidin-4-yl)-2,8-diazaspiro[4.5]decane-3-carboxylate | 648 |
| 63hl | 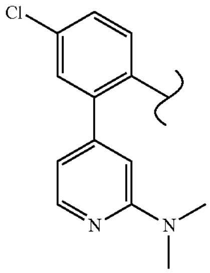 | B | (S)-ethyl 8-(2-amino-6-((R)-1-(4-chloro-2-(2-(dimethylamino)pyridin-4-yl)phenyl)-2,2,2-trifluoroethoxy)pyrimidin-4-yl)-2,8-diazaspiro[4.5]decane-3-carboxylate | 635 |
| 63hm | 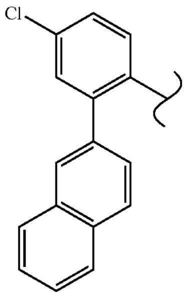 | B | (S)-ethyl 8-(2-amino-6-((R)-1-(4-chloro-2-(naphthalen-2-yl)phenyl)-2,2,2-trifluoroethoxy)pyrimidin-4-yl)-2,8-diazaspiro[4.5]decane-3-carboxylate | 641 |

TABLE 18a-continued

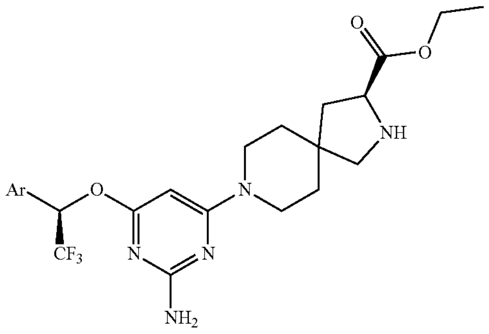

| Ex. No. | Ar | Method A or B | CAS Name | LCMS (MH+) |
|---|---|---|---|---|
| 63hn | 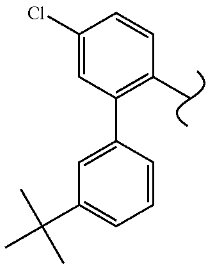 | B | (S)-ethyl 8-(2-amino-6-((R)-1-(3'-(tert-butyl)-5-chloro-[1,1'-biphenyl]-2-yl)-2,2,2-trifluoroethoxy)pyrimidin-4-yl)-2,8-diazaspiro[4.5]decane-3-carboxylate | 647 |
| 63ho | 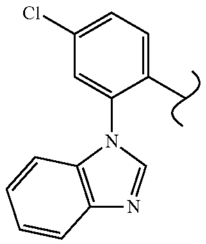 | B | (S)-ethyl 8-(6-((R)-1-(2-(1H-benzo[d]imidazol-1-yl)-4-chlorophenyl)-2,2,2-trifluoroethoxy)-2-aminopyrimidin-4-yl)-2,8-diazaspiro[4.5]decane-3-carboxylate | 631 |
| 63hp | 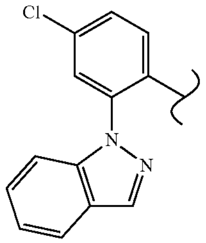 | B | (S)-ethyl 8-(2-amino-6-((R)-1-(4-chloro-2-(1H-indazol-1-yl)phenyl)-2,2,2-trifluoroethoxy)pyrimidin-4-yl)-2,8-diazaspiro[4.5]decane-3-carboxylate | 631 |
| 63hq | 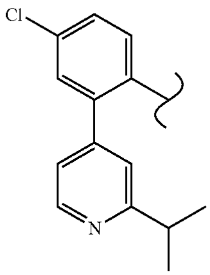 | B | (S)-ethyl 8-(2-amino-6-((R)-1-(4-chloro-2-(2-isopropylpyridin-4-yl)phenyl)-2,2,2-trifluoroethoxy)pyrimidin-4-yl)-2,8-diazaspiro[4.5]decane-3-carboxylate | 634 |

TABLE 18a-continued

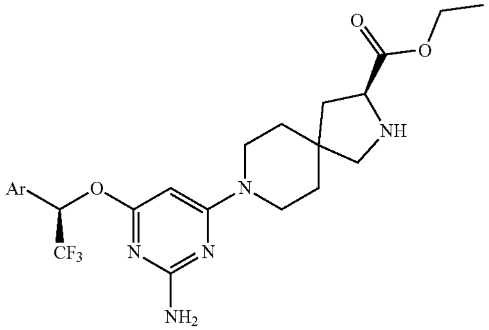

| Ex. No. | Ar | Method A or B | CAS Name | LCMS (MH+) |
|---|---|---|---|---|
| 63hr | 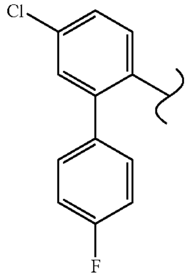 | B | (S)-ethyl 8-(2-amino-6-((R)-1-(5-chloro-4'-fluoro-[1,1'-biphenyl]-2-yl)-2,2,2-trifluoroethoxy)pyriinidin-4-yl)-2,8-diazaspiro[4.5]decane-3-carboxylate | 609 |
| 63hs | 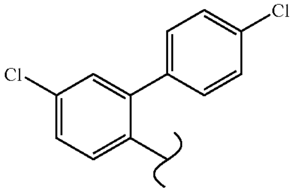 | B | (S)-ethyl 8-(2-amino-6-((R)-1-(4',5-dichloro-[1,1'-biphenyl]-2-yl)-2,2,2-trifluoroethoxy)pyrimidin-4-yl)-2,8-diazaspiro[4.5]decane-3-carboxylate | 625 |
| 63ht | 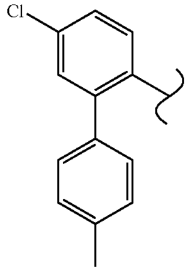 | B | (S)-ethyl 8-(2-amino-6-((R)-1-(5-chloro-4'-methyl-[1,1'-biphenyl]-2-yl)-2,2,2-trifluoroethoxy)pyrimidin-4-yl)-2,8-diazaspiro[4.5]decane-3-carboxylate | 605 |
| 63hu | 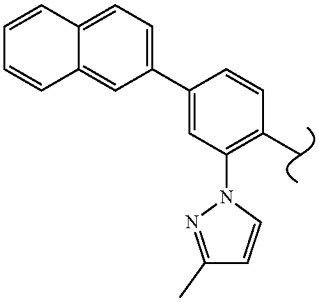 | A | (S)-ethyl 8-(2-amino-6-((R)-2,2,2-trifluoro-1-(2-(3-methyl-1H-pyrazol-1-yl)-4-(naphthalen-2-yl)phenyl)ethoxy)pyrimidin-4-yl)-2,8-diazaspiro[4.5]decane-3-carboxylate | 687 |

TABLE 18a-continued

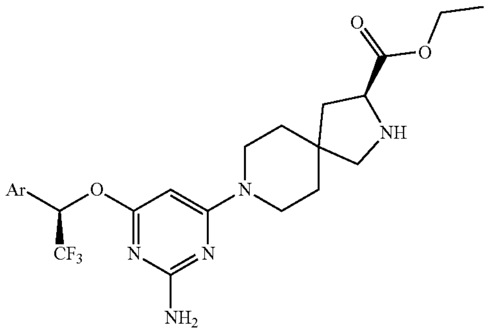

| Ex. No. | Ar | Method A or B | CAS Name | LCMS (MH+) |
|---|---|---|---|---|
| 63hv | 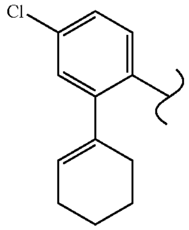 | B | (S)-ethyl 8-(2-amino-6-((R)-1-(5-chloro-2',3',4',5'-tetrahydro-[1,1'-biphenyl]-2-yl)-2,2,2-trifluoroethoxy)pyrimidin-4-yl)-2,8-diazaspiro[4.5]decane-3-carboxylate | 595 |
| 63hw | 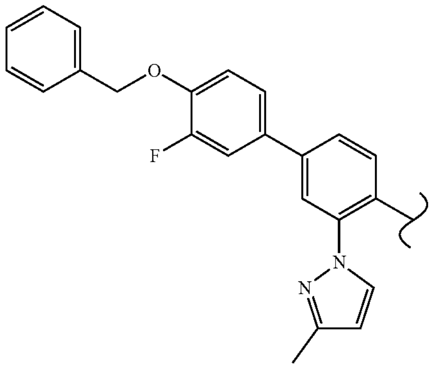 | A | (S)-ethyl 8-(2-amino-6-((R)-1-(4'-(benzyloxy)-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 761 |
| 63hx | 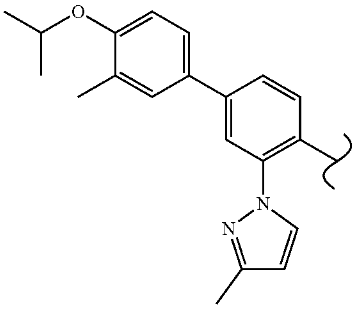 | A | (S)-ethyl 8-(2-amino-6-((R)-2,2,2-trifluoro-1-(4'-isopropoxy-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 709 |
| 63hy | 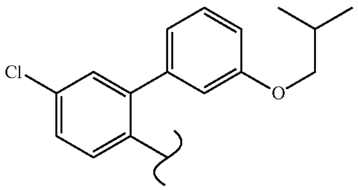 | B | (S)-ethyl 8-(2-amino-6-((R)-1-(5-chloro-3'-isobuloxy-[1,1'-biphenyl]-2-yl)-2,2,2-trifluoroethoxy)pyrimidin-4-yl)-2,8-diazaspiro[4.5]decane-3-carboxylate | 663 |

TABLE 18a-continued

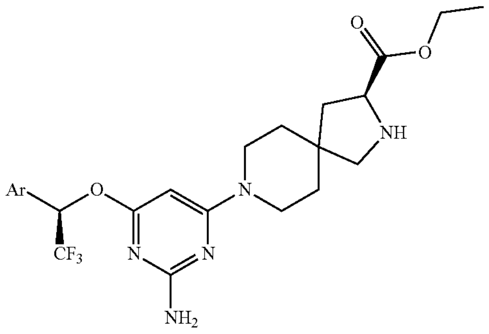

| Ex. No. | Ar | Method A or B | CAS Name | LCMS (MH+) |
|---|---|---|---|---|
| 63hz | 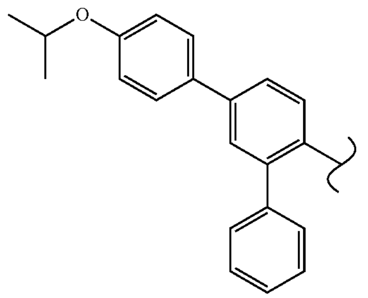 | A | (S)-ethyl 8-(2-amino-6-((R)-2,2,2-trifluoro-1-(4-isopropoxy-[1,1':3',1''-terphenyl]-4'-yl)ethoxy)pyrimidin-4-yl)-2,8-diazaspiro[4.5]decane-3-carboxylate | 690 |
| 63ia | 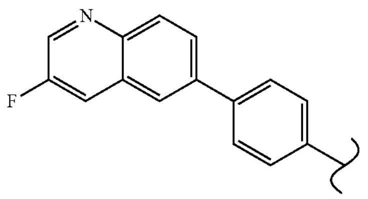 | A | (S)-ethyl 8-(2-amino-6-((R)-2,2,2-trifluoro-1-(4-(3-fluoroquinolin-6-yl)phenyl)ethoxy)pyrimidin-4-yl)-2,8-diazaspiro[4.5]decane-3-carboxylate | 626 |
| 63ib | 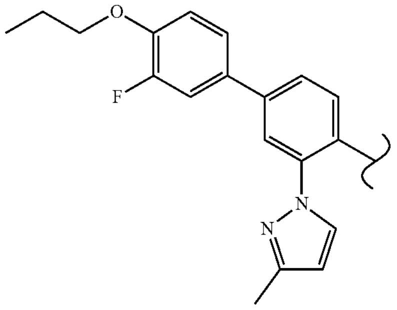 | A | (S)-ethyl 8-(2-amino-6-((R)-2,2,2-trifluoro-1-(3'-fluoro-3-(3-methyl-1H-pyrazol-1-yl)-4'-propoxy-[1,1'-biphenyl]-4-yl)ethoxy)pyrimidin-4-yl)-2,8-diazaspiro[4.5]decane-3-carboxylate | 713 |
| 63ic | 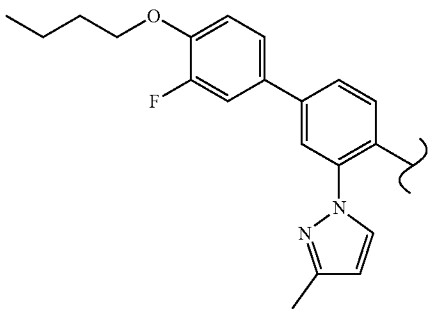 | A | (S)-ethyl 8-(2-amino-6-((R)-1-(4'-butoxy-3'-fluoro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 727 |

TABLE 18a-continued

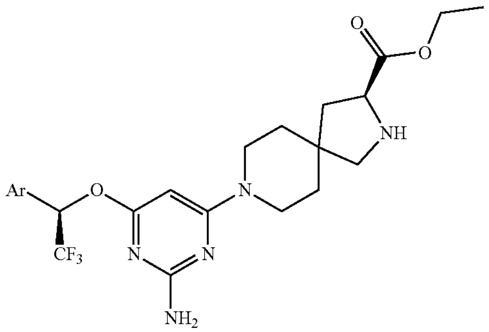

| Ex. No. | Ar | Method A or B | CAS Name | LCMS (MH+) |
|---|---|---|---|---|
| 63id | 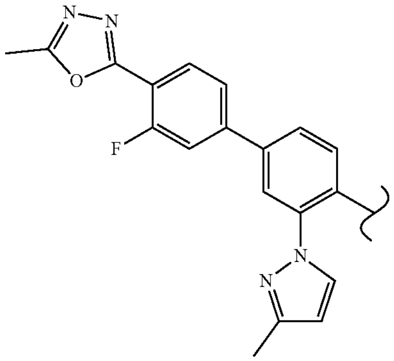 | A | (S)-ethyl 8-(2-amino-6-((R)-2,2,2-trifluoro-1-(3'-fluoro-4'-(5-methyl-1,3,4-oxadiazol-2-yl)-3-(3-methyl-1H-pyrazol-1-yl)-[1,1'-biphenyl]-4-yl)ethoxy)pyrimidin-4-yl)-2,8-diazaspiro[4.5]decane-3-carboxylate | 734 |
| 63ie | 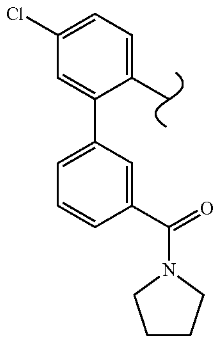 | B | (S)-ethyl 8-(2-amino-6-((R)-1-(5-chloro-3'-(pyrrolidine-1-carbonyl)-[1,1'-biphenyl]-2-yl)-2,2,2-trifluoroethoxy)pyrimidin-4-yl)-2,8-diazaspiro[4.5]decane-3-carboxylate | 688 |
| 63if | 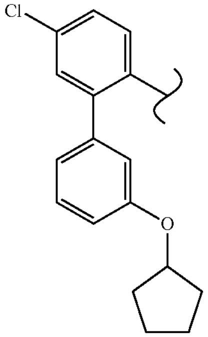 | B | (S)-ethyl 8-(2-amino-6-((R)-1-(5-chloro-3'-(cyclopentyloxy)-[1,1'-biphenyl]-2-yl)-2,2,2-trifluoroethoxy)pyrimidin-4-yl)-2,8-diazaspiro[4.5]decane-3-carboxylate | 675 |

TABLE 18a-continued

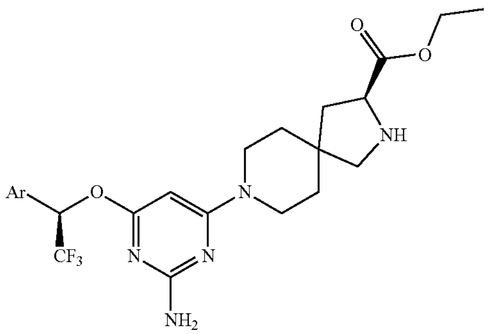

| Ex. No. | Ar | Method A or B | CAS Name | LCMS (MH+) |
|---|---|---|---|---|
| 63ig | 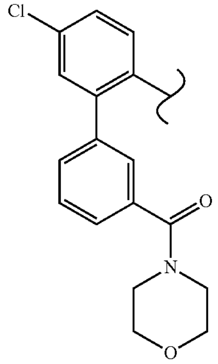 | B | (S)-ethyl 8-(2-amino-6-((R)-1-(5-chloro-3'-(morpholine-4-carbonyl)-[1,1'-biphenyl]-2-yl)-2,2,2-trifluoroethoxy)pyrimidin-4-yl)-2,8-diazaspiro[4.5]decane-3-carboxylate | 704 |
| 63ih | 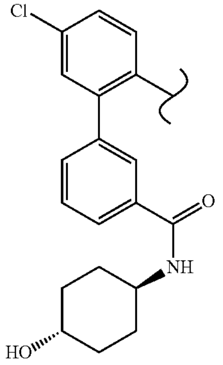 | B | (S)-ethyl 8-(2-amino-6-((R)-1-(5-chloro-3'-(((1R,4R)-4-hydroxycyclohexyl)carbamoyl)-[1,1'-biphenyl]-2-yl)-2,2,2-trifluoroethoxy)pyrimidin-4-yl)-2,8-diazaspiro[4.5]decane-3-carboxylate | 732 |
| 63ii | 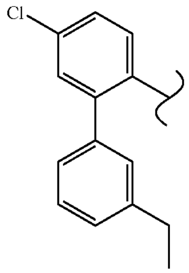 | B | (S)-ethyl 8-(2-amino-6-((R)-1-(5-chloro-3'-ethyl-[1,1'-biphenyl]-2-yl)-2,2,2-trifluoroethoxy)pyrimidin-4-yl)-2,8-diazaspiro[4.5]decane-3-carboxylate | 619 |

TABLE 18a-continued

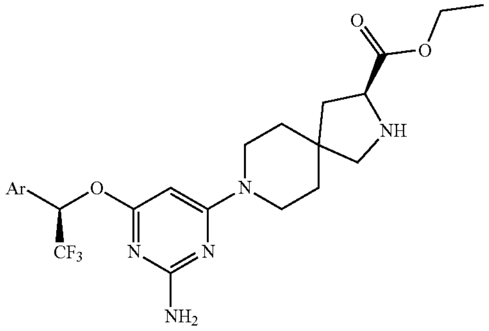

| Ex. No. | Ar | Method A or B | CAS Name | LCMS (MH+) |
|---|---|---|---|---|
| 63ij | 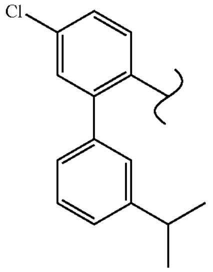 | B | (S)-ethyl 8-(2-amino-6-((R)-1-(5-chloro-3'-isopropyl-[1,1'-biphenyl]-2-yl)-2,2,2-trifluoroethoxy)pyrimidin-4-yl)-2,8-diazaspiro[4.5]decane-3-carboxylate | 633 |
| 63ik | 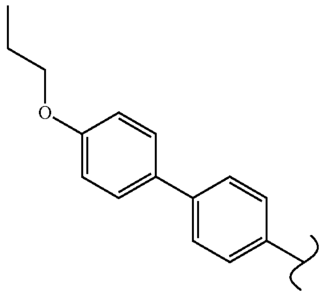 | A | (S)-ethyl 8-(2-amino-6-((R)-2,2,2-trifluoro-1-(4'-propoxy-[1,1'-biphenyl]-4-yl)ethoxy)pyrimidin-4-yl)-2,8-diazaspiro[4.5]decane-3-carboxylate | 614 |
| 63il | 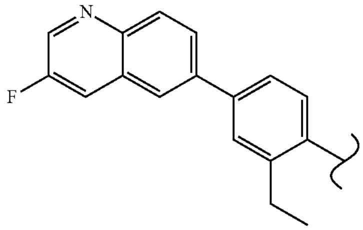 | A | (S)-ethyl 8-(2-amino-6-((R)-1-(2-ethyl-4-(3-fluoroquinolin-6-yl)phenyl)-2,2,2-trifluoroethoxy)pyrimidin-4-yl)-2,8-diazaspiro[4.5]decane-3-carboxylate | 654 |
| 63im | 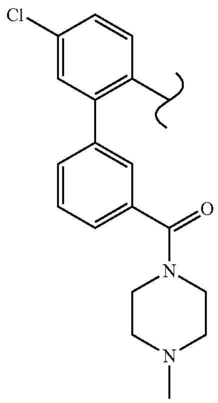 | B | (S)-ethyl 8-(2-amino-6-((R)-1-(5-chloro-3'-(4-methylpiperazine-1-carbonyl)-[1,1'-biphenyl]-2-yl)-2,2,2-trifluoroethoxy)pyrimidin-4-yl)-2,8-diazaspiro[4.5]decane-3-carboxylate | 717 |

TABLE 18a-continued

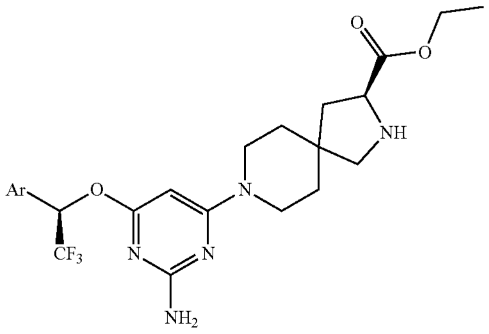

| Ex. No. | Ar | Method A or B | CAS Name | LCMS (MH+) |
|---|---|---|---|---|
| 63in | 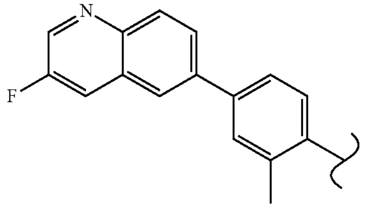 | A | (S)-ethyl 8-(2-amino-6-((R)-2,2,2-trifluoro-1-(4-(3-fluoroquinolin-6-yl)-2-methylphenyl)ethoxy)pyrimidin-4-yl)-2,8-diazaspiro[4.5]decane-3-carboxylate | 640 |
| 63io | 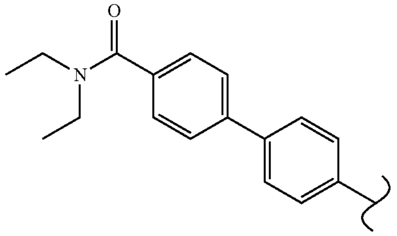 | A | (S)-ethyl 8-(2-amino-6-((R)-1-(4-(diethylcarbamoyl)-[1,1'-biphenyl]-4-yl)-2,2,2-trifluoroethoxy)pyrimidin-4-yl)-2,8-diazaspiro[4.5]decane-3-carboxylate | 656 |
| 63ip | 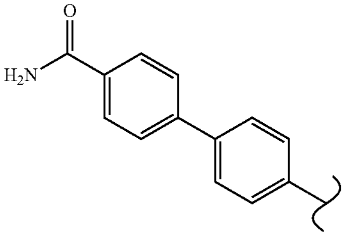 | A | (S)-ethyl 8-(2-amino-6-((R)-1-(4'-carbamoyl-[1,1'-biphenyl]-4-yl)-2,2,2-trifluoroethoxy)pyrimidin-4-yl)-2,8-diazaspiro[4.5]decane-3-carboxylate | 600 |
| 63iq | 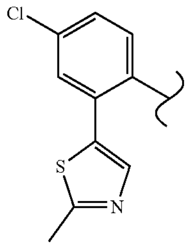 | B | (S)-ethyl 8-(2-amino-6-((R)-1-(4-chloro-2-(2-methylthiazol-5-yl)phenyl)-2,2,2-trifluoroethoxy)pyrimidin-4-yl)-2,8-diazaspiro[4.5]decane-3-carboxylate | 612 |

TABLE 18a-continued

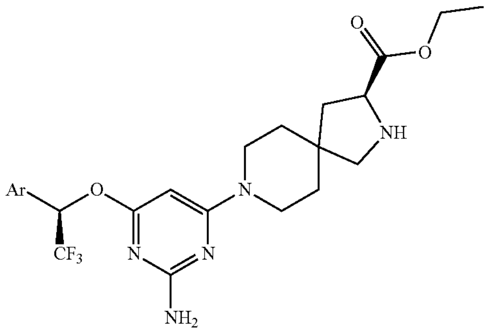

| Ex. No. | Ar | Method A or B | CAS Name | LCMS (MH+) |
|---|---|---|---|---|
| 63ir | 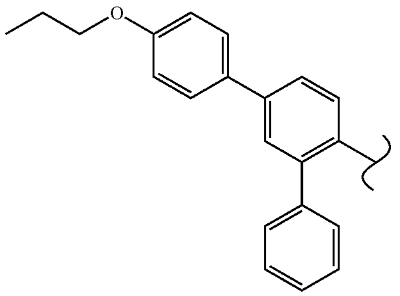 | A | (S)-ethyl 8-(2-amino-6-((R)-2,2,2-trifluoro-1-(4-propoxy-[1,1':3',1''-terphenyl]-4'-yl)ethoxy)pyrimidin-4-yl)-2,8-diazaspiro[4.5]decane-3-carboxylate | 691 |
| 63is | 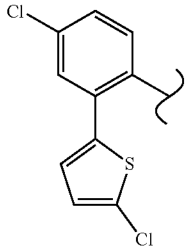 | B | (S)-ethyl 8-(2-amino-6-((R)-1-(4-chloro-2-(5-chlorothiophen-2-yl)phenyl)-2,2,2-trifluoroethoxy)pyrimidin-4-yl)-2,8-diazaspiro[4.5]decane-3-carboxylate | 631 |
| 63it | 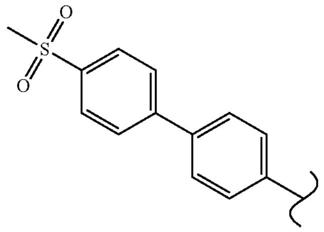 | A | (S)-ethyl 8-(2-amino-6-((R)-2,2,2-trifluoro-1-(4'-(methylsulfonyl)-[1,1'-biphenyl]-4-yl(ethoxy)pyrimidin-4-yl)-2,8-diazaspiro[4.5]decane-3-carboxylate | 635 |
| 63iu | 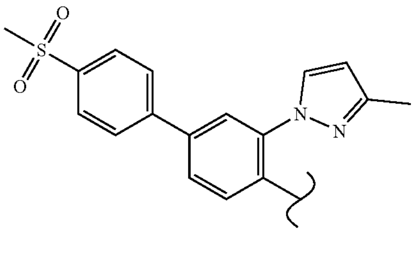 | A | (S)-ethyl 8-(2-amino-6-((R)-2,2,2-trifluoro-1-(3-(3-methyl-1H-pyrazol-1-yl)-4'-(methylsulfonyl)-[1,1'-biphenyl]-4-yl)ethoxy)pyrimidin-4-yl)-2,8-diazaspiro[4.5]decane-3-carboxylate | 715 |

TABLE 18a-continued

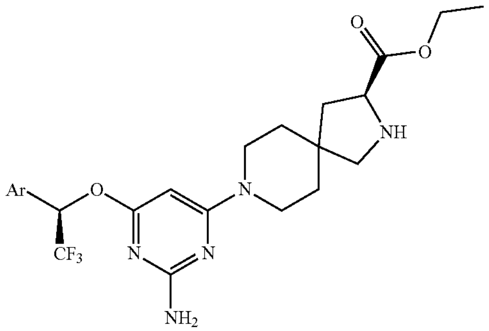

| Ex. No. | Ar | Method A or B | CAS Name | LCMS (MH+) |
|---|---|---|---|---|
| 63iv | 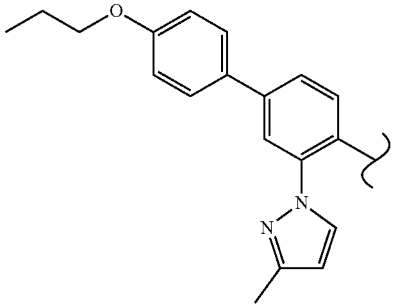 | A | (S)-ethyl 8-(2-amino-6-((R)-2,2,2-trifluoro-1-(3-(3-methyl-1H-pyrazol-1-yl)-4'-propoxy-[1,1'-biphenyl]-4-yl)ethoxy)pyrimidin-4-yl)-2,8-diazaspiro[4.5]decane-3-carboxylate | 695 |
| 63ix | 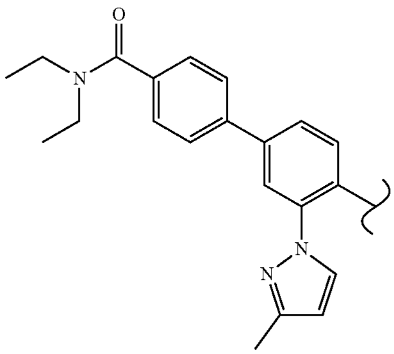 | A | (S)-ethyl 8-(2-amino-6-((R)-1-(4'-(diethylcarbamoyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 736 |
| 63iy | 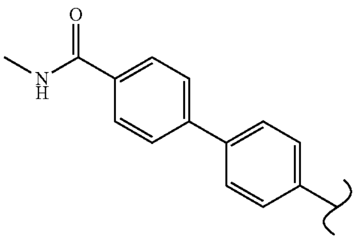 | A | (S)-ethyl 8-(2-amino-6-((R)-2,2,2-trifluoro-1-(4'-(methylcarbamoyl)-[1,1'-biphenyl]-4-yl)ethoxy)pyrimidin-4-yl)-2,8-diazaspiro[4.5]decane-3-carboxylate | 613 |

TABLE 18a-continued

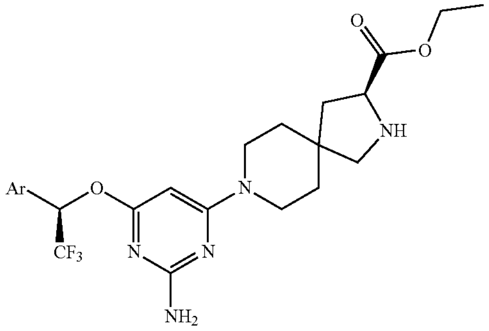

| Ex. No. | Ar | Method A or B | CAS Name | LCMS (MH+) |
|---|---|---|---|---|
| 63iz | 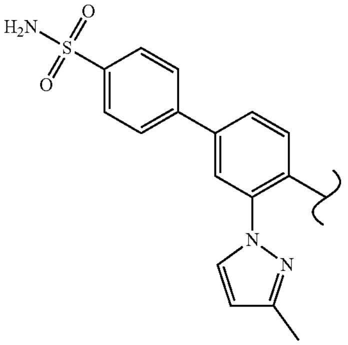 | A | (S)-ethyl 8-(2-amino-6-((R)-2,2,2-trifluoro-1-(3-(3-methyl-1H-pyrazol-1-yl)-4'-sulfamoyl-[1,1'-biphenyl]-4-yl)ethoxy)pyrimidin-4-yl)-2,8-diazaspiro[4.5]decane-3-carboxylate | 715 |
| 63ja | 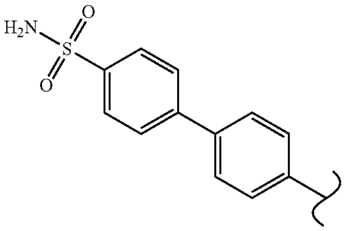 | A | (S)-ethyl 8-(2-amino-6-((R)-2,2,2-trifluoro-1-(4'-sulfamoyl-[1,1'-biphenyl]-4-yl)ethoxy)pyrimidin-4-yl)-2,8-diazaspiro[4.5]decane-3-carboxylate | 635 |
| 63jb | 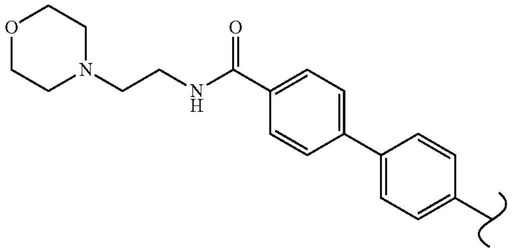 | A | (S)-ethyl 8-(2-amino-6-((R)-2,2,2-trifluoro-1-(4'-((2-morpholinoethyl)carbamoyl)-[1,1'-biphenyl]-4-yl)ethoxy)pyrimidin-4-yl)-2,8-diazaspiro[4.5]decane-3-carboxylate | 712 |
| 63jc | 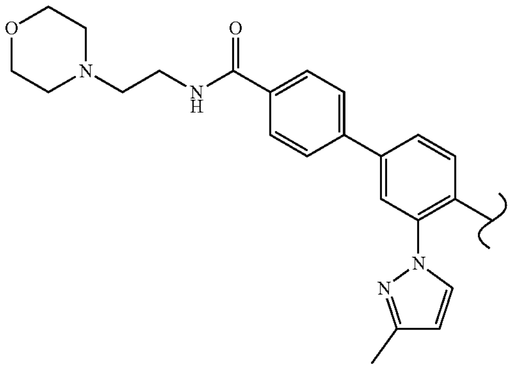 | A | (S)-ethyl 8-(2-amino-6-((R)-2,2,2-trifluoro-1-(3-(3-methyl-1H-pyrazol-1-yl)-4'-((2-morpholinoethyl)carbamoyl)-[1,1'-biphenyl]-4-yl)ethoxy)pyrimidin-4-yl)-2,8-diazaspiro[4.5]decane-3-carboxylate | 792 |

TABLE 18a-continued

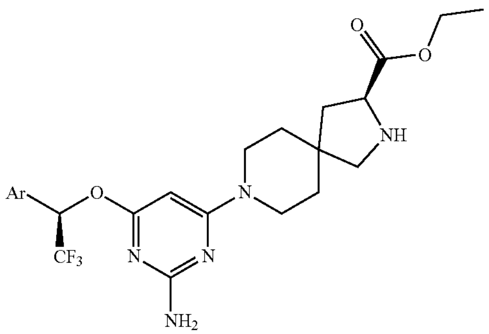

| Ex. No. | Ar | Method A or B | CAS Name | LCMS (MH+) |
|---|---|---|---|---|
| 63jd | 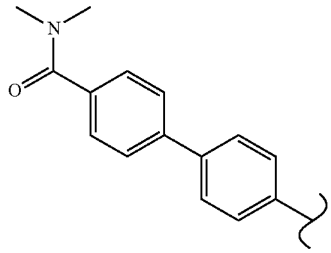 | A | (S)-ethyl 8-(2-amino-6-((R)-1-(4'-(dimethylcarbamoyl)-[1,1'-biphenyl]-4-yl)-2,2,2-trifluoroethoxy)pyrimidin-4-yl)-2,8-diazaspiro[4.5]decane-3-carboxylate | 628 |
| 63je | 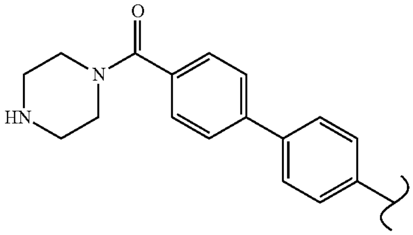 | A | (S)-ethyl 8-(2-amino-6-((R)-2,2,2-trifluoro-1-(4'-(piperazine-1-carbonyl)-[1,1'-biphenyl]-4-yl)ethoxy)pyrimidin-4-yl)-2,8-diazaspiro[4.5]decane-3-carboxylate | 669 |
| 63jf | 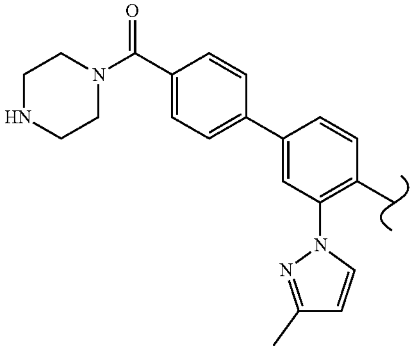 | A | (S)-ethyl 8-(2-amino-6-((R)-2,2,2-trifluoro-1-(3-(3-methyl-1H-pyrazol-1-yl)-4'-(piperazine-1-carbonyl)-[1,1'-biphenyl]-4-yl)ethoxy)pyrimidin-4-yl)-2,8-diazaspiro[4.5]decane-3-carboxylate | 749 |
| 63jg | 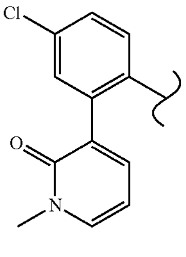 | B | (S)-ethyl 8-(2-amino-6-((R)-1-(4-chloro-2-(1-methyl-2-oxo-1,2-dihydropyridin-3-yl)phenyl)-2,2,2-trifluoroethoxy)pyrimidin-4-yl)-2,8-diazaspiro[4.5]decane-3-carboxylate | 622 |

TABLE 18a-continued

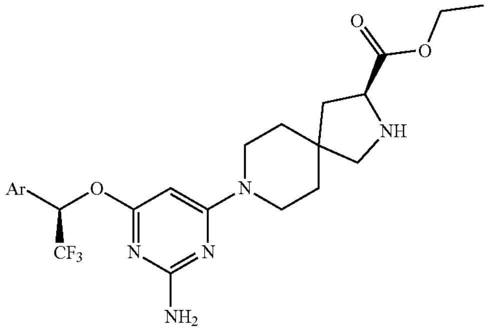

| Ex. No. | Ar | Method A or B | CAS Name | LCMS (MH+) |
|---|---|---|---|---|
| 63jh | 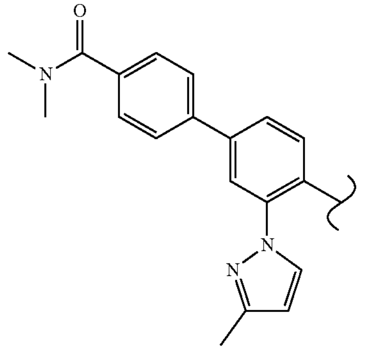 | A | (S)-ethyl 8-(2-amino-6-((R)-1-(4'-(dimethylcarbamoyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 708 |
| 63ji | 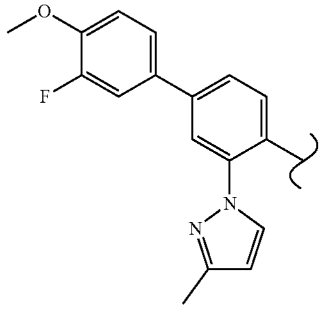 | A | (S)-ethyl 8-(2-amino-6-((R)-2,2,2-trifluoro-]-(3'-fluoro-4'-methoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 685 |
| 63jj | 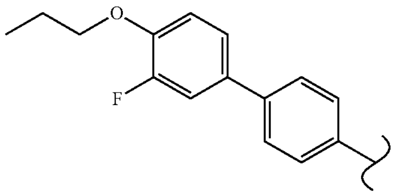 | A | (S)-ethyl 8-(2-amino-6-((R)-2,2,2-trifluoro-1-(3'-fluoro-4'-propoxy-[1,1'-biphenyl]-4-yl)ethoxy)pyrimidin-4-yl)-2,8-diazaspiro[4.5]decane-3-carboxylate | 633 |
| 63jk | 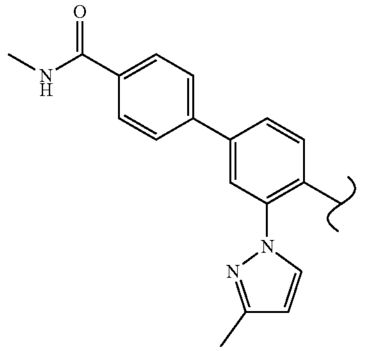 | A | (S)-ethyl 8-(2-amino-6-((R)-2,2,2-trifluoro-1-(3-(3-methyl-1H-pyrazol-1-yl)-4'-(methylcarbamoyl)-[1,1'-biphenyl]-4-yl)ethoxy)pyrimidin-4-yl)-2,8-diazaspiro[4.5]decane-3-carboxylate | 694 |

TABLE 18a-continued

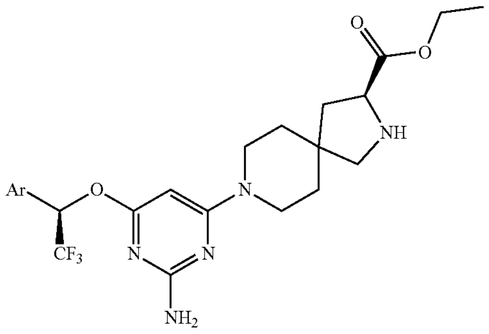

| Ex. No. | Ar | Method A or B | CAS Name | LCMS (MH+) |
|---|---|---|---|---|
| 63jl | 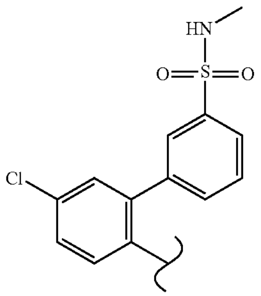 | B | (S)-ethyl 8-(2-amino-6-((R)-1-(5-chloro-3'-(N-methylsulfamoyl)-[1,1'-biphenyl]-2-yl)-2,2,2-trifluoroethoxy)pyrimidin-4-yl)-2,8-diazaspiro[4.5]decane-3-carboxylate | 684 |
| 63jm | 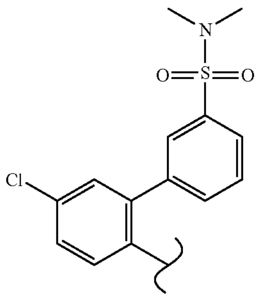 | B | (S)-ethyl 8-(2-amino-6-((R)-1-(5-chloro-3'-(N,N-dimethylsulfamoyl)-[1,1'-biphenyl]-2-yl)-2,2,2-trifluoroethoxy)pyrimidin-4-yl)-2,8-diazaspiro[4.5]decane-3-carboxylate | 698 |
| 63jn | 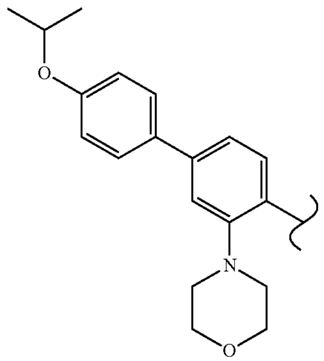 | A | (S)-ethyl 8-(2-amino-6-((R)-2,2,2-trifluoro-1-(4'-isopropoxy-3-morpholino-[1,1'-biphenyl]-4-yl)ethoxy)pyrimidin-4-yl)-2,8-diazaspiro[4.5]decane-3-carboxylate | 700 |

TABLE 18a-continued

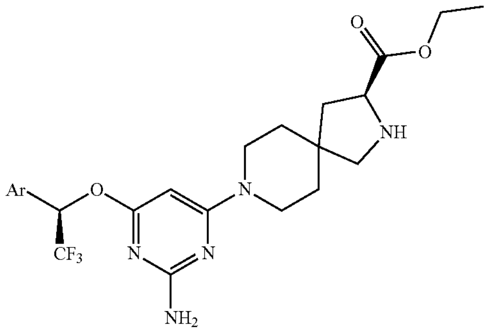

| Ex. No. | Ar | Method A or B | CAS Name | LCMS (MH+) |
|---|---|---|---|---|
| 63jo | 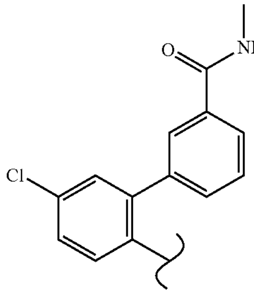 | B | (S)-ethyl 8-(2-amino-6-((R)-1-(5-chloro-3'-(methylcarbamoyl)-[1,1'-biphenyl]-2-yl)-2,2,2-trifluoroethoxy)pyrimidin-4-yl)-2,8-diazaspiro[4.5]decane-3-carboxylate | 648 |
| 63jp | 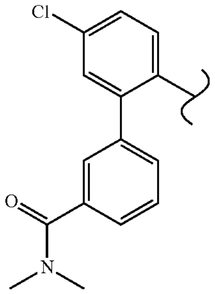 | B | (S)-ethyl 8-(2-amino-6-((R)-1-(5-chloro-3'-(dimethylcarbamoyl)-[1,1'-biphenyl]-2-yl)-2,2,2-trifluoroethoxy)pyrimidin-4-yl)-2,8-diazaspiro[4.5]decane-3-carboxylate | 662 |
| 63jq | 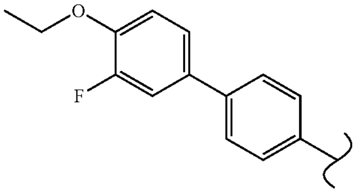 | A | (S)-ethyl 8-(2-amino-6-((R)-1-(4'-ethoxy-3'-fluoro-[1,1'-biphenyl]-4-yl)-2,2,2-trifluoroethoxy)pyrimidin-4-yl)-2,8-diazaspiro[4.5]decane-3-carboxylate | 618 |
| 63jr | 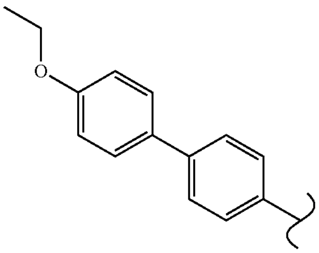 | A | (S)-ethyl 8-(2-amino-6-((R)-1-(4'-ethoxy-[1,1'-biphenyl]-4-yl)-2,2,2-trifluoroethoxy)pyrimidin-4-yl)-2,8-diazaspiro[4.5]decane-3-carboxylate | 601 |

TABLE 18a-continued

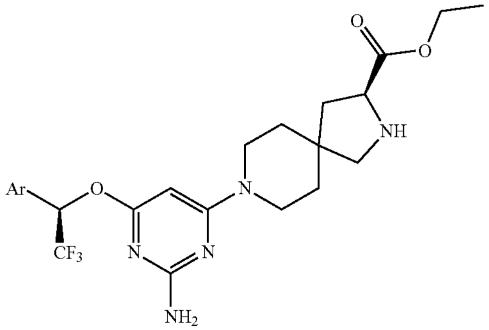

| Ex. No. | Ar | Method A or B | CAS Name | LCMS (MH+) |
|---|---|---|---|---|
| 63js | 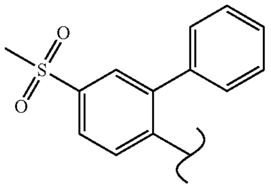 | A | (S)-ethyl 8-(2-amino-6-((R)-2,2,2-trifluoro-1-(5-(methylsulfonyl)-[1,1'-biphenyl]-2-yl)ethoxy)pyrimidin-4-yl)-2,8-diazaspiro[4.5]decane-3-carboxylate | 635 |
| 63jt | 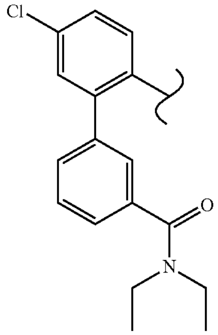 | B | (S)-ethyl 8-(2-amino-6-((R)-1-(5-chloro-3'-(diethylcarbamoyl)-[1,1'-biphenyl]-2-y])-2,2,2-trifluoroethoxy)pyrimidin-4-yl)-2,8-diazaspiro[4.5]decane-3-carboxylate | 690 |
| 63ju | 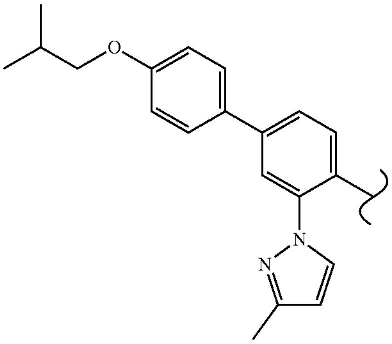 | A | (S)-ethyl 8-(2-amino-6-((R)-2,2,2-trifluoro-1-(4'-isobutoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 709 |
| 63jv | 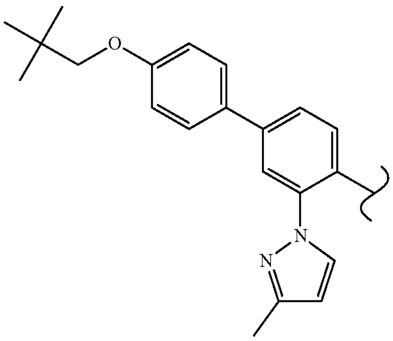 | A | (S)-ethyl 8-(2-amino-6-((R)-2,2,2-trifluoro-1-(3-(3-methyl-1H-pyrazol-1-yl)-4'-(neopentyloxy)-[1,1'-biphenyl]-4-yl)ethoxy)pyrimidin-4-yl)-2,8-diazaspiro[4.5]decane-3-carboxylate | 723 |

TABLE 18a-continued

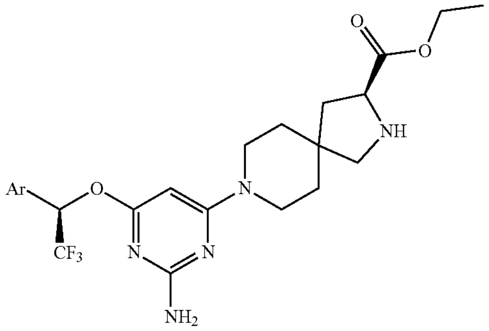

| Ex. No. | Ar | Method A or B | CAS Name | LCMS (MH+) |
|---|---|---|---|---|
| 63jw | 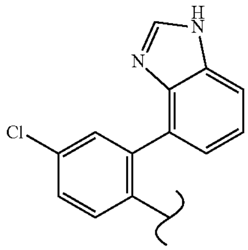 | B | (S)-ethyl 8-(6-((R)-1-(2-(1H-benzo[d]imidazol-4-yl)-4-chlorophenyl)-2,2,2-trifluoroethoxy)-2-aminopyrimidin-4-yl)-2,8-diazaspiro[4.5]decane-3-carboxylate | 631 |
| 63jx | 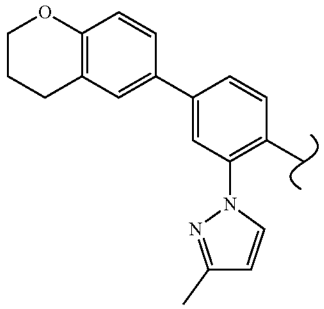 | A | (S)-ethyl 8-(2-amino-6-((R)-1-(4-(chroman-6-yl)-2-(3-methyl-1H-pyrazol-1-yl)phenyl)-2,2,2-trifluoroethoxy)pyrimidin-4-yl)-2,8-diazaspiro[4.5]decane-3-carboxylate | 693 |
| 63jy | 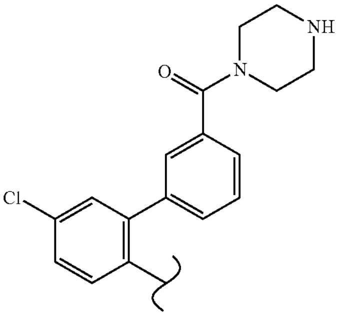 | B | (S)-ethyl 8-(2-amino-6-((R)-1-(5-chloro-3'-(piperazine-1-carbonyl)-[1,1'-biphenyl]-2-yl)-2,2,2-trifluoroethoxy)pyrimidin-4-yl)-2,8-diazaspiro[4.5]decane-3-carboxylate | 703 |
| 63jz | 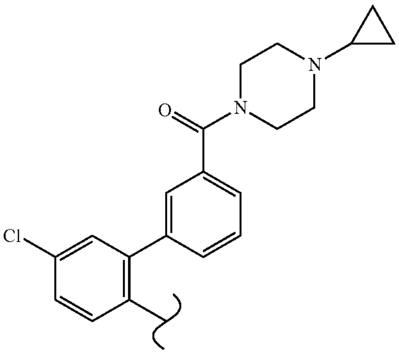 | A | (S)-ethyl 8-(2-amino-6-((R)-1-(5-chloro-3'-(4-cyclopropylpiperazine-1-carbonyl)-[1,1'-biphenyl]-2-yl)-2,2,2-trifluoroethoxy)pyrimidin-4-yl)-2,8-diazaspiro[4.5]decane-3-carboxylate | 743 |

TABLE 18a-continued

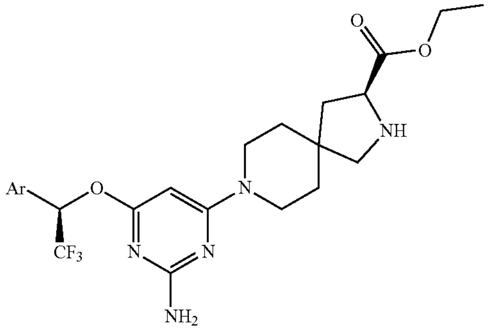

| Ex. No. | Ar | Method A or B | CAS Name | LCMS (MH+) |
|---|---|---|---|---|
| 63ka | 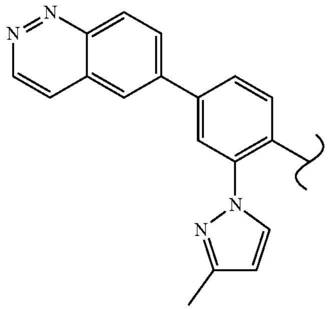 | A | (S)-ethyl 8-(2-amino-6-((R)-1-(4-(cinnolin-6-yl)-2-(3-methyl-1H-pyrazol-1-yl)phenyl)-2,2,2-trifluoroethoxy)pyrimidin-4-yl)-2,8-diazaspiro[4.5]decane-3-carboxylate | 689 |
| 63kb | 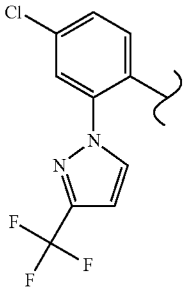 | B | (S)-ethyl 8-(2-amino-6-((R)-1-(4-chloro-2-(3-(trifluoromethyl)-1H-pyrazol-1-yl)phenyl)-2,2,2-trifluoroethoxy)pyrimidin-4-yl)-2,8-diazaspiro[4.5]decane-3-carboxylate | 649 |
| 63kc | 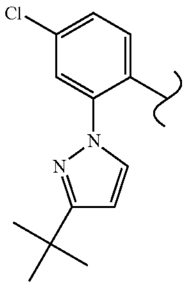 | B | (S)-ethyl 8-(2-amino-6-((R)-1-(2-(3-(tert-butyl)-1H-pyrazol-1-yl)-4-chlorophenyl)-2,2,2-trifluoroethoxy)pyrimidin-4-yl)-2,8-diazaspiro[4.5]decane-3-carboxylate | 637 |
| 63kd | 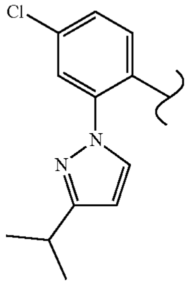 | B | (S)-ethyl 8-(2-amino-6-((R)-1-(4-chloro-2-(3-isopropyl-1H-pyrazol-1-yl)phenyl)-2,2,2-trifluoroethoxy)pyrimidin-4-yl)-2,8-diazaspiro[4.5]decane-3-carboxylate | 624 |

TABLE 18a-continued

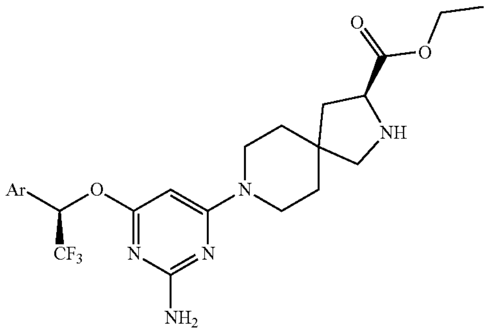

| Ex. No. | Ar | Method A or B | CAS Name | LCMS (MH+) |
|---|---|---|---|---|
| 63ke | 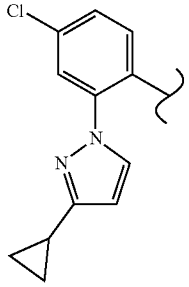 | B | (S)-ethyl 8-(2-amino-6-((R)-1-(4-chloro-2-(3-cyclopropyl-1H-pyrazol-1-yl)phenyl)-2,2,2-trifluoroethoxy)pyrimidin-4-yl)-2,8-diazaspiro[4.5]decane-3-carboxylate | 622 |
| 63kf | 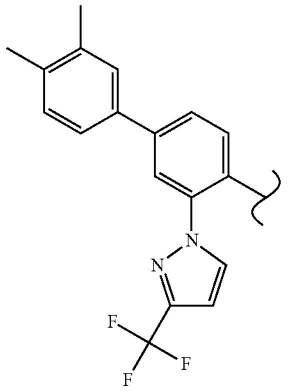 | A | (S)-ethyl 8-(2-amino-6-((R)-1-(3',4'-dimethyl-3-(3-(trifluoromethyl)-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 719 |
| 63kg | 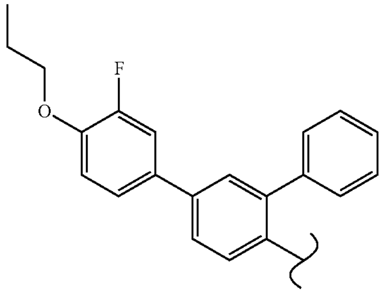 | A | (S)-ethyl 8-(2-amino-6-((R)-2,2,2-trifluoro-1-(3-fluoro-4-propoxy-[1,1':3',1''-terphenyl]-4'-yl)ethoxy)pyrimidin-4-yl)-2,8-diazaspiro[4.5]decane-3-carboxylate | 660 |

TABLE 18a-continued

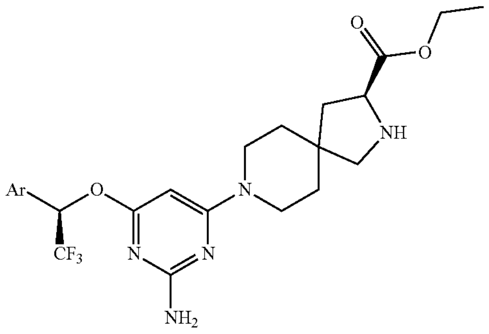

| Ex. No. | Ar | Method A or B | CAS Name | LCMS (MH+) |
|---|---|---|---|---|
| 63kh | 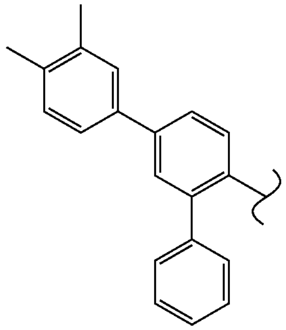 | A | (S)-ethyl 8-(2-amino-6-((R)-1-(3,4-dimethyl-[1,1':3',1''-terphenyl]-4'-yl)-2,2,2-trifluoroethoxy)pyrimidin-4-yl)-2,8-diazaspiro[4.5]decane-3-carboxylate | 708 |
| 63ki | 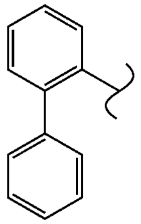 | A | (S)-ethyl 8-(6-((R)-1-([1,1'-biphenyl]-2-yl)-2,2,2-trifluoroethoxy)-2-aminopyrimidin-4-yl)-2,8-diazaspiro[4.5]decane-3-carboxylate | 556 |
| 63kj | 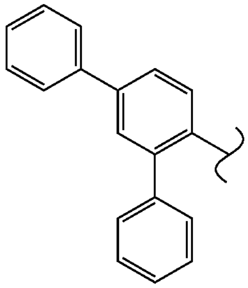 | A | (S)-ethyl 8-(6-((R)-1-([1,1':3',1''-terphenyl]-4'-yl)-2,2,2-trifluoroethoxy)-2-aminopyrimidin-4-yl)-2,8-diazaspiro[4.5]decane-3-carboxylate | 633 |

TABLE 18a-continued

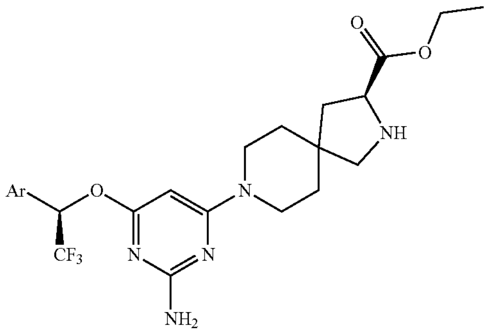

| Ex. No. | Ar | Method A or B | CAS Name | LCMS (MH+) |
|---|---|---|---|---|
| 63kl | 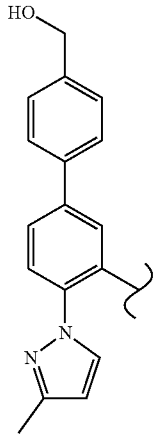 | A | (S)-ethyl 8-(2-amino-6-((R)-2,2,2-trifluoro-1-(4'-(hydroxymethyl)-4-(3-methyl-1H-pyrazol-1-yl)-[1,1'-biphenyl]-3-yl)ethoxy)pyrimidin-4-yl)-2,8-diazaspiro[4.5]decane-3-carboxylate | 667 |
| 63km | 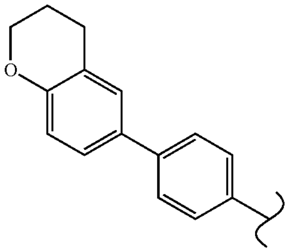 | A | (S)-ethyl 8-(2-amino-6-((R)-1-(4-(chroman-6-yl)phenyl)-2,2,2-trifluoroethoxy)pyrimidin-4-yl)-2,8-diazaspiro[4.5]decane-3-carboxylate | 612 |
| 63kn | 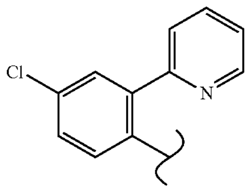 | B | (S)-ethyl 8-(2-amino-6-((R)-1-(4-chloro-2-(pyridin-2-yl)phenyl)-2,2,2-trifluoroethoxy)pyrimidin-4-yl)-2,8-diazaspiro[4.5]decane-3-carboxylate | 592 |
| 63ko | 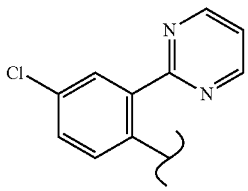 | B | (S)-ethyl 8-(2-amino-6-((R)-1-(4-chloro-2-(pyrimidin-2-yl)phenyl)-2,2,2-trifluoroethoxy)pyrimidin-4-yl)-2,8-diazaspiro[4.5]decane-3-carboxylate | 593 |

TABLE 18a-continued

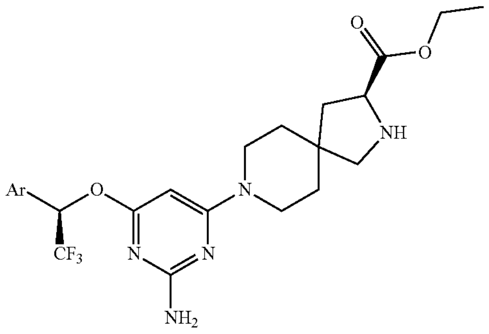

| Ex. No. | Ar | Method A or B | CAS Name | LCMS (MH+) |
|---|---|---|---|---|
| 63kp | 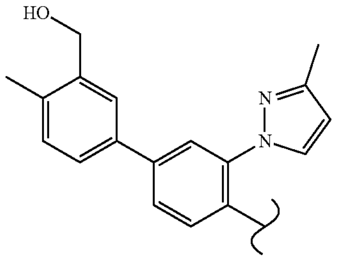 | A | (S)-ethyl 8-(2-amino-6-((R)-2,2,2-trifluoro-1-(3'-(hydroxymethyl)-4'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 681 |
| 63kq | 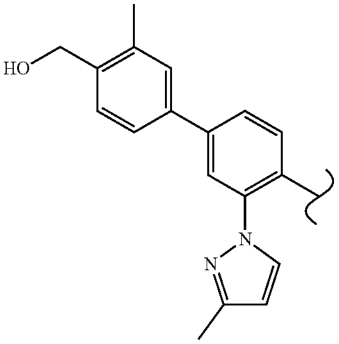 | A | (S)-ethyl 8-(2-amino-6-((R)-2,2,2-trifluoro-1-(4'-(hydroxymethyl)-3'-methyl-3-(3-methyl-1H-pyrazol-1-yl)-[1,1'-biphenyl]-4-yl)ethoxy)pyrimidin-4-yl)-2,8-diazaspiro[4.5]decane-3-carboxylate | 681 |
| 63kr | 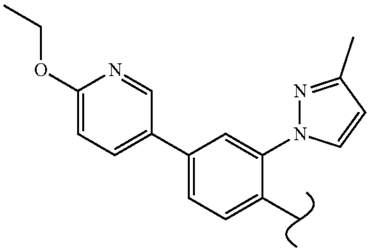 | A | (S)-ethyl 8-(2-amino-6-((R)-1-(4-(6-ethoxypyridin-3-yl)-2-(3-methyl-1H-pyrazol-1-yl)phenyl)-2,2,2-trifluoroethoxy)pyrimidin-4-yl)-2,8-diazaspiro[4.5]decane-3-carboxylate | 681 |
| 63ks | 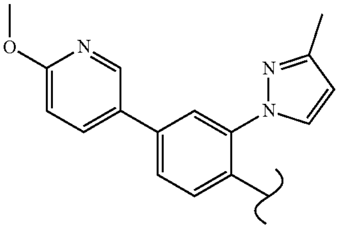 | A | (S)-ethyl 8-(2-amino-6-((R)-2,2,2-trifluoro-1-(4-(6-methoxypyridin-3-yl)-2-(3-methyl-1H-pyrazol-1-yl)phenyl)ethoxy)pyrimidin-4-yl)-2,8-diazaspiro[4.5]decane-3-carboxylate | 668 |

TABLE 18a-continued

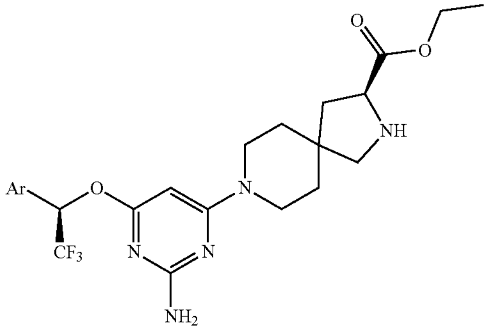

| Ex. No. | Ar | Method A or B | CAS Name | LCMS (MH+) |
|---|---|---|---|---|
| 63kt | 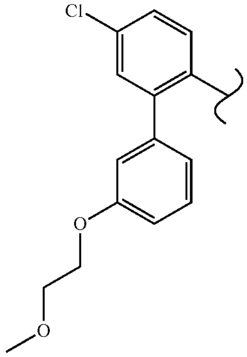 | A | (S)-ethyl 8-(2-amino-6-((R)-1-(5-chloro-3'-(2-methoxyethoxy)-[1,1'-biphenyl]-2-yl)-2,2,2-trifluoroethoxy)pyrimidin-4-yl)-2,8-diazaspiro[4.5]decane-3-carboxylate | 665 |
| 63ku | 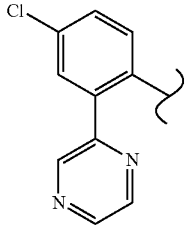 | B | (S)-ethyl 8-(2-amino-6-((R)-1-(4-chloro-2-(pyrazin-2-yl)phenyl)-2,2,2-trifluoroethoxy)pyrimidin-4-yl)-2,8-diazaspiro[4.5]decane-3-carboxylate | 594 |
| 63kv | 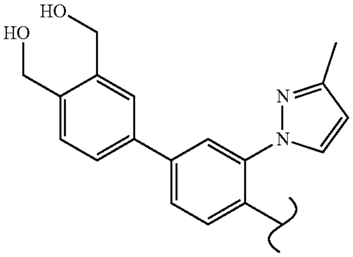 | B | (S)-ethyl 8-(2-amino-6-((S)-1-(3',4'-bis(hydroxymethyl)-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 697 |

TABLE 18b

| NMR Data for Compounds of Table 18a | |
|---|---|
| Ex. No. | NMR |
| 63a | $^1H$ NMR (400 MHz, MeOH-d4): δ PPM 1.26 (t, J = 7.1 Hz, 3H), 1.50 (m, 5H), 1.63 (s, 1H), 1.73 (dd, J = 13.0, 7.2 Hz, 1H), 2.07 (dd, J = 13.0, 8.7 Hz, 1H), 2.74 (d, J = 11.0 Hz, 1H), 2.88 (d, J = 11.0 Hz, 1H), 3.50 (pd, J = 13.6, 5.4 Hz, 5H), 3.81 (t, J = 8.0 Hz, 1H), 4.17 (qd, J = 7.0, 1.6 Hz, 2H), 4.92 (s, 6H), 5.55 (s, 1H), 6.66 (q, J = 7.2 Hz, 1H), 7.63 (d, J = 8.0 Hz, 2H), 7.77 (m, 4H), 8.10 (d, J = 8.6 Hz, 1H), 8.29 (d, J = 1.8 Hz, 1H), 9.24 (s, 1H) |

TABLE 18b-continued

| NMR Data for Compounds of Table 18a | |
|---|---|
| Ex. No. | NMR |
| 63b | $^1H$ NMR (400 MHz, CDCl3): δ ppm 1.28 (m, 5H), 1.59 (t, J = 5.6 Hz, 2H), 1.77 (dd, J = 13.1, 6.8 Hz, 1H), 2.09 (m, 1H), 2.87 (d, J = 10.6 Hz, 1H), 2.98 (d, J = 10.6 Hz, 1H), 3.51 (dt, J = 14.9, 5.0 Hz, 4H), 3.92 (m, 1H), 4.21 (q, J = 7.1 Hz, 2H), 4.62 (s, 2H), 5.54 (s, 1H), 6.63 (q, J = 7.0 Hz, 1H), 7.40 (dd, J = 8.5, 1.4 Hz, 1H), 7.62 (q, J = 8.3 Hz, 6H), 7.81 (d, J = 8.5 Hz, 1H), 8.11 (s, 1H) |
| 63c | $^1H$ NMR (400 MHz, CDCl3): δ ppm 0.87 (dd, J = 7.5, 3.2 Hz, 1H), 1.28 (dd, J = 14.0, 6.9 Hz, 7H), 1.57 (dt, J = 17.4, 5.6 Hz, 4H), 1.87 (m, 5H), 2.11 (dd, J = 13.1, 8.8 Hz, 1H), 2.89 (d, J = 10.6 Hz, 1H), 2.99 (d, J = 10.6 Hz, 1H), 3.28 (t, J = 6.7 Hz, 2H), 3.51 (m, 4H), 3.67 (t, J = 6.9 Hz, 2H), 3.89 (s, 4H), 4.21 (q, J = 7.1 Hz, 2H), 4.59 (s, 2H), 5.53 (s, 1H), 6.61 (q, J = 7.1 Hz, 1H), 7.07 (d, J = 1.5 Hz, 1H), 7.17 (dd, J = 7.7, 1.5 Hz, 1H), 7.33 (d, J = 7.8 Hz, 1H), 7.58 (s, 4H) |
| 63d | $^1H$-NMR (400 MHz, MeOH-d4): δ ppm 1.62(m, 4H), 2.09-2.04(m, 1H), 2.40-2.35(m, 1H), 3.14(m, 1H), 3.25(m, 1H), 3.47(m, 2H), 3.31-3.30(m, 2H), 4.22-4.20(m, 1H), 5.49(s, 1H), 5.83-5.80(m, 1H), 6.52-6.38(m, 2H), 6.65(m, 1H), 7.31(d, J = 2.0, 1H), 7.45-7.43 (d, J = 8.0, 3H), 7.68-7.66(d, J = 8.0, 1H), 7.80-7.78(d, J = 8.0, 2H) |
| 63e | $^1H$ NMR (400 MHz, CDCl3): δ ppm 0.07 (s, 1H), 0.87 (dd, J = 17.8, 8.8 Hz, 2H), 1.12 (s, 3H), 1.29 (m, 18H), 1.51 (s, 1H), 1.63 (dq, J = 29.6, 7.7, 6.6 Hz, 10H), 1.89 (dd, J = 13.2, 7.4 Hz, 2H), 2.23 (dd, J = 13.2, 8.6 Hz, 2H), 3.13 (m, 4H), 3.53 (h, J = 6.6 Hz, 16H), 4.04 (s, 1H), 4.20 (dq, J = 33.0, 7.5 Hz, 8H), 4.35 (s, 1H), 4.60 (m, 5H), 5.52 (d, J = 16.0 Hz, 2H), 6.64 (q, J = 7.0 Hz, 2H), 7.39 (m, 2H), 7.50 (d, J = 7.6 Hz, 1H), 7.65 (q, J = 7.9 Hz, 9H), 7.79 (dd, J = 24.7, 8.0 Hz, 3H), 8.03 (d, J = 8.5 Hz, 2H), 8.23 (s, 2H), 8.97 (s, 2H) |
| 63f | $^1H$ NMR (400 MHz, CDCl3): δ ppm 0.87 (dd, J = 16.5, 9.8 Hz, 2H), 1.28 (m, 12H), 1.58 (m, 4H), 1.79 (dd, J = 13.1, 6.9 Hz, 1H), 2.12 (dd, J = 13.1, 8.9 Hz, 1H), 2.90 (d, J = 10.7 Hz, 1H), 3.00 (d, J = 10.6 Hz, 1H), 3.52 (dt, J = 11.4, 5.4 Hz, 7H), 3.96 (t, J = 7.8 Hz, 1H), 4.21 (q, J = 7.2 Hz, 2H), 4.61 (s, 2H), 5.54 (s, 1H), 6.64 (q, J = 7.1 Hz, 1H), 7.66 (q, J = 8.4 Hz, 5H), 8.12 (t, J = 4.2 Hz, 2H), 8.94 (s, 1H) |
| 63g | $^1H$ NMR (400 MHz, MeOH-d4): δ ppm 1.32 (m, 4H), 1.64 (dq, J = 14.1, 8.9, 7.2 Hz, 4H), 2.03 (td, J = 13.3, 8.9 Hz, 1H), 2.49 (dd, J = 13.6, 8.7 Hz, 1H), 3.27 (s, 2H), 3.58 (m, 4H), 3.88 (d, J = 11.8 Hz, 6H), 4.32 (qd, J = 7.2, 2.5 Hz, 2H), 4.58 (t, J = 8.8 Hz, 1H), 6.62 (q, J = 7.1 Hz, 1H), 7.03 (m, 1H), 7.19 (m, 2H), 7.57 (d, J = 8.2 Hz, 2H), 7.64 (m, 2H) |
| 63h | $^1H$ NMR (400 MHz, CDCl3): δ ppm 7.769-7.796 (m, 1H), 7.707-7.740(m, 2H), 7.585-7.636(m, 4H), 7.422-7.444(m, 1H), 6.738-6.762(m, 1H), 6.579-6.658-6.537 (m, 1H), 5.521 (s, 1H), 4.612 (s, 2H), 4.200-4.253 (q, 2H), 4.114-4.154 (t, 1H), 3.747(s, 3H), 3.475-3.523 (m, 4H), 3.047-3.160 (m, 2H), 2.171-2.726 (m, 1H), 1.840-1.891 (m, 1H), 1.543-1.649 (m, 4H), 1.209-1.305 (t, 3H) |
| 63i | $^1H$ NMR (400 MHz, DMSO-d6): δ ppm 1.25 (t, J = 7.10 Hz, 3 H) 1.42-1.69 (m, 4 H) 1.92 (dd, J = 13.25, 9.35 Hz, 1 H) 2.35 (dd, J = 13.25, 8.47 Hz, 1 H) 3.14 (br. s., 2 H) 3.60 (br. s., 4 H) 4.24 (qd, J = 7.09, 2.10 Hz, 2 H) 4.54 (br. s., 1 H) 5.77 (br. s., 1 H) 6.70 (q, J = 6.65 Hz, 1 H) 7.37 (d, J = 2.10 Hz, 1 H) 7.43-7.52 (m, 3 H) 7.53-7.69 (m, 4 H) 9.23 (br. s., 1 H) 10.44 (br. s., 1 H) |
| 63j | $^1H$ NMR (400 MHz, CD3OD): δ ppm 7.66-7.64 (d, 1 H, J = 8.6 Hz), 7.43-7.41 (d, 1 H, J = 8.6 Hz), 7.26-7.20 (m, 2 H), 6.82-6.68 (m, 4 H), 5.42 (s, 1 H), 4.19-4.16 (q, 1 H, J = 7.0 Hz), 3.83-3.81 (t, 1 H), 3.49-3.47 (m, 4 H), 2.91-2.89 (d, 1 H, J = 10.9 Hz), 2.77-2.75 (d, 1 H, J = 10.9 Hz), 2.11-2.07 (m, 1 H), 2.12-2.10 (m, 1 H), 1.53-1.51 (m, 4 H), 1.28-1.25 (t, 3 H, J = 7.0 Hz Hz) |
| 63k | $^1H$ NMR (400 MHz, MeOH-d4): δ ppm 8.42 (s, 1 H), 8.30 (d, 1 H), 7.61 (m, 2 H), 7.31 (m, 1 H), 7.10 (s, 1 H), 6.58 (m, 1 H), 5.57 (s, 1 H), 4.20 (m, 2 H), 3.84 (m, 1 H), 3.48 (m, 4 H), 3.16 (s, 3 H), 2.77 (m, 1 H), 2.70 (m, 1 H), 2.61 (m, 1 H), 2.14 (m, 1 H), 1.77 (m, 1 H), 1.65 (m, 2 H), 1.54 (m, 4 H), 1.20 (m, 3 H), 0.98 (m, 3 H) |
| 63l | $^1H$ NMR (400 MHz, CD3OD-d4): δ ppm 1.28-1.24 (m, 4 H), 7.72-7.68 (m, 3 H), 1.52 (m, 4 H), 1.71 (m, 1 H), 2.10 (m, 1 H), 2.32 (s, 3 H), 2.76-2.73 (m, 1 H), 2.90-2.87 (m, 1 H), 3.49 (m, 4 H), 3.75 (s, 3 H), 3.81 (m, 2 H), 4.20-4.15 (m, 2 H), 5.54 (s. 1H), 6.65-6.59 (m, 1 H), 6.93 (s, 1 H), 7.37-7.34(m, 1 H), 7.45-7.42 (m, 1 H), 7.57-7.55 (m, 2 H) |
| 63m | $^1H$ NMR (400 MHz, MeOH-d4): δ ppm 8.19 (s, 1 H), 7.64 (d, 1 H), 7.53-7.42 (m, 5 H), 7.29 (s, 1 H), 7.16 (s, 2 H), 6.63 (q, 1 H), 6.52-6.35 (m, 3 H), 5.80-5.77 (d, 1 H), 5.50 (s, 1 H), 4.21-4.18 (m, 2 H), 3.97 (t, 1 H), 3.49 (m, 4 H), 2.98-2.95 (d, 1 H), 2.86-2.83 (d, 1 H), 2.16-2.14 (m, 1 H), 1.80-1.76 (m, 1 H), 1.54 (m, 4 H), 1.19-1.16 (t, 3 H) |
| 63n | $^1H$ NMR (400 MHz, MeOH-d4): δ ppm 1.27 (q, J = 7.1, 6.1 Hz, 4H), 1.52 (dt, J = 10.4, 5.7 Hz, 4H), 1.74 (dd, J = 13.0, 7.2 Hz, 1H), 2.09 (dd, J = 13.1, 8.8 Hz, 1H), 2.75 (d, J = 11.0 Hz, 1H), 2.89 (d, J = 11.0 Hz, 1H), 3.52 (tq, J = 14.5, 8.2 Hz, 4H), 3.82 (dd, J = 8.8, 7.2 Hz, 1H), 3.90 (s, 3H), 4.18 (qd, J = 7.1, 1.6 Hz, 2H), 4.89 (d, J = 1.5 Hz, 13H), 5.51 (d, J = 18.8 Hz, 2H), 6.62 (q, J = 7.1 Hz, 1H), 7.15 (t, J = 8.6 Hz, 1H), 7.39 (m, 2H), 7.59 (m, 4H) |
| 63o | $^1H$-NMR (400 MHz, MeOH-d4): δ ppm δ8.00(d, J = 2.36 Hz, 1H), 7.88(dd, J = 2.6, 6.76 Hz, 1H), 7.58(m, 4H), 6.62(m, 2H), 5.55(s, 1H), 4.22(m, 3H), 3.64(s, 3H), 3.52(m, 4H), 3.02(m, 2H), 2.27(m, 1H), 1.89(m, 1H), 1.59(m, 4H), 1.29(t, J = 7.16 Hz, 3H). |
| 63p | $^1H$ NMR (400 MHz, MeOH-d4): δ ppm 7.62(d, 2H, J = 8.0), 7.56(d, 2H, J = 8.0), 7.45(m, 2H), 6.93(d, 1H, J = 8.0), 6.62 (q, 1H, J = 8.0), 5.54 (s, 1H), 4.21 (t, 2H, J = 4.0), 3.99 (t, 1H, J = 4.0), 3.56δ3.49 (m, 4H), 3.00(dd, 3H, J = 20.0, 8.0), 2.86 (d, 1H, J = 8.0), 2.59-2.57 (m, 2H), 2.18 (dd, 2H, J = 12.0, 8.0), 1.80(dd, 2H, J = 8.0, 4.0), 1.54(m, 5), 1.28(t, 4H, J = 8.0) |

TABLE 18b-continued

| NMR Data for Compounds of Table 18a | |
|---|---|
| Ex. No. | NMR |
| 63q | $^1$H-NMR (400 MHz, CDCl3): δ ppm 11.76 (m, 1H), 7.84-7.86 (m, 1H), 7.70-7.73 (m, 2H), 7.59 (m, 4H), 7.43-7.45 (m, 1H), 6.73-6.75 (m, 1H), 6.57-6.63 (q, 1H), 5.53 (s, 1H), 4.61 (s, 2H), 4.17-4.23 (q, 2H), 3.90-3.94 (t, 1H), 3.48-3.51 (m, 4H), 2.86-2.99 (m, 2H), 2.07-2.12 (m, 2H), 1.74-1.79 (m, 1H), 1.53-1.59 (m, 4H), 1.24-1.29 (t, 3H). |
| 63r | $^1$H NMR (400 MHz, CD3OD-d4): δ ppm 8.42 (s, 1 H), 8.04 (d, 1 H), 7.79 (m, 3 H), 7.63 (m, 1 H), 7.46 (m, 1 H), 6.58 (m, 1 H), 6.40 (m, 1 H), 5.56 (m, 1 H), 4.18 (m, 2 H), 3.83 (m, 1 H), 3.50 (m, 4 H), 3.21(s, 3 H), 2.90 (m, 1 H), 2.78 (m, 1 H), 2.14 (m, 1 H), 1.86 (m, 3 H), 1.76(m, 1 H), 1.54 (m, 4 H), 1.26 (m, 3 H) |
| 63s | $^1$H NMR (MeOH-d4): δ ppm 0.90 (t, J = 6.9 Hz, 1H), 1.17 (p, J = 6.3 Hz, 3H), 1.29 (s, 2H), 1.56 (m, 4H), 1.80 (s, 1H), 2.29 (s, 1H), 2.41 (s, 3H), 2.80 (m, 4H), 3.26 (d, J = 11.3 Hz, 1H), 3.44 (s, 1H), 4.09 (tdd, J = 14.2, 7.9, 4.6 Hz, 2H), 4.48 (s, 1H), 4.87 (s, 2H), 5.56 (s, 1H), 6.42 (t, J = 2.2 Hz, 1H), 6.93 (m, 1H), 7.46 (m, 4H), 7.61 (m, 2H), 7.80 (dd, J = 8.3, 2.2 Hz, 1H), 7.93 (dd, J = 5.2, 2.5 Hz, 2H) |
| 63t | $^1$H NMR (MeOH-d4): δ ppm 0.91 (dd, J = 12.4, 6.3 Hz, 2H), 1.17 (q, J = 7.4 Hz, 3H), 1.31 (d, J = 16.3 Hz, 3H), 1.65 (m, 4H), 1.83 (s, 1H), 2.32 (s, 2H), 2.41 (s, 3H), 2.92 (ddt, J = 18.2, 14.3, 9.1 Hz, 5H), 3.28 (s, 1H), 4.11 (dtt, J = 10.7, 7.1, 3.9 Hz, 2H), 4.48 (s, 1H), 4.95 (d, J = 11.7 Hz, 1H), 6.43 (d, J = 2.2 Hz, 1H), 6.94 (q, J = 6.5 Hz, 1H), 7.50 (m, 3H), 7.61 (dd, J = 8.6, 2.1 Hz, 2H), 7.79 (dt, J = 8.3, 1.4 Hz, 1H), 7.93 (dd, J = 10.2, 3.2 Hz, 2H) |
| 63u | $^1$H NMR (400 MHz, $CDCl_3$-d): δ ppm 8.50 (s, 1H), 7.99-7.96 (m, 1H), 7.69-7.63 (m, 2H), 7.51 (s, 1H), 7.25-7.23 (m, 1H), 7.11 (d, J = 7.8 Hz, 1H), 6.57 (q, J = 6.6 Hz, 1H), 5.51 (s, 1H), 5.18 (s, 2H), 4.21 (q, J = 7.1 Hz, 2H), 3.93-3.89 (m, 1H), 3.53-3.48 (m, 4H), 3.14 (s, 3H), 2.93 (dd, J1 = 10.6 Hz, J2 = 42.0 Hz, 2H), 2.66-2.62 (m, 2H), 2.12-2.07 (m, 1H), 1.79-1.74 (m, 1H), 1.69-1.63 (m, 2H), 1.61-1.58 (m, 2H), 1.55-1.52 (m, 2H), 1.29 (t, J = 7.2 Hz, 3H), 0.95 (t, J = 7.3 Hz, 3H) |
| 63v | $^1$H NMR (400 MHz, $CDCl_3$): δ ppm 8.52 (d, J = 9.5 Hz, 1H), 7.99-7.97 (m, 1H), 7.69-7.62 (m, 3H), 7.38 (dd, J1 = 7.9 Hz, J2 = 20.6 Hz, 1H), 7.15 (dd, J1 = 7.9 Hz, J2 = 17.0 Hz, 1H), 6.57 (m, 1H), 6.46-6.42 (m, 1H), 6.34-5.84 (m, 1H), 5.51-5.50 (m, 1H), 5.18 (s, 2H), 4.20 (q, J = 7.2 Hz, 2H), 3.87 (t, J = 7.6 Hz, 1H), 3.52-3.50 (m, 4H), 3.15-3.14 (m, 3H), 2.90 (dd, J1 = 10.2 Hz, J2 = 47.8 Hz, 2H), 2.10-2.05 (m, 1H), 1.91 (d, J = 6.4 Hz, 3H), 1.78-1.73 (m, 1H), 1.58-1.53 (m, 4H), 1.28 (t, J = 7.1 Hz, 3H) |
| 63w | $^1$H NMR (400 MHz, MeOH-d4): δ ppm 8.49 (s, 1H), 7.98 (d, J = 7.5 Hz, 1H), 7.71 (t, J = 7.8 Hz, 1H), 7.65-7.63 (m, 2H), 7.42-7.40 (m, 1H), 7.23 (d, J = 1.9 Hz, 1H), 6.53 (q, J = 6.8 Hz, 1H), 5.48 (s, 1H), 5.26 (s, 2H), 4.22 (q, J = 7.1 Hz, 2H), 4.03 (t, J = 8.0 Hz, 1H), 3.52-3.51 (m, 4H), 3.21 (q, J = 7.4 Hz, 2H), 3.02 (dd, J1 = 10.9 Hz, J2 = 34.9 Hz, 2H), 2.18-2.12 (m, 1H), 1.85-1.80 (m, 1H), 1.62-1.61 (m, 2H), 1.56-1.55 (m, 2H), 1.31-1.28 (m, 6H) |
| 63x | 1H NMR (400 MHz, MeOH-d4): δ ppm 8.45 (s, 1H), 8.03(d, 1H, J = 8.0), 7.83(t, 1H, J = 8.0), 7.79-7.69(m, 2H), 7.50(d, 1H, J = 8.0), 7.37(s, 1H), 6.62 (q, 1H, J = 8.0), 5.61 (s, 1H), 4.38 (t, 1H, J = 8.0), 4.32-4.27 (m, 2H), 3.64-3.49(m, 4H), 3.16(q, 2H, J = 12.0), 2.39 (dd, 1H, J = 12.0, 8.0), 1.98 (dd, 1H, J = 12.0, 8.0), 1.70-1.62(m, 7H), 1.31(dd, 5H, J = 12.0, 8.0) 0.96(t, 4H, J = 8.0) |
| 63y | $^1$H NMR (400 MHz, MeOH-d4): δ ppm 8.50 (s, 1 H), 8.05-8.03 (d, 1 H), 7.82 (t, 1 H), 7.76-7.70 (m, 2 H), 7.52-7.51 (d, 1 H), 7.38-7.37 (d, 1 H), 6.62-6.60 (q, 1 H), 5.60 (s, 1 H), 4.20-4.19 (q, 2 H), 3.85 (t, 1 H), 3.57 (m, 4 H), 2.82 (d, 1 H), 2.77 (d, 1 H), 2.09 (m, 1 H), 1.77 (m, 1 H), 1.57 (m, 6 H), 1.31 (q, 2 H), 1.26 (m, 3 H), 0.84-0.81 (t, 3H) |
| 63z | $^1$H NMR (400 MHz, MeOH-d4): δ ppm 0.09 (dd, J = 4.2, 2.0 Hz, 1H), 0.90 (t, J = 6.5 Hz, 3H), 1.28 (m, 14H), 1.54 (dt, J = 10.5, 5.6 Hz, 6H), 1.76 (dd, J = 13.2, 7.3 Hz, 1H), 2.03 (s, 1H), 2.15 (ddd, J = 29.1, 14.1, 8.4 Hz, 2H), 2.78 (d, J = 10.9 Hz, 1H), 2.92 (d, J = 11.0 Hz, 1H), 3.53 (td, J = 13.8, 13.4, 6.0 Hz, 6H), 3.86 (dd, J = 8.8, 7.3 Hz, 1H), 4.20 (m, 3H), 5.46 (d, J = 22.4 Hz, 3H), 5.56 (s, 1H), 6.67 (q, J = 7.2 Hz, 2H), 7.66 (d, J = 8.1 Hz, 3H), 7.75 (m, 3H), 7.85 (m, 3H), 7.93 (d, J = 7.9 Hz, 2H) |
| 63aa | $^1$H NMR (400 MHz, MeOH-d4): δ ppm: 8.16 (d, J = 8.84 Hz, 1H), 8.03 (d, J = 1.84 Hz, 1H), 7.94-7.81(m, 2H), 7.77 (d, J = 8.32 Hz, 2H), 7.64(d, J = 8.24 Hz, 2H), 6.96 (d, J = 8.88 Hz, 1H), 6.65 (q, J = 7.08 Hz, 1H), 5.56 (s, 1H), 4.18 (m, 2H), 4.06(s, 3H), 3.82 (m, 1H), 3.53(m, 4H), 2.90 (d, J = 11.0 Hz, 1H), 2.76 (d, J = 11.0 Hz, 1H), 2.09 (m, 1H), 1.75(m, 1H), 1.53 (s, 4H), 1.27 (t, J = 7.12 Hz, 3H) |
| 63ab | $^1$H NMR (400 MHz, CDCl3): δ ppm 7.76 (s, 1H), 7.65 (d, J = 8.5 Hz, 1H), 7.43 (t, J = 7.6 Hz, 1H), 7.37 (dd, J1 = 2.2 Hz, J2 = 8.5 Hz, 1H), 7.33 (d, J = 7.6 Hz, 1H), 7.28 (d, J = 7.8 Hz, 1H), 7.24 (d, J = 2.2 Hz, 1H), 6.63 (q, J = 6.7 Hz, 1H), 5.41 (s, 1H), 5.02 (s, 2H), 4.80 (m, 2H), 4.21 (q, J = 7.1 Hz, 2H), 4.05-4.01 (m, 1H), 3.48-3.46 (m, 4H), 3.01 (dd, J1 = 10.9 Hz, J2 = 31.0 Hz, 2H), 2.17-2.11 (m, 1H), 1.83-1.78 (m, 1H), 1.59-1.50 (m, 4H), 1.28 (t, J = 7.1 Hz, 3H) |
| 63ac | $^1$H-NMR (400 MHz, MeOH-d4): δ ppm 7.97 (s, 1H), 7.60-7.67 (m, 2H), 7.52-7.56 (m, 1H), 7.43-7.45 (m, 1H), 7.31-7.31 (m, 1H), 7.22-7.24 (m, 1H), 6.621-6.663(m, 1H), 5.498(s, 1H), 4.16-4.22 (m, 2H), 4.92-4.03 (m, 2H), 3.83-3.87 (M, 1h), 3.46-3.53 (m, 4H), 2.90-2.92 (d, 1H), 2.76-2.78 (d, 1H), 2.59-2.63 (m, 2H), 2.10-2.22 (m, 3H), 1.71-1.78 (m, 1H), 1.52-1.55 (m, 4H), 1.25-1.28 (m, 3H) |
| 63ad | $^1$H-NMR (400 MHz, MeOH-d4) δ ppm: 7.98 (s, 1H), 7.63-7.65 (m, 1H), 7.42-7.50 (m, 3H), 7.30-7.30 (m, 1H), 7.05-7.07 (m, 1H), 6.62-6.67 (m, 1H), 5.49 (s, 1H), 4.15-4.22 (m, 2H), 3.80-3.98 (m, 3H), 3.46-3.56 (m, 6h), 2.73-2.92 (m, 4H), 2.73-2.78 (d, 1H), 2.07-2.13 (d, 1H), 1.73-1.78 (m, 1H), 1.49-1.57 (m, 4H), 1.25-1.29 (m, 3H) |

TABLE 18b-continued

NMR Data for Compounds of Table 18a

| Ex. No. | NMR |
|---|---|
| 63ae | $^1$H NMR (400 MHz, DMSO-d6) δ ppm: 1.25 (t, J = 7.10 Hz, 3 H) 1.42-1.69 (m, 4 H) 1.92 (dd, J = 13.25, 9.35 Hz, 1 H) 2.35 (dd, J = 13.25, 8.47 Hz, 1 H) 3.14 (br. s., 2 H) 3.60 (br. s., 4 H) 4.24 (qd, J = 7.09, 2.10 Hz, 2 H) 4.54 (br. s., 1 H) 5.77 (br. s., 1 H) 6.70 (q, J = 6.65 Hz, 1 H) 7.37 (d, J = 2.10 Hz, 1 H) 7.43-7.52 (m, 3 H) 7.53-7.69 (m, 4 H) 9.23 (br. s., 1 H) 10.44 (br. s., 1 H) |
| 63af | $^1$H NMR (400 MHz, MeOH-d4): δ ppm 7.66 (d, 1 H, J = 8.4 Hz), 7.50 (m, 3 H), 7.31 (d, 2 H, J = 8.7 Hz), 7.24 (d, 1 H, J = 7.2 Hz), 6.64 (m, 1 H), 5.50 (m, 1 H), 4.21 (m, 1 H), 3.87 (m, 1 H), 3.53 (m, 4 H), 3.01(s, 3 H), 3.18 (m, 1 H), 2.90 (m, 3 H), 2.79 (m, 1 H), 2.07 (m, 1 H), 1.74 (m, 1 H), 1.53 (m, 4 H), 1.27 (m, 3 H) |
| 63ag | $^1$H NMR (400 MHz, CDCl3): δ ppm 7.54 (d, J = 2.2 Hz, 1H), 7.51 (d, J = 8.6 Hz, 1H), 7.19 (dd, J1 = 2.6 Hz, J2 = 8.6 Hz, 1H), 6.85 (q, J = 6.6 Hz, 1H), 5.49 (s, 1H), 4.56 (s, 2H), 4.20 (q, J = 7.2 Hz, 2H), 3.90-3.86 (m, 1H), 3.53-3.47 (m, 4H), 2.90 (dd, J1 = 10.4 Hz, J2 = 47.6 Hz, 2H), 2.13-2.05 (m, 1H), 1.78-1.73 (m, 1H), 1.59-1.56 (m, 2H), 1.54-1.51 (m, 2H), 1.28 (t, J = 7.1 Hz, 3H) |
| 63ah | $^1$H NMR (400 MHz, CDCl3): δ ppm 7.54 (d, J = 2.2 Hz, 1H), 7.51 (d, J = 8.6 Hz, 1H), 7.19 (dd, J1 = 2.6 Hz, J2 = 8.6 Hz, 1H), 6.85 (q, J = 6.6 Hz, 1H), 5.49 (s, 1H), 4.56 (s, 2H), 4.20 (q, J = 7.2 Hz, 2H), 3.90-3.86 (m, 1H), 3.53-3.47 (m, 4H), 2.90 (dd, J1 = 10.4 Hz, J2 = 47.6 Hz, 2H), 2.13-2.05 (m, 1H), 1.78-1.73 (m, 1H), 1.59-1.56 (m, 2H), 1.54-1.51 (m, 2H), 1.28 (t, J = 7.1 Hz, 3H) |
| 63ai | $^1$H NMR (400 MHz, MeOH-d4): δ ppm 8.06 (d, J = 8.72 Hz, 1H), 8.01 (s, 1H), 7.94 (s, 2H), 7.76 (d, J = 8.28 Hz, 2H), 7.64 (d, J = 8.16 Hz, 2H), 7.31 (d, J = 8.68 Hz, 1H), 6.66 (q, J = 7.32 Hz, 1H), 5.56 (s, 1H), 4.18 (q, J = 7.04 Hz, 2H), 3.84-3.80 (m, 1H), 3.51 (m, 4H), 2.89 (d, J = 10.96 Hz, 1H), 2.75 (d, J = 11 Hz, 1H), 2.68(s, 3H), 2.10-2.01 (m, 1H), 1.76-1.71 (m, 1H), 1.54-1.49 (m, 4H), 1.25 (t, J = 7.12 Hz, 3H) |
| 63aj | $^1$H NMR (400 MHz, MeOH-d4): δ ppm 7.69 (d, J = 1.8 Hz, 1H), 7.60-7.57 (d, 1H), 7.48 (dd, J1 = 2.44, J2 = 8.6 Hz, 1H), 6.96 (q, J = 7.32 Hz, 1H), 5.56 (s, 1H), 4.19 (q, J = 7.12 Hz, 2H), 3.86-3.82 (m, 1H), 3.54 (m, 4H), 2.91 (d, J = 11 Hz, 1H), 2.77 (d, J = 11 Hz, 1H), 2.14-2.08 (m, 1H), 1.79-1.73 (m, 1H), 1.55 (m, 4H), 1.27 (t, J = 7.12 Hz, 3H) |
| 63ak | $^1$H NMR (400 MHz, MeOH-d4): δ ppm 7.91 (s, 1H), 7.71 (dd, J1 = 6.12 Hz, J2 = 1.96 Hz, 1H), 7.63 (m, 2H), 7.56-7.49 (m, 7H), 7.39-7.35 (m, 2H), 6.74 (q, J = 6.88 Hz, 1H), 5.50(s, 1H), 4.18 (q, J = 6.96 Hz, 2H), 3.83 (m, 1H), 3.50 (m, 4H), 2.89 (d, J = 11.04 Hz, 1H), 2.75 (d, J = 11 Hz, 1H), 2.12-2.06 (m, 1H), 1.76-1.71 (m, 1H), 1.54-1.49 (m, 4H), 1.27 (t, J = 7.12 Hz, 3H) |
| 63al | $^1$H NMR (400 MHz, MeOH-d4): δ ppm 0.84 (t, J = 7.1 Hz, 8H), 1.26 (t, J = 7.1 Hz, 8H), 1.50 (dt, J = 11.1, 5.8 Hz, 4H), 1.73 (dd, J = 13.1, 7.1 Hz, 1H), 2.06 (dd, J = 13.1, 8.8 Hz, 1H), 2.38 (s, 3H), 2.73 (d, J = 11.0 Hz, 1H), 2.88 (d, J = 11.0 Hz, 1H), 3.51 (m, 4H), 3.81 (dd, J = 8.7, 7.1 Hz, 1H), 4.00 (qd, J = 7.1, 4.5 Hz, 2H), 4.17 (qd, J = 7.1, 1.5 Hz, 2H), 5.74 (s, 1H), 6.39 (d, J = 2.3 Hz, 1H), 6.85 (q, J = 6.7 Hz, 1H), 7.45 (m, 5H), 7.80 (m, 2H), 7.90 (d, J = 2.4 Hz, 1H) |
| 63am | $^1$H NMR (400 MHz, MeOH-d4): δ ppm 0.89 (m, 1H), 1.26 (m, 7H), 1.40 (t, J = 7.1 Hz, 3H), 1.51 (m, 4H), 1.73 (dd, J = 13.1, 7.2 Hz, 1H), 2.05 (m, 1H), 2.40 (s, 3H), 2.74 (d, J = 11.0 Hz, 1H), 2.88 (d, J = 11.0 Hz, 1H), 3.53 (m, 4H), 3.81 (dd, J = 8.8, 7.1 Hz, 1H), 4.18 (qd, J = 7.1, 2.5 Hz, 2H), 4.39 (q, J = 7.1 Hz, 2H), 5.73 (s, 1H), 6.43 (d, J = 2.4 Hz, 1H), 6.82 (q, J = 6.6 Hz, 1H), 7.57 (t, J = 7.8 Hz, 1H), 7.68 (d, J = 1.9 Hz, 1H), 7.79 (m, 2H), 7.90 (dt, J = 8.0, 1.4 Hz, 1H), 8.02 (m, 2H), 8.28 (d, J = 1.9 Hz, 1H) |
| 63an | $^1$H NMR (400 MHz, MeOH-d4): δ ppm 1.33 (dt, J = 54.3, 7.1 Hz, 6H), 1.50 (dt, J = 10.8, 5.8 Hz, 4H), 1.73 (dd, J = 13.1, 7.2 Hz, 1H), 2.07 (dd, J = 13.1, 8.8 Hz, 1H), 2.40 (s, 3H), 2.74 (d, J = 11.0 Hz, 1H), 2.88 (d, J = 11.0 Hz, 1H), 3.52 (m, 4H), 3.82 (dd, J = 8.7, 7.2 Hz, 1H), 4.18 (qd, J = 7.1, 1.5 Hz, 2H), 4.38 (q, J = 7.1 Hz, 2H), 5.74 (s, 1H), 6.43 (d, J = 2.3 Hz, 1H), 6.84 (q, J = 6.6 Hz, 1H), 7.77 (m, 5H), 8.00 (d, J = 2.3 Hz, 1H), 8.09 (m, 2H) |
| 63ao | $^1$H NMR (400 MHz, MeOH-d4): δ ppm 1.27 (t, J = 7.1 Hz, 3H), 1.54 (m, 4H), 1.76 (dd, J = 13.1, 7.2 Hz, 1H), 2.11 (dd, J = 13.1, 8.7 Hz, 1H), 2.77 (dd, J = 11.0, 1.1 Hz, 1H), 2.91 (d, J = 11.0 Hz, 1H), 3.53 (td, J = 11.9, 11.4, 4.9 Hz, 4H), 3.84 (dd, J = 8.7, 7.2 Hz, 1H), 4.19 (qd, J = 7.2, 1.6 Hz, 2H), 5.53 (s, 1H), 7.15 (t, J = 8.0 Hz, 1H), 7.27 (q, J = 8.0 Hz, 1H), 7.69 (m, 2H) |
| 63ap | $^1$H NMR (400 MHz, CDCl3): δ ppm 1.28 (m, 4H), 1.56 (dq, J = 25.2, 5.5, 4.9 Hz, 4H), 1.78 (dd, J = 13.1, 6.9 Hz, 1H), 2.12 (m, 1H), 2.90 (d, J = 10.7 Hz, 1H), 2.99 (d, J = 10.6 Hz, 1H), 3.49 (dt, J = 11.5, 5.7 Hz, 4H), 3.94 (dd, J = 8.8, 6.9 Hz, 1H), 4.21 (q, J = 7.1 Hz, 2H), 4.58 (s, 2H), 5.43 (s, 1H), 6.55 (q, J = 6.8 Hz, 1H), 7.24 (m, 3H), 7.41 (m, 3H), 7.65 (m, 2H) |
| 63aq | $^1$H NMR (400 MHz, CDCl3): δ ppm 0.84 (m, 2H), 1.14 (s, 1H), 1.28 (t, J = 7.1 Hz, 3H), 1.53 (m, 4H), 1.74 (dd, J = 13.1, 6.8 Hz, 1H), 2.05 (m, 1H), 2.43 (s, 3H), 2.82 (d, J = 10.5 Hz, 1H), 2.94 (d, J = 10.5 Hz, 1H), 3.46 (dt, J = 14.0, 5.8 Hz, 4H), 3.86 (dd, J = 8.8, 6.7 Hz, 1H), 4.19 (q, J = 7.1 Hz, 2H), 4.35 (s, 2H), 5.40 (s, 1H), 6.61 (q, J = 6.8 Hz, 1H), 7.33 (m, 5H), 7.65 (d, J = 8.5 Hz, 1H) |
| 63ar | $^1$H NMR (400 MHz, MeOH-d4): δ ppm 1.27 (t, J = 7.1 Hz, 4H), 1.54 (dt, J = 7.9, 4.7 Hz, 4H), 1.76 (dd, J = 13.1, 7.2 Hz, 1H), 2.12 (m, 1H), 2.78 (m, 1H), 2.90 (m, 1H), 3.52 (m, 4H), 3.85 (td, J = 9.2, 8.8, 7.3 Hz, 1H), 4.19 (qd, J = 7.1, 1.6 Hz, 2H), 4.86 (d, J = 0.8 Hz, 11H), 5.51 (d, J = 13.8 Hz, 1H), 6.52 (q, J = 6.7 Hz, 1H), 7.34 (d, J = 2.2 Hz, 1H), 7.51 (dd, J = 8.5, 2.2 Hz, 1H), 7.75 (m, 5H) |

TABLE 18b-continued

| NMR Data for Compounds of Table 18a | |
|---|---|
| Ex. No. | NMR |
| 63as | $^1$H NMR (400 MHz, MeOH-d4): δ ppm 1.32 (t, J = 7.1 Hz, 3H), 1.67 (m, 4H), 2.05 (dd, J = 13.6, 8.8 Hz, 1H), 2.46 (d, J = 45.5 Hz, 7H), 2.66 (s, 1H), 3.28 (s, 2H), 3.69 (m, 4H), 4.32 (qd, J = 7.1, 2.3 Hz, 2H), 4.58 (t, J = 8.7 Hz, 1H), 6.43 (d, J = 2.4 Hz, 1H), 6.85 (q, J = 6.3 Hz, 1H), 7.37 (m, 2H), 7.66 (m, 3H), 7.79 (m, 2H), 7.97 (d, J = 2.4 Hz, 1H) |
| 63at | $^1$H NMR (MeOH-d4): δ ppm 1.28 (m, 15H), 1.53 (m, 13H), 1.76 (dd, J = 13.1, 7.3 Hz, 3H), 1.86 (s, 1H), 2.12 (dd, J = 13.1, 8.8 Hz, 3H), 2.79 (d, J = 11.0 Hz, 3H), 2.92 (d, J = 11.0 Hz, 3H), 3.51 (qdt, J = 18.0, 13.3, 5.9 Hz, 12H), 3.63 (d, J = 8.6 Hz, 1H), 3.87 (m, 3H), 4.19 (qd, J = 7.1, 1.6 Hz, 5H), 5.51 (s, 3H), 6.68 (q, J = 6.7 Hz, 3H), 7.29 (m, 6H), 7.47 (m, 19H), 7.65 (m, 5H) |
| 63au | $^1$H NMR (MeOH-d4): δ ppm 1.13 (s, 2H), 1.26 (t, J = 7.3 Hz, 4H), 1.49 (m, 6H), 1.73 (dd, J = 13.1, 7.2 Hz, 1H), 2.06 (dd, J = 13.1, 8.7 Hz, 1H), 2.38 (d, J = 12.1 Hz, 7H), 2.73 (d, J = 11.0 Hz, 1H), 2.87 (d, J = 11.0 Hz, 1H), 3.53 (tt, J = 14.1, 5.1 Hz, 5H), 3.81 (m, 1H), 4.18 (tt, J = 7.8, 3.6 Hz, 2H), 4.81 (s, 2H), 4.97 (d, J = 15.9 Hz, 1H), 5.74 (s, 1H), 6.41 (d, J = 2.1 Hz, 1H), 6.78 (q, J = 6.7 Hz, 1H), 7.26 (d, J = 7.9 Hz, 2H), 7.57 (m, 5H), 7.73 (m, 2H), 7.96 (d, J = 2.3 Hz, 1H) |
| 63av | $^1$H NMR (MeOH-d4): δ ppm 1.26 (m, 3H), 1.51 (dt, J = 10.6, 5.6 Hz, 4H), 1.74 (dd, J = 13.1, 7.2 Hz, 1H), 2.07 (dd, J = 13.1, 8.8 Hz, 1H), 2.40 (s, 7H), 2.74 (d, J = 10.9 Hz, 1H), 2.88 (d, J = 11.0 Hz, 1H), 3.54 (m, 4H), 3.81 (dd, J = 8.8, 7.1 Hz, 1H), 4.18 (qd, J = 7.1, 1.6 Hz, 2H), 5.74 (s, 1H), 6.42 (d, J = 2.4 Hz, 1H), 6.79 (q, J = 6.6 Hz, 1H), 7.21 (d, J = 7.5 Hz, 1H), 7.33 (t, J = 7.6 Hz, 1H), 7.46 (m, 2H), 7.62 (d, J = 1.9 Hz, 1H), 7.75 (m, 2H), 7.98 (d, J = 2.4 Hz, 1H) |
| 63aw | $^1$H NMR (MeOH-d4): δ ppm 0.90 (m, 1H), 1.27 (m, 5H), 1.51 (dt, J = 10.5, 5.6 Hz, 4H), 1.75 (dd, J = 13.1, 7.2 Hz, 1H), 2.09 (dd, J = 13.1, 8.7 Hz, 1H), 2.40 (s, 3H), 2.76 (d, J = 11.0 Hz, 1H), 2.90 (d, J = 11.0 Hz, 1H), 3.54 (m, 4H), 3.84 (dd, J = 8.7, 7.2 Hz, 1H), 4.19 (qd, J = 7.1, 1.7 Hz, 2H), 5.73 (s, 1H), 6.43 (d, J = 2.4 Hz, 1H), 6.84 (q, J = 6.5 Hz, 1H), 7.64 (m, 3H), 7.80 (m, 3H), 8.01 (d, J = 2.4 Hz, 1H) |
| 63ax | $^1$H NMR (400 MHz, Chloroform-d): δ ppm 1.27 (m, 9H), 1.52 (dt, J = 22.3, 5.4 Hz, 4H), 1.72 (d, J = 13.1 Hz, 1H), 2.05 (m, 1H), 2.25 (ddd, J = 18.1, 13.9, 8.2 Hz, 2H), 2.63 (m, 2H), 2.82 (d, J = 10.5 Hz, 1H), 2.94 (d, J = 10.4 Hz, 1H), 3.48 (dd, J = 13.6, 7.4 Hz, 5H), 3.63 (m, 1H), 3.81 (m, 4H), 4.19 (q, J = 7.1 Hz, 2H), 4.86 (s, 2H), 5.46 (s, 1H), 6.46 (m, 1H), 7.22 (d, J = 2.2 Hz, 1H), 7.34 (dd, J = 8.5, 2.2 Hz, 1H), 7.59 (d, J = 8.5 Hz, 1H) |
| 63ay | $^1$H NMR (400 MHz, MeOH-d4): δ ppm 1.35 (d, J = 2.64 Hz, 4 H) 1.61-1.86 (m, 5 H) 2.04-2.16 (m, 1 H) 2.42 (d, J = 1.27 Hz, 3 H) 2.48-2.60 (m, 1 H) 3.55-4.03 (m, 4 H) 4.25-4.44 (m, 2 H) 4.55-4.70 (m, 1 H) 6.45 (s, 1 H) 6.90-7.04 (m, 1 H) 7.61 (s, 2 H) 7.68-7.79 (m, 1 H) 7.88-8.00 (m, 1 H) |
| 63az | $^1$H NMR (400 MHz, MeOH-d4): δ ppm 1.25 (t, J = 7.15 Hz, 3 H) 1.43-1.60 (m, 4 H) 1.78 (dd, J = 13.13, 7.42 Hz, 1 H) 2.13 (dd, J = 13.08, 8.74 Hz, 1 H) 2.35 (s, 3 H) 2.73-3.01 (m, 2 H) 3.39-3.63 (m, 4 H) 3.94 (t, J = 7.91 Hz, 1 H) 4.18 (qd, J = 7.13, 1.78 Hz, 2 H) 5.65 (s, 1 H) 6.38 (d, J = 2.39 Hz, 1 H) 6.79 (q, J = 6.74 Hz, 1 H) 7.41-7.54 (m, 2 H) 7.68 (d, J = 8.35 Hz, 1 H) 7.91 (d, J = 2.34 Hz, 1 H) |
| 63ba | $^1$H NMR (400 MHz, MeOH-d4): δ ppm 1.33 (t, J = 7.13 Hz, 3 H), 1.53-1.75 (m, 4 H), 2.05 (dd, J = 13.62, 8.88 Hz, 1 H), 2.49 (dd, J = 13.57, 8.74 Hz, 1 H), 3.27 (s, 2 H), 3.42-3.74 (m, 4 H), 3.84(s, 3 H), 4.25-4.40 (m, 2 H), 4.58 (t, J = 8.79 Hz, 1 H), 5.60 (s, 1 H), 6.59-6.71 (m, 1 H), 6.92 (ddd, J = 8.22, 2.54, 0.76 Hz, 1 H), 7.11-7.16 (m, 1 H), 7.16-7.24 (m, 1 H), 7.31-7.38 (m, 1 H), 7.54-7.61 (m, 2 H), 7.62-7.70 (m, 2 H) |
| 63bb | $^1$H NMR (400 MHz, dichloromethane-d2): δ ppm 1.29 (t, J = 7.15 Hz, 3 H) 1.47-1.85 (m, 4 H) 2.01 (dd, J = 13.52, 8.30 Hz, 1 H) 2.30-2.36(m, 1 H) 2.38 (s, 3 H) 3.27-3.41 (m, 2 H) 3.41-3.67 (m, 4 H) 3.82 (s, 3 H) 4.26 (qd, J = 7.17, 4.00 Hz, 2 H) 4.45 (t, J = 8.49 Hz, 1 H) 4.96 (br. s, 2H) 5.49 (s, 1 H) 6.31 (d, J = 2.25 Hz, 1 H) 6.62 (q, J = 6.90 Hz, 1 H) 6.88 (d, J = 2.59 Hz, 1 H) 6.96 (dd, J = 8.81, 2.61 Hz, 1 H) 7.61 (d, J = 8.74 Hz, 1 H) 7.66 (d, J = 2.25 Hz, 1 H) |
| 63bc | $^1$H NMR (400 MHz, MeOH-d4): δ ppm 1.35 (t, J = 7.22 Hz, 3 H) 1.67-1.89 (m, 4 H) 2.05-2.18 (m, 1 H) 2.49-2.62 (m, 1 H) 3.56-3.90 (m, 4 H) 4.35 (dd, J = 7.13, 1.85 Hz, 2 H) 4.65 (s, 1 H) 5.97 (s, 1 H) 6.58-6.72 (m, 1 H) 7.14 (br. s., 1 H) 7.41 (d, J = 9.18 Hz, 1 H) 7.45-7.53 (m, 2 H) 7.64-7.72 (m, 2 H) 7.73-7.82 (m, 2 H) |
| 63bd | $^1$H NMR (400 MHz, MeOH-d4): δ ppm 1.28-1.39 (m, 4 H) 1.74 (d, J = 18.35 Hz, 4 H) 2.03-2.14 (m, 1 H) 2.35 (d, J = 12.89 Hz, 6 H) 2.43 (s, 3 H) 2.46-2.57 (m, 1 H) 3.62-3.96 (m, 4 H) 4.34 (dd, J = 7.13, 1.85 Hz, 2 H) 4.56-4.68 (m, 1 H) 6.44 (d, J = 2.34 Hz, 1 H) 6.50-6.61 (m, 1 H) 6.81-6.96 (m, 1 H) 7.26 (d, J = 7.81 Hz, 1 H) 7.40-7.47 (m, 1 H) 7.50 (s, 1 H) 7.68 (d, J = 1.37 Hz, 1 H) 7.78 (s, 1 H) 7.82 (d, J = 1.37 Hz, 1 H) 7.98; (d, J = 2.15 Hz, 1 H) |
| 63be | $^1$H NMR (400 MHz, MeOH-d4): δ ppm 1.30 (m, 6 H) 1.59 (m, 4 H) 2.02 (m, 1 H) 2.38 (s, 3 H) 2.45 (dd, J = 13.54, 8.76 Hz, 1 H) 2.72 (q, J = 7.60 Hz, 2 H) 3.24 (m, 2 H) 3.58 (m, 4 H) 4.32 (m, 2 H) 4.53 (t, J = 8.76 Hz, 1 H) 5.72 (s, 1 H) 6.38 (d, J = 2.20 Hz, 1 H) 6.71 (m, 1 H) 7.25 (d, J = 1.56 Hz, 1 H) 7.36 (dd, J = 8.10, 1.61 Hz, 1 H) 7.63 (d, J = 8.10 Hz, 1 H) 7.85 (d, J = 2.29 Hz, 1 H) |
| 63bf | $^1$H NMR (400 MHz, MeOH-d4): δ ppm 0.96 (t, J = 7.35 Hz, 2 H) 1.32 (t, J = 7.15 Hz, 4 H) 1.63 (m, 6 H) 2.00 (dd, J = 13.59, 8.61 Hz, 1 H) 2.37 (s, 3 H) 2.42 (m, 1 H) 2.66 (m, 2 H) 3.21 (m, 2 H) 3.58 (m, 4 H) 4.31 (m, 2 H) 4.49 (t, J = 8.69 Hz, 1 H) 5.72 (s, 1 H) 6.38 (d, J = 2.29 Hz, 1 H) 6.71 (q, J = 6.67 Hz, 1 H) 7.23 (d, J = 1.66 Hz, 1 H) 7.34 (dd, J = 8.10, 1.66 Hz, 1 H) 7.63 (d, J = 8.10 Hz, 1 H) 7.85 (d, J = 2.29 Hz, 1 H) |

TABLE 18b-continued

| NMR Data for Compounds of Table 18a | |
|---|---|
| Ex. No. | NMR |
| 63bg | $^1$H NMR (400 MHz, MeOH-d4): δ ppm 0.95 (t, J = 7.35 Hz, 3 H) 1.32 (t, J = 7.15 Hz, 4 H) 1.63 (m, 6 H) 2.02 (m, 1 H) 2.38 (s, 3 H) 2.45 (dd, J = 13.54, 8.76 Hz, 1 H) 2.69 (m, 2 H) 3.24 (m, 2 H) 3.58 (m, 4 H) 4.32 (m, 2 H) 4.53 (t, J = 8.74 Hz, 1 H) 5.72 (s, 1 H) 6.38 (d, J = 2.29 Hz, 1 H) 6.71 (m, 1 H) 7.23 (d, J = 1.61 Hz, 1 H) 7.34 (dd, J = 8.15, 1.61 Hz, 1 H) 7.62 (d, J = 8.15 Hz, 1 H) 7.85 (d, J = 2.34 Hz, 1 H) |
| 63bh | $^1$H NMR (400 MHz, CHLOROFORM-d): δ ppm 1.18-1.36 (m, 3 H) 1.43 (t, J = 6.74 Hz, 3 H) 1.54-2.29 (m, 6 H) 2.39 (br. s., 3 H) 3.78 (br. s., 4 H) 4.26 (br. s., 2 H) 4.42 (d J = 6.15 Hz, 2 H) 5.53 (br. s., 1 H) 6.36 (s, 1 H) 6.59 (br. s., 1 H) 7.48 (d, J = 7.96 Hz, 1 H)7.61(br. s., 1 H) 8.16 (d, J = 8.05 Hz, 1 H) 8.34 (br. s., 1 H) |
| 63bi | $^1$H NMR (400 MHz, MeOH-d4): δ ppm 1.24-1.30 (m, 5 H) 1.37 (t, J = 7.13 Hz, 3 H) 1.45-1.62 (m, 4 H) 1.84 (dd, J = 13.32, 7.86 Hz, 1 H) 1.95 (s, 4 H) 2.22 (dd, J = 13.30, 8.86 Hz, 1 H) 2.38 (s, 3 H) 2.88-3.09 (m, 2 H) 3.41-3.71 (m, 4 H) 4.10 (t, J = 8.25 Hz, 1 H) 4.22 (qd, J = 7.13, 2.00 Hz, 2 H) 4.37 (q, J = 7.13 Hz, 2 H) 5.66 (s, 1 H) 6.41 (d, J = 2.39 Hz, 1 H) 6.84 (q, J = 6.54 Hz, 1 H) 7.83 (d, J = 8.30 Hz, 1 H) 7.94 (d, J = 2.34 Hz, 1 H) 7.99 (d, J = 1.61 Hz, 1 H) 8.08 (dd, J = 8.27, 1.64 Hz, 1 H) |
| 63bj | $^1$H NMR (400 MHz, MeOH-d4): δ ppm 1.31 (td, J = 7.13, 3.22 Hz, 6 H) 1.52-1.64 (m, 4 H) 1.97 (s, 1 H) 2.01 (dd, J = 13.59, 8.81 Hz, 1 H) 2.37 (s, 3 H) 2.44 (dd, J = 13.62, 8.74 Hz, 1 H) 3.18-3.26 (m, 2 H) 3.43-3.68 (m, 4 H) 4.19-4.34 (m, 4 H) 4.53 (t, J = 8.74 Hz, 1 H) 5.75 (s, 1 H) 6.40 (d, J = 2.39 Hz, 1 H) 6.55 (d, J = 16.06 Hz, 1 H) 6.95 (q, J = 6.56 Hz, 1 H) 7.46 (d, J = 8.30 Hz, 1 H) 7.68 (d, J = 16.06 Hz, 1 H) 7.80 (dd, J = 8.32, 2.03 Hz, 1 H) 7.87 (s, 1 H) 7.91 (d, J = 2.39 Hz, 1 H) |
| 63bk | $^1$H NMR (400 MHz, MeOH-d4): δ ppm 0.92 (t, J = 7.37 Hz, 3 H) 1.32 (dq, J = 14.94, 7.38 Hz, 2 H) 1.50-1.68 (m, 6 H) 2.06 (dd, J = 13.37, 7.22 Hz, 1 H) 2.31 (dd, J = 13.45, 9.25 Hz, 1 H) 2.37 (s, 3 H) 2.69 (t, J = 7.59 Hz, 2 H) 3.06-3.29 (m, 2 H) 3.41-3.76 (m, 4 H) 4.08 (dd, J = 9.20, 7.25 Hz, 1 H) 5.75 (s, 1 H) 6.36 (d, J = 2.15 Hz, 1 H) 6.69 (q, J = 6.62 Hz, 1 H) 7.28-7.33 (m, 1 H) 7.34-7.39 (m, 1 H) 7.53 (s, 1 H) 7.82 (d, J = 2.29 Hz, 1 H) |
| 63bl | $^1$H NMR (400 MHz, DMSO-d6): δ ppm 1.50-1.73 (m, 4 H) 1.80 (quin, J = 7.52 Hz, 2 H) 1.90 (dd, J = 13.23, 9.22 Hz, 1 H) 2.15-2.26 (m, 2 H) 2.27-2.41 (m, 4 H) 2.69 (t, J = 7.66 Hz, 2 H) 3.00-3.20 (m, 2 H) 3.69 (br. s., 4 H) 4.33-4.52 (m, 1 H) 6.14 (br. s., 1 H) 6.38 (d, J = 2.29 Hz, 1 H) 7.05 (br. s., 1 H) 7.37-7.52 (m, 3 H) 7.76 (br. s., 1 H) 8.02 (d, J = 2.29 Hz, 1 H) 8.97 (d, J = 5.32 Hz, 1 H) 10.42 (br. s., 1 H) |
| 63bm | $^1$H NMR (400 MHz, MeOH-d4): δ ppm 1.31 (t, J = 7.15 Hz, 3 H) 1.52-1.70 (m, 4 H) 1.90 (dd, J = 6.30, 1.22 Hz, 3 H) 1.97 (dd, J = 13.52, 8.44 Hz, 1 H) 2.35-2.41 (m, 4 H) 3.06-3.24 (m, 2 H) 3.42-3.79 (m, 4 H) 4.21-4.35 (m, 2 H) 4.40 (t, J = 8.57 Hz, 1 H) 5.75 (s, 1 H) 6.27-6.54 (m, 3 H) 6.75 (q, J = 6.64 Hz, 1 H) 7.32 (d, J = 8.25 Hz, 1 H) 7.52 (dd, J = 8.30, 2.00 Hz, 1 H) 7.64 (s, 1 H) 7.83 (d, J = 2.29 Hz, 1 H) |
| 63bn | $^1$H NMR (400 MHz, MeOH-d4): δ ppm 1.32 (t, J = 7.15 Hz, 3 H) 1.49-1.70 (m, 4 H) 2.01 (dd, J = 13.59, 8.76 Hz, 1 H) 2.29 (s, 3 H) 2.32 (s, 3 H) 2.40 (s, 3 H) 2.40-2.44 (m, 1 H) 3.24 (s, 2 H) 3.43-3.71 (m, 4 H) 4.22-4.41 (m, 2 H) 4.56 (t, J = 8.74 Hz, 1 H) 5.80 (s, 1 H) 6.41 (d, J = 2.29 Hz, 1 H) 6.81-6.92 (m, 1 H) 7.20 (d, J = 7.81 Hz, 1 H) 7.26-7.32 (m, 1 H) 7.35 (s, 1 H) 7.45 (d, J = 8.30 Hz, 1 H) 7.73 (dd, J = 8.27, 2.12 Hz, 1 H) 7.88-7.90 (m, 2 H) |
| 63bo | $^1$H NMR (400 MHz, MeOH-d4): δ ppm 0.92 (t, J = 7.35 Hz, 3 H) 1.32 (t, J = 7.13 Hz, 3 H) 1.49-1.76 (m, 6 H) 1.94-2.06 (m, 1 H) 2.37 (s, 3 H) 2.43 (dd, J = 13.57, 8.79 Hz, 1 H) 2.66 (t, J = 7.52 Hz, 2 H)3.13-3.28 (m, 2 H) 3.43-3.76 (m, 4 H) 4.21-4.39 (m, 2 H) 4.50 (t, J = 8.66 Hz, 1 H) 5.74 (s, 1 H) 6.37 (d, J = 2.29 Hz, 1 H) 6.70 (q, J = 6.69 Hz, 1 H) 7.26-7.33 (m, 1 H) 7.34-7.42 (m, 1 H) 7.53 (s, 1 H) 7.82 (d, J = 2.29 Hz, 1 H) |
| 63bp | $^1$H NMR (400 MHz, MeOH-d4): δ ppm 1.25 (t, J = 7.61 Hz, 3 H) 1.33 (t, J = 7.15 Hz, 3 H) 1.57-1.71 (m, 4 H) 2.04 (dd, J = 13.93, 8.52 Hz, 1 H) 2.37 (s, 3 H) 2.47 (dd, J = 13.62, 8.74 Hz, 1 H) 2.72 (q, J = 7.61 Hz, 2 H) 3.26 (d, J = 1.51 Hz, 2 H) 3.44-3.77 (m, 4 H) 4.23-4.43 (m, 2 H) 4.57 (t, J = 8.79 Hz, 1 H) 5.76 (s, 1 H) 6.37 (d, J = 2.20 Hz, 1 H) 6.63-6.78 (m, 1 H) 7.27-7.35 (m, 1 H) 7.36-7.46 (m, 1 H) 7.55 (s, 1 H) 7.81 (d, J = 2.29 Hz, 1 H) |
| 63bq | $^1$H NMR (400 MHz, MeOH-d4): δ ppm 0.92 (t, J = 7.35 Hz, 3 H) 1.22-1.42 (m, 5 H) 1.49-1.75 (m, 6 H) 1.94-2.08 (m, 1 H) 2.37 (s, 3 H) 2.44 (dd, J = 13.57, 8.74 Hz, 1 H) 2.68 (t, J = 7.61 Hz, 2 H) 3.15-3.29 (m, 2 H) 3.42-3.76 (m, 4 H) 4.23-4.40 (m, 2 H) 4.53 (t, J = 8.74 Hz, 1 H) 5.75 (s, 1 H) 6.37 (d, J = 2.34 Hz, 1 H) 6.70 (q, J = 6.69 Hz, 1 H) 7.27-7.33 (m, 1 H) 7.34-7.41 (m, 1 H) 7.53 (s, 1 H) 7.82 (d, J = 2.34 Hz, 1 H) |
| 63br | $^1$H NMR (400 MHz, MeOH-d4): δ ppm 1.33 (t, J = 7.13 Hz, 3 H) 1.53-1.74 (m, 4 H) 2.05 (dd, J = 13.62, 8.83 Hz, 1 H) 2.38 (s, 3 H) 2.48 (dd, J = 13.62, 8.79 Hz, 1 H) 3.28 (s, 2 H) 3.44-3.79 (m, 4 H) 4.22-4.43 (m, 2 H) 4.59 (t, J = 8.79 Hz, 1 H) 5.37 (d, J = 11.08 Hz, 1 H) 5.73-5.96 (m, 2 H) 6.39 (d, J = 2.34 Hz, 1 H) 6.68-6.95 (m, 2 H) 7.40 (d, J = 8.25 Hz, 1 H) 7.65 (dd, J = 8.27, 1.98 Hz, 1 H) 7.73 (s, 1 H) 7.87 (d, J = 2.34 Hz, 1 H) |
| 63bs | $^1$H NMR (400 MHz, MeOH-d4): δ ppm 1.11 (t, J = 7.47 Hz, 3 H) 1.33 (t, J = 7.15 Hz, 3 H) 1.51-1.72 (m, 4 H) 2.04 (dd, J = 13.62, 8.83 Hz, 1 H) 2.18-2.33 (m, 2 H) 2.38 (s, 3 H) 2.47 (dd, J = 13.59, 8.81 Hz, 1 H) 3.26 (s, 2 H) 3.44-3.78 (m, 4 H) 4.19-4.43 (m, 2 H) 4.58 (t, J = 8.79 Hz, 1 H) 5.79 (s, 1 H) 6.30-6.53 (m, 3 H) 6.69-6.84 (m, 1 H) 7.33 (d, J = 8.25 Hz, 1 H) 7.55 (dd, J = 8.30, 2.00 Hz, 1 H) 7.65 (s, 1 H) 7.84 (d, J = 2.34 Hz, 1 H) |
| 63bt | $^1$H NMR (400 MHz, MeOH-d4): δ ppm 1.30 (t, J = 7.13 Hz, 3 H) 1.45-1.65 (m, 4 H) 1.79-1.91 (m, 1 H) 2.16-2.32 (m, 1 H) 3.03 (s, 2 H) 3.51 (br. s., 4 H) 3.75-3.81 (m, 1 H) 4.07-4.17 (m, 1 H) 4.20-4.32 (m, 2 H) 5.55 (s, 1 H) 6.65 (d, J = 2.34 Hz, 1 H) 7.15-7.28 (m, 1 H) 7.36-7.46 (m, 1 H) 7.57 (d, J = 2.15 Hz, 1 H) 7.62-7.70 (m, 1 H) 7.73 (d, J = 2.15 Hz, 1 H) |

TABLE 18b-continued

| NMR Data for Compounds of Table 18a | |
|---|---|
| Ex. No. | NMR |
| 63bu | $^1$H NMR (400 MHz, MeOH-d4): δ ppm 1.29 (t, J = 7.13 Hz, 3 H) 1.40-1.61 (m, 4 H) 1.71-1.86 (m, 1 H) 2.07-2.22 (m, 1 H) 2.86 (s, 1 H) 2.94 (s, 1 H) 3.50 (d, J = 4.69 Hz, 4 H) 4.00 (s, 4 H) 4.22 (dd, J = 7.22, 0.98 Hz, 2 H) 5.57 (s, 1 H) 6.61 (d, J = 2.15 Hz, 1 H) 7.13-7.28 (m, 1 H) 7.35-7.50 (m, 2 H) 7.55 (d, J = 1.17 Hz, 1 H) 7.72 (d, J = 2.34 Hz, 2 H) |
| 63bv | $^1$H NMR (400 MHz, MeOH-d4): δ ppm 1.35 (t, J = 7.13 Hz, 3 H) 1.57-1.83 (m, 4 H) 1.99-2.16 (m, 1 H) 2.56 (s, 4 H) 3.31 (s, 2 H) 3.68 (br. s., 4 H) 4.03 (s, 3 H) 4.35 (dd, J = 7.03, 2.15 Hz, 2 H) 4.62 (s, 1 H) 5.70 (s, 1 H) 6.70 (d, J = 6.83 Hz, 1 H) 7.42 (dd, J = 8.49, 0.88 Hz, 1 H) 7.60-7.72 (m, 3 H) 7.73-7.86 (m, 3 H) |
| 63bw | $^1$H NMR (400 MHz, MeOH-d4): δ ppm 1.35 (t, J = 7.13 Hz, 3 H) 1.67-1.90 (m, 4 H) 2.03-2.18 (m, 1 H) 2.47-2.61 (m, 1 H) 2.72 (s, 3 H) 3.34 (br. s., 2 H) 3.56-3.87 (m, 4 H) 4.17 (s, 3 H) 4.35 (dd, J = 7.13, 2.05 Hz, 2 H) 4.64 (s, 1 H) 5.89-6.04 (m, 1 H) 6.59-6.75 (m, 1 H) 7.45 (d, J = 0.98 Hz, 1 H) 7.70 (d, J = 8.20 Hz, 2 H) 7.77 (s, 1 H) 7.79-7.92 (m, 3 H) |
| 63bx | $^1$H NMR (400 MHz, MeOH-d4): δ ppm 1.35 (t, J = 7.13 Hz, 3 H) 1.77 (br. s., 4 H) 2.04-2.15 (m, 1 H) 2.47-2.58 (m, 1 H) 3.09 (s, 2 H) 3.57 (t, J = 6.74 Hz, 6 H) 4.28-4.43 (m, 2 H) 4.57-4.69 (m, 1H) 5.80-5.92 (m, 1 H) 6.60-6.75 (m, 1 H) 7.62 (s, 1 H) 7.69 (d, J = 8.40 Hz, 3 H) 7.74-7.85 (m, 2 H) 8.03 (d, J = 8.00 Hz, 1 H) |
| 63by | $^1$H NMR (400 MHz, MeOH-d4): δ ppm 1.35 (t, J = 7.13 Hz, 3 H) 1.61-1.81 (m, 4 H) 2.00-2.16 (m, 1 H) 2.44-2.59 (m, 1 H) 3.47-3.80 (m, 4 H) 4.35 (dd, J = 7.03, 2.54 Hz, 2 H) 4.63 (s, 1 H) 5.73 (s, 1 H) 6.64-6.83 (m, 1 H) 7.76 (d, J = 8.20 Hz, 2 H) 7.95 (d, J = 8.20 Hz, 2 H) 8.12-8.33 (m, 2 H) 8.36-8.47 (m, 2 H) 8.48-8.68 (m, 1 H) 9.39-9.76 (m, 1 H) |
| 63bz | $^1$H NMR (400 MHz, MeOH-d4): δ ppm 1.10-1.20 (m, 3 H) 1.26 (t, J = 7.13 Hz, 3 H) 1.42-1.64 (m, 4 H) 1.79 (dd, J = 13.15, 7.44 Hz, 1 H) 1.94 (s, 2 H) 2.15 (dd, J = 12.98, 8.69 Hz, 1 H) 2.35 (s, 3 H) 2.62-2.71 (m, 2 H) 2.81-2.87 (m, 1 H) 2.93-3.02 (m, 3 H) 3.40-3.66 (m, 4 H) 3.96 (t, J = 8.18 Hz, 1 H) 4.06 (q, J = 7.18 Hz, 2 H) 4.16-4.25 (m, 2 H) 5.69 (s, 1 H) 6.36 (d, J = 2.25 Hz, 1 H) 6.71 (q, J = 6.67 Hz, 1 H) 7.27 (d, J = 1.56 Hz, 1 H) 7.35 (dd, J = 8.13, 1.83 Hz, 1 H) 7.62 (d, J = 8.20 Hz, 1 H) 7.83 (d, J = 2.29 Hz, 1 H) |
| 63ca | $^1$H NMR (400 MHz, MeOH-d4): δ ppm 1.35 (t, J = 7.13 Hz, 3 H) 1.63-1.82 (m, 4 H) 2.03-2.17 (m, 1 H) 2.47-2.60 (m, 1 H) 3.51-3.83 (m, 4 H) 4.27-4.42 (m, 2 H) 4.57-4.69 (m, 1 H) 5.69-5.88 (m, 1 H) 6.65-6.85 (m, 1 H) 7.71-7.85 (m, 2 H) 7.89-8.01 (m, 2 H) 8.22-8.35 (m, 2 H) 8.36-8.49 (m, 1 H) 8.52-8.60 (m, 1 H) 8.62-8.72 (m, 1 H) 9.56-9.75 (m, 1 H) |
| 63cb | $^1$H NMR (400 MHz, DMSO-d6): δ ppm 1.18 (t, J = 7.10 Hz, 3 H) 1.24 (t, J = 7.13 Hz, 3 H) 1.37-1.63 (m, 4 H) 1.82 (quin, J = 7.52 Hz, 2 H) 1.90 (dd, J = 13.28, 9.42 Hz, 1 H) 2.19-2.41 (m, 6 H) 2.67 (t, J = 7.69 Hz, 2 H) 3.12 (br. s., 2 H) 3.18-3.74 (m, 4 H) 4.05 (q, J = 7.13 Hz, 2 H) 4.15-4.30 (m, 2 H) 4.52 (t, J = 8.49 Hz, 1 H) 5.72 (br. s., 1 H) 6.01 (br. s., 2 H) 6.37 (d, J = 2.15 Hz, 1 H) 6.99 (q, J = 6.87 Hz, 1 H) 7.33-7.44 (m, 2 H) 7.47 (s, 1 H) 8.01 (d, J = 2.25 Hz, 1 H) 9.20 (br. s., 1 H) 10.39 (br. s., 1 H) |
| 63cc | $^1$H NMR (400 MHz, DMSO-d6): δ ppm 1.10-1.20 (m, 3 H) 1.25 (t, J = 7.10 Hz, 3 H) 1.44-1.63 (m, 4 H) 1.82 (quin, J = 7.53 Hz, 2 H) 1.91 (dd, J = 13.28, 9.37 Hz, 1 H) 2.19-2.40 (m, 3 H) 2.60 (t, J = 7.71 Hz, 2 H) 3.13 (br. s., 2 H) 3.40-3.68 (m, 4 H) 4.02 (q, J = 7.09 Hz, 2 H) 4.13-4.33 (m, 2 H) 4.53 (br. s., 1 H) 5.70 (br. s., 1 H) 6.29 (br. s, 2 H) 6.62-6.76 (m, 1 H) 7.28 (d, J = 8.20 Hz, 2 H) 7.43 (d, J = 8.10 Hz, 2 H) 9.21 (br. s., 1 H) 10.43 (br. s., 1 H) |
| 63cd | $^1$H NMR (400 MHz, DMSO-d6): δ ppm 1.15 (t, J = 7.13 Hz, 3 H) 1.24 (t, J = 7.10 Hz, 3 H) 1.39-1.64 (m, 4 H) 1.78-1.97 (m, 3 H) 2.22-2.39 (m, 6 H) 2.66 (t, J = 7.71 Hz, 2 H) 3.11 (br. s., 2 H) 3.38-3.64 (m, 4 H) 3.93-4.07 (m, 2 H) 4.15-4.31 (m, 2 H) 4.52 (br. s., 1 H) 5.73 (br. s., 1 H) 6.05 (br. s., 2 H) 6.38 (d, J = 2.10 Hz, 1 H) 7.00 (q, J = 6.72 Hz, 1 H) 7.30 (d, J = 1.51 Hz, 1 H) 7.33-7.41 (m, 1 H) 7.59 (d, J = 8.05 Hz, 1 H) 8.04 (d, J = 2.29 Hz, 1 H) 9.20 (br. s., 1 H) 10.38 (br. s., 1 H) |
| 63ce | $^1$H NMR (400 MHz, MeOH-d4): δ ppm 1.22-1.30 (m, 3 H) 1.48-1.61 (m, 4 H) 1.82 (dd, J = 13.30, 7.74 Hz, 1 H) 1.94 (s, 3 H) 2.15-2.23 (m, 1 H) 2.38 (s, 3 H) 2.87-2.92 (m, 1 H) 2.96-3.02 (m, 1 H) 3.42-3.64 (m, 4 H) 4.01-4.08 (m, 1 H) 4.16-4.25 (m, 2 H) 5.72 (s, 1 H) 6.41 (d, J = 2.39 Hz, 1 H) 6.81-6.88 (m, 1 H) 7.61-7.66 (m, 1 H) 7.71 (d, J = 1.76 Hz, 1 H) 7.73-7.86 (m, 3 H) 7.97-8.02 (m, 2 H) 8.08 (s, 1 H) |
| 63cf | $^1$H NMR (400 MHz, DMSO-d6): δ ppm 1.25 (t, J = 7.13 Hz, 3 H) 1.45-1.66 (m, 4 H) 1.92 (dd, J = 13.18, 9.42 Hz, 1 H) 2.35 (dd, J = 13.28, 8.54 Hz, 1 H) 3.14 (br. s., 2 H) 3.60 (br. s., 4 H) 4.14-4.31 (m, 2H) 4.54 (br. s., 1 H) 5.75 (br. s., 1 H) 6.56 (q, J = 6.72 Hz, 1 H) 7.47 (t, J = 1.27 Hz, 1 H) 7.65 (s, 2 H) 7.75-7.84 (m, 1 H) 7.89 (d, J = 7.81 Hz, 1 H) 7.93-8.01 (m, 2 H) 9.21 (br. s., 1 H) 10.36 (br. s., 1 H) |
| 63cg | $^1$H NMR (400 MHz, DMSO-d6): δ ppm 1.25 (t, J = 7.10 Hz, 3 H) 1.57 (d, J = 5.37 Hz, 4 H) 1.83-1.99 (m, 1 H) 2.28-2.40 (m, 1 H) 3.14 (br. s., 2 H) 3.58 (br. s., 4 H) 3.81 (s, 3 H) 4.24 (dd, J = 7.13, 2.25 Hz, 2 H) 4.43-4.63 (m, 1 H) 5.62-5.85 (m, 1 H) 6.73 (d, J = 6.78 Hz, 1 H) 6.96-7.16 (m, 3 H) 7.39 (d, J = 2.15 Hz, 1 H) 7.50 (dd, J = 8.74, 7.61 Hz, 1 H) 7.55-7.69 (m, 2 H) 9.09-9.32 (m, 1 H) 10.26-10.47 (m, 1 H) |
| 63ch | $^1$H NMR (400 MHz, MeOH-d4): δ ppm 1.32 (t, J = 7.15 Hz, 3 H) 1.52-1.70 (m, 4 H) 1.93-2.02 (m, 1 H) 2.40 (dd, J = 13.45, 8.71 Hz, 1 H) 3.09-3.24 (m, 2 H) 3.43-3.74 (m, 4 H) 4.25-4.35 (m, 2 H) 4.40 (t, J = 8.57 Hz, 1 H) 5.59 (s, 1 H) 6.61 (q, J = 6.56 Hz, 1 H) 7.32 (d, J = 2.15 Hz, 1 H) 7.49 (dd, J = 8.49, 2.25 Hz, 1 H) 7.61 (d, J = 8.00 Hz, 1 H) 7.65-7.77 (m, 2 H) 7.97-8.10 (m, 1 H) 8.32 (br. s., 1 H) |

TABLE 18b-continued

| NMR Data for Compounds of Table 18a | |
|---|---|
| Ex. No. | NMR |
| 63ci | $^1$H NMR (400 MHz, MeOH-d4): δ ppm 1.32 (t, J = 7.13 Hz, 3 H) 1.50-1.70 (m, 4 H) 1.91-2.02 (m, 1 H) 2.39 (dd, J = 13.50, 8.76 Hz, 1 H) 3.08-3.23 (m, 2 H) 3.41-3.69 (m, 4 H) 4.24-4.34 (m, 2 H) 4.38 (t, J = 8.54 Hz, 1 H) 5.50 (s, 1 H) 6.75 (q, J = 6.96 Hz, 1 H) 6.87 (d, J = 7.66 Hz, 1 H) 6.91 (ddd, J = 8.21, 2.50, 0.90 Hz, 1 H) 7.06 (br. s., 1 H) 7.28 (d, J = 2.20 Hz, 1 H) 7.32 (t, J = 7.88 Hz, 1 H) 7.43 (dd, J = 8.47, 2.27 Hz, 1 H) 7.66 (d, J = 8.44 Hz, 1 H) |
| 63cj | $^1$H NMR (400 MHz, MeOH-d4): δ ppm 1.32 (t, J = 7.13 Hz, 3 H) 1.52-1.70 (m, 4 H) 1.93-2.06 (m, 1 H) 2.41 (dd, J = 13.42, 8.74 Hz, 1 H) 3.10-3.25 (m, 5 H) 3.44-3.74 (m, 4 H) 4.21-4.37 (m, 2 H) 4.42 (t, J = 8.59 Hz, 1 H) 5.61 (s, 1 H) 6.57 (q, J = 6.57 Hz, 1 H) 7.36 (d, J = 2.20 Hz, 1 H) 7.51 (dd, J = 8.54, 2.20 Hz, 1 H) 7.70 (d, J = 8.44 Hz, 1 H) 7.72-7.78 (m, 1 H) 7.78-7.89 (m, 1 H) 8.09 (dt, J = 7.85, 1.49 Hz, 1 H) 8.41 (d, J = 0.73 Hz, 1 H) |
| 63ck | $^1$H NMR (400 MHz, DMSO-d6): δ ppm 1.21 (t, J = 7.10 Hz, 3 H) 1.38-1.64 (m, 4 H) 1.88 (dd, J = 13.20, 9.35 Hz, 1 H) 2.30 (dd, J = 13.20, 8.47 Hz, 1 H) 3.09 (br. s., 2 H) 3.42-3.61 (m, 4 H) 3.95-4.11 (m, 2 H) 4.12-4.28 (m, 2 H) 4.48 (br. s., 1 H) 5.71 (br. s., 1 H) 6.32 (br. s., 1 H) 6.71 (q, J = 6.74 Hz, 1 H) 7.33 (d, J = 2.05 Hz, 1 H) 7.44-7.69 (m, 6 H) 8.52 (br. s., 3 H) 9.27 (br. s., 1 H) 10.62 (br. s., 1 H) |
| 63cl | $^1$H NMR (400 MHz, MeOH-d4): δ ppm 1.35 (t, J = 7.13 Hz, 4 H) 1.82 (br. s., 4 H) 2.03-2.21 (m, 1 H) 2.47-2.64 (m, 1 H) 3.35 (s, 2 H) 3.56-3.92 (m, 4 H) 4.27-4.43 (m, 2 H) 4.59-4.70 (m, 1 H) 6.65-6.82 (m, 1 H) 7.81 (d, J = 8.00 Hz, 2 H) 8.00 (d, J = 8.20 Hz, 2 H) 8.05-8.14 (m, 1 H) 8.29-8.40 (m, 1 H) 8.46-8.55 (m, 1 H) 8.63 (d, J = 1.56 Hz, 1 H) 9.21 (s, 2 H) |
| 63cm | $^1$H NMR (400 MHz, MeOH-d4): δ ppm 1.35 (t, J = 6.93 Hz, 5 H) 1.83 (br. s., 4 H) 2.04-2.22 (m, 1 H) 2.47-2.65 (m, 1 H) 3.36 (br. s., 2 H) 4.35 (d, J = 6.64 Hz, 2 H) 4.57-4.71 (m, 1 H) 6.64-6.85 (m, 1 H) 7.84 (d, J = 6.64 Hz, 2 H) 8.03 (d, J = 6.83 Hz, 2 H) 8.08-8.18 (m, 1 H) 8.27-8.41 (m, 1 H) 8.50 (br. s., 2 H) 9.26 (br. s., 2 H) |
| 63cn | $^1$H NMR (400 MHz, MeOH-d4): δ ppm 1.24-1.45 (m, 10 H) 1.75 (d, J = 18.55 Hz, 4 H) 2.01-2.18 (m, 1 H) 2.43 (s, 3 H) 2.47-2.62 (m, 1 H) 3.86 (br. s., 3 H) 4.34 (d, J = 5.86 Hz, 2 H) 4.54-4.75 (m, 2 H) 6.44 (d, J = 1.95 Hz, 1 H) 6.89 (d, J = 5.66 Hz, 1 H) 7.03 (d, J = 8.59 Hz, 2 H) 7.57-7.71 (m, 3 H) 7.72-7.87 (m, 2 H) 7.98 (d, J = 1.76 Hz, 1 H) |
| 63co | $^1$H NMR (400 MHz, MeOH-d4): δ ppm 1.35 (s, 3 H) 1.64-1.91 (m, 4 H) 2.03-2.20 (m, 1 H) 2.47-2.64 (m, 1 H) 3.35 (br. s., 2 H) 3.56-3.95 (m, 4 H) 4.25-4.44 (m, 2 H) 4.57-4.71 (m, 1 H) 6.57-6.84 (m, 1 H) 7.70-7.85 (m, 2 H) 7.90-8.07 (m, 2 H) 8.23 (s, 2 H) 8.33-8.47 (m, 1 H) 8.86-9.05 (m, 2 H) |
| 63cp | $^1$H NMR (400 MHz, MeOH-d4): δ ppm 1.18-1.31 (m, 3 H) 1.44-1.60 (m, 4 H) 1.79 (dd, J = 13.28, 7.61 Hz, 1 H) 1.93 (s, 2 H) 1.98 (s, 3 H)2.14 (dd, J = 13.18, 8.79 Hz, 1 H) 2.37 (s, 3 H) 2.80-2.89 (m, 1 H) 2.91-3.00 (m, 1 H) 3.40-3.64 (m, 4 H) 3.97 (t, J = 8.15 Hz, 1 H) 4.19 (qd, J = 7.13, 1.81 Hz, 2 H) 4.37 (s, 2 H) 5.72 (s, 1 H) 6.39 (d, J = 2.20 Hz, 1 H) 6.76 (q, J = 6.56 Hz, 1 H) 7.36 (d, J = 8.30 Hz, 2 H) 7.59-7.66 (m, 3 H) 7.69-7.81 (m, 2 H) 7.95 (d, J = 2.29 Hz, 1 H) |
| 63cq | $^1$H NMR (400 MHz, DMSO-d6): δ ppm 1.10-1.20 (m, 3 H) 1.25 (t, 3 = 7.10 Hz, 3 H) 1.44-1.63 (m, 4 H) 1H NMR (400 MHz, MeOH-d4): δ ppm 1.21-1.31 (m, 3 H) 1.52 (dt, J = 10.53, 5.35 Hz, 4 H) 1.79 (dd, J = 13.15, 7.44 Hz, 1 H) 1.89 (s, 3 H) 1.93 (s, 2 H) 2.14 (dd, J = 13.13, 8.79 Hz, 1 H) 2.38 (s, 3 H) 2.78-2.88 (m, 3 H) 2.91-2.99 (m, 1 H) 3.40 (t, J = 7.35 Hz, 2 H) 3.44-3.66 (m, 4 H) 3.95 (t, J = 8.13 Hz, 1 H) 4.12-4.25 (m, 2 H) 5.72 (s, 1 H) 6.40 (d, J = 2.29 Hz, 1 H) 6.77 (q, J = 6.74 Hz, 1 H) 7.31 (d, J = 8.25 Hz, 2 H) 7.58-7.64 (m, 3 H) 7.70-7.80 (m, 2 H) 7.95 (d, J = 2.29 Hz, 1 H) |
| 63cr | $^1$H NMR (400 MHz, MeOH-d4): δ ppm 1.25 (t, J = 7.13 Hz, 3 H) 1.47-1.58 (m, 4 H) 1.79 (dd, J = 13.20, 7.44 Hz, 1 H) 1.93 (s, 2 H) 2.15 (dd, J = 13.23, 8.74 Hz, 1 H) 2.40 (s, 3 H) 2.81-2.87 (m, 1 H) 2.92-2.98 (m, 1 H) 3.44-3.63 (m, 4 H) 3.97 (dd, J = 8.52, 7.83 Hz, 1 H) 4.14-4.24 (m, 2 H) 5.75 (s, 1 H) 6.42 (d, J = 2.29 Hz, 1 H) 6.84 (q, J = 6.69 Hz, 1 H) 7.55 (dd, J = 8.30, 4.34 Hz, 1 H) 7.83 (d, J = 1.76 Hz, 1 H) 7.85-7.99 (m, 3 H)8.00-8.07 (m, 2 H) 8.30 (d, J = 1.51 Hz, 1 H) 8.37-8.42 (m, 1 H) 8.88 (dd, 1 = 4.30, 1.66 Hz, 1 H) |
| 63cs | $^1$H NMR (400 MHz, MeOH-d4): δ ppm 1.34 (d, J = 6.05 Hz, 6 H) 1.60 (br. s., 4 H) 2.02-2.13 (m, 1 H) 2.26-2.37 (m, 1 H) 2.42 (s, 3 H) 3.04-3.18 (m, 1 H) 3.26 (d, J = 11.71 Hz, 1 H) 3.41-3.78 (m, 4 H) 4.02-4.17 (m, 1 H) 4.66 (s, 1 H) 5.78 (s, 1 H) 6.43 (d, J = 2.15 Hz, 1 H) 6.69-6.86 (m, 1 H) 6.99 (d, J = 8.79 Hz, 2 H) 7.50-7.66 (m, 3 H) 7.67-7.82 (m, 2 H) 7.97 (d, J = 2.34 Hz, 1 H) |
| 63ct | $^1$H NMR (400 MHz, MeOH-d4): δ ppm 1.35 (t, J = 7.13 Hz, 3 H) 1.58-1.78 (m, 4 H) 2.02-2.16 (m, 1 H) 2.43-2.60 (m, 1 H) 3.30 (s, 2 H) 3.46-3.78 (m, 4 H) 4.27-4.41 (m, 2 H) 4.55-4.66 (m, 1 H), 5.61-5.77 (m, 1 H) 6.42-6.53 (m, 1 H) 6.59-6.70 (m, 1 H) 7.25-7.39 (m, 2 H) 7.62 (s, 4 H) 7.72 (s, 2 H) |
| 63cu | $^1$H NMR (400 MHz, DMSO-d6): δ ppm 1.25 (t, J = 7.10 Hz, 3 H) 1.33 (t, J = 7.10 Hz, 3 H) 1.44-1.64 (m, 4 H) 1.92 (dd, J = 13.28, 9.27 Hz, 1 H) 2.35 (dd, J = 13.28, 8.49 Hz, 1 H) 3.14 (br. s., 2 H) 3.44-3.66 (m, 4 H) 4.14-4.29 (m, 2 H) 4.30-4.43 (m, 2 H) 4.54 (br. s., 1 H) 5.75 (br. s., 1 H) 6.43 (br. s., 1 H) 6.59 (q, J = 6.72 Hz, 1 H) 7.37-7.47 (m, 1 H) 7.57-7.67 (m, 2 H) 7.68-7.81 (m, 2 H) 8.08 (dt, J = 6.77, 1.96 Hz, 1 H) 8.24 (br. s., 1 H) 9.22 (br. s., 1 H) 10.41 (br. s, 1 H) |
| 63cv | $^1$H NMR (400 MHz, MeOH-d4): δ ppm 1.34 (t, J = 7.13 Hz, 3 H) 1.69-1.88 (m, 4 H) 2.11 (dd, J = 13.64, 8.96 Hz, 1 H) 2.55 (dd, J = 13.62, 8.69 Hz, 1 H) 3.34 (s, 2 H) 3.52-3.80 (m, 4 H) 4.35 (qd, J = 7.13, 1.93 Hz, 2 H) 4.63 (t, J = 8.79 Hz, 1 H) 6.55-6.67 (m, 1 H) 7.37 (d, J = 2.20 Hz, 1 H) 7.54 (dd, J = 8.52, 2.22 Hz, 1 H) 7.58-7.63 (m, 1 H) 7.65-7.70 (m, 1 H) 7.71 (d, J = 8.59 Hz, 1 H) 8.17 (dt, J = 7.74, 1.43 Hz, 1 H) 8.35 (br. s., 1 H) |

TABLE 18b-continued

| NMR Data for Compounds of Table 18a | |
|---|---|
| Ex. No. | NMR |
| 63cw | $^1$H NMR (400 MHz, DMSO-d6): δ ppm 1.44-1.69 (m, 4 H) 1.91 (dd, J = 13.28, 9.18 Hz, 1 H) 2.35 (dd, J = 13.15, 8.61 Hz, 1 H) 3.14 (br. s., 2 H) 3.64 (br. s., 4 H) 4.37-4.53 (m, 1 H) 5.87 (br. s., 1 H) 6.62 (q, J = 6.78 Hz, 1 H) 7.43 (t, J = 1.22 Hz, 1 H) 7.65 (s, 2 H) 7.70 (d, J = 4.78 Hz, 2 H) 7.99-8.12 (m, 1 H) 8.26 (br. s., 1 H) 8.96 (d, J = 5.03 Hz, 1 H) 10.25 (br. s., 1 H) |
| 63cx | $^1$H NMR (400 MHz, MeOH-d4): δ ppm 1.33 (t, J = 7.15 Hz, 3 H) 1.55-1.74 (m, 4 H) 2.04 (dd, J = 13.57, 8.79 Hz, 1 H) 2.48 (dd, J = 13.54, 8.76 Hz, 1 H) 3.26 (s, 2 H) 3.44-3.73 (m, 4 H) 4.25-4.41 (m, 2 H) 4.56 (t, J = 8.74 Hz, 1 H) 5.57 (s, 1 H) 6.63 (q, J = 6.80 Hz, 1 H) 7.30 (d, J = 2.20 Hz, 1 H) 7.47 (dd, J = 8.52, 2.22 Hz, 1 H) 7.52-7.59 (m, 1 H) 7.59-7.65 (m, 1 H) 7.67 (d, J = 8.54 Hz, 1 H) 7.90-8.04 (m, 1 H) 8.41 (br. s., 1 H) |
| 63cy | $^1$H NMR (400 MHz, MeOH-d4): δ ppm 1.33 (t, J = 7.15 Hz, 3 H) 1.53-1.74 (m, 4 H) 2.05 (dd, J = 13.57, 8.79 Hz, 1 H) 2.48 (dd, J = 13.54, 8.76 Hz, 1 H) 3.23 (s, 3 H) 3.27 (d, J = 1.22 Hz, 2 H) 3.42-3.79 (m, 4 H) 4.22-4.42 (m, 2 H) 4.57 (t, J = 8.79 Hz, 1 H) 5.54 (s, 1 H) 6.61 (q, J = 6.72 Hz, 1 H) 7.35 (d, J = 2.20 Hz, 1 H) 7.52 (dd, J = 8.54, 2.25 Hz, 1 H) 7.72 (d, J = 8.54 Hz, 1 H) 7.77 (d, J = 7.86 Hz, 2 H) 8.08-8.20 (m, 2 H) |
| 63cz | $^1$H NMR (400 MHz, MeOH-d4): δ ppm 1.33 (t, J = 7.13 Hz, 3 H) 1.54-1.72 (m, 4 H) 1.99-2.07 (m, 1 H) 2.46 (dd, J = 13.57, 8.74 Hz, 1 H) 3.17-3.28 (m, 2 H) 3.42-3.72 (m, 4 H) 4.26-4.39 (m, 2 H) 4.51 (t, J = 8.69 Hz, 1 H) 5.53 (s, 1 H) 6.56-6.66 (m, 1 H) 7.34 (d, J = 2.20 Hz, 1 H) 7.51 (dd, J = 8.52, 2.22 Hz, 1 H) 7.67 (d, J = 8.00 Hz, 2 H) 7.71 (d, J = 8.49 Hz, 1 H) 8.02-8.14 (m, 2 H) |
| 63da | $^1$H NMR (400 MHz, MeOH-d4): δ ppm 0.99 (t, J = 7.15 Hz, 3 H) 1.33 (t, J = 7.13 Hz, 3 H) 1.62-1.78 (m, 4 H) 2.07 (dd, J = 13.64, 8.86 Hz, 1 H) 2.41 (s, 3 H) 2.50 (dd, J = 13.67, 8.79 Hz, 1 H) 3.29-3.31 (m, 2 H) 3.55-3.84 (m, 4 H) 3.84-4.06 (m, 2 H) 4.23-4.42 (m, 2 H) 4.60 (t, J = 8.81 Hz, 1 H) 6.23-6.36 (m, 1 H) 6.43 (d, J = 2.34 Hz, 1 H) 6.89-7.01 (m, 1 H) 7.40 (dd, J = 7.66, 0.93 Hz, 1 H) 7.48-7.59 (m, 4 H) 7.60-7.69 (m, 1 H) 7.86 (dd, J = 7.79, 1.24 Hz, 1 H) 7.93 (d, J = 2.34 Hz, 1 H) |
| 63db | $^1$H NMR (400 MHz, MeOH-d4): δ ppm 1.30 (t, J = 7.15 Hz, 3 H) 1.40 (t, J = 7.13 Hz, 3 H) 1.52-1.67 (m, 4 H) 2.00 (dd, J = 13.59, 8.81 Hz, 1 H) 2.39 (s, 3 H) 2.44 (dd, J = 13.64, 8.76 Hz, 1 H) 3.17-3.27 (m, 2 H) 3.41-3.73 (m, 4 H) 4.23-4.36 (m, 2 H) 4.40 (q, J = 7.13 Hz, 2 H) 4.54 (t, J = 8.79 Hz, 1 H) 5.78 (s, 1 H) 6.41 (d, J = 2.15 Hz, 1 H) 6.92 (q, J = 6.62 Hz, 1 H) 7.52 (d, J = 8.25 Hz, 1 H) 7.58 (t, J = 7.74 Hz, 1 H) 7.77-7.87 (m, 2 H) 7.88-7.97 (m, 2 H) 8.03 (dt, J = 7.79, 1.33 Hz, 1 H) 8.21 (t, J = 1.61 Hz, 1 H) |
| 63dc | $^1$H NMR (400 MHz, MeOH-d4): δ ppm 1.32 (t, J = 7.13 Hz, 3 H) 1.41 (t, J = 7.13 Hz, 3 H) 1.56-1.69 (m, 4 H) 2.03 (dd, J = 13.62, 8.83 Hz, 1 H) 2.41 (s, 3 H) 2.47 (dd, J = 13.57, 8.79 Hz, 1 H) 3.26 (s, 2 H) 3.46-3.75 (m, 4 H) 4.32 (qd, J = 7.15, 2.37 Hz, 2 H) 4.40 (q, J = 7.14 Hz, 2 H) 4.57 (t, J = 8.79 Hz, 1 H) 5.87 (s, 1 H) 6.43 (d, J = 2.34 Hz, 1 H) 6.89-7.03 (m, 1 H) 7.55 (d, J = 8.30 Hz, 1 H) 7.68-7.79 (m, 2 H) 7.87 (dd, J = 8.30, 2.15 Hz, 1 H) 7.94 (d, J = 2.34 Hz, 1 H) 7.98 (d, J = 1.51 Hz, 1 H) 8.08-8.18 (m, 2H) |
| 63dd | $^1$H NMR (400 MHz, MeOH-d4): δ ppm 1.32 (t, J = 7.15 Hz, 3 H) 1.50-1.71 (m, 4 H) 2.00 (dd, J = 13.54, 8.61 Hz, 1 H) 2.38 (s, 3 H) 2.42 (dd, J = 13.59, 8.81 Hz, 1 H) 3.12-3.28 (m, 2 H) 3.42-3.77 (m, 6 H) 4.21-4.39 (m, 2 H) 4.48 (t, J = 8.69 Hz, 1 H) 4.69-4.79 (m, 1 H) 5.72 (d, J = 2.05 Hz, 1 H) 6.39 (d, J = 2.29 Hz, 1 H) 6.77 (q, J = 6.54 Hz, 1 H) 7.45 (d, J = 1.56 Hz, 1 H) 7.52 (dd, J = 8.20, 1.56 Hz, 1H) 7.70 (d, J = 8.15 Hz, 1 H) 7.88 (dd, J = 4.37, 2.37 Hz, 1 H) |
| 63de | $^1$H NMR (400 MHz, MeOH-d4): δ ppm 1.22-1.29 (m, 3 H) 1.51 (dt, J = 11.74, 5.65 Hz, 4 H) 1.75 (dd, J = 12.98, 7.32 Hz, 1 H) 1.90 (s, 4 H) 2.09 (dd, J = 13.13, 8.74 Hz, 1 H) 2.38 (s, 3 H) 2.73-2.93 (m, 2 H) 3.43-3.63 (m, 4 H) 3.85 (dd, J = 8.71, 7.39 Hz, 1 H) 4.10 (s, 2 H) 4.13-4.23 (m, 2 H) 5.70 (s, 1 H) 6.41 (d, J = 2.25 Hz, 1 H) 6.78 (q, J = 6.88 Hz, 1 H) 7.52 (d, J = 8.35 Hz, 2 H) 7.66 (d, J = 1.71 Hz, 1 H) 7.72-7.84 (m, 4 H) 7.97 (d, J = 2.34 Hz, 1 H) |
| 63df | $^1$H NMR (400 MHz, MeOH-d4): δ ppm 1.33 (dt, J = 10.30, 7.13 Hz, 6 H) 1.50-1.69 (m, 4 H) 2.01 (dd, J = 13.57, 8.74 Hz, 1 H) 2.40-2.45 (m, 1 H), 2.41 (s, 3 H) 3.22 (d, J = 2.00 Hz, 2 H) 3.44-3.74 (m, 4 H) 4.21-4.36 (m, 4 H) 4.52 (t, J = 8.74 Hz, 1 H) 5.80 (s, 1 H) 6.43 (d, J = 2.29 Hz, 1 H) 6.61 (d, J = 16.06 Hz, 1 H) 6.92 (q, J = 6.65 Hz, 1 H) 7.49-7.56 (m, 2 H) 7.61-7.70 (m, 2 H) 7.72-7.80 (m, 2 H) 7.83 (dd, J = 8.27, 2.17 Hz, 1 H) 7.94 (dd, J = 6.39, 1.85 Hz, 2 H) |
| 63dg | $^1$H NMR (400 MHz, MeOH-d4): δ ppm 1.26-1.39 (m, 6 H) 1.52-1.63 (m, 4 H) 1.94 (dd, J = 13.50, 8.32 Hz, 1 H) 2.34 (dd, J = 13.40, 8.76 Hz, 1 H) 2.40 (s, 3 H) 3.04-3.20 (m, 2 H) 3.44-3.69 (m, 4 H)4.21-4.31 (m, 4 H) 4.34 (t, J = 8.54 Hz, 1 H) 5.78 (s, 1 H) 6.42 (d, J = 2.20 Hz, 1 H) 6.58 (d, J = 16.06 Hz, 1 H) 6.92 (q, J = 6.67 Hz, 1 H) 7.51 (d, J = 8.25 Hz, 1 H) 7.62-7.77 (m, 5 H) 7.82 (dd, 1 = 8.30, 2.15 Hz, 1 H) 7.93 (d, J = 2.34 Hz, 1 H) 7.97 (d, J = 1.27 Hz, 1 H) |
| 63dh | $^1$H NMR (400 MHz, MeOH-d4): δ ppm 1.18 (t, J = 7.13 Hz, 3 H) 1.32 (t, J = 7.15 Hz, 3 H) 1.54-1.68 (m, 4 H) 2.03 (dd, J = 13.62, 8.83 Hz, 1 H) 2.40 (s, 3 H) 2.46 (dd, J = 13.59, 8.76 Hz, 1 H) 2.68 (t, J = 7.47 Hz, 2 H) 3.01 (t, J = 7.49 Hz, 2 H) 3.25 (s, 2 H) 3.45-3.75 (m, 4 H) 4.10 (q, J = 7.13 Hz, 2 H) 4.25-4.40 (m, 2 H) 4.57 (t, J = 8.79 Hz, 1 H) 5.82 (s, 1 H) 6.42 (d, J = 2.25 Hz, 1 H) 6.88 (q, J = 6.70 Hz, 1 H) 7.27 (d, J = 7.42 Hz, 1 H) 7.36-7.42 (m, 1 H) 7.42-7.47 (m, 2 H) 7.50 (d, J = 8.30 Hz, 1 H) 7.79 (dd, J = 8.27, 2.12 Hz, 1 H) 7.88-7.94 (m, 2 H) |
| 63di | $^1$H NMR (400 MHz, MeOH-d4): δ ppm 1.22 (t, J = 7.13 Hz, 3 H) 1.32 (t, J = 7.15 Hz, 3 H) 1.53-1.72 (m, 4 H) 2.03 (dd, J = 13.62, 8.83 Hz, 1 H) 2.40 (s, 3 H) 2.47 (dd, J = 13.59, 8.76 Hz, 1 H) 2.67 (t, J = 7.57 Hz, 2 H) 2.92-3.03 (m, 2 H) 3.25 (s, 2 H) 3.45-3.80 (m, 4 H) 4.11 (q, J = 7.13 Hz, 2 H) 4.32 (qd, J = 7.13, 2.32 Hz, 2 H) 4.57 (t, J = 8.79 Hz, 1 H) 5.84 (s, 1 H) 6.41 (d, J = 2.34 Hz, 1 H) 6.87 (q, J = 6.57 Hz, 1 H) 7.34 |

TABLE 18b-continued

| NMR Data for Compounds of Table 18a | |
|---|---|
| Ex. No. | NMR |
| | (d, J = 8.25 Hz, 2 H) 7.49 (d, J = 8.30 Hz, 1 H) 7.53 (d, J = 8.25 Hz, 2 H) 7.78 (dd, J = 8.30, 2.15 Hz, 1 H) 7.90 (d, J = 2.24 Hz, 2 H) |
| 63dj | $^1$H NMR (400 MHz, MeOH-d4): δ ppm 1.20-1.35 (m, 3 H) 1.42-1.60 (m, 4 H) 1.68-1.83 (m, 1 H) 1.99-2.15 (m, 1 H) 2.42 (s, 3 H) 2.75 (d, J = 10.93 Hz, 1 H) 2.89 (d, J = 10.93 Hz, 1 H) 3.55 (d, J = 5.86 Hz, 4 H) 3.82 (s, 1 H) 4.20 (dd, J = 7.13, 1.27 Hz, 2 H) 5.74 (s, 1 H) 6.44 (d, J = 2.15 Hz, 1 H) 6.85 (d, J = 6.64 Hz, 1 H) 7.04-7.24 (m, 1 H) 7.39-7.53 (m, 3 H) 7.67 (d, J = 1.56 Hz, 1 H) 7.76 (d, J = 1.76 Hz, 1 H) 7.79-7.88 (m, 1H) 8.01 (d, J = 2.15 Hz, 1 H) |
| 63dk | $^1$H NMR (400 MHz, MeOH-d4): δ ppm 1.28 (t, J = 7.13 Hz, 3 H) 1.42-1.63 (m, 4 H) 1.69-1.82 (m, 1 H) 2.01-2.16 (m, 1 H) 2.44 (s, 3 H) 2.77 (s, 1 H) 2.89 (s, 1 H) 3.57 (d, J = 5.86 Hz, 4 H) 3.76-3.89 (m, 1 H) 4.19 (dd, J = 7.22, 1.37 Hz, 2 H) 5.78 (s, 1 H) 6.46 (d, J = 2.15 Hz, 1 H) 6.78-6.96 (m, 1 H) 7.53-7.65 (m, 1 H) 7.79-7.98 (m, 3 H) 8.06 (d, J = 2.34 Hz, 1 H) 8.14 (s, 2 H) 8.28 (s, 1 H) 8.40-8.52 (m, 1 H) 8.80-8.96 (m, 1 H) |
| 63dl | $^1$H NMR (400 MHz, MeOH-d4): δ ppm 1.32 (t, J = 7.13 Hz, 3 H) 1.51-1.68 (m, 4 H) 1.96-2.06 (m, 1 H) 2.39 (s, 3 H) 2.43 (dd, J = 13.54, 8.81 Hz, 1 H) 3.15-3.27 (m, 2 H) 3.43-3.72 (m, 4 H) 4.26-4.36 (m, 2 H) 4.39-4.45 (m, 1 H) 4.49 (t, J = 8.69 Hz, 1 H) 4.90 (t, J = 8.44 Hz, 1 H) 5.70 (d, J = 2.83 Hz, 1 H) 5.87 (td, J = 7.86, 1.66 Hz, 1 H) 6.42 (d, J = 2.34 Hz, 1 H) 6.79-6.91 (m, 1 H) 7.52 (t, J = 1.85 Hz, 1 H) 7.58 (dt, J = 8.20, 2.17 Hz, 1 H) 7.82 (dd, J = 8.27, 1.54 Hz, 1 H) 7.95 (dd, J = 3.44, 2.61 Hz, 1 H) |
| 63dm | $^1$H NMR (400 MHz, MeOH-d4): δ ppm 1.29 (t, J = 7.13 Hz, 3 H) 1.43-1.62 (m, 4 H) 1.70-1.83 (m, 1 H) 2.03-2.18 (m, 1 H) 2.79 (s, 1 H) 2.90 (s, 1 H) 3.09 (s, 2 H) 3.17 (s, 3 H) 3.54 (br. s., 4 H) 3.65 (t, J = 6.74 Hz, 2 H) 3.80-3.96 (m, 1 H) 4.21 (d, J = 7.03 Hz, 2 H) 5.57 (s, 1 H) 6.60-6.76 (m, 1 H) 7.52 (s, 1 H) 7.56-7.67 (m, 3 H) 7.68-7.79 (m, 2 H) 8.01 (d, J = 8.20 Hz, 1 H) |
| 63dn | $^1$H NMR (400 MHz, MeOH-d4): δ ppm 1.28 (t, J = 7.13 Hz, 3 H) 1.55 (dt, J = 11.03, 5.37 Hz, 4 H) 1.89 (dd, J = 13.32, 8.10 Hz, 1 H) 1.96 (s, 3 H) 1.97 (s, 3 H) 2.28 (dd, J = 13.40, 8.86 Hz, 1 H) 2.36 (s, 3 H) 2.97-3.11 (m, 2 H) 3.41-3.68 (m, 4 H) 4.18-4.30 (m, 3 H) 4.39 (s, 2 H) 5.69 (s, 1 H) 6.37 (d, J = 2.34 Hz, 1 H) 6.73 (q, J = 6.30 Hz, 1 H) 7.31 (d, J = 1.51 Hz, 1 H) 7.40 (dd, J = 8.13, 1.59 Hz, 1 H), 7.67 (d, J = 8.05 Hz, 1 H), 7.85 (d, J = 2.25 Hz, 1 H) |
| 63do | $^1$H NMR (400 MHz, MeOH-d4): δ ppm 1.31 (t, J = 7.15 Hz, 3 H) 1.55-1.68 (m, 4 H) 1.97 (s, 1 H) 2.02 (dd, J = 13.59, 8.96 Hz, 1 H) 2.12 (ddt, J = 13.30, 7.49, 5.74, 5.74 Hz, 1 H) 2.39 (s, 3 H) 2.46 (dd, J = 13.57, 8.64 Hz, 1 H) 2.65-2.77 (m, 1 H) 2.91 (dt, J = 13.74, 7.04 Hz, 1 H) 3.04-3.14 (m, 1 H) 3.24 (d, J = 1.76 Hz, 2 H) 3.45-3.76 (m, 6 H) 3.81 (dd, J = 8.52, 5.88 Hz, 1 H) 4.25-4.45 (m, 4 H) 4.55 (t, J = 8.79 Hz, 1 H) 5.81 (s, 1 H) 6.41 (d, J = 2.29 Hz, 1 H) 6.82 (q, J = 6.65 Hz, 1 H) 7.71 (s, 1 H) 7.77-7.84 (m, 4 H) 7.90-8.01 (m, 3 H) |
| 63dp | $^1$H NMR (400 MHz, MeOH-d4): δ ppm 1.33 (t, J = 7.13 Hz, 3 H) 1.54-1.75 (m, 4 H) 2.02 (dd, J = 13.57, 8.69 Hz, 1 H) 2.28 (s, 3 H) 2.31 (s, 3 H) 2.45 (dd, J = 13.54, 8.76 Hz, 1 H) 3.20-3.27 (m, 2 H) 3.23 (s, 3 H) 3.42-3.79 (m, 4 H) 4.32 (qd, J = 7.13, 2.54 Hz, 2 H) 4.51 (t, J = 8.69 Hz, 1 H) 5.63 (s, 1 H) 6.63 (q, J = 6.64 Hz, 1 H) 7.19 (d, J = 7.86 Hz, 1 H) 7.36 (dd, J = 7.76, 1.76 Hz, 1 H) 7.41 (s, 1 H) 7.48 (d, J = 1.81 Hz, 1 H) 7.65-7.72 (m, 1 H) 7.72-7.77 (m, 1 H) 7.80-7.85 (m, 2 H) 8.07 (dt, J = 7.03, 1.93 Hz, 1 H) 8.47 (br. s., 1 H) |
| 63dq | $^1$H NMR (400 MHz, MeOH-d4): δ ppm 1.32 (t, J = 7.13 Hz, 3 H) 1.53-1.73 (m, 4 H) 1.93-2.08 (m, 1 H) 2.41 (dd, J = 13.45, 8.71 Hz, 1 H) 3.11-3.23 (m, 2 H) 3.24 (s, 3 H) 3.46-3.79 (m, 4 H) 4.30 (qd, J = 7.12, 2.46 Hz, 2 H) 4.43 (t, J = 8.59 Hz, 1 H) 5.65 (s, 1 H) 6.67 (q, J = 6.64 Hz, 1 H) 7.56 (dd, J = 8.32, 4.32 Hz, 1 H) 7.70 (d, J = 1.76 Hz, 1 H) 7.78-7.97 (m, 4 H) 8.07 δ 8.12 (m, 3 H) 8.23 (s, 1 H), 8.42 (dd, J = 8.44, 1.61 Hz, 1 H) 8.53 (br. s., 1 H) 8.85 (dd, J = 4.32, 1.68 Hz, 1 H) |
| 63dr | $^1$H NMR (400 MHz, MeOH-d4): δ ppm 1.32 (t, J = 7.13 Hz, 3 H) 1.51-1.71 (m, 4 H) 1.99-2.08 (m, 1 H) 2.40 (s, 3 H) 2.41 (s, 3 H) 2.46 (dd, J = 13.62, 8.74 Hz, 1 H) 3.25 (d, J = 1.07 Hz, 2 H) 3.43-3.77 (m, 4 H) 4.32 (qd, J = 7.13, 2.32 Hz, 2 H) 4.57 (t, J = 8.79 Hz, 1 H) 4.68 (s, 2 H) 5.85 (s, 1 H) 6.42 (d, J = 2.25 Hz, 1 H) 6.88 (q, J = 6.65 Hz, 1 H) 7.34-7.54 (m, 4 H) 7.79 (dd, J = 8.27, 2.12 Hz, 1 H) 7.91 (d, J = 2.25 Hz, 2 H) |
| 63ds | $^1$H NMR (400 MHz, MeOH-d4): δ ppm 1.32 (t, J = 7.15 Hz, 3 H) 1.55-1.77 (m, 4 H) 2.04 (dd, J = 9.32, 4.30 Hz, 1 H) 2.37 (s, 3 H) 2.40 (s, 3 H) 2.48 (dd, J = 13.62, 8.79 Hz, 1 H) 3.28 (s, 2 H) 3.50-3.87 (m, 4 H) 4.19-4.42 (m, 2 H) 4.59 (t, J = 8.79 Hz, 1 H) 4.71 (s, 2 H) 6.14 (br. s., 1 H) 6.42 (d, J = 2.34 Hz, 1 H) 6.91 (q, J = 6.41 Hz, 1 H) 7.28 (d, J = 7.91 Hz, 1 H) 7.44 (dd, J = 7.76, 2.05 Hz, 1 H) 7.51 (d, J = 8.25 Hz, 1 H) 7.65 (d, J = 1.81 Hz, 1 H) 7.85 (dd, J = 8.27, 2.12 Hz, 1 H) 7.88-7.96 (m, 2 H) |
| 63dt | $^1$H NMR (400 MHz, MeOH-d4): δ ppm 1.32 (t, J = 7.13 Hz, 3 H) 1.52-1.71 (m, 4 H) 1.98-2.08 (m, 1 H) 2.41 (s, 3 H) 2.45 (dd, J = 13.62, 8.79 Hz, 1 H) 3.24 (d, J = 1.61 Hz, 2 H) 3.42-3.73 (m, 4 H) 3.93 (s, 3 H) 4.24-4.40 (m, 2 H) 4.54 (t, J = 8.76 Hz, 1 H) 5.78 (s, 1 H) 6.43 (d, J = 2.29 Hz, 1 H) 6.95 (q, J = 6.62 Hz, 1 H) 7.54 (d, J = 8.30 Hz, 1 H) 7.67-7.77 (m, 2 H) 7.85 (dd, J = 8.30, 2.20 Hz, 1 H) 7.94 (d, J = 2.34 Hz, 1 H) 7.98 (d, J = 1.37 Hz, 1 H) 8.07-8.16 (m, 2 H) |
| 63du | $^1$H NMR (400 MHz, MeOH-d4): δ ppm 1.29 (t, J = 7.13 Hz, 3 H) 1.46-1.67 (m, 4 H) 1.90 (dd, J = 13.35, 8.22 Hz, 1 H) 2.30 (dd, J = 13.35, 8.71 Hz, 1 H) 2.40 (s, 3 H) 2.93-3.16 (m, 2 H) 3.38-3.74 (m, 4 H) 4.16-4.36 (m, 3 H) 5.77 (s, 1 H) 6.41 (d, J = 2.29 Hz, 1 H) 6.91 (q, J = 6.62 Hz, 1 H) 7.51 (d, J = 8.25 Hz, 1 H) 7.64 (d, J = 8.40 Hz, 2 H) 7.82 (dd, J = 8.30, 2.15 Hz, 1 H) 7.93 (d, J = 2.29 Hz, 1 H) 7.96 (s, 1 H) 8.07 (d, J = 8.30 Hz, 2 H) |

TABLE 18b-continued

| NMR Data for Compounds of Table 18a | |
|---|---|
| Ex. No. | NMR |
| 63dv | $^{1}$H NMR (400 MHz, MeOH-d4): δ ppm 1.35 (s, 4 H) 1.60-1.76 (m, 3 H) 2.02-2.13 (m, 1 H) 2.43 (s, 3 H) 2.46-2.56 (m, 1 H) 3.30 (s, 2 H) 3.53-3.83 (m, 4 H) 4.30-4.40 (m, 2 H) 4.56-4.66 (m, 1 H) 5.48 (s, 2 H) 6.01-6.11 (m, 1 H) 6.44-6.50 (m, 1 H) 6.89-6.98 (m, 1 H) 7.80-7.84 (m, 1 H) 7.86-8.02 (m, 5 H) 8.03-8.08 (m, 1 H) |
| 63dw | $^{1}$H NMR (400 MHz, MeOH -d4): δ ppm 1.28 (t, J = 7.13 Hz, 3 H) 1.55 (br. s., 4 H) 1.70-1.83 (m, 1 H) 2.03-2.18 (m, 1 H) 2.70-2.82 (m, 1 H) 2.86-2.97 (m, 1 H) 3.41-3.59 (m, 4 H) 3.79-3.94 (m, 1 H) 4.09-4.30 (m, 2 H) 5.59 (s, 1 H) 6.60-6.77 (m, 1 H) 7.71 (d, J = 8.20 Hz, 2 H) 7.84 (d, J = 8.20 Hz, 2 H) 8.03-8.15 (m, 1 H) 8.34 (s, 2 H) 9.26 (s, 1 H) 9.59 (s, 1 H) |
| 63dx | $^{1}$H NMR (400 MHz, Chloroform-d): δ ppm 1.27 (m, 7H), 1.55 (m, 3H), 1.77 (dd, J = 13.1, 7.0 Hz, 1H), 2.11 (dd, J = 13.1, 8.9 Hz, 1H), 2.42 (s, 3H), 2.96 (m, 2H), 3.47 (dt, J = 11.6, 5.7 Hz, 4H), 3.98 (dd, J = 8.8, 6.9 Hz, 1H), 4.21 (q, J = 7.1 Hz, 2H), 4.73 (s, 2H), 5.49 (s, 1H), 5.99 (m, 1H), 6.35 (d, J = 2.3 Hz, 1H), 6.63 (q, J = 6.7 Hz, 1H), 7.61 (m, 2H), 7.73 (d, J = 2.3 Hz, 1H), 7.88 (d, J = 8.3 Hz, 1H), 8.96 (s, 2H), 9.24 (s, 1H) |
| 63dy | $^{1}$H NMR (400 MHz, MeOH-d4): δ ppm 1.27 (m, 8H), 1.51 (dt, J = 10.8, 5.6 Hz, 8H), 1.74 (dd, J = 13.1, 7.3 Hz, 2H), 2.06 (m, 2H), 2.39 (s, 6H), 2.75 (d, J = 11.0 Hz, 2H), 2.89 (d, J = 11.0 Hz, 2H), 3.53 (dt, J = 22.5, 6.4 Hz, 8H), 3.82 (dd, J = 8.8, 7.2 Hz, 2H), 4.18 (qd, J = 7.1, 1.6 Hz, 3H), 5.73 (s, 2H), 6.00 (m, 1H), 6.42 (d, J = 2.4 Hz, 2H), 6.82 (q, J = 6.6 Hz, 2H), 7.35 (dt, J = 10.4, 8.4 Hz, 2H), 7.50 (m, 2H), 7.73 (m, 8H), 8.00 (d, J = 2.4 Hz, 2H) |
| 63dz | $^{1}$H NMR (400 MHz, MeOH-d4): δ ppm 1.26 (t, J = 7.1 Hz, 3H), 1.50 (dt, J = 10.6, 5.6 Hz, 4H), 1.73 (dd, J = 13.1, 7.2 Hz, 1H), 2.07 (dd, J = 13.1, 8.8 Hz, 1H), 2.39 (s, 3H), 2.74 (d, J = 11.0 Hz, 1H), 2.88 (d, J = 11.0 Hz, 1H), 3.52 (dq, J = 23.8, 7.6, 6.5 Hz, 4H), 3.81 (dd, J = 8.8, 7.1 Hz, 1H), 4.17 (qd, J = 7.1, 1.6 Hz, 2H), 5.73 (s, 1H), 6.41 (d, J = 2.4 Hz, 1H), 6.80 (q, J = 6.5 Hz, 1H), 7.46 (m, 2H), 7.71 (m, 5H), 7.98 (d, J = 2.3 Hz, 1H) |
| 63ea | $^{1}$H NMR (400 MHz, DMSO-d6): δ ppm 1.25 (t, J = 7.10 Hz, 3 H) 1.42-1.69 (m, 4 H) 1.92 (dd, J = 13.25, 9.35 Hz, 1 H) 2.35 (dd, J = 13.25, 8.47 Hz, 1 H) 3.14 (br. s., 2 H) 3.60 (br. s., 4 H) 4.24 (qd, J = 7.09, 2.10 Hz, 2 H) 4.54 (br. s., 1 H) 5.77 (br. s., 1 H) 6.70 (q, J = 6.65 Hz, 1 H) 7.37 (d, J = 2.10 Hz, 1 H) 7.43-7.52 (m, 3 H) 7.53-7.69 (m, 4 H) 9.23 (br. s., 1 H) 10.44 (br. s., 1 H) |
| 63eb | $^{1}$H NMR (400 MHz, MeOH-d4): δ ppm 1.25 (t, J = 7.1 Hz, 4H), 1.49 (dt, J = 10.6, 5.6 Hz, 4H), 1.73 (dd, J = 13.1, 7.2 Hz, 1H), 2.06 (dd, J = 13.1, 8.8 Hz, 1H), 2.39 (s, 3H), 2.74 (d, J = 11.0 Hz, 1H), 2.88 (d, J = 11.0 Hz, 1H), 3.50 (m, 4H), 3.82 (dd, J = 8.7, 7.2 Hz, 1H), 4.17 (qd, J = 7.1, 1.5 Hz, 2H), 5.76 (s, 1H), 6.41 (d, J = 2.4 Hz, 1H), 6.89 (q, J = 6.6 Hz, 1H), 7.51 (m, 6H), 7.76 (dd, J = 8.3, 2.2 Hz, 1H), 7.92 (t, J = 2.2 Hz, 2H) |
| 63ec | $^{1}$H NMR (400 MHz, MeOH-d4): δ ppm 1.26 (t, J = 7.1 Hz, 5H), 1.51 (dt, J = 10.1, 5.3 Hz, 4H), 1.77 (dd, J = 13.1, 7.4 Hz, 1H), 2.12 (dd, J = 13.2, 8.8 Hz, 1H), 2.39 (s, 3H), 2.80 (d, J = 11.1 Hz, 1H), 2.93 (d, J = 11.1 Hz, 1H), 3.53 (m, 4H), 3.91 (t, J = 8.0 Hz, 1H), 4.19 (qd, J = 7.2, 1.7 Hz, 2H), 5.77 (s, 1H), 6.41 (d, J = 2.3 Hz, 1H), 6.91 (q, J = 6.6 Hz, 1H), 7.37 (ddt, J = 16.6, 10.3, 8.6 Hz, 2H), 7.51 (m, 2H), 7.76 (dd, J = 8.3, 2.2 Hz, 1H), 7.91 (dd, J = 9.9, 2.4 Hz, 2H) |
| 63ed | $^{1}$H NMR (400 MHz, MeOH-d4): δ ppm 1.26 (m, 6H), 1.50 (dt, J = 10.4, 5.4 Hz, 5H), 1.73 (dd, J = 13.1, 7.2 Hz, 1H), 2.06 (m, 1H), 2.39 (s, 3H), 2.74 (d, J = 11.0 Hz, 1H), 2.88 (d, J = 11.0 Hz, 1H), 3.53 (m, 5H), 3.81 (dd, J = 8.7, 7.1 Hz, 1H), 4.17 (qd, J = 7.1, 1.5 Hz, 2H), 5.77 (s, 1H), 6.41 (d, J = 2.4 Hz, 1H), 6.87 (q, J = 6.7 Hz, 1H), 7.44 (m, 4H), 7.60 (m, 3H), 7.78 (dd, J = 8.3, 2.1 Hz, 1H), 7.92 (t, J = 2.6 Hz, 2H) |
| 63ee | $^{1}$H NMR (400 MHz, MeOH-d4): δ ppm 1.27 (q, J = 8.3, 7.1 Hz, 6H), 1.49 (m, 4H), 1.72 (dd, J = 13.1, 7.2 Hz, 1H), 2.06 (dd, J = 13.1, 8.8 Hz, 1H), 2.39 (s, 3H), 2.74 (d, J = 11.0 Hz, 1H), 2.88 (d, J = 11.0 Hz, 1H), 3.50 (m, 4H), 3.83 (dd, J = 8.8, 7.2 Hz, 1H), 4.18 (qd, J = 7.1, 1.5 Hz, 2H), 5.77 (s, 1H), 6.41 (d, J = 2.5 Hz, 1H), 6.93 (q, J = 6.6 Hz, 1H), 7.50 (m, 2H), 7.59 (d, J = 8.3 Hz, 1H), 7.73 (m, 2H), 7.92 (dd, J = 7.7, 2.3 Hz, 2H) |
| 63ef | $^{1}$H NMR (400 MHz, MeOH-d4): δ ppm 1.28 (t, J = 7.1 Hz, 5H), 1.54 (tt, J = 7.3, 4.4 Hz, 4H), 1.80 (dd, J = 13.2, 7.6 Hz, 1H), 2.17 (dd, J = 13.2, 8.8 Hz, 1H), 2.85 (d, J = 11.2 Hz, 1H), 2.97 (d, J = 11.2 Hz, 1H), 3.52 (ddt, J = 28.3, 12.4, 8.0 Hz, 4H), 3.97 (dd, J = 8.8, 7.5 Hz, 1H), 4.21 (qd, J = 7.1, 1.7 Hz, 2H), 5.50 (s, 1H), 6.68 (q, J = 6.9 Hz, 1H), 7.25 (m, 4H), 7.48 (m, 3H), 7.71 (m, 1H) |
| 63eg | $^{1}$H NMR (400 MHz, MeOH-d4): δ ppm 1.26 (t, J = 7.3 Hz, 4H), 1.51 (dt, J = 11.2, 5.5 Hz, 4H), 1.75 (dd, J = 13.1, 7.3 Hz, 1H), 2.10 (dd, J = 13.1, 8.8 Hz, 1H), 2.40 (s, 3H), 2.78 (d, J = 11.1 Hz, 1H), 2.91 (d, J = 11.0 Hz, 1H), 3.53 (m, 5H), 3.86 (dd, J = 8.6, 7.4 Hz, 1H), 4.18 (qd, J = 7.1, 1.6 Hz, 2H), 5.77 (s, 1H), 6.44 (d, J = 2.4 Hz, 1H), 7.00 (q, J = 6.7 Hz, 1H), 7.62 (d, J = 8.3 Hz, 1H), 7.97 (m, 3H), 9.06 (s, 2H), 9.17 (s, 1H) |
| 63eh | $^{1}$H NMR (400 MHz, MeOH-d4): δ ppm 1.26 (t, J = 7.1 Hz, 4H), 1.52 (dq, J = 12.0, 8.6, 7.2 Hz, 4H), 1.74 (dd, J = 13.1, 7.2 Hz, 1H), 2.09 (dd, J = 13.1, 8.8 Hz, 1H), 2.75 (d, J = 11.0 Hz, 1H), 2.90 (d, J = 11.0 Hz, 1H), 3.51 (m, 4H), 3.82 (dd, J = 8.7, 7.1 Hz, 1H), 4.18 (qd, J = 7.1, 1.6 Hz, 2H), 5.52 (s, 1H), 6.61 (q, J = 6.7 Hz, 1H), 7.33 (m, 2H), 7.47 (m, 2H), 7.66 (m, 2H) |
| 63ei | $^{1}$H NMR (400 MHz, MeOH-d4): δ ppm 1.26 (td, J = 7.1, 1.7 Hz, 6H), 1.41 (td, J = 7.0, 1.8 Hz, 3H), 1.52 (qd, J = 7.2, 4.7, 3.6 Hz, 4H), 1.75 (dd, J = 13.1, 7.3 Hz, 1H), 2.10 (dd, J = 13.1, 8.8 Hz, 1H), 2.77 (d, J = 10.9 Hz, 1H), 2.91 (d, J = 11.0 Hz, 1H), 3.29 (s, 1H), 3.51 (dq, J = 18.9, 6.1 Hz, 4H), 3.84 (m, 1H), 4.16 (m, 3H), 5.48 (d, J = 2.0 Hz, 1H), 6.73 (q, J = 6.8 Hz, 1H), 7.02 (m, 2H), 7.20 (s, 1H), 7.28 (d, J = 2.2 Hz, 1H), 7.43 (m, 2H), 7.67 (d, J = 8.4 Hz, 1H) |

TABLE 18b-continued

| NMR Data for Compounds of Table 18a | |
|---|---|
| Ex. No. | NMR |
| 63ej | $^1$H NMR (400 MHz, MeOH-d4): δ ppm 1.26 (m, 4H), 1.50 (dt, J = 22.1, 6.5 Hz, 7H), 1.74 (dd, J = 13.1, 7.2 Hz, 1H), 2.08 (dd, J = 13.1, 8.8 Hz, 1H), 2.75 (d, J = 11.0 Hz, 1H), 2.90 (d, J = 11.0 Hz, 1H), 3.31 (d, J = 1.8 Hz, 1H), 3.49 (dq, J = 25.8, 7.5, 6.6 Hz, 4H), 3.83 (dd, J = 8.7, 7.2 Hz, 1H), 4.18 (m, 4H), 5.49 (s, 1H), 6.62 (q, J = 6.8 Hz, 1H), 7.20 (d, J = 8.5 Hz, 1H), 7.26 (d, J = 2.2 Hz, 1H), 7.34 (m, 1H), 7.42 (dd, J = 8.5, 2.2 Hz, 1H), 7.58 (m, 1H), 7.65 (d, J = 8.5 Hz, 1H) |
| 63ek | $^1$H NMR (400 MHz, MeOH-d4): δ ppm 1.26 (t, J = 7.0 Hz, 4H), 1.53 (m, 4H), 1.75 (dd, J = 13.1, 7.2 Hz, 1H), 2.10 (dd, J = 13.1, 8.7 Hz, 1H), 2.76 (d, J = 10.9 Hz, 1H), 2.90 (d, J = 11.0 Hz, 1H), 3.51 (dq, J = 26.1, 7.5, 6.6 Hz, 4H), 3.83 (dd, J = 8.8, 7.2 Hz, 1H), 4.18 (qd, J = 7.1, 1.6 Hz, 2H), 5.53 (s, 1H), 6.59 (q, J = 6.7 Hz, 1H), 7.27 (d, J = 8.8 Hz, 1H), 7.34 (m, 2H), 7.49 (m, 2H), 7.69 (d, J = 8.5 Hz, 1H) |
| 63el | $^1$H NMR (400 MHz, MeOH-d4): δ ppm 0.89 (m, 2H), 1.31 (m, 15H), 1.52 (dt, J = 7.9, 4.5 Hz, 4H), 1.74 (dd, J = 13.1, 7.2 Hz, 1H), 2.09 (dd, J = 13.1, 8.8 Hz, 1H), 2.75 (d, J = 11.0 Hz, 1H), 2.89 (d, J = 11.0 Hz, 1H), 3.49 (ddt, J = 17.6, 11.8, 6.7 Hz, 4H), 3.82 (dd, J = 8.7, 7.2 Hz, 1H), 4.18 (qd, J = 7.2, 1.5 Hz, 2H), 5.44 (s, 1H), 6.60 (q, J = 6.8 Hz, 1H), 7.28 (m, 2H), 7.47 (m, 4H), 7.67 (d, J = 8.5 Hz, 1H) |
| 63em | $^1$H NMR (400 MHz, MeOH-d4): δ ppm 1.26 (m, 6H), 1.53 (m, 4H), 1.75 (dd, J = 13.1, 7.2 Hz, 1H), 2.10 (dd, J = 13.1, 8.7 Hz, 1H), 2.76 (d, J = 10.9 Hz, 1H), 2.91 (d, J = 11.0 Hz, 1H), 3.52 (m, 4H), 3.83 (dd, J = 8.8, 7.2 Hz, 1H), 4.18 (qd, J = 7.1, 1.7 Hz, 2H), 5.53 (s, 1H), 6.47 (q, J = 6.7 Hz, 1H), 7.36 (d, J = 2.2 Hz, 1H), 7.53 (dd, J = 8.6, 2.3 Hz, 1H), 7.72 (m, 2H), 7.85 (m, 2H) |
| 63en | $^1$H NMR (400 MHz, MeOH-d4): δ ppm 1.30 (t, J = 7.1 Hz, 7H), 1.59 (dt, J = 11.5, 5.7 Hz, 8H), 1.95 (m, 2H), 2.34 (dd, J = 13.3, 8.6 Hz, 2H), 3.10 (m, 4H), 3.56 (m, 8H), 3.75 (s, 1H), 4.28 (m, 6H), 5.55 (s, 1H), 6.52 (q, J = 6.7 Hz, 2H), 7.38 (d, J = 2.2 Hz, 2H), 7.53 (dd, J = 8.5, 2.2 Hz, 2H), 7.66 (m, 8H) |
| 63eo | $^1$H NMR (400 MHz, MeOH-d4): δ ppm 1.26 (td, J = 7.0, 0.7 Hz, 4H), 1.53 (m, 4H), 1.75 (dd, J = 13.1, 7.3 Hz, 1H), 2.09 (dd, J = 13.1, 8.7 Hz, 1H), 2.76 (d, J = 11.0 Hz, 1H), 2.90 (d, J = 11.0 Hz, 1H), 3.30 (m, 1H), 3.51 (dtd, J = 19.2, 13.4, 7.5 Hz, 4H), 3.82 (dd, J = 8.7, 7.2 Hz, 1H), 4.18 (m, 2H), 5.50 (s, 1H), 6.63 (q, J = 6.9 Hz, 1H), 7.25 (m, 1H), 7.47 (m, 6H), 7.71 (m, 1H) |
| 63ep | $^1$H NMR (400 MHz, MeOH-d4): δ ppm 1.33 (t, J = 7.1 Hz, 4H), 1.65 (m, 5H), 2.06 (dd, J = 13.6, 8.9 Hz, 1H), 2.50 (dd, J = 13.6, 8.8 Hz, 1H), 3.28 (s, 2H), 3.57 (m, 5H), 3.86 (s, 3H), 4.32 (qd, J = 7.2, 2.5 Hz, 2H), 4.59 (t, J = 8.8 Hz, 1H), 6.68 (q, J = 6.7 Hz, 1H), 6.98 (d, J = 7.5 Hz, 1H), 7.07 (m, 2H), 7.32 (d, J = 2.2 Hz, 1H), 7.46 (m, 2H), 7.68 (d, J = 8.5 Hz, 1H) |
| 63eq | $^1$H NMR (400 MHz, MeOH-d4): δ ppm 1.31 (m, 10H), 1.52 (m, 4H), 1.74 (dd, J = 13.1, 7.2 Hz, 1H), 2.09 (dd, J = 13.1, 8.7 Hz, 1H), 2.75 (d, J = 11.0 Hz, 1H), 2.90 (d, J = 11.0 Hz, 1H), 3.50 (m, 4H), 3.83 (dd, J = 8.7, 7.2 Hz, 1H), 4.18 (qd, J = 7.1, 1.5 Hz, 2H), 4.70 (h, J = 6.1 Hz, 1H), 5.48 (s, 1H), 6.73 (q, J = 6.9 Hz, 1H), 6.95 (d, J = 7.6 Hz, 1H), 7.04 (m, 1H), 7.21 (s, 1H), 7.27 (d, J = 2.3 Hz, 1H), 7.42 (m, 2H), 7.66 (d, J = 8.5 Hz, 1H) |
| 63er | $^1$H NMR (400 MHz, MeOH-d4): δ ppm 1.26 (td, J = 7.1, 1.4 Hz, 3H), 1.54 (m, 4H), 1.75 (dd, J = 13.1, 7.2 Hz, 1H), 2.10 (dd, J = 13.1, 8.7 Hz, 1H), 2.46 (s, 3H), 2.76 (d, J = 10.9 Hz, 1H), 2.91 (d, J = 11.0 Hz, 1H), 3.52 (m, 4H), 3.83 (dd, J = 8.7, 7.2 Hz, 1H), 4.18 (qd, J = 7.2, 1.6 Hz, 2H), 5.50 (d, J = 1.5 Hz, 1H), 6.60 (q, J = 6.8 Hz, 1H), 7.29 (m, 2H), 7.45 (m, 2H), 7.57 (s, 1H), 7.67 (m, 1H) |
| 63es | $^1$H NMR (400 MHz, MeOH-d4): δ ppm: 1.19 (s, 2H), 1.34 (m, 11H), 1.53 (m, 4H), 1.75 (dd, J = 13.1, 7.2 Hz, 1H), 2.10 (dd, J = 13.1, 8.8 Hz, 1H), 2.76 (d, J = 11.0 Hz, 1H), 2.91 (d, J = 11.0 Hz, 1H), 3.52 (m, 4H), 3.83 (m, 1H), 4.18 (m, 2H), 4.73 (h, J = 6.1 Hz, 1H), 5.50 (s, 1H), 6.62 (q, J = 6.6 Hz, 1H), 7.28 (m, 3H), 7.43 (dd, J = 8.5, 2.3 Hz, 1H), 7.59 (s, 1H), 7.65 (d, J = 8.5 Hz, 1H) |
| 63et | $^1$H NMR (400 MHz, MeOH-d4): δ ppm 0.88 (d, J = 8.3 Hz, 1H), 1.30 (m, 11H), 1.53 (m, 4H), 1.75 (dd, J = 13.1, 7.2 Hz, 1H), 2.10 (dd, J = 13.1, 8.8 Hz, 1H), 2.76 (d, J = 11.0 Hz, 1H), 2.91 (d, J = 11.0 Hz, 1H), 3.52 (m, 5H), 3.83 (dd, J = 8.7, 7.2 Hz, 1H), 4.18 (qd, J = 7.1, 1.6 Hz, 2H), 4.71 (h, J = 6.2 Hz, 1H), 5.49 (s, 1H), 6.66 (q, J = 6.8 Hz, 1H), 7.27 (m, 4H), 7.43 (dd, J = 8.5, 2.3 Hz, 1H), 7.65 (m, 1H) |
| 63eu | $^1$H NMR (400 MHz, MeOH-d4): δ ppm 1.30 (m, 4H), 1.60 (tt, J = 9.2, 4.2 Hz, 4H), 1.97 (m, 1H), 2.37 (dd, J = 13.6, 8.8 Hz, 1H), 3.14 (q, J = 11.6 Hz, 2H), 3.56 (m, 4H), 4.31 (m, 3H), 4.87 (d, J = 1.7 Hz, 18H), 5.54 (s, 1H), 6.49 (q, J = 6.6 Hz, 1H), 7.35 (d, J = 2.2 Hz, 1H), 7.51 (dd, J = 8.5, 2.2 Hz, 1H), 7.68 (d, J = 8.6 Hz, 1H), 7.82 (m, 3H) |
| 63ev | $^1$H NMR (400 MHz, MeOH-d4): δ ppm 1.27 (m, 4H), 1.54 (m, 4H), 1.78 (dd, J = 13.1, 7.4 Hz, 1H), 2.13 (dd, J = 13.1, 8.8 Hz, 1H), 2.81 (d, J = 11.1 Hz, 1H), 2.93 (d, J = 11.0 Hz, 1H), 3.53 (dq, J = 13.2, 6.0 Hz, 4H), 3.89 (dd, J = 8.8, 7.3 Hz, 1H), 4.20 (qd, J = 7.1, 1.7 Hz, 2H), 5.51 (s, 1H), 6.63 (q, J = 6.7 Hz, 1H), 7.28 (m, 4H), 7.52 (m, 2H), 7.68 (d, J = 8.5 Hz, 1H) |
| 63ew | $^1$H NMR (400 MHz, MeOH-d4): δ ppm 0.90 (d, J = 8.0 Hz, 1H), 1.27 (m, 5H), 1.53 (dt, J = 7.7, 4.7 Hz, 4H), 1.76 (dd, J = 13.1, 7.2 Hz, 1H), 2.11 (dd, J = 13.1, 8.8 Hz, 1H), 2.45 (s, 3H), 2.78 (d, J = 11.0 Hz, 1H), 2.91 (d, J = 11.0 Hz, 1H), 3.31 (s, 3H), 3.50 (dq, J = 27.7, 7.7, 6.6 Hz, 4H), 3.85 (t, J = 8.0 Hz, 1H), 4.19 (m, 2H), 5.49 (s, 1H), 6.61 (q, J = 6.8 Hz, 1H), 7.32 (m, 3H), 7.45 (dd, J = 8.6, 2.3 Hz, 1H), 7.52 (d, J = 8.1 Hz, 1H), 7.67 (d, J = 8.5 Hz, 1H) |
| 63ex | $^1$H NMR (400 MHz, MeOH-d4): δ ppm 1.27 (t, J = 7.1 Hz, 4H), 1.54 (m, 4H), 1.76 (dd, J = 13.1, 7.2 Hz, 1H), 2.11 (dd, J = 13.1, 8.8 Hz, 1H), 2.77 (d, J = 11.0 Hz, 1H), 2.91 (d, J = 11.0 Hz, 1H), 3.54 (m, 4H), 3.83 (dd, J = 8.7, 7.2 Hz, 1H), 4.19 (qd, J = |

TABLE 18b-continued

| NMR Data for Compounds of Table 18a | |
|---|---|
| Ex. No. | NMR |
| | 7.1, 1.7 Hz, 2H), 5.53 (s, 1H), 6.54 (q, J = 6.7 Hz, 1H), 7.36 (d, J = 2.2 Hz, 1H), 7.53 (dd, J = 8.6, 2.2 Hz, 1H), 7.68 (dd, J = 23.2, 8.4 Hz, 2H), 7.84 (s, 1H), 7.97 (d, J = 8.1 Hz, 1H) |
| 63ey | $^1$H NMR (400 MHz, MeOH-d4): δ ppm 1.27 (t, J = 7.1 Hz, 4H), 1.54 (ddd, J = 11.9, 6.5, 4.3 Hz, 4H), 1.76 (dd, J = 13.1, 7.2 Hz, 1H), 2.11 (dd, J = 13.1, 8.7 Hz, 1H), 2.77 (d, J = 11.0 Hz, 1H), 2.91 (d, J = 11.0 Hz, 1H), 3.52 (dq, J = 26.9, 7.7, 6.7 Hz, 4H), 3.84 (dd, J = 8.7, 7.2 Hz, 1H), 4.19 (qd, J = 7.2, 1.6 Hz, 2H), 5.53 (s, 1H), 6.63 (q, J = 6.7 Hz, 1H), 7.10 (tt, J = 9.2, 2.4 Hz, 1H), 7.19 (s, 2H), 7.34 (d, J = 2.2 Hz, 1H), 7.50 (dd, J = 8.6, 2.2 Hz, 1H), 7.70 (d, J = 8.5 Hz, 1H) |
| 63ez | $^1$H NMR (400 MHz, MeOH-d4): δ ppm 0.07 (d, J = 1.0 Hz, 1H), 0.88 (dd, J = 14.3, 7.9 Hz, 1H), 1.28 (m, 6H), 1.56 (m, 3H), 1.75 (dd, J = 13.1, 6.7 Hz, 1H), 2.07 (dd, J = 13.1, 8.8 Hz, 2H), 2.84 (d, J = 10.5 Hz, 1H), 2.96 (d, J = 10.5 Hz, 1H), 3.49 (m, 4H), 3.88 (m, 1H), 4.20 (m, 2H), 4.56 (s, 2H), 5.44 (d, J = 1.0 Hz, 1H), 6.52 (q, J = 6.7 Hz, 1H), 7.23 (m, 3H), 7.40 (m, 1H), 7.66 (m, 2H) |
| 63fa | $^1$H NMR (400 MHz, MeOH-d4): δ ppm 1.27 (t, J = 7.1 Hz, 3H), 1.53 (m, 4H), 1.75 (dd, J = 13.1, 7.2 Hz, 1H), 2.10 (dd, J = 13.1, 8.8 Hz, 1H), 2.76 (d, J = 11.0 Hz, 1H), 2.90 (d, J = 10.9 Hz, 1H), 3.52 (m, 4H), 3.82 (dd, J = 8.7, 7.2 Hz, 1H), 4.18 (qd, J = 7.2, 1.6 Hz, 2H), 5.52 (s, 1H), 6.60 (q, J = 6.8 Hz, 1H), 7.3 1 (d, J = 2.3 Hz, 1H), 7.45 (m, 3H), 7.67 (d, J = 8.5 Hz, 1H) |
| 63fb | $^1$H NMR (400 MHz, MeOH-$d_4$): δ ppm 0.89 (dd, J = 10.8, 3.8 Hz, 1H), 1.27 (t, J = 7.1 Hz, 4H), 1.53 (m, 4H), 1.75 (dd, J = 13.1, 7.2 Hz, 1H), 2.10 (dd, J = 13.1, 8.7 Hz, 1H), 2.25 (s, 1H), 2.35 (d, J = 3.2 Hz, 6H), 2.77 (d, J = 11.0 Hz, 1H), 2.91 (d, J = 11.0 Hz, 1H), 3.50 (m, 4H), 3.85 (dd, J = 8.7, 7.2 Hz, 1H), 4.19 (qd, J = 7.2, 1.6 Hz, 2H), 4.87 (d, J = 5.2 Hz, 13H), 5.44 (s, 1H), 6.64 (q, J = 6.8 Hz, 1H), 7.18 (d, J = 7.7 Hz, 2H), 7.26 (m, 2H), 7.41 (dd, J = 8.5, 2.3 Hz, 1H), 7.65 (d, J = 8.5 Hz, 1H) |
| 63fc | $^1$H NMR (400 MHz, MeOH-d4): δ ppm 0.89 (t, J = 6.7 Hz, 1H), 1.30 (m, 11H), 1.59 (dt, J = 7.7, 4.0 Hz, 9H), 1.94 (dd, J = 13.4, 8.3 Hz, 2H), 2.45 (s, 15H), 2.80 (s, 3H), 3.12 (m, 4H), 3.55 (tdd, J = 24.1, 17.0, 12.0 Hz, 9H), 4.28 (m, 6H), 5.51 (s, 2H), 6.64 (q, J = 6.8 Hz, 2H), 7.21 (s, 4H), 7.28 (d, J = 2.3 Hz, 2H), 7.44 (dd, J = 8.5, 2.3 Hz, 2H), 7.66 (d, J = 8.6 Hz, 2H) |
| 63fd | $^1$H NMR (400 MHz, MeOH-d4): δ ppm 0.08 (dd, J = 4.2, 1.7 Hz, 1H), 0.90 (q, J = 7.7 Hz, 1H), 1.26 (t, J = 7.1 Hz, 4H), 1.50 (dt, J = 33.9, 6.4 Hz, 7H), 1.75 (dd, J = 13.1, 7.2 Hz, 1H), 2.10 (dd, J = 13.1, 8.8 Hz, 1H), 2.76 (d, J = 11.0 Hz, 1H), 2.91 (d, J = 11.0 Hz, 1H), 3.50 (dq, J = 24.8, 7.5, 6.5 Hz, 4H), 3.83 (dd, J = 8.7, 7.2 Hz, 1H), 4.19 (ttd, J = 7.1, 4.5, 2.1 Hz, 4H), 5.49 (s, 1H), 6.66 (q, J = 6.8 Hz, 1H), 7.27 (m, 4H), 7.43 (dd, J = 8.5, 2.3 Hz, 1H), 7.65 (d, J = 8.5 Hz, 1H) |
| 63fe | $^1$H NMR (400 MHz, MeOH-d4): δ ppm 1.26 (td, J = 7.2, 1.1 Hz, 4H), 1.52 (dt, J = 11.8, 5.7 Hz, 4H), 1.74 (dd, J = 13.2, 7.2 Hz, 1H), 2.09 (dd, J = 13.2, 8.7 Hz, 1H), 2.38 (s, 6H), 2.75 (d, J = 11.0 Hz, 1H), 2.90 (d, J = 11.0 Hz, 1H), 3.50 (m, 5H), 3.82 (t, J = 8.0 Hz, 1H), 4.18 (m, 2H), 5.45 (s, 1H), 6.66 (q, J = 6.8 Hz, 1H), 7.04 (s, 2H), 7.12 (d, J = 1.8 Hz, 1H), 7.25 (d, J = 2.1 Hz, 1H), 7.41 (m, 1H), 7.66 (d, J = 8.5 Hz, 1H) |
| 63ff | $^1$H NMR (400 MHz, MeOH-d4): δ ppm 1.27 (t, J = 7.1 Hz, 3H), 1.54 (m, 4H), 1.76 (dd, J = 13.1, 7.3 Hz, 1H), 2.11 (dd, J = 13.1, 8.7 Hz, 1H), 2.43 (s, 3H), 2.78 (d, J = 11.0 Hz, 1H), 2.92 (d, J = 11.0 Hz, 1H), 3.52 (m, 4H), 3.86 (dd, J = 8.7, 7.3 Hz, 1H), 4.19 (qd, J = 7.1, 1.6 Hz, 2H), 5.50 (s, 1H), 6.61 (q, J = 6.8 Hz, 1H), 7.18 (s, 1H), 7.31 (m, 2H), 7.39 (s, 1H), 7.46 (dd, J = 8.5, 2.3 Hz, 1H), 7.68 (m, 1H) |
| 63fg | $^1$H NMR (400 MHz, MeOH-d4): δ ppm 0.89 (t, J = 6.9 Hz, 1H), 1.27 (m, 6H), 1.53 (dt, J = 7.9, 4.6 Hz, 4H), 1.76 (dd, J = 13.1, 7.3 Hz, 1H), 2.11 (m, 1H), 2.35 (d, J = 1.9 Hz, 3H), 2.77 (d, J = 11.0 Hz, 1H), 2.91 (d, J = 11.0 Hz, 1H), 3.49 (dp, J = 25.1, 5.9 Hz, 4H), 3.84 (dd, J = 8.7, 7.2 Hz, 1H), 4.19 (qd, J = 7.1, 1.6 Hz, 2H), 4.87 (s, 13H), 5.49 (s, 1H), 6.62 (q, J = 6.8 Hz, 1H), 7.26 (m, 4H), 7.43 (dd, J = 8.6, 2.3 Hz, 1H), 7.66 (d, J = 8.5 Hz, 1H) |
| 63fh | $^1$H NMR (400 MHz, MeOH-d4): δ ppm 1.27 (t, J = 7.1 Hz, 4H), 1.53 (dp, J = 7.3, 3.6, 2.9 Hz, 4H), 1.75 (dd, J = 13.1, 7.3 Hz, 1H), 2.10 (dd, J = 13.1, 8.7 Hz, 1H), 2.40 (s, 3H), 2.77 (d, J = 11.0 Hz, 1H), 2.91 (d, J = 11.0 Hz, 1H), 3.51 (m, 4H), 3.84 (dd, J = 8.7, 7.2 Hz, 1H), 4.19 (qd, J = 7.1, 1.6 Hz, 2H), 5.50 (s, 1H), 6.61 (q, J = 6.7 Hz, 1H), 7.30 (d, J = 2.3 Hz, 1H), 7.45 (m, 4H), 7.67 (d, J = 8.5 Hz, 1H) |
| 63fi | $^1$H NMR (400 MHz, MeOH-d4): δ ppm 1.26 (t, J = 7.1 Hz, 5H), 1.53 (m, 4H), 1.75 (dd, J = 13.1, 7.2 Hz, 1H), 2.09 (dd, J = 13.1, 8.7 Hz, 1H), 2.76 (d, J = 11.0 Hz, 1H), 2.90 (d, J = 11.0 Hz, 1H), 3.51 (dtt, J = 18.9, 13.4, 7.4 Hz, 4H), 3.82 (dd, J = 8.7, 7.2 Hz, 1H), 4.18 (qd, J = 7.2, 1.6 Hz, 2H), 5.50 (d, J = 10.3 Hz, 1H), 6.58 (q, J = 6.7 Hz, 1H), 7.32 (d, J = 2.2 Hz, 1H), 7.47 (m, 4H), 7.67 (m, 2H) |
| 63fj | $^1$H NMR (400 MHz, MeOH-d4): δ ppm 0.87 (dd, J = 11.5, 4.7 Hz, 1H), 1.26 (ddd, J = 19.3, 6.9, 5.5 Hz, 12H), 1.48 (m, 4H), 1.72 (dd, J = 13.1, 7.3 Hz, 1H), 2.05 (m, 1H), 2.74 (d, J = 11.0 Hz, 1H), 2.93 (m, 2H), 3.45 (m, 4H), 3.83 (dd, J = 8.7, 7.2 Hz, 1H), 4.17 (qd, J = 7.1, 1.4 Hz, 2H), 5.44 (s, 1H), 6.63 (q, J = 6.8 Hz, 1H), 7.34 (m, 7H), 7.66 (d, J = 8.5 Hz, 1H) |
| 63fk | $^1$H NMR (400 MHz, MeOH-d4): δ ppm 0.88 (d, J = 7.9 Hz, 1H), 1.19 (s, 2H), 1.26 (t, J = 7.1 Hz, 4H), 1.53 (dt, J = 8.3, 4.9 Hz, 4H), 1.75 (dd, J = 13.1, 7.2 Hz, 1H), 2.10 (dd, J = 13.1, 8.8 Hz, 1H), 2.76 (d, J = 11.0 Hz, 1H), 2.90 (d, J = 10.9 Hz, 1H), 3.51 (m, 4H), 3.83 (dd, J = 8.8, 7.2 Hz, 1H), 4.18 (qd, J = 7.1, 1.7 Hz, 2H), 4.87 (s, 7H), 5.52 (s, 1H), 6.40 (q, J = 6.6 Hz, 1H), 7.40 (d, J = 2.2 Hz, 1H), 7.55 (dd, J = 8.5, 2.3 Hz, 1H), 7.71 (d, J = 8.5 Hz, 1H), 8.11 (s, 2H) |
| 63fl | $^1$H NMR (400 MHz, MeOH-d4): δ ppm 1.27 (m, 6H), 1.54 (m, 7H), 1.77 (dd, J = 13.1, 7.3 Hz, 2H), 2.12 (dd, J = 13.1, 8.7 Hz, 2H), 2.23 (dd, J = 4.4, 1.5 Hz, 3H), 2.36 (d, J = 2.1 Hz, 5H), 2.79 (d, J = 11.1 Hz, 2H), 2.93 (d, J = 11.0 Hz, 2H), 3.30 (d, J = |

TABLE 18b-continued

| NMR Data for Compounds of Table 18a | |
|---|---|
| Ex. No. | NMR |
| | 9.7 Hz, 1H), 3.52 (dq, J = 19.4, 6.4 Hz, 7H), 3.88 (dd, J = 8.8, 7.3 Hz, 2H), 4.19 (dddd, J = 8.7, 7.1, 5.6, 1.7 Hz, 3H), 5.49 (q, J = 2.5, 1.9 Hz, 2H), 6.65 (q, J = 6.7 Hz, 2H), 7.22 (m, 6H), 7.43 (m, 3H), 7.67 (d, J = 8.5 Hz, 2H) |
| 63fm | $^1$H NMR (400 MHz, MeOH-d4): δ ppm1.30 (m, 5H), 1.61 (m, 4H), 1.96 (dd, J = 13.4, 8.4 Hz, 1H), 2.37 (dd, J = 13.4, 8.7 Hz, 1H), 2.81 (s, 1H), 3.13 (q, J = 11.6 Hz, 2H), 3.57 (m, 4H), 4.30 (m, 3H), 5.56 (s, 1H), 6.55 (q, J = 6.7 Hz, 1H), 7.34 (d, J = 2.2 Hz, 1H), 7.55 (m, 5H), 7.69 (d, J = 8.5 Hz, 1H) |
| 63fn | $^1$H NMR (400 MHz, MeOH-d4): δ ppm 1.27 (m, 4H), 1.53 (m, 4H), 1.75 (dd, J = 13.1, 7.2 Hz, 1H), 2.10 (dd, J = 13.1, 8.8 Hz, 1H), 2.76 (d, J = 10.9 Hz, 1H), 2.90 (d, J = 11.0 Hz, 1H), 3.51 (m, 4H), 3.82 (dd, J = 8.8, 7.2 Hz, 1H), 4.18 (qd, J = 7.1, 1.6 Hz, 2H), 5.53 (s, 1H), 6.49 (q, J = 6.7 Hz, 1H), 7.34 (d, J = 2.2 Hz, 1H), 7.52 (m, 2H), 7.68 (d, J = 8.6 Hz, 1H), 7.81 (s, 2H) |
| 63fo | $^1$H NMR (400 MHz, MeOH-d4): δ ppm1.27 (t, J = 7.1 Hz, 4H), 1.54 (m, 4H), 1.75 (dd, J = 13.1, 7.2 Hz, 1H), 2.10 (dd, J = 13.1, 8.8 Hz, 1H), 2.77 (d, J = 11.0 Hz, 1H), 2.83 (s, 1H), 2.91 (d, J = 11.0 Hz, 1H), 3.53 (m, 4H), 3.83 (dd, J = 8.7, 7.2 Hz, 1H), 4.19 (qd, J = 7.2, 1.6 Hz, 2H), 5.53 (s, 1H), 6.53 (q, J = 6.8 Hz, 1H), 7.37 (d, J = 2.2 Hz, 1H), 7.53 (dd, J = 8.5, 2.2 Hz, 1H), 7.62 (ddd, J = 7.9, 5.0, 0.9 Hz, 1H), 7.72 (d, J = 8.6 Hz, 1H), 7.98 (m, 1H), 8.67 (dd, J = 5.0, 1.6 Hz, 1H), 8.75 (d, J = 2.2 Hz, 1H) |
| 63fp | $^1$H NMR (400 MHz, MeOH-d4): δ ppm1.31 (m, 10H), 1.54 (m, 4H), 1.75 (dd, J = 13.1, 7.2 Hz, 1H), 2.10 (dd, J = 13.1, 8.8 Hz, 1H), 2.77 (d, J = 11.0 Hz, 1H), 2.91 (d, J = 11.0 Hz, 1H), 3.53 (m, 4H), 3.84 (dd, J = 8.7, 7.2 Hz, 1H), 4.19 (qd, J = 7.1, 1.6 Hz, 2H), 4.69 (p, J = 6.1 Hz, 1H), 5.51 (s, 1H), 6.72 (q, J = 7.0 Hz, 1H), 6.83 (dt, J = 11.3, 2.3 Hz, 1H), 7.03 (m, 1H), 7.30 (d, J = 2.2 Hz, 1H), 7.46 (dd, J = 8.5, 2.3 Hz, 1H), 7.67 (d, J = 8.5 Hz, 1H) |
| 63fq | $^1$H NMR (400 MHz, MeOH-d4): δ ppm0.88 (m, 1H), 1.37 (m, 22H), 1.75 (dd, J = 13.1, 7.4 Hz, 2H), 2.09 (dd, J = 13.1, 8.8 Hz, 2H), 2.21 (s, 2H), 2.78 (d, J = 11.1 Hz, 2H), 2.91 (d, J = 11.1 Hz, 2H), 3.49 (m, 8H), 3.88 (dd, J = 8.8, 7.4 Hz, 2H), 4.12 (m, 8H), 5.49 (s, 2H), 6.79 (m, 7H), 7.03 (s, 2H), 7.28 (d, J = 2.3 Hz, 2H), 7.42 (dd, J = 8.6, 2.2 Hz, 2H), 7.67 (d, J = 8.5 Hz, 2H) |
| 63fr | $^1$H NMR (400 MHz, MeOH-d4): δ ppm1.32 (m, 15H), 1.52 (m, 4H), 1.74 (dd, J = 13.1, 7.2 Hz, 1H), 2.09 (dd, J = 13.1, 8.8 Hz, 1H), 2.32 (d, J = 0.7 Hz, 1H), 2.43 (d, J = 0.8 Hz, 3H), 2.76 (d, J = 11.0 Hz, 1H), 2.90 (d, J = 11.0 Hz, 1H), 3.48 (m, 4H), 3.83 (dd, J = 8.7, 7.2 Hz, 1H), 4.18 (qd, J = 7.2, 1.5 Hz, 2H), 5.43 (s, 1H), 6.63 (q, J = 6.8 Hz, 1H), 7.06 (s, 1H), 7.26 (m, 2H), 7.34 (q, J = 1.3 Hz, 1H), 7.42 (dd, J = 8.5, 2.3 Hz, 1H), 7.66 (d, J = 8.5 Hz, 1H) |
| 63fs | $^1$H NMR (400 MHz, MeOH-d4): δ ppm 1.27 (t, J = 7.2 Hz, 3H), 1.55 (m, 4H), 1.77 (dd, J = 13.1, 7.3 Hz, 1H), 2.12 (dd, J = 13.2, 8.8 Hz, 1H), 2.79 (d, J = 11.0 Hz, 1H), 2.92 (d, J = 11.0 Hz, 1H), 3.53 (m, 4H), 3.86 (dd, J = 8.7, 7.3 Hz, 1H), 4.19 (qd, J = 7.1, 1.7 Hz, 2H), 4.86 (s, 3H), 5.53 (s, 1H), 6.57 (q, J = 6.8 Hz, 1H), 7.34 (d, J = 2.2 Hz, 1H), 7.51 (dd, J = 8.5, 2.3 Hz, 1H), 7.72 (m, 2H), 7.84 (m, 2H), 7.92 (s, 1H) |
| 63ft | $^1$H NMR (400 MHz, MeOH-d4): δ ppm 0.88 (m, 2H), 1.24 (m, 4H), 1.39 (t, J = 7.0 Hz, 3H), 1.50 (q, J = 7.7, 5.2 Hz, 4H), 1.74 (ddd, J = 13.3, 7.3, 1.8 Hz, 1H), 2.08 (ddd, J = 11.4, 8.7, 2.6 Hz, 1H), 2.39 (s, 3H), 2.76 (d, J = 11.1 Hz, 1H), 2.88 (dd, J = 11.0, 5.7 Hz, 1H), 3.58 (m, 4H), 3.85 (m, 1H), 4.13 (m, 4H), 5.73 (s, 1H), 6.42 (d, J = 2.4 Hz, 1H), 6.70 (dt, J = 10.7, 2.2 Hz, 1H), 6.80 (p, J = 6.5 Hz, 1H), 7.01 (m, 2H), 7.63 (d, J = 1.9 Hz, 1H), 7.76 (m, 2H), 8.00 (d, J = 2.4 Hz, 1H) |
| 63fu | $^1$H NMR (400 MHz, MeOH-d4): δ ppm 1.26 (t, J = 7.1 Hz, 4H), 1.50 (dt, J = 9.9, 5.2 Hz, 4H), 1.73 (dd, J = 13.1, 7.2 Hz, 1H), 2.07 (dd, J = 13.1, 8.7 Hz, 1H), 2.22 (s, 1H), 2.29 (d, J = 10.3 Hz, 6H), 2.39 (s, 3H), 2.75 (d, J = 11.0 Hz, 1H), 2.88 (d, J = 11.0 Hz, 1H), 3.52 (m, 4H), 3.83 (dd, J = 8.7, 7.2 Hz, 1H), 4.18 (qd, J = 7.1, 1.6 Hz, 2H), 5.74 (s, 1H), 6.41 (d, J = 2.3 Hz, 1H), 6.75 (m, 1H), 7.19 (d, J = 7.9 Hz, 1H), 7.39 (m, 2H), 7.59 (d, J = 1.8 Hz, 1H), 7.72 (m, 2H), 7.96 (d, J = 2.3 Hz, 1H) |
| 63fv | $^1$H NMR (400 MHz, MeOH-d4): δ ppm 1.26 (m, 4H), 1.51 (dt, J = 10.6, 5.6 Hz, 4H), 1.74 (dd, J = 13.1, 7.2 Hz, 1H), 2.08 (dd, J = 13.1, 8.7 Hz, 1H), 2.39 (s, 3H), 2.76 (d, J = 11.0 Hz, 1H), 2.89 (d, J = 11.0 Hz, 1H), 3.53 (m, 4H), 3.83 (m, 1H), 4.18 (m, 2H), 4.85 (d, J = 10.8 Hz, 1H), 5.73 (s, 1H), 6.42 (d, J = 2.4 Hz, 1H), 6.83 (q, J = 6.6 Hz, 1H), 7.60 (m, 4H), 7.79 (m, 2H), 8.00 (d, J = 2.4 Hz, 1H) |
| 63fw | $^1$H NMR (400 MHz, MeOH-d4): δ ppm 1.25 (t, J = 7.1 Hz, 3H), 1.46 (m, 7H), 1.73 (dd, J = 13.1, 7.2 Hz, 1H), 2.06 (dd, J = 13.1, 8.8 Hz, 1H), 2.39 (s, 3H), 2.73 (d, J = 11.0 Hz, 1H), 2.87 (d, J = 11.0 Hz, 1H), 3.52 (m, 4H), 3.80 (dd, J = 8.7, 7.1 Hz, 1H), 4.16 (m, 4H), 5.73 (s, 1H), 6.41 (d, J = 2.3 Hz, 1H), 6.78 (q, J = 6.6 Hz, 1H), 7.11 (d, J = 8.6 Hz, 1H), 7.57 (m, 2H), 7.71 (m, 3H), 7.98 (d, J = 2.4 Hz, 1H) |
| 63fx | $^1$H NMR (400 MHz, MeOH-d4): δ ppm 1.26 (m, 4H), 1.39 (t, J = 7.0 Hz, 3H), 1.51 (dt, J = 10.6, 5.6 Hz, 4H), 1.73 (dd, J = 13.1, 7.1 Hz, 1H), 2.07 (dd, J = 13.0, 8.8 Hz, 1H), 2.39 (s, 3H), 2.74 (d, J = 10.9 Hz, 1H), 2.88 (d, J = 11.0 Hz, 1H), 3.53 (m, 4H), 3.81 (dd, J = 8.8, 7.1 Hz, 1H), 4.13 (m, 4H), 4.87 (s, 13H), 5.74 (s, 1H), 6.41 (d, J = 2.4 Hz, 1H), 6.78 (q, J = 7.6, 7.0 Hz, 1H), 6.93 (m, 1H), 7.20 (m, 2H), 7.34 (t, J = 7.9 Hz, 1H), 7.62 (d, J = 1.8 Hz, 1H), 7.75 (m, 2H), 7.98 (d, J = 2.4 Hz, 1H) |
| 63fy | $^1$H NMR (400 MHz, MeOH-d4): δ ppm 1.26 (m, 3H), 1.50 (dt, J = 10.5, 5.8 Hz, 4H), 1.73 (dd, J = 13.1, 7.2 Hz, 1H), 2.07 (dd, J = 13.0, 8.8 Hz, 1H), 2.39 (s, 3H), 2.74 (d, J = 11.0 Hz, 1H), 2.88 (d, J = 11.0 Hz, 1H), 3.52 (m, 4H), 3.80 (m, 1H), 4.17 (qd, J = 7.1, 1.6 Hz, 2H), 5.73 (s, 1H), 6.42 (d, J = 2.3 Hz, 1H), 6.84 (q, J = 6.6 Hz, 1H), 6.99 (tt, J = 9.1, 2.4 Hz, 1H), 7.34 (m, 2H), 7.68 (d, J = 1.9 Hz, 1H), 7.79 (m, 2H), 8.01 (d, J = 2.4 Hz, 1H) |

TABLE 18b-continued

| NMR Data for Compounds of Table 18a | |
|---|---|
| Ex. No. | NMR |
| 63fz | $^1$H NMR (400 MHz, MeOH-d4): δ ppm 1.26 (m, 3H), 1.51 (dt, J = 10.6, 5.6 Hz, 4H), 1.73 (dd, J = 13.1, 7.2 Hz, 1H), 2.07 (dd, J = 13.1, 8.8 Hz, 1H), 2.40 (s, 3H), 2.74 (d, J = 11.0 Hz, 1H), 2.88 (d, J = 11.0 Hz, 1H), 3.52 (dq, J = 25.8, 8.1, 6.9 Hz, 4H), 3.81 (dd, 1 = 8.8, 7.1 Hz, 1H), 4.17 (qd, J = 7.1, 1.6 Hz, 2H), 5.73 (s, 1H), 6.43 (d, J = 2.4 Hz, 1H), 6.83 (q, J = 6.6 Hz, 1H), 7.69 (m, 3H), 7.82 (m, 2H), 7.98 (m, 3H) |
| 63ga | $^1$H NMR (400 MHz, MeOH-d4): δ ppm 1.27 (t, J = 7.1 Hz, 3H), 1.41 (t, J = 7.0 Hz, 3H), 1.53 (m, 4H), 1.75 (dd, J = 13.1, 7.3 Hz, 1H), 2.11 (m, 1H), 2.77 (d, J = 11.0 Hz, 1H), 2.91 (d, J = 11.0 Hz, 1H), 3.52 (m, 4H), 3.83 (dd, J = 8.7, 7.2 Hz, 1H), 4.17 (m, 4H), 5.49 (s, 1H), 6.66 (q, J = 6.8 Hz, 1H), 7.02 (s, 1H), 7.27 (m, 3H), 7.45 (dd, J = 8.5, 2.3 Hz, 1H), 7.66 (d, J = 8.5 Hz, 1H) |
| 63gb | $^1$H NMR (400 MHz, MeOH-d4): δ ppm 0.88 (m, 2H), 1.17 (t, J = 7.0 Hz, 1H), 1.31 (m, 12H), 1.51 (dt, J = 11.3, 5.6 Hz, 4H), 1.74 (ddd, J = 13.1, 7.3, 1.9 Hz, 1H), 2.08 (ddd, J = 11.9, 8.8, 2.8 Hz, 1H), 2.39 (s, 3H), 2.76 (d, J = 11.0 Hz, 1H), 2.89 (dd, J = 11.0, 5.9 Hz, 1H), 3.57 (m, 5H), 3.84 (dt, J = 8.6, 7.2 Hz, 1H), 4.18 (qd, J = 7.1, 1.7 Hz, 1H), 4.64 (p, J = 6.1 Hz, 1H), 5.74 (s, 1H), 6.41 (d, J = 2.3 Hz, 1H), 6.78 (q, J = 6.5 Hz, 1H), 7.16 (t, J = 8.6 Hz, 1H), 7.44 (m, 2H), 7.61 (d, J = 1.9 Hz, 1H), 7.73 (m, 2H), 7.98 (d, J = 2.4 Hz, 1H) |
| 63gc | $^1$H NMR (400 MHz, MeOH-d4): δ ppm 1.26 (m, 4H), 1.51 (dt, J = 10.6, 5.7 Hz, 4H), 1.74 (dd, J = 13.1, 7.2 Hz, 1H), 2.07 (dd, J = 13.1, 8.8 Hz, 1H), 2.28 (s, 1H), 2.37 (d, J = 16.9 Hz, 9H), 2.75 (d, J = 11.0 Hz, 1H), 2.89 (d, J = 11.0 Hz, 1H), 3.53 (dt, J = 22.1, 6.0 Hz, 4H), 3.82 (dd, J = 8.7, 7.2 Hz, 1H), 4.18 (qd, J = 7.1, 1.6 Hz, 2H), 5.74 (s, 1H), 6.41 (d, J = 2.3 Hz, 1H), 6.77 (q, J = 6.6 Hz, 1H), 7.03 (m, 1H), 7.27 (d, J = 1.5 Hz, 2H), 7.60 (d, J = 1.8 Hz, 1H), 7.74 (m, 2H), 7.97 (d, J = 2.4 Hz, 1H) |
| 63gd | $^1$H NMR (400 MHz, MeOH-d4): δ ppm 1.26 (q, J = 7.1, 6.4 Hz, 4H), 1.50 (dt, J = 10.3, 5.6 Hz, 4H), 1.73 (dd, J = 13.0, 7.2 Hz, 1H), 2.07 (dd, J = 13.1, 8.8 Hz, 1H), 2.39 (d, J = 3.0 Hz, 6H), 2.74 (d, J = 10.9 Hz, 1H), 2.88 (d, J = 10.9 Hz, 1H), 3.52 (dt, J = 22.1, 6.1 Hz, 4H), 3.81 (dd, J = 8.8, 7.1 Hz, 1H), 4.17 (qd, J = 7.1, 1.6 Hz, 2H), 4.87 (s, 9H), 5.73 (s, 1H), 6.42 (d, J = 2.3 Hz, 1H), 6.81 (q, J = 6.6 Hz, 1H), 7.23 (s, 1H), 7.42 (s, 1H), 7.48 (d, J = 2.0 Hz, 1H), 7.62 (d, J = 1.9 Hz, 1H), 7.71 (dd, J = 8.1, 1.9 Hz, 1H), 7.79 (d, J = 8.2 Hz, 1H), 8.00 (d, J = 2.4 Hz, 1H) |
| 63ge | $^1$H NMR (400 MHz, MeOH-d4): δ ppm 0.89 (t, J = 7.0 Hz, 1H), 1.26 (m, 5H), 1.50 (dt, J = 10.5, 5.4 Hz, 4H), 1.73 (dd, J = 13.1, 7.2 Hz, 1H), 2.07 (dd, J = 13.1, 8.8 Hz, 1H), 2.29 (d, J = 1.9 Hz, 3H), 2.39 (s, 3H), 2.74 (d, J = 10.9 Hz, 1H), 2.88 (d, J = 11.0 Hz, 1H), 3.52 (m, 4H), 3.81 (dd, J = 8.8, 7.2 Hz, 1H), 4.18 (qd, J = 7.1, 1.6 Hz, 2H), 5.73 (s, 1H), 6.41 (d, J = 2.4 Hz, 1H), 6.79 (q, J = 6.6 Hz, 1H), 7.37 (m, 3H), 7.63 (d, J = 1.9 Hz, 1H), 7.76 (m, 2H), 7.98 (d, J = 2.4 Hz, 1H) |
| 63gf | $^1$H NMR (400 MHz, MeOH-d4): δ ppm 0.08 (m, 1H), 1.26 (m, 4H), 1.36 (s, 9H), 1.51 (dt, J = 10.5, 5.5 Hz, 5H), 1.74 (dd, J = 13.1, 7.2 Hz, 1H), 2.08 (dd, J = 13.1, 8.8 Hz, 1H), 2.40 (s, 3H), 2.74 (d, J = 11.0 Hz, 1H), 2.89 (d, J = 11.0 Hz, 1H), 3.53 (dt, J = 23.0, 6.0 Hz, 4H), 3.81 (dd, J = 8.8, 7.1 Hz, 1H), 4.17 (qd, J = 7.1, 1.6 Hz, 2H), 5.74 (s, 1H), 6.42 (d, J = 2.4 Hz, 1H), 6.76 (q, J = 6.6 Hz, 1H), 7.43 (m, 3H), 7.61 (d, J = 1.9 Hz, 1H), 7.73 (m, 3H), 7.99 (d, J = 2.4 Hz, 1H) |
| 63gg | $^1$H NMR (400 MHz, MeOH-d4): δ ppm 1.26 (t, J = 7.3 Hz, 6H), 1.50 (dt, J = 10.5, 5.6 Hz, 4H), 1.74 (dd, J = 13.1, 7.2 Hz, 1H), 2.08 (dd, J = 13.1, 8.8 Hz, 1H), 2.39 (s, 3H), 2.75 (d, J = 11.0 Hz, 1H), 2.89 (d, J = 11.0 Hz, 1H), 3.52 (m, 4H), 3.83 (dd, J = 8.7, 7.2 Hz, 1H), 4.18 (qd, J = 7.1, 1.6 Hz, 2H), 5.73 (s, 1H), 6.42 (d, J = 2.4 Hz, 1H), 6.82 (q, J = 6.6 Hz, 1H), 7.41 (m, 2H), 7.61 (m, 2H), 7.74 (m, 3H), 8.00 (d, J = 2.4 Hz, 1H) |
| 63gh | $^1$H NMR (400 MHz, MeOH-d4): δ ppm 1.26 (t, J = 7.2 Hz, 3H), 1.51 (dt, J = 10.4, 5.5 Hz, 4H), 1.75 (dd, J = 13.1, 7.3 Hz, 1H), 2.10 (dd, J = 13.1, 8.8 Hz, 1H), 2.39 (s, 3H), 2.84 (m, 2H), 3.52 (ddq, J = 25.3, 13.2, 7.1, 5.7 Hz, 4H), 3.86 (dd, J = 8.8, 7.2 Hz, 1H), 4.18 (qd, J = 7.2, 1.6 Hz, 2H), 5.73 (s, 1H), 6.42 (d, J = 2.3 Hz, 1H), 6.82 (q, J = 6.6 Hz, 1H), 7.33 (t, J = 8.8 Hz, 1H), 7.63 (m, 2H), 7.73 (dd, J = 8.3, 1.9 Hz, 1H), 7.82 (m, 2H), 8.00 (d, J = 2.3 Hz, 1H) |
| 63gi | $^1$H NMR (400 MHz, MeOH-d4): δ ppm 1.28 (m, 4H), 1.53 (dt, J = 10.2, 5.5 Hz, 4H), 1.82 (dd, J = 13.2, 7.7 Hz, 1H), 2.19 (m, 1H), 2.39 (s, 3H), 2.88 (d, J = 11.2 Hz, 1H), 2.99 (d, J = 11.2 Hz, 1H), 3.55 (m, 4H), 4.02 (t, J = 8.2 Hz, 1H), 4.22 (qd, J = 7.1, 1.9 Hz, 2H), 5.74 (s, 1H), 6.42 (d, J = 2.3 Hz, 1H), 6.82 (m, 1H), 7.35 (dt, J = 10.4, 8.4 Hz, 1H), 7.50 (ddt, J = 7.9, 3.8, 1.8 Hz, 1H), 7.72 (m, 4H), 8.00 (d, J = 2.4 Hz, 1H) |
| 63gj | $^1$H NMR (400 MHz, MeOH-d4): δ ppm 1.31 (m, 3H), 1.65 (dt, J = 12.8, 6.2 Hz, 4H), 2.03 (m, 1H), 2.43 (m, 4H), 3.27 (s, 2H), 3.65 (m, 4H), 4.31 (qd, J = 7.1, 2.2 Hz, 2H), 4.58 (t, J = 8.8 Hz, 1H), 4.85 (m, 1H), 6.43 (d, J = 2.5 Hz, 1H), 6.89 (q, J = 6.4 Hz, 1H), 7.45 (m, 1H), 7.72 (d, J = 1.8 Hz, 1H), 7.81 (m, 2H), 8.00 (m, 3H) |
| 63gk | $^1$H NMR (400 MHz, MeOH-d4): δ ppm 1.32 (t, J = 7.1 Hz, 3H), 1.64 (q, J = 10.3, 8.1 Hz, 4H), 2.04 (dd, J = 13.6, 8.9 Hz, 1H), 2.44 (m, 4H), 2.80 (s, 1H), 3.25 (m, 2H), 3.56 (m, 1H), 3.70 (d, J = 5.7 Hz, 2H), 4.32 (qd, J = 7.1, 2.5 Hz, 2H), 4.57 (t, J = 8.8 Hz, 1H), 6.44 (d, J = 2.4 Hz, 1H), 6.90 (q, J = 6.5 Hz, 1H), 7.76 (q, J = 1.5, 1.0 Hz, 2H), 7.85 (m, 2H), 7.95 (m, 1H), 8.04 (m, 2H) |
| 63gl | $^1$H NMR (400 MHz, MeOH-d4): δ ppm 1.26 (t, J = 7.1 Hz, 4H), 1.51 (dt, J = 10.3, 5.5 Hz, 4H), 1.74 (dd, J = 13.1, 7.2 Hz, 1H), 2.08 (dd, J = 13.1, 8.8 Hz, 1H), 2.40 (s, 3H), 2.75 (d, J = 11.0 Hz, 1H), 2.89 (d, J = 11.0 Hz, 1H), 3.52 (m, 4H), 3.83 (dd, J = 8.7, 7.2 Hz, 1H), 4.18 (qd, J = 7.1, 1.6 Hz, 2H), 5.73 (s, 1H), 6.42 (d, J = 2.3 Hz, 1H), 6.82 (q, J = 6.6 Hz, 1H), 7.31 (ddt, J = 8.1, 2.3, 1.1 Hz, 1H), 7.57 (dd, J = 15.9, 7.9 Hz, 2H), 7.74 (m, 4H), 8.01 (d, J = 2.4 Hz, 1H) |

TABLE 18b-continued

| NMR Data for Compounds of Table 18a | |
|---|---|
| Ex. No. | NMR |
| 63gm | $^1$H NMR (400 MHz, MeOH-d4): δ ppm 1.30 (d, J = 34.9 Hz, 12H), 1.51 (dt, J = 10.4, 5.7 Hz, 4H), 1.74 (dd, J = 13.1, 7.2 Hz, 1H), 2.06 (m, 1H), 2.39 (d, J = 3.3 Hz, 6H), 2.74 (d, J = 11.0 Hz, 2H), 2.89 (d, J = 11.0 Hz, 1H), 3.53 (m, 5H), 3.81 (dd, J = 8.7, 7.1 Hz, 1H), 4.17 (qd, J = 7.2, 1.6 Hz, 2H), 4.87 (s, 3H), 5.73 (s, 1H), 6.41 (d, J = 2.4 Hz, 1H), 6.75 (q, J = 6.8 Hz, 1H), 7.28 (d, J = 9.0 Hz, 2H), 7.46 (t, J = 1.6 Hz, 1H), 7.59 (d, J = 1.8 Hz, 1H), 7.75 (m, 2H), 7.98 (d, J = 2.3 Hz, 1H) |
| 63gn | $^1$H NMR (400 MHz, MeOH-d4): δ ppm 1.26 (t, J = 7.1 Hz, 4H), 1.50 (dt, J = 10.8, 5.6 Hz, 4H), 1.73 (dd, J = 13.1, 7.2 Hz, 1H), 2.07 (dd, J = 13.1, 8.8 Hz, 1H), 2.41 (d, J = 11.8 Hz, 6H), 2.74 (d, J = 11.0 Hz, 1H), 2.88 (d, J = 11.0 Hz, 1H), 3.52 (dq, J = 24.2, 7.6, 6.3 Hz, 4H), 3.81 (dd, J = 8.7, 7.2 Hz, 1H), 4.18 (qd, J = 7.1, 1.6 Hz, 2H), 5.73 (s, 1H), 6.41 (d, J = 2.4 Hz, 1H), 6.79 (m, 1H), 7.45 (m, 2H), 7.63 (dd, J = 7.6, 2.0 Hz, 2H), 7.75 (m, 2H), 7.98 (d, J = 2.4 Hz, 1H) |
| 63go | $^1$H NMR (400 MHz, MeOH-d4): δ ppm 0.88 (d, J = 7.9 Hz, 1H), 1.26 (t, J = 7.1 Hz, 7H), 1.50 (dt, J = 10.5, 5.6 Hz, 8H), 1.74 (dd, J = 13.1, 7.2 Hz, 2H), 2.07 (dd, J = 13.1, 8.8 Hz, 2H), 2.34 (t, J = 0.6 Hz, 1H), 2.40 (d, J = 9.3 Hz, 16H), 2.75 (d, J = 11.0 Hz, 2H), 2.89 (d, J = 11.0 Hz, 2H), 3.52 (m, 8H), 3.82 (dd, J = 8.8, 7.2 Hz, 2H), 4.18 (qd, J = 7.1, 1.6 Hz, 4H), 5.73 (s, 2H), 6.41 (d, J = 2.3 Hz, 2H), 6.79 (q, J = 6.6 Hz, 2H), 7.44 (d, J = 0.9 Hz, 4H), 7.62 (d, J = 1.8 Hz, 2H), 7.74 (m, 4H), 7.98 (d, J = 2.4 Hz, 2H) |
| 63gp | $^1$H NMR (400 MHz, MeOH-d4): δ ppm 1.27 (q, J = 7.1, 5.7 Hz, 7H), 1.51 (dt, J = 10.7, 5.5 Hz, 4H), 1.74 (dd, J = 13.1, 7.2 Hz, 1H), 2.06 (td, J = 15.3, 14.1, 7.4 Hz, 1H), 2.32 (d, J = 2.1 Hz, 3H), 2.39 (s, 2H), 2.75 (d, J = 11.0 Hz, 1H), 2.89 (d, J = 11.0 Hz, 1H), 3.53 (dt, J = 22.2, 6.1 Hz, 4H), 3.83 (dd, J = 8.8, 7.2 Hz, 1H), 4.18 (m, 2H), 5.74 (s, 1H), 6.41 (d, J = 2.4 Hz, 1H), 6.78 (q, J = 6.5 Hz, 1H), 7.10 (t, J = 9.0 Hz, 1H), 7.56 (m, 3H), 7.74 (m, 2H), 7.98 (d, J = 2.4 Hz, 1H) |
| 63gq | $^1$H NMR (400 MHz, MeOH-d4): δ ppm 0.89 (m, 1H), 1.26 (dq, J = 10.3, 5.8, 3.2 Hz, 6H), 1.46 (m, 7H), 1.74 (dd, J = 13.1, 7.2 Hz, 1H), 2.09 (m, 1H), 2.39 (s, 3H), 2.75 (d, J = 11.0 Hz, 1H), 2.89 (d, J = 11.0 Hz, 1H), 3.53 (m, 4H), 3.82 (dd, J = 8.7, 7.2 Hz, 1H), 4.16 (m, 4H), 5.74 (s, 1H), 6.41 (d, J = 2.3 Hz, 1H), 6.78 (q, J = 6.5 Hz, 1H), 7.15 (t, J = 8.6 Hz, 1H), 7.47 (m, 4H), 7.73 (m, 2H), 7.97 (d, J = 2.3 Hz, 1H) |
| 63gr | $^1$H NMR (400 MHz, MeOH-d4): δ ppm 1.26 (t, J = 7.1 Hz, 3H), 1.52 (t, J = 8.0 Hz, 5H), 1.74 (dd, J = 13.1, 7.2 Hz, 1H), 2.08 (dd, J = 13.0, 8.7 Hz, 1H), 2.40 (s, 3H), 2.75 (d, J = 11.0 Hz, 1H), 2.89 (d, J = 10.9 Hz, 1H), 3.25 (p, J = 1.7 Hz, 1H), 3.53 (m, 5H), 3.81 (dd, J = 8.8, 7.1 Hz, 1H), 4.18 (qd, J = 7.1, 1.6 Hz, 2H), 4.82 (s, 1H), 5.73 (s, 1H), 6.00 (m, 1H), 6.42 (d, J = 2.4 Hz, 1H), 6.85 (d, J = 6.6 Hz, 1H), 7.48 (t, J = 1.9 Hz, 1H), 7.69 (m, 3H), 7.80 (m, 3H), 8.03 (d, J = 2.4 Hz, 1H) |
| 63gs | $^1$H NMR (400 MHz, MeOH-d4): δ ppm 1.26 (m, 10H), 1.50 (dt, J = 10.3, 5.6 Hz, 4H), 1.73 (dd, J = 13.1, 7.2 Hz, 1H), 2.07 (dd, J = 13.1, 8.8 Hz, 1H), 2.39 (s, 3H), 2.74 (d, J = 11.0 Hz, 1H), 2.93 (m, 2H), 3.52 (m, 5H), 3.82 (dd, J = 8.7, 7.2 Hz, 1H), 4.17 (qd, J = 7.1, 1.5 Hz, 2H), 5.74 (s, 1H), 6.41 (d, J = 2.3 Hz, 1H), 6.78 (q, J = 6.6 Hz, 1H), 7.26 (dt, J = 7.6, 1.4 Hz, 1H), 7.36 (t, J = 7.7 Hz, 1H), 7.47 (m, 2H), 7.61 (d, J = 1.9 Hz, 1H), 7.75 (m, 2H), 7.98 (d, J = 2.4 Hz, 1H) |
| 63gt | $^1$H NMR (400 MHz, MeOH-d4): δ ppm 1.26 (m, 4H), 1.51 (dt, J = 11.0, 5.6 Hz, 4H), 1.74 (dd, J = 13.1, 7.2 Hz, 1H), 2.07 (dd, J = 13.2, 8.8 Hz, 1H), 2.40 (s, 2H), 2.75 (d, J = 10.9 Hz, 1H), 2.89 (d, J = 11.0 Hz, 1H), 3.53 (m, 4H), 3.82 (dd, J = 8.8, 7.2 Hz, 1H), 4.18 (qd, J = 7.1, 1.6 Hz, 2H), 5.72 (s, 1H), 6.00 (m, 1H), 6.43 (d, J = 2.4 Hz, 1H), 6.84 (q, J = 6.5 Hz, 1H), 7.71 (m, 2H), 7.82 (m, 2H), 7.92 (dd, J = 8.4, 2.3 Hz, 1H), 8.05 (dd, J = 15.9, 2.3 Hz, 2H) |
| 63gu | $^1$H NMR (400 MHz, MeOH-d4): δ ppm 1.26 (t, J = 7.1 Hz, 3H), 1.51 (dt, J = 11.1, 5.5 Hz, 4H), 1.74 (dd, J = 13.1, 7.2 Hz, 1H), 2.07 (dd, J = 13.1, 8.8 Hz, 1H), 2.40 (s, 3H), 2.75 (d, J = 11.0 Hz, 1H), 2.89 (d, J = 11.0 Hz, 1H), 3.53 (dt, J = 22.4, 6.0 Hz, 4H), 3.81 (dd, J = 8.7, 7.1 Hz, 1H), 4.18 (qd, J = 7.1, 1.7 Hz, 2H), 5.73 (s, 1H), 6.43 (d, J = 2.4 Hz, 1H), 6.86 (q, J = 6.6 Hz, 1H), 7.81 (m, 5H), 7.97 (m, 1H), 8.03 (d, J = 2.4 Hz, 1H) |
| 63gv | $^1$H NMR (400 MHz, MeOH-d4): δ ppm 0.08 (m, 1H), 1.26 (m, 4H), 1.51 (dt, J = 10.7, 5.5 Hz, 5H), 1.73 (dd, J = 13.1, 7.2 Hz, 1H), 2.06 (m, 1H), 2.40 (s, 3H), 2.74 (d, J = 11.0 Hz, 1H), 2.88 (d, J = 11.0 Hz, 1H), 3.26 (s, 1H), 3.53 (dt, J = 22.3, 6.1 Hz, 5H), 3.81 (dd, J = 8.7, 7.1 Hz, 1H), 4.17 (qd, J = 7.1, 1.6 Hz, 2H), 5.74 (s, 1H), 6.42 (dd, J = 2.4, 0.6 Hz, 1H), 6.83 (q, J = 6.6 Hz, 1H), 7.57 (dd, J = 8.1, 7.5 Hz, 1H), 7.74 (t, J = 1.1 Hz, 1H), 7.87 (m, 4H), 8.00 (d, J = 2.4 Hz, 1H), 8.19 (m, 1H) |
| 63gw | $^1$H NMR (400 MHz, MeOH-d4): δ ppm 1.26 (t, J = 7.1 Hz, 3H), 1.52 (dt, J = 10.3, 5.5 Hz, 4H), 1.75 (dd, J = 13.1, 7.2 Hz, 1H), 2.09 (dd, J = 13.1, 8.8 Hz, 1H), 2.41 (s, 3H), 2.76 (d, J = 11.0 Hz, 1H), 2.90 (d, J = 11.0 Hz, 1H), 3.53 (dt, J = 23.4, 6.0 Hz, 4H), 3.83 (dd, J = 8.8, 7.1 Hz, 1H), 4.18 (qd, J = 7.2, 1.7 Hz, 2H), 5.72 (s, 1H), 6.44 (d, J = 2.4 Hz, 1H), 6.87 (q, J = 6.6 Hz, 1H), 7.80 (d, J = 1.6 Hz, 1H), 7.89 (m, 2H), 8.00 (s, 1H), 8.07 (d, J = 2.4 Hz, 1H), 8.30 (d, J = 1.5 Hz, 2H) |
| 63gx | $^1$H NMR (400 MHz, MeOH-d4): δ ppm 1.28 (m, 10H), 1.50 (dt, J = 10.2, 5.5 Hz, 4H), 1.73 (dd, J = 13.1, 7.2 Hz, 1H), 2.06 (m, 1H), 2.39 (s, 3H), 2.74 (d, J = 11.0 Hz, 1H), 2.88 (d, J = 10.9 Hz, 1H), 3.53 (m, 4H), 3.82 (dd, J = 8.7, 7.2 Hz, 1H), 4.17 (qd, J = 7.2, 1.6 Hz, 2H), 4.65 (h, J = 5.9 Hz, 1H), 5.73 (s, 1H), 6.41 (d, J = 2.3 Hz, 1H), 6.78 (q, J = 6.6 Hz, 1H), 6.92 (m, 1H), 7.19 (m, 2H), 7.33 (t, J = 7.9 Hz, 1H), 7.60 (d, J = 1.8 Hz, 1H), 7.74 (m, 2H), 7.98 (d, J = 2.3 Hz, 1H) |
| 63gy | $^1$H NMR (400 MHz, MeOH-d4): δ ppm 1.26 (t, J = 7.2 Hz, 4H), 1.46 (m, 7H), 1.75 (dd, J = 13.1, 7.3 Hz, 1H), 2.09 (dd, J = 13.1, 8.8 Hz, 1H), 2.39 (s, 3H), 2.76 (d, J = 11.0 Hz, 1H), 2.90 (d, J = 11.0 Hz, 1H), 3.52 (dq, J = 24.9, 7.0, 6.0 Hz, 4H), 3.84 (dd, J = 8.7, 7.2 Hz, 1H), 4.18 (ttd, J = 7.0, 5.2, 2.5 Hz, 4H), 5.74 (s, 1H), 6.41 (d, J = 2.3 Hz, 1H), 6.78 (q, J = 6.5 Hz, 1H), 7.18 (m, 2H), 7.35 (dd, J = 8.0, 2.1 Hz, 1H), 7.62 (d, J = 1.8 Hz, 1H), 7.74 (m, 2H), 7.99 (d, J = 2.3 Hz, 1H) |

TABLE 18b-continued

| NMR Data for Compounds of Table 18a | |
|---|---|
| Ex. No. | NMR |
| 63gz | $^1$H NMR (400 MHz, MeOH-d4): δ ppm 1.29 (m, 9H), 1.51 (dt, J = 10.4, 5.6 Hz, 4H), 1.73 (dd, J = 13.1, 7.2 Hz, 1H), 2.07 (dd, J = 13.0, 8.7 Hz, 1H), 2.39 (s, 3H), 2.74 (d, J = 11.0 Hz, 1H), 2.88 (d, J = 11.0 Hz, 1H), 3.53 (m, 4H), 3.81 (dd, J = 8.7, 7.1 Hz, 1H), 4.17 (qd, J = 7.1, 1.6 Hz, 2H), 4.66 (h, J = 6.1 Hz, 1H), 5.73 (s, 1H), 6.41 (d, J = 2.4 Hz, 1H), 6.70 (dt, J = 10.8, 2.2 Hz, 1H), 6.81 (q, J = 6.6 Hz, 1H), 6.99 (m, 2H), 7.62 (d, J = 1.8 Hz, 1H), 7.72 (dd, J = 8.3, 1.9 Hz, 1H), 7.79 (d, J = 8.3 Hz, 1H), 8.00 (d, J = 2.3 Hz, 1H) |
| 63ha | $^1$H NMR (400 MHz, MeOH-d4): δ ppm 1.29-1.40 (m, 3 H), 1.55-1.76 (m, 4 H), 2.06 (br. s., 1 H), 2.35-2.54 (m, 4 H), 3.29 (s, 2 H) 3.50-3.78 (m, 4H), 3.85 (s, 3H), 4.34 (dd, J = 7.03, 2.34 Hz, 2 H), 4.60 (s, 1 H), 5.96 (s, 1 H), 6.44 (d, J = 2.15 Hz, 1 H), 6.81 (d, J = 6.44 Hz, 1 H), 7.03 (d, J = 8.79 Hz, 2 H), 7.50-7.68 (m, 3 H), 7.70-7.82 (m, 2 H), 7.97 (d, J = 2.15 Hz, 1 H) |
| 63hb | $^1$H NMR (400 MHz, MeOH-d4): δ ppm 1.34 (t, J = 7.13 Hz, 3 H), 1.43 (t, J = 7.03 Hz, 3 H), 1.63-1.82 (m, 4 H), 2.01-2.14 (m, 1 H), 2.43 (s, 3 H) 2.46-2.57 (m, 1 H), 3.31 (br. s., 2 H), 3.59-3.93 (m, 4 H), 4.11 (d, J = 7.03 Hz, 2 H), 4.26-4.41 (m, 2 H), 4.56-4.68 (m, 1 H), 6.44 (d, J = 2.15 Hz, 1 H), 6.76-6.93 (m, 1 H), 7.04 (d, J = 8.79 Hz, 2 H), 7.66 (dd, J = 5.17, 3.61 Hz, 3 H), 7.72-7.85 (m, 2 H), 7.93-8.02 (m, 1 H) |
| 63hc | $^1$H NMR (400 MHz, MeOH-d4): δ ppm 1.26 (t, J = 7.2 Hz, 3H), 1.51 (dt, J = 11.0, 5.6 Hz, 4H), 1.74 (dd, J = 13.1, 7.3 Hz, 1H), 2.09 (dd, J = 13.1, 8.8 Hz, 1H), 2.39 (s, 3H), 2.76 (d, J = 11.0 Hz, 1H), 2.90 (d, J = 11.0 Hz, 1H), 3.52 (m, 4H), 3.84 (dd, J = 8.7, 7.2 Hz, 1H), 4.18 (qd, J = 7.1, 1.6 Hz, 2H), 4.88 (s, 7H), 5.72 (s, 1H), 6.42 (d, J = 2.4 Hz, 1H), 6.84 (q, J = 6.5 Hz, 1H), 7.52 (m, 2H), 7.67 (d, J = 1.9 Hz, 1H), 7.74 (dd, J = 8.3, 1.9 Hz, 1H), 7.81 (d, J = 8.3 Hz, 1H), 8.01 (d, J = 2.4 Hz, 1H) |
| 63hd | $^1$H NMR (400 MHz, MeOH-d4): δ ppm 1.27 (m, 4H), 1.54 (dt, J = 8.1, 4.7 Hz, 4H), 1.76 (dd, J = 13.1, 7.3 Hz, 1H), 2.11 (dd, J = 13.1, 8.8 Hz, 1H), 2.77 (d, J = 10.9 Hz, 1H), 2.91 (d, J = 10.9 Hz, 1H), 3.53 (dq, J = 16.3, 6.7, 6.2 Hz, 4H), 3.65 (s, 3H), 3.83 (dd, J = 8.8, 7.2 Hz, 1H), 4.19 (qd, J = 7.2, 1.6 Hz, 2H), 5.51 (d, J = 18.6 Hz, 1H), 6.49 (dd, J = 6.9, 2.0 Hz, 1H), 6.81 (q, J = 6.8 Hz, 1H), 6.91 (s, 1H), 7.35 (d, J = 2.2 Hz, 1H), 7.51 (dd, J = 8.5, 2.2 Hz, 1H), 7.70 (d, J = 8.6 Hz, 1H), 7.80 (d, J = 6.8 Hz, 1H) |
| 63he | $^1$H NMR (400 MHz, MeOH-d4): δ ppm 1.26 (t, J = 7.1 Hz, 4H), 1.51 (dt, J = 10.8, 5.6 Hz, 5H), 1.74 (dd, J = 13.1, 7.1 Hz, 1H), 2.07 (dd, J = 13.0, 8.7 Hz, 1H), 2.38 (d, J = 9.6 Hz, 6H), 2.74 (d, J = 10.9 Hz, 1H), 2.88 (d, J = 11.0 Hz, 1H), 3.53 (dt, J = 21.9, 6.3 Hz, 5H), 3.81 (dd, J = 8.7, 7.1 Hz, 1H), 4.18 (qd, J = 7.1, 1.7 Hz, 2H), 4.88 (s, 15H), 5.74 (s, 1H), 6.42 (d, J = 2.4 Hz, 1H), 6.81 (q, J = 6.6 Hz, 1H), 7.33 (m, 1H), 7.58 (m, 1H), 7.66 (t, J = 2.6 Hz, 2H), 7.77 (m, 2H), 7.99 (d, J = 2.4 Hz, 1H) |
| 63hf | $^1$H NMR (400 MHz, MeOH-d4): δ ppm 0.08 (m, 1H), 1.26 (t, J = 7.1 Hz, 4H), 1.51 (dt, J = 10.6, 5.6 Hz, 4H), 1.76 (dd, J = 13.2, 7.4 Hz, 1H), 2.11 (dd, J = 13.2, 8.8 Hz, 1H), 2.39 (s, 7H), 2.79 (d, J = 11.0 Hz, 1H), 2.92 (d, J = 11.1 Hz, 1H), 3.52 (dq, J = 29.5, 7.4, 6.4 Hz, 5H), 3.89 (dd, J = 8.7, 7.4 Hz, 1H), 4.19 (qd, J = 7.2, 1.7 Hz, 2H), 5.73 (s, 1H), 6.42 (d, J = 2.4 Hz, 1H), 6.80 (q, J = 6.6 Hz, 1H), 7.37 (d, J = 7.9 Hz, 1H), 7.51 (dd, J = 7.9, 1.9 Hz, 1H), 7.62 (d, J = 1.9 Hz, 1H), 7.73 (m, 3H), 7.99 (d, J = 2.4 Hz, 1H) |
| 63hg | $^1$H NMR (400 MHz, MeOH-d4): δ ppm 1.26 (t, J = 7.1 Hz, 3H), 1.51 (dt, J = 10.5, 5.6 Hz, 4H), 1.75 (dd, J = 13.1, 7.3 Hz, 1H), 2.10 (dd, J = 13.1, 8.8 Hz, 1H), 2.40 (s, 3H), 2.77 (d, J = 11.0 Hz, 1H), 2.91 (d, J = 11.0 Hz, 1H), 3.53 (m, 4H), 3.85 (dd, J = 8.7, 7.2 Hz, 1H), 4.18 (qd, J = 7.1, 1.7 Hz, 2H), 5.73 (s, 1H), 6.43 (d, J = 2.4 Hz, 1H), 6.86 (q, J = 6.6 Hz, 1H), 7.50 (dd, J = 8.4, 2.1 Hz, 1H), 7.79 (m, 6H), 8.04 (d, J = 2.4 Hz, 1H) |
| 63hh | $^1$H NMR (400 MHz, MeOH-d4): δ ppm 0.93 (m, 2H), 1.36 (m, 11H), 1.69 (td, J = 13.3, 6.6 Hz, 1H), 2.04 (dd, J = 13.1, 8.8 Hz, 1H), 2.39 (s, 3H), 2.72 (d, J = 11.0 Hz, 1H), 2.86 (d, J = 11.0 Hz, 1H), 3.50 (m, 4H), 3.80 (t, J = 7.9 Hz, 1H), 4.17 (m, 2H), 5.71 (s, 1H), 6.42 (d, J = 2.4 Hz, 1H), 6.85 (q, J = 6.6 Hz, 1H), 7.20 (dt, J = 8.5, 2.1 Hz, 1H), 7.39 (dt, J = 9.7, 2.0 Hz, 1H), 7.52 (t, J = 1.6 Hz, 1H), 7.67 (m, 2H), 7.80 (d, J = 8.3 Hz, 1H), 8.01 (d, J = 2.3 Hz, 1H) |
| 63hi | $^1$H NMR (400 MHz, MeOH-d4): δ ppm 0.75 (m, 2H), 1.01 (dq, J = 8.4, 2.4 Hz, 2H), 1.19 (s, 1H), 1.26 (t, J = 7.1 Hz, 4H), 1.52 (m, 4H), 1.74 (dd, J = 13.1, 7.2 Hz, 1H), 2.02 (m, 2H), 2.75 (d, J = 11.0 Hz, 1H), 2.89 (d, J = 11.0 Hz, 1H), 3.49 (m, 4H), 3.82 (dd, J = 8.8, 7.2 Hz, 1H), 4.18 (qd, J = 7.1, 1.5 Hz, 2H), 5.44 (s, 1H), 6.60 (q, J = 6.9 Hz, 1H), 7.20 (m, 4H), 7.41 (m, 2H), 7.66 (d, J = 8.5 Hz, 1H) |
| 63hj | $^1$H NMR (400 MHz, MeOH-d4): δ ppm 1.25 (t, J = 7.1 Hz, 3H), 1.35 (d, J = 6.0 Hz, 6H), 1.49 (ddd, J = 12.1, 7.6, 4.8 Hz, 4H), 1.72 (dd, J = 13.1, 7.2 Hz, 1H), 2.05 (dd, J = 13.1, 8.8 Hz, 1H), 2.39 (s, 3H), 2.72 (d, J = 11.0 Hz, 1H), 2.87 (d, J = 11.0 Hz, 1H), 3.51 (m, 4H), 3.80 (dd, J = 8.7, 7.1 Hz, 1H), 4.17 (qd, J = 7.1, 1.6 Hz, 2H), 4.67 (hept, J = 6.1 Hz, 1H), 5.73 (s, 1H), 6.41 (d, J = 2.4 Hz, 1H), 6.78 (q, J = 6.6 Hz, 1H), 7.12 (d, J = 8.6 Hz, 1H), 7.54 (m, 2H), 7.67 (m, 2H), 7.75 (d, J = 8.3 Hz, 1H), 7.98 (d, J = 2.4 Hz, 1H) |
| 63hk | $^1$H NMR (400 MHz, MeOH-d4): δ ppm 1.27 (m, 4H), 1.54 (m, 4H), 1.75 (dd, J = 13.1, 7.2 Hz, 1H), 2.11 (dd, J = 13.1, 8.8 Hz, 1H), 2.77 (d, J = 11.0 Hz, 1H), 2.91 (d, J = 11.0 Hz, 1H), 3.52 (dq, J = 27.4, 7.7, 6.5 Hz, 4H), 3.83 (dd, J = 8.7, 7.2 Hz, 1H), 4.19 (qd, J = 7.1, 1.6 Hz, 2H), 5.51 (d, J = 14.8 Hz, 2H), 6.79 (q, J = 6.8 Hz, 1H), 7.40 (d, J = 2.2 Hz, 1H), 7.52 (m, 2H), 7.73 (d, J = 8.5 Hz, 1H), 8.23 (d, J = 8.3 Hz, 1H), 8.47 (s, 1H), 9.34 (s, 1H) |
| 63hl | $^1$H NMR (400 MHz, MeOH-d4): δ ppm 1.25 (t, J = 7.1 Hz, 3H), 1.50 (dt, J = 7.8, 4.8 Hz, 4H), 1.73 (dd, J = 13.1, 7.2 Hz, 1H), 2.07 (dd, J = 13.1, 8.7 Hz, 1H), 2.74 (d, J = 10.9 Hz, 1H), 2.88 (d, J = 10.9 Hz, 1H), 3.10 (s, 6H), 3.49 (m, 4H), 3.81 (dd, J = 8.7, 7.2 Hz, 1H), 4.17 (qd, J = 7.1, 1.3 Hz, 2H), 5.47 (s, 1H), 6.69 (m, 3H), 7.32 (d, J = 2.2 Hz, 1H), 7.45 (dd, J = 8.5, 2.2 Hz, 1H), 7.68 (d, J = 8.5 Hz, 1H), 8.18 (d, J = 5.2 Hz, 1H) |

TABLE 18b-continued

| NMR Data for Compounds of Table 18a | |
|---|---|
| Ex. No. | NMR |
| 63hm | $^1$H NMR (400 MHz, MeOH-d4): δ ppm 1.24 (t, J = 7.1 Hz, 3H), 1.45 (dt, J = 9.4, 5.7 Hz, 4H), 1.70 (dd, J = 13.1, 7.2 Hz, 1H), 2.03 (dd, J = 13.1, 8.7 Hz, 1H), 2.70 (d, J = 11.0 Hz, 1H), 2.85 (d, J = 11.0 Hz, 1H), 3.40 (m, 4H), 3.79 (t, J = 7.9 Hz, 1H), 4.16 (q, J = 7.1 Hz, 2H), 5.45 (d, J = 17.0 Hz, 1H), 6.68 (q, J = 6.8 Hz, 1H), 7.37 (d, J = 2.3 Hz, 1H), 7.44 (dd, J = 8.6, 2.2 Hz, 1H), 7.56 (m, 3H), 7.71 (d, J = 8.5 Hz, 1H), 7.94 (m, 4H) |
| 63hn | $^1$H NMR (400 MHz, MeOH-d4): δ ppm 1.27 (t, J = 7.1 Hz, 3H), 1.36 (s, 9H), 1.52 (m, 4H), 1.77 (dd, J = 13.1, 7.4 Hz, 1H), 2.13 (dd, J = 13.1, 8.7 Hz, 1H), 2.80 (d, J = 11.1 Hz, 1H), 2.93 (d, J = 11.1 Hz, 1H), 3.48 (m, 4H), 3.91 (dd, J = 8.7, 7.4 Hz, 1H), 4.20 (qd, J = 7.2, 1.7 Hz, 2H), 5.41 (s, 1H), 6.64 (q, J = 6.9 Hz, 1H), 7.27 (m, 2H), 7.44 (m, 5H), 7.69 (d, J = 7.3 Hz, 1H) |
| 63ho | $^1$H NMR (400 MHz, MeOH-d4): δ ppm 1.26 (td, J = 7.1, 2.3 Hz, 3H), 1.53 (dt, J = 13.2, 6.2 Hz, 4H), 1.74 (dt, J = 13.6, 7.0 Hz, 1H), 2.09 (m, 1H), 2.75 (dd, J = 10.9, 7.2 Hz, 1H), 2.90 (dd, J = 11.0, 6.6 Hz, 1H), 3.29 (s, 1H), 3.52 (m, 4H), 3.83 (td, J = 8.2, 4.3 Hz, 1H), 4.18 (q, J = 7.1 Hz, 2H), 5.47 (m, 1H), 6.43 (dt, J = 11.2, 5.6 Hz, 1H), 7.22 (m, 1H), 7.38 (m, 2H), 7.61 (dd, J = 5.0, 2.2 Hz, 1H), 7.81 (m, 3H) |
| 63hp | $^1$H NMR (400 MHz, MeOH-d4): δ ppm 1.27 (t, J = 7.1 Hz, 4H), 1.51 (dt, J = 10.0, 5.2 Hz, 4H), 1.80 (m, 1H), 2.17 (dd, J = 13.3, 8.8 Hz, 1H), 2.86 (d, J = 11.2 Hz, 1H), 2.97 (d, J = 11.2 Hz, 1H), 3.50 (m, 4H), 4.01 (t, J = 8.2 Hz, 1H), 4.21 (qd, J = 7.1, 1.9 Hz, 2H), 5.63 (s, 1H), 6.69 (q, J = 6.6 Hz, 1H), 7.30 (ddd, J = 7.9, 6.9, 0.9 Hz, 1H), 7.46 (m, 2H), 7.75 (m, 4H), 8.39 (d, J = 1.0 Hz, 1H) |
| 63hq | $^1$H NMR (400 MHz, MeOH-d4): δ ppm 1.28 (t, J = 7.1 Hz, 3H), 1.36 (dd, J = 6.9, 3.7 Hz, 6H), 1.50 (m, 2H), 1.73 (dd, J = 13.1, 6.7 Hz, 1H), 2.05 (dd, J = 13.1, 8.8 Hz, 1H), 2.81 (d, J = 10.5 Hz, 1H), 2.94 (d, J = 10.5 Hz, 1H), 3.14 (p, J = 6.9 Hz, 1H), 3.47 (dt, J = 12.2, 5.6 Hz, 4H), 3.85 (dd, J = 8.8, 6.7 Hz, 1H), 4.19 (q, J = 7.1 Hz, 2H), 4.34 (s, 2H), 5.42 (s, 1H), 6.53 (q, J = 6.7 Hz, 1H), 7.25 (m, 3H), 7.42 (dd, J = 8.5, 2.2 Hz, 1H), 7.68 (d, J = 8.5 Hz, 1H), 8.65 (dd, J = 5.0, 0.8 Hz, 1H) |
| 63hr | $^1$H NMR (400 MHz, MeOH-d4): δ ppm 1.27 (t, J = 7.1 Hz, 3H), 1.53 (m, 4H), 1.76 (dd, J = 13.1, 7.3 Hz, 1H), 2.11 (dd, J = 13.1, 8.7 Hz, 1H), 2.77 (d, J = 11.0 Hz, 1H), 2.91 (d, J = 11.0 Hz, 1H), 3.51 (dq, J = 17.7, 6.1 Hz, 4H), 3.84 (dd, J = 8.7, 7.3 Hz, 1H), 4.19 (qd, J = 7.1, 1.6 Hz, 2H), 5.50 (s, 1H), 6.60 (q, J = 6.7 Hz, 1H), 7.28 (m, 3H), 7.48 (ddd, J = 25.4, 8.2, 3.7 Hz, 3H), 7.66 (d, J = 8.5 Hz, 1H) |
| 63hs | $^1$H NMR (400 MHz, MeOH-d4): δ ppm 1.26 (t, J = 7.1 Hz, 3H), 1.52 (m, 4H), 1.75 (dd, J = 13.1, 7.3 Hz, 1H), 2.10 (dd, J = 13.1, 8.8 Hz, 1H), 2.77 (d, J = 11.0 Hz, 1H), 2.91 (d, J = 11.0 Hz, 1H), 3.50 (dq, J = 25.8, 7.7, 6.9 Hz, 4H), 3.85 (dd, J = 8.7, 7.3 Hz, 1H), 4.19 (qd, J = 7.1, 1.5 Hz, 2H), 5.50 (s, 1H), 6.60 (q, J = 6.7 Hz, 1H), 7.28 (d, J = 2.2 Hz, 1H), 7.52 (m, 6H) |
| 63ht | $^1$H NMR (400 MHz, MeOH-d4): δ ppm 1.29 (t, J = 7.1 Hz, 3H), 1.56 (dt, J = 11.3, 5.3 Hz, 4H), 1.86 (dd, J = 13.3, 7.9 Hz, 1H), 2.25 (dd, J = 13.3, 8.7 Hz, 1H), 2.44 (s, 3H), 2.96 (d, J = 11.4 Hz, 1H), 3.05 (d, J = 11.3 Hz, 1H), 3.54 (m, 3H), 3.75 (s, 1H), 4.13 (t, J = 8.3 Hz, 1H), 4.24 (qd, J = 7.2, 2.0 Hz, 2H), 5.48 (s, 1H), 6.64 (q, J = 6.8 Hz, 1H), 7.26 (d, J = 2.3 Hz, 1H), 7.35 (s, 4H), 7.42 (dd, J = 8.5, 2.3 Hz, 1H), 7.65 (d, J = 8.5 Hz, 1H) |
| 63hu | $^1$H NMR (400 MHz, MeOH-d4): δ ppm 1.24 (m, 3H), 1.49 (dt, J = 10.2, 5.7 Hz, 4H), 1.72 (m, 1H), 2.04 (m, 1H), 2.41 (s, 2H), 2.72 (d, J = 10.9 Hz, 1H), 2.86 (d, J = 10.9 Hz, 1H), 3.52 (m, 4H), 3.79 (dd, J = 8.8, 7.1 Hz, 1H), 4.16 (qd, J = 7.1, 1.6 Hz, 2H), 5.76 (s, 1H), 6.43 (d, J = 2.4 Hz, 1H), 6.82 (q, J = 6.7 Hz, 1H), 7.49 (m, 2H), 7.84 (m, 7H), 8.01 (d, J = 2.4 Hz, 1H), 8.14 (d, J = 1.9 Hz, 1H) |
| 63hv | $^1$H NMR (400 MHz, MeOH-d4): δ ppm 1.26 (t, J = 7.1 Hz, 3H), 1.53 (m, 4H), 1.78 (m, 5H), 2.11 (m, 2H), 2.25 (dt, J = 7.9, 4.0 Hz, 2H), 2.41 (d, J = 18.1 Hz, 1H), 2.76 (d, J = 11.0 Hz, 1H), 2.90 (d, J = 11.0 Hz, 1H), 3.50 (dq, J = 24.8, 7.6, 6.8 Hz, 4H), 3.82 (dd, J = 8.7, 7.2 Hz, 1H), 4.18 (qd, J = 7.1, 1.5 Hz, 2H), 5.48 (s, 1H), 5.76 (h, J = 2.0 Hz, 1H), 6.93 (q, J = 6.9 Hz, 1H), 7.15 (d, J = 2.3 Hz, 1H), 7.30 (dd, J = 8.5, 2.3 Hz, 1H), 7.58 (d, J = 8.5 Hz, 1H) |
| 63hw | $^1$H NMR (400 MHz, MeOH-d4): δ ppm 1.27 (t, J = 7.1 Hz, 3H), 1.52 (dt, J = 8.9, 5.7 Hz, 4H), 1.81 (dd, J = 13.3, 7.7 Hz, 1H), 2.17 (dd, J = 13.3, 8.8 Hz, 1H), 2.39 (s, 3H), 2.88 (d, J = 11.3 Hz, 1H), 2.98 (d, J = 11.3 Hz, 1H), 3.53 (m, 4H), 4.04 (t, J = 8.2 Hz, 1H), 4.21 (qd, J = 7.2, 1.8 Hz, 2H), 4.90 (d, J = 1.1 Hz, 5H), 5.74 (s, 1H), 6.41 (d, J = 2.3 Hz, 1H), 6.78 (q, J = 6.6 Hz, 1H), 7.17 (t, J = 8.6 Hz, 1H), 7.40 (m, 7H), 7.62 (m, 2H), 7.74 (d, J = 8.2 Hz, 1H), 7.96 (d, J = 2.3 Hz, 1H) |
| 63hx | $^1$H NMR (400 MHz, MeOH-d4): δ ppm 1.32 (m, 9H), 1.55 (dt, J = 10.7, 5.8 Hz, 4H), 1.87 (dd, J = 13.3, 8.0 Hz, 1H), 2.24 (m, 4H), 2.39 (s, 3H), 2.98 (d, J = 11.4 Hz, 1H), 3.06 (d, J = 11.4 Hz, 1H), 3.58 (m, 4H), 4.22 (m, 3H), 4.63 (p, J = 6.0 Hz, 1H), 5.76 (s, 1H), 6.41 (d, J = 2.3 Hz, 1H), 6.75 (q, J = 6.6 Hz, 1H), 6.97 (d, J = 8.2 Hz, 1H), 7.45 (d, J = 8.1 Hz, 2H), 7.58 (d, J = 1.7 Hz, 1H), 7.71 (m, 2H), 7.96 (d, J = 2.3 Hz, 1H) |
| 63hy | $^1$H NMR (400 MHz, MeOH-d4): δ ppm 1.04 (m, 7H), 1.26 (t, J = 7.1 Hz, 4H), 1.52 (m, 4H), 1.74 (dd, J = 13.1, 7.3 Hz, 1H), 2.08 (m, 2H), 2.75 (d, J = 11.0 Hz, 1H), 2.90 (d, J = 11.0 Hz, 1H), 3.50 (m, 4H), 3.80 (m, 3H), 4.18 (qd, J = 7.1, 1.4 Hz, 2H), 5.48 (s, 1H), 6.70 (q, J = 6.9 Hz, 1H), 7.02 (m, 2H), 7.19 (s, 2H), 7.28 (d, J = 2.3 Hz, 1H), 7.42 (m, 2H), 7.66 (d, J = 8.5 Hz, 1H) |
| 63hz | $^1$H NMR (400 MHz, MeOH-d4): δ ppm 1.33 (t, J = 6.3 Hz, 9H), 1.68 (m, 4H), 2.04 (m, 1H), 2.50 (dd, J = 13.6, 8.7 Hz, 1H), 3.28 (s, 2H), 3.56 (m, 5H), 4.32 (qd, J = 7.2, 2.2 Hz, 2H), 4.62 (m, 2H), 6.59 (m, 1H), 6.97 (m, 2H), 7.53 (m, 9H), 7.66 (dd, J = 8.3, 2.0 Hz, 1H), 7.75 (d, J = 8.4 Hz, 1H) |

TABLE 18b-continued

| NMR Data for Compounds of Table 18a | |
|---|---|
| Ex. No. | NMR |
| 63ia | $^1$H NMR (400 MHz, MeOH-d4): δ ppm 1.26 (t, J = 7.1 Hz, 3H), 1.52 (dt, J = 9.7, 5.5 Hz, 4H), 1.74 (dd, J = 13.0, 7.3 Hz, 1H), 2.09 (dd, J = 13.1, 8.8 Hz, 1H), 2.75 (d, J = 11.0 Hz, 1H), 2.89 (d, J = 11.0 Hz, 1H), 3.51 (dq, J = 23.9, 7.7, 6.6 Hz, 4H), 3.82 (dd, J = 8.7, 7.2 Hz, 1H), 4.18 (qd, J = 7.1, 1.5 Hz, 2H), 5.56 (s, 1H), 6.68 (q, J = 7.2 Hz, 1H), 7.67 (d, J = 8.1 Hz, 2H), 7.82 (m, 2H), 8.03 (dd, J = 8.9, 2.0 Hz, 1H), 8.15 (m, 3H), 8.81 (dd, J = 2.9, 0.9 Hz, 1H) |
| 63ib | $^1$H NMR (400 MHz, MeOH-d4): δ ppm 1.06 (t, J = 7.4 Hz, 3H), 1.24 (m, 3H), 1.50 (dt, J = 10.7, 5.6 Hz, 4H), 1.79 (m, 3H), 2.07 (dd, J = 13.1, 8.8 Hz, 1H), 2.39 (s, 3H), 2.74 (d, J = 10.9 Hz, 1H), 2.87 (m, 1H), 3.55 (m, 5H), 3.81 (dd, J = 8.8, 7.2 Hz, 1H), 4.04 (t, J = 6.4 Hz, 2H), 4.17 (qd, J = 7.2, 1.7 Hz, 2H), 5.75 (s, 1H), 6.41 (d, J = 2.4 Hz, 1H), 6.78 (q, J = 6.6 Hz, 1H), 7.15 (t, J = 8.6 Hz, 1H), 7.45 (m, 2H), 7.60 (d, J = 1.8 Hz, 1H), 7.73 (m, 2H), 7.98 (d, J = 2.4 Hz, 1H) |
| 63ic | $^1$H NMR (400 MHz, MeOH-d4): δ ppm 1.00 (t, J = 7.4 Hz, 3H), 1.26 (t, J = 7.1 Hz, 3H), 1.51 (m, 6H), 1.76 (m, 3H), 2.07 (dd, J = 13.1, 8.8 Hz, 1H), 2.39 (s, 3H), 2.74 (d, J = 11.0 Hz, 1H), 2.88 (d, J = 11.0 Hz, 1H), 3.53 (qd, J = 13.9, 7.7 Hz, 4H), 3.81 (dd, J = 8.7, 7.2 Hz, 1H), 4.14 (m, 4H), 5.74 (s, 1H), 6.41 (d, J = 2.3 Hz, 1H), 6.78 (q, J = 6.6 Hz, 1H), 7.15 (m, 1H), 7.46 (m, 2H), 7.61 (d, J = 1.7 Hz, 1H), 7.73 (m, 2H), 7.98 (d, J = 2.4 Hz, 1H) |
| 63id | $^1$H NMR (400 MHz, MeOH-d4): δ ppm 1.25 (t, J = 7.1 Hz, 3H), 1.51 (m, 4H), 1.73 (dd, J = 13.1, 7.2 Hz, 1H), 2.07 (dd, J = 13.0, 8.8 Hz, 1H), 2.40 (s, 3H), 2.64 (s, 3H), 2.74 (d, J = 11.0 Hz, 1H), 2.88 (d, J = 11.0 Hz, 1H), 3.52 (m, 4H), 3.81 (dd, J = 8.7, 7.2 Hz, 1H), 4.17 (qd, J = 7.1, 1.6 Hz, 2H), 5.74 (s, 1H), 6.44 (d, J = 2.3 Hz, 1H), 6.86 (q, J = 6.6 Hz, 1H), 7.76 (m, 3H), 7.85 (d, J = 1.2 Hz, 2H), 8.08 (m, 2H) |
| 63ie | $^1$H NMR (400 MHz, MeOH-d4): δ ppm 0.89 (d, J = 6.7 Hz, 2H), 1.27 (t, J = 7.1 Hz, 3H), 1.53 (m, 4H), 1.72 (ddd, J = 23.9, 13.2, 7.0 Hz, 1H), 1.94 (m, 4H), 2.11 (dd, J = 13.1, 8.8 Hz, 1H), 2.77 (d, J = 10.9 Hz, 1H), 2.91 (d, J = 11.0 Hz, 1H), 3.55 (m, 9H), 3.85 (dd, J = 8.7, 7.3 Hz, 1H), 4.19 (qd, J = 7.1, 1.7 Hz, 2H), 5.53 (s, 1H), 6.69 (q, J = 6.7 Hz, 1H), 7.31 (d, J = 2.2 Hz, 1H), 7.48 (m, 2H), 7.64 (m, 3H), 7.93 (s, 1H) |
| 63if | $^1$H NMR (400 MHz, MeOH-d4): δ ppm 1.27 (td, J = 7.1, 0.8 Hz, 4H), 1.53 (m, 4H), 1.76 (m, 9H), 1.97 (dd, J = 13.4, 6.8 Hz, 2H), 2.11 (dd, J = 13.1, 8.8 Hz, 1H), 2.77 (d, J = 11.0 Hz, 1H), 2.91 (d, J = 10.9 Hz, 1H), 3.31 (m, 3H), 3.51 (dq, J = 19.6, 6.3 Hz, 4H), 3.84 (dd, J = 8.7, 7.3 Hz, 1H), 4.19 (m, 2H), 5.48 (s, 1H), 6.71 (q, J = 6.9 Hz, 1H), 6.94 (d, J = 7.6 Hz, 1H), 7.02 (dd, J = 8.4, 2.6 Hz, 1H), 7.18 (s, 1H), 7.28 (d, J = 2.2 Hz, 1H), 7.43 (m, 2H), 7.66 (d, J = 8.5 Hz, 1H) |
| 63ig | $^1$H NMR (400 MHz, MeOH-d4): δ ppm 0.89 (dd, J = 6.7, 0.7 Hz, 1H), 1.27 (td, J = 7.1, 0.7 Hz, 3H), 1.53 (m, 4H), 1.75 (dd, J = 13.1, 7.3 Hz, 1H), 2.11 (m, 1H), 2.76 (d, J = 11.0 Hz, 1H), 2.90 (d, J = 11.0 Hz, 1H), 3.30 (dq, J = 3.5, 1.8 Hz, 5H), 3.54 (m, 10H), 3.82 (m, 5H), 4.18 (qd, J = 7.2, 1.6 Hz, 2H), 5.53 (s, 1H), 6.70 (q, J = 6.7 Hz, 1H), 6.84 (m, 1H), 7.30 (m, 1H), 7.51 (m, 3H), 7.66 (m, 2H), 7.79 (s, 1H) |
| 63ih | $^1$H NMR (400 MHz, MeOH-d4): δ ppm 1.39 (m, 12H), 1.84 (dd, J = 13.2, 7.8 Hz, 1H), 1.98 (m, 5H), 2.24 (m, 1H), 2.92 (d, J = 11.3 Hz, 1H), 3.02 (d, J = 11.2 Hz, 1H), 3.54 (ddq, J = 27.6, 15.0, 7.8, 7.4 Hz, 6H), 3.89 (s, 1H), 4.07 (t, J = 8.2 Hz, 1H), 4.23 (qd, J = 7.1, 2.0 Hz, 2H), 4.93 (d, J = 1.4 Hz, 11H), 5.55 (s, 1H), 6.63 (q, J = 6.7 Hz, 1H), 7.30 (d, J = 2.2 Hz, 1H), 7.46 (dd, J = 8.5, 2.3 Hz, 1H), 7.63 (m, 3H), 7.89 (dt, J = 7.7, 1.6 Hz, 1H), 8.35 (s, 1H) |
| 63ii | $^1$H NMR (400 MHz, MeOH-d4): δ ppm 1.27 (td, J = 7.4, 5.4 Hz, 7H), 1.52 (dt, J = 7.6, 4.7 Hz, 4H), 1.74 (dd, J = 13.1, 7.2 Hz, 1H), 2.09 (dd, J = 13.1, 8.7 Hz, 1H), 2.74 (m, 3H), 2.90 (d, J = 11.0 Hz, 1H), 3.30 (d, J = 9.9 Hz, 1H), 3.49 (m, 4H), 3.83 (dd, J = 8.7, 7.2 Hz, 1H), 4.18 (qd, J = 7.1, 1.5 Hz, 2H), 5.46 (s, 1H), 6.64 (q, J = 6.8 Hz, 1H), 7.30 (m, 4H), 7.43 (m, 2H), 7.67 (d, J = 8.5 Hz, 1H) |
| 63ij | $^1$H NMR (400 MHz, MeOH-d4): δ ppm 1.30 (dd, J = 6.9, 5.1 Hz, 6H), 1.59 (d, J = 5.6 Hz, 4H), 2.03 (dd, J = 13.4, 7.2 Hz, 1H), 2.30 (dd, J = 13.4, 9.2 Hz, 1H), 3.03 (m, 2H), 3.22 (d, J = 11.7 Hz, 1H), 3.46 (tt, J = 16.4, 7.0 Hz, 2H), 3.62 (q, J = 8.5 Hz, 2H), 4.05 (dd, J = 9.1, 7.1 Hz, 1H), 5.48 (s, 1H), 6.62 (q, J = 6.7 Hz, 1H), 7.31 (m, 4H), 7.44 (m, 2H), 7.66 (d, J = 8.5 Hz, 1H) |
| 63ik | $^1$H NMR (400 MHz, MeOH-d4): δ ppm 1.05 (t, J = 7.4 Hz, 3H), 1.26 (td, J = 7.2, 0.6 Hz, 4H), 1.51 (dt, J = 10.0, 5.7 Hz, 4H), 1.77 (ddd, J = 27.5, 13.6, 7.1 Hz, 3H), 2.08 (dd, 1 = 13.1, 8.7 Hz, 1H), 2.74 (d, J = 11.0 Hz, 1H), 2.88 (d, J = 11.0 Hz, 1H), 3.30 (p, J = 1.6 Hz, 5H), 3.51 (m, 4H), 3.81 (dd, J = 8.7, 7.2 Hz, 1H), 3.95 (t, J = 6.5 Hz, 2H), 4.18 (qd, J = 7.1, 1.5 Hz, 2H), 5.53 (s, 1H), 6.61 (q, J = 7.2 Hz, 1H), 6.97 (m, 2H), 7.56 (m, 6H) |
| 63il | $^1$H NMR (400 MHz, MeOH-d4): δ ppm 1.26 (t, J = 7.1 Hz, 4H), 1.46 (m, 8H), 1.73 (dd, J = 13.0, 7.3 Hz, 1H), 2.08 (m, 1H), 2.74 (d, J = 11.0 Hz, 1H), 2.89 (d, J = 11.0 Hz, 1H), 3.02 (m, 2H), 3.50 (dd, J = 17.6, 11.2 Hz, 4H), 3.82 (dd, J = 8.7, 7.2 Hz, 1H), 4.18 (qd, J = 7.2, 1.5 Hz, 2H), 5.53 (s, 1H), 6.99 (q, J = 6.9 Hz, 1H), 7.67 (m, 3H), 8.03 (dd, J = 8.9, 2.1 Hz, 1H), 8.14 (m, 3H), 8.80 (dd, J = 2.8, 0.9 Hz, 1H) |
| 63im | $^1$H NMR (400 MHz, MeOH-d4): δ ppm 1.26 (t, J = 7.1 Hz, 5H), 1.53 (td, J = 7.3, 6.9, 4.5 Hz, 4H), 1.75 (dd, J = 13.1, 7.3 Hz, 1H), 2.10 (m, 1H), 2.29 (s, 3H), 2.39 (s, 3H), 2.53 (s, 2H), 2.76 (d, J = 11.0 Hz, 1H), 2.90 (d, J = 11.0 Hz, 1H), 3.52 (m, 6H), 3.83 (m, 3H), 4.18 (qd, J = 7.1, 1.7 Hz, 2H), 5.51 (d, J = 15.3 Hz, 1H), 6.71 (q, J = 6.6 Hz, 1H), 7.32 (d, J = 2.3 Hz, 1H), 7.50 (m, 3H), 7.66 (m, 2H), 7.80 (s, 1H) |
| 63in | $^1$H NMR (400 MHz, MeOH-d4): δ ppm 1.25 (m, 4H), 1.54 (m, 4H), 1.75 (dd, J = 13.1, 7.3 Hz, 1H), 2.10 (dd, J = 12.8, 8.5 Hz, 1H), 2.66 (s, 3H), 2.76 (d, J = 11.0 Hz, 1H), 2.90 (d, J = 11.0 Hz, 1H), 3.52 (dd, J = 14.8, 8.9 Hz, 5H), 3.83 (dd, J = 8.7, 7.3 Hz, 1H), 4.18 (qd, J = 7.1, 1.6 Hz, 2H), 5.54 (s, 1H), 6.85 (t, J = 7.0 Hz, 1H), 7.65 (d, J = 2.9 Hz, 3H), 8.04 (dd, J = 8.9, 2.0 Hz, 1H), 8.15 (m, 3H), 8.81 (d, J = 2.8 Hz, 1H) |

TABLE 18b-continued

| NMR Data for Compounds of Table 18a | |
|---|---|
| Ex. No. | NMR |
| 63io | $^1$H NMR (400 MHz, MeOH-d4): δ ppm 1.15 (t, J = 7.0 Hz, 3H), 1.26 (t, J = 7.1 Hz, 6H), 1.53 (dt, J = 10.1, 5.5 Hz, 4H), 1.75 (dd, J = 13.1, 7.2 Hz, 1H), 2.10 (dd, J = 13.1, 8.7 Hz, 1H), 2.76 (d, J = 11.0 Hz, 1H), 2.90 (d, J = 11.0 Hz, 1H), 3.36 (d, J = 7.7 Hz, 1H), 3.54 (m, 6H), 3.83 (dd, J = 8.7, 7.2 Hz, 1H), 4.18 (qd, J = 7.2, 1.6 Hz, 2H), 5.55 (s, 1H), 6.65 (q, J = 7.1 Hz, 1H), 7.46 (m, 2H), 7.62 (d, J = 8.1 Hz, 2H), 7.72 (m, 4H) |
| 63ip | $^1$H NMR (400 MHz, MeOH-d4): δ ppm 1.26 (td, J = 7.1, 1.0 Hz, 7H), 1.53 (m, 8H), 1.74 (dd, J = 13.1, 7.2 Hz, 2H), 2.09 (dd, J = 13.1, 8.7 Hz, 2H), 2.75 (d, J = 11.0 Hz, 2H), 2.89 (d, J = 11.0 Hz, 2H), 3.28 (d, J = 14.7 Hz, 1H), 3.53 (m, 9H), 3.82 (dd, J = 8.7, 7.2 Hz, 2H), 4.18 (qd, J = 7.1, 1.5 Hz, 4H), 5.55 (s, 2H), 6.66 (q, J = 7.1 Hz, 2H), 7.62 (d, J = 8.1 Hz, 4H), 7.72 (m, 8H), 7.95 (m, 4H) |
| 63iq | $^1$H NMR (400 MHz, MeOH-d4): δ ppm 1.27 (m, 6H), 1.54 (m, 4H), 1.78 (dd, J = 13.1, 7.4 Hz, 1H), 2.14 (dd, J = 13.2, 8.8 Hz, 1H), 2.81 (d, J = 13.9 Hz, 4H), 2.94 (d, J = 11.0 Hz, 1H), 3.22 (s, 2H), 3.52 (ddt, J = 19.7, 11.9, 6.0 Hz, 4H), 3.92 (t, J = 8.0 Hz, 1H), 4.21 (qd, J = 7.8, 6.4, 4.7 Hz, 2H), 4.88 (s, 1H), 5.51 (s, 1H), 6.75 (q, J = 6.7 Hz, 1H), 7.49 (m, 2H), 7.72 (m, 2H) |
| 63ir | $^1$H NMR (400 MHz, MeOH-d4): δ ppm 1.04 (t, J = 7.4 Hz, 3H), 1.26 (t, J = 7.1 Hz, 3H), 1.51 (m, 4H), 1.76 (ddd, J = 25.2, 13.5, 7.1 Hz, 3H), 2.08 (dd, J = 13.1, 8.8 Hz, 1H), 2.74 (d, J = 11.0 Hz, 1H), '2.89 (d, J = 11.0 Hz, 1H), 3.47 (dq, J = 26.7, 7.9, 6.9 Hz, 4H), 3.82 (dd, J = 8.7, 7.2 Hz, 1H), 3.95 (t, J = 6.5 Hz, 2H), 4.18 (m, 2H), 5.45 (s, 1H), 6.66 (q, J = 6.9 Hz, 1H), 6.97 (m, 2H), 7.55 (m, 9H), 7.73 (d, J = 8.3 Hz, 1H) |
| 63is | $^1$H NMR (400 MHz, MeOH-d4): δ ppm 1.28 (t, J = 7.1 Hz, 4H), 1.54 (m, 4H), 1.81 (dd, J = 13.2, 7.6 Hz, 1H), 2.18 (dd, J = 13.3, 8.8 Hz, 1H), 2.87 (d, J = 11.2 Hz, 1H), 2.98 (d, J = 11.1 Hz, 1H), 3.51 (m, 4H), 4.00 (t, J = 8.1 Hz, 1H), 4.21 (qd, J = 7.1, 1.8 Hz, 2H), 5.49 (d, J = 2.0 Hz, 1H), 6.82 (q, J = 6.7 Hz, 1H), 7.13 (m, 2H), 7.46 (m, 2H), 7.67 (d, J = 8.5 Hz, 1H) |
| 63it | $^1$H NMR (400 MHz, MeOH-d4): δ ppm 1.26 (t, J = 7.1 Hz, 3H), 1.53 (dt, J = 10.5, 5.6 Hz, 4H), 1.75 (dd, J = 13.0, 7.2 Hz, 1H), 2.10 (dd, J = 13.1, 8.7 Hz, 1H), 2.76 (d, J = 11.0 Hz, 1H), 2.90 (d, J = 11.0 Hz, 1H), 3.15 (s, 3H), 3.53 (m, 4H), 3.83 (dd, J = 8.8, 7.2 Hz, 1H), 4.18 (qd, J = 7.1, 1.6 Hz, 2H), 5.56 (s, 1H), 6.67 (q, J = 7.1 Hz, 1H), 7.66 (d, J = 8.2 Hz, 2H), 7.74 (m, 2H), 7.89 (m, 2H), 8.02 (m, 2H) |
| 63iu | $^1$H NMR (400 MHz, MeOH-d4): δ ppm 1.26 (t, J = 7.1 Hz, 3H), 1.51 (dt, J = 10.8, 5.6 Hz, 4H), 1.73 (dd, J = 13.1, 7.2 Hz, 1H), 2.08 (dd, J = 13.1, 8.8 Hz, 1H), 2.40 (s, 3H), 2.74 (d, J = 11.0 Hz, 1H), 2.88 (d, J = 11.0 Hz, 1H), 3.15 (s, 3H), 3.53 (m, 4H), 3.81 (dd, J = 8.8, 7.2 Hz, 1H), 4.18 (qd, J = 7.2, 1.7 Hz, 2H), 5.74 (s, 1H), 6.43 (d, J = 2.4 Hz, 1H), 6.85 (q, J = 6.6 Hz, 1H), 7.76 (dd, J = 1.7, 0.6 Hz, 1H), 7.83 (m, 2H), 7.95 (m, 2H), 8.03 (m, 3H) |
| 63iv | $^1$H NMR (400 MHz, MeOH-d4): δ ppm 1.05 (t, J = 7.4 Hz, 3H), 1.26 (m, 3H), 1.49 (dt, J = 10.7, 5.7 Hz, 4H), 1.78 (m, 3H), 2.08 (dd, J = 13.1, 8.8 Hz, 1H), 2.25 (d, J = 14.0 Hz, 1H), 2.39 (s, 3H), 2.75 (d, J = 11.0 Hz, 1H), 2.88 (d, J = 11.0 Hz, 1H), 3.53 (m, 4H), 3.83 (t, J = 8.0 Hz, 1H), 3.95 (t, J = 6.4 Hz, 2H), 4.18 (qd, J = 7.1, 1.6 Hz, 2H), 5.76 (s, 1H), 6.41 (d, J = 2.3 Hz, 1H), 6.75 (t, J = 6.7 Hz, 1H), 6.98 (m, 2H), 7.58 (m, 3H), 7.71 (m, 2H), 7.96 (d, J = 2.4 Hz, 1H) |
| 63ix | $^1$H NMR (400 MHz, MeOH-d4): δ ppm 1.14 (t, J = 7.0 Hz, 3H), 1.26 (t, J = 7.1 Hz, 7H), 1.51 (dt, J = 10.8, 5.7 Hz, 4H), 1.73 (dd, J = 13.0, 7.2 Hz, 1H), 2.08 (dd, J = 13.0, 8.8 Hz, 1H), 2.39 (d, J = 1.7 Hz, 3H), 2.74 (d, J = 10.9 Hz, 1H), 2.88 (d, J = 11.0 Hz, 1H), 3.31 (d, J = 16.3 Hz, 3H), 3.56 (s, 6H), 3.81 (dd, J = 8.7, 7.1 Hz, 1H), 4.18 (m, 2H), 5.75 (s, 1H), 6.42 (d, J = 2.4 Hz, 1H), 6.82 (q, J = 6.5 Hz, 1H), 7.47 (dd, J = 8.3, 2.0 Hz, 2H), 7.70 (d, J = 1.8 Hz, 1H), 7.79 (m, 4H), 8.01 (d, J = 2.4 Hz, 1H) |
| 63iy | $^1$H NMR (400 MHz, MeOH-d4): δ ppm 1.26 (t, J = 7.1 Hz, 5H), 1.53 (dt, J = 9.7, 5.4 Hz, 8H), 1.74 (dd, J = 13.0, 7.3 Hz, 2H), 2.09 (dd, J = 13.1, 8.8 Hz, 2H), 2.76 (d, J = 11.0 Hz, 2H), 2.91 (d, J = 19.4 Hz, 7H), 3.36 (s, 1H), 3.53 (m, 8H), 3.83 (dd, J = 8.7, 7.2 Hz, 2H), 4.18 (qd, J = 7.1, 1.6 Hz, 4H), 4.97 (s, 1H), 5.55 (s, 2H), 6.65 (q, J = 7.1 Hz, 2H), 7.62 (d, J = 8.1 Hz, 4H), 7.71 (m, 7H), 7.89 (m, 4H) |
| 63iz | $^1$H NMR (400 MHz, MeOH-d4): δ ppm 1.26 (t, J = 7.1 Hz, 4H), 1.51 (dt, J = 10.6, 5.5 Hz, 4H), 1.76 (dd, J = 13.1, 7.3 Hz, 1H), 2.11 (dd, J = 13.1, 8.8 Hz, 1H), 2.40 (s, 3H), 2.78 (d, J = 11.1 Hz, 1H), 2.91 (d, J = 11.0 Hz, 1H), 3.54 (qq, J = 14.0, 7.5, 6.5 Hz, 4H), 3.88 (dd, J = 8.7, 7.4 Hz, 1H), 4.19 (qd, J = 7.1, 1.7 Hz, 2H), 5.75 (s, 1H), 6.43 (d, J = 2.4 Hz, 1H), 6.83 (q, J = 6.6 Hz, 1H), 7.73 (d, J = 1.6 Hz, 1H), 7.84 (m, 4H), 7.99 (m, 3H) |
| 63ja | $^1$H NMR (400 MHz, MeOH-d4): δ ppm 1.27 (m, 7H), 1.53 (dt, J = 9.9, 5.5 Hz, 8H), 1.77 (dd, J = 13.1, 7.4 Hz, 2H), 2.17 (m, 2H), 2.81 (d, J = 11.1 Hz, 2H), 2.93 (d, J = 11.1 Hz, 2H), 3.33 (d, J = 12.6 Hz, 1H), 3.52 (ddt, J = 17.5, 11.5, 5.2 Hz, 8H), 3.90 (dd, J = 8.6, 7.5 Hz, 2H), 4.20 (qd, J = 7.2, 1.7 Hz, 3H), 5.56 (s, 2H), 6.66 (q, J = 7.1 Hz, 2H), 7.64 (d, J = 8.1 Hz, 4H), 7.71 (d, J = 8.3 Hz, 4H), 7.79 (m, 4H), 7.96 (m, 4H) |
| 63jb | $^1$H NMR (400 MHz, MeOH-d4): δ ppm 1.27 (t, J = 7.1 Hz, 5H), 1.53 (dt, J = 9.6, 5.3 Hz, 5H), 1.76 (dd, J = 13.1, 7.3 Hz, 1H), 2.11 (dd, J = 13.1, 8.7 Hz, 1H), 2.61 (m, 7H), 2.77 (d, J = 11.0 Hz, 1H), 2.91 (d, J = 11.0 Hz, 1H), 3.56 (m, 8H), 3.71 (t, J = 4.7 Hz, 5H), 3.85 (dd, J = 8.7, 7.2 Hz, 1H), 4.19 (qd, J = 7.1, 1.6 Hz, 2H), 5.55 (s, 1H), 6.66 (q, J = 7.2 Hz, 1H), 7.63 (d, J = 8.1 Hz, 2H), 7.73 (m, 4H), 7.91 (m, 2H) |
| 63jc | $^1$H NMR (400 MHz, MeOH-d4): δ ppm 1.21 (dt, J = 33.8, 7.2 Hz, 4H), 1.51 (dt, J = 10.8, 5.4 Hz, 4H), 1.74 (dd, J = 13.1, 7.3 Hz, 1H), 2.08 (m, 1H), 2.40 (s, 3H), 2.58 (dt, J = 23.6, 5.8 Hz, 6H), 2.75 (d, J = 11.0 Hz, 1H), 2.88 (dd, J = 11.0, 5.9 Hz, 1H), 3.32 (s, 1H), 3.57 (m, 6H), 3.70 (t, J = 4.7 Hz, 4H), 3.82 (m, 1H), 4.18 (qd, J = 7.1, 1.7 Hz, 2H), 5.75 (s, 1H), 6.43 (d, J = 2.4 Hz, 1H), 6.82 (q, J = 6.6 Hz, 1H), 7.72 (d, J = 1.5 Hz, 1H), 7.81 (m, 4H), 7.96 (m, 4H) |

TABLE 18b-continued

NMR Data for Compounds of Table 18a

| Ex. No. | NMR |
|---|---|
| 63jd | $^1$H NMR (400 MHz, MeOH-d4): δ ppm 1.26 (td, J = 7.1, 1.3 Hz, 3H), 1.52 (dt, J = 9.5, 5.5 Hz, 4H), 1.74 (dd, J = 13.1, 7.2 Hz, 1H), 2.09 (dd, J = 13.1, 8.8 Hz, 1H), 2.75 (d, J = 11.1 Hz, 1H), 2.89 (d, J = 10.9 Hz, 1H), 3.04 (d, J = 1.3 Hz, 3H), 3.11 (s, 3H), 3.52 (m, 4H), 3.82 (m, 1H), 4.18 (qt, J = 7.1, 1.4 Hz, 2H), 5.55 (d, J = 1.3 Hz, 1H), 6.66 (q, J = 7.1 Hz, 1H), 7.51 (m, 2H), 7.68 (m, 6H) |
| 63je | $^1$H NMR (400 MHz, MeOH-d4): δ ppm 1.27 (t, J = 7.1 Hz, 4H), 1.53 (dt, J = 9.5, 5.3 Hz, 4H), 1.75 (dd, J = 13.0, 7.3 Hz, 1H), 2.11 (dd, J = 13.1, 8.8 Hz, 1H), 2.78 (t, J = 9.8 Hz, 3H), 2.91 (d, J = 11.0 Hz, 4H), 3.50 (m, 7H), 3.75 (s, 2H), 3.85 (dd, J = 8.8, 7.3 Hz, 1H), 4.19 (qd, J = 7.2, 1.6 Hz, 2H), 5.55 (s, 1H), 6.66 (q, J = 7.0 Hz, 1H), 7.51 (m, 2H), 7.62 (d, J = 8.2 Hz, 2H), 7.72 (m, 4H) |
| 63jf | $^1$H NMR (400 MHz, MeOH-d4): δ ppm 1.26 (td, J = 7.4, 1.9 Hz, 8H), 1.50 (dt, J = 10.8, 5.8 Hz, 5H), 1.75 (dd, J = 13.1, 7.4 Hz, 1H), 2.10 (dd, J = 13.2, 8.9 Hz, 1H), 2.39 (s, 3H), 2.86 (m, 8H), 3.26 (s, 1H), 3.52 (m, 8H), 3.76 (s, 2H), 3.88 (dd, J = 8.8, 7.3 Hz, 1H), 4.18 (ddtd, J = 7.7, 5.3, 3.6, 2.0 Hz, 2H), 4.93 (s, 2H), 5.74 (s, 1H), 6.43 (d, J = 2.4 Hz, 1H), 6.82 (q, J = 6.6 Hz, 1H), 7.51 (dd, J = 8.3, 2.0 Hz, 2H), 7.75 (m, 7H), 8.01 (d, J = 2.4 Hz, 1H) |
| 63jg | $^1$H NMR (400 MHz, MeOH-d4): δ ppm 1.31 (t, J = 7.2 Hz, 8H), 1.57 (s, 10H), 1.95 (dd, J = 13.4, 8.4 Hz, 2H), 2.37 (t, J = 11.1 Hz, 2H), 3.12 (m, 4H), 3.61 (m, 15H), 4.31 (m, 6H), 5.49 (s, 1H), 5.62 (s, 1H), 6.25 (d, J = 6.9 Hz, 2H), 6.50 (t, J = 6.8 Hz, 2H), 7.31 (d, J = 2.2 Hz, 2H), 7.46 (dd, J = 15.4, 7.7 Hz, 4H), 7.65 (d, J = 8.5 Hz, 2H), 7.79 (d, J = 7.1 Hz, 2H) |
| 63jh | $^1$H NMR (400 MHz, MeOH-d4): δ ppm 1.26 (t, J = 7.1 Hz, 3H), 1.50 (dt, J = 10.4, 5.5 Hz, 4H), 1.74 (dd, J = 13.1, 7.2 Hz, 1H), 2.08 (dd, J = 13.1, 8.8 Hz, 1H), 2.39 (s, 3H), 2.75 (d, J = 11.0 Hz, 1H), 2.89 (d, J = 11.0 Hz, 1H), 3.53 (m, 4H), 3.83 (m, 1H), 3.90 (s, 3H), 4.18 (qd, J = 7.2, 1.6 Hz, 2H), 5.75 (s, 1H), 6.41 (d, J = 2.4 Hz, 1H), 6.78 (q, J = 6.7 Hz, 1H), 7.17 (t, J = 8.9 Hz, 1H), 7.48 (m, 2H), 7.61 (d, J = 1.8 Hz, 1H), 7.73 (m, 2H), 7.99 (d, J = 2.4 Hz, 1H) |
| 63ji | $^1$H NMR (400 MHz, MeOH-d4): δ ppm 1.30 (d, J = 11.1 Hz, 1H), 1.51 (q, J = 6.8, 6.0 Hz, 4H), 1.78 (dd, J = 13.0, 7.0 Hz, 1H), 1.89 (s, 2H), 2.07 (dd, J = 13.1, 9.1 Hz, 1H), 2.40 (s, 3H), 2.68 (d, J = 11.1 Hz, 1H), 2.95 (d, J = 11.1 Hz, 1H), 3.03 (s, 3H), 3.11 (s, 3H), 3.22 (s, 2H), 3.45 (m, 3H), 3.63 (q, J = 7.9, 7.5 Hz, 3H), 5.75 (s, 1H), 6.43 (d, J = 2.4 Hz, 1H), 6.82 (q, J = 6.6 Hz, 1H), 7.53 (d, J = 7.9 Hz, 2H), 7.70 (m, 1H), 7.80 (m, 4H), 8.01 (d, J = 2.5 Hz, 1H) |
| 63jj | $^1$H NMR (400 MHz, MeOH-d4): δ ppm 1.06 (t, J = 7.4 Hz, 4H), 1.30 (t, J = 7.1 Hz, 3H), 1.57 (m, 4H), 1.86 (m, 3H), 2.30 (m, 1H), 3.09 (m, 3H), 3.54 (m, 4H), 4.03 (t, J = 6.4 Hz, 2H), 4.27 (m, 3H), 5.55 (s, 1H), 6.64 (q, J = 7.2 Hz, 1H), 7.12 (t, J = 8.8 Hz, 1H), 7.37 (m, 2H), 7.58 (q, J = 8.4 Hz, 4H) |
| 63jk | $^1$H NMR (400 MHz, MeOH-d4): δ ppm 1.26 (t, J = 7.1 Hz, 5H), 1.50 (dt, J = 10.2, 5.2 Hz, 4H), 1.75 (dd, J = 13.1, 7.4 Hz, 1H), 2.10 (dd, J = 13.1, 8.8 Hz, 1H), 2.40 (s, 3H), 2.78 (d, J = 11.1 Hz, 1H), 2.91 (d, J = 13.6 Hz, 4H), 3.52 (m, 4H), 3.88 (dd, J = 8.7, 7.3 Hz, 1H), 4.18 (qd, J = 7.1, 1.6 Hz, 2H), 5.75 (s, 1H), 6.43 (d, J = 2.4 Hz, 1H), 6.82 (q, J = 6.5 Hz, 1H), 7.70 (d, J = 1.7 Hz, 1H), 7.78 (m, 4H), 7.90 (m, 2H), 8.01 (d, J = 2.4 Hz, 1H) |
| 63jl | $^1$H NMR (400 MHz, MeOH-d4): δ ppm 1.25 (m, 5H), 1.54 (dt, J = 11.2, 6.0 Hz, 4H), 1.75 (dd, J = 13.1, 7.2 Hz, 1H), 2.11 (dd, J = 13.1, 8.8 Hz, 1H), 2.58 (s, 3H), 2.77 (d, J = 11.0 Hz, 1H), 2.91 (d, J = 11.0 Hz, 1H), 3.55 (h, J = 7.5 Hz, 4H), 3.84 (dd, J = 8.7, 7.2 Hz, 1H), 4.18 (qd, J = 7.1, 1.7 Hz, 2H), 5.58 (s, 1H), 6.65 (q, J = 6.6 Hz, 1H), 7.34 (d, J = 2.2 Hz, 1H), 7.49 (dd, J = 8.5, 2.3 Hz, 1H), 7.73 (m, 3H), 7.94 (ddd, J = 7.9, 1.8, 1.1 Hz, 1H), 8.32 (s, 1H) |
| 63jm | $^1$H NMR (400 MHz, MeOH-d4): δ ppm 1.27 (t, J = 7.1 Hz, 4H), 1.54 (dt, J = 8.6, 4.8 Hz, 4H), 1.76 (dd, J = 13.1, 7.2 Hz, 1H), 2.11 (dd, J = 13.1, 8.8 Hz, 1H), 2.73 (s, 7H), 2.91 (d, J = 10.9 Hz, 1H), 3.55 (dp, J = 20.2, 7.2, 6.0 Hz, 4H), 3.84 (dd, J = 8.7, 7.2 Hz, 1H), 4.19 (qd, J = 7.1, 1.6 Hz, 2H), 5.59 (s, 1H), 6.69 (q, J = 6.4 Hz, 1H), 7.36 (d, J = 2.2 Hz, 1H), 7.50 (dd, J = 8.5, 2.2 Hz, 1H), 7.70 (dd, J = 13.1, 8.0 Hz, 2H), 7.85 (m, 2H), 8.34 (s, 1H) |
| 63jn | $^1$H NMR (400 MHz, MeOH-d4): δ ppm 1.30 (m, 10H), 1.52 (dt, J = 10.2, 5.7 Hz, 4H), 1.74 (dd, J = 13.1, 7.3 Hz, 1H), 2.08 (m, 1H), 2.83 (m, 4H), 3.20 (ddd, J = 11.9, 6.2, 3.0 Hz, 2H), 3.31 (s, 1H), 3.49 (ddd, J = 30.2, 13.4, 6.0 Hz, 4H), 3.90 (dddd, J = 32.2, 15.9, 7.4, 5.0 Hz, 5H), 4.18 (qd, J = 7.2, 1.5 Hz, 2H), 4.64 (p, J = 6.0 Hz, 1H), 5.52 (s, 1H), 6.96 (m, 2H), 7.40 (m, 2H), 7.54 (m, 4H) |
| 63jo | $^1$H NMR (400 MHz, MeOH-d4): δ ppm 1.27 (m, 4H), 1.54 (dt, J = 7.6, 4.8 Hz, 5H), 1.76 (dd, J = 13.1, 7.3 Hz, 1H), 2.11 (dd, J = 13.1, 8.8 Hz, 1H), 2.77 (d, J = 11.0 Hz, 1H), 2.92 (d, J = 18.5 Hz, 4H), 3.53 (m, 4H), 3.85 (dd, J = 8.7, 7.3 Hz, 1H), 4.19 (qd, J = 7.1, 1.6 Hz, 2H), 4.93 (s, 7H), 5.52 (d, J = 19.1 Hz, 1H), 6.63 (q, J = 6.7 Hz, 1H), 7.29 (d, J = 2.2 Hz, 1H), 7.46 (dd, J = 8.5, 2.3 Hz, 1H), 7.62 (m, 3H), 7.88 (dt, J = 7.7, 1.6 Hz, 1H), 8.37 (s, 1H) |
| 63jp | $^1$H NMR (400 MHz, MeOH-d4): δ ppm 1.26 (t, J = 7.1 Hz, 3H), 1.53 (dt, J = 7.7, 4.7 Hz, 4H), 1.75 (dd, J = 13.1, 7.2 Hz, 1H), 2.10 (dd, J = 13.1, 8.8 Hz, 1H), 2.76 (d, J = 11.0 Hz, 1H), 2.90 (d, J = 11.0 Hz, 1H), 3.06 (s, 3H), 3.12 (s, 3H), 3.51 (m, 4H), 3.83 (dd, J = 8.7, 7.2 Hz, 1H), 4.18 (qd, J = 7.1, 1.6 Hz, 2H), 5.53 (s, 1H), 6.70 (q, J = 6.7 Hz, 1H), 7.32 (d, J = 2.2 Hz, 1H), 7.56 (m, 5H), 7.79 (s, 1H) |
| 63jq | $^1$H NMR (400 MHz, MeOH-d4): δ ppm 1.26 (t, J = 7.1 Hz, 5H), 1.46 (m, 7H), 1.74 (dd, J = 13.1, 7.3 Hz, 1H), 2.09 (dd, J = 13.1, 8.7 Hz, 1H), 2.75 (d, J = 11.0 Hz, 1H), 2.89 (d, J = 11.0 Hz, 1H), 3.52 (m, 4H), 3.82 (dd, J = 8.7, 7.2 Hz, 1H), 4.15 (m, 4H), 5.53 (s, 1H), 6.62 (q, J = 7.1 Hz, 1H), 7.12 (t, J = 8.7 Hz, 1H), 7.38 (m, 2H), 7.58 (q, J = 8.4 Hz, 4H) |

TABLE 18b-continued

NMR Data for Compounds of Table 18a

| Ex. No. | NMR |
|---|---|
| 63jr | $^1$H NMR (400 MHz, MeOH-d4): δ ppm 1.26 (t, J = 7.1 Hz, 3H), 1.39 (t, J = 7.0 Hz, 3H), 1.51 (m, 4H), 1.73 (dd, J = 13.1, 7.3 Hz, 1H), 2.08 (dd, J = 13.1, 8.8 Hz, 1H), 2.74 (d, J = 11.0 Hz, 1H), 2.88 (d, J = 11.0 Hz, 1H), 3.49 (dtt, 1 = 19.6, 13.1, 6.9 Hz, 4H), 3.82 (dd, J = 8.8, 7.3 Hz, 1H), 4.05 (q, J = 7.0 Hz, 2H), 4.18 (qd, J = 7.1, 1.5 Hz, 2H), 5.53 (s, 1H), 6.61 (q, J = 7.1 Hz, 1H), 6.96 (m, 2H), 7.55 (m, 6H) |
| 63js | $^1$H NMR (400 MHz, MeOH-d4): δ ppm 1.26 (t, J = 7.1 Hz, 3H), 1.52 (m, 4H), 1.75 (dd, J = 13.1, 7.3 Hz, 1H), 2.10 (dd, J = 13.1, 8.8 Hz, 1H), 2.76 (d, J = 11.0 Hz, 1H), 2.90 (d, J = 11.0 Hz, 1H), 3.16 (s, 3H), 3.52 (m, 4H), 3.83 (dd, J = 8.7, 7.3 Hz, 1H), 4.18 (qd, J = 7.2, 1.5 Hz, 2H), 5.53 (s, 1H), 6.75 (q, J = 6.7 Hz, 1H), 7.56 (m, 5H), 7.84 (d, J = 1.9 Hz, 1H), 7.99 (m, 2H) |
| 63jt | $^1$H NMR (400 MHz, MeOH-d4): δ ppm 1.13 (t, J = 7.2 Hz, 3H), 1.27 (q, J = 6.8 Hz, 7H), 1.55 (m, 4H), 1.81 (dd, J = 13.2, 7.6 Hz, 1H), 2.18 (dd, J = 13.2, 8.7 Hz, 1H), 2.86 (d, J = 11.2 Hz, 1H), 2.98 (d, J = 11.2 Hz, 1H), 3.36 (q, J = 7.1 Hz, 2H), 3.56 (m, 6H), 3.98 (t, J = 8.1 Hz, 1H), 4.21 (qd, J = 7.2, 1.8 Hz, 2H), 5.54 (s, 1H), 6.74 (q, J = 6.8 Hz, 1H), 7.32 (d, J = 2.2 Hz, 1H), 7.49 (m, 3H), 7.65 (m, 3H) |
| 63ju | $^1$H NMR (400 MHz, MeOH-d4): δ ppm 1.04 (dd, J = 6.8, 1.9 Hz, 6H), 1.26 (t, J = 7.2 Hz, 3H), 1.50 (dt, J = 10.7, 5.7 Hz, 4H), 1.73 (dd, J = 13.1, 7.2 Hz, 1H), 2.07 (ddd, J = 13.0, 7.7, 4.9 Hz, 2H), 2.39 (s, 2H), 2.74 (d, J = 10.9 Hz, 1H), 2.88 (d, J = 11.0 Hz, 1H), 3.49 (d, J = 7.5 Hz, 1H), 3.56 (d, J = 7.9 Hz, 3H), 3.78 (m, 3H), 4.17 (qd, J = 7.1, 1.6 Hz, 2H), 5.75 (s, 1H), 6.41 (d, J = 2.4 Hz, 1H), 6.75 (q, J = 6.6 Hz, 1H), 6.99 (m, 2H), 7.60 (dd, J = 8.7, 1.9 Hz, 3H), 7.72 (m, 2H), 7.97 (d, J = 2.4 Hz, 1H) |
| 63jv | $^1$H NMR (400 MHz, MeOH-d4): δ ppm 1.04 (s, 9H), 1.25 (t, J = 7.1 Hz, 3H), 1.48 (dt, J = 10.6, 5.7 Hz, 4H), 1.71 (dd, J = 13.1, 7.2 Hz, 1H), 2.05 (dd, J = 13.1, 8.8 Hz, 1H), 2.39 (s, 3H), 2.72 (d, J = 11.0 Hz, 1H), 2.86 (d, J = 11.0 Hz, 1H), 3.52 (m, 4H), 3.64 (s, 2H), 3.80 (dd, J = 8.7, 7.1 Hz, 1H), 4.17 (qd, J = 7.1, 1.5 Hz, 2H), 5.75 (s, 1H), 6.41 (d, J = 2.3 Hz, 1H), 6.76 (q, J = 6.6 Hz, 1H), 6.98 (m, 2H), 7.57 (m, 3H), 7.70 (m, 2H), 7.96 (d, J = 2.4 Hz, 1H) |
| 63jw | $^1$H NMR (400 MHz, MeOH-d4): δ ppm<br>1H NMR (MeOH-d4) δ: 1.29 (t, J = 7.1 Hz, 7H), 1.53 (s, 8H), 1.79 (s, 2H), 2.14 (s, 2H), 2.81 (s, 2H), 2.94 (d, J = 10.8 Hz, 2H), 3.50 (s, 7H), 3.57 (s, 2H), 3.90 (t, J = 8.0 Hz, 2H), 4.22 (qd, J = 7.1, 1.7 Hz, 3H), 5.43 (s, 1H), 6.51 (s, 1H), 6.85 (s, 1H), 7.25 (s, 1H), 7.48 (d, J = 9.7 Hz, 4H), 7.55 (d, J = 7.5 Hz, 2H), 7.79 (s, 4H), 8.13 (s, 2H) |
| 63jx | $^1$H NMR (400 MHz, MeOH-d4): δ ppm 1.26 (t, J = 7.1 Hz, 3H), 1.49 (dt, J = 10.8, 5.8 Hz, 4H), 1.73 (dd, J = 13.1, 7.2 Hz, 1H), 2.03 (m, 3H), 2.39 (s, 3H), 2.73 (d, J = 11.0 Hz, 1H), 2.85 (m, 3H), 3.53 (m, 4H), 3.81 (dd, J = 8.7, 7.1 Hz, 1H), 4.17 (m, 4H), 5.75 (s, 1H), 6.40 (d, J = 2.3 Hz, 1H), 6.77 (dd, J = 17.0, 7.9 Hz, 2H), 7.36 (dq, J = 4.4, 2.5 Hz, 2H), 7.56 (d, J = 1.8 Hz, 1H), 7.69 (m, 2H), 7.96 (d, J = 2.3 Hz, 1H) |
| 63jy | $^1$H NMR (400 MHz, MeOH-d4): δ 1.27 (dd, J = 7.9, 6.4 Hz, 4H), 1.54 (dt, J = 10.7, 5.6 Hz, 4H), 1.76 (dd, J = 13.2, 7.4 Hz, 1H), 2.12 (dd, J = 13.1, 8.8 Hz, 1H), 2.78 (m, 3H), 2.92 (m, 3H), 3.53 (m, 6H), 3.76 (s, 2H), 3.85 (dd, J = 8.7, 7.2 Hz, 1H), 4.19 (qd, J = 7.1, 1.7 Hz, 2H), 5.51 (d, J = 15.6 Hz, 1H), 6.72 (q, J = 6.6 Hz, 1H), 7.33 (d, J = 2.2 Hz, 1H), 7.51 (m, 3H), 7.66 (m, 2H), 7.79 (s, 1H) |
| 63jz | $^1$H NMR (400 MHz, MeOH-d4): δ 0.46 (m, 4H), 1.27 (m, 4H), 1.53 (dt, J = 11.2, 5.6 Hz, 4H), 1.72 (m, 2H), 2.13 (dd, J = 13.1, 8.8 Hz, 1H), 2.58 (s, 2H), 2.73 (s, 2H), 2.80 (d, J = 11.1 Hz, 1H), 2.93 (d, J = 11.0 Hz, 1H), 3.52 (ddd, J = 25.7, 12.3, 6.8 Hz, 6H), 3.76 (s, 2H), 3.89 (dd, J = 8.7, 7.3 Hz, 1H), 4.19 (qd, J = 7.1, 1.7 Hz, 2H), 5.52 (d, J = 17.0 Hz, 1H), 6.71 (q, J = 6.7 Hz, 1H), 7.33 (d, J = 2.3 Hz, 1H), 7.57 (m, 5H), 7.80 (s, 1H) |
| 63ka | $^1$H NMR (400 MHz, MeOH-d4): δ ppm 1.25 (t, J = 7.1 Hz, 3H), 1.50 (dt, J = 10.3, 5.3 Hz, 4H), 1.73 (dd, J = 13.1, 7.3 Hz, 1H), 2.07 (dd, J = 13.1, 8.8 Hz, 1H), 2.41 (s, 3H), 2.75 (d, J = 11.0 Hz, 1H), 2.88 (d, J = 11.0 Hz, 1H), 3.51 (m, 4H), 3.82 (dd, J = 8.8, 7.2 Hz, 1H), 4.17 (qd, J = 7.1, 1.6 Hz, 2H), 5.76 (s, 1H), 6.45 (d, J = 2.4 Hz, 1H), 6.88 (q, J = 6.6 Hz, 1H), 7.92 (m, 3H), 8.07 (d, J = 2.4 Hz, 1H), 8.29 (m, 3H), 8.52 (d, J = 8.9 Hz, 1H), 9.32 (d, J = 5.9 Hz, 1H) |
| 63kb | $^1$H NMR (400 MHz, MeOH-d4): δ ppm 1.35 (t, J = 7.22 Hz, 3 H) 1.65-1.91 (m, 4 H) 2.12 (dd, J = 13.67, 8.79 Hz, 1 H) 2.53 (dd, J = 13.67, 8.79 Hz, 1 H) 3.35 (s, 2 H) 3.56-3.91 (m, 4 H) 4.35 (qd, J = 7.06, 3.03 Hz, 2 H) 4.65 (t, J = 8.69 Hz, 1 H) 6.66 (d, J = 5.66 Hz, 1 H) 7.02 (d, J = 2.34 Hz, 1H) 7.69-7.78 (m, 2 H) 7.79-7.88 (m, 1 H) 8.29 (d, J = 1.37 Hz, 1H) |
| 63kc | $^1$H NMR (400 MHz, MeOH-d4): δ ppm 1.35 (t, J = 7.13 Hz, 3 H) 1.40 (s, 9 H) 1.64-1.85 (m, 4 H) 2.03-2.18 (m, 1 H) 2.43-2.61 (m, 1 H)<br>3.53-3.87 (m, 4 H) 4.27-4.43 (m, 2 H) 4.56-4.70 (m, 1 H) 5.51 (s, 1 H) 6.56 (d, J = 2.34 Hz, 1 H) 7.30-7.42 (m, 1 H) 7.53-7.61 (m, 1 H) 7.69<br>(d, J = 1.95 Hz, 2 H) 8.01 (d, J = 2.54 Hz, 1 H) |
| 63kd | $^1$H NMR (400 MHz, MeOH-d4): δ ppm 1.22-1.42 (m, 9 H) 1.51-1.72 (m, 4 H) 1.90-2.09 (m, 1 H) 2.33-2.52 (m, 1 H) 3.09 (s, 1 H) 3.21 (d, 1 = 4.69 Hz, 2 H) 3.40-3.72 (m, 4 H) 4.31 (dd, J = 7.13, 2.25 Hz, 2 H) 4.48 (s, 1 H) 5.64 (s, 1 H) 6.47 (d, J = 2.34 Hz, 1 H) 7.02 (d, J = 6.64 Hz, 1 H) 7.43-7.60 (m, 2 H) 7.72 (d, J = 8.59 Hz, 1 H) 7.95 (d, J = 2.34 Hz, 1 H) |
| 63ke | $^1$H NMR (400 MHz, MeOH-d4): δ ppm 0.68-0.95 (m, 2 H) 1.05 (dd, J = 8.40, 2.15 Hz, 2 H) 1.35 (t, J = 7.13 Hz, 4 H) 1.63-1.89 (m, 4 H) 1.98-2.18 (m, 2 H) 2.44-2.63 (m, 1 H) 3.78 (d, J = 5.08 Hz, 4 H) 4.35 (d, J = 7.03 Hz, 2 H) 4.63 (s, 1 H) 6.31 (d, J = 2.34 Hz, 1 H) 7.09 (d, J = 6.25 Hz, 1 H) 7.51-7.67 (m, 2 H) 7.73 (d, J = 8.20 Hz, 1 H) 7.93 (d, J = 2.54 Hz, 1 H) |
| 63kf | $^1$H NMR (400 MHz, MeOH-d4): δ ppm 1.35 (t, J = 7.13 Hz, 4 H) 1.74 (br. s., 4 H) 2.04-2.15 (m, 1 H) 2.34 (s, 3 H) 2.37 (s, 3 H) 2.44-2.58 (m, 1 H) 3.31 (d, J = 2.34 Hz, 2 H) 3.54-3.89 (m, 3 H) 4.34 (dd, J = 7.13, 3.22 Hz, 2 H) 4.61 (s, 1 H) 6.10 (s, 1 H) 6.51- |

TABLE 18b-continued

| NMR Data for Compounds of Table 18a | |
|---|---|
| Ex. No. | NMR |
| | 6.65 (m, 1 H) 7.03 (d, J = 2.15 Hz, 1 H) 7.28 (s, 1 H) 7.42-7.50 (m, 1 H) 7.54 (s, 1 H) 7.76-7.88 (m, 2 H) 7.90-8.01 (m, 1 H) 8.33 (s, 1 H) |
| 63kg | $^1$H NMR (400 MHz, MeOH-d4): δ ppm 1.29 (t, J = 7.1 Hz, 3H), 1.55 (s, 3H), 1.58 (d, J = 5.8 Hz, 1H), 1.88 (m, 1H), 2.29 (m, 6H), 3.04 (m, 2H), 3.43 (s, 2H), 3.56 (s, 2H), 4.24 (m, 2H), 6.68 (q, J = 6.9 Hz, 1H), 7.17 (d, J = 7.9 Hz, 1H), 7.36 (m, 2H), 7.45 (m, 1H), 7.52 (s, 2H), 7.53 (d, J = 2.8 Hz, 1H), 7.63 (dd, J = 8.2, 2.0 Hz, 1H), 7.73 (d, J = 8.2 Hz, 1H) |
| 63kh | $^1$H NMR (400 MHz, MeOH-d4): δ ppm 1.05 (t, J = 7.4 Hz, 3H), 1.26 (td, J = 7.1, 2.1 Hz, 3H), 1.50 (s, 3H), 1.53 (d, J = 5.7 Hz, 1H), 1.79 (m, 3H), 2.09 (dd, J = 13.1, 8.8 Hz, 1H), 2.75 (d, J = 11.0 Hz, 1H), 2.89 (d, J = 11.0 Hz, 1H), 3.50 (s, 3H), 3.83 (dd, J = 8.8, 7.2 Hz, 1H), 4.02 (t, J = 6.5 Hz, 2H), 4.17 (m, 2H), 5.46 (s, 1H), 6.67 (q, J = 6.7 Hz, 1H), 7.12 (t, J = 8.6 Hz, 1H), 7.40 (m, 4H), 7.52 (s, 4H), 7.54 (s, 1H), 7.62 (dd, J = 8.2, 2.1 Hz, 1H), 7.74 (d, J = 8.3 Hz, 1H) |
| 63ki | $^1$H NMR (400 MHz, MeOH-d4): δ ppm 1.27 (t, J = 7.1 Hz, 3H), 1.53 (dd, J = 11.2, 5.2 Hz, 5H), 1.75 (dd, J = 13.1, 7.3 Hz, 1H), 2.10 (dd, J = 13.1, 8.8 Hz, 1H), 2.76 (d, J = 11.0 Hz, 1H), 2.90 (d, J = 11.0 Hz, 1H), 3.49 (m, 2H), 3.51 (s, 3H), 3.84 (dd, J = 8.7, 7.3 Hz, 1H), 4.18 (qd, J = 7.1, 1.6 Hz, 2H), 5.44 (s, 1H), 6.66 (q, J = 6.9 Hz, 1H), 7.26 (m, 1H), 7.45 (m, 8H), 7.70 (d, J = 7.2 Hz, 1H) |
| 63kj | $^1$H NMR (400 MHz, MeOH-d4): δ ppm 1.27 (t, J = 7.1 Hz, 3H), 1.53 (dd, J = 11.0, 5.2 Hz, 4H), 1.77 (dd, J = 13.2, 7.4 Hz, 1H), 2.13 (dd, J = 13.1, 8.8 Hz, 1H), 2.80 (d, J = 11.1 Hz, 1H), 2.93 (d, J = 11.1 Hz, 1H), 3.46 (m, 1H), 3.53 (m, 2H), 3.91 (t, J = 8.1 Hz, 1H), 4.19 (qd, J = 7.1, 1.4 Hz, 2H), 5.47 (s, 1H), 6.69 (q, J = 6.9 Hz, 1H), 7.35 (m, 1H), 7.45 (m, 4H), 7.54 (d, J = 4.6 Hz, 4H), 7.65 (m, 3H), 7.77 (d, J = 8.2 Hz, 1H) |
| 63kk | $^1$H NMR (400 MHz, MeOH-d4): δ ppm 1.25 (t, J = 7.1 Hz, 3H), 1.51 (m, 4H), 1.74 (dd, J = 13.1, 7.4 Hz, 1H), 2.10 (dd, J = 13.1, 8.8 Hz, 1H), 2.29 (d, J = 9.9 Hz, 6H), 2.39 (s, 3H), 2.77 (d, J = 11.1 Hz, 1H), 2.90 (d, J = 11.1 Hz, 1H), 3.54 (tq, J = 14.0, 7.9, 6.7 Hz, 4H), 3.88 (dd, J = 8.7, 7.4 Hz, 1H), 4.17 (m, 2H), 5.74 (s, 1H), 6.41 (d, J = 2.3 Hz, 1H), 6.77 (q, J = 6.6 Hz, 1H), 7.19 (d, J = 7.8 Hz, 1H), 7.36 (dd, J = 7.6, 2.1 Hz, 1H), 7.42 (d, J = 1.5 Hz, 1H), 7.59 (d, J = 1.9 Hz, 1H), 7.72 (m, 2H), 7.97 (d, J = 2.4 Hz, 1H) |
| 63kl | $^1$H NMR (400 MHz, MeOH-d4): δ ppm 1.26 (t, J = 7.1 Hz, 3H), 1.51 (dd, J = 11.1, 5.8 Hz, 5H), 1.74 (dd, J = 13.1, 7.3 Hz, 1H), 2.09 (dd, J = 13.1, 8.8 Hz, 1H), 2.39 (s, 3H), 2.76 (d, J = 11.0 Hz, 1H), 2.89 (d, J = 11.0 Hz, 1H), 3.55 (d, J = 5.0 Hz, 4H), 3.85 (dd, J = 8.7, 7.2 Hz, 1H), 4.18 (m, 2H), 4.65 (s, 2H), 5.78 (s, 1H), 6.41 (d, J = 2.4 Hz, 1H), 6.87 (q, J = 6.5 Hz, 1H), 7.47 (dd, J = 10.9, 8.2 Hz, 3H), 7.59 (m, 2H), 7.79 (dd, J = 8.3, 2.1 Hz, 1H), 7.93 (d, J = 2.3 Hz, 2H) |
| 63km | $^1$H NMR (400 MHz, MeOH-d4): δ ppm 7.61-7.49 (m, 4H), 7.35-7.27 (m, 2H), 6.77 (dd, J = 8.4, 1.8 Hz, 1H), 6.60 (q, J = 7.3 Hz, 1H), 5.55-5.46 (m, 1H), 4.24-4.13 (m, 4H), 3.83 (dd, J = 8.8, 7.2 Hz, 1H), 2.93-2.71 (m, 4H), 2.14-1.94 (m, 3H), 1.74 (dd, J = 13.1, 7.3 Hz, 1H), 1.56-1.48 (m, 1H), 1.51 (s, 3H), 1.27 (td, J = 7.1, 2.0 Hz, 3H). |
| 63kn | $^1$H NMR (400 MHz, MeOH-d4): δ ppm 8.71 (d, J = 5.2 Hz, 2H), 8.02 (td, J = 7.7, 1.7 Hz, 1H), 7.78-7.68 (m, 3H), 7.51 (tt, J = 7.9, 3.3 Hz, 5H), 6.92 (d, J = 6.5 Hz, 1H), 5.81 (d, J = 3.8 Hz, 2H), 4.18 (qd, J = 7.1, 1.7 Hz, 2H), 3.83 (s, 1H), 3.56 (s, 6H), 3.57-3.46 (m, 1H), 2.89 (d, J = 11.0 Hz, 2H), 2.76 (d, J = 11.0 Hz, 2H), 2.09 (dd, J = 13.1, 8.9 Hz, 1H), 1.74 (dd, J = 13.1, 7.3 Hz, 1H), 1.52 (dd, J = 10.9, 5.5 Hz, 5H), 1.31-1.22 (m, 6H) |
| 63ko | $^1$H NMR (400 MHz, MeOH-d4): δ ppm 8.99 (d, J = 4.9 Hz, 2H), 8.03 (s, 1H), 7.73 (dd, J = 15.2, 7.7 Hz, 2H), 7.60-7.48 (m, 2H), 5.69 (s, 1H), 4.18 (q, J = 7.1 Hz, 2H), 3.83 (t, J = 8.1 Hz, 1H), 3.54-3.43 (m, 4H), 2.89 (d, J = 11.1 Hz, 1H), 2.75 (d, J = 11.0 Hz, 1H), 2.14-2.04 (m, 1H), 1.74 (dd, J = 13.0, 7.4 Hz, 1H), 1.50 (dd, J = 10.6, 5.5 Hz, 5H), 1.26 (t, J = 7.2 Hz, 4H) |
| 63kp | $^1$H NMR (400 MHz, MeOH-d4): δ ppm 7.97 (s, 1H), 7.76 (s, 2H), 7.66 (d, J = 16.1 Hz, 2H), 7.49 (d, J = 7.9 Hz, 1H), 7.25 (d, J = 8.1 Hz, 1H), 6.77 (d, J = 7.1 Hz, 1H), 6.41 (s, 1H), 5.74 (d, J = 2.7 Hz, 1H), 4.68 (s, 2H), 4.18 (d, J = 7.6 Hz, 2H), 3.84 (t, J = 8.1 Hz, 1H), 3.56 (s, 3H), 3.49 (s, 1H), 3.30 (d, J = 3.4 Hz, 9H), 2.89 (d, J = 11.1 Hz, 1H), 2.76 (d, J = 11.0 Hz, 1H), 2.37 (d, J = 14.1 Hz, 5H), 1.79-1.69 (m, 1H), 1.51 (d, J = 8.8 Hz, 4H), 1.30-1.21 (m, 4H) |
| 63kq | $^1$H NMR (400 MHz, MeOH-d4): δ ppm 7.98 (s, 1H), 7.76 (d, J = 5.1 Hz, 2H), 7.63 (s, 1H), 7.48 (d, J = 13.3 Hz, 3H), 6.77 (d, J = 6.8 Hz, 1H), 6.41 (s, 1H), 5.74 (s, 1H), 4.66 (s, 2H), 4.18 (d, J = 7.4 Hz, 2H), 3.82 (t, J = 8.2 Hz, 1H), 3.56 (s, 3H), 3.50 (s, 1H), 2.89 (d, J = 11.0 Hz, 1H), 2.75 (d, J = 11.1 Hz, 1H), 2.39 (s, 6H), 1.74 (dd, J = 13.0, 7.2 Hz, 1H), 1.51 (s, 4H), 1.30-1.22 (m, 3H) |
| 63kr | $^1$H NMR (400 MHz, MeOH-d4): δ ppm 8.43 (d, J = 2.5 Hz, 1H), 7.98 (d, J = 10.3 Hz, 2H), 7.79 (d, J = 8.3 Hz, 1H), 7.71 (d, J = 8.5 Hz, 1H), 7.63 (s, 1H), 6.83 (dd, J = 19.6, 7.7 Hz, 2H), 6.42 (d, J = 2.3 Hz, 1H), 5.74 (s, 1H), 4.35 (q, J = 7.0 Hz, 2H), 4.17 (q, J = 7.1 Hz, 2H), 3.55 (s, 3H), 3.48 (d, J = 13.0 Hz, 1H), 2.88 (d, J = 11.0 Hz, 1H), 2.74 (d, J = 11.0 Hz, 1H), 2.39 (s, 3H), 2.07 (dd, J = 13.0, 8.9 Hz, 1H), 1.73 (dd, J = 13.0, 7.2 Hz, 1H), 1.50 (d, J = 8.3 Hz, 4H), 1.38 (t, J = 7.1 Hz, 3H), 1.26 (t, J = 7.2 Hz, 3H). |
| 63ks | $^1$H NMR (400 MHz, MeOH-d4): δ ppm 8.46 (s, 1H), 7.99 (s, 2H), 7.83-7.69 (m, 2H), 7.64 (s, 1H), 6.80 (d, J = 5.3 Hz, 1H), 6.42 (s, 1H), 5.74 (s, 1H), 4.18 (d, J = 7.3 Hz, 2H), 3.94 (d, J = 2.7 Hz, 3H), 3.86 (t, J = 8.1 Hz, 1H), 3.56 (s, 3H), 3.50 (s, 1H), 2.91 (d, J = 11.0 Hz, 1H), 2.77 (d, J = 11.6 Hz, 1H), 2.39 (d, J = 2.7 Hz, 3H), 2.10 (t, J = 10.9 Hz, 1H), 1.80-1.70 (m, 1H), 1.51 (s, 4H), 1.26 (dd, J = 8.3, 5.7 Hz, 3H). |

TABLE 18b-continued

NMR Data for Compounds of Table 18a

| Ex. No. | NMR |
|---|---|
| 63kt | $^1$H NMR (400 MHz, MeOH-d4): δ ppm 7.67 (d, J = 8.5 Hz, 1H), 7.44 (ddd, J = 8.0, 4.8, 2.6 Hz, 2H), 7.32-7.24 (m, 2H), 7.07 (dd, J = 8.4, 2.5 Hz, 1H), 6.99 (d, J = 7.6 Hz, 1H), 6.76 (q, J = 6.9 Hz, 1H), 5.51 (s, 1H), 4.27 (dd, J = 7.0, 2.0 Hz, 1H), 4.25-4.13 (m, 4H), 3.76 (s, 2H), 3.58 (s, 2H), 3.51 (d, J = 14.9 Hz, 2H), 3.42 (s, 3H), 3.08 (d, J = 11.4 Hz, 1H), 2.99 (d, J = 11.4 Hz, 1H), 2.28 (dd, J = 13.3, 8.7 Hz, 1H), 1.88 (dd, J = 13.3, 8.0 Hz, 1H), 1.57 (p, J = 5.4 Hz, 4H), 1.29 (t, J = 7.1 Hz, 3H) |
| 63ku | $^1$H NMR (400 MHz, MeOH-d4): δ ppm 8.97 (d, J = 1.5 Hz, 1H), 8.80 (dd, J = 2.6, 1.5 Hz, 1H), 8.71 (d, J = 2.6 Hz, 1H), 7.77 (d, J = 8.3 Hz, 1H), 7.64-7.55 (m, 1H), 6.87 (q, J = 6.7 Hz, 1H), 5.62 (s, 1H), 4.23-4.13 (m, 2H), 3.82 (dd, J = 8.7, 7.2 Hz, 1H), 3.60-3.42 (m, 3H), 2.89 (d, J = 11.0 Hz, 1H), 2.75 (d, J = 11.0 Hz, 1H), 2.09 (dd, J = 13.1, 8.7 Hz, 1H), 1.74 (dd, J = 13.1, 7.2 Hz, 1H), 1.51 (dt, J = 10.9, 5.6 Hz, 3H), 1.26 (t, J = 7.1 Hz, 2H) |

Example 64a (S)-Octyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate

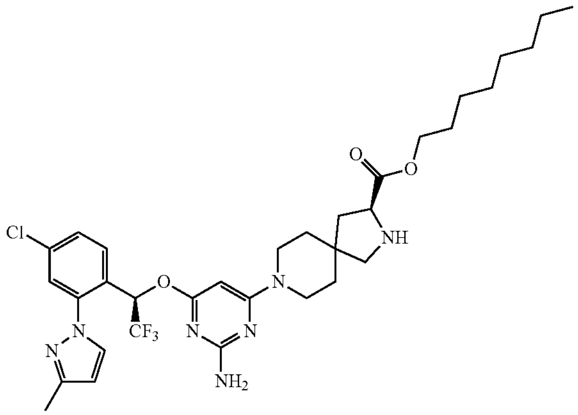 [SMILES: CCCCCCCCOC(=O)[C@@H]1CC2(CCN(c3cc(O[C@H](c4ccc(Cl)cc4-n4ccc(C)n4)C(F)(F)F)nc(N)n3)CC2)CN1]

To a flask equipped with a Dean Stark trap were added (2S)-8-[2-amino-6-[(1R)-1-[4-chloro-2-(3-methyl pyrazol-1-yl)phenyl]-2,2,2-trifluoroethoxy]pyrimidin-4-yl]-3,8-diazaspiro [4.5]decane-2-carboxylic acid (1 g, 1.78 mmol), toluene (25 mL), and p-toluene sulfonic acid monohydrate (336 mg, 1.77 mmol), and n-octanol (690 mg, 5.30 mmol). The reaction mixture was heated to reflux for 48 h, cooled to RT, and concentrated in vacuo. Purification on a 120 g Isco RediSep silica cartridge ($CH_2Cl_2$/MeOH/ $NH_4OH$) provided the title compound as a white solid.

Applying the generic scheme below, the following examples of Table 19a were prepared as described above for (S)-octyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate (Example 64a), using the appropriate alcohol.

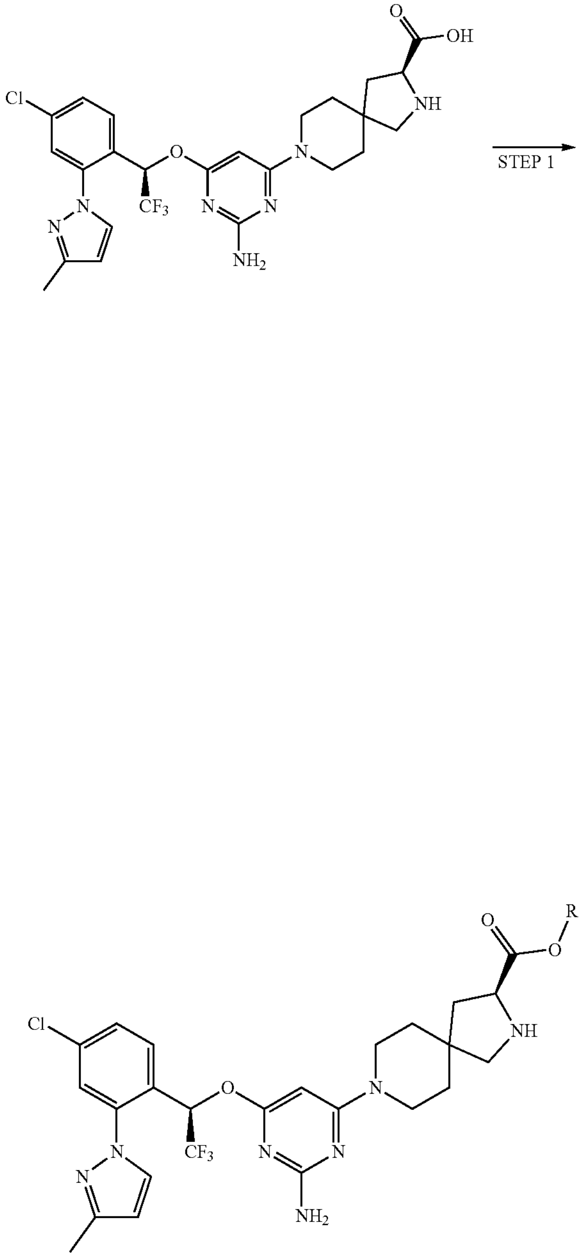

TABLE 19a

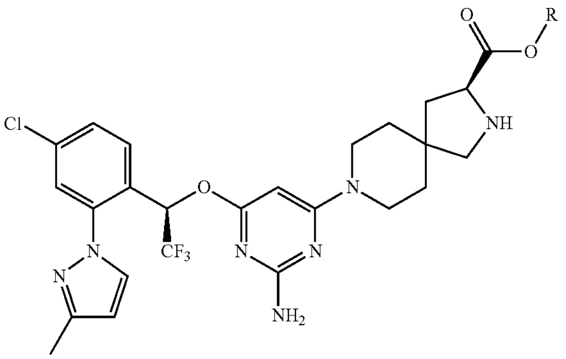

| Ex. No. | R | CAS Name | LCMS (MH+) |
|---|---|---|---|
| 64a | 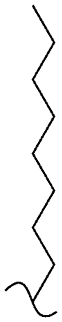 | (S)-Octyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 679.2 |
| 64b | 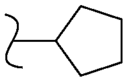 | (S)-cyclopentyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 635.1 |
| 64c | 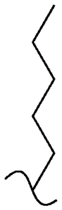 | (S)-pentyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 637 |
| 64d | 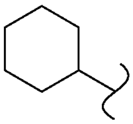 | (S)-cyclohexyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 648 |
| 64e | 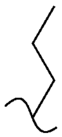 | (S)-propyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 608 |
| 64f | 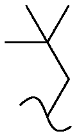 | (S)-neopentyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 636 |

TABLE 19a-continued

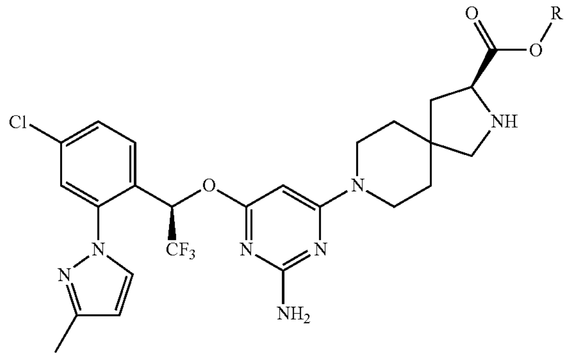

| Ex. No. | R | CAS Name | LCMS (MH+) |
|---|---|---|---|
| 64g | 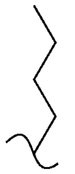 | (S)-butyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 622 |
| 64h | 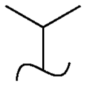 | (S)-isopropyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 622 |

TABLE 19b

NMR Data for Compounds of Table 19a

| Ex. No. | NMR |
|---|---|
| 64a | $^1$H NMR (400 MHz, MeOH-d4): δ ppm 0.82-0.96 (m, 3 H), 1.20-1.47 (m, 10 H), 1.53-1.79 (m, 6 H), 2.04 (dd, J = 13.6, 8.8 Hz, 1 H), 2.38 (s, 3 H), 2.49 (dd, J = 13.6, 8.8 Hz, 1 H), 3.28 (s, 2 H), 3.42-3.85 (m, 4 H), 4.16-4.39 (m, 2 H), 4.60 (t, J = 8.8 Hz, 1 H), 5.81 (s, 1 H), 6.42 (d, J = 2.2 Hz, 1 H), 6.85 (q, J = 6.6 Hz, 1 H), 7.46-7.60 (m, 2 H), 7.71 (d, J = 8.3 Hz, 1 H), 7.93 (d, J = 2.4 Hz, 1 H) |
| 64b | $^1$H NMR (400 MHz, MeOH-d4): δ ppm 1.50-2.10 (m, 13 H), 2.38 (s, 3 H), 2.45 (dd, J = 13.6, 8.8 Hz, 1 H), 3.27 (d, J = 1.2 Hz, 2 H), 3.43-3.76 (m, 4 H), 4.55 (t, J = 8.7 Hz, 1 H), 5.26-5.39 (m, 1 H), 5.74 (s, 1 H), 6.42 (d, J = 2.3 Hz, 1 H), 6.83 (q, J = 6.6 Hz, 1 H), 7.45-7.59 (m, 2 H), 7.71 (d, J = 8.4 Hz, 1 H), 7.93 (d, J = 2.3 Hz, 1 H) |
| 64c | $^1$H NMR (400 MHz, MeOH-d4): δ ppm 0.94 (t, J = 7.2 Hz, 3H), 1.35-1.39 (m, 4H), 1.52-1.56 (m, 4 H), 1.64-1.71 (m, 2H), 1.74-1.79 (m, 1H), 2.08-2.14 (m, 1H), 2.40 (s, 3 H), 2.77 (d, J = 10.8 Hz, 1H), 2.92 (d, J = 10.8 Hz, 1H), 3.48-3.58 (m, 4 H), 3.83-3.87 (m, 1H), 4.13-4.18 (m, 2H), 5.69 (s, 1 H), 6.43 (d, J = 2.0 Hz, 1H), 6.81-6.86 (m, 1H), 7.51-7.55 (m, 2H), 7.72 (d, J = 8.4 Hz, 1H), 7.95 (d, J = 2.0 Hz, 1H) |
| 64d | $^1$H NMR (400 MHz, MeOH-d4): δ ppm 1.31-1.56 (m, 10H), 1.75-1.80 (m, 3H), 1.85-1.89 (m, 2H), 2.08-2.13 (m, 1H), 2.39 (s, 3H), 2.76 (d, J = 10.8 Hz, 1 H), 2.93 (d, J = 10.8 Hz, 1H), 3.50-3.58 (m, 4H), 3.81-3.84 (m, 1H), 4.77-4.83 (m, 1H), 5.69 (s, 1 H), 6.42 (d, J = 2.0 Hz, 1H), 6.81-6.86 (m, 1H), 7.51-7.55 (m, 2H), 7.72 (d, J = 8.4 Hz, 1H), 7.95 (d, J = 2.4 Hz, 1H) |
| 64e | $^1$H NMR (400 MHz, MeOH-d4): δ ppm 0.98 (t, J = 7.6 Hz, 3H), 1.54-1.59 (m, 4 H), 1.66 (m, 2H), 1.81-1.86 (m, 1H), 2.17-2.23 (m, 1H), 2.40 (s, 3H), 2.89 (d, J = 11.2 Hz, 1H), 3.00 (d, J = 11.2 Hz, 1H), 3.47-3.62 (m, 4H), 4.03 (t, J = 8.0 Hz, 1H), 4.11-4.18 (m, 2H), 5.70 (s, 1H), 6.43 (d, J = 2.4 Hz, 1H), 6.84 (q, 1H), 7.51-7.55 (m, 2H), 7.73 (d, J = 8.4 Hz, 1H), 7.95 (d, J = 2.4 Hz, 1H) |
| 64f | $^1$H NMR (400 MHz, MeOH-d4): δ ppm 0.98 (s, 9H), 1.50-1.58 (m, 4 H), 1.77-1.82 (m, 1H), 2.12-2.17 (m, 1H), 2.40 (s, 3H), 2.79 (d, J = 11.2 Hz, 1H), 2.94 (d, J = 11.2 Hz, 1H), 3.52-3.58 (m, 4H), 3.83-3.93 (m, 3H), 5.70 (s, 1 H), 6.43 (d, J = 2.4 Hz, 1H), 6.81-6.86 (m, 1H), 7.52-7.55 (m, 2H), 7.73 (d, J = 8.4 Hz, 1H), 7.95 (d, J = 2.4 Hz, 1H) |
| 64g | $^1$H NMR (400 MHz, MeOH-d4): δ ppm 0.95 (t, J = 7.6 Hz, 3H), 1.37-1.43 (m, 2H), 1.50-1.54 (m, 4H), 1.60-1.67 (m, 2H), 1.72-1.77 (m, 1H), 2.06-2.12 (m, 1H), 2.38 (s, 3 H), 2.75 (d, J = 11.2 Hz, 1 H), 2.90 (d, J = 11.2 Hz, 1H), 3.45-3.58 (m, 4 H), 3.83-3.86 (m, 1H), 4.10-4.20 (m, 2H), 5.67 (s, 1H), 6.40 (d, J = 2.4 Hz, 1H), 6.80-6.85 (m, 1 H), 7.50-7.53 (m, 2H), 7.71 (d, J = 8.0 Hz, 1H), 7.93 (d, J = 2.0 Hz, 1H) |

TABLE 19b-continued

| NMR Data for Compounds of Table 19a | |
|---|---|
| Ex. No. | NMR |
| 64h | $^1$H NMR (400 MHz, MeOH-d4): δ ppm 0.85 (d, J = 6.8 Hz, 6H), 1.42-1.47 (m, 4H), 1.68-1.73 (m, 1H), 1.82-1.89 (m, 1H), 2.05-2.10 (m, 1H), 2.28 (s, 3H), 2.74 (d, J = 11.2 Hz, 1 H), 2.87 (d, J = 11.2 Hz, 1H), 3.37-3.48 (m, 4H), 3.81-3.91 (m, 3H), 5.58 (s, 1H), 6.30 (d, J = 2.0 Hz, 1H), 6.70-6.75 (m, 1 H), 7.40-7.43 (m, 2H), 7.60 (d, J = 8.4 Hz, 1H), 7.83 (d, J = 2.4 Hz, 1H) |

Example 65a (S)-Tert-butyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate

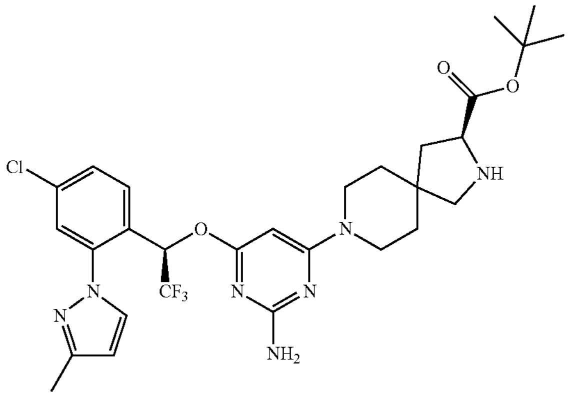 [SMILES: Cc1ccn(-c2cc(Cl)ccc2[C@@H](Oc2cc(N3CCC4(CC3)CN[C@H](C(=O)OC(C)(C)C)C4)nc(N)n2)C(F)(F)F)n1]

Step 1: To a mixture of (S)-8-(2-amino-6-((R)-1-(4-chloro-2-(3-methyl-1H-pyrazol-1-yl)phenyl)-2,2,2-trifluoroethoxy)pyrimidin-4-yl)-2-((benzyloxy)carbonyl)-2,8-diazaspiro[4.5]decane-3-carboxylic acid (2.8 g, 4.1 mmol) in t-BuOH (50 mL) were added $BOC_2O$ (3.5 g, 16.5 mmol) and DMAP (0.201 g, 1.65 mmol), and the reaction was heated to 50° C. for 45 min. Then the reaction was cooled to RT and concentrated in vacuo. Purification on a 220 g Isco RediSep silica cartridge (EtOAc/heptane) provided (S)-2-benzyl 3-tert-butyl 8-(2-amino-6-((R)-1-(4-chloro-2-(3-methyl-1H-pyrazol-1-yl)phenyl)-2,2,2-trifluoroethoxy) pyrimidin-4-yl)-2,8-diazaspiro[4.5]decane-2,3-dicarboxylate as an off-white solid.

Step 2: To a solution of (S)-2-benzyl 3-tert-butyl 8-(2-amino-6-((R)-1-(4-chloro-2-(3-methyl-1H-pyrazol-1-yl) phenyl)-2,2,2-trifluoroethoxy)pyrimidin-4-yl)-2,8-diazaspiro[4.5]decane-2,3-dicarboxylate (1.35 g, 1.7 mmol) in EtOAc (130 mL) was added 5% (w/w) Pd/C (130 mg). The solution was degassed, charged with 1 atm $H_2$ (balloon), and stirred at RT for 3.5 h. Then the solids were filtered through celite, washed with EtOAc/methanol, and the filtrate was concentrated in vacuo. Purification on a 220 g Isco RediSep silica cartridge ($CH_2Cl_2$/MeOH/$NH_4OH$) provided the title compound as an off-white solid.

Applying the generic scheme below, the following examples of Table 20a were prepared as described above for (S)-tert-butyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate (Example 65).

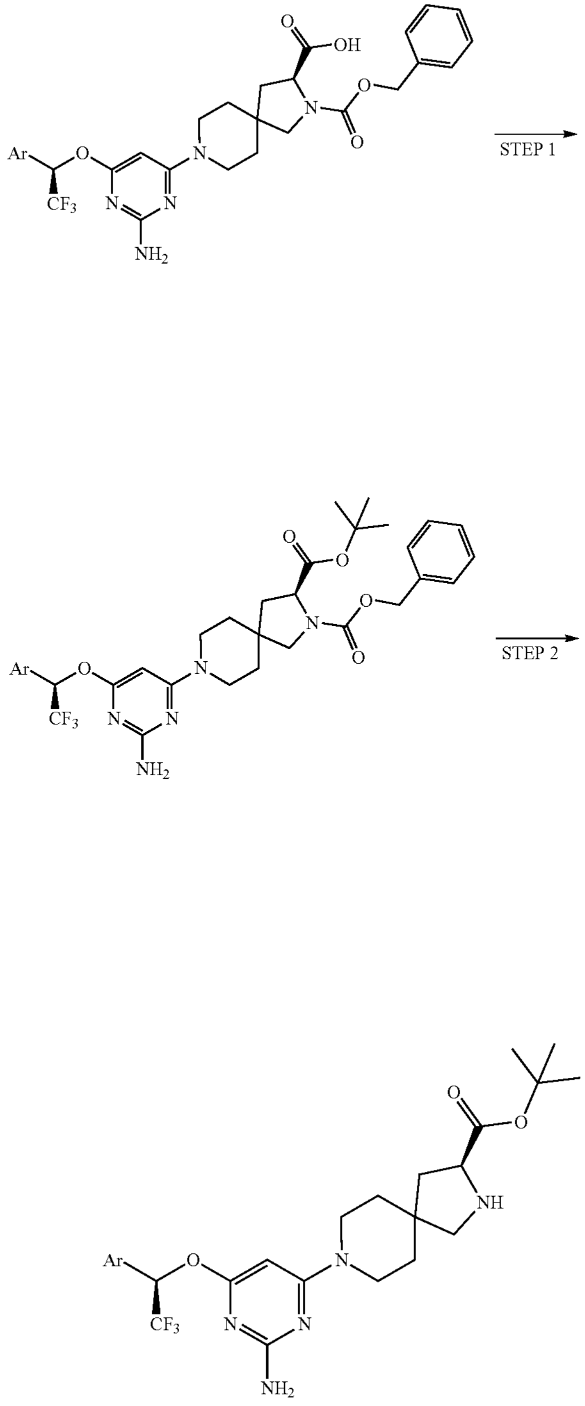

TABLE 20a

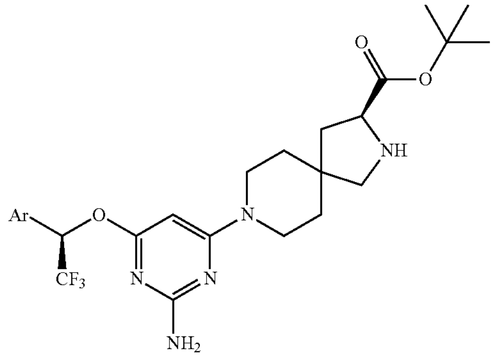

| Ex. No. | Ar | CAS Name | LCMS (MH+) |
|---|---|---|---|
| 65a | 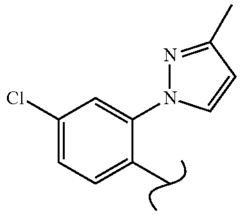 | (S)-tert-butyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 623 |
| 65b | 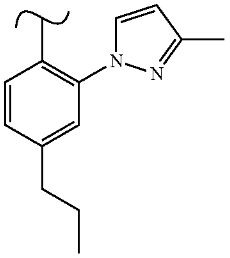 | (S)-tert-butyl 8-(2-amino-6-((R)-2,2,2-trifluoro-1-(2-(3-methyl-1H-pyrazol-1-yl)-4-propylphenyl)ethoxy)pyrimidin-4-yl)-2,8-diazaspiro[4.5]decane-3-carboxylate | 630 |
| 65c | 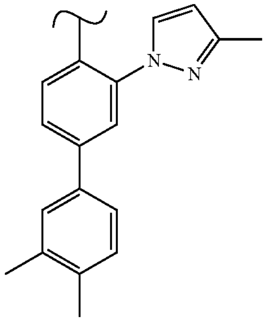 | (S)-tert-butyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 693 |
| 65d | 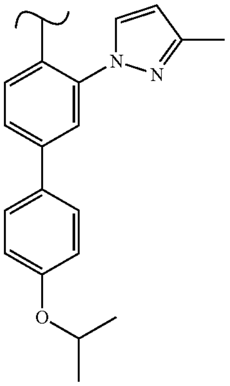 | (S)-tert-butyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 722 |

TABLE 20b

NMR Data for Compounds of Table 20a

| Ex. No. | NMR |
|---|---|
| 65a | $^1$H NMR (400 MHz, MeOH-d4): δ ppm 1.54 (s, 9 H), 1.57-1.72 (m, 4 H), 2.02 (dd, J = 13.62, 8.44 Hz, 1 H), 2.38 (s, 3 H), 2.40-2.47 (m, 1 H), 3.18-3.37 (m, 2 H), 3.47-3.75 (m, 4 H), 4.49 (t, J = 8.61 Hz, 1 H), 5.76 (s, 1 H), 6.42 (d, J = 2.34 Hz, 1 H), 6.84 (q, J = 6.57 Hz, 1 H), 7.46-7.59 (m, 2 H), 7.71 (d, J = 8.35 Hz, 1 H), 7.93 (d, J = 2.39 Hz, 1 H) |
| 65b | $^1$H NMR (400 MHz, MeOH-d4): δ ppm 0.96 (t, J = 7.35 Hz, 3 H) 1.53 (s, 9 H) 1.56-1.77 (m, 6 H) 1.99 (dd, J = 13.52, 8.25 Hz, 1 H) 2.37-2.42 (m, 4 H) 2.59-2.73 (m, 2 H) 3.14-3.29 (m, 2 H) 3.45-3.74 (m, 4 H) 4.43 (t, J = 8.47 Hz, 1 H) 5.72 (s, 1 H) 6.38 (d, J = 2.29 Hz, 1 H) 6.72 (q, J = 6.74 Hz, 1 H) 7.23 (d, J = 1.61 Hz, 1 H) 7.33 (dd, J = 8.10, 1.61 Hz, 1 H) 7.63 (d, J = 8.10 Hz, 1 H) 7.85 (d, J = 2.34 Hz, 1 H) |
| 65c | $^1$H NMR (400 MHz, MeOH-d4): δ ppm .49 (s, 4 H) 1.50 (s, 5 H) 1.53-1.64 (m, 4 H) 1.90-2.01 (m, 1 H) 2.27 (s, 3 H) 2.30 (s, 3 H) 2.31-2.37 (m, 1 H) 2.38 (s, 3 H) 3.09-3.25 (m, 2 H) 3.43-3.70 (m, 4 H) 4.32-4.42 (m, 1 H) 5.74 (s, 1 H) 6.39 (d, J = 2.29 Hz, 1 H) 6.75 (q, J = 6.67 Hz, 1 H) 7.19 (d, J = 7.91 Hz, 1 H) 7.36 (dd, J = 7.81, 1.81 Hz, 1 H) 7.42 (s, 1 H) 7.58 (s, 1 H) 7.68-7.78 (m, 2 H) 7.93 (d, J = 2.29 Hz, 1 H) |
| 65d | $^1$H NMR (400 MHz, MeOH-d4): δ ppm 1.31 (d, J = 6.05 Hz, 6 H) 1.50 (s, 4 H) 1.51 (s, 5 H) 1.55-1.70 (m, 4 H) 1.92-2.06 (m, 1 H) 2.38 (s, 3 H) 2.39-2.48 (m, 1 H) 3.16-3.27 (m, 2 H) 3.47-3.75 (m, 4 H) 4.46 (t, J = 8.64 Hz, 1 H) 4.63 (dt, J = 12.10, 6.05 Hz, 1 H) 5.85 (s, 1 H) 6.39 (d, J = 2.29 Hz, 1 H) 6.76 (q, J = 6.62 Hz, 1 H) 6.97 (d, J = 8.79 Hz, 2 H) 7.55-7.63 (m, 3 H) 7.67-7.77 (m, 2 H) 7.93 (d, J = 2.29 Hz, 1 H) |

Example 66a (S)-2-(Dimethylamino)ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro [4.5] decane-3-carboxylate

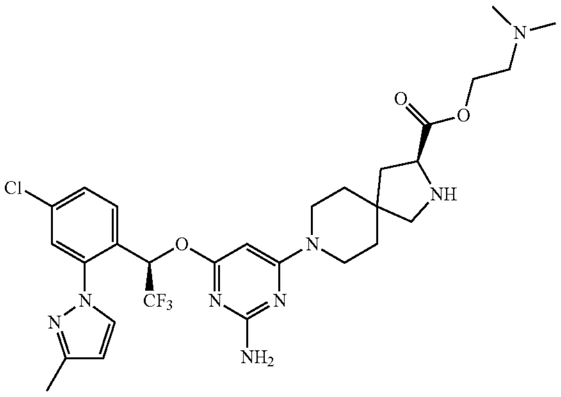 [SMILES: Cc1ccn(-c2cc(Cl)ccc2[C@@H](Oc2cc(N3CCC4(CC3)CN[C@H](C(=O)OCCN(C)C)C4)nc(N)n2)C(F)(F)F)n1]

Step 1: To a mixture of (S)-8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylic acid (85 mg, 0.16 mmol) in THF (10 mL) was added $BOC_2O$ (4 g, 18.6 mmol) in THF (10 mL), and the reaction mixture was stirred at RT for 16 h. Then the reaction was diluted with $CH_2Cl_2$, cooled to 0° C., and the pH adjusted to 2 with 2 N HCl. The reaction mixture was then extracted $CH_2Cl_2$ and concentrated in vacuo to provide (S)-8-(2-amino-6-((R)-1-(4-chloro-2-(3-methyl-1H-pyrazol-1-yl)phenyl)-2,2,2-trifluoroethoxy) pyrimidin-4-yl)-2-(tert-butoxycarbonyl)-2,8-diazaspiro[4.5]decane-3-carboxylic acid as an off-white solid that was used directly without further purification .

Step 2: To a solution of (S)-8-(2-amino-6-((R)-1-(4-chloro-2-(3-methyl-1H-pyrazol-1-yl)phenyl)-2,2,2-trifluoroethoxy)pyrimidin-4-yl)-2-(tert-butoxycarbonyl)-2,8-diazaspiro[4.5]decane-3-carboxylic acid (1.6 g, 2.45 mmol) in DMF (24 mL) were added (2-chloro-ethyl)-dimethyl-amine hydrochloride (535 mg, 3.7 mmol) and $K_2CO_3$ (1.0 g, 7.4 mmol), and the reaction mixture was heated at 65° C. for 16 h. Then the reaction was cooled to RT, partitioned between EtOAc and water, and extracted. The combined organic layers were washed with brine, dried over $Na_2SO_4$, filtered, and concentrated in vacuo. Purification via prep-HPLC column chromatography ($CH_2Cl_2$/MeOH/$NH_4OH$) provided (S)-2-tert-butyl 3-(2-(dimethylamino)ethyl) 8-(2-amino-6-((R)-1-(4-chloro-2-(3-methyl-1H-pyrazol-1-yl) phenyl)-2,2,2-trifluoroethoxy)pyrimidin-4-yl)-2,8-diazaspiro[4.5]decane-2,3-dicarboxylate as an off-white solid.

Step 3: To a solution of (S)-2-tert-butyl 3-(2-(dimethylamino)ethyl) 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-2,3-dicarboxylate (1.4 g, 1.86 mmol) in $CH_2Cl_2$ (9 mL) was added TFA (4.5 mL), and the reaction was stirred at RT for 2 h. Then the reaction was concentrated in vacuo and the residue was partitioned between $CH_2Cl_2$ and aqueous $NaHCO_3$, and extracted. The combined organic layers were washed with brine, dried over $Na_2SO_4$, and concentrated in vacuo. Purification via prep-HPLC column chromatography ($CH_2Cl_2$/EtOH/$NH_4OH$) provided the title compound as an off-white solid.

Applying the generic scheme below, the following examples of Table 21a were prepared as described above for (S)-2-(dimethylamino)ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate (Example 66a), using the appropriate alkylating agent.

-continued
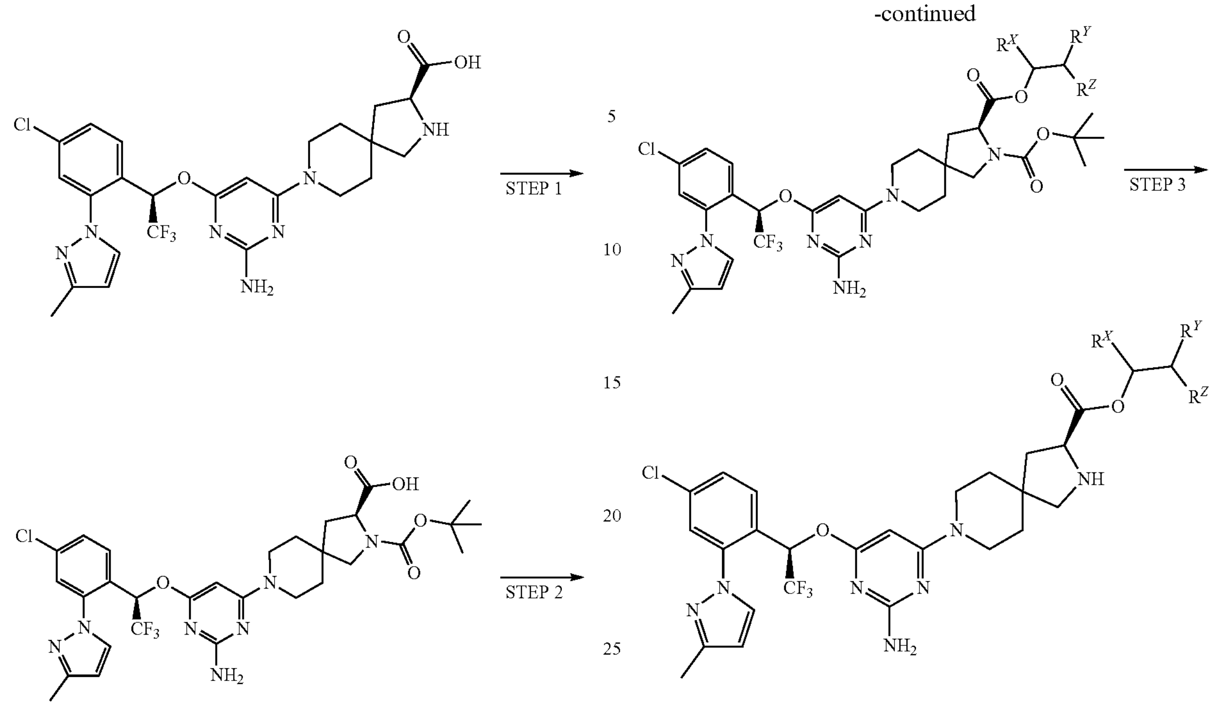
TABLE 21a
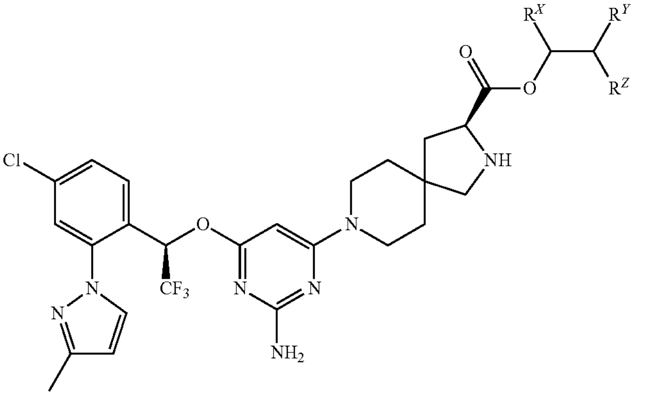
| Ex. No. | $R^X$ | $R^Y$ | $R^Z$ | CAS Name | LCMS (MH+) |
|---|---|---|---|---|---|
| 66a | H | 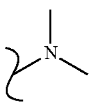 | H | (S)-2-(dimethylamino)ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 638 |
| 66b | H | 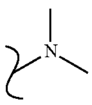 | 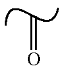 | (S)-2-(dimethylamino)-2-oxoethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 652 |

TABLE 21a-continued

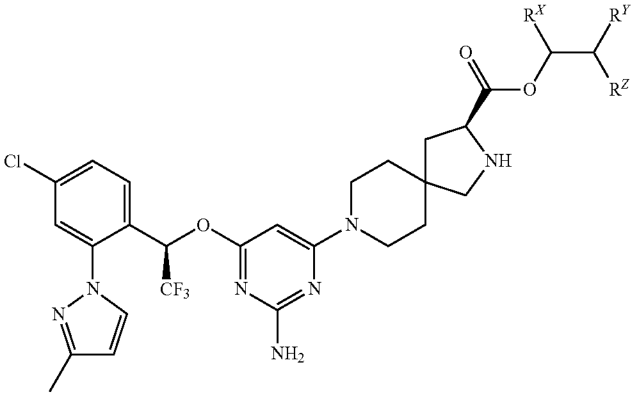

| Ex. No. | $R^X$ | $R^Y$ | $R^Z$ | CAS Name | LCMS (MH+) |
|---|---|---|---|---|---|
| 66c | H | 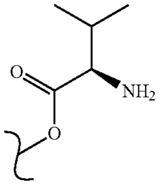 | H | (S)-2-(((R)-2-amino-3-methylbutanoyl)oxy)ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 710 |
| 66d | H | 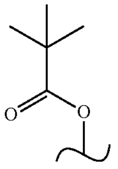 | H | (S)-2-(pivaloyloxy)ethyl 8-(2-amino-6-((R)-1-(4-chloro-2-(3-methyl-1H-pyrazol-1-yl)phenyl)-2,2,2-trifluoroethoxy)pyrimidin-4-yl)-2,8-diazaspiro[4.5]decane-3-carboxylate | 695 |

TABLE 21b

NMR Data for Compounds of Table 21a

| Ex. No. | NMR |
|---|---|
| 66a | $^1$H NMR (400 MHz, DMSO-d6): δ ppm 1.59 (d, J = 5.08 Hz, 4 H) 2.00 (dd, J = 13.15, 9.84 Hz, 1 H) 2.22-2.38 (m, 4 H) 2.77 (d, J = 3.37 Hz, 6 H) 3.14 (br. s., 2 H) 3.41 (br. s., 2 H) 3.60 (br. s., 2 H) 4.45 (dd, J = 5.71, 3.90 Hz, 1 H) 4.49-4.68 (m, 2 H) 5.90 (br. s., 1 H) 6.39 (d, J = 2.39 Hz, 1 H) 7.15 (d, J = 5.86 Hz, 1 H) 7.53-7.73 (m, 3 H) 8.14 (d, J = 2.39 Hz, 1 H) 9.65 (br. s., 1 H) 10.59 (br. s., 1 H), 10.80 (br. s., 1 H). |
| 66b | $^1$H NMR (400 MHz, DMSO-d6): δ ppm 1.46-1.77 (m, 4 H) 2.11 (dd, J = 13.42, 8.40 Hz, 1 H) 2.31 (s, 3 H) 2.38 (dd, J = 13.42, 9.08 Hz, 1 H) 2.78-2.88 (m, 3 H) 2.89-2.98 (m, 3 H) 3.16 (br. s., 2 H) 3.59-3.77 (m, 3 H) 4.65 (t, J = 6.17 Hz, 1 H) 4.83-4.97 (m, 1 H) 5.00-5.12 (m, 1 H) 6.03 (br. s., 1 H) 6.42 (d, J = 2.29 Hz, 1 H) 7.20 (d, J = 5.47 Hz, 1 H) 7.57-7.76 (m, 3 H) 8.17 (d, J = 2.34 Hz, 1 H) 9.22 (d, J = 4.44 Hz, 1 H) 10.63 (br. s., 1 H). |
| 66c | $^1$H NMR (400 MHz, DMSO-d6): δ ppm 0.98 (dd, J = 15.52, 6.93 Hz, 6 H) 1.46-1.70 (m, 4 H) 1.94 (dd, J = 13.15, 9.64 Hz, 1 H) 2.20 (td, J = 6.91, 4.88 Hz, 1 H) 2.26-2.38 (m, 4 H) 3.14 (br. s., 2 H) 3.51 (br. s., 2 H) 3.58-3.70 (m, 3 H) 3.88 (br. s., 1 H) 4.29-4.49 (m, 4 H) 4.55 (br. s., 1 H) 5.84 (br. s., 1 H) 6.42 (d, J = 2.34 Hz, 1 H) 7.16 (d, J = 5.66 Hz, 1 H) 7.50-7.76 (m, 3 H) 8.17 (d, J = 2.34 Hz, 1 H) 8.66 (br. s., 3 H) 9.47 (br. s., 1 H) 10.52-10.84 (m, 1 H). |
| 66d | $^1$H NMR (400 MHz, DMSO-d6): δ ppm 1.11-1.18 (m, 9 H) 1.48 (s, 3 H) 1.54-1.72 (m, 4 H) 1.74-2.01 (m, 1 H) 2.22-2.43 (m, 4 H) 3.15 (d, J = 3.56 Hz, 2 H) 3.58-3.80 (m, 4 H) 4.60 (d, J = 5.71 Hz, 1 H) 6.06 (br. s., 1 H) 6.42 (s, 1 H) 6.74-6.88 (m, 1 H) 7.22 (d, J = 5.47 Hz, 1 H) 7.57-7.76 (m, 4 H) 8.18 (s, 1 H) 9.19-9.56 (m, 1 H) 10.74 (br. s., 1 H). |

Example 67a (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate

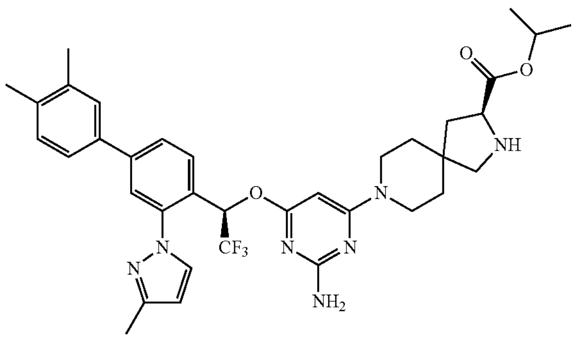 [SMILES: Cc1ccn(-c2cc(-c3ccc(C)c(C)c3)ccc2[C@@H](Oc2cc(N3CCC4(CC3)CN[C@H](C(=O)OC(C)C)C4)nc(N)n2)C(F)(F)F)n1]

To a solution of the compound of Example 1m (400 mg, 0.53 mmol) in propan-2-ol (5 mL) was added thionyl chloride (2 drops) at 0° C. The mixture was warmed to RT and then heated to reflux for 2 h. Then the reaction mixture was cooled to RT, concentrated and neutralized with saturated aqueous $NaHCO_3$ solution to pH 7-8. The aqueous layer was extracted with $CH_2Cl_2$. The combined organic layers were washed with brine, dried over $Na_2SO_4$, filtered, concentrated in vacuo and purified by flash column (0-10% MeOH in DCM) on silica gel to afford the title compound as a white solid.

$^1$H NMR (400 MHz, MeOH-d4): δ ppm 7.96 (d, J=2.3 Hz, 1H), 7.75 (d, J=8.2 Hz, 1H), 7.70 (dd, J=8.2, 1.8 Hz, 1H), 7.59 (d, J=1.8 Hz, 1H), 7.43 (s, 1H), 7.37 (d, J=7.8 Hz, 1H), 7.19 (d, J=8.0 Hz, 1H), 6.76 (q, J=6.8 Hz, 1H), 6.41 (d, J=2.3 Hz, 1H), 5.74 (s, 1H), 5.01 (m, 1H), 3.76 (dd, J=8.7, 7.0 Hz, 1H), 3.61-3.42 (m, 4H), 2.88 (d, J=11.1 Hz, 1H), 2.72 (d, J=11.0 Hz, 1H), 2.39 (s, 3H), 2.31 (s, 3H), 2.29 (s, 3H), 2.05 (dd, J=13.1, 8.9 Hz, 1H), 1.71 (dd, J=13.0, 7.0 Hz, 1H), 1.50 (m, 4H), 1.24 (dd, J=6.2, 3.9 Hz, 6H). LCMS ($MH^+$): 679.

Applying the generic scheme below, the following examples of Table 22 were prepared as described above for (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 67a), using the appropriate alcohol.

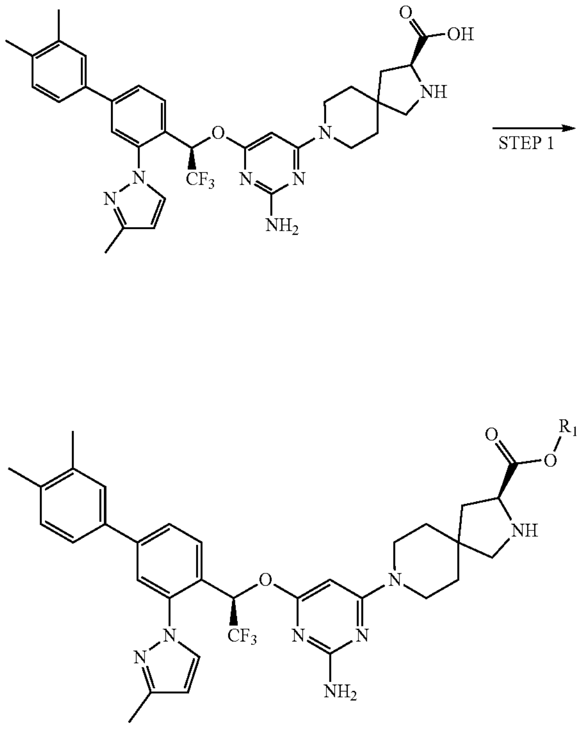

TABLE 22a

| Ex. No. | $R^1$ | CAS Name | LCMS (MH+) |
|---|---|---|---|
| 67b | 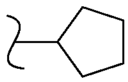 | (S)-cyclopentyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 705 |
| 67c | $CH_3$ | (S)-methyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 650 |
| 67d | 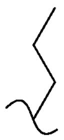 | (S)-propyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 679 |

TABLE 22b

| NMR Data for Compounds of Table 22 | |
|---|---|
| Ex. No. | NMR |
| 67b | $^1$H NMR (400 MHz, MeOH-d4): δ ppm 7.96 (d, J = 2.4 Hz, 1H), 7.75 (d, J = 8.2 Hz, 1H), 7.71 (dd, J = 8.2, 1.8 Hz, 1H), 7.60 (d, J = 1.7 Hz, 1H), 7.44 (s, 1H), 7.37 (dd, J = 7.9, 1.9 Hz, 1H), 7.20 (d, J = 7.8 Hz, 1H), 6.76 (q, J = 6.9 Hz, 1H), 6.41 (d, J = 2.3 Hz, 1H), 5.74 (s, 1H), 5.21-5.14 (m, 1H), 3.76 (dd, J = 8.8, 6.9 Hz, 1H), 3.61-3.42 (m, 4H), 2.88 (d, J = 11.0 Hz, 1H), 2.72 (d, J = 11.0 Hz, 1H), 2.39 (s, 3H), 2.31 (s, 3H), 2.28 (s, 3H), 2.04 (dd, J = 13.1, 8.8 Hz, 1H), 1.87 (d, J = 7.3 Hz, 2H), 1.77-1.56 (m, 7H), 1.50-1.45 (m, 4H) |
| 67c | $^1$H NMR (400 MHz, MeOH-d4): δ ppm 7.96 (d, J = 2.3 Hz, 1H), 7.76 (d, J = 8.3 Hz, 1H), 7.71 (dd, J = 8.2, 1.6 Hz, 1H), 7.60 (d, J = 1.6 Hz, 1H), 7.44 (s, 1H), 7.37 (dd, J = 7.8, 1.6 Hz, 1H), 7.20 (d, J = 7.9 Hz, 1H), 6.76 (q, J = 6.5 Hz, 1H), 6.41 (d, J = 2.3 Hz, 1H), 5.74 (s, 1H), 3.83 (t, J = 8.0 Hz, 1H), 3.71 (s, 3H), 3.61-3.41 (m, 4H), 2.86 (d, J = 11.0 Hz, 1H), 2.74 (d, J = 11.0 Hz, 1H), 2.39 (s, 3H), 2.31 (s, 3H), 2.28 (s, 3H), 2.06 (dd, J = 13.0, 8.7 Hz, 1H), 1.72 (dd, J = 13.0, 7.2 Hz, 1H), 1.55-1.43 (m, 4H) |
| 67d | $^1$H NMR (400 MHz, MeOH-d4): δ ppm 0.95 (m, 3H), 1.49 (dt, J = 12.0, 6.0 Hz, 4H), 1.69 (m, 3H), 2.06 (dd, J = 13.1, 8.8 Hz, 1H), 2.29 (d, J = 10.3 Hz, 6H), 2.39 (s, 3H), 2.73 (d, J = 11.0 Hz, 1H), 2.87 (d, J = 11.0 Hz, 1H), 3.30 (m, 4H), 3.51 (dt, J = 27.9, 6.6 Hz, 4H), 3.81 (dd, J = 8.7, 7.1 Hz, 1H), 4.08 (m, 2H), 5.74 (s, 1H), 6.41 (d, J = 2.3 Hz, 1H), 6.76 (q, J = 6.7 Hz, 1H), 7.19 (d, J = 7.9 Hz, 1H), 7.40 (m, 2H), 7.59 (d, J = 1.8 Hz, 1H), 7.72 (m, 2H), 7.96 (d, J = 2.4 Hz, 1H) |

Example 68a (S)-isopropyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro [4.5]decane-3-carboxylate

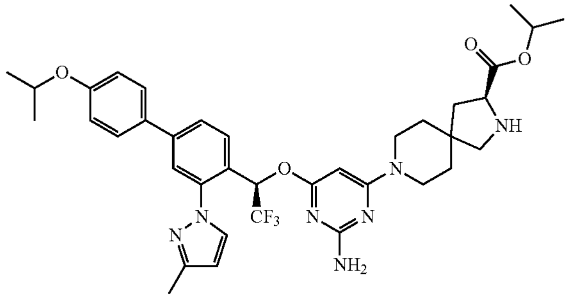

The title compound was prepared as described for (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 67a) starting with (S)-8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro [4.5]decane-3-carboxylic acid (Example 11).

Applying the generic scheme below, the following examples of Table 23 were prepared as described above for (S)-isopropyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro [4.5]decane-3-carboxylate (Example 68a), using the appropriate alcohol.

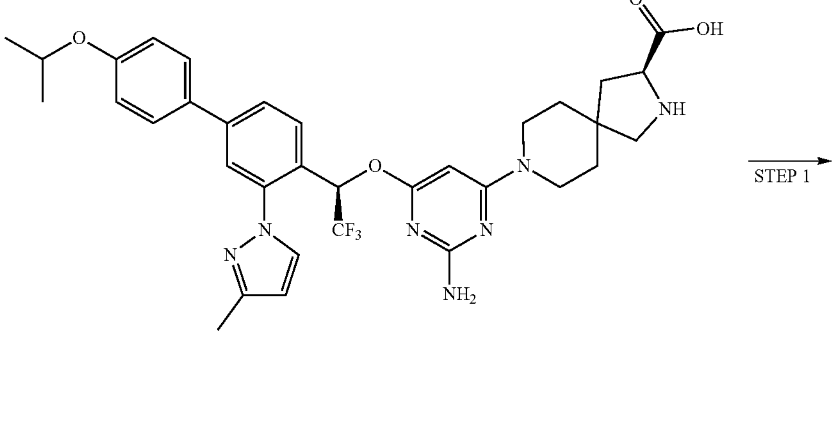

-continued

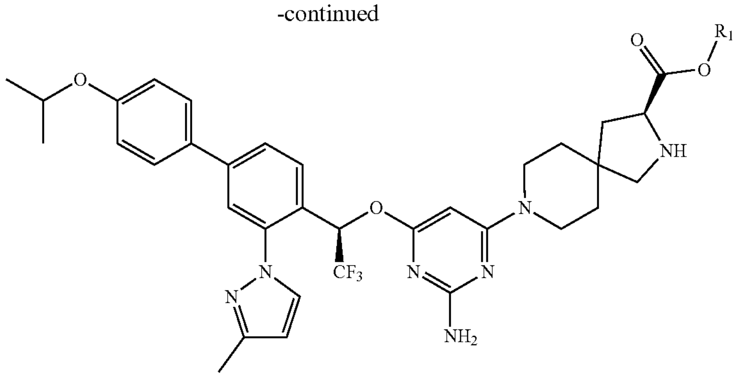

TABLE 23a

| Ex. No. | $R^1$ | CAS Name | LCMS (MH+) |
|---|---|---|---|
| 68a | 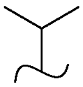 | (S)-isopropyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 709 |
| 68b | 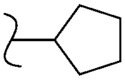 | (S)-cyclopentyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 735 |
| 68c | 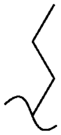 | (S)-propyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate | 709 |

TABLE 23b

| NMR Data for Compounds of Table 23 | |
|---|---|
| Ex. No. | NMR |
| 68a | $^1$H NMR (400 MHz, MeOH-d4): δ ppm 1.26 (m, 14H), 1.49 (dt, J = 10.9, 5.2 Hz, 4H), 1.72 (dd, J = 13.1, 7.0 Hz, 1H), 2.05 (dd, J = 13.1, 8.8 Hz, 1H), 2.39 (s, 3H), 2.72 (d, J = 11.0 Hz, 1H), 2.89 (d, J = 11.0 Hz, 1H), 3.52 (m, 4H), 3.77 (dd, J = 8.8, 7.0 Hz, 1H), 4.63 (hept, J = 6.0 Hz, 1H), 5.01 (p, J = 6.2 Hz, 1H), 5.74 (s, 1H), 6.40 (d, J = 2.3 Hz, 1H), 6.76 (q, J = 6.6 Hz, 1H), 6.96 (m, 2H), 7.57 (m, 3H), 7.70 (m, 2H), 7.95 (d, J = 2.3 Hz, 1H) |
| 68b | $^1$H NMR (400 MHz, MeOH-d4): δ ppm 1.32 (d, J = 6.0 Hz, 8H), 1.50 (m, 4H), 1.67 (ddd, J = 33.0, 12.8, 5.6 Hz, 8H), 1.88 (m, 3H), 2.05 (dd, J = 13.1, 8.9 Hz, 1H), 2.39 (s, 3H), 2.73 (d, J = 11.0 Hz, 1H), 2.89 (d, J = 11.0 Hz, 1H), 3.52 (dt, J = 21.1, 6.5 Hz, 4H), 3.78 (dd, J = 8.8, 7.0 Hz, 1H), 4.64 (p, J = 6.0 Hz, 1H), 5.18 (td, J = 5.9, 2.7 Hz, 1H), 5.75 (s, 1H), 6.40 (d, J = 2.4 Hz, 1H), 6.75 (q, J = 6.6 Hz, 1H), 6.97 (m, 2H), 7.59 (m, 3H), 7.71 (m, 2H), 7.95 (d, J = 2.4 Hz, 1H) |
| 68c | $^1$H NMR (400 MHz, MeOH-d4): δ ppm 0.94 (t, J = 7.4 Hz, 3H), 1.32 (d, J = 6.0 Hz, 6H), 1.50 (dt, J = 12.3, 6.0 Hz, 4H), 1.69 (m, 3H), 2.07 (dd, J = 13.1, 8.8 Hz, 1H), 2.39 (s, 3H), 2.73 (d, J = 11.0 Hz, 1H), 2.88 (d, J = 11.0 Hz, 1H), 3.52 (dp, J = 20.9, 7.5 Hz, 4H), 3.81 (dd, J = 8.7, 7.1 Hz, 1H), 4.09 (m, 2H), 4.64 (h, J = 6.0 Hz, 1H), 5.74 (s, 1H), 6.40 (d, J = 2.4 Hz, 1H), 6.76 (q, J = 6.7 Hz, 1H), 6.96 (m, 2H), 7.58 (m, 3H), 7.71 (m, 2H), 7.95 (d, J = 2.4 Hz, 1H) |

Example 69a (S)-isopropyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate

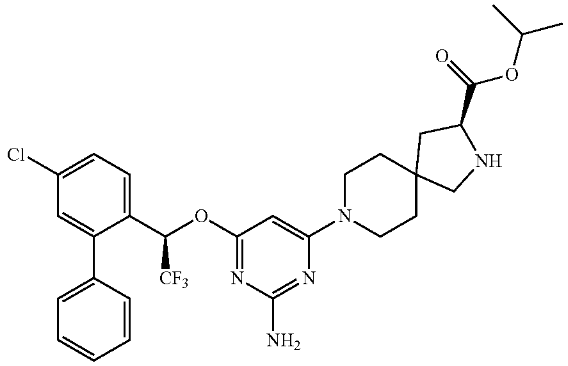

The title compound was prepared as described for (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 67a) starting with (S)-8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylic acid (Example 34c).

Applying the generic scheme below, the following examples of Table 24 were prepared as described above for (S)-isopropyl 8-(2-amino-6-((R)-2,2,2-trifluoro-1-(4'-isopropoxy-3-(3-methyl-1H-pyrazol-1-yl)-[1,1'-biphenyl]-4-yl)ethoxy)pyrimidin-4-yl)-2,8-diazaspiro[4.5]decane-3-carboxylate (Example 68a), using the appropriate alcohol.

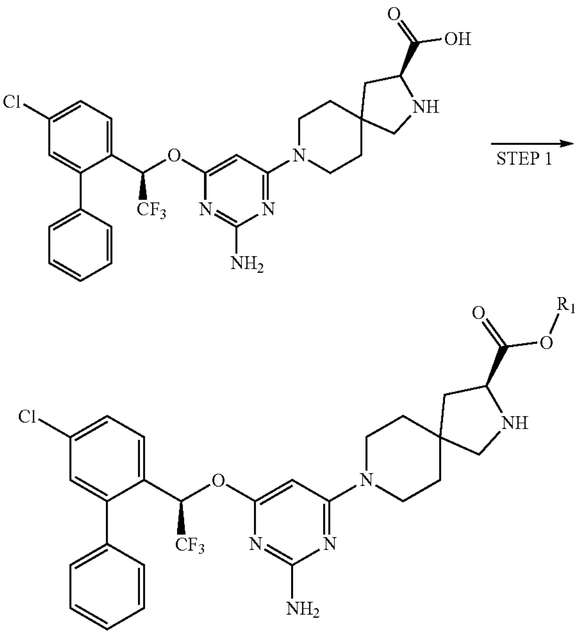

TABLE 24a

| Ex. No. | $R^1$ | CAS Name | LCMS (MH+) |
|---|---|---|---|
| 69a | 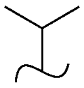 | (S)-isopropyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate | 605 |
| 69b | 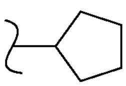 | (S)-cyclopentyl 8-(2-amino-6-((R)-1-(4'-chloro-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate | 735 |
| 69c | 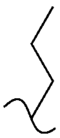 | (S)-propyl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate | 605 |
| 69d | 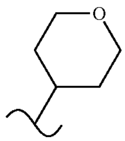 | (S)-tetrahydro-2H-pyran-4-yl 8-(2-amino-6-((R)-1-(5-chloro-[1,1'-biphenyl]-2-yl)-2,2,2-trifluoroethoxy)pyrimidin-4-yl)-2,8-diazaspiro[4.5]decane-3-carboxylate | 645 |

TABLE 24b

| NMR Data for Compounds of Table 24 | |
|---|---|
| Ex. No. | NMR |
| 69a | $^1$H NMR (400 MHz, MeOH-d4): δ ppm 1.25 (dd, J = 6.3, 3.2 Hz, 6H), 1.52 (m, 4H), 1.74 (dd, J = 13.1, 7.1 Hz, 1H), 2.09 (dd, J = 13.1, 8.8 Hz, 1H), 2.75 (d, J = 11.0 Hz, 1H), 2.91 (d, J = 11.0 Hz, 1H), 3.49 (m, 4H), 3.80 (dd, J = 8.8, 7.1 Hz, 1H), 5.02 (hept, J = 6.2 Hz, 1H), 5.47 (d, J = 7.8 Hz, 1H), 6.63 (q, J = 6.8 Hz, 1H), 7.28 (d, J = 2.2 Hz, 1H), 7.48 (m, 6H), 7.67 (d, J = 8.5 Hz, 1H) |
| 69b | $^1$H NMR (400 MHz, MeOH-d4): δ ppm 1.32 (d, J = 6.0 Hz, 8H), 1.50 (m, 4H), 1.67 (ddd, J = 33.0, 12.8, 5.6 Hz, 8H), 1.88 (m, 3H), 2.05 (dd, J = 13.1, 8.9 Hz, 1H), 2.39 (s, 3H), 2.73 (d, J = 11.0 Hz, 1H), 2.89 (d, J = 11.0 Hz, 1H), 3.52 (dt, J = 21.1, 6.5 Hz, 4H), 3.78 (dd, J = 8.8, 7.0 Hz, 1H), 4.64 (p, J = 6.0 Hz, 1H), 5.18 (td, J = 5.9, 2.7 Hz, 1H), 5.75 (s, 1H), 6.40 (d, J = 2.4 Hz, 1H), 6.75 (q, J = 6.6 Hz, 1H), 6.97 (m, 2H), 7.59 (m, 3H), 7.71 (m, 2H), 7.95 (d, J = 2.4 Hz, 1H) |
| 69c | $^1$H NMR (MeOH-d4): δ ppm 0.95 (t, J = 7.4 Hz, 3H), 1.52 (dt, J = 14.2, 4.9 Hz, 4H), 1.71 (ddd, J = 31.8, 13.7, 7.1 Hz, 3H), 2.10 (dd, J = 13.1, 8.8 Hz, 1H), 2.76 (d, J = 11.0 Hz, 1H), 2.91 (d, J = 11.0 Hz, 1H), 3.50 (ddd, J = 19.5, 7.9, 4.8 Hz, 4H), 3.84 (dd, J = 8.7, 7.2 Hz, 1H), 4.10 (m, 2H), 4.88 (s, 8H), 5.48 (d, J = 7.9 Hz, 1H), 6.63 (q, J = 6.9 Hz, 1H), 7.28 (d, J = 2.2 Hz, 1H), 7.47 (m, 6H), 7.67 (d, J = 8.6 Hz, 1H) |
| 69d | $^1$H NMR (MeOH-d4): δ ppm 1.61 (m, 6H), 1.82 (dd, J = 13.2, 7.5 Hz, 1H), 1.93 (dd, J = 11.6, 6.1 Hz, 2H), 2.03 (s, 1H), 2.20 (dd, J = 13.2, 8.8 Hz, 1H), 2.89 (d, J = 11.2 Hz, 1H), 2.99 (d, J = 11.2 Hz, 1H), 3.54 (m, 6H), 3.89 (dq, J = 12.1, 3.9 Hz, 2H), 4.04 (dd, J = 8.7, 7.5 Hz, 1H), 5.01 (tt, J = 8.3, 4.0 Hz, 1H), 5.48 (s, 1H), 6.64 (q, J = 6.9 Hz, 1H), 7.28 (d, J = 2.2 Hz, 1H), 7.47 (m, 6H), 7.67 (d, J = 8.5 Hz, 1H) |

Example 70

(S)-methyl 8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-3-carboxylate

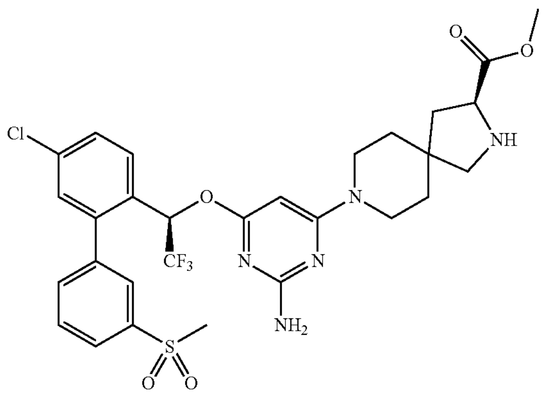 [SMILES: COC(=O)[C@@H]1CC2(CCN(c3cc(O[C@H](c4ccc(Cl)cc4-c4cccc(S(C)(=O)=O)c4)C(F)(F)F)nc(N)n3)CC2)CN1]

The title compound was prepared as described for (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 67a) starting with (S)-8-(2-amino-6-((R)-1-(5-chloro-3'-(methylsulfonyl)-[1,1'-biphenyl]-2-yl)-2,2,2-trifluoroethoxy)pyrimidin-4-yl)-2,8-diazaspiro[4.5]decane-3-carboxylic acid (Example 34w).

$^1$H NMR (400 MHz, MeOH-d4): δ ppm 1.51 (q, J=7.1, 6.7 Hz, 6H), 1.72 (dd, J=13.0, 7.3 Hz, 1H), 2.07 (dd, J=13.2, 8.7 Hz, 1H), 2.75 (d, J=11.0 Hz, 1H), 2.87 (d, J=11.0 Hz, 1H), 3.21 (s, 4H), 3.50 (tdt, J=20.3, 13.5, 7.0 Hz, 4H), 3.71 (s, 2H), 3.84 (t, J=8.0 Hz, 1H), 4.87 (m, 1H), 5.57 (s, 1H), 6.57 (q, J=6.6 Hz, 1H), 7.33 (d, J=2.3 Hz, 1H), 7.41 (s, 2H), 7.48 (dd, J=8.5, 2.2 Hz, 1H), 7.75 (m, 3H), 8.07 (d, J=7.8 Hz, 1H), 8.43 (s, 1H). LCMS (MH+): 655.

Example 71

(S)-methyl 8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylate

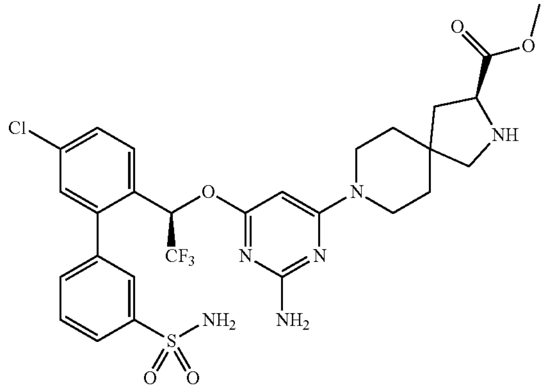 [SMILES: COC(=O)[C@@H]1CC2(CCN(c3cc(O[C@H](c4ccc(Cl)cc4-c4cccc(S(N)(=O)=O)c4)C(F)(F)F)nc(N)n3)CC2)CN1]

The title compound was prepared as described for (S)-isopropyl 8-(2-amino-6-((R)-1-(3',4'-dimethyl-3-(3-methyl-1H-pyrazol-1-yl)-[1,1'-biphenyl]-4-yl)-2,2,2-trifluoroethoxy)pyrimidin-4-yl)-2,8-diazaspiro[4.5]decane-3-carboxylate (Example 67a) starting with (S)-8-(2-amino-6-((R)-1-(5-chloro-3'-sulfamoyl-[1,1'-biphenyl]-2-yl)-2,2,2-trifluoroethoxy)pyrimidin-4-yl)-2,8-diazaspiro[4.5]decane-3-carboxylic acid (Example 34u).

$^1$H NMR (400 MHz, MeOH-d4): δ ppm 1.54 (dt, J=8.9, 6.0 Hz, 5H), 1.75 (dd, J=13.1, 7.4 Hz, 1H), 2.10 (dd, J=13.1, 8.7 Hz, 1H), 2.77 (d, J=11.0 Hz, 1H), 2.89 (d, J=11.0 Hz, 1H), 3.53 (qt, J=14.0, 7.8 Hz, 4H), 3.72 (s, 3H), 3.86 (dd, J=8.7, 7.3 Hz, 1H), 4.91 (s, 13H), 5.57 (s, 1H), 6.60 (q, J=6.5 Hz, 1H), 7.31 (d, J=2.2 Hz, 1H), 7.49 (dd, J=8.5, 2.3 Hz, 1H), 7.60 (d, J=7.7 Hz, 1H), 7.71 (m, 2H), 8.02 (ddd, J=7.9, 1.9, 1.1 Hz, 1H), 8.33 (s, 1H). LCMS (MH+):656. LCMS (MH+): 656.

Example A

In Vitro Inhibition Assays

TPH1 and $TPH_2$ Assays

Recombinant human TPH1 (rTPH1 GenBank TM accession no. NP_004179) was expressed by cloning full length human TPH1 cDNA in to a bacterial pMAL-c5E expression vector to produce maltose-binding protein (MBP) TPH1 fusion proteins. *E. coli* BL21 (DE3) containing pMAL-c5E-TPH1 was used for protein generation and the recombinant protein was purified utilizing standard column chromatography techniques. The MBP tagged TPH1 (MBP-TPH1) was used directly to screen compounds as described below. Recombinant human TPH2 ($rTPH_2$ GenBank TM accession no. 173353), PheOH (rPheOH GenBank TM accession no. K03020) and TH (rTH GenBank TM accession no. L20679) with an MBP tag were produced similarly.

TPH1 activities were measured in an assay containing 200 mM ammonium sulfate, 7 mM DTT, 50 μg/mL catalase, 25 μM ammonium iron sulfate, 50 mM MES, pH 7.1. Test compounds were diluted in 100% DMSO and added to the assay plate in 1 μL aliquots at 100× final concentration. Fifty microliters of assay buffer containing 30 nM TPH1 enzyme (MBP tagged) were added to the plate wells containing the test compound by the use of an Eppendorf repeater pipette. The reaction was initiated by the addition of 50 μL of assay buffer containing 60 μM tryptophan and 72 μM 6-6-methyltetra-hydropterin (2× final concentration) by the use of a Multidrop (LabSystems). Final reaction conditions were 15 nM TPH1 enzyme, 30 μM tryptophan, 36 μM 6-methyltetra-hydropterin, 200 mM ammonium sulfate, 7 mM DTT, 25 μg/mL catalase, 25 μM ferrous ammonium sulfate, 50 mM MES, pH 7.1, with atmospheric oxygen at room temperature. The plate was immediately placed onto an M5 plate reader (Molecular Devices) for kinetic fluorescence measurement using an excitation setting of 300 nm and an emission setting of 335 nm. Fluorescence reads are recorded in kinetic mode for 300 seconds (5 minutes).

Kinetic assay data for compounds at specific concentrations was translated into slopes using the Softmax Pro software on a Spectramax reader, and compound inhibition slopes were compared with wells containing enzyme, substrate and cofactor in the absence of inhibitor (100%), and wells containing substrate and cofactor in the absence of enzyme (0%). DMSO concentration in the assay was 1%. Typically, in the absence of enzyme, reaction slopes were ~0. $IC_{50}$'s were determined using Graphpad Prism.

Compounds having an $IC_{50}$ of 10,000 nM or less were considered active.

Inhibition of $TPH_2$ activity by the compounds of the invention was measured similarly. In some instances, compounds of the invention showed dual inhibition of both TPH1 and TPH2.

Data related to TPH1 inhibition activity of the compounds of the invention is provided below in Table 25. Compounds that inhibit TPH1 with an IC50 from 3,000 nM to 10,000 nM are indicated by +. Compounds that inhibit TPH1 with an $IC_{50}$ of less than 3,000 nM but more than 300 nM are indicated by ++. Compounds that inhibit TPH1 from 50 nM to 300 nM are indicated by +++. Compounds that inhibit TPH1 with an $IC_{50}$ less than 50 nM are indicatead by ++++. Ester prodrugs listed, for example, in Tables 18a, 19a, 20a, and 21a-24a, as well as in Examples 70 and 71, are not expected to be active in this in vitro assay.

TABLE 25

TPH1 Inhibition Data

| Ex. No. | TPH1 Range |
|---|---|
| 1a | ++++ |
| 1b | ++++ |
| 1c | ++++ |
| 1d | ++++ |
| 1e | ++++ |
| 1f | +++ |
| 1g | ++++ |
| 1h | ++++ |
| 1i | +++ |
| 1j | +++ |
| 1k | ++++ |
| 1l | ++++ |
| 1m | ++++ |
| 1n | ++++ |
| 1o | ++++ |
| 1p | ++++ |
| 1q | ++++ |
| 1r | ++++ |
| 1s | ++++ |
| 1u | ++++ |
| 1y | ++++ |
| 1w | ++++ |
| 1x | ++++ |
| 1y | ++++ |
| 1z | ++++ |
| 1aa | ++++ |
| 1ab | ++++ |
| 1ac | ++++ |
| 1ad | ++++ |
| 1ae | ++++ |
| 1af | ++++ |
| 1ag | ++++ |
| 1ah | ++++ |
| 1ai | ++++ |
| 1aj | ++++ |
| 1ak | +++ |
| 1al | ++++ |
| 1am | ++++ |
| 1an | ++++ |
| 1ao | ++++ |
| 1ap | ++++ |
| 1aq | +++ |
| 1ar | +++ |
| 1as | ++++ |
| 1at | ++++ |
| 1au | +++ |
| 1ay | ++++ |
| 1aw | +++ |
| 1ax | ++++ |
| 1ay | +++ |
| 1az | +++ |
| 1ba | ++++ |
| 1bb | ++++ |
| 1bc | ++++ |
| 1bd | ++++ |
| 1be | +++ |
| 1bf | +++ |
| 1bg | ++++ |
| 1bh | ++++ |
| 1bi | ++++ |
| 1bj | +++ |
| 1bk | ++++ |
| 1bl | ++++ |
| 1bm | ++++ |
| 1bn | ++++ |
| 1bo | +++ |
| 1bp | ++++ |
| 1bq | ++++ |
| 1bv | ++++ |
| 1bw | +++ |
| 1bx | ++++ |
| 1by | ++++ |
| 1bz | ++++ |
| 1ca | ++++ |
| 1cb | ++++ |

TABLE 25-continued

TPH1 Inhibition Data

| Ex. No. | TPH1 Range |
|---|---|
| 1cc | ++++ |
| 1cd | ++++ |
| 1ce | ++++ |
| 1cf | +++ |
| 1cg | ++++ |
| 1ch | +++ |
| 1ci | ++++ |
| 1cj | ++++ |
| 1ck | ++++ |
| 1dl | ++++ |
| 1cm | ++++ |
| 1cn | ++++ |
| 1co | ++++ |
| 1cp | ++++ |
| 1cq | ++++ |
| 1cr | ++++ |
| 1cs | ++++ |
| 10j | +++ |
| 10k | +++ |
| 10l | +++ |
| 10m | ++++ |
| 10n | ++++ |
| 10o | ++++ |
| 10p | +++ |
| 10q | ++++ |
| 10r | ++++ |
| 10pa | +++ |
| 1l | +++ |
| 12a | +++ |
| 12b | ++++ |
| 12c | ++++ |
| 13 | +++ |
| 14 | ++++ |
| 15 | +++ |
| 16 | ++ |
| 17 | ++++ |
| 18a | +++ |
| 18b | ++++ |
| 18c | ++++ |
| 18d | ++++ |
| 18e | ++++ |
| 18f | ++++ |
| 19a | ++++ |
| 19b | ++++ |
| 19c | ++++ |
| 19d | +++ |
| 19e | ++++ |
| 19f | ++++ |
| 19g | ++++ |
| 19h | ++++ |
| 19i | ++++ |
| 19j | ++++ |
| 19k | ++++ |
| 19l | ++++ |
| 19m | ++++ |
| 19n | ++++ |
| 19o | ++++ |
| 19p | ++++ |
| 19q | ++++ |
| 19r | ++++ |
| 20 | ++++ |
| 21 | ++++ |
| 22a | ++++ |
| 22b | ++++ |
| 22c | ++++ |
| 23 | ++++ |
| 24 | +++ |
| 25 | ++++ |
| 26 | + |
| 27 | +++ |
| 28 | +++ |
| 29a | ++++ |
| 29b | ++++ |
| 29c | +++ |
| 29d | ++++ |

TABLE 25-continued

TPH1 Inhibition Data

| Ex. No. | TPH1 Range |
|---|---|
| 29e | +++ |
| 29f | ++++ |
| 29g | ++++ |
| 29h | ++++ |
| 29i | ++++ |
| 29j | ++++ |
| 29k | +++ |
| 29l | ++++ |
| 29m | +++ |
| 29n | +++ |
| 29o | ++++ |
| 29p | ++++ |
| 29q | ++++ |
| 29r | ++++ |
| 29s | ++++ |
| 29t | +++ |
| 29u | +++ |
| 33 | +++ |
| 34a | ++++ |
| 34b | ++++ |
| 34c | +++ |
| 34d | +++ |
| 34e | +++ |
| 34f | +++ |
| 34g | +++ |
| 34h | ++ |
| 34i | +++ |
| 34j | +++ |
| 34k | +++ |
| 34l | +++ |
| 34m | +++ |
| 34n | +++ |
| 34o | +++ |
| 34p | +++ |
| 34q | ++++ |
| 34r | +++ |
| 34s | +++ |
| 34t | +++ |
| 34u | ++++ |
| 34v | ++++ |
| 34w | ++++ |
| 34x | ++++ |
| 34y | ++++ |
| 34z | ++++ |
| 34aa | ++++ |
| 34ab | ++ |
| 34ac | ++++ |
| 34ad | ++ |
| 34ae | ++ |
| 34af | ++++ |
| 34ag | ++++ |
| 34ah | ++++ |
| 34ai | +++ |
| 34aj | +++ |
| 34ak | +++ |
| 34al | + |
| 34am | +++ |
| 34an | ++++ |
| 34ao | ++++ |
| 34ap | +++ |
| 34aq | ++++ |
| 34ar | ++++ |
| 34as | ++++ |
| 34at | +++ |
| 34au | ++++ |
| 34av | ++++ |
| 34aw | ++++ |
| 34ax | +++ |
| 34ay | +++ |
| 34az | ++ |
| 34ba | ++++ |
| 34bb | +++ |
| 34bc | +++ |
| 34bd | ++++ |
| 34be | ++++ |

TABLE 25-continued

TPH1 Inhibition Data

| Ex. No. | TPH1 Range |
|---|---|
| 34bf | +++ |
| 34bg | +++ |
| 34bh | ++ |
| 34bi | ++++ |
| 34bj | ++++ |
| 34bk | +++ |
| 34bl | +++ |
| 34bm | +++ |
| 34bn | +++ |
| 34bo | +++ |
| 34bp | ++++ |
| 34bq | +++ |
| 34bu | +++ |
| 34bv | +++ |
| 34bw | +++ |
| 34bx | +++ |
| 34by | +++ |
| 34ca | +++ |
| 34cb | +++ |
| 34cc | +++ |
| 34cd | +++ |
| 34ce | +++ |
| 34cf | ++ |
| 34cg | +++ |
| 34ch | ++++ |
| 34ci | +++ |
| 34cj | +++ |
| 34ck | +++ |
| 34cl | +++ |
| 34cm | +++ |
| 34cn | +++ |
| 34co | +++ |
| 34cp | +++ |
| 34cq | ++++ |
| 34cr | +++ |
| 34cs | +++ |
| 34ct | ++++ |
| 34cu | ++++ |
| 34cv | ++++ |
| 35 | +++ |
| 36 | + |
| 36b | +++ |
| 36c | ++++ |
| 36d | + |
| 36e | ++ |
| 36f | +++ |
| 36g | ++++ |
| 37 | + |
| 38 | ++ |
| 39a | ++ |
| 39b | + |
| 39c | + |
| 39d | + |
| 39e | ++ |
| 40 | ++ |
| 41a | ++ |
| 41b | ++ |
| 41c | + |
| 41d | + |
| 42a | ++++ |
| 42b | +++ |
| 43 | + |
| 44 | ++ |
| 45 | +++ |
| 46 | + |
| 47 | ++ |
| 48 | ++ |
| 49 | ++++ |
| 50 | +++ |
| 51 | ++++ |
| 52a | ++++ |
| 52b | ++++ |
| 53 | ++++ |
| 54a | ++++ |
| 54b | +++ |

TABLE 25-continued

TPH1 Inhibition Data

| Ex. No. | TPH1 Range |
|---|---|
| 54c | ++++ |
| 54d | +++ |
| 54e | +++ |
| 54f | ++++ |
| 54g | +++ |
| 54h | + |
| 54i | + |
| 54j | +++ |
| 54k | +++ |
| 54l | + |
| 54m | ++ |
| 55a | +++ |
| 55b | ++++ |
| 55c | +++ |
| 55d | ++++ |
| 55e | +++ |
| 55f | +++ |
| 55g | ++ |
| 55h | +++ |
| 55i | ++++ |
| 55j | +++ |
| 55k | +++ |
| 55l | +++ |
| 55m | ++++ |
| 55n | ++ |
| 55o | +++ |
| 55p | +++ |
| 55q | ++++ |
| 55r | +++ |
| 55s | ++++ |
| 55t | +++ |
| 55u | +++ |
| 55v | ++++ |
| 55w | ++++ |
| 55x | +++ |
| 55y | +++ |
| 55z | +++ |
| 55aa | +++ |
| 55ab | +++ |
| 55ac | +++ |
| 55ad | +++ |
| 55ae | ++ |
| 55af | ++ |
| 55ag | +++ |
| 55ah | +++ |
| 55ai | ++++ |
| 55aj | +++ |
| 55ak | ++ |
| 55al | +++ |
| 55am | +++ |
| 55an | +++ |
| 55ao | +++ |
| 55ap | +++ |
| 55aq | +++ |
| 55ar | +++ |
| 55as | +++ |
| 55at | +++ |
| 55au | +++ |
| 55av | +++ |
| 55aw | ++ |
| 55ax | +++ |
| 55ay | ++ |
| 55az | ++++ |
| 55ba | ++++ |
| 55bb | ++++ |
| 55bc | ++++ |
| 55bd | ++++ |
| 55be | ++++ |
| 55bf | +++ |
| 55bg | ++++ |
| 55bh | +++ |
| 55bi | ++++ |
| 55bj | ++++ |
| 55bk | +++ |
| 55bl | ++ |

TABLE 25-continued

| TPH1 Inhibition Data | |
|---|---|
| Ex. No. | TPH1 Range |
| 55bm | ++ |
| 55bn | + |
| 55bo | +++ |
| 55bp | +++ |
| 55bq | ++ |
| 55br | ++ |
| 55bs | ++ |
| 55bt | ++ |
| 55bu | ++ |
| 55bv | ++ |
| 55bw | +++ |
| 55bx | ++ |
| 55by | ++ |
| 55bz | +++ |
| 55ca | +++ |
| 55cb | +++ |
| 55cc | +++ |
| 55cd | ++ |
| 55ce | ++ |
| 55cf | + |
| 55cg | ++ |
| 55ch | +++ |
| 55ci | ++ |
| 55cj | ++ |
| 55ck | ++ |
| 55cl | +++ |
| 55cm | ++ |
| 55cn | ++ |
| 55co | +++ |
| 55cp | ++ |
| 55cq | +++ |
| 55cr | ++ |
| 55cs | ++ |
| 55ct | ++ |
| 55cu | ++ |
| 55cv | ++ |
| 55cw | ++ |
| 55cx | ++ |
| 55cy | ++ |
| 55cz | +++ |
| 55da | ++ |
| 55db | ++ |
| 55dc | ++++ |
| 55dd | +++ |
| 55de | +++ |
| 55df | +++ |
| 55dg | +++ |
| 55dh | +++ |
| 55di | +++ |
| 55dj | +++ |
| 55dk | +++ |
| 55dl | +++ |
| 55dm | +++ |
| 55dn | +++ |
| 55do | ++++ |
| 55dp | ++++ |
| 55dq | ++++ |
| 56 | +++ |
| 57 | +++ |
| 58 | +++ |
| 59 | ++ |
| 59b | ++ |
| 59c | +++ |
| 59d | +++ |
| 60 | ++ |
| 61 | +++ |
| 62 | +++ |

PheOH and TH Inhibition Counter Assays

Certain compounds of the Examples were found to inhibit tryptophan hydroxylase (TPH) selectively over phenylalanine hydroxylase (PheOH). Inhibitory activity against PheOH can be assessed according to the methods described for example in *J. Med. Chem.* 10, 64-66 (1967), or *J. Antibiot.* 35, 458-462 (1982), or WO 2007/089335.

Certain compounds of the invention were found to inhibit tryptophan hydroxylase (TPH) selectively over tyrosine hydroxylase (TH). Inhibitory activity against TH can be assessed according to the methods described for example in Life Sci. 39, 2185-2189 (1986), or *Mol. Pharmacol.* 41, 339-344 (1992), or *J. Antibiot.* 35, 458-462 (1982), or WO 2007/089335.

Example B

Intestinal 5-HT Depletion Assay

The efficacy of the TPH1 inhibitors of the invention was assessed for the ability to decrease intestinal serotonin concentration in mice. Mice (C57 BL6) were administered a single 150 mg/kg dose of test article by oral gavage. Each animal was euthanized by exsanguination under isoflurane anesthesia. Jejunal intestinal mucosa was isolated and homogenized in 300 μL of a buffer containing 0.3M trichloroacetic acid, 0.1M sodium acetate, 10 mM EDTA, 20 mM sodium bisulfate and 50 mM ascorbic acid. Following centrifugation the 5-HT levels in the supernatants were measured by HPLC. The remaining mucosal pellet was solubilized overnight at 37° C. in a 0.1% sodium dodecyl sulfate buffer in 0.1N NaOH followed by determination of protein concentrations using a BCA protein assay (Pierce, Rockford, Ill. 5-HT levels were normalized to protein and data were expressed as mean percent reduction of mucosal 5-HT levels relative to vehicle control ±SEM (percent 5-HT reduction). All animal studies were carried out with protocols approved by the Institutional Animal Care and Use Committee.

The Examples listed in Table 26 below were tested and found to elicit a reduction in mean mucosal 5-HT concentrations relative to vehicle-treated animals according to the above-described in vivo assay. P-values, indicating statistical significance of the data (ANOVA) are provided in the table: * refers to $P<0.05$,  refers to $P<0.01$, * refers to $P<0.005$, and **** refers to $P<0.0005$.

TABLE 26

| In Vivo Efficacy of TPH1 Inhibitors In Mice (reduction of mucosal 5-HT concentrations one day after oral administration of a single 150 mg/kg dose) | |
|---|---|
| Example No. | Efficacy |
| 1g | *** |
| 1h | ** |
| 1l | **** |
| 1m | *** |
| 1n | ** |
| 1o | ** |
| 1p | ** |
| 1y | ** |
| 5 | ** |
| 10b | *** |
| 10d | *** |
| 10g | ** |
| 10h | *** |
| 10j | **** |
| 10k | * |
| 11 | **** |
| 12b | * |
| 12c | *** |
| 16 | ** |
| 22c | * |
| 28 | * |

TABLE 26-continued

| In Vivo Efficacy of TPH1 Inhibitors In Mice (reduction of mucosal 5-HT concentrations one day after oral administration of a single 150 mg/kg dose) | |
|---|---|
| Example No. | Efficacy |
| 29z | ** |
| 31 | * |
| 34r | *** |
| 34s | ** |
| 34u | * |
| 34v | * |
| 34w | *** |
| 55k | * |
| 55ak | ** |
| 55al | * |
| 55am | *** |
| 55an | *** |
| 55az | *** |
| 55bc | ** |
| 55bd | *** |
| 55bg | *** |
| 63g | *** |
| 63ay | *** |
| 63az | *** |
| 63ba | *** |
| 63bd | *** |
| 63be | *** |
| 63bf | **** |
| 63bg | **** |
| 63bh | ** |
| 63bi | ** |
| 63bn | **** |
| 63bo | **** |
| 63bp | **** |
| 63bq | **** |
| 63bx | *** |
| 63by | *** |
| 63bz | ** |
| 63ch | *** |
| 63cj | *** |
| 63cl | *** |
| 63cp | *** |
| 63da | *** |
| 63dc | *** |
| 63di | *** |
| 64c | **** |
| 64e | **** |
| 64f | **** |
| 64g | * |
| 64h | ** |
| 65a | **** |
| 66c | **** |
| 66d | **** |
| 101 | *** |

Example C

Reduction of Mucosal 5-HT Concentrations

The Examples listed in Table 27 below were tested and found to elicit a reduction in mean mucosal 5-HT concentrations relative to vehicle-treated animals according to the following in vivo assay.

The efficacy of the TPH1 inhibitors of the invention was assessed for the ability to decrease intestinal serotonin concentration in mice. Mice (C57 BL6) were administered an oral dose of 10 or 50 mg/kg of the test article in the evening. Approximately 16 h following the first dose, mice were administered a second oral dose of 50 mg/kg of the appropriate compound. A third oral dose of 50 mg/kg of the appropriate test article was administered 12 h after dose 2. Following an overnight fast, each animal was euthanized by exsanguination under isoflurane anesthesia. Jejunal intestinal mucosa was isolated and homogenized in 300 mL of a buffer containing 0.3M trichloroacetic acid, 0.1M sodium acetate, 10 mM EDTA, 20 mM sodium bisulfate and 50 mM ascorbic acid. Following centrifugation the 5-HT levels in the supernatants were measured by HPLC. The remaining mucosal pellet was solubilized overnight at 37° C. in a 0.1% sodium dodecyl sulfate buffer in 0.1N NaOH followed by determination of protein concentrations using a BCA protein assay (Pierce, Rockford, IL). 5-HT levels were normalized to protein and data were expressed as mean percent reduction of mucosal 5-HT levels relative to vehicle control ±SEM (percent 5-HT reduction). All animal studies were carried out with protocols approved by the Institutional Animal Care and Use Committee. P-values, indicating statistical significance of the data (ANOVA) are provided in the table: * refers to $P<0.05$,  refers to $P<0.01$, * refers to $P<0.005$, and **** refers to $P<0.0005$.

TABLE 27

| In Vivo Efficacy of TPH1 Inhibitors In Mice (reduction of mucosal 5-HT concentrations two days after oral administration of a single 50 mg/kg dose) | |
|---|---|
| Example No. | Efficacy |
| 1l | *** |
| 1m | * |
| 1n | *** |
| 1t | *** |
| 12c | *** |
| 55bg | *** |
| 63i | *** |
| 63ae | *** |
| 63aq | *** |
| 63ar | **** |
| 63aw | **** |
| 63az | *** |
| 63bd | *** |
| 63bf | *** |
| 63bg | *** |
| 63bn | **** |
| 63bo | *** |
| 63bp | *** |
| 63ch | *** |
| 63cj | ** |
| 63cl | *** |
| 63cn | **** |
| 63dc | *** |
| 63el | *** |
| 63eo | *** |
| 63ep | *** |
| 63ev | *** |
| 63ey | ** |
| 63fo | * |
| 63ha | ** |
| 64hb | *** |
| 69a | *** |
| 69b | *** |
| 69c | *** |

Example D

In Vivo Assay for Inflammatory Bowel Diseases

The utility of the compounds of the invention for the treatment of inflammatory bowel diseases can be measured, for example, using the experimental models of colitis induced by trinitrobenzene sulfonic acid (TNBS), dinitrobenzene sulfonic acid (DNBS), and dextran sodium sulfate (DSS), as described by Ghia, J.-E. et al. in *Gastroenterol.* 137,1649-60 (2009).

Example E

In Vivo Assay for Low Bone Mass Diseases

The utility of the compounds of the invention for the treatment of low bone mass diseases, such as osteoporosis, can be measured, for example, using the ovariectomy-induced osteopenia rat model, as described by Yadav, V. K. et al. in *Nature Med.* 16,308-12 (2010).

Example F

In Vivo Assay for PAH

The utility of the compounds of the invention for the treatment of pulmonary arterial hypertension (PAH), can be measured, for example, using the hypoxia mouse model, as described by Abid, S. et al. in *Am. J. Physiol., Lung Cellular and Molecular Physiology* 303, L500-8 (2012), or using the rat monocrotaline-induced PAH or the rat chronic hypoxia model, as described by Kay, J. M. et al. *Respiration* 47,48-56 (1985).

Example G

In Vivo Assay for Allergic Airway Inflammation

The utility of the compounds of the invention for the treatment of allergic airway inflammation, can be measured, for example, using the mouse model of allergic asthma, as described by Mirk, T. et al. in *Am. J. Respir. Crit. Care Med.* 187,476-485 (2013).

Example H

In Vivo Assay for Gastrointestinal Disorders

The utility of the compounds of the invention for the treatment of gastrointestinal disorders associated with dysregulation of the GI serotonergic system, such as chemotherapy-induced emesis and irritable bowel syndrome, can be measured, for example, using the a ferret model of chemotherapy-induced emesis, as described by Liu, Q. et al. in *J. Pharmacol. Exp. Ther.* 325,47-55 (2008).

Example I

In Vivo Assay for Tumor Growth

The utility of the compounds of the invention for the treatment of tumor growth, can be measured, for example, using the the xenograft model of cholangiocarcinoma tumor growth, as described by Alpini, G. et al. in *Cancer Res.* 68, 9184-93 (2008).

Example J

In Vivo Assay for Leukemia

The utility of the compounds of the invention for the treatment and prevention of leukemia and other cancers of the blood, can be measured, for example, using the mouse leukemia model, the osteoblast-deficient mouse model, or the murine model of acute myeloid leukemia, as described in WO 2013/074889.

Example K

In Vivo Assay for Atherosclerosis

The utility of the compounds of the invention for the treatment of atherosclerosis, and the reduction of plasma cholesterol and triglyceride levels, can be measured, for example, using the Apo E −/− or LDLR −/− mouse models of atherosclerotic plaque development, as described in WO 2012/058598.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating idiopathic pulmonary arterial hypertension in a patient, comprising administering to the patient in need thereof a therapeutically effective amount of (S)-8-(2-amino-6-((R)-1-(5-chloro-[1,1'-biphenyl]-2-yl)-2,2,2-trifluoroeth-oxy)pyrimidin-4-yl)-2,8-diazaspiro[4.5]decane-3-carboxylic acid or a pharmaceutically acceptable salt thereof.

2. The method of claim 1, wherein administration is by inhalation.

3. The method of claim 2, wherein inhalation is with a powder.

4. The method of claim 2, wherein inhalation is with a spray or an aerosol.

5. The method of claim 4, wherein the spray or aerosol is via a sonic nebulizer.

6. The method of claim 1, wherein administration is by injection.

7. The method of claim 6, wherein injection is subcutaneous, intravenous, or intramuscular.

8. The method of claim 1, wherein administration is by infusion.

9. The method of claim 1, wherein administration is oral.

10. A method of lowering peripheral serotonin in a patient having idiopathic pulmonary arterial hypertension, comprising administering to the patient in need thereof a therapeutically effective amount of (S)-8-(2-amino-6-((R)-1-(5-chloro-[1,1'-biphenyl]-2-yl)-2,2,2-trifluoroeth-oxy) pyrimidin-4-yl)-2,8-diazaspiro[4.5]decane-3-carboxylic acid or a pharmaceutically acceptable salt thereof.

11. The method of claim 10, wherein administration is by inhalation.

12. The method of claim 11, wherein inhalation is with a powder.

13. The method of claim 11, wherein inhalation is with a spray or an aerosol.

14. The method of claim 13, wherein the spray or aerosol is via a sonic nebulizer.

15. The method of claim 10, wherein administration is by injection.

16. The method of claim 15, wherein injection is subcutaneous, intravenous, or intramuscular.

17. The method of claim 10, wherein injection is subcutaneous, intravenous, or intramuscular.

18. The method of claim 10, wherein administration is oral.

* * * * *